(12) United States Patent
Whisstock et al.

(10) Patent No.: US 8,420,371 B2
(45) Date of Patent: Apr. 16, 2013

(54) CRYSTALS OF HUMAN GLUTAMIC ACID DECARBOXYLASE 65 (GAD65)

(75) Inventors: James Charles Whisstock, Murrumbeena (AU); Ashley Maurice Buckle, Mt. Dandenong (AU); Gustavo Fenalti, Sao Leopoldo (BR); Ruby Hong Ping Law, Caulfield (AU); Merrill Joy Rowley, Camberwell (AU)

(73) Assignee: Monash University, Clayton (AU)

( * ) Notice: Subject to any disclaimer, the term of this patent is extended or adjusted under 35 U.S.C. 154(b) by 0 days.

(21) Appl. No.: 12/310,958

(22) PCT Filed: Sep. 13, 2007

(86) PCT No.: PCT/AU2007/001362
§ 371 (c)(1),
(2), (4) Date: Nov. 4, 2009

(87) PCT Pub. No.: WO2008/031164
PCT Pub. Date: Mar. 20, 2008

(65) Prior Publication Data
US 2010/0216112 A1    Aug. 26, 2010

(30) Foreign Application Priority Data
Sep. 15, 2006    (AU) ............................... 2006905117

(51) Int. Cl.
*C12N 9/88*    (2006.01)
(52) U.S. Cl.
USPC ........................................................ 435/232

(58) Field of Classification Search .................... None
See application file for complete search history.

(56) References Cited

U.S. PATENT DOCUMENTS
2008/0201123 A1 *  8/2008  Cosgrove ........................ 703/11

OTHER PUBLICATIONS

"Crystallization of Nucleic Acids and Proteins, A Practical Approach", 2nd Ed., Ducruix and Giege, Oxford University Press, New York, 1999, p. 394.*
Powell et al., Clinica Chimica Acta 256:175-188, 1996.*
Corper et al., Science 288:505-511, 2000.*
Capitani et al., EMBO J. 22:4027-4037, 2003.*
Capitani, G. et al., "Structural model of human GAD65; prediction and interpretation of biochemical and immunogenic features," Proteins, 2005, vol. 59, No. 1, pp. 7-14.
Fenalti, G. et al., "GABA Production by Glutamic Acid Decarboxylase is regulated by a dynamic catalytic loop, " Nature Structural and Molecular Biology, 2007, vol. 14, No. 4, pp. 280-286.

* cited by examiner

*Primary Examiner* — David J Steadman
(74) *Attorney, Agent, or Firm* — Ohlandt, Greeley, Ruggiero & Perle, LLP.

(57) ABSTRACT

A crystal comprising an isoform of an N-terminally truncated glutamic acid decarboxylase (GAD) chosen from the group consisting of a monoclinic $P2_1$ space group with unit cell dimensions of a $=84.05\pm2.3$ Å, b$=62.74\pm2.3$ Å, c$=101.35\pm2.3$ Å and β $=106.69°$ (GAD67) or an orthorhombic $C222_1$ space group with unit cell dimensions of a$=78.25\pm2.3$ Å, b$=99.05\pm2.3$ Å and c$=120.01\pm2.3$ Å(GAD65).

2 Claims, 12 Drawing Sheets

GAD65

GAD67 a b

CRYSTALS OF HUMAN GLUTAMIC ACID DECARBOXYLASE 65 (GAD65)

FIELD OF THE INVENTION

The invention relates to crystal structures of the isoforms of human glutamic acid decarboxylase, GAD65 and GAD67. This invention also relates to a crystallographic model and methods for designing and selecting ligands that bind to and around the active binding site of GAD65 and GAD67.

INCORPORATION-BY-REFERENCE OF SEQUENCE LISTING

A sequence listing, created on May 7, 2012 as the ASCII text file "12310958 CRF Seq-3.txt" having a file size of 26 kilobytes, is incorporated herein by reference in its entirety.

BACKGROUND OF THE INVENTION

In this specification where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Incorporated herein by cross reference is the contents of a paper entitled "GABA production by glutamic acid decarboxylase is regulated by a dynamic catalytic loop" published in Nature *Structural & Molecular Biology*, volume 14, issue 4, pages 280-286.

Nature of GABA

Gamma-aminobutyric acid (GABA) and glutamate are the primary inhibitory and excitatory neurotransmitters in mammals. The balance between GABA and glutamate controls diverse processes such as neurogenesis, movement, circadian clocks, tissue development and blood glucose regulation. GABA is synthesized from glutamate by the 65 kDa and 67 kDa isoforms of the pyridoxal phosphate (PLP) dependant enzyme Glutamic Acid Decarboxylase (GAD65 and GAD67). Despite 81% sequence similarity, GAD65 (but not GAD67) cycles between an inactive apo-form and an active PLP-bound state; this activity represents a key control mechanism for GABA synthesis. Further, GAD65 (but not GAD67) is an important auto-antigen in diabetes and neurological disorders. The molecular basis for the catalytic and immune distinctions between the two GAD isoforms remains unknown.

Nature of GAD

GAD is a member of the pyroxidol-5-phosphate (PLP) dependant transferase superfamily. Members of this diverse superfamily play a major role in amino acid metabolism and catalyse decarboxylation as well as transamination, racemisation, aldol cleavage, and beta and gamma elimination. In GAD, PLP acts as an electrophilic catalyst while covalently bound to the glutamate, thereby stabilising the carbanionic reaction intermediate. This can be depicted diagrammatically as follows:

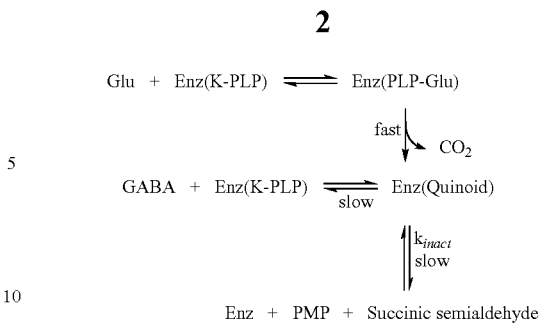

Vertebrates possess two closely related isoforms of GAD, GAD65 and GAD67, which are products of two independently regulated genes. Gene knockout studies together with clinical data demonstrate the necessity for this enzyme activity, and delineate distinct roles for each isoform. GAD67−/− mice exhibit substantially reduced GABA levels and die at birth of cleft palate. In contrast GAD65−/− mice have normal levels of GABA and appear normal at birth, but develop fatal seizures and anxiety phenotypes. In humans, mutation of GAD67 in humans results in spastic cerebral palsy.

In addition to its key role in neurotransmission, GAD65 is found in the human pancreas where GABA may regulate the first phase insulin response. The presence of GAD in the brain and pancreas is also of immunological importance, since autoantibodies to GAD65, but rarely to GAD67, are found in neurological conditions such as stiff person syndrome and most patients with type I diabetes.

Several mechanisms have been described in the regulation of GAD and GABA synthesis; these include post-translation modifications (including phosphorylation and palmitoylation), subcellular distributions (GAD67 is primarily cytosolic whereas GAD65 is associated with synaptic microvesicles) and transcription/translational control. Most notably, however, a side reaction in GAD65 causes dissociation of the co-factor PLP and enzyme inactivation as depicted in the reaction sequence above.

In this latter reaction free pyridoxal mono phosphate (PMP) together with succinic semialdehyde is released. Thus, it has been reported that ~80% of GAD67 isolated from cells exists in the active PLP bound state, while ~80% of GAD65 is in the inactive apo-form without PLP. Together with the physiological information derived from murine knockout studies, these data are consistent with a model where GAD67 is responsible for production of a basal pool of GABA and GAD65 is activated in response to a sudden requirements of extra GABA, for example in response to stress. The molecular basis for this difference remains to be elucidated.

There is therefore a need for a model of the structures of GAD that can reveal how the two closely related enzymes of GAD are able to perform strikingly different roles. Specifically there is a need for a structure model that shows how GAD65 is able to allow enzyme inactivation. Furthermore there is a need for a model structure and structural data that can facilitate the design of compounds that can perform functions such as prolonging GABA production by GAD65.

SUMMARY OF THE INVENTION

Crystal structure

The present invention therefore provides the structure coordinates of the two isoforms ofan N-terminal truncation ofGAD (GAD 65 and GAD67). The complete coordinates are listed in Table A. SEQ ID NO. 15 represents Asn88—Asp584 of GAD65. SEQ ID NO. 16 represents Thr93—Asp593 of GAD67. SEQ ID NO. 17 represents Thr93—Leu594 of GAD67 plus two His residues at the C-terminus.

The present invention further provides a crystal of GAD67 consisting of a monoclinic P2$_1$ space group with unit cell dimensions of a=84.05±2.3 Å, b=62.74±2.3 Å, c=101.35±2.3 Å and β=106.69.

The present invention further provides a crystal of GAD65 consisting of an orthorhombic C222$_1$ space group with unit cell dimensions of a=78.25±2.3 Å, b=99.05±2.3 Å and c=120.01±2.3 Å.

The present invention also provides a machine-readable data storage medium which comprises a data storage material encoded with machine readable data defined by the structure coordinates of GAD65 according to Table A or a homologue of this isoform.

The present invention also provides a machine-readable data storage medium which comprises a data storage material encoded with machine readable data defined by the structure coordinates of GAD67 according to Table A or a homologue of this isoform.

Catalytic Loop

The structure of GAD67 reveals a catalytic loop that covers the active binding site and introduces Tyr 434 as a catalytic switch. In contrast, the catalytic loop is mobile in GAD65. Mutational analysis reveals that destabilization of the catalytic loop in GAD67 promotes enzyme inactivation. It is further shown that many key residues implicated in auto-antibody binding map to mobile regions close to the active binding site of GAD65. The structure and model of the present invention show that mammals regulate the balance between GABA and glutamate by modulating the mobility of a catalytic loop. However, a cost of this mechanism may be that increased mobility in GAD65 may enhance the antigenicity of the molecule.

Accordingly, the present invention also provides a method for determining at least a portion of the three-dimensional structure of a species, such as a molecule or molecular complex which forms a binding partner of the catalytic loop (ie the loop that contains Tyr 434) or the region surrounding the catalytic loop of GAD65 and GAD 67. The molecule or molecular complex may for example stabilise, alter the conformation of, or interact with the catalytic loop. It is preferred that these molecules or molecular complexes correspond to at least a part of the active binding site defined by structure coordinates of GAD65 or GAD67 amino acids according to Table A, or a mutant or homologue thereof.

Accordingly the present invention further provides a method for identifying a binding partner for the catalytic loop or the region surrounding the catalytic loop of an isoform of an N-terminal truncation of GAD comprising the steps of:

(i) characterising the catalytic loop from the structure coordinates of Table A;

(ii) designing or selecting a binding partner that interacts with the catalytic loop or the region surrounding the catalytic loop; and (iii) obtaining or synthesizing said binding partner.

The present invention further provides an active binding site in GAD65 or GAD67 as well as methods for designing or selecting GAD modulators including agonists, partial agonists, antagonists, partial antagonists and/or selective GAD modulators using information about the crystal structures disclosed herein. The present invention further provides GAD modulators designed or selected according to said method.

In a preferred embodiment the methods or GAD modulators of the present invention are suitable for modulating the ability of either GAD65 or GAD67 to produce physiologically active compounds, such as GABA or succinic semialdehyde. Modulation in the production of GABA is expected to be useful of treating diseases such as movement disorders, Parkinson's disease, autism, schizophrenias, depression and other mental or physical illnesses that occur as a result of GABA deficiency, perturbations in GABA or GAD.

The structures of GAD reveal how two closely related enzymes are able to perform strikingly different roles. The work shows how mobility in the catalytic loop of GAD65 is able to allow enzyme inactivation. Indeed, our structural data may facilitate the design of compounds aimed at stabilising the catalytic loop and prolonging GABA production by GAD65.

GAD65 is highly auto-antigenic with respect to GAD67 and the structures of GAD65 and GAD67 thus provides a unique structural foundation for understanding auto-immune responses. The structures reveal that a key difference between the molecules is the flexibility of the C-terminal domain together with the catalytic loop. It has previously been reported by many others that flexible loops function in native proteins as efficient antigens.

The structural model of this invention thus also provides a high-resolution picture of how mammals regulate GABA production.

BRIEF DESCRIPTION OF THE DRAWINGS

FIG. 2(a) shows structural superposition between GAD67 A chain, GAD67 B chain and GAD65. Disordered regions in GAD65 are numbered.

FIG. 2(b) shows structural superposition of GAD67 dimer and GAD65 dimer. GABA moieties bound in active sites are shown as spheres. Catalytic loops are shaded. Both figures highlight the structural shifts in the C-terminus.

FIG. 2(c) shows the molecular surfaces of GAD65, FIG. 2(d) shows the molecular surfaces of GAD67. Flexibility, as measured by atomic temperature factors, is indicated by: Light shading=low (ordered) and dark shading=high (flexible). Disordered residues 436-485 in GAD65 are represented as dotted lines.

FIG. 4(a) shows the GAD67 monomer A.

FIG. 4(b) shows GAD67 monomer B.

FIG. 4(c) shows a close-up of GAD67 monomer A.

FIG. 4(d) shows GAD65.

FIG. 4(e) shows the superposition of active site residues of GAD67. The catalytic loop and Y434 sidechain (sticks) of GAD67 are shown. In panels A, B, and D, the $2F_o$-$F_c$ "omit" electron density contoured at 1σ is also shown (atoms from bound K-PLP cofactor, PLP-GABA and GABA product omitted from density calculation). The K405-PLP moiety, PLP-GABA atoms, and non covalently bound GABA are all visible. Hydrogen bonds are shown as dotted lines. Water molecules appear as spheres. The Y434 sidechain from the catalytic loop of chain B is also shown in both FIGS. 4(a) and 4(b). Protonation sites C4' and Cα are labelled; in (D) alternative conformations of bound GABA are shown.

FIG. 5(a) shows the "catalytic loop" (residues 430-450) of monomer A that forms a "flap" over the active site of monomer B in GAD67 can be seen. The K405-PLP adduct, PLP-GABA adduct and GABA product are shown as sticks.

FIG. 5(b) represents the interactions between the catalytic loop and adjacent monomer. Hydrogen bonds are shown as dotted lines. Water molecules are drawn as spheres. Residues that are different in GAD65 are lightly shaded. The alternative conformation of Y434 in monomer B is also shown. Residues 432-442 are disordered in GAD65.

FIG. 6(a) shows a comparison of % residual activity of WT GAD65 and GAD67 before and after incubation with glutamate.

FIG. 6(b) shows a comparison of % residual activity of GAD65 and GAD65 mutants.

FIG. 6(c) show a comparison of % residual activity of GAD67 and GAD67 mutants.

FIG. 12(a) shows the proposed mechanism for PLP-dependent formation of the Schiff base (Enz(PLP-Glu)) between PLP and glutamate and decarboxylation to give the quinoid (Enz(Quinoid)).

FIG. 12(b) shows how a GAD holoenzyme (i.e. PLP bound) catalyses the decarboxylation of glutamate bound to PLP; subsequent to the decarboxylation reaction, two alternate pathways have been characterised. The majority of the bound quinoid intermediate (or external aldimine) is converted to GABA alongside regeneration of the holoenzyme. Alternatively, decarboxylation-dependent transamination has been observed, where protonation of the C4' of PLP (instead of the Cα of the quinoid intermediate that results in GABA production) leads to the formation of succinate semialdehyde (SSA), pyridoxamine phosphate (PMP) and an inactive apoenzyme lacking PLP. Kinetic analysis reveals that the steps subsequent to product release (rather than the initial decarboxylation) are rate limiting. Further, the efficiency of decarboxylation-dependent transamination varies considerably between the two GAD isoforms, and therefore it appears to account for different physiological roles as well as different proportions of active holoenzymes in cells. It has been suggested that this difference is a result of different orientations of one or more proton-donating groups in the active site or, differences in the shielding of C4' from solvent.

DETAILED DESCRIPTION OF THE INVENTION

Structure Determination And Analysis

Figure 1:
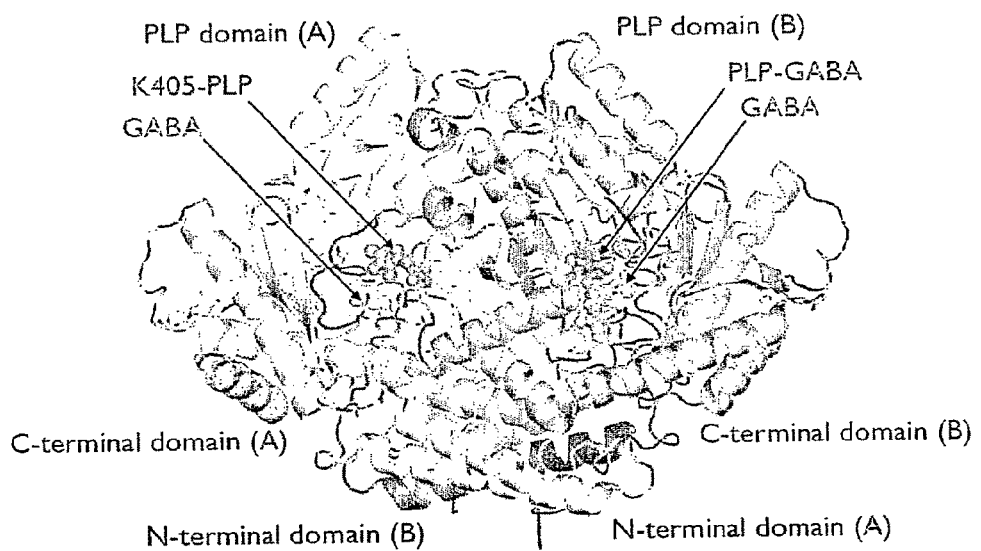
FIG. 1 is a dimeric structure of GAD67 within the asymmetric unit of the crystal. The N-terminal, PLP-binding and C-terminal domains are shaded differently and labelled. Monomer A is a slightly lighter shade than monomer B. Within the active sites, the K405-PLP Schiff base, and the PLP-GABA adduct are clearly labelled. Bound GABA product is also labelled. The "catalytic loop" (residues 430-450) forms a "flap" over the active site of an adjacent monomer.

The first crystal structures of GAD65 and GAD67 and their active binding domains have been determined to 2.3 Å resolution.

Protein Production And Crystallisation

The coding sequences of human GAD65 and GAD67, residues 84-585 and 90-594, respectively, were expressed in *Saccharomyces cerevisiae* as fusions to a C-terminal hexahistidine tag. Glutamate and PLP were added to all buffers. Recombinant proteins were purified from the cell lysate by immobilized metal affinity chromatography followed by size exclusion chromatography. Enzyme activity was measured by the $CO_2$ trapping method using benzethonium hydroxide as the trapping agent. Data generated were analysed using Prism and Ministat.

Prior to crystallization, purified holoenzymes were concentrated to 10 mg ml$^{-1}$ and equimolar chelidonic acid was added. The proteins were crystallized by the hanging drop method. GAD65 was crystallized in 20% (v/v) ethanol, 100 mM MES (pH6.2), 10 mM 2-mercaptoethanol and 20 mM $CaCl_2$, and GAD67 in 18% (w/v) PEG 8,000, 100 mM MES (ph 6.3), 10 mM 2-mercaptoethanol and 20 mM $CaCl_2$, at 20° C.

Mutagenesis

Amino acid substitutions were introduced into the GAD65 and GAD67 sequence using Quick-change mutagenesis kit (Stratagene). The amino acid substitutions were: X, Y and Z. All mutant proteins were prepared as described for the wild-type protein. The mutants and their forward and reverse primers are listed in Table 1.

Enzyme Activity Assay For GAD65Δ1-83

The procedure for measuring enzymatic activity of GAD65Δ1-83 was based on that described previously and was performed using an anion exchange resin AG1-X8 (Bio-Rad, Hercules, Calif.) to separate $^3$H-GABA from $^3$H-glutamate (Amersham) substrate by GAD65Δ1-83 catalysis in a reaction mix after 30 minutes at 37° C. Briefly, a stock solution (0.5M $KH_2PO_4$ pH 7.2, 10 mM 2-mercaptoethanol, 2 mM PLP, 10 mM AET and 100 mM glutamate). The reaction started after adding a solution containing a mixture of 200,000 cpm of $^3$H-glutamate and 100 mM of glutamate, to an eppendorf containing stock solution and purified GAD65$\Delta_{1-83}$. The reaction was stopped by the addition of 0.25M of $H_2SO_4$. For each tested sample, there were duplicate tubes both pre-stops (0 min) and active enzyme (30 min). After incubation, 500 µl of slurry (w/v) containing anion exchange resin in MQ water was added to each reaction. Eppendorfs were centrifuged at 2000 rpm for 1 minute at room temperature and 300 µl of supernatant was collected. 1 ml of scintilant was added to the sample and counted using a counting machine (WALLAC 1409 Liquid Scintillant Counting). Glutamate decarboxylase from rat brain was used as positive control for the enzyme assay experiments. Animal was killed by decapitation and brain was removed and homogenized with the stock buffer used in the enzyme assay. The homogeneous material was centrifuged in a TL-100 ultracentrifuge (Beckman) at 10,000 g for 10 minutes, and the clarified supernatant was collected and centrifuged again for 10 minutes and used in the assay run.

X-ray Data Collection, Structure Determination And Refinement

Data were collected at the IMCA-CAT beamline at the Advanced Photon Source, Chicago, USA. Both GAD65 and

TABLE 1

| Mutants | Forward primer | Reverse primer |
| --- | --- | --- |
| GAD65$_{F283Y}$ | 5'CATAGTCATTATTCTCTCAAGA AGGGAGCTG SEQ ID NO: 1 | 5'CTTGAGAGAATAATGACTATGTTCAGACG SEQ ID NO: 2 |
| GAD65$_{67loop}$ | 5'CAACCAAATGTGTGCCGGATA CCTCTTTCAG CCAGATAAACAGTATGACCTGTCC TATG SEQ ID NO: 3 | 5'CAGGTCATACTGTTTATCTGGCTGAAAGA GGTATCCGGCACACATTTGGTTGCAATTCCATC SEQ ID NO: 4 |
| GAD65$_{Y425F}$ | 5'GCCTCCTTCCTCTTTCAGCAAG ATAAAC SEQ ID NO: 5 | 5'CTGAAAGAGGAAGGAGGCATGCATTTGG SEQ ID NO: 6 |
| GAD67$_{Y292F}$ | 5'CAGAGTCACTTTTCCATAAAGA AAGCTGGG SEQ ID NO: 7 | 5'CTTTATGGAAAAGTGACTCTGTTCTGAGGTG SEQ ID NO: 8 |
| GAD67$_{65loop}$ | 5'CCAGATGCATGCATCCTACCTC TTCCAGCAA GACAAGCATTATGATGTCTCCTAC G SEQ ID NO: 9 | 5'GACATCATAATGCTTGTCTTGCTGGAAGAGG TAGGATGCATGCATCTGGTTGCATCC SEQ ID NO: 10 |
| GAD67$_{Y434F}$ | 5'GCAGGATTCCTCTTCCAGCCAG ACAAGC SEQ ID NO: 11 | 5'GGAAGAGGAATCCTGCACACATCTGG SEQ ID NO: 12 |

GAD67 crystals diffracted to 2.3A resolution. GAD67 crystals belong to space group P2$_1$, and have unit cell dimensions of a=84.05 Å, b=62.74 Å, c=101.35 Å, β=106.7°, consistent with two molecules per asymmetric unit; GAD65 crystals belong to space group C222$_1$, and have unit cell dimensions of a=78.25 Å, b =99.06 Å, c=120.1 Å, consistent with one molecule per asymmetric unit The data were merged and processed using MOSFLM and SCALA. (P. Evans, Scaling and assessment of data quality, *Acta Crystallogr. D. Biol. Crystallogr* (2006) 62, 72-82; A. Leslie, Joint CCP4+ESF-EAMCB *Newsletter on Protein Crystallography* (1992) 26). Subsequent crystallographic and structural analysis was performed using the CCP4i interface (E. Potterton et al, A graphical user interface to the CCP4 program suite, *Acta Crystallogr. D. Biol. Crystallogr* (2003) 59, 1131-7) to the CCP4 suite (The CCP4 suite: programs for protein crystallography, *Acta Crystallogr. D. Biol. Crystallogr*. (1994) 50, 760-3), unless stated otherwise. Five percent of the dataset was flagged for calculation of the free R factor (R$_{free}$) with neither a sigma, nor a low-resolution cut-off applied to the data. A summary of the data Collection and refinement statistics are provided in Table 2.

TABLE 2

|  | GAD67 | GAD65 |
|---|---|---|
| Data collection |  |  |
| Space Group | P2$_1$ | C222$_1$ |
| Cell dimensions (Å): a, b, c | 84.05, 62.74, 101.35, β = 106.69° | 78.25, 99.05, 120.1 |
| Resolution (Å) | 97.1-2.3 | 54.64-2.3 |
| Molecules per asymmetric unit | 2 | 1 |
| Total number of observations | 141888 | 78118 |
| Number of unique observations | 42284 | 20717 |
| Multiplicity | 3.4 (2.3) | 3.8 (3.8) |
| Data Completeness (%) | 93.7 (69.2) | 98.8 (98.8) |
| <I/σ> | 17.1 (4.4) | 14.9 (4.7) |
| R$_{pim}$ (%)[b] | 4.5 (19.4) | 3.5 (16.3) |
| Structure refinement |  |  |
| Nonhydrogen atoms |  | 3881 |
| Solvent | 359 | 93 |
| R$_{free}$ (%)[c] | 21.4 | 25.1 |
| R$_{cryst}$ (%) | 17.8 | 19.5 |
| Rms deviations from ideality |  |  |
| Bond lengths (Å) | 0.008 | 0.009 |
| Bond angles (°) | 1.2 | 1.3 |
| B factors (Å$^2$) |  |  |
| Mean main chain | 31.2 | 52.6 |
| Mean side chain | 32.8 | 54.3 |
| Mean water molecule | 34.7 | 52.4 |
| r.m.s. deviation bonded Bs | 0.7 | 0.7 |

[a]Values in parentheses refer to the highest resolution shell.
[b]Agreement between intensities of repeated measurements of the same reflections and can be defined as: Σ(I$_{h,i}$ − <I$_h$>)/ΣI$_{h,i}$, where I$_{h,i}$ are individual values and <I$_h$> is the mean value of the intensity of reflection h.
[c]The free R factor was calculated with the 5% of data omitted from the refinement.

The structure of GAD67 was solved using the molecular replacement method and the program PHASER (A. McCoy et al, Simple algorithm of a maximum likelihood SAD function, *Acta Crystallogr. D. Biol. Crystallogr* (2004) 60, 1220-8). A search model was constructed from the crystal structure of Pig Dopa Decarboxylase (DDC; PDB identifier 1JS3) (REF), the closest structural homologue identified using the FFAS server (L. Jaroszewski et al, FFAS03: a server for profile-profile sequence alignments, *Nucleic Acids Res* (2005) 33, W284-8) (sequence identity=20%). The structure was trimmed to remove regions of high sequence divergence, leaving predominantly residues belonging to the PLP-binding domain (representing ~60% of the total GAD67 structure). A "mixed" model consisting of conserved sidechains (all other non alanine/glycine residues truncated at Cγ atom) was then created using the SCRWL server (A. Canutescu et al, A graph-theory algorithm of rapid protein side-chain prediction, *Protein Sci* (2003) 12, 2001-14). Two outstanding solutions having Z-scores of 12 and 10 were produced, and packed well within the unit cell. Together with the unbiased features in the initial electron density maps, the correctness of the molecular replacement solution was confirmed.

Structure refinement and model building proceeded using one molecule in the asymmetric unit (the other Non-Crystallographic-Symmetry (NCS)-related molecule generated using NCS operators). Maximum likelihood refinement using REFMAC (G. Murshudov et al, Refinement of macromolecular structures by the maximum-likelihood method, *Acta Crystallographica* (1997) D53, 240-255), incorporating translation, libration, and screw-rotation displacement (TLS) refinement was carried out, employing a bulk solvent correction (Babinet model with mask). Throughout most stages of refinement, tight NCS-restraints were imposed on all residues in the two molecules in the asymmetric unit. At the later stages of refinement. All model building and structural validation was carried out using COOT (P. Emsley et al., K. Coot: Model-building tools for molecular graphics, *Acta Crystallogr. D. Biol. Crystallogr*. (2004) 60, 2126-32) Water molecules were added to the model using ARP/WARP (R. Morris et al, ARP/wARP and automatic interpretation of proteins electron density maps, *Methods Enzymol*, (2003) 374, 229-44) when the R$_{free}$ reached 30%. Solvent molecules were retained only if they had acceptable hydrogen bonding geometry contacts of 2.5-3.5 Å with protein atoms or with existing solvent, and were in good 2F$_o$-F$_c$ and F$_o$-F$_c$ electron density.

The structure of GAD65 was determined by molecular replacement using PHASER and the refined GAD67 model. Refinement proceeded as for GAD67.

Structural Analysis

Figure 4:
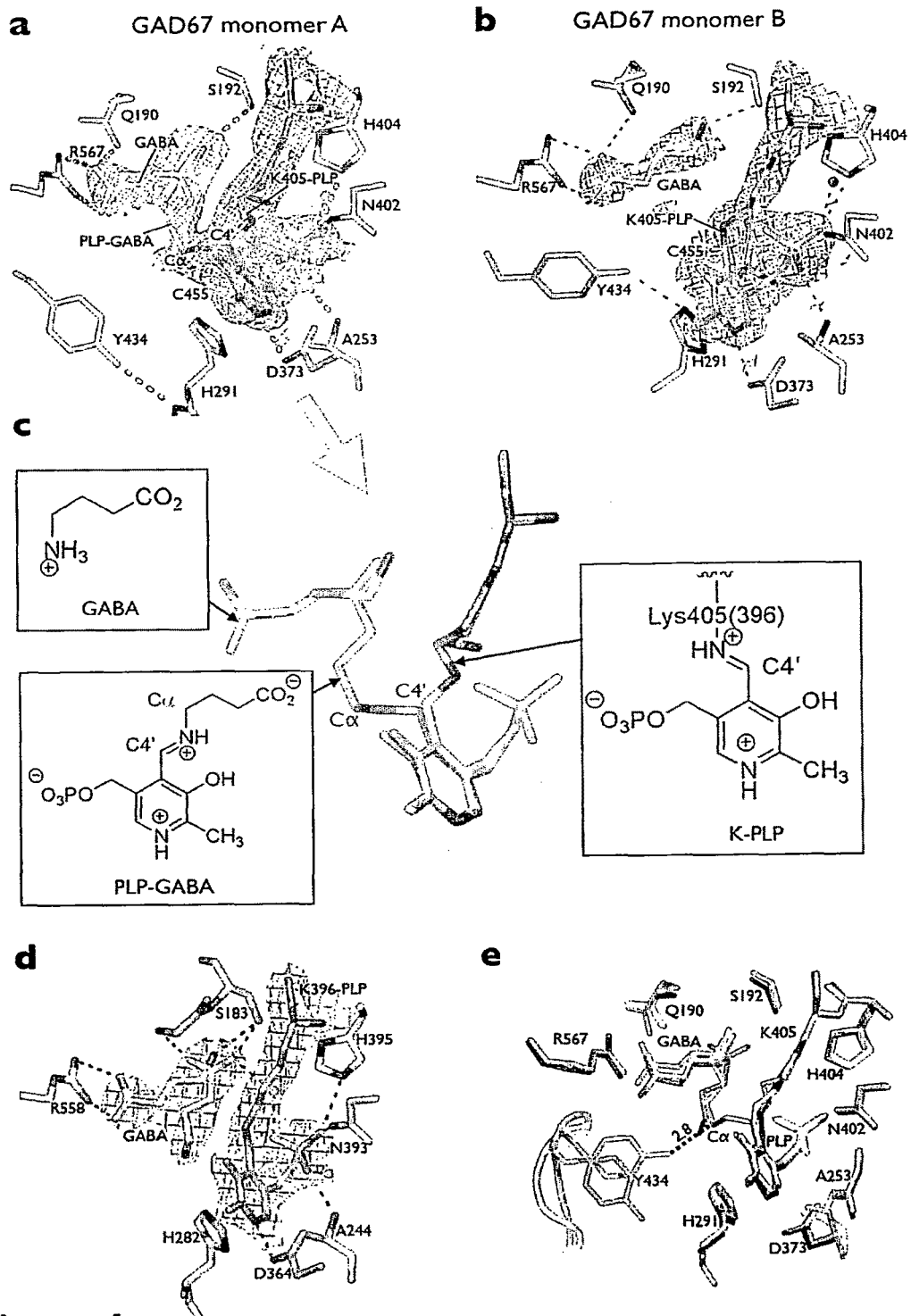
FIG. 4 is a view of the GAD65 catalytic loop interactions with active sites of GAD67 and GAD65.
Figure 5:
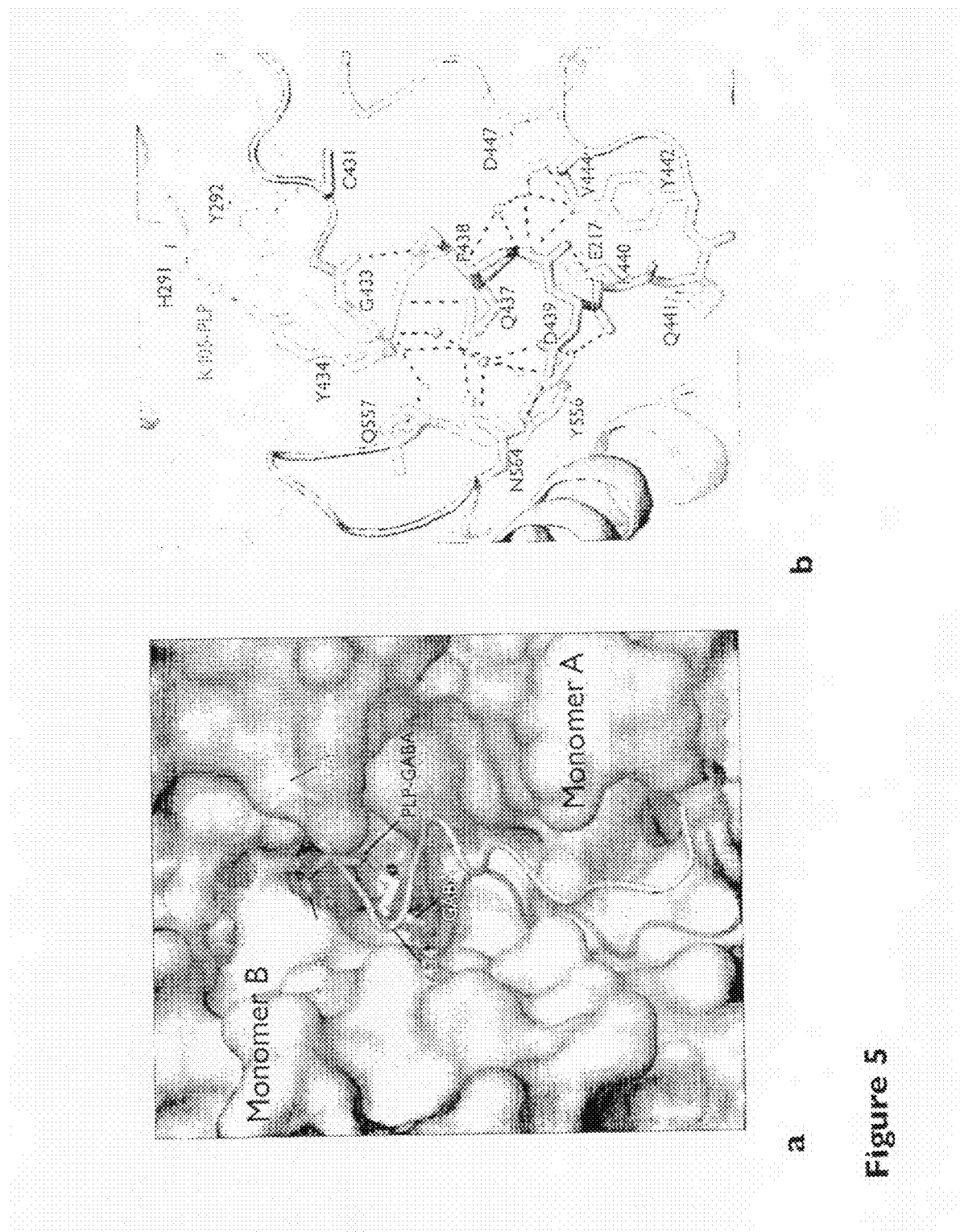
FIG. 5 is a structural superposition of GAD67 with Pig Dopa decarboxylase (PDB entry 1JS3) and *E. coli* GAD (PDB entry 1PMM).

PYMOL (W. DeLano, *The PyMOL User's Manual* from DeLano Scientific, San Carolos, Calif., USA (2002)) was used to produce FIGS. 2, 4 and 5. Structures were superimposed using the program MUSTANG (A. Konagurthu et al, Function, and Bioinformatics, MUSTANG: A multiple structural alignment algorithm; Proteins: Structure, Function, and Bioinformatics (2006)). Accessible surface areas were calculated using the CCP4 program AREAIMOL.

Overall Description of the X-Ray Crystal Structures of GAD65 And GAD67

Figure 7:
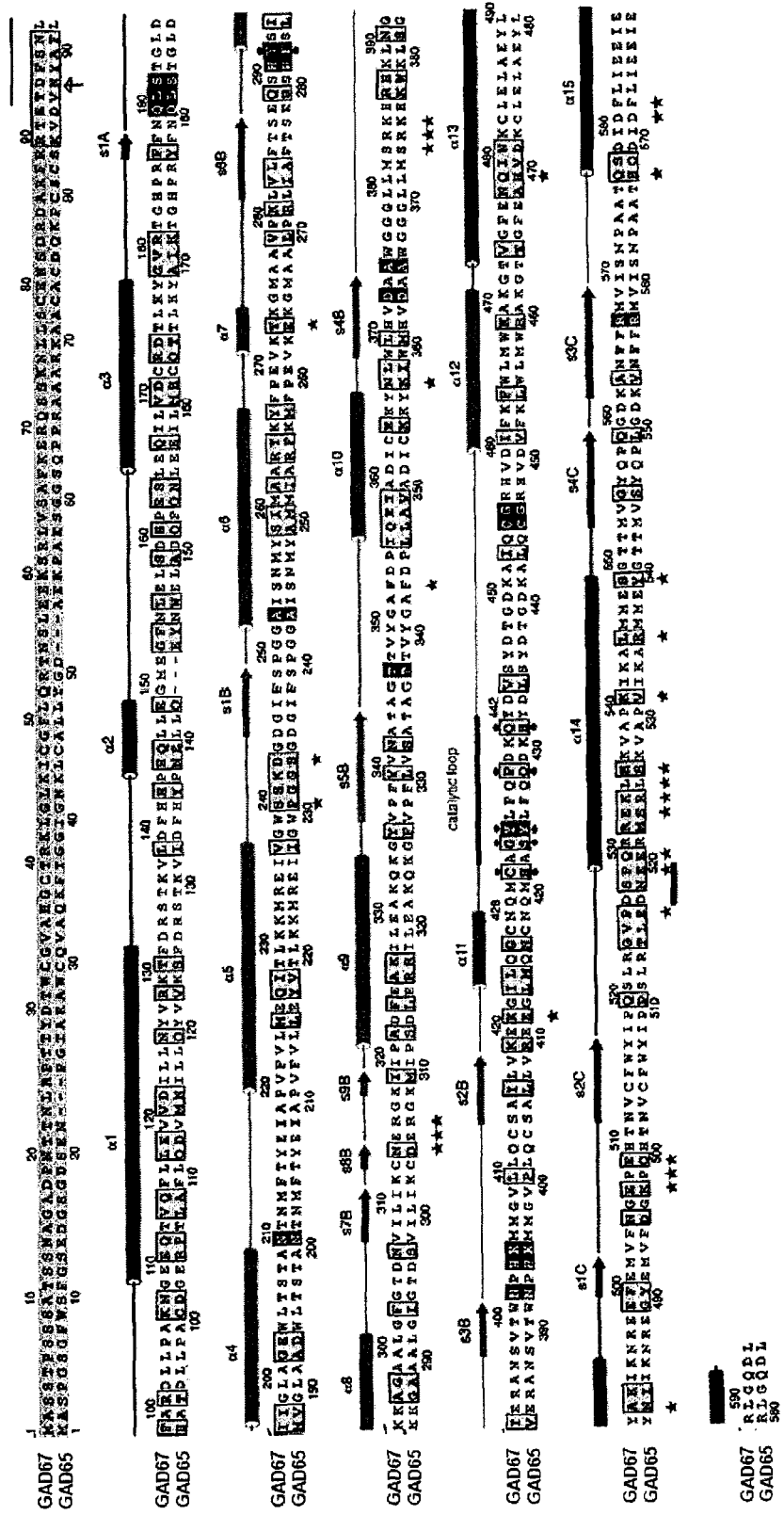
FIG. 7 depicts the sequence alignment of GAD65 (SEQ ID NO:14) and GAD67(SEQ ID NO:13) created using ALL-SCRIPT (G. J. Barton, ALLSCRIPT: A tool to format multiple sequence alignments, *Protein Eng.* (1993)6, 37-40). Residue numbering is indicated for both sequences. Shaded boxes indicate residues deleted in the constructs used in this study (GAD67Δ1-89 and GAD65Δ1-83). Differences in the primary sequences of GAD65 and GAD67 are indicated by boxes. The GAD67 secondary structure is shown above the sequence. GAD65 secondary structure is almost identical to GAD67, however, there is a difference located in the s3C β-strand of GAD67(residues XX-YY), which in GAD65 forms two contiguous smaller strands. GAD65 residues that form the GAD65 monoclonal autoantibody-binding epitope. Active site residues are boxed and critical functional residues boxed in black. Residues mutated in this study are indicated by an asterisk. The catalytic loop is labelled.

In order to understand the molecular regulation of GABA production, the crystal structures were determined for a truncated form of each isoform (referred to as GAD65 and GAD67 hereafter) that lack the first 83 and 89 residues, respectively. This is depicted visually in FIG. 7 for GAD65 (SEQ ID NO:14) and for GAD67(SEQ ID NO:13). A comparative analysis of the sequence differences between GAD65 and GAD67 is set out in Table 3.

TABLE 3

| Residue No. (GAD65 number in parentheses) | GAD67⇒GAD65 | Position, N-terminal domain (N), PLP domain (PLP) and C-terminal (C). | Exposed (E)/ Buried (B)/ Interface (I)*; GAD67 residues. | Exposed (E)/ Buried (B)/ Interface (I)*; GAD65 residues. | Active site (C); Implicated in AutoAb binding (Ab); Implicated in T cell epitope (T); Other (O). |
|---|---|---|---|---|---|
| 93(87) | Thr⇒Val | N | S | | |
| 94(88) | Asp⇒Asn | N | S | S | |
| 95(89) | Phe⇒Tyr | N | B | S | |
| 96(90) | Ser⇒Ala | N | S | S | |
| 97(91) | Asn⇒Phe | N | S | S | |
| 99(93) | Phe⇒His | N | S | S | |
| 101(95) | Arg⇒Thr | N | S | S | |
| 107(101) | Lys⇒Cys | N | S | S | |
| 108(102) | Asn⇒Asp | N | S | S | |
| 111(105) | Glu⇒Arg | α1 N | S | S | |
| 112(106) | Gln⇒Pro | α1 N | S | S | |
| 114(108) | Val⇒Leu | α1 N | S, I | S | |
| 115(109) | Gln⇒Ala | α1 N | S | S | |
| 118(112) | Leu⇒Gln | α1 N | S | S, I | |
| 119(113) | Glu⇒Asp | α1 N | S | S | |
| 121(115) | Val⇒Met | α1 N | B, I | B, I | |
| 122(116) | Asp⇒Asn | α1 N | B | S | T[1] |
| 126(120) | Asn⇒Gln | α1 N | S | S | T[1] |
| 129(123) | Arg⇒Val | α1 N | S, I | S | T[1] |
| 131(125) | Thr⇒Ser | α1 N | B | B, I | T[1] |
| 139(133) | Leu⇒Ile | N | B | B | |
| 143(137) | His⇒Tyr | N | S, I | S, I | |
| 145(139) | His⇒Asn | α2, N | S | S | |
| 146(140) | Gln⇒Glu | α2, N | S | S | |
| 149(143) | Glu⇒Gln | α2, N | S | S | |
| 150(del.) | | | | | |
| 151(del.) | | | | | |
| 152(del.) | | | | | |
| 153(144) | Gly⇒Glu | N | S | S | |
| 154(145) | Phe⇒Tyr | N | B | S | |
| 156(147) | Leu⇒Trp | N | B, I | B, I | |
| 159(150) | Ser⇒Ala | N | S, I | S, I | |
| 161(152) | His⇒Gln | N | S | S | |
| 163(154) | Glu⇒Gln | N | S, I | S, I | |
| 164(155) | Ser⇒Asn | N | S | S | |
| 167(158) | Gln⇒Glu | α3 N | S | S | |
| 170(161) | Val⇒Met | α3 N | S | S | |
| 171(162) | Asp⇒His | α3 N | B | B | |
| 173(164) | Arg⇒Gln | α3 N | S | S | |
| 174(165) | Asp⇒Thr | α3 N | S | B | |
| 179(170) | Gly⇒Ala | N | S | B | |
| 180(171) | Val⇒Ile | N | B, I | B, I | |
| 181(172) | Arg⇒Lys | N | S | S | |
| 187(178) | Phe⇒Tyr | s1A, N | B | B, I | |
| 197(188) | Ile⇒Met | α4 N | B, I | B, I | |
| 198(189) | Ile⇒Val | α4 N | B, I | B | |
| 202(193) | Gly⇒Ala | α4 N | B | B | |
| 203(194) | Glu⇒Asp | α4 N | B, I | B, I | |
| 225(216) | Met⇒Leu | α5 PLP | B, I | B | |
| 227(218) | Gln⇒Tyr | α5 PLP | S | S | |
| 228(219) | Ile⇒Val | α5 PLP | S, I | B, I | |
| 237(228) | Val⇒Ile | α5 PLP | B | B | |
| 240(231) | Ser⇒Pro | PLP | S | S | Ab[1], mAb DPC, structural differences between isoforms in this loop |
| 241(232) | Ser⇒Gly | PLP | S | S | structural differences between isoforms in this loop |
| 242(233) | Lys⇒Gly | PLP | S | B | structural differences between isoforms in this loop |
| 243(234) | Asp⇒Ser | PLP | S | S | Ab[1], mAb DPC, structural differences between isoforms in this loop |
| 259(250) | Ser⇒Ala | α6 PLP | B | B | |
| 260(251) | Ile⇒Met | α6 PLP | B | B | |
| 262(253) | Ala⇒Ile | α6 PLP | B | B | |
| 265(256) | Tyr⇒Phe | α6 PLP | S | S | |
| 267(258) | Tyr⇒Met | α6 PLP | S | S | |
| 273(264) | Thr⇒Glu | α7 PLP | S, I | S, I | Ab[1], mAb M10 and M6 |
| 279(270) | Val⇒Leu | PLP | B | S | |
| 281(272) | Lys⇒Arg | PLP | S, I | S | |
| 283(274) | Val⇒Ile | s2B, PLP | B | B | T[1] |
| 284(275) | Leu⇒Ala | s2B, PLP | B | B | T[1] |
| 289(280) | Gln⇒His | PLP | S | S | T[1], C(within 6 Å sphere) |
| 292(283) | Tyr⇒Phe | α8 PLP | S, I | S | T[1], C(within 6 Å sphere) |
| 294(285) | Ile⇒Leu | α8 PLP | B | B | |

TABLE 3-continued

| Residue No. (GAD65 number in parenthesis) | GAD67⇒GAD65 | Position, N-terminal domain (N), PLP domain (PLP) and C-terminal (C). | Exposed (E)/ Buried (B)/ Interface (I)*; GAD67 residues. | Exposed (E)/ Buried (B)/ Interface (I)*; GAD65 residues. | Active site (C); Implicated in AutoAb binding (Ab); Implicated in T cell epitope (T); Other (O). |
|---|---|---|---|---|---|
| 297(288) | Ala⇒Gly | α8 PLP | B | B | |
| 298(289) | Gly⇒Ala | α8 PLP | B | B | |
| 303(294) | Phe⇒Ile | PLP | B | B | Ab[4] |
| 307(298) | Asn⇒Ser | PLP | B | B | Ab[4] |
| 314(305) | Asn⇒Asp | s4B, PLP | S | S | Ab[2], mAb 96.11 |
| 319(310) | Ile⇒Met | s5B, PLP | B | B | |
| 322(313) | Ala⇒Ser | α9 PLP | S | S | |
| 324(315) | Phe⇒Leu | α9 PLP | B | B | |
| 326(317) | Ala⇒Arg | α9 PLP | S | S | Ab[1], Ab[3], T1D sera |
| 327(318) | Lys⇒Arg | α9 PLP | S | S | Ab[3], T1D sera |
| 336(327) | Tyr⇒Phe | PLP | S | S | |
| 340(331) | Tyr⇒Leu | s6B, PLP | B | B | C[1](within 6 Å) |
| 342(333) | Asn⇒Ser | s6B, PLP | B | B | C(within 6 Å) |
| 356(347) | Ile⇒Leu | α10 PLP | B | B | |
| 357(348) | Gln⇒Leu | α10 PLP | S | S | |
| 358(349) | Glu⇒Ala | α10 PLP | S | S | |
| 359(350) | Ile⇒Val | α10 PLP | B | B | |
| 364(355) | Glu⇒Lys | α10 PLP | S | S | |
| 367(358) | Asn⇒Lys | PLP | S | S | Ab[1], mAb M4 |
| 368(359) | Leu⇒Ile | PLP | B | B | |
| 370(361) | Leu⇒Met | s7B, PLP | | | |
| 387(378) | Arg⇒Lys | PLP | S | S | |
| 388(379) | His⇒Trp | PLP | S | S | |
| 391(382) | Asn⇒Ser | PLP | S | S | |
| 393(384) | Ile⇒Val | PLP | B | B | |
| 410(401) | Leu⇒Pro | PLP | B, I | B | |
| 416(407) | Ile⇒Leu | s9B, PLP | B | B | C(within 6 Å) |
| 419(410) | Lys⇒Arg | PLP | S | S, I | |
| 421(412) | Lys⇒Glu | PLP Connection between active sites | S | S | Ab[1], mAb DPC |
| 423(414) | Ile⇒Leu | PLP Connection between active sites α11 | B | B | |
| 424(415) | Leu⇒Met | PLP Connection between active sites α11 | B | B | |
| 426(417) | Gly⇒Gln | PLP Catalytic loop | B | S | |
| 431(422) | Cys⇒His | PLP Catalytic loop | S, no bonds within 5 Å distance | S | |
| 433(424) | Gly⇒Ser | PLP Catalytic loop | S, no bonds within 5 Å distance | No struct. | |
| 436(427) | Leu⇒Phe | PLP Catalytic loop | S, no bonds within 5 Å distance | No struct. | T[1] |
| 438(429) | Pro⇒Gln | PLP Catalytic loop | S, no bonds within 5 Å distance | No struct. | T[1] |
| 441(432) | Gln⇒His | PLP Catalytic loop | S, no bonds within 5 Å distance | No struct. | T[1] |
| 444(435) | Val⇒Leu | | S, no bonds within 5 Å distance | S | T[1] |
| 453(444) | Ile⇒Leu | PLP Catalytic loop | B | B | |
| 461(452) | Ile⇒Val | α12, PLP | B | B | |
| 464(455) | Phe⇒Leu | α12, PLP | B | B | |
| 469(460) | Lys⇒Arg | α12 | B, I | B, I | |
| 474(465) | Val⇒Thr | α13 C | S, I | S, I | |
| 478(469) | Asn⇒Ala | α13 C | S | S | |
| 479(470) | Gln⇒His | α13 C | S | S | Ab[1], mAb M8, M9 |
| 480(471) | Ile⇒Val | α13 C | B | B | |
| 481(472) | Asn⇒Asp | α13 C | S | S | |
| 492(483) | Ala⇒Asn | α13 C | S | S | Ab[1], T[1], mAb, M7, M3 and M1 |
| 493(484) | Lys⇒Ile | α13 C | S | S | T[1] |
| 499(490) | Glu⇒Gly | C | S | B | T[1] |
| 500(491) | Phe⇒Tyr | s1C, C | B | S | |
| 505(496) | Asn⇒Asp | C | S | S | |
| 507(498) | Glu⇒Lys | C | S | S | Ab[2], T[1], mAb b78 |
| 509(500) | Glu⇒Gln | C | S | S | Ab[2], mAb b78 |
| 520(511) | Gln⇒Pro | C | S | S | T[1] |
| 524(515) | Gly⇒Thr | C | S | S | T[1] |
| 525(516) | Val⇒Leu | C | S | S | T[1] |
| 526(517) | Pro⇒Glu | C | S | S | Ab[1], Ab[3], T[1], mAb M2 and M5 |
| 528(519) | Ser⇒Asn | C | S | S | T[1] |
| 529(520) | Pro⇒Glu | α14 C | S | S | Ab[1], T[1], M2 and M5 |
| 530(521) | Gln⇒Glu | α14 C | S | S | Ab[1], T[1], M5? |
| 532(523) | Arg⇒Met | α14 C | S | No struct. | T |
| 533(524) | Glu⇒Ser | α14 C | S | No struct. | Ab[1], Ab[3], T[1], M5 |
| 534(525) | Lys⇒Arg | α14 C | S | No struct. | Ab[3], T[1] |
| 536(527) | His⇒Ser | α14 C | S, I | S | Ab[1], M5 |
| 541(532) | Lys⇒Val | α14 C | S | S | Ab[1], b78 and M5 |

TABLE 3-continued

| Residue No. (GAD65 number in parenthesis) | GAD67⇒GAD65 | Position, N-terminal domain (N), PLP domain (PLP) and C-terminal (C). | Exposed (E)/ Buried (B)/ Interface (I)*; GAD67 residues. | Exposed (E)/ Buried (B)/ Interface (I)*; GAD65 residues. | Active site (C); Implicated in AutoAb binding (Ab); Implicated in T cell epitope (T); Other (O). |
|---|---|---|---|---|---|
| 545(536) | Leu⇒Arg | α14 C | S | S | Ab[1], M8 and M9 |
| 549(540) | Ser⇒Tyr | α14 C | S | S | Ab[1], M8 and M9 |
| 555(546) | Gly⇒Ser | s3C, C | B | S | |
| 559(550) | Gln⇒Leu | s3C, C | S | S | |
| 563(554) | Ala⇒Val | s4C, C | B | S | |
| 577(568) | Gln⇒His | C | S | S | Ab[1], M7 |
| 578(569) | Ser⇒Gln | C | S | S | |

GAD65 mutations with effect on antibody recognition:
Ab[1] - Schwartz et al., 1999. Glu264 is essential for mAb M10 epitope but not M4 and is replaced by threonine in GAD67. Lys358 completely abolished M4 reactivity (replaced by asparagine in GAD67). Asn483 and His568 are very important for the binding of M1, M3 and M7 antibodies. Glu517, Glu520 and Glu521 are essential for M2 and M5 epitope. Ser524 and Ser527 are critical for M5 recognition only. V532K affected M5 and b78 binding and is consistent with the inability of mAb b78 to inhibit GAD65 enzyme activity (unpublished?). Pro231 and Ser234 are important for DPC epitope and localized in a region of structural differences between GAD67 and GAD65. The location of this epitope away from the active site/catalytic loop is consistent with its inability to inhibit GAD65 activity. Arg536 and Tyr540 are critical for binding M8 and M9 only, and H470Q mutation affected these antibodies epitopes. Trp379 and Glu412 are also implicated in DPC epitope. Arg317 is critical for two GAD65-specific mAb (referred in text as unpublished) and also decrease reactivity of T1D patients by 17% (Myers, Fenalti.. et al.). Leu574 -Pro and Asn247Ser results in the loss of binding for all eleven tested antibodies in a another study (this may not be so relevant for Ab binding but could be important for protein folding or maintaining conformation, similar to residue). Leu574 -Pro affected C-terminal epitopes of M1, M3 and DPA. If this Leu is close to His362-need to check- the explanation is that it affects the folding since it is critical for folding in class II decarboxylases (Capitani et al., 2003).
Ab[2] - Mutation 305DER307, and 498KPQ500 decreased reactivity with b96.11 by 38% and 55% respectively. (Fenalti et al, 2006)
Ab[3] - O'Konnor et al., (2006). 524SRL526 mutated to AAA caused drastic reduction in reactivity with b78 (inhibts GAD65 activity). Although 572DF573 are the same in GAD67 and GAD65, mutation of these residues to A completely abolished reactivity with b78 and b96.11.
Ab[4] - Mutation 294IGTDS298 (note that Gly, Thr and Asp are in the interface of the dimer) completely abolished b96.11 and b78 antibody binding.
*3.6 Angstroms being the maximum distance between atoms used to calculate residues in the dimer interface.
T[1] - Patel et al., (Identification of immunodominant T cell epitopes of human glutamic acid decarboxylase 65 by using HLA-DR (alpha1*0101, beta1*0401) transgenic mice. Proc Natl Acad Sci USA, 1997 Jul. 22; 94(15): 8082-7
C[1] - Within 6 Å radius from PLP ring Preliminary studies revealed that the full length constructs were not suitable for structural studies because the N-terminal region is most likely unstructured and is extremely sensitive to proteolytic degradation. Previous studies as well as kinetic analysis revealed that N-terminally truncated GAD has comparable activity to full-length material.

Figure 2:
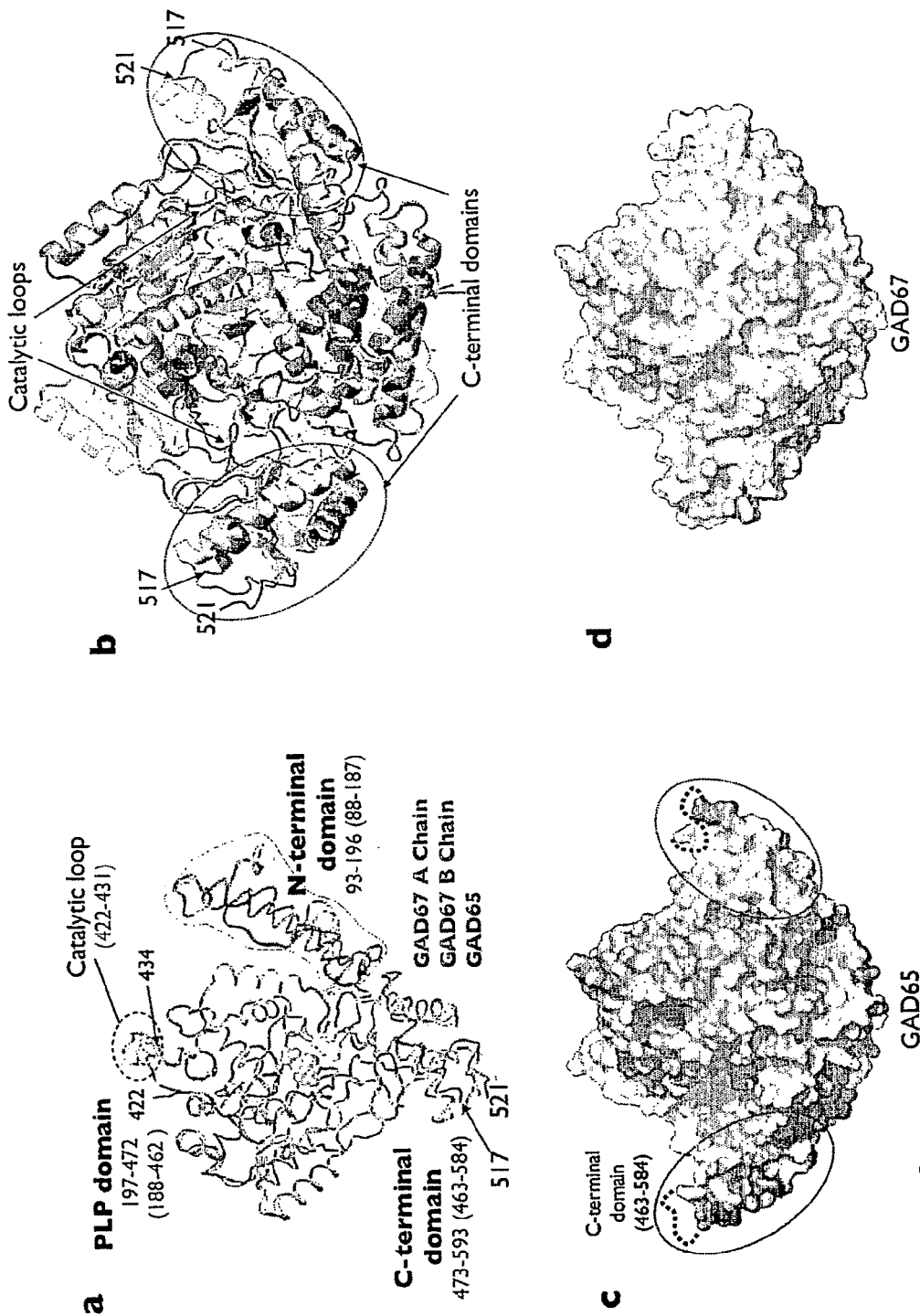
FIG. 2 is a view of the molecular surface of GAD67 dimer and GAD67 dimer interface shaded according to sequence conservation between GAD67 and GAD65.

The 2.3 Å structures of GAD67 and GAD65 are shown in FIG. 1 and FIG. 2. Both molecules form obligate functional dimers that bury a surface area of 6816 Å$^2$ and 5662 Å$^2$ respectively. The monomeric unit is made up of three distinct domains (termed N-terminal, PLP-binding and C-terminal; FIG. 1). The overall quality of the density in GAD67 is excellent, with all regions resolved in electron density. In GAD65 two loops (423-433 in the PLP domain and 518-520 in the C-terminal domain) are disordered. The contribution each domain makes to the dimer interface, and descriptions of the nature of the interfaces is detailed in the Table 4 which records the physical and chemical nature of the dimer interfaces. (Note that the discrepancy between the number of interface residues and surface areas of GAD67 and GAD65 dimers can be accounted for by the disorder of residues 423-433 in the PLP domain and 518-520 in the C-terminal domain of GAD65, both of which contribute to the dimer interface.)

TABLE 4

| | GAD67 | GAD65 |
|---|---|---|
| Buried Surface Area at interface | 6816 | 5662 |
| % Polar Atoms in Interface | 29 | 26 |
| % Non-Polar Atoms in Interface | 71 | 74 |
| Hydrogen Bonds | 42 | 36 |
| Total residues/ interface residues (%) | 1004/320 (32%) | 966/284 (29%) |
| Interface residues per domain (% composition per domain) | | |
| N-terminal | 102 (32%) | 102 (36%) |
| PLP-binding | 186 (58%) | 162 (57%) |
| C-terminal | 32 (10%) | 20 (7%) |

The N-terminal domain includes two parallel helices that pack against the N-terminal and PLP-binding domain of the other monomer. The PLP-binding domain adopts the type I PLP-dependant transferase-like fold and comprises nine helices surrounding a 7-stranded mainly parallel β-sheet which can be seen clearly in FIG. 1. The C-terminal domain contains the four remaining helices, together with a short 2 strand antiparallel β-sheet.

GAD65 and GAD67 are 71% identical in the region structurally characterised, adopt the same fold and superpose with an r.m.s.d of 0.8 Å$^2$ (474 residues; as shown in FIG. 2a). They do, however, differ in two important regions. Rigid body shifts of 1.5 Å are observed in the C-terminal domain of GAD65 with respect to GAD67 (see FIGS. 2a and 2b). Further, B-factor analysis reveals that this region is substantially more mobile in GAD65 and contains a region not visible in electron density (residue 518-520; FIG. 2). Importantly, residues 423-433 in the PLP domain of GAD65 are also not visible in electron density. This latter region accounts almost entirely for the difference of 1150 Å$^2$ interfacial surface area between the isoforms. In GAD67 the region corresponding to residues 423-433 forms a well-ordered loop that sits on top of the active site cleft as can be seen in FIG. 1. These differences are discussed below in relation to both GAD enzyme function and autoantigenicity.

Location of B-Cell Epitopes On GAD65

Figure 3:
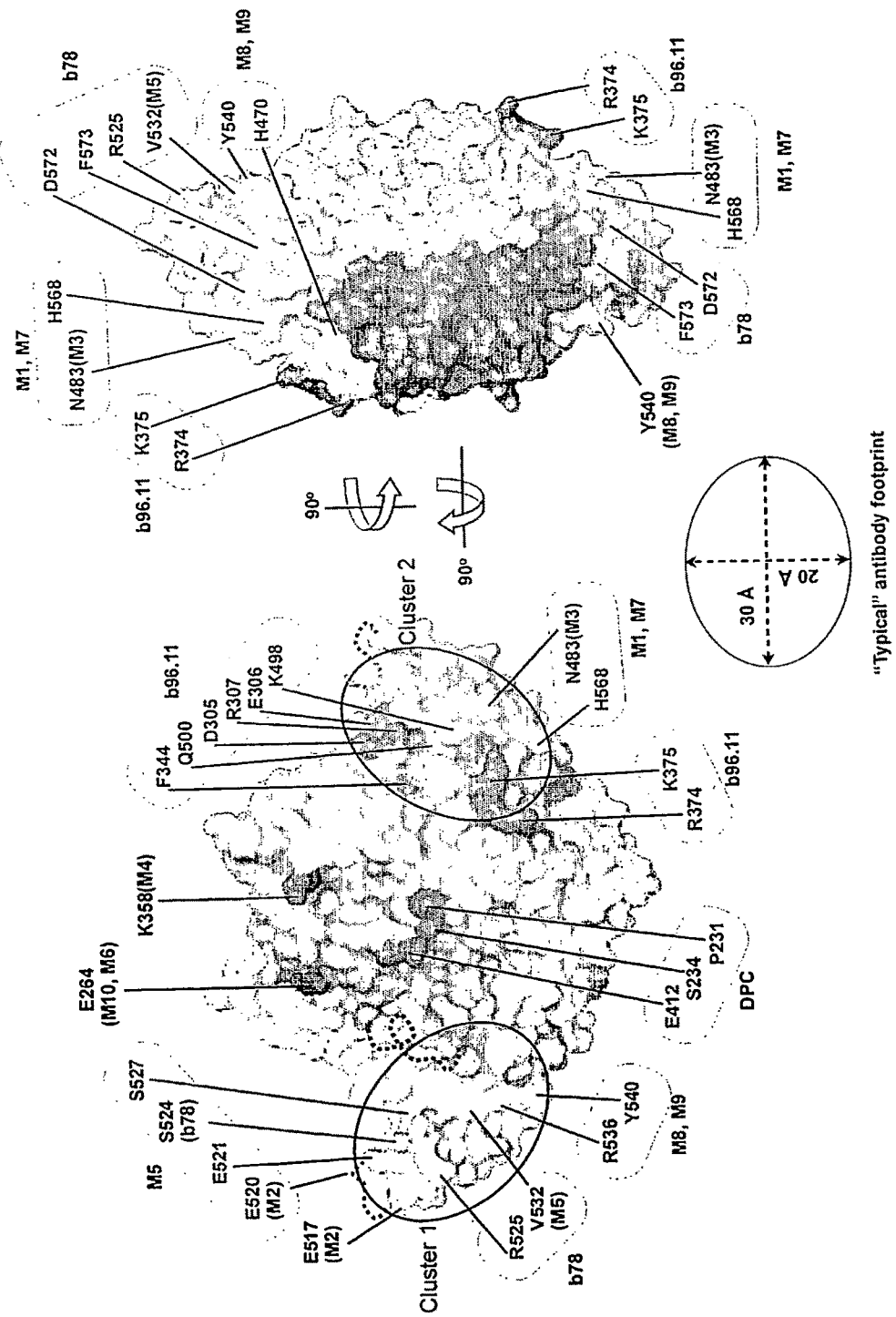
FIG. 3 is a view of the molecular surfaces of GAD65 and GAD67 shaded to show differing electrostatic potential. Location of amino acids on the structure of the dimer GAD65 are shown by mutation to reduce the binding of 13 human anti-GAD65 monoclonal antibodies. The human mAbs b78 and b96.11 are representatives of two major epitope regions on GAD65, indicated by the "typical antibody footprint". Epitopes for mAb M2, M5, M8, M9 and b78 (cluster 1) reside in one face of the C-terminal domain, in the region of the highly flexible loop for which there is no structure. Residues required for mAb binding within this cluster form a linear arrangement between the most flexible regions on the GAD65 structure, the catalytic loop and the C-terminal loop (black and doted lines respectively), being the representative mAb for this cluster (b78) enzymatically inhibitory. For two of these mAbs (M8, M9), the identified epitope residues also lie in the interface between the N-terminal and C-terminal domains (B). The epitopes within cluster 2 (M1, M3, M7, and b96.11) mapped to the opposite face of the C-terminal domain (Y). The epitope for mAb b96.11 is located in the border between the PLP and C-terminal domains, a region commonly recognised by autoantibodies present in Type 1 diabetes. The remaining 5 mAbs (M4, M6, M10, DPC) mapped to the PLP-domain, and form two sub-clusters: M4, M6 and M10, which can cross-inhibit each other, and the epitope for DPC
Figure 8:
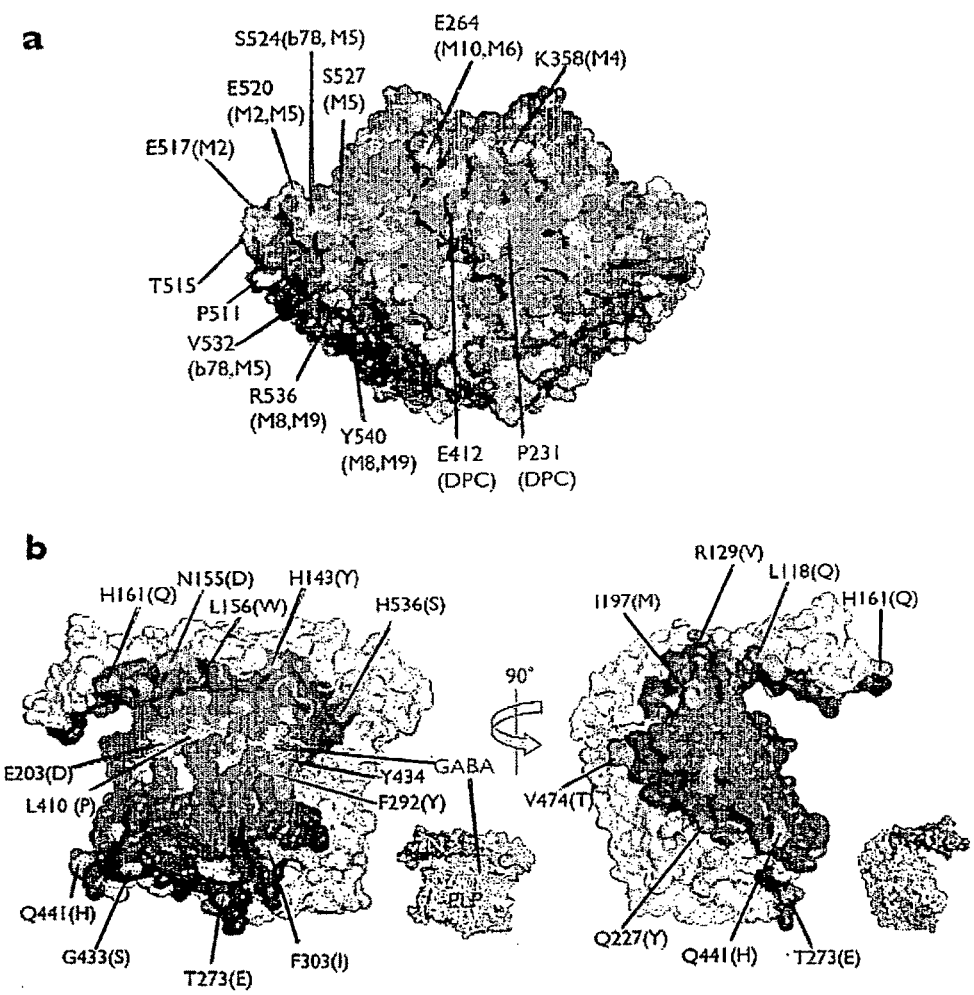
FIG. 8(a) shows surface-exposed differences in sequence between the two isoforms (GAD65 and GAD67) distributed over the entire structure of the molecule, with no obvious clustering apparent in any region.
FIG. 8(b) is the molecular surface of GAD67 dimer and GAD67 dimer interface shaded according to sequence conservation between GAD67 and GAD65. The molecular surface of the GAD67 dimer and GAD67 dimer interface are shaded according to sequence conservation between GAD67 and GAD65. Light shading=100% conserved, dark shading=50% conserved, red=non-conserved. Calculated using ESPript and displayed using CCP4MG (L. Potterton et al, Developments in the CCP4 molecular-graphics project, *Acta Crystallogr D. Biol. Crystallogr.* (2004) 60, 2288-94).
Figure 9:
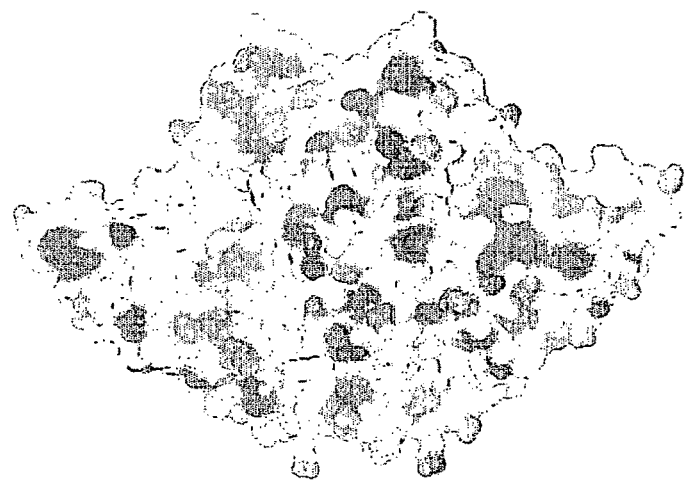
FIG. 9 is the molecular surfaces of GAD65 and GAD67 shaded according to electrostatic potential. Molecular surfaces of GAD65 and GAD67 are shaded according to electrostatic potential(ie positive or negative). Calculated using CCP4MG.
Figure 9:
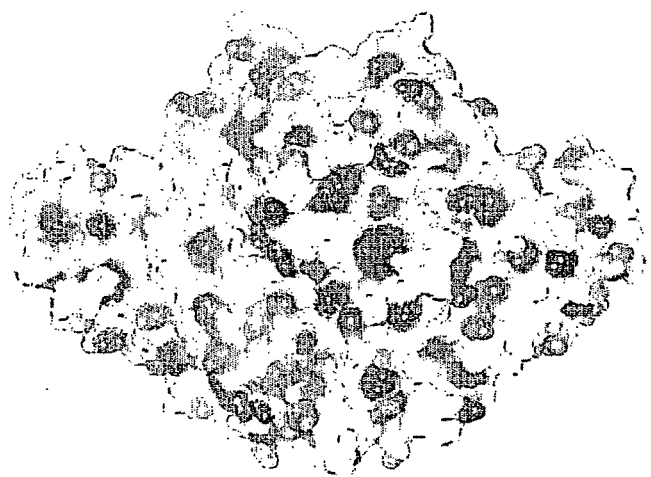
Figure 10:
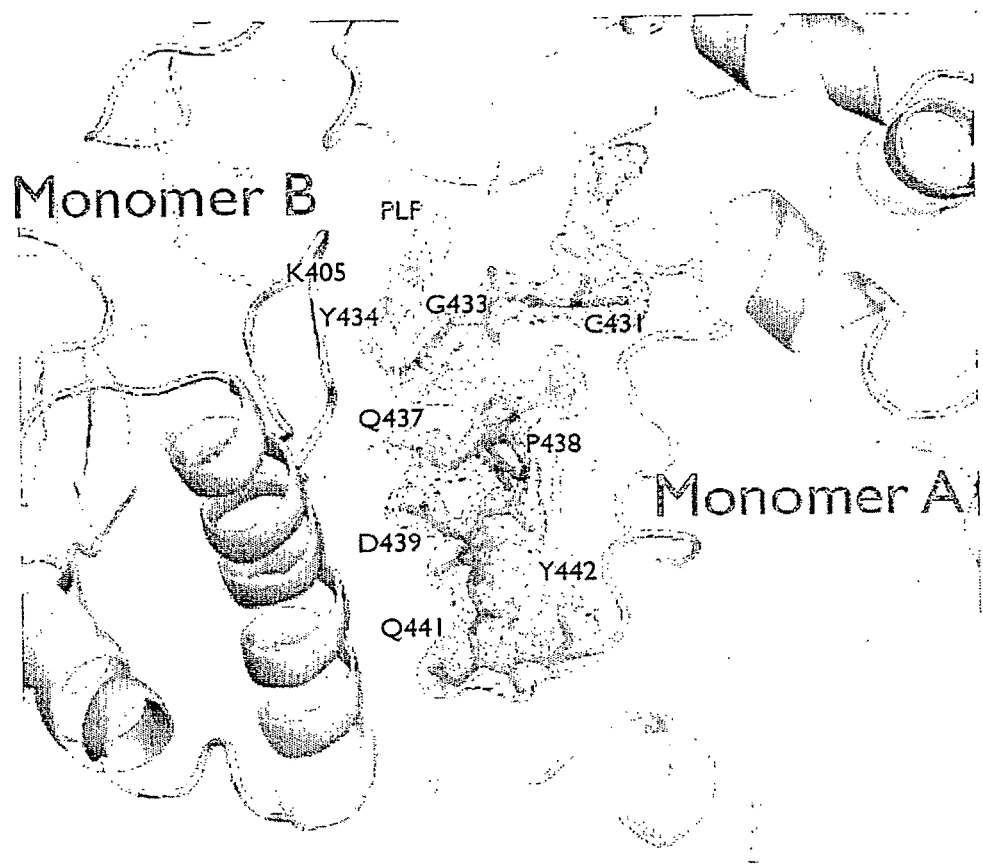
FIG. 10 depicts the GAD65 catalytic loop interactions. The "catalytic loop" (residues 430-450) of monomer A forms a "flap" over the active site of monomer B (green) in GAD67. The PLP moiety in the active site is shown as sticks.

Immune tolerance to GAD65 is labile since autoantibodies to GAD65 are detectable characteristically in Type 1 diabetes, whereas tolerance to GAD67 is solid; no structural basis for this differential autoreactivity has been discerned. Hence we mapped the differences in sequence onto the structure of each enzyme. The surface-exposed differences in sequence between the two isoforms were distributed over the entire structure of the molecule, with no obvious clustering apparent in any region as is evident from FIG. 8a. The differences in surface electrostatic potential of GAD isoforms are scattered throughout the molecule and do not cluster in any region and this can be seen in FIG. 9. However when we examined the location of amino acids known to influence binding of 15 human mAbs to GAD65 on the structure of the GAD65 dimer, epitopes for specific mAb localised in two distinct regions (FIG. 9). Interestingly, 10 of 15 mAb mutations that affect antibody binding localise to the C-terminal domain, or the interface between the C-terminal domain and the PLP binding domain (FIG. 3). The C-terminal domain is more mobile in GAD65 in comparison to GAD67, undergoes a 1.5 Å rigid body shift and includes a disordered region (FIG. 2).

The Active Site of Both GAD65 And GAD67 Reveals A Product Complex With GABA

Each GAD dimer contains two active sites, located in the middle of the PLP-binding domain at the dimer interface as shown in FIG. 1.

In summary, the active site is approximately tetrahedral in shape, and is constructed from residues in the PLP and C-terminal domains of both monomers. Two sides of the active site are formed by residues from the C-terminal domain and the PLP binding domain of monomer A respectively, the third face is formed by residues from the PLP binding domain of monomer B. PLP is located at the base of the cleft and is covalently attached via a Schiff base linkage to the absolutely conserved residue Lys 405 of monomer A (GAD67 numbering; FIG. 7). The conserved catalytic His 291 is found in the active site positioned on top of the PLP moiety as shown in FIG. 4.

GAD was purified in the presence of the substrate glutamate and examination of the active sites of both GAD65 and GAD67 revealed electron density consistent with the presence of the product GABA. This can be seen in FIG. 4. Continuous electron density in active sites of both GAD65 and GAD67 is compatible with the presence of a PLP cofactor covalently bonded to the active site lysine (K405) via a Schiff-base linkage (termed the internal aldimine; FIG. 4*a*). Notably, however, in the active site of GAD67 (monomer A) two discretely disordered conformations of GABA are observed. In one conformation, the carboxyl group of GABA forms a salt bridge with Arg567 and a hydrogen bond with Gln190. In the other conformation, continuous density between PLP and GABA reveals the presence of a trapped intermediate (termed the 'quinoid'; FIG. 4*a, b*) The second active site of GAD67 (monomer B) contains only a single GABA molecule (FIG. 4*b*). In both active sites of GAD65, GABA adopts two discretely disordered conformations (FIG. 4*d*) that form analogous interactions to those seen in GAD67. However, no density was observed that suggested the presence of a quinoid intermediate in GAD65 (FIG. 4*d*).

Comparison of the Active Site of GAD67 And GAD65 Reveals the Structural Basis For the Regulation of GABA Production GAD65, but not GAD67 has been reported to readily form the inactive apo-form and release PMP and succinic semialdehyde. We therefore attempted to identify key features of GAD67 that may explain this activity. Strikingly, the structure of GAD67 revealed that each active site is substantially occluded by an extended loop (residues 430-450, termed the 'catalytic loop') contributed in trans from the other monomer (FIGS. 1, 2*a*, 2*b*, 5, and FIG. 10). The catalytic loop is well ordered in electron density, buries ~1000 Å at its interface, and makes 12 hydrogen bonds, 4 water mediated hydrogen bonds, 2 salt bridges and 5 hydrophobic interactions with the body of GAD67 (FIG. 10). The interactions between catalytic loop (430-450) and the rest of the protein are listed in Table 5.

TABLE 5

| Loop residue | Partner | Type of bond |
|---|---|---|
| Interactions with other monomer | | |
| Tyr434 | Gln557 | vdw |
| Tyr434$^{O\eta}$ | Tyr292$^{N}$ (His291$^{N\epsilon2}$ in other monomer) | h-bond |
| Gln437$^{N\epsilon2}$ | Tyr556$^{O}$ | h-bond |
| Asp439$^{O\delta1}$ | Tyr556$^{O\eta}$ | h-bond |
| Asp439$^{O\delta2}$ | Asn564$^{O\delta1}$ | h-bond |
| Asp439$^{O}$ | Tyr556$^{O\eta}$ | h-bond |
| Gln441 | Ala544 | vdw |
| Tyr446 | Pro144 | vdw |
| Asp450$^{O\delta1}$ | Lys296$^{NZ}$ | h-bond* |
| Asp450$^{O}$ | Lys296$^{NZ}$ | h-bond |
| TOTAL: 3 vdw, 7 h-bonds | | |
| Interactions within loop | | |
| Met430$^{N}$ | Asp450$^{O\delta1,\,O\delta2}$ | 2 h-bonds |
| Met430$^{O}$ | Ala432$^{N}$ | h-bond |
| Cys431$^{N}$ | Asp450$^{O\delta2}$ | h-bond |
| Ala432$^{O}$ | Phe436$^{N}$ | h-bond |
| Tyr434$^{N}$ | Gln437$^{N\epsilon2}$ | h-bond |
| Leu435$^{N}$ | Gln437$^{O\epsilon1}$ | h-bond |
| Phe436 | Gly449 | vdw |
| Pro438$^{O}$ | Lys440$^{N}$ | h-bond |
| Lys440$^{NZ}$ | Asp447$^{O\delta2}$, Tyr442$^{O\eta}$ | 2 h-bonds* |
| Tyr442$^{O\eta}$ | Asp447$^{O\delta1,\,O\delta2}$ | 2 h-bonds |
| Tyr442$^{O}$ | Val444$^{N}$ | h-bond |
| Asp443$^{O\delta1}$ | Ser445$^{N,\,O\eta}$, Val444$^{N}$ | 3 h-bonds |
| Asp443$^{O\delta2}$ | Ser445$^{O\eta}$ | h-bond |
| Asp443$^{O}$ | Ser445$^{N}$, Tyr446$^{N}$ | 2 h-bonds |
| Val444$^{O}$ | Asp447$^{N}$, Tyr446$^{N}$ | 2 h-bonds |
| Ser445$^{O\eta}$ | Tyr446$^{N}$ | h-bond |
| Tyr446$^{O}$ | Thr448$^{N}$ | h-bond |
| Thr448$^{O}$ | Asp450$^{N}$ | h-bond |
| TOTAL: 1 vdw, 24 h-bonds | | |
| Interactions between loop and rest of monomer | | |
| Met430$^{N}$ | Asn428$^{O}$ | h-bond |
| Lys440$^{NZ}$ | Glu217$^{O\epsilon2}$ | h-bond* |
| Tyr442$^{O\eta}$ | Glu217$^{N}$ | h-bond |
| Asp447$^{O\delta1}$ | Tyr216$^{N}$ | h-bond |
| Thr448$^{N}$ | Phe214$^{O}$ | h-bond |
| Gly449$^{N}$ | Phe214$^{O}$ | h-bond |
| Asp450$^{O}$ | Gln429$^{N}$ | h-bond |
| Thr448 | Lys451 | vdw |
| Thr448$^{O}$ | Lys451$^{N}$ | vdw |
| Gly449$^{O}$ | Lys451$^{N}$, Ala452$^{N}$ | 2 h-bonds |
| TOTAL: 2 vdw, 9 h-bonds | | |
| GRAND TOTAL: 6 vdw, 40 h-bonds (3 charged) | | |

[a]*= charged interaction

Importantly, the catalytic loop brings the conserved residue Tyr 434 into the centre of the active site, in close proximity to the catalytic histidine 291 (FIG. 4*a, b, d*). Two conformations (termed A and B) of Tyr 434 are observed. In chain A the hydroxyl group of Tyr 434 hydrogen-bonds to the backbone nitrogen of Tyr 292 (the A conformation), whereas in chain B Tyr 434 is flipped to an alternative conformation (B) where its sidechain hydroxyl group forms a hydrogen bond to the Nϵ2 of the catalytic His 291 (FIG. 4*a, b, d, e*). In the B conformation the sidechain hydroxyl group of Tyr 434 is 2.8 Å from Ca atom of the PLP-GABA moiety In contrast, the structure of GAD65 reveals that the catalytic loop is flexible and is not visible in electron density. As a result the active site of GAD65 is completely exposed (FIG. 2*b* and FIG. 5*a*). A structural and sequence comparison between the two isoforms reveals that the majority of residues contacted by the catalytic loop in GAD67 are identical in sequence and conformation in GAD65 (FIGS. 5*b*, 7, and 8*b*).

One important exception is Phe 283, which corresponds to Tyr 292 in GAD65 and forms contacts with Tyr 434. Further, several non-conservative substitutions map to the catalytic loop of GAD65. Most notably, GAD65 contains a Gly⇒Ser substitution at position 433 and a Pro⇒In substitution at position 438. Pro438 is centred on a sharp kink in the catalytic loop and Gly 433 in GAD67 adopts a "+/+" conformation in chain A (FIG. 5b). It is therefore suggested that substitution of both of these residues in GAD65 may destabilise the conformation of the catalytic loop observed in the structure of GAD67.

Kinetic analysis confirms the importance of the catalytic loop in GAD65 auto-inactivation

Role of the Catalytic Loop

Figure 6:
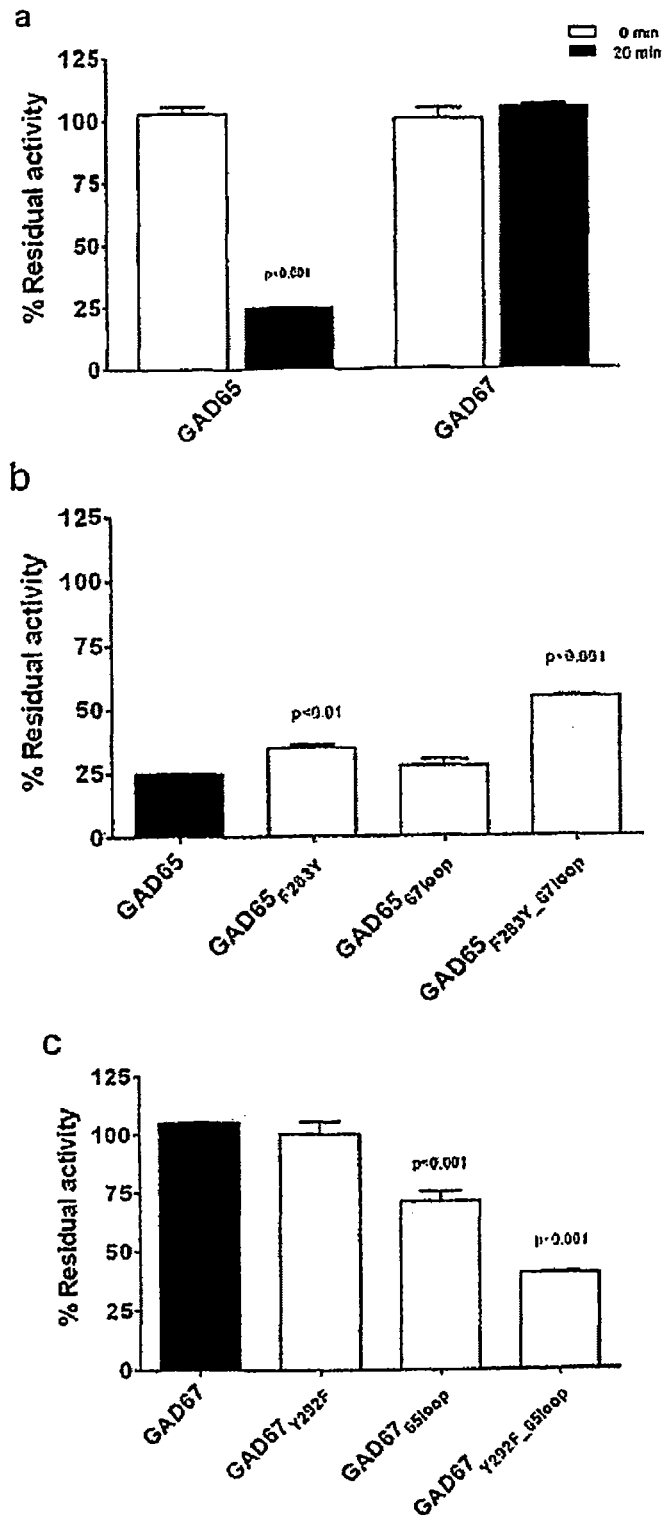
FIG. 6 are graphs relating to inactivation of GAD in the presence of glutamate as described in Example 1 (below).

In order to investigate the role of the catalytic loop we investigated the specific activity and inactivation of GAD65 and GAD67. Consistent with published literature, our data reveal that whereas GAD67 remains active after incubation with excess glutamate, GAD65 loses 75% of activity in 20 minutes (FIG. 6). GAD65 activity could be restored by addition of PLP (data not shown).

To test the role of the catalytic loop, we generated the mutations $GAD65_{Y425F}$ and $GAD67_{Y434F}$. Both mutants were inactive with respect to decarboxylation, confirming the essential catalytic role of the conserved tyrosine.

In order to investigate the role of the catalytic loop on the inactivation rate of holoenzymes, the catalytic loops of GAD65 and GAD67 were interchanged by mutagenesis (the mutants are named $GAD65_{67loop}$ and $GAD67_{65loop}$). Whilst the inactivation rate of $GAD65_{67loop}$ remains similar to that of GAD65, the inactivation rate of $GAD67_{65loop}$ increased significantly ($p<0.001$) (FIG. 6). We also investigated the role of Phe 283/Tyr 292 in GAD inactivation. The inactivation of $GAD65_{F283Y}$ and $GAD67_{Y292F}$ did not differ significantly from the respective wildtype enzymes. However, it is shown that the rate of inactivation of a $GAD65_{67loop\_F283Y}$ mutant is significantly slowed (FIG. 6) and loses 50% rather than 75% of activity after 20 minutes. Similarly it is shown that $GAD67_{65loop/Y292F}$ is rapidly inactivated in comparison to GAD67 or $GAD67_{65loop}$. While our mutations in GAD65 did not abolish enzyme inactivation, it is interesting to note that the C-terminal domain, against which the catalytic loop packs, is more mobile in GAD65 and has shifted 1.5 Å relative to its position in GAD67. It is therefore suggested that the mobility in the C-terminal domain may also contribute to destabilising the catalytic loop. Finally, it is notable that the position of catalytic loop is in close proximity to many of the residues important for auto-antibody binding in GAD65. Several auto-antibodies have been reported that inactivate GAD65 upon binding.

Tyr 434 Functions As A Key Catalytic Switch

Together, our mutational data show that the sequence of the catalytic loop plays a key role in inactivation of GAD67 and that Tyr 434 is plays a direct role in the catalytic machinery of the enzyme. Further, these data suggest that the stabilised conformation observed in the structure of GAD67 prevents enzyme inactivation and allows continuous GABA production. It is notable that in the A conformation, the hydroxyl group of Tyr 434 would be unable to protonate the PLP Cα atom, since the hydroxyl group is >5 Å away from the Cα position. Consistent with these data, we observe unambiguous density consistent with the quinoid GABA-PLP complex (i.e. an intermediate prior to protonation and GABA release). In the B conformation the hydroxyl group of Tyr 434 is 2.8 Å from the site of protonation (Cα) of the quinoid moiety In this conformation, we observe free GABA in the active site. It is therefore suggested that Tyr 434 is directly responsible for protonating the Cα position and that the H-bond interaction between Tyr434 and His291 in GAD67 favourably raises the pKa of the Tyr434.

Figure 11:
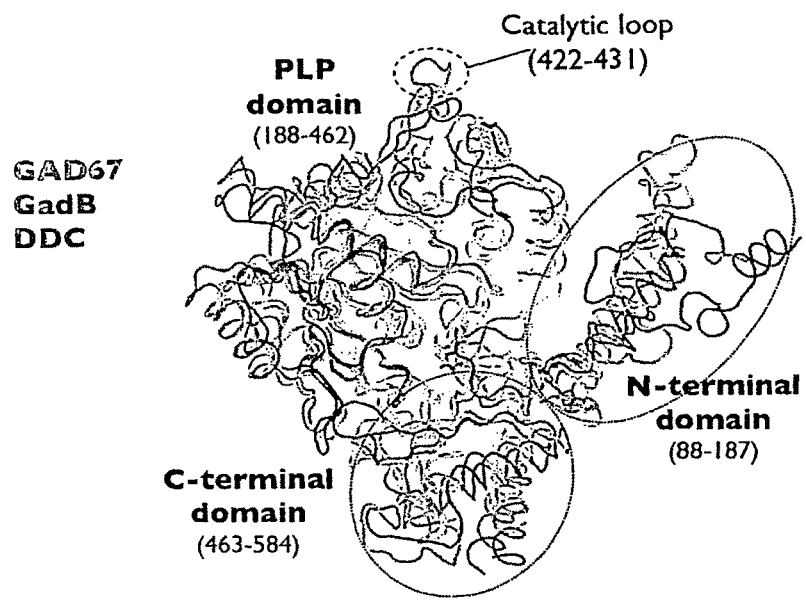
FIG. 11 shows a structural superposition of GAD67 with Pig Dopa decarboxylase (PDB entry 1JS3) and *E. coli* GAD (PDB entry 1PMM). Structural superposition of GAD67 with Pig Dopa decarboxylase (PDB entry 1JS3) and *E. coli* GADB (PDB entry 1PMM). (A) cartoon showing backbone. RMSD's=2.4 Å/347 residues (GAD67/GadB), 2.2 Å/422 residues (GAD67/DDC); (B) Active site residues of GAD67 and DDC. carbiDOPA inhibitor bound to DDC, GABA (GAD67) and K405-PLP-GABA (GAD67) covalent inhibitor are each shaded differently. Tyr434 from GAD67 catalytic loop is shown in dark shaking. Both GAD67 and DDC numbering is shown. The proposed H-bond between Tyr434/332 and the quinonoid Cα in DDC is shown as a dotted line.
Figure 11:
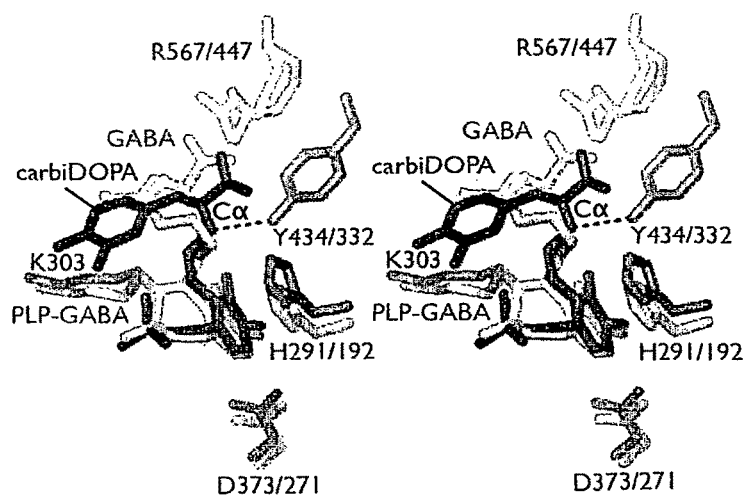

Structural studies on the related enzyme, DOPA decarboxylase (DDC), have revealed that, like GAD65, the region corresponding to the catalytic loop in this enzyme is disordered. DOPA decarboxylase catalyses predominantly the decarboxylation of L-aromatic amino acids into the corresponding aromatic amines, as well as half-transaminase and oxidative deaminase side reactions. Biochemical studies on DOPA decarboxylase have revealed that mutation of the equivalent residue to Tyr 434 (Tyr332) to a Phe converts the enzyme into a decarboxylation-dependant oxidative deaminase and promotes PMP release. It has thus been suggested that in DDC Tyr332 performs the protonation of the Cα atom of the quinoid intermediate that is critical for normal enzymatic activity. The position of Tyr 434 in GAD67 as shown in FIG. 11 is consistent with this hypothesis.

Figure 12:
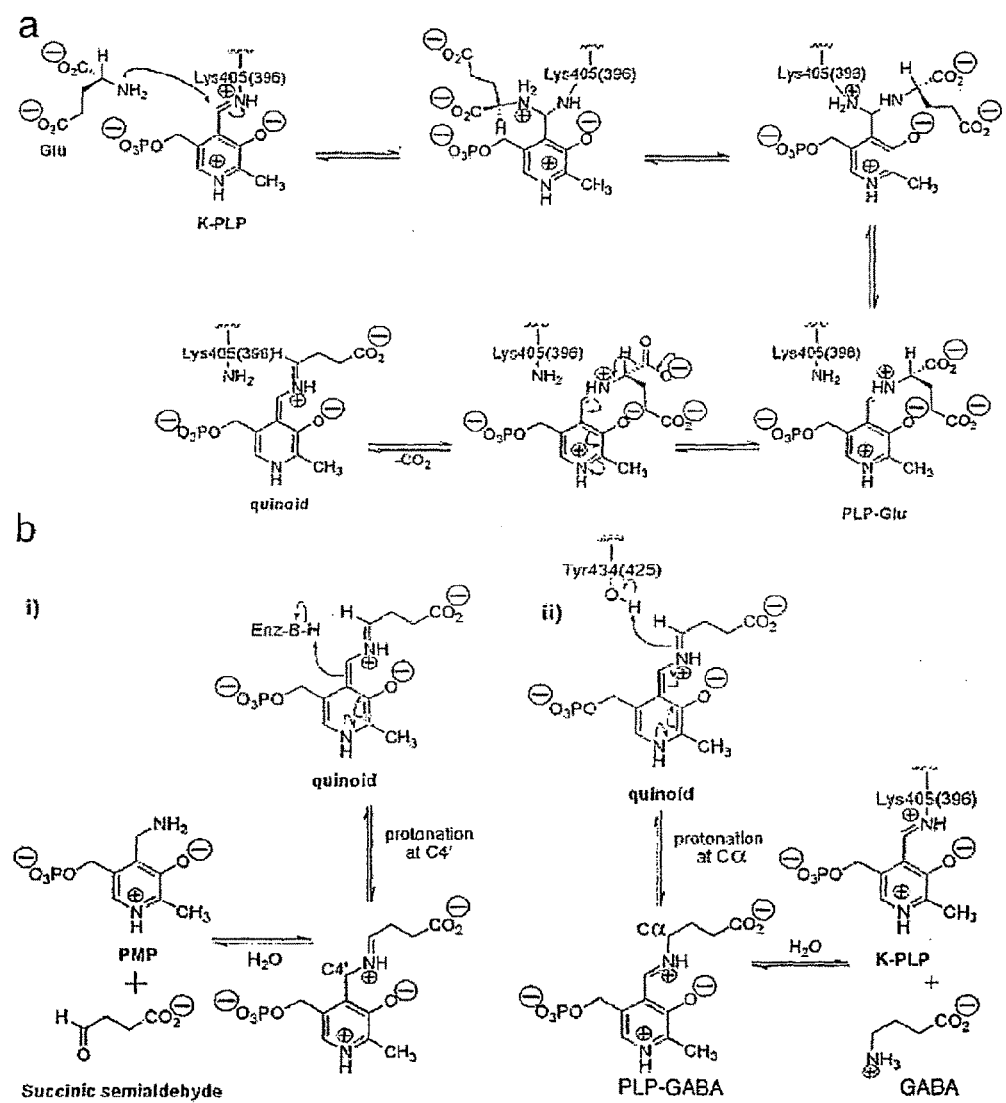
FIG. 12 depicts a proposed reaction mechanism of GAD.

Together, our data provide a plausible model for the autoregulation of GAD. In GAD67 it is suggested that the continuous presence of Tyr434 in the active site favours protonation of the Cα atom and uninterrupted GABA production (FIG. 12). Tyr425 is proposed to play the same catalytic role in GAD65. However, in the latter enzyme, the flexible nature of the catalytic loop ensures that the catalytic tyrosine is only transiently present in the active site. By analogy with DDC, it is suggested that in the absence of the catalytic tyrosine, protonation at C4' allows semialdehyde/PMP release and enzyme inactivation. In other PLP decarboxylaseas, it has been suggested that water or the catalytic lysine (396/405) may function as a proton donor at the C4' position. Together the structural data provides an elegant explanation for why GAD67 predominantly acts as a decarboxylase, whereas GAD65 is able to catalyse both decarboxylation and decarboxylation-dependant transamination reactions.

EXAMPLES

Example 1

Investigation of the Inactivation of GAD In the Presence of Glutamate

Purified holoenzymes (20 µg/ml) were preincubated at 30° C. for 20 min with 5 mM glutamate in the presence of 0.1% Triton X-100, 1 mM 2-mercaptoethanol, 1 mM 2-aminoethylisothiouronium bromide, 100 mM K/NaPO4, pH 7.2; enzyme activity was determined by adding L-[1-$^{14}$C]-glutamic acid and incubated at 30° C. for 30 min, $^{14}CO_2$ produced was trapped with benzethonium hydroxide. % Residual activity is calculated by taking the enzyme activity determined without the glutamate preincubation as 100%. Each bar is the mean of three determinations, with SD illustrated by the error bars. Statistical comparisons were performed using non-paired, two tailed Student's tests and the results are depicted in FIG. 6. FIG. 6(a) shows a comparison of % residual activity of WT GAD65 and GAD67 before and after incubation with glutamate. FIG. 6(b) shows a comparison of % residual activity of GAD65 and GAD65 mutants. FIG. 6(c) shows a comparison of % residual activity of GAD67 and GAD67 mutants.

The word 'comprising' and forms of the word 'comprising' as used in this description and in the claims does not limit the invention claimed to exclude any variants or additions.

Modifications and improvements to the invention will be readily apparent to those skilled in the art. Such modifications and improvements are intended to be within the scope of this invention.

TABLE A

Coordinates for GAD65

```
HEADER      ----                                            XX-XXX-9-     xxxx
COMPND      ---
REMARK 3
REMARK 3    REFINEMENT.
REMARK 3        PROGRAM          : REFMAC 5.2.0019
REMARK 3        AUTHORS          : MURSHUDOV,VAGIN,DODSON
REMARK 3
REMARK 3           REFINEMENT TARGET : MAXIMUM LIKELIHOOD
REMARK 3
REMARK 3    DATA USED IN REFINEMENT.
REMARK 3        RESOLUTION RANGE HIGH          (ANGSTROMS) :    2.30
REMARK 3        RESOLUTION RANGE LOW           (ANGSTROMS) :   61.43
REMARK 3        DATA CUTOFF                    (SIGMA(F))  : NONE
REMARK 3        COMPLETENESS FOR RANGE                (%) :   97.93
REMARK 3        NUMBER OF REFLECTIONS                      :   19571
REMARK 3
REMARK 3    FIT TO DATA USED IN REFINEMENT.
REMARK 3        CROSS-VALIDATION METHOD            : THROUGHOUT
REMARK 3        FREE R VALUE TEST SET SELECTION    : RANDOM
REMARK 3        R VALUE            (WORKING + TEST SET) : .19965
REMARK 3        R VALUE                  (WORKING SET) : .19649
REMARK 3        FREE R VALUE                          : .25594
REMARK 3        FREE R VALUE TEST SET SIZE       (%) : 5.2
REMARK 3        FREE R VALUE TEST SET COUNT        : 1077
REMARK 3
REMARK 3    FIT IN THE HIGHEST RESOLUTION BIN.
REMARK 3        TOTAL NUMBER OF BINS USED                  :   20
REMARK 3        BIN RESOLUTION RANGE HIGH                  : 2.300
REMARK 3        BIN RESOLUTION RANGE LOW                   : 2.360
REMARK 3        REFLECTION IN BIN        (WORKING SET) : 1389
REMARK 3        BIN COMPLETENESS    (WORKING+TEST) (%) : 94.85
REMARK 3        BIN R VALUE              (WORKING SET) : .247
REMARK 3        BIN FREE R VALUE SET COUNT                 :   66
REMARK 3        BIN FREE R VALUE                           : .354
REMARK 3
REMARK 3    NUMBER OF NON-HYDROGEN ATOMS USED IN REFINEMENT.
REMARK 3        ALL ATOMS                 :         3882
REMARK 3
REMARK 3    B VALUES.
REMARK 3        FROM WILSON PLOT         (A**2) : NULL
REMARK 3        MEAN B VALUE      (OVERALL, A**2) :  51.402
REMARK 3        OVERALL ANISOTROPIC B VALUE.
REMARK 3        B11 (A**2) :           -1.32
REMARK 3        B22 (A**2) :             .94
REMARK 3        B33 (A**2) :             .37
REMARK 3        B12 (A**2) :             .00
REMARK 3        B13 (A**2) :             .00
REMARK 3        B23 (A**2) :             .00
REMARK 3
REMARK 3    ESTIMATED OVERALL COORDINATE ERROR.
REMARK 3        ESU BASED ON R VALUE                        (A):   .454
REMARK 3        ESU BASED ON FREE R VALUE                   (A):   .269
REMARK 3        ESU BASED ON MAXIMUM LIKELIHOOD             (A):   .203
REMARK 3        ESU FOR B VALUES BASED ON MAXIMUM LIKELIHOOD  (A**2): 14.110
REMARK 3
REMARK 3    CORRELATION COEFFICIENTS.
REMARK 3        CORRELATION COEFFICIENT FO-FC       : .944
REMARK 3        CORRELATION COEFFICIENT FO-FC FREE  : .909
REMARK 3
REMARK 3    RMS DEVIATIONS FROM IDEAL VALUES           COUNT    RMS    WEIGHT
REMARK 3        BOND LENGTHS REFINED ATOMS     (A):   3877 ;   .009 ;   .022
REMARK 3        BOND ANGLES REFINED ATOMS (DEGREES):  5246 ; 1.352 ;  1.965
REMARK 3        TORSION ANGLES, PERIOD 1  (DEGREES):   480 ; 5.799 ;  5.000
REMARK 3        TORSION ANGLES, PERIOD 2  (DEGREES):   156 ;37.868 ; 24.038
REMARK 3        TORSION ANGLES, PERIOD 3  (DEGREES):   658 ;17.640 ; 15.000
REMARK 3        TORSION ANGLES, PERIOD 4  (DEGREES):    16 ;17.402 ; 15.000
REMARK 3        CHIRAL-CENTER RESTRAINTS      (A**3):   578 ;  .129 ;   .200
```

TABLE A-continued

| REMARK | 3 | | GENERAL PLANES REFINED ATOMS | | | (A): | 2879; | .004; | .020 |
| --- | --- | --- | --- | --- | --- | --- | --- | --- | --- |
| | | | gad65.pdb | | | | | | |
| REMARK | 3 | | NON-BONDED CONTACTS REFINED ATOMS | | | (A): | 1811; | .203; | .200 |
| REMARK | 3 | | NON-BONDED TORSION REFINED ATOMS | | | (A): | 2611; | .303; | .200 |
| REMARK | 3 | | H-BOND (X...Y) REFINED ATOMS | | | (A): | 165; | .143; | .200 |
| REMARK | 3 | | SYMMETRY VDW REFINED ATOMS | | | (A): | 111; | .174; | .200 |
| REMARK | 3 | | SYMMETRY H-BOND REFINED ATOMS | | | (A): | 11; | .117; | .200 |
| REMARK | 3 | | | | | | | | |
| REMARK | 3 | | ISOTROPIC THERMAL FACTOR RESTRAINTS. | | | | COUNT | RMS | WEIGHT |
| REMARK | 3 | | MAIN-CHAIN BOND REFINED ATOMS | | | (A**2): | 2463; | 1.021; | 2.000 |
| REMARK | 3 | | MAIN-CHAIN ANGLE REFINED ATOMS | | | (A**2): | 3849; | 1.908; | 5.000 |
| REMARK | 3 | | SIDE-CHAIN BOND REFINED ATOMS | | | (A**2): | 1629; | 3.756; | 7.000 |
| REMARK | 3 | | SIDE-CHAIN ANGLE REFINED ATOMS | | | (A**2): | 1397; | 5.202; | 10.000 |
| REMARK | 3 | | | | | | | | |
| REMARK | 3 | | NCS RESTRAINTS STATISTICS | | | | | | |
| REMARK | 3 | | NUMBER OF NCS GROUPS : NULL | | | | | | |
| REMARK | 3 | | | | | | | | |
| REMARK | 3 | | | | | | | | |
| REMARK | 3 | | TLS DETAILS | | | | | | |
| REMARK | 3 | | NUMBER OF TLS GROUPS : NULL | | | | | | |
| REMARK | 3 | | | | | | | | |
| REMARK | 3 | | | | | | | | |
| REMARK | 3 | | BULK SOLVENT MODELLING. | | | | | | |
| REMARK | 3 | | METHOD USED : BABINET MODEL WITH MASK | | | | | | |
| REMARK | 3 | | PARAMETERS FOR MASK CALCULATION | | | | | | |
| REMARK | 3 | | VDW PROBE RADIUS | | : | 1.40 | | | |
| REMARK | 3 | | ION PROBE RADIUS | | : | .80 | | | |
| REMARK | 3 | | SHRINKAGE RADIUS | | : | .80 | | | |
| REMARK | 3 | | | | | | | | |
| REMARK | 3 | | OTHER REFINEMENT REMARKS: | | | | | | |
| REMARK | 3 | | HYDROGENS HAVE BEEN ADDED IN THE RIDING POSITIONS | | | | | | |
| REMARK | 3 | | | | | | | | |
| CISPEP | 1 | LEU B | 98 | PRO B | 99 | | | .00 | |
| LINK | | HIS B 422 | | | ASP B 434 | | | | gap |
| CISPEP | 2 | ASP B | 438 | THR B | 439 | | | .00 | |
| CISPEP | 3 | GLN B | 500 | HIS B | 501 | | | .00 | |
| LINK | | GLU B 517 | | | GLU B 521 | | | | gap |
| CISPEP | 4 | GLN B | 583 | ASP B | 584 | | | .00 | |
| LINK | | GLU B 517 | | | ARG B 522 | | | | gap |
| LINK | | THR B 339 | | | ALA B 351 | | | | gap |
| LINK | | ASP B 434 | | | ASP B 438 | | | | gap |
| LINK | | THR B 338 | | | ALA B 351 | | | | gap |
| CRYST1 | 78.251 | 99.057 | 120.009 | 90.00 | 90.00 | 90.00 C 2 2 21 | | | |
| SCALE1 | 0.012779 | 0.000000 | 0.000000 | | 0.00000 | | | | |
| SCALE2 | 0.000000 | 0.010095 | 0.000000 | | 0.00000 | | | | |
| SCALE3 | 0.000000 | 0.000000 | 0.008333 | | 0.00000 | | | | |
| ATOM | 1 | N | ASN A | 88 | 5.865 | −17.438 | −47.031 | 1.00 58.48 | N |
| ATOM | 2 | CA | ASN A | 88 | 5.007 | −16.369 | −46.410 | 1.00 58.99 | C |
| ATOM | 3 | CB | ASN A | 88 | 5.014 | −16.481 | −44.872 | 1.00 59.66 | C |
| ATOM | 4 | CG | ASN A | 88 | 3.957 | −17.464 | −44.359 | 1.00 62.22 | C |
| ATOM | 5 | OD1 | ASN A | 88 | 4.285 | −18.316 | −43.512 | 1.00 67.32 | O |
| ATOM | 6 | ND2 | ASN A | 88 | 2.683 | −17.346 | −44.861 | 1.00 60.91 | N |
| ATOM | 7 | C | ASN A | 88 | 5.358 | −14.934 | −46.833 | 1.00 57.90 | C |
| ATOM | 8 | O | ASN A | 88 | 5.149 | −14.546 | −47.992 | 1.00 56.81 | O |
| ATOM | 9 | N | TYR A | 89 | 5.916 | −14.171 | −45.889 | 1.00 57.87 | N |
| ATOM | 10 | CA | TYR A | 89 | 6.036 | −12.710 | −46.000 | 1.00 57.61 | C |
| ATOM | 11 | CB | TYR A | 89 | 6.570 | −12.113 | −44.695 | 1.00 57.30 | C |
| ATOM | 12 | CG | TYR A | 89 | 5.727 | −12.392 | −43.465 | 1.00 56.53 | C |
| ATOM | 13 | CD1 | TYR A | 89 | 6.215 | −13.190 | −42.432 | 1.00 56.19 | C |
| ATOM | 14 | CE1 | TYR A | 89 | 5.452 | −13.444 | −41.294 | 1.00 55.74 | C |
| ATOM | 15 | CZ | TYR A | 89 | 4.183 | −12.901 | −41.183 | 1.00 57.78 | C |
| ATOM | 16 | OH | TYR A | 89 | 3.431 | −13.150 | −40.057 | 1.00 58.84 | O |
| ATOM | 17 | CE2 | TYR A | 89 | 3.668 | −12.106 | −42.195 | 1.00 56.17 | C |
| ATOM | 18 | CD2 | TYR A | 89 | 4.442 | −11.854 | −43.329 | 1.00 58.99 | C |
| ATOM | 19 | C | TYR A | 89 | 6.850 | −12.206 | −47.195 | 1.00 58.02 | C |
| ATOM | 20 | O | TYR A | 89 | 6.635 | −11.087 | −47.664 | 1.00 57.21 | O |
| ATOM | 21 | N | ALA A | 90 | 7.767 | −13.037 | −47.690 | 1.00 59.45 | N |
| ATOM | 22 | CA | ALA A | 90 | 8.564 | −12.708 | −48.876 | 1.00 60.48 | C |
| ATOM | 23 | CB | ALA A | 90 | 9.633 | −13.766 | −49.105 | 1.00 60.45 | C |
| ATOM | 24 | C | ALA A | 90 | 7.698 | −12.537 | −50.131 | 1.00 61.52 | C |
| | | | gad65.pdb | | | | | | |
| ATOM | 25 | O | ALA A | 90 | 8.064 | −11.806 | −51.056 | 1.00 62.22 | O |
| ATOM | 26 | N | PHE A | 91 | 6.550 | −13.209 | −50.152 | 1.00 61.81 | N |
| ATOM | 27 | CA | PHE A | 91 | 5.651 | −13.166 | −51.301 | 1.00 62.25 | C |
| ATOM | 28 | CB | PHE A | 91 | 5.428 | −14.586 | −51.840 | 1.00 62.81 | C |
| ATOM | 35 | C | PHE A | 91 | 4.325 | −12.482 | −50.932 | 1.00 62.20 | C |
| ATOM | 36 | O | PHE A | 91 | 3.290 | −12.677 | −51.588 | 1.00 62.12 | O |
| ATOM | 37 | N | LEU A | 92 | 4.375 | −11.680 | −49.873 | 1.00 61.49 | N |
| ATOM | 38 | CA | LEU A | 92 | 3.238 | −10.884 | −49.439 | 1.00 61.24 | C |
| ATOM | 39 | CB | LEU A | 92 | 2.831 | −11.253 | −48.008 | 1.00 61.43 | C |

TABLE A-continued

| | | | | | | | | | |
|---|---|---|---|---|---|---|---|---|---|
| ATOM | 40 | CG | LEU A | 92 | 2.117 | −12.595 | −47.784 | 1.00 | 63.12 | C |
| ATOM | 41 | CD1 | LEU A | 92 | 1.937 | −12.865 | −46.291 | 1.00 | 61.15 | C |
| ATOM | 42 | CD2 | LEU A | 92 | .766 | −12.643 | −48.502 | 1.00 | 62.42 | C |
| ATOM | 43 | C | LEU A | 92 | 3.549 | −9.396 | −49.536 | 1.00 | 60.92 | C |
| ATOM | 44 | O | LEU A | 92 | 4.714 | −8.996 | −49.552 | 1.00 | 60.83 | O |
| ATOM | 45 | N | HIS A | 93 | 2.493 | −8.588 | −49.621 | 1.00 | 59.97 | N |
| ATOM | 46 | CA | HIS A | 93 | 2.594 | −7.136 | −49.635 | 1.00 | 58.77 | C |
| ATOM | 47 | CB | HIS A | 93 | 2.561 | −6.588 | −51.070 | 1.00 | 59.30 | C |
| ATOM | 48 | CG | HIS A | 93 | 3.759 | −6.963 | −51.891 | 1.00 | 62.19 | C |
| ATOM | 49 | ND1 | HIS A | 93 | 3.735 | −7.979 | −52.822 | 1.00 | 64.96 | N |
| ATOM | 50 | CE1 | HIS A | 93 | 4.927 | −8.090 | −53.383 | 1.00 | 65.77 | C |
| ATOM | 51 | NE2 | HIS A | 93 | 5.724 | −7.181 | −52.852 | 1.00 | 64.08 | N |
| ATOM | 52 | CD2 | HIS A | 93 | 5.018 | −6.463 | −51.916 | 1.00 | 63.36 | C |
| ATOM | 53 | C | HIS A | 93 | 1.434 | −6.583 | −48.821 | 1.00 | 58.12 | C |
| ATOM | 54 | O | HIS A | 93 | .571 | −7.337 | −48.372 | 1.00 | 57.87 | O |
| ATOM | 55 | N | ALA A | 94 | 1.427 | −5.268 | −48.627 | 1.00 | 57.47 | N |
| ATOM | 56 | CA | ALA A | 94 | .412 | −4.590 | −47.838 | 1.00 | 57.35 | C |
| ATOM | 57 | CB | ALA A | 94 | .742 | −3.121 | −47.733 | 1.00 | 55.69 | C |
| ATOM | 58 | C | ALA A | 94 | −.966 | −4.786 | −48.467 | 1.00 | 58.69 | C |
| ATOM | 59 | O | ALA A | 94 | −1.961 | −4.971 | −47.767 | 1.00 | 58.85 | O |
| ATOM | 60 | N | THR A | 95 | −.989 | −4.764 | −49.797 | 1.00 | 59.22 | N |
| ATOM | 61 | CA | THR A | 95 | −2.189 | −4.911 | −50.601 | 1.00 | 59.95 | C |
| ATOM | 62 | CB | THR A | 95 | −1.856 | −4.703 | −52.087 | 1.00 | 60.08 | C |
| ATOM | 63 | OG1 | THR A | 95 | −.616 | −5.355 | −52.393 | 1.00 | 59.62 | O |
| ATOM | 64 | CG2 | THR A | 95 | −1.736 | −3.215 | −52.406 | 1.00 | 59.04 | C |
| ATOM | 65 | C | THR A | 95 | −2.868 | −6.269 | −50.426 | 1.00 | 60.79 | C |
| ATOM | 66 | O | THR A | 95 | −4.008 | −6.460 | −50.859 | 1.00 | 61.88 | O |
| ATOM | 67 | N | ASP A | 96 | −2.161 | −7.205 | −49.794 | 1.00 | 60.27 | N |
| ATOM | 68 | CA | ASP A | 96 | −2.688 | −8.545 | −49.515 | 1.00 | 58.53 | C |
| ATOM | 69 | CB | ASP A | 96 | −1.559 | −9.583 | −49.574 | 1.00 | 57.75 | C |
| ATOM | 70 | CG | ASP A | 96 | −.964 | −9.734 | −50.973 | 1.00 | 59.97 | C |
| ATOM | 71 | OD1 | ASP A | 96 | −1.701 | −9.558 | −51.973 | 1.00 | 60.40 | O |
| ATOM | 72 | OD2 | ASP A | 96 | .245 | −10.048 | −51.075 | 1.00 | 56.20 | O |
| ATOM | 73 | C | ASP A | 96 | −3.420 | −8.631 | −48.168 | 1.00 | 57.20 | C |
| ATOM | 74 | O | ASP A | 96 | −4.154 | −9.591 | −47.914 | 1.00 | 57.24 | O |
| ATOM | 75 | N | LEU A | 97 | −3.222 | −7.623 | −47.321 | 1.00 | 56.13 | N |
| ATOM | 76 | CA | LEO A | 97 | −3.796 | −7.596 | −45.973 | 1.00 | 55.89 | C |
| ATOM | 77 | CB | LEU A | 97 | −2.882 | −6.799 | −45.026 | 1.00 | 57.07 | C |
| ATOM | 78 | CG | LEU A | 97 | −1.392 | −7.153 | −44.915 | 1.00 | 57.16 | C |
| ATOM | 79 | CD1 | LEU A | 97 | −.666 | −6.089 | −44.107 | 1.00 | 56.49 | C |
| ATOM | 80 | CD2 | LEU A | 97 | −1.204 | −8.519 | −44.280 | 1.00 | 57.84 | C |
| ATOM | 81 | C | LEU A | 97 | −5.195 | −6.975 | −45.964 | 1.00 | 54.87 | C |
| ATOM | 82 | O | LEU A | 97 | −5.555 | −6.248 | −46.888 | 1.00 | 54.53 | O |
| ATOM | 83 | N | LEU A | 98 | −5.977 | −7.247 | −44.917 | 1.00 | 54.76 | N |
| ATOM | 84 | CA | LEU A | 98 | −7.252 | −6.533 | −44.704 | 1.00 | 54.57 | C |
| ATOM | 85 | CB | LEU A | 98 | −7.802 | −6.765 | −43.292 | 1.00 | 53.96 | C |
| ATOM | 86 | CG | LEU A | 98 | −8.417 | −8.139 | −42.983 | 1.00 | 52.88 | C |
| ATOM | 87 | CD1 | LEU A | 98 | −8.648 | −8.309 | −41.491 | 1.00 | 51.05 | C |
| ATOM | 88 | CD2 | LEU A | 98 | −9.711 | −8.374 | −43.762 | 1.00 | 55.10 | C |
| ATOM | 89 | C | LEU A | 98 | −7.069 | −5.038 | −44.954 | 1.00 | 54.96 | C |
| ATOM | 90 | O | LEU A | 98 | −6.097 | −4.456 | −44.465 | 1.00 | 54.07 | O |
| ATOM | 91 | N | PRO A | 99 | −8.013 | −4.394 | −45.685 | 1.00 | 55.66 | N |
| ATOM | 92 | CA | PRO A | 99 | −9.341 | −4.841 | −46.126 | 1.00 | 56.29 | C |
| ATOM | 93 | CB | PRO A | 99 | −10.080 | −3.522 | −46.342 | 1.00 | 56.16 | C |
| ATOM | 94 | CG | PRO A | 99 | −9.027 | −2.584 | −46.791 | 1.00 | 55.63 | C |
| ATOM | 95 | CD | PRO A | 99 | −7.742 | −3.012 | −46.129 | 1.00 | 55.41 | C |
| ATOM | 96 | C | PRO A | 99 | −9.431 | −5.685 | −47.409 | 1.00 | 57.07 | C |
| ATOM | 97 | O | PRO A | 99 | −10.527 | −5.826 | −47.957 | 1.00 | 56.87 | O |
| ATOM | 98 | N | ALA A | 100 | −8.315 | −6.228 | −47.887 | 1.00 | 57.70 | N |
| | | | | | gad65.pdb | | | | | |
| ATOM | 99 | CA | ALA A | 100 | −8.358 | −7.148 | −49.024 | 1.00 | 57.82 | C |
| ATOM | 100 | CB | ALA A | 100 | −6.959 | −7.532 | −49.459 | 1.00 | 56.97 | C |
| ATOM | 101 | C | ALA A | 100 | −9.163 | −8.384 | −48.643 | 1.00 | 58.45 | C |
| ATOM | 102 | O | ALA A | 100 | −9.141 | −8.804 | −47.483 | 1.00 | 58.13 | O |
| ATOM | 103 | N | CYS A | 101 | −9.878 | −8.950 | −49.618 | 1.00 | 59.74 | N |
| ATOM | 104 | CA | CYS A | 101 | −10.791 | −10.078 | −49.376 | 1.00 | 60.92 | C |
| ATOM | 105 | CB | CYS A | 101 | −11.672 | −10.337 | −50.603 | 1.00 | 61.63 | C |
| ATOM | 106 | SG | CYS A | 101 | −13.059 | −9.195 | −50.718 | 1.00 | 68.60 | S |
| ATOM | 107 | C | CYS A | 101 | −10.113 | −11.372 | −48.910 | 1.00 | 60.53 | C |
| ATOM | 108 | O | CYS A | 101 | −10.597 | −12.022 | −47.977 | 1.00 | 61.12 | O |
| ATOM | 109 | N | ASP A | 102 | −9.010 | −11.745 | −49.557 | 1.00 | 59.55 | N |
| ATOM | 110 | CA | ASP A | 102 | −8.171 | −12.837 | −49.067 | 1.00 | 59.47 | C |
| ATOM | 111 | CB | ASP A | 102 | −7.470 | −13.547 | −50.231 | 1.00 | 59.38 | C |
| ATOM | 115 | C | ASP A | 102 | −7.151 | −12.254 | −48.086 | 1.00 | 59.93 | C |
| ATOM | 116 | O | ASP A | 102 | −5.934 | −12.426 | −48.245 | 1.00 | 60.22 | O |
| ATOM | 117 | N | GLY A | 103 | −7.654 | −11.553 | −47.071 | 1.00 | 59.84 | N |
| ATOM | 118 | cA | GLY A | 103 | −6.791 | −10.765 | −46.194 | 1.00 | 59.46 | C |
| ATOM | 119 | C | GLY A | 103 | −6.729 | −11.140 | −44.728 | 1.00 | 58.85 | C |
| ATOM | 120 | O | GLY A | 103 | −5.760 | −10.793 | −44.060 | 1.00 | 59.96 | O |
| ATOM | 121 | N | GLU A | 104 | −7.743 | −11.839 | −44.220 | 1.00 | 57.65 | N |

TABLE A-continued

| | | | | | | | | | |
|---|---|---|---|---|---|---|---|---|---|
| ATOM | 122 | CA | GLU A | 104 | −7.857 | −12.074 | −42.776 | 1.00 57.74 | C |
| ATOM | 123 | CB | GLU A | 104 | −9.215 | −12.671 | −42.416 | 1.00 57.71 | C |
| ATOM | 124 | CG | GLU A | 104 | −9.459 | −12.827 | −40.909 | 1.00 59.11 | C |
| ATOM | 125 | CD | GLU A | 104 | −10.754 | −13.575 | −40.586 | 1.00 59.81 | C |
| ATOM | 126 | OE1 | GLU A | 104 | −11.756 | −13.419 | −41.330 | 1.00 65.19 | O |
| ATOM | 127 | OE2 | GLU A | 104 | −10.769 | −14.319 | −39.579 | 1.00 66.71 | O |
| ATOM | 128 | C | GLU A | 104 | −6.730 | −12.928 | −42.202 | 1.00 56.71 | C |
| ATOM | 129 | O | GLU A | 104 | −6.149 | −12.575 | −41.175 | 1.00 56.86 | O |
| ATOM | 130 | N | ARG A | 105 | −6.428 | −14.039 | −42.868 | 1.00 56.14 | N |
| ATOM | 131 | CA | ARG A | 105 | −5.355 | −14.946 | −42.436 | 1.00 55.32 | C |
| ATOM | 132 | CB | ARG A | 105 | −5.355 | −16.238 | −43.263 | 1.00 56.01 | C |
| ATOM | 139 | C | ARG A | 105 | −3.962 | −14.304 | −42.428 | 1.00 53.89 | C |
| ATOM | 140 | O | ARG A | 105 | −3.282 | −14.372 | −41.411 | 1.00 54.06 | O |
| ATOM | 141 | N | PRO A | 106 | −3.529 | −13.694 | −43.556 | 1.00 53.04 | N |
| ATOM | 142 | CA | PRO A | 106 | −2.225 | −13.007 | −43.567 | 1.00 52.20 | C |
| ATOM | 143 | CB | PRO A | 106 | −2.053 | −12.578 | −45.030 | 1.00 52.37 | C |
| ATOM | 144 | CG | PRO A | 106 | −3.430 | −12.586 | −45.610 | 1.00 54.00 | C |
| ATOM | 145 | CD | PRO A | 106 | −4.178 | −13.658 | −44.884 | 1.00 53.11 | C |
| ATOM | 146 | C | PRO A | 106 | −2.111 | −11.788 | −42.642 | 1.00 51.43 | C |
| ATOM | 147 | O | PRO A | 106 | −.998 | −11.430 | −42.257 | 1.00 51.17 | O |
| ATOM | 148 | N | THR A | 107 | −3.242 | −11.165 | −42.304 | 1.00 50.63 | N |
| ATOM | 149 | CA | THR A | 107 | −3.277 | −10.038 | −41.370 | 1.00 49.20 | C |
| ATOM | 150 | CB | THR A | 107 | −4.592 | −9.230 | −41.488 | 1.00 48.79 | C |
| ATOM | 151 | OG1 | THR A | 107 | −4.701 | −8.681 | −42.807 | 1.00 50.21 | O |
| ATOM | 152 | CG2 | THR A | 107 | −4.629 | −8.097 | −40.473 | 1.00 41.90 | C |
| ATOM | 153 | C | THR A | 107 | −3.064 | −10.460 | −39.910 | 1.00 49.16 | C |
| ATOM | 154 | O | THR A | 107 | −2.285 | −9.832 | −39.181 | 1.00 48.71 | O |
| ATOM | 155 | N | LEU A | 108 | −3.770 | −11.507 | −39.493 | 1.00 49.71 | N |
| ATOM | 156 | CA | LEU A | 108 | −3.628 | −12.084 | −38.155 | 1.00 50.32 | C |
| ATOM | 157 | CB | LEU A | 108 | −4.620 | −13.241 | −37.958 | 1.00 50.30 | C |
| ATOM | 158 | CG | LEU A | 108 | −6.115 | −12.898 | −37.876 | 1.00 51.95 | C |
| ATOM | 159 | CD1 | LEU A | 108 | −6.978 | −14.133 | −38.098 | 1.00 53.62 | C |
| ATOM | 160 | CD2 | LEU A | 108 | −6.473 | −12.234 | −36.548 | 1.00 53.41 | C |
| ATOM | 161 | C | LEU A | 108 | −2.204 | −12.577 | −37.902 | 1.00 50.71 | C |
| ATOM | 162 | O | LEU A | 108 | −1.697 | −12.482 | −36.780 | 1.00 50.66 | O |
| ATOM | 163 | N | ALA A | 109 | −1.568 | −13.095 | −38.954 | 1.00 51.02 | N |
| ATOM | 164 | CA | ALA A | 109 | −.214 | −13.614 | −38.864 | 1.00 51.49 | C |
| ATOM | 165 | CB | ALA A | 109 | .095 | −14.522 | −40.060 | 1.00 50.78 | C |
| ATOM | 166 | C | ALA A | 109 | .798 | −12.474 | −38.775 | 1.00 52.55 | C |
| ATOM | 167 | O | ALA A | 109 | 1.725 | −12.517 | −37.957 | 1.00 53.01 | O |
| ATOM | 168 | N | PHE A | 110 | .614 | −11.463 | −39.626 | 1.00 52.57 | N |
| ATOM | 169 | CA | PHE A | 110 | 1.543 | −10.339 | −39.718 | 1.00 51.86 | C |
| ATOM | 170 | CB | PHE A | 110 | 1.221 | −9.459 | −40.934 | 1.00 51.39 | C |
| ATOM | 171 | CG | PHE A | 110 | 1.947 | −8.137 | −40.945 | 1.00 52.07 | C |
| ATOM | 172 | CD1 | PHE A | 110 | 3.273 | −8.058 | −41.370 | 1.00 50.71 | C |
| ATOM | 173 | CE1 | PHE A | 110 | 3.950 | −6.842 | −41.379 | 1.00 50.31 | C |
| ATOM | 174 | CZ | PHE A | 110 | 3.302 | −5.686 | −40.964 | 1.00 48.26 | C |
| ATOM | 175 | CE2 | PHE A | 110 | 1.971 | −5.749 | −40.545 | 1.00 52.54 | C |
| | | | | gad65.pdb | | | | | |
| ATOM | 176 | CD2 | PHE A | 110 | 1.300 | −6.967 | −40.536 | 1.00 45.39 | C |
| ATOM | 177 | C | PHE A | 110 | 1.521 | −9.525 | −38.438 | 1.00 52.18 | C |
| ATOM | 178 | O | PHE A | 110 | 2.575 | −9.231 | −37.865 | 1.00 53.17 | O |
| ATOM | 179 | N | LEU A | 111 | .322 | −9.165 | −37.986 | 1.00 51.39 | N |
| ATOM | 180 | CA | LEU A | 111 | .188 | −8.406 | −36.755 | 1.00 50.72 | C |
| ATOM | 181 | CB | LEU A | 111 | −1.268 | −7.999 | −36.491 | 1.00 50.03 | C |
| ATOM | 182 | CG | LEU A | 111 | −1.940 | −6.996 | −37.448 | 1.00 48.29 | C |
| ATOM | 183 | CD1 | LEU A | 111 | −3.363 | −6.691 | −36.992 | 1.00 47.35 | C |
| ATOM | 184 | CD2 | LEU A | 111 | −1.139 | −5.717 | −37.621 | 1.00 42.10 | C |
| ATOM | 185 | C | LEU A | 111 | .746 | −9.188 | −35.574 | 1.00 51.25 | C |
| ATOM | 186 | O | LEU A | 111 | 1.336 | −8.609 | −34.676 | 1.00 50.97 | O |
| ATOM | 187 | N | GLN A | 112 | .562 | −10.507 | −35.570 | 1.00 52.56 | N |
| ATOM | 188 | CA | GLN A | 112 | 1.089 | −11.298 | −34.463 | 1.00 52.80 | C |
| ATOM | 189 | CB | GLN A | 112 | .415 | −12.662 | −34.356 | 1.00 53.06 | C |
| ATOM | 190 | CG | GLN A | 112 | .033 | −13.012 | −32.922 | 1.00 54.95 | C |
| ATOM | 191 | CD | GLN A | 112 | 1.230 | −13.415 | −32.087 | 1.00 59.79 | C |
| ATOM | 192 | OE1 | GLN A | 112 | 2.080 | −14.176 | −32.548 | 1.00 63.95 | O |
| ATOM | 193 | NE2 | GLN A | 112 | 1.306 | −12.911 | −30.853 | 1.00 55.55 | N |
| ATOM | 194 | C | GLN A | 112 | 2.615 | −11.405 | −34.513 | 1.00 51.49 | C |
| ATOM | 195 | O | GLN A | 112 | 3.263 | −11.430 | −33.479 | 1.00 50.90 | O |
| ATOM | 196 | N | ASP A | 113 | 3.180 | −11.424 | −35.715 | 1.00 51.62 | N |
| ATOM | 197 | CA | ASP A | 113 | 4.636 | −11.439 | −35.874 | 1.00 52.40 | C |
| ATOM | 198 | CB | ASP A | 113 | 5.040 | −11.792 | −37.306 | 1.00 52.26 | C |
| ATOM | 199 | CG | ASP A | 113 | 5.482 | −13.242 | −37.442 | 1.00 58.12 | C |
| ATOM | 200 | OD1 | ASP A | 113 | 6.706 | −13.464 | −37.585 | 1.00 59.09 | O |
| ATOM | 201 | OD2 | ASP A | 113 | 4.621 | −14.155 | −37.382 | 1.00 55.92 | O |
| ATOM | 202 | C | ASP A | 113 | 5.304 | −10.141 | −35.427 | 1.00 52.71 | C |
| ATOM | 203 | O | ASP A | 113 | 6.405 | −10.178 | −34.880 | 1.00 53.51 | O |
| ATOM | 204 | N | VAL A | 114 | 4.635 | −9.008 | −35.663 | 1.00 51.63 | N |
| ATOM | 205 | CA | VAL A | 114 | 5.066 | −7.709 | −35.140 | 1.00 50.63 | C |
| ATOM | 206 | CB | VAL A | 114 | 4.143 | −6.539 | −35.623 | 1.00 51.26 | C |

TABLE A-continued

| | | | | | | | | | |
|---|---|---|---|---|---|---|---|---|---|
| ATOM | 207 | CG1 | VAL A | 114 | 4.639 | −5.184 | −35.082 | 1.00 | 50.52 | C |
| ATOM | 208 | CG2 | VAL A | 114 | 4.037 | −6.499 | −37.139 | 1.00 | 47.72 | C |
| ATOM | 209 | C | VAL A | 114 | 5.038 | −7.749 | −33.617 | 1.00 | 49.87 | C |
| ATOM | 210 | O | VAL A | 114 | 5.975 | −7.305 | −32.956 | 1.00 | 49.68 | O |
| ATOM | 211 | N | MET A | 115 | 3.948 | −8.289 | −33.083 | 1.00 | 50.12 | N |
| ATOM | 212 | CA | MET A | 115 | 3.720 | −8.411 | −31.644 | 1.00 | 50.61 | C |
| ATOM | 213 | CB | MET A | 115 | 2.318 | −8.989 | −31.406 | 1.00 | 50.49 | C |
| ATOM | 214 | CG | MET A | 115 | 1.893 | −9.203 | −29.953 | 1.00 | 53.86 | C |
| ATOM | 215 | SD | MET A | 115 | 2.166 | −7.824 | −28.813 | 1.00 | 56.94 | S |
| ATOM | 216 | CE | MET A | 115 | 1.663 | −6.382 | −29.761 | 1.00 | 65.08 | C |
| ATOM | 217 | C | MET A | 115 | 4.812 | −9.237 | −30.939 | 1.00 | 50.38 | C |
| ATOM | 218 | O | MET A | 115 | 5.294 | −8.853 | −29.862 | 1.00 | 50.06 | O |
| ATOM | 219 | N | ASN A | 116 | 5.196 | −10.354 | −31.558 | 1.00 | 50.15 | N |
| ATOM | 220 | CA | ASN A | 116 | 6.313 | −11.180 | −31.090 | 1.00 | 50.01 | C |
| ATOM | 221 | CB | ASN A | 116 | 6.484 | −12.426 | −31.975 | 1.00 | 50.52 | C |
| ATOM | 222 | CG | ASN A | 116 | 5.318 | −13.417 | −31.843 | 1.00 | 52.80 | C |
| ATOM | 223 | OD1 | ASN A | 116 | 5.163 | −14.327 | −32.665 | 1.00 | 52.87 | O |
| ATOM | 224 | ND2 | ASN A | 116 | 4.505 | −13.248 | −30.801 | 1.00 | 52.90 | N |
| ATOM | 225 | C | ASN A | 116 | 7.618 | −10.388 | −31.004 | 1.00 | 49.59 | C |
| ATOM | 226 | O | ASN A | 116 | 8.328 | −10.467 | −30.003 | 1.00 | 49.95 | O |
| ATOM | 227 | N | ILE A | 117 | 7.915 | −9.603 | −32.039 | 1.00 | 49.67 | N |
| ATOM | 228 | CA | ILE A | 117 | 9.050 | −8.668 | −32.007 | 1.00 | 49.33 | C |
| ATOM | 229 | CB | ILE A | 117 | 9.208 | −7.912 | −33.355 | 1.00 | 49.93 | C |
| ATOM | 230 | CG1 | ILE A | 117 | 9.499 | −8.900 | −34.490 | 1.00 | 49.97 | C |
| ATOM | 231 | CD | ILE A | 117 | 9.266 | −8.342 | −35.890 | 1.00 | 49.91 | C |
| ATOM | 232 | CG2 | ILE A | 117 | 10.319 | −6.859 | −33.283 | 1.00 | 42.88 | C |
| ATOM | 233 | C | ILE A | 117 | 8.932 | −7.689 | −30.833 | 1.00 | 49.22 | C |
| ATOM | 234 | O | ILE A | 117 | 9.904 | −7.492 | −30.099 | 1.00 | 49.47 | O |
| ATOM | 235 | N | LEU A | 118 | 7.737 | −7.110 | −30.640 | 1.00 | 48.89 | N |
| ATOM | 236 | CA | LEU A | 118 | 7.485 | −6.135 | −29.566 | 1.00 | 47.14 | C |
| ATOM | 237 | CB | LEU A | 118 | 6.101 | −5.495 | −29.708 | 1.00 | 47.35 | C |
| ATOM | 238 | CG | LEU A | 118 | 5.721 | −4.755 | −30.998 | 1.00 | 44.65 | C |
| ATOM | 239 | CD1 | LEU A | 118 | 4.348 | −4.135 | −30.851 | 1.00 | 41.58 | C |
| ATOM | 240 | CD2 | LEU A | 118 | 6.736 | −3.696 | −31.354 | 1.00 | 45.39 | C |
| ATOM | 241 | C | LEU A | 118 | 7.646 | −6.729 | −28.159 | 1.00 | 46.88 | C |
| ATOM | 242 | O | LEU A | 118 | 8.251 | −6.107 | −27.270 | 1.00 | 46.40 | O |
| ATOM | 243 | N | LEU A | 119 | 7.112 | −7.933 | −27.981 | 1.00 | 46.77 | N |
| | | | | | gad65.pdb | | | | | |
| ATOM | 244 | CA | LEU A | 119 | 7.211 | −8.689 | −26.728 | 1.00 | 47.36 | C |
| ATOM | 245 | CB | LEU A | 119 | 6.401 | −9.988 | −26.844 | 1.00 | 47.03 | C |
| ATOM | 246 | CG | LEU A | 119 | 5.009 | −10.210 | −26.210 | 1.00 | 49.12 | C |
| ATOM | 247 | CD1 | LEU A | 119 | 4.171 | −8.961 | −25.994 | 1.00 | 52.27 | C |
| ATOM | 248 | CD2 | LEU A | 119 | 4.229 | −11.223 | −27.016 | 1.00 | 48.05 | C |
| ATOM | 249 | C | LEU A | 119 | 8.668 | −9.006 | −26.354 | 1.00 | 47.33 | C |
| ATOM | 250 | O | LEU A | 119 | 9.072 | −8.841 | −25.201 | 1.00 | 46.89 | O |
| ATOM | 251 | N | GLN A | 120 | 9.443 | −9.459 | −27.336 | 1.00 | 47.42 | N |
| ATOM | 252 | CA | GLN A | 120 | 10.849 | −9.771 | −27.136 | 1.00 | 48.69 | C |
| ATOM | 253 | CB | GLN A | 120 | 11.462 | −10.382 | −28.410 | 1.00 | 49.88 | C |
| ATOM | 254 | CG | GLN A | 120 | 12.988 | −10.537 | −28.375 | 1.00 | 55.78 | C |
| ATOM | 255 | CD | GLN A | 120 | 13.496 | −11.563 | −29.375 | 1.00 | 63.85 | C |
| ATOM | 258 | C | GLN A | 120 | 11.618 | −8.533 | −26.693 | 1.00 | 48.35 | C |
| ATOM | 259 | O | GLN A | 120 | 12.439 | −8.600 | −25.769 | 1.00 | 47.84 | O |
| ATOM | 260 | N | TYR A | 121 | 11.351 | −7.405 | −27.351 | 1.00 | 47.91 | N |
| ATOM | 261 | CA | TYR A | 121 | 12.005 | −6.137 | −27.006 | 1.00 | 46.91 | C |
| ATOM | 262 | CB | TYR A | 121 | 11.678 | −5.066 | −28.050 | 1.00 | 46.03 | C |
| ATOM | 263 | CG | TYR A | 121 | 12.035 | −3.637 | −27.666 | 1.00 | 45.69 | C |
| ATOM | 264 | CD1 | TYR A | 121 | 13.192 | −3.033 | −28.152 | 1.00 | 45.79 | C |
| ATOM | 265 | CE1 | TYR A | 121 | 13.512 | −1.717 | −27.823 | 1.00 | 43.23 | C |
| ATOM | 266 | CZ | TYR A | 121 | 12.672 | −.996 | −26.998 | 1.00 | 46.44 | C |
| ATOM | 267 | OH | TYR A | 121 | 12.990 | .301 | −26.667 | 1.00 | 46.31 | O |
| ATOM | 268 | CE2 | TYR A | 121 | 11.503 | −1.565 | −26.513 | 1.00 | 48.60 | C |
| ATOM | 269 | CD | TYR A | 121 | 11.189 | −2.874 | −26.852 | 1.00 | 48.21 | C |
| ATOM | 270 | C | TYR A | 121 | 11.595 | −5.692 | −25.593 | 1.00 | 47.29 | C |
| ATOM | 271 | O | TYR A | 121 | 12.418 | −5.136 | −24.842 | 1.00 | 46.40 | O |
| ATOM | 272 | N | VAL A | 122 | 10.335 | −5.964 | −25.237 | 1.00 | 47.86 | N |
| ATOM | 273 | CA | VAL A | 122 | 9.798 | −5.602 | −23.924 | 1.00 | 48.97 | C |
| ATOM | 274 | CB | VAL A | 122 | 8.254 | −5.841 | −23.808 | 1.00 | 49.86 | C |
| ATOM | 275 | CG1 | VAL A | 122 | 7.807 | −5.953 | −22.338 | 1.00 | 47.68 | C |
| ATOM | 276 | CG2 | VAL A | 122 | 7.473 | −4.731 | −24.535 | 1.00 | 46.70 | C |
| ATOM | 277 | C | VAL A | 122 | 10.562 | −6.345 | −22.845 | 1.00 | 49.90 | C |
| ATOM | 278 | O | VAL A | 122 | 11.123 | −5.721 | −21.947 | 1.00 | 50.69 | O |
| ATOM | 279 | N | VAL A | 123 | 10.630 | −7.670 | −22.950 | 1.00 | 51.34 | N |
| ATOM | 280 | CA | VAL A | 123 | 11.329 | −8.452 | −21.921 | 1.00 | 51.95 | C |
| ATOM | 281 | CB | VAL A | 123 | 11.095 | −9.994 | −22.041 | 1.00 | 52.24 | C |
| ATOM | 282 | CG1 | VAL A | 123 | 9.599 | −10.315 | −22.112 | 1.00 | 51.12 | C |
| ATOM | 283 | CG2 | VAL A | 123 | 11.836 | −10.606 | −23.230 | 1.00 | 57.68 | C |
| ATOM | 284 | C | VAL A | 123 | 12.815 | −8.066 | −21.804 | 1.00 | 52.22 | C |
| ATOM | 285 | O | VAL A | 123 | 13.337 | −7.946 | −20.695 | 1.00 | 51.97 | O |
| ATOM | 286 | N | LYS A | 124 | 13.466 | −7.812 | −22.942 | 1.00 | 52.78 | N |
| ATOM | 287 | CA | LYS A | 124 | 14.887 | −7.438 | −22.954 | 1.00 | 53.26 | C |

TABLE A-continued

| | | | | | | | | | |
|---|---|---|---|---|---|---|---|---|---|
| ATOM | 288 | CB | LYS A | 124 | 15.446 | −7.414 | −24.380 | 1.00 | 53.41 | C |
| ATOM | 289 | CG | LYS A | 124 | 15.794 | −8.791 | −24.940 | 1.00 | 56.24 | C |
| ATOM | 293 | C | LYS A | 124 | 15.138 | −6.100 | −22.273 | 1.00 | 53.69 | C |
| ATOM | 294 | O | LYS A | 124 | 16.179 | −5.914 | −21.636 | 1.00 | 54.24 | O |
| ATOM | 295 | N | SER A | 125 | 14.181 | −5.180 | −22.421 | 1.00 | 53.93 | N |
| ATOM | 296 | CA | SER A | 125 | 14.205 | −3.855 | −21.797 | 1.00 | 53.44 | C |
| ATOM | 297 | CB | SER A | 125 | 12.908 | −3.085 | −22.098 | 1.00 | 53.85 | C |
| ATOM | 298 | OG | SER A | 125 | 12.869 | −2.596 | −23.424 | 1.00 | 53.11 | O |
| ATOM | 299 | C | SER A | 125 | 14.386 | −3.932 | −20.291 | 1.00 | 53.00 | C |
| ATOM | 300 | O | SER A | 125 | 14.971 | −3.042 | −19.689 | 1.00 | 54.27 | O |
| ATOM | 301 | N | PHE A | 126 | 13.889 | −5.004 | −19.693 | 1.00 | 53.09 | N |
| ATOM | 302 | CA | PHE A | 126 | 14.002 | −5.213 | −18.252 | 1.00 | 53.04 | C |
| ATOM | 303 | CB | PHE A | 126 | 12.711 | −5.849 | −17.719 | 1.00 | 52.73 | C |
| ATOM | 304 | CG | PHE A | 126 | 11.507 | −4.988 | −17.925 | 1.00 | 51.48 | C |
| ATOM | 305 | CD1 | PHE A | 126 | 11.233 | −3.943 | −17.057 | 1.00 | 50.44 | C |
| ATOM | 306 | CE1 | PHE A | 126 | 10.123 | −3.125 | −17.258 | 1.00 | 58.51 | C |
| ATOM | 307 | CZ | PHE A | 126 | 9.281 | −3.347 | −18.338 | 1.00 | 54.50 | C |
| ATOM | 308 | CE2 | PHE A | 126 | 9.550 | −4.393 | −19.217 | 1.00 | 55.81 | C |
| ATOM | 309 | CD2 | PHE A | 126 | 10.662 | −5.200 | −19.009 | 1.00 | 54.33 | C |
| ATOM | 310 | C | PHE A | 126 | 15.245 | −6.018 | −17.850 | 1.00 | 51.97 | C |
| ATOM | 311 | O | PHE A | 126 | 15.600 | −6.076 | −16.671 | 1.00 | 51.14 | O |
| ATOM | 312 | N | ASP A | 127 | 15.898 | −6.616 | −18.843 | 1.00 | 51.74 | N |
| ATOM | 313 | CA | ASP A | 127 | 17.116 | −7.395 | −18.642 | 1.00 | 51.52 | C |
| ATOM | 314 | CB | ASP A | 127 | 17.337 | −8.335 | −19.833 | 1.00 | 50.67 | C |
| ATOM | 315 | CG | ASP A | 127 | 18.293 | −9.486 | −19.523 | 1.00 | 49.07 | C |
| ATOM | 316 | OD1 | ASP A | 127 | 19.329 | −9.269 | −18.859 | 1.00 | 48.31 | O |
| | | | | | gad65.pdb | | | | | |
| ATOM | 317 | OD2 | ASP A | 127 | 18.000 | −10.617 | −19.966 | 1.00 | 46.86 | O |
| ATOM | 318 | C | ASP A | 127 | 18.297 | −6.446 | −18.482 | 1.00 | 52.27 | C |
| ATOM | 319 | O | ASP A | 127 | 18.603 | −5.671 | −19.387 | 1.00 | 52.83 | O |
| ATOM | 320 | N | ARG A | 128 | 18.954 | −6.504 | −17.326 | 1.00 | 52.96 | N |
| ATOM | 321 | CA | ARG A | 128 | 20.097 | −5.625 | −17.038 | 1.00 | 52.70 | C |
| ATOM | 322 | CB | ARG A | 128 | 20.414 | −5.602 | −15.536 | 1.00 | 52.75 | C |
| ATOM | 323 | CG | ARG A | 128 | 19.586 | −4.572 | −14.772 | 1.00 | 52.02 | C |
| ATOM | 324 | CD | ARG A | 128 | 19.811 | −4.644 | −13.272 | 1.00 | 51.47 | C |
| ATOM | 325 | NE | ARG A | 128 | 18.810 | −3.862 | −12.543 | 1.00 | 41.70 | N |
| ATOM | 326 | CZ | ARG A | 128 | 17.589 | −4.304 | −12.230 | 1.00 | 46.63 | C |
| ATOM | 327 | NH1 | ARG A | 128 | 17.199 | −5.530 | −12.582 | 1.00 | 40.19 | N |
| ATOM | 328 | NH2 | ARG A | 128 | 16.743 | −3.513 | −11.577 | 1.00 | 43.16 | N |
| ATOM | 329 | C | ARG A | 128 | 21.360 | −5.923 | −17.859 | 1.00 | 53.02 | C |
| ATOM | 330 | O | ARG A | 128 | 22.278 | −5.104 | −17.896 | 1.00 | 54.10 | O |
| ATOM | 331 | N | SER A | 129 | 21.406 | −7.074 | −18.526 | 1.00 | 52.39 | N |
| ATOM | 332 | CA | SER A | 129 | 22.515 | −7.353 | −19.433 | 1.00 | 52.87 | C |
| ATOM | 333 | CB | SER A | 129 | 22.727 | −8.857 | −19.608 | 1.00 | 52.29 | C |
| ATOM | 334 | OG | SER A | 129 | 21.994 | −9.349 | −20.710 | 1.00 | 56.61 | O |
| ATOM | 335 | C | SER A | 129 | 22.357 | −6.646 | −20.792 | 1.00 | 53.52 | C |
| ATOM | 336 | O | SER A | 129 | 23.335 | −6.524 | −21.534 | 1.00 | 54.56 | O |
| ATOM | 337 | N | THR A | 130 | 21.130 | −6.203 | −21.107 | 1.00 | 52.55 | N |
| ATOM | 338 | CA | THR A | 130 | 20.826 | −5.406 | −22.303 | 1.00 | 51.56 | C |
| ATOM | 339 | CB | THR A | 130 | 19.271 | −5.272 | −22.519 | 1.00 | 52.80 | C |
| ATOM | 340 | OG1 | THR A | 130 | 18.643 | −6.560 | −22.439 | 1.00 | 53.61 | O |
| ATOM | 341 | CG2 | THR A | 130 | 18.908 | −4.636 | −23.875 | 1.00 | 51.47 | C |
| ATOM | 342 | C | THR A | 130 | 21.452 | −4.001 | −22.216 | 1.00 | 50.79 | C |
| ATOM | 343 | O | THR A | 130 | 21.451 | −3.360 | −21.160 | 1.00 | 50.44 | O |
| ATOM | 344 | N | LYS A | 131 | 21.996 | −3.529 | −23.331 | 1.00 | 50.48 | N |
| ATOM | 345 | CA | LYS A | 131 | 22.492 | −2.155 | −23.435 | 1.00 | 50.96 | C |
| ATOM | 346 | CB | LYS A | 131 | 23.361 | −2.009 | −24.696 | 1.00 | 51.36 | C |
| ATOM | 347 | CG | LYS A | 131 | 24.869 | −2.135 | −24.484 | 1.00 | 56.47 | C |
| ATOM | 348 | CD | LYS A | 131 | 25.265 | −3.232 | −23.509 | 1.00 | 61.85 | C |
| ATOM | 349 | CE | LYS A | 131 | 26.591 | −2.885 | −22.832 | 1.00 | 67.56 | C |
| ATOM | 350 | NZ | LYS A | 131 | 26.844 | −3.703 | −21.613 | 1.00 | 73.08 | N |
| ATOM | 351 | C | LYS A | 131 | 21.326 | −1.170 | −23.483 | 1.00 | 50.54 | C |
| ATOM | 352 | O | LYS A | 131 | 20.334 | −1.428 | −24.178 | 1.00 | 50.92 | O |
| ATOM | 353 | N | VAL A | 132 | 21.449 | −.064 | −22.741 | 1.00 | 49.36 | N |
| ATOM | 354 | CA | VAL A | 132 | 20.472 | 1.040 | −22.740 | 1.00 | 48.59 | C |
| ATOM | 355 | CB | VAL A | 132 | 20.842 | 2.145 | −21.695 | 1.00 | 48.27 | C |
| ATOM | 356 | CG1 | VAL A | 132 | 19.910 | 3.326 | −21.785 | 1.00 | 46.46 | C |
| ATOM | 357 | CG2 | VAL A | 132 | 20.861 | 1.611 | −20.267 | 1.00 | 49.08 | C |
| ATOM | 358 | C | VAL A | 132 | 20.414 | 1.682 | −24.127 | 1.00 | 48.26 | C |
| ATOM | 359 | O | VAL A | 132 | 19.342 | 2.060 | −24.613 | 1.00 | 48.14 | O |
| ATOM | 360 | N | ILE A | 133 | 21.586 | 1.800 | −24.749 | 1.00 | 46.98 | N |
| ATOM | 361 | CA | ILE A | 133 | 21.744 | 2.384 | −26.071 | 1.00 | 46.31 | C |
| ATOM | 362 | CB | ILE A | 133 | 22.049 | 3.925 | −25.998 | 1.00 | 45.91 | C |
| ATOM | 363 | CG1 | ILE A | 133 | 22.277 | 4.505 | −27.407 | 1.00 | 44.01 | C |
| ATOM | 364 | CD | ILE A | 133 | 22.606 | 5.987 | −27.457 | 1.00 | 46.37 | C |
| ATOM | 365 | CG2 | ILE A | 133 | 23.236 | 4.228 | −25.049 | 1.00 | 44.24 | C |
| ATOM | 366 | C | ILE A | 133 | 22.852 | 1.669 | −26.850 | 1.00 | 47.81 | C |
| ATOM | 367 | O | ILE A | 133 | 23.934 | 1.410 | −26.307 | 1.00 | 48.70 | O |
| ATOM | 368 | N | ASP A | 134 | 22.562 | 1.347 | −28.113 | 1.00 | 48.49 | N |
| ATOM | 369 | CA | ASP A | 134 | 23.567 | .969 | −29.113 | 1.00 | 48.73 | C |

TABLE A-continued

| | | | | | | | | | | |
|---|---|---|---|---|---|---|---|---|---|---|
| ATOM | 370 | CB | ASP A | 134 | 23.012 | −.138 | −30.029 | 1.00 | 48.78 | C |
| ATOM | 371 | CG | ASP A | 134 | 24.068 | −.707 | −30.994 | 1.00 | 52.34 | C |
| ATOM | 372 | OD1 | ASP A | 134 | 25.262 | −.331 | −30.890 | 1.00 | 57.62 | O |
| ATOM | 373 | OD2 | ASP A | 134 | 23.697 | −1.526 | −31.866 | 1.00 | 49.14 | O |
| ATOM | 374 | C | ASP A | 134 | 23.938 | 2.219 | −29.926 | 1.00 | 48.52 | C |
| ATOM | 375 | O | ASP A | 134 | 23.336 | 2.493 | −30.954 | 1.00 | 47.91 | O |
| ATOM | 376 | N | PHE A | 135 | 24.938 | 2.964 | −29.465 | 1.00 | 50.02 | N |
| ATOM | 377 | CA | PHE A | 135 | 25.200 | 4.311 | −29.981 | 1.00 | 50.71 | C |
| ATOM | 378 | CB | PHE A | 135 | 25.958 | 5.160 | −28.956 | 1.00 | 51.72 | C |
| ATOM | 379 | CG | PHE A | 135 | 26.322 | 6.527 | −29.461 | 1.00 | 53.21 | C |
| ATOM | 380 | CD1 | PHE A | 135 | 25.335 | 7.481 | −29.698 | 1.00 | 51.57 | C |
| ATOM | 381 | CE1 | PHE A | 135 | 25.662 | 8.743 | −30.176 | 1.00 | 54.13 | C |
| ATOM | 382 | CZ | PHE A | 135 | 26.987 | 9.060 | −30.426 | 1.00 | 57.62 | C |
| ATOM | 383 | CE2 | PHE A | 135 | 27.986 | 8.113 | −30.201 | 1.00 | 58.01 | C |
| ATOM | 384 | CD2 | PHE A | 135 | 27.649 | 6.854 | −29.719 | 1.00 | 56.18 | C |
| | | | | | gad65.pdb | | | | | |
| ATOM | 385 | C | PHE A | 135 | 25.905 | 4.400 | −31.332 | 1.00 | 51.22 | C |
| ATOM | 386 | O | PHE A | 135 | 26.955 | 3.795 | −31.547 | 1.00 | 51.27 | O |
| ATOM | 387 | N | HIS A | 136 | 25.327 | 5.207 | −32.219 | 1.00 | 51.05 | N |
| ATOM | 388 | CA | HIS A | 136 | 25.882 | 5.459 | −33.541 | 1.00 | 50.75 | C |
| ATOM | 389 | CB | HIS A | 136 | 25.102 | 4.680 | −34.606 | 1.00 | 51.32 | C |
| ATOM | 390 | CG | HIS A | 136 | 25.152 | 3.195 | −34.434 | 1.00 | 50.89 | C |
| ATOM | 391 | ND1 | HIS A | 136 | 26.091 | 2.404 | −35.060 | 1.00 | 55.39 | N |
| ATOM | 392 | CE1 | HIS A | 136 | 25.887 | 1.139 | −34.732 | 1.00 | 54.66 | C |
| ATOM | 393 | NE2 | HIS A | 136 | 24.848 | 1.084 | −33.916 | 1.00 | 52.16 | N |
| ATOM | 394 | CD2 | HIS A | 136 | 24.370 | 2.355 | −33.716 | 1.00 | 47.79 | C |
| ATOM | 395 | C | HIS A | 136 | 25.774 | 6.935 | −33.850 | 1.00 | 50.01 | C |
| ATOM | 396 | O | HIS A | 136 | 24.786 | 7.578 | −33.492 | 1.00 | 50.18 | O |
| ATOM | 397 | N | TYR A | 137 | 26.789 | 7.474 | −34.512 | 1.00 | 49.62 | N |
| ATOM | 398 | CA | TYR A | 137 | 26.701 | 8.817 | −35.056 | 1.00 | 50.08 | C |
| ATOM | 399 | CB | TYR A | 137 | 28.070 | 9.295 | −35.548 | 1.00 | 51.67 | C |
| ATOM | 400 | CG | TYR A | 137 | 29.097 | 9.433 | −34.436 | 1.00 | 58.44 | C |
| ATOM | 401 | CD1 | TYR A | 137 | 29.109 | 10.552 | −33.596 | 1.00 | 60.37 | C |
| ATOM | 402 | CE1 | TYR A | 137 | 30.051 | 10.668 | −32.566 | 1.00 | 63.93 | C |
| ATOM | 403 | CZ | TYR A | 137 | 30.991 | 9.654 | −32.381 | 1.00 | 63.07 | C |
| ATOM | 404 | OH | TYR A | 137 | 31.936 | 9.741 | −31.377 | 1.00 | 62.42 | O |
| ATOM | 405 | CE2 | TYR A | 137 | 30.991 | 8.539 | −33.204 | 1.00 | 63.98 | C |
| ATOM | 406 | CD2 | TYR A | 137 | 30.048 | 8.434 | −34.220 | 1.00 | 61.89 | C |
| ATOM | 407 | C | TYR A | 137 | 25.674 | 8.815 | −36.192 | 1.00 | 48.38 | C |
| ATOM | 408 | O | TYR A | 137 | 25.503 | 7.791 | −36.861 | 1.00 | 48.14 | O |
| ATOM | 409 | N | PRO A | 138 | 24.978 | 9.950 | −36.400 | 1.00 | 47.38 | N |
| ATOM | 410 | CA | PRO A | 138 | 23.950 | 10.051 | −37.449 | 1.00 | 47.84 | C |
| ATOM | 411 | CB | PRO A | 138 | 23.677 | 11.560 | −37.532 | 1.00 | 47.30 | C |
| ATOM | 412 | CG | PRO A | 138 | 23.924 | 12.041 | −36.139 | 1.00 | 45.91 | C |
| ATOM | 413 | CD | PRO A | 138 | 25.097 | 11.207 | −35.635 | 1.00 | 47.12 | C |
| ATOM | 414 | C | PRO A | 138 | 24.390 | 9.479 | −38.797 | 1.00 | 48.43 | C |
| ATOM | 415 | O | PRO A | 138 | 23.653 | 8.678 | −39.380 | 1.00 | 50.08 | O |
| ATOM | 416 | N | ASN A | 139 | 25.578 | 9.866 | −39.265 | 1.00 | 48.08 | N |
| ATOM | 417 | CA | ASN A | 139 | 26.150 | 9.339 | −40.512 | 1.00 | 49.00 | C |
| ATOM | 418 | CB | ASN A | 139 | 27.449 | 10.069 | −40.869 | 1.00 | 48.79 | C |
| ATOM | 422 | C | ASN A | 139 | 26.383 | 7.822 | −40.498 | 1.00 | 50.11 | C |
| ATOM | 423 | O | ASN A | 139 | 26.134 | 7.143 | −41.501 | 1.00 | 49.99 | O |
| ATOM | 424 | N | GLU A | 140 | 26.867 | 7.296 | −39.369 | 1.00 | 51.20 | N |
| ATOM | 425 | CA | GLU A | 140 | 26.999 | 5.843 | −39.188 | 1.00 | 51.63 | C |
| ATOM | 426 | CB | GLU A | 140 | 27.615 | 5.506 | −37.831 | 1.00 | 52.03 | C |
| ATOM | 427 | CG | GLU A | 140 | 29.113 | 5.285 | −37.845 | 1.00 | 60.52 | C |
| ATOM | 428 | CD | GLU A | 140 | 29.772 | 5.644 | −36.513 | 1.00 | 67.84 | C |
| ATOM | 429 | OE1 | GLU A | 140 | 29.156 | 5.401 | −35.443 | 1.00 | 65.23 | O |
| ATOM | 430 | OE2 | GLU A | 140 | 30.911 | 6.172 | −36.547 | 1.00 | 68.05 | O |
| ATOM | 431 | C | GLU A | 140 | 25.654 | 5.158 | −39.298 | 1.00 | 51.06 | C |
| ATOM | 432 | O | GLU A | 140 | 25.545 | 4.114 | −39.920 | 1.00 | 50.79 | O |
| ATOM | 433 | N | LEU A | 141 | 24.630 | 5.746 | −38.680 | 1.00 | 51.88 | N |
| ATOM | 434 | CA | LEU A | 141 | 23.304 | 5.130 | −38.678 | 1.00 | 51.92 | C |
| ATOM | 435 | CB | LEU A | 141 | 22.383 | 5.782 | −37.631 | 1.00 | 51.69 | C |
| ATOM | 436 | CG | LEU A | 141 | 21.297 | 4.924 | −36.952 | 1.00 | 52.28 | C |
| ATOM | 437 | CD1 | LEU A | 141 | 20.025 | 4.889 | −37.759 | 1.00 | 60.27 | C |
| ATOM | 438 | CD2 | LEU A | 141 | 21.759 | 3.485 | −36.662 | 1.00 | 54.83 | C |
| ATOM | 439 | C | LEU A | 141 | 22.708 | 5.161 | −40.089 | 1.00 | 51.87 | C |
| ATOM | 440 | O | LEU A | 141 | 22.142 | 4.173 | −40.542 | 1.00 | 50.42 | O |
| ATOM | 441 | N | LEU A | 142 | 22.880 | 6.287 | −40.783 | 1.00 | 54.14 | N |
| ATOM | 442 | CA | LEU A | 142 | 22.485 | 6.419 | −42.189 | 1.00 | 56.40 | C |
| ATOM | 443 | CB | LEU A | 142 | 22.753 | 7.836 | −42.700 | 1.00 | 56.70 | C |
| ATOM | 444 | CG | LEU A | 142 | 21.706 | 8.894 | −42.328 | 1.00 | 60.10 | C |
| ATOM | 445 | CD1 | LEU A | 142 | 22.256 | 10.300 | −42.562 | 1.00 | 64.88 | C |
| ATOM | 446 | CD2 | LEU A | 142 | 20.393 | 8.697 | −43.089 | 1.00 | 56.52 | C |
| ATOM | 447 | C | LEU A | 142 | 23.156 | 5.400 | −43.107 | 1.00 | 57.84 | C |
| ATOM | 448 | O | LEU A | 142 | 22.502 | 4.812 | −43.965 | 1.00 | 58.47 | O |
| ATOM | 449 | N | GLN A | 143 | 24.455 | 5.188 | −42.920 | 1.00 | 59.13 | N |
| ATOM | 450 | CA | GLN A | 143 | 25.208 | 4.233 | −43.734 | 1.00 | 60.85 | C |
| ATOM | 451 | CB | GLN A | 143 | 26.712 | 4.549 | −43.680 | 1.00 | 61.08 | C |

TABLE A-continued

| | | | | | | | | | | |
|---|---|---|---|---|---|---|---|---|---|---|
| ATOM | 452 | CG | GLN A | 143 | 27.103 | 5.851 | −44.395 | 1.00 | 64.21 | C |
| ATOM | 453 | CD | GLN A | 143 | 28.598 | 6.176 | −44.317 | 1.00 | 62.64 | C |
| ATOM | 454 | OE1 | GLN A | 143 | 28.991 | 7.157 | −43.682 | 1.00 | 69.59 | O |
| ATOM | 455 | NE2 | GLN A | 143 | 29.431 | 5.364 | −44.978 | 1.00 | 63.91 | N |
| | | | | gad65.pdb | | | | | | |
| ATOM | 456 | C | GLN A | 143 | 24.951 | 2.778 | −43.324 | 1.00 | 60.46 | C |
| ATOM | 457 | O | GLN A | 143 | 25.134 | 1.862 | −44.122 | 1.00 | 60.48 | O |
| ATOM | 458 | N | GLU A | 144 | 24.523 | 2.574 | −42.080 | 1.00 | 60.33 | N |
| ATOM | 459 | CA | GLU A | 144 | 24.365 | 1.234 | −41.513 | 1.00 | 60.73 | C |
| ATOM | 460 | CB | GLU A | 144 | 24.174 | 1.333 | −39.992 | 1.00 | 61.48 | C |
| ATOM | 461 | CG | GLU A | 144 | 24.242 | .013 | −39.239 | 1.00 | 66.12 | C |
| ATOM | 462 | CD | GLU A | 144 | 25.654 | −.519 | −39.117 | 1.00 | 71.57 | C |
| ATOM | 463 | OE1 | GLU A | 144 | 26.425 | .031 | −38.301 | 1.00 | 72.04 | O |
| ATOM | 464 | OE2 | GLU A | 144 | 25.988 | −1.490 | −39.838 | 1.00 | 75.21 | O |
| ATOM | 465 | C | GLU A | 144 | 23.186 | .491 | −42.128 | 1.00 | 60.24 | C |
| ATOM | 466 | O | GLU A | 144 | 23.170 | −.741 | −42.188 | 1.00 | 59.90 | O |
| ATOM | 467 | N | TYR A | 145 | 22.197 | 1.257 | −42.579 | 1.00 | 60.09 | N |
| ATOM | 468 | CA | TYR A | 145 | 20.933 | .707 | −43.033 | 1.00 | 59.47 | C |
| ATOM | 469 | CB | TYR A | 145 | 19.994 | .535 | −41.833 | 1.00 | 59.86 | C |
| ATOM | 470 | CG | TYR A | 145 | 18.860 | −.430 | −42.064 | 1.00 | 59.60 | C |
| ATOM | 471 | CD1 | TYR A | 145 | 19.105 | −1.798 | −42.209 | 1.00 | 60.53 | C |
| ATOM | 472 | CE1 | TYR A | 145 | 18.065 | −2.700 | −42.423 | 1.00 | 59.31 | C |
| ATOM | 473 | CZ | TYR A | 145 | 16.761 | −2.233 | −42.486 | 1.00 | 59.55 | C |
| ATOM | 474 | OH | TYR A | 145 | 15.735 | −3.132 | −42.693 | 1.00 | 62.73 | O |
| ATOM | 475 | CE2 | TYR A | 145 | 16.488 | −.880 | −42.338 | 1.00 | 57.59 | C |
| ATOM | 476 | CD2 | TYR A | 145 | 17.339 | .016 | −42.124 | 1.00 | 57.95 | C |
| ATOM | 477 | C | TYR A | 145 | 20.322 | 1.665 | −44.038 | 1.00 | 58.66 | C |
| ATOM | 478 | O | TYR A | 145 | 20.484 | 2.877 | −43.916 | 1.00 | 58.63 | O |
| ATOM | 479 | N | ASN A | 146 | 19.632 | 1.128 | −45.038 | 1.00 | 57.83 | N |
| ATOM | 480 | CA | ASN A | 146 | 18.919 | 1.977 | −45.983 | 1.00 | 57.32 | C |
| ATOM | 481 | CB | ASN A | 146 | 18.707 | 1.259 | −47.310 | 1.00 | 57.53 | C |
| ATOM | 482 | CG | ASN A | 146 | 17.993 | 2.121 | −48.327 | 1.00 | 58.91 | C |
| ATOM | 483 | OD1 | ASN A | 146 | 18.316 | 3.298 | −48.498 | 1.00 | 57.20 | O |
| ATOM | 484 | ND2 | ASN A | 146 | 17.014 | 1.537 | −49.011 | 1.00 | 60.00 | N |
| ATOM | 485 | C | ASN A | 146 | 17.580 | 2.449 | −45.406 | 1.00 | 56.54 | C |
| ATOM | 486 | O | ASN A | 146 | 16.662 | 1.650 | −45.221 | 1.00 | 57.00 | O |
| ATOM | 487 | N | TRP A | 147 | 17.484 | 3.741 | −45.109 | 1.00 | 55.03 | N |
| ATOM | 488 | CA | TRP A | 147 | 16.263 | 4.315 | −44.550 | 1.00 | 54.72 | C |
| ATOM | 489 | CB | TRP A | 147 | 16.588 | 5.180 | −43.330 | 1.00 | 54.14 | C |
| ATOM | 490 | CG | TRP A | 147 | 17.381 | 4.500 | −42.225 | 1.00 | 54.41 | C |
| ATOM | 491 | CD1 | TRP A | 147 | 18.716 | 4.659 | −41.953 | 1.00 | 50.96 | C |
| ATOM | 492 | NE1 | TRP A | 147 | 19.069 | 3.904 | −40.856 | 1.00 | 52.73 | N |
| ATOM | 493 | CE2 | TRP A | 147 | 17.960 | 3.246 | −40.388 | 1.00 | 52.29 | C |
| ATOM | 494 | CD2 | TRP A | 147 | 16.873 | 3.596 | −41.224 | 1.00 | 52.72 | C |
| ATOM | 495 | CE3 | TRP A | 147 | 15.609 | 3.049 | −40.956 | 1.00 | 50.73 | C |
| ATOM | 496 | CZ3 | TRP A | 147 | 15.473 | 2.173 | −39.881 | 1.00 | 51.22 | C |
| ATOM | 497 | CH2 | TRP A | 147 | 16.574 | 1.843 | −39.072 | 1.00 | 51.94 | C |
| ATOM | 498 | CZ2 | TRP A | 147 | 17.820 | 2.371 | −39.305 | 1.00 | 50.97 | C |
| ATOM | 499 | C | TRP A | 147 | 15.476 | 5.144 | −45.588 | 1.00 | 54.51 | C |
| ATOM | 500 | O | TRP A | 147 | 14.430 | 5.741 | −45.270 | 1.00 | 54.34 | O |
| ATOM | 501 | N | GLU A | 148 | 15.983 | 5.171 | −46.819 | 1.00 | 53.71 | N |
| ATOM | 502 | CA | GLU A | 148 | 15.402 | 5.965 | −47.906 | 1.00 | 53.17 | C |
| ATOM | 503 | CB | GLU A | 148 | 16.362 | 6.035 | −49.098 | 1.00 | 54.07 | C |
| ATOM | 504 | CG | GLU A | 148 | 17.664 | 6.784 | −48.833 | 1.00 | 59.98 | C |
| ATOM | 505 | CD | GLU A | 148 | 17.533 | 8.287 | −49.001 | 1.00 | 67.81 | C |
| ATOM | 506 | OE1 | GLU A | 148 | 17.885 | 8.800 | −50.085 | 1.00 | 74.52 | O |
| ATOM | 507 | OE2 | GLU A | 148 | 17.081 | 8.961 | −48.055 | 1.00 | 71.57 | O |
| ATOM | 508 | C | GLU A | 148 | 14.049 | 5.424 | −48.361 | 1.00 | 50.98 | C |
| ATOM | 509 | O | GLU A | 148 | 13.719 | 4.260 | −48.126 | 1.00 | 50.18 | O |
| ATOM | 510 | N | LEU A | 149 | 13.271 | 6.287 | −49.007 | 1.00 | 50.01 | N |
| ATOM | 511 | CA | LEU A | 149 | 11.935 | 5.930 | −49.483 | 1.00 | 49.44 | C |
| ATOM | 512 | CB | LEU A | 149 | 10.922 | 7.018 | −49.103 | 1.00 | 48.67 | C |
| ATOM | 513 | CG | LEU A | 149 | 10.529 | 7.064 | −47.626 | 1.00 | 45.82 | C |
| ATOM | 514 | CD1 | LEU A | 149 | 9.756 | 8.326 | −47.324 | 1.00 | 43.58 | C |
| ATOM | 515 | CD2 | LEU A | 149 | 9.724 | 5.827 | −47.253 | 1.00 | 42.03 | C |
| ATOM | 516 | C | LEU A | 149 | 11.924 | 5.690 | −50.986 | 1.00 | 49.53 | C |
| ATOM | 517 | O | LEU A | 149 | 12.724 | 6.283 | −51.711 | 1.00 | 50.00 | O |
| ATOM | 518 | N | ALA A | 150 | 11.010 | 4.832 | −51.443 | 1.00 | 49.76 | N |
| ATOM | 519 | CA | ALA A | 150 | 10.976 | 4.387 | −52.845 | 1.00 | 50.02 | C |
| ATOM | 520 | CB | ALA A | 150 | 11.561 | 2.974 | −52.967 | 1.00 | 49.79 | C |
| ATOM | 521 | C | ALA A | 150 | 9.580 | 4.449 | −53.478 | 1.00 | 50.70 | C |
| ATOM | 522 | O | ALA A | 150 | 8.564 | 4.531 | −52.772 | 1.00 | 51.10 | O |
| ATOM | 523 | N | ASP A | 151 | 9.543 | 4.405 | −54.810 | 1.00 | 50.70 | N |
| | | | | gad65.pdb | | | | | | |
| ATOM | 524 | CA | ASP A | 151 | 8.288 | 4.446 | −55.571 | 1.00 | 50.97 | C |
| ATOM | 525 | CB | ASP A | 151 | 8.557 | 4.808 | −57.035 | 1.00 | 50.92 | C |
| ATOM | 526 | CG | ASP A | 151 | 9.085 | 6.225 | −57.199 | 1.00 | 54.08 | C |
| ATOM | 529 | C | ASP A | 151 | 7.510 | 3.130 | −55.497 | 1.00 | 50.77 | C |
| ATOM | 530 | O | ASP A | 151 | 6.274 | 3.128 | −55.411 | 1.00 | 50.86 | O |
| ATOM | 531 | N | GLN A | 152 | 8.239 | 2.017 | −55.524 | 1.00 | 49.80 | N |

TABLE A-continued

| | | | | | | | | | | |
|---|---|---|---|---|---|---|---|---|---|---|
| ATOM | 532 | CA | GLN A | 152 | 7.635 | .685 | −55.547 | 1.00 | 48.90 | C |
| ATOM | 533 | CB | GLN A | 152 | 8.424 | −.241 | −56.487 | 1.00 | 48.86 | C |
| ATOM | 538 | C | GLN A | 152 | 7.551 | .093 | −54.141 | 1.00 | 48.04 | C |
| ATOM | 539 | O | GLN A | 152 | 8.384 | .419 | −53.294 | 1.00 | 46.79 | O |
| ATOM | 540 | N | PRO A | 153 | 6.548 | −.777 | −53.888 | 1.00 | 48.41 | N |
| ATOM | 541 | CA | PRO A | 153 | 6.359 | −1.352 | −52.552 | 1.00 | 49.19 | C |
| ATOM | 542 | CB | PRO A | 153 | 4.927 | −1.897 | −52.614 | 1.00 | 49.39 | C |
| ATOM | 543 | CG | PRO A | 153 | 4.719 | −2.253 | −54.033 | 1.00 | 45.75 | C |
| ATOM | 544 | CD | PRO A | 153 | 5.522 | −1.260 | −54.836 | 1.00 | 48.29 | C |
| ATOM | 545 | C | PRO A | 153 | 7.327 | −2.493 | −52.211 | 1.00 | 49.43 | C |
| ATOM | 546 | O | PRO A | 153 | 7.746 | −3.246 | −53.096 | 1.00 | 49.69 | O |
| ATOM | 547 | N | GLN A | 154 | 7.657 | −2.618 | −50.930 | 1.00 | 49.60 | N |
| ATOM | 548 | CA | GLN A | 154 | 8.475 | −3.723 | −50.432 | 1.00 | 50.25 | C |
| ATOM | 549 | CB | GLN A | 154 | 9.460 | −3.217 | −49.376 | 1.00 | 50.40 | C |
| ATOM | 550 | CG | GLN A | 154 | 10.739 | −2.631 | −49.955 | 1.00 | 50.59 | C |
| ATOM | 551 | CD | GLN A | 154 | 11.685 | −2.131 | −48.887 | 1.00 | 51.03 | C |
| ATOM | 552 | OE1 | GLN A | 154 | 11.267 | −1.475 | −47.940 | 1.00 | 57.85 | O |
| ATOM | 553 | NE2 | GLN A | 154 | 12.971 | −2.438 | −49.034 | 1.00 | 50.14 | N |
| ATOM | 554 | C | GLN A | 154 | 7.591 | −4.808 | −49.841 | 1.00 | 50.14 | C |
| ATOM | 555 | O | GLN A | 154 | 6.500 | −4.519 | −49.352 | 1.00 | 50.95 | O |
| ATOM | 556 | N | ASN A | 155 | 8.052 | −6.055 | −49.882 | 1.00 | 50.15 | N |
| ATOM | 557 | CA | ASN A | 155 | 7.288 | −7.158 | −49.291 | 1.00 | 49.86 | C |
| ATOM | 558 | CB | ASN A | 155 | 7.703 | −8.538 | −49.855 | 1.00 | 50.06 | C |
| ATOM | 559 | CG | ASN A | 155 | 9.155 | −8.917 | −49.547 | 1.00 | 54.94 | C |
| ATOM | 560 | OD1 | ASN A | 155 | 9.907 | −9.306 | −50.449 | 1.00 | 56.99 | O |
| ATOM | 561 | ND2 | ASN A | 155 | 9.540 | −8.848 | −48.276 | 1.00 | 55.83 | N |
| ATOM | 562 | C | ASN A | 155 | 7.298 | −7.123 | −47.764 | 1.00 | 49.24 | C |
| ATOM | 563 | O | ASN A | 155 | 8.113 | −6.414 | −47.159 | 1.00 | 48.95 | O |
| ATOM | 564 | N | LEU A | 156 | 6.397 | −7.890 | −47.155 | 1.00 | 49.07 | N |
| ATOM | 565 | CA | LEU A | 156 | 6.174 | −7.841 | −45.713 | 1.00 | 49.05 | C |
| ATOM | 566 | CB | LEU A | 156 | 4.852 | −8.525 | −45.338 | 1.00 | 48.26 | C |
| ATOM | 567 | CG | LEU A | 156 | 3.542 | −7.857 | −45.800 | 1.00 | 44.91 | C |
| ATOM | 568 | CD1 | LEU A | 156 | 2.359 | −8.650 | −45.293 | 1.00 | 44.49 | C |
| ATOM | 569 | CD2 | LEU A | 156 | 3.414 | −6.401 | −45.380 | 1.00 | 40.41 | C |
| ATOM | 570 | C | LEU A | 156 | 7.339 | −8.370 | −44.868 | 1.00 | 50.33 | C |
| ATOM | 571 | O | LEU A | 156 | 7.480 | −7.983 | −43.705 | 1.00 | 50.90 | O |
| ATOM | 572 | N | GLU A | 157 | 8.168 | −9.239 | −45.450 | 1.00 | 50.77 | N |
| ATOM | 573 | CA | GLU A | 157 | 9.392 | −9.709 | −44.788 | 1.00 | 51.43 | C |
| ATOM | 574 | CB | GLU A | 157 | 10.057 | −10.837 | −45.604 | 1.00 | 52.59 | C |
| ATOM | 575 | CG | GLU A | 157 | 11.482 | −11.243 | −45.169 | 1.00 | 60.13 | C |
| ATOM | 576 | CD | GLU A | 157 | 11.553 | −11.808 | −43.747 | 1.00 | 67.88 | C |
| ATOM | 577 | OE1 | GLU A | 157 | 11.087 | −12.948 | −43.525 | 1.00 | 66.08 | O |
| ATOM | 578 | OE2 | GLU A | 157 | 12.089 | −11.110 | −42.854 | 1.00 | 71.96 | O |
| ATOM | 579 | C | GLU A | 157 | 10.341 | −8.540 | −44.557 | 1.00 | 50.19 | C |
| ATOM | 580 | O | GLU A | 157 | 10.901 | −8.397 | −43.473 | 1.00 | 49.74 | O |
| ATOM | 581 | N | GLU A | 158 | 10.490 | −7.697 | −45.577 | 1.00 | 50.86 | N |
| ATOM | 582 | CA | GLU A | 158 | 11.304 | −6.479 | −45.506 | 1.00 | 52.14 | C |
| ATOM | 583 | CB | GLU A | 158 | 11.472 | −5.878 | −46.906 | 1.00 | 52.37 | C |
| ATOM | 584 | CG | GLU A | 158 | 12.241 | −6.786 | −47.875 | 1.00 | 57.91 | C |
| ATOM | 585 | CD | GLU A | 158 | 12.140 | −6.359 | −49.341 | 1.00 | 55.63 | C |
| ATOM | 586 | OE1 | GLU A | 158 | 11.032 | −6.441 | −49.927 | 1.00 | 65.89 | O |
| ATOM | 587 | OE2 | GLU A | 158 | 13.186 | −5.974 | −49.920 | 1.00 | 63.04 | O |
| ATOM | 588 | C | GLU A | 158 | 10.730 | −5.437 | −44.536 | 1.00 | 51.21 | C |
| ATOM | 589 | O | GLU A | 158 | 11.472 | −4.626 | −43.968 | 1.00 | 51.46 | O |
| ATOM | 590 | N | ILE A | 159 | 9.410 | −5.476 | −44.344 | 1.00 | 49.77 | N |
| ATOM | 591 | CA | ILE A | 159 | 8.719 | −4.576 | −43.420 | 1.00 | 47.70 | C |
| ATOM | 592 | CB | ILE A | 159 | 7.201 | −4.449 | −43.768 | 1.00 | 46.88 | C |
| ATOM | 593 | CG1 | ILE A | 159 | 7.019 | −3.746 | −45.119 | 1.00 | 38.53 | C |
| ATOM | 594 | CD | ILE A | 159 | 7.790 | −2.452 | −45.259 | 1.00 | 34.44 | C |
| ATOM | 595 | CG2 | ILE A | 159 | 6.417 | −3.750 | −42.653 | 1.00 | 47.89 | C |
| ATOM | 596 | C | ILE A | 159 | 8.939 | −5.012 | −41.976 | 1.00 | 47.30 | C |
| ATOM | 597 | O | ILE A | 159 | 9.186 | −4.177 | −41.098 | 1.00 | 45.98 | O |
| | | | | | gad65.pdb | | | | | |
| ATOM | 598 | N | LEU A | 160 | 8.865 | −6.319 | −41.740 | 1.00 | 47.79 | N |
| ATOM | 599 | CA | LEU A | 160 | 9.163 | −6.874 | −40.420 | 1.00 | 48.56 | C |
| ATOM | 600 | CB | LEU A | 160 | 8.806 | −8.359 | −40.354 | 1.00 | 48.85 | C |
| ATOM | 601 | CG | LEU A | 160 | 7.336 | −8.784 | −40.363 | 1.00 | 45.71 | C |
| ATOM | 602 | CD1 | LEU A | 160 | 7.266 | −10.280 | −40.601 | 1.00 | 49.06 | C |
| ATOM | 603 | CD2 | LEU A | 160 | 6.620 | −8.412 | −39.074 | 1.00 | 44.42 | C |
| ATOM | 604 | C | LEU A | 160 | 10.624 | −6.670 | −40.022 | 1.00 | 49.35 | C |
| ATOM | 605 | O | LEU A | 160 | 10.934 | −6.512 | −38.836 | 1.00 | 50.44 | O |
| ATOM | 606 | N | MET A | 161 | 11.516 | −6.658 | −41.010 | 1.00 | 49.46 | N |
| ATOM | 607 | CA | MET A | 161 | 12.928 | −6.386 | −40.753 | 1.00 | 50.38 | C |
| ATOM | 608 | CB | MET A | 161 | 13.805 | −6.750 | −41.950 | 1.00 | 51.18 | C |
| ATOM | 609 | CG | MET A | 161 | 14.640 | −8.009 | −41.728 | 1.00 | 58.54 | C |
| ATOM | 610 | SD | MET A | 161 | 15.946 | −7.748 | −40.499 | 1.00 | 68.14 | S |
| ATOM | 611 | CE | MET A | 161 | 16.654 | −9.395 | −40.394 | 1.00 | 65.72 | C |
| ATOM | 612 | C | MET A | 161 | 13.132 | −4.932 | −40.352 | 1.00 | 50.34 | C |
| ATOM | 613 | O | MET A | 161 | 13.927 | −4.633 | −39.461 | 1.00 | 51.08 | O |
| ATOM | 614 | N | HIS A | 162 | 12.395 | −4.039 | −41.003 | 1.00 | 49.39 | N |

TABLE A-continued

| | | | | | | | | | | |
|---|---|---|---|---|---|---|---|---|---|---|
| ATOM | 615 | CA | HIS A | 162 | 12.432 | −2.617 | −40.669 | 1.00 | 48.35 | C |
| ATOM | 616 | CB | HIS A | 162 | 11.528 | −1.820 | −41.613 | 1.00 | 48.81 | C |
| ATOM | 617 | CG | HIS A | 162 | 12.053 | −1.730 | −43.010 | 1.00 | 51.30 | C |
| ATOM | 618 | ND1 | HIS A | 162 | 11.238 | −1.817 | −44.118 | 1.00 | 55.38 | N |
| ATOM | 619 | CE1 | HIS A | 162 | 11.974 | −1.708 | −45.210 | 1.00 | 54.48 | C |
| ATOM | 620 | NE2 | HIS A | 162 | 13.235 | −1.551 | −44.851 | 1.00 | 54.10 | N |
| ATOM | 621 | CD2 | HIS A | 162 | 13.312 | −1.560 | −43.480 | 1.00 | 50.58 | C |
| ATOM | 622 | C | HIS A | 162 | 12.037 | −2.379 | −39.222 | 1.00 | 45.97 | C |
| ATOM | 623 | O | HIS A | 162 | 12.670 | −1.599 | −38.536 | 1.00 | 45.41 | O |
| ATOM | 624 | N | CYS A | 163 | 10.992 | −3.070 | −38.776 | 1.00 | 46.08 | N |
| ATOM | 625 | CA | CYS A | 163 | 10.561 | −3.065 | −37.383 | 1.00 | 46.03 | C |
| ATOM | 626 | CB | CYS A | 163 | 9.302 | −3.914 | −37.213 | 1.00 | 46.14 | C |
| ATOM | 627 | SG | CYS A | 163 | 7.871 | −3.339 | −38.151 | 1.00 | 49.30 | S |
| ATOM | 628 | C | CYS A | 163 | 11.649 | −3.581 | −36.448 | 1.00 | 46.62 | C |
| ATOM | 629 | O | CYS A | 163 | 11.874 | −3.007 | −35.396 | 1.00 | 46.75 | O |
| ATOM | 630 | N | GLN A | 164 | 12.326 | −4.659 | −36.846 | 1.00 | 48.26 | N |
| ATOM | 631 | CA | GLN A | 164 | 13.351 | −5.282 | −36.020 | 1.00 | 48.90 | C |
| ATOM | 632 | CB | GLN A | 164 | 13.771 | −6.606 | −36.647 | 1.00 | 49.41 | C |
| ATOM | 633 | CG | GLN A | 164 | 13.904 | −7.751 | −35.660 | 1.00 | 53.15 | C |
| ATOM | 634 | CD | GLN A | 164 | 14.446 | −9.014 | −36.309 | 1.00 | 51.62 | C |
| ATOM | 635 | OE1 | GLN A | 164 | 13.699 | −9.964 | −36.573 | 1.00 | 56.43 | O |
| ATOM | 636 | NE2 | GLN A | 164 | 15.749 | −9.024 | −36.587 | 1.00 | 55.96 | N |
| ATOM | 637 | C | GLN A | 164 | 14.555 | −4.348 | −35.884 | 1.00 | 48.32 | C |
| ATOM | 638 | O | GLN A | 164 | 15.070 | −4.127 | −34.783 | 1.00 | 48.53 | O |
| ATOM | 639 | N | THR A | 165 | 14.982 | −3.801 | −37.019 | 1.00 | 47.79 | N |
| ATOM | 640 | CA | THR A | 165 | 16.078 | −2.833 | −37.105 | 1.00 | 46.95 | C |
| ATOM | 641 | CB | THR A | 165 | 16.374 | −2.503 | −38.585 | 1.00 | 46.59 | C |
| ATOM | 642 | OG1 | THR A | 165 | 16.481 | −3.727 | −39.324 | 1.00 | 46.41 | O |
| ATOM | 643 | CG2 | THR A | 165 | 17.665 | −1.713 | −38.737 | 1.00 | 42.26 | C |
| ATOM | 644 | C | THR A | 165 | 15.798 | −1.547 | −36.319 | 1.00 | 46.88 | C |
| ATOM | 645 | O | THR A | 165 | 16.701 | −.991 | −35.695 | 1.00 | 47.51 | O |
| ATOM | 646 | N | THR A | 166 | 14.545 | −1.089 | −36.342 | 1.00 | 45.78 | N |
| ATOM | 647 | CA | THR A | 166 | 14.158 | .130 | −35.643 | 1.00 | 43.54 | C |
| ATOM | 648 | CB | THR A | 166 | 12.735 | .581 | −36.042 | 1.00 | 43.16 | C |
| ATOM | 649 | OG1 | THR A | 166 | 12.706 | .801 | −37.451 | 1.00 | 45.16 | O |
| ATOM | 650 | CG2 | THR A | 166 | 12.332 | 1.873 | −35.337 | 1.00 | 37.77 | C |
| ATOM | 651 | C | THR A | 166 | 14.280 | −.029 | −34.129 | 1.00 | 43.09 | C |
| ATOM | 652 | O | THR A | 166 | 14.849 | .838 | −33.461 | 1.00 | 42.44 | O |
| ATOM | 653 | N | LEU A | 167 | 13.762 | −1.136 | −33.596 | 1.00 | 42.88 | N |
| ATOM | 654 | CA | LEU A | 167 | 13.887 | −1.428 | −32.166 | 1.00 | 44.23 | C |
| ATOM | 655 | CB | LEU A | 167 | 12.891 | −2.522 | −31.733 | 1.00 | 44.91 | C |
| ATOM | 656 | CG | LEU A | 167 | 11.392 | −2.165 | −31.801 | 1.00 | 44.51 | C |
| ATOM | 657 | CD1 | LEU A | 167 | 10.498 | −3.400 | −31.661 | 1.00 | 40.63 | C |
| ATOM | 658 | CD2 | LEU A | 167 | 10.998 | −1.112 | −30.767 | 1.00 | 46.72 | C |
| ATOM | 659 | C | LEU A | 167 | 15.337 | −1.752 | −31.732 | 1.00 | 45.22 | C |
| ATOM | 660 | O | LEU A | 167 | 15.738 | −1.442 | −30.601 | 1.00 | 44.75 | O |
| ATOM | 661 | N | LYS A | 168 | 16.119 | −2.332 | −32.644 | 1.00 | 46.67 | N |
| ATOM | 662 | CA | LYS A | 168 | 17.561 | −2.540 | −32.442 | 1.00 | 47.38 | C |
| ATOM | 663 | CB | LYS A | 168 | 18.203 | −3.107 | −33.713 | 1.00 | 47.40 | C |
| ATOM | 664 | CG | LYS A | 168 | 19.654 | −3.574 | −33.562 | 1.00 | 47.53 | C |
| ATOM | 665 | CD | LYS A | 168 | 20.222 | −4.027 | −34.919 | 1.00 | 49.02 | C |
| | | | | | gad65.pdb | | | | | |
| ATOM | 666 | CE | LYS A | 168 | 21.335 | −5.075 | −34.780 | 1.00 | 58.00 | C |
| ATOM | 667 | NZ | LYS A | 168 | 22.394 | −4.690 | −33.799 | 1.00 | 58.33 | N |
| ATOM | 668 | C | LYS A | 168 | 18.286 | −1.251 | −32.032 | 1.00 | 47.65 | C |
| ATOM | 669 | O | LYS A | 168 | 19.054 | −1.242 | −31.060 | 1.00 | 47.57 | O |
| ATOM | 670 | N | TYR A | 169 | 18.054 | −.168 | −32.769 | 1.00 | 46.93 | N |
| ATOM | 671 | CA | TYR A | 169 | 18.773 | 1.085 | −32.493 | 1.00 | 45.91 | C |
| ATOM | 672 | CB | TYR A | 169 | 19.203 | 1.759 | −33.791 | 1.00 | 46.80 | C |
| ATOM | 673 | CG | TYR A | 169 | 20.054 | .872 | −34.678 | 1.00 | 51.46 | C |
| ATOM | 674 | CD1 | TYR A | 169 | 21.325 | .458 | −34.270 | 1.00 | 52.27 | C |
| ATOM | 675 | CE1 | TYR A | 169 | 22.110 | −.357 | −35.075 | 1.00 | 54.28 | C |
| ATOM | 676 | CZ | TYR A | 169 | 21.629 | −.759 | −36.307 | 1.00 | 52.13 | C |
| ATOM | 677 | OH | TYR A | 169 | 22.412 | −1.567 | −37.099 | 1.00 | 57.82 | O |
| ATOM | 678 | CE2 | TYR A | 169 | 20.369 | −.364 | −36.739 | 1.00 | 49.71 | C |
| ATOM | 679 | CD2 | TYR A | 169 | 19.590 | .446 | −35.924 | 1.00 | 49.70 | C |
| ATOM | 680 | C | TYR A | 169 | 18.016 | 2.060 | −31.591 | 1.00 | 44.90 | C |
| ATOM | 681 | O | TYR A | 169 | 18.539 | 3.105 | −31.220 | 1.00 | 45.82 | O |
| ATOM | 682 | N | ALA A | 170 | 16.787 | 1.715 | −31.230 | 1.00 | 44.05 | N |
| ATOM | 683 | CA | ALA A | 170 | 16.027 | 2.521 | −30.272 | 1.00 | 43.93 | C |
| ATOM | 684 | CB | ALA A | 170 | 14.597 | 1.986 | −30.148 | 1.00 | 42.56 | C |
| ATOM | 685 | C | ALA A | 170 | 16.720 | 2.518 | −28.897 | 1.00 | 43.81 | C |
| ATOM | 686 | O | ALA A | 170 | 17.295 | 1.504 | −28.486 | 1.00 | 43.58 | O |
| ATOM | 687 | N | ILE A | 171 | 16.672 | 3.655 | −28.202 | 1.00 | 43.65 | N |
| ATOM | 688 | CA | ILE A | 171 | 17.046 | 3.713 | −26.791 | 1.00 | 44.05 | C |
| ATOM | 689 | CB | ILE A | 171 | 17.036 | 5.162 | −26.244 | 1.00 | 45.35 | C |
| ATOM | 690 | CG1 | ILE A | 171 | 17.741 | 6.144 | −27.198 | 1.00 | 49.29 | C |
| ATOM | 691 | CD | ILE A | 171 | 19.132 | 5.797 | −27.592 | 1.00 | 45.21 | C |
| ATOM | 692 | CG2 | ILE A | 171 | 17.615 | 5.242 | −24.841 | 1.00 | 46.56 | C |
| ATOM | 693 | C | ILE A | 171 | 16.026 | 2.882 | −26.024 | 1.00 | 44.07 | C |

TABLE A-continued

| | | | | | | | | | | |
|---|---|---|---|---|---|---|---|---|---|---|
| ATOM | 694 | O | ILE A | 171 | 14.823 | 2.883 | −26.375 | 1.00 | 43.19 | O |
| ATOM | 695 | N | LYS A | 172 | 16.500 | 2.171 | −24.994 | 1.00 | 44.11 | N |
| ATOM | 696 | CA | LYS A | 172 | 15.632 | 1.366 | −24.126 | 1.00 | 44.08 | C |
| ATOM | 697 | CB | LYS A | 172 | 16.344 | .103 | −23.629 | 1.00 | 44.95 | C |
| ATOM | 698 | CG | LYS A | 172 | 17.108 | −.692 | −24.701 | 1.00 | 46.13 | C |
| ATOM | 699 | CD | LYS A | 172 | 16.182 | −1.456 | −25.625 | 1.00 | 49.89 | C |
| ATOM | 700 | CE | LYS A | 172 | 16.951 | −2.131 | −26.777 | 1.00 | 49.87 | C |
| ATOM | 701 | NZ | LYS A | 172 | 17.604 | −1.145 | −27.704 | 1.00 | 47.23 | N |
| ATOM | 702 | C | LYS A | 172 | 15.146 | 2.222 | −22.956 | 1.00 | 44.68 | C |
| ATOM | 703 | O | LYS A | 172 | 15.600 | 2.071 | −21.824 | 1.00 | 46.10 | O |
| ATOM | 704 | N | THR A | 173 | 14.215 | 3.127 | −23.252 | 1.00 | 44.05 | N |
| ATOM | 705 | CA | THR A | 173 | 13.659 | 4.069 | −22.285 | 1.00 | 43.65 | C |
| ATOM | 706 | CB | THR A | 173 | 12.651 | 5.010 | −22.971 | 1.00 | 43.39 | C |
| ATOM | 707 | OG1 | THR A | 173 | 11.706 | 4.220 | −23.699 | 1.00 | 44.57 | O |
| ATOM | 708 | CG2 | THR A | 173 | 13.373 | 5.986 | −23.930 | 1.00 | 35.11 | C |
| ATOM | 709 | C | THR A | 173 | 12.984 | 3.430 | −21.059 | 1.00 | 44.40 | C |
| ATOM | 710 | O | THR A | 173 | 12.663 | 4.125 | −20.092 | 1.00 | 44.49 | O |
| ATOM | 711 | N | GLY A | 174 | 12.773 | 2.117 | −21.097 | 1.00 | 45.00 | N |
| ATOM | 712 | CA | GLY A | 174 | 12.231 | 1.398 | −19.946 | 1.00 | 45.55 | C |
| ATOM | 713 | C | GLY A | 174 | 13.296 | .737 | −19.076 | 1.00 | 45.34 | C |
| ATOM | 714 | O | GLY A | 174 | 13.007 | .297 | −17.955 | 1.00 | 45.80 | O |
| ATOM | 715 | N | HIS A | 175 | 14.521 | .672 | −19.598 | 1.00 | 44.31 | N |
| ATOM | 716 | CA | HIS A | 175 | 15.660 | .029 | −18.928 | 1.00 | 43.40 | C |
| ATOM | 717 | CB | HIS A | 175 | 16.928 | .280 | −19.755 | 1.00 | 43.26 | C |
| ATOM | 718 | CG | HIS A | 175 | 18.058 | −.654 | −19.449 | 1.00 | 41.09 | C |
| ATOM | 719 | ND1 | HIS A | 175 | 18.929 | −.449 | −18.403 | 1.00 | 40.81 | N |
| ATOM | 720 | CE1 | HIS A | 175 | 19.827 | −1.419 | −18.383 | 1.00 | 38.13 | C |
| ATOM | 721 | NE2 | HIS A | 175 | 19.571 | −2.242 | −19.384 | 1.00 | 42.72 | N |
| ATOM | 722 | CD2 | HIS A | 175 | 18.472 | −1.785 | −20.069 | 1.00 | 40.82 | C |
| ATOM | 723 | C | HIS A | 175 | 15.875 | .565 | −17.512 | 1.00 | 43.20 | C |
| ATOM | 724 | O | HIS A | 175 | 15.769 | 1.770 | −17.302 | 1.00 | 42.47 | O |
| ATOM | 725 | N | PRO A | 176 | 16.198 | −.326 | −16.539 | 1.00 | 44.05 | N |
| ATOM | 726 | CA | PRO A | 176 | 16.509 | .085 | −15.158 | 1.00 | 43.80 | C |
| ATOM | 727 | CB | PRO A | 176 | 17.013 | −1.206 | −14.513 | 1.00 | 43.85 | C |
| ATOM | 728 | CG | PRO A | 176 | 16.295 | −2.282 | −15.258 | 1.00 | 43.07 | C |
| ATOM | 729 | CD | PRO A | 176 | 16.243 | −1.797 | −16.683 | 1.00 | 43.82 | C |
| ATOM | 730 | C | PRO A | 176 | 17.565 | 1.171 | −15.028 | 1.00 | 44.26 | C |
| ATOM | 731 | O | PRO A | 176 | 17.532 | 1.936 | −14.063 | 1.00 | 44.77 | O |
| ATOM | 732 | N | ARG A | 177 | 18.484 | 1.257 | −15.986 | 1.00 | 43.91 | N |
| ATOM | 733 | CA | ARG A | 177 | 19.581 | 2.214 | −15.874 gad65.pdb | 1.00 | 43.69 | C |
| ATOM | 734 | CB | ARG A | 177 | 20.922 | 1.503 | −15.958 | 1.00 | 44.29 | C |
| ATOM | 735 | CG | ARG A | 177 | 21.163 | .641 | −14.745 | 1.00 | 46.65 | C |
| ATOM | 736 | CD | ARG A | 177 | 22.247 | −.353 | −14.978 | 1.00 | 44.63 | C |
| ATOM | 737 | NE | ARG A | 177 | 22.252 | −1.334 | −13.902 | 1.00 | 47.93 | N |
| ATOM | 738 | CZ | ARG A | 177 | 23.047 | −2.392 | −13.870 | 1.00 | 48.97 | C |
| ATOM | 739 | NH1 | ARG A | 177 | 23.904 | −2.602 | −14.865 | 1.00 | 49.03 | N |
| ATOM | 740 | NH2 | ARG A | 177 | 22.977 | −3.240 | −12.852 | 1.00 | 50.58 | N |
| ATOM | 741 | C | ARG A | 177 | 19.492 | 3.380 | −16.849 | 1.00 | 42.97 | C |
| ATOM | 742 | O | ARG A | 177 | 20.460 | 4.114 | −17.048 | 1.00 | 41.65 | O |
| ATOM | 743 | N | TYR A | 178 | 18.309 | 3.556 | −17.431 | 1.00 | 42.59 | N |
| ATOM | 744 | CA | TYR A | 178 | 18.028 | 4.740 | −18.211 | 1.00 | 42.61 | C |
| ATOM | 745 | CB | TYR A | 178 | 16.973 | 4.438 | −19.270 | 1.00 | 42.75 | C |
| ATOM | 746 | CG | TYR A | 178 | 16.677 | 5.610 | −20.154 | 1.00 | 41.33 | C |
| ATOM | 747 | CD1 | TYR A | 178 | 17.602 | 6.037 | −21.105 | 1.00 | 40.29 | C |
| ATOM | 748 | CE1 | TYR A | 178 | 17.338 | 7.125 | −21.911 | 1.00 | 48.14 | C |
| ATOM | 749 | CZ | TYR A | 178 | 16.127 | 7.796 | −21.775 | 1.00 | 43.80 | C |
| ATOM | 750 | OH | TYR A | 178 | 15.861 | 8.872 | −22.570 | 1.00 | 47.66 | O |
| ATOM | 751 | CE2 | TYR A | 178 | 15.193 | 7.393 | −20.841 | 1.00 | 43.63 | C |
| ATOM | 752 | CD2 | TYR A | 178 | 15.474 | 6.301 | −20.035 | 1.00 | 44.72 | C |
| ATOM | 753 | C | TYR A | 178 | 17.574 | 5.864 | −17.271 | 1.00 | 42.63 | C |
| ATOM | 754 | O | TYR A | 178 | 16.522 | 5.761 | −16.646 | 1.00 | 42.02 | O |
| ATOM | 755 | N | PHE A | 179 | 18.392 | 6.916 | −17.165 | 1.00 | 43.40 | N |
| ATOM | 756 | CA | PHE A | 179 | 18.150 | 8.041 | −16.248 | 1.00 | 44.71 | C |
| ATOM | 757 | CB | PHE A | 179 | 19.151 | 8.026 | −15.075 | 1.00 | 44.25 | C |
| ATOM | 758 | CG | PHE A | 179 | 19.073 | 6.800 | −14.195 | 1.00 | 46.79 | C |
| ATOM | 759 | CD1 | PHE A | 179 | 20.157 | 5.923 | −14.113 | 1.00 | 47.74 | C |
| ATOM | 760 | CE1 | PHE A | 179 | 20.106 | 4.791 | −13.297 | 1.00 | 44.33 | C |
| ATOM | 761 | CZ | PHE A | 179 | 18.956 | 4.527 | −12.547 | 1.00 | 47.85 | C |
| ATOM | 762 | CE2 | PHE A | 179 | 17.863 | 5.398 | −12.620 | 1.00 | 44.20 | C |
| ATOM | 763 | CD2 | PHE A | 179 | 17.932 | 6.528 | −13.435 | 1.00 | 43.44 | C |
| ATOM | 764 | C | PHE A | 179 | 18.253 | 9.405 | −16.953 | 1.00 | 46.45 | C |
| ATOM | 765 | O | PHE A | 179 | 18.475 | 10.434 | −16.290 | 1.00 | 47.73 | O |
| ATOM | 766 | N | ASN A | 180 | 18.089 | 9.416 | −18.278 | 1.00 | 45.83 | N |
| ATOM | 767 | CA | ASN A | 180 | 18.462 | 10.574 | −19.105 | 1.00 | 46.52 | C |
| ATOM | 768 | CB | ASN A | 180 | 18.737 | 10.132 | −20.545 | 1.00 | 46.38 | C |
| ATOM | 769 | CG | ASN A | 180 | 19.672 | 11.086 | −21.281 | 1.00 | 51.53 | C |
| ATOM | 770 | OD1 | ASN A | 180 | 20.764 | 11.381 | −20.811 | 1.00 | 48.13 | O |
| ATOM | 771 | ND2 | ASN A | 180 | 19.248 | 11.559 | −22.445 | 1.00 | 53.82 | N |
| ATOM | 772 | C | ASN A | 180 | 17.456 | 11.729 | −19.146 | 1.00 | 46.61 | C |

TABLE A-continued

| | | | | | | | | | | |
|---|---|---|---|---|---|---|---|---|---|---|
| ATOM | 773 | O | ASN A | 180 | 17.828 | 12.880 | −19.419 | 1.00 | 46.83 | O |
| ATOM | 774 | N | GLN A | 181 | 16.188 | 11.414 | −18.907 | 1.00 | 46.03 | N |
| ATOM | 775 | CA | GLN A | 181 | 15.123 | 12.398 | −19.035 | 1.00 | 46.60 | C |
| ATOM | 776 | CB | GLN A | 181 | 14.309 | 12.185 | −20.328 | 1.00 | 46.33 | C |
| ATOM | 777 | CG | GLN A | 181 | 15.102 | 11.977 | −21.622 | 1.00 | 44.46 | C |
| ATOM | 778 | CD | GLN A | 181 | 15.797 | 13.235 | −22.136 | 1.00 | 50.57 | C |
| ATOM | 779 | OE1 | GLN A | 181 | 16.745 | 13.153 | −22.920 | 1.00 | 49.65 | O |
| ATOM | 780 | NE2 | GLN A | 181 | 15.322 | 14.397 | −21.714 | 1.00 | 48.83 | N |
| ATOM | 781 | C | GLN A | 181 | 14.198 | 12.283 | −17.843 | 1.00 | 47.60 | C |
| ATOM | 782 | O | GLN A | 181 | 14.341 | 11.376 | −17.029 | 1.00 | 47.51 | O |
| ATOM | 783 | N | LEU A | 182 | 13.246 | 13.207 | −17.757 | 1.00 | 48.28 | N |
| ATOM | 784 | CA | LEU A | 182 | 12.238 | 13.218 | −16.706 | 1.00 | 48.83 | C |
| ATOM | 785 | CB | LEU A | 182 | 11.534 | 14.584 | −16.697 | 1.00 | 47.83 | C |
| ATOM | 786 | CG | LEU A | 182 | 11.950 | 15.740 | −15.772 | 1.00 | 48.86 | C |
| ATOM | 787 | CD1 | LEU A | 182 | 13.412 | 15.748 | −15.382 | 1.00 | 49.70 | C |
| ATOM | 788 | CD2 | LEU A | 182 | 11.556 | 17.070 | −16.389 | 1.00 | 48.48 | C |
| ATOM | 789 | C | LEU A | 182 | 11.227 | 12.061 | −16.911 | 1.00 | 49.93 | C |
| ATOM | 790 | O | LEU A | 182 | 10.797 | 11.418 | −15.944 | 1.00 | 49.96 | O |
| ATOM | 791 | N | SER A | 183 | 10.874 | 11.821 | −18.175 | 1.00 | 50.13 | N |
| ATOM | 792 | CA | SER A | 183 | 10.073 | 10.677 | −18.589 | 1.00 | 52.40 | C |
| ATOM | 793 | CB | SER A | 183 | 9.282 | 11.005 | −19.865 | 1.00 | 52.89 | C |
| ATOM | 794 | OG | SER A | 183 | 8.550 | 12.212 | −19.728 | 1.00 | 52.85 | O |
| ATOM | 795 | C | SER A | 183 | 10.956 | 9.451 | −18.836 | 1.00 | 53.52 | C |
| ATOM | 796 | O | SER A | 183 | 11.693 | 9.399 | −19.826 | 1.00 | 54.79 | O |
| ATOM | 797 | N | THR A | 184 | 10.891 | 8.482 | −17.924 | 1.00 | 54.16 | N |
| ATOM | 798 | CA | THR A | 184 | 11.572 | 7.183 | −18.070 | 1.00 | 54.66 | C |
| ATOM | 799 | CB | THR A | 184 | 12.824 | 7.056 | −17.158 | 1.00 | 55.05 | C |
| ATOM | 800 | OG1 | THR A | 184 | 12.438 | 7.206 | −15.786 | 1.00 | 57.40 | O |
| ATOM | 801 | CG2 | THR A | 184 | 13.890 | 8.110 | −17.503 | 1.00 | 54.75 | C |
| | | | | | gad65.pdb | | | | | |
| ATOM | 802 | C | THR A | 184 | 10.608 | 6.056 | −17.696 | 1.00 | 54.68 | C |
| ATOM | 803 | O | THR A | 184 | 9.692 | 6.263 | −16.894 | 1.00 | 54.56 | O |
| ATOM | 804 | N | GLY A | 185 | 10.813 | 4.875 | −18.278 | 1.00 | 53.67 | N |
| ATOM | 805 | CA | GLY A | 185 | 10.039 | 3.693 | −17.909 | 1.00 | 52.22 | C |
| ATOM | 806 | C | GLY A | 185 | 9.094 | 3.198 | −18.993 | 1.00 | 50.79 | C |
| ATOM | 807 | O | GLY A | 185 | 8.792 | 3.904 | −19.955 | 1.00 | 49.90 | O |
| ATOM | 808 | N | LEU A | 186 | 8.651 | 1.957 | −18.843 | 1.00 | 49.90 | N |
| ATOM | 809 | CA | LEU A | 186 | 7.716 | 1.358 | −19.776 | 1.00 | 49.03 | C |
| ATOM | 810 | CB | LEU A | 186 | 8.439 | .464 | −20.807 | 1.00 | 48.84 | C |
| ATOM | 811 | CG | LEU A | 186 | 7.637 | −.184 | −21.956 | 1.00 | 50.75 | C |
| ATOM | 812 | CD1 | LEU A | 186 | 7.087 | .837 | −22.947 | 1.00 | 48.58 | C |
| ATOM | 813 | CD2 | LEU A | 186 | 8.470 | −1.253 | −22.701 | 1.00 | 48.75 | C |
| ATOM | 814 | C | LEU A | 186 | 6.681 | .601 | −18.962 | 1.00 | 48.41 | C |
| ATOM | 815 | O | LEU A | 186 | 6.932 | −.509 | −18.472 | 1.00 | 47.20 | O |
| ATOM | 816 | N | ASP A | 187 | 5.528 | 1.242 | −18.798 | 1.00 | 48.08 | N |
| ATOM | 817 | CA | ASP A | 187 | 4.439 | .694 | −18.016 | 1.00 | 48.62 | C |
| ATOM | 818 | CB | ASP A | 187 | 3.579 | 1.806 | −17.417 | 1.00 | 48.58 | C |
| ATOM | 819 | CG | ASP A | 187 | 2.543 | 1.263 | −16.464 | 1.00 | 52.46 | C |
| ATOM | 820 | OD1 | ASP A | 187 | 1.523 | .730 | −16.942 | 1.00 | 52.81 | O |
| ATOM | 821 | OD2 | ASP A | 187 | 2.766 | 1.333 | −15.238 | 1.00 | 56.45 | O |
| ATOM | 822 | C | ASP A | 187 | 3.564 | −.254 | −18.833 | 1.00 | 48.43 | C |
| ATOM | 823 | O | ASP A | 187 | 3.017 | .131 | −19.870 | 1.00 | 49.44 | O |
| ATOM | 824 | N | MET A | 188 | 3.412 | −1.476 | −18.325 | 1.00 | 46.47 | N |
| ATOM | 825 | CA | MET A | 188 | 2.775 | −2.570 | −19.045 | 1.00 | 45.49 | C |
| ATOM | 826 | CB | MET A | 188 | 3.039 | −3.891 | −18.320 | 1.00 | 45.15 | C |
| ATOM | 827 | CG | MET A | 188 | 4.502 | −4.331 | −18.319 | 1.00 | 44.83 | C |
| ATOM | 828 | SD | MET A | 188 | 5.217 | −4.578 | −19.957 | 1.00 | 48.73 | S |
| ATOM | 829 | CE | MET A | 188 | 5.898 | −2.981 | −20.353 | 1.00 | 47.55 | C |
| ATOM | 830 | C | MET A | 188 | 1.274 | −2.376 | −19.314 | 1.00 | 45.40 | C |
| ATOM | 831 | O | MET A | 188 | .809 | −2.632 | −20.426 | 1.00 | 46.08 | O |
| ATOM | 832 | N | VAL A | 189 | .523 | −1.939 | −18.306 | 1.00 | 44.22 | N |
| ATOM | 833 | CA | VAL A | 189 | −.887 | −1.582 | −18.510 | 1.00 | 44.22 | C |
| ATOM | 834 | CB | VAL A | 189 | −1.640 | −1.341 | −17.154 | 1.00 | 43.91 | C |
| ATOM | 835 | CG1 | VAL A | 189 | −3.059 | −.830 | −17.392 | 1.00 | 40.23 | C |
| ATOM | 836 | CG2 | VAL A | 189 | −1.682 | −2.611 | −16.339 | 1.00 | 38.95 | C |
| ATOM | 837 | C | VAL A | 189 | −.988 | −.371 | −19.461 | 1.00 | 43.90 | C |
| ATOM | 838 | O | VAL A | 189 | −1.762 | −.387 | −20.420 | 1.00 | 43.55 | O |
| ATOM | 839 | N | GLY A | 190 | −.167 | .647 | −19.207 | 1.00 | 43.72 | N |
| ATOM | 840 | CA | GLY A | 190 | −.055 | 1.820 | −20.073 | 1.00 | 44.81 | C |
| ATOM | 841 | C | GLY A | 190 | .223 | 1.536 | −21.540 | 1.00 | 45.66 | C |
| ATOM | 842 | O | GLY A | 190 | −.335 | 2.202 | −22.416 | 1.00 | 47.12 | O |
| ATOM | 843 | N | LEU A | 191 | 1.078 | .549 | −21.796 | 1.00 | 45.24 | N |
| ATOM | 844 | CA | LEU A | 191 | 1.385 | .076 | −23.140 | 1.00 | 45.72 | C |
| ATOM | 845 | CB | LEU A | 191 | 2.588 | −.888 | −23.087 | 1.00 | 45.07 | C |
| ATOM | 846 | CG | LEU A | 191 | 3.144 | −1.441 | −24.405 | 1.00 | 43.88 | C |
| ATOM | 847 | CD1 | LEU A | 191 | 3.558 | −.328 | −25.377 | 1.00 | 39.62 | C |
| ATOM | 848 | CD2 | LEU A | 191 | 4.321 | −2.391 | −24.146 | 1.00 | 45.98 | C |
| ATOM | 849 | C | LEU A | 191 | .187 | −.631 | −23.765 | 1.00 | 46.85 | C |
| ATOM | 850 | O | LEU A | 191 | −.179 | −.366 | −24.916 | 1.00 | 47.83 | O |
| ATOM | 851 | N | ALA A | 192 | −.415 | −1.543 | −23.006 | 1.00 | 46.80 | N |

TABLE A-continued

| | | | | | | | | | | |
|---|---|---|---|---|---|---|---|---|---|---|
| ATOM | 852 | CA | ALA A | 192 | −1.625 | −2.228 | −23.438 | 1.00 | 45.40 | C |
| ATOM | 853 | CB | ALA A | 192 | −2.110 | −3.174 | −22.360 | 1.00 | 44.43 | C |
| ATOM | 854 | C | ALA A | 192 | −2.710 | −1.208 | −23.793 | 1.00 | 45.10 | C |
| ATOM | 855 | O | ALA A | 192 | −3.375 | −1.342 | −24.823 | 1.00 | 44.94 | O |
| ATOM | 856 | N | ALA A | 193 | −2.868 | −.194 | −22.945 | 1.00 | 44.78 | N |
| ATOM | 857 | CA | ALA A | 193 | −3.859 | .863 | −23.150 | 1.00 | 46.40 | C |
| ATOM | 858 | CB | ALA A | 193 | −3.928 | 1.757 | −21.938 | 1.00 | 45.74 | C |
| ATOM | 859 | C | ALA A | 193 | −3.572 | 1.695 | −24.405 | 1.00 | 47.59 | C |
| ATOM | 860 | O | ALA A | 193 | −4.498 | 2.111 | −25.116 | 1.00 | 47.55 | O |
| ATOM | 861 | N | ASP A | 194 | −2.289 | 1.919 | −24.675 | 1.00 | 48.35 | N |
| ATOM | 862 | CA | ASP A | 194 | −1.874 | 2.649 | −25.867 | 1.00 | 48.60 | C |
| ATOM | 863 | CB | ASP A | 194 | −.402 | 3.030 | −25.773 | 1.00 | 49.08 | C |
| ATOM | 864 | CG | ASP A | 194 | −.121 | 4.403 | −26.352 | 1.00 | 60.57 | C |
| ATOM | 865 | OD1 | ASP A | 194 | 1.082 | 4.772 | −26.471 | 1.00 | 61.71 | O |
| ATOM | 866 | OD2 | ASP A | 194 | −1.110 | 5.118 | −26.676 | 1.00 | 66.29 | O |
| ATOM | 867 | C | ASP A | 194 | −2.156 | 1.849 | −27.149 | 1.00 | 47.46 | C |
| ATOM | 868 | O | ASP A | 194 | −2.554 | 2.422 | −28.181 | 1.00 | 45.90 | O |
| ATOM | 869 | N | TRP A | 195 | −1.963 | .530 | −27.063 | 1.00 | 46.18 | N |
| | | | | | gad65.pdb | | | | | |
| ATOM | 870 | CA | TRP A | 195 | −2.204 | −.370 | −28.186 | 1.00 | 45.77 | C |
| ATOM | 871 | CB | TRP A | 195 | −1.791 | −1.807 | −27.852 | 1.00 | 45.30 | C |
| ATOM | 872 | CG | TRP A | 195 | −.316 | −2.059 | −27.815 | 1.00 | 44.73 | C |
| ATOM | 873 | CD1 | TRP A | 195 | .674 | −1.239 | −28.266 | 1.00 | 45.44 | C |
| ATOM | 874 | NE1 | TRP A | 195 | 1.903 | −1.819 | −28.063 | 1.00 | 45.60 | N |
| ATOM | 875 | CE2 | TRP A | 195 | 1.724 | −3.043 | −27.480 | 1.00 | 46.54 | C |
| ATOM | 876 | CD2 | TRP A | 195 | .331 | −3.230 | −27.315 | 1.00 | 43.71 | C |
| ATOM | 877 | CE3 | TRP A | 195 | −.130 | −4.417 | −26.733 | 1.00 | 41.27 | C |
| ATOM | 878 | CZ3 | TRP A | 195 | .816 | −5.386 | −26.342 | 1.00 | 48.45 | C |
| ATOM | 879 | CH2 | TRP A | 195 | 2.196 | −5.164 | −26.517 | 1.00 | 46.49 | C |
| ATOM | 880 | CZ2 | TRP A | 195 | 2.669 | −4.007 | −27.089 | 1.00 | 48.01 | C |
| ATOM | 881 | C | TRP A | 195 | −3.664 | −.365 | −28.609 | 1.00 | 45.18 | C |
| ATOM | 882 | O | TRP A | 195 | −3.963 | −.354 | −29.804 | 1.00 | 44.96 | O |
| ATOM | 883 | N | LEU A | 196 | −4.553 | −.408 | −27.616 | 1.00 | 44.54 | N |
| ATOM | 884 | CA | LEU A | 196 | −5.999 | −.303 | −27.822 | 1.00 | 44.37 | C |
| ATOM | 885 | CB | LEU A | 196 | −6.746 | −.533 | −26.498 | 1.00 | 43.30 | C |
| ATOM | 886 | CG | LEU A | 196 | −8.272 | −.661 | −26.607 | 1.00 | 45.83 | C |
| ATOM | 887 | CD1 | LEU A | 196 | −8.801 | −1.600 | −25.530 | 1.00 | 41.00 | C |
| ATOM | 888 | CD2 | LEU A | 196 | −9.004 | .704 | −26.562 | 1.00 | 37.56 | C |
| ATOM | 889 | C | LEU A | 196 | −6.424 | 1.039 | −28.430 | 1.00 | 43.91 | C |
| ATOM | 890 | O | LEU A | 196 | −7.297 | 1.086 | −29.303 | 1.00 | 45.10 | O |
| ATOM | 891 | N | THR A | 197 | −5.835 | 2.120 | −27.935 | 1.00 | 43.00 | N |
| ATOM | 892 | CA | THR A | 197 | −6.137 | 3.474 | −28.395 | 1.00 | 44.28 | C |
| ATOM | 893 | CB | THR A | 197 | −5.262 | 4.490 | −27.645 | 1.00 | 44.82 | C |
| ATOM | 894 | OG1 | THR A | 197 | −5.548 | 4.409 | −26.242 | 1.00 | 46.21 | O |
| ATOM | 895 | CG2 | THR A | 197 | −5.527 | 5.884 | −28.137 | 1.00 | 43.09 | C |
| ATOM | 896 | C | THR A | 197 | −5.907 | 3.619 | −29.904 | 1.00 | 44.82 | C |
| ATOM | 897 | O | THR A | 197 | −6.781 | 4.122 | −30.635 | 1.00 | 44.77 | O |
| ATOM | 898 | N | SER A | 198 | −4.736 | 3.163 | −30.351 | 1.00 | 43.61 | N |
| ATOM | 899 | CA | SER A | 198 | −4.393 | 3.104 | −31.758 | 1.00 | 45.05 | C |
| ATOM | 900 | CB | SER A | 198 | −2.978 | 2.540 | −31.943 | 1.00 | 45.22 | C |
| ATOM | 901 | OG | SER A | 198 | −2.015 | 3.380 | −31.327 | 1.00 | 50.86 | O |
| ATOM | 902 | C | SER A | 198 | −5.398 | 2.274 | −32.556 | 1.00 | 45.04 | C |
| ATOM | 903 | O | SER A | 198 | −5.737 | 2.632 | −33.683 | 1.00 | 47.46 | O |
| ATOM | 904 | N | THR A | 199 | −5.876 | 1.181 | −31.972 | 1.00 | 43.92 | N |
| ATOM | 905 | CA | THR A | 199 | −6.825 | .278 | −32.646 | 1.00 | 43.98 | C |
| ATOM | 906 | CB | THR A | 199 | −7.008 | −1.025 | −31.844 | 1.00 | 44.04 | C |
| ATOM | 907 | OG1 | THR A | 199 | −5.724 | −1.605 | −31.562 | 1.00 | 44.39 | O |
| ATOM | 908 | CG2 | THR A | 199 | −7.851 | −2.030 | −32.615 | 1.00 | 44.80 | C |
| ATOM | 909 | C | THR A | 199 | −8.182 | .971 | −32.828 | 1.00 | 44.82 | C |
| ATOM | 910 | O | THR A | 199 | −8.835 | .815 | −33.860 | 1.00 | 43.98 | O |
| ATOM | 911 | N | ALA A | 200 | −8.584 | 1.738 | −31.812 | 1.00 | 44.82 | N |
| ATOM | 912 | CA | ALA A | 200 | −9.789 | 2.539 | −31.865 | 1.00 | 44.46 | C |
| ATOM | 913 | CB | ALA A | 200 | −10.182 | 3.010 | −30.471 | 1.00 | 42.50 | C |
| ATOM | 914 | C | ALA A | 200 | −9.640 | 3.721 | −32.827 | 1.00 | 45.73 | C |
| ATOM | 915 | O | ALA A | 200 | −10.609 | 4.089 | −33.493 | 1.00 | 47.36 | O |
| ATOM | 916 | N | ASN A | 201 | −8.442 | 4.310 | −32.886 | 1.00 | 46.97 | N |
| ATOM | 917 | CA | ASN A | 201 | −8.088 | 5.328 | −33.889 | 1.00 | 47.80 | C |
| ATOM | 918 | CB | ASN A | 201 | −7.601 | 4.638 | −35.171 | 1.00 | 48.46 | C |
| ATOM | 919 | CG | ASN A | 201 | −7.085 | 5.613 | −36.214 | 1.00 | 55.85 | C |
| ATOM | 920 | OD1 | ASN A | 201 | −7.443 | 5.522 | −37.390 | 1.00 | 63.68 | O |
| ATOM | 921 | ND2 | ASN A | 201 | −6.242 | 6.549 | −35.793 | 1.00 | 56.23 | N |
| ATOM | 922 | C | ASN A | 201 | −9.241 | 6.308 | −34.194 | 1.00 | 48.03 | C |
| ATOM | 923 | O | ASN A | 201 | −9.809 | 6.313 | −35.291 | 1.00 | 46.56 | O |
| ATOM | 924 | N | THR A | 202 | −9.604 | 7.109 | −33.196 | 1.00 | 48.70 | N |
| ATOM | 925 | CA | THR A | 202 | −10.652 | 8.115 | −33.367 | 1.00 | 49.31 | C |
| ATOM | 926 | CB | THR A | 202 | −11.987 | 7.691 | −32.689 | 1.00 | 49.54 | C |
| ATOM | 927 | OG1 | THR A | 202 | −13.038 | 8.607 | −33.043 | 1.00 | 48.79 | O |
| ATOM | 928 | CG2 | THR A | 202 | −11.837 | 7.636 | −31.171 | 1.00 | 47.19 | C |
| ATOM | 929 | C | THR A | 202 | −10.176 | 9.481 | −32.863 | 1.00 | 50.23 | C |
| ATOM | 930 | O | THR A | 202 | −9.138 | 9.587 | −32.198 | 1.00 | 50.18 | O |

TABLE A-continued

| | | | | | | | | | | |
|---|---|---|---|---|---|---|---|---|---|---|
| ATOM | 931 | N | ASN A | 203 | −10.926 | 10.521 | −33.217 | 1.00 | 50.73 | N |
| ATOM | 932 | CA | ASN A | 203 | −10.639 | 11.871 | −32.768 | 1.00 | 52.00 | C |
| ATOM | 933 | CB | ASN A | 203 | −10.972 | 12.880 | −33.863 | 1.00 | 53.33 | C |
| ATOM | 934 | CG | ASN A | 203 | −9.746 | 13.422 | −34.539 | 1.00 | 55.64 | C |
| ATOM | 935 | OD1 | ASN A | 203 | −8.920 | 14.063 | −33.902 | 1.00 | 63.72 | O |
| ATOM | 936 | ND2 | ASN A | 203 | −9.627 | 13.190 | −35.839 | 1.00 | 55.06 | N |
| ATOM | 937 | C | ASN A | 203 | −11.423 | 12.195 | −31.514 | 1.00 | 51.79 | C |
| | | | | gad65.pdb | | | | | | |
| ATOM | 938 | O | ASN A | 203 | −12.459 | 11.593 | −31.252 | 1.00 | 53.28 | O |
| ATOM | 939 | N | MET A | 204 | −10.930 | 13.165 | −30.759 | 1.00 | 50.81 | N |
| ATOM | 940 | CA | MET A | 204 | −11.504 | 13.515 | −29.481 | 1.00 | 50.69 | C |
| ATOM | 941 | CB | MET A | 204 | −10.412 | 14.048 | −28.530 | 1.00 | 50.47 | C |
| ATOM | 942 | CG | MET A | 204 | −9.707 | 13.007 | −27.665 | 1.00 | 45.01 | C |
| ATOM | 943 | SD | MET A | 204 | −10.749 | 11.759 | −26.843 | 1.00 | 53.45 | S |
| ATOM | 944 | CE | MET A | 204 | −11.622 | 12.711 | −25.601 | 1.00 | 53.18 | C |
| ATOM | 945 | C | MET A | 204 | −12.604 | 14.560 | −29.601 | 1.00 | 51.17 | C |
| ATOM | 946 | O | MET A | 204 | −13.332 | 14.781 | −28.637 | 1.00 | 51.72 | O |
| ATOM | 947 | N | PHE A | 205 | −12.735 | 15.207 | −30.759 | 1.00 | 51.02 | N |
| ATOM | 948 | CA | PHE A | 205 | −13.538 | 16.428 | −30.786 | 1.00 | 53.07 | C |
| ATOM | 949 | CB | PHE A | 205 | −13.226 | 17.376 | −31.969 | 1.00 | 53.81 | C |
| ATOM | 950 | CG | PHE A | 205 | −13.092 | 16.713 | −33.316 | 1.00 | 56.95 | C |
| ATOM | 951 | CD1 | PHE A | 205 | −12.056 | 17.104 | −34.176 | 1.00 | 57.47 | C |
| ATOM | 952 | CE1 | PHE A | 205 | −11.912 | 16.539 | −35.440 | 1.00 | 57.35 | C |
| ATOM | 953 | CZ | PHE A | 205 | −12.821 | 15.579 | −35.873 | 1.00 | 60.05 | C |
| ATOM | 954 | CE2 | PHE A | 205 | −13.873 | 15.189 | −35.027 | 1.00 | 65.13 | C |
| ATOM | 955 | CD2 | PHE A | 205 | −14.006 | 15.766 | −33.756 | 1.00 | 55.37 | C |
| ATOM | 956 | C | PHE A | 205 | −15.045 | 16.339 | −30.437 | 1.00 | 53.68 | C |
| ATOM | 957 | O | PHE A | 205 | −15.603 | 17.319 | −29.927 | 1.00 | 54.72 | O |
| ATOM | 958 | N | THR A | 206 | −15.676 | 15.178 | −30.647 | 1.00 | 52.27 | N |
| ATOM | 959 | CA | THR A | 206 | −17.088 | 14.983 | −30.264 | 1.00 | 50.73 | C |
| ATOM | 960 | CB | THR A | 206 | −18.043 | 15.107 | −31.461 | 1.00 | 50.81 | C |
| ATOM | 961 | OG1 | THR A | 206 | −17.703 | 14.123 | −32.438 | 1.00 | 50.42 | O |
| ATOM | 962 | CG2 | THR A | 206 | −17.988 | 16.504 | −32.091 | 1.00 | 53.36 | C |
| ATOM | 963 | C | THR A | 206 | −17.403 | 13.643 | −29.598 | 1.00 | 49.30 | C |
| ATOM | 964 | O | THR A | 206 | −16.757 | 12.615 | −29.871 | 1.00 | 49.29 | O |
| ATOM | 965 | N | TYR A | 207 | −18.407 | 13.673 | −28.720 | 1.00 | 47.75 | N |
| ATOM | 966 | CA | TYR A | 207 | −19.020 | 12.468 | −28.154 | 1.00 | 46.79 | C |
| ATOM | 967 | CB | TYR A | 207 | −20.203 | 12.841 | −27.246 | 1.00 | 45.92 | C |
| ATOM | 968 | CG | TYR A | 207 | −20.846 | 11.637 | −26.607 | 1.00 | 43.99 | C |
| ATOM | 969 | CD1 | TYR A | 207 | −20.381 | 11.143 | −25.383 | 1.00 | 38.99 | C |
| ATOM | 970 | CE1 | TYR A | 207 | −20.956 | 10.009 | −24.802 | 1.00 | 44.09 | C |
| ATOM | 971 | CZ | TYR A | 207 | −22.003 | 9.362 | −25.445 | 1.00 | 41.09 | C |
| ATOM | 972 | OH | TYR A | 207 | −22.561 | 8.238 | −24.867 | 1.00 | 45.16 | O |
| ATOM | 973 | CE2 | TYR A | 207 | −22.489 | 9.837 | −26.663 | 1.00 | 43.17 | C |
| ATOM | 974 | CD2 | TYR A | 207 | −21.905 | 10.967 | −27.239 | 1.00 | 44.01 | C |
| ATOM | 975 | C | TYR A | 207 | −19.491 | 11.517 | −29.261 | 1.00 | 47.72 | C |
| ATOM | 976 | O | TYR A | 207 | −19.426 | 10.302 | −29.114 | 1.00 | 47.73 | O |
| ATOM | 977 | N | GLU A | 208 | −19.965 | 12.094 | −30.363 | 1.00 | 48.44 | N |
| ATOM | 978 | CA | GLU A | 208 | −20.413 | 11.352 | −31.542 | 1.00 | 48.87 | C |
| ATOM | 979 | CB | GLU A | 208 | −20.807 | 12.326 | −32.669 | 1.00 | 47.86 | C |
| ATOM | 980 | CG | GLU A | 208 | −21.258 | 11.659 | −33.971 | 1.00 | 51.74 | C |
| ATOM | 981 | CD | GLU A | 208 | −21.861 | 12.640 | −34.972 | 1.00 | 50.92 | C |
| ATOM | 982 | OE1 | GLU A | 208 | −21.305 | 12.768 | −36.087 | 1.00 | 54.24 | O |
| ATOM | 983 | OE2 | GLU A | 208 | −22.889 | 13.280 | −34.643 | 1.00 | 60.19 | O |
| ATOM | 984 | C | GLU A | 208 | −19.426 | 10.273 | −32.048 | 1.00 | 47.50 | C |
| ATOM | 985 | O | GLU A | 208 | −19.855 | 9.185 | −32.432 | 1.00 | 49.26 | O |
| ATOM | 986 | N | ILE A | 209 | −18.131 | 10.563 | −32.068 | 1.00 | 46.00 | N |
| ATOM | 987 | CA | ILE A | 209 | −17.150 | 9.558 | −32.535 | 1.00 | 44.99 | C |
| ATOM | 988 | CB | ILE A | 209 | −16.358 | 10.001 | −33.813 | 1.00 | 46.01 | C |
| ATOM | 989 | CG1 | ILE A | 209 | −15.171 | 10.925 | −33.466 | 1.00 | 48.22 | C |
| ATOM | 990 | CD | ILE A | 209 | −15.455 | 12.388 | −33.452 | 1.00 | 54.45 | C |
| ATOM | 991 | CG2 | ILE A | 209 | −17.296 | 10.551 | −34.895 | 1.00 | 46.37 | C |
| ATOM | 992 | C | ILE A | 209 | −16.190 | 9.041 | −31.457 | 1.00 | 43.53 | C |
| ATOM | 993 | O | ILE A | 209 | −15.445 | 8.075 | −31.673 | 1.00 | 44.00 | O |
| ATOM | 994 | N | ALA A | 210 | −16.211 | 9.662 | −30.287 | 1.00 | 42.41 | N |
| ATOM | 995 | CA | ALA A | 210 | −15.397 | 9.166 | −29.181 | 1.00 | 41.45 | C |
| ATOM | 996 | CB | ALA A | 210 | −14.160 | 10.036 | −29.024 | 1.00 | 41.28 | C |
| ATOM | 997 | C | ALA A | 210 | −16.199 | 9.103 | −27.882 | 1.00 | 41.19 | C |
| ATOM | 998 | O | ALA A | 210 | −15.806 | 9.710 | −26.886 | 1.00 | 40.72 | O |
| ATOM | 999 | N | PRO A | 211 | −17.347 | 8.381 | −27.892 | 1.00 | 42.60 | N |
| ATOM | 1000 | CA | PRO A | 211 | −18.259 | 8.410 | −26.730 | 1.00 | 43.19 | C |
| ATOM | 1001 | CB | PRO A | 211 | −19.412 | 7.486 | −27.152 | 1.00 | 42.65 | C |
| ATOM | 1002 | CG | PRO A | 211 | −18.848 | 6.641 | −28.241 | 1.00 | 44.87 | C |
| ATOM | 1003 | CD | PRO A | 211 | −17.877 | 7.522 | −28.969 | 1.00 | 41.08 | C |
| ATOM | 1004 | C | PRO A | 211 | −17.637 | 7.973 | −25.393 | 1.00 | 43.66 | C |
| ATOM | 1005 | O | PRO A | 211 | −17.738 | 8.714 | −24.408 | 1.00 | 45.21 | O |
| | | | | gad65.pdb | | | | | | |
| ATOM | 1006 | N | VAL A | 212 | −16.987 | 6.813 | −25.350 | 1.00 | 42.98 | N |
| ATOM | 1007 | CA | VAL A | 212 | −16.294 | 6.396 | −24.121 | 1.00 | 44.04 | C |
| ATOM | 1008 | CB | VAL A | 212 | −15.682 | 4.974 | −24.240 | 1.00 | 43.75 | C |

TABLE A-continued

| | | | | | | | | | |
|---|---|---|---|---|---|---|---|---|---|
| ATOM | 1009 | CG1 | VAL A | 212 | −15.112 | 4.527 | −22.912 | 1.00 | 42.81 | C |
| ATOM | 1010 | CG2 | VAL A | 212 | −16.727 | 3.960 | −24.712 | 1.00 | 49.19 | C |
| ATOM | 1011 | C | VAL A | 212 | −15.181 | 7.395 | −23.727 | 1.00 | 44.59 | C |
| ATOM | 1012 | O | VAL A | 212 | −15.041 | 7.763 | −22.552 | 1.00 | 44.18 | O |
| ATOM | 1013 | N | PHE A | 213 | −14.397 | 7.836 | −24.713 | 1.00 | 44.24 | N |
| ATOM | 1014 | CA | PHE A | 213 | −13.202 | 8.624 | −24.415 | 1.00 | 44.45 | C |
| ATOM | 1015 | CB | PHE A | 213 | −12.257 | 8.678 | −25.614 | 1.00 | 43.97 | C |
| ATOM | 1016 | CG | PHE A | 213 | −11.808 | 7.325 | −26.084 | 1.00 | 43.78 | C |
| ATOM | 1017 | CD1 | PHE A | 213 | −11.291 | 6.399 | −25.179 | 1.00 | 39.40 | C |
| ATOM | 1018 | CE1 | PHE A | 213 | −10.864 | 5.136 | −25.604 | 1.00 | 41.56 | C |
| ATOM | 1019 | CZ | PHE A | 213 | −10.954 | 4.796 | −26.939 | 1.00 | 43.26 | C |
| ATOM | 1020 | CE2 | PHE A | 213 | −11.476 | 5.712 | −27.859 | 1.00 | 43.83 | C |
| ATOM | 1021 | CD2 | PHE A | 213 | −11.896 | 6.975 | −27.427 | 1.00 | 41.41 | C |
| ATOM | 1022 | C | PHE A | 213 | −13.524 | 10.011 | −23.904 | 1.00 | 44.92 | C |
| ATOM | 1023 | O | PHE A | 213 | −12.787 | 10.538 | −23.073 | 1.00 | 45.39 | O |
| ATOM | 1024 | N | VAL A | 214 | −14.625 | 10.597 | −24.383 | 1.00 | 44.92 | N |
| ATOM | 1025 | CA | VAL A | 214 | −15.064 | 11.894 | −23.881 | 1.00 | 45.02 | C |
| ATOM | 1026 | CB | VAL A | 214 | −16.213 | 12.506 | −24.724 | 1.00 | 46.32 | C |
| ATOM | 1027 | CG1 | VAL A | 214 | −16.788 | 13.739 | −24.030 | 1.00 | 49.19 | C |
| ATOM | 1028 | CG2 | VAL A | 214 | −15.726 | 12.876 | −26.118 | 1.00 | 46.03 | C |
| ATOM | 1029 | C | VAL A | 214 | −15.479 | 11.768 | −22.418 | 1.00 | 44.75 | C |
| ATOM | 1030 | O | VAL A | 214 | −15.157 | 12.639 | −21.604 | 1.00 | 44.61 | O |
| ATOM | 1031 | N | LEU A | 215 | −16.183 | 10.680 | −22.088 | 1.00 | 44.77 | N |
| ATOM | 1032 | CA | LEU A | 215 | −16.591 | 10.408 | −20.703 | 1.00 | 44.52 | C |
| ATOM | 1033 | CB | LEU A | 215 | −17.609 | 9.257 | −20.613 | 1.00 | 44.38 | C |
| ATOM | 1034 | CG | LEU A | 215 | −19.020 | 9.391 | −21.212 | 1.00 | 51.83 | C |
| ATOM | 1035 | CD1 | LEU A | 215 | −19.824 | 8.130 | −20.938 | 1.00 | 52.08 | C |
| ATOM | 1036 | CD2 | LEU A | 215 | −19.778 | 10.600 | −20.690 | 1.00 | 53.45 | C |
| ATOM | 1037 | C | LEU A | 215 | −15.393 | 10.148 | −19.773 | 1.00 | 44.04 | C |
| ATOM | 1038 | O | LEU A | 215 | −15.348 | 10.697 | −18.677 | 1.00 | 43.78 | O |
| ATOM | 1039 | N | LEU A | 216 | −14.430 | 9.332 | −20.198 | 1.00 | 43.89 | N |
| ATOM | 1040 | CA | LEU A | 216 | −13.227 | 9.114 | −19.381 | 1.00 | 45.69 | C |
| ATOM | 1041 | CB | LEU A | 216 | −12.276 | 8.079 | −20.009 | 1.00 | 46.11 | C |
| ATOM | 1042 | CG | LEU A | 216 | −12.756 | 6.637 | −20.288 | 1.00 | 47.34 | C |
| ATOM | 1043 | CD1 | LEU A | 216 | −11.574 | 5.714 | −20.586 | 1.00 | 43.64 | C |
| ATOM | 1044 | CD2 | LEU A | 216 | −13.596 | 6.057 | −19.150 | 1.00 | 46.09 | C |
| ATOM | 1045 | C | LEU A | 216 | −12.482 | 10.429 | −19.125 | 1.00 | 46.82 | C |
| ATOM | 1046 | O | LEU A | 216 | −11.943 | 10.653 | −18.036 | 1.00 | 46.75 | O |
| ATOM | 1047 | N | GLU A | 217 | −12.467 | 11.298 | −20.132 | 1.00 | 46.75 | N |
| ATOM | 1048 | CA | GLU A | 217 | −11.786 | 12.580 | −20.023 | 1.00 | 47.03 | C |
| ATOM | 1049 | CB | GLU A | 217 | −11.738 | 13.298 | −21.378 | 1.00 | 45.49 | C |
| ATOM | 1050 | CG | GLU A | 217 | −11.040 | 14.630 | −21.363 | 1.00 | 47.33 | C |
| ATOM | 1051 | CD | GLU A | 217 | −10.538 | 15.075 | −22.739 | 1.00 | 55.50 | C |
| ATOM | 1052 | OE1 | GLU A | 217 | −10.853 | 16.223 | −23.121 | 1.00 | 61.75 | O |
| ATOM | 1053 | OE2 | GLU A | 217 | −9.830 | 14.296 | −23.433 | 1.00 | 53.09 | O |
| ATOM | 1054 | C | GLU A | 217 | −12.477 | 13.418 | −18.955 | 1.00 | 47.61 | C |
| ATOM | 1055 | O | GLU A | 217 | −11.811 | 14.006 | −18.096 | 1.00 | 46.42 | O |
| ATOM | 1056 | N | TYR A | 218 | −13.809 | 13.441 | −18.972 | 1.00 | 48.48 | N |
| ATOM | 1057 | CA | TYR A | 218 | −14.512 | 14.129 | −17.904 | 1.00 | 50.01 | C |
| ATOM | 1058 | CB | TYR A | 218 | −16.025 | 14.215 | −18.113 | 1.00 | 51.12 | C |
| ATOM | 1059 | CG | TYR A | 218 | −16.694 | 14.887 | −16.925 | 1.00 | 57.57 | C |
| ATOM | 1060 | CD1 | TYR A | 218 | −17.313 | 14.134 | −15.923 | 1.00 | 58.78 | C |
| ATOM | 1061 | CE1 | TYR A | 218 | −17.907 | 14.750 | −14.822 | 1.00 | 61.45 | C |
| ATOM | 1062 | CZ | TYR A | 218 | −17.860 | 16.134 | −14.708 | 1.00 | 59.72 | C |
| ATOM | 1063 | OH | TYR A | 218 | −18.434 | 16.762 | −13.625 | 1.00 | 62.48 | O |
| ATOM | 1064 | CE2 | TYR A | 218 | −17.233 | 16.900 | −15.674 | 1.00 | 63.06 | C |
| ATOM | 1065 | CD2 | TYR A | 218 | −16.648 | 16.275 | −16.772 | 1.00 | 63.76 | C |
| ATOM | 1066 | C | TYR A | 218 | −14.179 | 13.558 | −16.509 | 1.00 | 49.62 | C |
| ATOM | 1067 | O | TYR A | 218 | −13.853 | 14.330 | −15.607 | 1.00 | 49.98 | O |
| ATOM | 1068 | N | VAL A | 219 | −14.251 | 12.235 | −16.330 | 1.00 | 48.42 | N |
| ATOM | 1069 | CA | VAL A | 219 | −13.976 | 11.653 | −15.000 | 1.00 | 48.80 | C |
| ATOM | 1070 | CB | VAL A | 219 | −14.501 | 10.167 | −14.794 | 1.00 | 48.94 | C |
| ATOM | 1071 | CG1 | VAL A | 219 | −15.759 | 9.871 | −15.612 | 1.00 | 48.63 | C |
| ATOM | 1072 | CG2 | VAL A | 219 | −13.419 | 9.112 | −15.059 | 1.00 | 51.19 | C |
| ATOM | 1073 | C | VAL A | 219 | −12.507 | 11.769 | −14.551 | 1.00 | 48.27 | C |
| | | | | | gad65.pdb | | | | | |
| ATOM | 1074 | O | VAL A | 219 | −12.229 | 11.959 | −13.361 | 1.00 | 48.92 | O |
| ATOM | 1075 | N | THR A | 220 | −11.574 | 11.645 | −15.488 | 1.00 | 46.81 | N |
| ATOM | 1076 | CA | THR A | 220 | −10.150 | 11.627 | −15.136 | 1.00 | 46.08 | C |
| ATOM | 1077 | CB | THR A | 220 | −9.290 | 11.094 | −16.304 | 1.00 | 45.93 | C |
| ATOM | 1078 | OG1 | THR A | 220 | −9.791 | 9.809 | −16.699 | 1.00 | 46.13 | O |
| ATOM | 1079 | CG2 | THR A | 220 | −7.869 | 10.933 | −15.875 | 1.00 | 43.81 | C |
| ATOM | 1080 | C | THR A | 220 | −9.673 | 13.010 | −14.704 | 1.00 | 44.93 | C |
| ATOM | 1081 | O | THR A | 220 | −8.968 | 13.151 | −13.702 | 1.00 | 44.27 | O |
| ATOM | 1082 | N | LEU A | 221 | −10.092 | 14.022 | −15.462 | 1.00 | 44.59 | N |
| ATOM | 1083 | CA | LEU A | 221 | −9.759 | 15.410 | −15.178 | 1.00 | 44.28 | C |
| ATOM | 1084 | CB | LEU A | 221 | −10.057 | 16.303 | −16.392 | 1.00 | 43.09 | C |
| ATOM | 1085 | CG | LEU A | 221 | −9.171 | 16.100 | −17.621 | 1.00 | 42.88 | C |
| ATOM | 1086 | CD1 | LEU A | 221 | −9.842 | 16.734 | −18.820 | 1.00 | 47.60 | C |
| ATOM | 1087 | CD2 | LEU A | 221 | −7.728 | 16.648 | −17.448 | 1.00 | 39.30 | C |

TABLE A-continued

| | | | | | | | | | | |
|---|---|---|---|---|---|---|---|---|---|---|
| ATOM | 1088 | C | LEU A | 221 | −10.450 | 15.960 | −13.931 | 1.00 | 44.55 | C |
| ATOM | 1089 | O | LEU A | 221 | −9.905 | 16.831 | −13.262 | 1.00 | 44.46 | O |
| ATOM | 1090 | N | LYS A | 222 | −11.647 | 15.464 | −13.631 | 1.00 | 45.51 | N |
| ATOM | 1091 | CA | LYS A | 222 | −12.338 | 15.834 | −12.393 | 1.00 | 46.30 | C |
| ATOM | 1092 | CB | LYS A | 222 | −13.787 | 15.345 | −12.403 | 1.00 | 45.65 | C |
| ATOM | 1093 | CG | LYS A | 222 | −14.651 | 15.983 | −11.314 | 1.00 | 49.93 | C |
| ATOM | 1094 | CD | LYS A | 222 | −15.999 | 15.287 | −11.201 | 1.00 | 53.31 | C |
| ATOM | 1095 | CE | LYS A | 222 | −16.640 | 15.553 | −9.856 | 1.00 | 55.59 | C |
| ATOM | 1096 | NZ | LYS A | 222 | −17.911 | 14.804 | −9.719 | 1.00 | 67.00 | N |
| ATOM | 1097 | C | LYS A | 222 | −11.587 | 15.306 | −11.147 | 1.00 | 45.52 | C |
| ATOM | 1098 | O | LYS A | 222 | −11.330 | 16.059 | −10.203 | 1.00 | 44.22 | O |
| ATOM | 1099 | N | LYS A | 223 | −11.243 | 14.019 | −11.157 | 1.00 | 44.69 | N |
| ATOM | 1100 | CA | LYS A | 223 | −10.433 | 13.431 | −10.097 | 1.00 | 45.06 | C |
| ATOM | 1101 | CB | LYS A | 223 | −10.136 | 11.968 | −10.410 | 1.00 | 45.13 | C |
| ATOM | 1102 | CG | LYS A | 223 | −9.523 | 11.196 | −9.264 | 1.00 | 52.40 | C |
| ATOM | 1103 | CD | LYS A | 223 | −10.579 | 10.594 | −8.362 | 1.00 | 60.42 | C |
| ATOM | 1104 | CE | LYS A | 223 | −9.937 | 9.937 | −7.156 | 1.00 | 64.51 | C |
| ATOM | 1105 | NZ | LYS A | 223 | −10.947 | 9.221 | −6.334 | 1.00 | 68.55 | N |
| ATOM | 1106 | C | LYS A | 223 | −9.126 | 14.216 | −9.891 | 1.00 | 45.39 | C |
| ATOM | 1107 | O | LYS A | 223 | −8.735 | 14.500 | −8.754 | 1.00 | 45.42 | O |
| ATOM | 1108 | N | MET A | 224 | −8.466 | 14.583 | −10.990 | 1.00 | 44.91 | N |
| ATOM | 1109 | CA | MET A | 224 | −7.231 | 15.357 | −10.908 | 1.00 | 45.79 | C |
| ATOM | 1110 | CB | MET A | 224 | −6.591 | 15.512 | −12.301 | 1.00 | 46.11 | C |
| ATOM | 1111 | CG | MET A | 224 | −6.058 | 14.193 | −12.885 | 1.00 | 43.32 | C |
| ATOM | 1112 | SD | MET A | 224 | −5.486 | 14.292 | −14.608 | 1.00 | 49.05 | S |
| ATOM | 1113 | CE | MET A | 224 | −4.018 | 15.314 | −14.399 | 1.00 | 38.39 | C |
| ATOM | 1114 | C | MET A | 224 | −7.482 | 16.715 | −10.227 | 1.00 | 44.86 | C |
| ATOM | 1115 | O | MET A | 224 | −6.683 | 17.172 | −9.407 | 1.00 | 44.22 | O |
| ATOM | 1116 | N | ARG A | 225 | −8.612 | 17.337 | −10.540 | 1.00 | 44.42 | N |
| ATOM | 1117 | CA | ARG A | 225 | −9.020 | 18.566 | −9.853 | 1.00 | 44.48 | C |
| ATOM | 1118 | CB | ARG A | 225 | −10.221 | 19.217 | −10.550 | 1.00 | 43.59 | C |
| ATOM | 1119 | CG | ARG A | 225 | −9.876 | 19.829 | −11.907 | 1.00 | 43.40 | C |
| ATOM | 1120 | CD | ARG A | 225 | −11.005 | 20.707 | −12.464 | 1.00 | 44.34 | C |
| ATOM | 1121 | NE | ARG A | 225 | −12.225 | 19.969 | −12.784 | 1.00 | 42.77 | N |
| ATOM | 1122 | CZ | ARG A | 225 | −12.457 | 19.323 | −13.928 | 1.00 | 41.41 | C |
| ATOM | 1123 | NH1 | ARG A | 225 | −11.547 | 19.274 | −14.894 | 1.00 | 47.09 | N |
| ATOM | 1124 | NH2 | ARG A | 225 | −13.608 | 18.707 | −14.106 | 1.00 | 45.97 | N |
| ATOM | 1125 | C | ARG A | 225 | −9.279 | 18.386 | −8.350 | 1.00 | 45.03 | C |
| ATOM | 1126 | O | ARG A | 225 | −8.994 | 19.284 | −7.562 | 1.00 | 43.87 | O |
| ATOM | 1127 | N | GLU A | 226 | −9.811 | 17.228 | −7.961 | 1.00 | 46.84 | N |
| ATOM | 1128 | CA | GLU A | 226 | −9.953 | 16.871 | −6.536 | 1.00 | 47.93 | C |
| ATOM | 1129 | CB | GLU A | 226 | −10.762 | 15.581 | −6.362 | 1.00 | 46.86 | C |
| ATOM | 1130 | CG | GLU A | 226 | −12.234 | 15.721 | −6.660 | 1.00 | 51.11 | C |
| ATOM | 1131 | CD | GLU A | 226 | −12.977 | 14.383 | −6.631 | 1.00 | 50.56 | C |
| ATOM | 1132 | OE1 | GLU A | 226 | −13.670 | 14.056 | −7.627 | 1.00 | 63.95 | O |
| ATOM | 1133 | OE2 | GLU A | 226 | −12.860 | 13.651 | −5.623 | 1.00 | 52.85 | O |
| ATOM | 1134 | C | GLU A | 226 | −8.591 | 16.714 | −5.856 | 1.00 | 46.85 | C |
| ATOM | 1135 | O | GLU A | 226 | −8.355 | 17.281 | −4.798 | 1.00 | 45.88 | O |
| ATOM | 1136 | N | ILE A | 227 | −7.705 | 15.939 | −6.480 | 1.00 | 47.82 | N |
| ATOM | 1137 | CA | ILE A | 227 | −6.346 | 15.741 | −5.987 | 1.00 | 47.91 | C |
| ATOM | 1138 | CB | ILE A | 227 | −5.519 | 14.822 | −6.945 | 1.00 | 48.99 | C |
| ATOM | 1139 | CG1 | ILE A | 227 | −6.222 | 13.468 | −7.176 | 1.00 | 48.69 | C |
| ATOM | 1140 | CD | ILE A | 227 | −5.562 | 12.273 | −6.516 | 1.00 | 49.40 | C |
| ATOM | 1141 | CG2 | ILE A | 227 | −4.080 | 14.646 | −6.441 | 1.00 | 48.40 | C |
| | | | | gad65.pdb | | | | | | |
| ATOM | 1142 | C | ILE A | 227 | −5.651 | 17.103 | −5.807 | 1.00 | 47.91 | C |
| ATOM | 1143 | O | ILE A | 227 | −4.941 | 17.311 | −4.819 | 1.00 | 48.51 | O |
| ATOM | 1144 | N | ILE A | 228 | −5.864 | 18.020 | −6.756 | 1.00 | 46.55 | N |
| ATOM | 1145 | CA | ILE A | 228 | −5.328 | 19.385 | −6.668 | 1.00 | 47.05 | C |
| ATOM | 1146 | CB | ILE A | 228 | −5.593 | 20.202 | −7.963 | 1.00 | 46.98 | C |
| ATOM | 1147 | CG1 | ILE A | 228 | −4.634 | 19.750 | −9.074 | 1.00 | 48.35 | C |
| ATOM | 1148 | CD | ILE A | 228 | −4.813 | 20.459 | −10.370 | 1.00 | 50.52 | C |
| ATOM | 1149 | CG2 | ILE A | 228 | −5.436 | 21.705 | −7.721 | 1.00 | 45.06 | C |
| ATOM | 1150 | C | ILE A | 228 | −5.865 | 20.118 | −5.435 | 1.00 | 48.91 | C |
| ATOM | 1151 | O | ILE A | 228 | −5.111 | 20.827 | −4.757 | 1.00 | 48.57 | O |
| ATOM | 1152 | N | GLY A | 229 | −7.157 | 19.924 | −5.144 | 1.00 | 49.31 | N |
| ATOM | 1153 | CA | GLY A | 229 | −7.788 | 20.494 | −3.955 | 1.00 | 50.14 | C |
| ATOM | 1154 | C | GLY A | 229 | −8.982 | 21.389 | −4.236 | 1.00 | 51.12 | C |
| ATOM | 1155 | O | GLY A | 229 | −9.529 | 22.009 | −3.320 | 1.00 | 50.98 | O |
| ATOM | 1156 | N | TRP A | 230 | −9.395 | 21.466 | −5.499 | 1.00 | 51.87 | N |
| ATOM | 1157 | CA | TRP A | 230 | −10.562 | 22.269 | −5.853 | 1.00 | 52.18 | C |
| ATOM | 1158 | CB | TRP A | 230 | −10.565 | 22.639 | −7.336 | 1.00 | 50.90 | C |
| ATOM | 1159 | CG | TRP A | 230 | −9.329 | 23.381 | −7.782 | 1.00 | 50.14 | C |
| ATOM | 1160 | CD1 | TRP A | 230 | −8.428 | 24.043 | −6.985 | 1.00 | 51.68 | C |
| ATOM | 1161 | NE1 | TRP A | 230 | −7.436 | 24.609 | −7.754 | 1.00 | 46.99 | N |
| ATOM | 1162 | CE2 | TRP A | 230 | −7.689 | 24.338 | −9.072 | 1.00 | 50.88 | C |
| ATOM | 1163 | CD2 | TRP A | 230 | −8.874 | 23.564 | −9.129 | 1.00 | 50.48 | C |
| ATOM | 1164 | CE3 | TRP A | 230 | −9.348 | 23.147 | −10.380 | 1.00 | 48.99 | C |
| ATOM | 1165 | CZ3 | TRP A | 230 | −8.630 | 23.502 | −11.517 | 1.00 | 47.36 | C |
| ATOM | 1166 | CH2 | TRP A | 230 | −7.460 | 24.273 | −11.427 | 1.00 | 47.29 | C |

TABLE A-continued

| | | | | | | | | | |
|---|---|---|---|---|---|---|---|---|---|
| ATOM | 1167 | CZ2 | TRP A | 230 | −6.973 | 24.699 | −10.220 | 1.00 | 49.34 | C |
| ATOM | 1168 | C | TRP A | 230 | −11.839 | 21.543 | −5.424 | 1.00 | 53.88 | C |
| ATOM | 1169 | O | TRP A | 230 | −12.019 | 20.358 | −5.740 | 1.00 | 54.00 | O |
| ATOM | 1170 | N | PRO A | 231 | −12.726 | 22.254 | −4.693 | 1.00 | 55.09 | N |
| ATOM | 1171 | CA | PRO A | 231 | −13.800 | 21.633 | −3.892 | 1.00 | 55.07 | C |
| ATOM | 1172 | CB | PRO A | 231 | −14.530 | 22.840 | −3.276 | 1.00 | 54.58 | C |
| ATOM | 1173 | CG | PRO A | 231 | −14.191 | 23.988 | −4.154 | 1.00 | 55.15 | C |
| ATOM | 1174 | CD | PRO A | 231 | −12.775 | 23.727 | −4.613 | 1.00 | 55.34 | C |
| ATOM | 1175 | C | PRO A | 231 | −14.756 | 20.792 | −4.719 | 1.00 | 54.82 | C |
| ATOM | 1176 | O | PRO A | 231 | −15.355 | 21.296 | −5.667 | 1.00 | 55.97 | O |
| ATOM | 1177 | N | GLY A | 232 | −14.891 | 19.517 | −4.360 | 1.00 | 54.16 | N |
| ATOM | 1178 | CA | GLY A | 232 | −15.669 | 18.558 | −5.158 | 1.00 | 53.84 | C |
| ATOM | 1179 | C | GLY A | 232 | −15.180 | 18.342 | −6.591 | 1.00 | 53.46 | C |
| ATOM | 1180 | O | GLY A | 232 | −15.919 | 17.818 | −7.433 | 1.00 | 53.76 | O |
| ATOM | 1181 | N | GLY A | 233 | −13.938 | 18.750 | −6.870 | 1.00 | 52.77 | N |
| ATOM | 1182 | CA | GLY A | 233 | −13.336 | 18.602 | −8.198 | 1.00 | 51.45 | C |
| ATOM | 1183 | C | GLY A | 233 | −13.898 | 19.566 | −9.222 | 1.00 | 51.10 | C |
| ATOM | 1184 | O | GLY A | 233 | −13.815 | 19.325 | −10.428 | 1.00 | 51.06 | O |
| ATOM | 1185 | N | SER A | 234 | −14.466 | 20.665 | −8.736 | 1.00 | 50.47 | N |
| ATOM | 1186 | CA | SER A | 234 | −14.991 | 21.719 | −9.592 | 1.00 | 50.99 | C |
| ATOM | 1187 | CB | SER A | 234 | −15.634 | 22.821 | −8.748 | 1.00 | 50.38 | C |
| ATOM | 1188 | OG | SER A | 234 | −16.518 | 22.266 | −7.799 | 1.00 | 60.61 | O |
| ATOM | 1189 | C | SER A | 234 | −13.871 | 22.330 | −10.438 | 1.00 | 50.25 | C |
| ATOM | 1190 | O | SER A | 234 | −12.696 | 22.284 | −10.061 | 1.00 | 48.89 | O |
| ATOM | 1191 | N | GLY A | 235 | −14.264 | 22.919 | −11.562 | 1.00 | 49.57 | N |
| ATOM | 1192 | CA | GLY A | 235 | −13.334 | 23.489 | −12.511 | 1.00 | 49.74 | C |
| ATOM | 1193 | C | GLY A | 235 | −13.483 | 22.860 | −13.880 | 1.00 | 49.93 | C |
| ATOM | 1194 | O | GLY A | 235 | −14.508 | 22.257 | −14.211 | 1.00 | 49.72 | O |
| ATOM | 1195 | N | ASP A | 236 | −12.431 | 22.993 | −14.668 | 1.00 | 49.97 | N |
| ATOM | 1196 | CA | ASP A | 236 | −12.432 | 22.606 | −16.050 | 1.00 | 50.52 | C |
| ATOM | 1197 | CB | ASP A | 236 | −12.601 | 23.874 | −16.874 | 1.00 | 52.31 | C |
| ATOM | 1198 | CG | ASP A | 236 | −13.325 | 23.646 | −18.164 | 1.00 | 60.14 | C |
| ATOM | 1199 | OD1 | ASP A | 236 | −13.404 | 22.482 | −18.636 | 1.00 | 66.87 | O |
| ATOM | 1200 | OD2 | ASP A | 236 | −13.819 | 24.659 | −18.707 | 1.00 | 69.05 | O |
| ATOM | 1201 | C | ASP A | 236 | −11.072 | 21.986 | −16.341 | 1.00 | 50.32 | C |
| ATOM | 1202 | O | ASP A | 236 | −10.162 | 22.049 | −15.510 | 1.00 | 49.59 | O |
| ATOM | 1203 | N | GLY A | 237 | −10.930 | 21.387 | −17.517 | 1.00 | 50.34 | N |
| ATOM | 1204 | CA | GLY A | 237 | −9.677 | 20.755 | −17.891 | 1.00 | 50.19 | C |
| ATOM | 1205 | C | GLY A | 237 | −9.649 | 20.309 | −19.335 | 1.00 | 50.14 | C |
| ATOM | 1206 | O | GLY A | 237 | −10.694 | 20.161 | −19.976 | 1.00 | 49.26 | O |
| ATOM | 1207 | N | ILE A | 238 | −8.432 | 20.105 | −19.832 | 1.00 | 49.73 | N |
| ATOM | 1208 | CA | ILE A | 238 | −8.180 | 19.565 | −21.159 | 1.00 | 49.43 | C |
| ATOM | 1209 | CB | ILE A | 238 | −8.189 | 20.692 | −22.276 | 1.00 | 50.37 | C |
| | | | | | gad65.pdb | | | | | |
| ATOM | 1210 | CG1 | ILE A | 238 | −8.373 | 20.100 | −23.686 | 1.00 | 53.15 | C |
| ATOM | 1211 | cD | ILE A | 238 | −9.789 | 19.757 | −24.064 | 1.00 | 60.28 | C |
| ATOM | 1212 | CG2 | ILE A | 238 | −6.923 | 21.571 | −22.225 | 1.00 | 47.24 | C |
| ATOM | 1213 | C | ILE A | 238 | −6.860 | 18.780 | −21.133 | 1.00 | 48.95 | C |
| ATOM | 1214 | O | ILE A | 238 | −5.970 | 19.047 | −20.319 | 1.00 | 49.46 | O |
| ATOM | 1215 | N | PHE A | 239 | −6.756 | 17.774 | −21.986 | 1.00 | 48.51 | N |
| ATOM | 1216 | CA | PHE A | 239 | −5.464 | 17.183 | −22.269 | 1.00 | 47.90 | C |
| ATOM | 1217 | CB | PHE A | 239 | −5.587 | 15.693 | −22.578 | 1.00 | 47.31 | C |
| ATOM | 1218 | CG | PHE A | 239 | −5.791 | 14.844 | −21.360 | 1.00 | 48.53 | C |
| ATOM | 1219 | CD1 | PHE A | 239 | −7.074 | 14.439 | −20.986 | 1.00 | 48.18 | C |
| ATOM | 1220 | CE1 | PHE A | 239 | −7.273 | 13.660 | −19.845 | 1.00 | 46.03 | C |
| ATOM | 1221 | CZ | PHE A | 239 | −6.179 | 13.285 | −19.060 | 1.00 | 46.49 | C |
| ATOM | 1222 | CE2 | PHE A | 239 | −4.891 | 13.690 | −19.426 | 1.00 | 48.00 | C |
| ATOM | 1223 | CD2 | PHE A | 239 | −4.704 | 14.462 | −20.569 | 1.00 | 46.76 | C |
| ATOM | 1224 | C | PHE A | 239 | −4.863 | 17.962 | −23.427 | 1.00 | 47.07 | C |
| ATOM | 1225 | O | PHE A | 239 | −5.561 | 18.301 | −24.380 | 1.00 | 47.40 | O |
| ATOM | 1226 | N | SER A | 240 | −3.586 | 18.295 | −23.309 | 1.00 | 47.12 | N |
| ATOM | 1227 | CA | SER A | 240 | −2.856 | 18.983 | −24.380 | 1.00 | 47.37 | C |
| ATOM | 1228 | CB | SER A | 240 | −2.376 | 20.353 | −23.898 | 1.00 | 47.01 | C |
| ATOM | 1229 | OG | SER A | 240 | −1.283 | 20.220 | −23.008 | 1.00 | 58.27 | O |
| ATOM | 1230 | C | SER A | 240 | −1.686 | 18.137 | −24.934 | 1.00 | 46.00 | C |
| ATOM | 1231 | O | SER A | 240 | −1.278 | 17.156 | −24.312 | 1.00 | 45.92 | O |
| ATOM | 1232 | N | PRO A | 241 | −1.166 | 18.493 | −26.123 | 1.00 | 46.06 | N |
| ATOM | 1233 | CA | PRO A | 241 | −.021 | 17.764 | −26.664 | 1.00 | 46.78 | C |
| ATOM | 1234 | CB | PRO A | 241 | −.134 | 18.021 | −28.161 | 1.00 | 46.76 | C |
| ATOM | 1235 | CG | PRO A | 241 | −.742 | 19.395 | −28.247 | 1.00 | 50.07 | C |
| ATOM | 1236 | CD | PRO A | 241 | −1.617 | 19.565 | −27.031 | 1.00 | 46.31 | C |
| ATOM | 1237 | C | PRO A | 241 | 1.314 | 18.293 | −26.095 | 1.00 | 46.85 | C |
| ATOM | 1238 | O | PRO A | 241 | 2.161 | 18.853 | −26.827 | 1.00 | 47.85 | O |
| ATOM | 1239 | N | GLY A | 242 | 1.479 | 18.118 | −24.791 | 1.00 | 44.24 | N |
| ATOM | 1240 | CA | GLY A | 242 | 2.673 | 18.573 | −24.085 | 1.00 | 43.00 | C |
| ATOM | 1241 | C | GLY A | 242 | 2.324 | 19.618 | −23.057 | 1.00 | 41.57 | C |
| ATOM | 1242 | O | GLY A | 242 | 1.435 | 20.441 | −23.272 | 1.00 | 42.68 | O |
| ATOM | 1243 | N | GLY A | 243 | 3.030 | 19.588 | −21.938 | 1.00 | 41.33 | N |
| ATOM | 1244 | CA | GLY A | 243 | 2.911 | 20.627 | −20.929 | 1.00 | 42.37 | C |
| ATOM | 1245 | C | GLY A | 243 | 3.375 | 21.987 | −21.410 | 1.00 | 43.08 | C |

TABLE A-continued

| | | | | | | | | | | |
|---|---|---|---|---|---|---|---|---|---|---|
| ATOM | 1246 | O | GLY A | 243 | 2.964 | 23.005 | −20.856 | 1.00 | 43.95 | O |
| ATOM | 1247 | N | ALA A | 244 | 4.245 | 22.021 | −22.418 | 1.00 | 42.86 | N |
| ATOM | 1248 | CA | ALA A | 244 | 4.628 | 23.308 | −23.019 | 1.00 | 44.21 | C |
| ATOM | 1249 | CB | ALA A | 244 | 5.756 | 23.143 | −24.049 | 1.00 | 42.46 | C |
| ATOM | 1250 | C | ALA A | 244 | 3.425 | 24.027 | −23.643 | 1.00 | 44.45 | C |
| ATOM | 1251 | O | ALA A | 244 | 3.318 | 25.242 | −23.545 | 1.00 | 44.53 | O |
| ATOM | 1252 | N | ILE A | 245 | 2.525 | 23.262 | −24.263 | 1.00 | 44.92 | N |
| ATOM | 1253 | CA | ILE A | 245 | 1.311 | 23.805 | −24.855 | 1.00 | 45.58 | C |
| ATOM | 1254 | CB | ILE A | 245 | .757 | 22.850 | −25.954 | 1.00 | 45.84 | C |
| ATOM | 1255 | CG1 | ILE A | 245 | 1.849 | 22.499 | −26.977 | 1.00 | 48.83 | C |
| ATOM | 1256 | CD | ILE A | 245 | 2.545 | 23.688 | −27.664 | 1.00 | 45.67 | C |
| ATOM | 1257 | CG2 | ILE A | 245 | −.490 | 23.421 | −26.637 | 1.00 | 41.47 | C |
| ATOM | 1258 | C | ILE A | 245 | .255 | 24.108 | −23.774 | 1.00 | 47.22 | C |
| ATOM | 1259 | O | ILE A | 245 | −.503 | 25.082 | −23.902 | 1.00 | 47.26 | O |
| ATOM | 1260 | N | SER A | 246 | .213 | 23.271 | −22.724 | 1.00 | 48.30 | N |
| ATOM | 1261 | CA | SER A | 246 | −.605 | 23.524 | −21.531 | 1.00 | 48.84 | C |
| ATOM | 1262 | CB | SER A | 246 | −.457 | 22.414 | −20.487 | 1.00 | 48.41 | C |
| ATOM | 1263 | OG | SER A | 246 | −1.135 | 21.236 | −20.863 | 1.00 | 52.24 | O |
| ATOM | 1264 | C | SER A | 246 | −.204 | 24.855 | −20.898 | 1.00 | 49.02 | C |
| ATOM | 1265 | O | SER A | 246 | −1.067 | 25.668 | −20.551 | 1.00 | 48.98 | O |
| ATOM | 1266 | N | ASN A | 247 | 1.104 | 25.073 | −20.745 | 1.00 | 48.81 | N |
| ATOM | 1267 | CA | ASN A | 247 | 1.589 | 26.380 | −20.312 | 1.00 | 48.99 | C |
| ATOM | 1268 | CB | ASN A | 247 | 3.114 | 26.432 | −20.165 | 1.00 | 47.63 | C |
| ATOM | 1269 | CG | ASN A | 247 | 3.638 | 25.600 | −19.007 | 1.00 | 45.44 | C |
| ATOM | 1270 | CD1 | ASN A | 247 | 4.787 | 25.154 | −19.043 | 1.00 | 53.29 | O |
| ATOM | 1271 | ND2 | ASN A | 247 | 2.822 | 25.388 | −17.985 | 1.00 | 39.37 | N |
| ATOM | 1272 | C | ASN A | 247 | 1.126 | 27.471 | −21.273 | 1.00 | 49.00 | C |
| ATOM | 1273 | O | ASN A | 247 | .676 | 28.522 | −20.838 | 1.00 | 50.80 | O |
| ATOM | 1274 | N | MET A | 248 | 1.228 | 27.219 | −22.570 | 1.00 | 48.75 | N |
| ATOM | 1275 | CA | MET A | 248 | .792 | 28.206 | −23.556 | 1.00 | 50.68 | C |
| ATOM | 1276 | CB | MET A | 248 | 1.135 | 27.758 | −24.978 | 1.00 | 50.17 | C |
| ATOM | 1277 | CG | MET A | 248 | .932 | 28.845 | −26.016 | 1.00 | 49.38 | C | gad65.pdb

| | | | | | | | | | | |
|---|---|---|---|---|---|---|---|---|---|---|
| ATOM | 1278 | SD | MET A | 248 | 1.103 | 28.246 | −27.704 | 1.00 | 56.31 | S |
| ATOM | 1279 | CE | MET A | 248 | −.377 | 27.252 | −27.847 | 1.00 | 57.11 | C |
| ATOM | 1280 | C | MET A | 248 | −.703 | 28.525 | −23.438 | 1.00 | 48.45 | C |
| ATOM | 1281 | O | MET A | 248 | −1.086 | 29.684 | −23.521 | 1.00 | 48.23 | O |
| ATOM | 1282 | N | TYR A | 249 | −1.525 | 27.490 | −23.246 | 1.00 | 47.26 | N |
| ATOM | 1283 | CA | TYR A | 249 | −2.969 | 27.644 | −23.013 | 1.00 | 45.79 | C |
| ATOM | 1284 | CB | TYR A | 249 | −3.656 | 26.286 | −22.857 | 1.00 | 46.30 | C |
| ATOM | 1285 | CG | TYR A | 249 | −3.750 | 25.438 | −24.095 | 1.00 | 49.26 | C |
| ATOM | 1286 | CD1 | TYR A | 249 | −3.650 | 25.998 | −25.365 | 1.00 | 56.70 | C |
| ATOM | 1287 | CE1 | TYR A | 249 | −3.762 | 25.212 | −26.514 | 1.00 | 60.10 | C |
| ATOM | 1288 | CZ | TYR A | 249 | −3.999 | 23.845 | −26.394 | 1.00 | 54.66 | C |
| ATOM | 1289 | OH | TYR A | 249 | −4.100 | 23.079 | −27.524 | 1.00 | 55.70 | O |
| ATOM | 1290 | CE2 | TYR A | 249 | −4.105 | 23.257 | −25.146 | 1.00 | 52.65 | C |
| ATOM | 1291 | CD2 | TYR A | 249 | −3.987 | 24.064 | −23.995 | 1.00 | 53.14 | C |
| ATOM | 1292 | C | TYR A | 249 | −3.286 | 28.472 | −21.768 | 1.00 | 44.00 | C |
| ATOM | 1293 | O | TYR A | 249 | −4.153 | 29.337 | −21.811 | 1.00 | 42.30 | O |
| ATOM | 1294 | N | ALA A | 250 | −2.599 | 28.187 | −20.662 | 1.00 | 44.33 | N |
| ATOM | 1295 | CA | ALA A | 250 | −2.802 | 28.930 | −19.415 | 1.00 | 45.26 | C |
| ATOM | 1296 | CB | ALA A | 250 | −1.887 | 28.386 | −18.304 | 1.00 | 43.76 | C |
| ATOM | 1297 | C | ALA A | 250 | −2.580 | 30.439 | −19.619 | 1.00 | 46.62 | C |
| ATOM | 1298 | O | ALA A | 250 | −3.381 | 31.266 | −19.175 | 1.00 | 46.09 | O |
| ATOM | 1299 | N | MET A | 251 | −1.501 | 30.777 | −20.319 | 1.00 | 47.97 | N |
| ATOM | 1300 | CA | MET A | 251 | −1.173 | 32.164 | −20.641 | 1.00 | 50.18 | C |
| ATOM | 1301 | CB | MET A | 251 | .205 | 32.211 | −21.301 | 1.00 | 50.18 | C |
| ATOM | 1302 | CG | MET A | 251 | .830 | 33.579 | −21.388 | 1.00 | 52.67 | C |
| ATOM | 1303 | SD | MET A | 251 | 2.515 | 33.482 | −22.032 | 1.00 | 54.71 | S |
| ATOM | 1304 | CE | MET A | 251 | 3.467 | 33.207 | −20.542 | 1.00 | 53.52 | C |
| ATOM | 1305 | C | MET A | 251 | −2.222 | 32.803 | −21.557 | 1.00 | 48.69 | C |
| ATOM | 1306 | O | MET A | 251 | −2.583 | 33.968 | −21.379 | 1.00 | 48.00 | O |
| ATOM | 1307 | N | MET A | 252 | −2.682 | 32.047 | −22.553 | 1.00 | 48.40 | N |
| ATOM | 1308 | CA | MET A | 252 | −3.774 | 32.491 | −23.420 | 1.00 | 49.08 | C |
| ATOM | 1309 | CB | MET A | 252 | −4.184 | 31.372 | −24.364 | 1.00 | 49.14 | C |
| ATOM | 1310 | CG | MET A | 252 | −3.570 | 31.454 | −25.711 | 1.00 | 53.56 | C |
| ATOM | 1311 | SD | MET A | 252 | −4.280 | 30.227 | −26.803 | 1.00 | 52.73 | S |
| ATOM | 1312 | CE | MET A | 252 | −5.951 | 30.831 | −26.946 | 1.00 | 47.45 | C |
| ATOM | 1313 | C | MET A | 252 | −4.992 | 32.878 | −22.601 | 1.00 | 47.17 | C |
| ATOM | 1314 | O | MET A | 252 | −5.551 | 33.958 | −22.787 | 1.00 | 46.49 | O |
| ATOM | 1315 | N | ILE A | 253 | −5.375 | 31.978 | −21.695 | 1.00 | 45.65 | N |
| ATOM | 1316 | CA | ILE A | 253 | −6.579 | 32.100 | −20.887 | 1.00 | 46.89 | C |
| ATOM | 1317 | CB | ILE A | 253 | −6.959 | 30.711 | −20.278 | 1.00 | 47.64 | C |
| ATOM | 1318 | CG1 | ILE A | 253 | −7.409 | 29.763 | −21.401 | 1.00 | 47.17 | C |
| ATOM | 1319 | CD | ILE A | 253 | −7.129 | 28.274 | −21.109 | 1.00 | 50.12 | C |
| ATOM | 1320 | CG2 | ILE A | 253 | −8.063 | 30.842 | −19.236 | 1.00 | 49.30 | C |
| ATOM | 1321 | C | ILE A | 253 | −6.484 | 33.190 | −19.805 | 1.00 | 46.00 | C |
| ATOM | 1322 | O | ILE A | 253 | −7.460 | 33.885 | −19.550 | 1.00 | 46.54 | O |
| ATOM | 1323 | N | ALA A | 254 | −5.318 | 33.333 | −19.174 | 1.00 | 44.28 | N |
| ATOM | 1324 | CA | ALA A | 254 | −5.082 | 34.436 | −18.230 | 1.00 | 43.36 | C |

TABLE A-continued

| | | | | | | | | | | |
|---|---|---|---|---|---|---|---|---|---|---|
| ATOM | 1325 | CB | ALA A | 254 | −3.708 | 34.314 | −17.600 | 1.00 | 43.55 | C |
| ATOM | 1326 | C | ALA A | 254 | −5.229 | 35.791 | −18.917 | 1.00 | 42.73 | C |
| ATOM | 1327 | O | ALA A | 254 | −5.795 | 36.726 | −18.341 | 1.00 | 43.30 | O |
| ATOM | 1328 | N | ARG A | 255 | −4.722 | 35.891 | −20.146 | 1.00 | 41.37 | N |
| ATOM | 1329 | CA | ARG A | 255 | −4.880 | 37.100 | −20.951 | 1.00 | 42.24 | C |
| ATOM | 1330 | CB | ARG A | 255 | −4.021 | 37.047 | −22.211 | 1.00 | 43.13 | C |
| ATOM | 1331 | CG | ARG A | 255 | −4.195 | 38.262 | −23.122 | 1.00 | 43.71 | C |
| ATOM | 1332 | CD | ARG A | 255 | −3.316 | 38.154 | −24.353 | 1.00 | 45.99 | C |
| ATOM | 1333 | NE | ARG A | 255 | −3.668 | 37.012 | −25.201 | 1.00 | 48.92 | N |
| ATOM | 1334 | CZ | ARG A | 255 | −2.984 | 36.644 | −26.280 | 1.00 | 45.12 | C |
| ATOM | 1335 | NH1 | ARG A | 255 | −1.904 | 37.322 | −26.651 | 1.00 | 41.51 | N |
| ATOM | 1336 | NH2 | ARG A | 255 | −3.382 | 35.599 | −26.985 | 1.00 | 44.30 | N |
| ATOM | 1337 | C | ARG A | 255 | −6.341 | 37.332 | −21.334 | 1.00 | 42.22 | C |
| ATOM | 1338 | O | ARG A | 255 | −6.874 | 38.424 | −21.132 | 1.00 | 41.46 | O |
| ATOM | 1339 | N | PHE A | 256 | −6.982 | 36.305 | −21.885 | 1.00 | 42.47 | N |
| ATOM | 1340 | CA | PHE A | 256 | −8.366 | 36.424 | −22.266 | 1.00 | 43.49 | C |
| ATOM | 1341 | CB | PHE A | 256 | −8.892 | 35.137 | −22.892 | 1.00 | 43.16 | C |
| ATOM | 1342 | CG | PHE A | 256 | −10.365 | 35.181 | −23.203 | 1.00 | 43.83 | C |
| ATOM | 1343 | CD1 | PHE A | 256 | −10.827 | 35.813 | −24.349 | 1.00 | 41.98 | C |
| ATOM | 1344 | CE1 | PHE A | 256 | −12.188 | 35.866 | −24.631 | 1.00 | 45.42 | C |
| ATOM | 1345 | CZ | PHE A | 256 | −13.099 | 35.284 | −23.758 | 1.00 | 41.79 | C |
| | | | gad65.pdb | | | | | | | |
| ATOM | 1346 | CE2 | PHE A | 256 | −12.648 | 34.648 | −22.607 | 1.00 | 45.11 | C |
| ATOM | 1347 | CD2 | PHE A | 256 | −11.290 | 34.598 | −22.336 | 1.00 | 47.94 | C |
| ATOM | 1348 | C | PHE A | 256 | −9.221 | 36.847 | −21.071 | 1.00 | 44.55 | C |
| ATOM | 1349 | O | PHE A | 256 | −10.139 | 37.639 | −21.226 | 1.00 | 44.02 | O |
| ATOM | 1350 | N | LYS A | 257 | −8.897 | 36.339 | −19.885 | 1.00 | 46.16 | N |
| ATOM | 1351 | CA | LYS A | 257 | −9.691 | 36.627 | −18.686 | 1.00 | 47.91 | C |
| ATOM | 1352 | CB | LYS A | 257 | −9.277 | 35.717 | −17.513 | 1.00 | 47.38 | C |
| ATOM | 1353 | CG | LYS A | 257 | −9.945 | 36.040 | −16.173 | 1.00 | 49.52 | C |
| ATOM | 1354 | CD | LYS A | 257 | −11.455 | 35.754 | −16.178 | 1.00 | 44.56 | C |
| ATOM | 1355 | CE | LYS A | 257 | −12.101 | 36.259 | −14.888 | 1.00 | 51.98 | C |
| ATOM | 1356 | NZ | LYS A | 257 | −13.531 | 35.843 | −14.755 | 1.00 | 58.95 | N |
| ATOM | 1357 | C | LYS A | 257 | −9.639 | 38.124 | −18.323 | 1.00 | 49.36 | C |
| ATOM | 1358 | O | LYS A | 257 | −10.680 | 38.747 | −18.029 | 1.00 | 48.20 | O |
| ATOM | 1359 | N | MET A | 258 | −8.439 | 38.701 | −18.400 | 1.00 | 50.15 | N |
| ATOM | 1360 | CA | MET A | 258 | −8.240 | 40.122 | −18.119 | 1.00 | 50.94 | C |
| ATOM | 1361 | CB | MET A | 258 | −6.792 | 40.388 | −17.721 | 1.00 | 49.75 | C |
| ATOM | 1362 | CG | MET A | 258 | −6.616 | 41.574 | −16.791 | 1.00 | 54.78 | C |
| ATOM | 1363 | SD | MET A | 258 | −4.964 | 41.623 | −16.050 | 1.00 | 56.68 | S |
| ATOM | 1364 | CE | MET A | 258 | −5.108 | 40.360 | −14.781 | 1.00 | 56.32 | C |
| ATOM | 1365 | C | MET A | 258 | −8.669 | 41.042 | −19.270 | 1.00 | 48.95 | C |
| ATOM | 1366 | O | MET A | 258 | −9.136 | 42.152 | −19.031 | 1.00 | 49.36 | O |
| ATOM | 1367 | N | PHE A | 259 | −8.526 | 40.578 | −20.508 | 1.00 | 47.12 | N |
| ATOM | 1368 | CA | PHE A | 259 | −8.858 | 41.382 | −21.680 | 1.00 | 45.97 | C |
| ATOM | 1369 | CB | PHE A | 259 | −7.593 | 42.050 | −22.252 | 1.00 | 46.07 | C |
| ATOM | 1370 | CG | PHE A | 259 | −6.898 | 42.973 | −21.283 | 1.00 | 47.12 | C |
| ATOM | 1371 | CD1 | PHE A | 259 | −7.420 | 44.243 | −21.005 | 1.00 | 47.07 | C |
| ATOM | 1372 | CE1 | PHE A | 259 | −6.779 | 45.104 | −20.099 | 1.00 | 45.58 | C |
| ATOM | 1373 | CZ | PHE A | 259 | −5.597 | 44.695 | −19.465 | 1.00 | 45.62 | C |
| ATOM | 1374 | CE2 | PHE A | 259 | −5.069 | 43.434 | −19.728 | 1.00 | 46.34 | C |
| ATOM | 1375 | CD2 | PHE A | 259 | −5.723 | 42.572 | −20.637 | 1.00 | 47.24 | C |
| ATOM | 1376 | C | PHE A | 259 | −9.562 | 40.551 | −22.763 | 1.00 | 46.38 | C |
| ATOM | 1377 | O | PHE A | 259 | −8.946 | 40.192 | −23.774 | 1.00 | 46.38 | O |
| ATOM | 1378 | N | PRO A | 260 | −10.863 | 40.242 | −22.563 | 1.00 | 46.48 | N |
| ATOM | 1379 | CA | PRO A | 260 | −11.532 | 39.376 | −23.538 | 1.00 | 46.21 | C |
| ATOM | 1380 | CB | PRO A | 260 | −12.967 | 39.245 | −22.994 | 1.00 | 46.65 | C |
| ATOM | 1381 | CG | PRO A | 260 | −13.127 | 40.330 | −21.969 | 1.00 | 46.40 | C |
| ATOM | 1382 | CD | PRO A | 260 | −11.755 | 40.641 | −21.451 | 1.00 | 46.52 | C |
| ATOM | 1383 | C | PRO A | 260 | −11.512 | 39.920 | −24.974 | 1.00 | 46.62 | C |
| ATOM | 1384 | O | PRO A | 260 | −11.594 | 39.141 | −25.922 | 1.00 | 47.32 | O |
| ATOM | 1385 | N | GLU A | 261 | −11.374 | 41.240 | −25.120 | 1.00 | 46.13 | N |
| ATOM | 1386 | CA | GLU A | 261 | −11.278 | 41.894 | −26.429 | 1.00 | 45.36 | C |
| ATOM | 1387 | CB | GLU A | 261 | −11.382 | 43.423 | −26.278 | 1.00 | 45.27 | C |
| ATOM | 1388 | CG | GLU A | 261 | −10.185 | 44.112 | −25.581 | 1.00 | 48.66 | C |
| ATOM | 1389 | CD | GLU A | 261 | −10.235 | 44.058 | −24.045 | 1.00 | 52.44 | C |
| ATOM | 1390 | OE1 | GLU A | 261 | −11.019 | 43.282 | −23.452 | 1.00 | 50.99 | O |
| ATOM | 1391 | OE2 | GLU A | 261 | −9.467 | 44.810 | −23.418 | 1.00 | 60.39 | O |
| ATOM | 1392 | C | GLU A | 261 | −10.043 | 41.506 | −27.286 | 1.00 | 44.63 | C |
| ATOM | 1393 | O | GLU A | 261 | −10.062 | 41.693 | −28.509 | 1.00 | 42.78 | O |
| ATOM | 1394 | N | VAL A | 262 | −8.988 | 40.980 | −26.655 | 1.00 | 44.25 | N |
| ATOM | 1395 | CA | VAL A | 262 | −7.778 | 40.565 | −27.395 | 1.00 | 45.10 | C |
| ATOM | 1396 | CB | VAL A | 262 | −6.680 | 39.974 | −26.469 | 1.00 | 45.21 | C |
| ATOM | 1397 | CG1 | VAL A | 262 | −7.086 | 38.603 | −25.906 | 1.00 | 38.83 | C |
| ATOM | 1398 | CG2 | VAL A | 262 | −5.349 | 39.896 | −27.213 | 1.00 | 42.14 | C |
| ATOM | 1399 | C | VAL A | 262 | −8.099 | 39.593 | −28.538 | 1.00 | 44.67 | C |
| ATOM | 1400 | O | VAL A | 262 | −7.492 | 39.640 | −29.591 | 1.00 | 43.41 | O |
| ATOM | 1401 | N | LYS A | 263 | −9.104 | 38.760 | −28.311 | 1.00 | 45.89 | N |
| ATOM | 1402 | CA | LYS A | 263 | −9.544 | 37.739 | −29.244 | 1.00 | 46.59 | C |
| ATOM | 1403 | CB | LYS A | 263 | −10.745 | 37.023 | −28.628 | 1.00 | 46.69 | C |

TABLE A-continued

| | | | | | | | | | |
|---|---|---|---|---|---|---|---|---|---|
| ATOM | 1404 | CG | LYS A | 263 | −11.123 | 35.711 | −29.278 | 1.00 | 45.23 | C |
| ATOM | 1405 | CD | LYS A | 263 | −12.225 | 35.061 | −28.477 | 1.00 | 45.22 | C |
| ATOM | 1406 | CE | LYS A | 263 | −12.919 | 34.005 | −29.286 | 1.00 | 51.40 | C |
| ATOM | 1407 | NZ | LYS A | 263 | −13.794 | 33.153 | −28.431 | 1.00 | 54.34 | N |
| ATOM | 1408 | C | LYS A | 263 | −9.919 | 38.335 | −30.595 | 1.00 | 46.39 | C |
| ATOM | 1409 | O | LYS A | 263 | −9.553 | 37.798 | −31.649 | 1.00 | 46.89 | O |
| ATOM | 1410 | N | GLU A | 264 | −10.644 | 39.450 | −30.551 | 1.00 | 45.08 | N |
| ATOM | 1411 | CA | GLU A | 264 | −11.101 | 40.132 | −31.750 | 1.00 | 44.23 | C |
| ATOM | 1412 | CB | GLU A | 264 | −12.452 | 40.813 | −31.469 | 1.00 | 44.39 | C |
| ATOM | 1413 | CG | GLU A | 264 | −13.643 | 39.842 | −31.363 | 1.00 | 50.00 | C |
| ATOM | 1414 | CD | GLU A | 264 | −13.805 | 39.230 | −29.967 | 1.00 | 60.15 | C |
| ATOM | 1415 | OE1 | GLU A | 264 | −13.189 | 39.735 | −28.997 | 1.00 | 59.33 | O |
| ATOM | 1416 | OE2 | GLU A | 264 | −14.561 | 38.241 | −29.839 | 1.00 | 61.19 | O |
| ATOM | 1417 | C | GLU A | 264 | −10.081 | 41.170 | −32.239 | 1.00 | 43.49 | C |
| ATOM | 1418 | O | GLU A | 264 | −9.847 | 41.307 | −33.443 | 1.00 | 42.78 | O |
| ATOM | 1419 | N | LYS A | 265 | −9.469 | 41.883 | −31.299 | 1.00 | 42.86 | N |
| ATOM | 1420 | CA | LYS A | 265 | −8.706 | 43.075 | −31.623 | 1.00 | 45.38 | C |
| ATOM | 1421 | CB | LYS A | 265 | −9.098 | 44.215 | −30.682 | 1.00 | 45.50 | C |
| ATOM | 1422 | CG | LYS A | 265 | −10.557 | 44.624 | −30.816 | 1.00 | 54.38 | C |
| ATOM | 1423 | CD | LYS A | 265 | −10.930 | 45.730 | −29.849 | 1.00 | 63.47 | C |
| ATOM | 1424 | CE | LYS A | 265 | −12.159 | 46.481 | −30.340 | 1.00 | 67.77 | C |
| ATOM | 1425 | NZ | LYS A | 265 | −11.834 | 47.382 | −31.497 | 1.00 | 70.72 | N |
| ATOM | 1426 | C | LYS A | 265 | −7.188 | 42.883 | −31.620 | 1.00 | 46.56 | C |
| ATOM | 1427 | O | LYS A | 265 | −6.465 | 43.684 | −32.224 | 1.00 | 46.61 | O |
| ATOM | 1428 | N | GLY A | 266 | −6.714 | 41.835 | −30.948 | 1.00 | 47.13 | N |
| ATOM | 1429 | CA | GLY A | 266 | −5.280 | 41.563 | −30.864 | 1.00 | 48.01 | C |
| ATOM | 1430 | C | GLY A | 266 | −4.604 | 42.352 | −29.759 | 1.00 | 49.54 | C |
| ATOM | 1431 | O | GLY A | 266 | −5.243 | 43.178 | −29.081 | 1.00 | 49.84 | O |
| ATOM | 1432 | N | MET A | 267 | −3.309 | 42.096 | −29.579 | 1.00 | 49.85 | N |
| ATOM | 1433 | CA | MET A | 267 | −2.505 | 42.729 | −28.525 | 1.00 | 49.92 | C |
| ATOM | 1434 | CB | MET A | 267 | −1.107 | 42.105 | −28.466 | 1.00 | 50.21 | C |
| ATOM | 1435 | CG | MET A | 267 | −1.058 | 40.738 | −27.834 | 1.00 | 46.09 | C |
| ATOM | 1436 | SD | MET A | 267 | −1.377 | 40.699 | −26.063 | 1.00 | 45.66 | S |
| ATOM | 1437 | CE | MET A | 267 | −.194 | 41.889 | −25.417 | 1.00 | 40.94 | C |
| ATOM | 1438 | C | MET A | 267 | −2.374 | 44.246 | −28.656 | 1.00 | 49.98 | C |
| ATOM | 1439 | O | MET A | 267 | −2.101 | 44.926 | −27.667 | 1.00 | 50.38 | O |
| ATOM | 1440 | N | ALA A | 268 | −2.567 | 44.773 | −29.866 | 1.00 | 49.89 | N |
| ATOM | 1441 | CA | ALA A | 268 | −2.515 | 46.222 | −30.103 | 1.00 | 50.50 | C |
| ATOM | 1442 | CB | ALA A | 268 | −2.630 | 46.524 | −31.580 | 1.00 | 51.08 | C |
| ATOM | 1443 | C | ALA A | 268 | −3.591 | 46.989 | −29.338 | 1.00 | 51.65 | C |
| ATOM | 1444 | O | ALA A | 268 | −3.454 | 48.199 | −29.120 | 1.00 | 53.05 | O |
| ATOM | 1445 | N | ALA A | 269 | −4.656 | 46.290 | −28.945 | 1.00 | 50.47 | N |
| ATOM | 1446 | CA | ALA A | 269 | −5.764 | 46.899 | −28.222 | 1.00 | 50.95 | C |
| ATOM | 1447 | CB | ALA A | 269 | −7.041 | 46.086 | −28.428 | 1.00 | 49.80 | C |
| ATOM | 1448 | C | ALA A | 269 | −5.470 | 47.003 | −26.736 | 1.00 | 50.96 | C |
| ATOM | 1449 | O | ALA A | 269 | −6.181 | 47.695 | −26.004 | 1.00 | 50.85 | O |
| ATOM | 1450 | N | LEU A | 270 | −4.440 | 46.293 | −26.284 | 1.00 | 50.22 | N |
| ATOM | 1451 | CA | LEU A | 270 | −4.254 | 46.111 | −24.853 | 1.00 | 49.38 | C |
| ATOM | 1452 | CB | LEU A | 270 | −3.968 | 44.639 | −24.529 | 1.00 | 49.99 | C |
| ATOM | 1453 | CG | LEU A | 270 | −4.848 | 43.520 | −25.109 | 1.00 | 45.84 | C |
| ATOM | 1454 | CD1 | LEU A | 270 | −4.622 | 42.247 | −24.323 | 1.00 | 45.85 | C |
| ATOM | 1455 | CD2 | LEU A | 270 | −6.317 | 43.854 | −25.163 | 1.00 | 48.64 | C |
| ATOM | 1456 | C | LEU A | 270 | −3.163 | 47.022 | −24.315 | 1.00 | 48.79 | C |
| ATOM | 1457 | O | LEU A | 270 | −2.385 | 47.577 | −25.097 | 1.00 | 48.49 | O |
| ATOM | 1458 | N | PRO A | 271 | −3.129 | 47.223 | −22.982 | 1.00 | 48.16 | N |
| ATOM | 1459 | CA | PRO A | 271 | −1.946 | 47.847 | −22.372 | 1.00 | 47.49 | C |
| ATOM | 1460 | CB | PRO A | 271 | −2.368 | 48.066 | −20.915 | 1.00 | 46.26 | C |
| ATOM | 1461 | CG | PRO A | 271 | −3.450 | 47.097 | −20.679 | 1.00 | 48.44 | C |
| ATOM | 1462 | CD | PRO A | 271 | −4.157 | 46.891 | −21.981 | 1.00 | 47.60 | C |
| ATOM | 1463 | C | PRO A | 271 | −.797 | 46.852 | −22.443 | 1.00 | 46.88 | C |
| ATOM | 1464 | O | PRO A | 271 | −1.011 | 45.722 | −22.874 | 1.00 | 47.32 | O |
| ATOM | 1465 | N | ARG A | 272 | .397 | 47.246 | −22.021 | 1.00 | 47.31 | N |
| ATOM | 1466 | CA | ARG A | 272 | 1.523 | 46.317 | −22.045 | 1.00 | 47.81 | C |
| ATOM | 1467 | CB | ARG A | 272 | 2.875 | 47.032 | −22.012 | 1.00 | 48.03 | C |
| ATOM | 1468 | CG | ARG A | 272 | 4.043 | 46.070 | −22.227 | 1.00 | 49.71 | C |
| ATOM | 1469 | CD | ARG A | 272 | 5.396 | 46.748 | −22.108 | 1.00 | 57.19 | C |
| ATOM | 1470 | NE | ARG A | 272 | 6.450 | 45.744 | −21.970 | 1.00 | 60.66 | N |
| ATOM | 1471 | CZ | ARG A | 272 | 7.741 | 46.013 | −21.823 | 1.00 | 59.94 | C |
| ATOM | 1472 | NH1 | ARG A | 272 | 8.166 | 47.271 | −21.799 | 1.00 | 59.50 | N |
| ATOM | 1473 | NH2 | ARG A | 272 | 8.608 | 45.014 | −21.695 | 1.00 | 58.99 | N |
| ATOM | 1474 | C | ARG A | 272 | 1.410 | 45.321 | −20.901 | 1.00 | 47.97 | C |
| ATOM | 1475 | O | ARG A | 272 | 1.475 | 45.691 | −19.722 | 1.00 | 48.19 | O |
| ATOM | 1476 | N | LEU A | 273 | 1.221 | 44.061 | −21.282 | 1.00 | 47.35 | N |
| ATOM | 1477 | CA | LEU A | 273 | 1.053 | 42.954 | −20.352 | 1.00 | 47.11 | C |
| ATOM | 1478 | CB | LEU A | 273 | .323 | 41.812 | −21.042 | 1.00 | 46.07 | C |
| ATOM | 1479 | CG | LEU A | 273 | −1.192 | 41.622 | −20.963 | 1.00 | 49.88 | C |
| ATOM | 1480 | CD1 | LEU A | 273 | −1.969 | 42.892 | −21.215 | 1.00 | 49.09 | C |
| ATOM | 1481 | CD2 | LEU A | 273 | −1.578 | 40.538 | −21.959 | 1.00 | 47.03 | C |

TABLE A-continued

| | | | | | | | | | |
|---|---|---|---|---|---|---|---|---|---|
| ATOM | 1482 | C | LEU A | 273 | 2.397 | 42.440 | −19.879 | 1.00 | 47.42 | C |
| ATOM | 1483 | O | LEU A | 273 | 3.347 | 42.345 | −20.665 | 1.00 | 47.58 | O |
| ATOM | 1484 | N | ILE A | 274 | 2.474 | 42.084 | −18.602 | 1.00 | 47.23 | N |
| ATOM | 1485 | CA | ILE A | 274 | 3.696 | 41.485 | −18.067 | 1.00 | 47.38 | C |
| ATOM | 1486 | CB | ILE A | 274 | 4.467 | 42.449 | −17.114 | 1.00 | 47.69 | C |
| ATOM | 1487 | CG1 | ILE A | 274 | 4.634 | 43.848 | −17.749 | 1.00 | 46.49 | C |
| ATOM | 1488 | CD | ILE A | 274 | 5.676 | 43.937 | −18.927 | 1.00 | 40.14 | C |
| ATOM | 1489 | CG2 | ILE A | 274 | 5.809 | 41.825 | −16.710 | 1.00 | 45.03 | C |
| ATOM | 1490 | C | ILE A | 274 | 3.382 | 40.194 | −17.336 | 1.00 | 47.33 | C |
| ATOM | 1491 | O | ILE A | 274 | 2.424 | 40.131 | −16.561 | 1.00 | 47.50 | O |
| ATOM | 1492 | N | ALA A | 275 | 4.207 | 39.180 | −17.605 | 1.00 | 47.67 | N |
| ATOM | 1493 | CA | ALA A | 275 | 4.147 | 37.877 | −16.959 | 1.00 | 47.99 | C |
| ATOM | 1494 | CB | ALA A | 275 | 4.018 | 36.770 | −18.012 | 1.00 | 47.03 | C |
| ATOM | 1495 | C | ALA A | 275 | 5.418 | 37.690 | −16.139 | 1.00 | 49.18 | C |
| ATOM | 1496 | O | ALA A | 275 | 6.469 | 38.199 | −16.524 | 1.00 | 50.40 | O |
| ATOM | 1497 | N | PHE A | 276 | 5.324 | 36.957 | −15.027 | 1.00 | 49.10 | N |
| ATOM | 1498 | CA | PHE A | 276 | 6.475 | 36.701 | −14.139 | 1.00 | 48.40 | C |
| ATOM | 1499 | CB | PHE A | 276 | 6.279 | 37.404 | −12.795 | 1.00 | 48.25 | C |
| ATOM | 1500 | CG | PHE A | 276 | 5.955 | 38.861 | −12.918 | 1.00 | 48.44 | C |
| ATOM | 1501 | CD1 | PHE A | 276 | 4.640 | 39.282 | −13.079 | 1.00 | 43.18 | C |
| ATOM | 1502 | CE1 | PHE A | 276 | 4.335 | 40.616 | −13.219 | 1.00 | 41.80 | C |
| ATOM | 1503 | CZ | PHE A | 276 | 5.341 | 41.555 | −13.175 | 1.00 | 47.04 | C |
| ATOM | 1504 | CE2 | PHE A | 276 | 6.662 | 41.154 | −13.015 | 1.00 | 49.95 | C |
| ATOM | 1505 | CD2 | PHE A | 276 | 6.962 | 39.811 | −12.889 | 1.00 | 46.68 | C |
| ATOM | 1506 | C | PHE A | 276 | 6.688 | 35.209 | −13.888 | 1.00 | 48.40 | C |
| ATOM | 1507 | O | PHE A | 276 | 5.729 | 34.454 | −13.700 | 1.00 | 47.82 | O |
| ATOM | 1508 | N | THR A | 277 | 7.949 | 34.789 | −13.871 | 1.00 | 47.67 | N |
| ATOM | 1509 | CA | THR A | 277 | 8.286 | 33.386 | −13.652 | 1.00 | 46.86 | C |
| ATOM | 1510 | CB | THR A | 277 | 8.018 | 32.517 | −14.942 | 1.00 | 47.82 | C |
| ATOM | 1511 | OG1 | THR A | 277 | 8.122 | 31.124 | −14.629 | 1.00 | 50.44 | O |
| ATOM | 1512 | CG2 | THR A | 277 | 8.961 | 32.861 | −16.086 | 1.00 | 48.13 | C |
| ATOM | 1513 | C | THR A | 277 | 9.716 | 33.261 | −13.094 | 1.00 | 46.41 | C |
| ATOM | 1514 | O | THR A | 277 | 10.493 | 34.224 | −13.136 | 1.00 | 46.14 | O |
| ATOM | 1515 | N | SER A | 278 | 10.065 | 32.105 | −12.540 | 1.00 | 45.81 | N |
| ATOM | 1516 | CA | SER A | 278 | 11.354 | 32.007 | −11.861 | 1.00 | 47.59 | C |
| ATOM | 1517 | CB | SER A | 278 | 11.335 | 30.917 | −10.779 | 1.00 | 48.25 | C |
| ATOM | 1518 | OG | SER A | 278 | 11.832 | 29.677 | −11.258 | 1.00 | 49.80 | O |
| ATOM | 1519 | C | SER A | 278 | 12.506 | 31.797 | −12.840 | 1.00 | 48.31 | C |
| ATOM | 1520 | O | SER A | 278 | 12.299 | 31.293 | −13.958 | 1.00 | 47.38 | O |
| ATOM | 1521 | N | GLU A | 279 | 13.707 | 32.201 | −12.416 | 1.00 | 48.81 | N |
| ATOM | 1522 | CA | GLU A | 279 | 14.966 | 31.940 | −13.145 | 1.00 | 49.87 | C |
| ATOM | 1523 | CB | GLU A | 279 | 16.185 | 32.468 | −12.366 | 1.00 | 49.94 | C |
| ATOM | 1524 | CG | GLU A | 279 | 16.395 | 33.961 | −12.381 | 1.00 | 52.70 | C |
| ATOM | 1525 | CD | GLU A | 279 | 17.635 | 34.382 | −11.575 | 1.00 | 53.88 | C |
| ATOM | 1526 | OE1 | GLU A | 279 | 17.648 | 34.211 | −10.332 | 1.00 | 59.87 | O |
| ATOM | 1527 | OE2 | GLU A | 279 | 18.603 | 34.885 | −12.192 | 1.00 | 64.15 | O |
| ATOM | 1528 | C | GLU A | 279 | 15.190 | 30.456 | −13.380 | 1.00 | 48.23 | C |
| ATOM | 1529 | O | GLU A | 279 | 15.982 | 30.075 | −14.242 | 1.00 | 48.06 | O |
| ATOM | 1530 | N | HIS A | 280 | 14.509 | 29.624 | −12.594 | 1.00 | 47.66 | N |
| ATOM | 1531 | CA | HIS A | 280 | 14.635 | 28.169 | −12.690 | 1.00 | 46.52 | C |
| ATOM | 1532 | CB | HIS A | 280 | 14.744 | 27.570 | −11.288 | 1.00 | 45.88 | C |
| ATOM | 1533 | CG | HIS A | 280 | 16.136 | 27.596 | −10.732 | 1.00 | 46.95 | C |
| ATOM | 1534 | ND1 | HIS A | 280 | 16.794 | 28.768 | −10.426 | 1.00 | 50.55 | N |
| ATOM | 1535 | CE1 | HIS A | 280 | 17.999 | 28.485 | −9.966 | 1.00 | 50.70 | C |
| ATOM | 1536 | NE2 | HIS A | 280 | 18.145 | 27.172 | −9.962 | 1.00 | 48.80 | N |
| ATOM | 1537 | CD2 | HIS A | 280 | 16.993 | 26.593 | −10.431 | 1.00 | 41.79 | C |
| ATOM | 1538 | C | HIS A | 280 | 13.493 | 27.509 | −13.459 | 1.00 | 46.88 | C |
| ATOM | 1539 | O | HIS A | 280 | 13.418 | 26.275 | −13.535 | 1.00 | 47.01 | O |
| ATOM | 1540 | N | SER A | 281 | 12.617 | 28.329 | −14.038 | 1.00 | 46.02 | N |
| ATOM | 1541 | CA | SER A | 281 | 11.398 | 27.828 | −14.650 | 1.00 | 45.76 | C |
| ATOM | 1542 | CB | SER A | 281 | 10.253 | 28.857 | −14.545 | 1.00 | 45.48 | C |
| ATOM | 1543 | OG | SER A | 281 | 10.319 | 29.853 | −15.559 | 1.00 | 47.30 | O |
| ATOM | 1544 | C | SER A | 281 | 11.629 | 27.366 | −16.089 | 1.00 | 46.70 | C |
| ATOM | 1545 | O | SER A | 281 | 12.675 | 27.627 | −16.684 | 1.00 | 46.83 | O |
| ATOM | 1546 | N | HIS A | 282 | 10.640 | 26.662 | −16.632 | 1.00 | 46.40 | N |
| ATOM | 1547 | CA | HIS A | 282 | 10.760 | 26.004 | −17.917 | 1.00 | 44.66 | C |
| ATOM | 1548 | CB | HIS A | 282 | 9.665 | 24.942 | −18.051 | 1.00 | 44.20 | C |
| ATOM | 1549 | CG | HIS A | 282 | 9.877 | 23.998 | −19.191 | 1.00 | 45.79 | C |
| | | | | | gad65.pdb | | | | | |
| ATOM | 1550 | ND1 | HIS A | 282 | 9.251 | 24.151 | −20.410 | 1.00 | 43.96 | N |
| ATOM | 1551 | CE1 | HIS A | 282 | 9.623 | 23.176 | −21.217 | 1.00 | 41.34 | C |
| ATOM | 1552 | NE2 | HIS A | 282 | 10.463 | 22.393 | −20.564 | 1.00 | 38.04 | N |
| ATOM | 1553 | CD2 | HIS A | 282 | 10.647 | 22.890 | −19.299 | 1.00 | 43.47 | C |
| ATOM | 1554 | C | HIS A | 282 | 10.661 | 27.029 | −19.025 | 1.00 | 44.18 | C |
| ATOM | 1555 | O | HIS A | 282 | 9.886 | 27.966 | −18.913 | 1.00 | 45.29 | O |
| ATOM | 1556 | N | PHE A | 283 | 11.450 | 26.849 | −20.084 | 1.00 | 44.44 | N |
| ATOM | 1557 | CA | PHE A | 283 | 11.498 | 27.796 | −21.202 | 1.00 | 46.29 | C |
| ATOM | 1558 | CB | PHE A | 283 | 12.663 | 27.474 | −22.150 | 1.00 | 46.86 | C |
| ATOM | 1559 | CG | PHE A | 283 | 12.668 | 26.058 | −22.670 | 1.00 | 55.64 | C |
| ATOM | 1560 | CD1 | PHE A | 283 | 13.536 | 25.106 | −22.124 | 1.00 | 65.82 | C |

TABLE A-continued

| | | | | | | | | | |
|---|---|---|---|---|---|---|---|---|---|
| ATOM | 1561 | CE1 | PHE A | 283 | 13.563 | 23.792 | −22.613 | 1.00 | 65.69 | C |
| ATOM | 1562 | CZ | PHE A | 283 | 12.713 | 23.425 | −23.659 | 1.00 | 57.17 | C |
| ATOM | 1563 | CE2 | PHE A | 283 | 11.856 | 24.366 | −24.211 | 1.00 | 57.85 | C |
| ATOM | 1564 | CD2 | PHE A | 283 | 11.838 | 25.675 | −23.720 | 1.00 | 54.46 | C |
| ATOM | 1565 | C | PHE A | 283 | 10.190 | 27.961 | −22.011 | 1.00 | 46.39 | C |
| ATOM | 1566 | O | PHE A | 283 | 10.094 | 28.870 | −22.824 | 1.00 | 47.34 | O |
| ATOM | 1567 | N | SER A | 284 | 9.197 | 27.105 | −21.775 | 1.00 | 45.18 | N |
| ATOM | 1568 | CA | SER A | 284 | 7.926 | 27.179 | −22.504 | 1.00 | 45.47 | C |
| ATOM | 1569 | CB | SER A | 284 | 7.022 | 25.955 | −22.221 | 1.00 | 45.39 | C |
| ATOM | 1570 | OG | SER A | 284 | 6.775 | 25.751 | −20.834 | 1.00 | 41.07 | O |
| ATOM | 1571 | C | SER A | 284 | 7.160 | 28.472 | −22.261 | 1.00 | 45.77 | C |
| ATOM | 1572 | O | SER A | 284 | 6.313 | 28.851 | −23.076 | 1.00 | 46.04 | O |
| ATOM | 1573 | N | LEU A | 285 | 7.461 | 29.145 | −21.152 | 1.00 | 46.30 | N |
| ATOM | 1574 | CA | LEU A | 285 | 6.802 | 30.399 | −20.798 | 1.00 | 47.07 | C |
| ATOM | 1575 | CB | LEU A | 285 | 7.000 | 30.715 | −19.307 | 1.00 | 47.51 | C |
| ATOM | 1576 | CG | LEU A | 285 | 6.038 | 30.115 | −18.261 | 1.00 | 54.74 | C |
| ATOM | 1577 | CD1 | LEU A | 285 | 4.620 | 30.692 | −18.376 | 1.00 | 54.01 | C |
| ATOM | 1578 | CD2 | LEU A | 285 | 5.988 | 28.575 | −18.289 | 1.00 | 56.38 | C |
| ATOM | 1579 | C | LEU A | 285 | 7.255 | 31.562 | −21.694 | 1.00 | 48.26 | C |
| ATOM | 1580 | O | LEU A | 285 | 6.418 | 32.357 | −22.163 | 1.00 | 48.06 | O |
| ATOM | 1581 | N | LYS A | 286 | 8.567 | 31.661 | −21.934 | 1.00 | 48.98 | N |
| ATOM | 1582 | CA | LYS A | 286 | 9.119 | 32.628 | −22.896 | 1.00 | 49.27 | C |
| ATOM | 1583 | CB | LYS A | 286 | 10.663 | 32.626 | −22.894 | 1.00 | 50.50 | C |
| ATOM | 1584 | CG | LYS A | 286 | 11.341 | 33.231 | −21.685 | 1.00 | 52.94 | C |
| ATOM | 1585 | CD | LYS A | 286 | 11.495 | 34.735 | −21.818 | 1.00 | 52.87 | C |
| ATOM | 1586 | CE | LYS A | 286 | 12.343 | 35.327 | −20.701 | 1.00 | 54.36 | C |
| ATOM | 1587 | NZ | LYS A | 286 | 12.562 | 36.795 | −20.910 | 1.00 | 47.96 | N |
| ATOM | 1588 | C | LYS A | 286 | 8.631 | 32.260 | −24.295 | 1.00 | 48.44 | C |
| ATOM | 1589 | O | LYS A | 286 | 8.127 | 33.112 | −25.023 | 1.00 | 49.09 | O |
| ATOM | 1590 | N | LYS A | 287 | 8.783 | 30.993 | −24.668 | 1.00 | 47.53 | N |
| ATOM | 1591 | CA | LYS A | 287 | 8.320 | 30.519 | −25.981 | 1.00 | 48.15 | C |
| ATOM | 1592 | CB | LYS A | 287 | 8.588 | 29.027 | −26.151 | 1.00 | 48.91 | C |
| ATOM | 1593 | CG | LYS A | 287 | 9.898 | 28.701 | −26.834 | 1.00 | 54.35 | C |
| ATOM | 1594 | CD | LYS A | 287 | 9.933 | 27.255 | −27.284 | 1.00 | 62.29 | C |
| ATOM | 1595 | CE | LYS A | 287 | 11.244 | 26.939 | −28.003 | 1.00 | 66.39 | C |
| ATOM | 1596 | NZ | LYS A | 287 | 11.262 | 25.565 | −28.596 | 1.00 | 67.27 | N |
| ATOM | 1597 | C | LYS A | 287 | 6.834 | 30.791 | −26.229 | 1.00 | 47.46 | C |
| ATOM | 1598 | O | LYS A | 287 | 6.450 | 31.175 | −27.332 | 1.00 | 47.88 | O |
| ATOM | 1599 | N | GLY A | 288 | 6.009 | 30.578 | −25.205 | 1.00 | 45.75 | N |
| ATOM | 1600 | CA | GLY A | 288 | 4.577 | 30.849 | −25.291 | 1.00 | 45.74 | C |
| ATOM | 1601 | C | GLY A | 288 | 4.292 | 32.321 | −25.499 | 1.00 | 44.82 | C |
| ATOM | 1602 | O | GLY A | 288 | 3.467 | 32.685 | −26.337 | 1.00 | 44.52 | O |
| ATOM | 1603 | N | ALA A | 289 | 5.001 | 33.171 | −24.759 | 1.00 | 44.33 | N |
| ATOM | 1604 | CA | ALA A | 289 | 4.800 | 34.623 | −24.854 | 1.00 | 42.60 | C |
| ATOM | 1605 | CB | ALA A | 289 | 5.566 | 35.349 | −23.785 | 1.00 | 41.29 | C |
| ATOM | 1606 | C | ALA A | 289 | 5.164 | 35.147 | −26.241 | 1.00 | 42.31 | C |
| ATOM | 1607 | O | ALA A | 289 | 4.409 | 35.943 | −26.827 | 1.00 | 41.97 | O |
| ATOM | 1608 | N | ALA A | 290 | 6.313 | 34.702 | −26.757 | 1.00 | 41.23 | N |
| ATOM | 1609 | CA | ALA A | 290 | 6.714 | 35.005 | −28.127 | 1.00 | 41.60 | C |
| ATOM | 1610 | CB | ALA A | 290 | 8.064 | 34.345 | −28.462 | 1.00 | 41.81 | C |
| ATOM | 1611 | C | ALA A | 290 | 5.633 | 34.564 | −29.124 | 1.00 | 42.25 | C |
| ATOM | 1612 | O | ALA A | 290 | 5.198 | 35.357 | −29.971 | 1.00 | 43.42 | O |
| ATOM | 1613 | N | ALA A | 291 | 5.186 | 33.311 | −29.021 | 1.00 | 41.10 | N |
| ATOM | 1614 | CA | ALA A | 291 | 4.107 | 32.819 | −29.870 | 1.00 | 40.91 | C |
| ATOM | 1615 | CB | ALA A | 291 | 3.800 | 31.378 | −29.556 | 1.00 | 41.53 | C |
| ATOM | 1616 | C | ALA A | 291 | 2.837 | 33.668 | −29.742 | 1.00 | 41.26 | C |
| ATOM | 1617 | O | ALA A | 291 | 2.187 | 33.945 | −30.723 | 1.00 | 40.16 | O |
| | | | | | gad65.pdb | | | | | |
| ATOM | 1618 | N | LEU A | 292 | 2.490 | 34.093 | −28.536 | 1.00 | 43.65 | N |
| ATOM | 1619 | CA | LEU A | 292 | 1.184 | 34.750 | −28.321 | 1.00 | 44.07 | C |
| ATOM | 1620 | CB | LEU A | 292 | .682 | 34.501 | −26.900 | 1.00 | 45.31 | C |
| ATOM | 1621 | CG | LEU A | 292 | .463 | 33.059 | −26.424 | 1.00 | 46.88 | C |
| ATOM | 1622 | CD1 | LEU A | 292 | .068 | 33.097 | −24.951 | 1.00 | 49.78 | C |
| ATOM | 1623 | CD2 | LEU A | 292 | −.557 | 32.279 | −27.243 | 1.00 | 50.10 | C |
| ATOM | 1624 | C | LEU A | 292 | 1.218 | 36.241 | −28.598 | 1.00 | 44.21 | C |
| ATOM | 1625 | O | LEU A | 292 | .247 | 36.956 | −28.322 | 1.00 | 44.60 | O |
| ATOM | 1626 | N | GLY A | 293 | 2.354 | 36.710 | −29.127 | 1.00 | 44.11 | N |
| ATOM | 1627 | CA | GLY A | 293 | 2.532 | 38.106 | −29.493 | 1.00 | 42.51 | C |
| ATOM | 1628 | C | GLY A | 293 | 2.647 | 38.976 | −28.265 | 1.00 | 43.82 | C |
| ATOM | 1629 | O | GLY A | 293 | 2.347 | 40.165 | −28.327 | 1.00 | 43.68 | O |
| ATOM | 1630 | N | ILE A | 294 | 3.071 | 38.378 | −27.148 | 1.00 | 44.09 | N |
| ATOM | 1631 | CA | ILE A | 294 | 3.272 | 39.105 | −25.889 | 1.00 | 44.91 | C |
| ATOM | 1632 | CB | ILE A | 294 | 2.914 | 38.200 | −24.662 | 1.00 | 45.99 | C |
| ATOM | 1633 | CG1 | ILE A | 294 | 1.390 | 38.111 | −24.491 | 1.00 | 48.13 | C |
| ATOM | 1634 | CD | ILE A | 294 | .909 | 36.916 | −23.679 | 1.00 | 45.36 | C |
| ATOM | 1635 | CG2 | ILE A | 294 | 3.519 | 38.719 | −23.374 | 1.00 | 42.19 | C |
| ATOM | 1636 | C | ILE A | 294 | 4.708 | 39.664 | −25.804 | 1.00 | 45.48 | C |
| ATOM | 1637 | O | ILE A | 294 | 4.919 | 40.745 | −25.262 | 1.00 | 45.66 | O |
| ATOM | 1638 | N | GLY A | 295 | 5.676 | 38.917 | −26.342 | 1.00 | 45.63 | N |
| ATOM | 1639 | CA | GLY A | 295 | 7.080 | 39.327 | −26.367 | 1.00 | 46.09 | C |

TABLE A-continued

| | | | | | | | | | |
|---|---|---|---|---|---|---|---|---|---|
| ATOM | 1640 | C | GLY A | 295 | 7.826 | 38.773 | −25.176 | 1.00 | 46.35 | C |
| ATOM | 1641 | O | GLY A | 295 | 7.393 | 38.957 | −24.041 | 1.00 | 45.92 | O |
| ATOM | 1642 | N | THR A | 296 | 8.939 | 38.084 | −25.424 | 1.00 | 46.88 | N |
| ATOM | 1643 | CA | THR A | 296 | 9.802 | 37.604 | −24.336 | 1.00 | 47.54 | C |
| ATOM | 1644 | CB | THR A | 296 | 11.004 | 36.766 | −24.841 | 1.00 | 49.21 | C |
| ATOM | 1645 | OG1 | THR A | 296 | 11.828 | 37.570 | −25.693 | 1.00 | 45.09 | O |
| ATOM | 1646 | CG2 | THR A | 296 | 10.542 | 35.510 | −25.588 | 1.00 | 47.43 | C |
| ATOM | 1647 | C | THR A | 296 | 10.342 | 38.747 | −23.464 | 1.00 | 48.21 | C |
| ATOM | 1648 | O | THR A | 296 | 10.721 | 38.512 | −22.324 | 1.00 | 48.54 | O |
| ATOM | 1649 | N | ASP A | 297 | 10.377 | 39.975 | −23.987 | 1.00 | 48.85 | N |
| ATOM | 1650 | CA | ASP A | 297 | 10.749 | 41.136 | −23.158 | 1.00 | 50.67 | C |
| ATOM | 1651 | CB | ASP A | 297 | 10.855 | 42.427 | −23.985 | 1.00 | 52.60 | C |
| ATOM | 1652 | CG | ASP A | 297 | 12.142 | 42.522 | −24.776 | 1.00 | 54.36 | C |
| ATOM | 1653 | OD1 | ASP A | 297 | 13.023 | 41.648 | −24.613 | 1.00 | 57.78 | O |
| ATOM | 1654 | OD2 | ASP A | 297 | 12.261 | 43.482 | −25.567 | 1.00 | 56.64 | O |
| ATOM | 1655 | C | ASP A | 297 | 9.756 | 41.379 | −22.023 | 1.00 | 49.49 | C |
| ATOM | 1656 | O | ASP A | 297 | 10.091 | 42.014 | −21.016 | 1.00 | 48.71 | O |
| ATOM | 1657 | N | SER A | 298 | 8.535 | 40.884 | −22.201 | 1.00 | 48.70 | N |
| ATOM | 1658 | CA | SER A | 298 | 7.484 | 41.093 | −21.211 | 1.00 | 48.98 | C |
| ATOM | 1659 | CB | SER A | 298 | 6.174 | 41.510 | −21.898 | 1.00 | 50.09 | C |
| ATOM | 1660 | OG | SER A | 298 | 6.334 | 42.772 | −22.544 | 1.00 | 51.26 | O |
| ATOM | 1661 | C | SER A | 298 | 7.296 | 39.883 | −20.298 | 1.00 | 48.06 | C |
| ATOM | 1662 | O | SER A | 298 | 6.317 | 39.803 | −19.565 | 1.00 | 47.60 | O |
| ATOM | 1663 | N | VAL A | 299 | 8.243 | 38.948 | −20.353 | 1.00 | 48.36 | N |
| ATOM | 1664 | CA | VAL A | 299 | 8.324 | 37.859 | −19.384 | 1.00 | 49.04 | C |
| ATOM | 1665 | CB | VAL A | 299 | 8.534 | 36.476 | −20.047 | 1.00 | 49.60 | C |
| ATOM | 1666 | CG1 | VAL A | 299 | 8.458 | 35.370 | −19.008 | 1.00 | 48.51 | C |
| ATOM | 1667 | CG2 | VAL A | 299 | 7.507 | 36.227 | −21.132 | 1.00 | 50.57 | C |
| ATOM | 1668 | C | VAL A | 299 | 9.495 | 38.155 | −18.461 | 1.00 | 49.54 | C |
| ATOM | 1669 | O | VAL A | 299 | 10.649 | 37.982 | −18.845 | 1.00 | 50.16 | O |
| ATOM | 1670 | N | ILE A | 300 | 9.194 | 38.609 | −17.249 | 1.00 | 48.93 | N |
| ATOM | 1671 | CA | ILE A | 300 | 10.234 | 38.963 | −16.282 | 1.00 | 49.11 | C |
| ATOM | 1672 | CB | ILE A | 300 | 9.798 | 40.148 | −15.368 | 1.00 | 48.52 | C |
| ATOM | 1673 | CG1 | ILE A | 300 | 9.268 | 41.336 | −16.188 | 1.00 | 46.09 | C |
| ATOM | 1674 | CD | ILE A | 300 | 10.265 | 41.976 | −17.149 | 1.00 | 52.61 | C |
| ATOM | 1675 | CG2 | ILE A | 300 | 10.941 | 40.557 | −14.428 | 1.00 | 47.79 | C |
| ATOM | 1676 | C | ILE A | 300 | 10.639 | 37.771 | −15.405 | 1.00 | 48.88 | C |
| ATOM | 1677 | O | ILE A | 300 | 9.788 | 37.107 | −14.807 | 1.00 | 48.36 | O |
| ATOM | 1678 | N | LEU A | 301 | 11.942 | 37.525 | −15.309 | 1.00 | 48.28 | N |
| ATOM | 1679 | CA | LEU A | 301 | 12.443 | 36.429 | −14.481 | 1.00 | 48.53 | C |
| ATOM | 1680 | CB | LEU A | 301 | 13.689 | 35.780 | −15.102 | 1.00 | 48.29 | C |
| ATOM | 1681 | CG | LEU A | 301 | 13.595 | 35.274 | −16.550 | 1.00 | 48.28 | C |
| ATOM | 1682 | CD1 | LEU A | 301 | 14.968 | 34.785 | −17.068 | 1.00 | 45.81 | C |
| ATOM | 1683 | CD2 | LEU A | 301 | 12.539 | 34.182 | −16.711 | 1.00 | 52.99 | C |
| ATOM | 1684 | C | LEU A | 301 | 12.706 | 36.871 | −13.046 | 1.00 | 48.50 | C |
| ATOM | 1685 | O | LEU A | 301 | 13.387 | 37.868 | −12.806 | 1.00 | 49.57 | O | gad65.pdb

| | | | | | | | | | |
|---|---|---|---|---|---|---|---|---|---|
| ATOM | 1686 | N | ILE A | 302 | 12.137 | 36.136 | −12.098 | 1.00 | 48.52 | N |
| ATOM | 1687 | CA | ILE A | 302 | 12.277 | 36.454 | −10.681 | 1.00 | 48.85 | C |
| ATOM | 1688 | CB | ILE A | 302 | 10.946 | 36.217 | −9.884 | 1.00 | 48.91 | C |
| ATOM | 1689 | CG1 | ILE A | 302 | 9.962 | 37.339 | −10.172 | 1.00 | 47.06 | C |
| ATOM | 1690 | CD | ILE A | 302 | 9.231 | 37.182 | −11.435 | 1.00 | 56.85 | C |
| ATOM | 1691 | CG2 | ILE A | 302 | 11.170 | 36.238 | −8.377 | 1.00 | 45.54 | C |
| ATOM | 1692 | C | ILE A | 302 | 13.448 | 35.672 | −10.099 | 1.00 | 49.32 | C |
| ATOM | 1693 | O | ILE A | 302 | 13.647 | 34.512 | −10.444 | 1.00 | 48.48 | O |
| ATOM | 1694 | N | LYS A | 303 | 14.223 | 36.332 | −9.235 | 1.00 | 50.53 | N |
| ATOM | 1695 | CA | LYS A | 303 | 15.416 | 35.734 | −8.625 | 1.00 | 50.93 | C |
| ATOM | 1696 | CB | LYS A | 303 | 16.155 | 36.756 | −7.753 | 1.00 | 51.05 | C |
| ATOM | 1697 | CG | LYS A | 303 | 16.896 | 37.821 | −8.533 | 1.00 | 56.44 | C |
| ATOM | 1701 | C | LYS A | 303 | 15.066 | 34.505 | −7.798 | 1.00 | 50.53 | C |
| ATOM | 1702 | O | LYS A | 303 | 14.006 | 34.446 | −7.180 | 1.00 | 50.19 | O |
| ATOM | 1703 | N | CYS A | 304 | 15.955 | 33.517 | −7.811 | 1.00 | 50.72 | N |
| ATOM | 1704 | CA | CYS A | 304 | 15.791 | 32.336 | −6.981 | 1.00 | 51.56 | C |
| ATOM | 1705 | CB | CYS A | 304 | 15.780 | 31.075 | −7.840 | 1.00 | 51.04 | C |
| ATOM | 1706 | SG | CYS A | 304 | 14.384 | 31.024 | −8.976 | 1.00 | 57.35 | S |
| ATOM | 1707 | C | CYS A | 304 | 16.875 | 32.253 | −5.911 | 1.00 | 52.23 | C |
| ATOM | 1708 | O | CYS A | 304 | 17.953 | 32.846 | −6.052 | 1.00 | 52.85 | O |
| ATOM | 1709 | N | ASP A | 305 | 16.572 | 31.529 | −4.838 | 1.00 | 52.32 | N |
| ATOM | 1710 | CA | ASP A | 305 | 17.543 | 31.267 | −3.787 | 1.00 | 52.62 | C |
| ATOM | 1711 | CB | ASP A | 305 | 16.836 | 31.007 | −2.442 | 1.00 | 52.37 | C |
| ATOM | 1712 | CG | ASP A | 305 | 15.930 | 29.767 | −2.459 | 1.00 | 55.26 | C |
| ATOM | 1713 | OD1 | ASP A | 305 | 15.953 | 28.998 | −3.441 | 1.00 | 58.07 | O |
| ATOM | 1714 | OD2 | ASP A | 305 | 15.192 | 29.555 | −1.468 | 1.00 | 59.21 | O |
| ATOM | 1715 | C | ASP A | 305 | 18.478 | 30.112 | −4.177 | 1.00 | 52.93 | C |
| ATOM | 1716 | O | ASP A | 305 | 18.332 | 29.508 | −5.252 | 1.00 | 51.68 | O |
| ATOM | 1717 | N | GLU A | 306 | 19.424 | 29.814 | −3.284 | 1.00 | 53.78 | N |
| ATOM | 1718 | CA | GLU A | 306 | 20.420 | 28.750 | −3.459 | 1.00 | 54.88 | C |
| ATOM | 1719 | CB | GLU A | 306 | 21.372 | 28.732 | −2.238 | 1.00 | 56.18 | C |
| ATOM | 1720 | CG | GLU A | 306 | 22.056 | 27.386 | −1.894 | 1.00 | 63.64 | C |
| ATOM | 1721 | CD | GLU A | 306 | 23.363 | 27.121 | −2.656 | 1.00 | 69.87 | C |

TABLE A-continued

| ATOM | 1722 | OE1 | GLU A | 306 | 23.597 | 27.726 | −3.732 | 1.00 | 72.64 | O |
|---|---|---|---|---|---|---|---|---|---|---|
| ATOM | 1723 | OE2 | GLU A | 306 | 24.161 | 26.285 | −2.171 | 1.00 | 69.72 | O |
| ATOM | 1724 | C | GLU A | 306 | 19.806 | 27.368 | −3.732 | 1.00 | 53.64 | C |
| ATOM | 1725 | O | GLU A | 306 | 20.444 | 26.511 | −4.354 | 1.00 | 53.91 | O |
| ATOM | 1726 | N | ARG A | 307 | 18.568 | 27.170 | −3.285 | 1.00 | 52.49 | N |
| ATOM | 1727 | CA | ARG A | 307 | 17.865 | 25.889 | −3.420 | 1.00 | 51.29 | C |
| ATOM | 1728 | CB | ARG A | 307 | 17.067 | 25.606 | −2.149 | 1.00 | 51.59 | C |
| ATOM | 1729 | CG | ARG A | 307 | 17.889 | 25.082 | −.991 | 1.00 | 53.46 | C |
| ATOM | 1730 | CD | ARG A | 307 | 17.334 | 25.568 | .352 | 1.00 | 61.30 | C |
| ATOM | 1731 | NE | ARG A | 307 | 15.986 | 25.071 | .629 | 1.00 | 61.45 | N |
| ATOM | 1735 | C | ARG A | 307 | 16.951 | 25.800 | −4.654 | 1.00 | 50.68 | C |
| ATOM | 1736 | O | ARG A | 307 | 16.255 | 24.801 | −4.843 | 1.00 | 49.85 | O |
| ATOM | 1737 | N | GLY A | 308 | 16.963 | 26.841 | −5.484 | 1.00 | 50.74 | N |
| ATOM | 1738 | CA | GLY A | 308 | 16.179 | 26.878 | −6.725 | 1.00 | 50.20 | C |
| ATOM | 1739 | C | GLY A | 308 | 14.783 | 27.500 | −6.636 | 1.00 | 49.81 | C |
| ATOM | 1740 | O | GLY A | 308 | 14.039 | 27.504 | −7.627 | 1.00 | 48.43 | O |
| ATOM | 1741 | N | LYS A | 309 | 14.428 | 28.032 | −5.464 | 1.00 | 49.53 | N |
| ATOM | 1742 | CA | LYS A | 309 | 13.072 | 28.561 | −5.227 | 1.00 | 50.34 | C |
| ATOM | 1743 | CB | LYS A | 309 | 12.584 | 28.260 | −3.802 | 1.00 | 49.14 | C |
| ATOM | 1744 | CG | LYS A | 309 | 12.641 | 26.818 | −3.372 | 1.00 | 45.80 | C |
| ATOM | 1745 | CD | LYS A | 309 | 12.363 | 26.728 | −1.883 | 1.00 | 48.61 | C |
| ATOM | 1746 | CE | LYS A | 309 | 12.887 | 25.434 | −1.271 | 1.00 | 47.53 | C |
| ATOM | 1747 | NZ | LYS A | 309 | 12.482 | 25.341 | .161 | 1.00 | 56.14 | N |
| ATOM | 1748 | C | LYS A | 309 | 12.974 | 30.063 | −5.450 | 1.00 | 52.23 | C |
| ATOM | 1749 | O | LYS A | 309 | 13.756 | 30.847 | −4.883 | 1.00 | 52.36 | O |
| ATOM | 1750 | N | MET A | 310 | 11.989 | 30.447 | −6.262 | 1.00 | 53.88 | N |
| ATOM | 1751 | CA | MET A | 310 | 11.585 | 31.843 | −6.458 | 1.00 | 56.12 | C |
| ATOM | 1752 | CB | MET A | 310 | 10.241 | 31.857 | −7.195 | 1.00 | 55.44 | C |
| ATOM | 1753 | CG | MET A | 310 | 9.551 | 33.205 | −7.343 | 1.00 | 59.11 | C |
| ATOM | 1754 | SD | MET A | 310 | 8.304 | 33.206 | −8.658 | 1.00 | 61.15 | S |
| ATOM | 1755 | CE | MET A | 310 | 7.144 | 31.969 | −8.078 | 1.00 | 67.07 | C |
| ATOM | 1756 | C | MET A | 310 | 11.512 | 32.624 | −5.128 | 1.00 | 54.72 | C |
| ATOM | 1757 | O | MET A | 310 | 10.887 | 32.161 | −4.177 | 1.00 | 53.86 | O |
| ATOM | 1758 | N | ILE A | 311 | 12.183 | 33.780 | −5.074 | 1.00 | 54.59 | N |
| ATOM | 1759 | CA | ILE A | 311 | 12.150 | 34.687 | −3.911 | 1.00 | 54.12 | C |
| ATOM | 1760 | CB | ILE A | 311 | 13.382 | 35.643 | −3.849 | 1.00 | 54.71 | C |
| ATOM | 1761 | CG1 | ILE A | 311 | 14.714 | 34.890 | −4.030 | 1.00 | 55.78 | C |
| ATOM | 1762 | CD | ILE A | 311 | 15.198 | 34.129 | −2.812 | 1.00 | 61.90 | C |
| ATOM | 1763 | CG2 | ILE A | 311 | 13.345 | 36.512 | −2.560 | 1.00 | 50.02 | C |
| ATOM | 1764 | C | ILE A | 311 | 10.894 | 35.565 | −3.944 | 1.00 | 53.59 | C |
| ATOM | 1765 | O | ILE A | 311 | 10.772 | 36.444 | −4.799 | 1.00 | 53.36 | O |
| ATOM | 1766 | N | PRO A | 312 | 9.961 | 35.340 | −3.006 | 1.00 | 53.74 | N |
| ATOM | 1767 | CA | PRO A | 312 | 8.696 | 36.085 | −2.998 | 1.00 | 54.08 | C |
| ATOM | 1768 | CB | PRO A | 312 | 8.029 | 35.617 | −1.701 | 1.00 | 54.43 | C |
| ATOM | 1769 | CG | PRO A | 312 | 8.594 | 34.254 | −1.472 | 1.00 | 54.13 | C |
| ATOM | 1770 | CD | PRO A | 312 | 10.022 | 34.364 | −1.901 | 1.00 | 53.49 | C |
| ATOM | 1771 | C | PRO A | 312 | 8.843 | 37.619 | −3.018 | 1.00 | 53.97 | C |
| ATOM | 1772 | O | PRO A | 312 | 8.020 | 38.299 | −3.639 | 1.00 | 53.46 | O |
| ATOM | 1773 | N | SER A | 313 | 9.884 | 38.149 | −2.369 | 1.00 | 53.52 | N |
| ATOM | 1774 | CA | SER A | 313 | 10.082 | 39.596 | −2.308 | 1.00 | 53.29 | C |
| ATOM | 1775 | CB | SER A | 313 | 10.908 | 40.014 | −1.074 | 1.00 | 53.76 | C |
| ATOM | 1776 | OG | SER A | 313 | 12.213 | 39.448 | −1.067 | 1.00 | 57.39 | O |
| ATOM | 1777 | C | SER A | 313 | 10.635 | 40.214 | −3.599 | 1.00 | 53.15 | C |
| ATOM | 1778 | O | SER A | 313 | 10.452 | 41.412 | −3.829 | 1.00 | 53.99 | O |
| ATOM | 1779 | N | ASP A | 314 | 11.303 | 39.417 | −4.435 | 1.00 | 51.88 | N |
| ATOM | 1780 | CA | ASP A | 314 | 11.726 | 39.900 | −5.751 | 1.00 | 50.82 | C |
| ATOM | 1781 | CB | ASP A | 314 | 12.855 | 39.044 | −6.346 | 1.00 | 51.06 | C |
| ATOM | 1782 | CG | ASP A | 314 | 13.616 | 39.769 | −7.468 | 1.00 | 56.00 | C |
| ATOM | 1783 | OD1 | ASP A | 314 | 14.022 | 40.936 | −7.260 | 1.00 | 59.90 | O |
| ATOM | 1784 | OD2 | ASP A | 314 | 13.812 | 39.177 | −8.558 | 1.00 | 58.52 | O |
| ATOM | 1785 | C | ASP A | 314 | 10.534 | 39.951 | −6.705 | 1.00 | 49.42 | C |
| ATOM | 1786 | O | ASP A | 314 | 10.488 | 40.781 | −7.613 | 1.00 | 48.38 | O |
| ATOM | 1787 | N | LEU A | 315 | 9.574 | 39.055 | −6.481 | 1.00 | 48.68 | N |
| ATOM | 1788 | CA | LEU A | 315 | 8.348 | 38.986 | −7.260 | 1.00 | 47.68 | C |
| ATOM | 1789 | CB | LEU A | 315 | 7.539 | 37.762 | −6.823 | 1.00 | 47.56 | C |
| ATOM | 1790 | CG | LEU A | 315 | 6.651 | 36.956 | −7.772 | 1.00 | 46.98 | C |
| ATOM | 1791 | CD1 | LEU A | 315 | 5.572 | 36.198 | −6.965 | 1.00 | 37.32 | C |
| ATOM | 1792 | CD2 | LEU A | 315 | 6.023 | 37.775 | −8.913 | 1.00 | 47.74 | C |
| ATOM | 1793 | C | LEU A | 315 | 7.524 | 40.254 | −7.042 | 1.00 | 48.41 | C |
| ATOM | 1794 | O | LEU A | 315 | 7.099 | 40.896 | −8.002 | 1.00 | 48.47 | O |
| ATOM | 1795 | N | GLU A | 316 | 7.296 | 40.601 | −5.773 | 1.00 | 48.70 | N |
| ATOM | 1796 | CA | GLU A | 316 | 6.552 | 41.804 | −5.404 | 1.00 | 48.79 | C |
| ATOM | 1797 | CB | GLU A | 316 | 6.326 | 41.846 | −3.893 | 1.00 | 48.36 | C |
| ATOM | 1798 | CG | GLU A | 316 | 5.519 | 43.039 | −3.419 | 1.00 | 53.17 | C |
| ATOM | 1799 | CD | GLU A | 316 | 4.901 | 42.853 | −2.037 | 1.00 | 57.48 | C |
| ATOM | 1800 | OE1 | GLU A | 316 | 3.915 | 43.558 | −1.736 | 1.00 | 54.87 | O |
| ATOM | 1801 | OE2 | GLU A | 316 | 5.394 | 42.014 | −1.250 | 1.00 | 61.30 | O |
| ATOM | 1802 | C | GLU A | 316 | 7.280 | 43.058 | −5.889 | 1.00 | 49.24 | C |
| ATOM | 1803 | O | GLU A | 316 | 6.666 | 43.946 | −6.482 | 1.00 | 49.61 | O | gad65.pdb

TABLE A-continued

| | | | | | | | | | | |
|---|---|---|---|---|---|---|---|---|---|---|
| ATOM | 1804 | N | ARG A | 317 | 8.590 | 43.114 | −5.653 | 1.00 | 49.12 | N |
| ATOM | 1805 | CA | ARG A | 317 | 9.436 | 44.195 | −6.166 | 1.00 | 49.47 | C |
| ATOM | 1806 | CB | ARG A | 317 | 10.920 | 43.901 | −5.880 | 1.00 | 49.50 | C |
| ATOM | 1807 | CG | ARG A | 317 | 11.897 | 44.987 | −6.330 | 1.00 | 55.22 | C |
| ATOM | 1808 | CD | ARG A | 317 | 13.197 | 44.375 | −6.849 | 1.00 | 61.71 | C |
| ATOM | 1809 | NE | ARG A | 317 | 13.605 | 44.951 | −8.135 | 1.00 | 67.92 | N |
| ATOM | 1810 | CZ | ARG A | 317 | 14.210 | 44.273 | −9.117 | 1.00 | 73.64 | C |
| ATOM | 1811 | NH1 | ARG A | 317 | 14.478 | 42.976 | −8.986 | 1.00 | 70.10 | N |
| ATOM | 1812 | NH2 | ARG A | 317 | 14.535 | 44.887 | −10.250 | 1.00 | 72.43 | N |
| ATOM | 1813 | C | ARG A | 317 | 9.199 | 44.388 | −7.669 | 1.00 | 48.80 | C |
| ATOM | 1814 | O | ARG A | 317 | 8.957 | 45.502 | −8.129 | 1.00 | 48.83 | O |
| ATOM | 1815 | N | ARG A | 318 | 9.234 | 43.291 | −8.421 | 1.00 | 47.90 | N |
| ATOM | 1816 | CA | ARG A | 318 | 9.066 | 43.351 | −9.869 | 1.00 | 47.16 | C |
| ATOM | 1817 | CB | ARG A | 318 | 9.532 | 42.047 | −10.515 | 1.00 | 47.29 | C |
| ATOM | 1818 | CG | ARG A | 318 | 11.052 | 41.834 | −10.424 | 1.00 | 43.68 | C |
| ATOM | 1819 | CD | ARG A | 318 | 11.780 | 42.842 | −11.269 | 1.00 | 47.92 | C |
| ATOM | 1820 | NE | ARG A | 318 | 12.869 | 42.220 | −12.016 | 1.00 | 55.20 | N |
| ATOM | 1821 | CZ | ARG A | 318 | 13.445 | 42.751 | −13.090 | 1.00 | 57.43 | C |
| ATOM | 1822 | NH1 | ARG A | 318 | 14.422 | 42.098 | −13.700 | 1.00 | 60.42 | N |
| ATOM | 1823 | NH2 | ARG A | 318 | 13.039 | 43.928 | −13.561 | 1.00 | 59.59 | N |
| ATOM | 1824 | C | ARG A | 318 | 7.652 | 43.740 | −10.320 | 1.00 | 46.71 | C |
| ATOM | 1825 | O | ARG A | 318 | 7.483 | 44.523 | −11.261 | 1.00 | 45.81 | O |
| ATOM | 1826 | N | ILE A | 319 | 6.644 | 43.197 | −9.639 | 1.00 | 47.00 | N |
| ATOM | 1827 | CA | ILE A | 319 | 5.254 | 43.560 | −9.892 | 1.00 | 47.82 | C |
| | | | | gad65.pdb | | | | | | |
| ATOM | 1828 | CB | ILE A | 319 | 4.294 | 42.772 | −8.979 | 1.00 | 47.66 | C |
| ATOM | 1829 | CG1 | ILE A | 319 | 4.337 | 41.287 | −9.324 | 1.00 | 48.94 | C |
| ATOM | 1830 | CD | ILE A | 319 | 3.684 | 40.416 | −8.280 | 1.00 | 52.13 | C |
| ATOM | 1831 | CG2 | ILE A | 319 | 2.858 | 43.283 | −9.110 | 1.00 | 48.77 | C |
| ATOM | 1832 | C | ILE A | 319 | 5.064 | 45.068 | −9.702 | 1.00 | 48.91 | C |
| ATOM | 1833 | O | ILE A | 319 | 4.460 | 45.737 | −10.551 | 1.00 | 49.45 | O |
| ATOM | 1834 | N | LEU A | 320 | 5.605 | 45.588 | −8.599 | 1.00 | 49.33 | N |
| ATOM | 1835 | CA | LEU A | 320 | 5.492 | 47.007 | −8.239 | 1.00 | 50.38 | C |
| ATOM | 1836 | CB | LEU A | 320 | 5.997 | 47.228 | −6.814 | 1.00 | 50.29 | C |
| ATOM | 1837 | CG | LEU A | 320 | 4.989 | 47.627 | −5.741 | 1.00 | 55.56 | C |
| ATOM | 1838 | CD1 | LEU A | 320 | 3.639 | 47.008 | −5.987 | 1.00 | 57.47 | C |
| ATOM | 1839 | CD2 | LEU A | 320 | 5.504 | 47.306 | −4.335 | 1.00 | 51.71 | C |
| ATOM | 1840 | C | LEU A | 320 | 6.192 | 47.960 | −9.210 | 1.00 | 49.74 | C |
| ATOM | 1841 | O | LEU A | 320 | 5.698 | 49.060 | −9.454 | 1.00 | 49.05 | O |
| ATOM | 1842 | N | GLU A | 321 | 7.339 | 47.539 | −9.744 | 1.00 | 50.25 | N |
| ATOM | 1843 | CA | GLU A | 321 | 8.031 | 48.257 | −10.826 | 1.00 | 51.94 | C |
| ATOM | 1844 | CB | GLU A | 321 | 9.389 | 47.610 | −11.145 | 1.00 | 51.98 | C |
| ATOM | 1845 | CG | GLU A | 321 | 10.461 | 47.847 | −10.091 | 1.00 | 53.37 | C |
| ATOM | 1846 | CD | GLU A | 321 | 11.767 | 47.126 | −10.376 | 1.00 | 54.37 | C |
| ATOM | 1847 | OE1 | GLU A | 321 | 12.698 | 47.245 | −9.539 | 1.00 | 61.14 | O |
| ATOM | 1848 | OE2 | GLU A | 321 | 11.876 | 46.453 | −11.432 | 1.00 | 61.36 | O |
| ATOM | 1849 | C | GLU A | 321 | 7.191 | 48.314 | −12.101 | 1.00 | 51.82 | C |
| ATOM | 1850 | O | GLU A | 321 | 7.089 | 49.376 | −12.722 | 1.00 | 51.98 | O |
| ATOM | 1851 | N | ALA A | 322 | 6.593 | 47.175 | −12.474 | 1.00 | 51.24 | N |
| ATOM | 1852 | CA | ALA A | 322 | 5.765 | 47.068 | −13.677 | 1.00 | 50.91 | C |
| ATOM | 1853 | CB | ALA A | 322 | 5.229 | 45.624 | −13.863 | 1.00 | 50.50 | C |
| ATOM | 1854 | C | ALA A | 322 | 4.611 | 48.063 | −13.677 | 1.00 | 50.84 | C |
| ATOM | 1855 | O | ALA A | 322 | 4.429 | 48.809 | −14.645 | 1.00 | 49.49 | O |
| ATOM | 1856 | N | LYS A | 323 | 3.838 | 48.079 | −12.591 | 1.00 | 52.02 | N |
| ATOM | 1857 | CA | LYS A | 323 | 2.705 | 49.007 | −12.487 | 1.00 | 53.04 | C |
| ATOM | 1858 | CB | LYS A | 323 | 1.620 | 48.513 | −11.529 | 1.00 | 53.04 | C |
| ATOM | 1859 | CG | LYS A | 323 | 2.040 | 47.466 | −10.525 | 1.00 | 54.75 | C |
| ATOM | 1860 | CD | LYS A | 323 | .902 | 46.482 | −10.275 | 1.00 | 42.43 | C |
| ATOM | 1861 | CE | LYS A | 323 | −.350 | 47.176 | −9.740 | 1.00 | 44.16 | C |
| ATOM | 1862 | NZ | LYS A | 323 | −.325 | 47.190 | −8.259 | 1.00 | 53.39 | N |
| ATOM | 1863 | C | LYS A | 323 | 3.085 | 50.441 | −12.181 | 1.00 | 54.26 | C |
| ATOM | 1864 | O | LYS A | 323 | 2.253 | 51.337 | −12.318 | 1.00 | 55.97 | O |
| ATOM | 1865 | N | GLN A | 324 | 4.333 | 50.664 | −11.777 | 1.00 | 55.00 | N |
| ATOM | 1866 | CA | GLN A | 324 | 4.860 | 52.018 | −11.618 | 1.00 | 55.26 | C |
| ATOM | 1867 | CB | GLN A | 324 | 6.206 | 51.992 | −10.881 | 1.00 | 55.79 | C |
| ATOM | 1868 | CG | GLN A | 324 | 6.475 | 53.202 | −9.997 | 1.00 | 59.44 | C |
| ATOM | 1869 | CD | GLN A | 324 | 6.755 | 54.477 | −10.786 | 1.00 | 64.45 | C |
| ATOM | 1870 | OE1 | GLN A | 324 | 7.690 | 54.533 | −11.589 | 1.00 | 62.52 | O |
| ATOM | 1871 | NE2 | GLN A | 324 | 5.945 | 55.511 | −10.550 | 1.00 | 59.86 | N |
| ATOM | 1872 | C | GLN A | 324 | 5.027 | 52.631 | −13.008 | 1.00 | 54.59 | C |
| ATOM | 1873 | O | GLN A | 324 | 4.712 | 53.805 | −13.230 | 1.00 | 54.93 | O |
| ATOM | 1874 | N | LYS A | 325 | 5.508 | 51.810 | −13.940 | 1.00 | 53.55 | N |
| ATOM | 1875 | CA | LYS A | 325 | 5.701 | 52.214 | −15.328 | 1.00 | 52.87 | C |
| ATOM | 1876 | CB | LYS A | 325 | 6.709 | 51.288 | −16.016 | 1.00 | 52.40 | C |
| ATOM | 1877 | CG | LYS A | 325 | 8.077 | 51.243 | −15.348 | 1.00 | 53.59 | C |
| ATOM | 1878 | CD | LYS A | 325 | 8.895 | 50.047 | −15.827 | 1.00 | 55.93 | C |
| ATOM | 1879 | CE | LYS A | 325 | 10.203 | 49.932 | −15.053 | 1.00 | 60.30 | C |
| ATOM | 1880 | NZ | LYS A | 325 | 11.200 | 49.048 | −15.736 | 1.00 | 67.02 | N |
| ATOM | 1881 | C | LYS A | 325 | 4.375 | 52.222 | −16.091 | 1.00 | 52.32 | C |
| ATOM | 1882 | O | LYS A | 325 | 4.331 | 52.569 | −17.276 | 1.00 | 52.29 | O |

TABLE A-continued

| | | | | | | | | | | |
|---|---|---|---|---|---|---|---|---|---|---|
| ATOM | 1883 | N | GLY A | 326 | 3.296 | 51.844 | −15.404 | 1.00 | 51.34 | N |
| ATOM | 1884 | CA | GLY A | 326 | 1.978 | 51.791 | −16.010 | 1.00 | 50.03 | C |
| ATOM | 1885 | C | GLY A | 326 | 1.795 | 50.552 | −16.866 | 1.00 | 50.37 | C |
| ATOM | 1886 | O | GLY A | 326 | .885 | 50.498 | −17.696 | 1.00 | 50.62 | O |
| ATOM | 1887 | N | PHE A | 327 | 2.667 | 49.560 | −16.673 | 1.00 | 50.22 | N |
| ATOM | 1888 | CA | PHE A | 327 | 2.517 | 48.251 | −17.309 | 1.00 | 49.53 | C |
| ATOM | 1889 | CB | PHE A | 327 | 3.866 | 47.529 | −17.422 | 1.00 | 49.44 | C |
| ATOM | 1890 | CG | PHE A | 327 | 4.904 | 48.271 | −18.235 | 1.00 | 50.23 | C |
| ATOM | 1891 | CD1 | PHE A | 327 | 6.249 | 47.968 | −18.086 | 1.00 | 47.27 | C |
| ATOM | 1892 | CE1 | PHE A | 327 | 7.219 | 48.636 | −18.828 | 1.00 | 53.27 | C |
| ATOM | 1893 | CZ | PHE A | 327 | 6.846 | 49.626 | −19.721 | 1.00 | 48.91 | C |
| ATOM | 1894 | CE2 | PHE A | 327 | 5.500 | 49.943 | −19.878 | 1.00 | 52.39 | C |
| ATOM | 1895 | CD2 | PHE A | 327 | 4.539 | 49.272 | −19.138 | 1.00 | 49.59 | C |
| | | | | gad65.pdb | | | | | | |
| ATOM | 1896 | C | PHE A | 327 | 1.533 | 47.407 | −16.502 | 1.00 | 49.74 | C |
| ATOM | 1897 | O | PHE A | 327 | 1.280 | 47.694 | −15.330 | 1.00 | 50.61 | O |
| ATOM | 1898 | N | VAL A | 328 | .977 | 46.370 | −17.123 | 1.00 | 49.89 | N |
| ATOM | 1899 | CA | VAL A | 328 | −.118 | 45.605 | −16.502 | 1.00 | 50.52 | C |
| ATOM | 1900 | CB | VAL A | 328 | −1.426 | 45.688 | −17.327 | 1.00 | 49.47 | C |
| ATOM | 1901 | CG1 | VAL A | 328 | −2.500 | 44.742 | −16.768 | 1.00 | 49.07 | C |
| ATOM | 1902 | CG2 | VAL A | 328 | −1.937 | 47.113 | −17.336 | 1.00 | 51.96 | C |
| ATOM | 1903 | C | VAL A | 328 | .273 | 44.149 | −16.250 | 1.00 | 50.72 | C |
| ATOM | 1904 | O | VAL A | 328 | .360 | 43.353 | −17.189 | 1.00 | 50.97 | O |
| ATOM | 1905 | N | PRO A | 329 | .528 | 43.806 | −14.976 | 1.00 | 50.67 | N |
| ATOM | 1906 | CA | PRO A | 329 | .760 | 42.414 | −14.592 | 1.00 | 49.94 | C |
| ATOM | 1907 | CB | PRO A | 329 | 1.002 | 42.503 | −13.083 | 1.00 | 50.20 | C |
| ATOM | 1908 | CG | PRO A | 329 | 1.432 | 43.919 | −12.843 | 1.00 | 48.97 | C |
| ATOM | 1909 | CD | PRO A | 329 | .628 | 44.718 | −13.819 | 1.00 | 50.68 | C |
| ATOM | 1910 | C | PRO A | 329 | −.485 | 41.600 | −14.869 | 1.00 | 48.92 | C |
| ATOM | 1911 | O | PRO A | 329 | −1.567 | 41.972 | −14.409 | 1.00 | 50.39 | O |
| ATOM | 1912 | N | PHE A | 330 | −.346 | 40.528 | −15.646 | 1.00 | 48.15 | N |
| ATOM | 1913 | CA | PHE A | 330 | −1.480 | 39.629 | −15.940 | 1.00 | 47.02 | C |
| ATOM | 1914 | CB | PHE A | 330 | −1.898 | 39.677 | −17.427 | 1.00 | 45.82 | C |
| ATOM | 1915 | CG | PHE A | 330 | −1.101 | 38.751 | −18.345 | 1.00 | 50.83 | C |
| ATOM | 1916 | CD1 | PHE A | 330 | −1.686 | 37.591 | −18.874 | 1.00 | 44.25 | C |
| ATOM | 1917 | CE1 | PHE A | 330 | −.969 | 36.752 | −19.741 | 1.00 | 45.08 | C |
| ATOM | 1918 | CZ | PHE A | 330 | .339 | 37.066 | −20.084 | 1.00 | 45.20 | C |
| ATOM | 1919 | CE2 | PHE A | 330 | .930 | 38.224 | −19.572 | 1.00 | 46.96 | C |
| ATOM | 1920 | CD2 | PHE A | 330 | .211 | 39.060 | −18.714 | 1.00 | 46.59 | C |
| ATOM | 1921 | C | PHE A | 330 | −1.236 | 38.200 | −15.494 | 1.00 | 45.92 | C |
| ATOM | 1922 | O | PHE A | 330 | −2.173 | 37.443 | −15.348 | 1.00 | 46.70 | O |
| ATOM | 1923 | N | LEU A | 331 | .021 | 37.832 | −15.277 | 1.00 | 46.30 | N |
| ATOM | 1924 | CA | LEU A | 331 | .354 | 36.442 | −14.986 | 1.00 | 45.94 | C |
| ATOM | 1925 | CB | LEU A | 331 | .543 | 35.663 | −16.297 | 1.00 | 45.83 | C |
| ATOM | 1926 | CG | LEU A | 331 | .945 | 34.181 | −16.239 | 1.00 | 48.94 | C |
| ATOM | 1927 | CD1 | LEU A | 331 | −.186 | 33.306 | −15.687 | 1.00 | 42.70 | C |
| ATOM | 1928 | CD2 | LEU A | 331 | 1.343 | 33.745 | −17.626 | 1.00 | 45.89 | C |
| ATOM | 1929 | C | LEU A | 331 | 1.570 | 36.254 | −14.089 | 1.00 | 46.00 | C |
| ATOM | 1930 | O | LEU A | 331 | 2.624 | 36.847 | −14.311 | 1.00 | 47.23 | O |
| ATOM | 1931 | N | VAL A | 332 | 1.423 | 35.421 | −13.069 | 1.00 | 45.66 | N |
| ATOM | 1932 | CA | VAL A | 332 | 2.605 | 34.828 | −12.459 | 1.00 | 46.46 | C |
| ATOM | 1933 | CB | VAL A | 332 | 3.009 | 35.429 | −11.054 | 1.00 | 46.57 | C |
| ATOM | 1934 | CG1 | VAL A | 332 | 1.929 | 36.318 | −10.480 | 1.00 | 45.29 | C |
| ATOM | 1935 | CG2 | VAL A | 332 | 3.503 | 34.359 | −10.069 | 1.00 | 48.77 | C |
| ATOM | 1936 | C | VAL A | 332 | 2.557 | 33.309 | −12.536 | 1.00 | 47.16 | C |
| ATOM | 1937 | O | VAL A | 332 | 1.566 | 32.670 | −12.176 | 1.00 | 47.49 | O |
| ATOM | 1938 | N | SER A | 333 | 3.627 | 32.759 | −13.093 | 1.00 | 47.37 | N |
| ATOM | 1939 | CA | SER A | 333 | 3.776 | 31.335 | −13.231 | 1.00 | 47.52 | C |
| ATOM | 1940 | CB | SER A | 333 | 4.222 | 31.007 | −14.651 | 1.00 | 47.12 | C |
| ATOM | 1941 | OG | SER A | 333 | 3.993 | 29.645 | −14.936 | 1.00 | 45.90 | O |
| ATOM | 1942 | C | SER A | 333 | 4.775 | 30.808 | −12.202 | 1.00 | 47.73 | C |
| ATOM | 1943 | O | SER A | 333 | 5.960 | 31.138 | −12.239 | 1.00 | 48.82 | O |
| ATOM | 1944 | N | ALA A | 334 | 4.277 | 30.009 | −11.272 | 1.00 | 48.20 | N |
| ATOM | 1945 | CA | ALA A | 334 | 5.109 | 29.400 | −10.253 | 1.00 | 48.25 | C |
| ATOM | 1946 | CB | ALA A | 334 | 4.419 | 29.465 | −8.891 | 1.00 | 47.50 | C |
| ATOM | 1947 | C | ALA A | 334 | 5.378 | 27.957 | −10.655 | 1.00 | 49.22 | C |
| ATOM | 1948 | O | ALA A | 334 | 4.513 | 27.297 | −11.242 | 1.00 | 51.52 | O |
| ATOM | 1949 | N | THR A | 335 | 6.575 | 27.472 | −10.355 | 1.00 | 48.21 | N |
| ATOM | 1950 | CA | THR A | 335 | 6.975 | 26.130 | −10.771 | 1.00 | 47.71 | C |
| ATOM | 1951 | CB | THR A | 335 | 8.360 | 26.136 | −11.475 | 1.00 | 47.88 | C |
| ATOM | 1952 | OG1 | THR A | 335 | 8.341 | 27.048 | −12.592 | 1.00 | 43.57 | O |
| ATOM | 1953 | CG2 | THR A | 335 | 8.727 | 24.733 | −11.981 | 1.00 | 48.24 | C |
| ATOM | 1954 | C | THR A | 335 | 6.968 | 25.188 | −9.572 | 1.00 | 48.50 | C |
| ATOM | 1955 | O | THR A | 335 | 7.617 | 25.440 | −8.548 | 1.00 | 49.50 | O |
| ATOM | 1956 | N | ALA A | 336 | 6.196 | 24.119 | −9.693 | 1.00 | 47.90 | N |
| ATOM | 1957 | CA | ALA A | 336 | 6.146 | 23.088 | −8.678 | 1.00 | 47.66 | C |
| ATOM | 1958 | CB | ALA A | 336 | 4.700 | 22.680 | −8.419 | 1.00 | 48.52 | C |
| ATOM | 1959 | C | ALA A | 336 | 6.982 | 21.897 | −9.134 | 1.00 | 46.20 | C |
| ATOM | 1960 | O | ALA A | 336 | 6.451 | 20.892 | −9.629 | 1.00 | 46.26 | O |
| ATOM | 1961 | N | GLY A | 337 | 8.294 | 22.011 | −8.971 | 1.00 | 44.65 | N |

TABLE A-continued

| | | | | | | | | | |
|---|---|---|---|---|---|---|---|---|---|
| ATOM | 1962 | CA | GLY A | 337 | 9.198 | 20.978 | −9.457 | 1.00 | 44.57 | C |
| ATOM | 1963 | C | GLY A | 337 | 9.895 | 21.407 | −10.736 | 1.00 | 43.85 | C |
| | | | | | gad65.pdb | | | | | |
| ATOM | 1964 | O | GLY A | 337 | 9.407 | 21.163 | −11.846 | 1.00 | 42.85 | O |
| ATOM | 1965 | N | THR A | 338 | 11.043 | 22.056 | −10.572 | 1.00 | 43.19 | N |
| ATOM | 1966 | CA | THR A | 338 | 11.821 | 22.516 | −11.699 | 1.00 | 43.87 | C |
| ATOM | 1967 | CB | THR A | 338 | 12.857 | 23.575 | −11.295 | 1.00 | 44.53 | C |
| ATOM | 1968 | OG1 | THR A | 338 | 13.762 | 23.002 | −10.346 | 1.00 | 41.38 | O |
| ATOM | 1969 | CG2 | THR A | 338 | 12.168 | 24.815 | −10.701 | 1.00 | 45.89 | C |
| ATOM | 1970 | C | THR A | 338 | 12.552 | 21.350 | −12.321 | 1.00 | 44.74 | C |
| ATOM | 1971 | O | THR A | 338 | 12.856 | 20.353 | −11.657 | 1.00 | 45.18 | O |
| ATOM | 1972 | N | THR A | 339 | 12.832 | 21.509 | −13.602 | 1.00 | 44.87 | N |
| ATOM | 1973 | CA | THR A | 339 | 13.496 | 20.510 | −14.439 | 1.00 | 47.26 | C |
| ATOM | 1974 | CB | THR A | 339 | 13.493 | 21.037 | −15.871 | 1.00 | 47.22 | C |
| ATOM | 1975 | OG1 | THR A | 339 | 12.241 | 20.674 | −16.464 | 1.00 | 52.79 | O |
| ATOM | 1976 | CG2 | THR A | 339 | 14.640 | 20.505 | −16.683 | 1.00 | 53.50 | C |
| ATOM | 1977 | C | THR A | 339 | 14.911 | 20.102 | −13.987 | 1.00 | 46.42 | C |
| ATOM | 1978 | O | THR A | 339 | 15.282 | 18.936 | −14.098 | 1.00 | 46.14 | O |
| ATOM | 1979 | N | VAL A | 340 | 15.685 | 21.050 | −13.459 | 1.00 | 45.50 | N |
| ATOM | 1980 | CA | VAL A | 340 | 17.049 | 20.739 | −13.036 | 1.00 | 45.04 | C |
| ATOM | 1981 | CB | VAL A | 340 | 18.055 | 21.830 | −13.477 | 1.00 | 46.18 | C |
| ATOM | 1982 | CG1 | VAL A | 340 | 19.497 | 21.380 | −13.211 | 1.00 | 44.04 | C |
| ATOM | 1983 | CG2 | VAL A | 340 | 17.854 | 22.158 | −14.972 | 1.00 | 43.32 | C |
| ATOM | 1984 | C | VAL A | 340 | 17.124 | 20.402 | −11.537 | 1.00 | 44.76 | C |
| ATOM | 1985 | O | VAL A | 340 | 17.299 | 19.237 | −11.181 | 1.00 | 43.13 | O |
| ATOM | 1986 | N | TYR A | 341 | 16.948 | 21.400 | −10.669 | 1.00 | 45.18 | N |
| ATOM | 1987 | CA | TYR A | 341 | 17.042 | 21.181 | −9.219 | 1.00 | 46.11 | C |
| ATOM | 1988 | CB | TYR A | 341 | 17.126 | 22.519 | −8.470 | 1.00 | 47.45 | C |
| ATOM | 1989 | CG | TYR A | 341 | 18.463 | 23.251 | −8.513 | 1.00 | 48.39 | C |
| ATOM | 1990 | CD1 | TYR A | 341 | 18.720 | 24.297 | −7.622 | 1.00 | 47.83 | C |
| ATOM | 1991 | CE1 | TYR A | 341 | 19.918 | 24.990 | −7.649 | 1.00 | 48.38 | C |
| ATOM | 1992 | CZ | TYR A | 341 | 20.888 | 24.633 | −8.564 | 1.00 | 47.70 | C |
| ATOM | 1993 | OH | TYR A | 341 | 22.073 | 25.317 | −8.583 | 1.00 | 55.19 | O |
| ATOM | 1994 | CE2 | TYR A | 341 | 20.673 | 23.597 | −9.459 | 1.00 | 49.52 | C |
| ATOM | 1995 | CD2 | TYR A | 341 | 19.458 | 22.911 | −9.431 | 1.00 | 45.49 | C |
| ATOM | 1996 | C | TYR A | 341 | 15.869 | 20.365 | −8.650 | 1.00 | 45.62 | C |
| ATOM | 1997 | O | TYR A | 341 | 15.979 | 19.778 | −7.572 | 1.00 | 46.73 | O |
| ATOM | 1998 | N | GLY A | 342 | 14.749 | 20.339 | −9.365 | 1.00 | 44.01 | N |
| ATOM | 1999 | CA | GLY A | 342 | 13.529 | 19.751 | −8.829 | 1.00 | 44.35 | C |
| ATOM | 2000 | C | GLY A | 342 | 12.954 | 20.621 | −7.720 | 1.00 | 43.73 | C |
| ATOM | 2001 | O | GLY A | 342 | 12.315 | 20.113 | −6.815 | 1.00 | 44.93 | O |
| ATOM | 2002 | N | ALA A | 343 | 13.198 | 21.930 | −7.794 | 1.00 | 43.64 | N |
| ATOM | 2003 | CA | ALA A | 343 | 12.785 | 22.880 | −6.752 | 1.00 | 43.88 | C |
| ATOM | 2004 | CB | ALA A | 343 | 13.619 | 24.153 | −6.828 | 1.00 | 42.20 | C |
| ATOM | 2005 | C | ALA A | 343 | 11.306 | 23.229 | −6.839 | 1.00 | 44.05 | C |
| ATOM | 2006 | O | ALA A | 343 | 10.720 | 23.207 | −7.922 | 1.00 | 45.82 | O |
| ATOM | 2007 | N | PHE A | 344 | 10.725 | 23.581 | −5.700 | 1.00 | 43.77 | N |
| ATOM | 2008 | CA | PHE A | 344 | 9.305 | 23.911 | −5.601 | 1.00 | 44.27 | C |
| ATOM | 2009 | CB | PHE A | 344 | 8.599 | 22.972 | −4.609 | 1.00 | 43.48 | C |
| ATOM | 2010 | CG | PHE A | 344 | 8.404 | 21.565 | −5.127 | 1.00 | 44.71 | C |
| ATOM | 2011 | CD1 | PHE A | 344 | 9.431 | 20.628 | −5.050 | 1.00 | 44.03 | C |
| ATOM | 2012 | CE1 | PHE A | 344 | 9.250 | 19.324 | −5.532 | 1.00 | 42.86 | C |
| ATOM | 2013 | CZ | PHE A | 344 | 8.031 | 18.951 | −6.093 | 1.00 | 42.83 | C |
| ATOM | 2014 | CE2 | PHE A | 344 | 6.999 | 19.871 | −6.169 | 1.00 | 38.18 | C |
| ATOM | 2015 | CD2 | PHE A | 344 | 7.188 | 21.174 | −5.685 | 1.00 | 43.36 | C |
| ATOM | 2016 | C | PHE A | 344 | 9.176 | 25.343 | −5.138 | 1.00 | 44.45 | C |
| ATOM | 2017 | O | PHE A | 344 | 9.672 | 25.689 | −4.070 | 1.00 | 45.16 | O |
| ATOM | 2018 | N | ASP A | 345 | 8.534 | 26.185 | −5.945 | 1.00 | 44.77 | N |
| ATOM | 2019 | CA | ASP A | 345 | 8.317 | 27.578 | −5.554 | 1.00 | 46.02 | C |
| ATOM | 2020 | CB | ASP A | 345 | 7.818 | 28.412 | −6.739 | 1.00 | 46.38 | C |
| ATOM | 2021 | CG | ASP A | 345 | 8.899 | 28.625 | −7.812 | 1.00 | 53.24 | C |
| ATOM | 2022 | OD1 | ASP A | 345 | 10.078 | 28.290 | −7.553 | 1.00 | 57.05 | O |
| ATOM | 2023 | OD2 | ASP A | 345 | 8.573 | 29.127 | −8.918 | 1.00 | 52.26 | O |
| ATOM | 2024 | C | ASP A | 345 | 7.364 | 27.654 | −4.344 | 1.00 | 45.84 | C |
| ATOM | 2025 | O | ASP A | 345 | 6.546 | 26.764 | −4.151 | 1.00 | 45.20 | O |
| ATOM | 2026 | N | PRO A | 346 | 7.495 | 28.701 | −3.507 | 1.00 | 46.07 | N |
| ATOM | 2027 | CA | PRO A | 346 | 6.630 | 28.756 | −2.334 | 1.00 | 45.86 | C |
| ATOM | 2028 | CB | PRO A | 346 | 7.379 | 29.692 | −1.387 | 1.00 | 45.74 | C |
| ATOM | 2029 | CG | PRO A | 346 | 8.261 | 30.537 | −2.270 | 1.00 | 45.68 | C |
| ATOM | 2030 | CD | PRO A | 346 | 8.398 | 29.867 | −3.599 | 1.00 | 46.17 | C |
| ATOM | 2031 | C | PRO A | 346 | 5.233 | 29.275 | −2.699 | 1.00 | 46.08 | C |
| | | | | | gad65.pdb | | | | | |
| ATOM | 2032 | O | PRO A | 346 | 4.995 | 30.479 | −2.725 | 1.00 | 45.52 | O |
| ATOM | 2033 | N | LEU A | 347 | 4.327 | 28.338 | −2.965 | 1.00 | 46.08 | N |
| ATOM | 2034 | CA | LEU A | 347 | 3.016 | 28.624 | −3.543 | 1.00 | 47.01 | C |
| ATOM | 2035 | CB | LEU A | 347 | 2.302 | 27.320 | −3.950 | 1.00 | 45.99 | C |
| ATOM | 2036 | CG | LEU A | 347 | 2.960 | 26.409 | −4.995 | 1.00 | 43.28 | C |
| ATOM | 2037 | CD1 | LEU A | 347 | 1.994 | 25.316 | −5.511 | 1.00 | 41.92 | C |
| ATOM | 2038 | CD2 | LEU A | 347 | 3.513 | 27.198 | −6.181 | 1.00 | 46.23 | C |
| ATOM | 2039 | C | LEU A | 347 | 2.105 | 29.491 | −2.672 | 1.00 | 48.39 | C |

TABLE A-continued

| | | | | | | | | | | |
|---|---|---|---|---|---|---|---|---|---|---|
| ATOM | 2040 | O | LEU A | 347 | 1.365 | 30.322 | −3.192 | 1.00 | 49.03 | O |
| ATOM | 2041 | N | LEU A | 348 | 2.173 | 29.297 | −1.357 | 1.00 | 49.45 | N |
| ATOM | 2042 | CA | LEU A | 348 | 1.348 | 30.037 | −.398 | 1.00 | 49.56 | C |
| ATOM | 2043 | CB | LEU A | 348 | 1.469 | 29.420 | 1.001 | 1.00 | 49.70 | C |
| ATOM | 2044 | CG | LEU A | 348 | .882 | 28.008 | 1.157 | 1.00 | 52.50 | C |
| ATOM | 2045 | CD1 | LEU A | 348 | 1.466 | 27.307 | 2.374 | 1.00 | 58.56 | C |
| ATOM | 2046 | CD2 | LEU A | 348 | −.642 | 28.018 | 1.221 | 1.00 | 53.83 | C |
| ATOM | 2047 | C | LEU A | 348 | 1.697 | 31.526 | −.359 | 1.00 | 50.05 | C |
| ATOM | 2048 | O | LEU A | 348 | .825 | 32.366 | −.122 | 1.00 | 50.07 | O |
| ATOM | 2049 | N | ALA A | 349 | 2.966 | 31.840 | −.609 | 1.00 | 49.96 | N |
| ATOM | 2050 | CA | ALA A | 349 | 3.441 | 33.221 | −.648 | 1.00 | 50.42 | C |
| ATOM | 2051 | CB | ALA A | 349 | 4.942 | 33.285 | −.317 | 1.00 | 50.88 | C |
| ATOM | 2052 | C | ALA A | 349 | 3.154 | 33.911 | −1.991 | 1.00 | 50.35 | C |
| ATOM | 2053 | O | ALA A | 349 | 2.794 | 35.099 | −2.008 | 1.00 | 50.24 | O |
| ATOM | 2054 | N | VAL A | 350 | 3.323 | 33.187 | −3.104 | 1.00 | 49.70 | N |
| ATOM | 2055 | CA | VAL A | 350 | 2.969 | 33.735 | −4.420 | 1.00 | 50.11 | C |
| ATOM | 2056 | CB | VAL A | 350 | 3.666 | 33.043 | −5.674 | 1.00 | 51.35 | C |
| ATOM | 2057 | CG1 | VAL A | 350 | 4.491 | 31.815 | −5.318 | 1.00 | 52.34 | C |
| ATOM | 2058 | CG2 | VAL A | 350 | 2.666 | 32.767 | −6.796 | 1.00 | 49.36 | C |
| ATOM | 2059 | C | VAL A | 350 | 1.458 | 33.876 | −4.590 | 1.00 | 50.52 | C |
| ATOM | 2060 | O | VAL A | 350 | .993 | 34.843 | −5.198 | 1.00 | 50.78 | O |
| ATOM | 2061 | N | ALA A | 351 | .708 | 32.921 | −4.035 | 1.00 | 50.08 | N |
| ATOM | 2062 | CA | ALA A | 351 | −.750 | 32.995 | −3.997 | 1.00 | 50.14 | C |
| ATOM | 2063 | CB | ALA A | 351 | −1.325 | 31.800 | −3.264 | 1.00 | 49.35 | C |
| ATOM | 2064 | C | ALA A | 351 | −1.190 | 34.289 | −3.326 | 1.00 | 51.12 | C |
| ATOM | 2065 | O | ALA A | 351 | −2.102 | 34.967 | −3.812 | 1.00 | 51.32 | O |
| ATOM | 2066 | N | ASP A | 352 | −.517 | 34.618 | −2.218 | 1.00 | 51.57 | N |
| ATOM | 2067 | CA | ASP A | 352 | −.753 | 35.838 | −1.441 | 1.00 | 51.31 | C |
| ATOM | 2068 | CB | ASP A | 352 | .051 | 35.798 | −.141 | 1.00 | 51.61 | C |
| ATOM | 2069 | CG | ASP A | 352 | −.594 | 34.918 | .907 | 1.00 | 54.25 | C |
| ATOM | 2070 | OD1 | ASP A | 352 | −1.807 | 34.651 | .781 | 1.00 | 54.78 | O |
| ATOM | 2071 | OD2 | ASP A | 352 | .108 | 34.489 | 1.847 | 1.00 | 56.16 | O |
| ATOM | 2072 | C | ASP A | 352 | −.416 | 37.103 | −2.202 | 1.00 | 50.32 | C |
| ATOM | 2073 | O | ASP A | 352 | −1.086 | 38.122 | −2.047 | 1.00 | 50.49 | O |
| ATOM | 2074 | N | ILE A | 353 | .631 | 37.031 | −3.015 | 1.00 | 50.20 | N |
| ATOM | 2075 | CA | ILE A | 353 | 1.042 | 38.150 | −3.858 | 1.00 | 49.47 | C |
| ATOM | 2076 | CB | ILE A | 353 | 2.539 | 37.980 | −4.309 | 1.00 | 49.75 | C |
| ATOM | 2077 | CG1 | ILE A | 353 | 3.474 | 38.396 | −3.166 | 1.00 | 47.42 | C |
| ATOM | 2078 | CD | ILE A | 353 | 4.847 | 37.709 | −3.187 | 1.00 | 53.67 | C |
| ATOM | 2079 | CG2 | ILE A | 353 | 2.871 | 38.775 | −5.566 | 1.00 | 45.61 | C |
| ATOM | 2080 | C | ILE A | 353 | .035 | 38.306 | −5.011 | 1.00 | 48.98 | C |
| ATOM | 2081 | O | ILE A | 353 | −.334 | 39.424 | −5.375 | 1.00 | 49.12 | O |
| ATOM | 2082 | N | CYS A | 354 | −.439 | 37.179 | −5.537 | 1.00 | 48.08 | N |
| ATOM | 2083 | CA | CYS A | 354 | −1.416 | 37.170 | −6.617 | 1.00 | 49.55 | C |
| ATOM | 2084 | CB | CYS A | 354 | −1.497 | 35.778 | −7.234 | 1.00 | 50.22 | C |
| ATOM | 2085 | SG | CYS A | 354 | −.038 | 35.330 | −8.191 | 1.00 | 49.46 | S |
| ATOM | 2086 | C | CYS A | 354 | −2.808 | 37.634 | −6.171 | 1.00 | 50.71 | C |
| ATOM | 2087 | O | CYS A | 354 | −3.551 | 38.225 | −6.955 | 1.00 | 50.91 | O |
| ATOM | 2088 | N | LYS A | 355 | −3.142 | 37.339 | −4.916 | 1.00 | 51.44 | N |
| ATOM | 2089 | CA | LYS A | 355 | −4.327 | 37.859 | −4.227 | 1.00 | 52.18 | C |
| ATOM | 2090 | CB | LYS A | 355 | −4.439 | 37.192 | −2.852 | 1.00 | 52.06 | C |
| ATOM | 2091 | CG | LYS A | 355 | −5.833 | 37.070 | −2.290 | 1.00 | 59.08 | C |
| ATOM | 2092 | CD | LYS A | 355 | −5.812 | 36.207 | −1.027 | 1.00 | 63.18 | C |
| ATOM | 2093 | CE | LYS A | 355 | −7.210 | 35.790 | −.611 | 1.00 | 69.58 | C |
| ATOM | 2094 | NZ | LYS A | 355 | −7.177 | 34.817 | .524 | 1.00 | 73.08 | N |
| ATOM | 2095 | C | LYS A | 355 | −4.210 | 39.370 | −4.039 | 1.00 | 51.64 | C |
| ATOM | 2096 | O | LYS A | 355 | −5.127 | 40.116 | −4.361 | 1.00 | 51.81 | O |
| ATOM | 2097 | N | LYS A | 356 | −3.068 | 39.810 | −3.517 | 1.00 | 51.49 | N |
| ATOM | 2098 | CA | LYS A | 356 | −2.812 | 41.227 | −3.277 | 1.00 | 51.27 | C |
| ATOM | 2099 | CB | LYS A | 356 | −1.418 | 41.402 | −2.675 | 1.00 | 50.67 | C |
| ATOM | 2100 | CG | LYS A | 356 | −1.074 | 42.804 | −2.184 | 1.00 | 54.27 | C |
| ATOM | 2101 | CD | LYS A | 356 | .294 | 42.776 | −1.518 | 1.00 | 56.36 | C |
| ATOM | 2102 | CE | LYS A | 356 | .480 | 43.892 | −.511 | 1.00 | 61.10 | C |
| ATOM | 2103 | NZ | LYS A | 356 | 1.112 | 45.104 | −1.095 | 1.00 | 62.51 | N |
| ATOM | 2104 | C | LYS A | 356 | −2.964 | 42.066 | −4.555 | 1.00 | 51.00 | C |
| ATOM | 2105 | O | LYS A | 356 | −3.657 | 43.092 | −4.559 | 1.00 | 50.73 | O |
| ATOM | 2106 | N | TYR A | 357 | −2.338 | 41.610 | −5.638 | 1.00 | 50.35 | N |
| ATOM | 2107 | CA | TYR A | 357 | −2.266 | 42.400 | −6.867 | 1.00 | 50.02 | C |
| ATOM | 2108 | CB | TYR A | 357 | −.837 | 42.385 | −7.413 | 1.00 | 50.30 | C |
| ATOM | 2109 | CG | TYR A | 357 | .139 | 43.044 | −6.463 | 1.00 | 53.42 | C |
| ATOM | 2110 | CD1 | TYR A | 357 | .109 | 44.423 | −6.245 | 1.00 | 52.96 | C |
| ATOM | 2111 | CE1 | TYR A | 357 | .997 | 45.027 | −5.368 | 1.00 | 51.57 | C |
| ATOM | 2112 | CZ | TYR A | 357 | 1.926 | 44.254 | −4.693 | 1.00 | 52.08 | C |
| ATOM | 2113 | OH | TYR A | 357 | 2.807 | 44.851 | −3.814 | 1.00 | 52.47 | O |
| ATOM | 2114 | CE2 | TYR A | 357 | 1.971 | 42.885 | −4.884 | 1.00 | 49.26 | C |
| ATOM | 2115 | CD2 | TYR A | 357 | 1.079 | 42.288 | −5.761 | 1.00 | 52.61 | C |
| ATOM | 2116 | C | TYR A | 357 | −3.300 | 42.035 | −7.935 | 1.00 | 49.26 | C |
| ATOM | 2117 | O | TYR A | 357 | −3.331 | 42.641 | −9.008 | 1.00 | 48.90 | O |
| ATOM | 2118 | N | LYS A | 358 | −4.153 | 41.062 | −7.610 | 1.00 | 49.15 | N | gad65.pdb

TABLE A-continued

| | | | | | | | | | | |
|---|---|---|---|---|---|---|---|---|---|---|
| ATOM | 2119 | CA | LYS A | 358 | −5.252 | 40.594 | −8.474 | 1.00 | 48.68 | C |
| ATOM | 2120 | CB | LYS A | 358 | −6.311 | 41.676 | −8.695 | 1.00 | 49.07 | C |
| ATOM | 2121 | CG | LYS A | 358 | −6.869 | 42.294 | −7.420 | 1.00 | 51.39 | C |
| ATOM | 2122 | CD | LYS A | 358 | −7.620 | 43.584 | −7.728 | 1.00 | 57.80 | C |
| ATOM | 2123 | CE | LYS A | 358 | −9.020 | 43.328 | −8.267 | 1.00 | 62.27 | C |
| ATOM | 2124 | NZ | LYS A | 358 | −9.985 | 42.991 | −7.176 | 1.00 | 69.10 | N |
| ATOM | 2125 | C | LYS A | 358 | −4.728 | 40.073 | −9.798 | 1.00 | 47.88 | C |
| ATOM | 2126 | O | LYS A | 358 | −5.137 | 40.524 | −10.877 | 1.00 | 47.90 | O |
| ATOM | 2127 | N | ILE A | 359 | −3.820 | 39.106 | −9.697 | 1.00 | 47.06 | N |
| ATOM | 2128 | CA | ILE A | 359 | −3.146 | 38.529 | −10.852 | 1.00 | 45.27 | C |
| ATOM | 2129 | CB | ILE A | 359 | −1.601 | 38.714 | −10.767 | 1.00 | 44.89 | C |
| ATOM | 2130 | CG1 | ILE A | 359 | −1.211 | 40.142 | −10.413 | 1.00 | 47.52 | C |
| ATOM | 2131 | CD | ILE A | 359 | .316 | 40.311 | −10.162 | 1.00 | 45.59 | C |
| ATOM | 2132 | CG2 | ILE A | 359 | −.914 | 38.281 | −12.066 | 1.00 | 45.27 | C |
| ATOM | 2133 | C | ILE A | 359 | −3.436 | 37.031 | −10.900 | 1.00 | 44.14 | C |
| ATOM | 2134 | O | ILE A | 359 | −3.454 | 36.371 | −9.865 | 1.00 | 44.28 | O |
| ATOM | 2135 | N | TRP A | 360 | −3.638 | 36.508 | −12.110 | 1.00 | 43.38 | N |
| ATOM | 2136 | CA | TRP A | 360 | −3.748 | 35.070 | −12.359 | 1.00 | 42.82 | C |
| ATOM | 2137 | CB | TRP A | 360 | −3.901 | 34.831 | −13.859 | 1.00 | 42.49 | C |
| ATOM | 2138 | CG | TRP A | 360 | −4.243 | 33.410 | −14.275 | 1.00 | 45.30 | C |
| ATOM | 2139 | CD1 | TRP A | 360 | −3.389 | 32.348 | −14.370 | 1.00 | 42.22 | C |
| ATOM | 2140 | NE1 | TRP A | 360 | −4.071 | 31.227 | −14.794 | 1.00 | 45.74 | N |
| ATOM | 2141 | CE2 | TRP A | 360 | −5.383 | 31.555 | −15.002 | 1.00 | 44.68 | C |
| ATOM | 2142 | CD2 | TRP A | 360 | −5.529 | 32.929 | −14.694 | 1.00 | 45.01 | C |
| ATOM | 2143 | CE3 | TRP A | 360 | −6.795 | 33.522 | −14.819 | 1.00 | 43.02 | C |
| ATOM | 2144 | CZ3 | TRP A | 360 | −7.865 | 32.733 | −15.254 | 1.00 | 43.00 | C |
| ATOM | 2145 | CH2 | TRP A | 360 | −7.684 | 31.367 | −15.562 | 1.00 | 41.18 | C |
| ATOM | 2146 | CZ2 | TRP A | 360 | −6.459 | 30.762 | −15.443 | 1.00 | 42.12 | C |
| ATOM | 2147 | C | TRP A | 360 | −2.508 | 34.332 | −11.852 | 1.00 | 42.64 | C |
| ATOM | 2148 | O | TRP A | 360 | −1.373 | 34.700 | −12.194 | 1.00 | 41.88 | O |
| ATOM | 2149 | N | MET A | 361 | −2.740 | 33.301 | −11.043 | 1.00 | 43.23 | N |
| ATOM | 2150 | CA | MET A | 361 | −1.690 | 32.381 | −10.599 | 1.00 | 45.52 | C |
| ATOM | 2151 | CB | MET A | 361 | −1.788 | 32.106 | −9.088 | 1.00 | 44.83 | C |
| ATOM | 2152 | CG | MET A | 361 | −.580 | 31.333 | −8.515 | 1.00 | 49.16 | C |
| ATOM | 2153 | SD | MET A | 361 | −.848 | 30.684 | −6.849 | 1.00 | 50.69 | S |
| ATOM | 2154 | CE | MET A | 361 | .491 | 29.517 | −6.676 | 1.00 | 55.42 | C |
| ATOM | 2155 | C | MET A | 361 | −1.734 | 31.062 | −11.387 | 1.00 | 43.41 | C |
| ATOM | 2156 | O | MET A | 361 | −2.699 | 30.309 | −11.312 | 1.00 | 42.13 | O |
| ATOM | 2157 | N | HIS A | 362 | −.678 | 30.788 | −12.144 | 1.00 | 42.35 | N |
| ATOM | 2158 | CA | HIS A | 362 | −.543 | 29.505 | −12.810 | 1.00 | 40.97 | C |
| ATOM | 2159 | CB | HIS A | 362 | −.139 | 29.710 | −14.271 | 1.00 | 42.12 | C |
| ATOM | 2160 | CG | HIS A | 362 | .131 | 28.436 | −15.012 | 1.00 | 41.99 | C |
| ATOM | 2161 | ND1 | HIS A | 362 | −.835 | 27.472 | −15.202 | 1.00 | 40.73 | N |
| ATOM | 2162 | CE1 | HIS A | 362 | −.314 | 26.461 | −15.875 | 1.00 | 44.15 | C |
| ATOM | 2163 | NE2 | HIS A | 362 | .953 | 26.739 | −16.135 | 1.00 | 45.22 | N |
| ATOM | 2164 | CD2 | HIS A | 362 | 1.259 | 27.965 | −15.598 | 1.00 | 36.70 | C |
| ATOM | 2165 | C | HIS A | 362 | .496 | 28.679 | −12.067 | 1.00 | 41.51 | C |
| ATOM | 2166 | O | HIS A | 362 | 1.493 | 29.223 | −11.572 | 1.00 | 42.07 | O |
| ATOM | 2167 | N | VAL A | 363 | .263 | 27.372 | −11.958 | 1.00 | 41.32 | N |
| ATOM | 2168 | CA | VAL A | 363 | 1.297 | 26.472 | −11.446 | 1.00 | 40.94 | C |
| ATOM | 2169 | CB | VAL A | 363 | .892 | 25.741 | −10.132 | 1.00 | 40.43 | C |
| ATOM | 2170 | CG1 | VAL A | 363 | 1.993 | 24.783 | −9.671 | 1.00 | 37.48 | C |
| ATOM | 2171 | CG2 | VAL A | 363 | .649 | 26.736 | −9.042 | 1.00 | 39.11 | C |
| ATOM | 2172 | C | VAL A | 363 | 1.742 | 25.483 | −12.515 | 1.00 | 40.94 | C |
| ATOM | 2173 | O | VAL A | 363 | .956 | 24.651 | −12.982 | 1.00 | 40.96 | O |
| ATOM | 2174 | N | ASP A | 364 | 3.002 | 25.601 | −12.925 | 1.00 | 41.19 | N |
| ATOM | 2175 | CA | ASP A | 364 | 3.613 | 24.592 | −13.786 | 1.00 | 40.37 | C |
| ATOM | 2176 | CB | ASP A | 364 | 4.831 | 25.140 | −14.555 | 1.00 | 39.72 | C |
| ATOM | 2177 | CG | ASP A | 364 | 5.393 | 24.129 | −15.557 | 1.00 | 44.48 | C |
| ATOM | 2178 | OD1 | ASP A | 364 | 4.884 | 22.984 | −15.589 | 1.00 | 36.63 | O |
| ATOM | 2179 | OD2 | ASP A | 364 | 6.345 | 24.467 | −16.310 | 1.00 | 43.39 | O |
| ATOM | 2180 | C | ASP A | 364 | 4.011 | 23.415 | −12.906 | 1.00 | 41.19 | C |
| ATOM | 2181 | O | ASP A | 364 | 5.103 | 23.391 | −12.335 | 1.00 | 41.71 | O |
| ATOM | 2182 | N | ALA A | 365 | 3.109 | 22.446 | −12.789 | 1.00 | 41.78 | N |
| ATOM | 2183 | CA | ALA A | 365 | 3.400 | 21.208 | −12.073 | 1.00 | 40.91 | C |
| ATOM | 2184 | CB | ALA A | 365 | 2.298 | 20.915 | −11.052 | 1.00 | 40.27 | C |
| ATOM | 2185 | C | ALA A | 365 | 3.610 | 20.020 | −13.037 | 1.00 | 41.05 | C |
| ATOM | 2186 | O | ALA A | 365 | 3.367 | 18.872 | −12.683 | 1.00 | 40.35 | O |
| ATOM | 2187 | N | ALA A | 366 | 4.088 | 20.306 | −14.247 | 1.00 | 42.19 | N |
| ATOM | 2188 | CA | ALA A | 366 | 4.361 | 19.269 | −15.248 | 1.00 | 43.64 | C |
| ATOM | 2189 | CB | ALA A | 366 | 5.124 | 19.860 | −16.433 | 1.00 | 44.98 | C |
| ATOM | 2190 | C | ALA A | 366 | 5.134 | 18.096 | −14.653 | 1.00 | 44.22 | C |
| ATOM | 2191 | O | ALA A | 366 | 4.776 | 16.935 | −14.862 | 1.00 | 46.58 | O |
| ATOM | 2192 | N | TRP A | 367 | 6.169 | 18.417 | −13.883 | 1.00 | 44.21 | N |
| ATOM | 2193 | CA | TRP A | 367 | 7.067 | 17.452 | −13.263 | 1.00 | 43.36 | C |
| ATOM | 2194 | CB | TRP A | 367 | 8.473 | 18.040 | −13.317 | 1.00 | 42.80 | C |
| ATOM | 2195 | CG | TRP A | 367 | 9.606 | 17.285 | −12.637 | 1.00 | 41.79 | C |
| ATOM | 2196 | CD1 | TRP A | 367 | 10.590 | 17.835 | −11.873 | 1.00 | 42.18 | C |
| ATOM | 2197 | NE1 | TRP A | 367 | 11.465 | 16.866 | −11.442 | 1.00 | 41.93 | N | gad65.pdb

TABLE A-continued

| | | | | | | | | | |
|---|---|---|---|---|---|---|---|---|---|
| ATOM | 2198 | CE2 | TRP A | 367 | 11.072 | 15.653 | −11.937 | 1.00 | 44.11 | C |
| ATOM | 2199 | CD2 | TRP A | 367 | 9.902 | 15.873 | −12.710 | 1.00 | 47.96 | C |
| ATOM | 2200 | CE3 | TRP A | 367 | 9.289 | 14.776 | −13.339 | 1.00 | 48.03 | C |
| ATOM | 2201 | CZ3 | TRP A | 367 | 9.853 | 13.515 | −13.174 | 1.00 | 47.57 | C |
| ATOM | 2202 | CH2 | TRP A | 367 | 11.032 | 13.332 | −12.402 | 1.00 | 44.02 | C |
| ATOM | 2203 | CZ2 | TRP A | 367 | 11.647 | 14.386 | −11.781 | 1.00 | 41.43 | C |
| ATOM | 2204 | C | TRP A | 367 | 6.645 | 17.146 | −11.812 | 1.00 | 44.17 | C |
| ATOM | 2205 | O | TRP A | 367 | 6.568 | 15.984 | −11.415 | 1.00 | 43.72 | O |
| ATOM | 2206 | N | GLY A | 368 | 6.366 | 18.194 | −11.038 | 1.00 | 44.17 | N |
| ATOM | 2207 | CA | GLY A | 368 | 6.035 | 18.053 | −9.624 | 1.00 | 44.81 | C |
| ATOM | 2208 | C | GLY A | 368 | 4.651 | 17.514 | −9.299 | 1.00 | 45.08 | C |
| ATOM | 2209 | O | GLY A | 368 | 4.420 | 17.060 | −8.181 | 1.00 | 46.14 | O |
| ATOM | 2210 | N | GLY A | 369 | 3.741 | 17.563 | −10.273 | 1.00 | 45.70 | N |
| ATOM | 2211 | CA | GLY A | 369 | 2.354 | 17.100 | −10.102 | 1.00 | 46.28 | C |
| ATOM | 2212 | C | GLY A | 369 | 2.166 | 15.690 | −9.560 | 1.00 | 46.79 | C |
| ATOM | 2213 | O | GLY A | 369 | 1.185 | 15.416 | −8.865 | 1.00 | 47.52 | O |
| ATOM | 2214 | N | GLY A | 370 | 3.098 | 14.791 | −9.872 | 1.00 | 46.42 | N |
| ATOM | 2215 | CA | GLY A | 370 | 3.063 | 13.414 | −9.351 | 1.00 | 45.80 | C |
| ATOM | 2216 | C | GLY A | 370 | 3.071 | 13.316 | −7.830 | 1.00 | 45.49 | C |
| ATOM | 2217 | O | GLY A | 370 | 2.434 | 12.427 | −7.255 | 1.00 | 44.44 | O |
| ATOM | 2218 | N | LEU A | 371 | 3.787 | 14.227 | −7.174 | 1.00 | 45.96 | N |
| ATOM | 2219 | CA | LEU A | 371 | 3.866 | 14.238 | −5.702 | 1.00 | 48.00 | C |
| ATOM | 2220 | CB | LEU A | 371 | 4.947 | 15.212 | −5.215 | 1.00 | 48.00 | C |
| ATOM | 2221 | CG | LEU A | 371 | 6.429 | 14.782 | −5.191 | 1.00 | 49.56 | C |
| ATOM | 2222 | CD1 | LEU A | 371 | 6.998 | 14.410 | −6.567 | 1.00 | 49.02 | C |
| ATOM | 2223 | CD2 | LEU A | 371 | 7.253 | 15.892 | −4.590 | 1.00 | 47.74 | C |
| ATOM | 2224 | C | LEU A | 371 | 2.521 | 14.556 | −5.027 | 1.00 | 48.73 | C |
| ATOM | 2225 | O | LEU A | 371 | 2.376 | 14.374 | −3.822 | 1.00 | 49.43 | O |
| ATOM | 2226 | N | LEU A | 372 | 1.549 | 15.023 | −5.814 | 1.00 | 48.72 | N |
| ATOM | 2227 | CA | LEU A | 372 | .188 | 15.260 | −5.334 | 1.00 | 49.50 | C |
| ATOM | 2228 | CB | LEU A | 372 | −.601 | 16.075 | −6.356 | 1.00 | 50.25 | C |
| ATOM | 2229 | CG | LEU A | 372 | −.254 | 17.555 | −6.426 | 1.00 | 48.39 | C |
| ATOM | 2230 | CD1 | LEU A | 372 | −.907 | 18.195 | −7.645 | 1.00 | 46.47 | C |
| ATOM | 2231 | CD2 | LEU A | 372 | −.678 | 18.242 | −5.129 | 1.00 | 46.71 | C |
| ATOM | 2232 | C | LEU A | 372 | −.542 | 13.953 | −5.044 | 1.00 | 49.03 | C |
| ATOM | 2233 | O | LEU A | 372 | −1.543 | 13.938 | −4.323 | 1.00 | 49.45 | O |
| ATOM | 2234 | N | MET A | 373 | −.021 | 12.865 | −5.599 | 1.00 | 49.03 | N |
| ATOM | 2235 | CA | MET A | 373 | −.538 | 11.520 | −5.352 | 1.00 | 49.64 | C |
| | | | | | gad65.pdb | | | | | |
| ATOM | 2236 | CB | MET A | 373 | −.188 | 10.591 | −6.517 | 1.00 | 48.87 | C |
| ATOM | 2237 | CG | MET A | 373 | −.557 | 11.123 | −7.897 | 1.00 | 53.03 | C |
| ATOM | 2238 | SD | MET A | 373 | −2.339 | 11.224 | −8.233 | 1.00 | 61.86 | S |
| ATOM | 2239 | CE | MET A | 373 | −2.825 | 9.513 | −8.051 | 1.00 | 55.30 | C |
| ATOM | 2240 | C | MET A | 373 | −.002 | 10.932 | −4.037 | 1.00 | 50.22 | C |
| ATOM | 2241 | O | MET A | 373 | −.494 | 9.904 | −3.562 | 1.00 | 50.77 | O |
| ATOM | 2242 | N | SER A | 374 | .993 | 11.595 | −3.454 | 1.00 | 50.12 | N |
| ATOM | 2243 | CA | SER A | 374 | 1.663 | 11.117 | −2.244 | 1.00 | 49.37 | C |
| ATOM | 2244 | CB | SER A | 374 | 3.179 | 11.203 | −2.434 | 1.00 | 48.53 | C |
| ATOM | 2245 | OG | SER A | 374 | 3.881 | 11.105 | −1.209 | 1.00 | 46.47 | O |
| ATOM | 2246 | C | SER A | 374 | 1.237 | 11.919 | −1.022 | 1.00 | 50.50 | C |
| ATOM | 2247 | O | SER A | 374 | 1.518 | 13.115 | −.937 | 1.00 | 50.66 | O |
| ATOM | 2248 | N | ARG A | 375 | .559 | 11.261 | −.079 | 1.00 | 52.37 | N |
| ATOM | 2249 | CA | ARG A | 375 | .199 | 11.886 | 1.206 | 1.00 | 53.86 | C |
| ATOM | 2250 | CB | ARG A | 375 | −.594 | 10.926 | 2.104 | 1.00 | 55.19 | C |
| ATOM | 2251 | CG | ARG A | 375 | −2.064 | 10.751 | 1.726 | 1.00 | 62.44 | C |
| ATOM | 2252 | CD | ARG A | 375 | −2.368 | 9.337 | 1.234 | 1.00 | 70.12 | C |
| ATOM | 2253 | NE | ARG A | 375 | −2.214 | 8.346 | 2.303 | 1.00 | 76.64 | N |
| ATOM | 2254 | CZ | ARG A | 375 | −2.409 | 7.033 | 2.166 | 1.00 | 79.07 | C |
| ATOM | 2255 | NH1 | ARG A | 375 | −2.771 | 6.512 | .998 | 1.00 | 78.53 | N |
| ATOM | 2256 | NH2 | ARG A | 375 | −2.243 | 6.232 | 3.209 | 1.00 | 80.94 | N |
| ATOM | 2257 | C | ARG A | 375 | 1.433 | 12.378 | 1.959 | 1.00 | 53.51 | C |
| ATOM | 2258 | O | ARG A | 375 | 1.386 | 13.407 | 2.640 | 1.00 | 53.27 | O |
| ATOM | 2259 | N | LYS A | 376 | 2.531 | 11.635 | 1.830 | 1.00 | 53.98 | N |
| ATOM | 2260 | CA | LYS A | 376 | 3.808 | 12.000 | 2.451 | 1.00 | 54.69 | C |
| ATOM | 2261 | CB | LYS A | 376 | 4.777 | 10.809 | 2.402 | 1.00 | 54.60 | C |
| ATOM | 2262 | CG | LYS A | 376 | 6.236 | 11.113 | 2.768 | 1.00 | 58.25 | C |
| ATOM | 2263 | CD | LYS A | 376 | 7.088 | 9.848 | 2.761 | 1.00 | 55.53 | C |
| ATOM | 2264 | CE | LYS A | 376 | 8.576 | 10.156 | 2.945 | 1.00 | 59.20 | C |
| ATOM | 2265 | NZ | LYS A | 376 | 8.937 | 10.627 | 4.313 | 1.00 | 57.27 | N |
| ATOM | 2266 | C | LYS A | 376 | 4.430 | 13.249 | 1.811 | 1.00 | 55.12 | C |
| ATOM | 2267 | O | LYS A | 376 | 4.946 | 14.114 | 2.516 | 1.00 | 55.03 | O |
| ATOM | 2268 | N | HIS A | 377 | 4.349 | 13.361 | .484 | 1.00 | 54.88 | N |
| ATOM | 2269 | CA | HIS A | 377 | 5.085 | 14.412 | −.224 | 1.00 | 54.69 | C |
| ATOM | 2270 | CB | HIS A | 377 | 5.896 | 13.806 | −1.373 | 1.00 | 55.04 | C |
| ATOM | 2271 | CG | HIS A | 377 | 7.000 | 12.908 | −.917 | 1.00 | 53.96 | C |
| ATOM | 2272 | ND1 | HIS A | 377 | 8.237 | 13.384 | −.542 | 1.00 | 56.22 | N |
| ATOM | 2273 | CE1 | HIS A | 377 | 9.005 | 12.370 | −.181 | 1.00 | 58.48 | C |
| ATOM | 2274 | NE2 | HIS A | 377 | 8.313 | 11.253 | −.316 | 1.00 | 58.68 | N |
| ATOM | 2275 | CD2 | HIS A | 377 | 7.052 | 11.563 | −.765 | 1.00 | 56.92 | C |
| ATOM | 2276 | C | HIS A | 377 | 4.288 | 15.617 | −.728 | 1.00 | 54.57 | C |

TABLE A-continued

| | | | | | | | | | |
|---|---|---|---|---|---|---|---|---|---|
| ATOM | 2277 | O | HIS A | 377 | 4.890 | 16.612 | −1.133 | 1.00 | 54.61 | O |
| ATOM | 2278 | N | LYS A | 378 | 2.956 | 15.547 | −.694 | 1.00 | 54.58 | N |
| ATOM | 2279 | CA | LYS A | 378 | 2.131 | 16.580 | −1.343 | 1.00 | 54.41 | C |
| ATOM | 2280 | CB | LYS A | 378 | .654 | 16.153 | −1.470 | 1.00 | 55.04 | C |
| ATOM | 2281 | CG | LYS A | 378 | −.260 | 16.379 | −.244 | 1.00 | 59.05 | C |
| ATOM | 2282 | CD | LYS A | 378 | −.729 | 17.849 | −.074 | 1.00 | 65.65 | C |
| ATOM | 2283 | CE | LYS A | 378 | −1.349 | 18.475 | −1.340 | 1.00 | 65.57 | C |
| ATOM | 2284 | NZ | LYS A | 378 | −2.845 | 18.483 | −1.319 | 1.00 | 69.35 | N |
| ATOM | 2285 | C | LYS A | 378 | 2.277 | 17.972 | −.734 | 1.00 | 53.51 | C |
| ATOM | 2286 | O | LYS A | 378 | 2.031 | 18.973 | −1.409 | 1.00 | 53.31 | O |
| ATOM | 2287 | N | TRP A | 379 | 2.708 | 18.030 | .524 | 1.00 | 52.87 | N |
| ATOM | 2288 | CA | TRP A | 379 | 2.933 | 19.300 | 1.222 | 1.00 | 52.85 | C |
| ATOM | 2289 | CB | TRP A | 379 | 3.453 | 19.057 | 2.649 | 1.00 | 52.66 | C |
| ATOM | 2290 | CG | TRP A | 379 | 4.821 | 18.434 | 2.699 | 1.00 | 52.55 | C |
| ATOM | 2291 | CD1 | TRP A | 379 | 5.115 | 17.100 | 2.714 | 1.00 | 53.16 | C |
| ATOM | 2292 | NE1 | TRP A | 379 | 6.475 | 16.910 | 2.762 | 1.00 | 51.44 | N |
| ATOM | 2293 | CE2 | TRP A | 379 | 7.091 | 18.135 | 2.763 | 1.00 | 53.93 | C |
| ATOM | 2294 | CD2 | TRP A | 379 | 6.076 | 19.120 | 2.723 | 1.00 | 51.79 | C |
| ATOM | 2295 | CE3 | TRP A | 379 | 6.446 | 20.473 | 2.728 | 1.00 | 53.97 | C |
| ATOM | 2296 | CZ3 | TRP A | 379 | 7.802 | 20.797 | 2.764 | 1.00 | 53.70 | C |
| ATOM | 2297 | CH2 | TRP A | 379 | 8.787 | 19.791 | 2.797 | 1.00 | 52.38 | C |
| ATOM | 2298 | CZ2 | TRP A | 379 | 8.453 | 18.460 | 2.801 | 1.00 | 51.72 | C |
| ATOM | 2299 | C | TRP A | 379 | 3.879 | 20.231 | .456 | 1.00 | 52.90 | C |
| ATOM | 2300 | O | TRP A | 379 | 3.839 | 21.453 | .637 | 1.00 | 52.84 | O |
| ATOM | 2301 | N | LYS A | 380 | 4.724 | 19.647 | −.397 | 1.00 | 52.73 | N |
| ATOM | 2302 | CA | LYS A | 380 | 5.598 | 20.417 | −1.292 | 1.00 | 53.03 | C |
| ATOM | 2303 | CB | LYS A | 380 | 6.562 | 19.488 | −2.028 | 1.00 | 52.16 | C |
| | | | | | gad65.pdb | | | | | |
| ATOM | 2304 | CG | LYS A | 380 | 7.738 | 19.077 | −1.175 | 1.00 | 52.99 | C |
| ATOM | 2305 | CD | LYS A | 380 | 8.161 | 17.655 | −1.459 | 1.00 | 51.71 | C |
| ATOM | 2306 | CE | LYS A | 380 | 9.258 | 17.223 | −.511 | 1.00 | 51.36 | C |
| ATOM | 2307 | NZ | LYS A | 380 | 9.761 | 15.870 | −.861 | 1.00 | 52.44 | N |
| ATOM | 2308 | C | LYS A | 380 | 4.816 | 21.275 | −2.288 | 1.00 | 53.78 | C |
| ATOM | 2309 | O | LYS A | 380 | 5.351 | 22.257 | −2.832 | 1.00 | 54.65 | O |
| ATOM | 2310 | N | LEU A | 381 | 3.559 | 20.897 | −2.527 | 1.00 | 53.47 | N |
| ATOM | 2311 | CA | LEU A | 381 | 2.684 | 21.650 | −3.424 | 1.00 | 53.79 | C |
| ATOM | 2312 | CB | LEU A | 381 | 2.066 | 20.743 | −4.501 | 1.00 | 53.42 | C |
| ATOM | 2313 | CG | LEU A | 381 | 3.006 | 20.159 | −5.556 | 1.00 | 54.70 | C |
| ATOM | 2314 | CD1 | LEU A | 381 | 3.426 | 18.749 | −5.149 | 1.00 | 56.20 | C |
| ATOM | 2315 | CD2 | LEU A | 381 | 2.358 | 20.134 | −6.940 | 1.00 | 56.25 | C |
| ATOM | 2316 | C | LEU A | 381 | 1.593 | 22.410 | −2.677 | 1.00 | 53.69 | C |
| ATOM | 2317 | O | LEU A | 381 | .590 | 22.792 | −3.275 | 1.00 | 54.72 | O |
| ATOM | 2318 | N | SER A | 382 | 1.788 | 22.640 | −1.378 | 1.00 | 52.75 | N |
| ATOM | 2319 | CA | SER A | 382 | .807 | 23.382 | −.585 | 1.00 | 51.59 | C |
| ATOM | 2320 | CB | SER A | 382 | 1.286 | 23.550 | .868 | 1.00 | 52.40 | C |
| ATOM | 2321 | OG | SER A | 382 | 1.210 | 22.328 | 1.581 | 1.00 | 59.26 | O |
| ATOM | 2322 | C | SER A | 382 | .570 | 24.751 | −1.204 | 1.00 | 49.47 | C |
| ATOM | 2323 | O | SER A | 382 | 1.520 | 25.498 | −1.435 | 1.00 | 49.78 | O |
| ATOM | 2324 | N | GLY A | 383 | −.691 | 25.082 | −1.457 | 1.00 | 47.12 | N |
| ATOM | 2325 | CA | GLY A | 383 | −1.036 | 26.358 | −2.072 | 1.00 | 46.07 | C |
| ATOM | 2326 | C | GLY A | 383 | −1.504 | 26.245 | −3.513 | 1.00 | 46.06 | C |
| ATOM | 2327 | O | GLY A | 383 | −2.045 | 27.206 | −4.055 | 1.00 | 45.91 | O |
| ATOM | 2328 | N | VAL A | 384 | −1.279 | 25.077 | −4.130 | 1.00 | 46.41 | N |
| ATOM | 2329 | CA | VAL A | 384 | −1.756 | 24.759 | −5.488 | 1.00 | 46.06 | C |
| ATOM | 2330 | CB | VAL A | 384 | −1.290 | 23.332 | −5.942 | 1.00 | 46.74 | C |
| ATOM | 2331 | CG1 | VAL A | 384 | −2.039 | 22.218 | −5.195 | 1.00 | 48.92 | C |
| ATOM | 2332 | CG2 | VAL A | 384 | −1.451 | 23.141 | −7.444 | 1.00 | 45.97 | C |
| ATOM | 2333 | C | VAL A | 384 | −3.280 | 24.872 | −5.587 | 1.00 | 45.83 | C |
| ATOM | 2334 | O | VAL A | 384 | −3.830 | 25.083 | −6.674 | 1.00 | 45.09 | O |
| ATOM | 2335 | N | GLU A | 385 | −3.957 | 24.751 | −4.441 | 1.00 | 44.97 | N |
| ATOM | 2336 | CA | GLU A | 385 | −5.421 | 24.777 | −4.409 | 1.00 | 44.05 | C |
| ATOM | 2337 | CB | GLU A | 385 | −5.965 | 24.144 | −3.110 | 1.00 | 43.59 | C |
| ATOM | 2338 | CG | GLU A | 385 | −5.791 | 24.968 | −1.808 | 1.00 | 43.52 | C |
| ATOM | 2339 | CD | GLU A | 385 | −4.396 | 24.873 | −1.171 | 1.00 | 49.27 | C |
| ATOM | 2340 | OE1 | GLU A | 385 | −4.228 | 25.431 | −.058 | 1.00 | 56.21 | O |
| ATOM | 2341 | OE2 | GLU A | 385 | −3.470 | 24.255 | −1.759 | 1.00 | 47.95 | O |
| ATOM | 2342 | C | GLU A | 385 | −5.925 | 26.205 | −4.633 | 1.00 | 44.00 | C |
| ATOM | 2343 | O | GLU A | 385 | −7.094 | 26.426 | −4.990 | 1.00 | 44.29 | O |
| ATOM | 2344 | N | ARG A | 386 | −5.013 | 27.161 | −4.459 | 1.00 | 42.69 | N |
| ATOM | 2345 | CA | ARG A | 386 | −5.303 | 28.580 | −4.648 | 1.00 | 42.35 | C |
| ATOM | 2346 | CB | ARG A | 386 | −4.527 | 29.407 | −3.632 | 1.00 | 41.95 | C |
| ATOM | 2347 | CG | ARG A | 386 | −5.237 | 29.532 | −2.317 | 1.00 | 46.92 | C |
| ATOM | 2348 | CD | ARG A | 386 | −5.071 | 30.930 | −1.801 | 1.00 | 49.86 | C |
| ATOM | 2349 | NE | ARG A | 386 | −4.019 | 31.007 | −.804 | 1.00 | 48.75 | N |
| ATOM | 2350 | CZ | ARG A | 386 | −3.397 | 32.135 | −.465 | 1.00 | 46.96 | C |
| ATOM | 2351 | NH1 | ARG A | 386 | −3.678 | 33.283 | −1.086 | 1.00 | 42.54 | N |
| ATOM | 2352 | NH2 | ARG A | 386 | −2.466 | 32.102 | .477 | 1.00 | 48.40 | N |
| ATOM | 2353 | C | ARG A | 386 | −5.006 | 29.091 | −6.061 | 1.00 | 41.97 | C |
| ATOM | 2354 | O | ARG A | 386 | −5.209 | 30.271 | −6.350 | 1.00 | 42.73 | O |
| ATOM | 2355 | N | ALA A | 387 | −4.546 | 28.196 | −6.929 | 1.00 | 41.47 | N |

TABLE A-continued

| | | | | | | | | | |
|---|---|---|---|---|---|---|---|---|---|
| ATOM | 2356 | CA | ALA A | 387 | −4.113 | 28.542 | −8.278 | 1.00 | 41.50 | C |
| ATOM | 2357 | CB | ALA A | 387 | −3.091 | 27.524 | −8.775 | 1.00 | 41.21 | C |
| ATOM | 2358 | C | ALA A | 387 | −5.277 | 28.615 | −9.243 | 1.00 | 41.77 | C |
| ATOM | 2359 | O | ALA A | 387 | −6.195 | 27.795 | −9.190 | 1.00 | 43.10 | O |
| ATOM | 2360 | N | ASN A | 388 | −5.233 | 29.596 | −10.137 | 1.00 | 40.61 | N |
| ATOM | 2361 | CA | ASN A | 388 | −6.226 | 29.702 | −11.196 | 1.00 | 38.47 | C |
| ATOM | 2362 | CB | ASN A | 388 | −6.205 | 31.093 | −11.820 | 1.00 | 37.60 | C |
| ATOM | 2363 | CG | ASN A | 388 | −6.385 | 32.187 | −10.798 | 1.00 | 38.50 | C |
| ATOM | 2364 | OD1 | ASN A | 388 | −5.422 | 32.622 | −10.163 | 1.00 | 40.62 | O |
| ATOM | 2365 | ND2 | ASN A | 388 | −7.619 | 32.650 | −10.634 | 1.00 | 36.86 | N |
| ATOM | 2366 | C | ASN A | 388 | −6.092 | 28.614 | −12.259 | 1.00 | 38.18 | C |
| ATOM | 2367 | O | ASN A | 388 | −7.084 | 28.197 | −12.839 | 1.00 | 38.06 | O |
| ATOM | 2368 | N | SER A | 389 | −4.864 | 28.157 | −12.512 | 1.00 | 38.33 | N |
| ATOM | 2369 | CA | SER A | 389 | −4.621 | 27.054 | −13.453 | 1.00 | 37.16 | C |
| ATOM | 2370 | CB | SER A | 389 | −4.330 | 27.563 | −14.879 | 1.00 | 36.92 | C |
| ATOM | 2371 | OG | SER A | 389 | −3.323 | 28.565 | −14.889 | 1.00 | 36.58 | O |
| | | | | | gad65.pdb | | | | | |
| ATOM | 2372 | C | SER A | 389 | −3.477 | 26.194 | −12.981 | 1.00 | 37.38 | C |
| ATOM | 2373 | O | SER A | 389 | −2.589 | 26.671 | −12.266 | 1.00 | 36.38 | O |
| ATOM | 2374 | N | VAL A | 390 | −3.492 | 24.928 | −13.387 | 1.00 | 38.18 | N |
| ATOM | 2375 | CA | VAL A | 390 | −2.364 | 24.024 | −13.137 | 1.00 | 39.97 | C |
| ATOM | 2376 | CB | VAL A | 390 | −2.610 | 23.086 | −11.911 | 1.00 | 40.81 | C |
| ATOM | 2377 | CG1 | VAL A | 390 | −1.426 | 22.135 | −11.700 | 1.00 | 42.38 | C |
| ATOM | 2378 | CG2 | VAL A | 390 | −2.877 | 23.889 | −10.641 | 1.00 | 42.05 | C |
| ATOM | 2379 | C | VAL A | 390 | −2.066 | 23.168 | −14.369 | 1.00 | 41.13 | C |
| ATOM | 2380 | O | VAL A | 390 | −2.988 | 22.690 | −15.036 | 1.00 | 42.71 | O |
| ATOM | 2381 | N | THR A | 391 | −.779 | 23.008 | −14.669 | 1.00 | 41.65 | N |
| ATOM | 2382 | CA | THR A | 391 | −.272 | 22.055 | −15.660 | 1.00 | 41.95 | C |
| ATOM | 2383 | CB | THR A | 391 | .866 | 22.683 | −16.512 | 1.00 | 42.54 | C |
| ATOM | 2384 | OG1 | THR A | 391 | .355 | 23.783 | −17.272 | 1.00 | 45.17 | O |
| ATOM | 2385 | CG2 | THR A | 391 | 1.499 | 21.649 | −17.469 | 1.00 | 43.76 | C |
| ATOM | 2386 | C | THR A | 391 | .298 | 20.814 | −14.944 | 1.00 | 42.09 | C |
| ATOM | 2387 | O | THR A | 391 | 1.005 | 20.927 | −13.955 | 1.00 | 41.22 | O |
| ATOM | 2388 | N | TRP A | 392 | .008 | 19.633 | −15.466 | 1.00 | 43.56 | N |
| ATOM | 2389 | CA | TRP A | 392 | .384 | 18.399 | −14.804 | 1.00 | 44.28 | C |
| ATOM | 2390 | CB | TRP A | 392 | −.741 | 17.986 | −13.845 | 1.00 | 45.31 | C |
| ATOM | 2391 | CG | TRP A | 392 | −.546 | 16.727 | −13.029 | 1.00 | 46.07 | C |
| ATOM | 2392 | CD1 | TRP A | 392 | .454 | 15.797 | −13.142 | 1.00 | 46.37 | C |
| ATOM | 2393 | NE1 | TRP A | 392 | .256 | 14.772 | −12.243 | 1.00 | 47.93 | N |
| ATOM | 2394 | CE2 | TRP A | 392 | −.892 | 15.017 | −11.534 | 1.00 | 44.54 | C |
| ATOM | 2395 | CD2 | TRP A | 392 | −1.435 | 16.235 | −12.015 | 1.00 | 47.25 | C |
| ATOM | 2396 | CE3 | TRP A | 392 | −2.625 | 16.720 | −11.444 | 1.00 | 45.66 | C |
| ATOM | 2397 | CZ3 | TRP A | 392 | −3.239 | 15.972 | −10.431 | 1.00 | 42.31 | C |
| ATOM | 2398 | CH2 | TRP A | 392 | −2.676 | 14.761 | −9.983 | 1.00 | 43.88 | C |
| ATOM | 2399 | CZ2 | TRP A | 392 | −1.508 | 14.266 | −10.521 | 1.00 | 42.96 | C |
| ATOM | 2400 | C | TRP A | 392 | .574 | 17.382 | −15.896 | 1.00 | 43.80 | C |
| ATOM | 2401 | O | TRP A | 392 | −.302 | 17.220 | −16.738 | 1.00 | 45.38 | O |
| ATOM | 2402 | N | ASN A | 393 | 1.726 | 16.714 | −15.883 | 1.00 | 43.61 | N |
| ATOM | 2403 | CA | ASN A | 393 | 2.074 | 15.725 | −16.879 | 1.00 | 45.26 | C |
| ATOM | 2404 | CB | ASN A | 393 | 3.424 | 16.058 | −17.534 | 1.00 | 46.09 | C |
| ATOM | 2405 | CG | ASN A | 393 | 3.354 | 17.233 | −18.489 | 1.00 | 50.35 | C |
| ATOM | 2406 | OD1 | ASN A | 393 | 2.381 | 17.992 | −18.510 | 1.00 | 52.80 | O |
| ATOM | 2407 | ND2 | ASN A | 393 | 4.397 | 17.386 | −19.297 | 1.00 | 48.36 | N |
| ATOM | 2408 | C | ASN A | 393 | 2.157 | 14.325 | −16.284 | 1.00 | 46.51 | C |
| ATOM | 2409 | O | ASN A | 393 | 3.228 | 13.904 | −15.820 | 1.00 | 47.44 | O |
| ATOM | 2410 | N | PRO A | 394 | 1.037 | 13.577 | −16.313 | 1.00 | 47.43 | N |
| ATOM | 2411 | CA | PRO A | 394 | 1.094 | 12.178 | −15.898 | 1.00 | 47.77 | C |
| ATOM | 2412 | CB | PRO A | 394 | −.334 | 11.687 | −16.164 | 1.00 | 48.14 | C |
| ATOM | 2413 | CG | PRO A | 394 | −1.157 | 12.923 | −16.022 | 1.00 | 50.58 | C |
| ATOM | 2414 | CD | PRO A | 394 | −.336 | 13.977 | −16.680 | 1.00 | 46.19 | C |
| ATOM | 2415 | C | PRO A | 394 | 2.111 | 11.360 | −16.704 | 1.00 | 47.93 | C |
| ATOM | 2416 | O | PRO A | 394 | 2.546 | 10.312 | −16.235 | 1.00 | 47.37 | O |
| ATOM | 2417 | N | HIS A | 395 | 2.505 | 11.839 | −17.885 | 1.00 | 48.02 | N |
| ATOM | 2418 | CA | HIS A | 395 | 3.510 | 11.120 | −18.662 | 1.00 | 49.82 | C |
| ATOM | 2419 | CB | HIS A | 395 | 3.479 | 11.476 | −20.164 | 1.00 | 49.74 | C |
| ATOM | 2420 | CG | HIS A | 395 | 4.124 | 12.779 | −20.517 | 1.00 | 52.73 | C |
| ATOM | 2421 | ND1 | HIS A | 395 | 3.440 | 13.794 | −21.157 | 1.00 | 54.18 | N |
| ATOM | 2422 | CE1 | HIS A | 395 | 4.257 | 14.814 | −21.359 | 1.00 | 49.14 | C |
| ATOM | 2423 | NE2 | HIS A | 395 | 5.449 | 14.491 | −20.885 | 1.00 | 54.87 | N |
| ATOM | 2424 | CD2 | HIS A | 395 | 5.396 | 13.222 | −20.359 | 1.00 | 48.12 | C |
| ATOM | 2425 | C | HIS A | 395 | 4.918 | 11.189 | −18.047 | 1.00 | 50.64 | C |
| ATOM | 2426 | O | HIS A | 395 | 5.779 | 10.395 | −18.395 | 1.00 | 51.49 | O |
| ATOM | 2427 | N | LLP A | 396 | 5.135 | 12.109 | −17.108 | 1.00 | 51.25 | N |
| ATOM | 2428 | CA | LLP A | 396 | 6.412 | 12.153 | −16.383 | 1.00 | 52.81 | C |
| ATOM | 2429 | CB | LLP A | 396 | 6.807 | 13.597 | −16.045 | 1.00 | 52.26 | C |
| ATOM | 2430 | CG | LLP A | 396 | 7.051 | 14.442 | −17.303 | 1.00 | 49.53 | C |
| ATOM | 2431 | CD | LLP A | 396 | 7.765 | 15.749 | −17.015 | 1.00 | 45.73 | C |
| ATOM | 2432 | CE | LLP A | 396 | 8.079 | 16.514 | −18.296 | 1.00 | 42.09 | C |
| ATOM | 2433 | NZ | LLP A | 396 | 8.592 | 17.883 | −17.989 | 1.00 | 47.12 | N |
| ATOM | 2434 | C4A | LLP A | 396 | 8.445 | 18.750 | −18.998 | 1.00 | 44.92 | C |

TABLE A-continued

| | | | | | | | | | |
|---|---|---|---|---|---|---|---|---|---|
| ATOM | 2435 | C4 | LLP A | 396 | 8.129 | 20.121 | −18.452 | 1.00 | 42.95 | C |
| ATOM | 2436 | C3 | LLP A | 396 | 8.515 | 20.482 | −17.160 | 1.00 | 41.62 | C |
| ATOM | 2437 | O3 | LLP A | 396 | 9.125 | 19.683 | −16.439 | 1.00 | 42.26 | O |
| ATOM | 2438 | C2 | LLP A | 396 | 8.193 | 21.747 | −16.674 | 1.00 | 43.62 | C |
| ATOM | 2439 | C2A | LLP A | 396 | 8.589 | 22.162 | −15.275 | 1.00 | 42.79 | C |
| | | | | gad65.pdb | | | | | | |
| ATOM | 2440 | N1 | LLP A | 396 | 7.503 | 22.638 | −17.473 | 1.00 | 41.95 | N |
| ATOM | 2441 | C5 | LLP A | 396 | 7.433 | 21.043 | −19.239 | 1.00 | 44.17 | C |
| ATOM | 2442 | C6 | LLP A | 396 | 7.112 | 22.302 | −18.742 | 1.00 | 44.51 | C |
| ATOM | 2443 | C5A | LLP A | 396 | 7.025 | 20.713 | −20.634 | 1.00 | 42.00 | C |
| ATOM | 2444 | O4P | LLP A | 396 | 6.346 | 19.479 | −20.890 | 1.00 | 46.46 | O |
| ATOM | 2445 | P | LLP A | 396 | 6.321 | 18.794 | −22.354 | 1.00 | 46.52 | P |
| ATOM | 2446 | O1P | LLP A | 396 | 5.310 | 17.772 | −22.022 | 1.00 | 43.06 | O |
| ATOM | 2447 | O2P | LLP A | 396 | 5.922 | 19.843 | −23.321 | 1.00 | 47.03 | O |
| ATOM | 2448 | O3P | LLP A | 396 | 7.693 | 18.288 | −22.589 | 1.00 | 47.80 | O |
| ATOM | 2449 | C | LLP A | 396 | 6.450 | 11.185 | −15.173 | 1.00 | 54.54 | C |
| ATOM | 2450 | O | LLP A | 396 | 6.716 | 10.001 | −15.355 | 1.00 | 55.97 | O |
| ATOM | 2451 | N | MET A | 397 | 6.139 | 11.656 | −13.971 | 1.00 | 56.20 | N |
| ATOM | 2452 | CA | MET A | 397 | 6.257 | 10.826 | −12.758 | 1.00 | 58.62 | C |
| ATOM | 2453 | CB | MET A | 397 | 6.213 | 11.696 | −11.498 | 1.00 | 59.84 | C |
| ATOM | 2454 | CG | MET A | 397 | 7.594 | 12.117 | −10.988 | 1.00 | 65.72 | C |
| ATOM | 2455 | SD | MET A | 397 | 8.524 | 10.760 | −10.240 | 1.00 | 77.13 | S |
| ATOM | 2456 | CE | MET A | 397 | 7.719 | 10.689 | −8.647 | 1.00 | 78.02 | C |
| ATOM | 2457 | C | MET A | 397 | 5.268 | 9.661 | −12.612 | 1.00 | 59.09 | C |
| ATOM | 2458 | O | MET A | 397 | 5.584 | 8.664 | −11.954 | 1.00 | 60.46 | O |
| ATOM | 2459 | N | MET A | 398 | 4.089 | 9.775 | −13.219 | 1.00 | 56.90 | N |
| ATOM | 2460 | CA | MET A | 398 | 3.076 | 8.720 | −13.103 | 1.00 | 54.91 | C |
| ATOM | 2461 | CB | MET A | 398 | 1.657 | 9.306 | −13.138 | 1.00 | 54.13 | C |
| ATOM | 2462 | CG | MET A | 398 | 1.334 | 10.160 | −11.919 | 1.00 | 51.63 | C |
| ATOM | 2463 | SD | MET A | 398 | −.149 | 11.162 | −12.109 | 1.00 | 55.92 | S |
| ATOM | 2464 | CE | MET A | 398 | −1.421 | 9.902 | −12.218 | 1.00 | 55.45 | C |
| ATOM | 2465 | C | MET A | 398 | 3.249 | 7.592 | −14.122 | 1.00 | 52.85 | C |
| ATOM | 2466 | O | MET A | 398 | 2.596 | 6.571 | −14.013 | 1.00 | 52.91 | O |
| ATOM | 2467 | N | GLY A | 399 | 4.139 | 7.772 | −15.095 | 1.00 | 51.64 | N |
| ATOM | 2468 | CA | GLY A | 399 | 4.512 | 6.687 | −16.015 | 1.00 | 51.13 | C |
| ATOM | 2469 | C | GLY A | 399 | 3.562 | 6.368 | −17.162 | 1.00 | 51.67 | C |
| ATOM | 2470 | O | GLY A | 399 | 3.674 | 5.318 | −17.797 | 1.00 | 51.86 | O |
| ATOM | 2471 | N | VAL A | 400 | 2.622 | 7.265 | −17.431 | 1.00 | 50.78 | N |
| ATOM | 2472 | CA | VAL A | 400 | 1.734 | 7.104 | −18.567 | 1.00 | 50.84 | C |
| ATOM | 2473 | CB | VAL A | 400 | .587 | 8.159 | −18.519 | 1.00 | 51.01 | C |
| ATOM | 2474 | CG1 | VAL A | 400 | −.428 | 7.909 | −19.619 | 1.00 | 46.54 | C |
| ATOM | 2475 | CG2 | VAL A | 400 | −.114 | 8.139 | −17.159 | 1.00 | 47.48 | C |
| ATOM | 2476 | C | VAL A | 400 | 2.564 | 7.207 | −19.862 | 1.00 | 51.67 | C |
| ATOM | 2477 | O | VAL A | 400 | 3.394 | 8.105 | −19.993 | 1.00 | 52.03 | O |
| ATOM | 2478 | N | PRO A | 401 | 2.378 | 6.274 | −20.814 | 1.00 | 52.24 | N |
| ATOM | 2479 | CA | PRO A | 401 | 3.168 | 6.429 | −22.046 | 1.00 | 52.63 | C |
| ATOM | 2480 | CB | PRO A | 401 | 2.662 | 5.292 | −22.945 | 1.00 | 51.66 | C |
| ATOM | 2481 | CG | PRO A | 401 | 2.184 | 4.257 | −21.979 | 1.00 | 49.40 | C |
| ATOM | 2482 | CD | PRO A | 401 | 1.552 | 5.052 | −20.851 | 1.00 | 52.13 | C |
| ATOM | 2483 | C | PRO A | 401 | 3.004 | 7.792 | −22.718 | 1.00 | 55.53 | C |
| ATOM | 2484 | O | PRO A | 401 | 1.945 | 8.440 | −22.602 | 1.00 | 55.09 | O |
| ATOM | 2485 | N | LEU A | 402 | 4.063 | 8.184 | −23.427 | 1.00 | 57.39 | N |
| ATOM | 2486 | CA | LEU A | 402 | 4.283 | 9.539 | −23.938 | 1.00 | 58.39 | C |
| ATOM | 2487 | CB | LEU A | 402 | 5.474 | 9.580 | −24.899 | 1.00 | 59.68 | C |
| ATOM | 2488 | CG | LEU A | 402 | 6.368 | 10.804 | −24.741 | 1.00 | 64.89 | C |
| ATOM | 2489 | CD1 | LEU A | 402 | 7.590 | 10.417 | −23.926 | 1.00 | 63.12 | C |
| ATOM | 2490 | CD2 | LEU A | 402 | 6.775 | 11.333 | −26.109 | 1.00 | 69.48 | C |
| ATOM | 2491 | C | LEU A | 402 | 3.102 | 10.270 | −24.572 | 1.00 | 58.61 | C |
| ATOM | 2492 | O | LEU A | 402 | 2.416 | 9.778 | −25.482 | 1.00 | 56.51 | O |
| ATOM | 2493 | N | GLN A | 403 | 2.988 | 11.497 | −24.075 | 1.00 | 59.37 | N |
| ATOM | 2494 | CA | GLN A | 403 | 1.919 | 12.474 | −24.246 | 1.00 | 58.00 | C |
| ATOM | 2495 | CB | GLN A | 403 | 1.720 | 12.964 | −25.679 | 1.00 | 58.64 | C |
| ATOM | 2496 | CG | GLN A | 403 | 3.012 | 13.564 | −26.239 | 1.00 | 63.76 | C |
| ATOM | 2497 | CD | GLN A | 403 | 2.850 | 14.959 | −26.800 | 1.00 | 63.14 | C |
| ATOM | 2498 | OE1 | GLN A | 403 | 1.992 | 15.208 | −27.649 | 1.00 | 64.21 | O |
| ATOM | 2499 | NE2 | GLN A | 403 | 3.705 | 15.873 | −26.351 | 1.00 | 58.53 | N |
| ATOM | 2500 | C | GLN A | 403 | .664 | 12.190 | −23.446 | 1.00 | 55.67 | C |
| ATOM | 2501 | O | GLN A | 403 | −.328 | 11.643 | −23.913 | 1.00 | 56.32 | O |
| ATOM | 2502 | N | CYS A | 404 | .785 | 12.569 | −22.189 | 1.00 | 52.92 | N |
| ATOM | 2503 | CA | CYS A | 404 | −.322 | 12.722 | −21.308 | 1.00 | 51.16 | C |
| ATOM | 2504 | CB | CYS A | 404 | −.444 | 11.524 | −20.374 | 1.00 | 52.34 | C |
| ATOM | 2505 | SG | CYS A | 404 | −2.086 | 11.395 | −19.669 | 1.00 | 53.15 | S |
| ATOM | 2506 | C | CYS A | 404 | .022 | 13.969 | −20.535 | 1.00 | 49.07 | C |
| ATOM | 2507 | O | CYS A | 404 | .818 | 13.935 | −19.587 | 1.00 | 49.39 | O |
| | | | | gad65.pdb | | | | | | |
| ATOM | 2508 | N | SER A | 405 | −.548 | 15.080 | −20.978 | 1.00 | 46.48 | N |
| ATOM | 2509 | CA | SER A | 405 | −.388 | 16.353 | −20.306 | 1.00 | 43.75 | C |
| ATOM | 2510 | CB | SER A | 405 | .531 | 17.263 | −21.113 | 1.00 | 42.89 | C |
| ATOM | 2511 | OG | SER A | 405 | .620 | 18.530 | −20.497 | 1.00 | 54.06 | O |
| ATOM | 2512 | C | SER A | 405 | −1.752 | 16.995 | −20.150 | 1.00 | 42.18 | C |

TABLE A-continued

| | | | | | | | | | | |
|---|---|---|---|---|---|---|---|---|---|---|
| ATOM | 2513 | O | SER A | 405 | −2.519 | 17.054 | −21.096 | 1.00 | 41.94 | O |
| ATOM | 2514 | N | ALA A | 406 | −2.042 | 17.494 | −18.959 | 1.00 | 41.78 | N |
| ATOM | 2515 | CA | ALA A | 406 | −3.323 | 18.148 | −18.699 | 1.00 | 41.41 | C |
| ATOM | 2516 | CB | ALA A | 406 | −4.090 | 17.387 | −17.610 | 1.00 | 40.53 | C |
| ATOM | 2517 | C | ALA A | 406 | −3.137 | 19.594 | −18.274 | 1.00 | 40.31 | C |
| ATOM | 2518 | O | ALA A | 406 | −2.186 | 19.912 | −17.564 | 1.00 | 41.47 | O |
| ATOM | 2519 | N | LEU A | 407 | −4.038 | 20.460 | −18.717 | 1.00 | 39.67 | N |
| ATOM | 2520 | CA | LEU A | 407 | −4.221 | 21.760 | −18.087 | 1.00 | 40.83 | C |
| ATOM | 2521 | CB | LEU A | 407 | −4.228 | 22.905 | −19.110 | 1.00 | 41.06 | C |
| ATOM | 2522 | CG | LEU A | 407 | −4.431 | 24.323 | −18.541 | 1.00 | 42.13 | C |
| ATOM | 2523 | CD1 | LEU A | 407 | −3.235 | 24.805 | −17.716 | 1.00 | 38.37 | C |
| ATOM | 2524 | CD2 | LEU A | 407 | −4.733 | 25.300 | −19.653 | 1.00 | 40.80 | C |
| ATOM | 2525 | C | LEU A | 407 | −5.543 | 21.755 | −17.330 | 1.00 | 40.94 | C |
| ATOM | 2526 | O | LEU A | 407 | −6.568 | 21.352 | −17.868 | 1.00 | 40.97 | O |
| ATOM | 2527 | N | LEU A | 408 | −5.495 | 22.218 | −16.084 | 1.00 | 41.26 | N |
| ATOM | 2528 | CA | LEU A | 408 | −6.675 | 22.350 | −15.229 | 1.00 | 40.51 | C |
| ATOM | 2529 | CB | LEU A | 408 | −6.496 | 21.516 | −13.949 | 1.00 | 39.85 | C |
| ATOM | 2530 | CG | LEU A | 408 | −6.171 | 20.089 | −14.423 | 1.00 | 46.41 | C |
| ATOM | 2531 | CD1 | LEU A | 408 | −4.912 | 19.479 | −13.799 | 1.00 | 42.62 | C |
| ATOM | 2532 | CD2 | LEU A | 408 | −7.384 | 19.158 | −14.402 | 1.00 | 44.00 | C |
| ATOM | 2533 | C | LEU A | 408 | −6.868 | 23.823 | −14.918 | 1.00 | 40.12 | C |
| ATOM | 2534 | O | LEU A | 408 | −5.916 | 24.521 | −14.588 | 1.00 | 39.23 | O |
| ATOM | 2535 | N | VAL A | 409 | −8.105 | 24.274 | −15.075 | 1.00 | 40.04 | N |
| ATOM | 2536 | CA | VAL A | 409 | −8.506 | 25.656 | −14.891 | 1.00 | 40.50 | C |
| ATOM | 2537 | CB | VAL A | 409 | −8.954 | 26.260 | −16.259 | 1.00 | 38.94 | C |
| ATOM | 2538 | CG1 | VAL A | 409 | −9.453 | 27.664 | −16.100 | 1.00 | 36.86 | C |
| ATOM | 2539 | CG2 | VAL A | 409 | −7.811 | 26.219 | −17.269 | 1.00 | 43.63 | C |
| ATOM | 2540 | C | VAL A | 409 | −9.681 | 25.664 | −13.895 | 1.00 | 42.07 | C |
| ATOM | 2541 | O | VAL A | 409 | −10.639 | 24.903 | −14.061 | 1.00 | 41.07 | O |
| ATOM | 2542 | N | ARG A | 410 | −9.608 | 26.523 | −12.877 | 1.00 | 44.13 | N |
| ATOM | 2543 | CA | ARG A | 410 | −10.610 | 26.541 | −11.817 | 1.00 | 47.18 | C |
| ATOM | 2544 | CB | ARG A | 410 | −10.086 | 27.238 | −10.550 | 1.00 | 48.27 | C |
| ATOM | 2545 | CG | ARG A | 410 | −10.663 | 26.659 | −9.246 | 1.00 | 51.66 | C |
| ATOM | 2546 | CD | ARG A | 410 | −11.797 | 27.482 | −8.708 | 1.00 | 60.67 | C |
| ATOM | 2547 | NE | ARG A | 410 | −12.933 | 26.674 | −8.254 | 1.00 | 68.59 | N |
| ATOM | 2548 | CZ | ARG A | 410 | −13.419 | 26.669 | −7.012 | 1.00 | 71.70 | C |
| ATOM | 2549 | NH1 | ARG A | 410 | −12.870 | 27.422 | −6.062 | 1.00 | 71.82 | N |
| ATOM | 2550 | NH2 | ARG A | 410 | −14.468 | 25.909 | −6.721 | 1.00 | 72.91 | N |
| ATOM | 2551 | C | ARG A | 410 | −11.943 | 27.138 | −12.253 | 1.00 | 47.98 | C |
| ATOM | 2552 | O | ARG A | 410 | −12.993 | 26.617 | −11.896 | 1.00 | 48.29 | O |
| ATOM | 2553 | N | GLU A | 411 | −11.902 | 28.224 | −13.017 | 1.00 | 48.61 | N |
| ATOM | 2554 | CA | GLU A | 411 | −13.128 | 28.859 | −13.487 | 1.00 | 49.06 | C |
| ATOM | 2555 | CB | GLU A | 411 | −12.879 | 30.333 | −13.825 | 1.00 | 48.76 | C |
| ATOM | 2556 | CG | GLU A | 411 | −14.146 | 31.135 | −14.086 | 1.00 | 51.05 | C |
| ATOM | 2557 | CD | GLU A | 411 | −13.866 | 32.576 | −14.479 | 1.00 | 51.22 | C |
| ATOM | 2558 | OE1 | GLU A | 411 | −14.354 | 32.996 | −15.554 | 1.00 | 57.86 | O |
| ATOM | 2559 | OE2 | GLU A | 411 | −13.169 | 33.291 | −13.717 | 1.00 | 55.51 | O |
| ATOM | 2560 | C | GLU A | 411 | −13.724 | 28.094 | −14.676 | 1.00 | 48.58 | C |
| ATOM | 2561 | O | GLU A | 411 | −13.142 | 28.041 | −15.758 | 1.00 | 47.87 | O |
| ATOM | 2562 | N | GLU A | 412 | −14.886 | 27.490 | −14.447 | 1.00 | 48.89 | N |
| ATOM | 2563 | CA | GLU A | 412 | −15.613 | 26.748 | −15.467 | 1.00 | 49.52 | C |
| ATOM | 2564 | CB | GLU A | 412 | −16.761 | 25.959 | −14.833 | 1.00 | 49.86 | C |
| ATOM | 2565 | CG | GLU A | 412 | −16.369 | 25.054 | −13.672 | 1.00 | 53.06 | C |
| ATOM | 2566 | CD | GLU A | 412 | −17.556 | 24.297 | −13.065 | 1.00 | 52.50 | C |
| ATOM | 2567 | OE1 | GLU A | 412 | −17.369 | 23.686 | −11.992 | 1.00 | 61.84 | O |
| ATOM | 2568 | OE2 | GLU A | 412 | −18.666 | 24.304 | −13.655 | 1.00 | 58.11 | O |
| ATOM | 2569 | C | GLU A | 412 | −16.178 | 27.703 | −16.520 | 1.00 | 47.40 | C |
| ATOM | 2570 | O | GLU A | 412 | −16.589 | 28.812 | −16.191 | 1.00 | 46.20 | O |
| ATOM | 2571 | N | GLY A | 413 | −16.177 | 27.266 | −17.778 | 1.00 | 46.79 | N |
| ATOM | 2572 | CA | GLY A | 413 | −16.643 | 28.088 | −18.902 | 1.00 | 47.42 | C |
| ATOM | 2573 | C | GLY A | 413 | −15.612 | 28.987 | −19.586 | 1.00 | 46.92 | C |
| ATOM | 2574 | O | GLY A | 413 | −15.782 | 29.339 | −20.755 | 1.00 | 46.98 | O |
| ATOM | 2575 | N | LEU A | 414 | −14.553 | 29.351 | −18.862 | 1.00 | 46.14 | N |
| | | | | gad65.pdb | | | | | | |
| ATOM | 2576 | CA | LEU A | 414 | −13.489 | 30.229 | −19.365 | 1.00 | 47.12 | C |
| ATOM | 2577 | CB | LEU A | 414 | −12.420 | 30.408 | −18.292 | 1.00 | 46.60 | C |
| ATOM | 2578 | CG | LEU A | 414 | −12.038 | 31.813 | −17.846 | 1.00 | 49.77 | C |
| ATOM | 2579 | CD1 | LEU A | 414 | −10.893 | 31.692 | −16.873 | 1.00 | 48.75 | C |
| ATOM | 2580 | CD2 | LEU A | 414 | −11.677 | 32.739 | −18.996 | 1.00 | 53.04 | C |
| ATOM | 2581 | C | LEU A | 414 | −12.814 | 29.730 | −20.650 | 1.00 | 47.40 | C |
| ATOM | 2582 | O | LEU A | 414 | −12.700 | 30.478 | −21.621 | 1.00 | 47.18 | O |
| ATOM | 2583 | N | MET A | 415 | −12.365 | 28.474 | −20.633 | 1.00 | 48.25 | N |
| ATOM | 2584 | CA | MET A | 415 | −11.693 | 27.838 | −21.769 | 1.00 | 50.21 | C |
| ATOM | 2585 | CB | MET A | 415 | −11.349 | 26.384 | −21.432 | 1.00 | 48.89 | C |
| ATOM | 2586 | CG | MET A | 415 | −10.052 | 26.172 | −20.688 | 1.00 | 51.10 | C |
| ATOM | 2587 | SD | MET A | 415 | −9.501 | 24.437 | −20.768 | 1.00 | 56.68 | S |
| ATOM | 2588 | CE | MET A | 415 | −9.757 | 23.951 | −19.077 | 1.00 | 60.46 | C |
| ATOM | 2589 | C | MET A | 415 | −12.508 | 27.880 | −23.072 | 1.00 | 48.44 | C |
| ATOM | 2590 | O | MET A | 415 | −11.969 | 28.201 | −24.142 | 1.00 | 47.06 | O |
| ATOM | 2591 | N | GLN A | 416 | −13.795 | 27.539 | −22.978 | 1.00 | 47.59 | N |

TABLE A-continued

| | | | | | | | | | | |
|---|---|---|---|---|---|---|---|---|---|---|
| ATOM | 2592 | CA | GLN A | 416 | −14.702 | 27.582 | −24.119 | 1.00 | 46.92 | C |
| ATOM | 2593 | CB | GLN A | 416 | −16.077 | 27.008 | −23.732 | 1.00 | 48.57 | C |
| ATOM | 2594 | CG | GLN A | 416 | −17.218 | 27.223 | −24.753 | 1.00 | 52.66 | C |
| ATOM | 2595 | CD | GLN A | 416 | −17.323 | 26.105 | −25.795 | 1.00 | 62.83 | C |
| ATOM | 2596 | OE1 | GLN A | 416 | −16.928 | 24.960 | −25.544 | 1.00 | 69.57 | O |
| ATOM | 2597 | NE2 | GLN A | 416 | −17.868 | 26.434 | −26.969 | 1.00 | 60.27 | N |
| ATOM | 2598 | C | GLN A | 416 | −14.845 | 29.018 | −24.620 | 1.00 | 45.57 | C |
| ATOM | 2599 | O | GLN A | 416 | −14.726 | 29.275 | −25.813 | 1.00 | 44.77 | O |
| ATOM | 2600 | N | ASN A | 417 | −15.107 | 29.948 | −23.704 | 1.00 | 45.35 | N |
| ATOM | 2601 | CA | ASN A | 417 | −15.256 | 31.352 | −24.064 | 1.00 | 45.81 | C |
| ATOM | 2602 | CB | ASN A | 417 | −15.498 | 32.209 | −22.819 | 1.00 | 45.72 | C |
| ATOM | 2603 | CG | ASN A | 417 | −16.971 | 32.426 | −22.520 | 1.00 | 47.24 | C |
| ATOM | 2604 | OD1 | ASN A | 417 | −17.319 | 33.343 | −21.781 | 1.00 | 53.13 | O |
| ATOM | 2605 | ND2 | ASN A | 417 | −17.841 | 31.597 | −23.091 | 1.00 | 49.56 | N |
| ATOM | 2606 | C | ASN A | 417 | −14.033 | 31.862 | −24.828 | 1.00 | 45.57 | C |
| ATOM | 2607 | O | ASN A | 417 | −14.166 | 32.509 | −25.870 | 1.00 | 43.78 | O |
| ATOM | 2608 | N | CYS A | 418 | −12.852 | 31.537 | −24.301 | 1.00 | 46.54 | N |
| ATOM | 2609 | CA | CYS A | 418 | −11.572 | 31.909 | −24.902 | 1.00 | 47.29 | C |
| ATOM | 2610 | CB | CYS A | 418 | −10.423 | 31.445 | −23.998 | 1.00 | 47.03 | C |
| ATOM | 2611 | SG | CYS A | 418 | −8.759 | 31.848 | −24.581 | 1.00 | 47.65 | S |
| ATOM | 2612 | C | CYS A | 418 | −11.418 | 31.339 | −26.316 | 1.00 | 47.93 | C |
| ATOM | 2613 | O | CYS A | 418 | −11.186 | 32.082 | −27.272 | 1.00 | 47.43 | O |
| ATOM | 2614 | N | ASN A | 419 | −11.596 | 30.029 | −26.445 | 1.00 | 48.97 | N |
| ATOM | 2615 | CA | ASN A | 419 | −11.263 | 29.333 | −27.682 | 1.00 | 51.29 | C |
| ATOM | 2616 | CB | ASN A | 419 | −10.640 | 27.973 | −27.381 | 1.00 | 50.74 | C |
| ATOM | 2617 | CG | ASN A | 419 | −9.211 | 28.101 | −26.931 | 1.00 | 56.10 | C |
| ATOM | 2618 | OD1 | ASN A | 419 | −8.339 | 28.465 | −27.721 | 1.00 | 59.56 | O |
| ATOM | 2619 | ND2 | ASN A | 419 | −8.957 | 27.834 | −25.651 | 1.00 | 58.35 | N |
| ATOM | 2620 | C | ASN A | 419 | −12.337 | 29.236 | −28.759 | 1.00 | 52.91 | C |
| ATOM | 2621 | O | ASN A | 419 | −11.994 | 29.094 | −29.925 | 1.00 | 54.05 | O |
| ATOM | 2622 | N | GLN A | 420 | −13.614 | 29.310 | −28.387 | 1.00 | 53.66 | N |
| ATOM | 2623 | CA | GLN A | 420 | −14.694 | 29.168 | −29.363 | 1.00 | 54.99 | C |
| ATOM | 2624 | CB | GLN A | 420 | −16.063 | 29.131 | −28.664 | 1.00 | 55.42 | C |
| ATOM | 2625 | CG | GLN A | 420 | −16.613 | 30.522 | −28.288 | 1.00 | 50.95 | C |
| ATOM | 2626 | CD | GLN A | 420 | −17.856 | 30.489 | −27.420 | 1.00 | 54.58 | C |
| ATOM | 2627 | OE1 | GLN A | 420 | −18.209 | 31.492 | −26.794 | 1.00 | 49.49 | O |
| ATOM | 2628 | NE2 | GLN A | 420 | −18.534 | 29.345 | −27.383 | 1.00 | 53.01 | N |
| ATOM | 2629 | C | GLN A | 420 | −14.656 | 30.313 | −30.378 | 1.00 | 57.21 | C |
| ATOM | 2630 | O | GLN A | 420 | −14.334 | 31.445 | −30.034 | 1.00 | 56.56 | O |
| ATOM | 2631 | N | MET A | 421 | −14.996 | 30.027 | −31.627 | 1.00 | 60.06 | N |
| ATOM | 2632 | CA | MET A | 421 | −15.043 | 31.092 | −32.630 | 1.00 | 62.69 | C |
| ATOM | 2633 | CB | MET A | 421 | −14.376 | 30.645 | −33.940 | 1.00 | 63.23 | C |
| ATOM | 2634 | CG | MET A | 421 | −12.839 | 30.711 | −33.928 | 1.00 | 61.27 | C |
| ATOM | 2635 | SD | MET A | 421 | −12.098 | 32.271 | −33.333 | 1.00 | 62.88 | S |
| ATOM | 2636 | CE | MET A | 421 | −11.358 | 31.780 | −31.771 | 1.00 | 58.37 | C |
| ATOM | 2637 | C | MET A | 421 | −16.461 | 31.632 | −32.850 | 1.00 | 64.48 | C |
| ATOM | 2638 | O | MET A | 421 | −16.645 | 32.792 | −33.238 | 1.00 | 64.89 | O |
| ATOM | 2639 | N | HIS A | 422 | −17.456 | 30.783 | −32.588 | 1.00 | 65.84 | N |
| ATOM | 2640 | CA | HIS A | 422 | −18.863 | 31.184 | −32.611 | 1.00 | 66.55 | C |
| ATOM | 2641 | CB | HIS A | 422 | −19.536 | 30.729 | −33.909 | 1.00 | 67.18 | C |
| ATOM | 2647 | C | HIS A | 422 | −19.610 | 30.621 | −31.401 | 1.00 | 66.44 | C |
| ATOM | 2648 | O | HIS A | 422 | −19.262 | 29.560 | −30.877 | 1.00 | 65.51 | O |
| | | | | | gad65.pdb | | | | | |
| ATOM | 2649 | N | ASP A | 434 | −27.317 | 16.288 | −26.385 | 1.00 | 93.04 | N |
| ATOM | 2650 | CA | ASP A | 434 | −26.568 | 16.939 | −25.315 | 1.00 | 93.57 | C |
| ATOM | 2651 | CB | ASP A | 434 | −26.445 | 16.007 | −24.101 | 1.00 | 93.31 | C |
| ATOM | 2652 | CG | ASP A | 434 | −25.790 | 16.681 | −22.905 | 1.00 | 92.71 | C |
| ATOM | 2653 | OD1 | ASP A | 434 | −26.163 | 17.830 | −22.579 | 1.00 | 91.30 | O |
| ATOM | 2654 | OD2 | ASP A | 434 | −24.904 | 16.052 | −22.284 | 1.00 | 91.00 | O |
| ATOM | 2655 | C | ASP A | 434 | −25.188 | 17.388 | −25.808 | 1.00 | 94.21 | C |
| ATOM | 2656 | O | ASP A | 434 | −24.224 | 16.610 | −25.809 | 1.00 | 94.01 | O |
| ATOM | 2657 | N | LEU A | 435 | −25.106 | 18.651 | −26.222 | 1.00 | 94.79 | N |
| ATOM | 2658 | CA | LEU A | 435 | −23.893 | 19.209 | −26.826 | 1.00 | 95.23 | C |
| ATOM | 2659 | CB | LEU A | 435 | −24.233 | 20.480 | −27.612 | 1.00 | 95.29 | C |
| ATOM | 2663 | C | LEU A | 435 | −22.765 | 19.491 | −25.822 | 1.00 | 95.51 | C |
| ATOM | 2664 | O | LEU A | 435 | −21.637 | 19.795 | −26.222 | 1.00 | 95.51 | O |
| ATOM | 2665 | N | SER A | 436 | −23.074 | 19.378 | −24.529 | 1.00 | 95.69 | N |
| ATOM | 2666 | CA | SER A | 436 | −22.119 | 19.646 | −23.447 | 1.00 | 95.88 | C |
| ATOM | 2667 | CB | SER A | 436 | −22.805 | 19.488 | −22.086 | 1.00 | 95.94 | C |
| ATOM | 2669 | C | SER A | 436 | −20.877 | 18.754 | −23.509 | 1.00 | 96.01 | C |
| ATOM | 2670 | O | SER A | 436 | −19.861 | 19.040 | −22.870 | 1.00 | 96.18 | O |
| ATOM | 2671 | N | TYR A | 437 | −20.971 | 17.679 | −24.287 | 1.00 | 96.12 | N |
| ATOM | 2672 | CA | TYR A | 437 | −19.881 | 16.724 | −24.452 | 1.00 | 95.95 | C |
| ATOM | 2673 | CB | TYR A | 437 | −20.449 | 15.315 | −24.650 | 1.00 | 96.12 | C |
| ATOM | 2681 | C | TYR A | 437 | −18.925 | 17.102 | −25.598 | 1.00 | 95.61 | C |
| ATOM | 2682 | O | TYR A | 437 | −17.970 | 16.369 | −25.879 | 1.00 | 95.91 | O |
| ATOM | 2683 | N | ASP A | 438 | −19.202 | 18.234 | −26.257 | 1.00 | 94.64 | N |
| ATOM | 2684 | CA | ASP A | 438 | −18.286 | 18.878 | −27.217 | 1.00 | 93.42 | C |
| ATOM | 2685 | CB | ASP A | 438 | −18.820 | 18.794 | −28.663 | 1.00 | 92.98 | C |
| ATOM | 2686 | CG | ASP A | 438 | −19.660 | 17.534 | −28.946 | 1.00 | 91.69 | C |

TABLE A-continued

| ATOM | 2687 | OD1 | ASP A | 438 | −19.523 | 16.505 | −28.248 | 1.00 | 89.14 | O |
|---|---|---|---|---|---|---|---|---|---|---|
| ATOM | 2688 | OD2 | ASP A | 438 | −20.460 | 17.581 | −29.907 | 1.00 | 84.23 | O |
| ATOM | 2689 | C | ASP A | 438 | −18.143 | 20.367 | −26.826 | 1.00 | 92.79 | C |
| ATOM | 2690 | O | ASP A | 438 | −19.120 | 21.103 | −26.985 | 1.00 | 93.13 | O |
| ATOM | 2691 | N | THR A | 439 | −17.002 | 20.877 | −26.328 | 1.00 | 91.65 | N |
| ATOM | 2692 | CA | THR A | 439 | −15.637 | 20.287 | −26.122 | 1.00 | 90.03 | C |
| ATOM | 2693 | CB | THR A | 439 | −15.568 | 18.820 | −25.608 | 1.00 | 90.18 | C |
| ATOM | 2694 | OG1 | THR A | 439 | −16.127 | 17.928 | −26.579 | 1.00 | 92.22 | O |
| ATOM | 2695 | CG2 | THR A | 439 | −16.256 | 18.676 | −24.245 | 1.00 | 90.83 | C |
| ATOM | 2696 | C | THR A | 439 | −14.611 | 20.529 | −27.245 | 1.00 | 87.80 | C |
| ATOM | 2697 | O | THR A | 439 | −13.429 | 20.752 | −26.963 | 1.00 | 87.47 | O |
| ATOM | 2698 | N | GLY A | 440 | −15.063 | 20.504 | −28.497 | 1.00 | 85.33 | N |
| ATOM | 2699 | CA | GLY A | 440 | −14.184 | 20.762 | −29.641 | 1.00 | 82.42 | C |
| ATOM | 2700 | C | GLY A | 440 | −13.590 | 22.164 | −29.670 | 1.00 | 79.70 | C |
| ATOM | 2701 | O | GLY A | 440 | −12.438 | 22.348 | −30.082 | 1.00 | 79.64 | O |
| ATOM | 2702 | N | ASP A | 441 | −14.377 | 23.145 | −29.230 | 1.00 | 76.61 | N |
| ATOM | 2703 | CA | ASP A | 441 | −13.978 | 24.555 | −29.249 | 1.00 | 73.95 | C |
| ATOM | 2704 | CB | ASP A | 441 | −15.146 | 25.443 | −29.705 | 1.00 | 73.96 | C |
| ATOM | 2705 | CG | ASP A | 441 | −15.071 | 25.809 | −31.183 | 1.00 | 73.09 | C |
| ATOM | 2706 | OD1 | ASP A | 441 | −14.076 | 25.453 | −31.851 | 1.00 | 76.15 | O |
| ATOM | 2707 | OD2 | ASP A | 441 | −16.008 | 26.466 | −31.675 | 1.00 | 67.23 | O |
| ATOM | 2708 | C | ASP A | 441 | −13.447 | 25.028 | −27.900 | 1.00 | 71.87 | C |
| ATOM | 2709 | O | ASP A | 441 | −13.483 | 26.223 | −27.577 | 1.00 | 71.64 | O |
| ATOM | 2710 | N | LYS A | 442 | −12.951 | 24.081 | −27.112 | 1.00 | 69.47 | N |
| ATOM | 2711 | CA | LYS A | 442 | −12.327 | 24.401 | −25.834 | 1.00 | 66.80 | C |
| ATOM | 2712 | CB | LYS A | 442 | −12.554 | 23.264 | −24.835 | 1.00 | 67.10 | C |
| ATOM | 2713 | CG | LYS A | 442 | −12.432 | 23.679 | −23.383 | 1.00 | 67.82 | C |
| ATOM | 2714 | CD | LYS A | 442 | −12.499 | 22.495 | −22.437 | 1.00 | 71.01 | C |
| ATOM | 2715 | CE | LYS A | 442 | −13.916 | 21.972 | −22.294 | 1.00 | 73.11 | C |
| ATOM | 2716 | NZ | LYS A | 442 | −14.034 | 21.048 | −21.137 | 1.00 | 76.98 | N |
| ATOM | 2717 | C | LYS A | 442 | −10.833 | 24.668 | −26.002 | 1.00 | 64.41 | C |
| ATOM | 2718 | O | LYS A | 442 | −10.246 | 25.413 | −25.225 | 1.00 | 64.92 | O |
| ATOM | 2719 | N | ALA A | 443 | −10.227 | 24.058 | −27.017 | 1.00 | 62.14 | N |
| ATOM | 2720 | CA | ALA A | 443 | −8.781 | 24.159 | −27.231 | 1.00 | 59.61 | C |
| ATOM | 2721 | CB | ALA A | 443 | −8.128 | 22.791 | −27.061 | 1.00 | 60.47 | C |
| ATOM | 2722 | C | ALA A | 443 | −8.408 | 24.753 | −28.582 | 1.00 | 56.83 | C |
| ATOM | 2723 | O | ALA A | 443 | −9.269 | 25.067 | −29.401 | 1.00 | 56.30 | O |
| ATOM | 2724 | N | LEU A | 444 | −7.104 | 24.898 | −28.799 | 1.00 | 55.41 | N |
| ATOM | 2725 | CA | LEU A | 444 | −6.564 | 25.318 | −30.085 | 1.00 | 53.21 | C |
| ATOM | 2726 | CB | LEU A | 444 | −5.128 | 25.821 | −29.929 | 1.00 | 54.01 | C |
| ATOM | 2727 | CG | LEU A | 444 | −5.009 | 27.325 | −29.708 | 1.00 | 55.89 | C |
| ATOM | 2728 | CD1 | LEU A | 444 | −3.546 | 27.698 | −29.504 | 1.00 | 53.15 | C |
| ATOM | 2729 | CD2 | LEU A | 444 | −5.633 | 28.080 | −30.900 | 1.00 | 56.12 | C |
| ATOM | 2730 | C | LEU A | 444 | −6.607 | 24.219 | −31.138 | 1.00 | 50.16 | C |
| ATOM | 2731 | O | LEU A | 444 | −6.915 | 24.494 | −32.289 | 1.00 | 49.23 | O |
| ATOM | 2732 | N | GLN A | 445 | −6.276 | 22.990 | −30.741 | 1.00 | 48.25 | N |
| ATOM | 2733 | CA | GLN A | 445 | −6.322 | 21.841 | −31.642 | 1.00 | 47.56 | C |
| ATOM | 2734 | CB | GLN A | 445 | −5.911 | 20.566 | −30.916 | 1.00 | 47.11 | C |
| ATOM | 2735 | CG | GLN A | 445 | −4.445 | 20.457 | −30.582 | 1.00 | 45.89 | C |
| ATOM | 2736 | CD | GLN A | 445 | −4.097 | 19.105 | −30.038 | 1.00 | 47.99 | C |
| ATOM | 2737 | OE1 | GLN A | 445 | −3.461 | 18.292 | −30.722 | 1.00 | 51.67 | O |
| ATOM | 2738 | NE2 | GLN A | 445 | −4.520 | 18.836 | −28.805 | 1.00 | 41.58 | N |
| ATOM | 2739 | C | GLN A | 445 | −7.709 | 21.626 | −32.238 | 1.00 | 47.71 | C |
| ATOM | 2740 | O | GLN A | 445 | −8.718 | 22.054 | −31.674 | 1.00 | 47.34 | O |
| ATOM | 2741 | N | CYS A | 446 | −7.740 | 20.976 | −33.391 | 1.00 | 47.55 | N |
| ATOM | 2742 | CA | CYS A | 446 | −8.974 | 20.521 | −33.982 | 1.00 | 47.00 | C |
| ATOM | 2743 | CB | CYS A | 446 | −9.009 | 20.901 | −35.455 | 1.00 | 47.04 | C |
| ATOM | 2744 | SG | CYS A | 446 | −10.447 | 20.365 | −36.359 | 1.00 | 50.09 | S |
| ATOM | 2745 | C | CYS A | 446 | −8.937 | 19.017 | −33.771 | 1.00 | 46.39 | C |
| ATOM | 2746 | O | CYS A | 446 | −9.430 | 18.513 | −32.753 | 1.00 | 45.74 | O |
| ATOM | 2747 | N | GLY A | 447 | −8.301 | 18.306 | −34.705 | 1.00 | 45.48 | N |
| ATOM | 2748 | CA | GLY A | 447 | −7.931 | 16.926 | −34.478 | 1.00 | 43.34 | C |
| ATOM | 2749 | C | GLY A | 447 | −7.198 | 16.817 | −33.160 | 1.00 | 43.94 | C |
| ATOM | 2750 | O | GLY A | 447 | −6.364 | 17.664 | −32.827 | 1.00 | 43.47 | O |
| ATOM | 2751 | N | ARG A | 448 | −7.526 | 15.786 | −32.391 | 1.00 | 44.73 | N |
| ATOM | 2752 | CA | ARG A | 448 | −6.886 | 15.574 | −31.108 | 1.00 | 45.57 | C |
| ATOM | 2753 | CB | ARG A | 448 | −7.626 | 16.307 | −29.985 | 1.00 | 45.11 | C |
| ATOM | 2754 | CG | ARG A | 448 | −6.904 | 16.244 | −28.648 | 1.00 | 44.87 | C |
| ATOM | 2755 | CD | ARG A | 448 | −7.353 | 17.329 | −27.680 | 1.00 | 51.60 | C |
| ATOM | 2756 | NE | ARG A | 448 | −8.750 | 17.199 | −27.250 | 1.00 | 53.09 | N |
| ATOM | 2757 | CZ | ARG A | 448 | −9.155 | 16.574 | −26.144 | 1.00 | 46.01 | C |
| ATOM | 2758 | NH1 | ARG A | 448 | −8.281 | 15.977 | −25.344 | 1.00 | 44.21 | N |
| ATOM | 2759 | NH2 | ARG A | 448 | −10.452 | 16.531 | −25.845 | 1.00 | 46.54 | N |
| ATOM | 2760 | C | ARG A | 448 | −6.792 | 14.082 | −30.837 | 1.00 | 46.84 | C |
| ATOM | 2761 | O | ARG A | 448 | −7.777 | 13.341 | −30.991 | 1.00 | 47.51 | O |
| ATOM | 2762 | N | HIS A | 449 | −5.588 | 13.648 | −30.475 | 1.00 | 45.65 | N |
| ATOM | 2763 | CA | HIS A | 449 | −5.321 | 12.247 | −30.209 | 1.00 | 45.72 | C |
| ATOM | 2764 | CB | HIS A | 449 | −3.820 | 11.979 | −30.298 | 1.00 | 45.88 | C |
| ATOM | 2765 | CG | HIS A | 449 | −3.432 | 10.588 | −29.918 | 1.00 | 42.24 | C | gad65.pdb

TABLE A-continued

| | | | | | | | | | | |
|---|---|---|---|---|---|---|---|---|---|---|
| ATOM | 2766 | ND1 | HIS A | 449 | −3.435 | 9.543 | −30.818 | 1.00 | 43.86 | N |
| ATOM | 2767 | CE1 | HIS A | 449 | −3.060 | 8.435 | −30.202 | 1.00 | 39.42 | C |
| ATOM | 2768 | NE2 | HIS A | 449 | −2.796 | 8.729 | −28.939 | 1.00 | 46.90 | N |
| ATOM | 2769 | CD2 | HIS A | 449 | −3.020 | 10.070 | −28.735 | 1.00 | 39.45 | C |
| ATOM | 2770 | C | HIS A | 449 | −5.863 | 11.858 | −28.837 | 1.00 | 46.03 | C |
| ATOM | 2771 | O | HIS A | 449 | −5.840 | 12.668 | −27.896 | 1.00 | 47.52 | O |
| ATOM | 2772 | N | VAL A | 450 | −6.357 | 10.626 | −28.730 | 1.00 | 44.07 | N |
| ATOM | 2773 | CA | VAL A | 450 | −6.860 | 10.097 | −27.467 | 1.00 | 43.32 | C |
| ATOM | 2774 | CS | VAL A | 450 | −7.792 | 8.872 | −27.712 | 1.00 | 43.54 | C |
| ATOM | 2775 | CG1 | VAL A | 450 | −8.289 | 8.266 | −26.404 | 1.00 | 42.01 | C |
| ATOM | 2776 | CG2 | VAL A | 450 | −8.952 | 9.259 | −28.600 | 1.00 | 44.12 | C |
| ATOM | 2777 | C | VAL A | 450 | −5.692 | 9.719 | −26.549 | 1.00 | 43.72 | C |
| ATOM | 2778 | O | VAL A | 450 | −4.979 | 8.762 | −26.808 | 1.00 | 44.53 | O |
| ATOM | 2779 | N | ASP A | 451 | −5.513 | 10.479 | −25.474 | 1.00 | 45.59 | N |
| ATOM | 2780 | CA | ASP A | 451 | −4.478 | 10.232 | −24.479 | 1.00 | 47.54 | C |
| ATOM | 2781 | CB | ASP A | 451 | −3.623 | 11.486 | −24.298 | 1.00 | 47.98 | C |
| ATOM | 2782 | CG | ASP A | 451 | −2.872 | 11.869 | −25.562 | 1.00 | 56.14 | C |
| ATOM | 2783 | OD1 | ASP A | 451 | −2.432 | 10.943 | −26.292 | 1.00 | 52.65 | O |
| ATOM | 2784 | OD2 | ASP A | 451 | −2.711 | 13.096 | −25.808 | 1.00 | 59.15 | O |
| ATOM | 2785 | C | ASP A | 451 | −5.060 | 9.816 | −23.126 | 1.00 | 47.91 | C |
| ATOM | 2786 | O | ASP A | 451 | −4.341 | 9.290 | −22.272 | 1.00 | 47.25 | O |
| ATOM | 2787 | N | VAL A | 452 | −6.355 | 10.061 | −22.937 | 1.00 | 46.98 | N |
| ATOM | 2788 | CA | VAL A | 452 | −7.021 | 9.750 | −21.673 | 1.00 | 46.86 | C |
| ATOM | 2789 | CB | VAL A | 452 | −8.480 | 10.316 | −21.633 | 1.00 | 46.07 | C |
| ATOM | 2790 | CG1 | VAL A | 452 | −9.402 | 9.595 | −22.624 | 1.00 | 39.81 | C |
| ATOM | 2791 | CG2 | VAL A | 452 | −9.045 | 10.249 | −20.214 | 1.00 | 47.58 | C |
| ATOM | 2792 | C | VAL A | 452 | −7.020 | 8.254 | −21.287 | 1.00 | 47.34 | C |
| ATOM | 2793 | O | VAL A | 452 | −6.831 | 7.917 | −20.115 | 1.00 | 48.12 | O |
| ATOM | 2794 | N | PHE A | 453 | −7.225 | 7.366 | −22.262 | 1.00 | 46.72 | N |
| ATOM | 2795 | CA | PHE A | 453 | −7.434 | 5.952 | −21.957 | 1.00 | 45.66 | C |
| | | | | | gad65.pdb | | | | | |
| ATOM | 2796 | CB | PHE A | 453 | −7.857 | 5.127 | −23.179 | 1.00 | 44.26 | C |
| ATOM | 2797 | CG | PHE A | 453 | −8.252 | 3.701 | −22.833 | 1.00 | 41.29 | C |
| ATOM | 2798 | CD1 | PHE A | 453 | −9.426 | 3.441 | −22.129 | 1.00 | 43.81 | C |
| ATOM | 2799 | CE1 | PHE A | 453 | −9.800 | 2.126 | −21.796 | 1.00 | 42.96 | C |
| ATOM | 2800 | CZ | PHE A | 453 | −8.980 | 1.060 | −22.161 | 1.00 | 43.40 | C |
| ATOM | 2801 | CE2 | PHE A | 453 | −7.805 | 1.306 | −22.863 | 1.00 | 40.92 | C |
| ATOM | 2802 | CD2 | PHE A | 453 | −7.445 | 2.626 | −23.196 | 1.00 | 39.96 | C |
| ATOM | 2803 | C | PHE A | 453 | −6.230 | 5.317 | −21.280 | 1.00 | 46.47 | C |
| ATOM | 2804 | O | PHE A | 453 | −6.397 | 4.503 | −20.375 | 1.00 | 45.11 | O |
| ATOM | 2805 | N | LYS A | 454 | −5.026 | 5.714 | −21.696 | 1.00 | 47.68 | N |
| ATOM | 2806 | CA | LYS A | 454 | −3.828 | 5.168 | −21.086 | 1.00 | 48.74 | C |
| ATOM | 2807 | CB | LYS A | 454 | −2.558 | 5.422 | −21.922 | 1.00 | 48.76 | C |
| ATOM | 2808 | CG | LYS A | 454 | −2.317 | 6.846 | −22.334 | 1.00 | 54.07 | C |
| ATOM | 2809 | CD | LYS A | 454 | −1.345 | 6.938 | −23.493 | 1.00 | 54.70 | C |
| ATOM | 2810 | CE | LYS A | 454 | −1.103 | 8.414 | −23.823 | 1.00 | 60.74 | C |
| ATOM | 2811 | NZ | LYS A | 454 | −.219 | 8.623 | −24.998 | 1.00 | 56.26 | N |
| ATOM | 2812 | C | LYS A | 454 | −3.699 | 5.577 | −19.621 | 1.00 | 49.50 | C |
| ATOM | 2813 | O | LYS A | 454 | −3.300 | 4.760 | −18.785 | 1.00 | 50.24 | O |
| ATOM | 2814 | N | LEU A | 455 | −4.073 | 6.815 | −19.301 | 1.00 | 48.81 | N |
| ATOM | 2815 | CA | LEU A | 455 | −4.094 | 7.266 | −17.903 | 1.00 | 47.81 | C |
| ATOM | 2816 | CB | LEU A | 455 | −4.217 | 8.803 | −17.805 | 1.00 | 47.69 | C |
| ATOM | 2817 | CG | LEU A | 455 | −4.398 | 9.462 | −16.417 | 1.00 | 49.83 | C |
| ATOM | 2818 | CD1 | LEU A | 455 | −3.323 | 9.036 | −15.403 | 1.00 | 48.07 | C |
| ATOM | 2819 | CD2 | LEU A | 455 | −4.451 | 10.987 | −16.496 | 1.00 | 47.62 | C |
| ATOM | 2820 | C | LEU A | 455 | −5.210 | 6.567 | −17.101 | 1.00 | 46.14 | C |
| ATOM | 2821 | O | LEU A | 455 | −4.978 | 6.071 | −15.988 | 1.00 | 46.65 | O |
| ATOM | 2822 | N | TRP A | 456 | −6.408 | 6.530 | −17.670 | 1.00 | 43.49 | N |
| ATOM | 2823 | CA | TRP A | 456 | −7.566 | 5.933 | −16.996 | 1.00 | 43.44 | C |
| ATOM | 2824 | CB | TRP A | 456 | −8.857 | 6.229 | −17.770 | 1.00 | 40.97 | C |
| ATOM | 2825 | CG | TRP A | 456 | −10.088 | 5.669 | −17.122 | 1.00 | 44.38 | C |
| ATOM | 2826 | CD1 | TRP A | 456 | −10.890 | 6.290 | −16.199 | 1.00 | 38.37 | C |
| ATOM | 2827 | NE1 | TRP A | 456 | −11.930 | 5.459 | −15.848 | 1.00 | 41.32 | N |
| ATOM | 2828 | CE2 | TRP A | 456 | −11.825 | 4.284 | −16.541 | 1.00 | 38.66 | C |
| ATOM | 2829 | CD2 | TRP A | 456 | −10.678 | 4.375 | −17.358 | 1.00 | 43.03 | C |
| ATOM | 2830 | CE3 | TRP A | 456 | −10.354 | 3.294 | −18.187 | 1.00 | 36.31 | C |
| ATOM | 2831 | CZ3 | TRP A | 456 | −11.156 | 2.161 | −18.154 | 1.00 | 39.02 | C |
| ATOM | 2832 | CH2 | TRP A | 456 | −12.282 | 2.100 | −17.325 | 1.00 | 38.93 | C |
| ATOM | 2833 | CZ2 | TRP A | 456 | −12.631 | 3.146 | −16.509 | 1.00 | 38.54 | C |
| ATOM | 2834 | C | TRP A | 456 | −7.402 | 4.416 | −16.703 | 1.00 | 43.32 | C |
| ATOM | 2835 | O | TRP A | 456 | −7.686 | 3.980 | −15.607 | 1.00 | 43.22 | O |
| ATOM | 2836 | N | LEU A | 457 | −6.938 | 3.630 | −17.678 | 1.00 | 42.98 | N |
| ATOM | 2837 | CA | LEU A | 457 | −6.694 | 2.196 | −17.465 | 1.00 | 42.58 | C |
| ATOM | 2838 | CB | LEU A | 457 | −6.316 | 1.477 | −18.778 | 1.00 | 42.41 | C |
| ATOM | 2839 | CG | LEU A | 457 | −6.598 | −.035 | −18.804 | 1.00 | 40.61 | C |
| ATOM | 2840 | CD1 | LEU A | 457 | −8.104 | −.318 | −18.599 | 1.00 | 40.63 | C |
| ATOM | 2841 | CD2 | LEU A | 457 | −6.100 | −.708 | −20.080 | 1.00 | 40.83 | C |
| ATOM | 2842 | C | LEU A | 457 | −5.640 | 1.934 | −16.379 | 1.00 | 42.84 | C |
| ATOM | 2843 | O | LEU A | 457 | −5.842 | 1.094 | −15.504 | 1.00 | 42.58 | O |
| ATOM | 2844 | N | MET A | 458 | −4.519 | 2.648 | −16.457 | 1.00 | 43.28 | N |

TABLE A-continued

| | | | | | | | | | |
|---|---|---|---|---|---|---|---|---|---|
| ATOM | 2845 | CA | MET A | 458 | −3.493 | 2.623 | −15.414 | 1.00 | 44.81 | C |
| ATOM | 2846 | CB | MET A | 458 | −2.333 | 3.544 | −15.784 | 1.00 | 43.84 | C |
| ATOM | 2847 | CG | MET A | 458 | −1.450 | 2.999 | −16.882 | 1.00 | 42.38 | C |
| ATOM | 2848 | SD | MET A | 458 | −.193 | 4.191 | −17.371 | 1.00 | 49.40 | S |
| ATOM | 2849 | CE | MET A | 458 | .874 | 4.205 | −15.935 | 1.00 | 43.59 | C |
| ATOM | 2850 | C | MET A | 458 | −4.028 | 3.000 | −14.036 | 1.00 | 44.51 | C |
| ATOM | 2851 | O | MET A | 458 | −3.751 | 2.318 | −13.060 | 1.00 | 45.84 | O |
| ATOM | 2852 | N | TRP A | 459 | −4.777 | 4.094 | −13.954 | 1.00 | 45.02 | N |
| ATOM | 2853 | CA | TRP A | 459 | −5.409 | 4.511 | −12.712 | 1.00 | 45.55 | C |
| ATOM | 2854 | CB | TRP A | 459 | −6.219 | 5.792 | −12.931 | 1.00 | 45.32 | C |
| ATOM | 2855 | CG | TRP A | 459 | −6.324 | 6.675 | −11.709 | 1.00 | 48.42 | C |
| ATOM | 2856 | CD1 | TRP A | 459 | −6.504 | 6.270 | −10.413 | 1.00 | 48.22 | C |
| ATOM | 2857 | NE1 | TRP A | 459 | −6.552 | 7.354 | −9.578 | 1.00 | 46.37 | N |
| ATOM | 2858 | CE2 | TRP A | 459 | −6.417 | 8.497 | −10.320 | 1.00 | 48.57 | C |
| ATOM | 2859 | CD2 | TRP A | 459 | −6.272 | 8.108 | −11.673 | 1.00 | 48.82 | C |
| ATOM | 2860 | CE3 | TRP A | 459 | −6.102 | 9.101 | −12.647 | 1.00 | 47.56 | C |
| ATOM | 2861 | CZ3 | TRP A | 459 | −6.087 | 10.440 | −12.244 | 1.00 | 48.78 | C |
| ATOM | 2862 | CH2 | TRP A | 459 | −6.248 | 10.795 | −10.888 | 1.00 | 45.56 | C |
| ATOM | 2863 | CZ2 | TRP A | 459 | −6.401 | 9.842 | −9.915 | 1.00 | 49.27 | C |
| | | | | | gad65.pdb | | | | | |
| ATOM | 2864 | C | TRP A | 459 | −6.321 | 3.391 | −12.196 | 1.00 | 46.71 | C |
| ATOM | 2865 | O | TRP A | 459 | −6.388 | 3.140 | −10.997 | 1.00 | 46.65 | O |
| ATOM | 2866 | N | ARG A | 460 | −7.000 | 2.713 | −13.114 | 1.00 | 46.73 | N |
| ATOM | 2867 | CA | ARG A | 460 | −7.889 | 1.622 | −12.765 | 1.00 | 48.35 | C |
| ATOM | 2868 | CB | ARG A | 460 | −8.727 | 1.214 | −13.980 | 1.00 | 47.55 | C |
| ATOM | 2869 | CG | ARG A | 460 | −10.220 | 1.105 | −13.708 | 1.00 | 54.02 | C |
| ATOM | 2870 | CD | ARG A | 460 | −10.894 | 2.468 | −13.573 | 1.00 | 51.19 | C |
| ATOM | 2875 | C | ARG A | 460 | −7.087 | .439 | −12.237 | 1.00 | 49.10 | C |
| ATOM | 2876 | O | ARG A | 460 | −7.432 | −.149 | −11.205 | 1.00 | 49.39 | O |
| ATOM | 2877 | N | ALA A | 461 | −6.006 | .113 | −12.943 | 1.00 | 49.21 | N |
| ATOM | 2878 | CA | ALA A | 461 | −5.187 | −1.058 | −12.634 | 1.00 | 49.19 | C |
| ATOM | 2879 | CB | ALA A | 461 | −4.294 | −1.400 | −13.816 | 1.00 | 49.60 | C |
| ATOM | 2880 | C | ALA A | 461 | −4.348 | −.892 | −11.372 | 1.00 | 48.69 | C |
| ATOM | 2881 | O | ALA A | 461 | −4.026 | −1.875 | −10.708 | 1.00 | 49.46 | O |
| ATOM | 2882 | N | LYS A | 462 | −4.013 | .353 | −11.050 | 1.00 | 48.08 | N |
| ATOM | 2883 | CA | LYS A | 462 | −3.111 | .678 | −9.945 | 1.00 | 47.62 | C |
| ATOM | 2884 | CB | LYS A | 462 | −2.080 | 1.713 | −10.414 | 1.00 | 47.99 | C |
| ATOM | 2885 | CG | LYS A | 462 | −1.060 | 1.194 | −11.417 | 1.00 | 51.80 | C |
| ATOM | 2886 | CD | LYS A | 462 | −.408 | 2.350 | −12.173 | 1.00 | 51.66 | C |
| ATOM | 2887 | CE | LYS A | 462 | 1.107 | 2.253 | −12.130 | 1.00 | 57.05 | C |
| ATOM | 2888 | NZ | LYS A | 462 | 1.668 | 1.117 | −12.928 | 1.00 | 58.26 | N |
| ATOM | 2889 | C | LYS A | 462 | −3.830 | 1.250 | −8.727 | 1.00 | 46.51 | C |
| ATOM | 2890 | O | LYS A | 462 | −3.360 | 1.103 | −7.594 | 1.00 | 45.89 | O |
| ATOM | 2891 | N | GLY A | 463 | −4.954 | 1.923 | −8.973 | 1.00 | 45.77 | N |
| ATOM | 2892 | CA | GLY A | 463 | −5.620 | 2.721 | −7.954 | 1.00 | 45.66 | C |
| ATOM | 2893 | C | GLY A | 463 | −4.779 | 3.940 | −7.621 | 1.00 | 45.51 | C |
| ATOM | 2894 | O | GLY A | 463 | −3.599 | 4.002 | −7.958 | 1.00 | 45.97 | O |
| ATOM | 2895 | N | THR A | 464 | −5.393 | 4.918 | −6.968 | 1.00 | 46.36 | N |
| ATOM | 2896 | CA | THR A | 464 | −4.680 | 6.086 | −6.465 | 1.00 | 47.95 | C |
| ATOM | 2897 | CB | THR A | 464 | −5.642 | 7.045 | −5.733 | 1.00 | 48.27 | C |
| ATOM | 2898 | OG1 | THR A | 464 | −6.639 | 7.500 | −6.652 | 1.00 | 51.34 | O |
| ATOM | 2899 | CG2 | THR A | 464 | −4.899 | 8.253 | −5.150 | 1.00 | 50.28 | C |
| ATOM | 2900 | C | THR A | 464 | −3.527 | 5.684 | −5.547 | 1.00 | 48.55 | C |
| ATOM | 2901 | O | THR A | 464 | −2.449 | 6.297 | −5.598 | 1.00 | 50.32 | O |
| ATOM | 2902 | N | THR A | 465 | −3.752 | 4.652 | −4.728 | 1.00 | 47.47 | N |
| ATOM | 2903 | CA | THR A | 465 | −2.716 | 4.091 | −3.844 | 1.00 | 47.29 | C |
| ATOM | 2904 | CB | THR A | 465 | −3.272 | 2.967 | −2.904 | 1.00 | 47.40 | C |
| ATOM | 2905 | OG1 | THR A | 465 | −4.161 | 2.112 | −3.634 | 1.00 | 51.14 | O |
| ATOM | 2906 | CG2 | THR A | 465 | −4.030 | 3.569 | −1.718 | 1.00 | 43.62 | C |
| ATOM | 2907 | C | THR A | 465 | −1.499 | 3.569 | −4.603 | 1.00 | 46.99 | C |
| ATOM | 2908 | O | THR A | 465 | −.382 | 3.688 | −4.129 | 1.00 | 47.48 | O |
| ATOM | 2909 | N | GLY A | 466 | −1.723 | 2.983 | −5.773 | 1.00 | 47.45 | N |
| ATOM | 2910 | CA | GLY A | 466 | −.642 | 2.497 | −6.626 | 1.00 | 47.58 | C |
| ATOM | 2911 | C | GLY A | 466 | .278 | 3.604 | −7.104 | 1.00 | 48.68 | C |
| ATOM | 2912 | O | GLY A | 466 | 1.504 | 3.472 | −7.038 | 1.00 | 48.94 | O |
| ATOM | 2913 | N | PHE A | 467 | −.307 | 4.704 | −7.575 | 1.00 | 49.54 | N |
| ATOM | 2914 | CA | PHE A | 467 | .482 | 5.851 | −8.025 | 1.00 | 49.27 | C |
| ATOM | 2915 | CB | PHE A | 467 | −.406 | 6.934 | −8.635 | 1.00 | 48.18 | C |
| ATOM | 2916 | CG | PHE A | 467 | −.878 | 6.631 | −10.031 | 1.00 | 47.51 | C |
| ATOM | 2917 | CD1 | PHE A | 467 | −2.227 | 6.692 | −10.346 | 1.00 | 50.71 | C |
| ATOM | 2918 | CE1 | PHE A | 467 | −2.675 | 6.436 | −11.646 | 1.00 | 49.35 | C |
| ATOM | 2919 | CZ | PHE A | 467 | −1.776 | 6.111 | −12.627 | 1.00 | 48.56 | C |
| ATOM | 2920 | CE2 | PHE A | 467 | −.415 | 6.057 | −12.333 | 1.00 | 49.46 | C |
| ATOM | 2921 | CD2 | PHE A | 467 | .023 | 6.318 | −11.039 | 1.00 | 49.15 | C |
| ATOM | 2922 | C | PHE A | 467 | 1.258 | 6.421 | −6.846 | 1.00 | 50.40 | C |
| ATOM | 2923 | O | PHE A | 467 | 2.449 | 6.748 | −6.962 | 1.00 | 50.89 | O |
| ATOM | 2924 | N | GLU A | 468 | .575 | 6.527 | −5.711 | 1.00 | 49.98 | N |
| ATOM | 2925 | CA | GLU A | 468 | 1.201 | 6.945 | −4.470 | 1.00 | 50.66 | C |
| ATOM | 2926 | CB | GLU A | 468 | .213 | 6.843 | −3.307 | 1.00 | 50.24 | C |
| ATOM | 2927 | CG | GLU A | 468 | .764 | 7.395 | −2.022 | 1.00 | 48.95 | C |

TABLE A-continued

| | | | | | | | | | |
|---|---|---|---|---|---|---|---|---|---|
| ATOM | 2928 | CD | GLU A | 468 | −.113 | 7.129 | −.816 | 1.00 | 52.14 | C |
| ATOM | 2929 | OE1 | GLU A | 468 | −1.040 | 6.286 | −.894 | 1.00 | 45.66 | O |
| ATOM | 2930 | OE2 | GLU A | 468 | .154 | 7.761 | .231 | 1.00 | 57.51 | O |
| ATOM | 2931 | C | GLU A | 468 | 2.457 | 6.133 | −4.155 | 1.00 | 51.66 | C |
| ATOM | 2932 | O | GLU A | 468 | 3.523 | 6.706 | −3.926 | 1.00 | 53.10 | O |
| ATOM | 2933 | N | ALA A | 469 | 2.326 | 4.808 | −4.131 | 1.00 | 51.30 | N |
| ATOM | 2934 | CA | ALA A | 469 | 3.427 | 3.934 | −3.735 | 1.00 | 52.00 | C |
| ATOM | 2935 | CB | ALA A | 469 | 2.969 | 2.480 | −3.697 | 1.00 | 51.88 | C |
| | | | gad65.pdb | | | | | | | |
| ATOM | 2936 | C | ALA A | 469 | 4.623 | 4.091 | −4.664 | 1.00 | 52.74 | C |
| ATOM | 2937 | O | ALA A | 469 | 5.786 | 4.054 | −4.223 | 1.00 | 52.12 | O |
| ATOM | 2938 | N | HIS A | 470 | 4.321 | 4.260 | −5.949 | 1.00 | 54.30 | N |
| ATOM | 2939 | CA | HIS A | 470 | 5.343 | 4.430 | −6.975 | 1.00 | 55.37 | C |
| ATOM | 2940 | CB | HIS A | 470 | 4.744 | 4.313 | −8.375 | 1.00 | 54.90 | C |
| ATOM | 2941 | CG | HIS A | 470 | 5.617 | 4.892 | −9.445 | 1.00 | 61.48 | C |
| ATOM | 2942 | ND1 | HIS A | 470 | 6.892 | 4.430 | −9.698 | 1.00 | 60.16 | N |
| ATOM | 2943 | CE1 | HIS A | 470 | 7.421 | 5.131 | −10.685 | 1.00 | 62.55 | C |
| ATOM | 2944 | NE2 | HIS A | 470 | 6.542 | 6.039 | −11.072 | 1.00 | 63.26 | N |
| ATOM | 2945 | CD2 | HIS A | 470 | 5.404 | 5.911 | −10.313 | 1.00 | 62.38 | C |
| ATOM | 2946 | C | HIS A | 470 | 6.095 | 5.751 | −6.824 | 1.00 | 54.65 | C |
| ATOM | 2947 | O | HIS A | 470 | 7.323 | 5.770 | −6.851 | 1.00 | 54.75 | O |
| ATOM | 2948 | N | VAL A | 471 | 5.348 | 6.843 | −6.672 | 1.00 | 54.16 | N |
| ATOM | 2949 | CA | VAL A | 471 | 5.929 | 8.159 | −6.430 | 1.00 | 54.14 | C |
| ATOM | 2950 | CB | VAL A | 471 | 4.822 | 9.264 | −6.325 | 1.00 | 54.21 | C |
| ATOM | 2951 | CG1 | VAL A | 471 | 5.346 | 10.569 | −5.723 | 1.00 | 52.50 | C |
| ATOM | 2952 | CG2 | VAL A | 471 | 4.227 | 9.539 | −7.700 | 1.00 | 52.31 | C |
| ATOM | 2953 | C | VAL A | 471 | 6.897 | 8.124 | −5.231 | 1.00 | 54.83 | C |
| ATOM | 2954 | O | VAL A | 471 | 8.001 | 8.658 | −5.325 | 1.00 | 55.11 | O |
| ATOM | 2955 | N | ASP A | 472 | 6.498 | 7.463 | −4.138 | 1.00 | 54.82 | N |
| ATOM | 2956 | CA | ASP A | 472 | 7.349 | 7.311 | −2.936 | 1.00 | 54.76 | C |
| ATOM | 2957 | CB | ASP A | 472 | 6.551 | 6.732 | −1.772 | 1.00 | 54.64 | C |
| ATOM | 2958 | CG | ASP A | 472 | 5.377 | 7.595 | −1.377 | 1.00 | 56.94 | C |
| ATOM | 2959 | OD1 | ASP A | 472 | 4.649 | 7.201 | −.435 | 1.00 | 53.83 | O |
| ATOM | 2960 | OD2 | ASP A | 472 | 5.184 | 8.661 | −2.002 | 1.00 | 59.59 | O |
| ATOM | 2961 | C | ASP A | 472 | 8.578 | 6.429 | −3.140 | 1.00 | 55.36 | C |
| ATOM | 2962 | O | ASP A | 472 | 9.622 | 6.650 | −2.515 | 1.00 | 55.31 | O |
| ATOM | 2963 | N | LYS A | 473 | 8.434 | 5.407 | −3.980 | 1.00 | 56.01 | N |
| ATOM | 2964 | CA | LYS A | 473 | 9.519 | 4.484 | −4.272 | 1.00 | 56.18 | C |
| ATOM | 2965 | CB | LYS A | 473 | 9.016 | 3.327 | −5.139 | 1.00 | 56.98 | C |
| ATOM | 2966 | CG | LYS A | 473 | 9.985 | 2.148 | −5.255 | 1.00 | 60.32 | C |
| ATOM | 2970 | C | LYS A | 473 | 10.634 | 5.243 | −4.980 | 1.00 | 55.95 | C |
| ATOM | 2971 | O | LYS A | 473 | 11.808 | 5.085 | −4.640 | 1.00 | 55.90 | O |
| ATOM | 2972 | N | CYS A | 474 | 10.251 | 6.083 | −5.946 | 1.00 | 55.33 | N |
| ATOM | 2973 | CA | CYS A | 474 | 11.200 | 6.907 | −6.682 | 1.00 | 54.29 | C |
| ATOM | 2974 | CB | CYS A | 474 | 10.511 | 7.636 | −7.840 | 1.00 | 52.54 | C |
| ATOM | 2975 | SG | CYS A | 474 | 9.753 | 6.536 | −9.061 | 1.00 | 52.69 | S |
| ATOM | 2976 | C | CYS A | 474 | 11.907 | 7.906 | −5.755 | 1.00 | 55.30 | C |
| ATOM | 2977 | O | CYS A | 474 | 13.132 | 8.053 | −5.816 | 1.00 | 54.58 | O |
| ATOM | 2978 | N | LEU A | 475 | 11.133 | 8.573 | −4.898 | 1.00 | 55.74 | N |
| ATOM | 2979 | CA | LEU A | 475 | 11.662 | 9.639 | −4.043 | 1.00 | 56.68 | C |
| ATOM | 2980 | CB | LEU A | 475 | 10.526 | 10.436 | −3.398 | 1.00 | 57.36 | C |
| ATOM | 2981 | CG | LEU A | 475 | 9.913 | 11.453 | −4.369 | 1.00 | 59.90 | C |
| ATOM | 2982 | CD1 | LEU A | 475 | 8.521 | 11.878 | −3.952 | 1.00 | 57.57 | C |
| ATOM | 2983 | CD2 | LEU A | 475 | 10.827 | 12.652 | −4.485 | 1.00 | 61.07 | C |
| ATOM | 2984 | C | LEU A | 475 | 12.642 | 9.148 | −2.989 | 1.00 | 56.71 | C |
| ATOM | 2985 | O | LEU A | 475 | 13.615 | 9.839 | −2.669 | 1.00 | 56.44 | O |
| ATOM | 2986 | N | GLU A | 476 | 12.380 | 7.952 | −2.464 | 1.00 | 56.89 | N |
| ATOM | 2987 | CA | GLU A | 476 | 13.272 | 7.307 | −1.510 | 1.00 | 57.37 | C |
| ATOM | 2988 | CB | GLU A | 476 | 12.599 | 6.082 | −.879 | 1.00 | 57.39 | C |
| ATOM | 2989 | CG | GLU A | 476 | 13.528 | 5.243 | −.019 | 1.00 | 60.23 | C |
| ATOM | 2993 | C | GLU A | 476 | 14.564 | 6.906 | −2.212 | 1.00 | 57.01 | C |
| ATOM | 2994 | O | GLU A | 476 | 15.649 | 7.045 | −1.654 | 1.00 | 57.43 | O |
| ATOM | 2995 | N | LEU A | 477 | 14.440 | 6.420 | −3.442 | 1.00 | 55.97 | N |
| ATOM | 2996 | CA | LEU A | 477 | 15.599 | 5.999 | −4.209 | 1.00 | 55.81 | C |
| ATOM | 2997 | CB | LEU A | 477 | 15.165 | 5.300 | −5.497 | 1.00 | 56.18 | C |
| ATOM | 2998 | CG | LEU A | 477 | 16.269 | 4.463 | −6.151 | 1.00 | 61.44 | C |
| ATOM | 2999 | CD1 | LEU A | 477 | 16.734 | 3.335 | −5.234 | 1.00 | 62.07 | C |
| ATOM | 3000 | CD2 | LEU A | 477 | 15.821 | 3.918 | −7.496 | 1.00 | 63.21 | C |
| ATOM | 3001 | C | LEU A | 477 | 16.529 | 7.178 | −4.495 | 1.00 | 54.93 | C |
| ATOM | 3002 | O | LEU A | 477 | 17.752 | 7.042 | −4.478 | 1.00 | 52.71 | O |
| ATOM | 3003 | N | ALA A | 478 | 15.929 | 8.337 | −4.753 | 1.00 | 55.87 | N |
| ATOM | 3004 | CA | ALA A | 478 | 16.669 | 9.587 | −4.885 | 1.00 | 55.95 | C |
| ATOM | 3005 | CB | ALA A | 478 | 15.746 | 10.671 | −5.374 | 1.00 | 54.74 | C |
| ATOM | 3006 | C | ALA A | 478 | 17.351 | 9.990 | −3.554 | 1.00 | 56.46 | C |
| ATOM | 3007 | O | ALA A | 478 | 18.470 | 10.515 | −3.552 | 1.00 | 55.97 | O |
| ATOM | 3008 | N | GLU A | 479 | 16.663 | 9.728 | −2.441 | 1.00 | 56.68 | N |
| ATOM | 3009 | CA | GLU A | 479 | 17.204 | 9.912 | −1.100 | 1.00 | 57.55 | C |
| | | | gad65.pdb | | | | | | | |
| ATOM | 3010 | CB | GLU A | 479 | 16.097 | 9.697 | −.043 | 1.00 | 57.59 | C |
| ATOM | 3011 | CG | GLU A | 479 | 16.576 | 9.644 | 1.417 | 1.00 | 59.04 | C |

TABLE A-continued

| | | | | | | | | | |
|---|---|---|---|---|---|---|---|---|---|
| ATOM | 3012 | CD   | GLU A | 479 | 15.458 | 9.339  | 2.425  | 1.00 | 59.60 | C |
| ATOM | 3013 | OE1  | GLU A | 479 | 15.415 | 10.002 | 3.482  | 1.00 | 64.00 | O |
| ATOM | 3014 | OE2  | GLU A | 479 | 14.627 | 8.435  | 2.178  | 1.00 | 67.75 | O |
| ATOM | 3015 | C    | GLU A | 479 | 18.382 | 8.957  | −.873  | 1.00 | 56.36 | C |
| ATOM | 3016 | O    | GLU A | 479 | 19.396 | 9.338  | −.263  | 1.00 | 56.60 | O |
| ATOM | 3017 | N    | TYR A | 480 | 18.245 | 7.725  | −1.365 | 1.00 | 54.54 | N |
| ATOM | 3018 | CA   | TYR A | 480 | 19.319 | 6.734  | −1.293 | 1.00 | 53.83 | C |
| ATOM | 3019 | CB   | TYR A | 480 | 18.825 | 5.376  | −1.798 | 1.00 | 52.86 | C |
| ATOM | 3020 | CG   | TYR A | 480 | 19.884 | 4.297  | −1.873 | 1.00 | 52.70 | C |
| ATOM | 3021 | CD1  | TYR A | 480 | 20.350 | 3.836  | −3.104 | 1.00 | 55.03 | C |
| ATOM | 3022 | CE1  | TYR A | 480 | 21.320 | 2.839  | −3.182 | 1.00 | 52.88 | C |
| ATOM | 3023 | CZ   | TYR A | 480 | 21.833 | 2.297  | −2.017 | 1.00 | 53.92 | C |
| ATOM | 3024 | OH   | TYR A | 480 | 22.802 | 1.323  | −2.078 | 1.00 | 53.28 | O |
| ATOM | 3025 | CE2  | TYR A | 480 | 21.396 | 2.746  | −.782  | 1.00 | 54.65 | C |
| ATOM | 3026 | CD2  | TYR A | 480 | 20.423 | 3.735  | −.715  | 1.00 | 57.32 | C |
| ATOM | 3027 | C    | TYR A | 480 | 20.567 | 7.192  | −2.077 | 1.00 | 54.29 | C |
| ATOM | 3028 | O    | TYR A | 480 | 21.705 | 6.973  | −1.642 | 1.00 | 53.55 | O |
| ATOM | 3029 | N    | LEU A | 481 | 20.340 | 7.821  | −3.230 | 1.00 | 54.14 | N |
| ATOM | 3030 | CA   | LEU A | 481 | 21.419 | 8.346  | −4.053 | 1.00 | 54.78 | C |
| ATOM | 3031 | CB   | LEU A | 481 | 20.874 | 8.830  | −5.395 | 1.00 | 54.25 | C |
| ATOM | 3032 | CG   | LEU A | 481 | 21.760 | 8.984  | −6.639 | 1.00 | 59.46 | C |
| ATOM | 3033 | CD1  | LEU A | 481 | 21.114 | 9.980  | −7.561 | 1.00 | 60.05 | C |
| ATOM | 3034 | CD2  | LEU A | 481 | 23.196 | 9.390  | −6.378 | 1.00 | 57.30 | C |
| ATOM | 3035 | C    | LEU A | 481 | 22.066 | 9.512  | −3.317 | 1.00 | 54.81 | C |
| ATOM | 3036 | O    | LEU A | 481 | 23.279 | 9.524  | −3.100 | 1.00 | 54.07 | O |
| ATOM | 3037 | N    | TYR A | 482 | 21.235 | 10.477 | −2.925 | 1.00 | 54.97 | N |
| ATOM | 3038 | CA   | TYR A | 482 | 21.691 | 11.675 | −2.222 | 1.00 | 54.88 | C |
| ATOM | 3039 | CB   | TYR A | 482 | 20.503 | 12.590 | −1.889 | 1.00 | 54.43 | C |
| ATOM | 3040 | CG   | TYR A | 482 | 20.854 | 13.830 | −1.088 | 1.00 | 55.63 | C |
| ATOM | 3041 | CD1  | TYR A | 482 | 20.456 | 13.954 | .241   | 1.00 | 53.96 | C |
| ATOM | 3042 | CE1  | TYR A | 482 | 20.747 | 15.092 | .976   | 1.00 | 55.97 | C |
| ATOM | 3043 | CZ   | TYR A | 482 | 21.467 | 16.124 | .394   | 1.00 | 56.38 | C |
| ATOM | 3044 | OH   | TYR A | 482 | 21.768 | 17.249 | 1.140  | 1.00 | 54.36 | O |
| ATOM | 3045 | CE2  | TYR A | 482 | 21.876 | 16.028 | −.926  | 1.00 | 56.16 | C |
| ATOM | 3046 | CD2  | TYR A | 482 | 21.562 | 14.884 | −1.663 | 1.00 | 54.83 | C |
| ATOM | 3047 | C    | TYR A | 482 | 22.512 | 11.356 | −.972  | 1.00 | 54.54 | C |
| ATOM | 3048 | O    | TYR A | 482 | 23.543 | 11.959 | −.753  | 1.00 | 52.94 | O |
| ATOM | 3049 | N    | ASN A | 483 | 22.063 | 10.389 | −.178  | 1.00 | 56.30 | N |
| ATOM | 3050 | CA   | ASN A | 483 | 22.781 | 10.015 | 1.044  | 1.00 | 57.73 | C |
| ATOM | 3051 | CB   | ASN A | 483 | 21.898 | 9.173  | 1.971  | 1.00 | 57.75 | C |
| ATOM | 3052 | CG   | ASN A | 483 | 20.729 | 9.968  | 2.555  | 1.00 | 62.98 | C |
| ATOM | 3053 | OD1  | ASN A | 483 | 19.692 | 9.401  | 2.906  | 1.00 | 63.27 | O |
| ATOM | 3054 | ND2  | ASN A | 483 | 20.895 | 11.285 | 2.662  | 1.00 | 63.25 | N |
| ATOM | 3055 | C    | ASN A | 483 | 24.123 | 9.327  | .803   | 1.00 | 58.10 | C |
| ATOM | 3056 | O    | ASN A | 483 | 25.026 | 9.429  | 1.635  | 1.00 | 58.53 | O |
| ATOM | 3057 | N    | ILE A | 484 | 24.254 | 8.629  | −.323  | 1.00 | 58.37 | N |
| ATOM | 3058 | CA   | ILE A | 484 | 25.515 | 7.971  | −.660  | 1.00 | 59.09 | C |
| ATOM | 3059 | CB   | ILE A | 484 | 25.356 | 6.870  | −1.744 | 1.00 | 59.32 | C |
| ATOM | 3060 | CG1  | ILE A | 484 | 24.588 | 5.665  | −1.203 | 1.00 | 57.00 | C |
| ATOM | 3061 | CD   | ILE A | 484 | 24.197 | 4.681  | −2.288 | 1.00 | 51.79 | C |
| ATOM | 3062 | CG2  | ILE A | 484 | 26.726 | 6.395  | −2.242 | 1.00 | 58.94 | C |
| ATOM | 3063 | C    | ILE A | 484 | 26.536 | 8.994  | −1.137 | 1.00 | 59.98 | C |
| ATOM | 3064 | O    | ILE A | 484 | 27.656 | 9.029  | −.630  | 1.00 | 60.87 | O |
| ATOM | 3065 | N    | ILE A | 485 | 26.151 | 9.821  | −2.110 | 1.00 | 59.97 | N |
| ATOM | 3066 | CA   | ILE A | 485 | 27.100 | 10.744 | −2.737 | 1.00 | 60.14 | C |
| ATOM | 3067 | CB   | ILE A | 485 | 26.655 | 11.207 | −4.138 | 1.00 | 59.87 | C |
| ATOM | 3068 | CG1  | ILE A | 485 | 25.226 | 11.770 | −4.120 | 1.00 | 57.66 | C |
| ATOM | 3069 | CD   | ILE A | 485 | 24.891 | 12.587 | −5.336 | 1.00 | 47.44 | C |
| ATOM | 3070 | CG2  | ILE A | 485 | 26.789 | 10.057 | −5.126 | 1.00 | 60.67 | C |
| ATOM | 3071 | C    | ILE A | 485 | 27.446 | 11.932 | −1.855 | 1.00 | 60.83 | C |
| ATOM | 3072 | O    | ILE A | 485 | 28.557 | 12.467 | −1.930 | 1.00 | 60.83 | O |
| ATOM | 3073 | N    | LYS A | 486 | 26.487 | 12.321 | −1.017 | 1.00 | 60.76 | N |
| ATOM | 3074 | CA   | LYS A | 486 | 26.668 | 13.363 | −.010  | 1.00 | 61.00 | C |
| ATOM | 3075 | CB   | LYS A | 486 | 25.391 | 13.470 | .828   | 1.00 | 60.18 | C |
| ATOM | 3076 | CG   | LYS A | 486 | 25.328 | 14.612 | 1.798  | 1.00 | 60.43 | C |
| ATOM | 3077 | CD   | LYS A | 486 | 23.898 | 14.831 | 2.285  | 1.00 | 61.61 | C |
| | | | | | gad65.pdb | | | | | |
| ATOM | 3078 | CE   | LYS A | 486 | 23.293 | 13.603 | 2.976  | 1.00 | 60.05 | C |
| ATOM | 3079 | NZ   | LYS A | 486 | 23.727 | 13.455 | 4.396  | 1.00 | 62.08 | N |
| ATOM | 3080 | C    | LYS A | 486 | 27.871 | 13.064 | .891   | 1.00 | 61.78 | C |
| ATOM | 3081 | O    | LYS A | 486 | 28.599 | 13.978 | 1.289  | 1.00 | 61.86 | O |
| ATOM | 3082 | N    | ASN A | 487 | 28.066 | 11.782 | 1.204  | 1.00 | 62.27 | N |
| ATOM | 3083 | CA   | ASN A | 487 | 29.169 | 11.340 | 2.059  | 1.00 | 62.82 | C |
| ATOM | 3084 | CB   | ASN A | 487 | 28.622 | 10.501 | 3.221  | 1.00 | 63.59 | C |
| ATOM | 3085 | CG   | ASN A | 487 | 27.475 | 11.188 | 3.958  | 1.00 | 68.51 | C |
| ATOM | 3086 | OD1  | ASN A | 487 | 26.340 | 10.697 | 3.959  | 1.00 | 69.23 | O |
| ATOM | 3087 | ND2  | ASN A | 487 | 27.766 | 12.328 | 4.584  | 1.00 | 69.09 | N |
| ATOM | 3088 | C    | ASN A | 487 | 30.272 | 10.568 | 1.305  | 1.00 | 62.17 | C |
| ATOM | 3089 | O    | ASN A | 487 | 31.109 | 9.897  | 1.921  | 1.00 | 62.47 | O |
| ATOM | 3090 | N    | ARG A | 488 | 30.282 | 10.675 | −.024  | 1.00 | 60.72 | N |

TABLE A-continued

| | | | | | | | | | |
|---|---|---|---|---|---|---|---|---|---|
| ATOM | 3091 | CA | ARG A | 488 | 31.248 | 9.936 | −.828 | 1.00 | 59.15 | C |
| ATOM | 3092 | CB | ARG A | 488 | 30.546 | 9.130 | −1.913 | 1.00 | 59.07 | C |
| ATOM | 3093 | CG | ARG A | 488 | 31.347 | 7.943 | −2.405 | 1.00 | 57.73 | C |
| ATOM | 3094 | CD | ARG A | 488 | 30.518 | 7.111 | −3.349 | 1.00 | 60.01 | C |
| ATOM | 3095 | NE | ARG A | 488 | 31.333 | 6.173 | −4.109 | 1.00 | 59.24 | N |
| ATOM | 3096 | CZ | ARG A | 488 | 31.357 | 4.859 | −3.909 | 1.00 | 65.09 | C |
| ATOM | 3097 | NH1 | ARG A | 488 | 30.600 | 4.308 | −2.963 | 1.00 | 65.13 | N |
| ATOM | 3098 | NH2 | ARG A | 488 | 32.139 | 4.094 | −4.664 | 1.00 | 65.91 | N |
| ATOM | 3099 | C | ARG A | 488 | 32.331 | 10.821 | −1.440 | 1.00 | 58.71 | C |
| ATOM | 3100 | O | ARG A | 488 | 32.038 | 11.871 | −2.022 | 1.00 | 58.21 | O |
| ATOM | 3101 | N | GLU A | 489 | 33.579 | 10.375 | −1.295 | 1.00 | 57.89 | N |
| ATOM | 3102 | CA | GLU A | 489 | 34.747 | 11.054 | −1.852 | 1.00 | 58.17 | C |
| ATOM | 3103 | CB | GLU A | 489 | 36.047 | 10.345 | −1.419 | 1.00 | 59.43 | C |
| ATOM | 3104 | CG | GLU A | 489 | 36.163 | 8.850 | −1.822 | 1.00 | 66.30 | C |
| ATOM | 3105 | CD | GLU A | 489 | 35.478 | 7.872 | −.849 | 1.00 | 72.02 | C |
| ATOM | 3106 | OE1 | GLU A | 489 | 34.298 | 8.084 | −.468 | 1.00 | 69.90 | O |
| ATOM | 3107 | OE2 | GLU A | 489 | 36.129 | 6.868 | −.480 | 1.00 | 72.21 | O |
| ATOM | 3108 | C | GLU A | 489 | 34.669 | 11.165 | −3.373 | 1.00 | 56.83 | C |
| ATOM | 3109 | O | GLU A | 489 | 34.402 | 10.186 | −4.064 | 1.00 | 57.14 | O |
| ATOM | 3110 | N | GLY A | 490 | 34.891 | 12.369 | −3.886 | 1.00 | 56.31 | N |
| ATOM | 3111 | CA | GLY A | 490 | 34.860 | 12.622 | −5.324 | 1.00 | 55.34 | C |
| ATOM | 3112 | C | GLY A | 490 | 33.566 | 13.256 | −5.792 | 1.00 | 55.68 | C |
| ATOM | 3113 | O | GLY A | 490 | 33.470 | 13.692 | −6.938 | 1.00 | 56.58 | O |
| ATOM | 3114 | N | TYR A | 491 | 32.580 | 13.316 | −4.900 | 1.00 | 55.20 | N |
| ATOM | 3115 | CA | TYR A | 491 | 31.239 | 13.798 | −5.224 | 1.00 | 56.70 | C |
| ATOM | 3116 | CB | TYR A | 491 | 30.205 | 12.702 | −4.935 | 1.00 | 56.60 | C |
| ATOM | 3117 | CG | TYR A | 491 | 30.171 | 11.575 | −5.951 | 1.00 | 58.26 | C |
| ATOM | 3118 | CD1 | TYR A | 491 | 30.958 | 10.430 | −5.784 | 1.00 | 58.95 | C |
| ATOM | 3119 | CE1 | TYR A | 491 | 30.927 | 9.391 | −6.712 | 1.00 | 58.55 | C |
| ATOM | 3120 | CZ | TYR A | 491 | 30.098 | 9.493 | −7.824 | 1.00 | 61.42 | C |
| ATOM | 3121 | OH | TYR A | 491 | 30.061 | 8.475 | −8.744 | 1.00 | 63.96 | O |
| ATOM | 3122 | CE2 | TYR A | 491 | 29.306 | 10.616 | −8.015 | 1.00 | 58.52 | C |
| ATOM | 3123 | CD2 | TYR A | 491 | 29.346 | 11.651 | −7.079 | 1.00 | 59.16 | C |
| ATOM | 3124 | C | TYR A | 491 | 30.877 | 15.060 | −4.437 | 1.00 | 57.44 | C |
| ATOM | 3125 | O | TYR A | 491 | 30.803 | 15.031 | −3.205 | 1.00 | 58.43 | O |
| ATOM | 3126 | N | GLU A | 492 | 30.634 | 16.156 | −5.151 | 1.00 | 57.36 | N |
| ATOM | 3127 | CA | GLU A | 492 | 30.273 | 17.430 | −4.531 | 1.00 | 58.46 | C |
| ATOM | 3128 | CB | GLU A | 492 | 31.323 | 18.500 | −4.861 | 1.00 | 58.36 | C |
| ATOM | 3129 | CG | GLU A | 492 | 31.234 | 19.767 | −4.014 | 1.00 | 62.68 | C |
| ATOM | 3130 | CD | GLU A | 492 | 32.054 | 20.930 | −4.573 | 1.00 | 61.38 | C |
| ATOM | 3131 | OE1 | GLU A | 492 | 31.608 | 22.090 | −4.408 | 1.00 | 69.05 | O |
| ATOM | 3132 | OE2 | GLU A | 492 | 33.131 | 20.696 | −5.174 | 1.00 | 65.89 | O |
| ATOM | 3133 | C | GLU A | 492 | 28.897 | 17.881 | −5.008 | 1.00 | 57.15 | C |
| ATOM | 3134 | O | GLU A | 492 | 28.649 | 17.963 | −6.220 | 1.00 | 56.45 | O |
| ATOM | 3135 | N | MET A | 493 | 28.009 | 18.183 | −4.059 | 1.00 | 56.46 | N |
| ATOM | 3136 | CA | MET A | 493 | 26.650 | 18.632 | −4.397 | 1.00 | 55.67 | C |
| ATOM | 3137 | CB | MET A | 493 | 25.718 | 18.618 | −3.179 | 1.00 | 55.77 | C |
| ATOM | 3138 | CG | MET A | 493 | 25.577 | 17.265 | −2.483 | 1.00 | 55.52 | C |
| ATOM | 3139 | SD | MET A | 493 | 25.157 | 15.906 | −3.592 | 1.00 | 64.12 | S |
| ATOM | 3140 | CE | MET A | 493 | 23.567 | 16.417 | −4.242 | 1.00 | 59.25 | C |
| ATOM | 3141 | C | MET A | 493 | 26.673 | 20.020 | −5.032 | 1.00 | 54.95 | C |
| ATOM | 3142 | O | MET A | 493 | 27.513 | 20.857 | −4.699 | 1.00 | 54.62 | O |
| ATOM | 3143 | N | VAL A | 494 | 25.741 | 20.245 | −5.949 | 1.00 | 53.91 | N |
| ATOM | 3144 | CA | VAL A | 494 | 25.700 | 21.464 | −6.752 | 1.00 | 52.82 | C |
| ATOM | 3145 | CB | VAL A | 494 | 24.956 | 21.170 | −8.082 | 1.00 | 51.57 | C |
| | | | | | gad65.pdb | | | | | |
| ATOM | 3146 | CG1 | VAL A | 494 | 24.462 | 22.438 | −8.777 | 1.00 | 50.67 | C |
| ATOM | 3147 | CG2 | VAL A | 494 | 25.881 | 20.392 | −8.986 | 1.00 | 44.78 | C |
| ATOM | 3148 | C | VAL A | 494 | 25.140 | 22.661 | −5.958 | 1.00 | 53.36 | C |
| ATOM | 3149 | O | VAL A | 494 | 25.534 | 23.815 | −6.170 | 1.00 | 53.18 | O |
| ATOM | 3150 | N | PHE A | 495 | 24.240 | 22.367 | −5.027 | 1.00 | 53.59 | N |
| ATOM | 3151 | CA | PHE A | 495 | 23.713 | 23.365 | −4.103 | 1.00 | 53.73 | C |
| ATOM | 3152 | CB | PHE A | 495 | 22.401 | 23.980 | −4.616 | 1.00 | 53.38 | C |
| ATOM | 3153 | CG | PHE A | 495 | 21.264 | 22.997 | −4.724 | 1.00 | 51.30 | C |
| ATOM | 3154 | CD1 | PHE A | 495 | 21.115 | 22.213 | −5.862 | 1.00 | 42.34 | C |
| ATOM | 3155 | CE1 | PHE A | 495 | 20.068 | 21.296 | −5.965 | 1.00 | 51.93 | C |
| ATOM | 3156 | CZ | PHE A | 495 | 19.150 | 21.163 | −4.925 | 1.00 | 53.39 | C |
| ATOM | 3157 | CE2 | PHE A | 495 | 19.294 | 21.944 | −3.774 | 1.00 | 55.76 | C |
| ATOM | 3158 | CD2 | PHE A | 495 | 20.345 | 22.859 | −3.686 | 1.00 | 50.70 | C |
| ATOM | 3159 | C | PHE A | 495 | 23.495 | 22.676 | −2.781 | 1.00 | 54.47 | C |
| ATOM | 3160 | O | PHE A | 495 | 23.329 | 21.461 | −2.732 | 1.00 | 55.33 | O |
| ATOM | 3161 | N | ASP A | 496 | 23.503 | 23.446 | −1.707 | 1.00 | 55.41 | N |
| ATOM | 3162 | CA | ASP A | 496 | 23.215 | 22.888 | −.398 | 1.00 | 56.81 | C |
| ATOM | 3163 | CB | ASP A | 496 | 23.950 | 23.657 | .700 | 1.00 | 57.29 | C |
| ATOM | 3164 | CG | ASP A | 496 | 24.239 | 22.795 | 1.910 | 1.00 | 62.31 | C |
| ATOM | 3165 | OD1 | ASP A | 496 | 23.274 | 22.319 | 2.561 | 1.00 | 59.55 | O |
| ATOM | 3166 | OD2 | ASP A | 496 | 25.441 | 22.600 | 2.205 | 1.00 | 65.41 | O |
| ATOM | 3167 | C | ASP A | 496 | 21.719 | 22.903 | −.146 | 1.00 | 56.55 | C |
| ATOM | 3168 | O | ASP A | 496 | 21.062 | 23.927 | −.341 | 1.00 | 56.84 | O |
| ATOM | 3169 | N | GLY A | 497 | 21.203 | 21.761 | .302 | 1.00 | 56.03 | N |

TABLE A-continued

| | | | | | | | | | |
|---|---|---|---|---|---|---|---|---|---|
| ATOM | 3170 | CA | GLY A | 497 | 19.789 | 21.578 | .597 | 1.00 | 55.49 | C |
| ATOM | 3171 | C | GLY A | 497 | 19.361 | 20.251 | .001 | 1.00 | 55.87 | C |
| ATOM | 3172 | O | GLY A | 497 | 19.675 | 19.965 | −1.163 | 1.00 | 56.21 | O |
| ATOM | 3173 | N | LYS A | 498 | 18.667 | 19.431 | .789 | 1.00 | 54.85 | N |
| ATOM | 3174 | CA | LYS A | 498 | 18.268 | 18.098 | .326 | 1.00 | 55.10 | C |
| ATOM | 3175 | CB | Lys A | 498 | 17.889 | 17.183 | 1.509 | 1.00 | 56.45 | C |
| ATOM | 3176 | CG | LYS A | 498 | 16.670 | 17.576 | 2.340 | 1.00 | 59.85 | C |
| ATOM | 3177 | CD | LYS A | 498 | 15.372 | 16.924 | 1.829 | 1.00 | 71.34 | C |
| ATOM | 3178 | CE | LYS A | 498 | 15.394 | 15.392 | 1.869 | 1.00 | 72.89 | C |
| ATOM | 3179 | NZ | LYS A | 498 | 15.301 | 14.824 | 3.243 | 1.00 | 76.68 | N |
| ATOM | 3180 | C | LYS A | 498 | 17.184 | 18.146 | −.787 | 1.00 | 54.01 | C |
| ATOM | 3181 | O | LYS A | 498 | 16.299 | 18.997 | −.737 | 1.00 | 53.61 | O |
| ATOM | 3182 | N | PRO A | 499 | 17.287 | 17.254 | −1.800 | 1.00 | 52.96 | N |
| ATOM | 3183 | CA | PRO A | 499 | 16.428 | 17.183 | −2.992 | 1.00 | 54.23 | C |
| ATOM | 3184 | CB | PRO A | 499 | 16.805 | 15.833 | −3.601 | 1.00 | 54.73 | C |
| ATOM | 3185 | CG | PRO A | 499 | 18.237 | 15.668 | −3.213 | 1.00 | 53.33 | C |
| ATOM | 3186 | CD | PRO A | 499 | 18.316 | 16.200 | −1.826 | 1.00 | 51.92 | C |
| ATOM | 3187 | C | PRO A | 499 | 14.945 | 17.198 | −2.677 | 1.00 | 54.01 | C |
| ATOM | 3188 | O | PRO A | 499 | 14.547 | 16.671 | −1.656 | 1.00 | 53.52 | O |
| ATOM | 3189 | N | GLN A | 500 | 14.133 | 17.754 | −3.574 | 1.00 | 56.34 | N |
| ATOM | 3190 | CA | GLN A | 500 | 12.710 | 18.010 | −3.263 | 1.00 | 57.08 | C |
| ATOM | 3191 | CB | GLN A | 500 | 12.337 | 19.490 | −3.485 | 1.00 | 57.01 | C |
| ATOM | 3192 | CG | GLN A | 500 | 12.793 | 20.405 | −2.354 | 1.00 | 56.76 | C |
| ATOM | 3193 | CD | GLN A | 500 | 12.020 | 21.707 | −2.296 | 1.00 | 54.90 | C |
| ATOM | 3194 | OE1 | GLN A | 500 | 11.337 | 21.986 | −1.309 | 1.00 | 52.17 | O |
| ATOM | 3195 | NE2 | GLN A | 500 | 12.121 | 22.512 | −3.350 | 1.00 | 48.45 | N |
| ATOM | 3196 | C | GLN A | 500 | 11.498 | 17.093 | −3.596 | 1.00 | 56.77 | C |
| ATOM | 3197 | O | GLN A | 500 | 10.449 | 17.395 | −3.077 | 1.00 | 59.08 | O |
| ATOM | 3198 | N | HIS A | 501 | 11.482 | 16.043 | −4.413 | 1.00 | 56.16 | N |
| ATOM | 3199 | CA | HIS A | 501 | 12.130 | 15.706 | −5.695 | 1.00 | 55.49 | C |
| ATOM | 3200 | CB | HIS A | 501 | 11.922 | 16.691 | −6.858 | 1.00 | 55.09 | C |
| ATOM | 3201 | CG | HIS A | 501 | 10.852 | 16.243 | −7.813 | 1.00 | 54.99 | C |
| ATOM | 3202 | ND1 | HIS A | 501 | 10.757 | 14.943 | −8.266 | 1.00 | 55.76 | N |
| ATOM | 3203 | CE1 | HIS A | 501 | 9.716 | 14.828 | −9.073 | 1.00 | 52.61 | C |
| ATOM | 3204 | NE2 | HIS A | 501 | 9.137 | 16.011 | −9.173 | 1.00 | 56.19 | N |
| ATOM | 3205 | CD2 | HIS A | 501 | 9.819 | 16.911 | −8.385 | 1.00 | 60.90 | C |
| ATOM | 3206 | C | HIS A | 501 | 13.223 | 14.629 | −5.899 | 1.00 | 54.64 | C |
| ATOM | 3207 | O | HIS A | 501 | 14.124 | 14.456 | −5.085 | 1.00 | 56.13 | O |
| ATOM | 3208 | N | THR A | 502 | 13.080 | 13.910 | −7.010 | 1.00 | 52.61 | N |
| ATOM | 3209 | CA | THR A | 502 | 14.016 | 12.869 | −7.425 | 1.00 | 50.84 | C |
| ATOM | 3210 | CB | THR A | 502 | 13.304 | 11.759 | −8.290 | 1.00 | 51.47 | C |
| ATOM | 3211 | OG1 | THR A | 502 | 13.198 | 12.174 | −9.664 | 1.00 | 46.78 | O |
| ATOM | 3212 | CG2 | THR A | 502 | 11.907 | 11.436 | −7.741 | 1.00 | 46.93 | C |
| ATOM | 3213 | C | THR A | 502 | 15.249 | 13.421 | −8.172 | 1.00 | 49.38 | C | gad65.pdb

| | | | | | | | | | |
|---|---|---|---|---|---|---|---|---|---|
| ATOM | 3214 | O | THR A | 502 | 16.171 | 12.663 | −8.470 | 1.00 | 49.23 | O |
| ATOM | 3215 | N | ASN A | 503 | 15.256 | 14.721 | −8.496 | 1.00 | 47.68 | N |
| ATOM | 3216 | CA | ASN A | 503 | 16.444 | 15.344 | −9.091 | 1.00 | 46.73 | C |
| ATOM | 3217 | CB | ASN A | 503 | 16.185 | 16.772 | −9.589 | 1.00 | 44.68 | C |
| ATOM | 3218 | CG | ASN A | 503 | 14.921 | 16.908 | −10.433 | 1.00 | 45.60 | C |
| ATOM | 3219 | OD1 | ASN A | 503 | 13.834 | 16.506 | −10.015 | 1.00 | 45.09 | O |
| ATOM | 3220 | ND2 | ASN A | 503 | 15.054 | 17.535 | −11.602 | 1.00 | 38.62 | N |
| ATOM | 3221 | C | ASN A | 503 | 17.611 | 15.386 | −8.094 | 1.00 | 48.27 | C |
| ATOM | 3222 | O | ASN A | 503 | 17.502 | 15.957 | −6.998 | 1.00 | 47.54 | O |
| ATOM | 3223 | N | VAL A | 504 | 18.726 | 14.774 | −8.471 | 1.00 | 49.69 | N |
| ATOM | 3224 | CA | VAL A | 504 | 19.950 | 14.889 | −7.681 | 1.00 | 50.22 | C |
| ATOM | 3225 | CB | VAL A | 504 | 20.356 | 13.553 | −7.029 | 1.00 | 50.81 | C |
| ATOM | 3226 | CG1 | VAL A | 504 | 21.543 | 13.756 | −6.036 | 1.00 | 53.57 | C |
| ATOM | 3227 | CG2 | VAL A | 504 | 19.171 | 12.921 | −6.302 | 1.00 | 47.22 | C |
| ATOM | 3228 | C | VAL A | 504 | 21.045 | 15.476 | −8.584 | 1.00 | 50.76 | C |
| ATOM | 3229 | O | VAL A | 504 | 21.400 | 14.889 | −9.609 | 1.00 | 50.46 | O |
| ATOM | 3230 | N | CYS A | 505 | 21.518 | 16.667 | −8.213 | 1.00 | 50.59 | N |
| ATOM | 3231 | CA | CYS A | 505 | 22.488 | 17.423 | −8.993 | 1.00 | 51.22 | C |
| ATOM | 3232 | CB | CYS A | 505 | 22.018 | 18.866 | −9.135 | 1.00 | 51.11 | C |
| ATOM | 3233 | SG | CYS A | 505 | 20.449 | 19.028 | −10.045 | 1.00 | 52.92 | S |
| ATOM | 3234 | C | CYS A | 505 | 23.883 | 17.372 | −8.354 | 1.00 | 52.81 | C |
| ATOM | 3235 | O | CYS A | 505 | 24.057 | 17.735 | −7.183 | 1.00 | 52.69 | O |
| ATOM | 3236 | N | PHE A | 506 | 24.870 | 16.911 | −9.123 | 1.00 | 53.22 | N |
| ATOM | 3237 | CA | PHE A | 506 | 26.206 | 16.674 | −8.591 | 1.00 | 52.95 | C |
| ATOM | 3238 | CB | PHE A | 506 | 26.264 | 15.329 | −7.863 | 1.00 | 52.75 | C |
| ATOM | 3239 | CG | PHE A | 506 | 26.085 | 14.124 | −8.765 | 1.00 | 53.69 | C |
| ATOM | 3240 | CD1 | PHE A | 506 | 27.189 | 13.530 | −9.392 | 1.00 | 54.28 | C |
| ATOM | 3241 | CE1 | PHE A | 506 | 27.031 | 12.405 | −10.211 | 1.00 | 51.56 | C |
| ATOM | 3242 | CZ | PHE A | 506 | 25.757 | 11.867 | −10.404 | 1.00 | 55.37 | C |
| ATOM | 3243 | CE2 | PHE A | 506 | 24.646 | 12.454 | −9.776 | 1.00 | 51.85 | C |
| ATOM | 3244 | CD2 | PHE A | 506 | 24.821 | 13.563 | −8.958 | 1.00 | 52.18 | C |
| ATOM | 3245 | C | PHE A | 506 | 27.326 | 16.758 | −9.621 | 1.00 | 54.17 | C |
| ATOM | 3246 | O | PHE A | 506 | 27.109 | 16.633 | −10.838 | 1.00 | 54.20 | O |
| ATOM | 3247 | N | TRP A | 507 | 28.532 | 16.988 | −9.113 | 1.00 | 54.11 | N |
| ATOM | 3248 | CA | TRP A | 507 | 29.735 | 16.842 | −9.902 | 1.00 | 53.86 | C |

TABLE A-continued

| | | | | | | | | | |
|---|---|---|---|---|---|---|---|---|---|
| ATOM | 3249 | CB  | TRP A | 507 | 30.670 | 18.026 | −9.677  | 1.00 | 52.98 | C |
| ATOM | 3250 | CG  | TRP A | 507 | 30.227 | 19.321 | −10.295 | 1.00 | 47.87 | C |
| ATOM | 3251 | CD1 | TRP A | 507 | 30.175 | 19.622 | −11.625 | 1.00 | 44.47 | C |
| ATOM | 3252 | NE1 | TRP A | 507 | 29.737 | 20.911 | −11.802 | 1.00 | 43.21 | N |
| ATOM | 3253 | CE2 | TRP A | 507 | 29.510 | 21.480 | −10.575 | 1.00 | 45.76 | C |
| ATOM | 3254 | CD2 | TRP A | 507 | 29.811 | 20.506 | −9.597  | 1.00 | 48.52 | C |
| ATOM | 3255 | CE3 | TRP A | 507 | 29.655 | 20.834 | −8.239  | 1.00 | 41.41 | C |
| ATOM | 3256 | CZ3 | TRP A | 507 | 29.223 | 22.117 | −7.909  | 1.00 | 46.71 | C |
| ATOM | 3257 | CH2 | TRP A | 507 | 28.931 | 23.069 | −8.910  | 1.00 | 47.89 | C |
| ATOM | 3258 | CZ2 | TRP A | 507 | 29.068 | 22.772 | −10.241 | 1.00 | 48.06 | C |
| ATOM | 3259 | C   | TRP A | 507 | 30.425 | 15.570 | −9.450  | 1.00 | 55.54 | C |
| ATOM | 3260 | O   | TRP A | 507 | 30.333 | 15.198 | −8.275  | 1.00 | 56.13 | O |
| ATOM | 3261 | N   | TYR A | 508 | 31.077 | 14.879 | −10.384 | 1.00 | 55.91 | N |
| ATOM | 3262 | CA  | TYR A | 508 | 32.087 | 13.898 | −10.017 | 1.00 | 56.07 | C |
| ATOM | 3263 | CB  | TYR A | 508 | 31.965 | 12.581 | −10.797 | 1.00 | 55.96 | C |
| ATOM | 3264 | CG  | TYR A | 508 | 33.018 | 11.565 | −10.388 | 1.00 | 54.69 | C |
| ATOM | 3265 | CD1 | TYR A | 508 | 34.056 | 11.207 | −11.254 | 1.00 | 55.56 | C |
| ATOM | 3266 | CE1 | TYR A | 508 | 35.036 | 10.291 | −10.865 | 1.00 | 48.75 | C |
| ATOM | 3267 | CZ  | TYR A | 508 | 34.990 | 9.746  | −9.593  | 1.00 | 53.92 | C |
| ATOM | 3268 | OH  | TYR A | 508 | 35.938 | 8.837  | −9.190  | 1.00 | 54.05 | O |
| ATOM | 3269 | CE2 | TYR A | 508 | 33.977 | 10.097 | −8.712  | 1.00 | 54.35 | C |
| ATOM | 3270 | CD2 | TYR A | 508 | 33.002 | 10.997 | −9.112  | 1.00 | 54.89 | C |
| ATOM | 3271 | C   | TYR A | 508 | 33.446 | 14.542 | −10.260 | 1.00 | 56.67 | C |
| ATOM | 3272 | O   | TYR A | 508 | 33.721 | 15.042 | −11.358 | 1.00 | 57.11 | O |
| ATOM | 3273 | N   | ILE A | 509 | 34.276 | 14.558 | −9.225  | 1.00 | 57.05 | N |
| ATOM | 3274 | CA  | ILE A | 509 | 35.636 | 15.087 | −9.339  | 1.00 | 58.24 | C |
| ATOM | 3275 | CB  | ILE A | 509 | 35.977 | 16.099 | −8.198  | 1.00 | 58.51 | C |
| ATOM | 3276 | CG1 | ILE A | 509 | 34.978 | 17.270 | −8.170  | 1.00 | 59.65 | C |
| ATOM | 3277 | CD  | ILE A | 509 | 33.817 | 17.104 | −7.181  | 1.00 | 60.18 | C |
| ATOM | 3278 | CG2 | ILE A | 509 | 37.381 | 16.692 | −8.379  | 1.00 | 60.29 | C |
| ATOM | 3279 | C   | ILE A | 509 | 36.611 | 13.901 | −9.384  | 1.00 | 57.95 | C |
| ATOM | 3280 | O   | ILE A | 509 | 36.790 | 13.206 | −8.389  | 1.00 | 56.97 | O |
| ATOM | 3281 | N   | PRO A | 510 | 37.216 | 13.646 | −10.556 | 1.00 | 59.31 | N |
| | | | gad65.pdb | | | | | | | |
| ATOM | 3282 | CA  | PRO A | 510 | 38.085 | 12.467 | −10.703 | 1.00 | 61.58 | C |
| ATOM | 3283 | CB  | PRO A | 510 | 38.490 | 12.505 | −12.188 | 1.00 | 61.65 | C |
| ATOM | 3284 | CG  | PRO A | 510 | 37.467 | 13.404 | −12.857 | 1.00 | 59.89 | C |
| ATOM | 3285 | CD  | PRO A | 510 | 37.145 | 14.432 | −11.801 | 1.00 | 59.23 | C |
| ATOM | 3286 | C   | PRO A | 510 | 39.315 | 12.586 | −9.799  | 1.00 | 63.55 | C |
| ATOM | 3287 | O   | PRO A | 510 | 39.721 | 13.709 | −9.487  | 1.00 | 62.60 | O |
| ATOM | 3288 | N   | PRO A | 511 | 39.896 | 11.446 | −9.367  | 1.00 | 66.12 | N |
| ATOM | 3289 | CA  | PRO A | 511 | 41.006 | 11.490 | −8.406  | 1.00 | 68.69 | C |
| ATOM | 3290 | CB  | PRO A | 511 | 41.512 | 10.042 | −8.386  | 1.00 | 68.65 | C |
| ATOM | 3291 | CG  | PRO A | 511 | 40.295 | 9.237  | −8.683  | 1.00 | 67.89 | C |
| ATOM | 3292 | CD  | PRO A | 511 | 39.549 | 10.054 | −9.717  | 1.00 | 66.39 | C |
| ATOM | 3293 | C   | PRO A | 511 | 42.124 | 12.461 | −8.777  | 1.00 | 70.48 | C |
| ATOM | 3294 | O   | PRO A | 511 | 42.820 | 12.946 | −7.889  | 1.00 | 70.77 | O |
| ATOM | 3295 | N   | SER A | 512 | 42.251 | 12.770 | −10.066 | 1.00 | 72.53 | N |
| ATOM | 3296 | CA  | SER A | 512 | 43.290 | 13.672 | −10.574 | 1.00 | 74.19 | C |
| ATOM | 3297 | CB  | SER A | 512 | 43.746 | 13.205 | −11.965 | 1.00 | 74.48 | C |
| ATOM | 3298 | OG  | SER A | 512 | 42.666 | 13.232 | −12.891 | 1.00 | 76.14 | O |
| ATOM | 3299 | C   | SER A | 512 | 42.867 | 15.151 | −10.623 | 1.00 | 74.91 | C |
| ATOM | 3300 | O   | SER A | 512 | 43.326 | 15.899 | −11.492 | 1.00 | 75.55 | O |
| ATOM | 3301 | N   | LEU A | 513 | 42.016 | 15.573 | −9.686  | 1.00 | 75.39 | N |
| ATOM | 3302 | CA  | LEU A | 513 | 41.488 | 16.944 | −9.669  | 1.00 | 75.33 | C |
| ATOM | 3303 | CB  | LEU A | 513 | 40.262 | 17.070 | −10.583 | 1.00 | 75.58 | C |
| ATOM | 3304 | CG  | LEU A | 513 | 40.364 | 17.632 | −12.005 | 1.00 | 78.34 | C |
| ATOM | 3305 | CD1 | LEU A | 513 | 38.985 | 17.622 | −12.654 | 1.00 | 80.46 | C |
| ATOM | 3306 | CD2 | LEU A | 513 | 40.936 | 19.045 | −12.022 | 1.00 | 78.89 | C |
| ATOM | 3307 | C   | LEU A | 513 | 41.103 | 17.434 | −8.279  | 1.00 | 75.55 | C |
| ATOM | 3308 | O   | LEU A | 513 | 40.910 | 18.639 | −8.076  | 1.00 | 74.93 | O |
| ATOM | 3309 | N   | ARG A | 514 | 40.991 | 16.506 | −7.331  | 1.00 | 76.52 | N |
| ATOM | 3310 | CA  | ARG A | 514 | 40.450 | 16.810 | −5.997  | 1.00 | 77.58 | C |
| ATOM | 3311 | CB  | ARG A | 514 | 40.255 | 15.525 | −5.198  | 1.00 | 77.44 | C |
| ATOM | 3312 | CG  | ARG A | 514 | 38.971 | 14.820 | −5.526  | 1.00 | 73.32 | C |
| ATOM | 3313 | CD  | ARG A | 514 | 39.111 | 13.341 | −5.318  | 1.00 | 69.46 | C |
| ATOM | 3314 | NE  | ARG A | 514 | 38.348 | 12.611 | −6.318  | 1.00 | 59.63 | N |
| ATOM | 3315 | CZ  | ARG A | 514 | 38.100 | 11.309 | −6.276  | 1.00 | 59.15 | C |
| ATOM | 3316 | NH1 | ARG A | 514 | 37.395 | 10.744 | −7.248  | 1.00 | 58.53 | N |
| ATOM | 3317 | NH2 | ARG A | 514 | 38.545 | 10.578 | −5.270  | 1.00 | 56.96 | N |
| ATOM | 3318 | C   | ARG A | 514 | 41.239 | 17.815 | −5.164  | 1.00 | 78.99 | C |
| ATOM | 3319 | O   | ARG A | 514 | 40.647 | 18.673 | −4.501  | 1.00 | 79.05 | O |
| ATOM | 3320 | N   | THR A | 515 | 42.564 | 17.706 | −5.204  | 1.00 | 80.45 | N |
| ATOM | 3321 | CA  | THR A | 515 | 43.440 | 18.526 | −4.369  | 1.00 | 82.19 | C |
| ATOM | 3322 | CB  | THR A | 515 | 44.450 | 17.645 | −3.600  | 1.00 | 82.21 | C |
| ATOM | 3325 | C   | THR A | 515 | 44.185 | 19.584 | −5.187  | 1.00 | 83.83 | C |
| ATOM | 3326 | O   | THR A | 515 | 45.251 | 20.069 | −4.785  | 1.00 | 83.99 | O |
| ATOM | 3327 | N   | LEU A | 516 | 43.617 | 19.938 | −6.339  | 1.00 | 84.84 | N |
| ATOM | 3328 | CA  | LEU A | 516 | 44.235 | 20.906 | −7.231  | 1.00 | 85.08 | C |
| ATOM | 3329 | CB  | LEU A | 516 | 43.713 | 20.724 | −8.658  | 1.00 | 85.20 | C |

TABLE A-continued

| | | | | | | | | | | |
|---|---|---|---|---|---|---|---|---|---|---|
| ATOM | 3330 | CG | LEU A | 516 | 44.722 | 20.960 | −9.784 | 1.00 | 85.62 | C |
| ATOM | 3331 | CD1 | LEU A | 516 | 45.793 | 19.876 | −9.790 | 1.00 | 88.21 | C |
| ATOM | 3332 | CD2 | LEU A | 516 | 44.024 | 21.017 | −11.125 | 1.00 | 85.06 | C |
| ATOM | 3333 | C | LEU A | 516 | 43.967 | 22.319 | −6.718 | 1.00 | 85.29 | C |
| ATOM | 3334 | O | LEU A | 516 | 42.822 | 22.677 | −6.427 | 1.00 | 85.44 | O |
| ATOM | 3335 | N | GLU A | 517 | 45.033 | 23.108 | −6.597 | 1.00 | 85.31 | N |
| ATOM | 3336 | CA | GLU A | 517 | 44.943 | 24.460 | −6.043 | 1.00 | 84.91 | C |
| ATOM | 3337 | CB | GLU A | 517 | 46.291 | 24.889 | −5.446 | 1.00 | 84.68 | C |
| ATOM | 3342 | C | GLU A | 517 | 44.458 | 25.478 | −7.077 | 1.00 | 84.50 | C |
| ATOM | 3343 | O | GLU A | 517 | 44.850 | 25.435 | −8.244 | 1.00 | 84.10 | O |
| ATOM | 3344 | N | GLU A | 521 | 40.947 | 27.413 | −9.933 | 1.00 | 75.57 | N |
| ATOM | 3345 | CA | GLU A | 521 | 40.319 | 27.303 | −11.248 | 1.00 | 76.27 | C |
| ATOM | 3346 | CB | GLU A | 521 | 40.760 | 28.448 | −12.173 | 1.00 | 76.44 | C |
| ATOM | 3347 | CG | GLU A | 521 | 39.944 | 29.728 | −12.006 | 1.00 | 76.60 | C |
| ATOM | 3351 | C | GLU A | 521 | 40.554 | 25.936 | −11.904 | 1.00 | 76.58 | C |
| ATOM | 3352 | O | GLU A | 521 | 40.908 | 25.843 | −13.083 | 1.00 | 76.96 | O |
| ATOM | 3353 | N | ARG A | 522 | 40.355 | 24.880 | −11.114 | 1.00 | 75.89 | N |
| ATOM | 3354 | CA | ARG A | 522 | 40.290 | 23.515 | −11.614 | 1.00 | 73.63 | C |
| ATOM | 3355 | CB | ARG A | 522 | 40.766 | 22.537 | −10.543 | 1.00 | 74.14 | C |
| ATOM | 3362 | C | ARG A | 522 | 38.831 | 23.239 | −11.972 | 1.00 | 72.37 | C |
| ATOM | 3363 | O | ARG A | 522 | 38.439 | 22.097 | −12.248 | 1.00 | 71.45 | O |
| ATOM | 3364 | N | MET A | 523 | 38.039 | 24.311 | −11.938 | 1.00 | 70.87 | N |
| | | | | | gad65.pdb | | | | | |
| ATOM | 3365 | CA | MET A | 523 | 36.651 | 24.308 | −12.373 | 1.00 | 70.15 | C |
| ATOM | 3366 | CB | MET A | 523 | 35.970 | 25.619 | −11.958 | 1.00 | 69.82 | C |
| ATOM | 3370 | C | MET A | 523 | 36.581 | 24.127 | −13.890 | 1.00 | 69.18 | C |
| ATOM | 3371 | O | MET A | 523 | 35.699 | 23.419 | −14.400 | 1.00 | 68.04 | O |
| ATOM | 3372 | N | SER A | 524 | 37.521 | 24.771 | −14.590 | 1.00 | 68.30 | N |
| ATOM | 3373 | CA | SER A | 524 | 37.646 | 24.686 | −16.044 | 1.00 | 68.16 | C |
| ATOM | 3374 | CB | SER A | 524 | 38.814 | 25.548 | −16.533 | 1.00 | 68.72 | C |
| ATOM | 3375 | OG | SER A | 524 | 39.109 | 25.287 | −17.900 | 1.00 | 71.25 | O |
| ATOM | 3376 | C | SER A | 524 | 37.822 | 23.238 | −16.502 | 1.00 | 67.31 | C |
| ATOM | 3377 | O | SER A | 524 | 37.262 | 22.828 | −17.524 | 1.00 | 67.16 | O |
| ATOM | 3378 | N | ARG A | 525 | 38.593 | 22.477 | −15.730 | 1.00 | 65.98 | N |
| ATOM | 3379 | CA | ARG A | 525 | 38.800 | 21.062 | −15.986 | 1.00 | 65.60 | C |
| ATOM | 3380 | CB | ARG A | 525 | 40.074 | 20.571 | −15.294 | 1.00 | 65.34 | C |
| ATOM | 3381 | CG | ARG A | 525 | 41.353 | 21.226 | −15.791 | 1.00 | 69.49 | C |
| ATOM | 3382 | CD | ARG A | 525 | 42.579 | 20.613 | −15.136 | 1.00 | 73.13 | C |
| ATOM | 3383 | NE | ARG A | 525 | 42.767 | 19.216 | −15.532 | 1.00 | 75.70 | N |
| ATOM | 3384 | CZ | ARG A | 525 | 43.672 | 18.394 | −15.006 | 1.00 | 74.77 | C |
| ATOM | 3385 | NH1 | ARG A | 525 | 44.492 | 18.816 | −14.048 | 1.00 | 69.74 | N |
| ATOM | 3386 | NH2 | ARG A | 525 | 43.753 | 17.142 | −15.441 | 1.00 | 73.43 | N |
| ATOM | 3387 | C | ARG A | 525 | 37.598 | 20.235 | −15.529 | 1.00 | 64.93 | C |
| ATOM | 3388 | O | ARG A | 525 | 37.304 | 19.176 | −16.100 | 1.00 | 65.19 | O |
| ATOM | 3389 | N | LEU A | 526 | 36.910 | 20.713 | −14.494 | 1.00 | 64.01 | N |
| ATOM | 3390 | CA | LEU A | 526 | 35.707 | 20.041 | −14.021 | 1.00 | 63.07 | C |
| ATOM | 3391 | CB | LEU A | 526 | 35.280 | 20.554 | −12.643 | 1.00 | 62.96 | C |
| ATOM | 3392 | CG | LEU A | 526 | 34.064 | 19.867 | −12.003 | 1.00 | 62.15 | C |
| ATOM | 3393 | CD1 | LEU A | 526 | 34.341 | 18.380 | −11.711 | 1.00 | 55.67 | C |
| ATOM | 3394 | CD2 | LEU A | 526 | 33.612 | 20.605 | −10.751 | 1.00 | 62.02 | C |
| ATOM | 3395 | C | LEU A | 526 | 34.576 | 20.208 | −15.036 | 1.00 | 62.66 | C |
| ATOM | 3396 | O | LEU A | 526 | 33.784 | 19.296 | −15.237 | 1.00 | 62.59 | O |
| ATOM | 3397 | N | SER A | 527 | 34.534 | 21.374 | −15.674 | 1.00 | 62.26 | N |
| ATOM | 3398 | CA | SER A | 527 | 33.552 | 21.692 | −16.693 | 1.00 | 62.41 | C |
| ATOM | 3399 | CB | SER A | 527 | 33.888 | 23.046 | −17.308 | 1.00 | 62.72 | C |
| ATOM | 3400 | OG | SER A | 527 | 32.736 | 23.693 | −17.827 | 1.00 | 68.12 | O |
| ATOM | 3401 | C | SER A | 527 | 33.488 | 20.626 | −17.792 | 1.00 | 62.65 | C |
| ATOM | 3402 | O | SER A | 527 | 32.462 | 20.472 | −18.459 | 1.00 | 62.96 | O |
| ATOM | 3403 | N | LYS A | 528 | 34.577 | 19.878 | −17.954 | 1.00 | 61.76 | N |
| ATOM | 3404 | CA | LYS A | 528 | 34.748 | 18.978 | −19.100 | 1.00 | 60.53 | C |
| ATOM | 3405 | CB | LYS A | 528 | 36.105 | 19.238 | −19.766 | 1.00 | 60.47 | C |
| ATOM | 3406 | CG | LYS A | 528 | 36.152 | 20.591 | −20.459 | 1.00 | 63.76 | C |
| ATOM | 3407 | CD | LYS A | 528 | 37.560 | 21.052 | −20.795 | 1.00 | 72.06 | C |
| ATOM | 3408 | CE | LYS A | 528 | 37.499 | 22.306 | −21.677 | 1.00 | 76.30 | C |
| ATOM | 3409 | NZ | LYS A | 528 | 38.826 | 22.867 | −22.050 | 1.00 | 76.71 | N |
| ATOM | 3410 | C | LYS A | 528 | 34.589 | 17.508 | −18.740 | 1.00 | 58.65 | C |
| ATOM | 3411 | O | LYS A | 528 | 34.606 | 16.644 | −19.611 | 1.00 | 58.51 | O |
| ATOM | 3412 | N | VAL A | 529 | 34.408 | 17.243 | −17.452 | 1.00 | 57.43 | N |
| ATOM | 3413 | CA | VAL A | 529 | 34.318 | 15.881 | −16.927 | 1.00 | 56.43 | C |
| ATOM | 3414 | CB | VAL A | 529 | 34.544 | 15.866 | −15.392 | 1.00 | 56.38 | C |
| ATOM | 3415 | CG1 | VAL A | 529 | 34.215 | 14.500 | −14.794 | 1.00 | 54.72 | C |
| ATOM | 3416 | CG2 | VAL A | 529 | 35.990 | 16.277 | −15.060 | 1.00 | 56.79 | C |
| ATOM | 3417 | C | VAL A | 529 | 32.996 | 15.182 | −17.295 | 1.00 | 55.98 | C |
| ATOM | 3418 | O | VAL A | 529 | 33.012 | 14.055 | −17.793 | 1.00 | 55.85 | O |
| ATOM | 3419 | N | ALA A | 530 | 31.867 | 15.847 | −17.048 | 1.00 | 54.44 | N |
| ATOM | 3420 | CA | ALA A | 530 | 30.557 | 15.263 | −17.351 | 1.00 | 53.99 | C |
| ATOM | 3421 | CB | ALA A | 530 | 29.405 | 16.143 | −16.816 | 1.00 | 53.51 | C |
| ATOM | 3422 | C | ALA A | 530 | 30.383 | 14.949 | −18.843 | 1.00 | 52.56 | C |
| ATOM | 3423 | O | ALA A | 530 | 29.992 | 13.836 | −19.178 | 1.00 | 52.62 | O |
| ATOM | 3424 | N | PRO A | 531 | 30.701 | 15.910 | −19.741 | 1.00 | 51.86 | N |

TABLE A-continued

| | | | | | | | | | | |
|---|---|---|---|---|---|---|---|---|---|---|
| ATOM | 3425 | CA | PRO A | 531 | 30.645 | 15.579 | −21.170 | 1.00 | 51.98 | C |
| ATOM | 3426 | CB | PRO A | 531 | 31.204 | 16.835 | −21.844 | 1.00 | 51.96 | C |
| ATOM | 3427 | CG | PRO A | 531 | 30.846 | 17.937 | −20.896 | 1.00 | 50.16 | C |
| ATOM | 3428 | CD | PRO A | 531 | 31.091 | 17.321 | −19.540 | 1.00 | 51.69 | C |
| ATOM | 3429 | C | PRO A | 531 | 31.439 | 14.329 | −21.579 | 1.00 | 52.46 | C |
| ATOM | 3430 | O | PRO A | 531 | 30.951 | 13.557 | −22.403 | 1.00 | 53.21 | O |
| ATOM | 3431 | N | VAL A | 532 | 32.625 | 14.119 | −21.003 | 1.00 | 52.78 | N |
| ATOM | 3432 | CA | VAL A | 532 | 33.439 | 12.938 | −21.328 | 1.00 | 52.58 | C |
| ATOM | 3433 | CB | VAL A | 532 | 34.931 | 13.095 | −20.889 | 1.00 | 53.74 | C |
| ATOM | 3434 | CG1 | VAL A | 532 | 35.698 | 11.768 | −21.015 | 1.00 | 53.53 | C |
| ATOM | 3435 | CG2 | VAL A | 532 | 35.622 | 14.193 | −21.697 | 1.00 | 53.71 | C |
| | | | | gad65.pdb | | | | | | |
| ATOM | 3436 | C | VAL A | 532 | 32.827 | 11.660 | −20.749 | 1.00 | 51.54 | C |
| ATOM | 3437 | O | VAL A | 532 | 32.713 | 10.661 | −21.449 | 1.00 | 51.72 | O |
| ATOM | 3438 | N | ILE A | 533 | 32.426 | 11.697 | −19.483 | 1.00 | 50.68 | N |
| ATOM | 3439 | CA | ILE A | 533 | 31.756 | 10.558 | −18.870 | 1.00 | 50.60 | C |
| ATOM | 3440 | CB | ILE A | 533 | 31.326 | 10.832 | −17.400 | 1.00 | 51.13 | C |
| ATOM | 3441 | CG1 | ILE A | 533 | 32.513 | 11.297 | −16.547 | 1.00 | 55.35 | C |
| ATOM | 3442 | CD | ILE A | 533 | 33.299 | 10.181 | −15.926 | 1.00 | 55.36 | C |
| ATOM | 3443 | CG2 | ILE A | 533 | 30.678 | 9.583 | −16.778 | 1.00 | 49.91 | C |
| ATOM | 3444 | C | ILE A | 533 | 30.518 | 10.189 | −19.690 | 1.00 | 50.18 | C |
| ATOM | 3445 | O | ILE A | 533 | 30.356 | 9.038 | −20.081 | 1.00 | 49.60 | O |
| ATOM | 3446 | N | LYS A | 534 | 29.657 | 11.173 | −19.950 | 1.00 | 49.89 | N |
| ATOM | 3447 | CA | LYS A | 534 | 28.437 | 10.945 | −20.721 | 1.00 | 49.28 | C |
| ATOM | 3448 | CB | LYS A | 534 | 27.673 | 12.255 | −20.943 | 1.00 | 49.20 | C |
| ATOM | 3449 | CG | LYS A | 534 | 26.388 | 12.121 | −21.756 | 1.00 | 51.82 | C |
| ATOM | 3450 | CD | LYS A | 534 | 25.405 | 11.134 | −21.116 | 1.00 | 53.99 | C |
| ATOM | 3451 | CE | LYS A | 534 | 24.082 | 11.053 | −21.899 | 1.00 | 53.88 | C |
| ATOM | 3452 | NZ | LYS A | 534 | 23.206 | 12.252 | −21.657 | 1.00 | 52.29 | N |
| ATOM | 3453 | C | LYS A | 534 | 28.752 | 10.273 | −22.050 | 1.00 | 47.90 | C |
| ATOM | 3454 | O | LYS A | 534 | 28.133 | 9.276 | −22.398 | 1.00 | 46.13 | O |
| ATOM | 3455 | N | ALA A | 535 | 29.725 | 10.823 | −22.776 | 1.00 | 48.79 | N |
| ATOM | 3456 | CA | ALA A | 535 | 30.165 | 10.231 | −24.038 | 1.00 | 49.15 | C |
| ATOM | 3457 | CB | ALA A | 535 | 31.330 | 11.019 | −24.645 | 1.00 | 47.40 | C |
| ATOM | 3458 | C | ALA A | 535 | 30.526 | 8.763 | −23.851 | 1.00 | 50.59 | C |
| ATOM | 3459 | O | ALA A | 535 | 30.100 | 7.919 | −24.644 | 1.00 | 51.61 | O |
| ATOM | 3460 | N | ARG A | 536 | 31.280 | 8.459 | −22.791 | 1.00 | 51.53 | N |
| ATOM | 3461 | CA | ARG A | 536 | 31.721 | 7.082 | −22.506 | 1.00 | 52.19 | C |
| ATOM | 3462 | CB | ARG A | 536 | 32.823 | 7.060 | −21.441 | 1.00 | 52.08 | C |
| ATOM | 3463 | CG | ARG A | 536 | 34.116 | 7.795 | −21.821 | 1.00 | 57.74 | C |
| ATOM | 3469 | C | ARG A | 536 | 30.568 | 6.178 | −22.068 | 1.00 | 52.51 | C |
| ATOM | 3470 | O | ARG A | 536 | 30.572 | 4.994 | −22.385 | 1.00 | 53.06 | O |
| ATOM | 3471 | N | MET A | 537 | 29.608 | 6.733 | −21.321 | 1.00 | 52.67 | N |
| ATOM | 3472 | CA | MET A | 537 | 28.354 | 6.040 | −20.967 | 1.00 | 54.33 | C |
| ATOM | 3473 | CB | MET A | 537 | 27.392 | 6.971 | −20.222 | 1.00 | 53.67 | C |
| ATOM | 3474 | CG | MET A | 537 | 27.641 | 7.168 | −18.745 | 1.00 | 55.63 | C |
| ATOM | 3475 | SD | MET A | 537 | 26.557 | 8.490 | −18.130 | 1.00 | 57.97 | S |
| ATOM | 3476 | CE | MET A | 537 | 26.887 | 8.416 | −16.366 | 1.00 | 58.51 | C |
| ATOM | 3477 | C | MET A | 537 | 27.626 | 5.507 | −22.202 | 1.00 | 53.38 | C |
| ATOM | 3478 | O | MET A | 537 | 27.175 | 4.375 | −22.204 | 1.00 | 53.27 | O |
| ATOM | 3479 | N | MET A | 538 | 27.516 | 6.347 | −23.233 | 1.00 | 53.18 | N |
| ATOM | 3480 | CA | MET A | 538 | 26.837 | 6.016 | −24.481 | 1.00 | 54.61 | C |
| ATOM | 3481 | CB | MET A | 538 | 26.500 | 7.296 | −25.244 | 1.00 | 54.18 | C |
| ATOM | 3482 | CG | MET A | 538 | 25.370 | 8.097 | −24.627 | 1.00 | 55.75 | C |
| ATOM | 3483 | SD | MET A | 538 | 25.318 | 9.726 | −25.361 | 1.00 | 57.54 | S |
| ATOM | 3484 | CE | MET A | 538 | 24.243 | 9.446 | −26.773 | 1.00 | 53.32 | C |
| ATOM | 3485 | C | MET A | 538 | 27.641 | 5.076 | −25.390 | 1.00 | 54.74 | C |
| ATOM | 3486 | O | MET A | 538 | 27.063 | 4.196 | −26.041 | 1.00 | 53.08 | O |
| ATOM | 3487 | N | GLU A | 539 | 28.962 | 5.276 | −25.450 | 1.00 | 54.87 | N |
| ATOM | 3488 | CA | GLU A | 539 | 29.828 | 4.370 | −26.205 | 1.00 | 55.93 | C |
| ATOM | 3489 | CB | GLU A | 539 | 31.285 | 4.858 | −26.237 | 1.00 | 57.05 | C |
| ATOM | 3490 | CG | GLU A | 539 | 31.541 | 6.144 | −27.046 | 1.00 | 64.73 | C |
| ATOM | 3491 | CD | GLU A | 539 | 31.522 | 5.955 | −28.567 | 1.00 | 74.53 | C |
| ATOM | 3492 | OE1 | GLU A | 539 | 31.056 | 4.901 | −29.064 | 1.00 | 75.00 | O |
| ATOM | 3493 | OE2 | GLU A | 539 | 31.975 | 6.886 | −29.275 | 1.00 | 80.32 | O |
| ATOM | 3494 | C | GLU A | 539 | 29.754 | 2.962 | −25.628 | 1.00 | 55.23 | C |
| ATOM | 3495 | O | GLU A | 539 | 29.733 | 1.990 | −26.372 | 1.00 | 55.42 | O |
| ATOM | 3496 | N | TYR A | 540 | 29.696 | 2.853 | −24.305 | 1.00 | 55.46 | N |
| ATOM | 3497 | CA | TYR A | 540 | 29.567 | 1.543 | −23.674 | 1.00 | 56.19 | C |
| ATOM | 3498 | CB | TYR A | 540 | 30.325 | 1.491 | −22.346 | 1.00 | 57.39 | C |
| ATOM | 3499 | CG | TYR A | 540 | 31.828 | 1.540 | −22.540 | 1.00 | 62.87 | C |
| ATOM | 3500 | CD1 | TYR A | 540 | 32.573 | 2.610 | −22.052 | 1.00 | 65.67 | C |
| ATOM | 3501 | CE1 | TYR A | 540 | 33.944 | 2.673 | −22.232 | 1.00 | 68.22 | C |
| ATOM | 3502 | CZ | TYR A | 540 | 34.589 | 1.661 | −22.918 | 1.00 | 66.59 | C |
| ATOM | 3503 | OH | TYR A | 540 | 35.950 | 1.739 | −23.087 | 1.00 | 66.36 | O |
| ATOM | 3504 | CE2 | TYR A | 540 | 33.874 | .579 | −23.420 | 1.00 | 67.27 | C |
| ATOM | 3505 | CD2 | TYR A | 540 | 32.498 | .527 | −23.232 | 1.00 | 62.91 | C |
| ATOM | 3506 | C | TYR A | 540 | 28.128 | 1.064 | −23.512 | 1.00 | 54.95 | C |
| ATOM | 3507 | O | TYR A | 540 | 27.890 | −.136 | −23.449 | 1.00 | 53.95 | O |

TABLE A-continued

| | | | | | | | | | |
|---|---|---|---|---|---|---|---|---|---|
| ATOM | 3508 | N | GLY A | 541 | 27.185 | 2.007 | −23.445 | 1.00 | 54.42 | N |
| | | | | | gad65.pdb | | | | | |
| ATOM | 3509 | CA | GLY A | 541 | 25.746 | 1.705 | −23.387 | 1.00 | 53.89 | C |
| ATOM | 3510 | C | GLY A | 541 | 25.264 | 1.163 | −22.058 | 1.00 | 52.82 | C |
| ATOM | 3511 | O | GLY A | 541 | 24.319 | .374 | −22.009 | 1.00 | 53.99 | O |
| ATOM | 3512 | N | THR A | 542 | 25.896 | 1.599 | −20.977 | 1.00 | 51.56 | N |
| ATOM | 3513 | CA | THR A | 542 | 25.672 | 1.001 | −19.661 | 1.00 | 52.08 | C |
| ATOM | 3514 | CB | THR A | 542 | 26.988 | .960 | −18.855 | 1.00 | 52.65 | C |
| ATOM | 3515 | OG1 | THR A | 542 | 27.610 | 2.250 | −18.897 | 1.00 | 53.13 | O |
| ATOM | 3516 | CG2 | THR A | 542 | 27.965 | −.069 | −19.459 | 1.00 | 51.76 | C |
| ATOM | 3517 | C | THR A | 542 | 24.610 | 1.756 | −18.857 | 1.00 | 52.62 | C |
| ATOM | 3518 | O | THR A | 542 | 23.929 | 1.186 | −18.004 | 1.00 | 52.87 | O |
| ATOM | 3519 | N | THR A | 543 | 24.497 | 3.050 | −19.131 | 1.00 | 52.80 | N |
| ATOM | 3520 | CA | THR A | 543 | 23.561 | 3.928 | −18.454 | 1.00 | 52.70 | C |
| ATOM | 3521 | CB | THR A | 543 | 24.011 | 4.241 | −16.995 | 1.00 | 53.80 | C |
| ATOM | 3522 | OG1 | THR A | 543 | 22.946 | 4.883 | −16.274 | 1.00 | 57.38 | O |
| ATOM | 3523 | CG2 | THR A | 543 | 25.263 | 5.124 | −16.972 | 1.00 | 53.17 | C |
| ATOM | 3524 | C | THR A | 543 | 23.484 | 5.192 | −19.293 | 1.00 | 51.45 | C |
| ATOM | 3525 | O | THR A | 543 | 24.275 | 5.366 | −20.227 | 1.00 | 51.70 | O |
| ATOM | 3526 | N | MET A | 544 | 22.521 | 6.051 | −18.981 | 1.00 | 49.53 | N |
| ATOM | 3527 | CA | MET A | 544 | 22.442 | 7.384 | −19.570 | 1.00 | 48.83 | C |
| ATOM | 3528 | CB | MET A | 544 | 21.473 | 7.422 | −20.756 | 1.00 | 48.63 | C |
| ATOM | 3529 | CG | MET A | 544 | 22.092 | 6.968 | −22.049 | 1.00 | 49.73 | C |
| ATOM | 3530 | SD | MET A | 544 | 20.955 | 6.823 | −23.436 | 1.00 | 49.40 | S |
| ATOM | 3531 | CE | MET A | 544 | 21.105 | 8.458 | −24.130 | 1.00 | 40.32 | C |
| ATOM | 3532 | C | MET A | 544 | 21.967 | 8.338 | −18.499 | 1.00 | 47.32 | C |
| ATOM | 3533 | O | MET A | 544 | 21.008 | 8.044 | −17.800 | 1.00 | 46.44 | O |
| ATOM | 3534 | N | VAL A | 545 | 22.667 | 9.459 | −18.357 | 1.00 | 46.38 | N |
| ATOM | 3535 | CA | VAL A | 545 | 22.310 | 10.501 | −17.398 | 1.00 | 46.20 | C |
| ATOM | 3536 | CB | VAL A | 545 | 23.193 | 10.449 | −16.122 | 1.00 | 46.62 | C |
| ATOM | 3537 | CG1 | VAL A | 545 | 22.628 | 11.346 | −15.020 | 1.00 | 46.95 | C |
| ATOM | 3538 | CG2 | VAL A | 545 | 23.318 | 9.025 | −15.603 | 1.00 | 48.94 | C |
| ATOM | 3539 | C | VAL A | 545 | 22.512 | 11.827 | −18.099 | 1.00 | 45.90 | C |
| ATOM | 3540 | O | VAL A | 545 | 23.442 | 11.970 | −18.886 | 1.00 | 46.96 | O |
| ATOM | 3541 | N | SER A | 546 | 21.643 | 12.795 | −17.847 | 1.00 | 46.15 | N |
| ATOM | 3542 | CA | SER A | 546 | 21.855 | 14.126 | −18.406 | 1.00 | 47.67 | C |
| ATOM | 3543 | CB | SER A | 546 | 20.522 | 14.863 | −18.637 | 1.00 | 49.37 | C |
| ATOM | 3544 | OG | SER A | 546 | 19.933 | 14.499 | −19.884 | 1.00 | 56.63 | O |
| ATOM | 3545 | C | SER A | 546 | 22.773 | 14.948 | −17.503 | 1.00 | 47.82 | C |
| ATOM | 3546 | O | SER A | 546 | 22.783 | 14.767 | −16.274 | 1.00 | 47.49 | O |
| ATOM | 3547 | N | TYR A | 547 | 23.546 | 15.831 | −18.132 | 1.00 | 48.03 | N |
| ATOM | 3548 | CA | TYR A | 547 | 24.377 | 16.813 | −17.445 | 1.00 | 49.87 | C |
| ATOM | 3549 | CB | TYR A | 547 | 25.879 | 16.490 | −17.610 | 1.00 | 49.97 | C |
| ATOM | 3550 | CG | TYR A | 547 | 26.383 | 16.703 | −19.032 | 1.00 | 50.07 | C |
| ATOM | 3551 | CD1 | TYR A | 547 | 26.372 | 15.664 | −19.960 | 1.00 | 49.08 | C |
| ATOM | 3552 | CE1 | TYR A | 547 | 26.811 | 15.862 | −21.275 | 1.00 | 46.19 | C |
| ATOM | 3553 | CZ | TYR A | 547 | 27.270 | 17.102 | −21.660 | 1.00 | 50.19 | C |
| ATOM | 3554 | OH | TYR A | 547 | 27.709 | 17.296 | −22.952 | 1.00 | 50.42 | O |
| ATOM | 3555 | CE2 | TYR A | 547 | 27.289 | 18.156 | −20.757 | 1.00 | 50.77 | C |
| ATOM | 3556 | CD2 | TYR A | 547 | 26.845 | 17.953 | −19.453 | 1.00 | 50.47 | C |
| ATOM | 3557 | C | TYR A | 547 | 24.077 | 18.157 | −18.092 | 1.00 | 51.12 | C |
| ATOM | 3558 | O | TYR A | 547 | 23.656 | 18.200 | −19.242 | 1.00 | 49.91 | O |
| ATOM | 3559 | N | GLN A | 548 | 24.310 | 19.248 | −17.364 | 1.00 | 52.84 | N |
| ATOM | 3560 | CA | GLN A | 548 | 24.145 | 20.591 | −17.914 | 1.00 | 54.60 | C |
| ATOM | 3561 | CB | GLN A | 548 | 22.653 | 20.936 | −18.134 | 1.00 | 55.28 | C |
| ATOM | 3562 | CG | GLN A | 548 | 21.813 | 21.141 | −16.866 | 1.00 | 58.79 | C |
| ATOM | 3563 | CD | GLN A | 548 | 21.480 | 19.837 | −16.153 | 1.00 | 64.28 | C |
| ATOM | 3564 | OE1 | GLN A | 548 | 21.987 | 19.567 | −15.063 | 1.00 | 66.45 | O |
| ATOM | 3565 | NE2 | GLN A | 548 | 20.628 | 19.020 | −16.771 | 1.00 | 67.96 | N |
| ATOM | 3566 | C | GLN A | 548 | 24.794 | 21.615 | −16.996 | 1.00 | 55.79 | C |
| ATOM | 3567 | O | GLN A | 548 | 25.061 | 21.312 | −15.833 | 1.00 | 55.39 | O |
| ATOM | 3568 | N | PRO A | 549 | 25.080 | 22.821 | −17.524 | 1.00 | 57.14 | N |
| ATOM | 3569 | CA | PRO A | 549 | 25.414 | 23.915 | −16.633 | 1.00 | 57.99 | C |
| ATOM | 3570 | CB | PRO A | 549 | 26.302 | 24.798 | −17.504 | 1.00 | 57.26 | C |
| ATOM | 3571 | CG | PRO A | 549 | 25.807 | 24.577 | −18.898 | 1.00 | 58.27 | C |
| ATOM | 3572 | CD | PRO A | 549 | 25.149 | 23.225 | −18.943 | 1.00 | 57.10 | C |
| ATOM | 3573 | C | PRO A | 549 | 24.145 | 24.660 | −16.211 | 1.00 | 59.79 | C |
| ATOM | 3574 | O | PRO A | 549 | 23.111 | 24.535 | −16.872 | 1.00 | 60.94 | O |
| ATOM | 3575 | N | LEU A | 550 | 24.217 | 25.418 | −15.120 | 1.00 | 61.06 | N |
| ATOM | 3576 | CA | LEU A | 550 | 23.100 | 26.274 | −14.711 | 1.00 | 62.99 | C |
| | | | | | gad65.pdb | | | | | |
| ATOM | 3577 | CB | LEU A | 550 | 22.097 | 25.506 | −13.831 | 1.00 | 63.30 | C |
| ATOM | 3578 | CG | LEU A | 550 | 20.800 | 26.216 | −13.424 | 1.00 | 67.07 | C |
| ATOM | 3579 | CD1 | LEU A | 550 | 19.652 | 25.241 | −13.351 | 1.00 | 70.45 | C |
| ATOM | 3580 | CD2 | LEU A | 550 | 20.951 | 26.965 | −12.099 | 1.00 | 73.28 | C |
| ATOM | 3581 | C | LEU A | 550 | 23.613 | 27.510 | −13.990 | 1.00 | 64.15 | C |
| ATOM | 3582 | O | LEU A | 550 | 24.207 | 27.410 | −12.917 | 1.00 | 64.44 | O |
| ATOM | 3583 | N | GLY A | 551 | 23.366 | 28.676 | −14.579 | 1.00 | 65.84 | N |
| ATOM | 3584 | CA | GLY A | 551 | 23.813 | 29.941 | −13.999 | 1.00 | 66.37 | C |
| ATOM | 3585 | C | GLY A | 551 | 25.322 | 29.952 | −13.909 | 1.00 | 66.34 | C |

TABLE A-continued

| | | | | | | | | | |
|---|---|---|---|---|---|---|---|---|---|
| ATOM | 3586 | O | GLY A | 551 | 26.002 | 29.784 | −14.916 | 1.00 | 66.06 | O |
| ATOM | 3587 | N | ASP A | 552 | 25.838 | 30.113 | −12.693 | 1.00 | 67.45 | N |
| ATOM | 3588 | CA | ASP A | 552 | 27.286 | 30.174 | −12.452 | 1.00 | 68.42 | C |
| ATOM | 3589 | CB | ASP A | 552 | 27.587 | 31.111 | −11.276 | 1.00 | 69.52 | C |
| ATOM | 3590 | CG | ASP A | 552 | 26.926 | 30.653 | −9.985 | 1.00 | 76.69 | C |
| ATOM | 3591 | OD1 | ASP A | 552 | 27.615 | 30.009 | −9.162 | 1.00 | 81.05 | O |
| ATOM | 3592 | OD2 | ASP A | 552 | 25.713 | 30.916 | −9.805 | 1.00 | 82.40 | O |
| ATOM | 3593 | C | ASP A | 552 | 27.914 | 28.795 | −12.196 | 1.00 | 67.38 | C |
| ATOM | 3594 | O | ASP A | 552 | 29.109 | 28.696 | −11.885 | 1.00 | 67.49 | O |
| ATOM | 3595 | N | LYS A | 553 | 27.108 | 27.741 | −12.315 | 1.00 | 65.62 | N |
| ATOM | 3596 | CA | LYS A | 553 | 27.585 | 26.369 | −12.155 | 1.00 | 64.06 | C |
| ATOM | 3597 | CB | LYS A | 553 | 26.505 | 25.495 | −11.509 | 1.00 | 64.23 | C |
| ATOM | 3598 | CG | LYS A | 553 | 25.777 | 26.145 | −10.325 | 1.00 | 67.22 | C |
| ATOM | 3599 | CD | LYS A | 553 | 26.498 | 25.920 | −9.002 | 1.00 | 71.88 | C |
| ATOM | 3600 | CE | LYS A | 553 | 25.827 | 26.676 | −7.859 | 1.00 | 73.27 | C |
| ATOM | 3601 | NZ | LYS A | 553 | 26.284 | 28.094 | −7.781 | 1.00 | 77.33 | N |
| ATOM | 3602 | C | LYS A | 553 | 27.995 | 25.792 | −13.512 | 1.00 | 62.62 | C |
| ATOM | 3603 | O | LYS A | 553 | 27.321 | 26.025 | −14.522 | 1.00 | 63.06 | O |
| ATOM | 3604 | N | VAL A | 554 | 29.108 | 25.059 | −13.533 | 1.00 | 60.21 | N |
| ATOM | 3605 | CA | VAL A | 554 | 29.578 | 24.394 | −14.745 | 1.00 | 58.09 | C |
| ATOM | 3606 | CB | VAL A | 554 | 31.134 | 24.267 | −14.802 | 1.00 | 58.09 | C |
| ATOM | 3607 | CG1 | VAL A | 554 | 31.790 | 25.637 | −14.896 | 1.00 | 56.79 | C |
| ATOM | 3608 | CG2 | VAL A | 554 | 31.674 | 23.479 | −13.608 | 1.00 | 57.25 | C |
| ATOM | 3609 | C | VAL A | 554 | 28.955 | 23.010 | −14.859 | 1.00 | 57.05 | C |
| ATOM | 3610 | O | VAL A | 554 | 28.413 | 22.490 | −13.877 | 1.00 | 56.81 | O |
| ATOM | 3611 | N | ASN A | 555 | 29.066 | 22.417 | −16.051 | 1.00 | 55.11 | N |
| ATOM | 3612 | CA | ASN A | 555 | 28.521 | 21.091 | −16.346 | 1.00 | 53.36 | C |
| ATOM | 3613 | CB | ASN A | 555 | 29.323 | 20.402 | −17.461 | 1.00 | 52.17 | C |
| ATOM | 3614 | CG | ASN A | 555 | 29.076 | 21.009 | −18.822 | 1.00 | 54.46 | C |
| ATOM | 3615 | OD1 | ASN A | 555 | 29.983 | 21.096 | −19.648 | 1.00 | 58.93 | O |
| ATOM | 3616 | ND2 | ASN A | 555 | 27.849 | 21.444 | −19.064 | 1.00 | 56.97 | N |
| ATOM | 3617 | C | ASN A | 555 | 28.466 | 20.171 | −15.144 | 1.00 | 52.61 | C |
| ATOM | 3618 | O | ASN A | 555 | 29.509 | 19.721 | −14.643 | 1.00 | 53.07 | O |
| ATOM | 3619 | N | PHE A | 556 | 27.251 | 19.894 | −14.692 | 1.00 | 50.80 | N |
| ATOM | 3620 | CA | PHE A | 556 | 27.033 | 18.925 | −13.625 | 1.00 | 50.01 | C |
| ATOM | 3621 | CB | PHE A | 556 | 26.643 | 19.624 | −12.317 | 1.00 | 49.03 | C |
| ATOM | 3622 | CG | PHE A | 556 | 25.397 | 20.469 | −12.406 | 1.00 | 49.85 | C |
| ATOM | 3623 | CD1 | PHE A | 556 | 25.467 | 21.801 | −12.819 | 1.00 | 42.95 | C |
| ATOM | 3624 | CE1 | PHE A | 556 | 24.323 | 22.590 | −12.890 | 1.00 | 42.65 | C |
| ATOM | 3625 | CZ | PHE A | 556 | 23.091 | 22.048 | −12.541 | 1.00 | 45.25 | C |
| ATOM | 3626 | CE2 | PHE A | 556 | 23.006 | 20.718 | −12.125 | 1.00 | 47.27 | C |
| ATOM | 3627 | CD2 | PHE A | 556 | 24.150 | 19.940 | −12.047 | 1.00 | 49.53 | C |
| ATOM | 3628 | C | PHE A | 556 | 25.977 | 17.911 | −14.022 | 1.00 | 50.16 | C |
| ATOM | 3629 | O | PHE A | 556 | 25.098 | 18.219 | −14.813 | 1.00 | 51.28 | O |
| ATOM | 3630 | N | PHE A | 557 | 26.077 | 16.702 | −13.476 | 1.00 | 50.92 | N |
| ATOM | 3631 | CA | PHE A | 557 | 25.107 | 15.642 | −13.724 | 1.00 | 50.66 | C |
| ATOM | 3632 | CB | PHE A | 557 | 25.603 | 14.298 | −13.181 | 1.00 | 50.54 | C |
| ATOM | 3633 | CG | PHE A | 557 | 26.757 | 13.711 | −13.942 | 1.00 | 54.52 | C |
| ATOM | 3634 | CD1 | PHE A | 557 | 26.558 | 13.106 | −15.179 | 1.00 | 54.45 | C |
| ATOM | 3635 | CE1 | PHE A | 557 | 27.625 | 12.550 | −15.878 | 1.00 | 58.28 | C |
| ATOM | 3636 | CZ | PHE A | 557 | 28.917 | 12.585 | −15.326 | 1.00 | 57.86 | C |
| ATOM | 3637 | CE2 | PHE A | 557 | 29.122 | 13.184 | −14.088 | 1.00 | 57.25 | C |
| ATOM | 3638 | CD2 | PHE A | 557 | 28.046 | 13.737 | −13.404 | 1.00 | 55.68 | C |
| ATOM | 3639 | C | PHE A | 557 | 23.804 | 15.984 | −13.034 | 1.00 | 50.23 | C |
| ATOM | 3640 | O | PHE A | 557 | 23.802 | 16.374 | −11.863 | 1.00 | 50.22 | O |
| ATOM | 3641 | N | ARG A | 558 | 22.703 | 15.865 | −13.766 | 1.00 | 49.92 | N |
| ATOM | 3642 | CA | ARG A | 558 | 21.386 | 15.942 | −13.156 | 1.00 | 50.11 | C |
| ATOM | 3643 | CB | ARG A | 558 | 20.486 | 16.999 | −13.786 | 1.00 | 50.69 | C |
| ATOM | 3644 | CG | ARG A | 558 | 19.185 gad65.pdb | 17.162 | −12.985 | 1.00 | 52.39 | C |
| ATOM | 3645 | CD | ARG A | 558 | 17.953 | 17.134 | −13.863 | 1.00 | 54.61 | C |
| ATOM | 3646 | NE | ARG A | 558 | 17.957 | 16.044 | −14.840 | 1.00 | 48.78 | N |
| ATOM | 3647 | CZ | ARG A | 558 | 17.211 | 16.048 | −15.942 | 1.00 | 50.38 | C |
| ATOM | 3648 | NH1 | ARG A | 558 | 17.270 | 15.036 | −16.799 | 1.00 | 40.46 | N |
| ATOM | 3649 | NH2 | ARG A | 558 | 16.399 | 17.073 | −16.183 | 1.00 | 43.86 | N |
| ATOM | 3650 | C | ARG A | 558 | 20.724 | 14.584 | −13.220 | 1.00 | 50.11 | C |
| ATOM | 3651 | O | ARG A | 558 | 20.096 | 14.207 | −14.207 | 1.00 | 50.04 | O |
| ATOM | 3652 | N | MET A | 559 | 20.897 | 13.844 | −12.145 | 1.00 | 49.78 | N |
| ATOM | 3653 | CA | MET A | 559 | 20.296 | 12.548 | −12.013 | 1.00 | 49.09 | C |
| ATOM | 3654 | CB | MET A | 559 | 21.022 | 11.822 | −10.892 | 1.00 | 48.28 | C |
| ATOM | 3655 | CG | MET A | 559 | 20.629 | 10.420 | −10.703 | 1.00 | 55.45 | C |
| ATOM | 3656 | SD | MET A | 559 | 20.985 | 9.316 | −12.070 | 1.00 | 50.85 | S |
| ATOM | 3657 | CE | MET A | 559 | 20.215 | 7.911 | −11.261 | 1.00 | 44.14 | C |
| ATOM | 3658 | C | MET A | 559 | 18.813 | 12.756 | −11.703 | 1.00 | 48.73 | C |
| ATOM | 3659 | O | MET A | 559 | 18.458 | 13.726 | −11.029 | 1.00 | 47.67 | O |
| ATOM | 3660 | N | VAL A | 560 | 17.967 | 11.870 | −12.235 | 1.00 | 49.74 | N |
| ATOM | 3661 | CA | VAL A | 560 | 16.510 | 11.884 | −12.019 | 1.00 | 51.45 | C |
| ATOM | 3662 | CB | VAL A | 560 | 15.731 | 12.632 | −13.156 | 1.00 | 52.22 | C |
| ATOM | 3663 | CG1 | VAL A | 560 | 15.698 | 14.143 | −12.924 | 1.00 | 48.74 | C |
| ATOM | 3664 | CG2 | VAL A | 560 | 16.284 | 12.282 | −14.530 | 1.00 | 50.09 | C |

TABLE A-continued

| | | | | | | | | | |
|---|---|---|---|---|---|---|---|---|---|
| ATOM | 3665 | C | VAL A | 560 | 15.937 | 10.463 | −11.947 | 1.00 | 52.66 | C |
| ATOM | 3666 | O | VAL A | 560 | 16.349 | 9.576 | −12.707 | 1.00 | 52.83 | O |
| ATOM | 3667 | N | ILE A | 561 | 14.973 | 10.245 | −11.051 | 1.00 | 52.62 | N |
| ATOM | 3668 | CA | ILE A | 561 | 14.330 | 8.934 | −10.960 | 1.00 | 53.21 | C |
| ATOM | 3669 | CB | ILE A | 561 | 14.724 | 8.194 | −9.645 | 1.00 | 54.33 | C |
| ATOM | 3670 | CG1 | ILE A | 561 | 16.256 | 8.103 | −9.545 | 1.00 | 54.14 | C |
| ATOM | 3671 | CD | ILE A | 561 | 16.779 | 7.584 | −8.242 | 1.00 | 57.30 | C |
| ATOM | 3672 | CG2 | ILE A | 561 | 14.078 | 6.783 | −9.571 | 1.00 | 55.10 | C |
| ATOM | 3673 | C | ILE A | 561 | 12.808 | 9.021 | −11.167 | 1.00 | 53.96 | C |
| ATOM | 3674 | O | ILE A | 561 | 12.123 | 9.826 | −10.521 | 1.00 | 53.35 | O |
| ATOM | 3675 | N | SER A | 562 | 12.295 | 8.210 | −12.093 | 1.00 | 54.66 | N |
| ATOM | 3676 | CA | SER A | 562 | 10.848 | 8.120 | −12.342 | 1.00 | 54.60 | C |
| ATOM | 3677 | CB | SER A | 562 | 10.393 | 9.211 | −13.314 | 1.00 | 53.81 | C |
| ATOM | 3678 | OG | SER A | 562 | 11.107 | 9.139 | −14.539 | 1.00 | 57.44 | O |
| ATOM | 3679 | C | SER A | 562 | 10.450 | 6.733 | −12.856 | 1.00 | 55.42 | C |
| ATOM | 3680 | O | SER A | 562 | 9.265 | 6.436 | −13.035 | 1.00 | 55.48 | O |
| ATOM | 3681 | N | ASN A | 563 | 11.452 | 5.888 | −13.076 | 1.00 | 55.13 | N |
| ATOM | 3682 | CA | ASN A | 563 | 11.255 | 4.555 | −13.611 | 1.00 | 55.50 | C |
| ATOM | 3683 | CB | ASN A | 563 | 12.501 | 4.163 | −14.411 | 1.00 | 54.50 | C |
| ATOM | 3684 | CG | ASN A | 563 | 12.376 | 2.834 | −15.153 | 1.00 | 55.05 | C |
| ATOM | 3685 | OD1 | ASN A | 563 | 13.303 | 2.438 | −15.862 | 1.00 | 55.02 | O |
| ATOM | 3686 | ND2 | ASN A | 563 | 11.249 | 2.150 | −15.008 | 1.00 | 55.08 | N |
| ATOM | 3687 | C | ASN A | 563 | 10.989 | 3.579 | −12.451 | 1.00 | 57.25 | C |
| ATOM | 3688 | O | ASN A | 563 | 11.755 | 3.546 | −11.476 | 1.00 | 58.67 | O |
| ATOM | 3689 | N | PRO A | 564 | 9.876 | 2.819 | −12.525 | 1.00 | 56.51 | N |
| ATOM | 3690 | CA | PRO A | 564 | 9.608 | 1.754 | −11.549 | 1.00 | 55.97 | C |
| ATOM | 3691 | CB | PRO A | 564 | 8.211 | 1.261 | −11.937 | 1.00 | 56.13 | C |
| ATOM | 3692 | CG | PRO A | 564 | 8.034 | 1.691 | −13.361 | 1.00 | 57.87 | C |
| ATOM | 3693 | CD | PRO A | 564 | 8.781 | 2.966 | −13.505 | 1.00 | 55.82 | C |
| ATOM | 3694 | C | PRO A | 564 | 10.611 | .589 | −11.584 | 1.00 | 54.89 | C |
| ATOM | 3695 | O | PRO A | 564 | 10.753 | −.111 | −10.590 | 1.00 | 54.33 | O |
| ATOM | 3696 | N | ALA A | 565 | 11.295 | .395 | −12.710 | 1.00 | 53.60 | N |
| ATOM | 3697 | CA | ALA A | 565 | 12.262 | −.689 | −12.861 | 1.00 | 52.57 | C |
| ATOM | 3698 | CB | ALA A | 565 | 12.435 | −1.048 | −14.333 | 1.00 | 51.55 | C |
| ATOM | 3699 | C | ALA A | 565 | 13.630 | −.416 | −12.211 | 1.00 | 53.68 | C |
| ATOM | 3700 | O | ALA A | 565 | 14.451 | −1.339 | −12.076 | 1.00 | 53.53 | O |
| ATOM | 3701 | N | ALA A | 566 | 13.871 | .835 | −11.820 | 1.00 | 54.04 | N |
| ATOM | 3702 | CA | ALA A | 566 | 15.127 | 1.228 | −11.171 | 1.00 | 55.15 | C |
| ATOM | 3703 | CB | ALA A | 566 | 15.369 | 2.709 | −11.331 | 1.00 | 53.92 | C |
| ATOM | 3704 | C | ALA A | 566 | 15.125 | .855 | −9.694 | 1.00 | 57.22 | C |
| ATOM | 3705 | O | ALA A | 566 | 14.221 | 1.248 | −8.943 | 1.00 | 57.99 | O |
| ATOM | 3706 | N | THR A | 567 | 16.147 | .105 | −9.284 | 1.00 | 58.53 | N |
| ATOM | 3707 | CA | THR A | 567 | 16.255 | −.397 | −7.909 | 1.00 | 59.96 | C |
| ATOM | 3708 | CB | THR A | 567 | 16.268 | −1.932 | −7.888 | 1.00 | 59.54 | C |
| ATOM | 3709 | OG1 | THR A | 567 | 17.422 | −2.405 | −8.584 | 1.00 | 63.56 | O |
| ATOM | 3710 | CG2 | THR A | 567 | 15.025 | −2.490 | −8.571 | 1.00 | 59.21 | C |
| ATOM | 3711 | C | THR A | 567 | 17.489 | .177 | −7.183 | 1.00 | 60.56 | C |
| ATOM | 3712 | O | THR A | 567 | 18.162 | 1.061 | −7.715 | 1.00 | 60.54 | O |
| | | | | | gad65.pdb | | | | | |
| ATOM | 3713 | N | HIS A | 568 | 17.763 | −.300 | −5.967 | 1.00 | 61.01 | N |
| ATOM | 3714 | CA | HIS A | 568 | 18.946 | .146 | −5.206 | 1.00 | 61.37 | C |
| ATOM | 3715 | CB | HIS A | 568 | 18.917 | −.359 | −3.752 | 1.00 | 62.14 | C |
| ATOM | 3716 | CG | HIS A | 568 | 17.918 | .345 | −2.884 | 1.00 | 66.36 | C |
| ATOM | 3717 | ND1 | HIS A | 568 | 16.640 | −.132 | −2.680 | 1.00 | 71.55 | N |
| ATOM | 3718 | CE1 | HIS A | 568 | 15.986 | .694 | −1.881 | 1.00 | 74.64 | C |
| ATOM | 3719 | NE2 | HIS A | 568 | 16.793 | 1.691 | −1.561 | 1.00 | 73.96 | N |
| ATOM | 3720 | CD2 | HIS A | 568 | 18.008 | 1.493 | −2.172 | 1.00 | 70.19 | C |
| ATOM | 3721 | C | HIS A | 568 | 20.261 | −.249 | −5.893 | 1.00 | 60.55 | C |
| ATOM | 3722 | O | HIS A | 568 | 21.206 | .545 | −5.935 | 1.00 | 60.00 | O |
| ATOM | 3723 | N | GLN A | 569 | 20.306 | −1.461 | −6.442 | 1.00 | 60.70 | N |
| ATOM | 3724 | CA | GLN A | 569 | 21.463 | −1.933 | −7.211 | 1.00 | 62.18 | C |
| ATOM | 3725 | CB | GLN A | 569 | 21.240 | −3.370 | −7.707 | 1.00 | 62.19 | C |
| ATOM | 3726 | CG | GLN A | 569 | 20.288 | −3.488 | −8.903 | 1.00 | 65.69 | C |
| ATOM | 3727 | CD | GLN A | 569 | 20.014 | −4.916 | −9.329 | 1.00 | 64.21 | C |
| ATOM | 3728 | OE1 | GLN A | 569 | 20.888 | −5.601 | −9.866 | 1.00 | 69.87 | O |
| ATOM | 3729 | NE2 | GLN A | 569 | 18.782 | −5.366 | −9.110 | 1.00 | 72.27 | N |
| ATOM | 3730 | C | GLN A | 569 | 21.825 | −1.015 | −8.397 | 1.00 | 61.67 | C |
| ATOM | 3731 | O | GLN A | 569 | 23.002 | −.833 | −8.706 | 1.00 | 61.93 | O |
| ATOM | 3732 | N | ASP A | 570 | 20.809 | −.450 | −9.052 | 1.00 | 60.46 | N |
| ATOM | 3733 | CA | ASP A | 570 | 21.011 | .376 | −10.243 | 1.00 | 59.64 | C |
| ATOM | 3734 | CB | ASP A | 570 | 19.699 | .563 | −11.008 | 1.00 | 59.27 | C |
| ATOM | 3735 | CG | ASP A | 570 | 19.116 | 31.748 | −11.457 | 1.00 | 63.11 | C |
| ATOM | 3736 | OD1 | ASP A | 570 | 19.782 | −1.448 | −12.254 | 1.00 | 59.23 | O |
| ATOM | 3737 | OD2 | ASP A | 570 | 18.001 | −1.090 | −10.995 | 1.00 | 68.96 | O |
| ATOM | 3738 | C | ASP A | 570 | 21.641 | 1.711 | −9.906 | 1.00 | 58.26 | C |
| ATOM | 3739 | O | ASP A | 570 | 22.415 | 2.247 | −10.692 | 1.00 | 57.92 | O |
| ATOM | 3740 | N | ILE A | 571 | 21.300 | 2.238 | −8.736 | 1.00 | 58.11 | N |
| ATOM | 3741 | CA | ILE A | 571 | 21.966 | 3.427 | −8.181 | 1.00 | 58.57 | C |
| ATOM | 3742 | CB | ILE A | 571 | 21.189 | 3.987 | −6.958 | 1.00 | 58.14 | C |
| ATOM | 3743 | CG1 | ILE A | 571 | 19.733 | 4.311 | −7.339 | 1.00 | 60.20 | C |

TABLE A-continued

| | | | | | | | | | | |
|---|---|---|---|---|---|---|---|---|---|---|
| ATOM | 3744 | CD | ILE A | 571 | 19.547 | 5.110 | −8.645 | 1.00 | 54.00 | C |
| ATOM | 3745 | CG2 | ILE A | 571 | 21.903 | 5.190 | −6.337 | 1.00 | 55.07 | C |
| ATOM | 3746 | C | ILE A | 571 | 23.429 | 3.112 | −7.815 | 1.00 | 59.27 | C |
| ATOM | 3747 | O | ILE A | 571 | 24.341 | 3.866 | −8.180 | 1.00 | 59.53 | O |
| ATOM | 3748 | N | ASP A | 572 | 23.626 | 1.995 | −7.105 | 1.00 | 58.80 | N |
| ATOM | 3749 | CA | ASP A | 572 | 24.949 | 1.465 | −6.775 | 1.00 | 58.47 | C |
| ATOM | 3750 | CB | ASP A | 572 | 24.820 | .126 | −6.047 | 1.00 | 58.38 | C |
| ATOM | 3751 | CG | ASP A | 572 | 24.194 | .257 | −4.671 | 1.00 | 58.70 | C |
| ATOM | 3752 | OD1 | ASP A | 572 | 24.213 | 1.361 | −4.091 | 1.00 | 61.73 | O |
| ATOM | 3753 | OD2 | ASP A | 572 | 23.687 | −.762 | −4.159 | 1.00 | 63.31 | O |
| ATOM | 3754 | C | ASP A | 572 | 25.813 | 1.281 | −8.021 | 1.00 | 58.89 | C |
| ATOM | 3755 | O | ASP A | 572 | 26.984 | 1.659 | −8.017 | 1.00 | 58.69 | O |
| ATOM | 3756 | N | PHE A | 573 | 25.232 | .702 | −9.078 | 1.00 | 59.50 | N |
| ATOM | 3757 | CA | PHE A | 573 | 25.928 | .528 | −10.351 | 1.00 | 59.53 | C |
| ATOM | 3758 | CB | PHE A | 573 | 25.070 | −.223 | −11.372 | 1.00 | 60.03 | C |
| ATOM | 3759 | CG | PHE A | 573 | 25.695 | −.293 | −12.740 | 1.00 | 63.02 | C |
| ATOM | 3760 | CD1 | PHE A | 573 | 26.510 | −1.366 | −13.094 | 1.00 | 65.03 | C |
| ATOM | 3761 | CE1 | PHE A | 573 | 27.111 | −1.422 | −14.358 | 1.00 | 67.05 | C |
| ATOM | 3762 | CZ | PHE A | 573 | 26.903 | −.393 | −15.274 | 1.00 | 64.69 | C |
| ATOM | 3763 | CE2 | PHE A | 573 | 26.099 | .689 | −14.927 | 1.00 | 64.59 | C |
| ATOM | 3764 | CD2 | PHE A | 573 | 25.499 | .734 | −13.667 | 1.00 | 63.91 | C |
| ATOM | 3765 | C | PHE A | 573 | 26.341 | 1.872 | −10.929 | 1.00 | 59.64 | C |
| ATOM | 3766 | O | PHE A | 573 | 27.474 | 2.039 | −11.389 | 1.00 | 59.74 | O |
| ATOM | 3767 | N | LEU A | 574 | 25.413 | 2.824 | −10.904 | 1.00 | 59.88 | N |
| ATOM | 3768 | CA | LEU A | 574 | 25.649 | 4.143 | −11.464 | 1.00 | 59.75 | C |
| ATOM | 3769 | CB | LEU A | 574 | 24.394 | 5.019 | −11.370 | 1.00 | 59.55 | C |
| ATOM | 3770 | CG | LEU A | 574 | 24.571 | 6.419 | −11.968 | 1.00 | 57.12 | C |
| ATOM | 3771 | CD1 | LEU A | 574 | 24.663 | 6.377 | −13.493 | 1.00 | 49.38 | C |
| ATOM | 3772 | CD2 | LEU A | 574 | 23.461 | 7.311 | −11.515 | 1.00 | 56.17 | C |
| ATOM | 3773 | C | LEU A | 574 | 26.828 | 4.842 | −10.801 | 1.00 | 59.91 | C |
| ATOM | 3774 | O | LEU A | 574 | 27.732 | 5.311 | −11.493 | 1.00 | 59.49 | O |
| ATOM | 3775 | N | ILE A | 575 | 26.808 | 4.916 | −9.469 | 1.00 | 60.77 | N |
| ATOM | 3776 | CA | ILE A | 575 | 27.904 | 5.530 | −8.712 | 1.00 | 61.71 | C |
| ATOM | 3777 | CB | ILE A | 575 | 27.799 | 5.262 | −7.185 | 1.00 | 61.83 | C |
| ATOM | 3778 | CG1 | ILE A | 575 | 26.387 | 5.537 | −6.640 | 1.00 | 60.99 | C |
| ATOM | 3779 | CD | ILE A | 575 | 25.933 | 6.973 | −6.714 | 1.00 | 61.27 | C |
| ATOM | 3780 | CG2 | ILE A | 575 | 28.878 | 6.042 | −6.437 | 1.00 | 61.13 | C |
| | | | | | gad65.pdb | | | | | |
| ATOM | 3781 | C | ILE A | 575 | 29.247 | 4.974 | −9.187 | 1.00 | 61.99 | C |
| ATOM | 3782 | O | ILE A | 575 | 30.167 | 5.728 | −9.512 | 1.00 | 62.13 | O |
| ATOM | 3783 | N | GLU A | 576 | 29.323 | 3.649 | −9.233 | 1.00 | 62.25 | N |
| ATOM | 3784 | CA | GLU A | 576 | 30.528 | 2.920 | −9.598 | 1.00 | 64.58 | C |
| ATOM | 3785 | CB | GLU A | 576 | 30.341 | 1.430 | −9.309 | 1.00 | 64.50 | C |
| ATOM | 3786 | CG | GLU A | 576 | 30.196 | 1.095 | −7.826 | 1.00 | 67.57 | C |
| ATOM | 3787 | CD | GLU A | 576 | 29.895 | −.385 | −7.570 | 1.00 | 67.72 | C |
| ATOM | 3788 | OE1 | GLU A | 576 | 30.164 | −.848 | −6.435 | 1.00 | 75.10 | O |
| ATOM | 3789 | OE2 | GLU A | 576 | 29.390 | −1.082 | −8.490 | 1.00 | 75.27 | O |
| ATOM | 3790 | C | GLU A | 576 | 30.946 | 3.124 | −11.057 | 1.00 | 64.01 | C |
| ATOM | 3791 | O | GLU A | 576 | 32.141 | 3.253 | −11.345 | 1.00 | 64.56 | O |
| ATOM | 3792 | N | GLU A | 577 | 29.965 | 3.151 | −11.964 | 1.00 | 62.07 | N |
| ATOM | 3793 | CA | GLU A | 577 | 30.222 | 3.363 | −13.388 | 1.00 | 59.52 | C |
| ATOM | 3794 | CB | GLU A | 577 | 28.933 | 3.193 | −14.202 | 1.00 | 59.80 | C |
| ATOM | 3795 | CG | GLU A | 577 | 29.120 | 3.288 | −15.718 | 1.00 | 58.07 | C |
| ATOM | 3796 | CD | GLU A | 577 | 29.765 | 2.050 | −16.329 | 1.00 | 60.20 | C |
| ATOM | 3797 | OE1 | GLU A | 577 | 29.950 | 2.032 | −17.565 | 1.00 | 62.71 | O |
| ATOM | 3798 | OE2 | GLU A | 577 | 30.084 | 1.093 | −15.589 | 1.00 | 62.99 | O |
| ATOM | 3799 | C | GLU A | 577 | 30.814 | 4.741 | −13.647 | 1.00 | 57.82 | C |
| ATOM | 3800 | O | GLU A | 577 | 31.706 | 4.891 | −14.481 | 1.00 | 56.84 | O |
| ATOM | 3801 | N | ILE A | 578 | 30.296 | 5.743 | −12.942 | 1.00 | 56.52 | N |
| ATOM | 3802 | CA | ILE A | 578 | 30.781 | 7.113 | −13.083 | 1.00 | 55.42 | C |
| ATOM | 3803 | CB | ILE A | 578 | 29.895 | 8.115 | −12.297 | 1.00 | 54.92 | C |
| ATOM | 3804 | CG1 | ILE A | 578 | 28.580 | 8.342 | −13.057 | 1.00 | 55.81 | C |
| ATOM | 3805 | CD | ILE A | 578 | 27.543 | 9.209 | −12.349 | 1.00 | 54.27 | C |
| ATOM | 3806 | CG2 | ILE A | 578 | 30.614 | 9.444 | −12.112 | 1.00 | 53.68 | C |
| ATOM | 3807 | C | ILE A | 578 | 32.261 | 7.186 | −12.669 | 1.00 | 55.02 | C |
| ATOM | 3808 | O | ILE A | 578 | 33.089 | 7.784 | −13.369 | 1.00 | 52.75 | O |
| ATOM | 3809 | N | GLU A | 579 | 32.571 | 6.539 | −11.547 | 1.00 | 56.04 | N |
| ATOM | 3810 | CA | GLU A | 579 | 33.934 | 6.436 | −11.039 | 1.00 | 57.61 | C |
| ATOM | 3811 | CB | GLU A | 579 | 33.934 | 5.734 | −9.671 | 1.00 | 57.34 | C |
| ATOM | 3812 | CG | GLU A | 579 | 33.498 | 6.651 | −8.546 | 1.00 | 58.41 | C |
| ATOM | 3813 | CD | GLU A | 579 | 33.043 | 5.924 | −7.281 | 1.00 | 63.67 | C |
| ATOM | 3814 | OE1 | GLU A | 579 | 32.683 | 6.621 | −6.310 | 1.00 | 60.13 | O |
| ATOM | 3815 | OE2 | GLU A | 579 | 33.044 | 4.676 | −7.246 | 1.00 | 64.70 | O |
| ATOM | 3816 | C | GLU A | 579 | 34.853 | 5.727 | −12.034 | 1.00 | 58.51 | C |
| ATOM | 3817 | O | GLU A | 579 | 35.949 | 6.197 | −12.323 | 1.00 | 59.02 | O |
| ATOM | 3818 | N | ARG A | 580 | 34.378 | 4.610 | −12.571 | 1.00 | 59.66 | N |
| ATOM | 3819 | CA | ARG A | 580 | 35.121 | 3.797 | −13.521 | 1.00 | 61.52 | C |
| ATOM | 3820 | CB | ARG A | 580 | 34.257 | 2.610 | −13.882 | 1.00 | 61.82 | C |
| ATOM | 3821 | CG | ARG A | 580 | 34.972 | 1.353 | −14.287 | 1.00 | 65.76 | C |
| ATOM | 3822 | CD | ARG A | 580 | 33.926 | .263 | −14.441 | 1.00 | 70.44 | C |

TABLE A-continued

| | | | | | | | | | |
|---|---|---|---|---|---|---|---|---|---|
| ATOM | 3823 | NE | ARG A | 580 | 33.217 | .033 | −13.181 | 1.00 | 73.59 | N |
| ATOM | 3824 | CZ | ARG A | 580 | 31.961 | −.390 | −13.085 | 1.00 | 77.56 | C |
| ATOM | 3825 | NH1 | ARG A | 580 | 31.246 | −.623 | −14.175 | 1.00 | 81.08 | N |
| ATOM | 3826 | NH2 | ARG A | 580 | 31.413 | −.573 | −11.891 | 1.00 | 78.42 | N |
| ATOM | 3827 | C | ARG A | 580 | 35.472 | 4.574 | −14.796 | 1.00 | 63.51 | C |
| ATOM | 3828 | O | ARG A | 580 | 36.591 | 4.464 | −15.326 | 1.00 | 63.17 | O |
| ATOM | 3829 | N | LEU A | 581 | 34.499 | 5.351 | −15.275 | 1.00 | 64.72 | N |
| ATOM | 3830 | CA | LEU A | 581 | 34.603 | 6.101 | −16.516 | 1.00 | 65.94 | C |
| ATOM | 3831 | CB | LEU A | 581 | 33.202 | 6.309 | −17.099 | 1.00 | 65.74 | C |
| ATOM | 3832 | CG | LEU A | 581 | 32.570 | 5.279 | −18.054 | 1.00 | 65.60 | C |
| ATOM | 3833 | CD1 | LEU A | 581 | 32.901 | 3.826 | −17.750 | 1.00 | 65.99 | C |
| ATOM | 3834 | CD2 | LEU A | 581 | 31.065 | 5.483 | −18.083 | 1.00 | 66.09 | C |
| ATOM | 3835 | C | LEU A | 581 | 35.326 | 7.444 | −16.344 | 1.00 | 68.11 | C |
| ATOM | 3836 | O | LEU A | 581 | 35.725 | 8.075 | −17.330 | 1.00 | 67.89 | O |
| ATOM | 3837 | N | GLY A | 582 | 35.502 | 7.871 | −15.095 | 1.00 | 70.13 | N |
| ATOM | 3838 | CA | GLY A | 582 | 36.159 | 9.138 | −14.796 | 1.00 | 72.86 | C |
| ATOM | 3839 | C | GLY A | 582 | 37.657 | 9.037 | −14.621 | 1.00 | 75.40 | C |
| ATOM | 3840 | O | GLY A | 582 | 38.161 | 9.179 | −13.511 | 1.00 | 75.98 | O |
| ATOM | 3841 | N | GLN A | 583 | 38.359 | 8.794 | −15.725 | 1.00 | 77.85 | N |
| ATOM | 3842 | CA | GLN A | 583 | 39.829 | 8.731 | −15.757 | 1.00 | 79.91 | C |
| ATOM | 3843 | CB | GLN A | 583 | 40.340 | 7.373 | −15.254 | 1.00 | 80.05 | C |
| ATOM | 3844 | CG | GLN A | 583 | 40.760 | 7.393 | −13.778 | 1.00 | 82.64 | C |
| ATOM | 3845 | CD | GLN A | 583 | 40.126 | 6.280 | −12.942 | 1.00 | 83.45 | C |
| ATOM | 3846 | OE1 | GLN A | 583 | 39.786 | 6.492 | −11.777 | 1.00 | 84.12 | O |
| ATOM | 3847 | NE2 | GLN A | 583 | 39.968 | 5.096 | −13.531 | 1.00 | 76.11 | N |
| ATOM | 3848 | C | GLN A | 583 | 40.397 | 9.082 | −17.151 | 1.00 | 80.80 | C |
| | | | | | gad65.pdb | | | | | |
| ATOM | 3849 | O | GLN A | 583 | 40.739 | 8.195 | −17.943 | 1.00 | 80.45 | O |
| ATOM | 3850 | N | ASP A | 584 | 40.499 | 10.380 | −17.443 | 1.00 | 81.65 | N |
| ATOM | 3851 | CA | ASP A | 584 | 40.130 | 11.441 | −16.499 | 1.00 | 82.17 | C |
| ATOM | 3852 | CB | ASP A | 584 | 41.382 | 12.059 | −15.867 | 1.00 | 82.62 | C |
| ATOM | 3856 | C | ASP A | 584 | 39.281 | 12.524 | −17.167 | 1.00 | 82.09 | C |
| ATOM | 3857 | O | ASP A | 584 | 38.076 | 12.356 | −17.358 | 1.00 | 81.77 | O |
| TER | | | | | | | | | | |
| ATOM | 1 | N | ASN B | 88 | −5.872 | −17.439 | −12.971 | 1.00 | 58.48 | N |
| ATOM | 2 | CA | ASN B | 88 | −5.014 | −16.370 | −13.592 | 1.00 | 58.99 | C |
| ATOM | 3 | CB | ASN B | 88 | −5.021 | −16.482 | −15.130 | 1.00 | 59.66 | C |
| ATOM | 4 | CG | ASN B | 88 | −3.965 | −17.465 | −15.643 | 1.00 | 62.22 | C |
| ATOM | 5 | OD1 | ASN B | 88 | −4.293 | −18.317 | −16.490 | 1.00 | 67.32 | O |
| ATOM | 6 | ND2 | ASN B | 88 | −2.691 | −17.348 | −15.141 | 1.00 | 60.91 | N |
| ATOM | 7 | C | ASN B | 88 | −5.365 | −14.935 | −13.169 | 1.00 | 57.90 | C |
| ATOM | 8 | O | ASN B | 88 | −5.155 | −14.547 | −12.010 | 1.00 | 56.81 | O |
| ATOM | 9 | N | TYR B | 89 | −5.923 | −14.172 | −14.113 | 1.00 | 57.87 | N |
| ATOM | 10 | CA | TYR B | 89 | −6.042 | −12.711 | −14.002 | 1.00 | 57.61 | C |
| ATOM | 11 | CB | TYR B | 89 | −6.576 | −12.114 | −15.307 | 1.00 | 57.30 | C |
| ATOM | 12 | CG | TYR B | 89 | −5.734 | −12.393 | −16.537 | 1.00 | 56.53 | C |
| ATOM | 13 | CD1 | TYR B | 89 | −6.222 | −13.191 | −17.570 | 1.00 | 56.19 | C |
| ATOM | 14 | CE1 | TYR B | 89 | −5.459 | −13.445 | −18.708 | 1.00 | 55.74 | C |
| ATOM | 15 | CZ | TYR B | 89 | −4.190 | −12.902 | −18.819 | 1.00 | 57.78 | C |
| ATOM | 16 | OH | TYR B | 89 | −3.438 | −13.152 | −19.945 | 1.00 | 58.84 | O |
| ATOM | 17 | CE2 | TYR B | 89 | −3.675 | −12.107 | −17.807 | 1.00 | 56.17 | C |
| ATOM | 18 | CD2 | TYR B | 89 | −4.448 | −11.855 | −16.673 | 1.00 | 58.99 | C |
| ATOM | 19 | C | TYR B | 89 | −6.856 | −12.207 | −12.807 | 1.00 | 58.02 | C |
| ATOM | 20 | O | TYR B | 89 | −6.640 | −11.088 | −12.338 | 1.00 | 57.21 | O |
| ATOM | 21 | N | ALA B | 90 | −7.773 | −13.037 | −12.311 | 1.00 | 59.45 | N |
| ATOM | 22 | CA | ALA B | 90 | −8.570 | −12.708 | −11.125 | 1.00 | 60.48 | C |
| ATOM | 23 | CB | ALA B | 90 | −9.639 | −13.766 | −10.896 | 1.00 | 60.45 | C |
| ATOM | 24 | C | ALA B | 90 | −7.703 | −12.537 | −9.870 | 1.00 | 61.52 | C |
| ATOM | 25 | O | ALA B | 90 | −8.069 | −11.806 | −8.945 | 1.00 | 62.22 | O |
| ATOM | 26 | N | PHE B | 91 | −6.556 | −13.209 | −9.850 | 1.00 | 61.81 | N |
| ATOM | 27 | CA | PHE B | 91 | −5.656 | −13.167 | −8.701 | 1.00 | 62.25 | C |
| ATOM | 28 | CB | PHE B | 91 | −5.434 | −14.587 | −8.162 | 1.00 | 62.81 | C |
| ATOM | 29 | C | PHE B | 91 | −4.330 | −12.483 | −9.070 | 1.00 | 62.20 | C |
| ATOM | 30 | O | PHE B | 91 | −3.295 | −12.678 | −8.414 | 1.00 | 62.12 | O |
| ATOM | 31 | N | LEU B | 92 | −4.380 | −11.681 | −10.129 | 1.00 | 61.49 | N |
| ATOM | 32 | CA | LEU B | 92 | −3.243 | −10.885 | −10.563 | 1.00 | 61.24 | C |
| ATOM | 33 | CB | LEU B | 92 | −2.836 | −11.254 | −11.994 | 1.00 | 61.43 | C |
| ATOM | 34 | CG | LEU B | 92 | −2.123 | −12.597 | −12.218 | 1.00 | 63.12 | C |
| ATOM | 35 | CD1 | LEU B | 92 | −1.943 | −12.867 | −13.711 | 1.00 | 61.15 | C |
| ATOM | 36 | CD2 | LEU B | 92 | −0.772 | −12.645 | −11.501 | 1.00 | 62.42 | C |
| ATOM | 37 | C | LEU B | 92 | −3.554 | −9.397 | −10.466 | 1.00 | 60.92 | C |
| ATOM | 38 | O | LEU B | 92 | −4.719 | −8.997 | −10.450 | 1.00 | 60.83 | O |
| ATOM | 39 | N | HIS B | 93 | −2.497 | −8.590 | −10.381 | 1.00 | 59.97 | N |
| ATOM | 40 | CA | HIS B | 93 | −2.598 | −7.137 | −10.367 | 1.00 | 58.77 | C |
| ATOM | 41 | CB | HIS B | 93 | −2.565 | −6.589 | −8.933 | 1.00 | 59.30 | C |
| ATOM | 42 | CG | HIS B | 93 | −3.763 | −6.964 | −8.111 | 1.00 | 62.19 | C |
| ATOM | 43 | ND1 | HIS B | 93 | −3.739 | −7.980 | −7.180 | 1.00 | 64.96 | N |
| ATOM | 44 | CE1 | HIS B | 93 | −4.931 | −8.091 | −6.619 | 1.00 | 65.77 | C |
| ATOM | 45 | NE2 | HIS B | 93 | −5.728 | −7.182 | −7.150 | 1.00 | 64.08 | N |
| ATOM | 46 | CD2 | HIS B | 93 | −5.022 | −6.464 | −8.086 | 1.00 | 63.36 | C |

TABLE A-continued

| | | | | | | | | | |
|---|---|---|---|---|---|---|---|---|---|
| ATOM | 47 | C | HIS B | 93 | −1.438 | −6.585 | −11.182 | 1.00 | 58.12 | C |
| ATOM | 48 | O | HIS B | 93 | −0.575 | −7.339 | −11.631 | 1.00 | 57.87 | O |
| ATOM | 49 | N | ALA B | 94 | −1.431 | −5.270 | −11.376 | 1.00 | 57.47 | N |
| ATOM | 50 | CA | ALA B | 94 | −0.416 | −4.592 | −12.165 | 1.00 | 57.35 | C |
| ATOM | 51 | CB | ALA B | 94 | −0.745 | −3.123 | −12.270 | 1.00 | 55.69 | C |
| ATOM | 52 | C | ALA B | 94 | 0.962 | −4.788 | −11.536 | 1.00 | 58.69 | C |
| ATOM | 53 | O | ALA B | 94 | 1.957 | −4.974 | −12.236 | 1.00 | 58.85 | O |
| ATOM | 54 | N | THR B | 95 | 0.986 | −4.766 | −10.206 | 1.00 | 59.22 | N |
| ATOM | 55 | CA | THR B | 95 | 2.186 | −4.914 | −9.402 | 1.00 | 59.95 | C |
| ATOM | 56 | CB | THR B | 95 | 1.853 | −4.706 | −7.916 | 1.00 | 60.08 | C |
| ATOM | 57 | OG1 | THR B | 95 | 0.613 | −5.357 | −7.610 | 1.00 | 59.62 | O |
| ATOM | 58 | CG2 | THR B | 95 | 1.733 | −3.217 | −7.597 | 1.00 | 59.04 | C |
| ATOM | 59 | C | THR B | 95 | 2.864 | −6.272 | −9.578 | 1.00 | 60.79 | C |
| ATOM | 60 | O | THR B | 95 | 4.004 | −6.463 | −9.145 | 1.00 | 61.88 | O |
| ATOM | 61 | N | ASP B | 96 | 2.157 | −7.208 | −10.209 | 1.00 | 60.27 | N |
| | | | | | gad65.pdb | | | | | |
| ATOM | 62 | CA | ASP B | 96 | 2.684 | −8.548 | −10.488 | 1.00 | 58.53 | C |
| ATOM | 63 | CB | ASP B | 96 | 1.554 | −9.586 | −10.429 | 1.00 | 57.75 | C |
| ATOM | 64 | CG | ASP B | 96 | 0.959 | −9.736 | −9.030 | 1.00 | 59.97 | C |
| ATOM | 65 | OD1 | ASP B | 96 | 1.697 | −9.560 | −8.030 | 1.00 | 60.40 | O |
| ATOM | 66 | OD2 | ASP B | 96 | −0.250 | −10.050 | −8.928 | 1.00 | 56.20 | O |
| ATOM | 67 | C | ASP B | 96 | 3.415 | −8.634 | −11.836 | 1.00 | 57.20 | C |
| ATOM | 68 | O | ASP B | 96 | 4.149 | −9.594 | −12.090 | 1.00 | 57.24 | O |
| ATOM | 69 | N | LEU B | 97 | 3.217 | −7.626 | −12.683 | 1.00 | 56.13 | N |
| ATOM | 70 | CA | LEU B | 97 | 3.791 | −7.599 | −14.031 | 1.00 | 55.89 | C |
| ATOM | 71 | CB | LEU B | 97 | 2.877 | −6.802 | −14.978 | 1.00 | 57.07 | C |
| ATOM | 72 | CG | LEU B | 97 | 1.387 | −7.156 | −15.088 | 1.00 | 57.16 | C |
| ATOM | 73 | CD1 | LEU B | 97 | 0.661 | −6.091 | −15.896 | 1.00 | 56.49 | C |
| ATOM | 74 | CD2 | LEU B | 97 | 1.199 | −8.522 | −15.723 | 1.00 | 57.84 | C |
| ATOM | 75 | C | LEU B | 97 | 5.190 | −6.979 | −14.040 | 1.00 | 54.87 | C |
| ATOM | 76 | O | LEU B | 97 | 5.551 | −6.252 | −13.116 | 1.00 | 54.53 | O |
| ATOM | 77 | N | LEU B | 98 | 5.972 | −7.251 | −15.087 | 1.00 | 54.76 | N |
| ATOM | 78 | CA | LEU B | 98 | 7.247 | −6.537 | −15.300 | 1.00 | 54.57 | C |
| ATOM | 79 | CB | LEU B | 98 | 7.797 | −6.769 | −16.712 | 1.00 | 53.96 | C |
| ATOM | 80 | CG | LEU B | 98 | 8.411 | −8.143 | −17.022 | 1.00 | 52.88 | C |
| ATOM | 81 | CD1 | LEU B | 98 | 8.642 | −8.314 | −18.514 | 1.00 | 51.05 | C |
| ATOM | 82 | CD2 | LEU B | 98 | 9.705 | −8.379 | −16.243 | 1.00 | 55.10 | C |
| ATOM | 83 | C | LEU B | 98 | 7.065 | −5.042 | −15.050 | 1.00 | 54.96 | C |
| ATOM | 84 | O | LEU B | 98 | 6.093 | −4.460 | −15.539 | 1.00 | 54.07 | O |
| ATOM | 85 | N | PRO B | 99 | 8.009 | −4.398 | −14.320 | 1.00 | 55.66 | N |
| ATOM | 86 | CA | PRO B | 99 | 9.337 | −4.846 | −13.879 | 1.00 | 56.29 | C |
| ATOM | 87 | CB | PRO B | 99 | 10.076 | −3.527 | −13.663 | 1.00 | 56.16 | C |
| ATOM | 88 | CG | PRO B | 99 | 9.023 | −2.588 | −13.214 | 1.00 | 55.63 | C |
| ATOM | 89 | CD | PRO B | 99 | 7.738 | −3.016 | −13.876 | 1.00 | 55.41 | C |
| ATOM | 90 | C | PRO B | 99 | 9.427 | −5.690 | −12.596 | 1.00 | 57.07 | C |
| ATOM | 91 | O | PRO B | 99 | 10.523 | −5.831 | −12.048 | 1.00 | 56.87 | O |
| ATOM | 92 | N | ALA B | 100 | 8.311 | −6.232 | −12.118 | 1.00 | 57.70 | N |
| ATOM | 93 | CA | ALA B | 100 | 8.354 | −7.152 | −10.981 | 1.00 | 57.82 | C |
| ATOM | 94 | CB | ALA B | 100 | 6.955 | −7.536 | −10.545 | 1.00 | 56.97 | C |
| ATOM | 95 | C | ALA B | 100 | 9.158 | −8.388 | −11.362 | 1.00 | 58.45 | C |
| ATOM | 96 | O | ALA B | 100 | 9.136 | −8.809 | −12.522 | 1.00 | 58.13 | O |
| ATOM | 97 | N | CYS B | 101 | 9.873 | −8.955 | −10.387 | 1.00 | 59.74 | N |
| ATOM | 98 | CA | CYS B | 101 | 10.786 | −10.083 | −10.629 | 1.00 | 60.92 | C |
| ATOM | 99 | CB | CYS B | 101 | 11.667 | −10.342 | −9.402 | 1.00 | 61.63 | C |
| ATOM | 100 | SG | CYS B | 101 | 13.055 | −9.200 | −9.287 | 1.00 | 68.60 | S |
| ATOM | 101 | C | CYS B | 101 | 10.108 | −11.377 | −11.095 | 1.00 | 60.53 | C |
| ATOM | 102 | O | CYS B | 101 | 10.591 | −12.027 | −12.028 | 1.00 | 61.12 | O |
| ATOM | 103 | N | ASP B | 102 | 9.005 | −11.749 | −10.448 | 1.00 | 59.55 | N |
| ATOM | 104 | CA | ASP B | 102 | 8.165 | −12.841 | −10.937 | 1.00 | 59.47 | C |
| ATOM | 105 | CB | ASP B | 102 | 7.464 | −13.551 | −9.773 | 1.00 | 59.38 | C |
| ATOM | 106 | C | ASP B | 102 | 7.145 | −12.258 | −11.918 | 1.00 | 59.93 | C |
| ATOM | 107 | O | ASP B | 102 | 5.928 | −12.430 | −11.759 | 1.00 | 60.22 | O |
| ATOM | 108 | N | GLY B | 103 | 7.648 | −11.557 | −12.933 | 1.00 | 59.84 | N |
| ATOM | 109 | CA | GLY B | 103 | 6.785 | −10.769 | −13.810 | 1.00 | 59.46 | C |
| ATOM | 110 | C | GLY B | 103 | 6.723 | −11.144 | −15.276 | 1.00 | 58.85 | C |
| ATOM | 111 | O | GLY B | 103 | 5.754 | −10.797 | −15.944 | 1.00 | 59.96 | O |
| ATOM | 112 | N | GLU B | 104 | 7.737 | −11.843 | −15.784 | 1.00 | 57.65 | N |
| ATOM | 113 | CA | GLU B | 104 | 7.850 | −12.078 | −17.228 | 1.00 | 57.74 | C |
| ATOM | 114 | CB | GLU B | 104 | 9.208 | −12.676 | −17.589 | 1.00 | 57.71 | C |
| ATOM | 115 | CG | GLU B | 104 | 9.452 | −12.832 | −19.096 | 1.00 | 59.11 | C |
| ATOM | 116 | CD | GLU B | 104 | 10.747 | −13.580 | −19.419 | 1.00 | 59.81 | C |
| ATOM | 117 | OE1 | GLU B | 104 | 11.749 | −13.424 | −18.675 | 1.00 | 65.19 | O |
| ATOM | 118 | OE2 | GLU B | 104 | 10.761 | −14.324 | −20.426 | 1.00 | 66.71 | O |
| ATOM | 119 | C | GLU B | 104 | 6.723 | −12.932 | −17.802 | 1.00 | 56.71 | C |
| ATOM | 120 | O | GLU B | 104 | 6.142 | −12.579 | −18.829 | 1.00 | 56.86 | O |
| ATOM | 121 | N | ARG B | 105 | 6.421 | −14.043 | −17.136 | 1.00 | 56.14 | N |
| ATOM | 122 | CA | ARG B | 105 | 5.348 | −14.950 | −17.568 | 1.00 | 55.32 | C |
| ATOM | 123 | CB | ARG B | 105 | 5.347 | −16.242 | −16.741 | 1.00 | 56.01 | C |
| ATOM | 124 | C | ARG B | 105 | 3.955 | −14.307 | −17.575 | 1.00 | 53.89 | C |
| ATOM | 125 | O | ARG B | 105 | 3.275 | −14.375 | −18.592 | 1.00 | 54.06 | O |

TABLE A-continued

| | | | | | | | | | |
|---|---|---|---|---|---|---|---|---|---|
| ATOM | 126 | N | PRO B | 106 | 3.522 | −13.697 | −16.447 | 1.00 | 53.04 | N |
| ATOM | 127 | CA | PRO B | 106 | 2.218 | −13.010 | −16.436 | 1.00 | 52.20 | C |
| ATOM | 128 | CB | PRO B | 106 | 2.047 | −12.581 | −14.973 | 1.00 | 52.37 | C |
| ATOM | 129 | CG | PRO B | 106 | 3.424 | −12.589 | −14.393 | 1.00 | 54.00 | C |
| | | | | gad65.pdb | | | | | | |
| ATOM | 130 | CD | PRO B | 106 | 4.171 | −13.661 | −15.120 | 1.00 | 53.11 | C |
| ATOM | 131 | C | PRO B | 106 | 2.104 | −11.791 | −17.361 | 1.00 | 51.43 | C |
| ATOM | 132 | O | PRO B | 106 | 0.991 | −11.433 | −17.746 | 1.00 | 51.17 | O |
| ATOM | 133 | N | THR B | 107 | 3.236 | −11.168 | −17.699 | 1.00 | 50.63 | N |
| ATOM | 134 | CA | THR B | 107 | 3.271 | −10.041 | −18.634 | 1.00 | 49.20 | C |
| ATOM | 135 | CB | THR B | 107 | 4.586 | −9.234 | −18.516 | 1.00 | 48.79 | C |
| ATOM | 136 | OG1 | THR B | 107 | 4.695 | −8.685 | −17.197 | 1.00 | 50.21 | O |
| ATOM | 137 | CG2 | THR B | 107 | 4.623 | −8.101 | −19.531 | 1.00 | 41.90 | C |
| ATOM | 138 | C | THR B | 107 | 3.057 | −10.463 | −20.093 | 1.00 | 49.16 | C |
| ATOM | 139 | O | THR B | 107 | 2.278 | −9.835 | −20.822 | 1.00 | 48.71 | O |
| ATOM | 140 | N | LEU B | 108 | 3.763 | −11.510 | −20.511 | 1.00 | 49.71 | N |
| ATOM | 141 | CA | LEU B | 108 | 3.621 | −12.087 | −21.849 | 1.00 | 50.32 | C |
| ATOM | 142 | CB | LEU B | 108 | 4.612 | −13.245 | −22.046 | 1.00 | 50.30 | C |
| ATOM | 143 | CG | LEU B | 108 | 6.107 | −12.902 | −22.128 | 1.00 | 51.95 | C |
| ATOM | 144 | CD1 | LEU B | 108 | 6.970 | −14.137 | −21.906 | 1.00 | 53.62 | C |
| ATOM | 145 | CD2 | LEU B | 108 | 6.465 | −12.238 | −23.456 | 1.00 | 53.41 | C |
| ATOM | 146 | C | LEU B | 108 | 2.196 | −12.580 | −22.101 | 1.00 | 50.71 | C |
| ATOM | 147 | O | LEU B | 108 | 1.689 | −12.485 | −23.223 | 1.00 | 50.66 | O |
| ATOM | 148 | N | ALA B | 109 | 1.560 | −13.098 | −21.049 | 1.00 | 51.02 | N |
| ATOM | 149 | CA | ALA B | 109 | 0.206 | −13.617 | −21.139 | 1.00 | 51.49 | C |
| ATOM | 150 | CB | ALA B | 109 | −0.103 | −14.524 | −19.943 | 1.00 | 50.78 | C |
| ATOM | 151 | C | ALA B | 109 | −0.805 | −12.476 | −21.228 | 1.00 | 52.55 | C |
| ATOM | 152 | O | ALA B | 109 | −1.733 | −12.519 | −22.045 | 1.00 | 53.01 | O |
| ATOM | 153 | N | PHE B | 110 | −0.621 | −11.465 | −20.377 | 1.00 | 52.57 | N |
| ATOM | 154 | CA | PHE B | 110 | −1.550 | −10.341 | −20.285 | 1.00 | 51.86 | C |
| ATOM | 155 | CB | PHE B | 110 | −1.227 | −9.461 | −19.069 | 1.00 | 51.39 | C |
| ATOM | 156 | CG | PHE B | 110 | −1.953 | −8.139 | −19.058 | 1.00 | 52.07 | C |
| ATOM | 157 | CD1 | PHE B | 110 | −3.279 | −8.060 | −18.632 | 1.00 | 50.71 | C |
| ATOM | 158 | CE1 | PHE B | 110 | −3.956 | −6.843 | −18.623 | 1.00 | 50.31 | C |
| ATOM | 159 | CZ | PHE B | 110 | −3.307 | −5.688 | −19.038 | 1.00 | 48.26 | C |
| ATOM | 160 | CE2 | PHE B | 110 | −1.976 | −5.751 | −19.458 | 1.00 | 52.54 | C |
| ATOM | 161 | CD2 | PHE B | 110 | −1.306 | −6.969 | −19.467 | 1.00 | 45.39 | C |
| ATOM | 162 | C | PHE B | 110 | −1.528 | −9.527 | −21.565 | 1.00 | 52.18 | C |
| ATOM | 163 | O | PHE B | 110 | −2.582 | −9.233 | −22.137 | 1.00 | 53.17 | O |
| ATOM | 164 | N | LEU B | 111 | −0.329 | −9.167 | −22.017 | 1.00 | 51.39 | N |
| ATOM | 165 | CA | LEU B | 111 | −0.195 | −8.409 | −23.248 | 1.00 | 50.72 | C |
| ATOM | 166 | CB | LEU B | 111 | 1.261 | −8.002 | −23.512 | 1.00 | 50.03 | C |
| ATOM | 167 | CG | LEU B | 111 | 1.934 | −6.999 | −22.555 | 1.00 | 48.29 | C |
| ATOM | 168 | CD1 | LEU B | 111 | 3.357 | −6.694 | −23.012 | 1.00 | 47.35 | C |
| ATOM | 169 | CD2 | LEU B | 111 | 1.133 | −5.720 | −22.382 | 1.00 | 42.10 | C |
| ATOM | 170 | C | LEU B | 111 | −0.753 | −9.190 | −24.429 | 1.00 | 51.25 | C |
| ATOM | 171 | O | LEU B | 111 | −1.343 | −8.611 | −25.327 | 1.00 | 50.97 | O |
| ATOM | 172 | N | GLN B | 112 | −0.570 | −10.509 | −24.433 | 1.00 | 52.56 | N |
| ATOM | 173 | CA | GLN B | 112 | −1.097 | −11.300 | −25.540 | 1.00 | 52.80 | C |
| ATOM | 174 | CB | GLN B | 112 | −0.423 | −12.665 | −25.647 | 1.00 | 53.06 | C |
| ATOM | 175 | CG | GLN B | 112 | −0.042 | −13.015 | −27.081 | 1.00 | 54.95 | C |
| ATOM | 176 | CD | GLN B | 112 | −1.239 | −13.417 | −27.916 | 1.00 | 59.79 | C |
| ATOM | 177 | OE1 | GLN B | 112 | −2.089 | −14.178 | −27.454 | 1.00 | 63.95 | O |
| ATOM | 178 | NE2 | GLN B | 112 | −1.315 | −12.913 | −29.150 | 1.00 | 55.55 | N |
| ATOM | 179 | C | GLN B | 112 | −2.623 | −11.407 | −25.489 | 1.00 | 51.49 | C |
| ATOM | 180 | O | GLN B | 112 | −3.271 | −11.432 | −26.523 | 1.00 | 50.90 | O |
| ATOM | 181 | N | ASP B | 113 | −3.188 | −11.426 | −24.287 | 1.00 | 51.62 | N |
| ATOM | 182 | CA | ASP B | 113 | −4.644 | −11.440 | −24.128 | 1.00 | 52.40 | C |
| ATOM | 183 | CB | ASP B | 113 | −5.048 | −11.793 | −22.696 | 1.00 | 52.26 | C |
| ATOM | 184 | CG | ASP B | 113 | −5.490 | −13.243 | −22.560 | 1.00 | 58.12 | C |
| ATOM | 185 | OD1 | ASP B | 113 | −6.714 | −13.465 | −22.417 | 1.00 | 59.09 | O |
| ATOM | 186 | OD2 | ASP B | 113 | −4.629 | −14.156 | −22.620 | 1.00 | 55.92 | O |
| ATOM | 187 | C | ASP B | 113 | −5.312 | −10.142 | −24.575 | 1.00 | 52.71 | C |
| ATOM | 188 | O | ASP B | 113 | −6.413 | −10.179 | −25.122 | 1.00 | 53.51 | O |
| ATOM | 189 | N | VAL B | 114 | −4.642 | −9.009 | −24.339 | 1.00 | 51.63 | N |
| ATOM | 190 | CA | VAL B | 114 | −5.073 | −7.710 | −24.862 | 1.00 | 50.63 | C |
| ATOM | 191 | CB | VAL B | 114 | −4.150 | −6.541 | −24.379 | 1.00 | 51.26 | C |
| ATOM | 192 | CG1 | VAL B | 114 | −4.645 | −5.185 | −24.920 | 1.00 | 50.52 | C |
| ATOM | 193 | CG2 | VAL B | 114 | −4.043 | −6.501 | −22.863 | 1.00 | 47.72 | C |
| ATOM | 194 | C | VAL B | 114 | −5.045 | −7.750 | −26.385 | 1.00 | 49.87 | C |
| ATOM | 195 | O | VAL B | 114 | −5.982 | −7.306 | −27.046 | 1.00 | 49.68 | O |
| ATOM | 196 | N | MET B | 115 | −3.955 | −8.291 | −26.919 | 1.00 | 50.12 | N |
| ATOM | 197 | CA | MET B | 115 | −3.728 | −8.413 | −28.358 | 1.00 | 50.61 | C |
| | | | | gad65.pdb | | | | | | |
| ATOM | 198 | CB | MET B | 115 | −2.326 | −8.991 | −28.596 | 1.00 | 50.49 | C |
| ATOM | 199 | CG | MET B | 115 | −1.901 | −9.205 | −30.050 | 1.00 | 53.86 | C |
| ATOM | 200 | SD | MET B | 115 | −2.174 | −7.826 | −31.190 | 1.00 | 56.94 | S |
| ATOM | 201 | CE | MET B | 115 | −1.671 | −6.384 | −30.242 | 1.00 | 65.08 | C |
| ATOM | 202 | C | MET B | 115 | −4.820 | −9.239 | −29.063 | 1.00 | 50.38 | C |
| ATOM | 203 | O | MET B | 115 | −5.302 | −8.854 | −30.140 | 1.00 | 50.06 | O |

TABLE A-continued

| | | | | | | | | | |
|---|---|---|---|---|---|---|---|---|---|
| ATOM | 204 | N | ASN B | 116 | −5.204 | −10.355 | −28.444 | 1.00 | 50.15 | N |
| ATOM | 205 | CA | ASN B | 116 | −6.322 | −11.181 | −28.912 | 1.00 | 50.01 | C |
| ATOM | 206 | CB | ASN B | 116 | −6.493 | −12.427 | −28.027 | 1.00 | 50.52 | C |
| ATOM | 207 | CG | ASN B | 116 | −5.327 | −13.418 | −28.159 | 1.00 | 52.80 | C |
| ATOM | 208 | OD1 | ASN B | 116 | −5.172 | −14.328 | −27.337 | 1.00 | 52.87 | O |
| ATOM | 209 | ND2 | ASN B | 116 | −4.514 | −13.250 | −29.201 | 1.00 | 52.90 | N |
| ATOM | 210 | C | ASN B | 116 | −7.626 | −10.389 | −28.997 | 1.00 | 49.59 | C |
| ATOM | 211 | O | ASN B | 116 | −8.337 | −10.468 | −29.998 | 1.00 | 49.95 | O |
| ATOM | 212 | N | ILE B | 117 | −7.923 | −9.604 | −27.962 | 1.00 | 49.67 | N |
| ATOM | 213 | CA | ILE B | 117 | −9.058 | −8.668 | −27.994 | 1.00 | 49.33 | C |
| ATOM | 214 | CB | ILE B | 117 | −9.215 | −7.912 | −26.646 | 1.00 | 49.93 | C |
| ATOM | 215 | CG1 | ILE B | 117 | −9.506 | −8.900 | −25.511 | 1.00 | 49.97 | C |
| ATOM | 216 | CD | ILE B | 117 | −9.273 | −8.342 | −24.111 | 1.00 | 49.91 | C |
| ATOM | 217 | CG2 | ILE B | 117 | −10.326 | −6.859 | −26.718 | 1.00 | 42.88 | C |
| ATOM | 218 | C | ILE B | 117 | −8.940 | −7.690 | −29.168 | 1.00 | 49.22 | C |
| ATOM | 219 | O | ILE B | 117 | −9.912 | −7.492 | −29.902 | 1.00 | 49.47 | O |
| ATOM | 220 | N | LEU B | 118 | −7.745 | −7.111 | −29.362 | 1.00 | 48.89 | N |
| ATOM | 221 | CA | LEU B | 118 | −7.493 | −6.136 | −30.436 | 1.00 | 47.14 | C |
| ATOM | 222 | CB | LEU B | 118 | −6.108 | −5.496 | −30.294 | 1.00 | 47.35 | C |
| ATOM | 223 | CG | LEU B | 118 | −5.728 | −4.756 | −29.004 | 1.00 | 44.65 | C |
| ATOM | 224 | CD1 | LEU B | 118 | −4.355 | −4.137 | −29.151 | 1.00 | 41.58 | C |
| ATOM | 225 | CD2 | LEU B | 118 | −6.743 | −3.697 | −28.648 | 1.00 | 45.39 | C |
| ATOM | 226 | C | LEU B | 118 | −7.654 | −6.730 | −31.843 | 1.00 | 46.88 | C |
| ATOM | 227 | O | LEU B | 118 | −8.259 | −6.108 | −32.731 | 1.00 | 46.40 | O |
| ATOM | 228 | N | LEU B | 119 | −7.120 | −7.934 | −32.021 | 1.00 | 46.77 | N |
| ATOM | 229 | CA | LEU B | 119 | −7.220 | −8.690 | −33.274 | 1.00 | 47.36 | C |
| ATOM | 230 | CB | LEU B | 119 | −6.410 | −9.989 | −33.158 | 1.00 | 47.03 | C |
| ATOM | 231 | CG | LEU B | 119 | −5.018 | −10.212 | −33.792 | 1.00 | 49.12 | C |
| ATOM | 232 | CD1 | LEU B | 119 | −4.180 | −8.963 | −34.008 | 1.00 | 52.27 | C |
| ATOM | 233 | CD2 | LEU B | 119 | −4.238 | −11.225 | −32.986 | 1.00 | 48.05 | C |
| ATOM | 234 | C | LEU B | 119 | −8.677 | −9.007 | −33.647 | 1.00 | 47.33 | C |
| ATOM | 235 | O | LEU B | 119 | −9.081 | −8.842 | −34.800 | 1.00 | 46.89 | O |
| ATOM | 236 | N | GLN B | 120 | −9.452 | −9.459 | −32.665 | 1.00 | 47.42 | N |
| ATOM | 237 | CA | GLN B | 120 | −10.858 | −9.771 | −32.865 | 1.00 | 48.69 | C |
| ATOM | 238 | CB | GLN B | 120 | −11.471 | −10.382 | −31.591 | 1.00 | 49.88 | C |
| ATOM | 239 | CG | GLN B | 120 | −12.997 | −10.537 | −31.625 | 1.00 | 55.78 | C |
| ATOM | 240 | CD | GLN B | 120 | −13.505 | −11.562 | −30.625 | 1.00 | 63.85 | C |
| ATOM | 241 | C | GLN B | 120 | −11.627 | −8.533 | −33.308 | 1.00 | 48.35 | C |
| ATOM | 242 | O | GLN B | 120 | −12.448 | −8.600 | −34.232 | 1.00 | 47.84 | O |
| ATOM | 243 | N | TYR B | 121 | −11.359 | −7.405 | −32.650 | 1.00 | 47.91 | N |
| ATOM | 244 | CA | TYR B | 121 | −12.013 | −6.137 | −32.995 | 1.00 | 46.91 | C |
| ATOM | 245 | CB | TYR B | 121 | −11.686 | −5.066 | −31.951 | 1.00 | 46.03 | C |
| ATOM | 246 | CG | TYR B | 121 | −12.042 | −3.637 | −32.335 | 1.00 | 45.69 | C |
| ATOM | 247 | CD1 | TYR B | 121 | −13.199 | −3.033 | −31.849 | 1.00 | 45.79 | C |
| ATOM | 248 | CE1 | TYR B | 121 | −13.519 | −1.716 | −32.178 | 1.00 | 43.23 | C |
| ATOM | 249 | CZ | TYR B | 121 | −12.679 | −0.996 | −33.003 | 1.00 | 46.44 | C |
| ATOM | 250 | OH | TYR B | 121 | −12.997 | 0.301 | −33.334 | 1.00 | 46.31 | O |
| ATOM | 251 | CE2 | TYR B | 121 | −11.510 | −1.565 | −33.488 | 1.00 | 48.60 | C |
| ATOM | 252 | CD2 | TYR B | 121 | −11.196 | −2.874 | −33.149 | 1.00 | 48.21 | C |
| ATOM | 253 | C | TYR B | 121 | −11.603 | −5.692 | −34.408 | 1.00 | 47.29 | C |
| ATOM | 254 | O | TYR B | 121 | −12.426 | −5.136 | −35.159 | 1.00 | 46.40 | O |
| ATOM | 255 | N | VAL B | 122 | −10.343 | −5.964 | −34.764 | 1.00 | 47.86 | N |
| ATOM | 256 | CA | VAL B | 122 | −9.807 | −5.603 | −36.077 | 1.00 | 48.97 | C |
| ATOM | 257 | CB | VAL B | 122 | −8.263 | −5.842 | −36.193 | 1.00 | 49.86 | C |
| ATOM | 258 | CG1 | VAL B | 122 | −7.816 | −5.954 | −37.664 | 1.00 | 47.68 | C |
| ATOM | 259 | CG2 | VAL B | 122 | −7.481 | −4.732 | −35.467 | 1.00 | 46.70 | C |
| ATOM | 260 | C | VAL B | 122 | −10.571 | −6.345 | −37.156 | 1.00 | 49.90 | C |
| ATOM | 261 | O | VAL B | 122 | −11.132 | −5.721 | −38.054 | 1.00 | 50.69 | O |
| ATOM | 262 | N | VAL B | 123 | −10.639 | −7.670 | −37.051 | 1.00 | 51.34 | N |
| ATOM | 263 | CA | VAL B | 123 | −11.339 | −8.452 | −38.080 | 1.00 | 51.95 | C |
| ATOM | 264 | CB | VAL B | 123 | −11.105 | −9.994 | −37.960 | 1.00 | 52.24 | C |
| ATOM | 265 | CG1 | VAL B | 123 | −9.609 | −10.316 | −37.889 | 1.00 | 51.12 | C |
| | | | | | gad65.pdb | | | | | |
| ATOM | 266 | CG2 | VAL B | 123 | −11.846 | −10.606 | −36.771 | 1.00 | 57.68 | C |
| ATOM | 267 | C | VAL B | 123 | −12.825 | −8.066 | −38.197 | 1.00 | 52.22 | C |
| ATOM | 268 | O | VAL B | 123 | −13.347 | −7.946 | −39.305 | 1.00 | 51.97 | O |
| ATOM | 269 | N | LYS B | 124 | −13.475 | −7.812 | −37.058 | 1.00 | 52.78 | N |
| ATOM | 270 | CA | LYS B | 124 | −14.896 | −7.437 | −37.046 | 1.00 | 53.26 | C |
| ATOM | 271 | CB | LYS B | 124 | −15.455 | −7.413 | −35.620 | 1.00 | 53.41 | C |
| ATOM | 272 | CG | LYS B | 124 | −15.803 | −8.790 | −35.060 | 1.00 | 56.24 | C |
| ATOM | 273 | C | LYS B | 124 | −15.147 | −6.099 | −37.727 | 1.00 | 53.69 | C |
| ATOM | 274 | O | LYS B | 124 | −16.188 | −5.913 | −38.364 | 1.00 | 54.24 | O |
| ATOM | 275 | N | SER B | 125 | −14.190 | −5.179 | −37.579 | 1.00 | 53.93 | N |
| ATOM | 276 | CA | SER B | 125 | −14.213 | −3.854 | −38.203 | 1.00 | 53.44 | C |
| ATOM | 277 | CB | SER B | 125 | −12.916 | −3.085 | −37.903 | 1.00 | 53.85 | C |
| ATOM | 278 | OG | SER B | 125 | −12.877 | −2.596 | −36.577 | 1.00 | 53.11 | O |
| ATOM | 279 | C | SER B | 125 | −14.395 | −3.931 | −39.709 | 1.00 | 53.00 | C |
| ATOM | 280 | O | SER B | 125 | −14.980 | −3.041 | −40.311 | 1.00 | 54.27 | O |
| ATOM | 281 | N | PHE B | 126 | −13.898 | −5.004 | −40.307 | 1.00 | 53.09 | N |
| ATOM | 282 | CA | PHE B | 126 | −14.011 | −5.213 | −41.748 | 1.00 | 53.04 | C |

TABLE A-continued

| | | | | | | | | | |
|---|---|---|---|---|---|---|---|---|---|
| ATOM | 283 | CB | PHE B | 126 | −12.721 | −5.849 | −42.282 | 1.00 | 52.73 | C |
| ATOM | 284 | CG | PHE B | 126 | −11.517 | −4.988 | −42.076 | 1.00 | 51.48 | C |
| ATOM | 285 | CD1 | PHE B | 126 | −11.242 | −3.943 | −42.944 | 1.00 | 50.44 | C |
| ATOM | 286 | CE1 | PHE B | 126 | −10.132 | −3.126 | −42.743 | 1.00 | 58.51 | C |
| ATOM | 287 | CZ | PHE B | 126 | −9.290 | −3.348 | −41.663 | 1.00 | 54.50 | C |
| ATOM | 288 | CE2 | PHE B | 126 | −9.559 | −4.394 | −40.784 | 1.00 | 55.81 | C |
| ATOM | 289 | CD2 | PHE B | 126 | −10.671 | −5.200 | −40.992 | 1.00 | 54.33 | C |
| ATOM | 290 | C | PHE B | 126 | −15.255 | −6.017 | −42.150 | 1.00 | 51.97 | C |
| ATOM | 291 | O | PHE B | 126 | −15.610 | −6.075 | −43.329 | 1.00 | 51.14 | O |
| ATOM | 292 | N | ASP B | 127 | −15.908 | −6.615 | −41.157 | 1.00 | 51.74 | N |
| ATOM | 293 | CA | ASP B | 127 | −17.126 | −7.394 | −41.358 | 1.00 | 51.52 | C |
| ATOM | 294 | CB | ASP B | 127 | −17.347 | −8.334 | −40.167 | 1.00 | 50.67 | C |
| ATOM | 295 | CG | ASP B | 127 | −18.303 | −9.485 | −40.476 | 1.00 | 49.07 | C |
| ATOM | 296 | OD1 | ASP B | 127 | −19.339 | −9.267 | −41.140 | 1.00 | 48.31 | O |
| ATOM | 297 | OD2 | ASP B | 127 | −18.011 | −10.616 | −40.034 | 1.00 | 46.86 | O |
| ATOM | 298 | C | ASP B | 127 | −18.307 | −6.445 | −41.518 | 1.00 | 52.27 | C |
| ATOM | 299 | O | ASP B | 127 | −18.612 | −5.669 | −40.613 | 1.00 | 52.83 | O |
| ATOM | 300 | N | ARG B | 128 | −18.964 | −6.502 | −42.673 | 1.00 | 52.96 | N |
| ATOM | 301 | CA | ARG B | 128 | −20.107 | −5.623 | −42.961 | 1.00 | 52.70 | C |
| ATOM | 302 | CB | ARG B | 128 | −20.424 | −5.600 | −44.463 | 1.00 | 52.75 | C |
| ATOM | 303 | CG | ARG B | 128 | −19.596 | −4.570 | −45.227 | 1.00 | 52.02 | C |
| ATOM | 304 | CD | ARG B | 128 | −19.821 | −4.642 | −46.727 | 1.00 | 51.47 | C |
| ATOM | 305 | NE | ARG B | 128 | −18.820 | −3.861 | −47.457 | 1.00 | 41.70 | N |
| ATOM | 306 | CZ | ARG B | 128 | −17.599 | −4.303 | −47.770 | 1.00 | 46.63 | C |
| ATOM | 307 | NH1 | ARG B | 128 | −17.210 | −5.529 | −47.418 | 1.00 | 40.19 | N |
| ATOM | 308 | NH2 | ARG B | 128 | −16.753 | −3.512 | −48.423 | 1.00 | 43.16 | N |
| ATOM | 309 | C | ARG B | 128 | −21.370 | −5.921 | −42.140 | 1.00 | 53.02 | C |
| ATOM | 310 | O | ARG B | 128 | −22.288 | −5.102 | −42.103 | 1.00 | 54.10 | O |
| ATOM | 311 | N | SER B | 129 | −21.416 | −7.072 | −41.473 | 1.00 | 52.39 | N |
| ATOM | 312 | CA | SER B | 129 | −22.525 | −7.350 | −40.566 | 1.00 | 52.87 | C |
| ATOM | 313 | CB | SER B | 129 | −22.737 | −8.854 | −40.391 | 1.00 | 52.29 | C |
| ATOM | 314 | OG | SER B | 129 | −22.004 | −9.347 | −39.289 | 1.00 | 56.61 | O |
| ATOM | 315 | C | SER B | 129 | −22.366 | −6.643 | −39.207 | 1.00 | 53.52 | C |
| ATOM | 316 | O | SER B | 129 | −23.344 | −6.521 | −38.465 | 1.00 | 54.56 | O |
| ATOM | 317 | N | THR B | 130 | −21.139 | −6.201 | −38.892 | 1.00 | 52.55 | N |
| ATOM | 318 | CA | THR B | 130 | −20.835 | −5.404 | −37.696 | 1.00 | 51.56 | C |
| ATOM | 319 | CB | THR B | 130 | −19.280 | −5.270 | −37.480 | 1.00 | 52.80 | C |
| ATOM | 320 | OG1 | THR B | 130 | −18.652 | −6.558 | −37.561 | 1.00 | 53.61 | O |
| ATOM | 321 | CG2 | THR B | 130 | −18.916 | −4.634 | −36.125 | 1.00 | 51.47 | C |
| ATOM | 322 | C | THR B | 130 | −21.460 | −3.999 | −37.783 | 1.00 | 50.79 | C |
| ATOM | 323 | O | THR B | 130 | −21.459 | −3.358 | −38.839 | 1.00 | 50.44 | O |
| ATOM | 324 | N | LYS B | 131 | −22.004 | −3.526 | −36.668 | 1.00 | 50.48 | N |
| ATOM | 325 | CA | LYS B | 131 | −22.500 | −2.152 | −36.564 | 1.00 | 50.96 | C |
| ATOM | 326 | CB | LYS B | 131 | −23.368 | −2.006 | −35.303 | 1.00 | 51.36 | C |
| ATOM | 327 | CG | LYS B | 131 | −24.877 | −2.132 | −35.514 | 1.00 | 56.47 | C |
| ATOM | 328 | CD | LYS B | 131 | −25.273 | −3.229 | −36.489 | 1.00 | 61.85 | C |
| ATOM | 329 | CE | LYS B | 131 | −26.599 | −2.881 | −37.166 | 1.00 | 67.56 | C |
| ATOM | 330 | NZ | LYS B | 131 | −26.852 | −3.699 | −38.385 | 1.00 | 73.08 | N |
| ATOM | 331 | C | LYS B | 131 | −21.334 | −1.168 | −36.516 | 1.00 | 50.54 | C |
| ATOM | 332 | O | LYS B | 131 | −20.341 | −1.426 | −35.821 | 1.00 | 50.92 | O |
| ATOM | 333 | N | VAL B | 132 | −21.456 | −0.062 | −37.258 | 1.00 | 49.36 | N | gad65.pdb

| | | | | | | | | | |
|---|---|---|---|---|---|---|---|---|---|
| ATOM | 334 | CA | VAL B | 132 | −20.479 | 1.042 | −37.259 | 1.00 | 48.59 | C |
| ATOM | 335 | CB | VAL B | 132 | −20.849 | 2.147 | −38.304 | 1.00 | 48.27 | C |
| ATOM | 336 | CG1 | VAL B | 132 | −19.917 | 3.328 | −38.215 | 1.00 | 46.46 | C |
| ATOM | 337 | CG2 | VAL B | 132 | −20.868 | 1.613 | −39.732 | 1.00 | 49.08 | C |
| ATOM | 338 | C | VAL B | 132 | −20.421 | 1.684 | −35.872 | 1.00 | 48.26 | C |
| ATOM | 339 | O | VAL B | 132 | −19.348 | 2.062 | −35.387 | 1.00 | 48.14 | O |
| ATOM | 340 | N | ILE B | 133 | −21.593 | 1.802 | −35.250 | 1.00 | 46.98 | N |
| ATOM | 341 | CA | ILE B | 133 | −21.750 | 2.387 | −33.928 | 1.00 | 46.31 | C |
| ATOM | 342 | CB | ILE B | 133 | −22.055 | 3.928 | −34.001 | 1.00 | 45.91 | C |
| ATOM | 343 | CG1 | ILE B | 133 | −22.282 | 4.508 | −32.592 | 1.00 | 44.01 | C |
| ATOM | 344 | CD | ILE B | 133 | −22.611 | 5.990 | −32.542 | 1.00 | 46.37 | C |
| ATOM | 345 | CG2 | ILE B | 133 | −23.242 | 4.231 | −34.950 | 1.00 | 44.24 | C |
| ATOM | 346 | C | ILE B | 133 | −22.858 | 1.672 | −33.149 | 1.00 | 47.81 | C |
| ATOM | 347 | O | ILE B | 133 | −23.940 | 1.413 | −33.692 | 1.00 | 48.70 | O |
| ATOM | 348 | N | ASP B | 134 | −22.568 | 1.350 | −31.886 | 1.00 | 48.49 | N |
| ATOM | 349 | CA | ASP B | 134 | −23.573 | 0.972 | −30.886 | 1.00 | 48.73 | C |
| ATOM | 350 | CB | ASP B | 134 | −23.018 | −0.135 | −29.970 | 1.00 | 48.78 | C |
| ATOM | 351 | CG | ASP B | 134 | −24.074 | −0.704 | −29.005 | 1.00 | 52.34 | C |
| ATOM | 352 | OD1 | ASP B | 134 | −25.268 | −0.327 | −29.108 | 1.00 | 57.62 | O |
| ATOM | 353 | OD2 | ASP B | 134 | −23.703 | −1.523 | −28.133 | 1.00 | 49.14 | O |
| ATOM | 354 | C | ASP B | 134 | −23.943 | 2.222 | −30.073 | 1.00 | 48.52 | C |
| ATOM | 355 | O | ASP B | 134 | −23.341 | 2.496 | −29.045 | 1.00 | 47.91 | O |
| ATOM | 356 | N | PHE B | 135 | −24.943 | 2.967 | −30.534 | 1.00 | 50.02 | N |
| ATOM | 357 | CA | PHE B | 135 | −25.205 | 4.315 | −30.018 | 1.00 | 50.71 | C |
| ATOM | 358 | CB | PHE B | 135 | −25.963 | 5.164 | −31.043 | 1.00 | 51.72 | C |
| ATOM | 359 | CG | PHE B | 135 | −26.326 | 6.531 | −30.537 | 1.00 | 53.21 | C |
| ATOM | 360 | CD1 | PHE B | 135 | −25.339 | 7.485 | −30.301 | 1.00 | 51.57 | C |
| ATOM | 361 | CE1 | PHE B | 135 | −25.666 | 8.747 | −29.823 | 1.00 | 54.13 | C |

TABLE A-continued

| ATOM | 362 | CZ  | PHE B | 135 | −26.991 | 9.064  | −29.572 | 1.00 | 57.62 | C |
| ---- | --- | --- | ----- | --- | ------- | ------ | ------- | ---- | ----- | - |
| ATOM | 363 | CE2 | PHE B | 135 | −27.990 | 8.117  | −29.797 | 1.00 | 58.01 | C |
| ATOM | 364 | CD2 | PHE B | 135 | −27.653 | 6.858  | −30.279 | 1.00 | 56.18 | C |
| ATOM | 365 | C   | PHE B | 135 | −25.910 | 4.404  | −28.667 | 1.00 | 51.22 | C |
| ATOM | 366 | O   | PHE B | 135 | −26.960 | 3.799  | −28.451 | 1.00 | 51.27 | O |
| ATOM | 367 | N   | HIS B | 136 | −25.331 | 5.211  | −27.780 | 1.00 | 51.05 | N |
| ATOM | 368 | CA  | HIS B | 136 | −25.886 | 5.463  | −26.458 | 1.00 | 50.75 | C |
| ATOM | 369 | CB  | HIS B | 136 | −25.106 | 4.684  | −25.393 | 1.00 | 51.32 | C |
| ATOM | 370 | CG  | HIS B | 136 | −25.156 | 3.199  | −25.565 | 1.00 | 50.89 | C |
| ATOM | 371 | ND1 | HIS B | 136 | −26.095 | 2.408  | −24.938 | 1.00 | 55.39 | N |
| ATOM | 372 | CE1 | HIS B | 136 | −25.892 | 1.143  | −25.266 | 1.00 | 54.66 | C |
| ATOM | 373 | NE2 | HIS B | 136 | −24.853 | 1.088  | −26.083 | 1.00 | 52.16 | N |
| ATOM | 374 | CD2 | HIS B | 136 | −24.375 | 2.358  | −26.283 | 1.00 | 47.79 | C |
| ATOM | 375 | C   | HIS B | 136 | −25.778 | 6.939  | −26.149 | 1.00 | 50.01 | C |
| ATOM | 376 | O   | HIS B | 136 | −24.789 | 7.582  | −26.507 | 1.00 | 50.18 | O |
| ATOM | 377 | N   | TYR B | 137 | −26.792 | 7.478  | −25.486 | 1.00 | 49.62 | N |
| ATOM | 378 | CA  | TYR B | 137 | −26.704 | 8.821  | −24.942 | 1.00 | 50.08 | C |
| ATOM | 379 | CB  | TYR B | 137 | −28.073 | 9.299  | −24.450 | 1.00 | 51.67 | C |
| ATOM | 380 | CG  | TYR B | 137 | −29.100 | 9.438  | −25.562 | 1.00 | 58.44 | C |
| ATOM | 381 | CD1 | TYR B | 137 | −29.112 | 10.557 | −26.402 | 1.00 | 60.37 | C |
| ATOM | 382 | CE1 | TYR B | 137 | −30.054 | 10.673 | −27.432 | 1.00 | 63.93 | C |
| ATOM | 383 | CZ  | TYR B | 137 | −30.994 | 9.659  | −27.617 | 1.00 | 63.07 | C |
| ATOM | 384 | OH  | TYR B | 137 | −31.939 | 9.746  | −28.621 | 1.00 | 62.42 | O |
| ATOM | 385 | CE2 | TYR B | 137 | −30.994 | 8.544  | −26.794 | 1.00 | 63.98 | C |
| ATOM | 386 | CD2 | TYR B | 137 | −30.051 | 8.439  | −25.778 | 1.00 | 61.89 | C |
| ATOM | 387 | C   | TYR B | 137 | −25.677 | 8.819  | −23.807 | 1.00 | 48.38 | C |
| ATOM | 388 | O   | TYR B | 137 | −25.506 | 7.795  | −23.138 | 1.00 | 48.14 | O |
| ATOM | 389 | N   | PRO B | 138 | −24.980 | 9.954  | −23.599 | 1.00 | 47.38 | N |
| ATOM | 390 | CA  | PRO B | 138 | −23.952 | 10.054 | −22.550 | 1.00 | 47.84 | C |
| ATOM | 391 | CB  | PRO B | 138 | −23.679 | 11.563 | −22.467 | 1.00 | 47.30 | C |
| ATOM | 392 | CG  | PRO B | 138 | −23.926 | 12.044 | −23.860 | 1.00 | 45.91 | C |
| ATOM | 393 | CD  | PRO B | 138 | −25.099 | 11.211 | −24.364 | 1.00 | 47.12 | C |
| ATOM | 394 | C   | PRO B | 138 | −24.392 | 9.483  | −21.202 | 1.00 | 48.43 | C |
| ATOM | 395 | O   | PRO B | 138 | −23.655 | 8.681  | −20.619 | 1.00 | 50.08 | O |
| ATOM | 396 | N   | ASN B | 139 | −25.580 | 9.870  | −20.734 | 1.00 | 48.08 | N |
| ATOM | 397 | CA  | ASN B | 139 | −26.152 | 9.343  | −19.487 | 1.00 | 49.00 | C |
| ATOM | 398 | CB  | ASN B | 139 | −27.450 | 10.073 | −19.129 | 1.00 | 48.79 | C |
| ATOM | 399 | C   | ASN B | 139 | −26.385 | 7.826  | −19.501 | 1.00 | 50.11 | C |
| ATOM | 400 | O   | ASN B | 139 | −26.136 | 7.147  | −18.498 | 1.00 | 49.99 | O |
| ATOM | 401 | N   | GLU B | 140 | −26.869 | 7.300  | −20.629 | 1.00 | 51.20 | N |
| ATOM | 402 | CA  | GLU B | 140 | −27.002 | 5.847  | −20.810 | 1.00 | 51.63 | C |
| ATOM | 403 | CB  | GLU B | 140 | −27.618 | 5.510  | −22.167 | 1.00 | 52.03 | C |
| ATOM | 404 | CG  | GLU B | 140 | −29.116 | 5.290  | −22.153 | 1.00 | 60.52 | C |
| ATOM | 405 | CD  | GLU B | 140 | −29.775 | 5.649  | −23.485 | 1.00 | 67.84 | C |
| ATOM | 406 | OE1 | GLU B | 140 | −29.160 | 5.406  | −24.555 | 1.00 | 65.23 | O |
| ATOM | 407 | OE2 | GLU B | 140 | −30.914 | 6.177  | −23.451 | 1.00 | 68.05 | O |
| ATOM | 408 | C   | GLU B | 140 | −25.657 | 5.162  | −20.701 | 1.00 | 51.06 | C |
| ATOM | 409 | O   | GLU B | 140 | −25.548 | 4.118  | −20.079 | 1.00 | 50.79 | O |
| ATOM | 410 | N   | LEU B | 141 | −24.633 | 5.750  | −21.319 | 1.00 | 51.88 | N |
| ATOM | 411 | CA  | LEU B | 141 | −23.307 | 5.133  | −21.321 | 1.00 | 51.92 | C |
| ATOM | 412 | CB  | LEU B | 141 | −22.386 | 5.785  | −22.368 | 1.00 | 51.69 | C |
| ATOM | 413 | CG  | LEU B | 141 | −21.300 | 4.927  | −23.047 | 1.00 | 52.28 | C |
| ATOM | 414 | CD1 | LEU B | 141 | −20.028 | 4.891  | −22.241 | 1.00 | 60.27 | C |
| ATOM | 415 | CD2 | LEU B | 141 | −21.763 | 3.488  | −23.337 | 1.00 | 54.83 | C |
| ATOM | 416 | C   | LEU B | 141 | −22.711 | 5.164  | −19.910 | 1.00 | 51.87 | C |
| ATOM | 417 | O   | LEU B | 141 | −22.145 | 4.176  | −19.457 | 1.00 | 50.42 | O |
| ATOM | 418 | N   | LEU B | 142 | −22.882 | 6.290  | −19.216 | 1.00 | 54.14 | N |
| ATOM | 419 | CA  | LEU B | 142 | −22.487 | 6.422  | −17.810 | 1.00 | 56.40 | C |
| ATOM | 420 | CB  | LEU B | 142 | −22.755 | 7.839  | −17.299 | 1.00 | 56.70 | C |
| ATOM | 421 | CG  | LEU B | 142 | −21.707 | 8.897  | −17.671 | 1.00 | 60.10 | C |
| ATOM | 422 | CD1 | LEU B | 142 | −22.257 | 10.303 | −17.437 | 1.00 | 64.88 | C |
| ATOM | 423 | CD2 | LEU B | 142 | −20.394 | 8.700  | −16.911 | 1.00 | 56.52 | C |
| ATOM | 424 | C   | LEU B | 142 | −23.158 | 5.403  | −16.892 | 1.00 | 57.84 | C |
| ATOM | 425 | O   | LEU B | 142 | −22.504 | 4.815  | −16.034 | 1.00 | 58.47 | O |
| ATOM | 426 | N   | GLN B | 143 | −24.457 | 5.192  | −17.079 | 1.00 | 59.13 | N |
| ATOM | 427 | CA  | GLN B | 143 | −25.210 | 4.237  | −16.265 | 1.00 | 60.85 | C |
| ATOM | 428 | CB  | GLN B | 143 | −26.714 | 4.553  | −16.318 | 1.00 | 61.08 | C |
| ATOM | 429 | CG  | GLN B | 143 | −27.105 | 5.855  | −15.603 | 1.00 | 64.21 | C |
| ATOM | 430 | CD  | GLN B | 143 | −28.600 | 6.181  | −15.681 | 1.00 | 62.64 | C |
| ATOM | 431 | OE1 | GLN B | 143 | −28.993 | 7.162  | −16.316 | 1.00 | 69.59 | O |
| ATOM | 432 | NE2 | GLN B | 143 | −29.433 | 5.369  | −15.020 | 1.00 | 63.91 | N |
| ATOM | 433 | C   | GLN B | 143 | −24.954 | 2.782  | −16.675 | 1.00 | 60.46 | C |
| ATOM | 434 | O   | GLN B | 143 | −25.137 | 1.866  | −15.877 | 1.00 | 60.48 | O |
| ATOM | 435 | N   | GLU B | 144 | −24.526 | 2.578  | −17.919 | 1.00 | 60.33 | N |
| ATOM | 436 | CA  | GLU B | 144 | −24.369 | 1.238  | −18.486 | 1.00 | 60.73 | C |
| ATOM | 437 | CB  | GLU B | 144 | −24.178 | 1.337  | −20.007 | 1.00 | 61.48 | C |
| ATOM | 438 | CG  | GLU B | 144 | −24.246 | 0.017  | −20.760 | 1.00 | 66.12 | C |
| ATOM | 439 | CD  | GLU B | 144 | −25.658 | −0.515 | −20.881 | 1.00 | 71.57 | C |
| ATOM | 440 | OE1 | GLU B | 144 | −26.429 | 0.035  | −21.697 | 1.00 | 72.04 | O | gad65.pdb

TABLE A-continued

| | | | | | | | | | |
|---|---|---|---|---|---|---|---|---|---|
| ATOM | 441 | OE2 | GLU B | 144 | −25.993 | −1.486 | −20.160 | 1.00 | 75.21 | O |
| ATOM | 442 | C | GLU B | 144 | −23.190 | 0.494 | −17.871 | 1.00 | 60.24 | C |
| ATOM | 443 | O | GLU B | 144 | −23.174 | −0.738 | −17.811 | 1.00 | 59.90 | O |
| ATOM | 444 | N | TYR B | 145 | −22.200 | 1.260 | −17.420 | 1.00 | 60.09 | N |
| ATOM | 445 | CA | TYR B | 145 | −20.936 | 0.710 | −16.966 | 1.00 | 59.47 | C |
| ATOM | 446 | CB | TYR B | 145 | −19.998 | 0.538 | −18.166 | 1.00 | 59.86 | C |
| ATOM | 447 | CG | TYR B | 145 | −18.864 | −0.428 | −17.936 | 1.00 | 59.60 | C |
| ATOM | 448 | CD1 | TYR B | 145 | −19.109 | −1.796 | −17.791 | 1.00 | 60.53 | C |
| ATOM | 449 | CE1 | TYR B | 145 | −18.069 | −2.698 | −17.577 | 1.00 | 59.31 | C |
| ATOM | 450 | CZ | TYR B | 145 | −16.765 | −2.231 | −17.514 | 1.00 | 59.55 | C |
| ATOM | 451 | OH | TYR B | 145 | −15.739 | −3.130 | −17.307 | 1.00 | 62.73 | O |
| ATOM | 452 | CE2 | TYR B | 145 | −16.492 | −0.878 | −17.662 | 1.00 | 57.59 | C |
| ATOM | 453 | CD2 | TYR B | 145 | −17.543 | 0.018 | −17.876 | 1.00 | 57.95 | C |
| ATOM | 454 | C | TYR B | 145 | −20.325 | 1.668 | −15.961 | 1.00 | 58.66 | C |
| ATOM | 455 | O | TYR B | 145 | −20.487 | 2.880 | −16.083 | 1.00 | 58.63 | O |
| ATOM | 456 | N | ASN B | 146 | −19.635 | 1.131 | −14.962 | 1.00 | 57.83 | N |
| ATOM | 457 | CA | ASN B | 146 | −18.922 | 1.979 | −14.017 | 1.00 | 57.32 | C |
| ATOM | 458 | CB | ASN B | 146 | −18.709 | 1.261 | −12.690 | 1.00 | 57.53 | C |
| ATOM | 459 | CG | ASN B | 146 | −17.995 | 2.123 | −11.673 | 1.00 | 58.91 | C |
| ATOM | 460 | OD1 | ASN B | 146 | −18.318 | 3.300 | −11.502 | 1.00 | 57.20 | O |
| ATOM | 461 | ND2 | ASN B | 146 | −17.016 | 1.539 | −10.989 | 1.00 | 60.00 | N |
| ATOM | 462 | C | ASN B | 146 | −17.583 | 2.451 | −14.594 | 1.00 | 56.54 | C |
| ATOM | 463 | O | ASN B | 146 | −16.665 | 1.652 | −14.779 | 1.00 | 57.00 | O |
| ATOM | 464 | N | TRP B | 147 | −17.486 | 3.743 | −14.891 | 1.00 | 55.03 | N |
| ATOM | 465 | CA | TRP B | 147 | −16.265 | 4.317 | −15.450 | 1.00 | 54.72 | C |
| ATOM | 466 | CB | TRP B | 147 | −16.590 | 5.182 | −16.670 | 1.00 | 54.14 | C |
| ATOM | 467 | CG | TRP B | 147 | −17.384 | 4.502 | −17.775 | 1.00 | 54.41 | C |
| ATOM | 468 | CD1 | TRP B | 147 | −18.719 | 4.661 | −18.047 | 1.00 | 50.96 | C |
| ATOM | 469 | NE1 | TRP B | 147 | −19.072 | 3.906 | −19.144 | 1.00 | 52.73 | N |
| | | | | | gad65.pdb | | | | | |
| ATOM | 470 | CE2 | TRP B | 147 | −17.963 | 3.248 | −19.612 | 1.00 | 52.29 | C |
| ATOM | 471 | CD2 | TRP B | 147 | −16.876 | 3.598 | −18.776 | 1.00 | 52.72 | C |
| ATOM | 472 | CE3 | TRP B | 147 | −15.612 | 3.050 | −19.044 | 1.00 | 50.73 | C |
| ATOM | 473 | CZ3 | TRP B | 147 | −15.477 | 2.174 | −20.119 | 1.00 | 51.22 | C |
| ATOM | 474 | CH2 | TRP B | 147 | −16.578 | 1.845 | −20.928 | 1.00 | 51.94 | C |
| ATOM | 475 | CZ2 | TRP B | 147 | −17.824 | 2.373 | −20.695 | 1.00 | 50.97 | C |
| ATOM | 476 | C | TRP B | 147 | −15.478 | 5.146 | −14.412 | 1.00 | 54.51 | C |
| ATOM | 477 | O | TRP B | 147 | −14.432 | 5.742 | −14.731 | 1.00 | 54.34 | O |
| ATOM | 478 | N | GLU B | 148 | −15.985 | 5.173 | −13.181 | 1.00 | 53.71 | N |
| ATOM | 479 | CA | GLU B | 148 | −15.403 | 5.967 | −12.095 | 1.00 | 53.17 | C |
| ATOM | 480 | CB | GLU B | 148 | −16.363 | 6.037 | −10.902 | 1.00 | 54.07 | C |
| ATOM | 481 | CG | GLU B | 148 | −17.665 | 6.786 | −11.167 | 1.00 | 59.98 | C |
| ATOM | 482 | CD | GLU B | 148 | −17.533 | 8.289 | −10.999 | 1.00 | 67.81 | C |
| ATOM | 483 | OE1 | GLU B | 148 | −17.885 | 8.802 | −9.915 | 1.00 | 74.52 | O |
| ATOM | 484 | OE2 | GLU B | 148 | −17.081 | 8.963 | −11.945 | 1.00 | 71.57 | O |
| ATOM | 485 | C | GLU B | 148 | −14.050 | 5.425 | −11.640 | 1.00 | 50.98 | C |
| ATOM | 486 | O | GLU B | 148 | −13.721 | 4.261 | −11.875 | 1.00 | 50.18 | O |
| ATOM | 487 | N | LEU B | 149 | −13.272 | 6.288 | −10.994 | 1.00 | 50.01 | N |
| ATOM | 488 | CA | LEU B | 149 | −11.936 | 5.931 | −10.518 | 1.00 | 49.44 | C |
| ATOM | 489 | CB | LEU B | 149 | −10.923 | 7.019 | −10.898 | 1.00 | 48.67 | C |
| ATOM | 490 | CG | LEU B | 149 | −10.530 | 7.064 | −12.375 | 1.00 | 45.82 | C |
| ATOM | 491 | CD1 | LEU B | 149 | −9.757 | 8.326 | −12.678 | 1.00 | 43.58 | C |
| ATOM | 492 | CD2 | LEU B | 149 | −9.725 | 5.827 | −12.749 | 1.00 | 42.03 | C |
| ATOM | 493 | C | LEU B | 149 | −11.925 | 5.691 | −9.015 | 1.00 | 49.53 | C |
| ATOM | 494 | O | LEU B | 149 | −12.724 | 6.284 | −8.290 | 1.00 | 50.00 | O |
| ATOM | 495 | N | ALA B | 150 | −11.011 | 4.833 | −8.558 | 1.00 | 49.76 | N |
| ATOM | 496 | CA | ALA B | 150 | −10.977 | 4.388 | −7.156 | 1.00 | 50.02 | C |
| ATOM | 497 | CB | ALA B | 150 | −11.562 | 2.975 | −7.034 | 1.00 | 49.79 | C |
| ATOM | 498 | C | ALA B | 150 | −9.580 | 4.449 | −6.524 | 1.00 | 50.70 | C |
| ATOM | 499 | O | ALA B | 150 | −8.565 | 4.531 | −7.230 | 1.00 | 51.10 | O |
| ATOM | 500 | N | ASP B | 151 | −9.543 | 4.405 | −5.192 | 1.00 | 50.70 | N |
| ATOM | 501 | CA | ASP B | 151 | −8.288 | 4.446 | −4.431 | 1.00 | 50.97 | C |
| ATOM | 502 | CB | ASP B | 151 | −8.557 | 4.808 | −2.967 | 1.00 | 50.92 | C |
| ATOM | 503 | CG | ASP B | 151 | −9.084 | 6.225 | −2.803 | 1.00 | 54.08 | C |
| ATOM | 504 | C | ASP B | 151 | −7.510 | 3.130 | −4.505 | 1.00 | 50.77 | C |
| ATOM | 505 | O | ASP B | 151 | −6.274 | 3.128 | −4.591 | 1.00 | 50.86 | O |
| ATOM | 506 | N | GLN B | 152 | −8.240 | 2.017 | −4.478 | 1.00 | 49.80 | N |
| ATOM | 507 | CA | GLN B | 152 | −7.636 | 0.685 | −4.455 | 1.00 | 48.90 | C |
| ATOM | 508 | CB | GLN B | 152 | −8.425 | −0.241 | −3.515 | 1.00 | 48.86 | C |
| ATOM | 509 | C | GLN B | 152 | −7.552 | 0.093 | −5.861 | 1.00 | 48.04 | C |
| ATOM | 510 | O | GLN B | 152 | −8.386 | 0.419 | −6.708 | 1.00 | 46.79 | O |
| ATOM | 511 | N | PRO B | 153 | −6.550 | −0.777 | −6.114 | 1.00 | 48.41 | N |
| ATOM | 512 | CA | PRO B | 153 | −6.361 | −1.352 | −7.450 | 1.00 | 49.19 | C |
| ATOM | 513 | CB | PRO B | 153 | −4.929 | −1.898 | −7.388 | 1.00 | 49.39 | C |
| ATOM | 514 | CG | PRO B | 153 | −4.721 | −2.254 | −5.969 | 1.00 | 45.75 | C |
| ATOM | 515 | CD | PRO B | 153 | −5.524 | −1.261 | −5.166 | 1.00 | 48.29 | C |
| ATOM | 516 | C | PRO B | 153 | −7.329 | −2.493 | −7.791 | 1.00 | 49.43 | C |
| ATOM | 517 | O | PRO B | 153 | −7.748 | −3.246 | −6.906 | 1.00 | 49.69 | O |
| ATOM | 518 | N | GLN B | 154 | −7.660 | −2.618 | −9.072 | 1.00 | 49.60 | N |
| ATOM | 519 | CA | GLN B | 154 | −8.478 | −3.723 | −9.570 | 1.00 | 50.25 | C |

TABLE A-continued

| | | | | | | | | | |
|---|---|---|---|---|---|---|---|---|---|
| ATOM | 520 | CB | GLN B | 154 | −9.463 | −3.217 | −10.625 | 1.00 | 50.40 | C |
| ATOM | 521 | CG | GLN B | 154 | −10.742 | −2.630 | −10.046 | 1.00 | 50.59 | C |
| ATOM | 522 | CD | GLN B | 154 | −11.688 | −2.130 | −11.114 | 1.00 | 51.03 | C |
| ATOM | 523 | OE1 | GLN B | 154 | −11.270 | −1.474 | −12.061 | 1.00 | 57.85 | O |
| ATOM | 524 | NE2 | GLN B | 154 | −12.974 | −2.437 | −10.967 | 1.00 | 50.14 | N |
| ATOM | 525 | C | GLN B | 154 | −7.594 | −4.808 | −10.161 | 1.00 | 50.14 | C |
| ATOM | 526 | O | GLN B | 154 | −6.504 | −4.520 | −10.650 | 1.00 | 50.95 | O |
| ATOM | 527 | N | ASN B | 155 | −8.056 | −6.055 | −10.120 | 1.00 | 50.15 | N |
| ATOM | 528 | CA | ASN B | 155 | −7.292 | −7.158 | −10.711 | 1.00 | 49.86 | C |
| ATOM | 529 | CB | ASN B | 155 | −7.707 | −8.538 | −10.146 | 1.00 | 50.06 | C |
| ATOM | 530 | CG | ASN B | 155 | −9.160 | −8.917 | −10.454 | 1.00 | 54.94 | C |
| ATOM | 531 | OD1 | ASN B | 155 | −9.912 | −9.306 | −9.552 | 1.00 | 56.99 | O |
| ATOM | 532 | ND2 | ASN B | 155 | −9.545 | −8.848 | −11.725 | 1.00 | 55.83 | N |
| ATOM | 533 | C | ASN B | 155 | −7.302 | −7.123 | −12.238 | 1.00 | 49.24 | C |
| ATOM | 534 | O | ASN B | 155 | −8.117 | −6.414 | −12.842 | 1.00 | 48.95 | O |
| ATOM | 535 | N | LEU B | 156 | −6.402 | −7.891 | −12.847 | 1.00 | 49.07 | N |
| ATOM | 536 | CA | LEU B | 156 | −6.179 | −7.842 | −14.289 | 1.00 | 49.05 | C |
| ATOM | 537 | CB | LEU B | 156 | −4.857 | −8.526 | −14.664 | 1.00 | 48.26 | C |
| ATOM | 538 | CG | LEU B | 156 | −3.547 | −7.858 | −14.202 | 1.00 | 44.91 | C |
| ATOM | 539 | CD1 | LEU B | 156 | −2.364 | −8.652 | −14.709 | 1.00 | 44.49 | C |
| ATOM | 540 | CD2 | LEU B | 156 | −3.419 | −6.402 | −14.622 | 1.00 | 40.41 | C |
| ATOM | 541 | C | LEU B | 156 | −7.344 | −8.370 | −15.134 | 1.00 | 50.33 | C |
| ATOM | 542 | O | LEU B | 156 | −7.485 | −7.983 | −16.297 | 1.00 | 50.90 | O |
| ATOM | 543 | N | GLU B | 157 | −8.173 | −9.239 | −14.551 | 1.00 | 50.77 | N |
| ATOM | 544 | CA | GLU B | 157 | −9.398 | −9.709 | −15.213 | 1.00 | 51.43 | C |
| ATOM | 545 | CB | GLU B | 157 | −10.063 | −10.837 | −14.397 | 1.00 | 52.59 | C |
| ATOM | 546 | CG | GLU B | 157 | −11.488 | −11.242 | −14.832 | 1.00 | 60.13 | C |
| ATOM | 547 | CD | GLU B | 157 | −11.559 | −11.807 | −16.254 | 1.00 | 67.88 | C |
| ATOM | 548 | OE1 | GLU B | 157 | −11.094 | −12.948 | −16.476 | 1.00 | 66.08 | O |
| ATOM | 549 | OE2 | GLU B | 157 | −12.095 | −11.109 | −17.147 | 1.00 | 71.96 | O |
| ATOM | 550 | C | GLU B | 157 | −10.346 | −8.540 | −15.444 | 1.00 | 50.19 | C |
| ATOM | 551 | O | GLU B | 157 | −10.907 | −8.397 | −16.528 | 1.00 | 49.74 | O |
| ATOM | 552 | N | GLU B | 158 | −10.495 | −7.697 | −14.424 | 1.00 | 50.86 | N |
| ATOM | 553 | CA | GLU B | 158 | −11.309 | −6.478 | −14.495 | 1.00 | 52.14 | C |
| ATOM | 554 | CB | GLU B | 158 | −11.476 | −5.877 | −13.095 | 1.00 | 52.37 | C |
| ATOM | 555 | CG | GLU B | 158 | −12.245 | −6.785 | −12.126 | 1.00 | 57.91 | C |
| ATOM | 556 | CD | GLU B | 158 | −12.144 | −6.358 | −10.660 | 1.00 | 55.63 | C |
| ATOM | 557 | OE1 | GLU B | 158 | −11.036 | −6.440 | −10.074 | 1.00 | 65.89 | O |
| ATOM | 558 | OE2 | GLU B | 158 | −13.190 | −5.973 | −10.081 | 1.00 | 63.04 | O |
| ATOM | 559 | C | GLU B | 158 | −10.735 | −5.437 | −15.465 | 1.00 | 51.21 | C |
| ATOM | 560 | O | GLU B | 158 | −11.477 | −4.625 | −16.033 | 1.00 | 51.46 | O |
| ATOM | 561 | N | ILE B | 159 | −9.415 | −5.476 | −15.657 | 1.00 | 49.77 | N |
| ATOM | 562 | CA | ILE B | 159 | −8.724 | −4.576 | −16.581 | 1.00 | 47.70 | C |
| ATOM | 563 | CB | ILE B | 159 | −7.206 | −4.450 | −16.234 | 1.00 | 46.88 | C |
| ATOM | 564 | CG1 | ILE B | 159 | −7.023 | −3.747 | −14.883 | 1.00 | 38.53 | C |
| ATOM | 565 | CD | ILE B | 159 | −7.794 | −2.452 | −14.743 | 1.00 | 34.44 | C |
| ATOM | 566 | CG2 | ILE B | 159 | −6.422 | −3.751 | −17.349 | 1.00 | 47.89 | C |
| ATOM | 567 | C | ILE B | 159 | −8.944 | −5.012 | −18.025 | 1.00 | 47.30 | C |
| ATOM | 568 | O | ILE B | 159 | −9.191 | −4.177 | −18.903 | 1.00 | 45.98 | O |
| ATOM | 569 | N | LEU B | 160 | −8.870 | −6.319 | −18.261 | 1.00 | 47.79 | N |
| ATOM | 570 | CA | LEU B | 160 | −9.169 | −6.874 | −19.581 | 1.00 | 48.56 | C |
| ATOM | 571 | CB | LEU B | 160 | −8.812 | −8.359 | −19.647 | 1.00 | 48.85 | C |
| ATOM | 572 | CG | LEU B | 160 | −7.342 | −8.785 | −19.639 | 1.00 | 45.71 | C |
| ATOM | 573 | CD1 | LEU B | 160 | −7.273 | −10.281 | −19.401 | 1.00 | 49.06 | C |
| ATOM | 574 | CD2 | LEU B | 160 | −6.626 | −8.413 | −20.928 | 1.00 | 44.42 | C |
| ATOM | 575 | C | LEU B | 160 | −10.630 | −6.670 | −19.979 | 1.00 | 49.35 | C |
| ATOM | 576 | O | LEU B | 160 | −10.940 | −6.512 | −21.165 | 1.00 | 50.44 | O |
| ATOM | 577 | N | MET B | 161 | −11.522 | −6.658 | −18.991 | 1.00 | 49.46 | N |
| ATOM | 578 | CA | MET B | 161 | −12.934 | −6.385 | −19.248 | 1.00 | 50.38 | C |
| ATOM | 579 | CB | MET B | 161 | −13.810 | −6.749 | −18.050 | 1.00 | 51.18 | C |
| ATOM | 580 | CG | MET B | 161 | −14.646 | −8.008 | −18.272 | 1.00 | 58.54 | C |
| ATOM | 581 | SD | MET B | 161 | −15.952 | −7.746 | −19.501 | 1.00 | 68.14 | S |
| ATOM | 582 | CE | MET B | 161 | −16.660 | −9.393 | −19.606 | 1.00 | 65.72 | C |
| ATOM | 583 | C | MET B | 161 | −13.137 | −4.931 | −19.649 | 1.00 | 50.34 | C |
| ATOM | 584 | O | MET B | 161 | −13.932 | −4.632 | −20.539 | 1.00 | 51.08 | O |
| ATOM | 585 | N | HIS B | 162 | −12.400 | −4.038 | −18.998 | 1.00 | 49.39 | N |
| ATOM | 586 | CA | HIS B | 162 | −12.437 | −2.616 | −19.332 | 1.00 | 48.35 | C |
| ATOM | 587 | CB | HIS B | 162 | −11.532 | −1.820 | −18.388 | 1.00 | 48.81 | C |
| ATOM | 588 | CG | HIS B | 162 | −12.057 | −1.729 | −16.991 | 1.00 | 51.30 | C |
| ATOM | 589 | ND1 | HIS B | 162 | −11.242 | −1.817 | −15.883 | 1.00 | 55.38 | N |
| ATOM | 590 | CE1 | HIS B | 162 | −11.978 | −1.707 | −14.791 | 1.00 | 54.48 | C |
| ATOM | 591 | NE2 | HIS B | 162 | −13.239 | −1.550 | −15.150 | 1.00 | 54.10 | N |
| ATOM | 592 | CD2 | HIS B | 162 | −13.316 | −1.559 | −16.521 | 1.00 | 50.58 | C |
| ATOM | 593 | C | HIS B | 162 | −12.042 | −2.378 | −20.779 | 1.00 | 45.97 | C |
| ATOM | 594 | O | HIS B | 162 | −12.675 | −1.598 | −21.465 | 1.00 | 45.41 | O |
| ATOM | 595 | N | CYS B | 163 | −10.997 | −3.070 | −21.225 | 1.00 | 46.08 | N |
| ATOM | 596 | CA | CYS B | 163 | −10.566 | −3.065 | −22.618 | 1.00 | 46.03 | C |
| ATOM | 597 | CB | CYS B | 163 | −9.308 | −3.914 | −22.788 | 1.00 | 46.14 | C |
| ATOM | 598 | SG | CYS B | 163 | −7.876 | −3.340 | −21.851 | 1.00 | 49.30 | S | gad65.pdb

TABLE A-continued

| | | | | | | | | | |
|---|---|---|---|---|---|---|---|---|---|
| ATOM | 599 | C | CYS B | 163 | −11.655 | −3.581 | −23.553 | 1.00 | 46.62 | C |
| ATOM | 600 | O | CYS B | 163 | −11.880 | −3.007 | −24.605 | 1.00 | 46.75 | O |
| ATOM | 601 | N | GLN B | 164 | −12.332 | −4.658 | −23.155 | 1.00 | 48.26 | N |
| ATOM | 602 | CA | GLN B | 164 | −13.357 | −5.281 | −23.981 | 1.00 | 48.90 | C |
| ATOM | 603 | CB | GLN B | 164 | −13.777 | −6.605 | −23.353 | 1.00 | 49.41 | C |
| ATOM | 604 | CG | GLN B | 164 | −13.911 | −7.750 | −24.340 | 1.00 | 53.15 | C |
| ATOM | 605 | CD | GLN B | 164 | −14.453 | −9.013 | −23.691 | 1.00 | 51.62 | C |
| ATOM | 606 | OE1 | GLN B | 164 | −13.706 | −9.963 | −23.427 | 1.00 | 56.43 | O |
| ATOM | 607 | NE2 | GLN B | 164 | −15.756 | −9.023 | −23.413 | 1.00 | 55.96 | N |
| ATOM | 608 | C | GLN B | 164 | −14.561 | −4.347 | −24.116 | 1.00 | 48.32 | C |
| ATOM | 609 | O | GLN B | 164 | −15.076 | −4.126 | −25.217 | 1.00 | 48.53 | O |
| ATOM | 610 | N | THR B | 165 | −14.988 | −3.800 | −22.981 | 1.00 | 47.79 | N |
| ATOM | 611 | CA | THR B | 165 | −16.083 | −2.832 | −22.895 | 1.00 | 46.95 | C |
| ATOM | 612 | CB | THR B | 165 | −16.379 | −2.501 | −21.415 | 1.00 | 46.59 | C |
| ATOM | 613 | OG1 | THR B | 165 | −16.486 | −3.725 | −20.676 | 1.00 | 46.41 | O |
| ATOM | 614 | CG2 | THR B | 165 | −17.670 | −1.711 | −21.263 | 1.00 | 42.26 | C |
| ATOM | 615 | C | THR B | 165 | −15.803 | −1.546 | −23.681 | 1.00 | 46.88 | C |
| ATOM | 616 | O | THR B | 165 | −16.706 | −0.989 | −24.305 | 1.00 | 47.51 | O |
| ATOM | 617 | N | THR B | 166 | −14.550 | −1.088 | −23.658 | 1.00 | 45.78 | N |
| ATOM | 618 | CA | THR B | 166 | −14.163 | 0.131 | −24.358 | 1.00 | 43.54 | C |
| ATOM | 619 | CB | THR B | 166 | −12.740 | 0.582 | −23.959 | 1.00 | 43.16 | C |
| ATOM | 620 | OG1 | THR B | 166 | −12.710 | 0.802 | −22.550 | 1.00 | 45.16 | O |
| ATOM | 621 | CG2 | THR B | 166 | −12.337 | 1.873 | −24.664 | 1.00 | 37.77 | C |
| ATOM | 622 | C | THR B | 166 | −14.285 | −0.028 | −25.872 | 1.00 | 43.09 | C |
| ATOM | 623 | O | THR B | 166 | −14.854 | 0.839 | −26.539 | 1.00 | 42.44 | O |
| ATOM | 624 | N | LEU B | 167 | −13.768 | −1.135 | −26.405 | 1.00 | 42.88 | N |
| ATOM | 625 | CA | LEU B | 167 | −13.893 | −1.427 | −27.835 | 1.00 | 44.23 | C |
| ATOM | 626 | CB | LEU B | 167 | −12.897 | −2.521 | −28.268 | 1.00 | 44.91 | C |
| ATOM | 627 | CG | LEU B | 167 | −11.398 | −2.165 | −28.200 | 1.00 | 44.51 | C |
| ATOM | 628 | CD1 | LEU B | 167 | −10.505 | −3.400 | −28.340 | 1.00 | 40.63 | C |
| ATOM | 629 | CD2 | LEU B | 167 | −11.004 | −1.112 | −29.234 | 1.00 | 46.72 | C |
| ATOM | 630 | C | LEU B | 167 | −15.343 | −1.751 | −28.268 | 1.00 | 45.22 | C |
| ATOM | 631 | O | LEU B | 167 | −15.744 | −1.441 | −29.399 | 1.00 | 44.75 | O |
| ATOM | 632 | N | LYS B | 168 | −16.125 | −2.331 | −27.356 | 1.00 | 46.67 | N |
| ATOM | 633 | CA | LYS B | 168 | −17.567 | −2.538 | −27.558 | 1.00 | 47.38 | C |
| ATOM | 634 | CB | LYS B | 168 | −18.209 | −3.105 | −26.287 | 1.00 | 47.40 | C |
| ATOM | 635 | CG | LYS B | 168 | −19.660 | −3.572 | −26.437 | 1.00 | 47.53 | C |
| ATOM | 636 | CD | LYS B | 168 | −20.228 | −4.025 | −25.080 | 1.00 | 49.02 | C |
| ATOM | 637 | CE | LYS B | 168 | −21.341 | −5.072 | −25.219 | 1.00 | 58.00 | C |
| ATOM | 638 | NZ | LYS B | 168 | −22.400 | −4.687 | −26.200 | 1.00 | 58.33 | N |
| ATOM | 639 | C | LYS B | 168 | −18.292 | −1.249 | −27.968 | 1.00 | 47.65 | C |
| ATOM | 640 | O | LYS B | 168 | −19.060 | −1.240 | −28.940 | 1.00 | 47.57 | O |
| ATOM | 641 | N | TYR B | 169 | −18.060 | −0.166 | −27.231 | 1.00 | 46.93 | N |
| ATOM | 642 | CA | TYR B | 169 | −18.778 | 1.087 | −27.507 | 1.00 | 45.91 | C |
| ATOM | 643 | CB | TYR B | 169 | −19.208 | 1.761 | −26.209 | 1.00 | 46.80 | C |
| ATOM | 644 | CG | TYR B | 169 | −20.059 | 0.874 | −25.321 | 1.00 | 51.46 | C |
| ATOM | 645 | CD1 | TYR B | 169 | −21.330 | 0.461 | −25.729 | 1.00 | 52.27 | C |
| ATOM | 646 | CE1 | TYR B | 169 | −22.115 | −0.354 | −24.924 | 1.00 | 54.28 | C |
| ATOM | 647 | CZ | TYR B | 169 | −21.634 | −0.756 | −23.692 | 1.00 | 52.13 | C |
| ATOM | 648 | OH | TYR B | 169 | −22.417 | −1.564 | −22.900 | 1.00 | 57.82 | O |
| ATOM | 649 | CE2 | TYR B | 169 | −20.374 | −0.361 | −23.260 | 1.00 | 49.71 | C |
| ATOM | 650 | CD2 | TYR B | 169 | −19.595 | 0.448 | −24.076 | 1.00 | 49.70 | C |
| ATOM | 651 | C | TYR B | 169 | −18.021 | 2.062 | −28.409 | 1.00 | 44.90 | C |
| ATOM | 652 | O | TYR B | 169 | −18.544 | 3.107 | −28.780 | 1.00 | 45.82 | O |
| ATOM | 653 | N | ALA B | 170 | −16.792 | 1.716 | −28.770 | 1.00 | 44.05 | N |
| ATOM | 654 | CA | ALA B | 170 | −16.032 | 2.522 | −29.728 | 1.00 | 43.93 | C |
| ATOM | 655 | CB | ALA B | 170 | −14.602 | 1.987 | −29.853 | 1.00 | 42.56 | C |
| ATOM | 656 | C | ALA B | 170 | −16.726 | 2.519 | −31.103 | 1.00 | 43.81 | C |
| ATOM | 657 | O | ALA B | 170 | −17.301 | 1.506 | −31.514 | 1.00 | 43.58 | O |
| ATOM | 658 | N | ILE B | 171 | −16.677 | 3.656 | −31.798 | 1.00 | 43.65 | N |
| ATOM | 659 | CA | ILE B | 171 | −17.052 | 3.714 | −33.209 | 1.00 | 44.05 | C |
| ATOM | 660 | CB | ILE B | 171 | −17.041 | 5.163 | −33.756 | 1.00 | 45.35 | C |
| ATOM | 661 | CG1 | ILE B | 171 | −17.746 | 6.146 | −32.802 | 1.00 | 49.29 | C |
| ATOM | 662 | CD | ILE B | 171 | −19.137 | 5.799 | −32.408 | 1.00 | 45.21 | C |
| ATOM | 663 | CG2 | ILE B | 171 | −17.621 | 5.243 | −35.159 | 1.00 | 46.56 | C |
| ATOM | 664 | C | ILE B | 171 | −16.032 | 2.883 | −33.976 | 1.00 | 44.07 | C |
| ATOM | 665 | O | ILE B | 171 | −14.829 | 2.884 | −33.626 | 1.00 | 43.19 | O |
| ATOM | 666 | N | LYS B | 172 | −16.506 | 2.172 | −35.006 | 1.00 | 44.11 | N |
| ATOM | 667 | CA | LYS B | 172 | −15.639 | 1.367 | −35.874 | 1.00 | 44.08 | C |
| ATOM | 668 | CB | LYS B | 172 | −16.351 | 0.104 | −36.371 | 1.00 | 44.95 | C |
| ATOM | 669 | CG | LYS B | 172 | −17.115 | −0.691 | −35.299 | 1.00 | 46.13 | C |
| ATOM | 670 | CD | LYS B | 172 | −16.189 | −1.455 | −34.375 | 1.00 | 49.89 | C |
| ATOM | 671 | CE | LYS B | 172 | −16.958 | −2.130 | −33.223 | 1.00 | 49.87 | C |
| ATOM | 672 | NZ | LYS B | 172 | −17.611 | −1.143 | −32.296 | 1.00 | 47.23 | N |
| ATOM | 673 | C | LYS B | 172 | −15.153 | 2.223 | −37.044 | 1.00 | 44.68 | C |
| ATOM | 674 | O | LYS B | 172 | −15.607 | 2.072 | −38.176 | 1.00 | 46.10 | O |
| ATOM | 675 | N | THR B | 173 | −14.221 | 3.128 | −36.749 | 1.00 | 44.05 | N |
| ATOM | 676 | CA | THR B | 173 | −13.665 | 4.069 | −37.716 | 1.00 | 43.65 | C |

TABLE A-continued

| | | | | | | | | | | |
|---|---|---|---|---|---|---|---|---|---|---|
| ATOM | 677 | CB | THR B | 173 | −12.657 | 5.010 | −37.030 | 1.00 | 43.39 | C |
| ATOM | 678 | OG1 | THR B | 173 | −11.712 | 4.220 | −36.302 | 1.00 | 44.57 | O |
| ATOM | 679 | CG2 | THR B | 173 | −13.379 | 5.986 | −36.071 | 1.00 | 35.11 | C |
| ATOM | 680 | C | THR B | 173 | −12.991 | 3.430 | −38.942 | 1.00 | 44.40 | C |
| ATOM | 681 | O | THR B | 173 | −12.670 | 4.125 | −39.909 | 1.00 | 44.49 | O |
| ATOM | 682 | N | GLY B | 174 | −12.780 | 2.117 | −38.904 | 1.00 | 45.00 | N |
| ATOM | 683 | CA | GLY B | 174 | −12.239 | 1.398 | −40.055 | 1.00 | 45.55 | C |
| ATOM | 684 | C | GLY B | 174 | −13.304 | 0.737 | −40.925 | 1.00 | 45.34 | C |
| ATOM | 685 | O | GLY B | 174 | −13.015 | 0.297 | −42.046 | 1.00 | 45.80 | O |
| ATOM | 686 | N | HIS B | 175 | −14.529 | 0.673 | −40.403 | 1.00 | 44.31 | N |
| ATOM | 687 | CA | HIS B | 175 | −15.668 | 0.030 | −41.072 | 1.00 | 43.40 | C |
| ATOM | 688 | CB | HIS B | 175 | −16.936 | 0.281 | −40.245 | 1.00 | 43.26 | C |
| ATOM | 689 | CG | HIS B | 175 | −18.066 | −0.653 | −40.551 | 1.00 | 41.09 | C |
| ATOM | 690 | ND1 | HIS B | 175 | −18.937 | −0.447 | −41.597 | 1.00 | 40.81 | N |
| ATOM | 691 | CE1 | HIS B | 175 | −19.836 | −1.417 | −41.616 | 1.00 | 38.13 | C |
| ATOM | 692 | NE2 | HIS B | 175 | −19.580 | −2.240 | −40.615 | 1.00 | 42.72 | N |
| ATOM | 693 | CD2 | HIS B | 175 | −18.480 | −1.783 | −39.931 | 1.00 | 40.82 | C |
| ATOM | 694 | C | HIS B | 175 | −15.883 | 0.566 | −42.488 | 1.00 | 43.20 | C |
| ATOM | 695 | O | HIS B | 175 | −15.777 | 1.771 | −42.698 | 1.00 | 42.47 | O |
| ATOM | 696 | N | PRO B | 176 | −16.207 | −0.325 | −43.461 | 1.00 | 44.05 | N |
| ATOM | 697 | CA | PRO B | 176 | −16.518 | 0.086 | −44.842 | 1.00 | 43.80 | C |
| ATOM | 698 | CB | PRO B | 176 | −17.022 | −1.205 | −45.487 | 1.00 | 43.85 | C |
| ATOM | 699 | CG | PRO B | 176 | −16.304 | −2.281 | −44.742 | 1.00 | 43.07 | C |
| ATOM | 700 | CD | PRO B | 176 | −16.252 | −1.796 | −43.317 | 1.00 | 43.82 | C |
| ATOM | 701 | C | PRO B | 176 | −17.574 | 1.172 | −44.972 | 1.00 | 44.26 | C |
| ATOM | 702 | O | PRO B | 176 | −17.540 | 1.937 | −45.937 | 1.00 | 44.77 | O |
| ATOM | 703 | N | ARG 8 | 177 | −18.492 | 1.258 | −44.014 | 1.00 | 43.91 | N |
| ATOM | 704 | CA | ARG B | 177 | −19.589 | 2.216 | −44.126 | 1.00 | 43.69 | C |
| ATOM | 705 | CB | ARG B | 177 | −20.930 | 1.505 | −44.041 | 1.00 | 44.29 | C |
| ATOM | 706 | CG | ARG B | 177 | −21.172 | 0.643 | −45.254 | 1.00 | 46.65 | C |
| ATOM | 707 | CD | ARG B | 177 | −22.256 | −0.351 | −45.021 | 1.00 | 44.63 | C |
| ATOM | 708 | NE | ARG B | 177 | −22.261 | −1.332 | −46.097 | 1.00 | 47.93 | N |
| ATOM | 709 | CZ | ARG B | 177 | −23.057 | −2.390 | −46.129 | 1.00 | 48.97 | C |
| ATOM | 710 | NH1 | ARG B | 177 | −23.913 | −2.599 | −45.134 | 1.00 | 49.03 | N |
| ATOM | 711 | NH2 | ARG B | 177 | −22.987 | −3.238 | −47.147 | 1.00 | 50.58 | N |
| ATOM | 712 | C | ARG B | 177 | −19.500 | 3.382 | −43.151 | 1.00 | 42.97 | C |
| ATOM | 713 | O | ARG B | 177 | −20.467 | 4.116 | −42.952 | 1.00 | 41.65 | O |
| ATOM | 714 | N | TYR B | 178 | −18.316 | 3.557 | −42.569 | 1.00 | 42.59 | N |
| ATOM | 715 | CA | TYR B | 178 | −18.035 | 4.741 | −41.789 | 1.00 | 42.61 | C |
| ATOM | 716 | CB | TYR B | 178 | −16.980 | 4.439 | −40.730 | 1.00 | 42.75 | C |
| ATOM | 717 | CG | TYR B | 178 | −16.683 | 5.611 | −39.846 | 1.00 | 41.33 | C |
| ATOM | 718 | CD1 | TYR B | 178 | −17.608 | 6.038 | −38.895 | 1.00 | 40.29 | C |
| ATOM | 719 | CE1 | TYR B | 178 | −17.344 | 7.126 | −38.089 | 1.00 | 48.14 | C |
| ATOM | 720 | CZ | TYR B | 178 | −16.133 | 7.797 | −38.225 | 1.00 | 43.80 | C |
| ATOM | 721 | OH | TYR B | 178 | −15.866 | 8.873 | −37.431 | 1.00 | 47.66 | O |
| ATOM | 722 | CE2 | TYR B | 178 | −15.199 | 7.394 | −39.160 | 1.00 | 43.63 | C |
| ATOM | 723 | CD2 | TYR B | 178 | −15.480 | 6.302 | −39.966 | 1.00 | 44.72 | C |
| ATOM | 724 | C | TYR B | 178 | −17.581 | 5.865 | −42.729 | 1.00 | 42.63 | C |
| ATOM | 725 | O | TYR B | 178 | −16.529 | 5.762 | −43.354 | 1.00 | 42.02 | O |
| ATOM | 726 | N | PHE B | 179 | −18.399 | 6.917 | −42.835 | 1.00 | 43.40 | N |
| ATOM | 727 | CA | PHE B | 179 | −18.157 | 8.042 | −43.752 | 1.00 | 44.71 | C |
| ATOM | 728 | CB | PHE B | 179 | −19.158 | 8.028 | −44.925 | 1.00 | 44.25 | C |
| ATOM | 729 | CG | PHE B | 179 | −19.080 | 6.801 | −45.805 | 1.00 | 46.79 | C |
| ATOM | 730 | CD1 | PHE B | 179 | −20.164 | 5.925 | −45.887 | 1.00 | 47.74 | C |
| ATOM | 731 | CE1 | PHE B | 179 | −20.114 | 4.793 | −46.703 | 1.00 | 44.33 | C |
| ATOM | 732 | CZ | PHE B | 179 | −18.964 | 4.528 | −47.453 | 1.00 | 47.85 | C |
| ATOM | 733 | CE2 | PHE B | 179 | −17.871 | 5.399 | −47.380 | 1.00 | 44.20 | C |
| ATOM | 734 | CD2 | PHE B | 179 | −17.939 | 6.529 | −46.565 | 1.00 | 43.44 | C |
| ATOM | 735 | C | PHE B | 179 | −18.259 | 9.406 | −43.047 | 1.00 | 46.45 | C |
| ATOM | 736 | O | PHE B | 179 | −18.481 | 10.435 | −43.710 | 1.00 | 47.73 | O |
| ATOM | 737 | N | ASN B | 180 | −18.095 | 9.417 | −41.722 | 1.00 | 45.83 | N |
| ATOM | 738 | CA | ASN B | 180 | −18.467 | 10.575 | −40.895 | 1.00 | 46.52 | C |
| ATOM | 739 | CB | ASN B | 180 | −18.742 | 10.134 | −39.455 | 1.00 | 46.38 | C |
| ATOM | 740 | CG | ASN B | 180 | −19.677 | 11.088 | −38.719 | 1.00 | 51.53 | C |
| ATOM | 741 | OD1 | ASN B | 180 | −20.769 gad65.pdb | 11.383 | −39.189 | 1.00 | 48.13 | O |
| ATOM | 742 | ND2 | ASN B | 180 | −19.253 | 11.561 | −37.555 | 1.00 | 53.82 | N |
| ATOM | 743 | C | ASN B | 180 | −17.461 | 11.730 | −40.854 | 1.00 | 46.61 | C |
| ATOM | 744 | O | ASN B | 180 | −17.833 | 12.881 | −40.581 | 1.00 | 46.83 | O |
| ATOM | 745 | N | GLN B | 181 | −16.193 | 11.415 | −41.094 | 1.00 | 46.03 | N |
| ATOM | 746 | CA | GLN B | 181 | −15.128 | 12.399 | −40.966 | 1.00 | 46.60 | C |
| ATOM | 747 | CB | GLN B | 181 | −14.314 | 12.185 | −39.673 | 1.00 | 46.33 | C |
| ATOM | 748 | CG | GLN B | 181 | −15.107 | 11.978 | −38.379 | 1.00 | 44.46 | C |
| ATOM | 749 | CD | GLN B | 181 | −15.801 | 13.236 | −37.865 | 1.00 | 50.57 | C |
| ATOM | 750 | OE1 | GLN B | 181 | −16.749 | 13.154 | −37.080 | 1.00 | 49.65 | O |
| ATOM | 751 | NE2 | GLN B | 181 | −15.326 | 14.398 | −38.287 | 1.00 | 48.83 | N |
| ATOM | 752 | C | GLN B | 181 | −14.203 | 12.283 | −42.158 | 1.00 | 47.60 | C |
| ATOM | 753 | O | GLN B | 181 | −14.347 | 11.376 | −42.972 | 1.00 | 47.51 | O |
| ATOM | 754 | N | LEU B | 182 | −13.251 | 13.207 | −42.244 | 1.00 | 48.28 | N |
| ATOM | 755 | CA | LEU B | 182 | −12.243 | 13.218 | −43.295 | 1.00 | 48.83 | C |

TABLE A-continued

| | | | | | | | | | |
|---|---|---|---|---|---|---|---|---|---|
| ATOM | 756 | CB | LEU B | 182 | −11.539 | 14.584 | −43.305 | 1.00 | 47.83 | C |
| ATOM | 757 | CG | LEU B | 182 | −11.955 | 15.740 | −44.229 | 1.00 | 48.86 | C |
| ATOM | 758 | CD1 | LEU B | 182 | −13.417 | 15.748 | −44.619 | 1.00 | 49.70 | C |
| ATOM | 759 | CD2 | LEU B | 182 | −11.560 | 17.070 | −43.613 | 1.00 | 48.48 | C |
| ATOM | 760 | C | LEU B | 182 | −11.232 | 12.061 | −43.090 | 1.00 | 49.93 | C |
| ATOM | 761 | O | LEU B | 182 | −10.803 | 11.417 | −44.058 | 1.00 | 49.96 | O |
| ATOM | 762 | N | SER B | 183 | −10.879 | 11.821 | −41.827 | 1.00 | 50.13 | N |
| ATOM | 763 | CA | SER B | 183 | −10.078 | 10.676 | −41.413 | 1.00 | 52.40 | C |
| ATOM | 764 | CB | SER B | 183 | −9.287 | 11.004 | −40.137 | 1.00 | 52.89 | C |
| ATOM | 765 | OG | SER B | 183 | −8.555 | 12.211 | −40.274 | 1.00 | 52.85 | O |
| ATOM | 766 | C | SER B | 183 | −10.962 | 9.451 | −41.165 | 1.00 | 53.52 | C |
| ATOM | 767 | O | SER B | 183 | −11.699 | 9.399 | −40.175 | 1.00 | 54.79 | O |
| ATOM | 768 | N | THR B | 184 | −10.897 | 8.482 | −42.077 | 1.00 | 54.16 | N |
| ATOM | 769 | CA | THR B | 184 | −11.578 | 7.183 | −41.931 | 1.00 | 54.66 | C |
| ATOM | 770 | CB | THR B | 184 | −12.831 | 7.056 | −42.843 | 1.00 | 55.05 | C |
| ATOM | 771 | OG1 | THR B | 184 | −12.445 | 7.206 | −44.215 | 1.00 | 57.40 | O |
| ATOM | 772 | CG2 | THR B | 184 | −13.896 | 8.110 | −42.498 | 1.00 | 54.75 | C |
| ATOM | 773 | C | THR B | 184 | −10.615 | 6.055 | −42.305 | 1.00 | 54.68 | C |
| ATOM | 774 | O | THR B | 184 | −9.699 | 6.262 | −43.108 | 1.00 | 54.56 | O |
| ATOM | 775 | N | GLY B | 185 | −10.820 | 4.875 | −41.723 | 1.00 | 53.67 | N |
| ATOM | 776 | CA | GLY B | 185 | −10.046 | 3.692 | −42.092 | 1.00 | 52.22 | C |
| ATOM | 777 | C | GLY B | 185 | −9.101 | 3.197 | −41.009 | 1.00 | 50.79 | C |
| ATOM | 778 | O | GLY B | 185 | −8.799 | 3.903 | −40.047 | 1.00 | 49.90 | O |
| ATOM | 779 | N | LEU B | 186 | −8.659 | 1.956 | −41.159 | 1.00 | 49.90 | N |
| ATOM | 780 | CA | LEU B | 186 | −7.724 | 1.357 | −40.226 | 1.00 | 49.03 | C |
| ATOM | 781 | CB | LEU B | 186 | −8.447 | 0.463 | −39.195 | 1.00 | 48.84 | C |
| ATOM | 782 | CG | LEU B | 186 | −7.645 | −0.185 | −38.046 | 1.00 | 50.75 | C |
| ATOM | 783 | CD1 | LEU B | 186 | −7.094 | 0.836 | −37.055 | 1.00 | 48.58 | C |
| ATOM | 784 | CD2 | LEU B | 186 | −8.478 | −1.254 | −37.301 | 1.00 | 48.75 | C |
| ATOM | 785 | C | LEU B | 186 | −6.689 | 0.600 | −41.040 | 1.00 | 48.41 | C |
| ATOM | 786 | O | LEU B | 186 | −6.940 | −0.510 | −41.530 | 1.00 | 47.20 | O |
| ATOM | 787 | N | ASP B | 187 | −5.536 | 1.240 | −41.204 | 1.00 | 48.08 | N |
| ATOM | 788 | CA | ASP B | 187 | −4.447 | 0.692 | −41.986 | 1.00 | 48.62 | C |
| ATOM | 789 | CB | ASP B | 187 | −3.587 | 1.804 | −42.586 | 1.00 | 48.58 | C |
| ATOM | 790 | CG | ASP B | 187 | −2.551 | 1.260 | −43.539 | 1.00 | 52.46 | C |
| ATOM | 791 | OD1 | ASP B | 187 | −1.531 | 0.727 | −43.061 | 1.00 | 52.81 | O |
| ATOM | 792 | OD2 | ASP B | 187 | −2.774 | 1.330 | −44.765 | 1.00 | 56.45 | O |
| ATOM | 793 | C | ASP B | 187 | −3.572 | −0.256 | −41.170 | 1.00 | 48.43 | C |
| ATOM | 794 | O | ASP B | 187 | −3.025 | 0.129 | −40.133 | 1.00 | 49.44 | O |
| ATOM | 795 | N | MET B | 188 | −3.421 | −1.478 | −41.678 | 1.00 | 46.47 | N |
| ATOM | 796 | CA | MET B | 188 | −2.784 | −2.572 | −40.958 | 1.00 | 45.49 | C |
| ATOM | 797 | CB | MET B | 188 | −3.048 | −3.893 | −41.683 | 1.00 | 45.15 | C |
| ATOM | 798 | CG | MET B | 188 | −4.511 | −4.333 | −41.683 | 1.00 | 44.83 | C |
| ATOM | 799 | SD | MET B | 188 | −5.226 | −4.580 | −40.045 | 1.00 | 48.73 | S |
| ATOM | 800 | CE | MET B | 188 | −5.907 | −2.983 | −39.649 | 1.00 | 47.55 | C |
| ATOM | 801 | C | MET B | 188 | −1.283 | −2.379 | −40.689 | 1.00 | 45.40 | C |
| ATOM | 802 | O | MET B | 188 | −0.817 | −2.635 | −39.577 | 1.00 | 46.08 | O |
| ATOM | 803 | N | VAL B | 189 | −0.532 | −1.942 | −41.697 | 1.00 | 44.22 | N |
| ATOM | 804 | CA | VAL B | 189 | 0.878 | −1.585 | −41.493 | 1.00 | 44.22 | C |
| ATOM | 805 | CB | VAL B | 189 | 1.631 | −1.345 | −42.849 | 1.00 | 43.91 | C |
| ATOM | 806 | CG1 | VAL B | 189 | 3.050 | −0.834 | −42.612 | 1.00 | 40.23 | C |
| ATOM | 807 | CG2 | VAL B | 189 | 1.673 | −2.615 | −43.664 | 1.00 | 38.95 | C |
| ATOM | 808 | C | VAL B | 189 | 0.980 | −0.374 | −40.542 | 1.00 | 43.90 | C |
| ATOM | 809 | O | VAL B | 189 | 1.754 | −0.391 | −39.584 | 1.00 | 43.55 | O |
| | | | | | gad65.pdb | | | | | |
| ATOM | 810 | N | GLY B | 190 | 0.159 | 0.644 | −40.796 | 1.00 | 43.72 | N |
| ATOM | 811 | CA | GLY B | 190 | 0.048 | 1.817 | −39.930 | 1.00 | 44.81 | C |
| ATOM | 812 | C | GLY B | 190 | −0.230 | 1.533 | −38.463 | 1.00 | 45.66 | C |
| ATOM | 813 | O | GLY B | 190 | 0.328 | 2.199 | −37.587 | 1.00 | 47.12 | O |
| ATOM | 814 | N | LEU B | 191 | −1.085 | 0.546 | −38.207 | 1.00 | 45.24 | N |
| ATOM | 815 | CA | LEU B | 191 | −1.392 | 0.073 | −36.863 | 1.00 | 45.72 | C |
| ATOM | 816 | CB | LEU B | 191 | −2.596 | −0.890 | −36.916 | 1.00 | 45.07 | C |
| ATOM | 817 | CG | LEU B | 191 | −3.151 | −1.443 | −35.598 | 1.00 | 43.88 | C |
| ATOM | 818 | CD1 | LEU B | 191 | −3.565 | −0.330 | −34.626 | 1.00 | 39.62 | C |
| ATOM | 819 | CD2 | LEU B | 191 | −4.329 | −2.393 | −35.856 | 1.00 | 45.98 | C |
| ATOM | 820 | C | LEU B | 191 | −0.194 | −0.634 | −36.238 | 1.00 | 46.85 | C |
| ATOM | 821 | O | LEU B | 191 | 0.172 | −0.369 | −35.087 | 1.00 | 47.83 | O |
| ATOM | 822 | N | ALA B | 192 | 0.407 | −1.546 | −36.997 | 1.00 | 46.80 | N |
| ATOM | 823 | CA | ALA B | 192 | 1.617 | −2.231 | −36.565 | 1.00 | 45.40 | C |
| ATOM | 824 | CB | ALA B | 192 | 2.102 | −3.178 | −37.644 | 1.00 | 44.43 | C |
| ATOM | 825 | C | ALA B | 192 | 2.703 | −1.212 | −36.211 | 1.00 | 45.10 | C |
| ATOM | 826 | O | ALA B | 192 | 3.368 | −1.346 | −35.181 | 1.00 | 44.94 | O |
| ATOM | 827 | N | ALA B | 193 | 2.861 | −0.198 | −37.059 | 1.00 | 44.78 | N |
| ATOM | 828 | CA | ALA B | 193 | 3.852 | 0.859 | −36.854 | 1.00 | 46.40 | C |
| ATOM | 829 | CB | ALA B | 193 | 3.921 | 1.753 | −38.066 | 1.00 | 45.74 | C |
| ATOM | 830 | C | ALA B | 193 | 3.565 | 1.691 | −35.599 | 1.00 | 47.59 | C |
| ATOM | 831 | O | ALA B | 193 | 4.492 | 2.107 | −34.888 | 1.00 | 47.55 | O |
| ATOM | 832 | N | ASP B | 194 | 2.282 | 1.915 | −35.329 | 1.00 | 48.35 | N |
| ATOM | 833 | CA | ASP B | 194 | 1.868 | 2.646 | −34.137 | 1.00 | 48.60 | C |
| ATOM | 834 | CB | ASP B | 194 | 0.396 | 3.027 | −34.230 | 1.00 | 49.08 | C |

TABLE A-continued

| | | | | | | | | | | |
|---|---|---|---|---|---|---|---|---|---|---|
| ATOM | 835 | CG | ASP B | 194 | 0.115 | 4.400 | −33.651 | 1.00 | 60.57 | C |
| ATOM | 836 | OD1 | ASP B | 194 | −1.087 | 4.769 | −33.532 | 1.00 | 61.71 | O |
| ATOM | 837 | OD2 | ASP B | 194 | 1.105 | 5.115 | −33.328 | 1.00 | 66.29 | O |
| ATOM | 838 | C | ASP B | 194 | 2.150 | 1.846 | −32.855 | 1.00 | 47.46 | C |
| ATOM | 839 | O | ASP B | 194 | 2.548 | 2.419 | −31.823 | 1.00 | 45.90 | O |
| ATOM | 840 | N | TRP B | 195 | 1.957 | 0.527 | −32.941 | 1.00 | 46.18 | N |
| ATOM | 841 | CA | TRP B | 195 | 2.198 | −0.373 | −31.818 | 1.00 | 45.77 | C |
| ATOM | 842 | CB | TRP B | 195 | 1.784 | −1.810 | −32.151 | 1.00 | 45.30 | C |
| ATOM | 843 | CG | TRP B | 195 | 0.309 | −2.062 | −32.188 | 1.00 | 44.73 | C |
| ATOM | 844 | CD1 | TRP B | 195 | −0.681 | −1.242 | −31.737 | 1.00 | 45.44 | C |
| ATOM | 845 | NE1 | TRP B | 195 | −1.910 | −1.821 | −31.940 | 1.00 | 45.60 | N |
| ATOM | 846 | CE2 | TRP B | 195 | −1.731 | −3.045 | −32.523 | 1.00 | 46.54 | C |
| ATOM | 847 | CD2 | TRP B | 195 | −0.338 | −3.233 | −32.688 | 1.00 | 43.71 | C |
| ATOM | 848 | CE3 | TRP B | 195 | 0.122 | −4.420 | −33.270 | 1.00 | 41.27 | C |
| ATOM | 849 | CZ3 | TRP B | 195 | −0.824 | −5.389 | −33.661 | 1.00 | 48.45 | C |
| ATOM | 850 | CH2 | TRP B | 195 | −2.204 | −5.166 | −33.486 | 1.00 | 46.49 | C |
| ATOM | 851 | CZ2 | TRP B | 195 | −2.677 | −4.009 | −32.914 | 1.00 | 48.01 | C |
| ATOM | 852 | C | TRP B | 195 | 3.658 | −0.369 | −31.395 | 1.00 | 45.18 | C |
| ATOM | 853 | O | TRP B | 195 | 3.957 | −0.358 | −30.200 | 1.00 | 44.96 | O |
| ATOM | 854 | N | LEU B | 196 | 4.546 | −0.412 | −32.388 | 1.00 | 44.54 | N |
| ATOM | 855 | CA | LEU B | 196 | 5.993 | −0.307 | −32.182 | 1.00 | 44.37 | C |
| ATOM | 856 | CB | LEU B | 196 | 6.739 | −0.538 | −33.506 | 1.00 | 43.30 | C |
| ATOM | 857 | CG | LEU B | 196 | 8.265 | −0.666 | −33.398 | 1.00 | 45.83 | C |
| ATOM | 858 | CD1 | LEU B | 196 | 8.794 | −1.605 | −34.475 | 1.00 | 41.00 | C |
| ATOM | 859 | CD2 | LEU B | 196 | 8.998 | 0.699 | −33.443 | 1.00 | 37.56 | C |
| ATOM | 860 | C | LEU B | 196 | 6.418 | 1.035 | −31.574 | 1.00 | 43.91 | C |
| ATOM | 861 | O | LEU B | 196 | 7.291 | 1.081 | −30.702 | 1.00 | 45.10 | O |
| ATOM | 862 | N | THR B | 197 | 5.829 | 2.116 | −32.069 | 1.00 | 43.00 | N |
| ATOM | 863 | CA | THR B | 197 | 6.132 | 3.470 | −31.609 | 1.00 | 44.28 | C |
| ATOM | 864 | CB | THR B | 197 | 5.257 | 4.486 | −32.359 | 1.00 | 44.82 | C |
| ATOM | 865 | OG1 | THR B | 197 | 5.542 | 4.405 | −33.762 | 1.00 | 46.21 | O |
| ATOM | 866 | CG2 | THR B | 197 | 5.522 | 5.880 | −31.867 | 1.00 | 43.09 | C |
| ATOM | 867 | C | THR B | 197 | 5.902 | 3.615 | −30.100 | 1.00 | 44.82 | C |
| ATOM | 868 | O | THR B | 197 | 6.776 | 4.118 | −29.370 | 1.00 | 44.77 | O |
| ATOM | 869 | N | SER B | 198 | 4.731 | 3.159 | −29.653 | 1.00 | 43.61 | N |
| ATOM | 870 | CA | SER B | 198 | 4.388 | 3.100 | −28.246 | 1.00 | 45.05 | C |
| ATOM | 871 | CB | SER B | 198 | 2.973 | 2.537 | −28.061 | 1.00 | 45.22 | C |
| ATOM | 872 | OG | SER B | 198 | 2.010 | 3.377 | −28.677 | 1.00 | 50.86 | O |
| ATOM | 873 | C | SER B | 198 | 5.393 | 2.270 | −27.448 | 1.00 | 45.04 | C |
| ATOM | 874 | O | SER B | 198 | 5.732 | 2.628 | −26.321 | 1.00 | 47.46 | O |
| ATOM | 875 | N | THR B | 199 | 5.871 | 1.177 | −28.032 | 1.00 | 43.92 | N |
| ATOM | 876 | CA | THR B | 199 | 6.820 | 0.274 | −27.358 | 1.00 | 43.98 | C |
| ATOM | 877 | CB | THR B | 199 | 7.002 | −1.029 | −28.160 | 1.00 | 44.04 | C |
| | | | | | gad65.pdb | | | | | |
| ATOM | 878 | OG1 | THR B | 199 | 5.718 | −1.609 | −28.442 | 1.00 | 44.39 | O |
| ATOM | 879 | CG2 | THR B | 199 | 7.845 | −2.035 | −27.390 | 1.00 | 44.80 | C |
| ATOM | 880 | C | THR B | 199 | 8.177 | 0.966 | −27.177 | 1.00 | 44.82 | C |
| ATOM | 881 | O | THR B | 199 | 8.830 | 0.810 | −26.145 | 1.00 | 43.98 | O |
| ATOM | 882 | N | ALA B | 200 | 8.579 | 1.733 | −28.193 | 1.00 | 44.82 | N |
| ATOM | 883 | CA | ALA B | 200 | 9.784 | 2.534 | −28.140 | 1.00 | 44.46 | C |
| ATOM | 884 | CB | ALA B | 200 | 10.177 | 3.005 | −29.534 | 1.00 | 42.50 | C |
| ATOM | 885 | C | ALA B | 200 | 9.635 | 3.716 | −27.178 | 1.00 | 45.73 | C |
| ATOM | 886 | O | ALA B | 200 | 10.605 | 4.084 | −26.512 | 1.00 | 47.36 | O |
| ATOM | 887 | N | ASN B | 201 | 8.438 | 4.305 | −27.119 | 1.00 | 46.97 | N |
| ATOM | 888 | CA | ASN B | 201 | 8.084 | 5.323 | −26.116 | 1.00 | 47.80 | C |
| ATOM | 889 | CB | ASN B | 201 | 7.597 | 4.633 | −24.834 | 1.00 | 48.46 | C |
| ATOM | 890 | CG | ASN B | 201 | 7.082 | 5.609 | −23.791 | 1.00 | 55.85 | C |
| ATOM | 891 | OD1 | ASN B | 201 | 7.440 | 5.518 | −22.615 | 1.00 | 63.68 | O |
| ATOM | 892 | ND2 | ASN B | 201 | 6.239 | 6.545 | −24.212 | 1.00 | 56.23 | N |
| ATOM | 893 | C | ASN B | 201 | 9.237 | 6.303 | −25.811 | 1.00 | 48.03 | C |
| ATOM | 894 | O | ASN B | 201 | 9.806 | 6.308 | −24.714 | 1.00 | 46.56 | O |
| ATOM | 895 | N | THR B | 202 | 9.600 | 7.104 | −26.809 | 1.00 | 48.70 | N |
| ATOM | 896 | CA | THR B | 202 | 10.649 | 8.110 | −26.638 | 1.00 | 49.31 | C |
| ATOM | 897 | CB | THR B | 202 | 11.983 | 7.685 | −27.317 | 1.00 | 49.54 | C |
| ATOM | 898 | OG1 | THR B | 202 | 13.035 | 8.601 | −26.963 | 1.00 | 48.79 | O |
| ATOM | 899 | CG2 | THR B | 202 | 11.833 | 7.630 | −28.835 | 1.00 | 47.19 | C |
| ATOM | 900 | C | THR B | 202 | 10.173 | 9.476 | −27.142 | 1.00 | 50.23 | C |
| ATOM | 901 | O | THR B | 202 | 9.135 | 9.582 | −27.807 | 1.00 | 50.18 | O |
| ATOM | 902 | N | ASN B | 203 | 10.923 | 10.516 | −26.789 | 1.00 | 50.73 | N |
| ATOM | 903 | CA | ASN B | 203 | 10.636 | 11.866 | −27.238 | 1.00 | 52.00 | C |
| ATOM | 904 | CB | ASN B | 203 | 10.970 | 12.875 | −26.143 | 1.00 | 53.33 | C |
| ATOM | 905 | CG | ASN B | 203 | 9.744 | 13.417 | −25.466 | 1.00 | 55.64 | C |
| ATOM | 906 | OD1 | ASN B | 203 | 8.918 | 14.058 | −26.103 | 1.00 | 63.72 | O |
| ATOM | 907 | ND2 | ASN B | 203 | 9.625 | 13.185 | −24.166 | 1.00 | 55.06 | N |
| ATOM | 908 | C | ASN B | 203 | 11.420 | 12.189 | −28.492 | 1.00 | 51.79 | C |
| ATOM | 909 | O | ASN B | 203 | 12.456 | 11.587 | −28.754 | 1.00 | 53.28 | O |
| ATOM | 910 | N | MET B | 204 | 10.927 | 13.160 | −29.247 | 1.00 | 50.81 | N |
| ATOM | 911 | CA | MET B | 204 | 11.501 | 13.509 | −30.525 | 1.00 | 50.69 | C |
| ATOM | 912 | CB | MET B | 204 | 10.409 | 14.043 | −31.476 | 1.00 | 50.47 | C |
| ATOM | 913 | CG | MET B | 204 | 9.704 | 13.002 | −32.340 | 1.00 | 45.01 | C |

TABLE A-continued

| | | | | | | | | | |
|---|---|---|---|---|---|---|---|---|---|
| ATOM | 914 | SD | MET B | 204 | 10.745 | 11.753 | −33.163 | 1.00 | 53.45 | S |
| ATOM | 915 | CE | MET B | 204 | 11.618 | 12.705 | −34.405 | 1.00 | 53.18 | C |
| ATOM | 916 | C | MET B | 204 | 12.602 | 14.554 | −30.405 | 1.00 | 51.17 | C |
| ATOM | 917 | O | MET B | 204 | 13.329 | 14.775 | −31.369 | 1.00 | 51.72 | O |
| ATOM | 918 | N | PHE B | 205 | 12.733 | 15.201 | −29.247 | 1.00 | 51.02 | N |
| ATOM | 919 | CA | PHE B | 205 | 13.536 | 16.422 | −29.220 | 1.00 | 53.07 | C |
| ATOM | 920 | CB | PHE B | 205 | 13.225 | 17.370 | −28.037 | 1.00 | 53.81 | C |
| ATOM | 921 | CG | PHE B | 205 | 13.091 | 16.707 | −26.690 | 1.00 | 56.95 | C |
| ATOM | 922 | CD1 | PHE B | 205 | 12.055 | 17.098 | −25.830 | 1.00 | 57.47 | C |
| ATOM | 923 | CE1 | PHE B | 205 | 11.911 | 16.533 | −24.566 | 1.00 | 57.35 | C |
| ATOM | 924 | CZ | PHE B | 205 | 12.820 | 15.573 | −24.133 | 1.00 | 60.05 | C |
| ATOM | 925 | CE2 | PHE B | 205 | 13.872 | 15.183 | −24.979 | 1.00 | 65.13 | C |
| ATOM | 926 | CD2 | PHE B | 205 | 14.005 | 15.760 | −26.250 | 1.00 | 55.37 | C |
| ATOM | 927 | C | PHE B | 205 | 15.043 | 16.332 | −29.570 | 1.00 | 53.68 | C |
| ATOM | 928 | O | PHE B | 205 | 15.601 | 17.312 | −30.080 | 1.00 | 54.72 | O |
| ATOM | 929 | N | THR B | 206 | 15.674 | 15.171 | −29.360 | 1.00 | 52.27 | N |
| ATOM | 930 | CA | THR B | 206 | 17.086 | 14.976 | −29.743 | 1.00 | 50.73 | C |
| ATOM | 931 | CB | THR B | 206 | 18.041 | 15.100 | −28.546 | 1.00 | 50.81 | C |
| ATOM | 932 | OG1 | THR B | 206 | 17.701 | 14.116 | −27.569 | 1.00 | 50.42 | O |
| ATOM | 933 | CG2 | THR B | 206 | 17.987 | 16.497 | −27.916 | 1.00 | 53.36 | C |
| ATOM | 934 | C | THR B | 206 | 17.400 | 13.636 | −30.409 | 1.00 | 49.30 | C |
| ATOM | 935 | O | THR B | 206 | 16.754 | 12.608 | −30.136 | 1.00 | 49.29 | O |
| ATOM | 936 | N | TYR B | 207 | 18.404 | 13.666 | −31.287 | 1.00 | 47.75 | N |
| ATOM | 937 | CA | TYR B | 207 | 19.017 | 12.460 | −31.853 | 1.00 | 46.79 | C |
| ATOM | 938 | CB | TYR B | 207 | 20.200 | 12.833 | −32.761 | 1.00 | 45.92 | C |
| ATOM | 939 | CG | TYR B | 207 | 20.842 | 11.629 | −33.400 | 1.00 | 43.99 | C |
| ATOM | 940 | CD1 | TYR B | 207 | 20.377 | 11.135 | −34.624 | 1.00 | 38.99 | C |
| ATOM | 941 | CE1 | TYR B | 207 | 20.952 | 10.001 | −35.205 | 1.00 | 44.09 | C |
| ATOM | 942 | CZ | TYR B | 207 | 21.998 | 9.354 | −34.563 | 1.00 | 41.09 | C |
| ATOM | 943 | OH | TYR B | 207 | 22.556 | 8.229 | −35.141 | 1.00 | 45.16 | O |
| ATOM | 944 | CE2 | TYR B | 207 | 22.485 | 9.828 | −33.345 | 1.00 | 43.17 | C |
| ATOM | 945 | CD2 | TYR B | 207 | 21.901 | 10.959 | −32.769 | 1.00 | 44.01 | C | gad65.pdb

| | | | | | | | | | |
|---|---|---|---|---|---|---|---|---|---|
| ATOM | 946 | C | TYR B | 207 | 19.488 | 11.509 | −30.746 | 1.00 | 47.72 | C |
| ATOM | 947 | O | TYR B | 207 | 19.422 | 10.294 | −30.893 | 1.00 | 47.73 | O |
| ATOM | 948 | N | GLU B | 208 | 19.962 | 12.086 | −29.644 | 1.00 | 48.44 | N |
| ATOM | 949 | CA | GLU B | 208 | 20.410 | 11.344 | −28.465 | 1.00 | 48.87 | C |
| ATOM | 950 | CB | GLU B | 208 | 20.805 | 12.318 | −27.338 | 1.00 | 47.86 | C |
| ATOM | 951 | CG | GLU B | 208 | 21.256 | 11.651 | −26.037 | 1.00 | 51.74 | C |
| ATOM | 952 | CD | GLU B | 208 | 21.859 | 12.632 | −25.036 | 1.00 | 50.92 | C |
| ATOM | 953 | OE1 | GLU B | 208 | 21.303 | 12.760 | −23.921 | 1.00 | 54.24 | O |
| ATOM | 954 | OE2 | GLU B | 208 | 22.887 | 13.272 | −25.365 | 1.00 | 60.19 | O |
| ATOM | 955 | C | GLU B | 208 | 19.423 | 10.265 | −27.959 | 1.00 | 47.50 | C |
| ATOM | 956 | O | GLU B | 208 | 19.852 | 9.177 | −27.575 | 1.00 | 49.26 | O |
| ATOM | 957 | N | ILE B | 209 | 18.128 | 10.556 | −27.939 | 1.00 | 46.00 | N |
| ATOM | 958 | CA | ILE B | 209 | 17.147 | 9.551 | −27.472 | 1.00 | 44.99 | C |
| ATOM | 959 | CB | ILE B | 209 | 16.355 | 9.994 | −26.194 | 1.00 | 46.01 | C |
| ATOM | 960 | CG1 | ILE B | 209 | 15.168 | 10.919 | −26.540 | 1.00 | 48.22 | C |
| ATOM | 961 | CD | ILE B | 209 | 15.453 | 12.381 | −26.554 | 1.00 | 54.45 | C |
| ATOM | 962 | CG2 | ILE B | 209 | 17.294 | 10.544 | −25.112 | 1.00 | 46.37 | C |
| ATOM | 963 | C | ILE B | 209 | 16.187 | 9.034 | −28.550 | 1.00 | 43.53 | C |
| ATOM | 964 | O | ILE B | 209 | 15.441 | 8.068 | −28.333 | 1.00 | 44.00 | O |
| ATOM | 965 | N | ALA B | 210 | 16.207 | 9.655 | −29.720 | 1.00 | 42.41 | N |
| ATOM | 966 | CA | ALA B | 210 | 15.393 | 9.159 | −30.825 | 1.00 | 41.45 | C |
| ATOM | 967 | CB | ALA B | 210 | 14.156 | 10.030 | −30.982 | 1.00 | 41.28 | C |
| ATOM | 968 | C | ALA B | 210 | 16.195 | 9.096 | −32.125 | 1.00 | 41.19 | C |
| ATOM | 969 | O | ALA B | 210 | 15.802 | 9.703 | −33.120 | 1.00 | 40.72 | O |
| ATOM | 970 | N | PRO B | 211 | 17.343 | 8.374 | −32.115 | 1.00 | 42.60 | N |
| ATOM | 971 | CA | PRO B | 211 | 18.254 | 8.403 | −33.277 | 1.00 | 43.19 | C |
| ATOM | 972 | CB | PRO B | 211 | 19.407 | 7.478 | −32.855 | 1.00 | 42.65 | C |
| ATOM | 973 | CG | PRO B | 211 | 18.843 | 6.633 | −31.766 | 1.00 | 44.87 | C |
| ATOM | 974 | CD | PRO B | 211 | 17.873 | 7.515 | −31.038 | 1.00 | 41.08 | C |
| ATOM | 975 | C | PRO B | 211 | 17.632 | 7.966 | −34.614 | 1.00 | 43.66 | C |
| ATOM | 976 | O | PRO B | 211 | 17.733 | 8.707 | −35.599 | 1.00 | 45.21 | O |
| ATOM | 977 | N | VAL B | 212 | 16.982 | 6.806 | −34.657 | 1.00 | 42.98 | N |
| ATOM | 978 | CA | VAL B | 212 | 16.289 | 6.389 | −35.885 | 1.00 | 44.04 | C |
| ATOM | 979 | CB | VAL B | 212 | 15.676 | 4.967 | −35.766 | 1.00 | 43.75 | C |
| ATOM | 980 | CG1 | VAL B | 212 | 15.106 | 4.520 | −37.094 | 1.00 | 42.81 | C |
| ATOM | 981 | CG2 | VAL B | 212 | 16.721 | 3.953 | −35.294 | 1.00 | 49.19 | C |
| ATOM | 982 | C | VAL B | 212 | 15.176 | 7.388 | −36.279 | 1.00 | 44.59 | C |
| ATOM | 983 | O | VAL B | 212 | 15.036 | 7.756 | −37.454 | 1.00 | 44.18 | O |
| ATOM | 984 | N | PHE B | 213 | 14.392 | 7.829 | −35.293 | 1.00 | 44.24 | N |
| ATOM | 985 | CA | PHE B | 213 | 13.197 | 8.618 | −35.591 | 1.00 | 44.45 | C |
| ATOM | 986 | CB | PHE B | 213 | 12.252 | 8.672 | −34.392 | 1.00 | 43.97 | C |
| ATOM | 987 | CG | PHE B | 213 | 11.803 | 7.319 | −33.922 | 1.00 | 43.78 | C |
| ATOM | 988 | CD1 | PHE B | 213 | 11.286 | 6.393 | −34.827 | 1.00 | 39.40 | C |
| ATOM | 989 | CE1 | PHE B | 213 | 10.858 | 5.130 | −34.401 | 1.00 | 41.56 | C |
| ATOM | 990 | CZ | PHE B | 213 | 10.949 | 4.790 | −33.066 | 1.00 | 43.26 | C |
| ATOM | 991 | CE2 | PHE B | 213 | 11.471 | 5.706 | −32.147 | 1.00 | 43.83 | C |
| ATOM | 992 | CD2 | PHE B | 213 | 11.891 | 6.969 | −32.579 | 1.00 | 41.41 | C |

TABLE A-continued

| | | | | | | | | | |
|---|---|---|---|---|---|---|---|---|---|
| ATOM | 993 | C | PHE B | 213 | 13.519 | 10.005 | −36.102 | 1.00 | 44.92 | C |
| ATOM | 994 | O | PHE B | 213 | 12.782 | 10.532 | −36.933 | 1.00 | 45.39 | O |
| ATOM | 995 | N | VAL B | 214 | 14.621 | 10.590 | −35.623 | 1.00 | 44.92 | N |
| ATOM | 996 | CA | VAL B | 214 | 15.060 | 11.887 | −36.125 | 1.00 | 45.02 | C |
| ATOM | 997 | CB | VAL B | 214 | 16.209 | 12.499 | −35.283 | 1.00 | 46.32 | C |
| ATOM | 998 | CG1 | VAL B | 214 | 16.784 | 13.732 | −35.977 | 1.00 | 49.19 | C |
| ATOM | 999 | CG2 | VAL B | 214 | 15.722 | 12.869 | −33.889 | 1.00 | 46.03 | C |
| ATOM | 1000 | C | VAL B | 214 | 15.475 | 11.761 | −37.588 | 1.00 | 44.75 | C |
| ATOM | 1001 | O | VAL B | 214 | 15.153 | 12.632 | −38.402 | 1.00 | 44.61 | O |
| ATOM | 1002 | N | LEU B | 215 | 16.178 | 10.673 | −37.919 | 1.00 | 44.77 | N |
| ATOM | 1003 | CA | LEU B | 215 | 16.586 | 10.401 | −39.304 | 1.00 | 44.52 | C |
| ATOM | 1004 | CB | LEU B | 215 | 17.604 | 9.250 | −39.394 | 1.00 | 44.38 | C |
| ATOM | 1005 | CG | LEU B | 215 | 19.015 | 9.383 | −38.795 | 1.00 | 51.83 | C |
| ATOM | 1006 | CD1 | LEU B | 215 | 19.818 | 8.122 | −39.069 | 1.00 | 52.08 | C |
| ATOM | 1007 | CD2 | LEU B | 215 | 19.773 | 10.592 | −39.317 | 1.00 | 53.45 | C |
| ATOM | 1008 | C | LEU B | 215 | 15.388 | 10.141 | −40.233 | 1.00 | 44.04 | C |
| ATOM | 1009 | O | LEU B | 215 | 15.343 | 10.690 | −41.329 | 1.00 | 43.78 | O |
| ATOM | 1010 | N | LEU B | 216 | 14.425 | 9.325 | −39.808 | 1.00 | 43.89 | N |
| ATOM | 1011 | CA | LEU B | 216 | 13.221 | 9.108 | −40.625 | 1.00 | 45.69 | C |
| ATOM | 1012 | CB | LEU B | 216 | 12.270 | 8.073 | −39.997 | 1.00 | 46.11 | C |
| ATOM | 1013 | CG | LEU B | 216 | 12.750 | 6.631 | −39.718 | 1.00 | 47.34 | C | gad65.pdb

| | | | | | | | | | |
|---|---|---|---|---|---|---|---|---|---|
| ATOM | 1014 | CD1 | LEU B | 216 | 11.568 | 5.708 | −39.420 | 1.00 | 43.64 | C |
| ATOM | 1015 | CD2 | LEU B | 216 | 13.589 | 6.050 | −40.856 | 1.00 | 46.09 | C |
| ATOM | 1016 | C | LEU B | 216 | 12.477 | 10.423 | −40.881 | 1.00 | 46.82 | C |
| ATOM | 1017 | O | LEU B | 216 | 11.937 | 10.647 | −41.970 | 1.00 | 46.75 | O |
| ATOM | 1018 | N | GLU B | 217 | 12.462 | 11.292 | −39.874 | 1.00 | 46.75 | N |
| ATOM | 1019 | CA | GLU B | 217 | 11.781 | 12.574 | −39.983 | 1.00 | 47.03 | C |
| ATOM | 1020 | CB | GLU B | 217 | 11.734 | 13.292 | −38.628 | 1.00 | 45.49 | C |
| ATOM | 1021 | CG | GLU B | 217 | 11.036 | 14.624 | −38.643 | 1.00 | 47.33 | C |
| ATOM | 1022 | CD | GLU B | 217 | 10.534 | 15.069 | −37.267 | 1.00 | 55.50 | C |
| ATOM | 1023 | OE1 | GLU B | 217 | 10.850 | 16.217 | −36.885 | 1.00 | 61.75 | O |
| ATOM | 1024 | OE2 | GLU B | 217 | 9.826 | 14.291 | −36.573 | 1.00 | 53.09 | O |
| ATOM | 1025 | C | GLU B | 217 | 12.472 | 13.412 | −41.051 | 1.00 | 47.61 | C |
| ATOM | 1026 | O | GLU B | 217 | 11.806 | 14.000 | −41.910 | 1.00 | 46.42 | O |
| ATOM | 1027 | N | TYR B | 218 | 13.804 | 13.434 | −41.034 | 1.00 | 48.48 | N |
| ATOM | 1028 | CA | TYR B | 218 | 14.507 | 14.122 | −42.102 | 1.00 | 50.01 | C |
| ATOM | 1029 | CB | TYR B | 218 | 16.020 | 14.208 | −41.894 | 1.00 | 51.12 | C |
| ATOM | 1030 | CG | TYR B | 218 | 16.689 | 14.880 | −43.082 | 1.00 | 57.57 | C |
| ATOM | 1031 | CD1 | TYR B | 218 | 17.308 | 14.126 | −44.084 | 1.00 | 58.78 | C |
| ATOM | 1032 | CE1 | TYR B | 218 | 17.902 | 14.742 | −45.185 | 1.00 | 61.45 | C |
| ATOM | 1033 | CZ | TYR B | 218 | 17.855 | 16.126 | −45.299 | 1.00 | 59.72 | C |
| ATOM | 1034 | OH | TYR B | 218 | 18.429 | 16.754 | −46.382 | 1.00 | 62.48 | O |
| ATOM | 1035 | CE2 | TYR B | 218 | 17.229 | 16.892 | −44.333 | 1.00 | 63.06 | C |
| ATOM | 1036 | CD2 | TYR B | 218 | 16.644 | 16.268 | −43.235 | 1.00 | 63.76 | C |
| ATOM | 1037 | C | TYR B | 218 | 14.174 | 13.551 | −43.497 | 1.00 | 49.62 | C |
| ATOM | 1038 | O | TYR B | 218 | 13.848 | 14.323 | −44.399 | 1.00 | 49.98 | O |
| ATOM | 1039 | N | VAL B | 219 | 14.246 | 12.228 | −43.676 | 1.00 | 48.42 | N |
| ATOM | 1040 | CA | VAL B | 219 | 13.970 | 11.646 | −45.006 | 1.00 | 48.80 | C |
| ATOM | 1041 | CB | VAL B | 219 | 14.495 | 10.160 | −45.212 | 1.00 | 48.94 | C |
| ATOM | 1042 | CG1 | VAL B | 219 | 15.753 | 9.864 | −44.394 | 1.00 | 48.63 | C |
| ATOM | 1043 | CG2 | VAL B | 219 | 13.412 | 9.105 | −44.947 | 1.00 | 51.19 | C |
| ATOM | 1044 | C | VAL B | 219 | 12.501 | 11.763 | −45.455 | 1.00 | 48.27 | C |
| ATOM | 1045 | O | VAL B | 219 | 12.223 | 11.953 | −46.645 | 1.00 | 48.92 | O |
| ATOM | 1046 | N | THR B | 220 | 11.568 | 11.639 | −44.518 | 1.00 | 46.81 | N |
| ATOM | 1047 | CA | THR B | 220 | 10.144 | 11.621 | −44.869 | 1.00 | 46.08 | C |
| ATOM | 1048 | CB | THR B | 220 | 9.284 | 11.088 | −43.701 | 1.00 | 45.93 | C |
| ATOM | 1049 | OG1 | THR B | 220 | 9.785 | 9.803 | −43.306 | 1.00 | 46.13 | O |
| ATOM | 1050 | CG2 | THR B | 220 | 7.863 | 10.928 | −44.130 | 1.00 | 43.81 | C |
| ATOM | 1051 | C | THR B | 220 | 9.667 | 13.004 | −45.301 | 1.00 | 44.93 | C |
| ATOM | 1052 | O | THR B | 220 | 8.962 | 13.145 | −46.303 | 1.00 | 44.27 | O |
| ATOM | 1053 | N | LEU B | 221 | 10.087 | 14.016 | −44.544 | 1.00 | 44.59 | N |
| ATOM | 1054 | CA | LEU B | 221 | 9.754 | 15.404 | −44.828 | 1.00 | 44.28 | C |
| ATOM | 1055 | CB | LEU B | 221 | 10.053 | 16.297 | −43.614 | 1.00 | 43.09 | C |
| ATOM | 1056 | CG | LEU B | 221 | 9.167 | 16.095 | −42.384 | 1.00 | 42.88 | C |
| ATOM | 1057 | CD1 | LEU B | 221 | 9.838 | 16.728 | −41.186 | 1.00 | 47.60 | C |
| ATOM | 1058 | CD2 | LEU B | 221 | 7.724 | 16.643 | −42.557 | 1.00 | 39.30 | C |
| ATOM | 1059 | C | LEU B | 221 | 10.445 | 15.954 | −46.075 | 1.00 | 44.55 | C |
| ATOM | 1060 | O | LEU B | 221 | 9.900 | 16.825 | −46.744 | 1.00 | 44.46 | O |
| ATOM | 1061 | N | LYS B | 222 | 11.642 | 15.458 | −46.375 | 1.00 | 45.51 | N |
| ATOM | 1062 | CA | LYS B | 222 | 12.333 | 15.828 | −47.613 | 1.00 | 46.30 | C |
| ATOM | 1063 | CB | LYS B | 222 | 13.782 | 15.338 | −47.603 | 1.00 | 45.65 | C |
| ATOM | 1064 | CG | LYS B | 222 | 14.646 | 15.976 | −48.692 | 1.00 | 49.93 | C |
| ATOM | 1065 | CD | LYS B | 222 | 15.993 | 15.280 | −48.806 | 1.00 | 53.31 | C |
| ATOM | 1066 | CE | LYS B | 222 | 16.634 | 15.545 | −50.151 | 1.00 | 55.59 | C |
| ATOM | 1067 | NZ | LYS B | 222 | 17.905 | 14.796 | −50.288 | 1.00 | 67.00 | N |
| ATOM | 1068 | C | LYS B | 222 | 11.581 | 15.300 | −48.859 | 1.00 | 45.52 | C |
| ATOM | 1069 | O | LYS B | 222 | 11.324 | 16.053 | −49.803 | 1.00 | 44.22 | O |
| ATOM | 1070 | N | LYS B | 223 | 11.237 | 14.013 | −48.849 | 1.00 | 44.69 | N |
| ATOM | 1071 | CA | LYS B | 223 | 10.427 | 13.425 | −49.909 | 1.00 | 45.06 | C |

TABLE A-continued

| | | | | | | | | | |
|---|---|---|---|---|---|---|---|---|---|
| ATOM | 1072 | CB | LYS B | 223 | 10.129 | 11.962 | −49.595 | 1.00 | 45.13 | C |
| ATOM | 1073 | CG | LYS B | 223 | 9.516 | 11.190 | −50.741 | 1.00 | 52.40 | C |
| ATOM | 1074 | CD | LYS B | 223 | 10.572 | 10.588 | −51.644 | 1.00 | 60.42 | C |
| ATOM | 1075 | CE | LYS B | 223 | 9.929 | 9.931 | −52.849 | 1.00 | 64.51 | C |
| ATOM | 1076 | NZ | LYS B | 223 | 10.939 | 9.215 | −53.672 | 1.00 | 68.55 | N |
| ATOM | 1077 | C | LYS B | 223 | 9.120 | 14.210 | −50.114 | 1.00 | 45.39 | C |
| ATOM | 1078 | O | LYS B | 223 | 8.729 | 14.494 | −51.251 | 1.00 | 45.42 | O |
| ATOM | 1079 | N | MET B | 224 | 8.460 | 14.578 | −49.015 | 1.00 | 44.91 | N |
| ATOM | 1080 | CA | MET B | 224 | 7.225 | 15.352 | −49.097 | 1.00 | 45.79 | C |
| ATOM | 1081 | CB | MET B | 224 | 6.586 | 15.507 | −47.704 | 1.00 | 46.11 | C | gad65.pdb

| | | | | | | | | | |
|---|---|---|---|---|---|---|---|---|---|
| ATOM | 1082 | CG | MET B | 224 | 6.052 | 14.188 | −47.120 | 1.00 | 43.32 | C |
| ATOM | 1083 | SD | MET B | 224 | 5.481 | 14.287 | −45.397 | 1.00 | 49.05 | S |
| ATOM | 1084 | CE | MET B | 224 | 4.013 | 15.310 | −45.605 | 1.00 | 38.39 | C |
| ATOM | 1085 | C | MET B | 224 | 7.476 | 16.710 | −49.778 | 1.00 | 44.86 | C |
| ATOM | 1086 | O | MET B | 224 | 6.677 | 17.167 | −50.598 | 1.00 | 44.22 | O |
| ATOM | 1087 | N | ARG B | 225 | 8.607 | 17.331 | −49.465 | 1.00 | 44.42 | N |
| ATOM | 1088 | CA | ARG B | 225 | 9.015 | 18.560 | −50.152 | 1.00 | 44.48 | C |
| ATOM | 1089 | CB | ARG B | 225 | 10.216 | 19.211 | −49.456 | 1.00 | 43.59 | C |
| ATOM | 1090 | CG | ARG B | 225 | 9.872 | 19.823 | −48.099 | 1.00 | 43.40 | C |
| ATOM | 1091 | CD | ARG B | 225 | 11.001 | 20.701 | −47.542 | 1.00 | 44.34 | C |
| ATOM | 1092 | NE | ARG B | 225 | 12.221 | 19.963 | −47.222 | 1.00 | 42.77 | N |
| ATOM | 1093 | CZ | ARG B | 225 | 12.453 | 19.317 | −46.078 | 1.00 | 41.41 | C |
| ATOM | 1094 | NH1 | ARG B | 225 | 11.543 | 19.268 | −45.112 | 1.00 | 47.09 | N |
| ATOM | 1095 | NH2 | ARG B | 225 | 13.604 | 18.700 | −45.900 | 1.00 | 45.97 | N |
| ATOM | 1096 | C | ARG B | 225 | 9.274 | 18.380 | −51.656 | 1.00 | 45.03 | C |
| ATOM | 1097 | O | ARG B | 225 | 8.989 | 19.278 | −52.444 | 1.00 | 43.87 | O |
| ATOM | 1098 | N | GLU B | 226 | 9.805 | 17.222 | −52.045 | 1.00 | 46.84 | N |
| ATOM | 1099 | CA | GLU B | 226 | 9.947 | 16.865 | −53.470 | 1.00 | 47.93 | C |
| ATOM | 1100 | CB | GLU B | 226 | 10.755 | 15.575 | −53.644 | 1.00 | 46.86 | C |
| ATOM | 1101 | CG | GLU B | 226 | 12.228 | 15.714 | −53.346 | 1.00 | 51.11 | C |
| ATOM | 1102 | CD | GLU B | 226 | 12.970 | 14.376 | −53.375 | 1.00 | 50.56 | C |
| ATOM | 1103 | OE1 | GLU B | 226 | 13.663 | 14.049 | −52.379 | 1.00 | 63.95 | O |
| ATOM | 1104 | OE2 | GLU B | 226 | 12.853 | 13.644 | −54.383 | 1.00 | 52.85 | O |
| ATOM | 1105 | C | GLU B | 226 | 8.585 | 16.708 | −54.149 | 1.00 | 46.85 | C |
| ATOM | 1106 | O | GLU B | 226 | 8.349 | 17.275 | −55.207 | 1.00 | 45.88 | O |
| ATOM | 1107 | N | ILE B | 227 | 7.699 | 15.934 | −53.525 | 1.00 | 47.82 | N |
| ATOM | 1108 | CA | ILE B | 227 | 6.339 | 15.736 | −54.018 | 1.00 | 47.91 | C |
| ATOM | 1109 | CB | ILE B | 227 | 5.512 | 14.817 | −53.060 | 1.00 | 48.99 | C |
| ATOM | 1110 | CG1 | ILE B | 227 | 6.215 | 13.463 | −52.829 | 1.00 | 48.69 | C |
| ATOM | 1111 | CD | ILE B | 227 | 5.555 | 12.268 | −53.489 | 1.00 | 49.40 | C |
| ATOM | 1112 | CG2 | ILE B | 227 | 4.073 | 14.641 | −53.563 | 1.00 | 48.40 | C |
| ATOM | 1113 | C | ILE B | 227 | 5.645 | 17.098 | −54.198 | 1.00 | 47.91 | C |
| ATOM | 1114 | O | ILE B | 227 | 4.935 | 17.306 | −55.186 | 1.00 | 48.51 | O |
| ATOM | 1115 | N | ILE B | 228 | 5.858 | 18.015 | −53.249 | 1.00 | 46.55 | N |
| ATOM | 1116 | CA | ILE B | 228 | 5.322 | 19.380 | −53.337 | 1.00 | 47.05 | C |
| ATOM | 1117 | CB | ILE B | 228 | 5.588 | 20.197 | −52.042 | 1.00 | 46.98 | C |
| ATOM | 1118 | CG1 | ILE B | 228 | 4.629 | 19.745 | −50.931 | 1.00 | 48.35 | C |
| ATOM | 1119 | CD | ILE B | 228 | 4.808 | 20.454 | −49.635 | 1.00 | 50.52 | C |
| ATOM | 1120 | CG2 | ILE B | 228 | 5.431 | 21.700 | −52.284 | 1.00 | 45.06 | C |
| ATOM | 1121 | C | ILE B | 228 | 5.859 | 20.113 | −54.570 | 1.00 | 48.91 | C |
| ATOM | 1122 | O | ILE B | 228 | 5.105 | 20.822 | −55.248 | 1.00 | 48.57 | O |
| ATOM | 1123 | N | GLY B | 229 | 7.151 | 19.919 | −54.861 | 1.00 | 49.31 | N |
| ATOM | 1124 | CA | GLY B | 229 | 7.782 | 20.488 | −56.050 | 1.00 | 50.14 | C |
| ATOM | 1125 | C | GLY B | 229 | 8.977 | 21.383 | −55.770 | 1.00 | 51.12 | C |
| ATOM | 1126 | O | GLY B | 229 | 9.524 | 22.003 | −56.686 | 1.00 | 50.98 | O |
| ATOM | 1127 | N | TRP B | 230 | 9.390 | 21.460 | −54.507 | 1.00 | 51.87 | N |
| ATOM | 1128 | CA | TRP B | 230 | 10.557 | 22.263 | −54.153 | 1.00 | 52.18 | C |
| ATOM | 1129 | CB | TRP B | 230 | 10.560 | 22.633 | −52.670 | 1.00 | 50.90 | C |
| ATOM | 1130 | CG | TRP B | 230 | 9.325 | 23.375 | −52.224 | 1.00 | 50.14 | C |
| ATOM | 1131 | CD1 | TRP B | 230 | 8.424 | 24.037 | −53.021 | 1.00 | 51.68 | C |
| ATOM | 1132 | NE1 | TRP B | 230 | 7.432 | 24.604 | −52.251 | 1.00 | 46.99 | N |
| ATOM | 1133 | CE2 | TRP B | 230 | 7.685 | 24.333 | −50.933 | 1.00 | 50.88 | C |
| ATOM | 1134 | CD2 | TRP B | 230 | 8.870 | 23.558 | −50.877 | 1.00 | 50.48 | C |
| ATOM | 1135 | CE3 | TRP B | 230 | 9.344 | 23.141 | −49.626 | 1.00 | 48.99 | C |
| ATOM | 1136 | CZ3 | TRP B | 230 | 8.626 | 23.496 | −48.489 | 1.00 | 47.36 | C |
| ATOM | 1137 | CH2 | TRP B | 230 | 7.457 | 24.268 | −48.578 | 1.00 | 47.29 | C |
| ATOM | 1138 | CZ2 | TRP B | 230 | 6.969 | 24.694 | −49.785 | 1.00 | 49.34 | C |
| ATOM | 1139 | C | TRP B | 230 | 11.834 | 21.536 | −54.582 | 1.00 | 53.88 | C |
| ATOM | 1140 | O | TRP B | 230 | 12.014 | 20.351 | −54.266 | 1.00 | 54.00 | O |
| ATOM | 1141 | N | PRO B | 231 | 12.721 | 22.247 | −55.313 | 1.00 | 55.09 | N |
| ATOM | 1142 | CA | PRO B | 231 | 13.795 | 21.626 | −56.114 | 1.00 | 55.07 | C |
| ATOM | 1143 | CB | PRO B | 231 | 14.525 | 22.833 | −56.731 | 1.00 | 54.58 | C |
| ATOM | 1144 | CG | PRO B | 231 | 14.186 | 23.981 | −55.853 | 1.00 | 55.15 | C |
| ATOM | 1145 | CD | PRO B | 231 | 12.770 | 23.720 | −55.393 | 1.00 | 55.34 | C |
| ATOM | 1146 | C | PRO B | 231 | 14.750 | 20.785 | −55.288 | 1.00 | 54.82 | C |
| ATOM | 1147 | O | PRO B | 231 | 15.350 | 21.289 | −54.340 | 1.00 | 55.97 | O |
| ATOM | 1148 | N | GLY B | 232 | 14.885 | 19.510 | −55.647 | 1.00 | 54.16 | N |
| ATOM | 1149 | CA | GLY B | 232 | 15.663 | 18.551 | −54.849 | 1.00 | 53.84 | C | gad65.pdb

TABLE A-continued

| | | | | | | | | | |
|---|---|---|---|---|---|---|---|---|---|
| ATOM | 1150 | C | GLY B | 232 | 15.174 | 18.335 | −53.416 | 1.00 | 53.46 | C |
| ATOM | 1151 | O | GLY B | 232 | 15.913 | 17.811 | −52.574 | 1.00 | 53.76 | O |
| ATOM | 1152 | N | GLY B | 233 | 13.932 | 18.743 | −53.136 | 1.00 | 52.77 | N |
| ATOM | 1153 | CA | GLY B | 233 | 13.331 | 18.595 | −51.808 | 1.00 | 51.45 | C |
| ATOM | 1154 | C | GLY B | 233 | 13.893 | 19.559 | −50.784 | 1.00 | 51.10 | C |
| ATOM | 1155 | O | GLY B | 233 | 13.810 | 19.318 | −49.578 | 1.00 | 51.06 | O |
| ATOM | 1156 | N | SER B | 234 | 14.461 | 20.658 | −51.271 | 1.00 | 50.47 | N |
| ATOM | 1157 | CA | SER B | 234 | 14.987 | 21.712 | −50.415 | 1.00 | 50.99 | C |
| ATOM | 1158 | CB | SER B | 234 | 15.630 | 22.814 | −51.259 | 1.00 | 50.38 | C |
| ATOM | 1159 | OG | SER B | 234 | 16.513 | 22.258 | −52.208 | 1.00 | 60.61 | O |
| ATOM | 1160 | C | SER B | 234 | 13.867 | 22.323 | −49.569 | 1.00 | 50.25 | C |
| ATOM | 1161 | O | SER B | 234 | 12.692 | 22.277 | −49.945 | 1.00 | 48.89 | O |
| ATOM | 1162 | N | GLY B | 235 | 14.260 | 22.912 | −48.445 | 1.00 | 49.57 | N |
| ATOM | 1163 | CA | GLY B | 235 | 13.331 | 23.482 | −47.495 | 1.00 | 49.74 | C |
| ATOM | 1164 | C | GLY B | 235 | 13.480 | 22.853 | −46.126 | 1.00 | 49.93 | C |
| ATOM | 1165 | O | GLY B | 235 | 14.505 | 22.250 | −45.796 | 1.00 | 49.72 | O |
| ATOM | 1166 | N | ASP B | 236 | 12.428 | 22.987 | −45.338 | 1.00 | 49.97 | N |
| ATOM | 1167 | CA | ASP B | 236 | 12.429 | 22.600 | −43.956 | 1.00 | 50.52 | C |
| ATOM | 1168 | CB | ASP B | 236 | 12.599 | 23.868 | −43.132 | 1.00 | 52.31 | C |
| ATOM | 1169 | CG | ASP B | 236 | 13.323 | 23.640 | −41.842 | 1.00 | 60.14 | C |
| ATOM | 1170 | OD1 | ASP B | 236 | 13.401 | 22.476 | −41.370 | 1.00 | 66.87 | O |
| ATOM | 1171 | OD2 | ASP B | 236 | 13.817 | 24.652 | −41.300 | 1.00 | 69.05 | O |
| ATOM | 1172 | C | ASP B | 236 | 11.069 | 21.980 | −43.665 | 1.00 | 50.32 | C |
| ATOM | 1173 | O | ASP B | 236 | 10.159 | 22.043 | −44.496 | 1.00 | 49.59 | O |
| ATOM | 1174 | N | GLY B | 237 | 10.927 | 21.381 | −42.489 | 1.00 | 50.34 | N |
| ATOM | 1175 | CA | GLY B | 237 | 9.674 | 20.749 | −42.115 | 1.00 | 50.19 | C |
| ATOM | 1176 | C | GLY B | 237 | 9.646 | 20.303 | −40.671 | 1.00 | 50.14 | C |
| ATOM | 1177 | O | GLY B | 237 | 10.691 | 20.155 | −40.030 | 1.00 | 49.26 | O |
| ATOM | 1178 | N | ILE B | 238 | 8.429 | 20.100 | −40.173 | 1.00 | 49.73 | N |
| ATOM | 1179 | CA | ILE B | 238 | 8.177 | 19.560 | −38.846 | 1.00 | 49.43 | C |
| ATOM | 1180 | CB | ILE B | 238 | 8.187 | 20.687 | −37.729 | 1.00 | 50.37 | C |
| ATOM | 1181 | CG1 | ILE B | 238 | 8.371 | 20.095 | −36.319 | 1.00 | 53.15 | C |
| ATOM | 1182 | CD | ILE B | 238 | 9.787 | 19.752 | −35.942 | 1.00 | 60.28 | C |
| ATOM | 1183 | CG2 | ILE B | 238 | 6.921 | 21.566 | −37.780 | 1.00 | 47.24 | C |
| ATOM | 1184 | C | ILE B | 238 | 6.857 | 18.775 | −38.872 | 1.00 | 48.95 | C |
| ATOM | 1185 | O | ILE B | 238 | 5.967 | 19.042 | −39.686 | 1.00 | 49.46 | O |
| ATOM | 1186 | N | PHE B | 239 | 6.753 | 17.769 | −38.019 | 1.00 | 48.51 | N |
| ATOM | 1187 | CA | PHE B | 239 | 5.461 | 17.179 | −37.736 | 1.00 | 47.90 | C |
| ATOM | 1188 | CB | PHE B | 239 | 5.584 | 15.689 | −37.427 | 1.00 | 47.31 | C |
| ATOM | 1189 | CG | PHE B | 239 | 5.787 | 14.840 | −38.645 | 1.00 | 48.53 | C |
| ATOM | 1190 | CD1 | PHE B | 239 | 7.070 | 14.434 | −39.019 | 1.00 | 48.18 | C |
| ATOM | 1191 | CE1 | PHE B | 239 | 7.269 | 13.655 | −40.160 | 1.00 | 46.03 | C |
| ATOM | 1192 | CZ | PHE B | 239 | 6.174 | 13.280 | −40.945 | 1.00 | 46.49 | C |
| ATOM | 1193 | CE2 | PHE B | 239 | 4.886 | 13.686 | −40.579 | 1.00 | 48.00 | C |
| ATOM | 1194 | CD2 | PHE B | 239 | 4.700 | 14.458 | −39.436 | 1.00 | 46.76 | C |
| ATOM | 1195 | C | PHE B | 239 | 4.860 | 17.958 | −36.578 | 1.00 | 47.07 | C |
| ATOM | 1196 | O | PHE B | 239 | 5.559 | 18.297 | −35.625 | 1.00 | 47.40 | O |
| ATOM | 1197 | N | SER B | 240 | 3.583 | 18.291 | −36.695 | 1.00 | 47.12 | N |
| ATOM | 1198 | CA | SER B | 240 | 2.854 | 18.979 | −35.624 | 1.00 | 47.37 | C |
| ATOM | 1199 | CB | SER B | 240 | 2.374 | 20.349 | −36.106 | 1.00 | 47.01 | C |
| ATOM | 1200 | OG | SER B | 240 | 1.281 | 20.217 | −36.996 | 1.00 | 58.27 | O |
| ATOM | 1201 | C | SER B | 240 | 1.684 | 18.134 | −35.070 | 1.00 | 46.00 | C |
| ATOM | 1202 | O | SER B | 240 | 1.275 | 17.153 | −35.692 | 1.00 | 45.92 | O |
| ATOM | 1203 | N | PRO B | 241 | 1.164 | 18.490 | −33.881 | 1.00 | 46.06 | N |
| ATOM | 1204 | CA | PRO B | 241 | 0.019 | 17.761 | −33.340 | 1.00 | 46.78 | C |
| ATOM | 1205 | CB | PRO B | 241 | 0.132 | 18.018 | −31.843 | 1.00 | 46.76 | C |
| ATOM | 1206 | CG | PRO B | 241 | 0.741 | 19.392 | −31.757 | 1.00 | 50.07 | C |
| ATOM | 1207 | CD | PRO B | 241 | 1.615 | 19.562 | −32.973 | 1.00 | 46.31 | C |
| ATOM | 1208 | C | PRO B | 241 | −1.316 | 18.290 | −33.909 | 1.00 | 46.85 | C |
| ATOM | 1209 | O | PRO B | 241 | −2.163 | 18.851 | −33.176 | 1.00 | 47.85 | O |
| ATOM | 1210 | N | GLY B | 242 | −1.481 | 18.115 | −35.213 | 1.00 | 44.24 | N |
| ATOM | 1211 | CA | GLY B | 242 | −2.675 | 18.571 | −35.918 | 1.00 | 43.00 | C |
| ATOM | 1212 | C | GLY B | 242 | −2.326 | 19.616 | −36.946 | 1.00 | 41.57 | C |
| ATOM | 1213 | O | GLY B | 242 | −1.437 | 20.438 | −36.732 | 1.00 | 42.68 | O |
| ATOM | 1214 | N | GLY B | 243 | −3.033 | 19.586 | −38.065 | 1.00 | 41.33 | N |
| ATOM | 1215 | CA | GLY B | 243 | −2.914 | 20.625 | −39.074 | 1.00 | 42.37 | C |
| ATOM | 1216 | C | GLY B | 243 | −3.377 | 21.985 | −38.593 | 1.00 | 43.08 | C |
| ATOM | 1217 | O | GLY B | 243 | −2.966 | 23.003 | −39.147 | 1.00 | 43.95 | O |
| | | | | | gad65.pdb | | | | | |
| ATOM | 1218 | N | ALA B | 244 | −4.247 | 22.019 | −37.585 | 1.00 | 42.86 | N |
| ATOM | 1219 | CA | ALA B | 244 | −4.629 | 23.306 | −36.984 | 1.00 | 44.21 | C |
| ATOM | 1220 | CB | ALA B | 244 | −5.757 | 23.141 | −35.954 | 1.00 | 42.46 | C |
| ATOM | 1221 | C | ALA B | 244 | −3.426 | 24.025 | −36.360 | 1.00 | 44.45 | C |
| ATOM | 1222 | O | ALA B | 244 | −3.319 | 25.240 | −36.458 | 1.00 | 44.53 | O |
| ATOM | 1223 | N | ILE B | 245 | −2.526 | 23.260 | −35.740 | 1.00 | 44.92 | N |
| ATOM | 1224 | CA | ILE B | 245 | −1.312 | 23.802 | −35.149 | 1.00 | 45.58 | C |
| ATOM | 1225 | CB | ILE B | 245 | −0.758 | 22.847 | −34.050 | 1.00 | 45.84 | C |
| ATOM | 1226 | CG1 | ILE B | 245 | −1.850 | 22.497 | −33.027 | 1.00 | 48.83 | C |
| ATOM | 1227 | CD | ILE B | 245 | −2.546 | 23.686 | −32.339 | 1.00 | 45.67 | C |
| ATOM | 1228 | CG2 | ILE B | 245 | 0.489 | 23.418 | −33.367 | 1.00 | 41.47 | C |

TABLE A-continued

| | | | | | | | | | |
|---|---|---|---|---|---|---|---|---|---|
| ATOM | 1229 | C | ILE B | 245 | −0.256 | 24.105 | −36.230 | 1.00 | 47.22 | C |
| ATOM | 1230 | O | ILE B | 245 | 0.502 | 25.079 | −36.102 | 1.00 | 47.26 | O |
| ATOM | 1231 | N | SER B | 246 | −0.215 | 23.268 | −37.280 | 1.00 | 48.30 | N |
| ATOM | 1232 | CA | SER B | 246 | 0.603 | 23.521 | −38.473 | 1.00 | 48.84 | C |
| ATOM | 1233 | CB | SER B | 246 | 0.455 | 22.411 | −39.517 | 1.00 | 48.41 | C |
| ATOM | 1234 | OG | SER B | 246 | 1.133 | 21.233 | −39.141 | 1.00 | 52.24 | O |
| ATOM | 1235 | C | SER B | 246 | 0.203 | 24.852 | −39.106 | 1.00 | 49.02 | C |
| ATOM | 1236 | O | SER B | 246 | 1.066 | 25.665 | −39.453 | 1.00 | 48.98 | O |
| ATOM | 1237 | N | ASN B | 247 | −1.105 | 25.070 | −39.259 | 1.00 | 48.81 | N |
| ATOM | 1238 | CA | ASN B | 247 | −1.590 | 26.377 | −39.692 | 1.00 | 48.99 | C |
| ATOM | 1239 | CB | ASN B | 247 | −3.115 | 26.430 | −39.838 | 1.00 | 47.63 | C |
| ATOM | 1240 | CG | ASN B | 247 | −3.640 | 25.598 | −40.996 | 1.00 | 45.44 | C |
| ATOM | 1241 | OD1 | ASN B | 247 | −4.789 | 25.152 | −40.960 | 1.00 | 53.29 | O |
| ATOM | 1242 | ND2 | ASN B | 247 | −2.824 | 25.386 | −42.018 | 1.00 | 39.37 | N |
| ATOM | 1243 | C | ASN B | 247 | −1.127 | 27.468 | −38.731 | 1.00 | 49.00 | C |
| ATOM | 1244 | O | ASN B | 247 | −0.677 | 28.519 | −39.166 | 1.00 | 50.80 | O |
| ATOM | 1245 | N | MET B | 248 | −1.229 | 27.216 | −37.434 | 1.00 | 48.75 | N |
| ATOM | 1246 | CA | MET B | 248 | −0.792 | 28.203 | −36.448 | 1.00 | 50.68 | C |
| ATOM | 1247 | CB | MET B | 248 | −1.135 | 27.755 | −35.026 | 1.00 | 50.17 | C |
| ATOM | 1248 | CG | MET B | 248 | −0.932 | 28.842 | −33.988 | 1.00 | 49.38 | C |
| ATOM | 1249 | SD | MET B | 248 | −1.102 | 28.243 | −32.300 | 1.00 | 56.31 | S |
| ATOM | 1250 | CE | MET B | 248 | 0.377 | 27.249 | −32.157 | 1.00 | 57.11 | C |
| ATOM | 1251 | C | MET B | 248 | 0.703 | 28.522 | −36.566 | 1.00 | 48.45 | C |
| ATOM | 1252 | O | MET B | 248 | 1.086 | 29.681 | −36.483 | 1.00 | 48.23 | O |
| ATOM | 1253 | N | TYR B | 249 | 1.525 | 27.487 | −36.758 | 1.00 | 47.26 | N |
| ATOM | 1254 | CA | TYR B | 249 | 2.969 | 27.640 | −36.992 | 1.00 | 45.79 | C |
| ATOM | 1255 | CB | TYR B | 249 | 3.655 | 26.282 | −37.148 | 1.00 | 46.30 | C |
| ATOM | 1256 | CG | TYR B | 249 | 3.749 | 25.434 | −35.910 | 1.00 | 49.26 | C |
| ATOM | 1257 | CD1 | TYR B | 249 | 3.650 | 25.994 | −34.640 | 1.00 | 56.70 | C |
| ATOM | 1258 | CE1 | TYR B | 249 | 3.762 | 25.208 | −33.491 | 1.00 | 60.10 | C |
| ATOM | 1259 | CZ | TYR B | 249 | 3.998 | 23.841 | −33.611 | 1.00 | 54.66 | C |
| ATOM | 1260 | OH | TYR B | 249 | 4.099 | 23.075 | −32.481 | 1.00 | 55.70 | O |
| ATOM | 1261 | CE2 | TYR B | 249 | 4.104 | 23.253 | −34.859 | 1.00 | 52.65 | C |
| ATOM | 1262 | CD2 | TYR B | 249 | 3.986 | 24.060 | −36.010 | 1.00 | 53.14 | C |
| ATOM | 1263 | C | TYR B | 249 | 3.286 | 28.468 | −38.237 | 1.00 | 44.00 | C |
| ATOM | 1264 | O | TYR B | 249 | 4.153 | 29.333 | −38.194 | 1.00 | 42.30 | O |
| ATOM | 1265 | N | ALA B | 250 | 2.598 | 28.183 | −39.343 | 1.00 | 43.33 | N |
| ATOM | 1266 | CA | ALA B | 250 | 2.801 | 28.926 | −40.590 | 1.00 | 45.26 | C |
| ATOM | 1267 | CB | ALA B | 250 | 1.886 | 28.382 | −41.700 | 1.00 | 43.76 | C |
| ATOM | 1268 | C | ALA B | 250 | 2.580 | 30.435 | −40.386 | 1.00 | 46.62 | C |
| ATOM | 1269 | O | ALA B | 250 | 3.381 | 31.262 | −40.830 | 1.00 | 46.09 | O |
| ATOM | 1270 | N | MET B | 251 | 1.501 | 30.774 | −39.685 | 1.00 | 47.97 | N |
| ATOM | 1271 | CA | MET B | 251 | 1.173 | 32.161 | −39.363 | 1.00 | 50.18 | C |
| ATOM | 1272 | CB | MET B | 251 | −0.205 | 32.208 | −38.703 | 1.00 | 50.18 | C |
| ATOM | 1273 | CG | MET B | 251 | −0.829 | 33.576 | −38.616 | 1.00 | 52.67 | C |
| ATOM | 1274 | SD | MET B | 251 | −2.514 | 33.480 | −37.972 | 1.00 | 54.71 | S |
| ATOM | 1275 | CE | MET B | 251 | −3.466 | 33.205 | −39.462 | 1.00 | 53.52 | C |
| ATOM | 1276 | C | MET B | 251 | 2.223 | 32.799 | −38.448 | 1.00 | 48.69 | C |
| ATOM | 1277 | O | MET B | 251 | 2.584 | 33.964 | −38.626 | 1.00 | 48.00 | O |
| ATOM | 1278 | N | MET B | 252 | 2.683 | 32.043 | −37.452 | 1.00 | 48.40 | N |
| ATOM | 1279 | CA | MET B | 252 | 3.775 | 32.487 | −36.585 | 1.00 | 49.08 | C |
| ATOM | 1280 | CB | MET B | 252 | 4.185 | 31.368 | −35.641 | 1.00 | 49.14 | C |
| ATOM | 1281 | CG | MET B | 252 | 3.571 | 31.450 | −34.294 | 1.00 | 53.56 | C |
| ATOM | 1282 | SD | MET B | 252 | 4.281 | 30.223 | −33.202 | 1.00 | 52.73 | S |
| ATOM | 1283 | CE | MET B | 252 | 5.952 | 30.827 | −33.059 | 1.00 | 47.45 | C |
| ATOM | 1284 | C | MET B | 252 | 4.993 | 32.874 | −37.404 | 1.00 | 47.17 | C |
| ATOM | 1285 | O | MET B | 252 | 5.552 | 33.954 | −37.218 | 1.00 | 46.49 | O |
| | | | | | gad65.pdb | | | | | |
| ATOM | 1286 | N | ILE B | 253 | 5.375 | 31.974 | −38.310 | 1.00 | 45.65 | N |
| ATOM | 1287 | CA | ILE B | 253 | 6.579 | 32.095 | −39.118 | 1.00 | 46.89 | C |
| ATOM | 1288 | CB | ILE B | 253 | 6.959 | 30.706 | −39.727 | 1.00 | 47.64 | C |
| ATOM | 1289 | CG1 | ILE B | 253 | 7.409 | 29.758 | −38.605 | 1.00 | 47.17 | C |
| ATOM | 1290 | CD | ILE B | 253 | 7.128 | 28.269 | −38.896 | 1.00 | 50.12 | C |
| ATOM | 1291 | CG2 | ILE B | 253 | 8.063 | 30.837 | −40.770 | 1.00 | 49.30 | C |
| ATOM | 1292 | C | ILE B | 253 | 6.484 | 33.185 | −40.200 | 1.00 | 46.00 | C |
| ATOM | 1293 | O | ILE B | 253 | 7.461 | 33.880 | −40.456 | 1.00 | 46.54 | O |
| ATOM | 1294 | N | ALA B | 254 | 5.318 | 33.329 | −40.831 | 1.00 | 44.28 | N |
| ATOM | 1295 | CA | ALA B | 254 | 5.082 | 34.432 | −41.775 | 1.00 | 43.36 | C |
| ATOM | 1296 | CB | ALA B | 254 | 3.708 | 34.310 | −42.405 | 1.00 | 43.55 | C |
| ATOM | 1297 | C | ALA B | 254 | 5.230 | 35.787 | −41.088 | 1.00 | 42.73 | C |
| ATOM | 1298 | O | ALA B | 254 | 5.796 | 36.721 | −41.664 | 1.00 | 43.30 | O |
| ATOM | 1299 | N | ARG B | 255 | 4.723 | 35.887 | −39.859 | 1.00 | 41.37 | N |
| ATOM | 1300 | CA | ARG B | 255 | 4.882 | 37.096 | −39.054 | 1.00 | 42.24 | C |
| ATOM | 1301 | CB | ARG B | 255 | 4.023 | 37.043 | −37.794 | 1.00 | 43.13 | C |
| ATOM | 1302 | CG | ARG B | 255 | 4.197 | 38.258 | −36.883 | 1.00 | 43.71 | C |
| ATOM | 1303 | CD | ARG B | 255 | 3.318 | 38.150 | −35.652 | 1.00 | 45.99 | C |
| ATOM | 1304 | NE | ARG B | 255 | 3.670 | 37.008 | −34.804 | 1.00 | 48.92 | N |
| ATOM | 1305 | CZ | ARG B | 255 | 2.986 | 36.640 | −33.725 | 1.00 | 45.12 | C |
| ATOM | 1306 | NH1 | ARG B | 255 | 1.907 | 37.319 | −33.354 | 1.00 | 41.51 | N |
| ATOM | 1307 | NH2 | ARG B | 255 | 3.384 | 35.595 | −33.020 | 1.00 | 44.30 | N |

TABLE A-continued

| | | | | | | | | | |
|---|---|---|---|---|---|---|---|---|---|
| ATOM | 1308 | C   | ARG B | 255 | 6.343  | 37.327 | −38.672 | 1.00 | 42.22 | C |
| ATOM | 1309 | O   | ARG B | 255 | 6.876  | 38.419 | −38.874 | 1.00 | 41.46 | O |
| ATOM | 1310 | N   | PHE B | 256 | 6.984  | 36.300 | −38.121 | 1.00 | 42.47 | N |
| ATOM | 1311 | CA  | PHE B | 256 | 8.368  | 36.419 | −37.740 | 1.00 | 43.49 | C |
| ATOM | 1312 | CB  | PHE B | 256 | 8.893  | 35.132 | −37.114 | 1.00 | 43.16 | C |
| ATOM | 1313 | CG  | PHE B | 256 | 10.367 | 35.175 | −36.803 | 1.00 | 43.83 | C |
| ATOM | 1314 | CD1 | PHE B | 256 | 10.829 | 35.807 | −35.657 | 1.00 | 41.98 | C |
| ATOM | 1315 | CE1 | PHE B | 256 | 12.190 | 35.860 | −35.376 | 1.00 | 45.42 | C |
| ATOM | 1316 | CZ  | PHE B | 256 | 13.101 | 35.278 | −36.249 | 1.00 | 41.79 | C |
| ATOM | 1317 | CE2 | PHE B | 256 | 12.649 | 34.642 | −37.400 | 1.00 | 45.11 | C |
| ATOM | 1318 | CD2 | PHE B | 256 | 11.291 | 34.592 | −37.670 | 1.00 | 47.94 | C |
| ATOM | 1319 | C   | PHE B | 256 | 9.223  | 36.842 | −38.935 | 1.00 | 44.55 | C |
| ATOM | 1320 | O   | PHE B | 256 | 10.141 | 37.633 | −38.780 | 1.00 | 44.02 | O |
| ATOM | 1321 | N   | LYS B | 257 | 8.898  | 36.334 | −40.121 | 1.00 | 46.16 | N |
| ATOM | 1322 | CA  | LYS B | 257 | 9.692  | 36.621 | −41.320 | 1.00 | 47.91 | C |
| ATOM | 1323 | CB  | LYS B | 257 | 9.278  | 35.712 | −42.493 | 1.00 | 47.38 | C |
| ATOM | 1324 | CG  | LYS B | 257 | 9.945  | 36.034 | −43.833 | 1.00 | 49.52 | C |
| ATOM | 1325 | CD  | LYS B | 257 | 11.455 | 35.748 | −43.828 | 1.00 | 44.56 | C |
| ATOM | 1326 | CE  | LYS B | 257 | 12.101 | 36.253 | −45.119 | 1.00 | 51.98 | C |
| ATOM | 1327 | NZ  | LYS B | 257 | 13.531 | 35.836 | −45.252 | 1.00 | 58.95 | N |
| ATOM | 1328 | C   | LYS B | 257 | 9.640  | 38.118 | −41.683 | 1.00 | 49.36 | C |
| ATOM | 1329 | O   | LYS B | 257 | 10.681 | 38.741 | −41.977 | 1.00 | 48.20 | O |
| ATOM | 1330 | N   | MET B | 258 | 8.441  | 38.696 | −41.606 | 1.00 | 50.15 | N |
| ATOM | 1331 | CA  | MET B | 258 | 8.242  | 40.117 | −41.887 | 1.00 | 50.94 | C |
| ATOM | 1332 | CB  | MET B | 258 | 6.794  | 40.383 | −42.285 | 1.00 | 49.75 | C |
| ATOM | 1333 | CG  | MET B | 258 | 6.618  | 41.569 | −43.215 | 1.00 | 54.78 | C |
| ATOM | 1334 | SD  | MET B | 258 | 4.966  | 41.619 | −43.955 | 1.00 | 56.68 | S |
| ATOM | 1335 | CE  | MET B | 258 | 5.109  | 40.355 | −45.224 | 1.00 | 56.32 | C |
| ATOM | 1336 | C   | MET B | 258 | 8.671  | 41.037 | −40.736 | 1.00 | 48.95 | C |
| ATOM | 1337 | O   | MET B | 258 | 9.138  | 42.147 | −40.975 | 1.00 | 49.36 | O |
| ATOM | 1338 | N   | PHE B | 259 | 8.528  | 40.573 | −39.498 | 1.00 | 47.12 | N |
| ATOM | 1339 | CA  | PHE B | 259 | 8.861  | 41.377 | −38.326 | 1.00 | 45.97 | C |
| ATOM | 1340 | CB  | PHE B | 259 | 7.596  | 42.045 | −37.754 | 1.00 | 46.07 | C |
| ATOM | 1341 | CG  | PHE B | 259 | 6.901  | 42.968 | −38.723 | 1.00 | 47.12 | C |
| ATOM | 1342 | CD1 | PHE B | 259 | 7.423  | 44.238 | −39.001 | 1.00 | 47.07 | C |
| ATOM | 1343 | CE1 | PHE B | 259 | 6.782  | 45.099 | −39.907 | 1.00 | 45.58 | C |
| ATOM | 1344 | CZ  | PHE B | 259 | 5.600  | 44.690 | −40.541 | 1.00 | 45.62 | C |
| ATOM | 1345 | CE2 | PHE B | 259 | 5.072  | 43.430 | −40.278 | 1.00 | 46.34 | C |
| ATOM | 1346 | CD2 | PHE B | 259 | 5.726  | 42.567 | −39.369 | 1.00 | 47.24 | C |
| ATOM | 1347 | C   | PHE B | 259 | 9.565  | 40.546 | −37.243 | 1.00 | 46.38 | C |
| ATOM | 1348 | O   | PHE B | 259 | 8.949  | 40.187 | −36.232 | 1.00 | 46.38 | O |
| ATOM | 1349 | N   | PRO B | 260 | 10.866 | 40.236 | −37.444 | 1.00 | 46.48 | N |
| ATOM | 1350 | CA  | PRO B | 260 | 11.535 | 39.370 | −36.469 | 1.00 | 46.21 | C |
| ATOM | 1351 | CB  | PRO B | 260 | 12.970 | 39.239 | −37.013 | 1.00 | 46.65 | C |
| ATOM | 1352 | CG  | PRO B | 260 | 13.130 | 40.324 | −38.038 | 1.00 | 46.40 | C |
| ATOM | 1353 | CD  | PRO B | 260 | 11.758 | 40.635 | −38.556 | 1.00 | 46.52 | C |
| | | | | | gad65.pdb | | | | | |
| ATOM | 1354 | C   | PRO B | 260 | 11.515 | 39.914 | −35.033 | 1.00 | 46.62 | C |
| ATOM | 1355 | O   | PRO B | 260 | 11.597 | 39.135 | −34.085 | 1.00 | 47.32 | O |
| ATOM | 1356 | N   | GLU B | 261 | 11.377 | 41.234 | −34.887 | 1.00 | 46.13 | N |
| ATOM | 1357 | CA  | GLU B | 261 | 11.282 | 41.888 | −33.578 | 1.00 | 45.36 | C |
| ATOM | 1358 | CB  | GLU B | 261 | 11.386 | 43.417 | −33.729 | 1.00 | 45.27 | C |
| ATOM | 1359 | CG  | GLU B | 261 | 10.189 | 44.107 | −34.426 | 1.00 | 48.66 | C |
| ATOM | 1360 | CD  | GLU B | 261 | 10.239 | 44.052 | −35.962 | 1.00 | 52.44 | C |
| ATOM | 1361 | OE1 | GLU B | 261 | 11.023 | 43.276 | −36.555 | 1.00 | 50.99 | O |
| ATOM | 1362 | OE2 | GLU B | 261 | 9.471  | 44.805 | −36.588 | 1.00 | 60.39 | O |
| ATOM | 1363 | C   | GLU B | 261 | 10.047 | 41.501 | −32.720 | 1.00 | 44.63 | C |
| ATOM | 1364 | O   | GLU B | 261 | 10.066 | 41.688 | −31.497 | 1.00 | 42.78 | O |
| ATOM | 1365 | N   | VAL B | 262 | 8.992  | 40.975 | −33.351 | 1.00 | 44.25 | N |
| ATOM | 1366 | CA  | VAL B | 262 | 7.782  | 40.560 | −32.611 | 1.00 | 45.10 | C |
| ATOM | 1367 | CB  | VAL B | 262 | 6.683  | 39.969 | −33.537 | 1.00 | 45.21 | C |
| ATOM | 1368 | CG1 | VAL B | 262 | 7.089  | 38.598 | −34.100 | 1.00 | 38.83 | C |
| ATOM | 1369 | CG2 | VAL B | 262 | 5.352  | 39.892 | −32.792 | 1.00 | 42.14 | C |
| ATOM | 1370 | C   | VAL B | 262 | 8.103  | 39.588 | −31.468 | 1.00 | 44.67 | C |
| ATOM | 1371 | O   | VAL B | 262 | 7.496  | 39.635 | −30.415 | 1.00 | 43.41 | O |
| ATOM | 1372 | N   | LYS B | 263 | 9.107  | 38.755 | −31.695 | 1.00 | 45.89 | N |
| ATOM | 1373 | CA  | LYS B | 263 | 9.547  | 37.734 | −30.762 | 1.00 | 46.59 | C |
| ATOM | 1374 | CB  | LYS B | 263 | 10.748 | 37.017 | −31.378 | 1.00 | 46.69 | C |
| ATOM | 1375 | CG  | LYS B | 263 | 11.126 | 35.705 | −30.728 | 1.00 | 45.23 | C |
| ATOM | 1376 | CD  | LYS B | 263 | 12.227 | 35.055 | −31.530 | 1.00 | 45.22 | C |
| ATOM | 1377 | CE  | LYS B | 263 | 12.921 | 33.999 | −30.721 | 1.00 | 51.40 | C |
| ATOM | 1378 | NZ  | LYS B | 263 | 13.796 | 33.147 | −31.576 | 1.00 | 54.34 | N |
| ATOM | 1379 | C   | LYS B | 263 | 9.923  | 38.330 | −29.411 | 1.00 | 46.39 | C |
| ATOM | 1380 | O   | LYS B | 263 | 9.557  | 37.793 | −28.357 | 1.00 | 46.89 | O |
| ATOM | 1381 | N   | GLU B | 264 | 10.648 | 39.445 | −29.455 | 1.00 | 45.08 | N |
| ATOM | 1382 | CA  | GLU B | 264 | 11.105 | 40.127 | −28.257 | 1.00 | 44.23 | C |
| ATOM | 1383 | CB  | GLU B | 264 | 12.456 | 40.807 | −28.538 | 1.00 | 44.39 | C |
| ATOM | 1384 | CG  | GLU B | 264 | 13.647 | 39.836 | −28.644 | 1.00 | 50.00 | C |
| ATOM | 1385 | CD  | GLU B | 264 | 13.809 | 39.224 | −30.040 | 1.00 | 60.15 | C |
| ATOM | 1386 | OE1 | GLU B | 264 | 13.193 | 39.729 | −31.010 | 1.00 | 59.33 | O |

TABLE A-continued

| | | | | | | | | | |
|---|---|---|---|---|---|---|---|---|---|
| ATOM | 1387 | OE2 | GLU B | 264 | 14.565 | 38.235 | −30.168 | 1.00 | 61.19 | O |
| ATOM | 1388 | C | GLU B | 264 | 10.086 | 41.165 | −27.767 | 1.00 | 43.49 | C |
| ATOM | 1389 | O | GLU B | 264 | 9.852 | 41.302 | −26.563 | 1.00 | 42.78 | O |
| ATOM | 1390 | N | LYS B | 265 | 9.474 | 41.878 | −28.707 | 1.00 | 42.86 | N |
| ATOM | 1391 | CA | LYS B | 265 | 8.711 | 43.070 | −28.383 | 1.00 | 45.38 | C |
| ATOM | 1392 | CB | LYS B | 265 | 9.103 | 44.210 | −29.324 | 1.00 | 45.50 | C |
| ATOM | 1393 | CG | LYS B | 265 | 10.562 | 44.619 | −29.191 | 1.00 | 54.38 | C |
| ATOM | 1394 | CD | LYS B | 265 | 10.935 | 45.724 | −30.158 | 1.00 | 63.47 | C |
| ATOM | 1395 | CE | LYS B | 265 | 12.165 | 46.475 | −29.667 | 1.00 | 67.77 | C |
| ATOM | 1396 | NZ | LYS B | 265 | 11.840 | 47.376 | −28.510 | 1.00 | 70.72 | N |
| ATOM | 1397 | C | LYS B | 265 | 7.193 | 42.878 | −28.386 | 1.00 | 46.56 | C |
| ATOM | 1398 | O | LYS B | 265 | 6.470 | 43.680 | −27.782 | 1.00 | 46.61 | O |
| ATOM | 1399 | N | GLY B | 266 | 6.719 | 41.831 | −29.058 | 1.00 | 47.13 | N |
| ATOM | 1400 | CA | GLY B | 266 | 5.285 | 41.559 | −29.142 | 1.00 | 48.01 | C |
| ATOM | 1401 | C | GLY B | 266 | 4.609 | 42.348 | −30.246 | 1.00 | 49.54 | C |
| ATOM | 1402 | O | GLY B | 266 | 5.248 | 43.174 | −30.925 | 1.00 | 49.84 | O |
| ATOM | 1403 | N | MET B | 267 | 3.313 | 42.092 | −30.426 | 1.00 | 49.85 | N |
| ATOM | 1404 | CA | MET B | 267 | 2.509 | 42.726 | −31.480 | 1.00 | 49.92 | C |
| ATOM | 1405 | CB | MET B | 267 | 1.111 | 42.102 | −31.539 | 1.00 | 50.21 | C |
| ATOM | 1406 | CG | MET B | 267 | 1.062 | 40.735 | −32.171 | 1.00 | 46.09 | C |
| ATOM | 1407 | SD | MET B | 267 | 1.380 | 40.696 | −33.942 | 1.00 | 45.66 | S |
| ATOM | 1408 | CE | MET B | 267 | 0.198 | 41.886 | −34.588 | 1.00 | 40.94 | C |
| ATOM | 1409 | C | MET B | 267 | 2.379 | 44.243 | −31.349 | 1.00 | 49.98 | C |
| ATOM | 1410 | O | MET B | 267 | 2.106 | 44.923 | −32.338 | 1.00 | 50.38 | O |
| ATOM | 1411 | N | ALA B | 268 | 2.572 | 44.770 | −30.139 | 1.00 | 49.89 | N |
| ATOM | 1412 | CA | ALA B | 268 | 2.521 | 46.219 | −29.902 | 1.00 | 50.50 | C |
| ATOM | 1413 | CB | ALA B | 268 | 2.636 | 46.521 | −28.425 | 1.00 | 51.08 | C |
| ATOM | 1414 | C | ALA B | 268 | 3.597 | 46.985 | −30.667 | 1.00 | 51.65 | C |
| ATOM | 1415 | O | ALA B | 268 | 3.460 | 48.195 | −30.885 | 1.00 | 53.05 | O |
| ATOM | 1416 | N | ALA B | 269 | 4.661 | 46.286 | −31.061 | 1.00 | 50.47 | N |
| ATOM | 1417 | CA | ALA B | 269 | 5.769 | 46.895 | −31.784 | 1.00 | 50.95 | C |
| ATOM | 1418 | CB | ALA B | 269 | 7.046 | 46.081 | −31.578 | 1.00 | 49.80 | C |
| ATOM | 1419 | C | ALA B | 269 | 5.475 | 46.999 | −33.270 | 1.00 | 50.96 | C |
| ATOM | 1420 | O | ALA B | 269 | 6.186 | 47.691 | −34.002 | 1.00 | 50.85 | O |
| ATOM | 1421 | N | LEU B | 270 | 4.445 | 46.289 | −33.722 | 1.00 | 50.22 | N |
| | | | | | gad65.pdb | | | | | |
| ATOM | 1422 | CA | LEU B | 270 | 4.259 | 46.107 | −35.152 | 1.00 | 49.38 | C |
| ATOM | 1423 | CB | LEU B | 270 | 3.972 | 44.635 | −35.476 | 1.00 | 49.99 | C |
| ATOM | 1424 | CG | LEU B | 270 | 4.852 | 43.516 | −34.897 | 1.00 | 45.84 | C |
| ATOM | 1425 | CD1 | LEU B | 270 | 4.626 | 42.243 | −35.682 | 1.00 | 45.85 | C |
| ATOM | 1426 | CD2 | LEU B | 270 | 6.321 | 43.849 | −34.843 | 1.00 | 48.64 | C |
| ATOM | 1427 | C | LEU B | 270 | 3.168 | 47.018 | −35.690 | 1.00 | 48.79 | C |
| ATOM | 1428 | O | LEU B | 270 | 2.390 | 47.573 | −34.908 | 1.00 | 48.49 | O |
| ATOM | 1429 | N | PRO B | 271 | 3.133 | 47.219 | −37.023 | 1.00 | 48.16 | N |
| ATOM | 1430 | CA | PRO B | 271 | 1.951 | 47.843 | −37.633 | 1.00 | 47.49 | C |
| ATOM | 1431 | CB | PRO B | 271 | 2.372 | 48.062 | −39.090 | 1.00 | 48.26 | C |
| ATOM | 1432 | CG | PRO B | 271 | 3.454 | 47.093 | −39.326 | 1.00 | 48.44 | C |
| ATOM | 1433 | CD | PRO B | 271 | 4.161 | 46.887 | −38.024 | 1.00 | 47.60 | C |
| ATOM | 1434 | C | PRO B | 271 | 0.801 | 46.849 | −37.562 | 1.00 | 46.88 | C |
| ATOM | 1435 | O | PRO B | 271 | 1.015 | 45.719 | −37.131 | 1.00 | 47.32 | O |
| ATOM | 1436 | N | ARG B | 272 | −0.393 | 47.243 | −37.984 | 1.00 | 47.31 | N |
| ATOM | 1437 | CA | ARG B | 272 | −1.519 | 46.314 | −37.959 | 1.00 | 47.81 | C |
| ATOM | 1438 | CB | ARG B | 272 | −2.871 | 47.030 | −37.992 | 1.00 | 48.03 | C |
| ATOM | 1439 | CG | ARG B | 272 | −4.039 | 46.068 | −37.777 | 1.00 | 49.71 | C |
| ATOM | 1440 | CD | ARG B | 272 | −5.392 | 46.746 | −37.896 | 1.00 | 57.19 | C |
| ATOM | 1441 | NE | ARG B | 272 | −6.446 | 45.743 | −38.033 | 1.00 | 60.66 | N |
| ATOM | 1442 | CZ | ARG B | 272 | −7.737 | 46.012 | −38.180 | 1.00 | 59.94 | C |
| ATOM | 1443 | NH1 | ARG B | 272 | −8.162 | 47.270 | −38.204 | 1.00 | 59.50 | N |
| ATOM | 1444 | NH2 | ARG B | 272 | −8.604 | 45.013 | −38.308 | 1.00 | 58.99 | N |
| ATOM | 1445 | C | ARG B | 272 | −1.406 | 45.318 | −39.103 | 1.00 | 47.97 | C |
| ATOM | 1446 | O | ARG B | 272 | −1.471 | 45.688 | −40.282 | 1.00 | 48.19 | O |
| ATOM | 1447 | N | LEU B | 273 | −1.218 | 44.058 | −38.722 | 1.00 | 47.35 | N |
| ATOM | 1448 | CA | LEU B | 273 | −1.050 | 42.951 | −39.652 | 1.00 | 47.11 | C |
| ATOM | 1449 | CB | LEU B | 273 | −0.320 | 41.809 | −38.962 | 1.00 | 46.07 | C |
| ATOM | 1450 | CG | LEU B | 273 | 1.195 | 41.619 | −39.042 | 1.00 | 49.88 | C |
| ATOM | 1451 | CD1 | LEU B | 273 | 1.972 | 42.888 | −38.790 | 1.00 | 49.09 | C |
| ATOM | 1452 | CD2 | LEU B | 273 | 1.581 | 40.535 | −38.046 | 1.00 | 47.03 | C |
| ATOM | 1453 | C | LEU B | 273 | −2.394 | 42.438 | −40.125 | 1.00 | 47.42 | C |
| ATOM | 1454 | O | LEU B | 273 | −3.344 | 42.343 | −39.339 | 1.00 | 47.58 | O |
| ATOM | 1455 | N | ILE B | 274 | −2.472 | 42.081 | −41.402 | 1.00 | 47.23 | N |
| ATOM | 1456 | CA | ILE B | 274 | −3.694 | 41.483 | −41.937 | 1.00 | 47.38 | C |
| ATOM | 1457 | CB | ILE B | 274 | −4.465 | 42.447 | −42.890 | 1.00 | 47.69 | C |
| ATOM | 1458 | CG1 | ILE B | 274 | −4.631 | 43.846 | −42.255 | 1.00 | 46.49 | C |
| ATOM | 1459 | CD | ILE B | 274 | −5.673 | 43.935 | −41.077 | 1.00 | 40.14 | C |
| ATOM | 1460 | CG2 | ILE B | 274 | −5.807 | 41.823 | −43.293 | 1.00 | 45.03 | C |
| ATOM | 1461 | C | ILE a | 274 | −3.380 | 40.192 | −42.668 | 1.00 | 47.33 | C |
| ATOM | 1462 | O | ILE B | 274 | −2.422 | 40.128 | −43.443 | 1.00 | 47.50 | O |
| ATOM | 1463 | N | ALA B | 275 | −4.206 | 39.178 | −42.399 | 1.00 | 47.67 | N |
| ATOM | 1464 | CA | ALA B | 275 | −4.146 | 37.875 | −43.045 | 1.00 | 47.99 | C |
| ATOM | 1465 | CB | ALA B | 275 | −4.017 | 36.768 | −41.992 | 1.00 | 47.03 | C |

TABLE A-continued

| | | | | | | | | | |
|---|---|---|---|---|---|---|---|---|---|
| ATOM | 1466 | C | ALA B | 275 | −5.417 | 37.688 | −43.864 | 1.00 | 49.18 | C |
| ATOM | 1467 | O | ALA B | 275 | −6.468 | 38.197 | −43.479 | 1.00 | 50.40 | O |
| ATOM | 1468 | N | PHE B | 276 | −5.324 | 36.955 | −44.976 | 1.00 | 49.10 | N |
| ATOM | 1469 | CA | PHE B | 276 | −6.475 | 36.699 | −45.864 | 1.00 | 48.40 | C |
| ATOM | 1470 | CB | PHE B | 276 | −6.279 | 37.402 | −47.208 | 1.00 | 48.25 | C |
| ATOM | 1471 | CG | PHE B | 276 | −5.954 | 38.859 | −47.085 | 1.00 | 48.44 | C |
| ATOM | 1472 | CD1 | PHE B | 276 | −4.639 | 39.280 | −46.925 | 1.00 | 43.18 | C |
| ATOM | 1473 | CE1 | PHE B | 276 | −4.334 | 40.614 | −46.785 | 1.00 | 41.80 | C |
| ATOM | 1474 | CZ | PHE B | 276 | −5.340 | 41.553 | −46.829 | 1.00 | 47.04 | C |
| ATOM | 1475 | CE2 | PHE B | 276 | −6.661 | 41.152 | −46.988 | 1.00 | 49.95 | C |
| ATOM | 1476 | CD2 | PHE B | 276 | −6.961 | 39.809 | −47.114 | 1.00 | 46.68 | C |
| ATOM | 1477 | C | PHE B | 276 | −6.688 | 35.207 | −46.115 | 1.00 | 48.40 | C |
| ATOM | 1478 | O | PHE B | 276 | −5.729 | 34.452 | −46.303 | 1.00 | 47.82 | O |
| ATOM | 1479 | N | THR B | 277 | −7.949 | 34.788 | −46.132 | 1.00 | 47.67 | N |
| ATOM | 1480 | CA | THR B | 277 | −8.287 | 33.385 | −46.351 | 1.00 | 46.86 | C |
| ATOM | 1481 | CB | THR B | 277 | −8.019 | 32.516 | −45.061 | 1.00 | 47.82 | C |
| ATOM | 1482 | OG1 | THR B | 277 | −8.123 | 31.123 | −45.374 | 1.00 | 50.44 | O |
| ATOM | 1483 | CG2 | THR B | 277 | −8.961 | 32.860 | −43.917 | 1.00 | 48.13 | C |
| ATOM | 1484 | C | THR B | 277 | −9.717 | 33.260 | −46.908 | 1.00 | 46.41 | C |
| ATOM | 1485 | O | THR B | 277 | −10.494 | 34.223 | −46.866 | 1.00 | 46.14 | O |
| ATOM | 1486 | N | SER B | 278 | −10.066 | 32.104 | −47.462 | 1.00 | 45.81 | N |
| ATOM | 1487 | CA | SER B | 278 | −11.355 | 32.006 | −48.141 | 1.00 | 47.59 | C |
| ATOM | 1488 | CB | SER B | 278 | −11.337 | 30.916 | −49.223 | 1.00 | 48.25 | C |
| ATOM | 1489 | OG | SER B | 278 | −11.834 | 29.677 | −48.744 | 1.00 | 49.80 | O |
| | | | | | gad65.pdb | | | | | |
| ATOM | 1490 | C | SER B | 278 | −12.507 | 31.797 | −47.162 | 1.00 | 48.31 | C |
| ATOM | 1491 | O | SER B | 278 | −12.300 | 31.293 | −46.044 | 1.00 | 47.38 | O |
| ATOM | 1492 | N | GLU B | 279 | −13.708 | 32.201 | −47.586 | 1.00 | 48.81 | N |
| ATOM | 1493 | CA | GLU B | 279 | −14.967 | 31.940 | −46.856 | 1.00 | 49.87 | C |
| ATOM | 1494 | CB | GLU B | 279 | −16.186 | 32.469 | −47.635 | 1.00 | 49.94 | C |
| ATOM | 1495 | CG | GLU B | 279 | −16.396 | 33.962 | −47.620 | 1.00 | 52.70 | C |
| ATOM | 1496 | CD | GLU B | 279 | −17.636 | 34.383 | −48.426 | 1.00 | 53.88 | C |
| ATOM | 1497 | OE1 | GLU B | 279 | −17.649 | 34.212 | −49.669 | 1.00 | 59.87 | O |
| ATOM | 1498 | OE2 | GLU B | 279 | −18.604 | 34.886 | −47.809 | 1.00 | 64.15 | O |
| ATOM | 1499 | C | GLU B | 279 | −15.191 | 30.456 | −46.621 | 1.00 | 48.23 | C |
| ATOM | 1500 | O | GLU B | 279 | −15.983 | 30.076 | −45.759 | 1.00 | 48.06 | O |
| ATOM | 1501 | N | HIS B | 280 | −14.511 | 29.624 | −47.407 | 1.00 | 47.66 | N |
| ATOM | 1502 | CA | HIS B | 280 | −14.637 | 28.169 | −47.311 | 1.00 | 46.52 | C |
| ATOM | 1503 | CB | HIS B | 280 | −14.747 | 27.570 | −48.713 | 1.00 | 45.88 | C |
| ATOM | 1504 | CG | HIS B | 280 | −16.139 | 27.597 | −49.269 | 1.00 | 46.95 | C |
| ATOM | 1505 | ND1 | HIS B | 280 | −16.796 | 28.769 | −49.575 | 1.00 | 50.55 | N |
| ATOM | 1506 | CE1 | HIS 8 | 280 | −18.002 | 28.486 | −50.035 | 1.00 | 50.70 | C |
| ATOM | 1507 | NE2 | HIS B | 280 | −18.148 | 27.173 | −50.039 | 1.00 | 48.80 | N |
| ATOM | 1508 | CD2 | HIS B | 280 | −16.996 | 26.594 | −49.570 | 1.00 | 41.79 | C |
| ATOM | 1509 | C | HIS B | 280 | −13.495 | 27.509 | −46.543 | 1.00 | 46.88 | C |
| ATOM | 1510 | O | HIS B | 280 | −13.421 | 26.275 | −46.467 | 1.00 | 47.01 | O |
| ATOM | 1511 | N | SER B | 281 | −12.619 | 28.329 | −45.964 | 1.00 | 46.02 | N |
| ATOM | 1512 | CA | SER B | 281 | −11.400 | 27.828 | −45.352 | 1.00 | 45.76 | C |
| ATOM | 1513 | CB | SER B | 281 | −10.255 | 28.856 | −45.457 | 1.00 | 45.48 | C |
| ATOM | 1514 | OG | SER B | 281 | −10.320 | 29.852 | −44.443 | 1.00 | 47.30 | O |
| ATOM | 1515 | C | SER B | 281 | −11.631 | 27.366 | −43.913 | 1.00 | 46.70 | C |
| ATOM | 1516 | O | SER B | 281 | −12.677 | 27.627 | −43.318 | 1.00 | 46.83 | O |
| ATOM | 1517 | N | HIS B | 282 | −10.642 | 26.661 | −43.370 | 1.00 | 46.40 | N |
| ATOM | 1518 | CA | HIS B | 282 | −10.762 | 26.004 | −42.085 | 1.00 | 44.66 | C |
| ATOM | 1519 | CB | HIS B | 282 | −9.667 | 24.941 | −41.951 | 1.00 | 44.20 | C |
| ATOM | 1520 | CG | HIS B | 282 | −9.879 | 23.997 | −40.811 | 1.00 | 45.79 | C |
| ATOM | 1521 | ND1 | HIS B | 282 | −9.253 | 24.150 | −39.592 | 1.00 | 43.96 | N |
| ATOM | 1522 | CE1 | HIS B | 282 | −9.625 | 23.175 | −38.785 | 1.00 | 41.34 | C |
| ATOM | 1523 | NE2 | HIS B | 282 | −10.465 | 22.393 | −39.438 | 1.00 | 38.04 | N |
| ATOM | 1524 | CD2 | HIS B | 282 | −10.649 | 22.890 | −40.703 | 1.00 | 43.47 | C |
| ATOM | 1525 | C | HIS B | 282 | −10.662 | 27.029 | −40.977 | 1.00 | 44.18 | C |
| ATOM | 1526 | O | HIS B | 282 | −9.887 | 27.965 | −41.089 | 1.00 | 45.29 | O |
| ATOM | 1527 | N | PHE B | 283 | −11.451 | 26.849 | −39.918 | 1.00 | 44.44 | N |
| ATOM | 1528 | CA | PHE B | 283 | −11.499 | 27.796 | −38.800 | 1.00 | 46.29 | C |
| ATOM | 1529 | CB | PHE B | 283 | −12.664 | 27.474 | −37.852 | 1.00 | 46.86 | C |
| ATOM | 1530 | CG | PHE B | 283 | −12.669 | 26.058 | −37.332 | 1.00 | 55.64 | C |
| ATOM | 1531 | CD1 | PHE B | 283 | −13.537 | 25.106 | −37.877 | 1.00 | 65.82 | C |
| ATOM | 1532 | CE1 | PHE B | 283 | −13.564 | 23.792 | −37.388 | 1.00 | 65.69 | C |
| ATOM | 1533 | CZ | PHE B | 283 | −12.714 | 23.425 | −36.343 | 1.00 | 57.17 | C |
| ATOM | 1534 | CE2 | PHE B | 283 | −11.857 | 24.366 | −35.791 | 1.00 | 57.85 | C |
| ATOM | 1535 | CD2 | PHE B | 283 | −11.839 | 25.675 | −36.282 | 1.00 | 54.46 | C |
| ATOM | 1536 | C | PHE B | 283 | −10.191 | 27.961 | −37.991 | 1.00 | 46.39 | C |
| ATOM | 1537 | O | PHE B | 283 | −10.094 | 28.870 | −37.178 | 1.00 | 47.34 | O |
| ATOM | 1538 | N | SER B | 284 | −9.198 | 27.104 | −38.227 | 1.00 | 45.18 | N |
| ATOM | 1539 | CA | SER B | 284 | −7.927 | 27.178 | −37.499 | 1.00 | 45.47 | C |
| ATOM | 1540 | CB | SER B | 284 | −7.023 | 25.954 | −37.782 | 1.00 | 45.39 | C |
| ATOM | 1541 | OG | SER B | 284 | −6.776 | 25.750 | −39.169 | 1.00 | 41.07 | O |
| ATOM | 1542 | C | SER B | 284 | −7.160 | 28.471 | −37.742 | 1.00 | 45.77 | C |
| ATOM | 1543 | O | SER B | 284 | −6.313 | 28.850 | −36.927 | 1.00 | 46.04 | O |
| ATOM | 1544 | N | LEU B | 285 | −7.461 | 29.144 | −38.851 | 1.00 | 46.30 | N |

TABLE A-continued

| | | | | | | | | | |
|---|---|---|---|---|---|---|---|---|---|
| ATOM | 1545 | CA | LEU B | 285 | −6.802 | 30.398 | −39.205 | 1.00 | 47.07 | C |
| ATOM | 1546 | CB | LEU B | 285 | −7.000 | 30.714 | −40.696 | 1.00 | 47.51 | C |
| ATOM | 1547 | CG | LEU B | 285 | −6.039 | 30.113 | −41.742 | 1.00 | 54.74 | C |
| ATOM | 1548 | CD1 | LEU B | 285 | −4.620 | 30.690 | −41.627 | 1.00 | 54.01 | C |
| ATOM | 1549 | CD2 | LEU B | 285 | −5.989 | 28.573 | −41.714 | 1.00 | 56.38 | C |
| ATOM | 1550 | C | LEU B | 285 | −7.255 | 31.561 | −38.309 | 1.00 | 48.26 | C |
| ATOM | 1551 | O | LEU B | 285 | −6.417 | 32.356 | −37.840 | 1.00 | 48.06 | O |
| ATOM | 1552 | N | LYS B | 286 | −8.567 | 31.660 | −38.069 | 1.00 | 48.98 | N |
| ATOM | 1553 | CA | LYS B | 286 | −9.118 | 32.627 | −37.107 | 1.00 | 49.27 | C |
| ATOM | 1554 | CB | LYS B | 286 | −10.662 | 32.626 | −37.108 | 1.00 | 50.50 | C |
| ATOM | 1555 | CG | LYS B | 286 | −11.340 | 33.231 | −38.317 | 1.00 | 52.94 | C |
| ATOM | 1556 | CD | LYS B | 286 | −11.494 | 34.735 | −38.184 | 1.00 | 52.87 | C |
| ATOM | 1557 | CE | LYS B | 286 | −12.342 | 35.327 | −39.301 | 1.00 | 54.36 | C |
| | | | | | gad65.pdb | | | | | |
| ATOM | 1558 | NZ | LYS B | 286 | −12.560 | 36.795 | −39.092 | 1.00 | 47.96 | N |
| ATOM | 1559 | C | LYS B | 286 | −8.630 | 32.259 | −35.708 | 1.00 | 48.44 | C |
| ATOM | 1560 | O | LYS B | 286 | −8.126 | 33.111 | −34.980 | 1.00 | 49.09 | O |
| ATOM | 1561 | N | LYS B | 287 | −8.782 | 30.992 | −35.335 | 1.00 | 47.53 | N |
| ATOM | 1562 | CA | LYS B | 287 | −8.319 | 30.518 | −34.022 | 1.00 | 48.15 | C |
| ATOM | 1563 | CB | LYS B | 287 | −8.587 | 29.026 | −33.852 | 1.00 | 48.91 | C |
| ATOM | 1564 | CG | LYS B | 287 | −9.897 | 28.701 | −33.168 | 1.00 | 54.35 | C |
| ATOM | 1565 | CD | LYS B | 287 | −9.933 | 27.255 | −32.718 | 1.00 | 62.29 | C |
| ATOM | 1566 | CE | LYS B | 287 | −11.244 | 26.939 | −31.999 | 1.00 | 66.39 | C |
| ATOM | 1567 | NZ | LYS B | 287 | −11.262 | 25.565 | −31.406 | 1.00 | 67.27 | N |
| ATOM | 1568 | C | LYS B | 287 | −6.833 | 30.790 | −33.774 | 1.00 | 47.46 | C |
| ATOM | 1569 | O | LYS B | 287 | −6.449 | 31.174 | −32.671 | 1.00 | 47.88 | O |
| ATOM | 1570 | N | GLY B | 288 | −6.008 | 30.577 | −34.798 | 1.00 | 45.75 | N |
| ATOM | 1571 | CA | GLY B | 288 | −4.576 | 30.847 | −34.712 | 1.00 | 45.74 | C |
| ATOM | 1572 | C | GLY B | 288 | −4.291 | 32.319 | −34.504 | 1.00 | 44.82 | C |
| ATOM | 1573 | O | GLY B | 288 | −3.466 | 32.683 | −33.667 | 1.00 | 44.52 | O |
| ATOM | 1574 | N | ALA B | 289 | −5.000 | 33.169 | −35.244 | 1.00 | 44.33 | N |
| ATOM | 1575 | CA | ALA B | 289 | −4.798 | 34.621 | −35.149 | 1.00 | 42.60 | C |
| ATOM | 1576 | CB | ALA B | 289 | −5.564 | 35.347 | −36.218 | 1.00 | 41.29 | C |
| ATOM | 1577 | C | ALA B | 289 | −5.162 | 35.145 | −33.762 | 1.00 | 42.31 | C |
| ATOM | 1578 | O | ALA B | 289 | −4.407 | 35.941 | −33.177 | 1.00 | 41.97 | O |
| ATOM | 1579 | N | ALA B | 290 | −6.311 | 34.701 | −33.246 | 1.00 | 41.23 | N |
| ATOM | 1580 | CA | ALA B | 290 | −6.712 | 35.004 | −31.876 | 1.00 | 41.60 | C |
| ATOM | 1581 | CB | ALA B | 290 | −8.062 | 34.344 | −31.541 | 1.00 | 41.81 | C |
| ATOM | 1582 | C | ALA B | 290 | −5.631 | 34.563 | −30.879 | 1.00 | 42.25 | C |
| ATOM | 1583 | O | ALA B | 290 | −5.195 | 35.356 | −30.032 | 1.00 | 43.42 | O |
| ATOM | 1584 | N | ALA B | 291 | −5.184 | 33.309 | −30.982 | 1.00 | 41.10 | N |
| ATOM | 1585 | CA | ALA B | 291 | −4.105 | 32.817 | −30.133 | 1.00 | 40.91 | C |
| ATOM | 1586 | CB | ALA B | 291 | −3.798 | 31.376 | −30.448 | 1.00 | 41.53 | C |
| ATOM | 1587 | C | ALA B | 291 | −2.835 | 33.666 | −30.262 | 1.00 | 41.26 | C |
| ATOM | 1588 | O | ALA B | 291 | −2.184 | 33.943 | −29.281 | 1.00 | 40.16 | O |
| ATOM | 1589 | N | LEU B | 292 | −2.488 | 34.091 | −31.468 | 1.00 | 43.65 | N |
| ATOM | 1590 | CA | LEU B | 292 | −1.182 | 34.747 | −31.683 | 1.00 | 44.07 | C |
| ATOM | 1591 | CB | LEU B | 292 | −0.680 | 34.498 | −33.104 | 1.00 | 45.31 | C |
| ATOM | 1592 | CG | LEU B | 292 | −0.461 | 33.056 | −33.580 | 1.00 | 46.88 | C |
| ATOM | 1593 | CD1 | LEU B | 292 | −0.067 | 33.094 | −35.053 | 1.00 | 49.78 | C |
| ATOM | 1594 | CD2 | LEU B | 292 | 0.559 | 32.276 | −32.761 | 1.00 | 50.10 | C |
| ATOM | 1595 | C | LEU B | 292 | −1.215 | 36.238 | −31.406 | 1.00 | 44.21 | C |
| ATOM | 1596 | O | LEU B | 292 | −0.244 | 36.953 | −31.682 | 1.00 | 44.60 | O |
| ATOM | 1597 | N | GLY B | 293 | −2.351 | 36.708 | −30.877 | 1.00 | 44.11 | N |
| ATOM | 1598 | CA | GLY B | 293 | −2.529 | 38.104 | −30.511 | 1.00 | 42.51 | C |
| ATOM | 1599 | C | GLY B | 293 | −2.644 | 38.974 | −31.739 | 1.00 | 43.82 | C |
| ATOM | 1600 | O | GLY B | 293 | −2.343 | 40.163 | −31.677 | 1.00 | 43.68 | O |
| ATOM | 1601 | N | ILE B | 294 | −3.068 | 38.376 | −32.856 | 1.00 | 44.09 | N |
| ATOM | 1602 | CA | ILE B | 294 | −3.269 | 39.103 | −34.115 | 1.00 | 44.91 | C |
| ATOM | 1603 | CB | ILE B | 294 | −2.911 | 38.198 | −35.342 | 1.00 | 45.99 | C |
| ATOM | 1604 | CG1 | ILE B | 294 | −1.388 | 38.108 | −35.513 | 1.00 | 48.13 | C |
| ATOM | 1605 | CD | ILE B | 294 | −0.907 | 36.913 | −36.325 | 1.00 | 45.36 | C |
| ATOM | 1606 | CG2 | ILE B | 294 | −3.517 | 38.717 | −36.630 | 1.00 | 42.19 | C |
| ATOM | 1607 | C | ILE B | 294 | −4.705 | 39.662 | −34.200 | 1.00 | 45.48 | C |
| ATOM | 1608 | O | ILE B | 294 | −4.916 | 40.743 | −34.742 | 1.00 | 45.66 | O |
| ATOM | 1609 | N | GLY B | 295 | −5.673 | 38.916 | −33.661 | 1.00 | 45.63 | N |
| ATOM | 1610 | CA | GLY B | 295 | −7.077 | 39.326 | −33.636 | 1.00 | 46.09 | C |
| ATOM | 1611 | C | GLY B | 295 | −7.823 | 38.772 | −34.827 | 1.00 | 46.35 | C |
| ATOM | 1612 | O | GLY B | 295 | −7.390 | 38.956 | −35.962 | 1.00 | 45.92 | O |
| ATOM | 1613 | N | THR B | 296 | −8.936 | 38.083 | −34.579 | 1.00 | 46.88 | N |
| ATOM | 1614 | CA | THR B | 296 | −9.800 | 37.603 | −35.667 | 1.00 | 47.54 | C |
| ATOM | 1615 | CB | THR B | 296 | −11.002 | 36.766 | −35.161 | 1.00 | 49.21 | C |
| ATOM | 1616 | OG1 | THR B | 296 | −11.825 | 37.570 | −34.309 | 1.00 | 45.09 | O |
| ATOM | 1617 | CG2 | THR B | 296 | −10.540 | 35.510 | −34.414 | 1.00 | 47.43 | C |
| ATOM | 1618 | C | THR B | 296 | −10.340 | 38.747 | −36.539 | 1.00 | 48.21 | C |
| ATOM | 1619 | O | THR B | 296 | −10.719 | 38.512 | −37.678 | 1.00 | 48.54 | O |
| ATOM | 1620 | N | ASP B | 297 | −10.374 | 39.975 | −36.016 | 1.00 | 48.85 | N |
| ATOM | 1621 | CA | ASP B | 297 | −10.746 | 41.136 | −36.845 | 1.00 | 50.67 | C |
| ATOM | 1622 | CB | ASP B | 297 | −10.852 | 42.427 | −36.018 | 1.00 | 52.60 | C |
| ATOM | 1623 | CG | ASP B | 297 | −12.138 | 42.522 | −35.226 | 1.00 | 54.36 | C |

TABLE A-continued

| | | | | | | | | | |
|---|---|---|---|---|---|---|---|---|---|
| ATOM | 1624 | OD1 | ASP B | 297 | −13.020 | 41.648 | −35.389 | 1.00 | 57.78 | O |
| ATOM | 1625 | OD2 | ASP B | 297 | −12.257 | 43.482 | −34.435 | 1.00 | 56.64 | O |
| | | | | | gad65.pdb | | | | | |
| ATOM | 1626 | C | ASP B | 297 | −9.753 | 41.378 | −37.980 | 1.00 | 49.49 | C |
| ATOM | 1627 | O | ASP B | 297 | −10.088 | 42.013 | −38.987 | 1.00 | 48.71 | O |
| ATOM | 1628 | N | SER B | 298 | −8.532 | 40.883 | −37.802 | 1.00 | 48.70 | N |
| ATOM | 1629 | CA | SER B | 298 | −7.481 | 41.092 | −38.792 | 1.00 | 48.98 | C |
| ATOM | 1630 | CB | SER B | 298 | −6.171 | 41.509 | −38.105 | 1.00 | 50.09 | C |
| ATOM | 1631 | OG | SER B | 298 | −6.331 | 42.771 | −37.459 | 1.00 | 51.26 | O |
| ATOM | 1632 | C | SER B | 298 | −7.294 | 39.882 | −39.705 | 1.00 | 48.06 | C |
| ATOM | 1633 | O | SER B | 298 | −6.315 | 39.801 | −40.438 | 1.00 | 47.60 | O |
| ATOM | 1634 | N | VAL B | 299 | −8.241 | 38.947 | −39.650 | 1.00 | 48.36 | N |
| ATOM | 1635 | CA | VAL B | 299 | −8.323 | 37.858 | −40.619 | 1.00 | 49.04 | C |
| ATOM | 1636 | CB | VAL B | 299 | −8.533 | 36.475 | −39.956 | 1.00 | 49.60 | C |
| ATOM | 1637 | CG1 | VAL B | 299 | −8.457 | 35.369 | −40.995 | 1.00 | 48.51 | C |
| ATOM | 1638 | CG2 | VAL B | 299 | −7.506 | 36.226 | −38.871 | 1.00 | 50.57 | C |
| ATOM | 1639 | C | VAL B | 299 | −9.494 | 38.154 | −41.542 | 1.00 | 49.54 | C |
| ATOM | 1640 | O | VAL B | 299 | −10.648 | 37.982 | −41.157 | 1.00 | 50.16 | O |
| ATOM | 1641 | N | ILE B | 300 | −9.193 | 38.608 | −42.754 | 1.00 | 48.93 | N |
| ATOM | 1642 | CA | ILE B | 300 | −10.233 | 38.962 | −43.721 | 1.00 | 49.11 | C |
| ATOM | 1643 | CB | ILE B | 300 | −9.797 | 40.147 | −44.635 | 1.00 | 48.52 | C |
| ATOM | 1644 | CG1 | ILE B | 300 | −9.266 | 41.335 | −43.815 | 1.00 | 46.09 | C |
| ATOM | 1645 | CD | ILE B | 300 | −10.263 | 41.975 | −42.854 | 1.00 | 52.61 | C |
| ATOM | 1646 | CG2 | ILE B | 300 | −10.940 | 40.556 | −45.574 | 1.00 | 47.79 | C |
| ATOM | 1647 | C | ILE B | 300 | −10.638 | 37.770 | −44.597 | 1.00 | 48.88 | C |
| ATOM | 1648 | O | ILE B | 300 | −9.788 | 37.106 | −45.196 | 1.00 | 48.36 | O |
| ATOM | 1649 | N | LEU B | 301 | −11.941 | 37.525 | −44.693 | 1.00 | 48.28 | N |
| ATOM | 1650 | CA | LEU B | 301 | −12.443 | 36.429 | −45.521 | 1.00 | 48.53 | C |
| ATOM | 1651 | CB | LEU B | 301 | −13.689 | 35.780 | −44.900 | 1.00 | 48.29 | C |
| ATOM | 1652 | CG | LEU B | 301 | −13.595 | 35.274 | −43.452 | 1.00 | 48.28 | C |
| ATOM | 1653 | CD1 | LEU B | 301 | −14.968 | 34.786 | −42.934 | 1.00 | 45.81 | C |
| ATOM | 1654 | CD2 | LEU B | 301 | −12.539 | 34.182 | −43.291 | 1.00 | 52.99 | C |
| ATOM | 1655 | C | LEU B | 301 | −12.706 | 36.871 | −46.956 | 1.00 | 48.50 | C |
| ATOM | 1656 | O | LEU B | 301 | −13.387 | 37.868 | −47.196 | 1.00 | 49.57 | O |
| ATOM | 1657 | N | ILE B | 302 | −12.137 | 36.136 | −47.904 | 1.00 | 48.52 | N |
| ATOM | 1658 | CA | ILE B | 302 | −12.277 | 36.454 | −49.321 | 1.00 | 48.85 | C |
| ATOM | 1659 | CB | ILE B | 302 | −10.947 | 36.216 | −50.118 | 1.00 | 48.91 | C |
| ATOM | 1660 | CG1 | ILE B | 302 | −9.962 | 37.338 | −49.831 | 1.00 | 47.06 | C |
| ATOM | 1661 | CD | ILE B | 302 | −9.231 | 37.181 | −48.568 | 1.00 | 56.85 | C |
| ATOM | 1662 | CG2 | ILE B | 302 | −11.171 | 36.237 | −51.625 | 1.00 | 45.54 | C |
| ATOM | 1663 | C | ILE B | 302 | −13.449 | 35.672 | −49.903 | 1.00 | 49.32 | C |
| ATOM | 1664 | O | ILE B | 302 | −13.648 | 34.512 | −49.558 | 1.00 | 48.48 | O |
| ATOM | 1665 | N | LYS B | 303 | −14.224 | 36.332 | −50.767 | 1.00 | 50.53 | N |
| ATOM | 1666 | CA | LYS B | 303 | −15.417 | 35.734 | −51.376 | 1.00 | 50.93 | C |
| ATOM | 1667 | CB | LYS B | 303 | −16.156 | 36.757 | −52.248 | 1.00 | 51.05 | C |
| ATOM | 1668 | CG | LYS B | 303 | −16.897 | 37.822 | −51.468 | 1.00 | 56.44 | C |
| ATOM | 1669 | C | LYS B | 303 | −15.068 | 34.505 | −52.203 | 1.00 | 50.53 | C |
| ATOM | 1670 | O | LYS B | 303 | −14.008 | 34.446 | −52.822 | 1.00 | 50.19 | O |
| ATOM | 1671 | N | CYS B | 304 | −15.957 | 33.518 | −52.190 | 1.00 | 50.72 | N |
| ATOM | 1672 | CA | CYS B | 304 | −15.793 | 32.336 | −53.020 | 1.00 | 51.56 | C |
| ATOM | 1673 | CB | CYS B | 304 | −15.782 | 31.075 | −52.161 | 1.00 | 51.04 | C |
| ATOM | 1674 | SG | CYS B | 304 | −14.386 | 31.024 | −51.026 | 1.00 | 57.35 | S |
| ATOM | 1675 | C | CYS B | 304 | −16.877 | 32.254 | −54.090 | 1.00 | 52.23 | C |
| ATOM | 1676 | O | CYS B | 304 | −17.955 | 32.847 | −53.949 | 1.00 | 52.85 | O |
| ATOM | 1677 | N | ASP B | 305 | −16.575 | 31.530 | −55.163 | 1.00 | 52.32 | N |
| ATOM | 1678 | CA | ASP B | 305 | −17.546 | 31.268 | −56.214 | 1.00 | 52.62 | C |
| ATOM | 1679 | CB | ASP B | 305 | −16.839 | 31.008 | −57.559 | 1.00 | 52.37 | C |
| ATOM | 1680 | CG | ASP B | 305 | −15.934 | 29.767 | −57.542 | 1.00 | 55.26 | C |
| ATOM | 1681 | OD1 | ASP B | 305 | −15.957 | 28.998 | −56.560 | 1.00 | 58.07 | O |
| ATOM | 1682 | OD2 | ASP B | 305 | −15.196 | 29.555 | −58.533 | 1.00 | 59.21 | O |
| ATOM | 1683 | C | ASP B | 305 | −18.481 | 30.113 | −55.824 | 1.00 | 52.93 | C |
| ATOM | 1684 | O | ASP B | 305 | −18.335 | 29.509 | −54.749 | 1.00 | 51.68 | O |
| ATOM | 1685 | N | GLU B | 306 | −19.428 | 29.815 | −56.717 | 1.00 | 53.78 | N |
| ATOM | 1686 | CA | GLU B | 306 | −20.424 | 28.751 | −56.541 | 1.00 | 54.88 | C |
| ATOM | 1687 | CB | GLU B | 306 | −21.376 | 28.734 | −57.762 | 1.00 | 56.18 | C |
| ATOM | 1688 | CG | GLU B | 306 | −22.060 | 27.388 | −58.106 | 1.00 | 63.64 | C |
| ATOM | 1689 | CD | GLU B | 306 | −23.367 | 27.123 | −57.344 | 1.00 | 69.87 | C |
| ATOM | 1690 | OE1 | GLU B | 306 | −23.601 | 27.728 | −56.268 | 1.00 | 72.64 | O |
| ATOM | 1691 | OE2 | GLU B | 306 | −24.166 | 26.287 | −57.829 | 1.00 | 69.72 | O |
| ATOM | 1692 | C | GLU B | 306 | −19.810 | 27.369 | −56.268 | 1.00 | 53.64 | C |
| ATOM | 1693 | O | GLU B | 306 | −20.448 | 26.513 | −55.646 | 1.00 | 53.91 | O |
| | | | | | gad65.pdb | | | | | |
| ATOM | 1694 | N | ARG B | 307 | −18.572 | 27.171 | −56.716 | 1.00 | 52.49 | N |
| ATOM | 1695 | CA | ARG B | 307 | −17.869 | 25.890 | −56.581 | 1.00 | 51.29 | C |
| ATOM | 1696 | CB | ARG B | 307 | −17.072 | 25.607 | −57.852 | 1.00 | 51.59 | C |
| ATOM | 1697 | CG | ARG B | 307 | −17.894 | 25.083 | −59.010 | 1.00 | 53.46 | C |
| ATOM | 1698 | CD | ARG B | 307 | −17.339 | 25.569 | −60.353 | 1.00 | 61.30 | C |
| ATOM | 1699 | NE | ARG B | 307 | −15.991 | 25.071 | −60.630 | 1.00 | 61.45 | N |
| ATOM | 1700 | C | ARG B | 307 | −16.955 | 25.801 | −55.347 | 1.00 | 50.68 | C |
| ATOM | 1701 | O | ARG B | 307 | −16.260 | 24.801 | −55.158 | 1.00 | 49.85 | O |

TABLE A-continued

| | | | | | | | | | |
|---|---|---|---|---|---|---|---|---|---|
| ATOM | 1702 | N | GLY B | 308 | −16.967 | 26.842 | −54.517 | 1.00 | 50.74 | N |
| ATOM | 1703 | CA | GLY B | 308 | −16.183 | 26.879 | −53.276 | 1.00 | 50.20 | C |
| ATOM | 1704 | C | GLY B | 308 | −14.786 | 27.500 | −53.365 | 1.00 | 49.81 | C |
| ATOM | 1705 | O | GLY B | 308 | −14.042 | 27.504 | −52.374 | 1.00 | 48.43 | O |
| ATOM | 1706 | N | LYS B | 309 | −14.432 | 28.032 | −54.537 | 1.00 | 49.53 | N |
| ATOM | 1707 | CA | LYS B | 309 | −13.075 | 28.561 | −54.775 | 1.00 | 50.34 | C |
| ATOM | 1708 | CB | LYS B | 309 | −12.588 | 28.260 | −56.200 | 1.00 | 49.14 | C |
| ATOM | 1709 | CG | LYS B | 309 | −12.645 | 26.818 | −56.630 | 1.00 | 45.80 | C |
| ATOM | 1710 | CD | LYS B | 309 | −12.368 | 26.727 | −58.119 | 1.00 | 48.61 | C |
| ATOM | 1711 | CE | LYS B | 309 | −12.892 | 25.434 | −58.731 | 1.00 | 47.53 | C |
| ATOM | 1712 | NZ | LYS B | 309 | −12.487 | 25.340 | −60.163 | 1.00 | 56.14 | N |
| ATOM | 1713 | C | LYS B | 309 | −12.977 | 30.063 | −54.552 | 1.00 | 52.23 | C |
| ATOM | 1714 | O | LYS B | 309 | −13.759 | 30.847 | −55.119 | 1.00 | 52.36 | O |
| ATOM | 1715 | N | MET B | 310 | −11.992 | 30.446 | −53.740 | 1.00 | 53.88 | N |
| ATOM | 1716 | CA | MET B | 310 | −11.587 | 31.842 | −53.544 | 1.00 | 56.12 | C |
| ATOM | 1717 | CB | MET B | 310 | −10.243 | 31.856 | −52.807 | 1.00 | 55.44 | C |
| ATOM | 1718 | CG | MET B | 310 | −9.553 | 33.204 | −52.659 | 1.00 | 59.11 | C |
| ATOM | 1719 | SD | MET B | 310 | −8.306 | 33.205 | −51.345 | 1.00 | 61.15 | S |
| ATOM | 1720 | CE | MET B | 310 | −7.146 | 31.967 | −51.925 | 1.00 | 67.07 | C |
| ATOM | 1721 | C | MET B | 310 | −11.514 | 32.623 | −54.874 | 1.00 | 54.72 | C |
| ATOM | 1722 | O | MET B | 310 | −10.890 | 32.160 | −55.825 | 1.00 | 53.86 | O |
| ATOM | 1723 | N | ILE B | 311 | −12.185 | 33.779 | −54.928 | 1.00 | 54.59 | N |
| ATOM | 1724 | CA | ILE B | 311 | −12.152 | 34.686 | −56.091 | 1.00 | 54.12 | C |
| ATOM | 1725 | CB | ILE B | 311 | −13.384 | 35.643 | −56.153 | 1.00 | 54.71 | C |
| ATOM | 1726 | CG1 | ILE B | 311 | −14.716 | 34.890 | −55.972 | 1.00 | 55.78 | C |
| ATOM | 1727 | CD | ILE B | 311 | −15.201 | 34.129 | −57.189 | 1.00 | 61.90 | C |
| ATOM | 1728 | CG2 | ILE B | 311 | −13.347 | 36.512 | −57.442 | 1.00 | 50.02 | C |
| ATOM | 1729 | C | ILE B | 311 | −10.896 | 35.564 | −56.058 | 1.00 | 53.59 | C |
| ATOM | 1730 | O | ILE B | 311 | −10.774 | 36.443 | −55.203 | 1.00 | 53.36 | O |
| ATOM | 1731 | N | PRO B | 312 | −9.963 | 35.339 | −56.996 | 1.00 | 53.74 | N |
| ATOM | 1732 | CA | PRO B | 312 | −8.698 | 36.084 | −57.005 | 1.00 | 54.08 | C |
| ATOM | 1733 | CB | PRO B | 312 | −8.031 | 35.615 | −58.302 | 1.00 | 54.43 | C |
| ATOM | 1734 | CG | PRO B | 312 | −8.597 | 34.252 | −58.531 | 1.00 | 54.13 | C |
| ATOM | 1735 | CD | PRO B | 312 | −10.025 | 34.363 | −58.101 | 1.00 | 53.49 | C |
| ATOM | 1736 | C | PRO B | 312 | −8.845 | 37.618 | −56.985 | 1.00 | 53.97 | C |
| ATOM | 1737 | O | PRO B | 312 | −8.021 | 38.297 | −56.364 | 1.00 | 53.46 | O |
| ATOM | 1738 | N | SER B | 313 | −9.886 | 38.148 | −57.634 | 1.00 | 53.52 | N |
| ATOM | 1739 | CA | SER B | 313 | −10.083 | 39.595 | −57.695 | 1.00 | 53.29 | C |
| ATOM | 1740 | CB | SER B | 313 | −10.909 | 40.013 | −58.928 | 1.00 | 53.76 | C |
| ATOM | 1741 | OG | SER B | 313 | −12.215 | 39.447 | −58.935 | 1.00 | 57.39 | O |
| ATOM | 1742 | C | SER B | 313 | −10.636 | 40.213 | −56.404 | 1.00 | 53.15 | C |
| ATOM | 1743 | O | SER B | 313 | −10.453 | 41.411 | −56.174 | 1.00 | 53.99 | O |
| ATOM | 1744 | N | ASP B | 314 | −11.304 | 39.416 | −55.567 | 1.00 | 51.88 | N |
| ATOM | 1745 | CA | ASP B | 314 | −11.727 | 39.899 | −54.251 | 1.00 | 50.82 | C |
| ATOM | 1746 | CB | ASP B | 314 | −12.856 | 39.044 | −53.656 | 1.00 | 51.06 | C |
| ATOM | 1747 | CG | ASP B | 314 | −13.616 | 39.769 | −52.534 | 1.00 | 56.00 | C |
| ATOM | 1748 | OD1 | ASP B | 314 | −14.022 | 40.936 | −52.742 | 1.00 | 59.90 | O |
| ATOM | 1749 | OD2 | ASP B | 314 | −13.812 | 39.177 | −51.444 | 1.00 | 58.52 | O |
| ATOM | 1750 | C | ASP B | 314 | −10.534 | 39.950 | −53.298 | 1.00 | 49.42 | C |
| ATOM | 1751 | O | ASP B | 314 | −10.488 | 40.780 | −52.390 | 1.00 | 48.38 | O |
| ATOM | 1752 | N | LEU B | 315 | −9.575 | 39.054 | −53.522 | 1.00 | 48.68 | N |
| ATOM | 1753 | CA | LEU B | 315 | −8.349 | 38.985 | −52.743 | 1.00 | 47.68 | C |
| ATOM | 1754 | CB | LEU B | 315 | −7.540 | 37.760 | −53.180 | 1.00 | 47.56 | C |
| ATOM | 1755 | CG | LEU B | 315 | −6.652 | 36.954 | −52.231 | 1.00 | 46.98 | C |
| ATOM | 1756 | CD1 | LEU B | 315 | −5.573 | 36.196 | −53.038 | 1.00 | 37.32 | C |
| ATOM | 1757 | CD2 | LEU B | 315 | −6.023 | 37.773 | −51.090 | 1.00 | 47.74 | C |
| ATOM | 1758 | C | LEU B | 315 | −7.524 | 40.252 | −52.961 | 1.00 | 48.41 | C |
| ATOM | 1759 | O | LEU B | 315 | −7.099 | 40.894 | −52.001 | 1.00 | 48.47 | O |
| ATOM | 1760 | N | GLU B | 316 | −7.296 | 40.599 | −54.230 | 1.00 | 48.70 | N |
| ATOM | 1761 | CA | GLU B | 316 | −6.552 | 41.802 | −54.599 | 1.00 | 48.79 | C |
| ATOM | 1762 | CB | GLU B | 316 | −6.326 | 41.844 | −56.110 | 1.00 | 48.36 | C |
| ATOM | 1763 | CG | GLU B | 316 | −5.519 | 43.037 | −56.585 | 1.00 | 53.17 | C |
| ATOM | 1764 | CD | GLU B | 316 | −4.902 | 42.851 | −57.967 | 1.00 | 57.48 | C |
| ATOM | 1765 | OE1 | GLU B | 316 | −3.915 | 43.555 | −58.268 | 1.00 | 54.87 | O |
| ATOM | 1766 | OE2 | GLU B | 316 | −5.395 | 42.012 | −58.754 | 1.00 | 61.30 | O |
| ATOM | 1767 | C | GLU B | 316 | −7.280 | 43.056 | −54.114 | 1.00 | 49.24 | C |
| ATOM | 1768 | O | GLU B | 316 | −6.665 | 43.944 | −53.521 | 1.00 | 49.61 | O |
| ATOM | 1769 | N | ARG B | 317 | −8.590 | 43.113 | −54.350 | 1.00 | 49.12 | N |
| ATOM | 1770 | CA | ARG B | 317 | −9.435 | 44.194 | −53.837 | 1.00 | 49.47 | C |
| ATOM | 1771 | CB | ARG B | 317 | −10.920 | 43.900 | −54.123 | 1.00 | 49.50 | C |
| ATOM | 1772 | CG | ARG B | 317 | −11.896 | 44.986 | −53.672 | 1.00 | 55.22 | C |
| ATOM | 1773 | CD | ARG B | 317 | −13.196 | 44.375 | −53.153 | 1.00 | 61.71 | C |
| ATOM | 1774 | NE | ARG B | 317 | −13.604 | 44.951 | −51.867 | 1.00 | 67.92 | N |
| ATOM | 1775 | CZ | ARG B | 317 | −14.209 | 44.273 | −50.885 | 1.00 | 73.64 | C |
| ATOM | 1776 | NH1 | ARG B | 317 | −14.477 | 42.976 | −51.016 | 1.00 | 70.10 | N |
| ATOM | 1777 | NH2 | ARG B | 317 | −14.533 | 44.887 | −49.752 | 1.00 | 72.43 | N |
| ATOM | 1778 | C | ARG B | 317 | −9.198 | 44.387 | −52.334 | 1.00 | 48.80 | C |
| ATOM | 1779 | O | ARG B | 317 | −8.956 | 45.501 | −51.874 | 1.00 | 48.83 | O |
| ATOM | 1780 | N | ARG B | 318 | −9.233 | 43.290 | −51.582 | 1.00 | 47.90 | N | gad65.pdb

TABLE A-continued

| | | | | | | | | | | |
|---|---|---|---|---|---|---|---|---|---|---|
| ATOM | 1781 | CA | ARG B | 318 | −9.065 | 43.350 | −50.134 | 1.00 | 47.16 | C |
| ATOM | 1782 | CB | ARG B | 318 | −9.531 | 42.046 | −49.488 | 1.00 | 47.29 | C |
| ATOM | 1783 | CG | ARG B | 318 | −11.051 | 41.833 | −49.578 | 1.00 | 43.68 | C |
| ATOM | 1784 | CD | ARG B | 318 | −11.779 | 42.842 | −48.733 | 1.00 | 47.92 | C |
| ATOM | 1785 | NE | ARG B | 318 | −12.868 | 42.220 | −47.986 | 1.00 | 55.20 | N |
| ATOM | 1786 | CZ | ARG B | 318 | −13.443 | 42.751 | −46.912 | 1.00 | 57.43 | C |
| ATOM | 1787 | NH1 | ARG B | 318 | −14.421 | 42.098 | −46.302 | 1.00 | 60.42 | N |
| ATOM | 1788 | NH2 | ARG B | 318 | −13.037 | 43.928 | −46.441 | 1.00 | 59.59 | N |
| ATOM | 1789 | C | ARG B | 318 | −7.651 | 43.739 | −49.683 | 1.00 | 46.71 | C |
| ATOM | 1790 | O | ARG B | 318 | −7.481 | 44.521 | −48.742 | 1.00 | 45.81 | O |
| ATOM | 1791 | N | ILE B | 319 | −6.643 | 43.195 | −50.364 | 1.00 | 47.00 | N |
| ATOM | 1792 | CA | ILE B | 319 | −5.253 | 43.558 | −50.112 | 1.00 | 47.82 | C |
| ATOM | 1793 | CB | ILE B | 319 | −4.293 | 42.770 | −51.025 | 1.00 | 47.66 | C |
| ATOM | 1794 | CG1 | ILE B | 319 | −4.337 | 41.285 | −50.680 | 1.00 | 48.94 | C |
| ATOM | 1795 | CD | ILE B | 319 | −3.684 | 40.413 | −51.724 | 1.00 | 52.13 | C |
| ATOM | 1796 | CG2 | ILE B | 319 | −2.857 | 43.280 | −50.894 | 1.00 | 48.77 | C |
| ATOM | 1797 | C | ILE B | 319 | −5.063 | 45.066 | −50.302 | 1.00 | 48.91 | C |
| ATOM | 1798 | O | ILE B | 319 | −4.458 | 45.735 | −49.453 | 1.00 | 49.45 | O |
| ATOM | 1799 | N | LEU B | 320 | −5.604 | 45.586 | −51.405 | 1.00 | 49.33 | N |
| ATOM | 1800 | CA | LEU B | 320 | −5.490 | 47.005 | −51.765 | 1.00 | 50.38 | C |
| ATOM | 1801 | CB | LEU B | 320 | −5.996 | 47.226 | −53.190 | 1.00 | 50.29 | C |
| ATOM | 1802 | CG | LEU B | 320 | −4.988 | 47.625 | −54.263 | 1.00 | 55.56 | C |
| ATOM | 1803 | CD1 | LEU B | 320 | −3.638 | 47.005 | −54.017 | 1.00 | 57.47 | C |
| ATOM | 1804 | CD2 | LEU B | 320 | −5.503 | 47.304 | −55.669 | 1.00 | 51.71 | C |
| ATOM | 1805 | C | LEU B | 320 | −6.190 | 47.958 | −50.794 | 1.00 | 49.74 | C |
| ATOM | 1806 | O | LEU B | 320 | −5.696 | 49.058 | −50.550 | 1.00 | 49.05 | O |
| ATOM | 1807 | N | GLU B | 321 | −7.337 | 47.537 | −50.259 | 1.00 | 50.25 | N |
| ATOM | 1808 | CA | GLU B | 321 | −8.029 | 48.256 | −49.177 | 1.00 | 51.94 | C |
| ATOM | 1809 | CB | GLU B | 321 | −9.387 | 47.609 | −48.858 | 1.00 | 51.98 | C |
| ATOM | 1810 | CG | GLU B | 321 | −10.459 | 47.846 | −49.912 | 1.00 | 53.37 | C |
| ATOM | 1811 | CD | GLU B | 321 | −11.765 | 47.126 | −49.627 | 1.00 | 54.37 | C |
| ATOM | 1812 | OE1 | GLU B | 321 | −12.696 | 47.245 | −50.463 | 1.00 | 61.14 | O |
| ATOM | 1813 | OE2 | GLU B | 321 | −11.874 | 46.453 | −48.570 | 1.00 | 61.36 | O |
| ATOM | 1814 | C | GLU B | 321 | −7.188 | 48.312 | −47.902 | 1.00 | 51.82 | C |
| ATOM | 1815 | O | GLU B | 321 | −7.086 | 49.374 | −47.281 | 1.00 | 51.98 | O |
| ATOM | 1816 | N | ALA B | 322 | −6.590 | 47.173 | −47.529 | 1.00 | 51.24 | N |
| ATOM | 1817 | CA | ALA B | 322 | −5.762 | 47.066 | −46.327 | 1.00 | 50.91 | C |
| ATOM | 1818 | CB | ALA B | 322 | −5.227 | 45.622 | −46.141 | 1.00 | 50.50 | C |
| ATOM | 1819 | C | ALA B | 322 | −4.608 | 48.061 | −46.327 | 1.00 | 50.84 | C |
| ATOM | 1820 | O | ALA B | 322 | −4.426 | 48.807 | −45.359 | 1.00 | 49.49 | O |
| ATOM | 1821 | N | LYS B | 323 | −3.835 | 48.077 | −47.413 | 1.00 | 52.02 | N |
| ATOM | 1822 | CA | LYS B | 323 | −2.702 | 49.004 | −47.517 | 1.00 | 53.04 | C |
| ATOM | 1823 | CB | LYS B | 323 | −1.617 | 48.510 | −48.475 | 1.00 | 53.04 | C |
| ATOM | 1824 | CG | LYS B | 323 | −2.038 | 47.463 | −49.479 | 1.00 | 54.75 | C |
| ATOM | 1825 | CD | LYS B | 323 | −0.900 | 46.479 | −49.730 | 1.00 | 42.43 | C |
| ATOM | 1826 | CE | LYS B | 323 | 0.352 | 47.172 | −50.265 | 1.00 | 44.16 | C |
| ATOM | 1827 | NZ | LYS B | 323 | 0.327 | 47.186 | −51.746 | 1.00 | 53.39 | N |
| ATOM | 1828 | C | LYS B | 323 | −3.082 | 50.438 | −47.823 | 1.00 | 54.26 | C |
| ATOM | 1829 | O | LYS B | 323 | −2.249 | 51.334 | −47.686 | 1.00 | 55.97 | O |
| | | | | | gad65.pdb | | | | | |
| ATOM | 1830 | N | GLN B | 324 | −4.330 | 50.662 | −48.227 | 1.00 | 55.00 | N |
| ATOM | 1831 | CA | GLN B | 324 | −4.856 | 52.016 | −48.386 | 1.00 | 55.26 | C |
| ATOM | 1832 | CB | GLN B | 324 | −6.203 | 51.990 | −49.123 | 1.00 | 55.79 | C |
| ATOM | 1833 | CG | GLN B | 324 | −6.471 | 53.200 | −50.007 | 1.00 | 59.44 | C |
| ATOM | 1834 | CD | GLN B | 324 | −6.751 | 54.475 | −49.218 | 1.00 | 64.45 | C |
| ATOM | 1835 | OE1 | GLN B | 324 | −7.686 | 54.532 | −48.415 | 1.00 | 62.52 | O |
| ATOM | 1836 | NE2 | GLN B | 324 | −5.941 | 55.509 | −49.454 | 1.00 | 59.86 | N |
| ATOM | 1837 | C | GLN B | 324 | −5.023 | 52.629 | −46.996 | 1.00 | 54.59 | C |
| ATOM | 1838 | O | GLN B | 324 | −4.708 | 53.803 | −46.774 | 1.00 | 54.93 | O |
| ATOM | 1839 | N | LYS B | 325 | −5.504 | 51.808 | −46.064 | 1.00 | 53.55 | N |
| ATOM | 1840 | CA | LYS B | 325 | −5.697 | 52.212 | −44.676 | 1.00 | 52.87 | C |
| ATOM | 1841 | CB | LYS B | 325 | −6.705 | 51.286 | −43.988 | 1.00 | 52.40 | C |
| ATOM | 1842 | CG | LYS B | 325 | −8.073 | 51.242 | −44.655 | 1.00 | 53.59 | C |
| ATOM | 1843 | CD | LYS B | 325 | −8.891 | 50.046 | −44.176 | 1.00 | 55.93 | C |
| ATOM | 1844 | CE | LYS B | 325 | −10.199 | 49.931 | −44.950 | 1.00 | 60.30 | C |
| ATOM | 1845 | NZ | LYS B | 325 | −11.196 | 49.048 | −44.267 | 1.00 | 67.02 | N |
| ATOM | 1846 | C | LYS B | 325 | −4.371 | 52.220 | −43.913 | 1.00 | 52.32 | C |
| ATOM | 1847 | O | LYS B | 325 | −4.326 | 52.567 | −42.728 | 1.00 | 52.29 | O |
| ATOM | 1848 | N | GLY B | 326 | −3.292 | 51.842 | −44.600 | 1.00 | 51.34 | N |
| ATOM | 1849 | CA | GLY B | 326 | −1.974 | 51.788 | −43.994 | 1.00 | 50.03 | C |
| ATOM | 1850 | C | GLY B | 326 | −1.791 | 50.549 | −43.138 | 1.00 | 50.37 | C |
| ATOM | 1851 | O | GLY B | 326 | −0.881 | 50.495 | −42.309 | 1.00 | 50.62 | O |
| ATOM | 1852 | N | PHE B | 327 | −2.663 | 49.557 | −43.331 | 1.00 | 50.22 | N |
| ATOM | 1853 | CA | PHE B | 327 | −2.513 | 48.248 | −42.695 | 1.00 | 49.53 | C |
| ATOM | 1854 | CB | PHE B | 327 | −3.862 | 47.527 | −42.582 | 1.00 | 49.44 | C |
| ATOM | 1855 | CG | PHE B | 327 | −4.900 | 48.269 | −41.769 | 1.00 | 50.23 | C |
| ATOM | 1856 | CD1 | PHE B | 327 | −6.245 | 47.966 | −41.918 | 1.00 | 47.27 | C |
| ATOM | 1857 | CE1 | PHE B | 327 | −7.215 | 48.635 | −41.175 | 1.00 | 53.27 | C |
| ATOM | 1858 | CZ | PHE B | 327 | −6.842 | 49.625 | −40.283 | 1.00 | 48.91 | C |
| ATOM | 1859 | CE2 | PHE B | 327 | −5.495 | 49.941 | −40.126 | 1.00 | 52.39 | C |

TABLE A-continued

| | | | | | | | | | |
|---|---|---|---|---|---|---|---|---|---|
| ATOM | 1860 | CD2 | PHE B | 327 | −4.535 | 49.270 | −40.866 | 1.00 | 49.59 | C |
| ATOM | 1861 | C | PHE B | 327 | −1.530 | 47.404 | −43.502 | 1.00 | 49.74 | C |
| ATOM | 1862 | O | PHE B | 327 | −1.277 | 47.691 | −44.674 | 1.00 | 50.61 | O |
| ATOM | 1863 | N | VAL B | 328 | −0.974 | 46.367 | −42.882 | 1.00 | 49.89 | N |
| ATOM | 1864 | CA | VAL B | 328 | 0.121 | 45.602 | −43.503 | 1.00 | 50.52 | C |
| ATOM | 1865 | CB | VAL B | 328 | 1.429 | 45.684 | −42.678 | 1.00 | 49.47 | C |
| ATOM | 1866 | CG1 | VAL B | 328 | 2.503 | 44.738 | −43.237 | 1.00 | 49.07 | C |
| ATOM | 1867 | CG2 | VAL B | 328 | 1.940 | 47.109 | −42.669 | 1.00 | 51.96 | C |
| ATOM | 1868 | C | VAL B | 328 | −0.271 | 44.146 | −43.755 | 1.00 | 50.72 | C |
| ATOM | 1869 | O | VAL B | 328 | −0.358 | 43.350 | −42.816 | 1.00 | 50.97 | O |
| ATOM | 1870 | N | PRO B | 329 | −0.526 | 43.803 | −45.029 | 1.00 | 50.67 | N |
| ATOM | 1871 | CA | PRO B | 329 | −0.758 | 42.411 | −45.412 | 1.00 | 49.94 | C |
| ATOM | 1872 | CB | PRO B | 329 | −1.001 | 42.500 | −46.921 | 1.00 | 50.20 | C |
| ATOM | 1873 | CG | PRO B | 329 | −1.430 | 43.916 | −47.161 | 1.00 | 48.97 | C |
| ATOM | 1874 | CD | PRO B | 329 | −0.626 | 44.715 | −46.186 | 1.00 | 50.68 | C |
| ATOM | 1875 | C | PRO B | 329 | 0.487 | 41.597 | −45.136 | 1.00 | 48.92 | C |
| ATOM | 1876 | O | PRO B | 329 | 1.569 | 41.968 | −45.596 | 1.00 | 50.39 | O |
| ATOM | 1877 | N | PHE B | 330 | 0.347 | 40.525 | −44.359 | 1.00 | 48.15 | N |
| ATOM | 1878 | CA | PHE B | 330 | 1.481 | 39.625 | −44.065 | 1.00 | 47.02 | C |
| ATOM | 1879 | CB | PHE B | 330 | 1.900 | 39.673 | −42.578 | 1.00 | 45.82 | C |
| ATOM | 1880 | CG | PHE B | 330 | 1.103 | 38.748 | −41.660 | 1.00 | 50.83 | C |
| ATOM | 1881 | CD1 | PHE B | 330 | 1.687 | 37.587 | −41.131 | 1.00 | 44.25 | C |
| ATOM | 1882 | CE1 | PHE B | 330 | 0.970 | 36.749 | −40.264 | 1.00 | 45.08 | C |
| ATOM | 1883 | CZ | PHE B | 330 | −0.338 | 37.063 | −39.920 | 1.00 | 45.20 | C |
| ATOM | 1884 | CE2 | PHE B | 330 | −0.928 | 38.221 | −40.432 | 1.00 | 46.96 | C |
| ATOM | 1885 | CD2 | PHE B | 330 | −0.209 | 39.057 | −41.290 | 1.00 | 46.59 | C |
| ATOM | 1886 | C | PHE B | 330 | 1.237 | 38.196 | −44.511 | 1.00 | 45.92 | C |
| ATOM | 1887 | O | PHE B | 330 | 2.174 | 37.439 | −44.657 | 1.00 | 46.70 | O |
| ATOM | 1888 | N | LEU B | 331 | −0.020 | 37.829 | −44.727 | 1.00 | 46.30 | N |
| ATOM | 1889 | CA | LEU B | 331 | −0.354 | 36.439 | −45.018 | 1.00 | 45.94 | C |
| ATOM | 1890 | CB | LEU B | 331 | −0.543 | 35.660 | −43.707 | 1.00 | 45.83 | C |
| ATOM | 1891 | CG | LEU B | 331 | −0.945 | 34.178 | −43.765 | 1.00 | 48.94 | C |
| ATOM | 1892 | CD1 | LEU B | 331 | 0.186 | 33.303 | −44.317 | 1.00 | 42.70 | C |
| ATOM | 1893 | CD2 | LEU B | 331 | −1.343 | 33.742 | −42.378 | 1.00 | 45.89 | C |
| ATOM | 1894 | C | LEU B | 331 | −1.570 | 36.251 | −45.915 | 1.00 | 46.00 | C |
| ATOM | 1895 | O | LEU B | 331 | −2.624 | 36.844 | −45.693 | 1.00 | 47.23 | O |
| ATOM | 1896 | N | VAL B | 332 | −1.423 | 35.418 | −46.935 | 1.00 | 45.66 | N |
| ATOM | 1897 | CA | VAL B | 332 | −2.606 | 34.825 | −47.545 | 1.00 | 46.46 | C |
| | | | | | gad65.pdb | | | | | |
| ATOM | 1898 | CB | VAL B | 332 | −3.010 | 35.426 | −48.950 | 1.00 | 46.57 | C |
| ATOM | 1899 | CG1 | VAL B | 332 | −1.930 | 36.315 | −49.524 | 1.00 | 45.29 | C |
| ATOM | 1900 | CG2 | VAL B | 332 | −3.504 | 34.356 | −49.935 | 1.00 | 48.77 | C |
| ATOM | 1901 | C | VAL B | 332 | −2.558 | 33.306 | −47.468 | 1.00 | 47.16 | C |
| ATOM | 1902 | O | VAL B | 332 | −1.567 | 32.667 | −47.828 | 1.00 | 47.49 | O |
| ATOM | 1903 | N | SER B | 333 | −3.628 | 32.757 | −46.911 | 1.00 | 47.37 | N |
| ATOM | 1904 | CA | SER B | 333 | −3.777 | 31.333 | −46.773 | 1.00 | 47.52 | C |
| ATOM | 1905 | CB | SER B | 333 | −4.223 | 31.005 | −45.352 | 1.00 | 47.12 | C |
| ATOM | 1906 | OG | SER B | 333 | −3.994 | 29.643 | −45.067 | 1.00 | 45.90 | O |
| ATOM | 1907 | C | SER B | 333 | −4.777 | 30.806 | −47.801 | 1.00 | 47.73 | C |
| ATOM | 1908 | O | SER B | 333 | −5.962 | 31.136 | −47.764 | 1.00 | 48.82 | O |
| ATOM | 1909 | N | ALA B | 334 | −4.279 | 30.007 | −48.731 | 1.00 | 47.20 | N |
| ATOM | 1910 | CA | ALA B | 334 | −5.111 | 29.398 | −49.750 | 1.00 | 48.25 | C |
| ATOM | 1911 | CB | ALA B | 334 | −4.422 | 29.463 | −51.112 | 1.00 | 47.50 | C |
| ATOM | 1912 | C | ALA B | 334 | −5.381 | 27.955 | −49.348 | 1.00 | 49.22 | C |
| ATOM | 1913 | O | ALA B | 334 | −4.516 | 27.295 | −48.761 | 1.00 | 51.52 | O |
| ATOM | 1914 | N | THR B | 335 | −6.578 | 27.470 | −49.648 | 1.00 | 48.21 | N |
| ATOM | 1915 | CA | THR B | 335 | −6.978 | 26.128 | −49.232 | 1.00 | 47.71 | C |
| ATOM | 1916 | CB | THR B | 335 | −8.363 | 26.135 | −48.527 | 1.00 | 47.88 | C |
| ATOM | 1917 | OG1 | THR B | 335 | −8.343 | 27.047 | −47.411 | 1.00 | 43.57 | O |
| ATOM | 1918 | CG2 | THR B | 335 | −8.730 | 24.732 | −48.021 | 1.00 | 48.24 | C |
| ATOM | 1919 | C | THR B | 335 | −6.972 | 25.186 | −50.431 | 1.00 | 48.50 | C |
| ATOM | 1920 | O | THR B | 335 | −7.621 | 25.438 | −51.455 | 1.00 | 49.50 | O |
| ATOM | 1921 | N | ALA B | 336 | −6.200 | 24.117 | −50.310 | 1.00 | 47.90 | N |
| ATOM | 1922 | CA | ALA B | 336 | −6.150 | 23.086 | −51.325 | 1.00 | 47.66 | C |
| ATOM | 1923 | CB | ALA B | 336 | −4.704 | 22.678 | −51.584 | 1.00 | 48.52 | C |
| ATOM | 1924 | C | ALA B | 336 | −6.986 | 21.895 | −50.869 | 1.00 | 46.20 | C |
| ATOM | 1925 | O | ALA B | 336 | −6.456 | 20.890 | −50.374 | 1.00 | 46.26 | O |
| ATOM | 1926 | N | GLY B | 337 | −8.298 | 22.010 | −51.031 | 1.00 | 44.65 | N |
| ATOM | 1927 | CA | GLY B | 337 | −9.203 | 20.977 | −50.545 | 1.00 | 44.57 | C |
| ATOM | 1928 | C | GLY B | 337 | −9.899 | 21.406 | −49.266 | 1.00 | 43.85 | C |
| ATOM | 1929 | O | GLY 8 | 337 | −9.411 | 21.162 | −48.156 | 1.00 | 42.85 | O |
| ATOM | 1930 | N | THR B | 338 | −11.047 | 22.055 | −49.430 | 1.00 | 43.19 | N |
| ATOM | 1931 | CA | THR B | 338 | −11.825 | 22.516 | −48.303 | 1.00 | 43.87 | C |
| ATOM | 1932 | CB | THR B | 338 | −12.861 | 23.575 | −48.707 | 1.00 | 44.53 | C |
| ATOM | 1933 | OG1 | THR B | 338 | −13.766 | 23.002 | −49.655 | 1.00 | 41.38 | O |
| ATOM | 1934 | CG2 | THR B | 338 | −12.171 | 24.815 | −49.301 | 1.00 | 45.89 | C |
| ATOM | 1935 | C | THR B | 338 | −12.556 | 21.350 | −47.681 | 1.00 | 44.74 | C |
| ATOM | 1936 | O | THR B | 338 | −12.860 | 20.353 | −48.344 | 1.00 | 45.18 | O |
| ATOM | 1937 | N | THR B | 339 | −12.836 | 21.509 | −46.399 | 1.00 | 44.87 | N |
| ATOM | 1938 | CA | THR B | 339 | −13.500 | 20.510 | −45.562 | 1.00 | 47.26 | C |

TABLE A-continued

| | | | | | | | | | |
|---|---|---|---|---|---|---|---|---|---|
| ATOM | 1939 | CB | THR B | 339 | −13.496 | 21.037 | −44.130 | 1.00 | 47.22 | C |
| ATOM | 1940 | OG1 | THR B | 339 | −12.244 | 20.674 | −43.538 | 1.00 | 52.79 | O |
| ATOM | 1941 | CG2 | THR B | 339 | −14.643 | 20.505 | −43.318 | 1.00 | 53.50 | C |
| ATOM | 1942 | C | THR B | 339 | −14.915 | 20.102 | −46.014 | 1.00 | 46.42 | C |
| ATOM | 1943 | O | THR B | 339 | −15.286 | 18.937 | −45.903 | 1.00 | 46.14 | O |
| ATOM | 1944 | N | VAL B | 340 | −15.689 | 21.051 | −46.542 | 1.00 | 45.50 | N |
| ATOM | 1945 | CA | VAL B | 340 | −17.053 | 20.740 | −46.965 | 1.00 | 45.04 | C |
| ATOM | 1946 | CB | VAL B | 340 | −18.059 | 21.831 | −46.524 | 1.00 | 46.18 | C |
| ATOM | 1947 | CG1 | VAL B | 340 | −19.501 | 21.382 | −46.789 | 1.00 | 44.04 | C |
| ATOM | 1948 | CG2 | VAL B | 340 | −17.857 | 22.159 | −45.029 | 1.00 | 43.32 | C |
| ATOM | 1949 | C | VAL B | 340 | −17.128 | 20.403 | −48.464 | 1.00 | 44.76 | C |
| ATOM | 1950 | O | VAL B | 340 | −17.304 | 19.238 | −48.820 | 1.00 | 43.13 | O |
| ATOM | 1951 | N | TYR B | 341 | −16.952 | 21.401 | −49.332 | 1.00 | 45.18 | N |
| ATOM | 1952 | CA | TYR B | 341 | −17.047 | 21.182 | −50.782 | 1.00 | 46.11 | C |
| ATOM | 1953 | CB | TYR B | 341 | −17.130 | 22.520 | −51.531 | 1.00 | 47.45 | C |
| ATOM | 1954 | CG | TYR B | 341 | −18.467 | 23.252 | −51.488 | 1.00 | 48.39 | C |
| ATOM | 1955 | CD1 | TYR B | 341 | −18.724 | 24.298 | −52.378 | 1.00 | 47.83 | C |
| ATOM | 1956 | CE1 | TYR B | 341 | −19.922 | 24.991 | −52.351 | 1.00 | 48.38 | C |
| ATOM | 1957 | CZ | TYR B | 341 | −20.892 | 24.635 | −51.436 | 1.00 | 47.70 | C |
| ATOM | 1958 | OH | TYR B | 341 | −22.077 | 25.319 | −51.417 | 1.00 | 55.19 | O |
| ATOM | 1959 | CE2 | TYR B | 341 | −20.677 | 23.599 | −50.541 | 1.00 | 49.52 | C |
| ATOM | 1960 | CD2 | TYR B | 341 | −19.462 | 22.912 | −50.569 | 1.00 | 45.49 | C |
| ATOM | 1961 | C | TYR B | 341 | −15.874 | 20.366 | −51.351 | 1.00 | 45.62 | C |
| ATOM | 1962 | O | TYR B | 341 | −15.984 | 19.779 | −52.429 | 1.00 | 46.73 | O |
| ATOM | 1963 | N | GLY B | 342 | −14.754 | 20.339 | −50.636 | 1.00 | 44.01 | N |
| ATOM | 1964 | CA | GLY B | 342 | −13.534 | 19.751 | −51.172 | 1.00 | 44.35 | C |
| ATOM | 1965 | C | GLY B | 342 | −12.959 | 20.621 | −52.281 | 1.00 | 43.73 | C |
| | | | | | gad65.pdb | | | | | |
| ATOM | 1966 | O | GLY B | 342 | −12.320 | 20.113 | −53.187 | 1.00 | 44.93 | O |
| ATOM | 1967 | N | ALA B | 343 | −13.203 | 21.930 | −52.207 | 1.00 | 43.64 | N |
| ATOM | 1968 | CA | ALA B | 343 | −12.790 | 22.880 | −53.250 | 1.00 | 43.88 | C |
| ATOM | 1969 | CB | ALA B | 343 | −13.623 | 24.153 | −53.173 | 1.00 | 42.20 | C |
| ATOM | 1970 | C | ALA B | 343 | −11.311 | 23.228 | −53.163 | 1.00 | 44.05 | C |
| ATOM | 1971 | O | ALA B | 343 | −10.724 | 23.206 | −52.080 | 1.00 | 45.82 | O |
| ATOM | 1972 | N | PHE B | 344 | −10.730 | 23.580 | −54.302 | 1.00 | 43.77 | N |
| ATOM | 1973 | CA | PHE B | 344 | −9.310 | 23.910 | −54.401 | 1.00 | 44.27 | C |
| ATOM | 1974 | CB | PHE B | 344 | −8.604 | 22.971 | −55.393 | 1.00 | 43.48 | C |
| ATOM | 1975 | CG | PHE B | 344 | −8.409 | 21.564 | −54.875 | 1.00 | 44.71 | C |
| ATOM | 1976 | CD1 | PHE B | 344 | −9.437 | 20.627 | −54.952 | 1.00 | 44.03 | C |
| ATOM | 1977 | CE1 | PHE B | 344 | −9.256 | 19.323 | −54.470 | 1.00 | 42.86 | C |
| ATOM | 1978 | CZ | PHE B | 344 | −8.037 | 18.949 | −53.909 | 1.00 | 42.83 | C |
| ATOM | 1979 | CE2 | PHE B | 344 | −7.004 | 19.869 | −53.834 | 1.00 | 38.18 | C |
| ATOM | 1980 | CD2 | PHE B | 344 | −7.193 | 21.172 | −54.318 | 1.00 | 43.36 | C |
| ATOM | 1981 | C | PHE B | 344 | −9.180 | 25.342 | −54.864 | 1.00 | 44.45 | C |
| ATOM | 1982 | O | PHE B | 344 | −9.676 | 25.688 | −55.932 | 1.00 | 45.16 | O |
| ATOM | 1983 | N | ASP B | 345 | −8.538 | 26.184 | −54.057 | 1.00 | 44.77 | N |
| ATOM | 1984 | CA | ASP B | 345 | −8.321 | 27.577 | −54.449 | 1.00 | 46.02 | C |
| ATOM | 1985 | CB | ASP B | 345 | −7.821 | 28.410 | −53.264 | 1.00 | 46.38 | C |
| ATOM | 1986 | CG | ASP B | 345 | −8.902 | 28.624 | −52.190 | 1.00 | 53.24 | C |
| ATOM | 1987 | OD1 | ASP B | 345 | −10.081 | 28.289 | −52.449 | 1.00 | 57.05 | O |
| ATOM | 1988 | OD2 | ASP B | 345 | −8.576 | 29.126 | −51.085 | 1.00 | 52.26 | O |
| ATOM | 1989 | C | ASP B | 345 | −7.368 | 27.652 | −55.659 | 1.00 | 45.84 | C |
| ATOM | 1990 | O | ASP B | 345 | −6.550 | 26.762 | −55.852 | 1.00 | 45.20 | O |
| ATOM | 1991 | N | PRO B | 346 | −7.499 | 28.699 | −56.496 | 1.00 | 46.07 | N |
| ATOM | 1992 | CA | PRO B | 346 | −6.634 | 28.754 | −57.669 | 1.00 | 45.86 | C |
| ATOM | 1993 | CB | PRO B | 346 | −7.383 | 29.690 | −58.616 | 1.00 | 45.74 | C |
| ATOM | 1994 | CG | PRO B | 346 | −8.265 | 30.535 | −57.733 | 1.00 | 45.68 | C |
| ATOM | 1995 | CD | PRO B | 346 | −8.401 | 29.865 | −56.404 | 1.00 | 46.17 | C |
| ATOM | 1996 | C | PRO B | 346 | −5.237 | 29.273 | −57.304 | 1.00 | 46.08 | C |
| ATOM | 1997 | O | PRO B | 346 | −4.998 | 30.477 | −57.278 | 1.00 | 45.52 | O |
| ATOM | 1998 | N | LEU B | 347 | −4.331 | 28.335 | −57.038 | 1.00 | 46.08 | N |
| ATOM | 1999 | CA | LEU B | 347 | −3.020 | 28.621 | −56.461 | 1.00 | 47.01 | C |
| ATOM | 2000 | CB | LEU B | 347 | −2.306 | 27.317 | −56.054 | 1.00 | 45.99 | C |
| ATOM | 2001 | CG | LEU B | 347 | −2.964 | 26.406 | −55.008 | 1.00 | 43.28 | C |
| ATOM | 2002 | CD1 | LEU B | 347 | −1.998 | 25.313 | −54.493 | 1.00 | 41.92 | C |
| ATOM | 2003 | CD2 | LEU B | 347 | −3.517 | 27.195 | −53.822 | 1.00 | 46.23 | C |
| ATOM | 2004 | C | LEU B | 347 | −2.109 | 29.488 | −57.332 | 1.00 | 48.39 | C |
| ATOM | 2005 | O | LEU B | 347 | −1.368 | 30.319 | −56.812 | 1.00 | 49.03 | O |
| ATOM | 2006 | N | LEU B | 348 | −2.177 | 29.294 | −58.647 | 1.00 | 49.45 | N |
| ATOM | 2007 | CA | LEU B | 348 | −1.352 | 30.034 | −59.606 | 1.00 | 49.56 | C |
| ATOM | 2008 | CB | LEU B | 348 | −1.473 | 29.417 | −61.005 | 1.00 | 49.70 | C |
| ATOM | 2009 | CG | LEU B | 348 | −0.887 | 28.004 | −61.161 | 1.00 | 52.50 | C |
| ATOM | 2010 | CD1 | LEU B | 348 | −1.471 | 27.304 | −62.378 | 1.00 | 58.56 | C |
| ATOM | 2011 | CD2 | LEU B | 348 | 0.637 | 28.014 | −61.225 | 1.00 | 53.83 | C |
| ATOM | 2012 | C | LEU B | 348 | −1.701 | 31.523 | −59.645 | 1.00 | 50.05 | C |
| ATOM | 2013 | O | LEU B | 348 | −0.828 | 32.362 | −59.882 | 1.00 | 50.07 | O |
| ATOM | 2014 | N | ALA B | 349 | −2.970 | 31.837 | −59.395 | 1.00 | 49.96 | N |
| ATOM | 2015 | CA | ALA B | 349 | −3.444 | 33.218 | −59.356 | 1.00 | 50.42 | C |
| ATOM | 2016 | CB | ALA B | 349 | −4.945 | 33.283 | −59.686 | 1.00 | 50.88 | C |
| ATOM | 2017 | C | ALA B | 349 | −3.157 | 33.908 | −58.013 | 1.00 | 50.35 | C |

TABLE A-continued

| | | | | | | | | | |
|---|---|---|---|---|---|---|---|---|---|
| ATOM | 2018 | O | ALA B | 349 | −2.796 | 35.096 | −57.996 | 1.00 | 50.24 | O |
| ATOM | 2019 | N | VAL B | 350 | −3.326 | 33.184 | −56.900 | 1.00 | 49.70 | N |
| ATOM | 2020 | CA | VAL B | 350 | −2.971 | 33.732 | −55.584 | 1.00 | 50.11 | C |
| ATOM | 2021 | CB | VAL B | 350 | −3.668 | 33.040 | −54.330 | 1.00 | 51.35 | C |
| ATOM | 2022 | CG1 | VAL B | 350 | −4.494 | 31.813 | −54.685 | 1.00 | 52.34 | C |
| ATOM | 2023 | CG2 | VAL B | 350 | −2.668 | 32.764 | −53.208 | 1.00 | 49.36 | C |
| ATOM | 2024 | C | VAL B | 350 | −1.460 | 33.873 | −55.414 | 1.00 | 50.52 | C |
| ATOM | 2025 | O | VAL B | 350 | −0.995 | 34.840 | −54.806 | 1.00 | 50.78 | O |
| ATOM | 2026 | N | ALA B | 351 | −0.711 | 32.918 | −55.969 | 1.00 | 50.08 | N |
| ATOM | 2027 | CA | ALA B | 351 | 0.747 | 32.991 | −56.007 | 1.00 | 50.14 | C |
| ATOM | 2028 | CB | ALA B | 351 | 1.322 | 31.796 | −56.740 | 1.00 | 49.35 | C |
| ATOM | 2029 | C | ALA B | 351 | 1.188 | 34.285 | −56.679 | 1.00 | 51.12 | C |
| ATOM | 2030 | O | ALA B | 351 | 2.100 | 34.963 | −56.193 | 1.00 | 51.32 | O |
| ATOM | 2031 | N | ASP B | 352 | 0.514 | 34.614 | −57.786 | 1.00 | 51.57 | N |
| ATOM | 2032 | CA | ASP B | 352 | 0.751 | 35.834 | −58.563 | 1.00 | 51.31 | C |
| ATOM | 2033 | CB | ASP B | 352 | −0.054 | 35.794 | −59.863 | 1.00 | 51.61 | C |
| | | | | gad65.pdb | | | | | | |
| ATOM | 2034 | CG | ASP B | 352 | 0.591 | 34.914 | −60.911 | 1.00 | 54.25 | C |
| ATOM | 2035 | OD1 | ASP B | 352 | 1.804 | 34.647 | −60.786 | 1.00 | 54.78 | O |
| ATOM | 2036 | OD2 | ASP B | 352 | −0.111 | 34.485 | −61.851 | 1.00 | 56.16 | O |
| ATOM | 2037 | C | ASP B | 352 | 0.414 | 37.099 | −57.802 | 1.00 | 50.32 | C |
| ATOM | 2038 | O | ASP B | 352 | 1.084 | 38.118 | −57.958 | 1.00 | 50.49 | O |
| ATOM | 2039 | N | ILE B | 353 | −0.633 | 37.028 | −56.989 | 1.00 | 50.20 | N |
| ATOM | 2040 | CA | ILE B | 353 | −1.043 | 38.147 | −56.146 | 1.00 | 49.47 | C |
| ATOM | 2041 | CB | ILE B | 353 | −2.540 | 37.977 | −55.695 | 1.00 | 49.75 | C |
| ATOM | 2042 | CG1 | ILE B | 353 | −3.475 | 38.393 | −56.838 | 1.00 | 47.42 | C |
| ATOM | 2043 | CD | ILE B | 353 | −4.849 | 37.707 | −56.817 | 1.00 | 53.67 | C |
| ATOM | 2044 | CG2 | ILE B | 353 | −2.872 | 38.772 | −54.438 | 1.00 | 45.61 | C |
| ATOM | 2045 | C | ILE B | 353 | −0.036 | 38.302 | −54.993 | 1.00 | 48.98 | C |
| ATOM | 2046 | O | ILE B | 353 | 0.333 | 39.420 | −54.630 | 1.00 | 49.12 | O |
| ATOM | 2047 | N | CYS B | 354 | 0.438 | 37.175 | −54.467 | 1.00 | 48.08 | N |
| ATOM | 2048 | CA | CYS B | 354 | 1.415 | 37.166 | −53.388 | 1.00 | 49.55 | C |
| ATOM | 2049 | CB | CYS B | 354 | 1.496 | 35.774 | −52.771 | 1.00 | 50.22 | C |
| ATOM | 2050 | SG | CYS B | 354 | 0.037 | 35.327 | −51.813 | 1.00 | 49.46 | S |
| ATOM | 2051 | C | CYS B | 354 | 2.807 | 37.630 | −53.834 | 1.00 | 50.71 | C |
| ATOM | 2052 | O | CYS B | 354 | 3.550 | 38.221 | −53.050 | 1.00 | 50.91 | O |
| ATOM | 2053 | N | LYS B | 355 | 3.141 | 37.335 | −55.089 | 1.00 | 51.44 | N |
| ATOM | 2054 | CA | LYS B | 355 | 4.326 | 37.854 | −55.778 | 1.00 | 52.18 | C |
| ATOM | 2055 | CB | LYS B | 355 | 4.437 | 37.187 | −57.153 | 1.00 | 52.06 | C |
| ATOM | 2056 | CG | LYS B | 355 | 5.831 | 37.065 | −57.715 | 1.00 | 59.08 | C |
| ATOM | 2057 | CD | LYS B | 355 | 5.810 | 36.202 | −58.978 | 1.00 | 63.18 | C |
| ATOM | 2058 | CE | LYS B | 355 | 7.207 | 35.784 | −59.395 | 1.00 | 69.58 | C |
| ATOM | 2059 | NZ | LYS B | 355 | 7.174 | 34.811 | −60.530 | 1.00 | 73.08 | N |
| ATOM | 2060 | C | LYS B | 355 | 4.209 | 39.365 | −55.966 | 1.00 | 51.64 | C |
| ATOM | 2061 | O | LYS B | 355 | 5.126 | 40.111 | −55.644 | 1.00 | 51.81 | O |
| ATOM | 2062 | N | LYS B | 356 | 3.067 | 39.806 | −56.488 | 1.00 | 51.49 | N |
| ATOM | 2063 | CA | LYS B | 356 | 2.811 | 41.223 | −56.728 | 1.00 | 51.27 | C |
| ATOM | 2064 | CB | LYS B | 356 | 1.417 | 41.398 | −57.330 | 1.00 | 50.67 | C |
| ATOM | 2065 | CG | LYS B | 356 | 1.074 | 42.800 | −57.821 | 1.00 | 54.27 | C |
| ATOM | 2066 | CD | LYS B | 356 | −0.295 | 42.772 | −58.487 | 1.00 | 56.36 | C |
| ATOM | 2067 | CE | LYS B | 356 | −0.481 | 43.888 | −59.494 | 1.00 | 61.10 | C |
| ATOM | 2068 | NZ | LYS B | 356 | −1.112 | 45.101 | −58.909 | 1.00 | 62.51 | N |
| ATOM | 2069 | C | LYS B | 356 | 2.964 | 42.062 | −55.450 | 1.00 | 51.00 | C |
| ATOM | 2070 | O | LYS B | 356 | 3.657 | 43.087 | −55.446 | 1.00 | 50.73 | O |
| ATOM | 2071 | N | TYR B | 357 | 2.338 | 41.606 | −54.367 | 1.00 | 50.35 | N |
| ATOM | 2072 | CA | TYR B | 357 | 2.266 | 42.396 | −53.138 | 1.00 | 50.02 | C |
| ATOM | 2073 | CB | TYR B | 357 | 0.837 | 42.381 | −52.592 | 1.00 | 50.30 | C |
| ATOM | 2074 | CG | TYR B | 357 | −0.139 | 43.041 | −53.542 | 1.00 | 53.42 | C |
| ATOM | 2075 | CD1 | TYR B | 357 | −0.108 | 44.419 | −53.760 | 1.00 | 52.96 | C |
| ATOM | 2076 | CE1 | TYR B | 357 | −0.996 | 45.024 | −54.636 | 1.00 | 51.57 | C |
| ATOM | 2077 | CZ | TYR B | 357 | −1.926 | 44.251 | −55.311 | 1.00 | 52.08 | C |
| ATOM | 2078 | OH | TYR B | 357 | −2.807 | 44.848 | −56.190 | 1.00 | 52.47 | O |
| ATOM | 2079 | CE2 | TYR B | 357 | −1.971 | 42.882 | −55.120 | 1.00 | 49.26 | C |
| ATOM | 2080 | CD2 | TYR B | 357 | −1.079 | 42.285 | −54.243 | 1.00 | 52.61 | C |
| ATOM | 2081 | C | TYR B | 357 | 3.300 | 42.031 | −52.070 | 1.00 | 49.26 | C |
| ATOM | 2082 | O | TYR B | 357 | 3.332 | 42.637 | −50.997 | 1.00 | 48.90 | O |
| ATOM | 2083 | N | LYS B | 358 | 4.153 | 41.057 | −52.395 | 1.00 | 49.15 | N |
| ATOM | 2084 | CA | LYS B | 358 | 5.252 | 40.589 | −51.531 | 1.00 | 48.68 | C |
| ATOM | 2085 | CB | LYS B | 358 | 6.311 | 41.671 | −51.311 | 1.00 | 49.07 | C |
| ATOM | 2086 | CG | LYS B | 358 | 6.869 | 42.289 | −52.586 | 1.00 | 51.39 | C |
| ATOM | 2087 | CD | LYS B | 358 | 7.621 | 43.579 | −52.278 | 1.00 | 57.80 | C |
| ATOM | 2088 | CE | LYS B | 358 | 9.021 | 43.322 | −51.739 | 1.00 | 62.27 | C |
| ATOM | 2089 | NZ | LYS B | 358 | 9.985 | 42.985 | −52.830 | 1.00 | 69.10 | N |
| ATOM | 2090 | C | LYS B | 358 | 4.728 | 40.068 | −50.207 | 1.00 | 47.88 | C |
| ATOM | 2091 | O | LYS B | 358 | 5.138 | 40.519 | −49.128 | 1.00 | 47.90 | O |
| ATOM | 2092 | N | ILE B | 359 | 3.820 | 39.102 | −50.308 | 1.00 | 47.06 | N |
| ATOM | 2093 | CA | ILE B | 359 | 3.146 | 38.525 | −49.153 | 1.00 | 45.27 | C |
| ATOM | 2094 | CB | ILE B | 359 | 1.601 | 38.710 | −49.238 | 1.00 | 44.89 | C |
| ATOM | 2095 | CG1 | ILE B | 359 | 1.211 | 40.138 | −49.592 | 1.00 | 47.52 | C |
| ATOM | 2096 | CD | ILE B | 359 | −0.316 | 40.308 | −49.842 | 1.00 | 45.59 | C |

TABLE A-continued

| | | | | | | | | | |
|---|---|---|---|---|---|---|---|---|---|
| ATOM | 2097 | CG2 | ILE B | 359 | 0.914 | 38.277 | −47.939 | 1.00 | 45.27 | C |
| ATOM | 2098 | C | ILE B | 359 | 3.436 | 37.027 | −49.105 | 1.00 | 44.14 | C |
| ATOM | 2099 | O | ILE B | 359 | 3.453 | 36.367 | −50.140 | 1.00 | 44.28 | O |
| ATOM | 2100 | N | TRP B | 360 | 3.638 | 36.504 | −47.895 | 1.00 | 43.38 | N |
| ATOM | 2101 | CA | TRP B | 360 | 3.747 | 35.066 | −47.646 | 1.00 | 42.82 | C | gad65.pdb

| | | | | | | | | | |
|---|---|---|---|---|---|---|---|---|---|
| ATOM | 2102 | CB | TRP B | 360 | 3.901 | 34.827 | −46.146 | 1.00 | 42.49 | C |
| ATOM | 2103 | CG | TRP B | 360 | 4.242 | 33.406 | −45.730 | 1.00 | 45.30 | C |
| ATOM | 2104 | CD1 | TRP B | 360 | 3.388 | 32.344 | −45.635 | 1.00 | 42.22 | C |
| ATOM | 2105 | NE1 | TRP B | 360 | 4.070 | 31.223 | −45.211 | 1.00 | 45.74 | N |
| ATOM | 2106 | CE2 | TRP B | 360 | 5.382 | 31.550 | −45.003 | 1.00 | 44.68 | C |
| ATOM | 2107 | CD2 | TRP B | 360 | 5.528 | 32.924 | −45.311 | 1.00 | 45.01 | C |
| ATOM | 2108 | CE3 | TRP B | 360 | 6.795 | 33.517 | −45.187 | 1.00 | 43.02 | C |
| ATOM | 2109 | CZ3 | TRP B | 360 | 7.864 | 32.728 | −44.752 | 1.00 | 43.00 | C |
| ATOM | 2110 | CH2 | TRP B | 360 | 7.683 | 31.362 | −44.444 | 1.00 | 41.18 | C |
| ATOM | 2111 | CZ2 | TRP B | 360 | 6.458 | 30.757 | −44.562 | 1.00 | 42.12 | C |
| ATOM | 2112 | C | TRP B | 360 | 2.507 | 34.328 | −48.153 | 1.00 | 42.64 | C |
| ATOM | 2113 | O | TRP B | 360 | 1.372 | 34.696 | −47.811 | 1.00 | 41.88 | O |
| ATOM | 2114 | N | MET B | 361 | 2.739 | 33.297 | −48.962 | 1.00 | 43.23 | N |
| ATOM | 2115 | CA | MET B | 361 | 1.688 | 32.377 | −49.406 | 1.00 | 45.52 | C |
| ATOM | 2116 | CB | MET B | 361 | 1.786 | 32.102 | −50.917 | 1.00 | 44.83 | C |
| ATOM | 2117 | CG | MET B | 361 | 0.578 | 31.329 | −51.489 | 1.00 | 49.16 | C |
| ATOM | 2118 | SD | MET B | 361 | 0.845 | 30.680 | −53.155 | 1.00 | 50.69 | S |
| ATOM | 2119 | CE | MET B | 361 | −0.494 | 29.514 | −53.328 | 1.00 | 55.42 | C |
| ATOM | 2120 | C | MET B | 361 | 1.732 | 31.058 | −48.618 | 1.00 | 43.41 | C |
| ATOM | 2121 | O | MET B | 361 | 2.697 | 30.305 | −48.693 | 1.00 | 42.13 | O |
| ATOM | 2122 | N | HIS B | 362 | 0.676 | 30.784 | −47.860 | 1.00 | 42.35 | N |
| ATOM | 2123 | CA | HIS B | 362 | 0.541 | 29.502 | −47.194 | 1.00 | 40.97 | C |
| ATOM | 2124 | CB | HIS B | 362 | 0.137 | 29.707 | −45.733 | 1.00 | 42.12 | C |
| ATOM | 2125 | CG | HIS B | 362 | −0.133 | 28.433 | −44.992 | 1.00 | 41.99 | C |
| ATOM | 2126 | ND1 | HIS B | 362 | 0.833 | 27.469 | −44.802 | 1.00 | 40.73 | N |
| ATOM | 2127 | CE1 | HIS B | 362 | 0.312 | 26.458 | −44.129 | 1.00 | 44.15 | C |
| ATOM | 2128 | NE2 | HIS B | 362 | −0.955 | 26.736 | −43.869 | 1.00 | 45.22 | N |
| ATOM | 2129 | CD2 | HIS B | 362 | −1.261 | 27.962 | −44.406 | 1.00 | 36.70 | C |
| ATOM | 2130 | C | HIS B | 362 | −0.498 | 28.676 | −47.937 | 1.00 | 41.51 | C |
| ATOM | 2131 | O | HIS B | 362 | −1.495 | 29.220 | −48.432 | 1.00 | 42.07 | O |
| ATOM | 2132 | N | VAL B | 363 | −0.266 | 27.369 | −48.046 | 1.00 | 41.32 | N |
| ATOM | 2133 | CA | VAL B | 363 | −1.300 | 26.469 | −48.558 | 1.00 | 40.94 | C |
| ATOM | 2134 | CB | VAL B | 363 | −0.895 | 25.738 | −49.872 | 1.00 | 40.43 | C |
| ATOM | 2135 | CG1 | VAL B | 363 | −1.997 | 24.780 | −50.333 | 1.00 | 37.48 | C |
| ATOM | 2136 | CG2 | VAL B | 363 | −0.652 | 26.733 | −50.962 | 1.00 | 39.11 | C |
| ATOM | 2137 | C | VAL B | 363 | −1.745 | 25.480 | −47.489 | 1.00 | 40.94 | C |
| ATOM | 2138 | O | VAL B | 363 | −0.959 | 24.648 | −47.022 | 1.00 | 40.96 | O |
| ATOM | 2139 | N | ASP B | 364 | −3.005 | 25.598 | −47.078 | 1.00 | 41.19 | N |
| ATOM | 2140 | CA | ASP B | 364 | −3.616 | 24.590 | −46.217 | 1.00 | 40.37 | C |
| ATOM | 2141 | CB | ASP B | 364 | −4.834 | 25.138 | −45.448 | 1.00 | 39.72 | C |
| ATOM | 2142 | CG | ASP B | 364 | −5.396 | 24.127 | −44.446 | 1.00 | 44.48 | C |
| ATOM | 2143 | OD1 | ASP B | 364 | −4.887 | 22.982 | −44.414 | 1.00 | 36.63 | O |
| ATOM | 2144 | OD2 | ASP B | 364 | −6.347 | 24.465 | −43.693 | 1.00 | 43.39 | O |
| ATOM | 2145 | C | ASP B | 364 | −4.014 | 23.413 | −47.097 | 1.00 | 41.19 | C |
| ATOM | 2146 | O | ASP B | 364 | −5.106 | 23.389 | −47.668 | 1.00 | 41.71 | O |
| ATOM | 2147 | N | ALA B | 365 | −3.113 | 22.443 | −47.214 | 1.00 | 41.78 | N |
| ATOM | 2148 | CA | ALA B | 365 | −3.404 | 21.206 | −47.930 | 1.00 | 40.91 | C |
| ATOM | 2149 | CB | ALA B | 365 | −2.302 | 20.912 | −48.951 | 1.00 | 40.27 | C |
| ATOM | 2150 | C | ALA B | 365 | −3.614 | 20.018 | −46.966 | 1.00 | 41.05 | C |
| ATOM | 2151 | O | ALA B | 365 | −3.372 | 18.870 | −47.320 | 1.00 | 40.35 | O |
| ATOM | 2152 | N | ALA B | 366 | −4.092 | 20.304 | −45.756 | 1.00 | 42.19 | N |
| ATOM | 2153 | CA | ALA B | 366 | −4.365 | 19.267 | −44.755 | 1.00 | 43.64 | C |
| ATOM | 2154 | CB | ALA B | 366 | −5.128 | 19.858 | −43.570 | 1.00 | 44.98 | C |
| ATOM | 2155 | C | ALA B | 366 | −5.138 | 18.094 | −45.350 | 1.00 | 44.22 | C |
| ATOM | 2156 | O | ALA B | 366 | −4.781 | 16.933 | −45.141 | 1.00 | 46.58 | O |
| ATOM | 2157 | N | TRP B | 367 | −6.173 | 18.415 | −46.120 | 1.00 | 44.21 | N |
| ATOM | 2158 | CA | TRP B | 367 | −7.072 | 17.450 | −46.739 | 1.00 | 43.36 | C |
| ATOM | 2159 | CB | TRP B | 367 | −8.478 | 18.039 | −46.685 | 1.00 | 42.80 | C |
| ATOM | 2160 | CG | TRP B | 367 | −9.611 | 17.284 | −47.365 | 1.00 | 41.79 | C |
| ATOM | 2161 | CD1 | TRP B | 367 | −10.595 | 17.834 | −48.129 | 1.00 | 42.18 | C |
| ATOM | 2162 | NE1 | TRP B | 367 | −11.470 | 16.866 | −48.560 | 1.00 | 41.93 | N |
| ATOM | 2163 | CE2 | TRP B | 367 | −11.077 | 15.652 | −48.065 | 1.00 | 44.11 | C |
| ATOM | 2164 | CD2 | TRP B | 367 | −9.907 | 15.872 | −47.292 | 1.00 | 47.96 | C |
| ATOM | 2165 | CE3 | TRP B | 367 | −9.294 | 14.775 | −46.663 | 1.00 | 48.03 | C |
| ATOM | 2166 | CZ3 | TRP B | 367 | −9.859 | 13.514 | −46.828 | 1.00 | 47.57 | C |
| ATOM | 2167 | CH2 | TRP B | 367 | −11.038 | 13.331 | −47.600 | 1.00 | 44.02 | C |
| ATOM | 2168 | CZ2 | TRP B | 367 | −11.653 | 14.386 | −48.220 | 1.00 | 41.43 | C |
| ATOM | 2169 | C | TRP B | 367 | −6.650 | 17.144 | −48.191 | 1.00 | 44.17 | C | gad65.pdb

| | | | | | | | | | |
|---|---|---|---|---|---|---|---|---|---|
| ATOM | 2170 | O | TRP B | 367 | −6.573 | 15.982 | −48.587 | 1.00 | 43.72 | O |
| ATOM | 2171 | N | GLY B | 368 | −6.371 | 18.192 | −48.965 | 1.00 | 44.17 | N |
| ATOM | 2172 | CA | GLY B | 368 | −6.040 | 18.051 | −50.379 | 1.00 | 44.81 | C |
| ATOM | 2173 | C | GLY B | 368 | −4.656 | 17.512 | −50.704 | 1.00 | 45.08 | C |
| ATOM | 2174 | O | GLY B | 368 | −4.426 | 17.058 | −51.822 | 1.00 | 46.14 | O |

TABLE A-continued

| | | | | | | | | | |
|---|---|---|---|---|---|---|---|---|---|
| ATOM | 2175 | N | GLY B | 369 | −3.746 | 17.561 | −49.730 | 1.00 | 45.70 | N |
| ATOM | 2176 | CA | GLY B | 369 | −2.359 | 17.097 | −49.901 | 1.00 | 46.28 | C |
| ATOM | 2177 | C | GLY B | 369 | −2.172 | 15.687 | −50.443 | 1.00 | 46.79 | C |
| ATOM | 2178 | O | GLY B | 369 | −1.191 | 15.413 | −51.138 | 1.00 | 47.52 | O |
| ATOM | 2179 | N | GLY B | 370 | −3.104 | 14.788 | −50.131 | 1.00 | 46.42 | N |
| ATOM | 2180 | CA | GLY B | 370 | −3.070 | 13.411 | −50.652 | 1.00 | 45.80 | C |
| ATOM | 2181 | C | GLY B | 370 | −3.078 | 13.313 | −52.173 | 1.00 | 45.49 | C |
| ATOM | 2182 | O | GLY B | 370 | −2.441 | 12.424 | −52.748 | 1.00 | 44.44 | O |
| ATOM | 2183 | N | LEU B | 371 | −3.794 | 14.224 | −52.829 | 1.00 | 45.96 | N |
| ATOM | 2184 | CA | LEU B | 371 | −3.873 | 14.235 | −54.301 | 1.00 | 48.00 | C |
| ATOM | 2185 | CB | LEU B | 371 | −4.954 | 15.210 | −54.788 | 1.00 | 48.00 | C |
| ATOM | 2186 | CG | LEU B | 371 | −6.436 | 14.780 | −54.811 | 1.00 | 49.56 | C |
| ATOM | 2187 | CD1 | LEU B | 371 | −7.005 | 14.408 | −53.435 | 1.00 | 49.02 | C |
| ATOM | 2188 | CD2 | LEU B | 371 | −7.260 | 15.890 | −55.412 | 1.00 | 47.74 | C |
| ATOM | 2189 | C | LEU B | 371 | −2.528 | 14.553 | −54.976 | 1.00 | 48.73 | C |
| ATOM | 2190 | O | LEU B | 371 | −2.383 | 14.371 | −56.181 | 1.00 | 49.43 | O |
| ATOM | 2191 | N | LEU B | 372 | −1.556 | 15.020 | −54.189 | 1.00 | 48.72 | N |
| ATOM | 2192 | CA | LEU B | 372 | −0.195 | 15.256 | −54.670 | 1.00 | 49.50 | C |
| ATOM | 2193 | CB | LEU B | 372 | 0.595 | 16.071 | −53.648 | 1.00 | 50.25 | C |
| ATOM | 2194 | CG | LEU B | 372 | 0.248 | 17.551 | −53.578 | 1.00 | 48.39 | C |
| ATOM | 2195 | CD1 | LEU B | 372 | 0.901 | 18.191 | −52.359 | 1.00 | 46.47 | C |
| ATOM | 2196 | CD2 | LEU B | 372 | 0.672 | 18.238 | −54.875 | 1.00 | 46.71 | C |
| ATOM | 2197 | C | LEU B | 372 | 0.535 | 13.949 | −54.960 | 1.00 | 49.03 | C |
| ATOM | 2198 | O | LEU B | 372 | 1.536 | 13.934 | −55.681 | 1.00 | 49.45 | O |
| ATOM | 2199 | N | MET B | 373 | 0.014 | 12.861 | −54.405 | 1.00 | 49.03 | N |
| ATOM | 2200 | CA | MET B | 373 | 0.530 | 11.516 | −54.652 | 1.00 | 49.64 | C |
| ATOM | 2201 | CB | MET B | 373 | 0.180 | 10.587 | −53.487 | 1.00 | 48.87 | C |
| ATOM | 2202 | CG | MET B | 373 | 0.550 | 11.119 | −52.107 | 1.00 | 53.03 | C |
| ATOM | 2203 | SD | MET B | 373 | 2.332 | 11.220 | −51.771 | 1.00 | 61.86 | S |
| ATOM | 2204 | CE | MET B | 373 | 2.817 | 9.509 | −51.953 | 1.00 | 55.30 | C |
| ATOM | 2205 | C | MET B | 373 | −0.006 | 10.928 | −55.967 | 1.00 | 50.22 | C |
| ATOM | 2206 | O | MET B | 373 | 0.486 | 9.900 | −56.442 | 1.00 | 50.77 | O |
| ATOM | 2207 | N | SER B | 374 | −1.001 | 11.592 | −56.549 | 1.00 | 50.12 | N |
| ATOM | 2208 | CA | SER B | 374 | −1.671 | 11.114 | −57.759 | 1.00 | 49.37 | C |
| ATOM | 2209 | CB | SER B | 374 | −3.187 | 11.200 | −57.569 | 1.00 | 48.53 | C |
| ATOM | 2210 | OG | SER B | 374 | −3.890 | 11.102 | −58.794 | 1.00 | 46.47 | O |
| ATOM | 2211 | C | SER B | 374 | −1.245 | 11.916 | −58.981 | 1.00 | 50.50 | C |
| ATOM | 2212 | O | SER B | 374 | −1.526 | 13.112 | −59.066 | 1.00 | 50.66 | O |
| ATOM | 2213 | N | ARG B | 375 | −0.568 | 11.257 | −59.924 | 1.00 | 52.37 | N |
| ATOM | 2214 | CA | ARG B | 375 | −0.208 | 11.882 | −61.210 | 1.00 | 53.86 | C |
| ATOM | 2215 | CB | ARG B | 375 | 0.585 | 10.922 | −62.108 | 1.00 | 55.19 | C |
| ATOM | 2216 | CG | ARG B | 375 | 2.055 | 10.747 | −61.730 | 1.00 | 62.44 | C |
| ATOM | 2217 | CD | ARG B | 375 | 2.358 | 9.333 | −61.238 | 1.00 | 70.12 | C |
| ATOM | 2218 | NE | ARG B | 375 | 2.204 | 8.342 | −62.307 | 1.00 | 76.64 | N |
| ATOM | 2219 | CZ | ARG B | 375 | 2.399 | 7.029 | −62.170 | 1.00 | 79.07 | C |
| ATOM | 2220 | NH1 | ARG B | 375 | 2.761 | 6.508 | −61.002 | 1.00 | 78.53 | N |
| ATOM | 2221 | NH2 | ARG B | 375 | 2.232 | 6.228 | −63.213 | 1.00 | 80.94 | N |
| ATOM | 2222 | C | ARG B | 375 | −1.442 | 12.375 | −61.962 | 1.00 | 53.51 | C |
| ATOM | 2223 | O | ARG B | 375 | −1.395 | 13.404 | −62.643 | 1.00 | 53.27 | O |
| ATOM | 2224 | N | LYS B | 376 | −2.540 | 11.632 | −61.833 | 1.00 | 53.98 | N |
| ATOM | 2225 | CA | LYS B | 376 | −3.817 | 11.997 | −62.454 | 1.00 | 54.69 | C |
| ATOM | 2226 | CB | LYS B | 376 | −4.786 | 10.806 | −62.405 | 1.00 | 54.60 | C |
| ATOM | 2227 | CG | LYS B | 376 | −6.245 | 11.111 | −62.770 | 1.00 | 58.25 | C |
| ATOM | 2228 | CD | LYS B | 376 | −7.098 | 9.846 | −62.763 | 1.00 | 55.53 | C |
| ATOM | 2229 | CE | LYS B | 376 | −8.586 | 10.154 | −62.947 | 1.00 | 59.20 | C |
| ATOM | 2230 | NZ | LYS B | 376 | −8.947 | 10.625 | −64.315 | 1.00 | 57.27 | N |
| ATOM | 2231 | C | LYS B | 376 | −4.439 | 13.246 | −61.814 | 1.00 | 55.12 | C |
| ATOM | 2232 | O | LYS B | 376 | −4.955 | 14.111 | −62.519 | 1.00 | 55.03 | O |
| ATOM | 2233 | N | HIS B | 377 | −4.357 | 13.358 | −60.487 | 1.00 | 54.88 | N |
| ATOM | 2234 | CA | HIS B | 377 | −5.093 | 14.410 | −59.779 | 1.00 | 54.69 | C |
| ATOM | 2235 | CB | HIS B | 377 | −5.904 | 13.804 | −58.630 | 1.00 | 55.04 | C |
| ATOM | 2236 | CG | HIS B | 377 | −7.008 | 12.906 | −59.085 | 1.00 | 53.96 | C |
| ATOM | 2237 | ND1 | HIS B | 377 | −8.382 | 13.382 | −59.460 | 1.00 | 56.22 | N |
| ATOM | 2238 | CE1 | HIS B | 377 | −9.013 | 12.369 | −59.821 | 1.00 | 58.48 | C |
| ATOM | 2239 | NE2 | HIS B | 377 | −8.322 | 11.251 | −59.686 | 1.00 | 58.68 | N |
| ATOM | 2240 | CD2 | HIS B | 377 | −7.061 | 11.561 | −59.237 | 1.00 | 56.92 | C |
| ATOM | 2241 | C | HIS B | 377 | −4.296 | 15.614 | −59.275 | 1.00 | 54.57 | C |
| ATOM | 2242 | O | HIS B | 377 | −4.897 | 16.610 | −58.870 | 1.00 | 54.61 | O |
| ATOM | 2243 | N | LYS B | 378 | −2.964 | 15.544 | −59.309 | 1.00 | 54.58 | N |
| ATOM | 2244 | CA | LYS B | 378 | −2.138 | 16.577 | −58.660 | 1.00 | 54.41 | C |
| ATOM | 2245 | CB | LYS B | 378 | −0.661 | 16.149 | −58.534 | 1.00 | 55.04 | C |
| ATOM | 2246 | CG | LYS B | 378 | 0.253 | 16.375 | −59.760 | 1.00 | 59.05 | C |
| ATOM | 2247 | CD | LYS B | 378 | 0.722 | 17.845 | −59.930 | 1.00 | 65.65 | C |
| ATOM | 2248 | CE | LYS B | 378 | 1.342 | 18.471 | −58.664 | 1.00 | 65.57 | C |
| ATOM | 2249 | NZ | LYS B | 378 | 2.838 | 18.479 | −58.685 | 1.00 | 69.35 | N |
| ATOM | 2250 | C | LYS B | 378 | −2.284 | 17.969 | −59.269 | 1.00 | 53.51 | C |
| ATOM | 2251 | O | LYS B | 378 | −2.038 | 18.970 | −58.594 | 1.00 | 53.31 | O |
| ATOM | 2252 | N | TRP B | 379 | −2.715 | 18.027 | −60.527 | 1.00 | 52.87 | N |
| ATOM | 2253 | CA | TRP B | 379 | −2.940 | 19.297 | −61.225 | 1.00 | 52.85 | C | gad65.pdb

TABLE A-continued

| | | | | | | | | | |
|---|---|---|---|---|---|---|---|---|---|
| ATOM | 2254 | CB | TRP B | 379 | −3.460 | 19.054 | −62.652 | 1.00 | 52.66 | C |
| ATOM | 2255 | CG | TRP B | 379 | −4.829 | 18.431 | −62.702 | 1.00 | 52.55 | C |
| ATOM | 2256 | CD1 | TRP B | 379 | −5.123 | 17.097 | −62.717 | 1.00 | 53.16 | C |
| ATOM | 2257 | NE1 | TRP B | 379 | −6.483 | 16.908 | −62.765 | 1.00 | 51.44 | N |
| ATOM | 2258 | CE2 | TRP B | 379 | −7.099 | 18.133 | −62.765 | 1.00 | 53.93 | C |
| ATOM | 2259 | CD2 | TRP B | 379 | −6.083 | 19.118 | −62.726 | 1.00 | 51.79 | C |
| ATOM | 2260 | CE3 | TRP B | 379 | −6.453 | 20.471 | −62.731 | 1.00 | 53.97 | C |
| ATOM | 2261 | CZ3 | TRP B | 379 | −7.809 | 20.795 | −62.766 | 1.00 | 53.70 | C |
| ATOM | 2262 | CH2 | TRP B | 379 | −8.794 | 19.789 | −62.799 | 1.00 | 52.38 | C |
| ATOM | 2263 | CZ2 | TRP B | 379 | −8.461 | 18.458 | −62.803 | 1.00 | 51.72 | C |
| ATOM | 2264 | C | TRP B | 379 | −3.886 | 20.228 | −60.459 | 1.00 | 52.90 | C |
| ATOM | 2265 | O | TRP B | 379 | −3.845 | 21.450 | −60.640 | 1.00 | 52.84 | O |
| ATOM | 2266 | N | LYS B | 380 | −4.731 | 19.644 | −59.606 | 1.00 | 52.73 | N |
| ATOM | 2267 | CA | LYS B | 380 | −5.604 | 20.415 | −58.711 | 1.00 | 53.03 | C |
| ATOM | 2268 | CB | LYS B | 380 | −6.568 | 19.486 | −57.975 | 1.00 | 52.16 | C |
| ATOM | 2269 | CG | LYS B | 380 | −7.745 | 19.075 | −58.827 | 1.00 | 52.99 | C |
| ATOM | 2270 | CD | LYS B | 380 | −8.168 | 17.653 | −58.543 | 1.00 | 51.71 | C |
| ATOM | 2271 | CE | LYS B | 380 | −9.265 | 17.222 | −59.491 | 1.00 | 51.36 | C |
| ATOM | 2272 | NZ | LYS B | 380 | −9.768 | 15.869 | −59.141 | 1.00 | 52.44 | N |
| ATOM | 2273 | C | LYS B | 380 | −4.822 | 21.273 | −57.715 | 1.00 | 53.78 | C |
| ATOM | 2274 | O | LYS B | 380 | −5.357 | 22.255 | −57.171 | 1.00 | 54.65 | O |
| ATOM | 2275 | N | LEU B | 381 | −3.565 | 20.894 | −57.476 | 1.00 | 53.47 | N |
| ATOM | 2276 | CA | LEU B | 381 | −2.690 | 21.647 | −56.579 | 1.00 | 53.79 | C |
| ATOM | 2277 | CB | LEU B | 381 | −2.072 | 20.740 | −55.502 | 1.00 | 53.42 | C |
| ATOM | 2278 | CG | LEU B | 381 | −3.012 | 20.156 | −54.447 | 1.00 | 54.70 | C |
| ATOM | 2279 | CD1 | LEU B | 381 | −3.432 | 18.746 | −54.854 | 1.00 | 56.20 | C |
| ATOM | 2280 | CD2 | LEU B | 381 | −2.363 | 20.131 | −53.063 | 1.00 | 56.25 | C |
| ATOM | 2281 | C | LEU B | 381 | −1.599 | 22.407 | −57.327 | 1.00 | 53.69 | C |
| ATOM | 2282 | O | LEU B | 381 | −0.595 | 22.789 | −56.729 | 1.00 | 54.72 | O |
| ATOM | 2283 | N | SER B | 382 | −1.794 | 22.637 | −58.626 | 1.00 | 52.75 | N |
| ATOM | 2284 | CA | SER B | 382 | −0.813 | 23.378 | −59.419 | 1.00 | 51.59 | C |
| ATOM | 2285 | CB | SER B | 382 | −1.292 | 23.547 | −60.872 | 1.00 | 52.40 | C |
| ATOM | 2286 | OG | SER B | 382 | −1.216 | 22.325 | −61.585 | 1.00 | 59.26 | O |
| ATOM | 2287 | C | SER B | 382 | −0.575 | 24.747 | −58.800 | 1.00 | 49.47 | C |
| ATOM | 2288 | O | SER B | 382 | −1.525 | 25.495 | −58.569 | 1.00 | 49.78 | O |
| ATOM | 2289 | N | GLY B | 383 | 0.686 | 25.078 | −58.547 | 1.00 | 47.12 | N |
| ATOM | 2290 | CA | GLY B | 383 | 1.031 | 26.354 | −57.932 | 1.00 | 46.07 | C |
| ATOM | 2291 | C | GLY B | 383 | 1.500 | 26.241 | −56.491 | 1.00 | 46.06 | C |
| ATOM | 2292 | O | GLY B | 383 | 2.041 | 27.202 | −55.949 | 1.00 | 45.91 | O |
| ATOM | 2293 | N | VAL B | 384 | 1.274 | 25.073 | −55.874 | 1.00 | 46.41 | N |
| ATOM | 2294 | CA | VAL B | 384 | 1.752 | 24.755 | −54.516 | 1.00 | 46.06 | C |
| ATOM | 2295 | CB | VAL B | 384 | 1.285 | 23.328 | −54.062 | 1.00 | 46.74 | C |
| ATOM | 2296 | CG1 | VAL B | 384 | 2.034 | 22.214 | −54.809 | 1.00 | 48.92 | C |
| ATOM | 2297 | CG2 | VAL B | 384 | 1.447 | 23.137 | −52.560 | 1.00 | 45.97 | C |
| ATOM | 2298 | C | VAL B | 384 | 3.276 | 24.868 | −54.418 | 1.00 | 45.83 | C |
| ATOM | 2299 | O | VAL B | 384 | 3.826 | 25.079 | −53.331 | 1.00 | 45.09 | O |
| ATOM | 2300 | N | GLU B | 385 | 3.952 | 24.746 | −55.564 | 1.00 | 44.97 | N |
| ATOM | 2301 | CA | GLU B | 385 | 5.416 | 24.772 | −55.596 | 1.00 | 44.05 | C |
| ATOM | 2302 | CB | GLU B | 385 | 5.960 | 24.139 | −56.895 | 1.00 | 43.59 | C |
| ATOM | 2303 | CG | GLU B | 385 | 5.786 | 24.963 | −58.197 | 1.00 | 43.52 | C |
| ATOM | 2304 | CD | GLU B | 385 | 4.391 | 24.868 | −58.834 | 1.00 | 49.27 | C |
| ATOM | 2305 | OE1 | GLU B | 385 | 4.223 | 25.426 | −59.947 | 1.00 | 56.21 | O |
| | | | | | gad65.pdb | | | | | |
| ATOM | 2306 | OE2 | GLU B | 385 | 3.465 | 24.250 | −58.246 | 1.00 | 47.95 | O |
| ATOM | 2307 | C | GLU B | 385 | 5.921 | 26.200 | −55.372 | 1.00 | 44.00 | C |
| ATOM | 2308 | O | GLU B | 385 | 7.090 | 26.421 | −55.015 | 1.00 | 44.29 | O |
| ATOM | 2309 | N | ARG B | 386 | 5.009 | 27.156 | −55.546 | 1.00 | 42.69 | N |
| ATOM | 2310 | CA | ARG B | 386 | 5.299 | 28.575 | −55.357 | 1.00 | 42.35 | C |
| ATOM | 2311 | CB | ARG B | 386 | 4.523 | 29.402 | −56.373 | 1.00 | 41.95 | C |
| ATOM | 2312 | CG | ARG B | 386 | 5.233 | 29.527 | −57.688 | 1.00 | 46.92 | C |
| ATOM | 2313 | CD | ARG B | 386 | 5.067 | 30.925 | −58.204 | 1.00 | 49.86 | C |
| ATOM | 2314 | NE | ARG B | 386 | 4.015 | 31.002 | −59.201 | 1.00 | 48.75 | N |
| ATOM | 2315 | CZ | ARG B | 386 | 3.394 | 32.130 | −59.540 | 1.00 | 46.96 | C |
| ATOM | 2316 | NH1 | ARG B | 386 | 3.675 | 33.278 | −58.919 | 1.00 | 42.54 | N |
| ATOM | 2317 | NH2 | ARG B | 386 | 2.462 | 32.098 | −60.482 | 1.00 | 48.40 | N |
| ATOM | 2318 | C | ARG B | 386 | 5.003 | 29.086 | −53.944 | 1.00 | 41.97 | C |
| ATOM | 2319 | O | ARG B | 386 | 5.206 | 30.266 | −53.655 | 1.00 | 42.73 | O |
| ATOM | 2320 | N | ALA B | 387 | 4.543 | 28.191 | −53.076 | 1.00 | 41.47 | N |
| ATOM | 2321 | CA | ALA B | 387 | 4.110 | 28.538 | −51.727 | 1.00 | 41.50 | C |
| ATOM | 2322 | CB | ALA B | 387 | 3.088 | 27.520 | −51.230 | 1.00 | 41.21 | C |
| ATOM | 2323 | C | ALA B | 387 | 5.274 | 28.610 | −50.762 | 1.00 | 41.77 | C |
| ATOM | 2324 | O | ALA B | 387 | 6.192 | 27.790 | −50.815 | 1.00 | 43.10 | O |
| ATOM | 2325 | N | ASN B | 388 | 5.231 | 29.591 | −49.868 | 1.00 | 40.61 | N |
| ATOM | 2326 | CA | ASN B | 388 | 6.224 | 29.697 | −48.809 | 1.00 | 38.47 | C |
| ATOM | 2327 | CB | ASN B | 388 | 6.203 | 31.088 | −48.185 | 1.00 | 37.60 | C |
| ATOM | 2328 | CG | ASN B | 388 | 6.383 | 32.182 | −49.207 | 1.00 | 38.50 | C |
| ATOM | 2329 | OD1 | ASN B | 388 | 5.420 | 32.617 | −49.842 | 1.00 | 40.62 | O |
| ATOM | 2330 | ND2 | ASN B | 388 | 7.618 | 32.645 | −49.372 | 1.00 | 36.86 | N |
| ATOM | 2331 | C | ASN B | 388 | 6.090 | 28.609 | −47.746 | 1.00 | 38.18 | C |
| ATOM | 2332 | O | ASN B | 388 | 7.082 | 28.192 | −47.166 | 1.00 | 38.06 | O |

TABLE A-continued

| | | | | | | | | | |
|---|---|---|---|---|---|---|---|---|---|
| ATOM | 2333 | N | SER B | 389 | 4.862 | 28.152 | −47.493 | 1.00 | 38.33 | N |
| ATOM | 2334 | CA | SER B | 389 | 4.619 | 27.050 | −46.552 | 1.00 | 37.16 | C |
| ATOM | 2335 | CB | SER B | 389 | 4.328 | 27.559 | −45.126 | 1.00 | 36.92 | C |
| ATOM | 2336 | OG | SER B | 389 | 3.321 | 28.561 | −45.116 | 1.00 | 36.58 | O |
| ATOM | 2337 | C | SER B | 389 | 3.474 | 26.190 | −47.024 | 1.00 | 37.38 | C |
| ATOM | 2338 | O | SER B | 389 | 2.586 | 26.667 | −47.739 | 1.00 | 36.38 | O |
| ATOM | 2339 | N | VAL B | 390 | 3.489 | 24.924 | −46.618 | 1.00 | 38.18 | N |
| ATOM | 2340 | CA | VAL B | 390 | 2.361 | 24.020 | −46.867 | 1.00 | 39.97 | C |
| ATOM | 2341 | CB | VAL B | 390 | 2.606 | 23.082 | −48.093 | 1.00 | 40.81 | C |
| ATOM | 2342 | CG1 | VAL B | 390 | 1.422 | 22.131 | −48.304 | 1.00 | 42.38 | C |
| ATOM | 2343 | CG2 | VAL B | 390 | 2.873 | 23.885 | −49.364 | 1.00 | 42.05 | C |
| ATOM | 2344 | C | VAL B | 390 | 2.063 | 23.164 | −45.635 | 1.00 | 41.13 | C |
| ATOM | 2345 | O | VAL B | 390 | 2.985 | 22.686 | −44.968 | 1.00 | 42.71 | O |
| ATOM | 2346 | N | THR B | 391 | 0.776 | 23.005 | −45.335 | 1.00 | 41.65 | N |
| ATOM | 2347 | CA | THR B | 391 | 0.269 | 22.052 | −44.344 | 1.00 | 41.95 | C |
| ATOM | 2348 | CB | THR B | 391 | −0.869 | 22.680 | −43.492 | 1.00 | 42.54 | C |
| ATOM | 2349 | OG1 | THR B | 391 | −0.357 | 23.780 | −42.732 | 1.00 | 45.17 | O |
| ATOM | 2350 | CG2 | THR B | 391 | −1.502 | 21.646 | −42.535 | 1.00 | 43.76 | C |
| ATOM | 2351 | C | THR B | 391 | −0.302 | 20.811 | −45.060 | 1.00 | 42.09 | C |
| ATOM | 2352 | O | THR B | 391 | −1.009 | 20.924 | −46.049 | 1.00 | 41.22 | O |
| ATOM | 2353 | N | TRP B | 392 | −0.012 | 19.630 | −44.538 | 1.00 | 43.56 | N |
| ATOM | 2354 | CA | TRP B | 392 | −0.388 | 18.396 | −45.200 | 1.00 | 44.28 | C |
| ATOM | 2355 | CB | TRP B | 392 | 0.736 | 17.983 | −46.159 | 1.00 | 45.31 | C |
| ATOM | 2356 | CG | TRP B | 392 | 0.541 | 16.724 | −46.975 | 1.00 | 46.07 | C |
| ATOM | 2357 | CD1 | TRP B | 392 | −0.459 | 15.794 | −46.862 | 1.00 | 46.37 | C |
| ATOM | 2358 | NE1 | TRP B | 392 | −0.262 | 14.769 | −47.761 | 1.00 | 47.93 | N |
| ATOM | 2359 | CE2 | TRP B | 392 | 0.886 | 15.013 | −48.470 | 1.00 | 44.54 | C |
| ATOM | 2360 | CD2 | TRP B | 392 | 1.430 | 16.231 | −47.989 | 1.00 | 47.25 | C |
| ATOM | 2361 | CE3 | TRP B | 392 | 2.620 | 16.716 | −48.560 | 1.00 | 45.66 | C |
| ATOM | 2362 | CZ3 | TRP B | 392 | 3.233 | 15.968 | −49.573 | 1.00 | 42.31 | C |
| ATOM | 2363 | CH2 | TRP B | 392 | 2.670 | 14.757 | −50.021 | 1.00 | 43.88 | C |
| ATOM | 2364 | CZ2 | TRP B | 392 | 1.502 | 14.262 | −49.483 | 1.00 | 42.96 | C |
| ATOM | 2365 | C | TRP B | 392 | −0.578 | 17.379 | −44.108 | 1.00 | 43.80 | C |
| ATOM | 2366 | O | TRP B | 392 | 0.298 | 17.217 | −43.266 | 1.00 | 45.38 | O |
| ATOM | 2367 | N | ASN B | 393 | −1.730 | 16.711 | −44.120 | 1.00 | 43.61 | N |
| ATOM | 2368 | CA | ASN B | 393 | −2.079 | 15.722 | −43.124 | 1.00 | 45.26 | C |
| ATOM | 2369 | CB | ASN B | 393 | −3.428 | 16.056 | −42.469 | 1.00 | 46.09 | C |
| ATOM | 2370 | CG | ASN B | 393 | −3.358 | 17.231 | −41.514 | 1.00 | 50.35 | C |
| ATOM | 2371 | OD1 | ASN B | 393 | −2.385 | 17.989 | −41.493 | 1.00 | 52.80 | O |
| ATOM | 2372 | ND2 | ASN B | 393 | −4.401 | 17.384 | −40.706 | 1.00 | 48.36 | N |
| ATOM | 2373 | C | ASN B | 393 | −2.162 | 14.322 | −43.719 | 1.00 | 46.51 | C |
| | | | | | gad65.pdb | | | | | |
| ATOM | 2374 | O | ASN B | 393 | −3.233 | 13.902 | −44.183 | 1.00 | 47.44 | O |
| ATOM | 2375 | N | PRO B | 394 | −1.042 | 13.574 | −43.690 | 1.00 | 47.43 | N |
| ATOM | 2376 | CA | PRO B | 394 | −1.100 | 12.175 | −44.105 | 1.00 | 47.77 | C |
| ATOM | 2377 | CB | PRO B | 394 | 0.328 | 11.684 | −43.840 | 1.00 | 48.14 | C |
| ATOM | 2378 | CG | PRO B | 394 | 1.152 | 12.919 | −43.982 | 1.00 | 50.58 | C |
| ATOM | 2379 | CD | PRO B | 394 | 0.331 | 13.974 | −43.324 | 1.00 | 46.19 | C |
| ATOM | 2380 | C | PRO B | 394 | −2.117 | 11.357 | −43.299 | 1.00 | 47.93 | C |
| ATOM | 2381 | O | PRO B | 394 | −2.552 | 10.309 | −43.768 | 1.00 | 47.37 | O |
| ATOM | 2382 | N | HIS B | 395 | −2.510 | 11.836 | −42.118 | 1.00 | 48.02 | N |
| ATOM | 2383 | CA | HIS B | 395 | −3.515 | 11.118 | −41.341 | 1.00 | 49.82 | C |
| ATOM | 2384 | CB | HIS B | 395 | −3.484 | 11.474 | −39.839 | 1.00 | 49.74 | C |
| ATOM | 2385 | CG | HIS B | 395 | −4.129 | 12.777 | −39.486 | 1.00 | 52.73 | C |
| ATOM | 2386 | ND1 | HIS B | 395 | −3.444 | 13.792 | −38.846 | 1.00 | 54.18 | N |
| ATOM | 2387 | CE1 | HIS B | 395 | −4.261 | 14.812 | −38.644 | 1.00 | 49.14 | C |
| ATOM | 2388 | NE2 | HIS B | 395 | −5.453 | 14.489 | −39.118 | 1.00 | 54.87 | N |
| ATOM | 2389 | CD2 | HIS B | 395 | −5.400 | 13.220 | −39.644 | 1.00 | 48.12 | C |
| ATOM | 2390 | C | HIS B | 395 | −4.923 | 11.187 | −41.956 | 1.00 | 50.64 | C |
| ATOM | 2391 | O | HIS B | 395 | −5.785 | 10.393 | −41.607 | 1.00 | 51.49 | O |
| ATOM | 2392 | N | LLP B | 396 | −5.140 | 12.107 | −42.895 | 1.00 | 51.25 | N |
| ATOM | 2393 | CA | LLP B | 396 | −6.418 | 12.151 | −43.619 | 1.00 | 52.81 | C |
| ATOM | 2394 | CB | LLP B | 396 | −6.812 | 13.595 | −43.957 | 1.00 | 52.26 | C |
| ATOM | 2395 | CG | LLP B | 396 | −7.056 | 14.441 | −42.699 | 1.00 | 49.53 | C |
| ATOM | 2396 | CD | LLP B | 396 | −7.769 | 15.748 | −42.987 | 1.00 | 45.73 | C |
| ATOM | 2397 | CE | LLP B | 396 | −8.083 | 16.513 | −41.706 | 1.00 | 42.09 | C |
| ATOM | 2398 | NZ | LLP B | 396 | −8.596 | 17.882 | −42.013 | 1.00 | 47.12 | N |
| ATOM | 2399 | C4A | LLP B | 396 | −8.448 | 18.749 | −41.004 | 1.00 | 44.92 | C |
| ATOM | 2400 | C4 | LLP B | 396 | −8.132 | 20.120 | −41.550 | 1.00 | 42.95 | C |
| ATOM | 2401 | C3 | LLP B | 396 | −8.518 | 20.481 | −42.842 | 1.00 | 41.62 | C |
| ATOM | 2402 | O3 | LLP B | 396 | −9.129 | 19.682 | −43.563 | 1.00 | 42.26 | O |
| ATOM | 2403 | C2 | LLP B | 396 | −8.196 | 21.746 | −43.328 | 1.00 | 43.62 | C |
| ATOM | 2404 | C2A | LLP B | 396 | −8.592 | 22.161 | −44.727 | 1.00 | 42.79 | C |
| ATOM | 2405 | N1 | LLP B | 396 | −7.506 | 22.637 | −42.530 | 1.00 | 41.95 | N |
| ATOM | 2406 | C5 | LLP B | 396 | −7.436 | 21.042 | −40.763 | 1.00 | 44.17 | C |
| ATOM | 2407 | C6 | LLP B | 396 | −7.115 | 22.301 | −41.261 | 1.00 | 44.51 | C |
| ATOM | 2408 | C5A | LLP B | 396 | −7.028 | 20.712 | −39.369 | 1.00 | 42.00 | C |
| ATOM | 2409 | O4P | LLP B | 396 | −6.349 | 19.478 | −39.113 | 1.00 | 46.46 | O |
| ATOM | 2410 | P | LLP B | 396 | −6.324 | 18.793 | −37.649 | 1.00 | 46.52 | P |
| ATOM | 2411 | O1P | LLP B | 396 | −5.313 | 17.770 | −37.981 | 1.00 | 43.06 | O |

TABLE A-continued

| | | | | | | | | | |
|---|---|---|---|---|---|---|---|---|---|
| ATOM | 2412 | O2P | LLP B | 396 | −5.924 | 19.841 | −36.682 | 1.00 | 47.03 | O |
| ATOM | 2413 | O3P | LLP B | 396 | −7.696 | 18.287 | −37.413 | 1.00 | 47.80 | O |
| ATOM | 2414 | C | LLP B | 396 | −6.456 | 11.183 | −44.829 | 1.00 | 54.54 | C |
| ATOM | 2415 | O | LLP B | 396 | −6.722 | 9.999 | −44.647 | 1.00 | 55.97 | O |
| ATOM | 2416 | N | MET B | 397 | −6.145 | 11.654 | −46.031 | 1.00 | 56.20 | N |
| ATOM | 2417 | CA | MET B | 397 | −6.264 | 10.824 | −47.244 | 1.00 | 58.62 | C |
| ATOM | 2418 | CB | MET B | 397 | −6.220 | 11.694 | −48.504 | 1.00 | 59.84 | C |
| ATOM | 2419 | CG | MET B | 397 | −7.601 | 12.116 | −49.014 | 1.00 | 65.72 | C |
| ATOM | 2420 | SD | MET B | 397 | −8.531 | 10.759 | −49.762 | 1.00 | 77.13 | S |
| ATOM | 2421 | CE | MET B | 397 | −7.726 | 10.687 | −51.355 | 1.00 | 78.02 | C |
| ATOM | 2422 | C | MET B | 397 | −5.275 | 9.659 | −47.391 | 1.00 | 59.09 | C |
| ATOM | 2423 | O | MET B | 397 | −5.591 | 8.662 | −48.048 | 1.00 | 60.46 | O |
| ATOM | 2424 | N | MET B | 398 | −4.096 | 9.773 | −46.784 | 1.00 | 56.90 | N |
| ATOM | 2425 | CA | MET B | 398 | −3.083 | 8.717 | −46.900 | 1.00 | 54.91 | C |
| ATOM | 2426 | CB | MET B | 398 | −1.664 | 9.303 | −46.865 | 1.00 | 54.13 | C |
| ATOM | 2427 | CG | MET B | 398 | −1.341 | 10.157 | −48.084 | 1.00 | 51.63 | C |
| ATOM | 2428 | SD | MET B | 398 | 0.142 | 11.159 | −47.895 | 1.00 | 55.92 | S |
| ATOM | 2429 | CE | MET B | 398 | 1.414 | 9.898 | −47.786 | 1.00 | 55.45 | C |
| ATOM | 2430 | C | MET B | 398 | −3.256 | 7.590 | −45.881 | 1.00 | 52.85 | C |
| ATOM | 2431 | O | MET B | 398 | −2.603 | 6.568 | −45.990 | 1.00 | 52.91 | O |
| ATOM | 2432 | N | GLY B | 399 | −4.146 | 7.770 | −44.908 | 1.00 | 51.64 | N |
| ATOM | 2433 | CA | GLY B | 399 | −4.519 | 6.685 | −43.988 | 1.00 | 51.13 | C |
| ATOM | 2434 | C | GLY B | 399 | −3.569 | 6.366 | −42.841 | 1.00 | 51.67 | C |
| ATOM | 2435 | O | GLY B | 399 | −3.681 | 5.316 | −42.206 | 1.00 | 51.86 | O |
| ATOM | 2436 | N | VAL B | 400 | −2.629 | 7.262 | −42.572 | 1.00 | 50.78 | N |
| ATOM | 2437 | CA | VAL B | 400 | −1.740 | 7.101 | −41.436 | 1.00 | 50.84 | C |
| ATOM | 2438 | CB | VAL B | 400 | −0.593 | 8.156 | −41.484 | 1.00 | 51.01 | C |
| ATOM | 2439 | CG1 | VAL B | 400 | 0.422 | 7.906 | −40.385 | 1.00 | 46.54 | C |
| ATOM | 2440 | CG2 | VAL B | 400 | 0.108 | 8.136 | −42.844 | 1.00 | 47.48 | C |
| ATOM | 2441 | C | VAL B | 400 | −2.570 | 7.205 | −40.141 | 1.00 | 51.67 | C |
| | | | | | gad65.pdb | | | | | |
| ATOM | 2442 | O | VAL B | 400 | −3.400 | 8.103 | −40.010 | 1.00 | 52.03 | O |
| ATOM | 2443 | N | PRO B | 401 | −2.384 | 6.272 | −39.189 | 1.00 | 52.24 | N |
| ATOM | 2444 | CA | PRO B | 401 | −3.174 | 6.427 | −37.957 | 1.00 | 52.63 | C |
| ATOM | 2445 | CB | PRO B | 401 | −2.668 | 5.290 | −37.058 | 1.00 | 51.66 | C |
| ATOM | 2446 | CG | PRO B | 401 | −2.190 | 4.255 | −38.024 | 1.00 | 49.40 | C |
| ATOM | 2447 | CD | PRO B | 401 | −1.558 | 5.049 | −39.152 | 1.00 | 52.13 | C |
| ATOM | 2448 | C | PRO B | 401 | −3.009 | 7.790 | −37.285 | 1.00 | 55.53 | C |
| ATOM | 2449 | O | PRO B | 401 | −1.950 | 8.437 | −37.401 | 1.00 | 55.09 | O |
| ATOM | 2450 | N | LEU B | 402 | −4.068 | 8.182 | −36.576 | 1.00 | 57.39 | N |
| ATOM | 2451 | CA | LEU B | 402 | −4.288 | 9.537 | −36.065 | 1.00 | 58.39 | C |
| ATOM | 2452 | CB | LEU B | 402 | −5.479 | 9.578 | −35.103 | 1.00 | 59.68 | C |
| ATOM | 2453 | CG | LEU B | 402 | −6.372 | 10.803 | −35.261 | 1.00 | 64.89 | C |
| ATOM | 2454 | CD1 | LEU B | 402 | −7.595 | 10.416 | −36.076 | 1.00 | 63.12 | C |
| ATOM | 2455 | CD2 | LEU B | 402 | −6.779 | 11.332 | −33.893 | 1.00 | 69.48 | C |
| ATOM | 2456 | C | LEU B | 402 | −3.106 | 10.268 | −35.431 | 1.00 | 58.61 | C |
| ATOM | 2457 | O | LEU B | 402 | −2.420 | 9.776 | −34.521 | 1.00 | 56.51 | O |
| ATOM | 2458 | N | GLN B | 403 | −2.992 | 11.495 | −35.928 | 1.00 | 59.37 | N |
| ATOM | 2459 | CA | GLN B | 403 | −1.923 | 12.472 | −35.757 | 1.00 | 58.00 | C |
| ATOM | 2460 | CB | GLN B | 403 | −1.724 | 12.962 | −34.324 | 1.00 | 58.64 | C |
| ATOM | 2461 | CG | GLN B | 403 | −3.015 | 13.562 | −33.764 | 1.00 | 63.76 | C |
| ATOM | 2462 | CD | GLN B | 403 | −2.853 | 14.957 | −33.203 | 1.00 | 63.14 | C |
| ATOM | 2463 | OE1 | GLN B | 403 | −1.995 | 15.206 | −32.354 | 1.00 | 64.21 | O |
| ATOM | 2464 | NE2 | GLN B | 403 | −3.708 | 15.871 | −33.652 | 1.00 | 58.53 | N |
| ATOM | 2465 | C | GLN B | 403 | −0.668 | 12.187 | −36.557 | 1.00 | 55.67 | C |
| ATOM | 2466 | O | GLN B | 403 | 0.324 | 11.640 | −36.091 | 1.00 | 56.32 | O |
| ATOM | 2467 | N | CYS B | 404 | −0.789 | 12.566 | −37.814 | 1.00 | 52.92 | N |
| ATOM | 2468 | CA | CYS B | 404 | 0.318 | 12.719 | −38.696 | 1.00 | 51.16 | C |
| ATOM | 2469 | CB | CYS B | 404 | 0.439 | 11.521 | −39.630 | 1.00 | 52.34 | C |
| ATOM | 2470 | SG | CYS B | 404 | 2.081 | 11.391 | −40.335 | 1.00 | 53.15 | S |
| ATOM | 2471 | C | CYS B | 404 | −0.026 | 13.966 | −39.469 | 1.00 | 49.07 | C |
| ATOM | 2472 | O | CYS B | 404 | −0.822 | 13.932 | −40.417 | 1.00 | 49.39 | O |
| ATOM | 2473 | N | SER B | 405 | 0.544 | 15.077 | −39.026 | 1.00 | 46.48 | N |
| ATOM | 2474 | CA | SER B | 405 | 0.384 | 16.350 | −39.698 | 1.00 | 43.75 | C |
| ATOM | 2475 | CB | SER B | 405 | −0.534 | 17.260 | −38.891 | 1.00 | 42.89 | C |
| ATOM | 2476 | OG | SER B | 405 | −0.623 | 18.527 | −39.507 | 1.00 | 54.06 | O |
| ATOM | 2477 | C | SER B | 405 | 1.748 | 16.991 | −39.854 | 1.00 | 42.18 | C |
| ATOM | 2478 | O | SER B | 405 | 2.516 | 17.050 | −38.908 | 1.00 | 41.94 | O |
| ATOM | 2479 | N | ALA B | 406 | 2.038 | 17.490 | −41.045 | 1.00 | 41.78 | N |
| ATOM | 2480 | CA | ALA B | 406 | 3.319 | 18.144 | −41.305 | 1.00 | 41.41 | C |
| ATOM | 2481 | CB | ALA B | 406 | 4.086 | 17.383 | −42.395 | 1.00 | 40.53 | C |
| ATOM | 2482 | C | ALA B | 406 | 3.134 | 19.590 | −41.730 | 1.00 | 40.31 | C |
| ATOM | 2483 | O | ALA B | 406 | 2.183 | 19.908 | −42.440 | 1.00 | 41.47 | O |
| ATOM | 2484 | N | LEU B | 407 | 4.035 | 20.456 | −41.288 | 1.00 | 39.67 | N |
| ATOM | 2485 | CA | LEU B | 407 | 4.218 | 21.756 | −41.918 | 1.00 | 40.83 | C |
| ATOM | 2486 | CB | LEU B | 407 | 4.226 | 22.901 | −40.895 | 1.00 | 41.06 | C |
| ATOM | 2487 | CG | LEU B | 407 | 4.429 | 24.319 | −41.464 | 1.00 | 42.13 | C |
| ATOM | 2488 | CD1 | LEU B | 407 | 3.233 | 24.801 | −42.289 | 1.00 | 38.37 | C |
| ATOM | 2489 | CD2 | LEU B | 407 | 4.731 | 25.296 | −40.352 | 1.00 | 40.80 | C |
| ATOM | 2490 | C | LEU B | 407 | 5.540 | 21.750 | −42.675 | 1.00 | 40.94 | C |

TABLE A-continued

| | | | | | | | | | |
|---|---|---|---|---|---|---|---|---|---|
| ATOM | 2491 | O | LEU B | 407 | 6.565 | 21.347 | −42.137 | 1.00 | 40.97 | O |
| ATOM | 2492 | N | LEU B | 408 | 5.492 | 22.213 | −43.921 | 1.00 | 41.26 | N |
| ATOM | 2493 | CA | LEU B | 408 | 6.672 | 22.345 | −44.776 | 1.00 | 40.51 | C |
| ATOM | 2494 | CB | LEU B | 408 | 6.492 | 21.511 | −46.056 | 1.00 | 39.85 | C |
| ATOM | 2495 | CG | LEU B | 408 | 6.167 | 20.084 | −45.582 | 1.00 | 46.41 | C |
| ATOM | 2496 | CD1 | LEU B | 408 | 4.908 | 19.474 | −46.206 | 1.00 | 42.62 | C |
| ATOM | 2497 | CD2 | LEU B | 408 | 7.380 | 19.153 | −45.603 | 1.00 | 44.00 | C |
| ATOM | 2498 | C | LEU B | 408 | 6.865 | 23.818 | −45.087 | 1.00 | 40.12 | C |
| ATOM | 2499 | O | LEU B | 408 | 5.913 | 24.516 | −45.417 | 1.00 | 39.23 | O |
| ATOM | 2500 | N | VAL B | 409 | 8.102 | 24.269 | −44.931 | 1.00 | 40.04 | N |
| ATOM | 2501 | CA | VAL B | 409 | 8.504 | 25.651 | −45.115 | 1.00 | 40.50 | C |
| ATOM | 2502 | CB | VAL B | 409 | 8.952 | 26.255 | −43.747 | 1.00 | 38.94 | C |
| ATOM | 2503 | CG1 | VAL B | 409 | 9.451 | 27.658 | −43.906 | 1.00 | 36.86 | C |
| ATOM | 2504 | CG2 | VAL B | 409 | 7.809 | 26.214 | −42.737 | 1.00 | 43.63 | C |
| ATOM | 2505 | C | VAL B | 409 | 9.678 | 25.658 | −46.111 | 1.00 | 42.07 | C |
| ATOM | 2506 | O | VAL B | 409 | 10.636 | 24.897 | −45.945 | 1.00 | 41.07 | O |
| ATOM | 2507 | N | ARG B | 410 | 9.605 | 26.517 | −47.129 | 1.00 | 44.13 | N |
| ATOM | 2508 | CA | ARG B | 410 | 10.607 | 26.535 | −48.189 | 1.00 | 47.18 | C |
| ATOM | 2509 | CB | ARG B | 410 | 10.083 | 27.232 | −49.456 | 1.00 | 48.27 | C |
| | | | | | gad65.pdb | | | | | |
| ATOM | 2510 | CG | ARG B | 410 | 10.660 | 26.653 | −50.760 | 1.00 | 51.66 | C |
| ATOM | 2511 | CD | ARG B | 410 | 11.794 | 27.476 | −51.298 | 1.00 | 60.67 | C |
| ATOM | 2512 | NE | ARG B | 410 | 12.930 | 26.667 | −51.752 | 1.00 | 68.59 | N |
| ATOM | 2513 | CZ | ARG B | 410 | 13.415 | 26.662 | −52.995 | 1.00 | 71.70 | C |
| ATOM | 2514 | NH1 | ARG B | 410 | 12.866 | 27.415 | −53.944 | 1.00 | 71.82 | N |
| ATOM | 2515 | NH2 | ARG B | 410 | 14.464 | 25.902 | −53.286 | 1.00 | 72.91 | N |
| ATOM | 2516 | C | ARG B | 410 | 11.940 | 27.132 | −47.753 | 1.00 | 47.98 | C |
| ATOM | 2517 | O | ARG B | 410 | 12.990 | 26.610 | −48.110 | 1.00 | 48.29 | O |
| ATOM | 2518 | N | GLU B | 411 | 11.900 | 28.218 | −46.989 | 1.00 | 48.61 | N |
| ATOM | 2519 | CA | GLU B | 411 | 13.126 | 28.852 | −46.520 | 1.00 | 49.06 | C |
| ATOM | 2520 | CB | GLU B | 411 | 12.878 | 30.326 | −46.182 | 1.00 | 48.76 | C |
| ATOM | 2521 | CG | GLU B | 411 | 14.145 | 31.128 | −45.921 | 1.00 | 51.05 | C |
| ATOM | 2522 | CD | GLU B | 411 | 13.865 | 32.569 | −45.528 | 1.00 | 51.22 | C |
| ATOM | 2523 | OE1 | GLU B | 411 | 14.354 | 32.989 | −44.453 | 1.00 | 57.86 | O |
| ATOM | 2524 | OE2 | GLU B | 411 | 13.168 | 33.284 | −46.290 | 1.00 | 55.51 | O |
| ATOM | 2525 | C | GLU B | 411 | 13.722 | 28.087 | −45.331 | 1.00 | 48.58 | C |
| ATOM | 2526 | O | GLU B | 411 | 13.140 | 28.034 | −44.249 | 1.00 | 47.87 | O |
| ATOM | 2527 | N | GLU B | 412 | 14.884 | 27.483 | −45.560 | 1.00 | 48.89 | N |
| ATOM | 2528 | CA | GLU B | 412 | 15.611 | 26.741 | −44.540 | 1.00 | 49.52 | C |
| ATOM | 2529 | CB | GLU B | 412 | 16.759 | 25.952 | −45.174 | 1.00 | 49.86 | C |
| ATOM | 2530 | CG | GLU B | 412 | 16.366 | 25.047 | −46.335 | 1.00 | 53.06 | C |
| ATOM | 2531 | CD | GLU B | 412 | 17.553 | 24.289 | −46.942 | 1.00 | 52.50 | C |
| ATOM | 2532 | OE1 | GLU B | 412 | 17.366 | 23.678 | −48.015 | 1.00 | 61.84 | O |
| ATOM | 2533 | OE2 | GLU B | 412 | 18.663 | 24.296 | −46.352 | 1.00 | 58.11 | O |
| ATOM | 2534 | C | GLU B | 412 | 16.176 | 27.696 | −43.487 | 1.00 | 47.40 | C |
| ATOM | 2535 | O | GLU B | 412 | 16.588 | 28.805 | −43.816 | 1.00 | 46.20 | O |
| ATOM | 2536 | N | GLY B | 413 | 16.176 | 27.259 | −42.229 | 1.00 | 46.79 | N |
| ATOM | 2537 | CA | GLY B | 413 | 16.642 | 28.081 | −41.105 | 1.00 | 47.42 | C |
| ATOM | 2538 | C | GLY B | 413 | 15.611 | 28.980 | −40.421 | 1.00 | 46.92 | C |
| ATOM | 2539 | O | GLY B | 413 | 15.782 | 29.332 | −39.252 | 1.00 | 46.98 | O |
| ATOM | 2540 | N | LEU B | 414 | 14.552 | 29.344 | −41.145 | 1.00 | 46.14 | N |
| ATOM | 2541 | CA | LEU B | 414 | 13.489 | 30.223 | −40.642 | 1.00 | 47.12 | C |
| ATOM | 2542 | CB | LEU B | 414 | 12.419 | 30.402 | −41.715 | 1.00 | 46.60 | C |
| ATOM | 2543 | CG | LEU B | 414 | 12.038 | 31.807 | −42.160 | 1.00 | 49.77 | C |
| ATOM | 2544 | CD1 | LEU B | 414 | 10.892 | 31.686 | −43.133 | 1.00 | 48.75 | C |
| ATOM | 2545 | CD2 | LEU B | 414 | 11.677 | 32.733 | −41.010 | 1.00 | 53.04 | C |
| ATOM | 2546 | C | LEU B | 414 | 12.814 | 29.724 | −39.357 | 1.00 | 47.40 | C |
| ATOM | 2547 | O | LEU B | 414 | 12.700 | 30.472 | −38.386 | 1.00 | 47.18 | O |
| ATOM | 2548 | N | MET B | 415 | 12.364 | 28.468 | −39.373 | 1.00 | 48.25 | N |
| ATOM | 2549 | CA | MET B | 415 | 11.692 | 27.832 | −38.237 | 1.00 | 50.21 | C |
| ATOM | 2550 | CB | MET B | 415 | 11.348 | 26.378 | −38.574 | 1.00 | 48.89 | C |
| ATOM | 2551 | CG | MET B | 415 | 10.051 | 26.166 | −39.318 | 1.00 | 51.10 | C |
| ATOM | 2552 | SD | MET B | 415 | 9.499 | 24.432 | −39.238 | 1.00 | 56.68 | S |
| ATOM | 2553 | CE | MET B | 415 | 9.755 | 23.945 | −40.929 | 1.00 | 60.46 | C |
| ATOM | 2554 | C | MET B | 415 | 12.508 | 27.874 | −36.934 | 1.00 | 48.44 | C |
| ATOM | 2555 | O | MET B | 415 | 11.969 | 28.195 | −35.864 | 1.00 | 47.06 | O |
| ATOM | 2556 | N | GLN B | 416 | 13.795 | 27.533 | −37.029 | 1.00 | 47.59 | N |
| ATOM | 2557 | CA | GLN B | 416 | 14.702 | 27.575 | −35.888 | 1.00 | 46.92 | C |
| ATOM | 2558 | CB | GLN B | 416 | 16.077 | 27.001 | −36.275 | 1.00 | 48.57 | C |
| ATOM | 2559 | CG | GLN B | 416 | 17.218 | 27.216 | −35.254 | 1.00 | 52.66 | C |
| ATOM | 2560 | CD | GLN B | 416 | 17.323 | 26.098 | −34.212 | 1.00 | 62.83 | C |
| ATOM | 2561 | OE1 | GLN B | 416 | 16.927 | 24.953 | −34.463 | 1.00 | 69.57 | O |
| ATOM | 2562 | NE2 | GLN B | 416 | 17.868 | 26.427 | −33.038 | 1.00 | 60.27 | N |
| ATOM | 2563 | C | GLN B | 416 | 14.845 | 29.011 | −35.387 | 1.00 | 45.57 | C |
| ATOM | 2564 | O | GLN B | 416 | 14.727 | 29.268 | −34.194 | 1.00 | 44.77 | O |
| ATOM | 2565 | N | ASN B | 417 | 15.107 | 29.941 | −36.303 | 1.00 | 45.35 | N |
| ATOM | 2566 | CA | ASN B | 417 | 15.257 | 31.345 | −35.943 | 1.00 | 45.81 | C |
| ATOM | 2567 | CB | ASN B | 417 | 15.499 | 32.202 | −37.188 | 1.00 | 45.72 | C |
| ATOM | 2568 | CG | ASN B | 417 | 16.972 | 32.419 | −37.487 | 1.00 | 47.24 | C |
| ATOM | 2569 | OD1 | ASN B | 417 | 17.320 | 33.336 | −38.227 | 1.00 | 53.13 | O |

TABLE A-continued

| | | | | | | | | | | |
|---|---|---|---|---|---|---|---|---|---|---|
| ATOM | 2570 | ND2 | ASN B | 417 | 17.842 | 31.590 | −36.917 | 1.00 | 49.56 | N |
| ATOM | 2571 | C | ASN B | 417 | 14.034 | 31.856 | −35.179 | 1.00 | 45.57 | C |
| ATOM | 2572 | O | ASN B | 417 | 14.167 | 32.503 | −34.137 | 1.00 | 43.78 | O |
| ATOM | 2573 | N | CYS B | 418 | 12.853 | 31.531 | −35.706 | 1.00 | 46.54 | N |
| ATOM | 2574 | CA | CYS B | 418 | 11.573 | 31.903 | −35.104 | 1.00 | 47.29 | C |
| ATOM | 2575 | CB | CYS B | 418 | 10.424 | 31.439 | −36.008 | 1.00 | 47.03 | C |
| ATOM | 2576 | SG | CYS B | 418 | 8.760 | 31.843 | −35.425 | 1.00 | 47.65 | S |
| ATOM | 2577 | C | CYS B | 418 | 11.419 | 31.333 | −33.690 | 1.00 | 47.93 | C |
| | | | | | gad65.pdb | | | | | |
| ATOM | 2578 | O | CYS B | 418 | 11.188 | 32.076 | −32.734 | 1.00 | 47.43 | O |
| ATOM | 2579 | N | ASN B | 419 | 11.597 | 30.023 | −33.561 | 1.00 | 48.97 | N |
| ATOM | 2580 | CA | ASN B | 419 | 11.264 | 29.327 | −32.324 | 1.00 | 51.29 | C |
| ATOM | 2581 | CB | ASN B | 419 | 10.641 | 27.967 | −32.625 | 1.00 | 50.74 | C |
| ATOM | 2582 | CG | ASN B | 419 | 9.211 | 28.096 | −33.075 | 1.00 | 56.10 | C |
| ATOM | 2583 | OD1 | ASN B | 419 | 8.340 | 28.460 | −32.285 | 1.00 | 59.56 | O |
| ATOM | 2584 | ND2 | ASN B | 419 | 8.957 | 27.829 | −34.355 | 1.00 | 58.35 | N |
| ATOM | 2585 | C | ASN B | 419 | 12.338 | 29.230 | −31.247 | 1.00 | 52.91 | C |
| ATOM | 2586 | O | ASN B | 419 | 11.995 | 29.088 | −30.081 | 1.00 | 54.05 | O |
| ATOM | 2587 | N | GLN B | 420 | 13.615 | 29.304 | −31.620 | 1.00 | 53.66 | N |
| ATOM | 2588 | CA | GLN B | 420 | 14.695 | 29.162 | −30.644 | 1.00 | 54.99 | C |
| ATOM | 2589 | CB | GLN B | 420 | 16.064 | 29.124 | −31.343 | 1.00 | 55.42 | C |
| ATOM | 2590 | CG | GLN B | 420 | 16.614 | 30.515 | −31.719 | 1.00 | 50.95 | C |
| ATOM | 2591 | CD | GLN B | 420 | 17.857 | 30.482 | −32.588 | 1.00 | 54.58 | C |
| ATOM | 2592 | OE1 | GLN B | 420 | 18.210 | 31.485 | −33.214 | 1.00 | 49.49 | O |
| ATOM | 2593 | NE2 | GLN B | 420 | 18.535 | 29.338 | −32.625 | 1.00 | 53.01 | N |
| ATOM | 2594 | C | GLN B | 420 | 14.658 | 30.307 | −29.629 | 1.00 | 57.21 | C |
| ATOM | 2595 | O | GLN B | 420 | 14.336 | 31.439 | −29.973 | 1.00 | 56.56 | O |
| ATOM | 2596 | N | MET B | 421 | 14.998 | 30.021 | −28.380 | 1.00 | 60.06 | N |
| ATOM | 2597 | CA | MET B | 421 | 15.045 | 31.086 | −27.377 | 1.00 | 62.69 | C |
| ATOM | 2598 | CB | MET B | 421 | 14.378 | 30.639 | −26.067 | 1.00 | 63.23 | C |
| ATOM | 2599 | CG | MET B | 421 | 12.841 | 30.705 | −26.079 | 1.00 | 61.27 | C |
| ATOM | 2600 | SD | MET B | 421 | 12.101 | 32.265 | −26.674 | 1.00 | 62.88 | S |
| ATOM | 2601 | CE | MET B | 421 | 11.360 | 31.774 | −28.235 | 1.00 | 58.37 | C |
| ATOM | 2602 | C | MET B | 421 | 16.463 | 31.625 | −27.157 | 1.00 | 64.48 | C |
| ATOM | 2603 | O | MET B | 421 | 16.648 | 32.785 | −26.769 | 1.00 | 64.89 | O |
| ATOM | 2604 | N | HIS B | 422 | 17.458 | 30.776 | −27.419 | 1.00 | 65.84 | N |
| ATOM | 2605 | CA | HIS B | 422 | 18.865 | 31.177 | −27.397 | 1.00 | 66.55 | C |
| ATOM | 2606 | CB | HIS B | 422 | 19.538 | 30.721 | −26.099 | 1.00 | 67.18 | C |
| ATOM | 2607 | C | HIS B | 422 | 19.612 | 30.613 | −28.607 | 1.00 | 66.44 | C |
| ATOM | 2608 | O | HIS B | 422 | 19.264 | 29.552 | −29.131 | 1.00 | 65.51 | O |
| ATOM | 2609 | N | ASP B | 434 | 27.314 | 16.278 | −33.624 | 1.00 | 93.04 | N |
| ATOM | 2610 | CA | ASP B | 434 | 26.565 | 16.929 | −34.694 | 1.00 | 93.57 | C |
| ATOM | 2611 | CB | ASP B | 434 | 26.442 | 15.997 | −35.908 | 1.00 | 93.31 | C |
| ATOM | 2612 | CG | ASP B | 434 | 25.787 | 16.672 | −37.104 | 1.00 | 92.71 | C |
| ATOM | 2613 | OD1 | ASP B | 434 | 26.160 | 17.820 | −37.430 | 1.00 | 91.30 | O |
| ATOM | 2614 | OD2 | ASP B | 434 | 24.901 | 16.043 | −37.724 | 1.00 | 91.00 | O |
| ATOM | 2615 | C | ASP B | 434 | 25.186 | 17.379 | −34.200 | 1.00 | 94.21 | C |
| ATOM | 2616 | O | ASP B | 434 | 24.221 | 16.601 | −34.199 | 1.00 | 94.01 | O |
| ATOM | 2617 | N | LEU B | 435 | 25.104 | 18.642 | −33.787 | 1.00 | 94.79 | N |
| ATOM | 2618 | CA | LEU B | 435 | 23.891 | 19.200 | −33.182 | 1.00 | 95.23 | C |
| ATOM | 2619 | CB | LEU B | 435 | 24.232 | 20.471 | −32.396 | 1.00 | 95.29 | C |
| ATOM | 2620 | C | LEU B | 435 | 22.763 | 19.482 | −34.186 | 1.00 | 95.51 | C |
| ATOM | 2621 | O | LEU B | 435 | 21.635 | 19.787 | −33.786 | 1.00 | 95.51 | O |
| ATOM | 2622 | N | SER B | 436 | 23.072 | 19.369 | −35.479 | 1.00 | 95.69 | N |
| ATOM | 2623 | CA | SER B | 436 | 22.117 | 19.637 | −36.561 | 1.00 | 95.88 | C |
| ATOM | 2624 | CB | SER B | 436 | 22.802 | 19.479 | −37.922 | 1.00 | 95.94 | C |
| ATOM | 2625 | C | SER B | 436 | 20.874 | 18.746 | −36.499 | 1.00 | 96.01 | C |
| ATOM | 2626 | O | SER B | 436 | 19.858 | 19.032 | −37.138 | 1.00 | 96.18 | O |
| ATOM | 2627 | N | TYR B | 437 | 20.968 | 17.671 | −35.721 | 1.00 | 96.12 | N |
| ATOM | 2628 | CA | TYR B | 437 | 19.878 | 16.716 | −35.555 | 1.00 | 95.95 | C |
| ATOM | 2629 | CB | TYR B | 437 | 20.446 | 15.307 | −35.358 | 1.00 | 96.12 | C |
| ATOM | 2630 | C | TYR B | 437 | 18.922 | 17.094 | −34.409 | 1.00 | 95.61 | C |
| ATOM | 2631 | O | TYR B | 437 | 17.967 | 16.362 | −34.128 | 1.00 | 95.91 | O |
| ATOM | 2632 | N | ASP B | 438 | 19.200 | 18.226 | −33.750 | 1.00 | 94.64 | N |
| ATOM | 2633 | CA | ASP B | 438 | 18.284 | 18.871 | −32.790 | 1.00 | 93.42 | C |
| ATOM | 2634 | CB | ASP B | 438 | 18.818 | 18.786 | −31.344 | 1.00 | 92.98 | C |
| ATOM | 2635 | CG | ASP B | 438 | 19.658 | 17.526 | −31.061 | 1.00 | 91.69 | C |
| ATOM | 2636 | OD1 | ASP B | 438 | 19.521 | 16.497 | −31.759 | 1.00 | 89.14 | O |
| ATOM | 2637 | OD2 | ASP B | 438 | 20.458 | 17.573 | −30.101 | 1.00 | 84.23 | O |
| ATOM | 2638 | C | ASP B | 438 | 18.141 | 20.360 | −33.181 | 1.00 | 92.79 | C |
| ATOM | 2639 | O | ASP B | 438 | 19.119 | 21.095 | −33.022 | 1.00 | 93.13 | O |
| ATOM | 2640 | N | THR B | 439 | 17.001 | 20.870 | −33.679 | 1.00 | 91.65 | N |
| ATOM | 2641 | CA | THR B | 439 | 15.635 | 20.280 | −33.885 | 1.00 | 90.03 | C |
| ATOM | 2642 | CB | THR B | 439 | 15.566 | 18.813 | −34.399 | 1.00 | 90.18 | C |
| ATOM | 2643 | OG1 | THR B | 439 | 16.125 | 17.921 | −33.428 | 1.00 | 92.22 | O |
| ATOM | 2644 | CG2 | THR B | 439 | 16.254 | 18.669 | −35.762 | 1.00 | 90.83 | C |
| ATOM | 2645 | C | THR B | 439 | 14.610 | 20.522 | −32.762 | 1.00 | 87.80 | C |
| | | | | | gad65.pdb | | | | | |
| ATOM | 2646 | O | THR B | 439 | 13.428 | 20.746 | −33.043 | 1.00 | 87.47 | O |
| ATOM | 2647 | N | GLY B | 440 | 15.062 | 20.497 | −31.510 | 1.00 | 85.33 | N |

TABLE A-continued

| | | | | | | | | | |
|---|---|---|---|---|---|---|---|---|---|
| ATOM | 2648 | CA | GLY B | 440 | 14.183 | 20.756 | −30.366 | 1.00 | 82.42 | C |
| ATOM | 2649 | C | GLY B | 440 | 13.589 | 22.158 | −30.336 | 1.00 | 79.70 | C |
| ATOM | 2650 | O | GLY B | 440 | 12.438 | 22.342 | −29.924 | 1.00 | 79.64 | O |
| ATOM | 2651 | N | ASP B | 441 | 14.377 | 23.139 | −30.777 | 1.00 | 76.61 | N |
| ATOM | 2652 | CA | ASP B | 441 | 13.978 | 24.549 | −30.758 | 1.00 | 73.95 | C |
| ATOM | 2653 | CB | ASP B | 441 | 15.146 | 25.436 | −30.302 | 1.00 | 73.96 | C |
| ATOM | 2654 | CG | ASP B | 441 | 15.072 | 25.802 | −28.824 | 1.00 | 73.09 | C |
| ATOM | 2655 | OD1 | ASP B | 441 | 14.077 | 25.447 | −28.156 | 1.00 | 76.15 | O |
| ATOM | 2656 | OD2 | ASP B | 441 | 16.009 | 26.459 | −28.332 | 1.00 | 67.23 | O |
| ATOM | 2657 | C | ASP B | 441 | 13.447 | 25.022 | −32.107 | 1.00 | 71.87 | C |
| ATOM | 2658 | O | ASP B | 441 | 13.483 | 26.217 | −32.430 | 1.00 | 71.64 | O |
| ATOM | 2659 | N | LYS B | 442 | 12.950 | 24.075 | −32.894 | 1.00 | 69.47 | N |
| ATOM | 2660 | CA | LYS B | 442 | 12.326 | 24.395 | −34.172 | 1.00 | 66.80 | C |
| ATOM | 2661 | CB | LYS B | 442 | 12.553 | 23.258 | −35.171 | 1.00 | 67.10 | C |
| ATOM | 2662 | CG | LYS B | 442 | 12.431 | 23.673 | −36.623 | 1.00 | 67.82 | C |
| ATOM | 2663 | CD | LYS B | 442 | 12.497 | 22.489 | −37.569 | 1.00 | 71.01 | C |
| ATOM | 2664 | CE | LYS B | 442 | 13.914 | 21.966 | −37.713 | 1.00 | 73.11 | C |
| ATOM | 2665 | NZ | LYS B | 442 | 14.032 | 21.041 | −38.870 | 1.00 | 76.98 | N |
| ATOM | 2666 | C | LYS B | 442 | 10.832 | 24.662 | −34.004 | 1.00 | 64.41 | C |
| ATOM | 2667 | O | LYS B | 442 | 10.245 | 25.408 | −34.781 | 1.00 | 64.92 | O |
| ATOM | 2668 | N | ALA B | 443 | 10.226 | 24.053 | −32.989 | 1.00 | 62.14 | N |
| ATOM | 2669 | CA | ALA B | 443 | 8.781 | 24.154 | −32.775 | 1.00 | 59.61 | C |
| ATOM | 2670 | CB | ALA B | 443 | 8.127 | 22.786 | −32.944 | 1.00 | 60.47 | C |
| ATOM | 2671 | C | ALA B | 443 | 8.408 | 24.748 | −31.424 | 1.00 | 56.83 | C |
| ATOM | 2672 | O | ALA B | 443 | 9.269 | 25.062 | −30.605 | 1.00 | 56.30 | O |
| ATOM | 2673 | N | LEU B | 444 | 7.104 | 24.893 | −31.206 | 1.00 | 55.41 | N |
| ATOM | 2674 | CA | LEU B | 444 | 6.564 | 25.314 | −29.920 | 1.00 | 53.21 | C |
| ATOM | 2675 | CB | LEU B | 444 | 5.128 | 25.817 | −30.076 | 1.00 | 54.01 | C |
| ATOM | 2676 | CG | LEU B | 444 | 5.010 | 27.321 | −30.297 | 1.00 | 55.89 | C |
| ATOM | 2677 | CD1 | LEU B | 444 | 3.547 | 27.694 | −30.501 | 1.00 | 53.15 | C |
| ATOM | 2678 | CD2 | LEU B | 444 | 5.634 | 28.076 | −29.105 | 1.00 | 56.12 | C |
| ATOM | 2679 | C | LEU B | 444 | 6.607 | 24.215 | −28.867 | 1.00 | 50.16 | C |
| ATOM | 2680 | O | LEU B | 444 | 6.916 | 24.490 | −27.716 | 1.00 | 49.23 | O |
| ATOM | 2681 | N | GLN B | 445 | 6.276 | 22.986 | −29.264 | 1.00 | 48.25 | N |
| ATOM | 2682 | CA | GLN B | 445 | 6.322 | 21.837 | −28.363 | 1.00 | 47.56 | C |
| ATOM | 2683 | CB | GLN B | 445 | 5.910 | 20.562 | −29.089 | 1.00 | 47.11 | C |
| ATOM | 2684 | CG | GLN B | 445 | 4.444 | 20.453 | −29.423 | 1.00 | 45.89 | C |
| ATOM | 2685 | CD | GLN B | 445 | 4.096 | 19.101 | −29.967 | 1.00 | 47.99 | C |
| ATOM | 2686 | OE1 | GLN B | 445 | 3.460 | 18.288 | −29.282 | 1.00 | 51.67 | O |
| ATOM | 2687 | NE2 | GLN B | 445 | 4.518 | 18.832 | −31.200 | 1.00 | 41.58 | N |
| ATOM | 2688 | C | GLN B | 445 | 7.709 | 21.621 | −27.767 | 1.00 | 47.71 | C |
| ATOM | 2689 | O | GLN B | 445 | 8.718 | 22.049 | −28.332 | 1.00 | 47.34 | O |
| ATOM | 2690 | N | CYS B | 446 | 7.740 | 20.971 | −26.614 | 1.00 | 47.55 | N |
| ATOM | 2691 | CA | CYS B | 446 | 8.974 | 20.516 | −26.024 | 1.00 | 47.00 | C |
| ATOM | 2692 | CB | CYS B | 446 | 9.009 | 20.896 | −24.551 | 1.00 | 47.04 | C |
| ATOM | 2693 | SG | CYS B | 446 | 10.447 | 20.360 | −23.647 | 1.00 | 50.09 | S |
| ATOM | 2694 | C | CYS B | 446 | 8.936 | 19.012 | −26.234 | 1.00 | 46.39 | C |
| ATOM | 2695 | O | CYS B | 446 | 9.429 | 18.508 | −27.253 | 1.00 | 45.74 | O |
| ATOM | 2696 | N | GLY B | 447 | 8.300 | 18.301 | −25.300 | 1.00 | 45.48 | N |
| ATOM | 2697 | CA | GLY B | 447 | 7.930 | 16.921 | −25.527 | 1.00 | 43.34 | C |
| ATOM | 2698 | C | GLY B | 447 | 7.197 | 16.813 | −26.845 | 1.00 | 43.94 | C |
| ATOM | 2699 | O | GLY B | 447 | 6.363 | 17.660 | −27.178 | 1.00 | 43.47 | O |
| ATOM | 2700 | N | ARG B | 448 | 7.524 | 15.781 | −27.614 | 1.00 | 44.73 | N |
| ATOM | 2701 | CA | ARG B | 448 | 6.884 | 15.570 | −28.897 | 1.00 | 45.57 | C |
| ATOM | 2702 | CB | ARG B | 448 | 7.624 | 16.302 | −30.020 | 1.00 | 45.11 | C |
| ATOM | 2703 | CG | ARG B | 448 | 6.902 | 16.239 | −31.357 | 1.00 | 44.87 | C |
| ATOM | 2704 | CD | ARG B | 448 | 7.351 | 17.324 | −32.325 | 1.00 | 51.60 | C |
| ATOM | 2705 | NE | ARG B | 448 | 8.748 | 17.194 | −32.755 | 1.00 | 53.09 | N |
| ATOM | 2706 | CZ | ARG B | 448 | 9.152 | 16.569 | −33.861 | 1.00 | 46.01 | C |
| ATOM | 2707 | NH1 | ARG B | 448 | 8.278 | 15.972 | −34.661 | 1.00 | 44.21 | N |
| ATOM | 2708 | NH2 | ARG B | 448 | 10.449 | 16.525 | −34.161 | 1.00 | 46.54 | N |
| ATOM | 2709 | C | ARG B | 448 | 6.790 | 14.078 | −29.168 | 1.00 | 46.84 | C |
| ATOM | 2710 | O | ARG B | 448 | 7.775 | 13.336 | −29.014 | 1.00 | 47.51 | O |
| ATOM | 2711 | N | HIS B | 449 | 5.586 | 13.644 | −29.530 | 1.00 | 45.65 | N |
| ATOM | 2712 | CA | HIS B | 449 | 5.318 | 12.243 | −29.796 | 1.00 | 45.72 | C |
| ATOM | 2713 | CB | HIS B | 449 | 3.817 | 11.975 | −29.706 | 1.00 | 45.88 | C |
| | | | | | gad65.pdb | | | | | |
| ATOM | | | | | | | | | | |
| ATOM | 2714 | CG | HIS B | 449 | 3.429 | 10.584 | −30.086 | 1.00 | 42.24 | C |
| ATOM | 2715 | ND1 | HIS B | 449 | 3.432 | 9.539 | −29.186 | 1.00 | 43.86 | N |
| ATOM | 2716 | CE1 | HIS B | 449 | 3.056 | 8.431 | −29.802 | 1.00 | 39.42 | C |
| ATOM | 2717 | NE2 | HIS B | 449 | 2.792 | 8.725 | −31.065 | 1.00 | 46.90 | N |
| ATOM | 2718 | CD2 | HIS B | 449 | 3.016 | 10.066 | −31.269 | 1.00 | 39.45 | C |
| ATOM | 2719 | C | HIS B | 449 | 5.860 | 11.854 | −31.168 | 1.00 | 46.03 | C |
| ATOM | 2720 | O | HIS B | 449 | 5.837 | 12.664 | −32.109 | 1.00 | 47.52 | O |
| ATOM | 2721 | N | VAL B | 450 | 6.353 | 10.622 | −31.275 | 1.00 | 44.07 | N |
| ATOM | 2722 | CA | VAL B | 450 | 6.856 | 10.092 | −32.538 | 1.00 | 43.32 | C |
| ATOM | 2723 | CB | VAL B | 450 | 7.788 | 8.867 | −32.293 | 1.00 | 43.54 | C |
| ATOM | 2724 | CG1 | VAL B | 450 | 8.284 | 8.261 | −33.601 | 1.00 | 42.01 | C |
| ATOM | 2725 | CG2 | VAL B | 450 | 8.948 | 9.254 | −31.405 | 1.00 | 44.12 | C |

TABLE A-continued

| | | | | | | | | | |
|---|---|---|---|---|---|---|---|---|---|
| ATOM | 2726 | C | VAL B | 450 | 5.688 | 9.715 | −33.456 | 1.00 | 43.72 | C |
| ATOM | 2727 | O | VAL B | 450 | 4.975 | 8.758 | −33.196 | 1.00 | 44.53 | O |
| ATOM | 2728 | N | ASP B | 451 | 5.509 | 10.475 | −34.531 | 1.00 | 45.59 | N |
| ATOM | 2729 | CA | ASP B | 451 | 4.474 | 10.228 | −35.525 | 1.00 | 47.54 | C |
| ATOM | 2730 | CB | ASP B | 451 | 3.619 | 11.482 | −35.706 | 1.00 | 47.98 | C |
| ATOM | 2731 | CG | ASP B | 451 | 2.868 | 11.865 | −34.442 | 1.00 | 56.14 | C |
| ATOM | 2732 | OD1 | ASP B | 451 | 2.428 | 10.939 | −33.712 | 1.00 | 52.65 | O |
| ATOM | 2733 | OD2 | ASP B | 451 | 2.707 | 13.092 | −34.196 | 1.00 | 59.15 | O |
| ATOM | 2734 | C | ASP B | 451 | 5.055 | 9.812 | −36.878 | 1.00 | 47.91 | C |
| ATOM | 2735 | O | ASP B | 451 | 4.336 | 9.286 | −37.732 | 1.00 | 47.25 | O |
| ATOM | 2736 | N | VAL B | 452 | 6.350 | 10.056 | −37.068 | 1.00 | 46.98 | N |
| ATOM | 2737 | CA | VAL B | 452 | 7.016 | 9.745 | −38.332 | 1.00 | 46.86 | C |
| ATOM | 2738 | CB | VAL B | 452 | 8.475 | 10.311 | −38.372 | 1.00 | 46.07 | C |
| ATOM | 2739 | CG1 | VAL B | 452 | 9.397 | 9.590 | −37.381 | 1.00 | 39.81 | C |
| ATOM | 2740 | CG2 | VAL B | 452 | 9.040 | 10.244 | −39.791 | 1.00 | 47.58 | C |
| ATOM | 2741 | C | VAL B | 452 | 7.014 | 8.249 | −38.718 | 1.00 | 47.34 | C |
| ATOM | 2742 | O | VAL B | 452 | 6.825 | 7.912 | −39.890 | 1.00 | 48.12 | O |
| ATOM | 2743 | N | PHE B | 453 | 7.219 | 7.361 | −37.743 | 1.00 | 46.72 | N |
| ATOM | 2744 | CA | PHE B | 453 | 7.428 | 5.947 | −38.048 | 1.00 | 45.66 | C |
| ATOM | 2745 | CB | PHE B | 453 | 7.851 | 5.122 | −36.826 | 1.00 | 44.26 | C |
| ATOM | 2746 | CG | PHE B | 453 | 8.246 | 3.696 | −37.172 | 1.00 | 41.29 | C |
| ATOM | 2747 | CD1 | PHE B | 453 | 9.419 | 3.436 | −37.876 | 1.00 | 43.81 | C |
| ATOM | 2748 | CE1 | PHE B | 453 | 9.793 | 2.121 | −38.209 | 1.00 | 42.96 | C |
| ATOM | 2749 | CZ | PHE B | 453 | 8.973 | 1.055 | −37.844 | 1.00 | 43.40 | C |
| ATOM | 2750 | CE2 | PHE B | 453 | 7.798 | 1.301 | −37.142 | 1.00 | 40.92 | C |
| ATOM | 2751 | CD2 | PHE B | 453 | 7.438 | 2.621 | −36.809 | 1.00 | 39.96 | C |
| ATOM | 2752 | C | PHE B | 453 | 6.224 | 5.312 | −38.725 | 1.00 | 46.47 | C |
| ATOM | 2753 | O | PHE B | 453 | 6.390 | 4.498 | −39.630 | 1.00 | 45.11 | O |
| ATOM | 2754 | N | LYS B | 454 | 5.020 | 5.710 | −38.308 | 1.00 | 47.68 | N |
| ATOM | 2755 | CA | LYS B | 454 | 3.822 | 5.164 | −38.918 | 1.00 | 48.74 | C |
| ATOM | 2756 | CB | LYS B | 454 | 2.552 | 5.418 | −38.082 | 1.00 | 48.76 | C |
| ATOM | 2757 | CG | LYS B | 454 | 2.311 | 6.842 | −37.670 | 1.00 | 54.07 | C |
| ATOM | 2758 | CD | LYS B | 454 | 1.340 | 6.935 | −36.511 | 1.00 | 54.70 | C |
| ATOM | 2759 | CE | LYS B | 454 | 1.098 | 8.411 | −36.181 | 1.00 | 60.74 | C |
| ATOM | 2760 | NZ | LYS B | 454 | 0.214 | 8.620 | −35.006 | 1.00 | 56.26 | N |
| ATOM | 2761 | C | LYS B | 454 | 3.692 | 5.573 | −40.383 | 1.00 | 49.50 | C |
| ATOM | 2762 | O | LYS B | 454 | 3.293 | 4.756 | −41.219 | 1.00 | 50.24 | O |
| ATOM | 2763 | N | LEU B | 455 | 4.067 | 6.811 | −40.703 | 1.00 | 48.81 | N |
| ATOM | 2764 | CA | LEU B | 455 | 4.088 | 7.262 | −42.101 | 1.00 | 47.81 | C |
| ATOM | 2765 | CB | LEU B | 455 | 4.211 | 8.799 | −42.199 | 1.00 | 47.69 | C |
| ATOM | 2766 | CG | LEU B | 455 | 4.392 | 9.458 | −43.587 | 1.00 | 49.83 | C |
| ATOM | 2767 | CD1 | LEU B | 455 | 3.317 | 9.032 | −44.601 | 1.00 | 48.07 | C |
| ATOM | 2768 | CD2 | LEU B | 455 | 4.445 | 10.983 | −43.508 | 1.00 | 47.62 | C |
| ATOM | 2769 | C | LEU B | 455 | 5.203 | 6.563 | −42.903 | 1.00 | 46.14 | C |
| ATOM | 2770 | O | LEU B | 455 | 4.971 | 6.067 | −44.016 | 1.00 | 46.65 | O |
| ATOM | 2771 | N | TRP B | 456 | 6.401 | 6.525 | −42.335 | 1.00 | 43.49 | N |
| ATOM | 2772 | CA | TRP B | 456 | 7.559 | 5.928 | −43.009 | 1.00 | 43.44 | C |
| ATOM | 2773 | CB | TRP B | 456 | 8.850 | 6.224 | −42.235 | 1.00 | 40.97 | C |
| ATOM | 2774 | CG | TRP B | 456 | 10.081 | 5.663 | −42.883 | 1.00 | 44.38 | C |
| ATOM | 2775 | CD1 | TRP B | 456 | 10.883 | 6.284 | −43.806 | 1.00 | 38.37 | C |
| ATOM | 2776 | NE1 | TRP B | 456 | 11.923 | 5.453 | −44.158 | 1.00 | 41.32 | N |
| ATOM | 2777 | CE2 | TRP B | 456 | 11.818 | 4.278 | −43.465 | 1.00 | 38.66 | C |
| ATOM | 2778 | CD2 | TRP B | 456 | 10.671 | 4.369 | −42.647 | 1.00 | 43.03 | C |
| ATOM | 2779 | CE3 | TRP B | 456 | 10.347 | 3.288 | −41.818 | 1.00 | 36.31 | C |
| ATOM | 2780 | CZ3 | TRP B | 456 | 11.148 | 2.155 | −41.851 | 1.00 | 39.02 | C |
| ATOM | 2781 | CH2 | TRP B | 456 | 12.274 | 2.094 | −42.681 | 1.00 | 38.93 | C |
| | | | | | gad65.pdb | | | | | |
| ATOM | 2782 | CZ2 | TRP B | 456 | 12.623 | 3.140 | −43.497 | 1.00 | 38.54 | C |
| ATOM | 2783 | C | TRP B | 456 | 7.395 | 4.411 | −43.302 | 1.00 | 43.32 | C |
| ATOM | 2784 | O | TRP B | 456 | 7.678 | 3.975 | −44.398 | 1.00 | 43.22 | O |
| ATOM | 2785 | N | LEU B | 457 | 6.931 | 3.625 | −42.327 | 1.00 | 42.98 | N |
| ATOM | 2786 | CA | LEU B | 457 | 6.686 | 2.191 | −42.540 | 1.00 | 42.58 | C |
| ATOM | 2787 | CB | LEU B | 457 | 6.308 | 1.472 | −41.226 | 1.00 | 42.41 | C |
| ATOM | 2788 | CG | LEU B | 457 | 6.590 | −0.040 | −41.200 | 1.00 | 40.61 | C |
| ATOM | 2789 | CD1 | LEU B | 457 | 8.096 | −0.323 | −41.406 | 1.00 | 40.63 | C |
| ATOM | 2790 | CD2 | LEU B | 457 | 6.092 | −0.713 | −39.924 | 1.00 | 40.83 | C |
| ATOM | 2791 | C | LEU B | 457 | 5.632 | 1.929 | −43.625 | 1.00 | 42.84 | C |
| ATOM | 2792 | O | LEU B | 457 | 5.834 | 1.089 | −44.500 | 1.00 | 42.58 | O |
| ATOM | 2793 | N | MET B | 458 | 4.511 | 2.644 | −43.547 | 1.00 | 43.28 | N |
| ATOM | 2794 | CA | MET B | 458 | 3.485 | 2.619 | −44.590 | 1.00 | 44.81 | C |
| ATOM | 2795 | CB | MET B | 458 | 2.325 | 3.540 | −44.220 | 1.00 | 43.84 | C |
| ATOM | 2796 | CG | MET B | 458 | 1.442 | 2.995 | −43.122 | 1.00 | 42.38 | C |
| ATOM | 2797 | SD | MET B | 458 | 0.186 | 4.188 | −42.632 | 1.00 | 49.40 | S |
| ATOM | 2798 | CE | MET B | 458 | −0.882 | 4.202 | −44.068 | 1.00 | 43.59 | C |
| ATOM | 2799 | C | MET B | 458 | 4.020 | 2.996 | −45.968 | 1.00 | 44.51 | C |
| ATOM | 2800 | O | MET B | 458 | 3.742 | 2.314 | −46.944 | 1.00 | 45.84 | O |
| ATOM | 2801 | N | TRP B | 459 | 4.769 | 4.090 | −46.050 | 1.00 | 45.02 | N |
| ATOM | 2802 | CA | TRP B | 459 | 5.401 | 4.506 | −47.292 | 1.00 | 45.55 | C |
| ATOM | 2803 | CB | TRP B | 459 | 6.211 | 5.787 | −47.074 | 1.00 | 45.32 | C |
| ATOM | 2804 | CG | TRP B | 459 | 6.316 | 6.670 | −48.296 | 1.00 | 48.42 | C |

TABLE A-continued

| | | | | | | | | | |
|---|---|---|---|---|---|---|---|---|---|
| ATOM | 2805 | CD1 | TRP B | 459 | 6.496 | 6.265 | −49.592 | 1.00 | 48.22 | C |
| ATOM | 2806 | NE1 | TRP B | 459 | 6.544 | 7.349 | −50.427 | 1.00 | 46.37 | N |
| ATOM | 2807 | CE2 | TRP B | 459 | 6.409 | 8.492 | −49.685 | 1.00 | 48.57 | C |
| ATOM | 2808 | CD2 | TRP B | 459 | 6.265 | 8.103 | −48.332 | 1.00 | 48.82 | C |
| ATOM | 2809 | CE3 | TRP B | 459 | 6.095 | 9.096 | −47.358 | 1.00 | 47.56 | C |
| ATOM | 2810 | CZ3 | TRP B | 459 | 6.080 | 10.435 | −47.761 | 1.00 | 48.78 | C |
| ATOM | 2811 | CH2 | TRP B | 459 | 6.241 | 10.790 | −49.117 | 1.00 | 45.56 | C |
| ATOM | 2812 | CZ2 | TRP B | 459 | 6.394 | 9.837 | −50.090 | 1.00 | 49.27 | C |
| ATOM | 2813 | C | TRP B | 459 | 6.313 | 3.386 | −47.809 | 1.00 | 46.71 | C |
| ATOM | 2814 | O | TRP B | 459 | 6.379 | 3.135 | −49.008 | 1.00 | 46.65 | O |
| ATOM | 2815 | N | ARG B | 460 | 6.992 | 2.708 | −46.891 | 1.00 | 46.73 | N |
| ATOM | 2816 | CA | ARG B | 460 | 7.880 | 1.617 | −47.240 | 1.00 | 48.35 | C |
| ATOM | 2817 | CB | ARG B | 460 | 8.718 | 1.209 | −46.025 | 1.00 | 47.55 | C |
| ATOM | 2818 | CG | ARG B | 460 | 10.211 | 1.099 | −46.297 | 1.00 | 54.02 | C |
| ATOM | 2819 | CD | ARG B | 460 | 10.886 | 2.462 | −46.432 | 1.00 | 51.19 | C |
| ATOM | 2820 | C | ARG B | 460 | 7.078 | 0.434 | −47.768 | 1.00 | 49.10 | C |
| ATOM | 2821 | O | ARG B | 460 | 7.422 | −0.154 | −48.800 | 1.00 | 49.39 | O |
| ATOM | 2822 | N | ALA B | 461 | 5.997 | 0.108 | −47.061 | 1.00 | 49.21 | N |
| ATOM | 2823 | CA | ALA B | 461 | 5.177 | −1.063 | −47.370 | 1.00 | 49.19 | C |
| ATOM | 2824 | CB | ALA B | 461 | 4.285 | −1.404 | −46.188 | 1.00 | 49.60 | C |
| ATOM | 2825 | C | ALA B | 461 | 4.338 | −0.896 | −48.632 | 1.00 | 48.69 | C |
| ATOM | 2826 | O | ALA B | 461 | 4.016 | −1.879 | −49.296 | 1.00 | 49.46 | O |
| ATOM | 2827 | N | LYS B | 462 | 4.004 | 0.349 | −48.954 | 1.00 | 48.08 | N |
| ATOM | 2828 | CA | LYS B | 462 | 3.101 | 0.674 | −50.059 | 1.00 | 47.62 | C |
| ATOM | 2829 | CB | LYS B | 462 | 2.071 | 1.709 | −49.590 | 1.00 | 47.99 | C |
| ATOM | 2830 | CG | LYS B | 462 | 1.051 | 1.190 | −48.586 | 1.00 | 51.80 | C |
| ATOM | 2831 | CD | LYS B | 462 | 0.399 | 2.347 | −47.830 | 1.00 | 51.66 | C |
| ATOM | 2832 | CE | LYS B | 462 | −1.116 | 2.250 | −47.873 | 1.00 | 57.05 | C |
| ATOM | 2833 | NZ | LYS B | 462 | −1.677 | 1.114 | −47.075 | 1.00 | 58.26 | N |
| ATOM | 2834 | C | LYS B | 462 | 3.820 | 1.246 | −51.277 | 1.00 | 46.51 | C |
| ATOM | 2835 | O | LYS B | 462 | 3.350 | 1.099 | −52.410 | 1.00 | 45.89 | O |
| ATOM | 2836 | N | GLY B | 463 | 4.945 | 1.918 | −51.031 | 1.00 | 45.77 | N |
| ATOM | 2837 | CA | GLY B | 463 | 5.611 | 2.716 | −52.050 | 1.00 | 45.66 | C |
| ATOM | 2838 | C | GLY B | 463 | 4.770 | 3.935 | −52.383 | 1.00 | 45.51 | C |
| ATOM | 2839 | O | GLY B | 463 | 3.590 | 3.998 | −52.046 | 1.00 | 45.97 | O |
| ATOM | 2840 | N | THR B | 464 | 5.384 | 4.913 | −53.036 | 1.00 | 46.36 | N |
| ATOM | 2841 | CA | THR B | 464 | 4.671 | 6.081 | −53.539 | 1.00 | 47.95 | C |
| ATOM | 2842 | CB | THR B | 464 | 5.633 | 7.040 | −54.271 | 1.00 | 48.27 | C |
| ATOM | 2843 | OG1 | THR B | 464 | 6.631 | 7.495 | −53.353 | 1.00 | 51.34 | O |
| ATOM | 2844 | CG2 | THR B | 464 | 4.890 | 8.248 | −54.854 | 1.00 | 50.28 | C |
| ATOM | 2845 | C | THR B | 464 | 3.518 | 5.680 | −54.457 | 1.00 | 48.55 | C |
| ATOM | 2846 | O | THR B | 464 | 2.440 | 6.293 | −54.406 | 1.00 | 50.32 | O |
| ATOM | 2847 | N | THR B | 465 | 3.742 | 4.647 | −55.276 | 1.00 | 47.47 | N |
| ATOM | 2848 | CA | THR B | 465 | 2.706 | 4.087 | −56.160 | 1.00 | 47.29 | C |
| ATOM | 2849 | CB | THR B | 465 | 3.262 | 2.963 | −57.100 | 1.00 | 47.40 | C |
| | | | | | gad65.pdb | | | | | |
| ATOM | 2850 | OG1 | THR B | 465 | 4.151 | 2.107 | −56.370 | 1.00 | 51.14 | O |
| ATOM | 2851 | CG2 | THR B | 465 | 4.020 | 3.564 | −58.286 | 1.00 | 43.62 | C |
| ATOM | 2852 | C | THR B | 465 | 1.489 | 3.565 | −55.401 | 1.00 | 46.99 | C |
| ATOM | 2853 | O | THR B | 465 | 0.372 | 3.684 | −55.874 | 1.00 | 47.48 | O |
| ATOM | 2854 | N | GLY B | 466 | 1.713 | 2.979 | −54.231 | 1.00 | 47.45 | N |
| ATOM | 2855 | CA | GLY B | 466 | 0.632 | 2.493 | −53.377 | 1.00 | 47.58 | C |
| ATOM | 2856 | C | GLY B | 466 | −0.287 | 3.601 | −52.899 | 1.00 | 48.68 | C |
| ATOM | 2857 | O | GLY B | 466 | −1.513 | 3.469 | −52.965 | 1.00 | 48.94 | O |
| ATOM | 2858 | N | PHE B | 467 | 0.298 | 4.700 | −52.428 | 1.00 | 49.54 | N |
| ATOM | 2859 | CA | PHE B | 467 | −0.491 | 5.848 | −51.978 | 1.00 | 49.27 | C |
| ATOM | 2860 | CB | PHE B | 467 | 0.398 | 6.930 | −51.369 | 1.00 | 48.18 | C |
| ATOM | 2861 | CG | PHE B | 467 | 0.870 | 6.627 | −49.973 | 1.00 | 47.51 | C |
| ATOM | 2862 | CD1 | PHE B | 467 | 2.219 | 6.688 | −49.658 | 1.00 | 50.71 | C |
| ATOM | 2863 | CE1 | PHE B | 467 | 2.667 | 6.432 | −48.358 | 1.00 | 49.35 | C |
| ATOM | 2864 | CZ | PHE B | 467 | 1.768 | 6.107 | −47.377 | 1.00 | 48.56 | C |
| ATOM | 2865 | CE2 | PHE B | 467 | 0.407 | 6.054 | −47.670 | 1.00 | 49.46 | C |
| ATOM | 2866 | CD2 | PHE B | 467 | −0.031 | 6.315 | −48.964 | 1.00 | 49.15 | C |
| ATOM | 2867 | C | PHE B | 467 | −1.267 | 6.418 | −53.157 | 1.00 | 50.40 | C |
| ATOM | 2868 | O | PHE B | 467 | −2.458 | 6.745 | −53.041 | 1.00 | 50.89 | O |
| ATOM | 2869 | N | GLU B | 468 | −0.584 | 6.524 | −54.292 | 1.00 | 49.98 | N |
| ATOM | 2870 | CA | GLU B | 468 | −1.210 | 6.942 | −55.533 | 1.00 | 50.66 | C |
| ATOM | 2871 | CB | GLU B | 468 | −0.222 | 6.839 | −56.696 | 1.00 | 50.24 | C |
| ATOM | 2872 | CG | GLU B | 468 | −0.773 | 7.392 | −57.981 | 1.00 | 48.95 | C |
| ATOM | 2873 | CD | GLU B | 468 | 0.103 | 7.125 | −59.187 | 1.00 | 52.14 | C |
| ATOM | 2874 | OE1 | GLU B | 468 | 1.030 | 6.282 | −59.110 | 1.00 | 45.66 | O |
| ATOM | 2875 | OE2 | GLU B | 468 | −0.164 | 7.757 | −60.234 | 1.00 | 57.51 | O |
| ATOM | 2876 | C | GLU B | 468 | −2.466 | 6.130 | −55.848 | 1.00 | 51.66 | C |
| ATOM | 2877 | O | GLU B | 468 | −3.532 | 6.703 | −56.077 | 1.00 | 53.10 | O |
| ATOM | 2878 | N | ALA B | 469 | −2.336 | 4.805 | −55.872 | 1.00 | 51.30 | N |
| ATOM | 2879 | CA | ALA B | 469 | −3.437 | 3.931 | −56.268 | 1.00 | 52.00 | C |
| ATOM | 2880 | CB | ALA B | 469 | −2.979 | 2.477 | −56.306 | 1.00 | 51.88 | C |
| ATOM | 2881 | C | ALA B | 469 | −4.633 | 4.089 | −55.338 | 1.00 | 52.74 | C |
| ATOM | 2882 | O | ALA B | 469 | −5.796 | 4.052 | −55.779 | 1.00 | 52.12 | O |
| ATOM | 2883 | N | HIS B | 470 | −4.330 | 4.258 | −54.054 | 1.00 | 54.30 | N |

TABLE A-continued

| | | | | | | | | | | |
|---|---|---|---|---|---|---|---|---|---|---|
| ATOM | 2884 | CA | HIS B | 470 | −5.352 | 4.428 | −53.027 | 1.00 | 55.37 | C |
| ATOM | 2885 | CB | HIS B | 470 | −4.753 | 4.311 | −51.627 | 1.00 | 54.90 | C |
| ATOM | 2886 | CG | HIS B | 470 | −5.626 | 4.890 | −50.557 | 1.00 | 61.48 | C |
| ATOM | 2887 | ND1 | HIS B | 470 | −6.901 | 4.428 | −50.304 | 1.00 | 60.16 | N |
| ATOM | 2888 | CE1 | HIS B | 470 | −7.429 | 5.129 | −49.317 | 1.00 | 62.55 | C |
| ATOM | 2889 | NE2 | HIS B | 470 | −6.550 | 6.037 | −48.930 | 1.00 | 63.26 | N |
| ATOM | 2890 | CD2 | HIS B | 470 | −5.412 | 5.909 | −49.689 | 1.00 | 62.38 | C |
| ATOM | 2891 | C | HIS B | 470 | −6.104 | 5.749 | −53.178 | 1.00 | 54.65 | C |
| ATOM | 2892 | O | HIS B | 470 | −7.332 | 5.768 | −53.151 | 1.00 | 54.75 | O |
| ATOM | 2893 | N | VAL B | 471 | −5.357 | 6.841 | −53.330 | 1.00 | 54.16 | N |
| ATOM | 2894 | CA | VAL B | 471 | −5.937 | 8.157 | −53.572 | 1.00 | 54.14 | C |
| ATOM | 2895 | CB | VAL B | 471 | −4.830 | 9.262 | −53.678 | 1.00 | 54.21 | C |
| ATOM | 2896 | CG1 | VAL B | 471 | −5.354 | 10.567 | −54.280 | 1.00 | 52.50 | C |
| ATOM | 2897 | CG2 | VAL B | 471 | −4.235 | 9.537 | −52.303 | 1.00 | 52.31 | C |
| ATOM | 2898 | C | VAL B | 471 | −6.906 | 8.122 | −54.771 | 1.00 | 54.83 | C |
| ATOM | 2899 | O | VAL B | 471 | −8.009 | 8.656 | −54.677 | 1.00 | 55.11 | O |
| ATOM | 2900 | N | ASP B | 472 | −6.507 | 7.461 | −55.864 | 1.00 | 54.82 | N |
| ATOM | 2901 | CA | ASP B | 472 | −7.358 | 7.309 | −57.066 | 1.00 | 54.76 | C |
| ATOM | 2902 | CB | ASP B | 472 | −6.561 | 6.730 | −58.230 | 1.00 | 54.64 | C |
| ATOM | 2903 | CG | ASP B | 472 | −5.386 | 7.593 | −58.625 | 1.00 | 56.94 | C |
| ATOM | 2904 | OD1 | ASP B | 472 | −4.659 | 7.198 | −59.568 | 1.00 | 53.83 | O |
| ATOM | 2905 | OD2 | ASP B | 472 | −5.193 | 8.659 | −58.001 | 1.00 | 59.59 | O |
| ATOM | 2906 | C | ASP B | 472 | −8.587 | 6.428 | −56.862 | 1.00 | 55.36 | C |
| ATOM | 2907 | O | ASP B | 472 | −9.631 | 6.649 | −57.487 | 1.00 | 55.31 | O |
| ATOM | 2908 | N | LYS B | 473 | −8.444 | 5.406 | −56.022 | 1.00 | 56.01 | N |
| ATOM | 2909 | CA | LYS B | 473 | −9.529 | 4.483 | −55.730 | 1.00 | 56.18 | C |
| ATOM | 2910 | CB | LYS B | 473 | −9.026 | 3.326 | −54.863 | 1.00 | 56.98 | C |
| ATOM | 2911 | CG | LYS B | 473 | −9.995 | 2.147 | −54.746 | 1.00 | 60.32 | C |
| ATOM | 2912 | C | LYS B | 473 | −10.643 | 5.242 | −55.021 | 1.00 | 55.95 | C |
| ATOM | 2913 | O | LYS B | 473 | −11.817 | 5.084 | −55.361 | 1.00 | 55.90 | O |
| ATOM | 2914 | N | CYS B | 474 | −10.260 | 6.082 | −54.055 | 1.00 | 55.33 | N |
| ATOM | 2915 | CA | CYS B | 474 | −11.209 | 6.906 | −53.319 | 1.00 | 54.29 | C |
| ATOM | 2916 | CB | CYS B | 474 | −10.519 | 7.635 | −52.161 | 1.00 | 52.54 | C |
| ATOM | 2917 | SG | CYS B | 474 | −9.761 gad65.pdb | 6.535 | −50.941 | 1.00 | 52.69 | S |
| ATOM | 2918 | C | CYS B | 474 | −11.916 | 7.905 | −54.246 | 1.00 | 55.30 | C |
| ATOM | 2919 | O | CYS B | 474 | −13.141 | 8.053 | −54.185 | 1.00 | 54.58 | O |
| ATOM | 2920 | N | LEU B | 475 | −11.142 | 8.572 | −55.103 | 1.00 | 55.74 | N |
| ATOM | 2921 | CA | LEU B | 475 | −11.670 | 9.638 | −55.958 | 1.00 | 56.68 | C |
| ATOM | 2922 | CB | LEU B | 475 | −10.534 | 10.435 | −56.604 | 1.00 | 57.36 | C |
| ATOM | 2923 | CG | LEU B | 475 | −9.921 | 11.452 | −55.633 | 1.00 | 59.90 | C |
| ATOM | 2924 | CD1 | LEU B | 475 | −8.529 | 11.877 | −56.050 | 1.00 | 57.57 | C |
| ATOM | 2925 | CD2 | LEU B | 475 | −10.835 | 12.651 | −55.517 | 1.00 | 61.07 | C |
| ATOM | 2926 | C | LEU B | 475 | −12.651 | 9.148 | −57.012 | 1.00 | 56.71 | C |
| ATOM | 2927 | O | LEU B | 475 | −13.624 | 9.839 | −57.332 | 1.00 | 56.44 | O |
| ATOM | 2928 | N | GLU B | 476 | −12.389 | 7.951 | −57.537 | 1.00 | 56.89 | N |
| ATOM | 2929 | CA | GLU B | 476 | −13.281 | 7.307 | −58.491 | 1.00 | 57.37 | C |
| ATOM | 2930 | CB | GLU B | 476 | −12.609 | 6.081 | −59.122 | 1.00 | 57.39 | C |
| ATOM | 2931 | CG | GLU B | 476 | −13.538 | 5.243 | −59.982 | 1.00 | 60.23 | C |
| ATOM | 2932 | C | GLU B | 476 | −14.573 | 6.906 | −57.789 | 1.00 | 57.01 | C |
| ATOM | 2933 | O | GLU B | 476 | −15.659 | 7.045 | −58.347 | 1.00 | 57.43 | O |
| ATOM | 2934 | N | LEU B | 477 | −14.449 | 6.420 | −56.559 | 1.00 | 55.97 | N |
| ATOM | 2935 | CA | LEU B | 477 | −15.608 | 5.999 | −55.791 | 1.00 | 55.81 | C |
| ATOM | 2936 | CB | LEU B | 477 | −15.174 | 5.300 | −54.504 | 1.00 | 56.18 | C |
| ATOM | 2937 | CG | LEU B | 477 | −16.278 | 4.464 | −53.849 | 1.00 | 61.44 | C |
| ATOM | 2938 | CD1 | LEU B | 477 | −16.744 | 3.336 | −54.766 | 1.00 | 62.07 | C |
| ATOM | 2939 | CD2 | LEU B | 477 | −15.830 | 3.918 | −52.504 | 1.00 | 63.21 | C |
| ATOM | 2940 | C | LEU B | 477 | −16.538 | 7.179 | −55.505 | 1.00 | 54.93 | C |
| ATOM | 2941 | O | LEU B | 477 | −17.761 | 7.043 | −55.522 | 1.00 | 52.71 | O |
| ATOM | 2942 | N | ALA B | 478 | −15.938 | 8.337 | −55.247 | 1.00 | 55.87 | N |
| ATOM | 2943 | CA | ALA B | 478 | −16.677 | 9.588 | −55.115 | 1.00 | 55.95 | C |
| ATOM | 2944 | CB | ALA B | 478 | −15.754 | 10.671 | −54.627 | 1.00 | 54.74 | C |
| ATOM | 2945 | C | ALA B | 478 | −17.359 | 9.991 | −56.446 | 1.00 | 56.46 | C |
| ATOM | 2946 | O | ALA B | 478 | −18.478 | 10.516 | −56.448 | 1.00 | 55.97 | O |
| ATOM | 2947 | N | GLU B | 479 | −16.672 | 9.729 | −57.559 | 1.00 | 56.68 | N |
| ATOM | 2948 | CA | GLU B | 479 | −17.213 | 9.913 | −58.900 | 1.00 | 57.55 | C |
| ATOM | 2949 | CB | GLU B | 479 | −16.106 | 9.697 | −59.958 | 1.00 | 57.59 | C |
| ATOM | 2950 | CG | GLU B | 479 | −16.585 | 9.644 | −61.417 | 1.00 | 59.04 | C |
| ATOM | 2951 | CD | GLU B | 479 | −15.468 | 9.339 | −62.426 | 1.00 | 59.60 | C |
| ATOM | 2952 | OE1 | GLU B | 479 | −15.425 | 10.002 | −63.483 | 1.00 | 64.00 | O |
| ATOM | 2953 | OE2 | GLU B | 479 | −14.637 | 8.435 | −62.179 | 1.00 | 67.75 | O |
| ATOM | 2954 | C | GLU B | 479 | −18.391 | 8.958 | −59.127 | 1.00 | 56.36 | C |
| ATOM | 2955 | O | GLU B | 479 | −19.405 | 9.339 | −59.737 | 1.00 | 56.60 | O |
| ATOM | 2956 | N | TYR B | 480 | −18.254 | 7.726 | −58.635 | 1.00 | 54.54 | N |
| ATOM | 2957 | CA | TYR B | 480 | −19.329 | 6.735 | −57.707 | 1.00 | 53.83 | C |
| ATOM | 2958 | CB | TYR B | 480 | −18.835 | 5.377 | −58.202 | 1.00 | 52.86 | C |
| ATOM | 2959 | CG | TYR B | 480 | −19.894 | 4.298 | −58.127 | 1.00 | 52.70 | C |
| ATOM | 2960 | CD1 | TYR B | 480 | −20.360 | 3.837 | −56.896 | 1.00 | 55.03 | C |
| ATOM | 2961 | CE1 | TYR B | 480 | −21.330 | 2.841 | −56.817 | 1.00 | 52.88 | C |
| ATOM | 2962 | CZ | TYR B | 480 | −21.844 | 2.299 | −57.982 | 1.00 | 53.92 | C |

TABLE A-continued

| | | | | | | | | | | |
|---|---|---|---|---|---|---|---|---|---|---|
| ATOM | 2963 | OH | TYR B | 480 | −22.813 | 1.325 | −57.921 | 1.00 | 53.28 | O |
| ATOM | 2964 | CE2 | TYR B | 480 | −21.407 | 2.748 | −59.217 | 1.00 | 54.65 | C |
| ATOM | 2965 | CD2 | TYR B | 480 | −20.434 | 3.736 | −59.285 | 1.00 | 57.32 | C |
| ATOM | 2966 | C | TYR B | 480 | −20.576 | 7.193 | −57.923 | 1.00 | 54.29 | C |
| ATOM | 2967 | O | TYR B | 480 | −21.715 | 6.975 | −58.357 | 1.00 | 53.55 | O |
| ATOM | 2968 | N | LEU B | 481 | −20.349 | 7.822 | −56.770 | 1.00 | 54.14 | N |
| ATOM | 2969 | CA | LEU B | 481 | −21.428 | 8.348 | −55.946 | 1.00 | 54.78 | C |
| ATOM | 2970 | CB | LEU B | 481 | −20.882 | 8.832 | −54.605 | 1.00 | 54.25 | C |
| ATOM | 2971 | CG | LEU B | 481 | −21.768 | 8.986 | −53.360 | 1.00 | 59.46 | C |
| ATOM | 2972 | CD1 | LEU B | 481 | −21.122 | 9.982 | −52.439 | 1.00 | 60.05 | C |
| ATOM | 2973 | CD2 | LEU B | 481 | −23.204 | 9.392 | −53.621 | 1.00 | 57.30 | C |
| ATOM | 2974 | C | LEU B | 481 | −22.075 | 9.514 | −56.682 | 1.00 | 54.81 | C |
| ATOM | 2975 | O | LEU B | 481 | −23.288 | 9.526 | −56.899 | 1.00 | 54.07 | O |
| ATOM | 2976 | N | TYR B | 482 | −21.243 | 10.479 | −57.075 | 1.00 | 54.97 | N |
| ATOM | 2977 | CA | TYR B | 482 | −21.699 | 11.677 | −57.778 | 1.00 | 54.88 | C |
| ATOM | 2978 | CB | TYR B | 482 | −20.511 | 12.591 | −58.111 | 1.00 | 54.43 | C |
| ATOM | 2979 | CG | TYR B | 482 | −20.862 | 13.832 | −58.912 | 1.00 | 55.63 | C |
| ATOM | 2980 | CD1 | TYR B | 482 | −20.464 | 13.955 | −60.241 | 1.00 | 53.96 | C |
| ATOM | 2981 | CE1 | TYR B | 482 | −20.755 | 15.093 | −60.976 | 1.00 | 55.97 | C |
| ATOM | 2982 | CZ | TYR B | 482 | −21.475 | 16.126 | −60.394 | 1.00 | 56.38 | C |
| ATOM | 2983 | OH | TYR B | 482 | −21.776 | 17.251 | −61.140 | 1.00 | 54.36 | O |
| ATOM | 2984 | CE2 | TYR B | 482 | −21.883 | 16.030 | −59.074 | 1.00 | 56.16 | C |
| ATOM | 2985 | CD2 | TYR B | 482 | −21.570 | 14.886 | −58.337 | 1.00 | 54.83 | C |
| | | | | | gad65.pdb | | | | | |
| ATOM | 2986 | C | TYR B | 482 | −22.521 | 11.358 | −59.027 | 1.00 | 54.54 | C |
| ATOM | 2987 | O | TYR B | 482 | −23.551 | 11.961 | −59.246 | 1.00 | 52.94 | O |
| ATOM | 2988 | N | ASN B | 483 | −22.072 | 10.391 | −59.821 | 1.00 | 56.30 | N |
| ATOM | 2989 | CA | ASN B | 483 | −22.790 | 10.017 | −61.043 | 1.00 | 57.73 | C |
| ATOM | 2990 | CB | ASN B | 483 | −21.908 | 9.175 | −61.970 | 1.00 | 57.75 | C |
| ATOM | 2991 | CG | ASN B | 483 | −20.739 | 9.969 | −62.555 | 1.00 | 62.98 | C |
| ATOM | 2992 | OD1 | ASN B | 483 | −19.702 | 9.402 | −62.906 | 1.00 | 63.27 | O |
| ATOM | 2993 | ND2 | ASN B | 483 | −20.904 | 11.286 | −62.662 | 1.00 | 63.25 | N |
| ATOM | 2994 | C | ASN B | 483 | −24.132 | 9.329 | −60.802 | 1.00 | 58.10 | C |
| ATOM | 2995 | O | ASN B | 483 | −25.036 | 9.431 | −61.634 | 1.00 | 58.53 | O |
| ATOM | 2996 | N | ILE B | 484 | −24.263 | 8.631 | −59.676 | 1.00 | 58.37 | N |
| ATOM | 2997 | CA | ILE B | 484 | −25.524 | 7.974 | −59.339 | 1.00 | 59.09 | C |
| ATOM | 2998 | CB | ILE B | 484 | −25.366 | 6.873 | −58.255 | 1.00 | 59.32 | C |
| ATOM | 2999 | CG1 | ILE B | 484 | −24.598 | 5.667 | −58.796 | 1.00 | 57.00 | C |
| ATOM | 3000 | CD | ILE B | 484 | −24.207 | 4.683 | −57.711 | 1.00 | 51.79 | C |
| ATOM | 3001 | CG2 | ILE B | 484 | −26.736 | 6.398 | −57.756 | 1.00 | 58.94 | C |
| ATOM | 3002 | C | ILE B | 484 | −26.545 | 8.997 | −58.862 | 1.00 | 59.98 | C |
| ATOM | 3003 | O | ILE B | 484 | −27.665 | 9.032 | −59.368 | 1.00 | 60.87 | O |
| ATOM | 3004 | N | ILE B | 485 | −26.160 | 9.824 | −57.889 | 1.00 | 59.97 | N |
| ATOM | 3005 | CA | ILE B | 485 | −27.108 | 10.747 | −57.261 | 1.00 | 60.14 | C |
| ATOM | 3006 | CB | ILE B | 485 | −26.663 | 11.210 | −55.861 | 1.00 | 59.87 | C |
| ATOM | 3007 | CG1 | ILE B | 485 | −25.234 | 11.773 | −55.879 | 1.00 | 57.66 | C |
| ATOM | 3008 | CD | ILE B | 485 | −24.898 | 12.590 | −54.663 | 1.00 | 47.44 | C |
| ATOM | 3009 | CG2 | ILE B | 485 | −26.797 | 10.060 | −54.873 | 1.00 | 60.67 | C |
| ATOM | 3010 | C | ILE B | 485 | −27.454 | 11.935 | −58.143 | 1.00 | 60.83 | C |
| ATOM | 3011 | O | ILE B | 485 | −28.565 | 12.470 | −58.068 | 1.00 | 60.83 | O |
| ATOM | 3012 | N | LYS B | 486 | −26.495 | 12.324 | −58.982 | 1.00 | 60.76 | N |
| ATOM | 3013 | CA | LYS B | 486 | −26.676 | 13.366 | −59.989 | 1.00 | 61.00 | C |
| ATOM | 3014 | CB | LYS B | 486 | −25.399 | 13.473 | −60.827 | 1.00 | 60.18 | C |
| ATOM | 3015 | CG | LYS B | 486 | −25.336 | 14.615 | −61.797 | 1.00 | 60.43 | C |
| ATOM | 3016 | CD | LYS B | 486 | −23.906 | 14.833 | −62.284 | 1.00 | 61.61 | C |
| ATOM | 3017 | CE | LYS B | 486 | −23.302 | 13.605 | −62.975 | 1.00 | 60.05 | C |
| ATOM | 3018 | NZ | LYS B | 486 | −23.736 | 13.457 | −64.395 | 1.00 | 62.08 | N |
| ATOM | 3019 | C | LYS B | 486 | −27.880 | 13.067 | −60.889 | 1.00 | 61.78 | C |
| ATOM | 3020 | O | LYS B | 486 | −28.607 | 13.981 | −61.287 | 1.00 | 61.86 | O |
| ATOM | 3021 | N | ASN B | 487 | −28.075 | 11.785 | −61.202 | 1.00 | 62.27 | N |
| ATOM | 3022 | CA | ASN B | 487 | −29.178 | 11.343 | −62.057 | 1.00 | 62.82 | C |
| ATOM | 3023 | CB | ASN B | 487 | −28.632 | 10.504 | −63.219 | 1.00 | 63.59 | C |
| ATOM | 3024 | CG | ASN B | 487 | −27.485 | 11.191 | −63.956 | 1.00 | 68.51 | C |
| ATOM | 3025 | OD1 | ASN B | 487 | −26.350 | 10.700 | −63.958 | 1.00 | 69.23 | O |
| ATOM | 3026 | ND2 | ASN B | 487 | −27.775 | 12.331 | −64.582 | 1.00 | 69.09 | N |
| ATOM | 3027 | C | ASN B | 487 | −30.281 | 10.572 | −61.303 | 1.00 | 62.17 | C |
| ATOM | 3028 | O | ASN B | 487 | −31.118 | 9.901 | −61.919 | 1.00 | 62.47 | O |
| ATOM | 3029 | N | ARG B | 488 | −30.291 | 10.679 | −59.974 | 1.00 | 60.72 | N |
| ATOM | 3030 | CA | ARG B | 488 | −31.257 | 9.940 | −59.170 | 1.00 | 59.15 | C |
| ATOM | 3031 | CB | ARG B | 488 | −30.555 | 9.134 | −58.085 | 1.00 | 59.07 | C |
| ATOM | 3032 | CG | ARG B | 488 | −31.356 | 7.947 | −57.593 | 1.00 | 57.73 | C |
| ATOM | 3033 | CD | ARG B | 488 | −30.527 | 7.115 | −56.649 | 1.00 | 60.01 | C |
| ATOM | 3034 | NE | ARG B | 488 | −31.342 | 6.177 | −55.889 | 1.00 | 59.24 | N |
| ATOM | 3035 | CZ | ARG B | 488 | −31.367 | 4.863 | −56.089 | 1.00 | 65.09 | C |
| ATOM | 3036 | NH1 | ARG B | 488 | −30.610 | 4.312 | −57.035 | 1.00 | 65.13 | N |
| ATOM | 3037 | NH2 | ARG B | 488 | −32.149 | 4.098 | −55.333 | 1.00 | 65.91 | N |
| ATOM | 3038 | C | ARG B | 488 | −32.340 | 10.825 | −58.558 | 1.00 | 58.71 | C |
| ATOM | 3039 | O | ARG B | 488 | −32.046 | 11.875 | −57.976 | 1.00 | 58.21 | O |
| ATOM | 3040 | N | GLU B | 489 | −33.588 | 10.380 | −58.702 | 1.00 | 57.89 | N |
| ATOM | 3041 | CA | GLU B | 489 | −34.755 | 11.059 | −58.145 | 1.00 | 58.17 | C |

TABLE A-continued

| ATOM | 3042 | CB  | GLU B | 489 | −36.056 | 10.350 | −58.578 | 1.00 | 59.43 | C |
| ATOM | 3043 | CG  | GLU B | 489 | −36.172 | 8.855  | −58.175 | 1.00 | 66.30 | C |
| ATOM | 3044 | CD  | GLU B | 489 | −35.487 | 7.877  | −59.148 | 1.00 | 72.02 | C |
| ATOM | 3045 | OE1 | GLU B | 489 | −34.307 | 8.089  | −59.529 | 1.00 | 69.90 | O |
| ATOM | 3046 | OE2 | GLU B | 489 | −36.139 | 6.873  | −59.517 | 1.00 | 72.21 | O |
| ATOM | 3047 | C   | GLU B | 489 | −34.677 | 11.170 | −56.624 | 1.00 | 56.83 | C |
| ATOM | 3048 | O   | GLU B | 489 | −34.410 | 10.191 | −55.933 | 1.00 | 57.14 | O |
| ATOM | 3049 | N   | GLY B | 490 | −34.899 | 12.374 | −56.111 | 1.00 | 56.31 | N |
| ATOM | 3050 | CA  | GLY B | 490 | −34.867 | 12.627 | −54.673 | 1.00 | 55.34 | C |
| ATOM | 3051 | C   | GLY B | 490 | −33.573 | 13.261 | −54.205 | 1.00 | 55.68 | C |
| ATOM | 3052 | O   | GLY B | 490 | −33.477 | 13.697 | −53.059 | 1.00 | 56.58 | O |
| ATOM | 3053 | N   | TYR B | 491 | −32.587 | 13.321 | −55.098 | 1.00 | 55.20 | N | gad65.pdb

| ATOM | 3054 | CA  | TYR B | 491 | −31.246 | 13.802 | −54.774 | 1.00 | 56.70 | C |
| ATOM | 3055 | CB  | TYR B | 491 | −30.213 | 12.706 | −55.063 | 1.00 | 56.60 | C |
| ATOM | 3056 | CG  | TYR B | 491 | −30.179 | 11.579 | −54.047 | 1.00 | 58.26 | C |
| ATOM | 3057 | CD1 | TYR B | 491 | −30.966 | 10.434 | −54.214 | 1.00 | 58.95 | C |
| ATOM | 3058 | CE1 | TYR B | 491 | −30.935 | 9.395  | −53.286 | 1.00 | 58.55 | C |
| ATOM | 3059 | CZ  | TYR B | 491 | −30.106 | 9.497  | −52.174 | 1.00 | 61.42 | C |
| ATOM | 3060 | OH  | TYR B | 491 | −30.069 | 8.479  | −51.254 | 1.00 | 63.96 | O |
| ATOM | 3061 | CE2 | TYR B | 491 | −29.313 | 10.620 | −51.983 | 1.00 | 58.52 | C |
| ATOM | 3062 | CD2 | TYR B | 491 | −29.353 | 11.655 | −52.919 | 1.00 | 59.16 | C |
| ATOM | 3063 | C   | TYR B | 491 | −30.884 | 15.064 | −55.561 | 1.00 | 57.44 | C |
| ATOM | 3064 | O   | TYR B | 491 | −30.810 | 15.035 | −56.793 | 1.00 | 58.43 | O |
| ATOM | 3065 | N   | GLU B | 492 | −30.641 | 16.160 | −54.847 | 1.00 | 57.36 | N |
| ATOM | 3066 | CA  | GLU B | 492 | −30.279 | 17.434 | −55.467 | 1.00 | 58.46 | C |
| ATOM | 3067 | CB  | GLU B | 492 | −31.329 | 18.504 | −55.137 | 1.00 | 58.36 | C |
| ATOM | 3068 | CG  | GLU B | 492 | −31.240 | 19.771 | −55.984 | 1.00 | 62.68 | C |
| ATOM | 3069 | CD  | GLU B | 492 | −32.060 | 20.934 | −55.425 | 1.00 | 61.38 | C |
| ATOM | 3070 | OE1 | GLU B | 492 | −31.613 | 22.094 | −55.590 | 1.00 | 69.05 | O |
| ATOM | 3071 | OE2 | GLU B | 492 | −33.136 | 20.701 | −54.824 | 1.00 | 65.89 | O |
| ATOM | 3072 | C   | GLU B | 492 | −28.903 | 17.885 | −54.990 | 1.00 | 57.15 | C |
| ATOM | 3073 | O   | GLU B | 492 | −28.655 | 17.967 | −53.778 | 1.00 | 56.45 | O |
| ATOM | 3074 | N   | MET B | 493 | −28.015 | 18.186 | −55.940 | 1.00 | 56.46 | N |
| ATOM | 3075 | CA  | MET B | 493 | −26.656 | 18.635 | −55.602 | 1.00 | 55.67 | C |
| ATOM | 3076 | CB  | MET B | 493 | −25.724 | 18.621 | −56.820 | 1.00 | 55.77 | C |
| ATOM | 3077 | CG  | MET B | 493 | −25.584 | 17.268 | −57.516 | 1.00 | 55.52 | C |
| ATOM | 3078 | SD  | MET B | 493 | −25.164 | 15.909 | −56.407 | 1.00 | 64.12 | S |
| ATOM | 3079 | CE  | MET B | 493 | −23.574 | 16.419 | −55.757 | 1.00 | 59.25 | C |
| ATOM | 3080 | C   | MET B | 493 | −26.679 | 20.023 | −54.967 | 1.00 | 54.95 | C |
| ATOM | 3081 | O   | MET B | 493 | −27.519 | 20.860 | −55.300 | 1.00 | 54.62 | O |
| ATOM | 3082 | N   | VAL B | 494 | −25.746 | 20.248 | −54.050 | 1.00 | 53.91 | N |
| ATOM | 3083 | CA  | VAL B | 494 | −25.705 | 21.467 | −53.247 | 1.00 | 52.82 | C |
| ATOM | 3084 | CB  | VAL B | 494 | −24.961 | 21.173 | −51.917 | 1.00 | 51.57 | C |
| ATOM | 3085 | CG1 | VAL B | 494 | −24.466 | 22.441 | −51.222 | 1.00 | 50.67 | C |
| ATOM | 3086 | CG2 | VAL B | 494 | −25.886 | 20.395 | −51.013 | 1.00 | 44.78 | C |
| ATOM | 3087 | C   | VAL B | 494 | −25.145 | 22.664 | −54.041 | 1.00 | 53.36 | C |
| ATOM | 3088 | O   | VAL B | 494 | −25.538 | 23.818 | −53.829 | 1.00 | 53.18 | O |
| ATOM | 3089 | N   | PHE B | 495 | −24.245 | 22.369 | −54.972 | 1.00 | 53.59 | N |
| ATOM | 3090 | CA  | PHE B | 495 | −23.718 | 23.367 | −55.897 | 1.00 | 53.73 | C |
| ATOM | 3091 | CB  | PHE B | 495 | −22.406 | 23.982 | −55.384 | 1.00 | 53.38 | C |
| ATOM | 3092 | CG  | PHE B | 495 | −21.269 | 22.999 | −55.276 | 1.00 | 51.30 | C |
| ATOM | 3093 | CD1 | PHE B | 495 | −21.120 | 22.215 | −54.138 | 1.00 | 42.34 | C |
| ATOM | 3094 | CE1 | PHE B | 495 | −20.073 | 21.297 | −54.035 | 1.00 | 51.93 | C |
| ATOM | 3095 | CZ  | PHE B | 495 | −19.155 | 21.164 | −55.075 | 1.00 | 53.39 | C |
| ATOM | 3096 | CE2 | PHE B | 495 | −19.299 | 21.945 | −56.226 | 1.00 | 55.76 | C |
| ATOM | 3097 | CD2 | PHE B | 495 | −20.350 | 22.860 | −56.314 | 1.00 | 50.70 | C |
| ATOM | 3098 | C   | PHE B | 495 | −23.500 | 22.678 | −57.219 | 1.00 | 54.47 | C |
| ATOM | 3099 | O   | PHE B | 495 | −23.335 | 21.463 | −57.268 | 1.00 | 55.33 | O |
| ATOM | 3100 | N   | ASP B | 496 | −23.508 | 23.448 | −58.293 | 1.00 | 55.41 | N |
| ATOM | 3101 | CA  | ASP B | 496 | −23.221 | 22.890 | −59.602 | 1.00 | 56.81 | C |
| ATOM | 3102 | CB  | ASP B | 496 | −23.956 | 23.659 | −60.699 | 1.00 | 57.29 | C |
| ATOM | 3103 | CG  | ASP B | 496 | −24.245 | 22.797 | −61.909 | 1.00 | 62.31 | C |
| ATOM | 3104 | OD1 | ASP B | 496 | −23.281 | 22.321 | −62.561 | 1.00 | 59.55 | O |
| ATOM | 3105 | OD2 | ASP B | 496 | −25.447 | 22.603 | −62.204 | 1.00 | 65.41 | O |
| ATOM | 3106 | C   | ASP B | 496 | −21.725 | 22.905 | −59.854 | 1.00 | 56.55 | C |
| ATOM | 3107 | O   | ASP B | 496 | −21.068 | 23.929 | −59.659 | 1.00 | 56.84 | O |
| ATOM | 3108 | N   | GLY B | 497 | −21.209 | 21.763 | −60.302 | 1.00 | 56.03 | N |
| ATOM | 3109 | CA  | GLY B | 497 | −19.795 | 21.579 | −60.597 | 1.00 | 55.49 | C |
| ATOM | 3110 | C   | GLY B | 497 | −19.368 | 20.252 | −60.001 | 1.00 | 55.87 | C |
| ATOM | 3111 | O   | GLY B | 497 | −19.681 | 19.966 | −58.837 | 1.00 | 56.21 | O |
| ATOM | 3112 | N   | LYS B | 498 | −18.674 | 19.432 | −60.789 | 1.00 | 54.85 | N |
| ATOM | 3113 | CA  | LYS B | 498 | −18.275 | 18.099 | −60.326 | 1.00 | 55.10 | C |
| ATOM | 3114 | CB  | LYS B | 498 | −17.897 | 17.184 | −61.509 | 1.00 | 56.45 | C |
| ATOM | 3115 | CG  | LYS B | 498 | −16.678 | 17.576 | −62.341 | 1.00 | 59.85 | C |
| ATOM | 3116 | CD  | LYS B | 498 | −15.380 | 16.924 | −61.830 | 1.00 | 71.34 | C |
| ATOM | 3117 | CE  | LYS B | 498 | −15.402 | 15.392 | −61.870 | 1.00 | 72.89 | C |
| ATOM | 3118 | NZ  | LYS B | 498 | −15.310 | 14.824 | −63.244 | 1.00 | 76.68 | N |
| ATOM | 3119 | C   | LYS B | 498 | −17.191 | 18.147 | −59.214 | 1.00 | 54.01 | C |
| ATOM | 3120 | O   | LYS B | 498 | −16.306 | 18.997 | −59.264 | 1.00 | 53.61 | O |

TABLE A-continued

| | | | | | | | | | | |
|---|---|---|---|---|---|---|---|---|---|---|
| ATOM | 3121 | N | PRO B | 499 | −17.294 | 17.255 | −58.201 | 1.00 | 52.96 | N |
| | | | | | gad65.pdb | | | | | |
| ATOM | 3122 | CA | PRO B | 499 | −16.435 | 17.183 | −57.009 | 1.00 | 54.23 | C |
| ATOM | 3123 | CB | PRO B | 499 | −16.812 | 15.834 | −56.400 | 1.00 | 54.73 | C |
| ATOM | 3124 | CG | PRO B | 499 | −18.244 | 15.669 | −56.787 | 1.00 | 53.33 | C |
| ATOM | 3125 | CD | PRO B | 499 | −18.323 | 16.201 | −58.174 | 1.00 | 51.92 | C |
| ATOM | 3126 | C | PRO B | 499 | −14.952 | 17.198 | −57.324 | 1.00 | 54.01 | C |
| ATOM | 3127 | O | PRO B | 499 | −14.554 | 16.671 | −58.345 | 1.00 | 53.52 | O |
| ATOM | 3128 | N | GLN B | 500 | −14.140 | 17.754 | −56.427 | 1.00 | 56.34 | N |
| ATOM | 3129 | CA | GLN B | 500 | −12.716 | 18.010 | −56.738 | 1.00 | 57.08 | C |
| ATOM | 3130 | CB | GLN B | 500 | −12.343 | 19.489 | −56.517 | 1.00 | 57.01 | C |
| ATOM | 3131 | CG | GLN B | 500 | −12.799 | 20.405 | −57.647 | 1.00 | 56.76 | C |
| ATOM | 3132 | CD | GLN B | 500 | −12.026 | 21.706 | −57.706 | 1.00 | 54.90 | C |
| ATOM | 3133 | OE1 | GLN B | 500 | −11.343 | 21.985 | −58.693 | 1.00 | 52.17 | O |
| ATOM | 3134 | NE2 | GLN B | 500 | −12.126 | 22.511 | −56.652 | 1.00 | 48.45 | N |
| ATOM | 3135 | C | GLN B | 500 | −11.505 | 17.092 | −56.406 | 1.00 | 56.77 | C |
| ATOM | 3136 | O | GLN B | 500 | −10.456 | 17.394 | −56.925 | 1.00 | 59.08 | O |
| ATOM | 3137 | N | HIS B | 501 | −11.489 | 16.042 | −55.589 | 1.00 | 56.16 | N |
| ATOM | 3138 | CA | HIS B | 501 | −12.137 | 15.705 | −54.306 | 1.00 | 55.49 | C |
| ATOM | 3139 | CB | HIS B | 501 | −11.928 | 16.690 | −53.144 | 1.00 | 55.09 | C |
| ATOM | 3140 | CG | HIS B | 501 | −10.858 | 16.242 | −52.189 | 1.00 | 54.99 | C |
| ATOM | 3141 | ND1 | HIS B | 501 | −10.763 | 14.942 | −51.736 | 1.00 | 55.76 | N |
| ATOM | 3142 | CE1 | HIS B | 501 | −9.722 | 14.827 | −50.929 | 1.00 | 52.61 | C |
| ATOM | 3143 | NE2 | HIS B | 501 | −9.143 | 16.010 | −50.829 | 1.00 | 56.19 | N |
| ATOM | 3144 | CD2 | HIS B | 501 | −9.825 | 16.910 | −51.617 | 1.00 | 60.90 | C |
| ATOM | 3145 | C | HIS B | 501 | −13.230 | 14.629 | −54.102 | 1.00 | 54.64 | C |
| ATOM | 3146 | O | HIS B | 501 | −14.131 | 14.456 | −54.916 | 1.00 | 56.13 | O |
| ATOM | 3147 | N | THR B | 502 | −13.087 | 13.910 | −52.991 | 1.00 | 52.61 | N |
| ATOM | 3148 | CA | THR B | 502 | −14.023 | 12.869 | −52.576 | 1.00 | 50.84 | C |
| ATOM | 3149 | CB | THR B | 502 | −13.311 | 11.759 | −51.711 | 1.00 | 51.47 | C |
| ATOM | 3150 | OG1 | THR B | 502 | −13.205 | 12.174 | −50.337 | 1.00 | 46.78 | O |
| ATOM | 3151 | CG2 | THR B | 502 | −11.914 | 11.435 | −52.260 | 1.00 | 46.93 | C |
| ATOM | 3152 | C | THR B | 502 | −15.256 | 13.421 | −51.829 | 1.00 | 49.38 | C |
| ATOM | 3153 | O | THR B | 502 | −16.178 | 12.664 | −51.531 | 1.00 | 49.23 | O |
| ATOM | 3154 | N | ASN B | 503 | −15.262 | 14.721 | −51.505 | 1.00 | 47.68 | N |
| ATOM | 3155 | CA | ASN B | 503 | −16.450 | 15.345 | −50.910 | 1.00 | 46.73 | C |
| ATOM | 3156 | CB | ASN B | 503 | −16.191 | 16.773 | −50.412 | 1.00 | 44.68 | C |
| ATOM | 3157 | CG | ASN B | 503 | −14.926 | 16.908 | −49.568 | 1.00 | 45.60 | C |
| ATOM | 3158 | OD1 | ASN B | 503 | −13.840 | 16.506 | −49.986 | 1.00 | 45.09 | O |
| ATOM | 3159 | ND2 | ASN B | 503 | −15.059 | 17.535 | −48.399 | 1.00 | 38.62 | N |
| ATOM | 3160 | C | ASN B | 503 | −17.617 | 15.387 | −51.906 | 1.00 | 48.27 | C |
| ATOM | 3161 | O | ASN B | 503 | −17.508 | 15.958 | −53.002 | 1.00 | 47.54 | O |
| ATOM | 3162 | N | VAL B | 504 | −18.732 | 14.775 | −51.529 | 1.00 | 49.69 | N |
| ATOM | 3163 | CA | VAL B | 504 | −19.956 | 14.891 | −52.319 | 1.00 | 50.22 | C |
| ATOM | 3164 | CB | VAL B | 504 | −20.363 | 13.555 | −52.971 | 1.00 | 50.81 | C |
| ATOM | 3165 | CG1 | VAL B | 504 | −21.550 | 13.758 | −53.964 | 1.00 | 53.57 | C |
| ATOM | 3166 | CG2 | VAL B | 504 | −19.178 | 12.922 | −53.698 | 1.00 | 47.22 | C |
| ATOM | 3167 | C | VAL B | 504 | −21.051 | 15.478 | −51.416 | 1.00 | 50.76 | C |
| ATOM | 3168 | O | VAL B | 504 | −21.406 | 14.891 | −50.391 | 1.00 | 50.46 | O |
| ATOM | 3169 | N | CYS B | 505 | −21.524 | 16.669 | −51.787 | 1.00 | 50.59 | N |
| ATOM | 3170 | CA | CYS B | 505 | −22.494 | 17.425 | −51.007 | 1.00 | 51.22 | C |
| ATOM | 3171 | CB | CYS B | 505 | −22.023 | 18.868 | −50.865 | 1.00 | 51.11 | C |
| ATOM | 3172 | SG | CYS B | 505 | −20.454 | 19.030 | −49.955 | 1.00 | 52.92 | S |
| ATOM | 3173 | C | CYS B | 505 | −23.889 | 17.375 | −51.645 | 1.00 | 52.81 | C |
| ATOM | 3174 | O | CYS B | 505 | −24.063 | 17.738 | −52.816 | 1.00 | 52.69 | O |
| ATOM | 3175 | N | PHE B | 506 | −24.876 | 16.914 | −50.876 | 1.00 | 53.22 | N |
| ATOM | 3176 | CA | PHE B | 506 | −26.212 | 16.677 | −51.408 | 1.00 | 52.95 | C |
| ATOM | 3177 | CB | PHE B | 506 | −26.270 | 15.332 | −52.136 | 1.00 | 52.75 | C |
| ATOM | 3178 | CG | PHE B | 506 | −26.091 | 14.127 | −51.234 | 1.00 | 53.69 | C |
| ATOM | 3179 | CD1 | PHE B | 506 | −27.195 | 13.533 | −50.607 | 1.00 | 54.28 | C |
| ATOM | 3180 | CE1 | PHE B | 506 | −27.038 | 12.408 | −49.788 | 1.00 | 51.56 | C |
| ATOM | 3181 | CZ | PHE B | 506 | −25.764 | 11.870 | −49.595 | 1.00 | 55.37 | C |
| ATOM | 3182 | CE2 | PHE B | 506 | −24.653 | 12.457 | −50.223 | 1.00 | 51.85 | C |
| ATOM | 3183 | CD2 | PHE B | 506 | −24.828 | 13.566 | −51.041 | 1.00 | 52.18 | C |
| ATOM | 3184 | C | PHE B | 506 | −27.332 | 16.761 | −50.378 | 1.00 | 54.17 | C |
| ATOM | 3185 | O | PHE B | 506 | −27.114 | 16.636 | −49.161 | 1.00 | 54.20 | O |
| ATOM | 3186 | N | TRP B | 507 | −28.538 | 16.992 | −50.885 | 1.00 | 54.11 | N |
| ATOM | 3187 | CA | TRP B | 507 | −29.741 | 16.846 | −50.096 | 1.00 | 53.86 | C |
| ATOM | 3188 | CB | TRP B | 507 | −30.675 | 18.030 | −50.321 | 1.00 | 52.98 | C |
| ATOM | 3189 | CG | TRP B | 507 | −30.232 | 19.325 | −49.703 | 1.00 | 47.87 | C |
| | | | | | gad65.pdb | | | | | |
| ATOM | 3190 | CD1 | TRP B | 507 | −30.180 | 19.626 | −48.373 | 1.00 | 44.47 | C |
| ATOM | 3191 | NE1 | TRP B | 507 | −29.741 | 20.915 | −48.196 | 1.00 | 43.21 | N |
| ATOM | 3192 | CE2 | TRP B | 507 | −29.514 | 21.484 | −49.423 | 1.00 | 45.76 | C |
| ATOM | 3193 | CD2 | TRP B | 507 | −29.816 | 20.510 | −50.401 | 1.00 | 48.52 | C |
| ATOM | 3194 | CE3 | TRP B | 507 | −29.660 | 20.838 | −51.759 | 1.00 | 41.41 | C |
| ATOM | 3195 | CZ3 | TRP B | 507 | −29.228 | 22.121 | −52.089 | 1.00 | 46.71 | C |
| ATOM | 3196 | CH2 | TRP B | 507 | −28.935 | 23.073 | −51.089 | 1.00 | 47.89 | C |
| ATOM | 3197 | CZ2 | TRP B | 507 | −29.072 | 22.776 | −49.758 | 1.00 | 48.06 | C |
| ATOM | 3198 | C | TRP B | 507 | −30.431 | 15.574 | −50.548 | 1.00 | 55.54 | C |

TABLE A-continued

| | | | | | | | | | |
|---|---|---|---|---|---|---|---|---|---|
| ATOM | 3199 | O | TRP B | 507 | −30.339 | 15.202 | −51.723 | 1.00 | 56.13 | O |
| ATOM | 3200 | N | TYR B | 508 | −31.083 | 14.883 | −49.614 | 1.00 | 55.91 | N |
| ATOM | 3201 | CA | TYR B | 508 | −32.093 | 13.903 | −49.981 | 1.00 | 56.07 | C |
| ATOM | 3202 | CB | TYR B | 508 | −31.971 | 12.586 | −49.201 | 1.00 | 55.96 | C |
| ATOM | 3203 | CG | TYR B | 508 | −33.025 | 11.570 | −49.609 | 1.00 | 54.69 | C |
| ATOM | 3204 | CD1 | TYR B | 508 | −34.063 | 11.212 | −48.743 | 1.00 | 55.56 | C |
| ATOM | 3205 | CE1 | TYR B | 508 | −35.043 | 10.296 | −49.132 | 1.00 | 48.75 | C |
| ATOM | 3206 | CZ | TYR B | 508 | −34.997 | 9.751 | −50.404 | 1.00 | 53.92 | C |
| ATOM | 3207 | OH | TYR B | 508 | −35.946 | 8.843 | −50.807 | 1.00 | 54.05 | O |
| ATOM | 3208 | CE2 | TYR B | 508 | −33.984 | 10.102 | −51.285 | 1.00 | 54.35 | C |
| ATOM | 3209 | CD2 | TYR B | 508 | −33.009 | 11.002 | −50.885 | 1.00 | 54.89 | C |
| ATOM | 3210 | C | TYR B | 508 | −33.452 | 14.547 | −49.737 | 1.00 | 56.67 | C |
| ATOM | 3211 | O | TYR B | 508 | −33.727 | 15.047 | −48.639 | 1.00 | 57.11 | O |
| ATOM | 3212 | N | ILE B | 509 | −34.282 | 14.563 | −50.772 | 1.00 | 57.05 | N |
| ATOM | 3213 | CA | ILE B | 509 | −35.642 | 15.092 | −50.658 | 1.00 | 58.24 | C |
| ATOM | 3214 | CB | ILE B | 509 | −35.983 | 16.105 | −51.799 | 1.00 | 58.51 | C |
| ATOM | 3215 | CG1 | ILE B | 509 | −34.984 | 17.275 | −51.827 | 1.00 | 59.65 | C |
| ATOM | 3216 | CD | ILE B | 509 | −33.823 | 17.109 | −52.816 | 1.00 | 60.18 | C |
| ATOM | 3217 | CG2 | ILE B | 509 | −37.387 | 16.698 | −51.618 | 1.00 | 60.29 | C |
| ATOM | 3218 | C | ILE B | 509 | −36.617 | 13.907 | −50.613 | 1.00 | 57.95 | C |
| ATOM | 3219 | O | ILE B | 509 | −36.797 | 13.212 | −51.608 | 1.00 | 56.97 | O |
| ATOM | 3220 | N | PRO B | 510 | −37.222 | 13.652 | −49.441 | 1.00 | 59.31 | N |
| ATOM | 3221 | CA | PRO B | 510 | −38.091 | 12.473 | −49.293 | 1.00 | 61.58 | C |
| ATOM | 3222 | CB | PRO B | 510 | −38.496 | 12.511 | −47.808 | 1.00 | 61.65 | C |
| ATOM | 3223 | CG | PRO B | 510 | −37.473 | 13.410 | −47.140 | 1.00 | 59.89 | C |
| ATOM | 3224 | CD | PRO B | 510 | −37.151 | 14.438 | −48.196 | 1.00 | 59.23 | C |
| ATOM | 3225 | C | PRO B | 510 | −39.322 | 12.592 | −50.197 | 1.00 | 63.55 | C |
| ATOM | 3226 | O | PRO B | 510 | −39.727 | 13.716 | −50.509 | 1.00 | 62.60 | O |
| ATOM | 3227 | N | PRO B | 511 | −39.903 | 11.453 | −50.629 | 1.00 | 66.12 | N |
| ATOM | 3228 | CA | PRO B | 511 | −41.013 | 11.497 | −51.590 | 1.00 | 68.69 | C |
| ATOM | 3229 | CB | PRO B | 511 | −41.520 | 10.049 | −51.610 | 1.00 | 68.65 | C |
| ATOM | 3230 | CG | PRO B | 511 | −40.303 | 9.244 | −51.313 | 1.00 | 67.89 | C |
| ATOM | 3231 | CD | PRO B | 511 | −39.556 | 10.060 | −50.279 | 1.00 | 66.39 | C |
| ATOM | 3232 | C | PRO B | 511 | −42.131 | 12.468 | −51.219 | 1.00 | 70.48 | C |
| ATOM | 3233 | O | PRO B | 511 | −42.827 | 12.953 | −52.107 | 1.00 | 70.77 | O |
| ATOM | 3234 | N | SER B | 512 | −42.258 | 12.777 | −49.930 | 1.00 | 72.53 | N |
| ATOM | 3235 | CA | SER B | 512 | −43.296 | 13.679 | −49.422 | 1.00 | 74.19 | C |
| ATOM | 3236 | CB | SER B | 512 | −43.752 | 13.213 | −48.030 | 1.00 | 74.48 | C |
| ATOM | 3237 | OG | SER B | 512 | −42.672 | 13.239 | −47.105 | 1.00 | 76.14 | O |
| ATOM | 3238 | C | SER B | 512 | −42.873 | 15.158 | −49.373 | 1.00 | 74.91 | C |
| ATOM | 3239 | O | SER B | 512 | −43.331 | 15.906 | −48.504 | 1.00 | 75.55 | O |
| ATOM | 3240 | N | LEU B | 513 | −42.022 | 15.580 | −50.310 | 1.00 | 75.39 | N |
| ATOM | 3241 | CA | LEU B | 513 | −41.494 | 16.951 | −50.327 | 1.00 | 75.33 | C |
| ATOM | 3242 | CB | LEU B | 513 | −40.267 | 17.077 | −49.413 | 1.00 | 75.58 | C |
| ATOM | 3243 | CG | LEU B | 513 | −40.369 | 17.639 | −47.991 | 1.00 | 78.34 | C |
| ATOM | 3244 | CD1 | LEU B | 513 | −38.990 | 17.628 | −47.342 | 1.00 | 80.46 | C |
| ATOM | 3245 | CD2 | LEU B | 513 | −40.941 | 19.052 | −47.974 | 1.00 | 78.89 | C |
| ATOM | 3246 | C | LEU B | 513 | −41.109 | 17.441 | −51.717 | 1.00 | 75.55 | C |
| ATOM | 3247 | O | LEU B | 513 | −40.915 | 18.646 | −51.920 | 1.00 | 74.93 | O |
| ATOM | 3248 | N | ARG B | 514 | −40.997 | 16.513 | −52.665 | 1.00 | 76.52 | N |
| ATOM | 3249 | CA | ARG B | 514 | −40.456 | 16.817 | −53.999 | 1.00 | 77.58 | C |
| ATOM | 3250 | CB | ARG B | 514 | −40.262 | 15.531 | −54.798 | 1.00 | 77.44 | C |
| ATOM | 3251 | CG | ARG B | 514 | −38.978 | 14.826 | −54.470 | 1.00 | 73.32 | C |
| ATOM | 3252 | CD | ARG B | 514 | −39.118 | 13.347 | −54.678 | 1.00 | 69.46 | C |
| ATOM | 3253 | NE | ARG B | 514 | −38.355 | 12.617 | −53.678 | 1.00 | 59.63 | N |
| ATOM | 3254 | CZ | ARG B | 514 | −38.108 | 11.315 | −53.720 | 1.00 | 59.15 | C |
| ATOM | 3255 | NH1 | ARG B | 514 | −37.403 | 10.750 | −52.749 | 1.00 | 58.53 | N |
| ATOM | 3256 | NH2 | ARG B | 514 | −38.553 | 10.584 | −54.726 | 1.00 | 56.96 | N |
| ATOM | 3257 | C | ARG B | 514 | −41.245 | 17.822 | −54.832 | 1.00 | 78.99 | C |
| | | | | | gad65.pdb | | | | | |
| ATOM | 3258 | O | ARG B | 514 | −40.653 | 18.680 | −55.495 | 1.00 | 79.05 | O |
| ATOM | 3259 | N | THR B | 515 | −42.570 | 17.713 | −54.792 | 1.00 | 80.45 | N |
| ATOM | 3260 | CA | THR B | 515 | −43.446 | 18.533 | −55.627 | 1.00 | 82.19 | C |
| ATOM | 3261 | CB | THR B | 515 | −44.457 | 17.652 | −56.395 | 1.00 | 82.21 | C |
| ATOM | 3262 | C | THR B | 515 | −44.191 | 19.591 | −54.809 | 1.00 | 83.83 | C |
| ATOM | 3263 | O | THR B | 515 | −45.257 | 20.077 | −55.210 | 1.00 | 83.99 | O |
| ATOM | 3264 | N | LEU B | 516 | −43.622 | 19.945 | −53.657 | 1.00 | 84.84 | N |
| ATOM | 3265 | CA | LEU B | 516 | −44.240 | 20.914 | −52.765 | 1.00 | 85.08 | C |
| ATOM | 3266 | CB | LEU B | 516 | −43.718 | 20.731 | −51.338 | 1.00 | 85.20 | C |
| ATOM | 3267 | CG | LEU B | 516 | −44.727 | 20.968 | −50.212 | 1.00 | 85.62 | C |
| ATOM | 3268 | CD1 | LEU B | 516 | −45.798 | 19.884 | −50.205 | 1.00 | 88.21 | C |
| ATOM | 3269 | CD2 | LEU B | 516 | −44.028 | 21.025 | −48.871 | 1.00 | 85.06 | C |
| ATOM | 3270 | C | LEU B | 516 | −43.972 | 22.326 | −53.278 | 1.00 | 85.29 | C |
| ATOM | 3271 | O | LEU B | 516 | −42.827 | 22.684 | −53.569 | 1.00 | 85.44 | O |
| ATOM | 3272 | N | GLU B | 517 | −45.038 | 23.116 | −53.399 | 1.00 | 85.31 | N |
| ATOM | 3273 | CA | GLU B | 517 | −44.947 | 24.468 | −53.953 | 1.00 | 84.91 | C |
| ATOM | 3274 | CB | GLU B | 517 | −46.295 | 24.897 | −54.549 | 1.00 | 84.68 | C |
| ATOM | 3275 | C | GLU B | 517 | −44.462 | 25.486 | −52.919 | 1.00 | 84.50 | C |
| ATOM | 3276 | O | GLU B | 517 | −44.854 | 25.443 | −51.752 | 1.00 | 84.10 | O |
| ATOM | 3277 | N | GLU B | 521 | −40.950 | 27.420 | −50.063 | 1.00 | 75.57 | N |

TABLE A-continued

| | | | | | | | | | |
|---|---|---|---|---|---|---|---|---|---|
| ATOM | 3278 | CA | GLU B | 521 | −40.322 | 27.310 | −48.749 | 1.00 | 76.27 | C |
| ATOM | 3279 | CB | GLU B | 521 | −40.762 | 28.455 | −47.823 | 1.00 | 76.44 | C |
| ATOM | 3280 | CG | GLU B | 521 | −39.946 | 29.735 | −47.991 | 1.00 | 76.60 | C |
| ATOM | 3281 | C | GLU B | 521 | −40.557 | 25.943 | −48.092 | 1.00 | 76.58 | C |
| ATOM | 3282 | O | GLU B | 521 | −40.911 | 25.850 | −46.913 | 1.00 | 76.96 | O |
| ATOM | 3283 | N | ARG B | 522 | −40.358 | 24.887 | −48.882 | 1.00 | 75.89 | N |
| ATOM | 3284 | CA | ARG B | 522 | −40.294 | 23.522 | −48.382 | 1.00 | 73.63 | C |
| ATOM | 3285 | CB | ARG B | 522 | −40.770 | 22.544 | −49.453 | 1.00 | 74.14 | C |
| ATOM | 3286 | C | ARG B | 522 | −38.835 | 23.245 | −48.025 | 1.00 | 72.37 | C |
| ATOM | 3287 | O | ARG B | 522 | −38.443 | 22.103 | −47.749 | 1.00 | 71.45 | O |
| ATOM | 3288 | N | MET B | 523 | −38.042 | 24.317 | −48.059 | 1.00 | 70.87 | N |
| ATOM | 3289 | CA | MET B | 523 | −36.654 | 24.314 | −47.624 | 1.00 | 70.15 | C |
| ATOM | 3290 | CB | MET B | 523 | −35.973 | 25.625 | −48.039 | 1.00 | 69.82 | C |
| ATOM | 3291 | C | MET B | 523 | −36.584 | 24.133 | −46.107 | 1.00 | 69.18 | C |
| ATOM | 3292 | O | MET B | 523 | −35.702 | 23.425 | −45.597 | 1.00 | 68.04 | O |
| ATOM | 3293 | N | SER B | 524 | −37.524 | 24.777 | −45.407 | 1.00 | 68.30 | N |
| ATOM | 3294 | CA | SER B | 524 | −37.648 | 24.692 | −43.953 | 1.00 | 68.16 | C |
| ATOM | 3295 | CB | SER B | 524 | −38.816 | 25.555 | −43.464 | 1.00 | 68.72 | C |
| ATOM | 3296 | OG | SER B | 524 | −39.111 | 25.294 | −42.097 | 1.00 | 71.25 | O |
| ATOM | 3297 | C | SER B | 524 | −37.825 | 23.244 | −43.495 | 1.00 | 67.31 | C |
| ATOM | 3298 | O | SER B | 524 | −37.265 | 22.834 | −42.473 | 1.00 | 67.16 | O |
| ATOM | 3299 | N | ARG B | 525 | −38.596 | 22.483 | −44.267 | 1.00 | 65.98 | N |
| ATOM | 3300 | CA | ARG B | 525 | −38.803 | 21.068 | −44.011 | 1.00 | 65.60 | C |
| ATOM | 3301 | CB | ARG B | 525 | −40.078 | 20.578 | −44.702 | 1.00 | 65.34 | C |
| ATOM | 3302 | CG | ARG B | 525 | −41.356 | 21.233 | −44.205 | 1.00 | 69.49 | C |
| ATOM | 3303 | CD | ARG B | 525 | −42.583 | 20.620 | −44.860 | 1.00 | 73.13 | C |
| ATOM | 3304 | NE | ARG B | 525 | −42.771 | 19.223 | −44.464 | 1.00 | 75.70 | N |
| ATOM | 3305 | CZ | ARG B | 525 | −43.676 | 18.402 | −44.990 | 1.00 | 74.77 | C |
| ATOM | 3306 | NH1 | ARG B | 525 | −44.496 | 18.824 | −45.947 | 1.00 | 69.74 | N |
| ATOM | 3307 | NH2 | ARG B | 525 | −43.757 | 17.150 | −44.555 | 1.00 | 73.43 | N |
| ATOM | 3308 | C | ARG B | 525 | −37.602 | 20.241 | −44.468 | 1.00 | 64.93 | C |
| ATOM | 3309 | O | ARG B | 525 | −37.308 | 19.182 | −43.897 | 1.00 | 65.19 | O |
| ATOM | 3310 | N | LEU B | 526 | −36.914 | 20.719 | −45.503 | 1.00 | 64.01 | N |
| ATOM | 3311 | CA | LEU B | 526 | −35.711 | 20.047 | −45.976 | 1.00 | 63.07 | C |
| ATOM | 3312 | CB | LEU B | 526 | −35.284 | 20.559 | −47.354 | 1.00 | 62.96 | C |
| ATOM | 3313 | CG | LEU B | 526 | −34.068 | 19.872 | −47.994 | 1.00 | 62.15 | C |
| ATOM | 3314 | CD1 | LEU B | 526 | −34.346 | 18.385 | −48.286 | 1.00 | 55.67 | C |
| ATOM | 3315 | CD2 | LEU B | 526 | −33.616 | 20.610 | −49.247 | 1.00 | 62.02 | C |
| ATOM | 3316 | C | LEU B | 526 | −34.580 | 20.213 | −44.961 | 1.00 | 62.66 | C |
| ATOM | 3317 | O | LEU B | 526 | −33.788 | 19.301 | −44.761 | 1.00 | 62.59 | O |
| ATOM | 3318 | N | SER B | 527 | −34.537 | 21.379 | −44.323 | 1.00 | 62.26 | N |
| ATOM | 3319 | CA | SER B | 527 | −33.555 | 21.697 | −43.305 | 1.00 | 62.41 | C |
| ATOM | 3320 | CB | SER B | 527 | −33.891 | 23.051 | −42.690 | 1.00 | 62.72 | C |
| ATOM | 3321 | OG | SER B | 527 | −32.738 | 23.698 | −42.171 | 1.00 | 68.12 | O |
| ATOM | 3322 | C | SER B | 527 | −33.491 | 20.631 | −42.206 | 1.00 | 62.65 | C |
| ATOM | 3323 | O | SER B | 527 | −32.465 | 20.477 | −41.539 | 1.00 | 62.96 | O |
| ATOM | 3324 | N | LYS B | 528 | −34.580 | 19.883 | −42.043 | 1.00 | 61.76 | N |
| ATOM | 3325 | CA | LYS B | 528 | −34.751 | 18.984 | −40.897 | 1.00 | 60.53 | C |
| | | | | | gad65.pdb | | | | | |
| ATOM | 3326 | CB | LYS B | 528 | −36.108 | 19.244 | −40.231 | 1.00 | 60.47 | C |
| ATOM | 3327 | CG | LYS B | 528 | −36.155 | 20.597 | −39.538 | 1.00 | 63.76 | C |
| ATOM | 3328 | CD | LYS B | 528 | −37.562 | 21.058 | −39.202 | 1.00 | 72.06 | C |
| ATOM | 3329 | CE | LYS B | 528 | −37.501 | 22.312 | −38.320 | 1.00 | 76.30 | C |
| ATOM | 3330 | NZ | LYS B | 528 | −38.828 | 22.874 | −37.947 | 1.00 | 76.71 | N |
| ATOM | 3331 | C | LYS B | 528 | −34.593 | 17.514 | −41.257 | 1.00 | 58.65 | C |
| ATOM | 3332 | O | LYS B | 528 | −34.610 | 16.650 | −40.386 | 1.00 | 58.51 | O |
| ATOM | 3333 | N | VAL B | 529 | −34.412 | 17.248 | −42.545 | 1.00 | 57.43 | N |
| ATOM | 3334 | CA | VAL B | 529 | −34.322 | 15.886 | −43.070 | 1.00 | 56.43 | C |
| ATOM | 3335 | CB | VAL B | 529 | −34.549 | 15.871 | −44.605 | 1.00 | 56.38 | C |
| ATOM | 3336 | CG1 | VAL B | 529 | −34.220 | 14.505 | −45.203 | 1.00 | 54.72 | C |
| ATOM | 3337 | CG2 | VAL B | 529 | −35.995 | 16.283 | −44.937 | 1.00 | 56.79 | C |
| ATOM | 3338 | C | VAL B | 529 | −33.001 | 15.187 | −42.703 | 1.00 | 55.98 | C |
| ATOM | 3339 | O | VAL B | 529 | −33.017 | 14.060 | −42.204 | 1.00 | 55.85 | O |
| ATOM | 3340 | N | ALA B | 530 | −31.871 | 15.852 | −42.950 | 1.00 | 54.44 | N |
| ATOM | 3341 | CA | ALA B | 530 | −30.562 | 15.267 | −42.647 | 1.00 | 53.99 | C |
| ATOM | 3342 | CB | ALA B | 530 | −29.409 | 16.147 | −43.182 | 1.00 | 53.51 | C |
| ATOM | 3343 | C | ALA B | 530 | −30.387 | 14.953 | −41.155 | 1.00 | 52.56 | C |
| ATOM | 3344 | O | ALA B | 530 | −29.997 | 13.840 | −40.820 | 1.00 | 52.62 | O |
| ATOM | 3345 | N | PRO B | 531 | −30.705 | 15.915 | −40.257 | 1.00 | 51.86 | N |
| ATOM | 3346 | CA | PRO B | 531 | −30.649 | 15.584 | −38.828 | 1.00 | 51.98 | C |
| ATOM | 3347 | CB | PRO B | 531 | −31.207 | 16.840 | −38.154 | 1.00 | 51.96 | C |
| ATOM | 3348 | CG | PRO B | 531 | −30.849 | 17.942 | −39.102 | 1.00 | 50.16 | C |
| ATOM | 3349 | CD | PRO B | 531 | −31.095 | 17.326 | −40.458 | 1.00 | 51.69 | C |
| ATOM | 3350 | C | PRO B | 531 | −31.443 | 14.334 | −38.419 | 1.00 | 52.46 | C |
| ATOM | 3351 | O | PRO B | 531 | −30.955 | 13.562 | −37.595 | 1.00 | 53.21 | O |
| ATOM | 3352 | N | VAL B | 532 | −32.629 | 14.124 | −38.995 | 1.00 | 52.78 | N |
| ATOM | 3353 | CA | VAL B | 532 | −33.443 | 12.943 | −38.669 | 1.00 | 52.58 | C |
| ATOM | 3354 | CB | VAL B | 532 | −34.935 | 13.101 | −39.108 | 1.00 | 53.74 | C |
| ATOM | 3355 | CG1 | VAL B | 532 | −35.703 | 11.774 | −38.982 | 1.00 | 53.53 | C |
| ATOM | 3356 | CG2 | VAL B | 532 | −35.626 | 14.199 | −38.300 | 1.00 | 53.71 | C |

TABLE A-continued

| | | | | | | | | | | |
|---|---|---|---|---|---|---|---|---|---|---|
| ATOM | 3357 | C | VAL B | 532 | −32.832 | 11.665 | −39.248 | 1.00 | 51.54 | C |
| ATOM | 3358 | O | VAL B | 532 | −32.718 | 10.666 | −38.548 | 1.00 | 51.72 | O |
| ATOM | 3359 | N | ILE B | 533 | −32.431 | 11.702 | −40.515 | 1.00 | 50.68 | N |
| ATOM | 3360 | CA | ILE B | 533 | −31.761 | 10.563 | −41.128 | 1.00 | 50.60 | C |
| ATOM | 3361 | CB | ILE B | 533 | −31.332 | 10.837 | −42.598 | 1.00 | 51.13 | C |
| ATOM | 3362 | CG1 | ILE B | 533 | −32.519 | 11.302 | −43.450 | 1.00 | 55.35 | C |
| ATOM | 3363 | CD | ILE B | 533 | −33.305 | 10.186 | −44.071 | 1.00 | 55.36 | C |
| ATOM | 3364 | CG2 | ILE B | 533 | −30.684 | 9.587 | −43.220 | 1.00 | 49.91 | C |
| ATOM | 3365 | C | ILE B | 533 | −30.523 | 10.194 | −40.308 | 1.00 | 50.18 | C |
| ATOM | 3366 | O | ILE B | 533 | −30.362 | 9.042 | −39.917 | 1.00 | 49.60 | O |
| ATOM | 3367 | N | LYS B | 534 | −29.662 | 11.177 | −40.048 | 1.00 | 49.89 | N |
| ATOM | 3368 | CA | LYS B | 534 | −28.442 | 10.949 | −39.277 | 1.00 | 49.28 | C |
| ATOM | 3369 | CB | LYS B | 534 | −27.678 | 12.259 | −39.055 | 1.00 | 49.20 | C |
| ATOM | 3370 | CG | LYS B | 534 | −26.393 | 12.125 | −38.243 | 1.00 | 51.82 | C |
| ATOM | 3371 | CD | LYS B | 534 | −25.410 | 11.137 | −38.883 | 1.00 | 53.99 | C |
| ATOM | 3372 | CE | LYS B | 534 | −24.087 | 11.056 | −38.100 | 1.00 | 53.88 | C |
| ATOM | 3373 | NZ | LYS B | 534 | −23.210 | 12.255 | −38.342 | 1.00 | 52.29 | N |
| ATOM | 3374 | C | LYS B | 534 | −28.757 | 10.277 | −37.948 | 1.00 | 47.90 | C |
| ATOM | 3375 | O | LYS B | 534 | −28.138 | 9.280 | −37.600 | 1.00 | 46.13 | O |
| ATOM | 3376 | N | ALA B | 535 | −29.730 | 10.827 | −37.222 | 1.00 | 48.79 | N |
| ATOM | 3377 | CA | ALA B | 535 | −30.170 | 10.236 | −35.960 | 1.00 | 49.15 | C |
| ATOM | 3378 | CB | ALA B | 535 | −31.334 | 11.024 | −35.353 | 1.00 | 47.40 | C |
| ATOM | 3379 | C | ALA B | 535 | −30.531 | 8.768 | −36.147 | 1.00 | 50.59 | C |
| ATOM | 3380 | O | ALA B | 535 | −30.105 | 7.924 | −35.354 | 1.00 | 51.61 | O |
| ATOM | 3381 | N | ARG B | 536 | −31.285 | 8.464 | −37.207 | 1.00 | 51.53 | N |
| ATOM | 3382 | CA | ARG B | 536 | −31.727 | 7.087 | −37.492 | 1.00 | 52.19 | C |
| ATOM | 3383 | CB | ARG B | 536 | −32.829 | 7.065 | −38.556 | 1.00 | 52.08 | C |
| ATOM | 3384 | CG | ARG B | 536 | −34.122 | 7.800 | −38.176 | 1.00 | 57.74 | C |
| ATOM | 3385 | C | ARG B | 536 | −30.574 | 6.183 | −37.930 | 1.00 | 52.51 | C |
| ATOM | 3386 | O | ARG B | 536 | −30.578 | 4.999 | −37.613 | 1.00 | 53.06 | O |
| ATOM | 3387 | N | MET B | 537 | −29.614 | 6.737 | −38.677 | 1.00 | 52.67 | N |
| ATOM | 3388 | CA | MET B | 537 | −28.360 | 6.044 | −39.031 | 1.00 | 54.33 | C |
| ATOM | 3389 | CB | MET B | 537 | −27.398 | 6.975 | −39.776 | 1.00 | 53.67 | C |
| ATOM | 3390 | CG | MET B | 537 | −27.647 | 7.172 | −41.253 | 1.00 | 55.63 | C |
| ATOM | 3391 | SD | MET B | 537 | −26.563 | 8.493 | −41.869 | 1.00 | 57.97 | S |
| ATOM | 3392 | CE | MET B | 537 | −26.893 | 8.420 | −43.632 | 1.00 | 58.51 | C |
| ATOM | 3393 | C | MET B | 537 | −27.632 | 5.511 | −37.796 | 1.00 | 53.38 | C |
| | | | | | gad65.pdb | | | | | |
| ATOM | 3394 | O | MET B | 537 | −27.181 | 4.379 | −37.794 | 1.00 | 53.27 | O |
| ATOM | 3395 | N | MET B | 538 | −27.522 | 6.351 | −36.765 | 1.00 | 53.18 | N |
| ATOM | 3396 | CA | MET B | 538 | −26.843 | 6.020 | −35.517 | 1.00 | 54.61 | C |
| ATOM | 3397 | CB | MET B | 538 | −26.505 | 7.300 | −34.754 | 1.00 | 54.18 | C |
| ATOM | 3398 | CG | MET B | 538 | −25.375 | 8.100 | −35.372 | 1.00 | 55.75 | C |
| ATOM | 3399 | SD | MET B | 538 | −25.322 | 9.729 | −34.638 | 1.00 | 57.54 | S |
| ATOM | 3400 | CE | MET B | 538 | −24.247 | 9.449 | −33.226 | 1.00 | 53.32 | C |
| ATOM | 3401 | C | MET B | 538 | −27.647 | 5.080 | −34.608 | 1.00 | 54.74 | C |
| ATOM | 3402 | O | MET B | 538 | −27.069 | 4.200 | −33.957 | 1.00 | 53.08 | O |
| ATOM | 3403 | N | GLU B | 539 | −28.968 | 5.280 | −34.548 | 1.00 | 54.87 | N |
| ATOM | 3404 | CA | GLU B | 539 | −29.834 | 4.375 | −33.793 | 1.00 | 55.93 | C |
| ATOM | 3405 | CB | GLU B | 539 | −31.290 | 4.863 | −33.761 | 1.00 | 57.05 | C |
| ATOM | 3406 | CG | GLU B | 539 | −31.546 | 6.149 | −32.952 | 1.00 | 64.73 | C |
| ATOM | 3407 | CD | GLU B | 539 | −31.527 | 5.960 | −31.431 | 1.00 | 74.53 | C |
| ATOM | 3408 | OE1 | GLU B | 539 | −31.061 | 4.906 | −30.934 | 1.00 | 75.00 | O |
| ATOM | 3409 | OE2 | GLU B | 539 | −31.979 | 6.891 | −30.722 | 1.00 | 80.32 | O |
| ATOM | 3410 | C | GLU B | 539 | −29.760 | 2.967 | −34.370 | 1.00 | 55.23 | C |
| ATOM | 3411 | O | GLU B | 539 | −29.739 | 1.995 | −33.626 | 1.00 | 55.42 | O |
| ATOM | 3412 | N | TYR B | 540 | −29.702 | 2.857 | −35.693 | 1.00 | 55.46 | N |
| ATOM | 3413 | CA | TYR B | 540 | −29.574 | 1.547 | −36.324 | 1.00 | 56.19 | C |
| ATOM | 3414 | CB | TYR B | 540 | −30.332 | 1.496 | −37.652 | 1.00 | 57.39 | C |
| ATOM | 3415 | CG | TYR B | 540 | −31.835 | 1.545 | −37.457 | 1.00 | 62.87 | C |
| ATOM | 3416 | CD1 | TYR B | 540 | −32.580 | 2.615 | −37.945 | 1.00 | 65.67 | C |
| ATOM | 3417 | CE1 | TYR B | 540 | −33.951 | 2.678 | −37.765 | 1.00 | 68.22 | C |
| ATOM | 3418 | CZ | TYR B | 540 | −34.596 | 1.667 | −37.079 | 1.00 | 66.59 | C |
| ATOM | 3419 | OH | TYR B | 540 | −35.957 | 1.745 | −36.910 | 1.00 | 66.36 | O |
| ATOM | 3420 | CE2 | TYR B | 540 | −33.881 | 0.584 | −36.577 | 1.00 | 67.27 | C |
| ATOM | 3421 | CD2 | TYR B | 540 | −32.505 | 0.532 | −36.765 | 1.00 | 62.91 | C |
| ATOM | 3422 | C | TYR B | 540 | −28.135 | 1.068 | −36.486 | 1.00 | 54.95 | C |
| ATOM | 3423 | O | TYR B | 540 | −27.897 | −0.132 | −36.549 | 1.00 | 53.95 | O |
| ATOM | 3424 | N | GLY B | 541 | −27.192 | 2.011 | −36.553 | 1.00 | 54.42 | N |
| ATOM | 3425 | CA | GLY B | 541 | −25.753 | 1.708 | −36.611 | 1.00 | 53.89 | C |
| ATOM | 3426 | C | GLY B | 541 | −25.271 | 1.166 | −37.941 | 1.00 | 52.82 | C |
| ATOM | 3427 | O | GLY B | 541 | −24.326 | 0.377 | −37.990 | 1.00 | 53.99 | O |
| ATOM | 3428 | N | THR B | 542 | −25.903 | 1.602 | −39.021 | 1.00 | 51.56 | N |
| ATOM | 3429 | CA | THR B | 542 | −25.680 | 1.004 | −40.337 | 1.00 | 52.08 | C |
| ATOM | 3430 | CB | THR B | 542 | −26.996 | 0.964 | −41.143 | 1.00 | 52.65 | C |
| ATOM | 3431 | OG1 | THR B | 542 | −27.618 | 2.254 | −41.101 | 1.00 | 53.13 | O |
| ATOM | 3432 | CG2 | THR B | 542 | −27.973 | −0.065 | −40.539 | 1.00 | 51.76 | C |
| ATOM | 3433 | C | THR B | 542 | −24.618 | 1.759 | −41.142 | 1.00 | 52.62 | C |
| ATOM | 3434 | O | THR B | 542 | −23.937 | 1.189 | −41.995 | 1.00 | 52.87 | O |
| ATOM | 3435 | N | THR B | 543 | −24.504 | 3.053 | −40.868 | 1.00 | 52.80 | N |

TABLE A-continued

| | | | | | | | | | |
|---|---|---|---|---|---|---|---|---|---|
| ATOM | 3436 | CA | THR B | 543 | −23.568 | 3.931 | −41.545 | 1.00 | 52.70 | C |
| ATOM | 3437 | CB | THR B | 543 | −24.018 | 4.244 | −43.004 | 1.00 | 53.80 | C |
| ATOM | 3438 | OG1 | THR B | 543 | −22.953 | 4.886 | −43.725 | 1.00 | 57.38 | O |
| ATOM | 3439 | CG2 | THR B | 543 | −25.270 | 5.127 | −43.027 | 1.00 | 53.17 | C |
| ATOM | 3440 | C | THR B | 543 | −23.491 | 5.195 | −40.706 | 1.00 | 51.45 | C |
| ATOM | 3441 | O | THR B | 543 | −24.281 | 5.369 | −39.772 | 1.00 | 51.70 | O |
| ATOM | 3442 | N | MET B | 544 | −22.528 | 6.054 | −41.018 | 1.00 | 49.53 | N |
| ATOM | 3443 | CA | MET B | 544 | −22.448 | 7.387 | −40.429 | 1.00 | 48.83 | C |
| ATOM | 3444 | CB | MET B | 544 | −21.479 | 7.424 | −39.243 | 1.00 | 48.63 | C |
| ATOM | 3445 | CG | MET B | 544 | −22.098 | 6.970 | −37.950 | 1.00 | 49.73 | C |
| ATOM | 3446 | SD | MET B | 544 | −20.961 | 6.825 | −36.564 | 1.00 | 49.40 | S |
| ATOM | 3447 | CE | MET B | 544 | −21.110 | 8.460 | −35.870 | 1.00 | 40.32 | C |
| ATOM | 3448 | C | MET B | 544 | −21.973 | 8.340 | −41.500 | 1.00 | 47.32 | C |
| ATOM | 3449 | O | MET B | 544 | −21.014 | 8.046 | −42.200 | 1.00 | 46.44 | O |
| ATOM | 3450 | N | VAL B | 545 | −22.673 | 9.462 | −41.642 | 1.00 | 46.38 | N |
| ATOM | 3451 | CA | VAL B | 545 | −22.316 | 10.503 | −42.601 | 1.00 | 46.20 | C |
| ATOM | 3452 | CB | VAL B | 545 | −23.199 | 10.452 | −43.877 | 1.00 | 46.62 | C |
| ATOM | 3453 | CG1 | VAL B | 545 | −22.634 | 11.348 | −44.979 | 1.00 | 46.95 | C |
| ATOM | 3454 | CG2 | VAL B | 545 | −23.324 | 9.028 | −44.396 | 1.00 | 48.94 | C |
| ATOM | 3455 | C | VAL B | 545 | −22.517 | 11.829 | −41.900 | 1.00 | 45.90 | C |
| ATOM | 3456 | O | VAL B | 545 | −23.447 | 11.973 | −41.113 | 1.00 | 46.96 | O |
| ATOM | 3457 | N | SER B | 546 | −21.648 | 12.797 | −42.153 | 1.00 | 46.15 | N |
| ATOM | 3458 | CA | SER B | 546 | −21.860 | 14.128 | −41.594 | 1.00 | 47.67 | C |
| ATOM | 3459 | CB | SER B | 546 | −20.526 | 14.865 | −41.363 | 1.00 | 49.37 | C |
| ATOM | 3460 | OG | SER B | 546 | −19.937 | 14.501 | −40.116 | 1.00 | 56.63 | O |
| ATOM | 3461 | C | SER B | 546 | −22.778 | 14.951 | −42.496 | 1.00 | 47.82 | C |
| | | | | | gad65.pdb | | | | | |
| ATOM | 3462 | O | SER B | 546 | −22.788 | 14.769 | −43.725 | 1.00 | 47.49 | O |
| ATOM | 3463 | N | TYR B | 547 | −23.550 | 15.834 | −41.867 | 1.00 | 48.03 | N |
| ATOM | 3464 | CA | TYR B | 547 | −24.381 | 16.816 | −42.554 | 1.00 | 49.87 | C |
| ATOM | 3465 | CB | TYR B | 547 | −25.883 | 16.493 | −42.389 | 1.00 | 49.97 | C |
| ATOM | 3466 | CG | TYR B | 547 | −26.387 | 16.706 | −40.967 | 1.00 | 50.07 | C |
| ATOM | 3467 | CD1 | TYR B | 547 | −26.376 | 15.667 | −40.039 | 1.00 | 49.08 | C |
| ATOM | 3468 | CE1 | TYR B | 547 | −26.815 | 15.866 | −38.724 | 1.00 | 46.19 | C |
| ATOM | 3469 | CZ | TYR B | 547 | −27.273 | 17.106 | −38.339 | 1.00 | 50.19 | C |
| ATOM | 3470 | OH | TYR B | 547 | −27.712 | 17.300 | −37.047 | 1.00 | 50.42 | O |
| ATOM | 3471 | CE2 | TYR B | 547 | −27.292 | 18.160 | −39.242 | 1.00 | 50.77 | C |
| ATOM | 3472 | CD2 | TYR B | 547 | −26.848 | 17.957 | −40.546 | 1.00 | 50.47 | C |
| ATOM | 3473 | C | TYR B | 547 | −24.081 | 18.160 | −41.907 | 1.00 | 51.12 | C |
| ATOM | 3474 | O | TYR B | 547 | −23.659 | 18.203 | −40.757 | 1.00 | 49.91 | O |
| ATOM | 3475 | N | GLN B | 548 | −24.314 | 19.251 | −42.635 | 1.00 | 52.84 | N |
| ATOM | 3476 | CA | GLN B | 548 | −24.148 | 20.594 | −42.085 | 1.00 | 54.60 | C |
| ATOM | 3477 | CB | GLN B | 548 | −22.656 | 20.939 | −41.866 | 1.00 | 55.28 | C |
| ATOM | 3478 | CG | GLN B | 548 | −21.816 | 21.143 | −43.134 | 1.00 | 58.79 | C |
| ATOM | 3479 | CD | GLN B | 548 | −21.484 | 19.839 | −43.847 | 1.00 | 64.28 | C |
| ATOM | 3480 | OE1 | GLN B | 548 | −21.991 | 19.569 | −44.937 | 1.00 | 66.45 | O |
| ATOM | 3481 | NE2 | GLN B | 548 | −20.632 | 19.022 | −43.229 | 1.00 | 67.96 | N |
| ATOM | 3482 | C | GLN B | 548 | −24.797 | 21.618 | −43.003 | 1.00 | 55.79 | C |
| ATOM | 3483 | O | GLN B | 548 | −25.064 | 21.315 | −44.166 | 1.00 | 55.39 | O |
| ATOM | 3484 | N | PRO B | 549 | −25.083 | 22.824 | −42.475 | 1.00 | 57.14 | N |
| ATOM | 3485 | CA | PRO B | 549 | −25.417 | 23.918 | −43.366 | 1.00 | 57.99 | C |
| ATOM | 3486 | CB | PRO B | 549 | −26.304 | 24.801 | −42.495 | 1.00 | 57.26 | C |
| ATOM | 3487 | CG | PRO B | 549 | −25.809 | 24.580 | −41.101 | 1.00 | 58.27 | C |
| ATOM | 3488 | CD | PRO B | 549 | −25.151 | 23.228 | −41.056 | 1.00 | 57.10 | C |
| ATOM | 3489 | C | PRO B | 549 | −24.147 | 24.663 | −43.788 | 1.00 | 59.79 | C |
| ATOM | 3490 | O | PRO B | 549 | −23.113 | 24.538 | −43.128 | 1.00 | 60.94 | O |
| ATOM | 3491 | N | LEU B | 550 | −24.219 | 25.421 | −44.879 | 1.00 | 61.06 | N |
| ATOM | 3492 | CA | LEU B | 550 | −23.102 | 26.277 | −45.289 | 1.00 | 62.99 | C |
| ATOM | 3493 | CB | LEU B | 550 | −22.100 | 25.508 | −46.169 | 1.00 | 63.30 | C |
| ATOM | 3494 | CG | LEU B | 550 | −20.803 | 26.218 | −46.576 | 1.00 | 67.07 | C |
| ATOM | 3495 | CD1 | LEU B | 550 | −19.655 | 25.243 | −46.649 | 1.00 | 70.45 | C |
| ATOM | 3496 | CD2 | LEU B | 550 | −20.954 | 26.967 | −47.901 | 1.00 | 73.28 | C |
| ATOM | 3497 | C | LEU B | 550 | −23.615 | 27.513 | −46.010 | 1.00 | 64.15 | C |
| ATOM | 3498 | O | LEU B | 550 | −24.209 | 27.413 | −47.083 | 1.00 | 64.44 | O |
| ATOM | 3499 | N | GLY B | 551 | −23.368 | 28.679 | −45.421 | 1.00 | 65.84 | N |
| ATOM | 3500 | CA | GLY B | 551 | −23.815 | 29.944 | −46.001 | 1.00 | 66.37 | C |
| ATOM | 3501 | C | GLY B | 551 | −25.324 | 29.955 | −46.090 | 1.00 | 66.34 | C |
| ATOM | 3502 | O | GLY B | 551 | −26.003 | 29.787 | −45.083 | 1.00 | 66.06 | O |
| ATOM | 3503 | N | ASP B | 552 | −25.840 | 30.116 | −47.306 | 1.00 | 67.45 | N |
| ATOM | 3504 | CA | ASP B | 552 | −27.288 | 30.177 | −47.547 | 1.00 | 68.42 | C |
| ATOM | 3505 | CB | ASP B | 552 | −27.589 | 31.115 | −48.723 | 1.00 | 69.52 | C |
| ATOM | 3506 | CG | ASP B | 552 | −26.928 | 30.656 | −50.014 | 1.00 | 76.69 | C |
| ATOM | 3507 | OD1 | ASP B | 552 | −27.617 | 30.012 | −50.837 | 1.00 | 81.05 | O |
| ATOM | 3508 | OD2 | ASP B | 552 | −25.715 | 30.919 | −50.194 | 1.00 | 82.40 | O |
| ATOM | 3509 | C | ASP B | 552 | −27.916 | 28.799 | −47.803 | 1.00 | 67.38 | C |
| ATOM | 3510 | O | ASP B | 552 | −29.111 | 28.700 | −48.114 | 1.00 | 67.49 | O |
| ATOM | 3511 | N | LYS B | 553 | −27.110 | 27.744 | −47.684 | 1.00 | 65.62 | N |
| ATOM | 3512 | CA | LYS B | 553 | −27.588 | 26.373 | −47.844 | 1.00 | 64.06 | C |
| ATOM | 3513 | CB | LYS B | 553 | −26.508 | 25.498 | −48.490 | 1.00 | 64.23 | C |
| ATOM | 3514 | CG | LYS B | 553 | −25.780 | 26.148 | −49.674 | 1.00 | 67.22 | C |

TABLE A-continued

| | | | | | | | | | | |
|---|---|---|---|---|---|---|---|---|---|---|
| ATOM | 3515 | CD | LYS B | 553 | −26.501 | 25.923 | −50.997 | 1.00 | 71.88 | C |
| ATOM | 3516 | CE | LYS B | 553 | −25.830 | 26.679 | −52.140 | 1.00 | 73.27 | C |
| ATOM | 3517 | NZ | LYS B | 553 | −26.287 | 28.097 | −52.218 | 1.00 | 77.33 | N |
| ATOM | 3518 | C | LYS B | 553 | −27.998 | 25.796 | −46.487 | 1.00 | 62.62 | C |
| ATOM | 3519 | O | LYS B | 553 | −27.323 | 26.029 | −45.477 | 1.00 | 63.06 | O |
| ATOM | 3520 | N | VAL B | 554 | −29.111 | 25.063 | −46.466 | 1.00 | 60.21 | N |
| ATOM | 3521 | CA | VAL B | 554 | −29.581 | 24.398 | −45.253 | 1.00 | 58.09 | C |
| ATOM | 3522 | CB | VAL B | 554 | −31.137 | 24.272 | −45.196 | 1.00 | 58.09 | C |
| ATOM | 3523 | CG1 | VAL B | 554 | −31.792 | 25.642 | −45.102 | 1.00 | 56.79 | C |
| ATOM | 3524 | CG2 | VAL B | 554 | −31.677 | 23.484 | −46.390 | 1.00 | 57.25 | C |
| ATOM | 3525 | C | VAL B | 554 | −28.958 | 23.014 | −45.140 | 1.00 | 57.05 | C |
| ATOM | 3526 | O | VAL B | 554 | −28.416 | 22.494 | −46.122 | 1.00 | 56.81 | O |
| ATOM | 3527 | N | ASN B | 555 | −29.069 | 22.421 | −43.947 | 1.00 | 55.11 | N |
| ATOM | 3528 | CA | ASN B | 555 | −28.524 | 21.095 | −43.653 | 1.00 | 53.36 | C |
| ATOM | 3529 | CB | ASN B | 555 | −29.326 | 20.406 | −42.537 | 1.00 | 52.17 | C |
| | | | | | gad65.pdb | | | | | |
| ATOM | 3530 | CG | ASN B | 555 | −29.079 | 21.013 | −41.176 | 1.00 | 54.46 | C |
| ATOM | 3531 | OD1 | ASN B | 555 | −29.986 | 21.100 | −40.350 | 1.00 | 58.93 | O |
| ATOM | 3532 | ND2 | ASN B | 555 | −27.852 | 21.448 | −40.935 | 1.00 | 56.97 | N |
| ATOM | 3533 | C | ASN B | 555 | −28.470 | 20.175 | −44.855 | 1.00 | 52.61 | C |
| ATOM | 3534 | O | ASN B | 555 | −29.513 | 19.725 | −45.355 | 1.00 | 53.07 | O |
| ATOM | 3535 | N | PHE B | 556 | −27.255 | 19.898 | −45.307 | 1.00 | 50.80 | N |
| ATOM | 3536 | CA | PHE B | 556 | −27.037 | 18.928 | −46.374 | 1.00 | 50.01 | C |
| ATOM | 3537 | CB | PHE B | 556 | −26.647 | 19.627 | −47.682 | 1.00 | 49.03 | C |
| ATOM | 3538 | CG | PHE B | 556 | −25.401 | 20.472 | −47.593 | 1.00 | 49.85 | C |
| ATOM | 3539 | CD1 | PHE B | 556 | −25.471 | 21.804 | −47.180 | 1.00 | 42.95 | C |
| ATOM | 3540 | CE1 | PHE B | 556 | −24.327 | 22.593 | −47.109 | 1.00 | 42.65 | C |
| ATOM | 3541 | CZ | PHE B | 556 | −23.095 | 22.050 | −47.459 | 1.00 | 45.25 | C |
| ATOM | 3542 | CE2 | PHE B | 556 | −23.010 | 20.720 | −47.875 | 1.00 | 47.27 | C |
| ATOM | 3543 | CD2 | PHE B | 556 | −24.154 | 19.943 | −47.952 | 1.00 | 49.53 | C |
| ATOM | 3544 | C | PHE B | 556 | −25.982 | 17.914 | −45.977 | 1.00 | 50.16 | C |
| ATOM | 3545 | O | PHE B | 556 | −25.102 | 18.222 | −45.186 | 1.00 | 51.28 | O |
| ATOM | 3546 | N | PHE B | 557 | −26.082 | 16.705 | −46.523 | 1.00 | 50.92 | N |
| ATOM | 3547 | CA | PHE B | 557 | −25.112 | 15.645 | −46.275 | 1.00 | 50.66 | C |
| ATOM | 3548 | CB | PHE B | 557 | −25.609 | 14.301 | −46.818 | 1.00 | 50.54 | C |
| ATOM | 3549 | CG | PHE B | 557 | −26.763 | 13.714 | −46.057 | 1.00 | 54.52 | C |
| ATOM | 3550 | CD1 | PHE B | 557 | −26.563 | 13.109 | −44.820 | 1.00 | 54.45 | C |
| ATOM | 3551 | CE1 | PHE B | 557 | −27.630 | 12.554 | −44.120 | 1.00 | 58.28 | C |
| ATOM | 3552 | CZ | PHE B | 557 | −28.923 | 12.589 | −44.672 | 1.00 | 57.86 | C |
| ATOM | 3553 | CE2 | PHE B | 557 | −29.128 | 13.188 | −45.910 | 1.00 | 57.25 | C |
| ATOM | 3554 | CD2 | PHE B | 557 | −28.052 | 13.741 | −46.594 | 1.00 | 55.68 | C |
| ATOM | 3555 | C | PHE B | 557 | −23.809 | 15.987 | −46.965 | 1.00 | 50.23 | C |
| ATOM | 3556 | O | PHE B | 557 | −23.807 | 16.377 | −48.136 | 1.00 | 50.22 | O |
| ATOM | 3557 | N | ARG B | 558 | −22.708 | 15.867 | −46.233 | 1.00 | 49.92 | N |
| ATOM | 3558 | CA | ARG B | 558 | −21.391 | 15.944 | −46.844 | 1.00 | 50.11 | C |
| ATOM | 3559 | CB | ARG B | 558 | −20.491 | 17.001 | −46.214 | 1.00 | 50.69 | C |
| ATOM | 3560 | CG | ARG B | 558 | −19.190 | 17.163 | −47.015 | 1.00 | 52.39 | C |
| ATOM | 3561 | CD | ARG B | 558 | −17.958 | 17.135 | −46.137 | 1.00 | 54.61 | C |
| ATOM | 3562 | NE | ARG B | 558 | −17.962 | 16.045 | −45.160 | 1.00 | 48.78 | N |
| ATOM | 3563 | CZ | ARG B | 558 | −17.216 | 16.049 | −44.059 | 1.00 | 50.38 | C |
| ATOM | 3564 | NH1 | ARG B | 558 | −17.275 | 15.037 | −43.201 | 1.00 | 40.46 | N |
| ATOM | 3565 | NH2 | ARG B | 558 | −16.403 | 17.074 | −43.818 | 1.00 | 43.86 | N |
| ATOM | 3566 | C | ARG B | 558 | −20.729 | 14.586 | −46.780 | 1.00 | 50.11 | C |
| ATOM | 3567 | O | ARG B | 558 | −20.101 | 14.209 | −45.793 | 1.00 | 50.04 | O |
| ATOM | 3568 | N | MET B | 559 | −20.903 | 13.846 | −47.855 | 1.00 | 49.78 | N |
| ATOM | 3569 | CA | MET B | 559 | −20.302 | 12.550 | −47.987 | 1.00 | 49.09 | C |
| ATOM | 3570 | CB | MET B | 559 | −21.029 | 11.824 | −49.108 | 1.00 | 48.28 | C |
| ATOM | 3571 | CG | MET B | 559 | −20.636 | 10.422 | −49.297 | 1.00 | 55.45 | C |
| ATOM | 3572 | SD | MET B | 559 | −20.992 | 9.318 | −47.930 | 1.00 | 50.85 | S |
| ATOM | 3573 | CE | MET B | 559 | −20.223 | 7.913 | −48.739 | 1.00 | 44.14 | C |
| ATOM | 3574 | C | MET B | 559 | −18.819 | 12.757 | −48.297 | 1.00 | 48.73 | C |
| ATOM | 3575 | O | MET B | 559 | −18.464 | 13.727 | −48.971 | 1.00 | 47.67 | O |
| ATOM | 3576 | N | VAL B | 560 | −17.973 | 11.871 | −47.765 | 1.00 | 49.74 | N |
| ATOM | 3577 | CA | VAL B | 560 | −16.516 | 11.885 | −47.982 | 1.00 | 51.45 | C |
| ATOM | 3578 | CB | VAL B | 560 | −15.737 | 12.633 | −46.845 | 1.00 | 52.22 | C |
| ATOM | 3579 | CG1 | VAL B | 560 | −15.704 | 14.144 | −47.077 | 1.00 | 48.74 | C |
| ATOM | 3580 | CG2 | VAL B | 560 | −16.290 | 12.283 | −45.471 | 1.00 | 50.09 | C |
| ATOM | 3581 | C | VAL B | 560 | −15.944 | 10.464 | −48.054 | 1.00 | 52.66 | C |
| ATOM | 3582 | O | VAL B | 560 | −16.356 | 9.577 | −47.293 | 1.00 | 52.83 | O |
| ATOM | 3583 | N | ILE B | 561 | −14.980 | 10.245 | −48.950 | 1.00 | 52.62 | N |
| ATOM | 3584 | CA | ILE B | 561 | −14.337 | 8.934 | −49.041 | 1.00 | 53.21 | C |
| ATOM | 3585 | CB | ILE B | 561 | −14.732 | 8.194 | −50.356 | 1.00 | 54.33 | C |
| ATOM | 3586 | CG1 | ILE B | 561 | −16.264 | 8.104 | −50.455 | 1.00 | 54.14 | C |
| ATOM | 3587 | CD | ILE B | 561 | −16.787 | 7.585 | −51.758 | 1.00 | 57.30 | C |
| ATOM | 3588 | CG2 | ILE B | 561 | −14.086 | 6.783 | −50.430 | 1.00 | 55.10 | C |
| ATOM | 3589 | C | ILE B | 561 | −12.815 | 9.021 | −48.834 | 1.00 | 53.96 | C |
| ATOM | 3590 | O | ILE B | 561 | −12.130 | 9.826 | −49.480 | 1.00 | 53.35 | O |
| ATOM | 3591 | N | SER B | 562 | −12.302 | 8.210 | −47.908 | 1.00 | 54.66 | N |
| ATOM | 3592 | CA | SER B | 562 | −10.855 | 8.119 | −47.659 | 1.00 | 54.60 | C |
| ATOM | 3593 | CB | SER B | 562 | −10.400 | 9.210 | −46.688 | 1.00 | 53.81 | C |

TABLE A-continued

| | | | | | | | | | | |
|---|---|---|---|---|---|---|---|---|---|---|
| ATOM | 3594 | OG | SER B | 562 | −11.114 | 9.139 | −45.462 | 1.00 | 57.44 | O |
| ATOM | 3595 | C | SER B | 562 | −10.458 | 6.732 | −47.145 | 1.00 | 55.42 | C |
| ATOM | 3596 | O | SER B | 562 | −9.273 | 6.435 | −46.967 | 1.00 | 55.48 | O |
| ATOM | 3597 | N | ASN B | 563 | −11.460 | 5.888 | −46.925 | 1.00 | 55.13 | N |
| | | | | | gad65.pdb | | | | | |
| ATOM | 3598 | CA | ASN B | 563 | −11.263 | 4.555 | −46.390 | 1.00 | 55.50 | C |
| ATOM | 3599 | CB | ASN B | 563 | −12.509 | 4.163 | −45.590 | 1.00 | 54.50 | C |
| ATOM | 3600 | CG | ASN B | 563 | −12.384 | 2.834 | −44.848 | 1.00 | 55.05 | C |
| ATOM | 3601 | OD1 | ASN B | 563 | −13.311 | 2.438 | −44.139 | 1.00 | 55.02 | O |
| ATOM | 3602 | ND2 | ASN B | 563 | −11.257 | 2.150 | −44.993 | 1.00 | 55.08 | N |
| ATOM | 3603 | C | ASN B | 563 | −10.997 | 3.578 | −47.550 | 1.00 | 57.25 | C |
| ATOM | 3604 | O | ASN B | 563 | −11.764 | 3.546 | −48.525 | 1.00 | 58.67 | O |
| ATOM | 3605 | N | PRO B | 564 | −9.885 | 2.818 | −47.476 | 1.00 | 56.51 | N |
| ATOM | 3606 | CA | PRO B | 564 | −9.617 | 1.753 | −48.452 | 1.00 | 55.97 | C |
| ATOM | 3607 | CB | PRO B | 564 | −8.220 | 1.260 | −48.065 | 1.00 | 56.13 | C |
| ATOM | 3608 | CG | PRO B | 564 | −8.043 | 1.690 | −46.641 | 1.00 | 57.87 | C |
| ATOM | 3609 | CD | PRO B | 564 | −8.789 | 2.965 | −46.497 | 1.00 | 55.82 | C |
| ATOM | 3610 | C | PRO B | 564 | −10.620 | 0.588 | −48.417 | 1.00 | 54.89 | C |
| ATOM | 3611 | O | PRO B | 564 | −10.763 | −0.112 | −49.411 | 1.00 | 54.33 | O |
| ATOM | 3612 | N | ALA B | 565 | −11.304 | 0.394 | −47.291 | 1.00 | 53.60 | N |
| ATOM | 3613 | CA | ALA B | 565 | −12.271 | −0.689 | −47.140 | 1.00 | 52.57 | C |
| ATOM | 3614 | CB | ALA B | 565 | −12.444 | −1.048 | −45.668 | 1.00 | 51.55 | C |
| ATOM | 3615 | C | ALA B | 565 | −13.639 | −0.416 | −47.790 | 1.00 | 53.68 | C |
| ATOM | 3616 | O | ALA B | 565 | −14.461 | −1.339 | −47.924 | 1.00 | 53.53 | O |
| ATOM | 3617 | N | ALA B | 566 | −13.880 | 0.835 | −48.181 | 1.00 | 54.04 | N |
| ATOM | 3618 | CA | ALA B | 566 | −15.136 | 1.228 | −48.829 | 1.00 | 55.15 | C |
| ATOM | 3619 | CB | ALA B | 566 | −15.378 | 2.709 | −48.669 | 1.00 | 53.92 | C |
| ATOM | 3620 | C | ALA B | 566 | −15.135 | 0.855 | −50.306 | 1.00 | 57.22 | C |
| ATOM | 3621 | O | ALA B | 566 | −14.231 | 1.248 | −51.058 | 1.00 | 57.99 | O |
| ATOM | 3622 | N | THR B | 567 | −16.157 | 0.106 | −50.716 | 1.00 | 58.53 | N |
| ATOM | 3623 | CA | THR B | 567 | −16.265 | −0.396 | −52.091 | 1.00 | 59.96 | C |
| ATOM | 3624 | CB | THR B | 567 | −16.279 | −1.931 | −52.112 | 1.00 | 59.54 | C |
| ATOM | 3625 | OG1 | THR B | 567 | −17.433 | −2.404 | −51.416 | 1.00 | 63.56 | O |
| ATOM | 3626 | CG2 | THR B | 567 | −15.036 | −2.490 | −51.429 | 1.00 | 59.21 | C |
| ATOM | 3627 | C | THR B | 567 | −17.499 | 0.178 | −52.817 | 1.00 | 60.56 | C |
| ATOM | 3628 | O | THR B | 567 | −18.172 | 1.062 | −52.285 | 1.00 | 60.54 | O |
| ATOM | 3629 | N | HIS B | 568 | −17.774 | −0.299 | −54.033 | 1.00 | 61.01 | N |
| ATOM | 3630 | CA | HIS B | 568 | −18.957 | 0.147 | −54.794 | 1.00 | 61.37 | C |
| ATOM | 3631 | CB | HIS B | 568 | −18.928 | −0.358 | −56.248 | 1.00 | 62.14 | C |
| ATOM | 3632 | CG | HIS B | 568 | −17.929 | 0.346 | −57.116 | 1.00 | 66.36 | C |
| ATOM | 3633 | ND1 | HIS B | 568 | −16.651 | −0.131 | −57.320 | 1.00 | 71.55 | N |
| ATOM | 3634 | CE1 | HIS B | 568 | −15.997 | 0.694 | −58.119 | 1.00 | 74.64 | C |
| ATOM | 3635 | NE2 | HIS B | 568 | −16.804 | 1.692 | −58.439 | 1.00 | 73.96 | N |
| ATOM | 3636 | CD2 | HIS B | 568 | −18.019 | 1.494 | −57.828 | 1.00 | 70.19 | C |
| ATOM | 3637 | C | HIS B | 568 | −20.272 | −0.247 | −54.106 | 1.00 | 60.55 | C |
| ATOM | 3638 | O | HIS B | 568 | −21.216 | 0.547 | −54.064 | 1.00 | 60.00 | O |
| ATOM | 3639 | N | GLN B | 569 | −20.317 | −1.459 | −53.557 | 1.00 | 60.70 | N |
| ATOM | 3640 | CA | GLN B | 569 | −21.474 | −1.931 | −52.788 | 1.00 | 62.18 | C |
| ATOM | 3641 | CB | GLN B | 569 | −21.251 | −3.368 | −52.292 | 1.00 | 62.19 | C |
| ATOM | 3642 | CG | GLN B | 569 | −20.299 | −3.486 | −51.096 | 1.00 | 65.69 | C |
| ATOM | 3643 | CD | GLN B | 569 | −20.025 | −4.914 | −50.670 | 1.00 | 64.21 | C |
| ATOM | 3644 | OE1 | GLN B | 569 | −20.899 | −5.599 | −50.133 | 1.00 | 69.87 | O |
| ATOM | 3645 | NE2 | GLN B | 569 | −18.793 | −5.365 | −50.890 | 1.00 | 72.27 | N |
| ATOM | 3646 | C | GLN B | 569 | −21.835 | −1.013 | −51.602 | 1.00 | 61.67 | C |
| ATOM | 3647 | O | GLN B | 569 | −23.012 | −0.831 | −51.293 | 1.00 | 61.93 | O |
| ATOM | 3648 | N | ASP B | 570 | −20.819 | −0.448 | −50.947 | 1.00 | 60.46 | N |
| ATOM | 3649 | CA | ASP B | 570 | −21.021 | 0.378 | −49.756 | 1.00 | 59.64 | C |
| ATOM | 3650 | CB | ASP B | 570 | −19.708 | 0.565 | −48.992 | 1.00 | 59.27 | C |
| ATOM | 3651 | CG | ASP B | 570 | −19.126 | −0.747 | −48.543 | 1.00 | 63.11 | C |
| ATOM | 3652 | OD1 | ASP B | 570 | −19.792 | −1.446 | −47.745 | 1.00 | 59.23 | O |
| ATOM | 3653 | OD2 | ASP B | 570 | −18.011 | −1.089 | −49.005 | 1.00 | 68.96 | O |
| ATOM | 3654 | C | ASP B | 570 | −21.650 | 1.713 | −50.093 | 1.00 | 58.26 | C |
| ATOM | 3655 | O | ASP B | 570 | −22.424 | 2.249 | −49.307 | 1.00 | 57.92 | O |
| ATOM | 3656 | N | ILE B | 571 | −21.309 | 2.240 | −51.263 | 1.00 | 58.11 | N |
| ATOM | 3657 | CA | ILE B | 571 | −21.975 | 3.429 | −51.818 | 1.00 | 58.57 | C |
| ATOM | 3658 | CB | ILE B | 571 | −21.198 | 3.989 | −53.041 | 1.00 | 58.14 | C |
| ATOM | 3659 | CG1 | ILE B | 571 | −19.742 | 4.312 | −52.661 | 1.00 | 60.20 | C |
| ATOM | 3660 | CD | ILE B | 571 | −19.556 | 5.111 | −51.355 | 1.00 | 54.00 | C |
| ATOM | 3661 | CG2 | ILE B | 571 | −21.912 | 5.192 | −53.662 | 1.00 | 55.07 | C |
| ATOM | 3662 | C | ILE B | 571 | −23.438 | 3.114 | −52.184 | 1.00 | 59.27 | C |
| ATOM | 3663 | O | ILE B | 571 | −24.350 | 3.869 | −51.819 | 1.00 | 59.53 | O |
| ATOM | 3664 | N | ASP B | 572 | −23.636 | 1.997 | −52.894 | 1.00 | 58.80 | N |
| ATOM | 3665 | CA | ASP B | 572 | −24.959 | 1.468 | −53.224 | 1.00 | 58.47 | C |
| | | | | | gad65.pdb | | | | | |
| ATOM | 3666 | CB | ASP B | 572 | −24.830 | 0.129 | −53.952 | 1.00 | 58.38 | C |
| ATOM | 3667 | CG | ASP B | 572 | −24.205 | 0.259 | −55.328 | 1.00 | 58.70 | C |
| ATOM | 3668 | OD1 | ASP B | 572 | −24.224 | 1.363 | −55.908 | 1.00 | 61.73 | O |
| ATOM | 3669 | OD2 | ASP B | 572 | −23.698 | −0.760 | −55.840 | 1.00 | 63.31 | O |
| ATOM | 3670 | C | ASP B | 572 | −25.823 | 1.284 | −51.977 | 1.00 | 58.89 | C |
| ATOM | 3671 | O | ASP B | 572 | −26.994 | 1.662 | −51.981 | 1.00 | 58.69 | O |

TABLE A-continued

| | | | | | | | | | |
|---|---|---|---|---|---|---|---|---|---|
| ATOM | 3672 | N | PHE B | 573 | −25.242 | 0.705 | −50.921 | 1.00 | 59.50 | N |
| ATOM | 3673 | CA | PHE B | 573 | −25.938 | 0.531 | −49.647 | 1.00 | 59.53 | C |
| ATOM | 3674 | CB | PHE B | 573 | −25.080 | −0.220 | −48.627 | 1.00 | 60.03 | C |
| ATOM | 3675 | CG | PHE B | 573 | −25.704 | −0.290 | −47.258 | 1.00 | 63.02 | C |
| ATOM | 3676 | CD1 | PHE B | 573 | −26.519 | −1.363 | −46.904 | 1.00 | 65.03 | C |
| ATOM | 3677 | CE1 | PHE B | 573 | −27.120 | −1.418 | −45.640 | 1.00 | 67.05 | C |
| ATOM | 3678 | CZ | PHE B | 573 | −26.912 | −0.390 | −44.724 | 1.00 | 64.69 | C |
| ATOM | 3679 | CE2 | PHE B | 573 | −26.108 | 0.692 | −45.071 | 1.00 | 64.59 | C |
| ATOM | 3680 | CD2 | PHE B | 573 | −25.508 | 0.737 | −46.331 | 1.00 | 63.91 | C |
| ATOM | 3681 | C | PHE B | 573 | −26.350 | 1.875 | −49.069 | 1.00 | 59.64 | C |
| ATOM | 3682 | O | PHE B | 573 | −27.483 | 2.043 | −48.609 | 1.00 | 59.74 | O |
| ATOM | 3683 | N | LEU B | 574 | −25.422 | 2.827 | −49.095 | 1.00 | 59.88 | N |
| ATOM | 3684 | CA | LEU B | 574 | −25.657 | 4.146 | −48.535 | 1.00 | 59.75 | C |
| ATOM | 3685 | CB | LEU B | 574 | −24.402 | 5.022 | −48.629 | 1.00 | 59.55 | C |
| ATOM | 3686 | CG | LEU B | 574 | −24.579 | 6.422 | −48.031 | 1.00 | 57.12 | C |
| ATOM | 3687 | CD1 | LEU B | 574 | −24.670 | 6.380 | −46.506 | 1.00 | 49.38 | C |
| ATOM | 3688 | CD2 | LEU B | 574 | −23.469 | 7.314 | −48.484 | 1.00 | 56.17 | C |
| ATOM | 3689 | C | LEU B | 574 | −26.836 | 4.845 | −49.197 | 1.00 | 59.91 | C |
| ATOM | 3690 | O | LEU B | 574 | −27.740 | 5.315 | −48.505 | 1.00 | 59.49 | O |
| ATOM | 3691 | N | ILE B | 575 | −26.817 | 4.919 | −50.529 | 1.00 | 60.77 | N |
| ATOM | 3692 | CA | ILE B | 575 | −27.913 | 5.534 | −51.286 | 1.00 | 61.71 | C |
| ATOM | 3693 | CB | ILE B | 575 | −27.808 | 5.265 | −52.813 | 1.00 | 61.83 | C |
| ATOM | 3694 | CG1 | ILE B | 575 | −26.396 | 5.540 | −53.358 | 1.00 | 60.99 | C |
| ATOM | 3695 | CD | ILE B | 575 | −25.942 | 6.976 | −53.285 | 1.00 | 61.27 | C |
| ATOM | 3696 | CG2 | ILE B | 575 | −28.887 | 6.046 | −53.561 | 1.00 | 61.13 | C |
| ATOM | 3697 | C | ILE B | 575 | −29.256 | 4.978 | −50.811 | 1.00 | 61.99 | C |
| ATOM | 3698 | O | ILE B | 575 | −30.175 | 5.732 | −50.486 | 1.00 | 62.13 | O |
| ATOM | 3699 | N | GLU B | 576 | −29.332 | 3.653 | −50.765 | 1.00 | 62.25 | N |
| ATOM | 3700 | CA | GLU B | 576 | −30.537 | 2.924 | −50.400 | 1.00 | 64.58 | C |
| ATOM | 3701 | CB | GLU B | 576 | −30.351 | 1.434 | −50.689 | 1.00 | 64.50 | C |
| ATOM | 3702 | CG | GLU B | 576 | −30.206 | 1.099 | −52.172 | 1.00 | 67.57 | C |
| ATOM | 3703 | CD | GLU B | 576 | −29.905 | −0.381 | −52.428 | 1.00 | 67.72 | C |
| ATOM | 3704 | OE1 | GLU B | 576 | −30.175 | −0.844 | −53.563 | 1.00 | 75.10 | O |
| ATOM | 3705 | OE2 | GLU B | 576 | −29.400 | −1.078 | −51.508 | 1.00 | 75.27 | O |
| ATOM | 3706 | C | GLU B | 576 | −30.955 | 3.128 | −48.941 | 1.00 | 64.01 | C |
| ATOM | 3707 | O | GLU B | 576 | −32.150 | 3.258 | −48.652 | 1.00 | 64.56 | O |
| ATOM | 3708 | N | GLU B | 577 | −29.974 | 3.155 | −48.034 | 1.00 | 62.07 | N |
| ATOM | 3709 | CA | GLU B | 577 | −30.230 | 3.367 | −46.610 | 1.00 | 59.52 | C |
| ATOM | 3710 | CB | GLU B | 577 | −28.941 | 3.197 | −45.796 | 1.00 | 59.80 | C |
| ATOM | 3711 | CG | GLU B | 577 | −29.128 | 3.292 | −44.280 | 1.00 | 58.07 | C |
| ATOM | 3712 | CD | GLU B | 577 | −29.773 | 2.054 | −43.669 | 1.00 | 60.20 | C |
| ATOM | 3713 | OE1 | GLU B | 577 | −29.958 | 2.036 | −42.433 | 1.00 | 62.71 | O |
| ATOM | 3714 | OE2 | GLU B | 577 | −30.092 | 1.097 | −44.409 | 1.00 | 62.99 | O |
| ATOM | 3715 | C | GLU B | 577 | −30.822 | 4.745 | −46.351 | 1.00 | 57.82 | C |
| ATOM | 3716 | O | GLU B | 577 | −31.714 | 4.896 | −45.516 | 1.00 | 56.84 | O |
| ATOM | 3717 | N | ILE B | 578 | −30.304 | 5.747 | −47.056 | 1.00 | 56.52 | N |
| ATOM | 3718 | CA | ILE B | 578 | −30.788 | 7.117 | −46.915 | 1.00 | 55.42 | C |
| ATOM | 3719 | CB | ILE B | 578 | −29.902 | 8.119 | −47.701 | 1.00 | 54.92 | C |
| ATOM | 3720 | CG1 | ILE B | 578 | −28.587 | 8.346 | −46.941 | 1.00 | 55.81 | C |
| ATOM | 3721 | CD | ILE B | 578 | −27.550 | 9.213 | −47.649 | 1.00 | 54.27 | C |
| ATOM | 3722 | CG2 | ILE B | 578 | −30.621 | 9.448 | −47.886 | 1.00 | 53.68 | C |
| ATOM | 3723 | C | ILE B | 578 | −32.268 | 7.191 | −47.328 | 1.00 | 55.02 | C |
| ATOM | 3724 | O | ILE B | 578 | −33.096 | 7.789 | −46.628 | 1.00 | 52.75 | O |
| ATOM | 3725 | N | GLU B | 579 | −32.579 | 6.544 | −48.450 | 1.00 | 56.04 | N |
| ATOM | 3726 | CA | GLU B | 579 | −33.942 | 6.441 | −48.958 | 1.00 | 57.61 | C |
| ATOM | 3727 | CB | GLU B | 579 | −33.942 | 5.739 | −50.326 | 1.00 | 57.34 | C |
| ATOM | 3728 | CG | GLU B | 579 | −33.506 | 6.656 | −51.451 | 1.00 | 58.41 | C |
| ATOM | 3729 | CD | GLU B | 579 | −33.052 | 5.929 | −52.716 | 1.00 | 63.67 | C |
| ATOM | 3730 | OE1 | GLU B | 579 | −32.692 | 6.626 | −53.687 | 1.00 | 60.13 | O |
| ATOM | 3731 | OE2 | GLU B | 579 | −33.053 | 4.681 | −52.751 | 1.00 | 64.70 | O |
| ATOM | 3732 | C | GLU B | 579 | −34.861 | 5.732 | −47.963 | 1.00 | 58.51 | C |
| ATOM | 3733 | O | GLU B | 579 | −35.957 | 6.203 | −47.674 | 1.00 | 59.02 | O |
| | | | | gad65.pdb | | | | | | |
| ATOM | 3734 | N | ARG B | 580 | −34.386 | 4.615 | −47.426 | 1.00 | 59.66 | N |
| ATOM | 3735 | CA | ARG B | 580 | −35.129 | 3.802 | −46.476 | 1.00 | 61.52 | C |
| ATOM | 3736 | CB | ARG B | 580 | −34.265 | 2.615 | −46.115 | 1.00 | 61.82 | C |
| ATOM | 3737 | CG | ARG B | 580 | −34.981 | 1.358 | −45.710 | 1.00 | 65.76 | C |
| ATOM | 3738 | CD | ARG B | 580 | −33.935 | 0.268 | −45.556 | 1.00 | 70.44 | C |
| ATOM | 3739 | NE | ARG B | 580 | −33.226 | 0.038 | −46.816 | 1.00 | 73.59 | N |
| ATOM | 3740 | CZ | ARG B | 580 | −31.970 | −0.385 | −46.912 | 1.00 | 77.56 | C |
| ATOM | 3741 | NH1 | ARG B | 580 | −31.255 | −0.618 | −45.822 | 1.00 | 81.08 | N |
| ATOM | 3742 | NH2 | ARG B | 580 | −31.423 | −0.568 | −48.106 | 1.00 | 78.42 | N |
| ATOM | 3743 | C | ARG B | 580 | −35.480 | 4.580 | −45.201 | 1.00 | 63.51 | C |
| ATOM | 3744 | O | ARG B | 580 | −36.599 | 4.470 | −44.671 | 1.00 | 63.17 | O |
| ATOM | 3745 | N | LEU B | 581 | −34.506 | 5.356 | −44.722 | 1.00 | 64.72 | N |
| ATOM | 3746 | CA | LEU B | 581 | −34.610 | 6.106 | −43.481 | 1.00 | 65.94 | C |
| ATOM | 3747 | CB | LEU B | 581 | −33.209 | 6.314 | −42.898 | 1.00 | 65.74 | C |
| ATOM | 3748 | CG | LEU B | 581 | −32.577 | 5.284 | −41.943 | 1.00 | 65.60 | C |
| ATOM | 3749 | CD1 | LEU B | 581 | −32.908 | 3.831 | −42.247 | 1.00 | 65.99 | C |
| ATOM | 3750 | CD2 | LEU B | 581 | −31.072 | 5.488 | −41.915 | 1.00 | 66.09 | C |

TABLE A-continued

| | | | | | | | | | |
|---|---|---|---|---|---|---|---|---|---|
| ATOM | 3751 | C | LEU B | 581 | −35.333 | 7.450 | −43.653 | 1.00 | 68.11 | C |
| ATOM | 3752 | O | LEU B | 581 | −35.731 | 8.081 | −42.667 | 1.00 | 67.89 | O |
| ATOM | 3753 | N | GLY B | 582 | −35.509 | 7.877 | −44.902 | 1.00 | 70.13 | N |
| ATOM | 3754 | CA | GLY B | 582 | −36.166 | 9.144 | −45.201 | 1.00 | 72.86 | C |
| ATOM | 3755 | C | GLY B | 582 | −37.664 | 9.043 | −45.375 | 1.00 | 75.40 | C |
| ATOM | 3756 | O | GLY B | 582 | −38.168 | 9.185 | −46.485 | 1.00 | 75.98 | O |
| ATOM | 3757 | N | GLN B | 583 | −38.365 | 8.800 | −44.271 | 1.00 | 77.85 | N |
| ATOM | 3758 | CA | GLN B | 583 | −39.835 | 8.738 | −44.239 | 1.00 | 79.91 | C |
| ATOM | 3759 | CB | GLN B | 583 | −40.347 | 7.380 | −44.742 | 1.00 | 80.05 | C |
| ATOM | 3760 | CG | GLN B | 583 | −40.767 | 7.400 | −46.218 | 1.00 | 82.64 | C |
| ATOM | 3761 | CD | GLN B | 583 | −40.134 | 6.287 | −47.054 | 1.00 | 83.45 | C |
| ATOM | 3762 | OE1 | GLN B | 583 | −39.794 | 6.499 | −48.219 | 1.00 | 84.12 | O |
| ATOM | 3763 | NE2 | GLN B | 583 | −39.976 | 5.103 | −46.465 | 1.00 | 76.11 | N |
| ATOM | 3764 | C | GLN B | 583 | −40.403 | 9.089 | −42.845 | 1.00 | 80.80 | C |
| ATOM | 3765 | O | GLN B | 583 | −40.745 | 8.202 | −42.053 | 1.00 | 80.45 | O |
| ATOM | 3766 | N | ASP B | 584 | −40.505 | 10.387 | −42.553 | 1.00 | 81.65 | N |
| ATOM | 3767 | CA | ASP B | 584 | −40.136 | 11.448 | −43.497 | 1.00 | 82.17 | C |
| ATOM | 3768 | CB | ASP B | 584 | −41.388 | 12.066 | −44.129 | 1.00 | 82.62 | C |
| ATOM | 3769 | C | ASP B | 584 | −39.286 | 12.531 | −42.829 | 1.00 | 82.09 | C |
| ATOM | 3770 | O | ASP B | 584 | −38.081 | 12.362 | −42.638 | 1.00 | 81.77 | O |
| ATOM | 3858 | OE2 | GBA C | 1 | 15.162 | 17.936 | −18.957 | .50 | 36.04 | O |
| ATOM | 3859 | CD | GBA C | 1 | 14.586 | 16.897 | −19.322 | .50 | 32.41 | C |
| ATOM | 3860 | OE1 | GBA C | 1 | 15.165 | 15.797 | −19.295 | .50 | 34.12 | O |
| ATOM | 3861 | CG | GBA C | 1 | 13.147 | 16.998 | −19.786 | .50 | 35.80 | C |
| ATOM | 3862 | CB | GBA C | 1 | 12.720 | 15.799 | −20.623 | .50 | 35.91 | C |
| ATOM | 3863 | CA | GBA C | 1 | 11.291 | 15.349 | −20.335 | .50 | 36.65 | C |
| ATOM | 3864 | N | GBA C | 1 | 11.205 | 13.902 | −20.465 | .50 | 36.57 | N |
| ATOM | 3865 | OE2 | GBA D | 1 | 11.872 | 14.883 | −20.292 | .50 | 47.32 | O |
| ATOM | 3866 | CD | GBA D | 1 | 10.823 | 15.372 | −20.772 | .50 | 43.97 | C |
| ATOM | 3867 | OE1 | GBA D | 1 | 9.837 | 14.664 | −21.060 | .50 | 38.56 | O |
| ATOM | 3868 | CG | GBA D | 1 | 10.737 | 16.865 | −21.018 | .50 | 42.60 | C |
| ATOM | 3869 | CB | GBA D | 1 | 11.693 | 17.627 | −20.110 | .50 | 43.54 | C |
| ATOM | 3870 | CA | GBA D | 1 | 11.403 | 19.120 | −20.116 | .50 | 43.57 | C |
| ATOM | 3871 | N | GBA D | 1 | 12.168 | 19.772 | −21.157 | .50 | 44.03 | N |
| ATOM | 3872 | O3 | GOL E | 1 | 15.003 | 27.954 | −19.230 | 1.00 | 82.79 | O |
| ATOM | 3873 | C3 | GOL E | 1 | 14.616 | 29.273 | −19.556 | 1.00 | 86.19 | C |
| ATOM | 3874 | C2 | GOL E | 1 | 13.599 | 29.799 | −18.544 | 1.00 | 84.73 | C |
| ATOM | 3875 | O2 | GOL E | 1 | 14.273 | 30.120 | −17.345 | 1.00 | 85.45 | O |
| ATOM | 3876 | C1 | GOL E | 1 | 12.880 | 31.034 | −19.086 | 1.00 | 82.29 | C |
| ATOM | 3877 | O1 | GOL E | 1 | 11.483 | 30.817 | −19.159 | 1.00 | 80.07 | O |
| ATOM | 3771 | OE2 | GBA F | 1 | −15.166 | 17.937 | −41.044 | 0.50 | 36.04 | O |
| ATOM | 3772 | CD | GBA F | 1 | −14.590 | 16.898 | −40.679 | 0.50 | 32.41 | C |
| ATOM | 3773 | OE1 | GBA F | 1 | −15.169 | 15.798 | −40.706 | 0.50 | 34.12 | O |
| ATOM | 3774 | CG | GBA F | 1 | −13.151 | 16.998 | −40.215 | 0.50 | 35.80 | C |
| ATOM | 3775 | CB | GBA F | 1 | −12.724 | 15.799 | −39.378 | 0.50 | 35.91 | C |
| ATOM | 3776 | CA | GBA F | 1 | −11.295 | 15.349 | −39.667 | 0.50 | 36.65 | C |
| ATOM | 3777 | N | GBA F | 1 | −11.209 | 13.902 | −39.537 | 0.50 | 36.57 | N |
| ATOM | 3778 | OE2 | GBA G | 1 | −11.876 | 14.883 | −39.709 | 0.50 | 47.32 | O |
| ATOM | 3779 | CD | GBA G | 1 | −10.827 | 15.372 | −39.230 | 0.50 | 43.97 | C |
| ATOM | 3780 | OE1 | GBA G | 1 | −9.841 | 14.663 | −38.942 | 0.50 | 38.56 | O |
| ATOM | 3781 | CG | GBA G | 1 | −10.740 | 16.865 | −38.984 | 0.50 | 42.60 | C | gad65.pdb

| | | | | | | | | | |
|---|---|---|---|---|---|---|---|---|---|
| ATOM | 3782 | CB | GBA G | 1 | −11.696 | 17.627 | −39.892 | 0.50 | 43.54 | C |
| ATOM | 3783 | CA | GBA G | 1 | −11.406 | 19.120 | −39.886 | 0.50 | 43.57 | C |
| ATOM | 3784 | N | GBA G | 1 | −12.171 | 19.772 | −38.845 | 0.50 | 44.03 | N |
| ATOM | 3785 | O3 | GOL H | 1 | −15.004 | 27.955 | −40.771 | 1.00 | 82.79 | O |
| ATOM | 3786 | C3 | GOL H | 1 | −14.617 | 29.274 | −40.445 | 1.00 | 86.19 | C |
| ATOM | 3787 | C2 | GOL H | 1 | −13.600 | 29.799 | −41.458 | 1.00 | 84.73 | C |
| ATOM | 3788 | O2 | GOL H | 1 | −14.274 | 30.120 | −42.657 | 1.00 | 85.45 | O |
| ATOM | 3789 | C1 | GOL H | 1 | −12.880 | 31.034 | −40.916 | 1.00 | 82.29 | C |
| ATOM | 3790 | O1 | GOL H | 1 | −11.483 | 30.817 | −40.843 | 1.00 | 80.07 | O |
| END | | | | | | | | | | |

Coordinates for GAD67

```
HEADER     ----                                          XX-XXX-XX    xxxx
COMPND     ---
REMARK   3
REMARK   3  REFINEMENT.
REMARK   3     PROGRAM     : REFMAC 5.2.0019
REMARK   3     AUTHORS     : MURSHUDOV,VAGIN,DODSON
REMARK   3
REMARK   3     REFINEMENT TARGET : MAXIMUM LIKELIHOOD
REMARK   3
REMARK   3  DATA USED IN REFINEMENT.
REMARK   3     RESOLUTION RANGE HIGH    (ANGSTROMS) :   2.30
REMARK   3     RESOLUTION RANGE LOW     (ANGSTROMS) :  97.13
REMARK   3     DATA CUTOFF              (SIGMA(F))  :  NONE
REMARK   3     COMPLETENESS FOR RANGE         (%)   :  93.38
REMARK   3     NUMBER OF REFLECTIONS                :  40153
REMARK   3
```

TABLE A-continued

| | | | | | | |
|---|---|---|---|---|---|---|
| REMARK | 3 | FIT TO DATA USED IN REFINEMENT. | | | | |
| REMARK | 3 | CROSS-VALIDATION METHOD | : THROUGHOUT | | | |
| REMARK | 3 | FREE R VALUE TEST SET SELECTION | : RANDOM | | | |
| REMARK | 3 | R VALUE     (WORKING + TEST SET) | : .18835 | | | |
| REMARK | 3 | R VALUE          (WORKING SET) | : .18645 | | | |
| REMARK | 3 | FREE R VALUE | : .22381 | | | |
| REMARK | 3 | FREE R VALUE TEST SET SIZE   (%) | : 5.0 | | | |
| REMARK | 3 | FREE R VALUE TEST SET COUNT | : 2118 | | | |
| REMARK | 3 | | | | | |
| REMARK | 3 | FIT IN THE HIGHEST RESOLUTION BIN. | | | | |
| REMARK | 3 | TOTAL NUMBER OF BINS USED | : 20 | | | |
| REMARK | 3 | BIN RESOLUTION RANGE HIGH | : 2.300 | | | |
| REMARK | 3 | BIN RESOLUTION RANGE LOW | : 2.360 | | | |
| REMARK | 3 | REFLECTION IN BIN        (WORKING SET) | : 1955 | | | |
| REMARK | 3 | BIN COMPLETENESS  (WORKING+TEST) (%) | : 62.50 | | | |
| REMARK | 3 | BIN R VALUE           (WORKING SET) | : .214 | | | |
| REMARK | 3 | BIN FREE R VALUE SET COUNT | : 112 | | | |
| REMARK | 3 | BIN FREE R VALUE | : .258 | | | |
| REMARK | 3 | | | | | |
| REMARK | 3 | NUMBER OF NON-HYDROGEN ATOMS USED IN REFINEMENT. | | | | |
| REMARK | 3 | ALL ATOMS          :    8292 | | | | |
| REMARK | 3 | | | | | |
| REMARK | 3 | B VALUES. | | | | |
| REMARK | 3 | FROM WILSON PLOT         (A**2) : NULL | | | | |
| REMARK | 3 | MEAN B VALUE      (OVERALL, A**2) : 24.368 | | | | |
| REMARK | 3 | OVERALL ANISOTROPIC B VALUE. | | | | |
| REMARK | 3 | B11 (A**2) :        −.39 | | | | |
| REMARK | 3 | B22 (A**2) :         .07 | | | | |
| REMARK | 3 | B33 (A**2) :        −.90 | | | | |
| REMARK | 3 | B12 (A**2) :         .00 | | | | |
| REMARK | 3 | B13 (A**2) :       −2.12 | | | | |
| REMARK | 3 | B23 (A**2) :         .00 | | | | |
| REMARK | 3 | | | | | |
| REMARK | 3 | ESTIMATED OVERALL COORDINATE ERROR. | | | | |
| REMARK | 3 | ESU BASED ON R VALUE                    (A): | .486 | | | |
| REMARK | 3 | ESU BASED ON FREE R VALUE               (A): | .243 | | | |
| REMARK | 3 | ESU BASED ON MAXIMUM LIKELIHOOD         (A): | .164 | | | |
| REMARK | 3 | ESU FOR B VALUES BASED ON MAXIMUM LIKELIHOOD  (A**2): | 6.687 | | | |
| REMARK | 3 | | | | | |
| REMARK | 3 | CORRELATION COEFFICIENTS. | | | | |
| REMARK | 3 | CORRELATION COEFFICIENT FO-FC       : .938 | | | | |
| REMARK | 3 | CORRELATION COEFFICIENT FO-FC FREE  : .912 | | | | |
| REMARK | 3 | | | | | |
| REMARK | 3 | RMS DEVIATIONS FROM IDEAL VALUES | | COUNT | RMS | WEIGHT |
| REMARK | 3 | BOND LENGTHS REFINED ATOMS | (A): | 8120 ; | .009 ; | .022 |
| REMARK | 3 | BOND ANGLES REFINED ATOMS | (DEGREES): | 10980 ; | 1.125 ; | 1.956 |
| REMARK | 3 | TORSION ANGLES, PERIOD 1 | (DEGREES): | 1003 ; | 6.807 ; | 5.000 |
| REMARK | 3 | TORSION ANGLES, PERIOD 2 | (DEGREES): | 360 ; | 35.222 ; | 24.250 |
| REMARK | 3 | TORSION ANGLES, PERIOD 3 | (DEGREES): | 1390 ; | 15.756 ; | 15.000 |
| REMARK | 3 | TORSION ANGLES, PERIOD 4 | (DEGREES): | 37 ; | 15.757 ; | 15.000 |
| REMARK | 3 | CHIRAL-CENTER RESTRAINTS | (A**3): | 1187 ; | .095 ; | .200 |
| REMARK | 3 | GENERAL PLANES REFINED ATOMS | (A): | 6129 ; | .003 ; | .020 |
| | | gad67.pdb | | | | |
| REMARK | 3 | NON-BONDED CONTACTS REFINED ATOMS | (A): | 3996 ; | .193 ; | .200 |
| REMARK | 3 | NON-BONDED TORSION REFINED ATOMS | (A): | 5601 ; | .301 ; | .200 |
| REMARK | 3 | H-BOND (X...Y) REFINED ATOMS | (A): | 485 ; | .125 ; | .200 |
| REMARK | 3 | SYMMETRY VDW REFINED ATOMS | (A): | 46 ; | .212 ; | .200 |
| REMARK | 3 | SYMMETRY H-BOND REFINED ATOMS | (A): | 8 ; | .085 ; | .200 |
| REMARK | 3 | | | | | |
| REMARK | 3 | ISOTROPIC THERMAL FACTOR RESTRAINTS. | | COUNT | RMS | WEIGHT |
| REMARK | 3 | MAIN-CHAIN BOND REFINED ATOMS | (A**2): | 5135 ; | .911 ; | 3.000 |
| REMARK | 3 | MAIN-CHAIN ANGLE REFINED ATOMS | (A**2): | 7999 ; | 1.610 ; | 5.000 |
| REMARK | 3 | SIDE-CHAIN BOND REFINED ATOMS | (A**2): | 3434 ; | 2.582 ; | 7.000 |
| REMARK | 3 | SIDE-CHAIN ANGLE REFINED ATOMS | (A**2): | 2981 ; | 3.932 ; | 10.000 |
| REMARK | 3 | | | | | |
| REMARK | 3 | NCS RESTRAINTS STATISTICS | | | | |
| REMARK | 3 | NUMBER OF DIFFERENT NCS GROUPS :   24 | | | | |
| REMARK | 3 | | | | | |
| REMARK | 3 | NCS GROUP NUMBER           :   1 | | | | |
| REMARK | 3 | CHAIN NAMES          : A B | | | | |
| REMARK | 3 | NUMBER OF COMPONENTS NCS GROUP  :   1 | | | | |
| REMARK | 3 | COMPONENT C   SSSEQI TO C   SSSEQI CODE | | | | |
| REMARK | 3 | 1     A     98    A    106    1 | | | | |
| REMARK | 3 | 1     B     98    B    106    1 | | | | |
| REMARK | 3 | | GROUP | CHAIN | COUNT | RMS | WEIGHT |
| REMARK | 3 | TIGHT POSITIONAL | 1 | A   (A): | 71 ; | .02 ; | .05 |
| REMARK | 3 | TIGHT THERMAL | 1 | A   (A**2): | 71 ; | .05 ; | .50 |

TABLE A-continued

```
REMARK  3
REMARK  3    NCS GROUP NUMBER               :    2
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    113   A    138      1
REMARK  3              1      B    113   B    138      1
REMARK  3                   GROUP   CHAIN           COUNT   RMS   WEIGHT
REMARK  3       TIGHT POSITIONAL     2       A     (A):   212 ;   .01 ;   .05
REMARK  3       TIGHT THERMAL        2       A    (A**2):  212 ;   .20 ;   .50
REMARK  3
REMARK  3    NCS GROUP NUMBER               :    3
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    139   A    149      4
REMARK  3              1      B    139   B    149      4
REMARK  3                   GROUP   CHAIN           COUNT   RMS   WEIGHT
REMARK  3       MEDIUM POSITIONAL    3       A     (A):    97 ;   .12 ;   .50
REMARK  3       MEDIUM THERMAL       3       A    (A**2):   97 ;   .33 ;  2.00
REMARK  3
REMARK  3    NCS GROUP NUMBER               :    4
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    158   A    172      1
REMARK  3              1      B    158   B    172      1
REMARK  3                   GROUP   CHAIN           COUNT   RMS   WEIGHT
REMARK  3       TIGHT POSITIONAL     4       A     (A):   117 ;   .02 ;   .05
REMARK  3       TIGHT THERMAL        4       A    (A**2):  117 ;   .04 ;   .50
REMARK  3
REMARK  3    NCS GROUP NUMBER               :    5
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    174   A    239      1
REMARK  3              1      B    174   B    239      1
REMARK  3                   GROUP   CHAIN           COUNT   RMS   WEIGHT
REMARK  3       TIGHT POSITIONAL     5       A     (A):   529 ;   .02 ;   .05
REMARK  3       TIGHT THERMAL        5       A    (A**2):  529 ;   .04 ;   .50
REMARK  3
REMARK  3    NCS GROUP NUMBER               :    6
REMARK  3       CHAIN NAMES                 : A B
REMARK  3       NUMBER OF COMPONENTS NCS GROUP :    1
                              gad67.pdb
REMARK  3          COMPONENT C   SSSEQI TO  C   SSSEQI  CODE
REMARK  3              1      A    245   A    278      4
REMARK  3              1      B    245   B    278      4
REMARK  3                   GROUP   CHAIN           COUNT   RMS   WEIGHT
REMARK  3       MEDIUM POSITIONAL    6       A     (A):   256 ;   .11 ;   .50
REMARK  3       MEDIUM THERMAL       6       A    (A**2):  256 ;   .36 ;  2.00
REMARK  3
REMARK  3    NCS GROUP NUMBER               :    7
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    284   A    286      4
REMARK  3              1      B    284   B    286      4
REMARK  3                   GROUP   CHAIN           COUNT   RMS   WEIGHT
REMARK  3       MEDIUM POSITIONAL    7       A     (A):    26 ;   .10 ;   .50
REMARK  3       MEDIUM THERMAL       7       A    (A**2):   26 ;   .46 ;  2.00
REMARK  3
REMARK  3    NCS GROUP NUMBER               :    8
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    287   A    301      1
REMARK  3              1      B    287   B    301      1
REMARK  3                   GROUP   CHAIN           COUNT   RMS   WEIGHT
REMARK  3       TIGHT POSITIONAL     8       A     (A):   111 ;   .01 ;   .05
REMARK  3       TIGHT THERMAL        8       A    (A**2):  111 ;   .04 ;   .50
REMARK  3
REMARK  3    NCS GROUP NUMBER               :    9
REMARK  3       CHAIN NAMES                 : A B
REMARK  3       NUMBER OF COMPONENTS NCS GROUP :    1
REMARK  3          COMPONENT C   SSSEQI TO  C   SSSEQI  CODE
REMARK  3              1      A    302   A    319      1
REMARK  3              1      B    302   B    319      1
REMARK  3                   GROUP   CHAIN           COUNT   RMS   WEIGHT
REMARK  3       TIGHT POSITIONAL     9       A     (A):   137 ;   .02 ;   .05
```

TABLE A-continued

```
REMARK  3       TIGHT THERMAL           9       A       (A**2):  137;  .04;   .50
REMARK  3
REMARK  3       NCS GROUP NUMBER                       :  10
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    321   A    340    4
REMARK  3              1      B    321   B    340    4
REMARK  3                              GROUP  CHAIN           COUNT  RMS  WEIGHT
REMARK  3       MEDIUM POSITIONAL       10      A       (A):    158;  .15;   .50
REMARK  3       MEDIUM THERMAL          10      A       (A**2): 158;  .34;  2.00
REMARK  3
REMARK  3       NCS GROUP NUMBER                       :  11
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    341   A    404    1
REMARK  3              1      B    341   B    404    1
REMARK  3                              GROUP  CHAIN           COUNT  RMS  WEIGHT
REMARK  3       TIGHT POSITIONAL        11      A       (A):    501;  .02;   .05
REMARK  3       TIGHT THERMAL           11      A       (A**2): 501;  .04;   .50
REMARK  3
REMARK  3       NCS GROUP NUMBER                       :  12
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    406   A    410    1
REMARK  3              1      B    406   B    410    1
REMARK  3                              GROUP  CHAIN           COUNT  RMS  WEIGHT
REMARK  3       TIGHT POSITIONAL        12      A       (A):     35;  .02;   .05
REMARK  3       TIGHT THERMAL           12      A       (A**2):  35;  .05;   .50
REMARK  3
REMARK  3       NCS GROUP NUMBER                       :  13
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    411   A    412    4
REMARK  3              1      B    411   B    412    4
REMARK  3                              GROUP  CHAIN           COUNT  RMS  WEIGHT
REMARK  3       MEDIUM POSITIONAL       13      A       (A):     14;  .07;   .50
REMARK  3       MEDIUM THERMAL          13      A       (A**2):  14;  .38;  2.00
REMARK  3
REMARK  3       NCS GROUP NUMBER                       :  14
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    413   A    430    1
REMARK  3              1      B    413   B    430    1
REMARK  3                              GROUP  CHAIN           COUNT  RMS  WEIGHT
REMARK  3       TIGHT POSITIONAL        14      A       (A):    131;  .02;   .05
REMARK  3       TIGHT THERMAL           14      A       (A**2): 131;  .99;   .50
REMARK  3
REMARK  3       NCS GROUP NUMBER                       :  15
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    449   A    481    1
REMARK  3              1      B    449   B    481    1
REMARK  3                              GROUP  CHAIN           COUNT  RMS  WEIGHT
REMARK  3       TIGHT POSITIONAL        15      A       (A):    270;  .01;   .05
REMARK  3       TIGHT THERMAL           15      A       (A**2): 270;  .03;   .50
REMARK  3
REMARK  3       NCS GROUP NUMBER                       :  16
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    483   A    517    1
REMARK  3              1      B    483   B    517    1
REMARK  3                              GROUP  CHAIN           COUNT  RMS  WEIGHT
REMARK  3       TIGHT POSITIONAL        16      A       (A):    296;  .01;   .05
REMARK  3       TIGHT THERMAL           16      A       (A**2): 296;  .04;   .50
REMARK  3
REMARK  3       NCS GROUP NUMBER                       :  17
REMARK  3          CHAIN NAMES                         : A B
REMARK  3          NUMBER OF COMPONENTS NCS GROUP      :   1
REMARK  3          COMPONENT C    SSSEQI TO  C    SSSEQI  CODE
REMARK  3              1      A    518   A    523    6
REMARK  3              1      B    518   B    523    6
REMARK  3                              GROUP  CHAIN           COUNT  RMS  WEIGHT
REMARK  3       LOOSE POSITIONAL        17      A       (A):     49;  .19;  5.00
```

TABLE A-continued

```
REMARK  3       LOOSE THERMAL        17    A       (A**2):   49;    3.88;   10.00
REMARK  3
REMARK  3    NCS GROUP NUMBER                  :   18
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    531   A    538     4
REMARK  3              1      B    531   B    538     4
REMARK  3                         GROUP  CHAIN         COUNT   RMS   WEIGHT
REMARK  3       MEDIUM POSITIONAL    18    A       (A):      62;    .12;    .50
REMARK  3       MEDIUM THERMAL       18    A       (A**2):   62;    .36;   2.00
REMARK  3
REMARK  3    NCS GROUP. NUMBER                 :   19
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    539   A    555     1
REMARK  3              1      B    539   B    555     1
REMARK  3                         GROUP  CHAIN         COUNT   RMS   WEIGHT
REMARK  3       TIGHT POSITIONAL     19    A       (A):     115;    .01;    .05
REMARK  3       TIGHT THERMAL        19    A       (A**2):  115;    .03;    .50
                                      gad67.pdb
REMARK  3
REMARK  3    NCS GROUP NUMBER                  :   20
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    556   A    566     4
REMARK  3              1      B    556   B    566     4
REMARK  3                         GROUP  CHAIN         COUNT   RMS   WEIGHT
REMARK  3       MEDIUM POSITIONAL    20    A       (A):      93;    .06;    .50
REMARK  3       MEDIUM THERMAL       20    A       (A**2):   93;    .32 ;          2.00
REMARK  3
REMARK  3    NCS GROUP NUMBER                  :   21
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    567   A    573     1
REMARK  3              1      B    567   B    573     1
REMARK  3                         GROUP  CHAIN         COUNT   RMS   WEIGHT
REMARK  3       TIGHT POSITIONAL     21    A       (A):      55;    .01;    .05
REMARK  3       TIGHT THERMAL        21    A       (A**2):   55;    .03;    .50
REMARK  3
REMARK  3    NCS GROUP NUMBER                  :   22
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    574   A    587     4
REMARK  3              1      B    574   B    587     4
REMARK  3                         GROUP  CHAIN         COUNT   RMS   WEIGHT
REMARK  3       MEDIUM POSITIONAL    22    A       (A):     106;    .10;    .50
REMARK  3       MEDIUM THERMAL       22    A       (A**2):  106;    .28;   2.00
REMARK  3
REMARK  3    NCS GROUP NUMBER                  :   23
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    588   A    593     6
REMARK  3              1      B    588   B    593     6
REMARK  3                         GROUP  CHAIN         COUNT   RMS   WEIGHT
REMARK  3       LOOSE POSITIONAL     23    A       (A):      46;    .47;   5.00
REMARK  3       LOOSE THERMAL        23    A       (A**2):   46;   1.70;  10.00
REMARK  3
REMARK  3    NCS GROUP NUMBER                  :   24
REMARK  3       CHAIN NAMES                    : A B
REMARK  3       NUMBER OF COMPONENTS NCS GROUP :    1
REMARK  3          COMPONENT  C   SSSEQI TO  C   SSSEQI  CODE
REMARK  3              1      A    432   A    438     6
REMARK  3              1      B    432   B    438     6
REMARK  3                         GROUP  CHAIN         COUNT   RMS   WEIGHT
REMARK  3       LOOSE POSITIONAL     24    A       (A):      56;    .62;   5.00
REMARK  3       LOOSE THERMAL        24    A       (A**2):   56;   2.06;  10.00
REMARK  3
REMARK  3
REMARK  3    TLS DETAILS
REMARK  3       NUMBER OF TLS GROUPS  : NULL
REMARK  3
REMARK  3
REMARK  3    BULK SOLVENT MODELLING.
REMARK  3       METHOD USED : BABINET MODEL WITH MASK
```

TABLE A-continued

| | | | | | | | | | | |
|---|---|---|---|---|---|---|---|---|---|---|
| REMARK | 3 | PARAMETERS FOR MASK CALCULATION | | | | | | | | |
| REMARK | 3 | VDW PROBE RADIUS | : | 1.40 | | | | | | |
| REMARK | 3 | ION PROBE RADIUS | : | .80 | | | | | | |
| REMARK | 3 | SHRINKAGE RADIUS | : | .80 | | | | | | |
| REMARK | 3 | | | | | | | | | |
| REMARK | 3 | OTHER REFINEMENT REMARKS: | | | | | | | | |
| REMARK | 3 | HYDROGENS HAVE BEEN ADDED IN THE RIDING POSITIONS | | | | | | | | |
| REMARK | 3 | | | | | | | | | |
| CISPEP | 1 | LEU A | 104 | PRO A | 105 | | | .00 | | |
| CISPEP | 2 | ALA A | 322 | ASP A | 323 | | | .00 | | |
| | | | | gad67.pdb | | | | | | |
| CISPEP | 3 | THR A | 344 | ALA A | 345 | | | .00 | | |
| CISPEP | 4 | LEU A | 411 | GLN A | 412 | | | .00 | | |
| CISPEP | 5 | GLY A | 433 | TYR A | 434 | | | .00 | | |
| CISPEP | 6 | TYR A | 434 | LEU A | 435 | | | .00 | | |
| CISPEP | 7 | LEU A | 435 | PHE A | 436 | | | .00 | | |
| CISPEP | 8 | PHE A | 436 | GLN A | 437 | | | .00 | | |
| CISPEP | 9 | ARG A | 523 | GLY A | 524 | | | .00 | | |
| CISPEP | 10 | GLY A | 524 | VAL A | 525 | | | .00 | | |
| CISPEP | 11 | VAL A | 525 | PRO A | 526 | | | .00 | | |
| CISPEP | 12 | LEU B | 104 | PRO B | 105 | | | .00 | | |
| CISPEP | 13 | MET B | 151 | GLU B | 152 | | | .00 | | |
| CISPEP | 14 | GLU B | 152 | GLY B | 153 | | | .00 | | |
| CISPEP | 15 | THR B | 344 | ALA B | 345 | | | .00 | | |
| CISPEP | 16 | LEU B | 411 | GLN B | 412 | | | .00 | | |
| CISPEP | 17 | GLY B | 433 | TYR B | 434 | | | .00 | | |
| CISPEP | 18 | PHE B | 436 | GLN B | 437 | | | .00 | | |
| CISPEP | 19 | VAL B | 525 | PRO B | 526 | | | .00 | | |
| CRYST1 | 84.048 | | 62.739 | | 101.346 | | 90.00 106.68 | 90.00 P 1 21 1 | | |
| SCALE1 | | .011898 | | .000000 | | .003566 | | .00000 | | |
| SCALE2 | | .000000 | | .015939 | | .000000 | | .00000 | | |
| SCALE3 | | .000000 | | .000000 | | .010301 | | .00000 | | |
| ATOM | 1 | N | THR A | 93 | −8.093 | 38.670 | −24.807 | 1.00 | 46.52 | N |
| ATOM | 2 | CA | THR A | 93 | −7.187 | 37.484 | −24.731 | 1.00 | 46.43 | C |
| ATOM | 3 | CB | THR A | 93 | −5.819 | 37.849 | −24.098 | 1.00 | 46.82 | C |
| ATOM | 6 | C | THR A | 93 | −7.844 | 36.321 | −23.977 | 1.00 | 45.70 | C |
| ATOM | 7 | O | THR A | 93 | −8.783 | 35.707 | −24.489 | 1.00 | 46.26 | O |
| ATOM | 8 | N | ASP A | 94 | −7.350 | 36.036 | −22.770 | 1.00 | 44.46 | N |
| ATOM | 9 | CA | ASP A | 94 | −7.829 | 34.932 | −21.921 | 1.00 | 42.95 | C |
| ATOM | 10 | CB | ASP A | 94 | −9.246 | 35.211 | −21.388 | 1.00 | 43.84 | C |
| ATOM | 11 | CG | ASP A | 94 | −9.559 | 34.447 | −20.107 | 1.00 | 45.97 | C |
| ATOM | 12 | OD1 | ASP A | 94 | −8.641 | 34.247 | −19.280 | 1.00 | 46.78 | O |
| ATOM | 13 | OD2 | ASP A | 94 | −10.735 | 34.061 | −19.922 | 1.00 | 46.70 | O |
| ATOM | 14 | C | ASP A | 94 | −7.728 | 33.567 | −22.618 | 1.00 | 40.90 | C |
| ATOM | 15 | O | ASP A | 94 | −6.641 | 32.990 | −22.682 | 1.00 | 41.05 | O |
| ATOM | 16 | N | PHE A | 95 | −8.843 | 33.063 | −23.147 | 1.00 | 38.41 | N |
| ATOM | 17 | CA | PHE A | 95 | −8.860 | 31.755 | −23.818 | 1.00 | 35.89 | C |
| ATOM | 18 | CB | PHE A | 95 | −10.065 | 30.920 | −23.367 | 1.00 | 35.15 | C |
| ATOM | 19 | CG | PHE A | 95 | −9.959 | 30.407 | −21.964 | 1.00 | 33.95 | C |
| ATOM | 20 | CD1 | PHE A | 95 | −10.760 | 30.939 | −20.959 | 1.00 | 32.86 | C |
| ATOM | 21 | CE1 | PHE A | 95 | −10.673 | 30.467 | −19.654 | 1.00 | 32.64 | C |
| ATOM | 22 | CZ | PHE A | 95 | −9.776 | 29.449 | −19.344 | 1.00 | 34.40 | C |
| ATOM | 23 | CE2 | PHE A | 95 | −8.968 | 28.909 | −20.341 | 1.00 | 33.64 | C |
| ATOM | 24 | CD2 | PHE A | 95 | −9.066 | 29.388 | −21.646 | 1.00 | 32.51 | C |
| ATOM | 25 | C | PHE A | 95 | −8.853 | 31.840 | −25.342 | 1.00 | 34.20 | C |
| ATOM | 26 | O | PHE A | 95 | −8.808 | 30.810 | −26.021 | 1.00 | 33.69 | O |
| ATOM | 27 | N | SER A | 96 | −8.902 | 33.063 | −25.868 | 1.00 | 32.91 | N |
| ATOM | 28 | CA | SER A | 96 | −8.958 | 33.306 | −27.314 | 1.00 | 31.92 | C |
| ATOM | 29 | CB | SER A | 96 | −9.137 | 34.801 | −27.592 | 1.00 | 31.91 | C |
| ATOM | 31 | C | SER A | 96 | −7.741 | 32.774 | −28.083 | 1.00 | 31.06 | C |
| ATOM | 32 | O | SER A | 96 | −7.841 | 32.464 | −29.270 | 1.00 | 31.38 | O |
| ATOM | 33 | N | ASN A | 97 | −6.600 | 32.681 | −27.405 | 1.00 | 30.12 | N |
| ATOM | 34 | CA | ASN A | 97 | −5.363 | 32.209 | −28.024 | 1.00 | 30.00 | C |
| ATOM | 35 | CB | ASN A | 97 | −4.415 | 33.387 | −28.295 | 1.00 | 31.24 | C |
| ATOM | 36 | CG | ASN A | 97 | −3.427 | 33.100 | −29.419 | 1.00 | 35.68 | C |
| ATOM | 37 | OD1 | ASN A | 97 | −2.212 | 33.151 | −29.218 | 1.00 | 38.99 | O |
| ATOM | 38 | ND2 | ASN A | 97 | −3.945 | 32.790 | −30.608 | 1.00 | 37.18 | N |
| ATOM | 39 | C | ASN A | 97 | −4.669 | 31.117 | −27.200 | 1.00 | 28.10 | C |
| ATOM | 40 | O | ASN A | 97 | −3.442 | 30.962 | −27.251 | 1.00 | 27.72 | O |
| ATOM | 41 | N | LEU A | 98 | −5.468 | 30.381 | −26.428 | 1.00 | 25.03 | N |
| ATOM | 42 | CA | LEU A | 98 | −5.029 | 29.153 | −25.777 | 1.00 | 24.08 | C |
| ATOM | 43 | CB | LEU A | 98 | −5.413 | 29.127 | −24.292 | 1.00 | 24.75 | C |
| ATOM | 44 | CG | LEU A | 98 | −4.662 | 30.022 | −23.298 | 1.00 | 29.35 | C |
| ATOM | 45 | CD1 | LEU A | 98 | −5.267 | 29.885 | −21.904 | 1.00 | 31.78 | C |
| ATOM | 46 | CD2 | LEU A | 98 | −3.161 | 29.718 | −23.267 | 1.00 | 32.80 | C |
| ATOM | 47 | C | LEU A | 98 | −5.657 | 27.967 | −26.495 | 1.00 | 22.65 | C |
| ATOM | 48 | O | LEU A | 98 | −6.765 | 28.067 | −27.036 | 1.00 | 22.35 | O |
| ATOM | 49 | N | PHE A | 99 | −4.937 | 26.850 | −26.494 | 1.00 | 21.43 | N |
| ATOM | 50 | CA | PHE A | 99 | −5.363 | 25.637 | −27.184 | 1.00 | 20.76 | C |
| | | | gad67.pdb | | | | | | | |

TABLE A-continued

| | | | | | | | | | | |
|---|---|---|---|---|---|---|---|---|---|---|
| ATOM | 51 | CB | PHE A | 99 | −4.542 | 25.438 | −28.467 | 1.00 | 20.58 | C |
| ATOM | 52 | CG | PHE A | 99 | −4.775 | 26.509 | −29.505 | 1.00 | 20.79 | C |
| ATOM | 53 | CD1 | PHE A | 99 | −5.687 | 26.310 | −30.535 | 1.00 | 20.26 | C |
| ATOM | 54 | CE1 | PHE A | 99 | −5.914 | 27.304 | −31.489 | 1.00 | 20.89 | C |
| ATOM | 55 | CZ | PHE A | 99 | −5.226 | 28.517 | −31.406 | 1.00 | 22.57 | C |
| ATOM | 56 | CE2 | PHE A | 99 | −4.318 | 28.726 | −30.377 | 1.00 | 22.90 | C |
| ATOM | 57 | CD2 | PHE A | 99 | −4.098 | 27.726 | −29.436 | 1.00 | 21.67 | C |
| ATOM | 58 | C | PHE A | 99 | −5.244 | 24.435 | −26.257 | 1.00 | 20.40 | C |
| ATOM | 59 | O | PHE A | 99 | −4.546 | 24.491 | −25.245 | 1.00 | 20.27 | O |
| ATOM | 60 | N | ALA A | 100 | −5.940 | 23.355 | −26.604 | 1.00 | 20.30 | N |
| ATOM | 61 | CA | ALA A | 100 | −5.939 | 22.123 | −25.812 | 1.00 | 20.30 | C |
| ATOM | 62 | CB | ALA A | 100 | −6.865 | 21.103 | −26.438 | 1.00 | 19.38 | C |
| ATOM | 63 | C | ALA A | 100 | −4.537 | 21.539 | −25.643 | 1.00 | 21.67 | C |
| ATOM | 64 | O | ALA A | 100 | −4.233 | 20.930 | −24.618 | 1.00 | 22.23 | O |
| ATOM | 65 | N | ARG A | 101 | −3.688 | 21.737 | −26.650 | 1.00 | 22.30 | N |
| ATOM | 66 | CA | ARG A | 101 | −2.304 | 21.263 | −26.616 | 1.00 | 23.36 | C |
| ATOM | 67 | CB | ARG A | 101 | −1.650 | 21.435 | −27.991 | 1.00 | 23.49 | C |
| ATOM | 68 | CG | ARG A | 101 | −1.517 | 22.883 | −28.437 | 1.00 | 24.28 | C |
| ATOM | 69 | CD | ARG A | 101 | −1.296 | 22.983 | −29.932 | 1.00 | 26.25 | C |
| ATOM | 70 | NE | ARG A | 101 | −1.442 | 24.361 | −30.395 | 1.00 | 26.80 | N |
| ATOM | 71 | CZ | ARG A | 101 | −1.644 | 24.714 | −31.660 | 1.00 | 24.82 | C |
| ATOM | 72 | NH1 | ARG A | 101 | −1.725 | 23.793 | −32.614 | 1.00 | 22.61 | N |
| ATOM | 73 | NH2 | ARG A | 101 | −1.768 | 25.996 | −31.971 | 1.00 | 26.25 | N |
| ATOM | 74 | C | ARG A | 101 | −1.465 | 21.955 | −25.538 | 1.00 | 23.71 | C |
| ATOM | 75 | O | ARG A | 101 | −.389 | 21.468 | −25.182 | 1.00 | 24.70 | O |
| ATOM | 76 | N | ASP A | 102 | −1.963 | 23.082 | −25.027 | 1.00 | 24.16 | N |
| ATOM | 77 | CA | ASP A | 102 | −1.274 | 23.856 | −23.986 | 1.00 | 24.34 | C |
| ATOM | 78 | CB | ASP A | 102 | −1.534 | 25.360 | −24.164 | 1.00 | 25.01 | C |
| ATOM | 79 | CG | ASP A | 102 | −1.035 | 25.893 | −25.503 | 1.00 | 28.27 | C |
| ATOM | 80 | OD1 | ASP A | 102 | .053 | 25.469 | −25.957 | 1.00 | 30.58 | O |
| ATOM | 81 | OD2 | ASP A | 102 | −1.732 | 26.746 | −26.098 | 1.00 | 29.17 | O |
| ATOM | 82 | C | ASP A | 102 | −1.661 | 23.427 | −22.569 | 1.00 | 23.77 | C |
| ATOM | 83 | O | ASP A | 102 | −1.016 | 23.834 | −21.599 | 1.00 | 23.96 | O |
| ATOM | 84 | N | LEU A | 103 | −2.713 | 22.614 | −22.455 | 1.00 | 22.66 | N |
| ATOM | 85 | CA | LEU A | 103 | −3.187 | 22.120 | −21.157 | 1.00 | 21.57 | C |
| ATOM | 86 | CB | LEU A | 103 | −4.701 | 21.857 | −21.197 | 1.00 | 20.38 | C |
| ATOM | 87 | CG | LEU A | 103 | −5.658 | 22.946 | −21.683 | 1.00 | 18.99 | C |
| ATOM | 88 | CD1 | LEU A | 103 | −7.093 | 22.435 | −21.665 | 1.00 | 19.82 | C |
| ATOM | 89 | CD2 | LEU A | 103 | −5.535 | 24.215 | −20.850 | 1.00 | 20.57 | C |
| ATOM | 90 | C | LEU A | 103 | −2.450 | 20.840 | −20.756 | 1.00 | 21.25 | C |
| ATOM | 91 | O | LEU A | 103 | −1.728 | 20.257 | −21.569 | 1.00 | 21.02 | O |
| ATOM | 92 | N | LEU A | 104 | −2.634 | 20.407 | −19.508 | 1.00 | 21.06 | N |
| ATOM | 93 | CA | LEU A | 104 | −2.084 | 19.129 | −19.040 | 1.00 | 21.56 | C |
| ATOM | 94 | CB | LEU A | 104 | −2.603 | 18.786 | −17.635 | 1.00 | 20.40 | C |
| ATOM | 95 | CG | LEU A | 104 | −2.061 | 19.586 | −16.442 | 1.00 | 19.98 | C |
| ATOM | 96 | CD1 | LEU A | 104 | −2.806 | 19.223 | −15.161 | 1.00 | 16.80 | C |
| ATOM | 97 | CD2 | LEU A | 104 | −.544 | 19.408 | −16.258 | 1.00 | 13.89 | C |
| ATOM | 98 | C | LEU A | 104 | −2.440 | 18.017 | −20.030 | 1.00 | 22.61 | C |
| ATOM | 99 | O | LEU A | 104 | −3.585 | 17.945 | −20.483 | 1.00 | 22.70 | O |
| ATOM | 100 | N | PRO A | 105 | −1.481 | 17.125 | −20.353 | 1.00 | 23.85 | N |
| ATOM | 101 | CA | PRO A | 105 | −.162 | 16.888 | −19.755 | 1.00 | 24.83 | C |
| ATOM | 102 | CB | PRO A | 105 | .149 | 15.462 | −20.202 | 1.00 | 24.74 | C |
| ATOM | 103 | CG | PRO A | 105 | −.488 | 15.361 | −21.539 | 1.00 | 25.06 | C |
| ATOM | 104 | CD | PRO A | 105 | −1.737 | 16.196 | −21.471 | 1.00 | 23.84 | C |
| ATOM | 105 | C | PRO A | 105 | .993 | 17.809 | −20.173 | 1.00 | 26.13 | C |
| ATOM | 106 | O | PRO A | 105 | 2.129 | 17.557 | −19.767 | 1.00 | 26.25 | O |
| ATOM | 107 | N | ALA A | 106 | .725 | 18.851 | −20.961 | 1.00 | 27.59 | N |
| ATOM | 108 | CA | ALA A | 106 | 1.772 | 19.817 | −21.323 | 1.00 | 28.73 | C |
| ATOM | 109 | CB | ALA A | 106 | 1.218 | 20.927 | −22.192 | 1.00 | 27.80 | C |
| ATOM | 110 | C | ALA A | 106 | 2.415 | 20.382 | −20.054 | 1.00 | 30.44 | C |
| ATOM | 111 | O | ALA A | 106 | 1.713 | 20.700 | −19.084 | 1.00 | 30.63 | O |
| ATOM | 112 | N | LYS A | 107 | 3.745 | 20.494 | −20.079 | 1.00 | 32.68 | N |
| ATOM | 113 | CA | LYS A | 107 | 4.569 | 20.739 | −18.882 | 1.00 | 34.53 | C |
| ATOM | 114 | CB | LYS A | 107 | 6.032 | 20.984 | −19.280 | 1.00 | 35.10 | C |
| ATOM | 119 | C | LYS A | 107 | 4.085 | 21.846 | −17.932 | 1.00 | 35.18 | C |
| ATOM | 120 | O | LYS A | 107 | 3.971 | 21.625 | −16.724 | 1.00 | 35.91 | O |
| ATOM | 121 | N | ASN A | 108 | 3.796 | 23.022 | −18.480 | 1.00 | 35.20 | N |
| ATOM | 122 | CA | ASN A | 108 | 3.455 | 24.190 | −17.669 | 1.00 | 35.56 | C |
| | | | | | gad67.pdb | | | | | |
| ATOM | 123 | CB | ASN A | 108 | 4.317 | 25.385 | −18.094 | 1.00 | 36.55 | C |
| ATOM | 124 | CG | ASN A | 108 | 5.803 | 25.096 | −17.999 | 1.00 | 37.60 | C |
| ATOM | 125 | OD1 | ASN A | 108 | 6.334 | 24.866 | −16.912 | 1.00 | 38.86 | O |
| ATOM | 126 | ND2 | ASN A | 108 | 6.483 | 25.105 | −19.141 | 1.00 | 37.43 | N |
| ATOM | 127 | C | ASN A | 108 | 1.971 | 24.561 | −17.726 | 1.00 | 35.13 | C |
| ATOM | 128 | O | ASN A | 108 | 1.592 | 25.696 | −17.416 | 1.00 | 34.84 | O |
| ATOM | 129 | N | GLY A | 109 | 1.135 | 23.598 | −18.105 | 1.00 | 34.13 | N |
| ATOM | 130 | CA | GLY A | 109 | −.276 | 23.866 | −18.361 | 1.00 | 33.65 | C |
| ATOM | 131 | C | GLY A | 109 | −1.235 | 23.666 | −17.201 | 1.00 | 32.77 | C |
| ATOM | 132 | O | GLY A | 109 | −2.449 | 23.689 | −17.402 | 1.00 | 32.40 | O |
| ATOM | 133 | N | GLU A | 110 | −.702 | 23.487 | −15.994 | 1.00 | 32.21 | N |

TABLE A-continued

| | | | | | | | | | | |
|---|---|---|---|---|---|---|---|---|---|---|
| ATOM | 134 | CA | GLU A | 110 | −1.524 | 23.167 | −14.823 | 1.00 | 32.84 | C |
| ATOM | 135 | CB | GLU A | 110 | −.652 | 22.772 | −13.626 | 1.00 | 32.94 | C |
| ATOM | 136 | CG | GLU A | 110 | −1.439 | 22.215 | −12.441 | 1.00 | 33.91 | C |
| ATOM | 137 | CD | GLU A | 110 | −.568 | 21.903 | −11.239 | 1.00 | 34.98 | C |
| ATOM | 138 | OE1 | GLU A | 110 | .437 | 21.174 | −11.390 | 1.00 | 40.78 | O |
| ATOM | 139 | OE2 | GLU A | 110 | −.899 | 22.379 | −10.133 | 1.00 | 39.78 | O |
| ATOM | 140 | C | GLU A | 110 | −2.502 | 24.278 | −14.429 | 1.00 | 31.72 | C |
| ATOM | 141 | O | GLU A | 110 | −3.666 | 24.003 | −14.133 | 1.00 | 32.00 | O |
| ATOM | 142 | N | GLU A | 111 | −2.024 | 25.521 | −14.429 | 1.00 | 30.80 | N |
| ATOM | 143 | CA | GLU A | 111 | −2.843 | 26.677 | −14.057 | 1.00 | 30.10 | C |
| ATOM | 149 | C | GLU A | 111 | −3.984 | 26.913 | −15.043 | 1.00 | 29.11 | C |
| ATOM | 150 | O | GLU A | 111 | −5.112 | 27.209 | −14.647 | 1.00 | 28.85 | O |
| ATOM | 151 | N | GLN A | 112 | −3.675 | 26.775 | −16.327 | 1.00 | 28.36 | N |
| ATOM | 152 | CA | GLN A | 112 | −4.650 | 26.971 | −17.396 | 1.00 | 27.37 | C |
| ATOM | 153 | CB | GLN A | 112 | −3.928 | 27.181 | −18.732 | 1.00 | 28.16 | C |
| ATOM | 154 | CG | GLN A | 112 | −3.107 | 28.482 | −18.772 | 1.00 | 32.31 | C |
| ATOM | 155 | CD | GLN A | 112 | −1.971 | 28.466 | −19.792 | 1.00 | 37.32 | C |
| ATOM | 156 | OE1 | GLN A | 112 | −1.510 | 27.403 | −20.220 | 1.00 | 40.99 | O |
| ATOM | 157 | NE2 | GLN A | 112 | −1.509 | 29.657 | −20.180 | 1.00 | 37.62 | N |
| ATOM | 158 | C | GLN A | 112 | −5.665 | 25.822 | −17.474 | 1.00 | 25.03 | C |
| ATOM | 159 | O | GLN A | 112 | −6.816 | 26.037 | −17.846 | 1.00 | 24.68 | O |
| ATOM | 160 | N | THR A | 113 | −5.228 | 24.614 | −17.112 | 1.00 | 22.44 | N |
| ATOM | 161 | CA | THR A | 113 | −6.098 | 23.436 | −17.044 | 1.00 | 20.30 | C |
| ATOM | 162 | CB | THR A | 113 | −5.290 | 22.145 | −16.734 | 1.00 | 19.42 | C |
| ATOM | 163 | OG1 | THR A | 113 | −4.301 | 21.941 | −17.750 | 1.00 | 18.13 | O |
| ATOM | 164 | CG2 | THR A | 113 | −6.193 | 20.926 | −16.682 | 1.00 | 13.78 | C |
| ATOM | 165 | C | THR A | 113 | −7.180 | 23.637 | −15.981 | 1.00 | 20.64 | C |
| ATOM | 166 | O | THR A | 113 | −8.363 | 23.439 | −16.253 | 1.00 | 21.04 | O |
| ATOM | 167 | N | VAL A | 114 | −6.764 | 24.039 | −14.780 | 1.00 | 20.86 | N |
| ATOM | 168 | CA | VAL A | 114 | −7.689 | 24.310 | −13.677 | 1.00 | 21.17 | C |
| ATOM | 169 | CB | VAL A | 114 | −6.932 | 24.658 | −12.369 | 1.00 | 21.23 | C |
| ATOM | 170 | CG1 | VAL A | 114 | −7.876 | 25.236 | −11.313 | 1.00 | 22.61 | C |
| ATOM | 171 | CG2 | VAL A | 114 | −6.225 | 23.421 | −11.828 | 1.00 | 20.14 | C |
| ATOM | 172 | C | VAL A | 114 | −8.678 | 25.410 | −14.055 | 1.00 | 21.67 | C |
| ATOM | 173 | O | VAL A | 114 | −9.891 | 25.261 | −13.846 | 1.00 | 22.17 | O |
| ATOM | 174 | N | GLN A | 115 | −8.162 | 26.501 | −14.623 | 1.00 | 21.40 | N |
| ATOM | 175 | CA | GLN A | 115 | −9.004 | 27.626 | −15.029 | 1.00 | 21.67 | C |
| ATOM | 176 | CB | GLN A | 115 | −8.166 | 28.837 | −15.455 | 1.00 | 22.12 | C |
| ATOM | 177 | CG | GLN A | 115 | −7.618 | 29.662 | −14.285 | 1.00 | 26.13 | C |
| ATOM | 178 | CD | GLN A | 115 | −8.666 | 29.961 | −13.210 | 1.00 | 32.12 | C |
| ATOM | 179 | OE1 | GLN A | 115 | −8.492 | 29.597 | −12.042 | 1.00 | 33.26 | O |
| ATOM | 180 | NE2 | GLN A | 115 | −9.763 | 30.612 | −13.605 | 1.00 | 32.37 | N |
| ATOM | 181 | C | GLN A | 115 | −10.000 | 27.252 | −16.117 | 1.00 | 20.75 | C |
| ATOM | 182 | O | GLN A | 115 | −11.169 | 27.625 | −16.036 | 1.00 | 20.85 | O |
| ATOM | 183 | N | PHE A | 116 | −9.539 | 26.512 | −17.124 | 1.00 | 19.49 | N |
| ATOM | 184 | CA | PHE A | 116 | −10.423 | 26.035 | −18.179 | 1.00 | 18.59 | C |
| ATOM | 185 | CB | PHE A | 116 | −9.656 | 25.245 | −19.246 | 1.00 | 17.71 | C |
| ATOM | 186 | CG | PHE A | 116 | −10.550 | 24.563 | −20.244 | 1.00 | 17.07 | C |
| ATOM | 187 | CD1 | PHE A | 116 | −11.194 | 25.296 | −21.235 | 1.00 | 16.86 | C |
| ATOM | 188 | CE1 | PHE A | 116 | −12.041 | 24.668 | −22.152 | 1.00 | 14.58 | C |
| ATOM | 189 | CZ | PHE A | 116 | −12.251 | 23.296 | −22.074 | 1.00 | 15.48 | C |
| ATOM | 190 | CE2 | PHE A | 116 | −11.617 | 22.555 | −21.083 | 1.00 | 16.13 | C |
| ATOM | 191 | CD2 | PHE A | 116 | −10.773 | 23.190 | −20.172 | 1.00 | 17.79 | C |
| ATOM | 192 | C | PHE A | 116 | −11.574 | 25.198 | −17.613 | 1.00 | 18.45 | C |
| ATOM | 193 | O | PHE A | 116 | −12.745 | 25.460 | −17.911 | 1.00 | 18.85 | O |
| ATOM | 194 | N | LEU A | 117 | −11.233 | 24.205 | −16.795 | 1.00 | 17.81 | N |
| ATOM | 195 | CA | LEU A | 117 | −12.225 | 23.294 | −16.228 | 1.00 | 18.01 | C |
| | | | | | gad67.pdb | | | | | |
| ATOM | 196 | CB | LEU A | 117 | −11.554 | 22.117 | −15.511 | 1.00 | 16.49 | C |
| ATOM | 197 | CG | LEU A | 117 | −10.882 | 21.056 | −16.393 | 1.00 | 14.95 | C |
| ATOM | 198 | CD1 | LEU A | 117 | −10.110 | 20.054 | −15.539 | 1.00 | 14.38 | C |
| ATOM | 199 | CD2 | LEU A | 117 | −11.885 | 20.326 | −17.287 | 1.00 | 13.72 | C |
| ATOM | 200 | C | LEU A | 117 | −13.216 | 24.010 | −15.312 | 1.00 | 18.67 | C |
| ATOM | 201 | O | LEU A | 117 | −14.394 | 23.656 | −15.275 | 1.00 | 19.53 | O |
| ATOM | 202 | N | LEU A | 118 | −12.738 | 25.027 | −14.596 | 1.00 | 19.61 | N |
| ATOM | 203 | CA | LEU A | 118 | −13.608 | 25.884 | −13.786 | 1.00 | 19.70 | C |
| ATOM | 204 | CB | LEU A | 118 | −12.786 | 26.773 | −12.852 | 1.00 | 19.89 | C |
| ATOM | 205 | CG | LEU A | 118 | −12.202 | 26.113 | −11.596 | 1.00 | 21.11 | C |
| ATOM | 206 | CD1 | LEU A | 118 | −11.270 | 27.082 | −10.888 | 1.00 | 21.74 | C |
| ATOM | 207 | CD2 | LEU A | 118 | −13.294 | 25.618 | −10.640 | 1.00 | 20.59 | C |
| ATOM | 208 | C | LEU A | 118 | −14.566 | 26.731 | −14.628 | 1.00 | 19.42 | C |
| ATOM | 209 | O | LEU A | 118 | −15.684 | 27.016 | −14.195 | 1.00 | 18.72 | O |
| ATOM | 210 | N | GLU A | 119 | −14.128 | 27.122 | −15.824 | 1.00 | 19.43 | N |
| ATOM | 211 | CA | GLU A | 119 | −14.992 | 27.828 | −16.772 | 1.00 | 19.86 | C |
| ATOM | 212 | CB | GLU A | 119 | −14.178 | 28.462 | −17.905 | 1.00 | 20.91 | C |
| ATOM | 213 | CG | GLU A | 119 | −13.288 | 29.639 | −17.488 | 1.00 | 26.70 | C |
| ATOM | 214 | CD | GLU A | 119 | −14.066 | 30.888 | −17.090 | 1.00 | 35.80 | C |
| ATOM | 215 | OE1 | GLU A | 119 | −13.489 | 31.729 | −16.365 | 1.00 | 40.83 | O |
| ATOM | 216 | OE2 | GLU A | 119 | −15.245 | 31.033 | −17.491 | 1.00 | 37.85 | O |
| ATOM | 217 | C | GLU A | 119 | −16.062 | 26.903 | −17.357 | 1.00 | 18.87 | C |

TABLE A-continued

| | | | | | | | | | | |
|---|---|---|---|---|---|---|---|---|---|---|
| ATOM | 218 | O | GLU A | 119 | −17.195 | 27.332 | −17.600 | 1.00 | 18.86 | O |
| ATOM | 219 | N | VAL A | 120 | −15.694 | 25.645 | −17.593 | 1.00 | 17.94 | N |
| ATOM | 220 | CA | VAL A | 120 | −16.651 | 24.627 | −18.030 | 1.00 | 17.74 | C |
| ATOM | 221 | CB | VAL A | 120 | −15.963 | 23.282 | −18.381 | 1.00 | 17.81 | C |
| ATOM | 222 | CG1 | VAL A | 120 | −17.002 | 22.200 | −18.696 | 1.00 | 15.89 | C |
| ATOM | 223 | CG2 | VAL A | 120 | −15.004 | 23.452 | −19.547 | 1.00 | 15.94 | C |
| ATOM | 224 | C | VAL A | 120 | −17.687 | 24.409 | −16.927 | 1.00 | 18.57 | C |
| ATOM | 225 | O | VAL A | 120 | −18.891 | 24.479 | −17.181 | 1.00 | 18.81 | O |
| ATOM | 226 | N | VAL A | 121 | −17.212 | 24.175 | −15.705 | 1.00 | 18.29 | N |
| ATOM | 227 | CA | VAL A | 121 | −18.087 | 23.934 | −14.553 | 1.00 | 19.73 | C |
| ATOM | 228 | CB | VAL A | 121 | −17.265 | 23.687 | −13.256 | 1.00 | 19.28 | C |
| ATOM | 229 | CG1 | VAL A | 121 | −18.143 | 23.769 | −12.014 | 1.00 | 19.41 | C |
| ATOM | 230 | CG2 | VAL A | 121 | −16.565 | 22.339 | −13.320 | 1.00 | 17.67 | C |
| ATOM | 231 | C | VAL A | 121 | −19.108 | 25.064 | −14.364 | 1.00 | 21.54 | C |
| ATOM | 232 | O | VAL A | 121 | −20.282 | 24.808 | −14.072 | 1.00 | 22.52 | O |
| ATOM | 233 | N | ASP A | 122 | −18.658 | 26.302 | −14.565 | 1.00 | 22.66 | N |
| ATOM | 234 | CA | ASP A | 122 | −19.508 | 27.481 | −14.435 | 1.00 | 23.72 | C |
| ATOM | 235 | CB | ASP A | 122 | −18.686 | 28.753 | −14.619 | 1.00 | 25.42 | C |
| ATOM | 236 | CG | ASP A | 122 | −19.057 | 29.838 | −13.622 | 1.00 | 32.49 | C |
| ATOM | 237 | OD1 | ASP A | 122 | −20.309 | 29.771 | −13.056 | 1.00 | 38.33 | O |
| ATOM | 238 | OD2 | ASP A | 122 | −18.072 | 30.802 | −13.393 | 1.00 | 37.64 | O |
| ATOM | 239 | C | ASP A | 122 | −20.649 | 27.470 | −15.442 | 1.00 | 23.14 | C |
| ATOM | 240 | O | ASP A | 122 | −21.767 | 27.874 | −15.120 | 1.00 | 23.21 | O |
| ATOM | 241 | N | ILE A | 123 | −20.357 | 27.018 | −16.661 | 1.00 | 22.26 | N |
| ATOM | 242 | CA | ILE A | 123 | −21.378 | 26.845 | −17.696 | 1.00 | 21.19 | C |
| ATOM | 243 | CB | ILE A | 123 | −20.752 | 26.433 | −19.055 | 1.00 | 20.72 | C |
| ATOM | 244 | CG1 | ILE A | 123 | −19.860 | 27.557 | −19.597 | 1.00 | 20.74 | C |
| ATOM | 245 | CD1 | ILE A | 123 | −18.910 | 27.126 | −20.706 | 1.00 | 20.87 | C |
| ATOM | 246 | CG2 | ILE A | 123 | −21.837 | 26.074 | −20.068 | 1.00 | 19.58 | C |
| ATOM | 247 | C | ILE A | 123 | −22.414 | 25.804 | −17.252 | 1.00 | 20.62 | C |
| ATOM | 248 | O | ILE A | 123 | −23.624 | 26.002 | −17.422 | 1.00 | 20.15 | O |
| ATOM | 249 | N | LEU A | 124 | −21.925 | 24.712 | −16.667 | 1.00 | 19.66 | N |
| ATOM | 250 | CA | LEU A | 124 | −22.768 | 23.602 | −16.232 | 1.00 | 20.34 | C |
| ATOM | 251 | CB | LEU A | 124 | −21.921 | 22.352 | −15.946 | 1.00 | 19.49 | C |
| ATOM | 252 | CG | LEU A | 124 | −20.928 | 21.922 | −17.036 | 1.00 | 17.58 | C |
| ATOM | 253 | CD1 | LEU A | 124 | −20.084 | 20.739 | −16.580 | 1.00 | 13.52 | C |
| ATOM | 254 | CD2 | LEU A | 124 | −21.642 | 21.628 | −18.344 | 1.00 | 12.08 | C |
| ATOM | 255 | C | LEU A | 124 | −23.613 | 23.967 | −15.015 | 1.00 | 20.72 | C |
| ATOM | 256 | O | LEU A | 124 | −24.774 | 23.575 | −14.924 | 1.00 | 20.55 | O |
| ATOM | 257 | N | LEU A | 125 | −23.020 | 24.724 | −14.095 | 1.00 | 21.86 | N |
| ATOM | 258 | CA | LEU A | 125 | −23.725 | 25.227 | −12.921 | 1.00 | 23.24 | C |
| ATOM | 259 | CB | LEU A | 125 | −22.749 | 25.923 | −11.969 | 1.00 | 23.35 | C |
| ATOM | 260 | CG | LEU A | 125 | −22.239 | 25.172 | −10.728 | 1.00 | 24.90 | C |
| ATOM | 261 | CD1 | LEU A | 125 | −22.217 | 23.652 | −10.883 | 1.00 | 22.86 | C |
| ATOM | 262 | CD2 | LEU A | 125 | −20.870 | 25.686 | −10.335 | 1.00 | 24.11 | C |
| ATOM | 263 | C | LEU A | 125 | −24.886 | 26.151 | −13.285 | 1.00 | 24.12 | C |
| | | | gad67.pdb | | | | | | | |
| ATOM | 264 | O | LEU A | 125 | −25.971 | 26.036 | −12.706 | 1.00 | 25.04 | O |
| ATOM | 265 | N | ASN A | 126 | −24.663 | 27.052 | −14.245 | 1.00 | 23.72 | N |
| ATOM | 266 | CA | ASN A | 126 | −25.729 | 27.920 | −14.760 | 1.00 | 24.47 | C |
| ATOM | 267 | CB | ASN A | 126 | −25.179 | 28.914 | −15.794 | 1.00 | 25.14 | C |
| ATOM | 268 | CG | ASN A | 126 | −26.264 | 29.825 | −16.372 | 1.00 | 30.96 | C |
| ATOM | 269 | OD1 | ASN A | 126 | −26.574 | 29.760 | −17.564 | 1.00 | 34.49 | O |
| ATOM | 270 | ND2 | ASN A | 126 | −26.859 | 30.664 | −15.520 | 1.00 | 33.35 | N |
| ATOM | 271 | C | ASN A | 126 | −26.874 | 27.117 | −15.370 | 1.00 | 23.58 | C |
| ATOM | 272 | O | ASN A | 126 | −28.044 | 27.466 | −15.204 | 1.00 | 24.78 | O |
| ATOM | 273 | N | TYR A | 127 | −26.523 | 26.045 | −16.076 | 1.00 | 22.21 | N |
| ATOM | 274 | CA | TYR A | 127 | −27.497 | 25.139 | −16.670 | 1.00 | 21.25 | C |
| ATOM | 275 | CB | TYR A | 127 | −26.801 | 24.157 | −17.617 | 1.00 | 21.20 | C |
| ATOM | 276 | CG | TYR A | 127 | −27.735 | 23.219 | −18.356 | 1.00 | 21.65 | C |
| ATOM | 277 | CD1 | TYR A | 127 | −28.324 | 23.595 | −19.565 | 1.00 | 23.32 | C |
| ATOM | 278 | CE1 | TYR A | 127 | −29.179 | 22.730 | −20.249 | 1.00 | 24.01 | C |
| ATOM | 279 | CZ | TYR A | 127 | −29.445 | 21.471 | −19.721 | 1.00 | 23.18 | C |
| ATOM | 280 | OH | TYR A | 127 | −30.284 | 20.610 | −20.386 | 1.00 | 23.58 | O |
| ATOM | 281 | CE2 | TYR A | 127 | −28.869 | 21.073 | −18.526 | 1.00 | 22.37 | C |
| ATOM | 282 | CD2 | TYR A | 127 | −28.019 | 21.948 | −17.850 | 1.00 | 19.22 | C |
| ATOM | 283 | C | TYR A | 127 | −28.289 | 24.396 | −15.593 | 1.00 | 20.94 | C |
| ATOM | 284 | O | TYR A | 127 | −29.503 | 24.226 | −15.725 | 1.00 | 19.77 | O |
| ATOM | 285 | N | VAL A | 128 | −27.596 | 23.958 | −14.540 | 1.00 | 21.05 | N |
| ATOM | 286 | CA | VAL A | 128 | −28.234 | 23.298 | −13.398 | 1.00 | 21.73 | C |
| ATOM | 287 | CB | VAL A | 128 | −27.196 | 22.746 | −12.379 | 1.00 | 22.22 | C |
| ATOM | 288 | CG1 | VAL A | 128 | −27.883 | 22.283 | −11.089 | 1.00 | 22.33 | C |
| ATOM | 289 | CG2 | VAL A | 128 | −26.395 | 21.602 | −12.987 | 1.00 | 21.34 | C |
| ATOM | 290 | C | VAL A | 128 | −29.230 | 24.239 | −12.709 | 1.00 | 22.71 | C |
| ATOM | 291 | O | VAL A | 128 | −30.358 | 23.840 | −12.423 | 1.00 | 22.52 | O |
| ATOM | 292 | N | ARG A | 129 | −28.813 | 25.484 | −12.467 | 1.00 | 23.76 | N |
| ATOM | 293 | CA | ARG A | 129 | −29.697 | 26.522 | −11.907 | 1.00 | 25.88 | C |
| ATOM | 294 | CB | ARG A | 129 | −28.993 | 27.879 | −11.858 | 1.00 | 25.02 | C |
| ATOM | 295 | CG | ARG A | 129 | −27.875 | 28.044 | −10.842 | 1.00 | 28.33 | C |
| ATOM | 296 | CD | ARG A | 129 | −27.254 | 29.435 | −11.025 | 1.00 | 30.30 | C |

TABLE A-continued

| | | | | | | | | | | |
|---|---|---|---|---|---|---|---|---|---|---|
| ATOM | 297 | NE | ARG A | 129 | −26.033 | 29.649 | −10.249 | 1.00 | 38.08 | N |
| ATOM | 298 | CZ | ARG A | 129 | −25.994 | 30.209 | −9.042 | 1.00 | 42.25 | C |
| ATOM | 299 | NH1 | ARG A | 129 | −24.831 | 30.365 | −8.423 | 1.00 | 44.17 | N |
| ATOM | 300 | NH2 | ARG A | 129 | −27.111 | 30.611 | −8.446 | 1.00 | 40.82 | N |
| ATOM | 301 | C | ARG A | 129 | −30.984 | 26.686 | −12.721 | 1.00 | 25.75 | C |
| ATOM | 302 | O | ARG A | 129 | −32.089 | 26.680 | −12.164 | 1.00 | 26.01 | O |
| ATOM | 303 | N | LYS A | 130 | −30.828 | 26.835 | −14.037 | 1.00 | 25.90 | N |
| ATOM | 304 | CA | LYS A | 130 | −31.951 | 27.091 | −14.944 | 1.00 | 26.66 | C |
| ATOM | 305 | CB | LYS A | 130 | −31.443 | 27.602 | −16.296 | 1.00 | 26.29 | C |
| ATOM | 306 | CG | LYS A | 130 | −30.975 | 29.052 | −16.276 | 1.00 | 28.40 | C |
| ATOM | 310 | C | LYS A | 130 | −32.876 | 25.888 | −15.150 | 1.00 | 26.81 | C |
| ATOM | 311 | O | LYS A | 130 | −34.038 | 26.052 | −15.532 | 1.00 | 27.37 | O |
| ATOM | 312 | N | THR A | 131 | −32.355 | 24.689 | −14.900 | 1.00 | 26.89 | N |
| ATOM | 313 | CA | THR A | 131 | −33.116 | 23.450 | −15.040 | 1.00 | 27.76 | C |
| ATOM | 314 | CB | THR A | 131 | −32.215 | 22.217 | −14.787 | 1.00 | 27.79 | C |
| ATOM | 315 | OG1 | THR A | 131 | −31.394 | 21.975 | −15.936 | 1.00 | 29.39 | O |
| ATOM | 316 | CG2 | THR A | 131 | −33.042 | 20.977 | −14.496 | 1.00 | 27.54 | C |
| ATOM | 317 | C | THR A | 131 | −34.321 | 23.426 | −14.098 | 1.00 | 27.99 | C |
| ATOM | 318 | O | THR A | 131 | −35.402 | 22.965 | −14.471 | 1.00 | 27.87 | O |
| ATOM | 319 | N | PHE A | 132 | −34.129 | 23.945 | −12.889 | 1.00 | 28.64 | N |
| ATOM | 320 | CA | PHE A | 132 | −35.159 | 23.906 | −11.854 | 1.00 | 30.75 | C |
| ATOM | 321 | CB | PHE A | 132 | −34.514 | 23.625 | −10.495 | 1.00 | 29.80 | C |
| ATOM | 322 | CG | PHE A | 132 | −33.777 | 22.316 | −10.442 | 1.00 | 28.48 | C |
| ATOM | 323 | CD1 | PHE A | 132 | −34.442 | 21.143 | −10.104 | 1.00 | 25.56 | C |
| ATOM | 324 | CE1 | PHE A | 132 | −33.762 | 19.928 | −10.059 | 1.00 | 25.79 | C |
| ATOM | 325 | CZ | PHE A | 132 | −32.405 | 19.880 | −10.362 | 1.00 | 26.12 | C |
| ATOM | 326 | CE2 | PHE A | 132 | −31.734 | 21.043 | −10.707 | 1.00 | 23.59 | C |
| ATOM | 327 | CD2 | PHE A | 132 | −32.421 | 22.252 | −10.748 | 1.00 | 25.48 | C |
| ATOM | 328 | C | PHE A | 132 | −36.021 | 25.171 | −11.817 | 1.00 | 32.57 | C |
| ATOM | 329 | O | PHE A | 132 | −36.872 | 25.330 | −10.938 | 1.00 | 33.60 | O |
| ATOM | 330 | N | ASP A | 133 | −35.796 | 26.054 | −12.789 | 1.00 | 33.99 | N |
| ATOM | 331 | CA | ASP A | 133 | −36.546 | 27.296 | −12.939 | 1.00 | 35.30 | C |
| ATOM | 332 | CB | ASP A | 133 | −35.588 | 28.426 | −13.331 | 1.00 | 35.87 | C |
| ATOM | 333 | CG | ASP A | 133 | −36.255 | 29.796 | −13.366 | 1.00 | 40.15 | C |
| ATOM | 334 | OD1 | ASP A | 133 | −37.479 | 29.901 | −13.126 | 1.00 | 43.79 | O |
| | | | | | gad67.pdb | | | | | |
| ATOM | 335 | OD2 | ASP A | 133 | −35.540 | 30.785 | −13.645 | 1.00 | 43.82 | O |
| ATOM | 336 | C | ASP A | 133 | −37.630 | 27.101 | −14.002 | 1.00 | 35.44 | C |
| ATOM | 337 | O | ASP A | 133 | −37.327 | 26.790 | −15.156 | 1.00 | 35.51 | O |
| ATOM | 338 | N | ARG A | 134 | −38.888 | 27.288 | −13.607 | 1.00 | 35.31 | N |
| ATOM | 339 | CA | ARG A | 134 | −40.033 | 27.027 | −14.488 | 1.00 | 35.58 | C |
| ATOM | 340 | CB | ARG A | 134 | −41.310 | 26.822 | −13.670 | 1.00 | 35.74 | C |
| ATOM | 341 | CG | ARG A | 134 | −41.414 | 25.449 | −13.031 | 1.00 | 35.17 | C |
| ATOM | 342 | CD | ARG A | 134 | −42.460 | 25.430 | −11.935 | 1.00 | 34.42 | C |
| ATOM | 343 | NE | ARG A | 134 | −42.475 | 24.158 | −11.217 | 1.00 | 34.10 | N |
| ATOM | 344 | CZ | ARG A | 134 | −41.665 | 23.852 | −10.207 | 1.00 | 32.72 | C |
| ATOM | 345 | NH1 | ARG A | 134 | −40.756 | 24.724 | −9.784 | 1.00 | 30.57 | N |
| ATOM | 346 | NH2 | ARG A | 134 | −41.761 | 22.665 | −9.625 | 1.00 | 29.70 | N |
| ATOM | 347 | C | ARG A | 134 | −40.262 | 28.087 | −15.570 | 1.00 | 35.95 | C |
| ATOM | 348 | O | ARG A | 134 | −41.067 | 27.880 | −16.482 | 1.00 | 36.09 | O |
| ATOM | 349 | N | SER A | 135 | −39.564 | 29.217 | −15.463 | 1.00 | 35.67 | N |
| ATOM | 350 | CA | SER A | 135 | −39.597 | 30.244 | −16.506 | 1.00 | 35.48 | C |
| ATOM | 351 | CB | SER A | 135 | −39.117 | 31.595 | −15.965 | 1.00 | 35.35 | C |
| ATOM | 352 | OG | SER A | 135 | −37.803 | 31.514 | −15.441 | 1.00 | 36.79 | O |
| ATOM | 353 | C | SER A | 135 | −38.774 | 29.819 | −17.729 | 1.00 | 35.22 | C |
| ATOM | 354 | O | SER A | 135 | −39.002 | 30.305 | −18.839 | 1.00 | 35.74 | O |
| ATOM | 355 | N | THR A | 136 | −37.822 | 28.913 | −17.511 | 1.00 | 34.10 | N |
| ATOM | 356 | CA | THR A | 136 | −37.014 | 28.342 | −18.586 | 1.00 | 33.25 | C |
| ATOM | 357 | CB | THR A | 136 | −35.785 | 27.589 | −18.024 | 1.00 | 33.81 | C |
| ATOM | 358 | OG1 | THR A | 136 | −35.127 | 28.398 | −17.041 | 1.00 | 36.19 | O |
| ATOM | 359 | CG2 | THR A | 136 | −34.796 | 27.243 | −19.132 | 1.00 | 34.39 | C |
| ATOM | 360 | C | THR A | 136 | −37.857 | 27.371 | −19.416 | 1.00 | 31.78 | C |
| ATOM | 361 | O | THR A | 136 | −38.652 | 26.602 | −18.869 | 1.00 | 31.90 | O |
| ATOM | 362 | N | LYS A | 137 | −37.689 | 27.424 | −20.735 | 1.00 | 30.17 | N |
| ATOM | 363 | CA | LYS A | 137 | −38.338 | 26.473 | −21.637 | 1.00 | 29.09 | C |
| ATOM | 364 | CB | LYS A | 137 | −38.236 | 26.950 | −23.088 | 1.00 | 28.45 | C |
| ATOM | 365 | CG | LYS A | 137 | −39.246 | 28.024 | −23.463 | 1.00 | 29.68 | C |
| ATOM | 366 | CD | LYS A | 137 | −38.937 | 28.627 | −24.833 | 1.00 | 30.67 | C |
| ATOM | 369 | C | LYS A | 137 | −37.729 | 25.078 | −21.496 | 1.00 | 27.04 | C |
| ATOM | 370 | O | LYS A | 137 | −36.535 | 24.941 | −21.228 | 1.00 | 26.52 | O |
| ATOM | 371 | N | VAL A | 138 | −38.564 | 24.054 | −21.668 | 1.00 | 25.47 | N |
| ATOM | 372 | CA | VAL A | 138 | −38.117 | 22.661 | −21.671 | 1.00 | 23.70 | C |
| ATOM | 373 | CB | VAL A | 138 | −39.315 | 21.679 | −21.724 | 1.00 | 22.70 | C |
| ATOM | 374 | CG1 | VAL A | 138 | −38.844 | 20.234 | −21.779 | 1.00 | 20.58 | C |
| ATOM | 375 | CG2 | VAL A | 138 | −40.226 | 21.885 | −20.521 | 1.00 | 22.29 | C |
| ATOM | 376 | C | VAL A | 138 | −37.175 | 22.434 | −22.857 | 1.00 | 24.08 | C |
| ATOM | 377 | O | VAL A | 138 | −36.146 | 21.766 | −22.731 | 1.00 | 23.79 | O |
| ATOM | 378 | N | LEU A | 139 | −37.533 | 23.012 | −24.000 | 1.00 | 24.77 | N |
| ATOM | 379 | CA | LEU A | 139 | −36.710 | 22.955 | −25.201 | 1.00 | 25.93 | C |
| ATOM | 380 | CB | LEU A | 139 | −36.877 | 21.604 | −25.914 | 1.00 | 25.64 | C |

TABLE A-continued

| | | | | | | | | | | |
|---|---|---|---|---|---|---|---|---|---|---|
| ATOM | 381 | CG | LEU A | 139 | −38.066 | 21.395 | −26.861 | 1.00 | 26.22 | C |
| ATOM | 382 | CD1 | LEU A | 139 | −37.815 | 20.188 | −27.744 | 1.00 | 23.61 | C |
| ATOM | 383 | CD2 | LEU A | 139 | −39.403 | 21.273 | −26.117 | 1.00 | 26.85 | C |
| ATOM | 384 | C | LEU A | 139 | −37.052 | 24.098 | −26.155 | 1.00 | 26.68 | C |
| ATOM | 385 | O | LEU A | 139 | −38.148 | 24.664 | −26.099 | 1.00 | 26.57 | O |
| ATOM | 386 | N | ASP A | 140 | −36.095 | 24.426 | −27.017 | 1.00 | 27.77 | N |
| ATOM | 387 | CA | ASP A | 140 | −36.284 | 25.365 | −28.112 | 1.00 | 29.28 | C |
| ATOM | 388 | CB | ASP A | 140 | −35.169 | 26.421 | −28.096 | 1.00 | 30.89 | C |
| ATOM | 389 | CG | ASP A | 140 | −35.391 | 27.544 | −29.105 | 1.00 | 36.04 | C |
| ATOM | 390 | OD1 | ASP A | 140 | −36.553 | 27.790 | −29.507 | 1.00 | 40.84 | O |
| ATOM | 391 | OD2 | ASP A | 140 | −34.391 | 28.193 | −29.487 | 1.00 | 41.18 | O |
| ATOM | 392 | C | ASP A | 140 | −36.212 | 24.516 | −29.371 | 1.00 | 28.80 | C |
| ATOM | 393 | O | ASP A | 140 | −35.121 | 24.270 | −29.897 | 1.00 | 28.64 | O |
| ATOM | 394 | N | PHE A | 141 | −37.371 | 24.044 | −29.835 | 1.00 | 27.85 | N |
| ATOM | 395 | CA | PHE A | 141 | −37.409 | 23.027 | −30.890 | 1.00 | 26.43 | C |
| ATOM | 396 | CB | PHE A | 141 | −38.792 | 22.375 | −31.032 | 1.00 | 25.57 | C |
| ATOM | 397 | CG | PHE A | 141 | −38.846 | 21.327 | −32.117 | 1.00 | 25.15 | C |
| ATOM | 398 | CD1 | PHE A | 141 | −38.168 | 20.116 | −31.969 | 1.00 | 23.05 | C |
| ATOM | 399 | CE1 | PHE A | 141 | −38.189 | 19.152 | −32.976 | 1.00 | 20.92 | C |
| ATOM | 400 | CZ | PHE A | 141 | −38.889 | 19.397 | −34.147 | 1.00 | 23.37 | C |
| ATOM | 401 | CE2 | PHE A | 141 | −39.563 | 20.606 | −34.313 | 1.00 | 25.93 | C |
| ATOM | 402 | CD2 | PHE A | 141 | −39.532 | 21.566 | −33.303 | 1.00 | 25.75 | C |
| ATOM | 403 | C | PHE A | 141 | −36.933 | 23.519 | −32.248 | 1.00 | 25.91 | C |
| ATOM | 404 | O | PHE A | 141 | −37.284 | 24.612 | −32.687 | 1.00 | 25.67 | O |
| | | | | gad67.pdb | | | | | | |
| ATOM | 405 | N | HIS A | 142 | −36.131 | 22.682 | −32.902 | 1.00 | 25.87 | N |
| ATOM | 406 | CA | HIS A | 142 | −35.652 | 22.936 | −34.258 | 1.00 | 25.07 | C |
| ATOM | 407 | CB | HIS A | 142 | −34.238 | 23.522 | −34.244 | 1.00 | 24.43 | C |
| ATOM | 408 | CG | HIS A | 142 | −34.126 | 24.828 | −33.523 | 1.00 | 25.05 | C |
| ATOM | 409 | ND1 | HIS A | 142 | −34.621 | 26.008 | −34.036 | 1.00 | 28.12 | N |
| ATOM | 410 | CE1 | HIS A | 142 | −34.376 | 26.991 | −33.187 | 1.00 | 29.00 | C |
| ATOM | 411 | NE2 | HIS A | 142 | −33.736 | 26.491 | −32.145 | 1.00 | 28.21 | N |
| ATOM | 412 | CD2 | HIS A | 142 | −33.563 | 25.141 | −32.333 | 1.00 | 25.88 | C |
| ATOM | 413 | C | HIS A | 142 | −35.644 | 21.629 | −35.034 | 1.00 | 24.17 | C |
| ATOM | 414 | O | HIS A | 142 | −35.244 | 20.593 | −34.505 | 1.00 | 23.29 | O |
| ATOM | 415 | N | HIS A | 143 | −36.101 | 21.683 | −36.282 | 1.00 | 23.98 | N |
| ATOM | 416 | CA | HIS A | 143 | −35.974 | 20.557 | −37.202 | 1.00 | 23.48 | C |
| ATOM | 417 | CB | HIS A | 143 | −36.653 | 20.876 | −38.536 | 1.00 | 23.18 | C |
| ATOM | 418 | CG | HIS A | 143 | −38.145 | 20.781 | −38.487 | 1.00 | 23.59 | C |
| ATOM | 419 | ND1 | HIS A | 143 | −38.826 | 19.620 | −38.784 | 1.00 | 23.85 | N |
| ATOM | 420 | CE1 | HIS A | 143 | −40.124 | 19.829 | −38.653 | 1.00 | 23.07 | C |
| ATOM | 421 | NE2 | HIS A | 143 | −40.309 | 21.081 | −38.277 | 1.00 | 21.57 | N |
| ATOM | 422 | CD2 | HIS A | 143 | −39.088 | 21.698 | −38.165 | 1.00 | 22.39 | C |
| ATOM | 423 | C | HIS A | 143 | −34.496 | 20.263 | −37.418 | 1.00 | 23.18 | C |
| ATOM | 424 | O | HIS A | 143 | −33.677 | 21.172 | −37.324 | 1.00 | 22.42 | O |
| ATOM | 425 | N | PRO A | 144 | −34.145 | 18.991 | −37.688 | 1.00 | 24.12 | N |
| ATOM | 426 | CA | PRO A | 144 | −32.735 | 18.653 | −37.900 | 1.00 | 25.46 | C |
| ATOM | 427 | CB | PRO A | 144 | −32.797 | 17.223 | −38.440 | 1.00 | 25.05 | C |
| ATOM | 428 | CG | PRO A | 144 | −34.043 | 16.663 | −37.852 | 1.00 | 24.62 | C |
| ATOM | 429 | CD | PRO A | 144 | −35.017 | 17.805 | −37.799 | 1.00 | 23.67 | C |
| ATOM | 430 | C | PRO A | 144 | −32.027 | 19.581 | −38.896 | 1.00 | 27.42 | C |
| ATOM | 431 | O | PRO A | 144 | −30.911 | 20.029 | −38.620 | 1.00 | 27.07 | O |
| ATOM | 432 | N | HIS A | 145 | −32.681 | 19.890 | −40.017 | 1.00 | 29.52 | N |
| ATOM | 433 | CA | HIS A | 145 | −32.067 | 20.709 | −41.065 | 1.00 | 31.93 | C |
| ATOM | 434 | CB | HIS A | 145 | −32.875 | 20.663 | −42.371 | 1.00 | 32.34 | C |
| ATOM | 435 | CG | HIS A | 145 | −34.254 | 21.245 | −42.267 | 1.00 | 34.13 | C |
| ATOM | 436 | ND1 | HIS A | 145 | −34.500 | 22.599 | −42.347 | 1.00 | 35.13 | N |
| ATOM | 437 | CE1 | HIS A | 145 | −35.799 | 22.816 | −42.237 | 1.00 | 34.52 | C |
| ATOM | 438 | NE2 | HIS A | 145 | −36.406 | 21.650 | −42.105 | 1.00 | 34.60 | N |
| ATOM | 439 | CD2 | HIS A | 145 | −35.463 | 20.651 | −42.125 | 1.00 | 34.93 | C |
| ATOM | 440 | C | HIS A | 145 | −31.790 | 22.147 | −40.627 | 1.00 | 33.49 | C |
| ATOM | 441 | O | HIS A | 145 | −30.840 | 22.765 | −41.105 | 1.00 | 33.13 | O |
| ATOM | 442 | N | GLN A | 146 | −32.615 | 22.661 | −39.715 | 1.00 | 35.34 | N |
| ATOM | 443 | CA | GLN A | 146 | −32.444 | 24.003 | −39.152 | 1.00 | 37.46 | C |
| ATOM | 444 | CB | GLN A | 146 | −33.619 | 24.366 | −38.242 | 1.00 | 37.66 | C |
| ATOM | 445 | CG | GLN A | 146 | −34.978 | 24.412 | −38.922 | 1.00 | 38.50 | C |
| ATOM | 446 | CD | GLN A | 146 | −36.097 | 24.779 | −37.960 | 1.00 | 39.33 | C |
| ATOM | 447 | OE1 | GLN A | 146 | −37.185 | 24.207 | −38.011 | 1.00 | 42.78 | O |
| ATOM | 448 | NE2 | GLN A | 146 | −35.834 | 25.740 | −37.075 | 1.00 | 43.34 | N |
| ATOM | 449 | C | GLN A | 146 | −31.143 | 24.127 | −38.361 | 1.00 | 38.53 | C |
| ATOM | 450 | O | GLN A | 146 | −30.440 | 25.134 | −38.470 | 1.00 | 39.43 | O |
| ATOM | 451 | N | LEU A | 147 | −30.833 | 23.106 | −37.562 | 1.00 | 39.13 | N |
| ATOM | 452 | CA | LEU A | 147 | −29.600 | 23.084 | −36.781 | 1.00 | 40.16 | C |
| ATOM | 453 | CB | LEU A | 147 | −29.688 | 22.070 | −35.635 | 1.00 | 39.68 | C |
| ATOM | 454 | CG | LEU A | 147 | −30.532 | 22.393 | −34.396 | 1.00 | 38.57 | C |
| ATOM | 455 | CD1 | LEU A | 147 | −30.540 | 21.202 | −33.450 | 1.00 | 36.36 | C |
| ATOM | 456 | CD2 | LEU A | 147 | −30.028 | 23.638 | −33.669 | 1.00 | 36.61 | C |
| ATOM | 457 | C | LEU A | 147 | −28.382 | 22.795 | −37.656 | 1.00 | 41.54 | C |
| ATOM | 458 | O | LEU A | 147 | −27.325 | 23.405 | −37.473 | 1.00 | 41.58 | O |
| ATOM | 459 | N | LEU A | 148 | −28.542 | 21.871 | −38.604 | 1.00 | 42.80 | N |

TABLE A-continued

| | | | | | | | | | |
|---|---|---|---|---|---|---|---|---|---|
| ATOM | 460 | CA | LEU A | 148 | −27.481 | 21.515 | −39.550 | 1.00 | 44.29 | C |
| ATOM | 461 | CB | LEU A | 148 | −27.928 | 20.373 | −40.468 | 1.00 | 43.57 | C |
| ATOM | 462 | CG | LEU A | 148 | −27.874 | 18.939 | −39.931 | 1.00 | 43.27 | C |
| ATOM | 463 | CD1 | LEU A | 148 | −28.622 | 17.992 | −40.864 | 1.00 | 42.33 | C |
| ATOM | 464 | CD2 | LEU A | 148 | −26.436 | 18.468 | −39.723 | 1.00 | 41.74 | C |
| ATOM | 465 | C | LEU A | 148 | −27.016 | 22.702 | −40.392 | 1.00 | 46.29 | C |
| ATOM | 466 | O | LEU A | 148 | −25.810 | 22.919 | −40.556 | 1.00 | 46.59 | O |
| ATOM | 467 | N | GLU A | 149 | −27.973 | 23.470 | −40.912 | 1.00 | 48.43 | N |
| ATOM | 468 | CA | GLU A | 149 | −27.678 | 24.630 | −41.757 | 1.00 | 50.84 | C |
| ATOM | 469 | CB | GLU A | 149 | −28.938 | 25.104 | −42.489 | 1.00 | 50.69 | C |
| ATOM | 470 | CG | GLU A | 149 | −29.202 | 24.337 | −43.788 | 1.00 | 52.51 | C |
| ATOM | 471 | CD | GLU A | 149 | −30.669 | 24.309 | −44.192 | 1.00 | 54.45 | C |
| ATOM | 472 | OE1 | GLU A | 149 | −31.425 | 25.234 | −43.816 | 1.00 | 55.53 | O | gad67.pdb

| | | | | | | | | | |
|---|---|---|---|---|---|---|---|---|---|
| ATOM | 473 | OE2 | GLU A | 149 | −31.066 | 23.351 | −44.892 | 1.00 | 54.20 | O |
| ATOM | 474 | C | GLU A | 149 | −27.012 | 25.772 | −40.986 | 1.00 | 52.64 | C |
| ATOM | 475 | O | GLU A | 149 | −26.951 | 26.911 | −41.463 | 1.00 | 53.40 | O |
| ATOM | 476 | N | GLY A | 150 | −26.506 | 25.450 | −39.797 | 1.00 | 54.23 | N |
| ATOM | 477 | CA | GLY A | 150 | −25.692 | 26.370 | −39.016 | 1.00 | 54.99 | C |
| ATOM | 478 | C | GLY A | 150 | −26.482 | 27.230 | −38.056 | 1.00 | 55.49 | C |
| ATOM | 479 | O | GLY A | 150 | −27.481 | 27.852 | −38.433 | 1.00 | 55.69 | O |
| ATOM | 480 | N | MET A | 151 | −26.040 | 27.238 | −36.803 | 1.00 | 55.44 | N |
| ATOM | 481 | CA | MET A | 151 | −26.494 | 28.224 | −35.830 | 1.00 | 55.39 | C |
| ATOM | 482 | CB | MET A | 151 | −26.980 | 27.557 | −34.540 | 1.00 | 55.95 | C |
| ATOM | 483 | CG | MET A | 151 | −28.367 | 26.923 | −34.648 | 1.00 | 58.21 | C |
| ATOM | 484 | SD | MET A | 151 | −29.663 | 28.084 | −35.152 | 1.00 | 64.60 | S |
| ATOM | 485 | CE | MET A | 151 | −31.131 | 27.066 | −35.017 | 1.00 | 59.27 | C |
| ATOM | 486 | C | MET A | 151 | −25.350 | 29.201 | −35.566 | 1.00 | 54.39 | C |
| ATOM | 487 | O | MET A | 151 | −24.183 | 28.875 | −35.814 | 1.00 | 53.88 | O |
| ATOM | 488 | N | GLU A | 152 | −25.694 | 30.394 | −35.082 | 1.00 | 53.35 | N |
| ATOM | 489 | CA | GLU A | 152 | −24.737 | 31.493 | −34.922 | 1.00 | 52.02 | C |
| ATOM | 490 | CB | GLU A | 152 | −25.407 | 32.704 | −34.262 | 1.00 | 52.04 | C |
| ATOM | 491 | CG | GLU A | 152 | −26.375 | 33.452 | −35.166 | 1.00 | 52.46 | C |
| ATOM | 495 | C | GLU A | 152 | −23.485 | 31.082 | −34.148 | 1.00 | 50.77 | C |
| ATOM | 496 | O | GLU A | 152 | −23.573 | 30.605 | −33.016 | 1.00 | 50.06 | O |
| ATOM | 497 | N | GLY A | 153 | −22.331 | 31.249 | −34.792 | 1.00 | 49.96 | N |
| ATOM | 498 | CA | GLY A | 153 | −21.024 | 30.943 | −34.201 | 1.00 | 49.47 | C |
| ATOM | 499 | C | GLY A | 153 | −20.820 | 29.502 | −33.765 | 1.00 | 48.83 | C |
| ATOM | 500 | O | GLY A | 153 | −19.957 | 29.220 | −32.930 | 1.00 | 49.23 | O |
| ATOM | 501 | N | PHE A | 154 | −21.603 | 28.593 | −34.345 | 1.00 | 47.89 | N |
| ATOM | 502 | CA | PHE A | 154 | −21.653 | 27.199 | −33.904 | 1.00 | 46.80 | C |
| ATOM | 503 | CB | PHE A | 154 | −22.915 | 26.963 | −33.060 | 1.00 | 47.32 | C |
| ATOM | 504 | CG | PHE A | 154 | −23.000 | 25.591 | −32.436 | 1.00 | 47.56 | C |
| ATOM | 505 | CD1 | PHE A | 154 | −21.904 | 25.029 | −31.782 | 1.00 | 47.11 | C |
| ATOM | 506 | CE1 | PHE A | 154 | −21.988 | 23.765 | −31.201 | 1.00 | 46.45 | C |
| ATOM | 507 | CZ | PHE A | 154 | −23.185 | 23.057 | −31.255 | 1.00 | 48.22 | C |
| ATOM | 508 | CE2 | PHE A | 154 | −24.294 | 23.612 | −31.894 | 1.00 | 49.53 | C |
| ATOM | 509 | CD2 | PHE A | 154 | −24.197 | 24.874 | −32.476 | 1.00 | 48.99 | C |
| ATOM | 510 | C | PHE A | 154 | −21.582 | 26.225 | −35.082 | 1.00 | 45.30 | C |
| ATOM | 511 | O | PHE A | 154 | −22.596 | 25.921 | −35.728 | 1.00 | 45.21 | O |
| ATOM | 512 | N | ASN A | 155 | −20.370 | 25.741 | −35.345 | 1.00 | 42.77 | N |
| ATOM | 513 | CA | ASN A | 155 | −20.108 | 24.818 | −36.445 | 1.00 | 40.62 | C |
| ATOM | 514 | CB | ASN A | 155 | −18.870 | 25.287 | −37.222 | 1.00 | 40.76 | C |
| ATOM | 515 | CG | ASN A | 155 | −18.471 | 24.335 | −38.337 | 1.00 | 40.64 | C |
| ATOM | 516 | OD1 | ASN A | 155 | −19.318 | 23.751 | −39.021 | 1.00 | 38.96 | O |
| ATOM | 517 | ND2 | ASN A | 155 | −17.165 | 24.184 | −38.531 | 1.00 | 40.84 | N |
| ATOM | 518 | C | ASN A | 155 | −19.938 | 23.374 | −35.959 | 1.00 | 38.81 | C |
| ATOM | 519 | O | ASN A | 155 | −19.050 | 23.082 | −35.158 | 1.00 | 38.26 | O |
| ATOM | 520 | N | LEU A | 156 | −20.795 | 22.482 | −36.452 | 1.00 | 37.02 | N |
| ATOM | 521 | CA | LEU A | 156 | −20.738 | 21.060 | −36.102 | 1.00 | 35.51 | C |
| ATOM | 522 | CB | LEU A | 156 | −22.097 | 20.385 | −36.325 | 1.00 | 35.58 | C |
| ATOM | 523 | CG | LEU A | 156 | −23.257 | 20.798 | −35.409 | 1.00 | 36.51 | C |
| ATOM | 524 | CD1 | LEU A | 156 | −24.568 | 20.235 | −35.921 | 1.00 | 39.21 | C |
| ATOM | 525 | CD2 | LEU A | 156 | −23.022 | 20.367 | −33.969 | 1.00 | 37.34 | C |
| ATOM | 526 | C | LEU A | 156 | −19.652 | 20.303 | −36.864 | 1.00 | 34.43 | C |
| ATOM | 527 | O | LEU A | 156 | −19.201 | 19.243 | −36.424 | 1.00 | 33.98 | O |
| ATOM | 528 | N | GLU A | 157 | −19.233 | 20.853 | −38.000 | 1.00 | 33.78 | N |
| ATOM | 529 | CA | GLU A | 157 | −18.250 | 20.198 | −38.863 | 1.00 | 32.91 | C |
| ATOM | 530 | CB | GLU A | 157 | −18.103 | 20.943 | −40.196 | 1.00 | 33.45 | C |
| ATOM | 531 | CG | GLU A | 157 | −19.385 | 21.024 | −41.024 | 1.00 | 37.75 | C |
| ATOM | 532 | CD | GLU A | 157 | −19.889 | 19.664 | −41.480 | 1.00 | 41.79 | C |
| ATOM | 533 | OE1 | GLU A | 157 | −19.091 | 18.882 | −42.044 | 1.00 | 44.28 | O |
| ATOM | 534 | OE2 | GLU A | 157 | −21.090 | 19.380 | −41.279 | 1.00 | 43.11 | O |
| ATOM | 535 | C | GLU A | 157 | −16.898 | 20.080 | −38.180 | 1.00 | 30.91 | C |
| ATOM | 536 | O | GLU A | 157 | −16.524 | 20.924 | −37.365 | 1.00 | 31.06 | O |
| ATOM | 537 | N | LEU A | 158 | −16.175 | 19.020 | −38.516 | 1.00 | 28.61 | N |
| ATOM | 538 | CA | LEU A | 158 | −14.850 | 18.784 | −37.963 | 1.00 | 27.20 | C |
| ATOM | 539 | CB | LEU A | 158 | −14.702 | 17.315 | −37.551 | 1.00 | 26.63 | C |
| ATOM | 540 | CG | LEU A | 158 | −15.756 | 16.775 | −36.576 | 1.00 | 25.35 | C |
| ATOM | 541 | CD1 | LEU A | 158 | −15.818 | 15.262 | −36.634 | 1.00 | 23.78 | C |

TABLE A-continued

| | | | | | | | | | | |
|---|---|---|---|---|---|---|---|---|---|---|
| ATOM | 542 | CD2 | LEU A | 158 | −15.515 | 17.265 | −35.150 | 1.00 | 21.46 | C |
| ATOM | 543 | C | LEU A | 158 | −13.795 | 19.171 | −38.990 | 1.00 | 26.96 | C |
| | | | | | gad67.pdb | | | | | |
| ATOM | 544 | O | LEU A | 158 | −14.069 | 19.173 | −40.186 | 1.00 | 26.87 | O |
| ATOM | 545 | N | SER A | 159 | −12.593 | 19.505 | −38.526 | 1.00 | 26.82 | N |
| ATOM | 546 | CA | SER A | 159 | −11.524 | 19.945 | −39.427 | 1.00 | 26.22 | C |
| ATOM | 547 | CB | SER A | 159 | −11.565 | 21.467 | −39.616 | 1.00 | 26.31 | C |
| ATOM | 548 | OG | SER A | 159 | −11.412 | 22.146 | −38.382 | 1.00 | 28.16 | O |
| ATOM | 549 | C | SER A | 159 | −10.135 | 19.492 | −38.984 | 1.00 | 25.59 | C |
| ATOM | 550 | O | SER A | 159 | −9.975 | 18.884 | −37.921 | 1.00 | 25.09 | O |
| ATOM | 551 | N | ASP A | 160 | −9.143 | 19.798 | −39.820 | 1.00 | 24.80 | N |
| ATOM | 552 | CA | ASP A | 160 | −7.751 | 19.431 | −39.586 | 1.00 | 24.13 | C |
| ATOM | 553 | CB | ASP A | 160 | −6.900 | 19.764 | −40.819 | 1.00 | 25.28 | C |
| ATOM | 554 | CG | ASP A | 160 | −7.260 | 18.925 | −42.031 | 1.00 | 29.29 | C |
| ATOM | 555 | OD1 | ASP A | 160 | −7.934 | 17.887 | −41.864 | 1.00 | 32.88 | O |
| ATOM | 556 | OD2 | ASP A | 160 | −6.858 | 19.306 | −43.155 | 1.00 | 34.68 | O |
| ATOM | 557 | C | ASP A | 160 | −7.140 | 20.129 | −38.381 | 1.00 | 23.32 | C |
| ATOM | 558 | O | ASP A | 160 | −6.318 | 19.546 | −37.672 | 1.00 | 23.15 | O |
| ATOM | 559 | N | HIS A | 161 | −7.533 | 21.381 | −38.160 | 1.00 | 23.04 | N |
| ATOM | 560 | CA | HIS A | 161 | −6.867 | 22.225 | −37.174 | 1.00 | 23.20 | C |
| ATOM | 561 | CB | HIS A | 161 | −6.344 | 23.504 | −37.840 | 1.00 | 24.13 | C |
| ATOM | 562 | CG | HIS A | 161 | −5.338 | 23.243 | −38.919 | 1.00 | 28.47 | C |
| ATOM | 563 | ND1 | HIS A | 161 | −4.021 | 22.936 | −38.650 | 1.00 | 30.23 | N |
| ATOM | 564 | CE1 | HIS A | 161 | −3.376 | 22.740 | −39.787 | 1.00 | 33.40 | C |
| ATOM | 565 | NE2 | HIS A | 161 | −4.228 | 22.906 | −40.783 | 1.00 | 34.36 | N |
| ATOM | 566 | CD2 | HIS A | 161 | −5.463 | 23.217 | −40.268 | 1.00 | 30.80 | C |
| ATOM | 567 | C | HIS A | 161 | −7.733 | 22.544 | −35.955 | 1.00 | 22.20 | C |
| ATOM | 568 | O | HIS A | 161 | −8.959 | 22.633 | −36.068 | 1.00 | 22.16 | O |
| ATOM | 569 | N | PRO A | 162 | −7.090 | 22.705 | −34.783 | 1.00 | 21.07 | N |
| ATOM | 570 | CA | PRO A | 162 | −7.783 | 22.962 | −33.523 | 1.00 | 20.68 | C |
| ATOM | 571 | CB | PRO A | 162 | −6.648 | 22.950 | −32.493 | 1.00 | 20.51 | C |
| ATOM | 572 | CG | PRO A | 162 | −5.416 | 23.273 | −33.279 | 1.00 | 19.72 | C |
| ATOM | 573 | CD | PRO A | 162 | −5.628 | 22.623 | −34.596 | 1.00 | 20.16 | C |
| ATOM | 574 | C | PRO A | 162 | −8.493 | 24.306 | −33.468 | 1.00 | 21.53 | C |
| ATOM | 575 | O | PRO A | 162 | −8.036 | 25.283 | −34.071 | 1.00 | 21.90 | O |
| ATOM | 576 | N | GLU A | 163 | −9.609 | 24.342 | −32.742 | 1.00 | 20.82 | N |
| ATOM | 577 | CA | GLU A | 163 | −10.238 | 25.590 | −32.350 | 1.00 | 20.41 | C |
| ATOM | 578 | CB | GLU A | 163 | −11.730 | 25.389 | −32.133 | 1.00 | 21.21 | C |
| ATOM | 579 | CG | GLU A | 163 | −12.546 | 25.200 | −33.387 | 1.00 | 26.82 | C |
| ATOM | 580 | CD | GLU A | 163 | −14.030 | 25.103 | −33.085 | 1.00 | 33.42 | C |
| ATOM | 581 | OE1 | GLU A | 163 | −14.390 | 24.780 | −31.928 | 1.00 | 28.61 | O |
| ATOM | 582 | OE2 | GLU A | 163 | −14.840 | 25.357 | −34.003 | 1.00 | 39.39 | O |
| ATOM | 583 | C | GLU A | 163 | −9.614 | 26.038 | −31.039 | 1.00 | 19.39 | C |
| ATOM | 584 | O | GLU A | 163 | −9.080 | 25.216 | −30.290 | 1.00 | 19.15 | O |
| ATOM | 585 | N | SER A | 164 | −9.694 | 27.336 | −30.756 | 1.00 | 18.24 | N |
| ATOM | 586 | CA | SER A | 164 | −9.255 | 27.870 | −29.475 | 1.00 | 17.99 | C |
| ATOM | 587 | CB | SER A | 164 | −9.279 | 29.401 | −29.497 | 1.00 | 18.05 | C |
| ATOM | 588 | OG | SER A | 164 | −10.610 | 29.888 | −29.443 | 1.00 | 19.95 | O |
| ATOM | 589 | C | SER A | 164 | −10.155 | 27.347 | −28.349 | 1.00 | 17.69 | C |
| ATOM | 590 | O | SER A | 164 | −11.308 | 26.962 | −28.588 | 1.00 | 16.55 | O |
| ATOM | 591 | N | LEU A | 165 | −9.622 | 27.349 | −27.130 | 1.00 | 17.83 | N |
| ATOM | 592 | CA | LEU A | 165 | −10.377 | 26.933 | −25.949 | 1.00 | 19.34 | C |
| ATOM | 593 | CB | LEU A | 165 | −9.472 | 26.874 | −24.709 | 1.00 | 19.38 | C |
| ATOM | 594 | CG | LEU A | 165 | −8.358 | 25.815 | −24.702 | 1.00 | 20.84 | C |
| ATOM | 595 | CD1 | LEU A | 165 | −7.444 | 25.994 | −23.501 | 1.00 | 17.08 | C |
| ATOM | 596 | CD2 | LEU A | 165 | −8.913 | 24.385 | −24.751 | 1.00 | 17.97 | C |
| ATOM | 597 | C | LEU A | 165 | −11.592 | 27.823 | −25.691 | 1.00 | 20.16 | C |
| ATOM | 598 | O | LEU A | 165 | −12.594 | 27.366 | −25.143 | 1.00 | 20.56 | O |
| ATOM | 599 | N | GLU A | 166 | −11.507 | 29.088 | −26.097 | 1.00 | 21.07 | N |
| ATOM | 600 | CA | GLU A | 166 | −12.654 | 29.988 | −26.021 | 1.00 | 22.78 | C |
| ATOM | 601 | CB | GLU A | 166 | −12.259 | 31.423 | −26.402 | 1.00 | 23.41 | C |
| ATOM | 602 | CG | GLU A | 166 | −13.403 | 32.452 | −26.337 | 1.00 | 30.52 | C |
| ATOM | 603 | CD | GLU A | 166 | −14.152 | 32.446 | −25.000 | 1.00 | 40.52 | C |
| ATOM | 604 | OE1 | GLU A | 166 | −13.502 | 32.397 | −23.928 | 1.00 | 43.15 | O |
| ATOM | 605 | OE2 | GLU A | 166 | −15.401 | 32.498 | −25.021 | 1.00 | 44.96 | O |
| ATOM | 606 | C | GLU A | 166 | −13.789 | 29.476 | −26.909 | 1.00 | 22.47 | C |
| ATOM | 607 | O | GLU A | 166 | −14.952 | 29.470 | −26.500 | 1.00 | 22.92 | O |
| ATOM | 608 | N | GLN A | 167 | −13.436 | 29.034 | −28.115 | 1.00 | 22.23 | N |
| ATOM | 609 | CA | GLN A | 167 | −14.407 | 28.471 | −29.049 | 1.00 | 21.75 | C |
| ATOM | 610 | CB | GLN A | 167 | −13.800 | 28.335 | −30.452 | 1.00 | 22.01 | C |
| ATOM | 611 | CG | GLN A | 167 | −14.826 | 28.102 | −31.571 | 1.00 | 26.53 | C |
| | | | | | gad67.pdb | | | | | |
| ATOM | 612 | CD | GLN A | 167 | −15.949 | 29.137 | −31.587 | 1.00 | 31.70 | C |
| ATOM | 613 | OE1 | GLN A | 167 | −15.699 | 30.344 | −31.626 | 1.00 | 33.83 | O |
| ATOM | 614 | NE2 | GLN A | 167 | −17.190 | 28.664 | −31.561 | 1.00 | 31.11 | N |
| ATOM | 615 | C | GLN A | 167 | −14.964 | 27.132 | −28.545 | 1.00 | 20.42 | C |
| ATOM | 616 | O | GLN A | 167 | −16.126 | 26.818 | −28.783 | 1.00 | 20.57 | O |
| ATOM | 617 | N | ILE A | 168 | −14.130 | 26.369 | −27.838 | 1.00 | 19.19 | N |
| ATOM | 618 | CA | ILE A | 168 | −14.546 | 25.132 | −27.174 | 1.00 | 18.66 | C |
| ATOM | 619 | CB | ILE A | 168 | −13.324 | 24.361 | −26.599 | 1.00 | 17.99 | C |

TABLE A-continued

| | | | | | | | | | | |
|---|---|---|---|---|---|---|---|---|---|---|
| ATOM | 620 | CG1 | ILE A | 168 | −12.453 | 23.795 | −27.732 | 1.00 | 17.27 | C |
| ATOM | 621 | CD1 | ILE A | 168 | −13.166 | 22.826 | −28.679 | 1.00 | 18.12 | C |
| ATOM | 622 | CG2 | ILE A | 168 | −13.757 | 23.258 | −25.637 | 1.00 | 18.15 | C |
| ATOM | 623 | C | ILE A | 168 | −15.590 | 25.408 | −26.082 | 1.00 | 19.35 | C |
| ATOM | 624 | O | ILE A | 168 | −16.607 | 24.710 | −25.994 | 1.00 | 19.48 | O |
| ATOM | 625 | N | LEU A | 169 | −15.341 | 26.434 | −25.268 | 1.00 | 19.37 | N |
| ATOM | 626 | CA | LEU A | 169 | −16.304 | 26.881 | −24.258 | 1.00 | 20.17 | C |
| ATOM | 627 | CB | LEU A | 169 | −15.701 | 27.977 | −23.368 | 1.00 | 19.98 | C |
| ATOM | 628 | CG | LEU A | 169 | −14.565 | 27.542 | −22.433 | 1.00 | 20.64 | C |
| ATOM | 629 | CD1 | LEU A | 169 | −13.884 | 28.752 | −21.791 | 1.00 | 18.22 | C |
| ATOM | 630 | CD2 | LEU A | 169 | −15.072 | 26.580 | −21.372 | 1.00 | 19.19 | C |
| ATOM | 631 | C | LEU A | 169 | −17.613 | 27.356 | −24.887 | 1.00 | 20.35 | C |
| ATOM | 632 | O | LEU A | 169 | −18.695 | 27.093 | −24.350 | 1.00 | 20.05 | O |
| ATOM | 633 | N | VAL A | 170 | −17.506 | 28.043 | −26.024 | 1.00 | 20.36 | N |
| ATOM | 634 | CA | VAL A | 170 | −18.678 | 28.492 | −26.785 | 1.00 | 20.24 | C |
| ATOM | 635 | CB | VAL A | 170 | −18.279 | 29.445 | −27.949 | 1.00 | 20.58 | C |
| ATOM | 636 | CG1 | VAL A | 170 | −19.438 | 29.667 | −28.909 | 1.00 | 18.94 | C |
| ATOM | 637 | CG2 | VAL A | 170 | −17.783 | 30.787 | −27.402 | 1.00 | 17.08 | C |
| ATOM | 638 | C | VAL A | 170 | −19.490 | 27.297 | −27.305 | 1.00 | 21.10 | C |
| ATOM | 639 | O | VAL A | 170 | −20.723 | 27.299 | −27.234 | 1.00 | 21.95 | O |
| ATOM | 640 | N | ASP A | 171 | −18.789 | 26.280 | −27.805 | 1.00 | 21.04 | N |
| ATOM | 641 | CA | ASP A | 171 | −19.419 | 25.050 | −28.287 | 1.00 | 21.46 | C |
| ATOM | 642 | CB | ASP A | 171 | −18.379 | 24.120 | −28.917 | 1.00 | 21.76 | C |
| ATOM | 643 | CG | ASP A | 171 | −17.802 | 24.667 | −30.214 | 1.00 | 24.77 | C |
| ATOM | 644 | OD1 | ASP A | 171 | −18.430 | 25.546 | −30.845 | 1.00 | 27.64 | O |
| ATOM | 645 | OD2 | ASP A | 171 | −16.711 | 24.205 | −30.603 | 1.00 | 22.54 | O |
| ATOM | 646 | C | ASP A | 171 | −20.166 | 24.317 | −27.172 | 1.00 | 21.24 | C |
| ATOM | 647 | O | ASP A | 171 | −21.220 | 23.736 | −27.408 | 1.00 | 20.22 | O |
| ATOM | 648 | N | CYS A | 172 | −19.609 | 24.351 | −25.964 | 1.00 | 21.16 | N |
| ATOM | 649 | CA | CYS A | 172 | −20.259 | 23.784 | −24.783 | 1.00 | 21.68 | C |
| ATOM | 650 | CB | CYS A | 172 | −19.318 | 23.821 | −23.576 | 1.00 | 21.53 | C |
| ATOM | 651 | SG | CYS A | 172 | −17.976 | 22.638 | −23.623 | 1.00 | 20.96 | S |
| ATOM | 652 | C | CYS A | 172 | −21.551 | 24.527 | −24.448 | 1.00 | 22.40 | C |
| ATOM | 653 | O | CYS A | 172 | −22.581 | 23.900 | −24.198 | 1.00 | 23.12 | O |
| ATOM | 654 | N | ARG A | 173 | −21.486 | 25.861 | −24.456 | 1.00 | 22.93 | N |
| ATOM | 655 | CA | ARG A | 173 | −22.638 | 26.718 | −24.164 | 1.00 | 23.60 | C |
| ATOM | 656 | CB | ARG A | 173 | −22.244 | 28.200 | −24.155 | 1.00 | 23.36 | C |
| ATOM | 657 | CG | ARG A | 173 | −21.397 | 28.625 | −22.972 | 1.00 | 24.87 | C |
| ATOM | 658 | CD | ARG A | 173 | −21.223 | 30.144 | −22.922 | 1.00 | 24.73 | C |
| ATOM | 659 | NE | ARG A | 173 | −20.038 | 30.513 | −22.151 | 1.00 | 27.17 | N |
| ATOM | 660 | CZ | ARG A | 173 | −18.858 | 30.818 | −22.686 | 1.00 | 27.01 | C |
| ATOM | 661 | NH1 | ARG A | 173 | −18.698 | 30.816 | −24.003 | 1.00 | 28.92 | N |
| ATOM | 662 | NH2 | ARG A | 173 | −17.835 | 31.129 | −21.903 | 1.00 | 25.82 | N |
| ATOM | 663 | C | ARG A | 173 | −23.756 | 26.507 | −25.170 | 1.00 | 23.41 | C |
| ATOM | 664 | O | ARG A | 173 | −24.925 | 26.401 | −24.794 | 1.00 | 23.73 | O |
| ATOM | 665 | N | ASP A | 174 | −23.381 | 26.453 | −26.447 | 1.00 | 23.55 | N |
| ATOM | 666 | CA | ASP A | 174 | −24.339 | 26.285 | −27.540 | 1.00 | 23.60 | C |
| ATOM | 667 | CB | ASP A | 174 | −23.676 | 26.539 | −28.899 | 1.00 | 24.02 | C |
| ATOM | 668 | CG | ASP A | 174 | −23.443 | 28.023 | −29.182 | 1.00 | 26.11 | C |
| ATOM | 669 | OD1 | ASP A | 174 | −22.662 | 28.331 | −30.107 | 1.00 | 29.89 | O |
| ATOM | 670 | OD2 | ASP A | 174 | −24.035 | 28.882 | −28.494 | 1.00 | 29.98 | O |
| ATOM | 671 | C | ASP A | 174 | −24.979 | 24.904 | −27.522 | 1.00 | 22.95 | C |
| ATOM | 672 | O | ASP A | 174 | −26.180 | 24.769 | −27.773 | 1.00 | 23.57 | O |
| ATOM | 673 | N | THR A | 175 | −24.175 | 23.886 | −27.222 | 1.00 | 21.78 | N |
| ATOM | 674 | CA | THR A | 175 | −24.665 | 22.512 | −27.121 | 1.00 | 21.58 | C |
| ATOM | 675 | CB | THR A | 175 | −23.520 | 21.515 | −26.789 | 1.00 | 21.40 | C |
| ATOM | 676 | OG1 | THR A | 175 | −22.591 | 21.482 | −27.879 | 1.00 | 23.92 | O |
| ATOM | 677 | CG2 | THR A | 175 | −24.057 | 20.107 | −26.560 | 1.00 | 19.87 | C |
| ATOM | 678 | C | THR A | 175 | −25.799 | 22.415 | −26.095 | 1.00 | 20.96 | C |
| ATOM | 679 | O | THR A | 175 | −26.833 | 21.810 | −26.368 | 1.00 | 20.72 | O |
| | | | | | gad67.pdb | | | | | |
| ATOM | 680 | N | LEU A | 176 | −25.606 | 23.036 | −24.935 | 1.00 | 20.94 | N |
| ATOM | 681 | CA | LEU A | 176 | −26.621 | 23.036 | −23.885 | 1.00 | 21.81 | C |
| ATOM | 682 | CB | LEU A | 176 | −26.006 | 23.425 | −22.539 | 1.00 | 20.92 | C |
| ATOM | 683 | CG | LEU A | 176 | −25.054 | 22.398 | −21.912 | 1.00 | 19.89 | C |
| ATOM | 684 | CD1 | LEU A | 176 | −24.224 | 23.036 | −20.802 | 1.00 | 17.68 | C |
| ATOM | 685 | CD2 | LEU A | 176 | −25.811 | 21.174 | −21.397 | 1.00 | 17.95 | C |
| ATOM | 686 | C | LEU A | 176 | −27.822 | 23.926 | −24.214 | 1.00 | 22.79 | C |
| ATOM | 687 | O | LEU A | 176 | −28.939 | 23.642 | −23.793 | 1.00 | 23.17 | O |
| ATOM | 688 | N | LYS A | 177 | −27.582 | 24.992 | −24.975 | 1.00 | 23.54 | N |
| ATOM | 689 | CA | LYS A | 177 | −28.635 | 25.927 | −25.375 | 1.00 | 24.69 | C |
| ATOM | 690 | CB | LYS A | 177 | −28.018 | 27.135 | −26.094 | 1.00 | 24.77 | C |
| ATOM | 691 | CG | LYS A | 177 | −29.004 | 28.223 | −26.512 | 1.00 | 25.01 | C |
| ATOM | 692 | CD | LYS A | 177 | −28.277 | 29.384 | −27.168 | 1.00 | 26.60 | C |
| ATOM | 693 | CE | LYS A | 177 | −29.205 | 30.560 | −27.437 | 1.00 | 33.80 | C |
| ATOM | 694 | NZ | LYS A | 177 | −30.082 | 30.354 | −28.618 | 1.00 | 36.77 | N |
| ATOM | 695 | C | LYS A | 177 | −29.688 | 25.263 | −26.264 | 1.00 | 24.47 | C |
| ATOM | 696 | O | LYS A | 177 | −30.883 | 25.561 | −26.159 | 1.00 | 25.32 | O |
| ATOM | 697 | N | TYR A | 178 | −29.238 | 24.357 | −27.128 | 1.00 | 24.00 | N |
| ATOM | 698 | CA | TYR A | 178 | −30.105 | 23.759 | −28.139 | 1.00 | 23.14 | C |

TABLE A-continued

| | | | | | | | | | | |
|---|---|---|---|---|---|---|---|---|---|---|
| ATOM | 699 | CB | TYR A | 178 | −29.448 | 23.853 | −29.522 | 1.00 | 23.22 | C |
| ATOM | 700 | CG | TYR A | 178 | −29.294 | 25.279 | −29.997 | 1.00 | 24.18 | C |
| ATOM | 701 | CD1 | TYR A | 178 | −30.416 | 26.058 | −30.296 | 1.00 | 23.86 | C |
| ATOM | 702 | CE1 | TYR A | 178 | −30.285 | 27.381 | −30.721 | 1.00 | 24.94 | C |
| ATOM | 703 | CZ | TYR A | 178 | −29.021 | 27.934 | −30.851 | 1.00 | 25.78 | C |
| ATOM | 704 | OH | TYR A | 178 | −28.895 | 29.239 | −31.272 | 1.00 | 26.59 | O |
| ATOM | 705 | CE2 | TYR A | 178 | −27.889 | 27.182 | −30.556 | 1.00 | 23.76 | C |
| ATOM | 706 | CD2 | TYR A | 178 | −28.032 | 25.862 | −30.129 | 1.00 | 23.51 | C |
| ATOM | 707 | C | TYR A | 178 | −30.539 | 22.331 | −27.822 | 1.00 | 22.69 | C |
| ATOM | 708 | O | TYR A | 178 | −31.152 | 21.662 | −28.657 | 1.00 | 22.07 | O |
| ATOM | 709 | N | GLY A | 179 | −30.229 | 21.875 | −26.613 | 1.00 | 22.54 | N |
| ATOM | 710 | CA | GLY A | 179 | −30.656 | 20.560 | −26.154 | 1.00 | 23.39 | C |
| ATOM | 711 | C | GLY A | 179 | −31.961 | 20.612 | −25.382 | 1.00 | 23.60 | C |
| ATOM | 712 | O | GLY A | 179 | −32.553 | 21.677 | −25.209 | 1.00 | 24.47 | O |
| ATOM | 713 | N | VAL A | 180 | −32.404 | 19.451 | −24.915 | 1.00 | 23.49 | N |
| ATOM | 714 | CA | VAL A | 180 | −33.644 | 19.334 | −24.159 | 1.00 | 23.69 | C |
| ATOM | 715 | CB | VAL A | 180 | −34.469 | 18.101 | −24.622 | 1.00 | 23.93 | C |
| ATOM | 716 | CG1 | VAL A | 180 | −35.761 | 17.955 | −23.816 | 1.00 | 21.61 | C |
| ATOM | 717 | CG2 | VAL A | 180 | −34.776 | 18.195 | −26.116 | 1.00 | 21.43 | C |
| ATOM | 718 | C | VAL A | 180 | −33.314 | 19.228 | −22.675 | 1.00 | 24.20 | C |
| ATOM | 719 | O | VAL A | 180 | −32.430 | 18.465 | −22.284 | 1.00 | 24.91 | O |
| ATOM | 720 | N | ARG A | 181 | −34.018 | 20.003 | −21.854 | 1.00 | 24.26 | N |
| ATOM | 721 | CA | ARG A | 181 | −33.824 | 19.956 | −20.406 | 1.00 | 24.38 | C |
| ATOM | 722 | CB | ARG A | 181 | −34.181 | 21.294 | −19.762 | 1.00 | 24.54 | C |
| ATOM | 723 | CG | ARG A | 181 | −33.176 | 22.389 | −20.066 | 1.00 | 26.39 | C |
| ATOM | 724 | CD | ARG A | 181 | −33.600 | 23.710 | −19.468 | 1.00 | 33.60 | C |
| ATOM | 725 | NE | ARG A | 181 | −32.663 | 24.784 | −19.804 | 1.00 | 37.53 | N |
| ATOM | 726 | CZ | ARG A | 181 | −31.615 | 25.136 | −19.062 | 1.00 | 39.07 | C |
| ATOM | 727 | NH1 | ARG A | 181 | −31.346 | 24.499 | −17.926 | 1.00 | 38.68 | N |
| ATOM | 728 | NH2 | ARG A | 181 | −30.830 | 26.130 | −19.460 | 1.00 | 38.29 | N |
| ATOM | 729 | C | ARG A | 181 | −34.612 | 18.810 | −19.786 | 1.00 | 23.63 | C |
| ATOM | 730 | O | ARG A | 181 | −35.795 | 18.943 | −19.488 | 1.00 | 23.78 | O |
| ATOM | 731 | N | THR A | 182 | −33.935 | 17.677 | −19.609 | 1.00 | 23.26 | N |
| ATOM | 732 | CA | THR A | 182 | −34.568 | 16.450 | −19.120 | 1.00 | 22.30 | C |
| ATOM | 733 | CB | THR A | 182 | −33.767 | 15.188 | −19.518 | 1.00 | 22.31 | C |
| ATOM | 734 | OG1 | THR A | 182 | −32.440 | 15.270 | −18.986 | 1.00 | 23.93 | O |
| ATOM | 735 | CG2 | THR A | 182 | −33.697 | 15.049 | −21.033 | 1.00 | 20.15 | C |
| ATOM | 736 | C | THR A | 182 | −34.789 | 16.475 | −17.606 | 1.00 | 21.53 | C |
| ATOM | 737 | O | THR A | 182 | −35.452 | 15.594 | −17.053 | 1.00 | 20.55 | O |
| ATOM | 738 | N | GLY A | 183 | −34.237 | 17.493 | −16.947 | 1.00 | 20.59 | N |
| ATOM | 739 | CA | GLY A | 183 | −34.433 | 17.694 | −15.514 | 1.00 | 19.53 | C |
| ATOM | 740 | C | GLY A | 183 | −35.568 | 18.643 | −15.162 | 1.00 | 19.00 | C |
| ATOM | 741 | O | GLY A | 183 | −35.931 | 18.774 | −13.992 | 1.00 | 20.06 | O |
| ATOM | 742 | N | HIS A | 184 | −36.118 | 19.307 | −16.176 | 1.00 | 18.19 | N |
| ATOM | 743 | CA | HIS A | 184 | −37.179 | 20.296 | −16.018 | 1.00 | 17.92 | C |
| ATOM | 744 | CB | HIS A | 184 | −37.548 | 20.857 | −17.391 | 1.00 | 18.08 | C |
| ATOM | 745 | CG | HIS A | 184 | −38.265 | 22.171 | −17.347 | 1.00 | 21.00 | C |
| ATOM | 746 | ND1 | HIS A | 184 | −39.600 | 22.282 | −17.022 | 1.00 | 21.20 | N |
| ATOM | 747 | CE1 | HIS A | 184 | −39.961 gad67.pdb | 23.552 | −17.079 | 1.00 | 20.32 | C |
| ATOM | 748 | NE2 | HIS A | 184 | −38.910 | 24.267 | −17.439 | 1.00 | 21.57 | N |
| ATOM | 749 | CD2 | HIS A | 184 | −37.838 | 23.427 | −17.619 | 1.00 | 20.27 | C |
| ATOM | 750 | C | HIS A | 184 | −38.420 | 19.692 | −15.346 | 1.00 | 17.93 | C |
| ATOM | 751 | O | HIS A | 184 | −38.851 | 18.598 | −15.715 | 1.00 | 17.45 | O |
| ATOM | 752 | N | PRO A | 185 | −38.987 | 20.399 | −14.345 | 1.00 | 17.66 | N |
| ATOM | 753 | CA | PRO A | 185 | −40.199 | 19.952 | −13.642 | 1.00 | 17.43 | C |
| ATOM | 754 | CB | PRO A | 185 | −40.597 | 21.177 | −12.816 | 1.00 | 17.54 | C |
| ATOM | 755 | CG | PRO A | 185 | −39.322 | 21.885 | −12.568 | 1.00 | 17.26 | C |
| ATOM | 756 | CD | PRO A | 185 | −38.479 | 21.670 | −13.799 | 1.00 | 17.60 | C |
| ATOM | 757 | C | PRO A | 185 | −41.342 | 19.564 | −14.583 | 1.00 | 17.61 | C |
| ATOM | 758 | O | PRO A | 185 | −42.144 | 18.690 | −14.247 | 1.00 | 17.71 | O |
| ATOM | 759 | N | ARG A | 186 | −41.399 | 20.203 | −15.751 | 1.00 | 17.52 | N |
| ATOM | 760 | CA | ARG A | 186 | −42.458 | 19.954 | −16.728 | 1.00 | 17.04 | C |
| ATOM | 761 | CB | ARG A | 186 | −43.081 | 21.278 | −17.180 | 1.00 | 17.46 | C |
| ATOM | 762 | CG | ARG A | 186 | −43.959 | 21.901 | −16.105 | 1.00 | 17.63 | C |
| ATOM | 763 | CD | ARG A | 186 | −44.133 | 23.383 | −16.304 | 1.00 | 20.24 | C |
| ATOM | 764 | NE | ARG A | 186 | −44.824 | 23.995 | −15.172 | 1.00 | 22.25 | N |
| ATOM | 765 | CZ | ARG A | 186 | −45.250 | 25.254 | −15.144 | 1.00 | 24.88 | C |
| ATOM | 766 | NH1 | ARG A | 186 | −45.057 | 26.051 | −16.189 | 1.00 | 23.23 | N |
| ATOM | 767 | NH2 | ARG A | 186 | −45.874 | 25.716 | −14.066 | 1.00 | 25.30 | N |
| ATOM | 768 | C | ARG A | 186 | −42.024 | 19.091 | −17.922 | 1.00 | 17.04 | C |
| ATOM | 769 | O | ARG A | 186 | −42.681 | 19.086 | −18.964 | 1.00 | 17.29 | O |
| ATOM | 770 | N | PHE A | 187 | −40.922 | 18.364 | −17.757 | 1.00 | 16.56 | N |
| ATOM | 771 | CA | PHE A | 187 | −40.523 | 17.336 | −18.711 | 1.00 | 16.52 | C |
| ATOM | 772 | CB | PHE A | 187 | −38.996 | 17.257 | −18.812 | 1.00 | 16.18 | C |
| ATOM | 773 | CG | PHE A | 187 | −38.494 | 16.238 | −19.801 | 1.00 | 17.38 | C |
| ATOM | 774 | CD1 | PHE A | 187 | −38.501 | 16.508 | −21.166 | 1.00 | 17.93 | C |
| ATOM | 775 | CE1 | PHE A | 187 | −38.020 | 15.578 | −22.080 | 1.00 | 14.51 | C |
| ATOM | 776 | CZ | PHE A | 187 | −37.518 | 14.359 | −21.632 | 1.00 | 16.88 | C |
| ATOM | 777 | CE2 | PHE A | 187 | −37.496 | 14.080 | −20.266 | 1.00 | 15.37 | C |

TABLE A-continued

| | | | | | | | | | | |
|---|---|---|---|---|---|---|---|---|---|---|
| ATOM | 778 | CD2 | PHE A | 187 | −37.980 | 15.022 | −19.363 | 1.00 | 17.56 | C |
| ATOM | 779 | C | PHE A | 187 | −41.113 | 15.992 | −18.285 | 1.00 | 15.83 | C |
| ATOM | 780 | O | PHE A | 187 | −40.681 | 15.404 | −17.289 | 1.00 | 14.67 | O |
| ATOM | 781 | N | PHE A | 188 | −42.111 | 15.531 | −19.039 | 1.00 | 16.04 | N |
| ATOM | 782 | CA | PHE A | 188 | −42.790 | 14.255 | −18.789 | 1.00 | 16.98 | C |
| ATOM | 783 | CB | PHE A | 188 | −44.270 | 14.490 | −18.470 | 1.00 | 17.31 | C |
| ATOM | 784 | CG | PHE A | 188 | −44.518 | 15.452 | −17.343 | 1.00 | 18.25 | C |
| ATOM | 785 | CD1 | PHE A | 188 | −45.054 | 16.709 | −17.596 | 1.00 | 18.35 | C |
| ATOM | 786 | CE1 | PHE A | 188 | −45.302 | 17.604 | −16.553 | 1.00 | 17.46 | C |
| ATOM | 787 | CZ | PHE A | 188 | −45.015 | 17.239 | −15.248 | 1.00 | 17.06 | C |
| ATOM | 788 | CE2 | PHE A | 188 | −44.479 | 15.982 | −14.981 | 1.00 | 19.50 | C |
| ATOM | 789 | CD2 | PHE A | 188 | −44.237 | 15.096 | −16.025 | 1.00 | 18.62 | C |
| ATOM | 790 | C | PHE A | 188 | −42.708 | 13.306 | −19.988 | 1.00 | 18.00 | C |
| ATOM | 791 | O | PHE A | 188 | −43.520 | 12.380 | −20.111 | 1.00 | 18.76 | O |
| ATOM | 792 | N | ASN A | 189 | −41.731 | 13.529 | −20.865 | 1.00 | 18.18 | N |
| ATOM | 793 | CA | ASN A | 189 | −41.660 | 12.823 | −22.145 | 1.00 | 18.46 | C |
| ATOM | 794 | CB | ASN A | 189 | −40.754 | 13.588 | −23.113 | 1.00 | 18.38 | C |
| ATOM | 795 | CG | ASN A | 189 | −41.097 | 13.327 | −24.561 | 1.00 | 18.96 | C |
| ATOM | 796 | OD1 | ASN A | 189 | −42.174 | 13.689 | −25.032 | 1.00 | 19.08 | O |
| ATOM | 797 | ND2 | ASN A | 189 | −40.172 | 12.714 | −25.284 | 1.00 | 16.48 | N |
| ATOM | 798 | C | ASN A | 189 | −41.211 | 11.362 | −22.060 | 1.00 | 19.13 | C |
| ATOM | 799 | O | ASN A | 189 | −41.589 | 10.550 | −22.904 | 1.00 | 19.43 | O |
| ATOM | 800 | N | GLN A | 190 | −40.403 | 11.040 | −21.051 | 1.00 | 20.89 | N |
| ATOM | 801 | CA | GLN A | 190 | −39.788 | 9.714 | −20.919 | 1.00 | 21.97 | C |
| ATOM | 802 | CB | GLN A | 190 | −38.273 | 9.783 | −21.182 | 1.00 | 21.96 | C |
| ATOM | 803 | CG | GLN A | 190 | −37.825 | 10.547 | −22.436 | 1.00 | 26.08 | C |
| ATOM | 804 | CD | GLN A | 190 | −38.217 | 9.877 | −23.749 | 1.00 | 31.07 | C |
| ATOM | 805 | OE1 | GLN A | 190 | −38.617 | 10.549 | −24.701 | 1.00 | 37.40 | O |
| ATOM | 806 | NE2 | GLN A | 190 | −38.096 | 8.557 | −23.809 | 1.00 | 34.58 | N |
| ATOM | 807 | C | GLN A | 190 | −40.019 | 9.118 | −19.528 | 1.00 | 23.01 | C |
| ATOM | 808 | O | GLN A | 190 | −40.518 | 9.791 | −18.621 | 1.00 | 22.66 | O |
| ATOM | 809 | N | LEU A | 191 | −39.642 | 7.851 | −19.374 | 1.00 | 24.37 | N |
| ATOM | 810 | CA | LEU A | 191 | −39.674 | 7.164 | −18.082 | 1.00 | 26.30 | C |
| ATOM | 811 | CB | LEU A | 191 | −39.630 | 5.644 | −18.279 | 1.00 | 25.72 | C |
| ATOM | 812 | CG | LEU A | 191 | −40.964 | 4.885 | −18.320 | 1.00 | 27.00 | C |
| ATOM | 813 | CD1 | LEU A | 191 | −42.048 | 5.619 | −19.092 | 1.00 | 22.92 | C |
| ATOM | 814 | CD2 | LEU A | 191 | −40.771 | 3.478 | −18.873 | 1.00 | 25.72 | C |
| ATOM | 815 | C | LEU A | 191 | −38.542 | 7.618 | −17.160 | 1.00 | 27.82 | C |
| | | | gad67.pdb | | | | | | | |
| ATOM | 816 | O | LEU A | 191 | −38.675 | 7.559 | −15.936 | 1.00 | 28.66 | O |
| ATOM | 817 | N | SER A | 192 | −37.436 | 8.064 | −17.753 | 1.00 | 28.95 | N |
| ATOM | 818 | CA | SER A | 192 | −36.331 | 8.654 | −17.002 | 1.00 | 30.38 | C |
| ATOM | 819 | CB | SER A | 192 | −34.987 | 8.125 | −17.506 | 1.00 | 30.49 | C |
| ATOM | 820 | OG | SER A | 192 | −35.018 | 6.720 | −17.663 | 1.00 | 35.21 | O |
| ATOM | 821 | C | SER A | 192 | −36.374 | 10.180 | −17.112 | 1.00 | 30.63 | C |
| ATOM | 822 | O | SER A | 192 | −36.088 | 10.741 | −18.171 | 1.00 | 30.18 | O |
| ATOM | 823 | N | THR A | 193 | −36.750 | 10.837 | −16.015 | 1.00 | 31.29 | N |
| ATOM | 824 | CA | THR A | 193 | −36.809 | 12.300 | −15.947 | 1.00 | 31.77 | C |
| ATOM | 825 | CB | THR A | 193 | −38.261 | 12.833 | −16.003 | 1.00 | 31.91 | C |
| ATOM | 826 | OG1 | THR A | 193 | −38.980 | 12.402 | −14.842 | 1.00 | 35.38 | O |
| ATOM | 827 | CG2 | THR A | 193 | −38.982 | 12.344 | −17.246 | 1.00 | 30.53 | C |
| ATOM | 828 | C | THR A | 193 | −36.147 | 12.825 | −14.668 | 1.00 | 31.48 | C |
| ATOM | 829 | O | THR A | 193 | −36.105 | 12.135 | −13.649 | 1.00 | 31.93 | O |
| ATOM | 830 | N | GLY A | 194 | −35.626 | 14.047 | −14.729 | 1.00 | 30.55 | N |
| ATOM | 831 | CA | GLY A | 194 | −35.051 | 14.692 | −13.554 | 1.00 | 28.74 | C |
| ATOM | 832 | C | GLY A | 194 | −33.537 | 14.725 | −13.539 | 1.00 | 27.65 | C |
| ATOM | 833 | O | GLY A | 194 | −32.881 | 14.020 | −14.306 | 1.00 | 27.82 | O |
| ATOM | 834 | N | LEU A | 195 | −32.988 | 15.558 | −12.662 | 1.00 | 26.14 | N |
| ATOM | 835 | CA | LEU A | 195 | −31.548 | 15.650 | −12.475 | 1.00 | 24.92 | C |
| ATOM | 836 | CB | LEU A | 195 | −30.998 | 16.946 | −13.087 | 1.00 | 24.52 | C |
| ATOM | 837 | CG | LEU A | 195 | −29.478 | 17.146 | −13.075 | 1.00 | 24.45 | C |
| ATOM | 838 | CD1 | LEU A | 195 | −28.751 | 16.045 | −13.848 | 1.00 | 20.35 | C |
| ATOM | 839 | CD2 | LEU A | 195 | −29.114 | 18.521 | −13.627 | 1.00 | 24.05 | C |
| ATOM | 840 | C | LEU A | 195 | −31.195 | 15.559 | −10.995 | 1.00 | 24.85 | C |
| ATOM | 841 | O | LEU A | 195 | −31.398 | 16.512 | −10.236 | 1.00 | 25.71 | O |
| ATOM | 842 | N | ASP A | 196 | −30.678 | 14.402 | −10.594 | 1.00 | 23.32 | N |
| ATOM | 843 | CA | ASP A | 196 | −30.254 | 14.186 | −9.223 | 1.00 | 22.04 | C |
| ATOM | 844 | CB | ASP A | 196 | −30.294 | 12.699 | −8.876 | 1.00 | 22.16 | C |
| ATOM | 845 | CG | ASP A | 196 | −30.135 | 12.449 | −7.397 | 1.00 | 24.11 | C |
| ATOM | 846 | OD1 | ASP A | 196 | −28.983 | 12.470 | −6.907 | 1.00 | 23.22 | O |
| ATOM | 847 | OD2 | ASP A | 196 | −31.167 | 12.226 | −6.727 | 1.00 | 28.08 | O |
| ATOM | 848 | C | ASP A | 196 | −28.856 | 14.746 | −9.005 | 1.00 | 20.78 | C |
| ATOM | 849 | O | ASP A | 196 | −27.911 | 14.359 | −9.694 | 1.00 | 20.07 | O |
| ATOM | 850 | N | ILE A | 197 | −28.735 | 15.647 | −8.033 | 1.00 | 19.69 | N |
| ATOM | 851 | CA | ILE A | 197 | −27.485 | 16.371 | −7.776 | 1.00 | 18.72 | C |
| ATOM | 852 | CB | ILE A | 197 | −27.699 | 17.526 | −6.756 | 1.00 | 18.94 | C |
| ATOM | 853 | CG1 | ILE A | 197 | −28.770 | 18.505 | −7.266 | 1.00 | 18.97 | C |
| ATOM | 854 | CD1 | ILE A | 197 | −28.506 | 19.088 | −8.667 | 1.00 | 20.30 | C |
| ATOM | 855 | CG2 | ILE A | 197 | −26.376 | 18.239 | −6.428 | 1.00 | 14.59 | C |
| ATOM | 856 | C | ILE A | 197 | −26.343 | 15.456 | −7.329 | 1.00 | 18.46 | C |

TABLE A-continued

| | | | | | | | | | | |
|---|---|---|---|---|---|---|---|---|---|---|
| ATOM | 857 | O | ILE A | 197 | −25.201 | 15.616 | −7.771 | 1.00 | 18.05 | O |
| ATOM | 858 | N | ILE A | 198 | −26.663 | 14.501 | −6.460 | 1.00 | 17.97 | N |
| ATOM | 859 | CA | ILE A | 198 | −25.699 | 13.512 | −5.994 | 1.00 | 17.52 | C |
| ATOM | 860 | CB | ILE A | 198 | −26.261 | 12.690 | −4.806 | 1.00 | 17.29 | C |
| ATOM | 861 | CG1 | ILE A | 198 | −26.724 | 13.614 | −3.667 | 1.00 | 16.72 | C |
| ATOM | 862 | CD1 | ILE A | 198 | −25.645 | 14.530 | −3.076 | 1.00 | 15.41 | C |
| ATOM | 863 | CG2 | ILE A | 198 | −25.242 | 11.658 | −4.321 | 1.00 | 14.16 | C |
| ATOM | 864 | C | ILE A | 198 | −25.283 | 12.587 | −7.139 | 1.00 | 17.80 | C |
| ATOM | 865 | O | ILE A | 198 | −24.105 | 12.242 | −7.259 | 1.00 | 17.96 | O |
| ATOM | 866 | N | GLY A | 199 | −26.253 | 12.202 | −7.972 | 1.00 | 17.06 | N |
| ATOM | 867 | CA | GLY A | 199 | −25.994 | 11.412 | −9.173 | 1.00 | 16.24 | C |
| ATOM | 868 | C | GLY A | 199 | −25.055 | 12.128 | −10.128 | 1.00 | 16.50 | C |
| ATOM | 869 | O | GLY A | 199 | −24.169 | 11.507 | −10.718 | 1.00 | 15.10 | O |
| ATOM | 870 | N | LEU A | 200 | −25.257 | 13.439 | −10.264 | 1.00 | 16.20 | N |
| ATOM | 871 | CA | LEU A | 200 | −24.416 | 14.289 | −11.097 | 1.00 | 17.40 | C |
| ATOM | 872 | CB | LEU A | 200 | −25.005 | 15.703 | −11.206 | 1.00 | 17.58 | C |
| ATOM | 873 | CG | LEU A | 200 | −24.264 | 16.668 | −12.143 | 1.00 | 17.00 | C |
| ATOM | 874 | CD1 | LEU A | 200 | −24.316 | 16.164 | −13.570 | 1.00 | 13.08 | C |
| ATOM | 875 | CD2 | LEU A | 200 | −24.822 | 18.086 | −12.049 | 1.00 | 17.29 | C |
| ATOM | 876 | C | LEU A | 200 | −22.985 | 14.348 | −10.574 | 1.00 | 17.73 | C |
| ATOM | 877 | O | LEU A | 200 | −22.033 | 14.178 | −11.338 | 1.00 | 17.40 | O |
| ATOM | 878 | N | ALA A | 201 | −22.847 | 14.594 | −9.272 | 1.00 | 17.56 | N |
| ATOM | 879 | CA | ALA A | 201 | −21.549 | 14.563 | −8.602 | 1.00 | 17.66 | C |
| ATOM | 880 | CB | ALA A | 201 | −21.713 | 14.840 | −7.115 | 1.00 | 17.65 | C |
| ATOM | 881 | C | ALA A | 201 | −20.852 | 13.221 | −8.826 | 1.00 | 17.53 | C |
| ATOM | 882 | O | ALA A | 201 | −19.671 | 13.182 | −9.179 | 1.00 | 17.68 | O |
| ATOM | 883 | N | GLY A | 202 | −21.596 | 12.133 | −8.635 | 1.00 | 16.70 | N |
| | | | | | gad67.pdb | | | | | |
| ATOM | 884 | CA | GLY A | 202 | −21.083 | 10.777 | −8.827 | 1.00 | 16.41 | C |
| ATOM | 885 | C | GLY A | 202 | −20.570 | 10.547 | −10.236 | 1.00 | 16.48 | C |
| ATOM | 886 | O | GLY A | 202 | −19.513 | 9.941 | −10.433 | 1.00 | 16.30 | O |
| ATOM | 887 | N | GLU A | 203 | −21.324 | 11.044 | −11.212 | 1.00 | 15.91 | N |
| ATOM | 888 | CA | GLU A | 203 | −20.947 | 10.971 | −12.619 | 1.00 | 16.56 | C |
| ATOM | 889 | CB | GLU A | 203 | −22.067 | 11.525 | −13.504 | 1.00 | 17.97 | C |
| ATOM | 890 | CG | GLU A | 203 | −23.241 | 10.573 | −13.736 | 1.00 | 23.21 | C |
| ATOM | 891 | CD | GLU A | 203 | −22.940 | 9.479 | −14.753 | 1.00 | 33.84 | C |
| ATOM | 892 | OE1 | GLU A | 203 | −21.823 | 8.909 | −14.729 | 1.00 | 37.18 | O |
| ATOM | 893 | OE2 | GLU A | 203 | −23.835 | 9.178 | −15.573 | 1.00 | 36.23 | O |
| ATOM | 894 | C | GLU A | 203 | −19.646 | 11.716 | −12.907 | 1.00 | 15.31 | C |
| ATOM | 895 | O | GLU A | 203 | −18.783 | 11.201 | −13.618 | 1.00 | 15.25 | O |
| ATOM | 896 | N | TRP A | 204 | −19.517 | 12.921 | −12.352 | 1.00 | 14.54 | N |
| ATOM | 897 | CA | TRP A | 204 | −18.319 | 13.742 | −12.533 | 1.00 | 14.29 | C |
| ATOM | 898 | CB | TRP A | 204 | −18.497 | 15.135 | −11.919 | 1.00 | 13.74 | C |
| ATOM | 899 | CG | TRP A | 204 | −19.474 | 16.027 | −12.659 | 1.00 | 13.17 | C |
| ATOM | 900 | CD1 | TRP A | 204 | −20.129 | 15.744 | −13.823 | 1.00 | 12.72 | C |
| ATOM | 901 | NE1 | TRP A | 204 | −20.926 | 16.801 | −14.192 | 1.00 | 13.38 | N |
| ATOM | 902 | CE2 | TRP A | 204 | −20.781 | 17.808 | −13.275 | 1.00 | 14.39 | C |
| ATOM | 903 | CD2 | TRP A | 204 | −19.868 | 17.357 | −12.293 | 1.00 | 13.26 | C |
| ATOM | 904 | CE3 | TRP A | 204 | −19.538 | 18.213 | −11.230 | 1.00 | 13.07 | C |
| ATOM | 905 | CZ3 | TRP A | 204 | −20.125 | 19.475 | −11.184 | 1.00 | 14.33 | C |
| ATOM | 906 | CH2 | TRP A | 204 | −21.032 | 19.895 | −12.181 | 1.00 | 13.81 | C |
| ATOM | 907 | CZ2 | TRP A | 204 | −21.370 | 19.080 | −13.230 | 1.00 | 11.88 | C |
| ATOM | 908 | C | TRP A | 204 | −17.070 | 13.070 | −11.972 | 1.00 | 14.64 | C |
| ATOM | 909 | O | TRP A | 204 | −16.001 | 13.136 | −12.581 | 1.00 | 14.81 | O |
| ATOM | 910 | N | LEU A | 205 | −17.215 | 12.414 | −10.822 | 1.00 | 14.63 | N |
| ATOM | 911 | CA | LEU A | 205 | −16.119 | 11.652 | −10.218 | 1.00 | 14.56 | C |
| ATOM | 912 | CB | LEU A | 205 | −16.464 | 11.237 | −8.785 | 1.00 | 14.17 | C |
| ATOM | 913 | CG | LEU A | 205 | −15.353 | 10.572 | −7.964 | 1.00 | 13.23 | C |
| ATOM | 914 | CD1 | LEU A | 205 | −15.422 | 11.027 | −6.525 | 1.00 | 14.00 | C |
| ATOM | 915 | CD2 | LEU A | 205 | −15.406 | 9.047 | −8.047 | 1.00 | 11.38 | C |
| ATOM | 916 | C | LEU A | 205 | −15.734 | 10.430 | −11.049 | 1.00 | 15.13 | C |
| ATOM | 917 | O | LEU A | 205 | −14.545 | 10.177 | −11.261 | 1.00 | 15.34 | O |
| ATOM | 918 | N | THR A | 206 | −16.742 | 9.681 | −11.500 | 1.00 | 14.99 | N |
| ATOM | 919 | CA | THR A | 206 | −16.546 | 8.481 | −12.314 | 1.00 | 15.71 | C |
| ATOM | 920 | CB | THR A | 206 | −17.900 | 7.851 | −12.715 | 1.00 | 16.17 | C |
| ATOM | 921 | OG1 | THR A | 206 | −18.688 | 7.604 | −11.543 | 1.00 | 17.34 | O |
| ATOM | 922 | CG2 | THR A | 206 | −17.689 | 6.546 | −13.459 | 1.00 | 15.39 | C |
| ATOM | 923 | C | THR A | 206 | −15.723 | 8.793 | −13.570 | 1.00 | 15.65 | C |
| ATOM | 924 | O | THR A | 206 | −14.790 | 8.069 | −13.906 | 1.00 | 14.51 | O |
| ATOM | 925 | N | SER A | 207 | −16.076 | 9.884 | −14.244 | 1.00 | 16.26 | N |
| ATOM | 926 | CA | SER A | 207 | −15.369 | 10.345 | −15.438 | 1.00 | 17.15 | C |
| ATOM | 927 | CB | SER A | 207 | −16.104 | 11.534 | −16.061 | 1.00 | 16.55 | C |
| ATOM | 928 | OG | SER A | 207 | −17.401 | 11.150 | −16.482 | 1.00 | 17.46 | O |
| ATOM | 929 | C | SER A | 207 | −13.915 | 10.712 | −15.138 | 1.00 | 17.75 | C |
| ATOM | 930 | O | SER A | 207 | −13.030 | 10.465 | −15.952 | 1.00 | 18.34 | O |
| ATOM | 931 | N | THR A | 208 | −13.684 | 11.293 | −13.964 | 1.00 | 17.89 | N |
| ATOM | 932 | CA | THR A | 208 | −12.339 | 11.637 | −13.500 | 1.00 | 18.24 | C |
| ATOM | 933 | CB | THR A | 208 | −12.394 | 12.559 | −12.264 | 1.00 | 17.90 | C |
| ATOM | 934 | OG1 | THR A | 208 | −13.304 | 13.633 | −12.519 | 1.00 | 17.27 | O |
| ATOM | 935 | CG2 | THR A | 208 | −11.026 | 13.138 | −11.954 | 1.00 | 18.59 | C |

TABLE A-continued

| | | | | | | | | | |
|---|---|---|---|---|---|---|---|---|---|
| ATOM | 936 | C | THR A | 208 | −11.517 | 10.387 | −13.187 | 1.00 | 18.51 | C |
| ATOM | 937 | O | THR A | 208 | −10.321 | 10.336 | −13.478 | 1.00 | 18.80 | O |
| ATOM | 938 | N | ALA A | 209 | −12.174 | 9.385 | −12.606 | 1.00 | 18.47 | N |
| ATOM | 939 | CA | ALA A | 209 | −11.552 | 8.098 | −12.304 | 1.00 | 18.35 | C |
| ATOM | 940 | CB | ALA A | 209 | −12.450 | 7.279 | −11.389 | 1.00 | 17.47 | C |
| ATOM | 941 | C | ALA A | 209 | −11.234 | 7.323 | −13.584 | 1.00 | 19.20 | C |
| ATOM | 942 | O | ALA A | 209 | −10.232 | 6.605 | −13.641 | 1.00 | 20.05 | O |
| ATOM | 943 | N | ASN A | 210 | −12.098 | 7.476 | −14.592 | 1.00 | 18.93 | N |
| ATOM | 944 | CA | ASN A | 210 | −11.900 | 6.934 | −15.945 | 1.00 | 19.69 | C |
| ATOM | 945 | CB | ASN A | 210 | −11.079 | 7.917 | −16.797 | 1.00 | 19.47 | C |
| ATOM | 946 | CG | ASN A | 210 | −11.043 | 7.538 | −18.271 | 1.00 | 19.33 | C |
| ATOM | 947 | OD1 | ASN A | 210 | −10.012 | 7.667 | −18.929 | 1.00 | 24.11 | O |
| ATOM | 948 | ND2 | ASN A | 210 | −12.169 | 7.073 | −18.793 | 1.00 | 16.99 | N |
| ATOM | 949 | C | ASN A | 210 | −11.291 | 5.526 | −15.993 | 1.00 | 19.76 | C |
| ATOM | 950 | O | ASN A | 210 | −10.141 | 5.343 | −16.402 | 1.00 | 19.06 | O |
| ATOM | 951 | N | THR A | 211 | −12.070 | 4.534 | −15.572 | 1.00 | 19.94 | N |
| gad67.pdb | | | | | | | | | | |
| ATOM | 952 | CA | THR A | 211 | −11.587 | 3.156 | −15.528 | 1.00 | 19.75 | C |
| ATOM | 953 | CB | THR A | 211 | −11.074 | 2.783 | −14.105 | 1.00 | 20.05 | C |
| ATOM | 954 | OG1 | THR A | 211 | −10.348 | 1.547 | −14.154 | 1.00 | 18.88 | O |
| ATOM | 955 | CG2 | THR A | 211 | −12.226 | 2.688 | −13.092 | 1.00 | 18.28 | C |
| ATOM | 956 | C | THR A | 211 | −12.622 | 2.147 | −16.046 | 1.00 | 20.78 | C |
| ATOM | 957 | O | THR A | 211 | −13.783 | 2.499 | −16.279 | 1.00 | 21.14 | O |
| ATOM | 958 | N | ASN A | 212 | −12.171 | .909 | −16.248 | 1.00 | 21.74 | N |
| ATOM | 959 | CA | ASN A | 212 | −13.000 | −.209 | −16.686 | 1.00 | 22.66 | C |
| ATOM | 960 | CB | ASN A | 212 | −12.205 | −1.099 | −17.642 | 1.00 | 24.21 | C |
| ATOM | 961 | CG | ASN A | 212 | −12.401 | −.737 | −19.087 | 1.00 | 28.36 | C |
| ATOM | 962 | OD1 | ASN A | 212 | −13.494 | −.881 | −19.629 | 1.00 | 37.98 | O |
| ATOM | 963 | ND2 | ASN A | 212 | −11.333 | −.291 | −19.735 | 1.00 | 34.92 | N |
| ATOM | 964 | C | ASN A | 212 | −13.432 | −1.068 | −15.503 | 1.00 | 22.69 | C |
| ATOM | 965 | O | ASN A | 212 | −12.676 | −1.218 | −14.542 | 1.00 | 22.92 | O |
| ATOM | 966 | N | MET A | 213 | −14.624 | −1.658 | −15.596 | 1.00 | 21.41 | N |
| ATOM | 967 | CA | MET A | 213 | −15.156 | −2.517 | −14.535 | 1.00 | 21.52 | C |
| ATOM | 968 | CB | MET A | 213 | −16.692 | −2.534 | −14.571 | 1.00 | 21.44 | C |
| ATOM | 969 | CG | MET A | 213 | −17.385 | −1.324 | −13.954 | 1.00 | 20.16 | C |
| ATOM | 970 | SD | MET A | 213 | −16.992 | −1.063 | −12.216 | 1.00 | 21.07 | S |
| ATOM | 971 | CE | MET A | 213 | −17.641 | −2.544 | −11.442 | 1.00 | 17.41 | C |
| ATOM | 972 | C | MET A | 213 | −14.658 | −3.967 | −14.573 | 1.00 | 21.77 | C |
| ATOM | 973 | O | MET A | 213 | −14.935 | −4.728 | −13.644 | 1.00 | 22.77 | O |
| ATOM | 974 | N | PHE A | 214 | −13.929 | −4.354 | −15.623 | 1.00 | 20.97 | N |
| ATOM | 975 | CA | PHE A | 214 | −13.674 | −5.786 | −15.873 | 1.00 | 20.30 | C |
| ATOM | 976 | CB | PHE A | 214 | −13.305 | −6.088 | −17.346 | 1.00 | 21.12 | C |
| ATOM | 977 | CG | PHE A | 214 | −12.188 | −5.239 | −17.920 | 1.00 | 20.41 | C |
| ATOM | 978 | CD1 | PHE A | 214 | −12.204 | −4.907 | −19.273 | 1.00 | 21.90 | C |
| ATOM | 979 | CE1 | PHE A | 214 | −11.188 | −4.143 | −19.838 | 1.00 | 22.71 | C |
| ATOM | 980 | CZ | PHE A | 214 | −10.133 | −3.697 | −19.045 | 1.00 | 23.33 | C |
| ATOM | 981 | CE2 | PHE A | 214 | −10.101 | −4.022 | −17.694 | 1.00 | 20.34 | C |
| ATOM | 982 | CD2 | PHE A | 214 | −11.122 | −4.797 | −17.140 | 1.00 | 19.46 | C |
| ATOM | 983 | C | PHE A | 214 | −12.761 | −6.543 | −14.891 | 1.00 | 19.88 | C |
| ATOM | 984 | O | PHE A | 214 | −12.843 | −7.771 | −14.796 | 1.00 | 20.24 | O |
| ATOM | 985 | N | THR A | 215 | −11.906 | −5.826 | −14.166 | 1.00 | 18.44 | N |
| ATOM | 986 | CA | THR A | 215 | −11.019 | −6.454 | −13.182 | 1.00 | 16.90 | C |
| ATOM | 987 | CB | THR A | 215 | −9.568 | −6.635 | −13.709 | 1.00 | 17.03 | C |
| ATOM | 988 | OG1 | THR A | 215 | −8.993 | −5.354 | −13.976 | 1.00 | 15.96 | O |
| ATOM | 989 | CG2 | THR A | 215 | −9.525 | −7.491 | −14.973 | 1.00 | 14.78 | C |
| ATOM | 990 | C | THR A | 215 | −10.948 | −5.641 | −11.893 | 1.00 | 16.10 | C |
| ATOM | 991 | O | THR A | 215 | −11.101 | −4.416 | −11.908 | 1.00 | 15.90 | O |
| ATOM | 992 | N | TYR A | 216 | −10.700 | −6.332 | −10.783 | 1.00 | 15.74 | N |
| ATOM | 993 | CA | TYR A | 216 | −10.439 | −5.685 | −9.497 | 1.00 | 15.78 | C |
| ATOM | 994 | CB | TYR A | 216 | −10.400 | −6.726 | −8.370 | 1.00 | 14.62 | C |
| ATOM | 995 | CG | TYR A | 216 | −10.071 | −6.136 | −7.024 | 1.00 | 14.49 | C |
| ATOM | 996 | CD1 | TYR A | 216 | −11.076 | −5.614 | −6.204 | 1.00 | 13.21 | C |
| ATOM | 997 | CE1 | TYR A | 216 | −10.769 | −5.052 | −4.964 | 1.00 | 14.23 | C |
| ATOM | 998 | CZ | TYR A | 216 | −9.445 | −5.014 | −4.539 | 1.00 | 13.76 | C |
| ATOM | 999 | OH | TYR A | 216 | −9.125 | −4.463 | −3.320 | 1.00 | 13.00 | O |
| ATOM | 1000 | CE2 | TYR A | 216 | −8.432 | −5.528 | −5.338 | 1.00 | 13.98 | C |
| ATOM | 1001 | CD2 | TYR A | 216 | −8.750 | −6.085 | −6.571 | 1.00 | 12.08 | C |
| ATOM | 1002 | C | TYR A | 216 | −9.119 | −4.909 | −9.548 | 1.00 | 16.77 | C |
| ATOM | 1003 | O | TYR A | 216 | −8.942 | −3.899 | −8.865 | 1.00 | 17.16 | O |
| ATOM | 1004 | N | GLU A | 217 | −8.203 | −5.403 | −10.374 | 1.00 | 17.69 | N |
| ATOM | 1005 | CA | GLU A | 217 | −6.886 | −4.812 | −10.590 | 1.00 | 18.82 | C |
| ATOM | 1006 | CB | GLU A | 217 | −6.200 | −5.564 | −11.731 | 1.00 | 19.77 | C |
| ATOM | 1007 | CG | GLU A | 217 | −4.737 | −5.259 | −11.923 | 1.00 | 22.55 | C |
| ATOM | 1008 | CD | GLU A | 217 | −4.117 | −6.135 | −12.986 | 1.00 | 26.96 | C |
| ATOM | 1009 | OE1 | GLU A | 217 | −3.469 | −5.598 | −13.905 | 1.00 | 29.72 | O |
| ATOM | 1010 | OE2 | GLU A | 217 | −4.288 | −7.366 | −12.908 | 1.00 | 32.13 | O |
| ATOM | 1011 | C | GLU A | 217 | −6.909 | −3.301 | −10.879 | 1.00 | 18.17 | C |
| ATOM | 1012 | O | GLU A | 217 | −6.103 | −2.551 | −10.321 | 1.00 | 18.30 | O |
| ATOM | 1013 | N | ILE A | 218 | −7.825 | −2.855 | −11.740 | 1.00 | 17.48 | N |
| ATOM | 1014 | CA | ILE A | 218 | −7.908 | −1.427 | −12.089 | 1.00 | 17.02 | C |

TABLE A-continued

| | | | | | | | | | |
|---|---|---|---|---|---|---|---|---|---|
| ATOM | 1015 | CB | ILE A | 218 | −7.550 | −1.130 | −13.611 | 1.00 | 17.37 | C |
| ATOM | 1016 | CG1 | ILE A | 218 | −8.725 | −1.359 | −14.588 | 1.00 | 19.13 | C |
| ATOM | 1017 | CD1 | ILE A | 218 | −9.558 | −2.605 | −14.394 | 1.00 | 23.05 | C |
| ATOM | 1018 | CG2 | ILE A | 218 | −6.256 | −1.831 | −14.045 | 1.00 | 14.99 | C |
| ATOM | 1019 | C | ILE A | 218 | −9.202 | −.712 | −11.635 | 1.00 | 16.59 | C | gad67.pdb

| | | | | | | | | | |
|---|---|---|---|---|---|---|---|---|---|
| ATOM | 1020 | O | ILE A | 218 | −9.383 | .483 | −11.882 | 1.00 | 17.48 | O |
| ATOM | 1021 | N | ALA A | 219 | −10.083 | −1.438 | −10.952 | 1.00 | 16.10 | N |
| ATOM | 1022 | CA | ALA A | 219 | −11.296 | −.837 | −10.388 | 1.00 | 15.23 | C |
| ATOM | 1023 | CB | ALA A | 219 | −12.471 | −1.010 | −11.351 | 1.00 | 13.82 | C |
| ATOM | 1024 | C | ALA A | 219 | −11.633 | −1.409 | −9.004 | 1.00 | 15.04 | C |
| ATOM | 1025 | O | ALA A | 219 | −12.755 | −1.861 | −8.776 | 1.00 | 15.57 | O |
| ATOM | 1026 | N | PRO A | 220 | −10.673 | −1.366 | −8.065 | 1.00 | 14.86 | N |
| ATOM | 1027 | CA | PRO A | 220 | −10.862 | −2.075 | −6.796 | 1.00 | 14.80 | C |
| ATOM | 1028 | CB | PRO A | 220 | −9.559 | −1.787 | −6.031 | 1.00 | 14.13 | C |
| ATOM | 1029 | CG | PRO A | 220 | −8.981 | −.575 | −6.677 | 1.00 | 12.47 | C |
| ATOM | 1030 | CD | PRO A | 220 | −9.377 | −.658 | −8.111 | 1.00 | 14.72 | C |
| ATOM | 1031 | C | PRO A | 220 | −12.085 | −1.614 | −5.990 | 1.00 | 15.41 | C |
| ATOM | 1032 | O | PRO A | 220 | −12.878 | −2.446 | −5.537 | 1.00 | 15.49 | O |
| ATOM | 1033 | N | VAL A | 221 | −12.239 | −.302 | −5.835 | 1.00 | 15.62 | N |
| ATOM | 1034 | CA | VAL A | 221 | −13.335 | .258 | −5.047 | 1.00 | 16.16 | C |
| ATOM | 1035 | CB | VAL A | 221 | −13.133 | 1.770 | −4.790 | 1.00 | 16.70 | C |
| ATOM | 1036 | CG1 | VAL A | 221 | −14.296 | 2.347 | −3.985 | 1.00 | 14.25 | C |
| ATOM | 1037 | CG2 | VAL A | 221 | −11.806 | 2.014 | −4.064 | 1.00 | 14.75 | C |
| ATOM | 1038 | C | VAL A | 221 | −14.683 | .009 | −5.720 | 1.00 | 16.16 | C |
| ATOM | 1039 | O | VAL A | 221 | −15.629 | −.433 | −5.071 | 1.00 | 16.76 | O |
| ATOM | 1040 | N | PHE A | 222 | −14.748 | .274 | −7.022 | 1.00 | 15.96 | N |
| ATOM | 1041 | CA | PHE A | 222 | −15.981 | .137 | −7.789 | 1.00 | 15.69 | C |
| ATOM | 1042 | CB | PHE A | 222 | −15.812 | .719 | −9.197 | 1.00 | 15.03 | C |
| ATOM | 1043 | CG | PHE A | 222 | −15.429 | 2.176 | −9.217 | 1.00 | 15.10 | C |
| ATOM | 1044 | CD1 | PHE A | 222 | −16.109 | 3.104 | −8.428 | 1.00 | 10.54 | C |
| ATOM | 1045 | CE1 | PHE A | 222 | −15.762 | 4.449 | −8.452 | 1.00 | 13.94 | C |
| ATOM | 1046 | CZ | PHE A | 222 | −14.728 | 4.883 | −9.280 | 1.00 | 12.70 | C |
| ATOM | 1047 | CE2 | PHE A | 222 | −14.047 | 3.963 | −10.083 | 1.00 | 13.72 | C |
| ATOM | 1048 | CD2 | PHE A | 222 | −14.399 | 2.622 | −10.047 | 1.00 | 13.17 | C |
| ATOM | 1049 | C | PHE A | 222 | −16.491 | −1.300 | −7.868 | 1.00 | 15.95 | C |
| ATOM | 1050 | O | PHE A | 222 | −17.701 | −1.527 | −7.834 | 1.00 | 17.13 | O |
| ATOM | 1051 | N | VAL A | 223 | −15.571 | −2.258 | −7.982 | 1.00 | 15.38 | N |
| ATOM | 1052 | CA | VAL A | 223 | −15.917 | −3.682 | −7.990 | 1.00 | 15.36 | C |
| ATOM | 1053 | CB | VAL A | 223 | −14.664 | −4.573 | −8.252 | 1.00 | 15.52 | C |
| ATOM | 1054 | CG1 | VAL A | 223 | −14.937 | −6.041 | −7.935 | 1.00 | 12.72 | C |
| ATOM | 1055 | CG2 | VAL A | 223 | −14.185 | −4.425 | −9.699 | 1.00 | 16.44 | C |
| ATOM | 1056 | C | VAL A | 223 | −16.605 | −4.084 | −6.681 | 1.00 | 16.40 | C |
| ATOM | 1057 | O | VAL A | 223 | −17.614 | −4.791 | −6.691 | 1.00 | 16.85 | O |
| ATOM | 1058 | N | LEU A | 224 | −16.057 | −3.623 | −5.560 | 1.00 | 16.71 | N |
| ATOM | 1059 | CA | LEU A | 224 | −16.614 | −3.927 | −4.248 | 1.00 | 16.95 | C |
| ATOM | 1060 | CB | LEU A | 224 | −15.645 | −3.527 | −3.138 | 1.00 | 16.37 | C |
| ATOM | 1061 | CG | LEU A | 224 | −14.306 | −4.270 | −3.079 | 1.00 | 17.86 | C |
| ATOM | 1062 | CD1 | LEU A | 224 | −13.503 | −3.774 | −1.888 | 1.00 | 17.84 | C |
| ATOM | 1063 | CD2 | LEU A | 224 | −14.469 | −5.785 | −3.013 | 1.00 | 15.16 | C |
| ATOM | 1064 | C | LEU A | 224 | −17.968 | −3.257 | −4.049 | 1.00 | 17.48 | C |
| ATOM | 1065 | O | LEU A | 224 | −18.890 | −3.865 | −3.505 | 1.00 | 16.54 | O |
| ATOM | 1066 | N | MET A | 225 | −18.081 | −2.013 | −4.513 | 1.00 | 17.97 | N |
| ATOM | 1067 | CA | MET A | 225 | −19.347 | −1.283 | −4.476 | 1.00 | 19.11 | C |
| ATOM | 1068 | CB | MET A | 225 | −19.178 | .132 | −5.033 | 1.00 | 18.39 | C |
| ATOM | 1069 | CG | MET A | 225 | −18.552 | 1.099 | −4.064 | 1.00 | 17.46 | C |
| ATOM | 1070 | SD | MET A | 225 | −18.205 | 2.690 | −4.828 | 1.00 | 18.54 | S |
| ATOM | 1071 | CE | MET A | 225 | −17.612 | 3.599 | −3.406 | 1.00 | 15.30 | C |
| ATOM | 1072 | C | MET A | 225 | −20.444 | −2.018 | −5.238 | 1.00 | 20.02 | C |
| ATOM | 1073 | O | MET A | 225 | −21.583 | −2.087 | −4.773 | 1.00 | 20.71 | O |
| ATOM | 1074 | N | GLU A | 226 | −20.091 | −2.570 | −6.398 | 1.00 | 20.99 | N |
| ATOM | 1075 | CA | GLU A | 226 | −21.031 | −3.329 | −7.216 | 1.00 | 22.53 | C |
| ATOM | 1076 | CB | GLU A | 226 | −20.419 | −3.666 | −8.584 | 1.00 | 22.33 | C |
| ATOM | 1077 | CG | GLU A | 226 | −21.391 | −4.309 | −9.567 | 1.00 | 25.73 | C |
| ATOM | 1078 | CD | GLU A | 226 | −20.942 | −4.200 | −11.016 | 1.00 | 28.00 | C |
| ATOM | 1079 | OE1 | GLU A | 226 | −20.986 | −3.082 | −11.577 | 1.00 | 31.93 | O |
| ATOM | 1080 | OE2 | GLU A | 226 | −20.566 | −5.240 | −11.602 | 1.00 | 31.74 | O |
| ATOM | 1081 | C | GLU A | 226 | −21.506 | −4.587 | −6.492 | 1.00 | 21.91 | C |
| ATOM | 1082 | O | GLU A | 226 | −22.699 | −4.876 | −6.476 | 1.00 | 21.61 | O |
| ATOM | 1083 | N | GLN A | 227 | −20.568 | −5.310 | −5.881 | 1.00 | 21.61 | N |
| ATOM | 1084 | CA | GLN A | 227 | −20.868 | −6.519 | −5.110 | 1.00 | 22.65 | C |
| ATOM | 1085 | CB | GLN A | 227 | −19.566 | −7.172 | −4.623 | 1.00 | 22.22 | C |
| ATOM | 1086 | CG | GLN A | 227 | −19.756 | −8.388 | −3.714 | 1.00 | 27.61 | C |
| ATOM | 1087 | CD | GLN A | 227 | −18.446 | −8.902 | −3.123 | 1.00 | 27.97 | C | gad67.pdb

| | | | | | | | | | |
|---|---|---|---|---|---|---|---|---|---|
| ATOM | 1088 | OE1 | GLN A | 227 | −18.283 | −8.970 | −1.899 | 1.00 | 34.28 | O |
| ATOM | 1089 | NE2 | GLN A | 227 | −17.504 | −9.262 | −3.993 | 1.00 | 34.90 | N |
| ATOM | 1090 | C | GLN A | 227 | −21.807 | −6.234 | −3.928 | 1.00 | 20.93 | C |
| ATOM | 1091 | O | GLN A | 227 | −22.787 | −6.952 | −3.728 | 1.00 | 20.38 | O |
| ATOM | 1092 | N | ILE A | 228 | −21.495 | −5.190 | −3.159 | 1.00 | 19.88 | N |

TABLE A-continued

| | | | | | | | | | | |
|---|---|---|---|---|---|---|---|---|---|---|
| ATOM | 1093 | CA | ILE A | 228 | −22.317 | −4.754 | −2.028 | 1.00 | 20.25 | C |
| ATOM | 1094 | CB | ILE A | 228 | −21.669 | −3.543 | −1.285 | 1.00 | 20.31 | C |
| ATOM | 1095 | CG1 | ILE A | 228 | −20.303 | −3.907 | −.677 | 1.00 | 23.35 | C |
| ATOM | 1096 | CD1 | ILE A | 228 | −20.310 | −5.051 | .320 | 1.00 | 28.36 | C |
| ATOM | 1097 | CG2 | ILE A | 228 | −22.614 | −2.950 | −.232 | 1.00 | 20.91 | C |
| ATOM | 1098 | C | ILE A | 228 | −23.729 | −4.374 | −2.477 | 1.00 | 19.71 | C |
| ATOM | 1099 | O | ILE A | 228 | −24.714 | −4.814 | −1.883 | 1.00 | 18.75 | O |
| ATOM | 1100 | N | THR A | 229 | −23.807 | −3.561 | −3.532 | 1.00 | 19.29 | N |
| ATOM | 1101 | CA | THR A | 229 | −25.077 | −3.040 | −4.039 | 1.00 | 19.41 | C |
| ATOM | 1102 | CB | THR A | 229 | −24.847 | −1.876 | −5.026 | 1.00 | 18.88 | C |
| ATOM | 1103 | OG1 | THR A | 229 | −24.000 | −.900 | −4.409 | 1.00 | 18.73 | O |
| ATOM | 1104 | CG2 | THR A | 229 | −26.154 | −1.219 | −5.417 | 1.00 | 16.75 | C |
| ATOM | 1105 | C | THR A | 229 | −25.962 | −4.127 | −4.657 | 1.00 | 19.67 | C |
| ATOM | 1106 | O | THR A | 229 | −27.155 | −4.184 | −4.368 | 1.00 | 20.26 | O |
| ATOM | 1107 | N | LEU A | 230 | −25.375 | −4.986 | −5.490 | 1.00 | 19.98 | N |
| ATOM | 1108 | CA | LEU A | 230 | −26.110 | −6.096 | −6.104 | 1.00 | 19.84 | C |
| ATOM | 1109 | CB | LEU A | 230 | −25.223 | −6.895 | −7.065 | 1.00 | 18.35 | C |
| ATOM | 1110 | CG | LEU A | 230 | −24.882 | −6.223 | −8.398 | 1.00 | 19.57 | C |
| ATOM | 1111 | CD1 | LEU A | 230 | −23.827 | −7.021 | −9.148 | 1.00 | 16.46 | C |
| ATOM | 1112 | CD2 | LEU A | 230 | −26.134 | −6.001 | −9.261 | 1.00 | 16.34 | C |
| ATOM | 1113 | C | LEU A | 230 | −26.726 | −7.037 | −5.079 | 1.00 | 20.42 | C |
| ATOM | 1114 | O | LEU A | 230 | −27.856 | −7.494 | −5.257 | 1.00 | 20.26 | O |
| ATOM | 1115 | N | LYS A | 231 | −25.991 | −7.332 | −4.012 | 1.00 | 20.83 | N |
| ATOM | 1116 | CA | LYS A | 231 | −26.516 | −8.237 | −2.994 | 1.00 | 22.38 | C |
| ATOM | 1117 | CB | LYS A | 231 | −25.402 | −8.815 | −2.103 | 1.00 | 23.04 | C |
| ATOM | 1118 | CG | LYS A | 231 | −24.958 | −7.968 | −.940 | 1.00 | 27.61 | C |
| ATOM | 1119 | CD | LYS A | 231 | −24.281 | −8.815 | .133 | 1.00 | 31.05 | C |
| ATOM | 1120 | CE | LYS A | 231 | −25.295 | −9.633 | .919 | 1.00 | 34.23 | C |
| ATOM | 1121 | NZ | LYS A | 231 | −24.772 | −10.055 | 2.248 | 1.00 | 36.40 | N |
| ATOM | 1122 | C | LYS A | 231 | −27.656 | −7.605 | −2.193 | 1.00 | 21.17 | C |
| ATOM | 1123 | O | LYS A | 231 | −28.615 | −8.282 | −1.836 | 1.00 | 21.27 | O |
| ATOM | 1124 | N | LYS A | 232 | −27.545 | −6.300 | −1.952 | 1.00 | 20.40 | N |
| ATOM | 1125 | CA | LYS A | 232 | −28.591 | −5.509 | −1.312 | 1.00 | 19.77 | C |
| ATOM | 1126 | CB | LYS A | 232 | −28.102 | −4.073 | −1.088 | 1.00 | 20.23 | C |
| ATOM | 1127 | CG | LYS A | 232 | −29.098 | −3.143 | −.394 | 1.00 | 23.14 | C |
| ATOM | 1128 | CD | LYS A | 232 | −29.134 | −3.347 | 1.103 | 1.00 | 26.81 | C |
| ATOM | 1129 | CE | LYS A | 232 | −29.737 | −2.140 | 1.804 | 1.00 | 30.98 | C |
| ATOM | 1130 | NZ | LYS A | 232 | −29.815 | −2.354 | 3.278 | 1.00 | 33.43 | N |
| ATOM | 1131 | C | LYS A | 232 | −29.862 | −5.517 | −2.157 | 1.00 | 19.15 | C |
| ATOM | 1132 | O | LYS A | 232 | −30.965 | −5.667 | −1.625 | 1.00 | 18.66 | O |
| ATOM | 1133 | N | MET A | 233 | −29.697 | −5.373 | −3.472 | 1.00 | 18.14 | N |
| ATOM | 1134 | CA | MET A | 233 | −30.820 | −5.420 | −4.407 | 1.00 | 17.72 | C |
| ATOM | 1135 | CB | MET A | 233 | −30.367 | −5.053 | −5.819 | 1.00 | 17.28 | C |
| ATOM | 1136 | CG | MET A | 233 | −29.943 | −3.597 | −5.980 | 1.00 | 17.16 | C |
| ATOM | 1137 | SD | MET A | 233 | −29.152 | −3.304 | −7.575 | 1.00 | 18.74 | S |
| ATOM | 1138 | CE | MET A | 233 | −30.574 | −2.999 | −8.629 | 1.00 | 14.40 | C |
| ATOM | 1139 | C | MET A | 233 | −31.503 | −6.784 | −4.414 | 1.00 | 16.82 | C |
| ATOM | 1140 | O | MET A | 233 | −32.727 | −6.867 | −4.517 | 1.00 | 16.00 | O |
| ATOM | 1141 | N | ARG A | 234 | −30.706 | −7.846 | −4.299 | 1.00 | 16.90 | N |
| ATOM | 1142 | CA | ARG A | 234 | −31.240 | −9.206 | −4.224 | 1.00 | 17.13 | C |
| ATOM | 1143 | CB | ARG A | 234 | −30.132 | −10.253 | −4.360 | 1.00 | 16.19 | C |
| ATOM | 1144 | CG | ARG A | 234 | −29.477 | −10.299 | −5.748 | 1.00 | 16.83 | C |
| ATOM | 1145 | CD | ARG A | 234 | −28.611 | −11.541 | −5.929 | 1.00 | 14.71 | C |
| ATOM | 1146 | NE | ARG A | 234 | −27.433 | −11.533 | −5.058 | 1.00 | 15.99 | N |
| ATOM | 1147 | CZ | ARG A | 234 | −26.256 | −11.001 | −5.381 | 1.00 | 16.04 | C |
| ATOM | 1148 | NH1 | ARG A | 234 | −26.082 | −10.426 | −6.563 | 1.00 | 13.95 | N |
| ATOM | 1149 | NH2 | ARG A | 234 | −25.247 | −11.041 | −4.523 | 1.00 | 15.63 | N |
| ATOM | 1150 | C | ARG A | 234 | −32.036 | −9.427 | −2.939 | 1.00 | 18.46 | C |
| ATOM | 1151 | O | ARG A | 234 | −33.040 | −10.130 | −2.949 | 1.00 | 18.22 | O |
| ATOM | 1152 | N | GLU A | 235 | −31.583 | −8.819 | −1.846 | 1.00 | 20.07 | N |
| ATOM | 1153 | CA | GLU A | 235 | −32.293 | −8.864 | −.569 | 1.00 | 23.35 | C |
| ATOM | 1154 | CB | GLU A | 235 | −31.440 | −8.260 | .552 | 1.00 | 23.48 | C |
| ATOM | 1155 | CG | GLU A | 235 | −30.248 | −9.126 | .960 | 1.00 | 27.18 | C | gad67.pdb

| | | | | | | | | | | |
|---|---|---|---|---|---|---|---|---|---|---|
| ATOM | 1156 | CD | GLU A | 235 | −29.220 | −8.390 | 1.809 | 1.00 | 28.61 | C |
| ATOM | 1157 | OE1 | GLU A | 235 | −28.354 | −9.065 | 2.401 | 1.00 | 36.77 | O |
| ATOM | 1158 | OE2 | GLU A | 235 | −29.264 | −7.143 | 1.885 | 1.00 | 34.89 | O |
| ATOM | 1159 | C | GLU A | 235 | −33.634 | −8.143 | −.674 | 1.00 | 22.59 | C |
| ATOM | 1160 | O | GLU A | 235 | −34.644 | −8.637 | −.186 | 1.00 | 22.84 | O |
| ATOM | 1161 | N | ILE A | 236 | −33.639 | −6.990 | −1.339 | 1.00 | 22.74 | N |
| ATOM | 1162 | CA | ILE A | 236 | −34.864 | −6.215 | −1.535 | 1.00 | 22.97 | C |
| ATOM | 1163 | CB | ILE A | 236 | −34.556 | −4.796 | −2.074 | 1.00 | 22.76 | C |
| ATOM | 1164 | CG1 | ILE A | 236 | −33.856 | −3.978 | −.984 | 1.00 | 22.23 | C |
| ATOM | 1165 | CD1 | ILE A | 236 | −32.972 | −2.865 | −1.501 | 1.00 | 24.95 | C |
| ATOM | 1166 | CG2 | ILE A | 236 | −35.830 | −4.080 | −2.521 | 1.00 | 21.90 | C |
| ATOM | 1167 | C | ILE A | 236 | −35.864 | −6.980 | −2.414 | 1.00 | 22.85 | C |
| ATOM | 1168 | O | ILE A | 236 | −37.076 | −6.954 | −2.167 | 1.00 | 23.01 | O |
| ATOM | 1169 | N | VAL A | 237 | −35.341 | −7.683 | −3.415 | 1.00 | 21.98 | N |
| ATOM | 1170 | CA | VAL A | 237 | −36.152 | −8.560 | −4.259 | 1.00 | 21.08 | C |
| ATOM | 1171 | CB | VAL A | 237 | −35.328 | −9.093 | −5.461 | 1.00 | 20.52 | C |

TABLE A-continued

| | | | | | | | | | | |
|---|---|---|---|---|---|---|---|---|---|---|
| ATOM | 1172 | CG1 | VAL A | 237 | −35.977 | −10.309 | −6.102 | 1.00 | 17.98 | C |
| ATOM | 1173 | CG2 | VAL A | 237 | −35.133 | −7.983 | −6.490 | 1.00 | 16.87 | C |
| ATOM | 1174 | C | VAL A | 237 | −36.785 | −9.698 | −3.437 | 1.00 | 22.23 | C |
| ATOM | 1175 | O | VAL A | 237 | −37.894 | −10.142 | −3.738 | 1.00 | 23.49 | O |
| ATOM | 1176 | N | GLY A | 238 | −36.084 | −10.147 | −2.396 | 1.00 | 21.89 | N |
| ATOM | 1177 | CA | GLY A | 238 | −36.600 | −11.182 | −1.502 | 1.00 | 21.87 | C |
| ATOM | 1178 | C | GLY A | 238 | −35.863 | −12.505 | −1.592 | 1.00 | 22.46 | C |
| ATOM | 1179 | O | GLY A | 238 | −36.313 | −13.515 | −1.041 | 1.00 | 22.37 | O |
| ATOM | 1180 | N | TRP A | 239 | −34.734 | −12.506 | −2.298 | 1.00 | 21.62 | N |
| ATOM | 1181 | CA | TRP A | 239 | −33.879 | −13.682 | −2.378 | 1.00 | 21.66 | C |
| ATOM | 1182 | CB | TRP A | 239 | −33.037 | −13.661 | −3.656 | 1.00 | 20.91 | C |
| ATOM | 1183 | CG | TRP A | 239 | −33.801 | −13.690 | −4.942 | 1.00 | 20.02 | C |
| ATOM | 1184 | CD1 | TRP A | 239 | −35.103 | −14.070 | −5.128 | 1.00 | 20.85 | C |
| ATOM | 1185 | NE1 | TRP A | 239 | −35.437 | −13.976 | −6.456 | 1.00 | 20.56 | N |
| ATOM | 1186 | CE2 | TRP A | 239 | −34.342 | −13.551 | −7.163 | 1.00 | 20.55 | C |
| ATOM | 1187 | CD2 | TRP A | 239 | −33.291 | −13.361 | −6.240 | 1.00 | 19.95 | C |
| ATOM | 1188 | CE3 | TRP A | 239 | −32.047 | −12.922 | −6.711 | 1.00 | 17.92 | C |
| ATOM | 1189 | CZ3 | TRP A | 239 | −31.894 | −12.684 | −8.074 | 1.00 | 21.23 | C |
| ATOM | 1190 | CH2 | TRP A | 239 | −32.962 | −12.880 | −8.970 | 1.00 | 20.33 | C |
| ATOM | 1191 | CZ2 | TRP A | 239 | −34.189 | −13.312 | −8.535 | 1.00 | 20.26 | C |
| ATOM | 1192 | C | TRP A | 239 | −32.940 | −13.747 | −1.175 | 1.00 | 23.18 | C |
| ATOM | 1193 | O | TRP A | 239 | −32.852 | −12.798 | −.383 | 1.00 | 22.83 | O |
| ATOM | 1194 | N | SER A | 240 | −32.211 | −14.857 | −1.079 | 1.00 | 24.39 | N |
| ATOM | 1195 | CA | SER A | 240 | −31.225 | −15.090 | −.029 | 1.00 | 25.61 | C |
| ATOM | 1196 | CB | SER A | 240 | −30.560 | −16.448 | −.249 | 1.00 | 25.47 | C |
| ATOM | 1197 | OG | SER A | 240 | −29.370 | −16.557 | .504 | 1.00 | 27.96 | O |
| ATOM | 1198 | C | SER A | 240 | −30.156 | −14.001 | .044 | 1.00 | 27.02 | C |
| ATOM | 1199 | O | SER A | 240 | −29.823 | −13.371 | −.961 | 1.00 | 27.86 | O |
| ATOM | 1200 | N | SER A | 241 | −29.632 | −13.785 | 1.247 | 1.00 | 28.30 | N |
| ATOM | 1201 | CA | SER A | 241 | −28.550 | −12.833 | 1.479 | 1.00 | 29.20 | C |
| ATOM | 1202 | CB | SER A | 241 | −28.553 | −12.365 | 2.936 | 1.00 | 29.37 | C |
| ATOM | 1203 | OG | SER A | 241 | −29.651 | −11.508 | 3.191 | 1.00 | 30.60 | O |
| ATOM | 1204 | C | SER A | 241 | −27.193 | −13.441 | 1.127 | 1.00 | 29.85 | C |
| ATOM | 1205 | O | SER A | 241 | −26.216 | −12.722 | .934 | 1.00 | 29.62 | O |
| ATOM | 1206 | N | LYS A | 242 | −27.139 | −14.769 | 1.063 | 1.00 | 31.04 | N |
| ATOM | 1207 | CA | LYS A | 242 | −25.929 | −15.474 | .657 | 1.00 | 31.98 | C |
| ATOM | 1208 | CB | LYS A | 242 | −25.672 | −16.697 | 1.557 | 1.00 | 32.02 | C |
| ATOM | 1209 | CG | LYS A | 242 | −26.719 | −17.799 | 1.443 | 1.00 | 34.38 | C |
| ATOM | 1210 | CD | LYS A | 242 | −26.445 | −18.974 | 2.368 | 1.00 | 34.81 | C |
| ATOM | 1211 | CE | LYS A | 242 | −27.479 | −20.080 | 2.140 | 1.00 | 40.39 | C |
| ATOM | 1212 | NZ | LYS A | 242 | −27.424 | −21.150 | 3.179 | 1.00 | 42.94 | N |
| ATOM | 1213 | C | LYS A | 242 | −26.054 | −15.884 | −.804 | 1.00 | 31.02 | C |
| ATOM | 1214 | O | LYS A | 242 | −27.164 | −16.089 | −1.304 | 1.00 | 30.48 | O |
| ATOM | 1215 | N | ASP A | 243 | −24.912 | −16.000 | −1.479 | 1.00 | 31.14 | N |
| ATOM | 1216 | CA | ASP A | 243 | −24.859 | −16.391 | −2.892 | 1.00 | 31.27 | C |
| ATOM | 1217 | CB | ASP A | 243 | −25.325 | −17.848 | −3.086 | 1.00 | 32.45 | C |
| ATOM | 1218 | CG | ASP A | 243 | −24.591 | −18.835 | −2.180 | 1.00 | 36.82 | C |
| ATOM | 1219 | OD1 | ASP A | 243 | −23.349 | −18.736 | −2.056 | 1.00 | 37.66 | O |
| ATOM | 1220 | OD2 | ASP A | 243 | −25.264 | −19.719 | −1.599 | 1.00 | 39.45 | O |
| ATOM | 1221 | C | ASP A | 243 | −25.667 | −15.425 | −3.771 | 1.00 | 29.89 | C |
| ATOM | 1222 | O | ASP A | 243 | −25.706 | −14.219 | −3.506 | 1.00 | 30.21 | O |
| ATOM | 1223 | N | GLY A | 244 | −26.318 | −15.956 | −4.803 | 1.00 | 27.86 | N |
| | | | | | gad67.pdb | | | | | |
| ATOM | 1224 | CA | GLY A | 244 | −26.978 | −15.128 | −5.805 | 1.00 | 25.49 | C |
| ATOM | 1225 | C | GLY A | 244 | −25.966 | −14.504 | −6.750 | 1.00 | 23.95 | C |
| ATOM | 1226 | O | GLY A | 244 | −24.756 | −14.611 | −6.545 | 1.00 | 22.50 | O |
| ATOM | 1227 | N | ASP A | 245 | −26.463 | −13.838 | −7.787 | 1.00 | 22.56 | N |
| ATOM | 1228 | CA | ASP A | 245 | −25.597 | −13.295 | −8.819 | 1.00 | 21.33 | C |
| ATOM | 1229 | CB | ASP A | 245 | −25.367 | −14.347 | −9.909 | 1.00 | 21.17 | C |
| ATOM | 1230 | CG | ASP A | 245 | −23.997 | −14.237 | −10.556 | 1.00 | 23.83 | C |
| ATOM | 1231 | OD1 | ASP A | 245 | −23.255 | −13.275 | −10.257 | 1.00 | 23.35 | O |
| ATOM | 1232 | OD2 | ASP A | 245 | −23.662 | −15.126 | −11.366 | 1.00 | 23.87 | O |
| ATOM | 1233 | C | ASP A | 245 | −26.199 | −12.040 | −9.432 | 1.00 | 21.05 | C |
| ATOM | 1234 | O | ASP A | 245 | −27.324 | −11.648 | −9.108 | 1.00 | 20.63 | O |
| ATOM | 1235 | N | GLY A | 246 | −25.440 | −11.414 | −10.322 | 1.00 | 20.15 | N |
| ATOM | 1236 | CA | GLY A | 246 | −25.908 | −10.246 | −11.041 | 1.00 | 18.86 | C |
| ATOM | 1237 | C | GLY A | 246 | −24.765 | −9.437 | −11.609 | 1.00 | 18.61 | C |
| ATOM | 1238 | O | GLY A | 246 | −23.603 | −9.654 | −11.266 | 1.00 | 17.99 | O |
| ATOM | 1239 | N | ILE A | 247 | −25.108 | −8.501 | −12.488 | 1.00 | 18.19 | N |
| ATOM | 1240 | CA | ILE A | 247 | −24.141 | −7.583 | −13.075 | 1.00 | 18.17 | C |
| ATOM | 1241 | CB | ILE A | 247 | −23.263 | −8.279 | −14.177 | 1.00 | 17.95 | C |
| ATOM | 1242 | CG1 | ILE A | 247 | −22.073 | −7.395 | −14.583 | 1.00 | 19.74 | C |
| ATOM | 1243 | CD1 | ILE A | 247 | −20.910 | −8.153 | −15.213 | 1.00 | 18.67 | C |
| ATOM | 1244 | CG2 | ILE A | 247 | −24.102 | −8.710 | −15.380 | 1.00 | 17.55 | C |
| ATOM | 1245 | C | ILE A | 247 | −24.883 | −6.355 | −13.607 | 1.00 | 17.82 | C |
| ATOM | 1246 | O | ILE A | 247 | −26.075 | −6.419 | −13.909 | 1.00 | 17.24 | O |
| ATOM | 1247 | N | PHE A | 248 | −24.183 | −5.232 | −13.681 | 1.00 | 17.95 | N |
| ATOM | 1248 | CA | PHE A | 248 | −24.726 | −4.048 | −14.312 | 1.00 | 17.38 | C |
| ATOM | 1249 | CB | PHE A | 248 | −24.148 | −2.782 | −13.674 | 1.00 | 17.46 | C |
| ATOM | 1250 | CG | PHE A | 248 | −24.762 | −2.455 | −12.337 | 1.00 | 19.11 | C |

TABLE A-continued

| | | | | | | | | | | |
|---|---|---|---|---|---|---|---|---|---|---|
| ATOM | 1251 | CD1 | PHE A | 248 | −24.279 | −3.042 | −11.170 | 1.00 | 19.44 | C |
| ATOM | 1252 | CE1 | PHE A | 248 | −24.853 | −2.757 | −9.930 | 1.00 | 20.13 | C |
| ATOM | 1253 | CZ | PHE A | 248 | −25.936 | −1.885 | −9.849 | 1.00 | 19.66 | C |
| ATOM | 1254 | CE2 | PHE A | 248 | −26.434 | −1.294 | −11.010 | 1.00 | 22.24 | C |
| ATOM | 1255 | CD2 | PHE A | 248 | −25.847 | −1.586 | −12.248 | 1.00 | 20.31 | C |
| ATOM | 1256 | C | PHE A | 248 | −24.480 | −4.125 | −15.813 | 1.00 | 18.10 | C |
| ATOM | 1257 | O | PHE A | 248 | −23.414 | −4.562 | −16.252 | 1.00 | 18.39 | O |
| ATOM | 1258 | N | SER A | 249 | −25.490 | −3.737 | −16.590 | 1.00 | 18.18 | N |
| ATOM | 1259 | CA | SER A | 249 | −25.441 | −3.832 | −18.043 | 1.00 | 18.56 | C |
| ATOM | 1260 | CB | SER A | 249 | −26.420 | −4.906 | −18.535 | 1.00 | 18.89 | C |
| ATOM | 1261 | OG | SER A | 249 | −27.725 | −4.389 | −18.698 | 1.00 | 22.39 | O |
| ATOM | 1262 | C | SER A | 249 | −25.752 | −2.478 | −18.685 | 1.00 | 17.79 | C |
| ATOM | 1263 | O | SER A | 249 | −26.373 | −1.630 | −18.043 | 1.00 | 17.84 | O |
| ATOM | 1264 | N | PRO A | 250 | −25.329 | −2.274 | −19.953 | 1.00 | 17.01 | N |
| ATOM | 1265 | CA | PRO A | 250 | −25.602 | −1.010 | −20.639 | 1.00 | 17.03 | C |
| ATOM | 1266 | CB | PRO A | 250 | −24.600 | −1.017 | −21.799 | 1.00 | 16.73 | C |
| ATOM | 1267 | CG | PRO A | 250 | −24.374 | −2.445 | −22.094 | 1.00 | 15.81 | C |
| ATOM | 1268 | CD | PRO A | 250 | −24.572 | −3.208 | −20.809 | 1.00 | 17.01 | C |
| ATOM | 1269 | C | PRO A | 250 | −27.050 | −.900 | −21.146 | 1.00 | 16.75 | C |
| ATOM | 1270 | O | PRO A | 250 | −27.292 | −.838 | −22.358 | 1.00 | 16.55 | O |
| ATOM | 1271 | N | GLY A | 251 | −27.996 | −.864 | −20.211 | 1.00 | 16.26 | N |
| ATOM | 1272 | CA | GLY A | 251 | −29.412 | −.735 | −20.541 | 1.00 | 15.85 | C |
| ATOM | 1273 | C | GLY A | 251 | −30.217 | −1.954 | −20.141 | 1.00 | 15.90 | C |
| ATOM | 1274 | O | GLY A | 251 | −29.698 | −3.073 | −20.134 | 1.00 | 16.41 | O |
| ATOM | 1275 | N | GLY A | 252 | −31.486 | −1.731 | −19.803 | 1.00 | 14.92 | N |
| ATOM | 1276 | CA | GLY A | 252 | −32.408 | −2.807 | −19.431 | 1.00 | 15.30 | C |
| ATOM | 1277 | C | GLY A | 252 | −32.714 | −3.762 | −20.574 | 1.00 | 15.25 | C |
| ATOM | 1278 | O | GLY A | 252 | −33.065 | −4.922 | −20.342 | 1.00 | 14.57 | O |
| ATOM | 1279 | N | ALA A | 253 | −32.592 | −3.264 | −21.805 | 1.00 | 14.87 | N |
| ATOM | 1280 | CA | ALA A | 253 | −32.748 | −4.080 | −23.004 | 1.00 | 15.39 | C |
| ATOM | 1281 | CB | ALA A | 253 | −32.622 | −3.226 | −24.253 | 1.00 | 15.66 | C |
| ATOM | 1282 | C | ALA A | 253 | −31.712 | −5.191 | −23.023 | 1.00 | 15.34 | C |
| ATOM | 1283 | O | ALA A | 253 | −32.023 | −6.329 | −23.352 | 1.00 | 15.66 | O |
| ATOM | 1284 | N | ILE A | 254 | −30.481 | −4.848 | −22.659 | 1.00 | 16.16 | N |
| ATOM | 1285 | CA | ILE A | 254 | −29.387 | −5.820 | −22.602 | 1.00 | 15.70 | C |
| ATOM | 1286 | CB | ILE A | 254 | −28.018 | −5.132 | −22.825 | 1.00 | 16.20 | C |
| ATOM | 1287 | CG1 | ILE A | 254 | −27.931 | −4.670 | −24.287 | 1.00 | 17.82 | C |
| ATOM | 1288 | CD1 | ILE A | 254 | −26.692 | −3.873 | −24.635 | 1.00 | 22.73 | C |
| ATOM | 1289 | CG2 | ILE A | 254 | −26.848 | −6.065 | −22.472 | 1.00 | 16.52 | C |
| ATOM | 1290 | C | ILE A | 254 | −29.456 | −6.689 | −21.336 | 1.00 | 14.55 | C |
| ATOM | 1291 | O | ILE A | 254 | −29.084 | −7.862 | −21.367 | 1.00 | 14.89 | O |
| | | | gad67.pdb | | | | | | | |
| ATOM | 1292 | N | SER A | 255 | −29.962 | −6.125 | −20.240 | 1.00 | 13.40 | N |
| ATOM | 1293 | CA | SER A | 255 | −30.313 | −6.922 | −19.056 | 1.00 | 12.82 | C |
| ATOM | 1294 | CB | SER A | 255 | −30.827 | −6.031 | −17.931 | 1.00 | 12.38 | C |
| ATOM | 1295 | OG | SER A | 255 | −29.773 | −5.250 | −17.399 | 1.00 | 15.16 | O |
| ATOM | 1296 | C | SER A | 255 | −31.337 | −8.017 | −19.381 | 1.00 | 12.42 | C |
| ATOM | 1297 | O | SER A | 255 | −31.149 | −9.173 | −18.999 | 1.00 | 12.43 | O |
| ATOM | 1298 | N | ASN A | 256 | −32.406 | −7.656 | −20.093 | 1.00 | 12.21 | N |
| ATOM | 1299 | CA | ASN A | 256 | −33.354 | −8.644 | −20.618 | 1.00 | 13.22 | C |
| ATOM | 1300 | CB | ASN A | 256 | −34.492 | −7.970 | −21.398 | 1.00 | 12.41 | C |
| ATOM | 1301 | CG | ASN A | 256 | −35.535 | −7.307 | −20.485 | 1.00 | 15.86 | C |
| ATOM | 1302 | OD1 | ASN A | 256 | −36.393 | −6.549 | −20.955 | 1.00 | 18.21 | O |
| ATOM | 1303 | ND2 | ASN A | 256 | −35.465 | −7.585 | −19.189 | 1.00 | 11.14 | N |
| ATOM | 1304 | C | ASN A | 256 | −32.659 | −9.704 | −21.481 | 1.00 | 13.80 | C |
| ATOM | 1305 | O | ASN A | 256 | −32.905 | −10.901 | −21.314 | 1.00 | 13.70 | O |
| ATOM | 1306 | N | MET A | 257 | −31.776 | −9.257 | −22.377 | 1.00 | 14.36 | N |
| ATOM | 1307 | CA | MET A | 257 | −30.996 | −10.155 | −23.238 | 1.00 | 15.19 | C |
| ATOM | 1308 | CB | MET A | 257 | −30.118 | −9.345 | −24.201 | 1.00 | 15.16 | C |
| ATOM | 1309 | CG | MET A | 257 | −29.400 | −10.165 | −25.268 | 1.00 | 16.29 | C |
| ATOM | 1310 | SD | MET A | 257 | −28.330 | −9.178 | −26.340 | 1.00 | 19.22 | S |
| ATOM | 1311 | CE | MET A | 257 | −27.012 | −8.757 | −25.211 | 1.00 | 26.86 | C |
| ATOM | 1312 | C | MET A | 257 | −30.155 | −11.150 | −22.428 | 1.00 | 14.33 | C |
| ATOM | 1313 | O | MET A | 257 | −30.137 | −12.336 | −22.748 | 1.00 | 14.67 | O |
| ATOM | 1314 | N | TYR A | 258 | −29.477 | −10.661 | −21.384 | 1.00 | 14.64 | N |
| ATOM | 1315 | CA | TYR A | 258 | −28.752 | −11.507 | −20.419 | 1.00 | 15.23 | C |
| ATOM | 1316 | CB | TYR A | 258 | −28.270 | −10.685 | −19.220 | 1.00 | 16.67 | C |
| ATOM | 1317 | CG | TYR A | 258 | −26.887 | −10.085 | −19.307 | 1.00 | 19.60 | C |
| ATOM | 1318 | CD1 | TYR A | 258 | −25.747 | −10.883 | −19.198 | 1.00 | 23.41 | C |
| ATOM | 1319 | CE1 | TYR A | 258 | −24.470 | −10.326 | −19.255 | 1.00 | 22.82 | C |
| ATOM | 1320 | CZ | TYR A | 258 | −24.332 | −8.955 | −19.401 | 1.00 | 22.65 | C |
| ATOM | 1321 | OH | TYR A | 258 | −23.078 | −8.391 | −19.458 | 1.00 | 22.85 | O |
| ATOM | 1322 | CE2 | TYR A | 258 | −25.452 | −8.142 | −19.493 | 1.00 | 20.68 | C |
| ATOM | 1323 | CD2 | TYR A | 258 | −26.717 | −8.707 | −19.436 | 1.00 | 18.42 | C |
| ATOM | 1324 | C | TYR A | 258 | −29.621 | −12.635 | −19.860 | 1.00 | 15.30 | C |
| ATOM | 1325 | O | TYR A | 258 | −29.162 | −13.776 | −19.744 | 1.00 | 15.27 | O |
| ATOM | 1326 | N | SER A | 259 | −30.866 | −12.305 | −19.501 | 1.00 | 14.04 | N |
| ATOM | 1327 | CA | SER A | 259 | −31.760 | −13.251 | −18.831 | 1.00 | 14.19 | C |
| ATOM | 1328 | CB | SER A | 259 | −33.009 | −12.547 | −18.297 | 1.00 | 14.14 | C |
| ATOM | 1329 | OG | SER A | 259 | −33.985 | −12.349 | −19.310 | 1.00 | 14.66 | O |

TABLE A-continued

| | | | | | | | | | |
|---|---|---|---|---|---|---|---|---|---|
| ATOM | 1330 | C | SER A | 259 | −32.146 | −14.402 | −19.745 | 1.00 | 14.40 | C |
| ATOM | 1331 | O | SER A | 259 | −32.264 | −15.544 | −19.302 | 1.00 | 15.09 | O |
| ATOM | 1332 | N | ILE A | 260 | −32.331 | −14.092 | −21.023 | 1.00 | 14.79 | N |
| ATOM | 1333 | CA | ILE A | 260 | −32.653 | −15.098 | −22.023 | 1.00 | 14.08 | C |
| ATOM | 1334 | CB | ILE A | 260 | −33.204 | −14.453 | −23.319 | 1.00 | 13.72 | C |
| ATOM | 1335 | CG1 | ILE A | 260 | −34.443 | −13.610 | −22.992 | 1.00 | 12.01 | C |
| ATOM | 1336 | CD1 | ILE A | 260 | −34.880 | −12.648 | −24.086 | 1.00 | 12.13 | C |
| ATOM | 1337 | CG2 | ILE A | 260 | −33.532 | −15.530 | −24.361 | 1.00 | 12.48 | C |
| ATOM | 1338 | C | ILE A | 260 | −31.423 | −15.970 | −22.294 | 1.00 | 15.49 | C |
| ATOM | 1339 | O | ILE A | 260 | −31.536 | −17.188 | −22.448 | 1.00 | 15.56 | O |
| ATOM | 1340 | N | MET A | 261 | −30.251 | −15.342 | −22.322 | 1.00 | 16.34 | N |
| ATOM | 1341 | CA | MET A | 261 | −28.989 | −16.064 | −22.511 | 1.00 | 16.38 | C |
| ATOM | 1342 | CB | MET A | 261 | −27.825 | −15.083 | −22.641 | 1.00 | 15.64 | C |
| ATOM | 1343 | CG | MET A | 261 | −27.820 | −14.313 | −23.950 | 1.00 | 18.54 | C |
| ATOM | 1344 | SD | MET A | 261 | −26.488 | −13.103 | −24.053 | 1.00 | 18.17 | S |
| ATOM | 1345 | CE | MET A | 261 | −25.077 | −14.195 | −24.115 | 1.00 | 17.59 | C |
| ATOM | 1346 | C | MET A | 261 | −28.730 | −17.031 | −21.361 | 1.00 | 15.43 | C |
| ATOM | 1347 | O | MET A | 261 | −28.328 | −18.174 | −21.587 | 1.00 | 13.88 | O |
| ATOM | 1348 | N | ALA A | 262 | −28.976 | −16.557 | −20.138 | 1.00 | 15.18 | N |
| ATOM | 1349 | CA | ALA A | 262 | −28.799 | −17.341 | −18.914 | 1.00 | 14.77 | C |
| ATOM | 1350 | CB | ALA A | 262 | −29.021 | −16.463 | −17.687 | 1.00 | 14.08 | C |
| ATOM | 1351 | C | ALA A | 262 | −29.723 | −18.554 | −18.872 | 1.00 | 14.90 | C |
| ATOM | 1352 | O | ALA A | 262 | −29.274 | −19.666 | −18.609 | 1.00 | 15.31 | O |
| ATOM | 1353 | N | ALA A | 263 | −31.010 | −18.322 | −19.129 | 1.00 | 15.14 | N |
| ATOM | 1354 | CA | ALA A | 263 | −32.022 | −19.376 | −19.194 | 1.00 | 15.35 | C |
| ATOM | 1355 | CB | ALA A | 263 | −33.388 | −18.775 | −19.498 | 1.00 | 14.70 | C |
| ATOM | 1356 | C | ALA A | 263 | −31.676 | −20.429 | −20.242 | 1.00 | 15.48 | C |
| ATOM | 1357 | O | ALA A | 263 | −31.855 | −21.630 | −20.010 | 1.00 | 15.08 | O |
| ATOM | 1358 | N | ARG A | 264 | −31.190 | −19.968 | −21.394 | 1.00 | 15.84 | N |
| ATOM | 1359 | CA | ARG A | 264 | −30.806 | −20.856 | −22.482 | 1.00 | 15.68 | C | gad67.pdb

| | | | | | | | | | |
|---|---|---|---|---|---|---|---|---|---|
| ATOM | 1360 | CB | ARG A | 264 | −30.482 | −20.072 | −23.754 | 1.00 | 15.51 | C |
| ATOM | 1361 | CG | ARG A | 264 | −30.191 | −20.963 | −24.967 | 1.00 | 15.85 | C |
| ATOM | 1362 | CD | ARG A | 264 | −30.080 | −20.157 | −26.236 | 1.00 | 16.49 | C |
| ATOM | 1363 | NE | ARG A | 264 | −28.999 | −19.175 | −26.179 | 1.00 | 17.57 | N |
| ATOM | 1364 | CZ | ARG A | 264 | −28.724 | −18.310 | −27.149 | 1.00 | 15.14 | C |
| ATOM | 1365 | NH1 | ARG A | 264 | −29.440 | −18.304 | −28.266 | 1.00 | 12.76 | N |
| ATOM | 1366 | NH2 | ARG A | 264 | −27.727 | −17.455 | −27.003 | 1.00 | 16.34 | N |
| ATOM | 1367 | C | ARG A | 264 | −29.631 | −21.726 | −22.079 | 1.00 | 15.86 | C |
| ATOM | 1368 | O | ARG A | 264 | −29.627 | −22.917 | −22.362 | 1.00 | 17.21 | O |
| ATOM | 1369 | N | TYR A | 265 | −28.644 | −21.135 | −21.412 | 1.00 | 16.54 | N |
| ATOM | 1370 | CA | TYR A | 265 | −27.482 | −21.885 | −20.941 | 1.00 | 17.11 | C |
| ATOM | 1371 | CB | TYR A | 265 | −26.377 | −20.946 | −20.446 | 1.00 | 17.94 | C |
| ATOM | 1372 | CG | TYR A | 265 | −25.089 | −21.686 | −20.140 | 1.00 | 19.71 | C |
| ATOM | 1373 | CD1 | TYR A | 265 | −24.722 | −21.973 | −18.826 | 1.00 | 18.49 | C |
| ATOM | 1374 | CE1 | TYR A | 265 | −23.548 | −22.670 | −18.546 | 1.00 | 20.70 | C |
| ATOM | 1375 | CZ | TYR A | 265 | −22.737 | −23.094 | −19.592 | 1.00 | 20.50 | C |
| ATOM | 1376 | OH | TYR A | 265 | −21.574 | −23.780 | −19.330 | 1.00 | 22.70 | O |
| ATOM | 1377 | CE2 | TYR A | 265 | −23.085 | −22.824 | −20.904 | 1.00 | 20.23 | C |
| ATOM | 1378 | CD2 | TYR A | 265 | −24.257 | −22.128 | −21.172 | 1.00 | 18.35 | C |
| ATOM | 1379 | C | TYR A | 265 | −27.834 | −22.901 | −19.847 | 1.00 | 17.17 | C |
| ATOM | 1380 | O | TYR A | 265 | −27.281 | −24.001 | −19.813 | 1.00 | 16.54 | O |
| ATOM | 1381 | N | LYS A | 266 | −28.742 | −22.510 | −18.954 | 1.00 | 17.92 | N |
| ATOM | 1382 | CA | LYS A | 266 | −29.218 | −23.364 | −17.867 | 1.00 | 18.34 | C |
| ATOM | 1383 | CB | LYS A | 266 | −30.152 | −22.565 | −16.947 | 1.00 | 18.90 | C |
| ATOM | 1384 | CG | LYS A | 266 | −31.016 | −23.396 | −15.988 | 1.00 | 21.30 | C |
| ATOM | 1385 | CD | LYS A | 266 | −30.414 | −23.510 | −14.593 | 1.00 | 29.11 | C |
| ATOM | 1386 | CE | LYS A | 266 | −29.472 | −24.696 | −14.456 | 1.00 | 33.55 | C |
| ATOM | 1387 | NZ | LYS A | 266 | −29.216 | −25.033 | −13.025 | 1.00 | 34.44 | N |
| ATOM | 1388 | C | LYS A | 266 | −29.929 | −24.608 | −18.407 | 1.00 | 18.47 | C |
| ATOM | 1389 | O | LYS A | 266 | −29.697 | −25.721 | −17.936 | 1.00 | 18.34 | O |
| ATOM | 1390 | N | TYR A | 267 | −30.784 | −24.406 | −19.403 | 1.00 | 18.99 | N |
| ATOM | 1391 | CA | TYR A | 267 | −31.594 | −25.483 | −19.957 | 1.00 | 19.65 | C |
| ATOM | 1392 | CB | TYR A | 267 | −32.961 | −24.946 | −20.392 | 1.00 | 20.81 | C |
| ATOM | 1393 | CG | TYR A | 267 | −33.928 | −24.746 | −19.245 | 1.00 | 24.02 | C |
| ATOM | 1394 | CD1 | TYR A | 267 | −34.829 | −25.749 | −18.888 | 1.00 | 28.09 | C |
| ATOM | 1395 | CE1 | TYR A | 267 | −35.719 | −25.575 | −17.828 | 1.00 | 27.85 | C |
| ATOM | 1396 | CZ | TYR A | 267 | −35.711 | −24.386 | −17.119 | 1.00 | 26.16 | C |
| ATOM | 1397 | OH | TYR A | 267 | −36.591 | −24.210 | −16.075 | 1.00 | 28.79 | O |
| ATOM | 1398 | CE2 | TYR A | 267 | −34.825 | −23.375 | −17.452 | 1.00 | 25.24 | C |
| ATOM | 1399 | CD2 | TYR A | 267 | −33.940 | −23.560 | −18.513 | 1.00 | 23.54 | C |
| ATOM | 1400 | C | TYR A | 267 | −30.917 | −26.225 | −21.111 | 1.00 | 19.09 | C |
| ATOM | 1401 | O | TYR A | 267 | −31.040 | −27.448 | −21.221 | 1.00 | 17.54 | O |
| ATOM | 1402 | N | PHE A | 268 | −30.205 | −25.487 | −21.963 | 1.00 | 18.39 | N |
| ATOM | 1403 | CA | PHE A | 268 | −29.605 | −26.065 | −23.171 | 1.00 | 18.87 | C |
| ATOM | 1404 | CB | PHE A | 268 | −30.443 | −25.708 | −24.405 | 1.00 | 19.78 | C |
| ATOM | 1405 | CG | PHE A | 268 | −31.858 | −26.202 | −24.335 | 1.00 | 22.80 | C |
| ATOM | 1406 | CD1 | PHE A | 268 | −32.174 | −27.499 | −24.721 | 1.00 | 26.57 | C |
| ATOM | 1407 | CE1 | PHE A | 268 | −33.482 | −27.965 | −24.652 | 1.00 | 27.13 | C |
| ATOM | 1408 | CZ | PHE A | 268 | −34.482 | −27.131 | −24.190 | 1.00 | 24.45 | C |

TABLE A-continued

| | | | | | | | | | |
|---|---|---|---|---|---|---|---|---|---|
| ATOM | 1409 | CE2 | PHE A | 268 | −34.179 | −25.833 | −23.799 | 1.00 | 25.78 | C |
| ATOM | 1410 | CD2 | PHE A | 268 | −32.874 | −25.375 | −23.874 | 1.00 | 22.90 | C |
| ATOM | 1411 | C | PHE A | 268 | −28.168 | −25.599 | −23.369 | 1.00 | 18.13 | C |
| ATOM | 1412 | O | PHE A | 268 | −27.892 | −24.855 | −24.313 | 1.00 | 18.00 | O |
| ATOM | 1413 | N | PRO A | 269 | −27.248 | −26.038 | −22.484 | 1.00 | 17.44 | N |
| ATOM | 1414 | CA | PRO A | 269 | −25.867 | −25.549 | −22.512 | 1.00 | 18.08 | C |
| ATOM | 1415 | CB | PRO A | 269 | −25.229 | −26.212 | −21.284 | 1.00 | 18.15 | C |
| ATOM | 1416 | CG | PRO A | 269 | −26.074 | −27.414 | −21.016 | 1.00 | 17.65 | C |
| ATOM | 1417 | CD | PRO A | 269 | −27.461 | −27.015 | −21.396 | 1.00 | 17.12 | C |
| ATOM | 1418 | C | PRO A | 269 | −25.091 | −25.906 | −23.787 | 1.00 | 19.01 | C |
| ATOM | 1419 | O | PRO A | 269 | −24.031 | −25.319 | −24.041 | 1.00 | 19.15 | O |
| ATOM | 1420 | N | GLU A | 270 | −25.622 | −26.844 | −24.573 | 1.00 | 18.50 | N |
| ATOM | 1421 | CA | GLU A | 270 | −25.002 | −27.261 | −25.834 | 1.00 | 19.32 | C |
| ATOM | 1422 | CB | GLU A | 270 | −25.606 | −28.581 | −26.346 | 1.00 | 19.41 | C |
| ATOM | 1423 | CG | GLU A | 270 | −27.107 | −28.554 | −26.630 | 1.00 | 21.79 | C |
| ATOM | 1424 | CD | GLU A | 270 | −27.962 | −29.004 | −25.446 | 1.00 | 26.52 | C |
| ATOM | 1425 | OE1 | GLU A | 270 | −27.549 | −28.820 | −24.275 | 1.00 | 23.40 | O |
| ATOM | 1426 | OE2 | GLU A | 270 | −29.064 | −29.544 | −25.692 | 1.00 | 28.68 | O |
| ATOM | 1427 | C | GLU A | 270 | −25.069 | −26.180 | −26.920 | 1.00 | 19.66 | C |
| | | | | | gad67.pdb | | | | | |
| ATOM | 1428 | O | GLU A | 270 | −24.278 | −26.203 | −27.869 | 1.00 | 19.00 | O |
| ATOM | 1429 | N | VAL A | 271 | −26.007 | −25.240 | −26.775 | 1.00 | 19.39 | N |
| ATOM | 1430 | CA | VAL A | 271 | −26.153 | −24.131 | −27.726 | 1.00 | 18.44 | C |
| ATOM | 1431 | CB | VAL A | 271 | −27.366 | −23.218 | −27.374 | 1.00 | 18.55 | C |
| ATOM | 1432 | CG1 | VAL A | 271 | −27.337 | −21.903 | −28.167 | 1.00 | 16.24 | C |
| ATOM | 1433 | CG2 | VAL A | 271 | −28.664 | −23.949 | −27.635 | 1.00 | 18.19 | C |
| ATOM | 1434 | C | VAL A | 271 | −24.863 | −23.311 | −27.845 | 1.00 | 17.82 | C |
| ATOM | 1435 | O | VAL A | 271 | −24.468 | −22.930 | −28.946 | 1.00 | 18.00 | O |
| ATOM | 1436 | N | LYS A | 272 | −24.214 | −23.056 | −26.711 | 1.00 | 17.33 | N |
| ATOM | 1437 | CA | LYS A | 272 | −22.970 | −22.284 | −26.669 | 1.00 | 17.19 | C |
| ATOM | 1438 | CB | LYS A | 272 | −22.385 | −22.285 | −25.249 | 1.00 | 16.45 | C |
| ATOM | 1439 | CG | LYS A | 272 | −21.170 | −21.375 | −25.098 | 1.00 | 18.13 | C |
| ATOM | 1440 | CD | LYS A | 272 | −20.664 | −21.279 | −23.676 | 1.00 | 16.36 | C |
| ATOM | 1441 | CE | LYS A | 272 | −19.497 | −20.303 | −23.618 | 1.00 | 15.66 | C |
| ATOM | 1442 | NZ | LYS A | 272 | −18.963 | −20.103 | −22.242 | 1.00 | 15.79 | N |
| ATOM | 1443 | C | LYS A | 272 | −21.916 | −22.758 | −27.695 | 1.00 | 17.86 | C |
| ATOM | 1444 | O | LYS A | 272 | −21.277 | −21.936 | −28.356 | 1.00 | 16.39 | O |
| ATOM | 1445 | N | THR A | 273 | −21.755 | −24.077 | −27.822 | 1.00 | 17.93 | N |
| ATOM | 1446 | CA | THR A | 273 | −20.767 | −24.661 | −28.730 | 1.00 | 18.67 | C |
| ATOM | 1447 | CB | THR A | 273 | −20.051 | −25.892 | −28.107 | 1.00 | 19.27 | C |
| ATOM | 1448 | OG1 | THR A | 273 | −21.023 | −26.814 | −27.596 | 1.00 | 20.16 | O |
| ATOM | 1449 | CG2 | THR A | 273 | −19.106 | −25.470 | −26.977 | 1.00 | 16.84 | C |
| ATOM | 1450 | C | THR A | 273 | −21.350 | −25.061 | −30.082 | 1.00 | 19.00 | C |
| ATOM | 1451 | O | THR A | 273 | −20.700 | −24.896 | −31.113 | 1.00 | 19.20 | O |
| ATOM | 1452 | N | LYS A | 274 | −22.572 | −25.586 | −30.081 | 1.00 | 19.12 | N |
| ATOM | 1453 | CA | LYS A | 274 | −23.153 | −26.165 | −31.295 | 1.00 | 19.37 | C |
| ATOM | 1454 | CB | LYS A | 274 | −23.919 | −27.443 | −30.965 | 1.00 | 19.34 | C |
| ATOM | 1455 | CG | LYS A | 274 | −23.034 | −28.628 | −30.635 | 1.00 | 20.83 | C |
| ATOM | 1456 | CD | LYS A | 274 | −23.874 | −29.828 | −30.227 | 1.00 | 25.26 | C |
| ATOM | 1457 | CE | LYS A | 274 | −23.029 | −31.088 | −30.101 | 1.00 | 30.78 | C |
| ATOM | 1458 | NZ | LYS A | 274 | −21.990 | −30.966 | −29.048 | 1.00 | 35.36 | N |
| ATOM | 1459 | C | LYS A | 274 | −24.046 | −25.207 | −32.078 | 1.00 | 19.36 | C |
| ATOM | 1460 | O | LYS A | 274 | −24.202 | −25.348 | −33.298 | 1.00 | 19.57 | O |
| ATOM | 1461 | N | GLY A | 275 | −24.628 | −24.239 | −31.379 | 1.00 | 17.52 | N |
| ATOM | 1462 | CA | GLY A | 275 | −25.524 | −23.289 | −32.011 | 1.00 | 18.14 | C |
| ATOM | 1463 | C | GLY A | 275 | −26.974 | −23.676 | −31.813 | 1.00 | 18.44 | C |
| ATOM | 1464 | O | GLY A | 275 | −27.275 | −24.763 | −31.315 | 1.00 | 17.58 | O |
| ATOM | 1465 | N | MET A | 276 | −27.867 | −22.778 | −32.219 | 1.00 | 18.63 | N |
| ATOM | 1466 | CA | MET A | 276 | −29.306 | −22.955 | −32.056 | 1.00 | 18.68 | C |
| ATOM | 1467 | CB | MET A | 276 | −30.035 | −21.654 | −32.392 | 1.00 | 18.12 | C |
| ATOM | 1468 | CG | MET A | 276 | −29.953 | −20.610 | −31.299 | 1.00 | 17.91 | C |
| ATOM | 1469 | SD | MET A | 276 | −30.849 | −21.077 | −29.798 | 1.00 | 17.82 | S |
| ATOM | 1470 | CE | MET A | 276 | −32.540 | −20.826 | −30.327 | 1.00 | 19.15 | C |
| ATOM | 1471 | C | MET A | 276 | −29.893 | −24.107 | −32.867 | 1.00 | 19.68 | C |
| ATOM | 1472 | O | MET A | 276 | −30.938 | −24.654 | −32.501 | 1.00 | 21.14 | O |
| ATOM | 1473 | N | ALA A | 277 | −29.224 | −24.485 | −33.956 | 1.00 | 20.29 | N |
| ATOM | 1474 | CA | ALA A | 277 | −29.699 | −25.586 | −34.809 | 1.00 | 20.80 | C |
| ATOM | 1475 | CB | ALA A | 277 | −28.987 | −25.576 | −36.156 | 1.00 | 20.21 | C |
| ATOM | 1476 | C | ALA A | 277 | −29.578 | −26.960 | −34.142 | 1.00 | 21.72 | C |
| ATOM | 1477 | O | ALA A | 277 | −30.138 | −27.940 | −34.634 | 1.00 | 22.73 | O |
| ATOM | 1478 | N | ALA A | 278 | −28.845 | −27.022 | −33.030 | 1.00 | 22.65 | N |
| ATOM | 1479 | CA | ALA A | 278 | −28.681 | −28.248 | −32.251 | 1.00 | 24.25 | C |
| ATOM | 1480 | CB | ALA A | 278 | −27.384 | −28.201 | −31.466 | 1.00 | 23.46 | C |
| ATOM | 1481 | C | ALA A | 278 | −29.863 | −28.512 | −31.308 | 1.00 | 26.11 | C |
| ATOM | 1482 | O | ALA A | 278 | −30.046 | −29.639 | −30.844 | 1.00 | 26.20 | O |
| ATOM | 1483 | N | VAL A | 279 | −30.633 | −27.467 | −31.006 | 1.00 | 28.65 | N |
| ATOM | 1484 | CA | VAL A | 279 | −31.885 | −27.597 | −30.248 | 1.00 | 31.36 | C |
| ATOM | 1485 | CB | VAL A | 279 | −31.769 | −27.076 | −28.779 | 1.00 | 31.23 | C |
| ATOM | 1486 | CG1 | VAL A | 279 | −30.737 | −27.867 | −27.999 | 1.00 | 31.07 | C |
| ATOM | 1487 | CG2 | VAL A | 279 | −31.439 | −25.595 | −28.742 | 1.00 | 31.04 | C |

TABLE A-continued

| | | | | | | | | | |
|---|---|---|---|---|---|---|---|---|---|
| ATOM | 1488 | C | VAL A | 279 | −33.015 | −26.861 | −30.981 | 1.00 | 33.62 | C |
| ATOM | 1489 | O | VAL A | 279 | −33.363 | −25.725 | −30.630 | 1.00 | 33.96 | O |
| ATOM | 1490 | N | PRO A | 280 | −33.582 | −27.496 | −32.020 | 1.00 | 34.70 | N |
| ATOM | 1491 | CA | PRO A | 280 | −34.597 | −26.805 | −32.821 | 1.00 | 35.27 | C |
| ATOM | 1492 | CB | PRO A | 280 | −34.991 | −27.851 | −33.876 | 1.00 | 35.43 | C |
| ATOM | 1493 | CG | PRO A | 280 | −33.817 | −28.775 | −33.948 | 1.00 | 36.67 | C |
| ATOM | 1494 | CD | PRO A | 280 | −33.315 | −28.852 | −32.531 | 1.00 | 36.09 | C |
| ATOM | 1495 | C | PRO A | 280 | −35.824 | −26.346 | −32.020 | 1.00 | 34.47 | C |
| | | | gad67.pdb | | | | | | | |
| ATOM | 1496 | O | PRO A | 280 | −36.203 | −26.974 | −31.030 | 1.00 | 34.07 | O |
| ATOM | 1497 | N | LYS A | 281 | −36.396 | −25.230 | −32.461 | 1.00 | 33.97 | N |
| ATOM | 1498 | CA | LYS A | 281 | −37.654 | −24.674 | −31.954 | 1.00 | 32.64 | C |
| ATOM | 1499 | CB | LYS A | 281 | −38.856 | −25.368 | −32.608 | 1.00 | 34.91 | C |
| ATOM | 1500 | CG | LYS A | 281 | −39.603 | −24.499 | −33.644 | 1.00 | 38.16 | C |
| ATOM | 1501 | CD | LYS A | 281 | −38.708 | −23.855 | −34.707 | 1.00 | 41.99 | C |
| ATOM | 1502 | CE | LYS A | 281 | −39.533 | −22.922 | −35.591 | 1.00 | 42.09 | C |
| ATOM | 1503 | NZ | LYS A | 281 | −38.706 | −21.954 | −36.376 | 1.00 | 45.46 | N |
| ATOM | 1504 | C | LYS A | 281 | −37.817 | −24.519 | −30.433 | 1.00 | 30.35 | C |
| ATOM | 1505 | O | LYS A | 281 | −38.696 | −25.125 | −29.814 | 1.00 | 29.61 | O |
| ATOM | 1506 | N | LEU A | 282 | −36.947 | −23.694 | −29.855 | 1.00 | 27.81 | N |
| ATOM | 1507 | CA | LEU A | 282 | −37.141 | −23.132 | −28.526 | 1.00 | 25.30 | C |
| ATOM | 1508 | CB | LEU A | 282 | −35.800 | −22.675 | −27.944 | 1.00 | 25.66 | C |
| ATOM | 1509 | CG | LEU A | 282 | −34.964 | −23.557 | −27.008 | 1.00 | 27.12 | C |
| ATOM | 1510 | CD1 | LEU A | 282 | −35.012 | −25.035 | −27.369 | 1.00 | 27.73 | C |
| ATOM | 1511 | CD2 | LEU A | 282 | −33.523 | −23.060 | −26.972 | 1.00 | 25.31 | C |
| ATOM | 1512 | C | LEU A | 282 | −38.062 | −21.927 | −28.679 | 1.00 | 23.19 | C |
| ATOM | 1513 | O | LEU A | 282 | −37.931 | −21.168 | −29.646 | 1.00 | 21.88 | O |
| ATOM | 1514 | N | VAL A | 283 | −39.002 | −21.768 | −27.748 | 1.00 | 21.31 | N |
| ATOM | 1515 | CA | VAL A | 283 | −39.893 | −20.598 | −27.750 | 1.00 | 21.04 | C |
| ATOM | 1516 | CB | VAL A | 283 | −41.389 | −20.956 | −28.037 | 1.00 | 20.53 | C |
| ATOM | 1517 | CG1 | VAL A | 283 | −41.524 | −21.762 | −29.326 | 1.00 | 21.12 | C |
| ATOM | 1518 | CG2 | VAL A | 283 | −42.025 | −21.693 | −26.868 | 1.00 | 20.69 | C |
| ATOM | 1519 | C | VAL A | 283 | −39.775 | −19.760 | −26.469 | 1.00 | 20.50 | C |
| ATOM | 1520 | O | VAL A | 283 | −39.443 | −20.280 | −25.404 | 1.00 | 19.79 | O |
| ATOM | 1521 | N | LEU A | 284 | −40.031 | −18.460 | −26.601 | 1.00 | 20.21 | N |
| ATOM | 1522 | CA | LEU A | 284 | −40.064 | −17.536 | −25.469 | 1.00 | 19.80 | C |
| ATOM | 1523 | CB | LEU A | 284 | −39.132 | −16.339 | −25.700 | 1.00 | 19.77 | C |
| ATOM | 1524 | CG | LEU A | 284 | −37.668 | −16.495 | −26.112 | 1.00 | 21.50 | C |
| ATOM | 1525 | CD1 | LEU A | 284 | −37.554 | −16.897 | −27.565 | 1.00 | 23.04 | C |
| ATOM | 1526 | CD2 | LEU A | 284 | −36.958 | −15.177 | −25.905 | 1.00 | 22.05 | C |
| ATOM | 1527 | C | LEU A | 284 | −41.487 | −17.017 | −25.327 | 1.00 | 18.43 | C |
| ATOM | 1528 | O | LEU A | 284 | −42.187 | −16.846 | −26.326 | 1.00 | 17.92 | O |
| ATOM | 1529 | N | PHE A | 285 | −41.904 | −16.756 | −24.092 | 1.00 | 16.99 | N |
| ATOM | 1530 | CA | PHE A | 285 | −43.209 | −16.161 | −23.832 | 1.00 | 16.00 | C |
| ATOM | 1531 | CB | PHE A | 285 | −44.072 | −17.070 | −22.951 | 1.00 | 16.02 | C |
| ATOM | 1532 | CG | PHE A | 285 | −44.458 | −18.356 | −23.612 | 1.00 | 15.42 | C |
| ATOM | 1533 | CD1 | PHE A | 285 | −43.770 | −19.529 | −23.326 | 1.00 | 14.81 | C |
| ATOM | 1534 | CE1 | PHE A | 285 | −44.114 | −20.721 | −23.943 | 1.00 | 14.99 | C |
| ATOM | 1535 | CZ | PHE A | 285 | −45.157 | −20.753 | −24.859 | 1.00 | 15.28 | C |
| ATOM | 1536 | CE2 | PHE A | 285 | −45.852 | −19.586 | −25.158 | 1.00 | 15.77 | C |
| ATOM | 1537 | CD2 | PHE A | 285 | −45.500 | −18.394 | −24.533 | 1.00 | 14.50 | C |
| ATOM | 1538 | C | PHE A | 285 | −43.079 | −14.789 | −23.198 | 1.00 | 15.49 | C |
| ATOM | 1539 | O | PHE A | 285 | −42.246 | −14.578 | −22.318 | 1.00 | 14.95 | O |
| ATOM | 1540 | N | THR A | 286 | −43.917 | −13.865 | −23.656 | 1.00 | 14.96 | N |
| ATOM | 1541 | CA | THR A | 286 | −43.943 | −12.507 | −23.142 | 1.00 | 15.70 | C |
| ATOM | 1542 | CB | THR A | 286 | −42.781 | −11.637 | −23.739 | 1.00 | 15.50 | C |
| ATOM | 1543 | OG1 | THR A | 286 | −42.619 | −10.441 | −22.965 | 1.00 | 15.66 | O |
| ATOM | 1544 | CG2 | THR A | 286 | −43.035 | −11.278 | −25.193 | 1.00 | 14.15 | C |
| ATOM | 1545 | C | THR A | 286 | −45.318 | −11.884 | −23.399 | 1.00 | 16.95 | C |
| ATOM | 1546 | O | THR A | 286 | −46.058 | −12.327 | −24.286 | 1.00 | 17.43 | O |
| ATOM | 1547 | N | SER A | 287 | −45.661 | −10.875 | −22.607 | 1.00 | 18.22 | N |
| ATOM | 1548 | CA | SER A | 287 | −46.927 | −10.160 | −22.759 | 1.00 | 20.00 | C |
| ATOM | 1549 | CB | SER A | 287 | −47.098 | −9.175 | −21.602 | 1.00 | 20.53 | C |
| ATOM | 1550 | OG | SER A | 287 | −48.227 | −8.348 | −21.781 | 1.00 | 21.67 | O |
| ATOM | 1551 | C | SER A | 287 | −47.013 | −9.405 | −24.087 | 1.00 | 21.13 | C |
| ATOM | 1552 | O | SER A | 287 | −45.993 | −8.972 | −24.635 | 1.00 | 21.51 | O |
| ATOM | 1553 | N | GLU A | 288 | −48.236 | −9.243 | −24.588 | 1.00 | 21.82 | N |
| ATOM | 1554 | CA | GLU A | 288 | −48.511 | −8.370 | −25.731 | 1.00 | 23.91 | C |
| ATOM | 1555 | CB | GLU A | 288 | −50.007 | −8.370 | −26.060 | 1.00 | 23.61 | C |
| ATOM | 1556 | CG | GLU A | 288 | −50.499 | −9.585 | −26.819 | 1.00 | 28.19 | C |
| ATOM | 1557 | CD | GLU A | 288 | −52.017 | −9.618 | −26.980 | 1.00 | 28.30 | C |
| ATOM | 1558 | OE1 | GLU A | 288 | −52.733 | −8.888 | −26.250 | 1.00 | 32.28 | O |
| ATOM | 1559 | OE2 | GLU A | 288 | −52.493 | −10.390 | −27.844 | 1.00 | 33.37 | O |
| ATOM | 1560 | C | GLU A | 288 | −48.073 | −6.928 | −25.457 | 1.00 | 23.16 | C |
| ATOM | 1561 | O | GLU A | 288 | −47.809 | −6.166 | −26.388 | 1.00 | 23.48 | O |
| ATOM | 1562 | N | GLN A | 289 | −48.010 | −6.560 | −24.178 | 1.00 | 22.71 | N |
| ATOM | 1563 | CA | GLN A | 289 | −47.667 | −5.200 | −23.771 | 1.00 | 22.21 | C |
| | | | gad67.pdb | | | | | | | |
| ATOM | 1564 | CB | GLN A | 289 | −48.792 | −4.618 | −22.908 | 1.00 | 22.32 | C |
| ATOM | 1565 | CG | GLN A | 289 | −50.099 | −4.458 | −23.684 | 1.00 | 22.47 | C |

TABLE A-continued

| | | | | | | | | | | |
|---|---|---|---|---|---|---|---|---|---|---|
| ATOM | 1566 | CD | GLN A | 289 | −51.209 | −3.809 | −22.889 | 1.00 | 23.40 | C |
| ATOM | 1567 | OE1 | GLN A | 289 | −52.374 | −4.183 | −23.023 | 1.00 | 29.42 | O |
| ATOM | 1568 | NE2 | GLN A | 289 | −50.862 | −2.829 | −22.063 | 1.00 | 24.43 | N |
| ATOM | 1569 | C | GLN A | 289 | −46.303 | −5.103 | −23.075 | 1.00 | 21.28 | C |
| ATOM | 1570 | O | GLN A | 289 | −45.978 | −4.089 | −22.449 | 1.00 | 21.12 | O |
| ATOM | 1571 | N | SER A | 290 | −45.502 | −6.158 | −23.206 | 1.00 | 19.80 | N |
| ATOM | 1572 | CA | SER A | 290 | −44.144 | −6.162 | −22.680 | 1.00 | 19.51 | C |
| ATOM | 1573 | CB | SER A | 290 | −43.622 | −7.590 | −22.550 | 1.00 | 20.05 | C |
| ATOM | 1574 | OG | SER A | 290 | −43.441 | −8.189 | −23.820 | 1.00 | 20.92 | O |
| ATOM | 1575 | C | SER A | 290 | −43.218 | −5.344 | −23.578 | 1.00 | 18.92 | C |
| ATOM | 1576 | O | SER A | 290 | −43.578 | −4.998 | −24.705 | 1.00 | 17.93 | O |
| ATOM | 1577 | N | HIS A | 291 | −42.028 | −5.042 | −23.067 | 1.00 | 18.19 | N |
| ATOM | 1578 | CA | HIS A | 291 | −41.052 | −4.238 | −23.793 | 1.00 | 17.77 | C |
| ATOM | 1579 | CB | HIS A | 291 | −39.923 | −3.804 | −22.855 | 1.00 | 17.29 | C |
| ATOM | 1580 | CG | HIS A | 291 | −39.057 | −2.727 | −23.420 | 1.00 | 17.42 | C |
| ATOM | 1581 | ND1 | HIS A | 291 | −37.863 | −2.991 | −24.053 | 1.00 | 19.90 | N |
| ATOM | 1582 | CE1 | HIS A | 291 | −37.319 | −1.857 | −24.455 | 1.00 | 16.42 | C |
| ATOM | 1583 | NE2 | HIS A | 291 | −38.118 | −.867 | −24.102 | 1.00 | 18.31 | N |
| ATOM | 1584 | CD2 | HIS A | 291 | −39.215 | −1.385 | −23.459 | 1.00 | 15.64 | C |
| ATOM | 1585 | C | HIS A | 291 | −40.484 | −4.986 | −25.002 | 1.00 | 17.21 | C |
| ATOM | 1586 | O | HIS A | 291 | −40.205 | −6.187 | −24.927 | 1.00 | 15.04 | O |
| ATOM | 1587 | N | TYR A | 292 | −40.297 | −4.251 | −26.099 | 1.00 | 18.73 | N |
| ATOM | 1588 | CA | TYR A | 292 | −39.856 | −4.819 | −27.380 | 1.00 | 19.87 | C |
| ATOM | 1589 | CB | TYR A | 292 | −39.930 | −3.769 | −28.500 | 1.00 | 21.31 | C |
| ATOM | 1590 | CG | TYR A | 292 | −38.901 | −2.654 | −28.417 | 1.00 | 24.15 | C |
| ATOM | 1591 | CD1 | TYR A | 292 | −39.163 | −1.491 | −27.699 | 1.00 | 26.13 | C |
| ATOM | 1592 | CE1 | TYR A | 292 | −38.231 | −.460 | −27.628 | 1.00 | 27.12 | C |
| ATOM | 1593 | CZ | TYR A | 292 | −37.021 | −.585 | −28.283 | 1.00 | 27.66 | C |
| ATOM | 1594 | OH | TYR A | 292 | −36.102 | .433 | −28.208 | 1.00 | 28.74 | O |
| ATOM | 1595 | CE2 | TYR A | 292 | −36.730 | −1.730 | −29.005 | 1.00 | 28.55 | C |
| ATOM | 1596 | CD2 | TYR A | 292 | −37.675 | −2.756 | −29.076 | 1.00 | 28.16 | C |
| ATOM | 1597 | C | TYR A | 292 | −38.476 | −5.483 | −27.349 | 1.00 | 19.66 | C |
| ATOM | 1598 | O | TYR A | 292 | −38.097 | −6.170 | −28.296 | 1.00 | 19.61 | O |
| ATOM | 1599 | N | SER A | 293 | −37.739 | −5.282 | −26.258 | 1.00 | 19.51 | N |
| ATOM | 1600 | CA | SER A | 293 | −36.401 | −5.851 | −26.111 | 1.00 | 19.55 | C |
| ATOM | 1601 | CB | SER A | 293 | −35.673 | −5.264 | −24.897 | 1.00 | 19.41 | C |
| ATOM | 1602 | OG | SER A | 293 | −36.396 | −5.463 | −23.697 | 1.00 | 20.36 | O |
| ATOM | 1603 | C | SER A | 293 | −36.398 | −7.379 | −26.062 | 1.00 | 19.24 | C |
| ATOM | 1604 | O | SER A | 293 | −35.376 | −8.002 | −26.359 | 1.00 | 19.76 | O |
| ATOM | 1605 | N | ILE A | 294 | −37.538 | −7.974 | −25.702 | 1.00 | 17.86 | N |
| ATOM | 1606 | CA | ILE A | 294 | −37.681 | −9.433 | −25.711 | 1.00 | 17.06 | C |
| ATOM | 1607 | CB | ILE A | 294 | −38.961 | −9.925 | −24.958 | 1.00 | 17.65 | C |
| ATOM | 1608 | CG1 | ILE A | 294 | −39.033 | −9.359 | −23.527 | 1.00 | 15.19 | C |
| ATOM | 1609 | CD1 | ILE A | 294 | −37.854 | −9.727 | −22.617 | 1.00 | 16.11 | C |
| ATOM | 1610 | CG2 | ILE A | 294 | −39.043 | −11.463 | −24.958 | 1.00 | 14.94 | C |
| ATOM | 1611 | C | ILE A | 294 | −37.658 | −9.970 | −27.144 | 1.00 | 16.92 | C |
| ATOM | 1612 | O | ILE A | 294 | −36.907 | −10.896 | −27.444 | 1.00 | 17.19 | O |
| ATOM | 1613 | N | LYS A | 295 | −38.480 | −9.384 | −28.015 | 1.00 | 17.39 | N |
| ATOM | 1614 | CA | LYS A | 295 | −38.490 | −9.711 | −29.447 | 1.00 | 18.57 | C |
| ATOM | 1615 | CB | LYS A | 295 | −39.573 | −8.905 | −30.174 | 1.00 | 18.55 | C |
| ATOM | 1616 | CG | LYS A | 295 | −40.985 | −9.453 | −30.035 | 1.00 | 22.85 | C |
| ATOM | 1617 | CD | LYS A | 295 | −41.310 | −10.478 | −31.114 | 1.00 | 24.37 | C |
| ATOM | 1618 | CE | LYS A | 295 | −42.748 | −10.954 | −30.987 | 1.00 | 22.57 | C |
| ATOM | 1619 | NZ | LYS A | 295 | −43.102 | −11.924 | −32.047 | 1.00 | 21.83 | N |
| ATOM | 1620 | C | LYS A | 295 | −37.139 | −9.434 | −30.102 | 1.00 | 18.67 | C |
| ATOM | 1621 | O | LYS A | 295 | −36.666 | −10.212 | −30.934 | 1.00 | 19.07 | O |
| ATOM | 1622 | N | LYS A | 296 | −36.528 | −8.321 | −29.707 | 1.00 | 18.84 | N |
| ATOM | 1623 | CA | LYS A | 296 | −35.230 | −7.898 | −30.217 | 1.00 | 19.76 | C |
| ATOM | 1624 | CB | LYS A | 296 | −34.899 | −6.513 | −29.673 | 1.00 | 21.08 | C |
| ATOM | 1625 | CG | LYS A | 296 | −34.125 | −5.629 | −30.628 | 1.00 | 28.06 | C |
| ATOM | 1626 | CD | LYS A | 296 | −34.668 | −4.211 | −30.584 | 1.00 | 32.24 | C |
| ATOM | 1627 | CE | LYS A | 296 | −33.780 | −3.263 | −31.354 | 1.00 | 35.80 | C |
| ATOM | 1628 | NZ | LYS A | 296 | −34.507 | −2.048 | −31.811 | 1.00 | 37.10 | N |
| ATOM | 1629 | C | LYS A | 296 | −34.140 | −8.902 | −29.849 | 1.00 | 19.09 | C |
| ATOM | 1630 | O | LYS A | 296 | −33.330 | −9.282 | −30.696 | 1.00 | 18.30 | O |
| ATOM | 1631 | N | ALA A | 297 | −34.139 | −9.342 | −28.592 | 1.00 | 18.11 | N |
| | | | gad67.pdb | | | | | | | |
| ATOM | 1632 | CA | ALA A | 297 | −33.216 | −10.387 | −28.141 | 1.00 | 18.09 | C |
| ATOM | 1633 | CB | ALA A | 297 | −33.228 | −10.508 | −26.623 | 1.00 | 17.70 | C |
| ATOM | 1634 | C | ALA A | 297 | −33.532 | −11.734 | −28.796 | 1.00 | 17.84 | C |
| ATOM | 1635 | O | ALA A | 297 | −32.619 | −12.476 | −29.165 | 1.00 | 17.39 | O |
| ATOM | 1636 | N | GLY A | 298 | −34.823 | −12.033 | −28.950 | 1.00 | 16.32 | N |
| ATOM | 1637 | CA | GLY A | 298 | −35.263 | −13.213 | −29.689 | 1.00 | 16.26 | C |
| ATOM | 1638 | C | GLY A | 298 | −34.646 | −13.293 | −31.074 | 1.00 | 16.64 | C |
| ATOM | 1639 | O | GLY A | 298 | −34.100 | −14.330 | −31.460 | 1.00 | 18.01 | O |
| ATOM | 1640 | N | ALA A | 299 | −34.726 | −12.189 | −31.817 | 1.00 | 16.55 | N |
| ATOM | 1641 | CA | ALA A | 299 | −34.151 | −12.100 | −33.158 | 1.00 | 15.30 | C |
| ATOM | 1642 | CB | ALA A | 299 | −34.586 | −10.812 | −33.838 | 1.00 | 14.81 | C |
| ATOM | 1643 | C | ALA A | 299 | −32.629 | −12.199 | −33.129 | 1.00 | 15.36 | C |
| ATOM | 1644 | O | ALA A | 299 | −32.038 | −12.976 | −33.881 | 1.00 | 15.65 | O |

TABLE A-continued

| | | | | | | | | | | |
|---|---|---|---|---|---|---|---|---|---|---|
| ATOM | 1645 | N | ALA A | 300 | −32.008 | −11.416 | −32.250 | 1.00 | 14.70 | N |
| ATOM | 1646 | CA | ALA A | 300 | −30.553 | −11.331 | −32.171 | 1.00 | 14.50 | C |
| ATOM | 1647 | CB | ALA A | 300 | −30.139 | −10.224 | −31.207 | 1.00 | 14.45 | C |
| ATOM | 1648 | C | ALA A | 300 | −29.891 | −12.659 | −31.783 | 1.00 | 14.57 | C |
| ATOM | 1649 | O | ALA A | 300 | −28.870 | −13.034 | −32.365 | 1.00 | 14.39 | O |
| ATOM | 1650 | N | LEU A | 301 | −30.485 | −13.357 | −30.813 | 1.00 | 13.68 | N |
| ATOM | 1651 | CA | LEU A | 301 | −29.917 | −14.585 | −30.240 | 1.00 | 13.44 | C |
| ATOM | 1652 | CB | LEU A | 301 | −30.376 | −14.762 | −28.784 | 1.00 | 12.78 | C |
| ATOM | 1653 | CG | LEU A | 301 | −30.123 | −13.600 | −27.812 | 1.00 | 14.03 | C |
| ATOM | 1654 | CD1 | LEU A | 301 | −30.890 | −13.795 | −26.504 | 1.00 | 11.82 | C |
| ATOM | 1655 | CD2 | LEU A | 301 | −28.640 | −13.387 | −27.546 | 1.00 | 9.89 | C |
| ATOM | 1656 | C | LEU A | 301 | −30.181 | −15.870 | −31.047 | 1.00 | 13.54 | C |
| ATOM | 1657 | O | LEU A | 301 | −29.677 | −16.942 | −30.697 | 1.00 | 13.95 | O |
| ATOM | 1658 | N | GLY A | 302 | −30.968 | −15.762 | −32.116 | 1.00 | 13.42 | N |
| ATOM | 1659 | CA | GLY A | 302 | −31.166 | −16.874 | −33.049 | 1.00 | 13.35 | C |
| ATOM | 1660 | C | GLY A | 302 | −32.439 | −17.683 | −32.869 | 1.00 | 13.51 | C |
| ATOM | 1661 | O | GLY A | 302 | −32.592 | −18.747 | −33.471 | 1.00 | 13.10 | O |
| ATOM | 1662 | N | PHE A | 303 | −33.353 | −17.182 | −32.041 | 1.00 | 14.31 | N |
| ATOM | 1663 | CA | PHE A | 303 | −34.642 | −17.840 | −31.809 | 1.00 | 14.27 | C |
| ATOM | 1664 | CB | PHE A | 303 | −35.281 | −17.332 | −30.511 | 1.00 | 14.20 | C |
| ATOM | 1665 | CG | PHE A | 303 | −34.556 | −17.749 | −29.257 | 1.00 | 14.22 | C |
| ATOM | 1666 | CD1 | PHE A | 303 | −34.915 | −18.915 | −28.586 | 1.00 | 13.08 | C |
| ATOM | 1667 | CE1 | PHE A | 303 | −34.261 | −19.295 | −27.421 | 1.00 | 13.62 | C |
| ATOM | 1668 | CZ | PHE A | 303 | −33.241 | −18.500 | −26.907 | 1.00 | 12.77 | C |
| ATOM | 1669 | CE2 | PHE A | 303 | −32.879 | −17.333 | −27.563 | 1.00 | 10.87 | C |
| ATOM | 1670 | CD2 | PHE A | 303 | −33.540 | −16.961 | −28.730 | 1.00 | 12.65 | C |
| ATOM | 1671 | C | PHE A | 303 | −35.615 | −17.588 | −32.957 | 1.00 | 14.62 | C |
| ATOM | 1672 | O | PHE A | 303 | −36.433 | −18.449 | −33.288 | 1.00 | 15.79 | O |
| ATOM | 1673 | N | GLY A | 304 | −35.530 | −16.397 | −33.549 | 1.00 | 14.21 | N |
| ATOM | 1674 | CA | GLY A | 304 | −36.515 | −15.936 | −34.523 | 1.00 | 14.22 | C |
| ATOM | 1675 | C | GLY A | 304 | −37.702 | −15.308 | −33.820 | 1.00 | 15.95 | C |
| ATOM | 1676 | O | GLY A | 304 | −38.162 | −15.818 | −32.791 | 1.00 | 16.59 | O |
| ATOM | 1677 | N | THR A | 305 | −38.205 | −14.201 | −34.365 | 1.00 | 16.44 | N |
| ATOM | 1678 | CA | THR A | 305 | −39.353 | −13.512 | −33.768 | 1.00 | 17.13 | C |
| ATOM | 1679 | CB | THR A | 305 | −39.590 | −12.116 | −34.383 | 1.00 | 17.32 | C |
| ATOM | 1680 | OG1 | THR A | 305 | −39.785 | −12.237 | −35.797 | 1.00 | 18.50 | O |
| ATOM | 1681 | CG2 | THR A | 305 | −38.413 | −11.192 | −34.097 | 1.00 | 15.97 | C |
| ATOM | 1682 | C | THR A | 305 | −40.653 | −14.324 | −33.828 | 1.00 | 18.09 | C |
| ATOM | 1683 | O | THR A | 305 | −41.558 | −14.102 | −33.022 | 1.00 | 17.86 | O |
| ATOM | 1684 | N | ASP A | 306 | −40.738 | −15.260 | −34.776 | 1.00 | 18.60 | N |
| ATOM | 1685 | CA | ASP A | 306 | −41.874 | −16.191 | −34.867 | 1.00 | 19.19 | C |
| ATOM | 1686 | CB | ASP A | 306 | −41.706 | −17.154 | −36.054 | 1.00 | 19.78 | C |
| ATOM | 1687 | CG | ASP A | 306 | −41.838 | −16.468 | −37.414 | 1.00 | 23.78 | C |
| ATOM | 1688 | OD1 | ASP A | 306 | −42.177 | −15.262 | −37.471 | 1.00 | 23.13 | O |
| ATOM | 1689 | OD2 | ASP A | 306 | −41.598 | −17.149 | −38.440 | 1.00 | 24.77 | O |
| ATOM | 1690 | C | ASP A | 306 | −42.004 | −17.016 | −33.588 | 1.00 | 18.75 | C |
| ATOM | 1691 | O | ASP A | 306 | −43.101 | −17.468 | −33.235 | 1.00 | 18.46 | O |
| ATOM | 1692 | N | ASN A | 307 | −40.873 | −17.213 | −32.911 | 1.00 | 18.11 | N |
| ATOM | 1693 | CA | ASN A | 307 | −40.806 | −18.064 | −31.725 | 1.00 | 17.92 | C |
| ATOM | 1694 | CB | ASN A | 307 | −39.622 | −19.022 | −31.845 | 1.00 | 17.98 | C |
| ATOM | 1695 | CG | ASN A | 307 | −39.747 | −19.933 | −33.054 | 1.00 | 17.42 | C |
| ATOM | 1696 | OD1 | ASN A | 307 | −40.777 | −20.586 | −33.244 | 1.00 | 17.35 | O |
| ATOM | 1697 | ND2 | ASN A | 307 | −38.711 | −19.964 | −33.891 | 1.00 | 14.01 | N |
| ATOM | 1698 | C | ASN A | 307 | −40.794 | −17.288 | −30.406 | 1.00 | 18.27 | C |
| ATOM | 1699 | O | ASN A | 307 | −40.509 | −17.841 | −29.339 | 1.00 | 18.63 | O |
| | | | | gad67.pdb | | | | | | |
| ATOM | 1700 | N | VAL A | 308 | −41.114 | −15.999 | −30.502 | 1.00 | 17.72 | N |
| ATOM | 1701 | CA | VAL A | 308 | −41.398 | −15.168 | −29.345 | 1.00 | 16.76 | C |
| ATOM | 1702 | CB | VAL A | 308 | −40.647 | −13.812 | −29.397 | 1.00 | 15.75 | C |
| ATOM | 1703 | CG1 | VAL A | 308 | −40.960 | −12.972 | −28.164 | 1.00 | 14.52 | C |
| ATOM | 1704 | CG2 | VAL A | 308 | −39.141 | −14.034 | −29.506 | 1.00 | 15.04 | C |
| ATOM | 1705 | C | VAL A | 308 | −42.912 | −14.985 | −29.349 | 1.00 | 18.02 | C |
| ATOM | 1706 | O | VAL A | 308 | −43.463 | −14.246 | −30.173 | 1.00 | 17.98 | O |
| ATOM | 1707 | N | ILE A | 309 | −43.577 | −15.692 | −28.440 | 1.00 | 19.16 | N |
| ATOM | 1708 | CA | ILE A | 309 | −45.034 | −15.796 | −28.437 | 1.00 | 19.35 | C |
| ATOM | 1709 | CB | ILE A | 309 | −45.498 | −17.243 | −28.075 | 1.00 | 20.11 | C |
| ATOM | 1710 | CG1 | ILE A | 309 | −44.852 | −18.287 | −29.005 | 1.00 | 21.10 | C |
| ATOM | 1711 | CD1 | ILE A | 309 | −45.292 | −18.202 | −30.486 | 1.00 | 23.25 | C |
| ATOM | 1712 | CG2 | ILE A | 309 | −47.029 | −17.355 | −28.080 | 1.00 | 16.61 | C |
| ATOM | 1713 | C | ILE A | 309 | −45.646 | −14.793 | −27.473 | 1.00 | 19.60 | C |
| ATOM | 1714 | O | ILE A | 309 | −45.299 | −14.766 | −26.291 | 1.00 | 19.48 | O |
| ATOM | 1715 | N | LEU A | 310 | −46.567 | −13.981 | −27.989 | 1.00 | 20.58 | N |
| ATOM | 1716 | CA | LEU A | 310 | −47.217 | −12.930 | −27.207 | 1.00 | 20.39 | C |
| ATOM | 1717 | CB | LEU A | 310 | −47.576 | −11.732 | −28.100 | 1.00 | 20.27 | C |
| ATOM | 1718 | CG | LEU A | 310 | −46.474 | −11.096 | −28.964 | 1.00 | 20.66 | C |
| ATOM | 1719 | CD1 | LEU A | 310 | −47.000 | −9.849 | −29.672 | 1.00 | 21.86 | C |
| ATOM | 1720 | CD2 | LEU A | 310 | −45.218 | −10.761 | −28.162 | 1.00 | 15.93 | C |
| ATOM | 1721 | C | LEU A | 310 | −48.450 | −13.446 | −26.463 | 1.00 | 20.80 | C |
| ATOM | 1722 | O | LEU A | 310 | −49.334 | −14.070 | −27.055 | 1.00 | 21.20 | O |
| ATOM | 1723 | N | ILE A | 311 | −48.493 | −13.185 | −25.159 | 1.00 | 20.83 | N |

TABLE A-continued

| | | | | | | | | | |
|---|---|---|---|---|---|---|---|---|---|
| ATOM | 1724 | CA | ILE A | 311 | −49.598 | −13.614 | −24.301 | 1.00 | 20.88 | C |
| ATOM | 1725 | CB | ILE A | 311 | −49.091 | −14.016 | −22.886 | 1.00 | 21.00 | C |
| ATOM | 1726 | CG1 | ILE A | 311 | −48.006 | −15.094 | −22.990 | 1.00 | 20.46 | C |
| ATOM | 1727 | CD1 | ILE A | 311 | −47.067 | −15.132 | −21.801 | 1.00 | 23.12 | C |
| ATOM | 1728 | CG2 | ILE A | 311 | −50.240 | −14.505 | −22.000 | 1.00 | 17.64 | C |
| ATOM | 1729 | C | ILE A | 311 | −50.635 | −12.502 | −24.186 | 1.00 | 21.27 | C |
| ATOM | 1730 | O | ILE A | 311 | −50.279 | −11.340 | −23.981 | 1.00 | 21.63 | O |
| ATOM | 1731 | N | LYS A | 312 | −51.909 | −12.870 | −24.314 | 1.00 | 21.47 | N |
| ATOM | 1732 | CA | LYS A | 312 | −53.021 | −11.920 | −24.239 | 1.00 | 21.78 | C |
| ATOM | 1733 | CB | LYS A | 312 | −54.362 | −12.606 | −24.527 | 1.00 | 23.04 | C |
| ATOM | 1734 | CG | LYS A | 312 | −54.569 | −12.978 | −25.993 | 1.00 | 27.67 | C |
| ATOM | 1735 | CD | LYS A | 312 | −56.038 | −13.259 | −26.302 | 1.00 | 33.98 | C |
| ATOM | 1736 | CE | LYS A | 312 | −56.209 | −13.921 | −27.673 | 1.00 | 39.09 | C |
| ATOM | 1737 | NZ | LYS A | 312 | −55.748 | −15.342 | −27.681 | 1.00 | 39.64 | N |
| ATOM | 1738 | C | LYS A | 312 | −53.087 | −11.204 | −22.898 | 1.00 | 21.02 | C |
| ATOM | 1739 | O | LYS A | 312 | −52.828 | −11.801 | −21.845 | 1.00 | 19.56 | O |
| ATOM | 1740 | N | CYS A | 313 | −53.430 | −9.920 | −22.961 | 1.00 | 20.66 | N |
| ATOM | 1741 | CA | CYS A | 313 | −53.592 | −9.085 | −21.781 | 1.00 | 21.64 | C |
| ATOM | 1742 | CB | CYS A | 313 | −52.787 | −7.792 | −21.936 | 1.00 | 22.03 | C |
| ATOM | 1743 | SG | CYS A | 313 | −50.990 | −8.031 | −21.868 | 1.00 | 24.02 | S |
| ATOM | 1744 | C | CYS A | 313 | −55.061 | −8.758 | −21.547 | 1.00 | 21.99 | C |
| ATOM | 1745 | O | CYS A | 313 | −55.838 | −8.670 | −22.495 | 1.00 | 21.68 | O |
| ATOM | 1746 | N | ASN A | 314 | −55.440 | −8.583 | −20.286 | 1.00 | 22.19 | N |
| ATOM | 1747 | CA | ASN A | 314 | −56.792 | −8.138 | −19.963 | 1.00 | 22.86 | C |
| ATOM | 1748 | CB | ASN A | 314 | −57.212 | −8.604 | −18.558 | 1.00 | 22.67 | C |
| ATOM | 1749 | CG | ASN A | 314 | −56.387 | −7.971 | −17.444 | 1.00 | 23.49 | C |
| ATOM | 1750 | OD1 | ASN A | 314 | −55.702 | −6.966 | −17.642 | 1.00 | 22.75 | O |
| ATOM | 1751 | ND2 | ASN A | 314 | −56.461 | −8.563 | −16.254 | 1.00 | 21.47 | N |
| ATOM | 1752 | C | ASN A | 314 | −56.960 | −6.619 | −20.145 | 1.00 | 23.87 | C |
| ATOM | 1753 | O | ASN A | 314 | −56.034 | −5.932 | −20.599 | 1.00 | 24.38 | O |
| ATOM | 1754 | N | GLU A | 315 | −58.140 | −6.110 | −19.792 | 1.00 | 24.02 | N |
| ATOM | 1755 | CA | GLU A | 315 | −58.465 | −4.683 | −19.889 | 1.00 | 24.75 | C |
| ATOM | 1756 | CB | GLU A | 315 | −59.838 | −4.422 | −19.246 | 1.00 | 25.63 | C |
| ATOM | 1757 | CG | GLU A | 315 | −60.315 | −2.967 | −19.245 | 1.00 | 30.48 | C |
| ATOM | 1758 | CD | GLU A | 315 | −60.610 | −2.416 | −20.635 | 1.00 | 35.19 | C |
| ATOM | 1759 | OE1 | GLU A | 315 | −60.638 | −1.174 | −20.777 | 1.00 | 35.38 | O |
| ATOM | 1760 | OE2 | GLU A | 315 | −60.815 | −3.210 | −21.582 | 1.00 | 38.86 | O |
| ATOM | 1761 | C | GLU A | 315 | −57.398 | −3.776 | −19.259 | 1.00 | 24.10 | C |
| ATOM | 1762 | O | GLU A | 315 | −57.074 | −2.718 | −19.805 | 1.00 | 23.76 | O |
| ATOM | 1763 | N | ARG A | 316 | −56.855 | −4.209 | −18.122 | 1.00 | 23.63 | N |
| ATOM | 1764 | CA | ARG A | 316 | −55.882 | −3.427 | −17.361 | 1.00 | 23.49 | C |
| ATOM | 1765 | CB | ARG A | 316 | −56.017 | −3.737 | −15.868 | 1.00 | 23.56 | C |
| ATOM | 1766 | CG | ARG A | 316 | −57.368 | −3.345 | −15.264 | 1.00 | 26.26 | C |
| ATOM | 1767 | CD | ARG A | 316 | −57.542 | −3.941 | −13.873 | 1.00 | 28.85 | C |
| ATOM | 1768 | NE | ARG A | 316 | −56.557 | −3.413 | −12.930 | 1.00 | 35.91 | N |
| ATOM | 1769 | CZ | ARG A | 316 | −56.155 | −4.038 | −11.825 | 1.00 | 39.04 | C |
| ATOM | 1770 | NH1 | ARG A | 316 | −56.648 | −5.233 | −11.511 | 1.00 | 38.20 | N |
| ATOM | 1771 | NH2 | ARG A | 316 | −55.247 | −3.470 | −11.037 | 1.00 | 38.25 | N |
| ATOM | 1772 | C | ARG A | 316 | −54.431 | −3.630 | −17.825 | 1.00 | 22.76 | C |
| ATOM | 1773 | O | ARG A | 316 | −53.502 | −3.114 | −17.197 | 1.00 | 23.47 | O |
| ATOM | 1774 | N | GLY A | 317 | −54.246 | −4.380 | −18.914 | 1.00 | 21.21 | N |
| ATOM | 1775 | CA | GLY A | 317 | −52.928 | −4.579 | −19.525 | 1.00 | 20.24 | C |
| ATOM | 1776 | C | GLY A | 317 | −52.058 | −5.619 | −18.840 | 1.00 | 20.24 | C |
| ATOM | 1777 | O | GLY A | 317 | −50.828 | −5.610 | −18.983 | 1.00 | 19.28 | O |
| ATOM | 1778 | N | LYS A | 318 | −52.699 | −6.515 | −18.094 | 1.00 | 20.26 | N |
| ATOM | 1779 | CA | LYS A | 318 | −52.010 | −7.581 | −17.379 | 1.00 | 19.74 | C |
| ATOM | 1780 | CB | LYS A | 318 | −52.680 | −7.827 | −16.024 | 1.00 | 19.33 | C |
| ATOM | 1781 | CG | LYS A | 318 | −52.602 | −6.689 | −15.027 | 1.00 | 20.93 | C |
| ATOM | 1782 | CD | LYS A | 318 | −53.424 | −7.031 | −13.789 | 1.00 | 21.83 | C |
| ATOM | 1783 | CE | LYS A | 318 | −53.259 | −6.008 | −12.675 | 1.00 | 24.73 | C |
| ATOM | 1784 | NZ | LYS A | 318 | −51.975 | −6.173 | −11.926 | 1.00 | 24.87 | N |
| ATOM | 1785 | C | LYS A | 318 | −52.074 | −8.872 | −18.193 | 1.00 | 20.15 | C |
| ATOM | 1786 | O | LYS A | 318 | −53.067 | −9.123 | −18.883 | 1.00 | 20.51 | O |
| ATOM | 1787 | N | ILE A | 319 | −51.028 | −9.692 | −18.096 | 1.00 | 19.72 | N |
| ATOM | 1788 | CA | ILE A | 319 | −51.054 | −11.043 | −18.651 | 1.00 | 20.15 | C |
| ATOM | 1789 | CB | ILE A | 319 | −49.727 | −11.816 | −18.390 | 1.00 | 19.87 | C |
| ATOM | 1790 | CG1 | ILE A | 319 | −48.740 | −11.585 | −19.535 | 1.00 | 19.55 | C |
| ATOM | 1791 | CD1 | ILE A | 319 | −47.350 | −12.183 | −19.296 | 1.00 | 19.09 | C |
| ATOM | 1792 | CG2 | ILE A | 319 | −49.973 | −13.325 | −18.237 | 1.00 | 19.35 | C |
| ATOM | 1793 | C | ILE A | 319 | −52.233 | −11.821 | −18.073 | 1.00 | 20.71 | C |
| ATOM | 1794 | O | ILE A | 319 | −52.464 | −11.800 | −16.861 | 1.00 | 20.65 | O |
| ATOM | 1795 | N | ILE A | 320 | −52.993 | −12.459 | −18.961 | 1.00 | 21.50 | N |
| ATOM | 1796 | CA | ILE A | 320 | −53.998 | −13.438 | −18.569 | 1.00 | 22.17 | C |
| ATOM | 1797 | CB | ILE A | 320 | −55.138 | −13.549 | −19.620 | 1.00 | 21.76 | C |
| ATOM | 1798 | CG1 | ILE A | 320 | −55.828 | −12.199 | −19.815 | 1.00 | 21.91 | C |
| ATOM | 1799 | CD1 | ILE A | 320 | −56.670 | −12.114 | −21.085 | 1.00 | 22.26 | C |
| ATOM | 1800 | CG2 | ILE A | 320 | −56.155 | −14.623 | −19.208 | 1.00 | 22.63 | C |
| ATOM | 1801 | C | ILE A | 320 | −53.267 | −14.777 | −18.427 | 1.00 | 21.66 | C |
| ATOM | 1802 | O | ILE A | 320 | −52.842 | −15.356 | −19.424 | 1.00 | 21.13 | O | gad67.pdb

TABLE A-continued

| | | | | | | | | | |
|---|---|---|---|---|---|---|---|---|---|
| ATOM | 1803 | N | PRO A | 321 | −53.100 | −15.265 | −17.185 | 1.00 | 22.81 | N |
| ATOM | 1804 | CA | PRO A | 321 | −52.289 | −16.465 | −16.954 | 1.00 | 23.62 | C |
| ATOM | 1805 | CB | PRO A | 321 | −52.455 | −16.709 | −15.448 | 1.00 | 23.83 | C |
| ATOM | 1806 | CG | PRO A | 321 | −52.804 | −15.370 | −14.882 | 1.00 | 23.70 | C |
| ATOM | 1807 | CD | PRO A | 321 | −53.643 | −14.716 | −15.927 | 1.00 | 22.60 | C |
| ATOM | 1808 | C | PRO A | 321 | −52.746 | −17.705 | −17.736 | 1.00 | 24.31 | C |
| ATOM | 1809 | O | PRO A | 321 | −52.065 | −18.729 | −17.717 | 1.00 | 23.31 | O |
| ATOM | 1810 | N | ALA A | 322 | −53.853 | −17.596 | −18.462 | 1.00 | 25.51 | N |
| ATOM | 1811 | CA | ALA A | 322 | −54.614 | −18.783 | −18.805 | 1.00 | 25.68 | C |
| ATOM | 1812 | CB | ALA A | 322 | −56.026 | −18.677 | −18.190 | 1.00 | 25.61 | C |
| ATOM | 1813 | C | ALA A | 322 | −54.734 | −19.372 | −20.223 | 1.00 | 25.90 | C |
| ATOM | 1814 | O | ALA A | 322 | −54.696 | −20.594 | −20.324 | 1.00 | 26.52 | O |
| ATOM | 1815 | N | ASP A | 323 | −54.784 | −18.620 | −21.327 | 1.00 | 26.35 | N |
| ATOM | 1816 | CA | ASP A | 323 | −53.694 | −17.879 | −22.004 | 1.00 | 26.14 | C |
| ATOM | 1817 | CB | ASP A | 323 | −53.942 | −16.414 | −22.366 | 1.00 | 26.38 | C |
| ATOM | 1818 | CG | ASP A | 323 | −53.654 | −16.159 | −23.857 | 1.00 | 28.44 | C |
| ATOM | 1819 | OD1 | ASP A | 323 | −54.374 | −16.741 | −24.701 | 1.00 | 29.41 | O |
| ATOM | 1820 | OD2 | ASP A | 323 | −52.691 | −15.435 | −24.199 | 1.00 | 28.81 | O |
| ATOM | 1821 | C | ASP A | 323 | −52.226 | −18.293 | −21.925 | 1.00 | 25.26 | C |
| ATOM | 1822 | O | ASP A | 323 | −51.743 | −18.934 | −22.858 | 1.00 | 25.28 | O |
| ATOM | 1823 | N | PHE A | 324 | −51.510 | −17.899 | −20.876 | 1.00 | 24.77 | N |
| ATOM | 1824 | CA | PHE A | 324 | −50.122 | −18.329 | −20.740 | 1.00 | 23.40 | C |
| ATOM | 1825 | CB | PHE A | 324 | −49.484 | −17.780 | −19.460 | 1.00 | 22.46 | C |
| ATOM | 1826 | CG | PHE A | 324 | −48.071 | −18.253 | −19.222 | 1.00 | 20.05 | C |
| ATOM | 1827 | CD1 | PHE A | 324 | −47.622 | −18.483 | −17.931 | 1.00 | 17.62 | C |
| ATOM | 1828 | CE1 | PHE A | 324 | −46.321 | −18.912 | −17.692 | 1.00 | 17.96 | C |
| ATOM | 1829 | CZ | PHE A | 324 | −45.455 | −19.124 | −18.753 | 1.00 | 17.72 | C |
| ATOM | 1830 | CE2 | PHE A | 324 | −45.884 | −18.897 | −20.054 | 1.00 | 17.89 | C |
| ATOM | 1831 | CD2 | PHE A | 324 | −47.186 | −18.461 | −20.285 | 1.00 | 19.82 | C |
| ATOM | 1832 | C | PHE A | 324 | −50.059 | −19.853 | −20.799 | 1.00 | 24.17 | C |
| ATOM | 1833 | O | PHE A | 324 | −49.379 | −20.409 | −21.664 | 1.00 | 24.65 | O |
| ATOM | 1834 | N | GLU A | 325 | −50.800 | −20.513 | −19.908 | 1.00 | 24.33 | N |
| ATOM | 1835 | CA | GLU A | 325 | −50.861 | −21.978 | −19.861 | 1.00 | 25.18 | C |
| | | | | gad67.pdb | | | | | | |
| ATOM | 1836 | CB | GLU A | 325 | −51.759 | −22.453 | −18.707 | 1.00 | 25.12 | C |
| ATOM | 1837 | CG | GLU A | 325 | −51.768 | −23.973 | −18.502 | 1.00 | 26.72 | C |
| ATOM | 1838 | CD | GLU A | 325 | −52.234 | −24.404 | −17.112 | 1.00 | 26.78 | C |
| ATOM | 1839 | OE1 | GLU A | 325 | −52.037 | −25.590 | −16.774 | 1.00 | 27.13 | O |
| ATOM | 1840 | OE2 | GLU A | 325 | −52.786 | −23.568 | −16.357 | 1.00 | 29.44 | O |
| ATOM | 1841 | C | GLU A | 325 | −51.306 | −22.598 | −21.190 | 1.00 | 24.84 | C |
| ATOM | 1842 | O | GLU A | 325 | −50.714 | −23.579 | −21.640 | 1.00 | 25.15 | O |
| ATOM | 1843 | N | ALA A | 326 | −52.338 | −22.020 | −21.808 | 1.00 | 24.73 | N |
| ATOM | 1844 | CA | ALA A | 326 | −52.861 | −22.508 | −23.092 | 1.00 | 25.08 | C |
| ATOM | 1845 | CB | ALA A | 326 | −54.117 | −21.731 | −23.494 | 1.00 | 24.59 | C |
| ATOM | 1846 | C | ALA A | 326 | −51.823 | −22.458 | −24.219 | 1.00 | 25.41 | C |
| ATOM | 1847 | O | ALA A | 326 | −51.728 | −23.387 | −25.026 | 1.00 | 25.53 | O |
| ATOM | 1848 | N | LYS A | 327 | −51.053 | −21.371 | −24.267 | 1.00 | 25.47 | N |
| ATOM | 1849 | CA | LYS A | 327 | −50.015 | −21.201 | −25.287 | 1.00 | 25.07 | C |
| ATOM | 1850 | CB | LYS A | 327 | −49.506 | −19.755 | −25.313 | 1.00 | 25.76 | C |
| ATOM | 1851 | CG | LYS A | 327 | −50.544 | −18.722 | −25.732 | 1.00 | 26.24 | C |
| ATOM | 1852 | CD | LYS A | 327 | −50.470 | −18.404 | −27.218 | 1.00 | 31.87 | C |
| ATOM | 1853 | CE | LYS A | 327 | −51.656 | −17.551 | −27.675 | 1.00 | 32.76 | C |
| ATOM | 1854 | NZ | LYS A | 327 | −51.755 | −16.256 | −26.941 | 1.00 | 33.64 | N |
| ATOM | 1855 | C | LYS A | 327 | −48.857 | −22.178 | −25.082 | 1.00 | 23.99 | C |
| ATOM | 1856 | O | LYS A | 327 | −48.252 | −22.632 | −26.053 | 1.00 | 24.18 | O |
| ATOM | 1857 | N | ILE A | 328 | −48.555 | −22.497 | −23.823 | 1.00 | 23.33 | N |
| ATOM | 1858 | CA | ILE A | 328 | −47.547 | −23.510 | −23.498 | 1.00 | 23.56 | C |
| ATOM | 1859 | CB | ILE A | 328 | −47.324 | −23.654 | −21.966 | 1.00 | 23.30 | C |
| ATOM | 1860 | CG1 | ILE A | 328 | −46.777 | −22.360 | −21.359 | 1.00 | 22.80 | C |
| ATOM | 1861 | CD1 | ILE A | 328 | −46.776 | −22.359 | −19.831 | 1.00 | 22.56 | C |
| ATOM | 1862 | CG2 | ILE A | 328 | −46.376 | −24.826 | −21.657 | 1.00 | 22.24 | C |
| ATOM | 1863 | C | ILE A | 328 | −47.961 | −24.870 | −24.064 | 1.00 | 25.00 | C |
| ATOM | 1864 | O | ILE A | 328 | −47.160 | −25.553 | −24.704 | 1.00 | 25.06 | O |
| ATOM | 1865 | N | LEU A | 329 | −49.216 | −25.244 | −23.818 | 1.00 | 26.21 | N |
| ATOM | 1866 | CA | LEU A | 329 | −49.766 | −26.527 | −24.252 | 1.00 | 27.80 | C |
| ATOM | 1867 | CB | LEU A | 329 | −51.161 | −26.733 | −23.646 | 1.00 | 28.44 | C |
| ATOM | 1868 | CG | LEU A | 329 | −51.342 | −27.508 | −22.331 | 1.00 | 29.02 | C |
| ATOM | 1869 | CD1 | LEU A | 329 | −50.084 | −27.619 | −21.488 | 1.00 | 30.37 | C |
| ATOM | 1870 | CD2 | LEU A | 329 | −52.492 | −26.927 | −21.516 | 1.00 | 30.84 | C |
| ATOM | 1871 | C | LEU A | 329 | −49.821 | −26.624 | −25.769 | 1.00 | 27.88 | C |
| ATOM | 1872 | O | LEU A | 329 | −49.474 | −27.653 | −26.338 | 1.00 | 27.44 | O |
| ATOM | 1873 | N | GLU A | 330 | −50.252 | −25.537 | −26.406 | 1.00 | 28.78 | N |
| ATOM | 1874 | CA | GLU A | 330 | −50.265 | −25.407 | −27.860 | 1.00 | 29.96 | C |
| ATOM | 1875 | CB | GLU A | 330 | −50.841 | −24.042 | −28.250 | 1.00 | 29.63 | C |
| ATOM | 1876 | CG | GLU A | 330 | −51.176 | −23.886 | −29.732 | 1.00 | 33.68 | C |
| ATOM | 1877 | CD | GLU A | 330 | −51.469 | −22.441 | −30.130 | 1.00 | 33.76 | C |
| ATOM | 1878 | OE1 | GLU A | 330 | −52.113 | −21.707 | −29.343 | 1.00 | 37.85 | O |
| ATOM | 1879 | OE2 | GLU A | 330 | −51.055 | −22.041 | −31.242 | 1.00 | 40.21 | O |
| ATOM | 1880 | C | GLU A | 330 | −48.864 | −25.571 | −28.452 | 1.00 | 29.79 | C |
| ATOM | 1881 | O | GLU A | 330 | −48.694 | −26.245 | −29.473 | 1.00 | 29.89 | O |

TABLE A-continued

| | | | | | | | | | | |
|---|---|---|---|---|---|---|---|---|---|---|
| ATOM | 1882 | N | ALA A | 331 | −47.871 | −24.961 | −27.799 | 1.00 | 29.44 | N |
| ATOM | 1883 | CA | ALA A | 331 | −46.484 | −24.968 | −28.270 | 1.00 | 28.86 | C |
| ATOM | 1884 | CB | ALA A | 331 | −45.633 | −23.991 | −27.462 | 1.00 | 28.38 | C |
| ATOM | 1885 | C | ALA A | 331 | −45.862 | −26.360 | −28.244 | 1.00 | 29.02 | C |
| ATOM | 1886 | O | ALA A | 331 | −45.264 | −26.797 | −29.231 | 1.00 | 28.86 | O |
| ATOM | 1887 | N | LYS A | 332 | −45.994 | −27.057 | −27.119 | 1.00 | 29.05 | N |
| ATOM | 1888 | CA | LYS A | 332 | −45.418 | −28.397 | −27.025 | 1.00 | 29.91 | C |
| ATOM | 1889 | CB | LYS A | 332 | −45.075 | −28.784 | −25.577 | 1.00 | 29.73 | C |
| ATOM | 1890 | CG | LYS A | 332 | −46.222 | −28.805 | −24.580 | 1.00 | 29.21 | C |
| ATOM | 1891 | CD | LYS A | 332 | −45.752 | −28.352 | −23.189 | 1.00 | 30.19 | C |
| ATOM | 1892 | CE | LYS A | 332 | −44.529 | −29.120 | −22.666 | 1.00 | 31.45 | C |
| ATOM | 1893 | NZ | LYS A | 332 | −44.880 | −30.193 | −21.692 | 1.00 | 33.66 | N |
| ATOM | 1894 | C | LYS A | 332 | −46.254 | −29.449 | −27.760 | 1.00 | 30.66 | C |
| ATOM | 1895 | O | LYS A | 332 | −45.760 | −30.534 | −28.066 | 1.00 | 30.84 | O |
| ATOM | 1896 | N | GLN A | 333 | −47.502 | −29.097 | −28.074 | 1.00 | 31.66 | N |
| ATOM | 1897 | CA | GLN A | 333 | −48.379 | −29.940 | −28.882 | 1.00 | 33.25 | C |
| ATOM | 1898 | CB | GLN A | 333 | −49.822 | −29.434 | −28.812 | 1.00 | 34.13 | C |
| ATOM | 1899 | CG | GLN A | 333 | −50.887 | −30.492 | −29.088 | 1.00 | 39.01 | C |
| ATOM | 1900 | CD | GLN A | 333 | −51.264 | −30.595 | −30.559 | 1.00 | 45.37 | C |
| ATOM | 1901 | OE1 | GLN A | 333 | −50.957 | −29.708 | −31.361 | 1.00 | 46.75 | O |
| ATOM | 1902 | NE2 | GLN A | 333 | −51.944 | −31.679 | −30.917 | 1.00 | 47.58 | N |
| ATOM | 1903 | C | GLN A | 333 | −47.893 | −29.980 | −30.328 | 1.00 | 33.53 | C |
| | | | | | gad67.pdb | | | | | |
| ATOM | 1904 | O | GLN A | 333 | −47.996 | −31.013 | −30.993 | 1.00 | 34.14 | O |
| ATOM | 1905 | N | LYS A | 334 | −47.359 | −28.857 | −30.807 | 1.00 | 33.22 | N |
| ATOM | 1906 | CA | LYS A | 334 | −46.765 | −28.796 | −32.142 | 1.00 | 33.00 | C |
| ATOM | 1907 | CB | LYS A | 334 | −47.019 | −27.436 | −32.813 | 1.00 | 33.52 | C |
| ATOM | 1908 | CG | LYS A | 334 | −46.539 | −26.219 | −32.040 | 1.00 | 36.80 | C |
| ATOM | 1912 | C | LYS A | 334 | −45.274 | −29.178 | −32.148 | 1.00 | 32.54 | C |
| ATOM | 1913 | O | LYS A | 334 | −44.608 | −29.092 | −33.184 | 1.00 | 32.56 | O |
| ATOM | 1914 | N | GLY A | 335 | −44.765 | −29.604 | −30.992 | 1.00 | 31.83 | N |
| ATOM | 1915 | CA | GLY A | 335 | −43.403 | −30.126 | −30.879 | 1.00 | 31.61 | C |
| ATOM | 1916 | C | GLY A | 335 | −42.347 | −29.112 | −30.464 | 1.00 | 32.02 | C |
| ATOM | 1917 | O | GLY A | 335 | −41.151 | −29.426 | −30.454 | 1.00 | 31.81 | O |
| ATOM | 1918 | N | TYR A | 336 | −42.782 | −27.900 | −30.118 | 1.00 | 31.15 | N |
| ATOM | 1919 | CA | TYR A | 336 | −41.852 | −26.841 | −29.716 | 1.00 | 30.36 | C |
| ATOM | 1920 | CB | TYR A | 336 | −42.410 | −25.449 | −30.045 | 1.00 | 30.76 | C |
| ATOM | 1921 | CG | TYR A | 336 | −42.770 | −25.220 | −31.505 | 1.00 | 32.57 | C |
| ATOM | 1922 | CD1 | TYR A | 336 | −43.539 | −24.122 | −31.881 | 1.00 | 33.64 | C |
| ATOM | 1923 | CE1 | TYR A | 336 | −43.874 | −23.896 | −33.214 | 1.00 | 33.55 | C |
| ATOM | 1924 | CZ | TYR A | 336 | −43.448 | −24.782 | −34.187 | 1.00 | 34.31 | C |
| ATOM | 1925 | OH | TYR A | 336 | −43.783 | −24.560 | −35.504 | 1.00 | 34.88 | O |
| ATOM | 1926 | CE2 | TYR A | 336 | −42.690 | −25.891 | −33.845 | 1.00 | 34.95 | C |
| ATOM | 1927 | CD2 | TYR A | 336 | −42.355 | −26.105 | −32.508 | 1.00 | 35.05 | C |
| ATOM | 1928 | C | TYR A | 336 | −41.508 | −26.952 | −28.232 | 1.00 | 28.95 | C |
| ATOM | 1929 | O | TYR A | 336 | −42.218 | −27.616 | −27.474 | 1.00 | 29.47 | O |
| ATOM | 1930 | N | VAL A | 337 | −40.414 | −26.306 | −27.831 | 1.00 | 26.80 | N |
| ATOM | 1931 | CA | VAL A | 337 | −39.895 | −26.422 | −26.472 | 1.00 | 24.49 | C |
| ATOM | 1932 | CB | VAL A | 337 | −38.455 | −27.007 | −26.469 | 1.00 | 24.61 | C |
| ATOM | 1933 | CG1 | VAL A | 337 | −37.919 | −27.154 | −25.045 | 1.00 | 23.10 | C |
| ATOM | 1934 | CG2 | VAL A | 337 | −38.418 | −28.356 | −27.186 | 1.00 | 24.12 | C |
| ATOM | 1935 | C | VAL A | 337 | −39.957 | −25.082 | −25.712 | 1.00 | 24.09 | C |
| ATOM | 1936 | O | VAL A | 337 | −39.099 | −24.213 | −25.907 | 1.00 | 23.46 | O |
| ATOM | 1937 | N | PRO A | 338 | −40.991 | −24.907 | −24.857 | 1.00 | 23.08 | N |
| ATOM | 1938 | CA | PRO A | 338 | −41.079 | −23.754 | −23.963 | 1.00 | 22.04 | C |
| ATOM | 1939 | CB | PRO A | 338 | −42.516 | −23.830 | −23.417 | 1.00 | 22.04 | C |
| ATOM | 1940 | CG | PRO A | 338 | −43.221 | −24.839 | −24.261 | 1.00 | 22.89 | C |
| ATOM | 1941 | CD | PRO A | 338 | −42.158 | −25.792 | −24.694 | 1.00 | 22.99 | C |
| ATOM | 1942 | C | PRO A | 338 | −40.086 | −23.888 | −22.820 | 1.00 | 20.96 | C |
| ATOM | 1943 | O | PRO A | 338 | −39.913 | −24.984 | −22.281 | 1.00 | 22.08 | O |
| ATOM | 1944 | N | PHE A | 339 | −39.440 | −22.784 | −22.449 | 1.00 | 19.16 | N |
| ATOM | 1945 | CA | PHE A | 339 | −38.418 | −22.817 | −21.398 | 1.00 | 17.31 | C |
| ATOM | 1946 | CB | PHE A | 339 | −37.046 | −23.161 | −22.001 | 1.00 | 16.75 | C |
| ATOM | 1947 | CG | PHE A | 339 | −36.393 | −22.015 | −22.728 | 1.00 | 15.88 | C |
| ATOM | 1948 | CD1 | PHE A | 339 | −35.240 | −21.423 | −22.217 | 1.00 | 15.32 | C |
| ATOM | 1949 | CE1 | PHE A | 339 | −34.628 | −20.360 | −22.880 | 1.00 | 14.57 | C |
| ATOM | 1950 | CZ | PHE A | 339 | −35.175 | −19.872 | −24.066 | 1.00 | 16.36 | C |
| ATOM | 1951 | CE2 | PHE A | 339 | −36.334 | −20.455 | −24.587 | 1.00 | 15.94 | C |
| ATOM | 1952 | CD2 | PHE A | 339 | −36.931 | −21.523 | −23.918 | 1.00 | 14.05 | C |
| ATOM | 1953 | C | PHE A | 339 | −38.327 | −21.515 | −20.608 | 1.00 | 16.50 | C |
| ATOM | 1954 | O | PHE A | 339 | −37.717 | −21.485 | −19.541 | 1.00 | 17.03 | O |
| ATOM | 1955 | N | TYR A | 340 | −38.948 | −20.456 | −21.130 | 1.00 | 16.04 | N |
| ATOM | 1956 | CA | TYR A | 340 | −38.761 | −19.092 | −20.625 | 1.00 | 15.33 | C |
| ATOM | 1957 | CB | TYR A | 340 | −37.602 | −18.431 | −21.386 | 1.00 | 14.63 | C |
| ATOM | 1958 | CG | TYR A | 340 | −37.343 | −16.968 | −21.058 | 1.00 | 14.50 | C |
| ATOM | 1959 | CD1 | TYR A | 340 | −38.134 | −15.956 | −21.607 | 1.00 | 11.86 | C |
| ATOM | 1960 | CE1 | TYR A | 340 | −37.893 | −14.626 | −21.322 | 1.00 | 13.73 | C |
| ATOM | 1961 | CZ | TYR A | 340 | −36.840 | −14.283 | −20.491 | 1.00 | 13.86 | C |
| ATOM | 1962 | OH | TYR A | 340 | −36.598 | −12.959 | −20.216 | 1.00 | 14.45 | O |
| ATOM | 1963 | CE2 | TYR A | 340 | −36.036 | −15.261 | −19.938 | 1.00 | 12.87 | C |

TABLE A-continued

| | | | | | | | | | |
|---|---|---|---|---|---|---|---|---|---|
| ATOM | 1964 | CD2 | TYR A | 340 | −36.291 | −16.600 | −20.226 | 1.00 | 12.51 | C |
| ATOM | 1965 | C | TYR A | 340 | −40.017 | −18.226 | −20.756 | 1.00 | 15.60 | C |
| ATOM | 1966 | O | TYR A | 340 | −40.690 | −18.232 | −21.796 | 1.00 | 15.35 | O |
| ATOM | 1967 | N | VAL A | 341 | −40.315 | −17.473 | −19.697 | 1.00 | 15.41 | N |
| ATOM | 1968 | CA | VAL A | 341 | −41.357 | −16.445 | −19.735 | 1.00 | 14.12 | C |
| ATOM | 1969 | CB | VAL A | 341 | −42.656 | −16.886 | −18.984 | 1.00 | 14.50 | C |
| ATOM | 1970 | CG1 | VAL A | 341 | −42.425 | −16.979 | −17.495 | 1.00 | 13.24 | C |
| ATOM | 1971 | CG2 | VAL A | 341 | −43.818 | −15.934 | −19.276 | 1.00 | 10.94 | C |
| ATOM | 1972 | C | VAL A | 341 | −40.822 | −15.123 | −19.172 | 1.00 | 14.42 | C |
| ATOM | 1973 | O | VAL A | 341 | −40.024 | −15.112 | −18.226 | 1.00 | 14.47 | O |
| ATOM | 1974 | N | ASN A | 342 | −41.256 | −14.020 | −19.771 | 1.00 | 14.49 | N |
| | | | | | gad67.pdb | | | | | |
| ATOM | 1975 | CA | ASN A | 342 | −40.975 | −12.691 | −19.248 | 1.00 | 15.21 | C |
| ATOM | 1976 | CB | ASN A | 342 | −40.398 | −11.791 | −20.347 | 1.00 | 14.70 | C |
| ATOM | 1977 | CG | ASN A | 342 | −40.338 | −10.334 | −19.937 | 1.00 | 15.20 | C |
| ATOM | 1978 | OD1 | ASN A | 342 | −39.708 | −9.986 | −18.944 | 1.00 | 17.47 | O |
| ATOM | 1979 | ND2 | ASN A | 342 | −41.002 | −9.475 | −20.698 | 1.00 | 15.36 | N |
| ATOM | 1980 | C | ASN A | 342 | −42.238 | −12.067 | −18.658 | 1.00 | 15.17 | C |
| ATOM | 1981 | O | ASN A | 342 | −43.232 | −11.883 | −19.361 | 1.00 | 15.32 | O |
| ATOM | 1982 | N | ALA A | 343 | −42.192 | −11.749 | −17.369 | 1.00 | 15.30 | N |
| ATOM | 1983 | CA | ALA A | 343 | −43.277 | −11.021 | −16.708 | 1.00 | 16.04 | C |
| ATOM | 1984 | CB | ALA A | 343 | −43.739 | −11.771 | −15.460 | 1.00 | 15.23 | C |
| ATOM | 1985 | C | ALA A | 343 | −42.841 | −9.587 | −16.364 | 1.00 | 15.76 | C |
| ATOM | 1986 | O | ALA A | 343 | −41.733 | −9.378 | −15.876 | 1.00 | 15.59 | O |
| ATOM | 1987 | N | THR A | 344 | −43.721 | −8.623 | −16.643 | 1.00 | 15.76 | N |
| ATOM | 1988 | CA | THR A | 344 | −43.532 | −7.193 | −16.366 | 1.00 | 16.99 | C |
| ATOM | 1989 | CB | THR A | 344 | −43.664 | −6.395 | −17.705 | 1.00 | 16.94 | C |
| ATOM | 1990 | OG1 | THR A | 344 | −43.293 | −7.224 | −18.815 | 1.00 | 16.46 | O |
| ATOM | 1991 | CG2 | THR A | 344 | −42.822 | −5.127 | −17.708 | 1.00 | 15.87 | C |
| ATOM | 1992 | C | THR A | 344 | −44.718 | −6.801 | −15.471 | 1.00 | 17.89 | C |
| ATOM | 1993 | O | THR A | 344 | −45.838 | −6.863 | −15.958 | 1.00 | 20.35 | O |
| ATOM | 1994 | N | ALA A | 345 | −44.585 | −6.363 | −14.212 | 1.00 | 20.06 | N |
| ATOM | 1995 | CA | ALA A | 345 | −43.450 | −5.733 | −13.508 | 1.00 | 18.80 | C |
| ATOM | 1996 | CB | ALA A | 345 | −42.155 | −6.459 | −13.740 | 1.00 | 21.19 | C |
| ATOM | 1997 | C | ALA A | 345 | −43.346 | −4.225 | −13.789 | 1.00 | 17.07 | C |
| ATOM | 1998 | O | ALA A | 345 | −42.351 | −3.580 | −13.451 | 1.00 | 16.33 | O |
| ATOM | 1999 | N | GLY A | 346 | −44.411 | −3.672 | −14.368 | 1.00 | 15.89 | N |
| ATOM | 2000 | CA | GLY A | 346 | −44.475 | −2.263 | −14.746 | 1.00 | 15.91 | C |
| ATOM | 2001 | C | GLY A | 346 | −44.224 | −2.089 | −16.234 | 1.00 | 16.06 | C |
| ATOM | 2002 | O | GLY A | 346 | −43.077 | −1.935 | −16.663 | 1.00 | 16.84 | O |
| ATOM | 2003 | N | THR A | 347 | −45.290 | −2.126 | −17.025 | 1.00 | 15.35 | N |
| ATOM | 2004 | CA | THR A | 347 | −45.169 | −1.976 | −18.474 | 1.00 | 15.32 | C |
| ATOM | 2005 | CB | THR A | 347 | −46.430 | −2.466 | −19.232 | 1.00 | 14.93 | C |
| ATOM | 2006 | OG1 | THR A | 347 | −47.578 | −1.748 | −18.765 | 1.00 | 16.26 | O |
| ATOM | 2007 | CG2 | THR A | 347 | −46.642 | −3.954 | −19.027 | 1.00 | 14.43 | C |
| ATOM | 2008 | C | THR A | 347 | −44.874 | −.526 | −18.853 | 1.00 | 15.11 | C |
| ATOM | 2009 | O | THR A | 347 | −45.199 | .403 | −18.111 | 1.00 | 14.41 | O |
| ATOM | 2010 | N | THR A | 348 | −44.266 | −.352 | −20.020 | 1.00 | 15.52 | N |
| ATOM | 2011 | CA | THR A | 348 | −43.804 | .950 | −20.482 | 1.00 | 15.71 | C |
| ATOM | 2012 | CB | THR A | 348 | −42.958 | .792 | −21.766 | 1.00 | 16.71 | C |
| ATOM | 2013 | OG1 | THR A | 348 | −41.919 | −.167 | −21.525 | 1.00 | 20.33 | O |
| ATOM | 2014 | CG2 | THR A | 348 | −42.331 | 2.116 | −22.182 | 1.00 | 13.86 | C |
| ATOM | 2015 | C | THR A | 348 | −44.948 | 1.945 | −20.701 | 1.00 | 15.16 | C |
| ATOM | 2016 | O | THR A | 348 | −44.812 | 3.129 | −20.382 | 1.00 | 15.21 | O |
| ATOM | 2017 | N | VAL A | 349 | −46.073 | 1.462 | −21.224 | 1.00 | 14.62 | N |
| ATOM | 2018 | CA | VAL A | 349 | −47.201 | 2.334 | −21.560 | 1.00 | 14.91 | C |
| ATOM | 2019 | CB | VAL A | 349 | −47.832 | 1.965 | −22.934 | 1.00 | 15.53 | C |
| ATOM | 2020 | CG1 | VAL A | 349 | −48.993 | 2.899 | −23.266 | 1.00 | 14.48 | C |
| ATOM | 2021 | CG2 | VAL A | 349 | −46.779 | 2.033 | −24.039 | 1.00 | 12.42 | C |
| ATOM | 2022 | C | VAL A | 349 | −48.252 | 2.424 | −20.431 | 1.00 | 15.56 | C |
| ATOM | 2023 | O | VAL A | 349 | −48.437 | 3.492 | −19.853 | 1.00 | 15.75 | O |
| ATOM | 2024 | N | TYR A | 350 | −48.908 | 1.310 | −20.107 | 1.00 | 15.68 | N |
| ATOM | 2025 | CA | TYR A | 350 | −49.939 | 1.282 | −19.053 | 1.00 | 16.12 | C |
| ATOM | 2026 | CB | TYR A | 350 | −50.772 | −.003 | −19.141 | 1.00 | 16.13 | C |
| ATOM | 2027 | CG | TYR A | 350 | −51.892 | −.007 | −20.162 | 1.00 | 15.74 | C |
| ATOM | 2028 | CD1 | TYR A | 350 | −52.927 | −.938 | −20.072 | 1.00 | 17.85 | C |
| ATOM | 2029 | CE1 | TYR A | 350 | −53.964 | −.959 | −21.007 | 1.00 | 15.25 | C |
| ATOM | 2030 | CZ | TYR A | 350 | −53.966 | −.029 | −22.039 | 1.00 | 17.34 | C |
| ATOM | 2031 | OH | TYR A | 350 | −54.979 | −.032 | −22.967 | 1.00 | 19.28 | O |
| ATOM | 2032 | CE2 | TYR A | 350 | −52.951 | .911 | −22.144 | 1.00 | 15.91 | C |
| ATOM | 2033 | CD2 | TYR A | 350 | −51.925 | .918 | −21.211 | 1.00 | 15.08 | C |
| ATOM | 2034 | C | TYR A | 350 | −49.378 | 1.389 | −17.638 | 1.00 | 16.57 | C |
| ATOM | 2035 | O | TYR A | 350 | −50.058 | 1.874 | −16.736 | 1.00 | 17.30 | O |
| ATOM | 2036 | N | GLY A | 351 | −48.149 | .918 | −17.442 | 1.00 | 16.67 | N |
| ATOM | 2037 | CA | GLY A | 351 | −47.572 | .810 | −16.102 | 1.00 | 15.90 | C |
| ATOM | 2038 | C | GLY A | 351 | −48.210 | −.330 | −15.329 | 1.00 | 16.08 | C |
| ATOM | 2039 | O | GLY A | 351 | −48.265 | −.306 | −14.102 | 1.00 | 14.96 | O |
| ATOM | 2040 | N | ALA A | 352 | −48.696 | −1.325 | −16.068 | 1.00 | 16.62 | N |
| ATOM | 2041 | CA | ALA A | 352 | −49.376 | −2.482 | −15.500 | 1.00 | 16.32 | C |

TABLE A-continued

| | | | | | | | | | | |
|---|---|---|---|---|---|---|---|---|---|---|
| ATOM | 2042 | CB | ALA A | 352 | −50.247 | −3.139 | −16.549 | 1.00 | 15.57 | C |
| | | | | | gad67.pdb | | | | | |
| ATOM | 2043 | C | ALA A | 352 | −48.383 | −3.488 | −14.938 | 1.00 | 17.46 | C |
| ATOM | 2044 | O | ALA A | 352 | −47.229 | −3.544 | −15.367 | 1.00 | 17.07 | O |
| ATOM | 2045 | N | PHE A | 353 | −48.846 | −4.286 | −13.980 | 1.00 | 17.93 | N |
| ATOM | 2046 | CA | PHE A | 353 | −48.031 | −5.333 | −13.384 | 1.00 | 18.11 | C |
| ATOM | 2047 | CB | PHE A | 353 | −47.902 | −5.100 | −11.875 | 1.00 | 17.30 | C |
| ATOM | 2048 | CG | PHE A | 353 | −46.998 | −3.950 | −11.513 | 1.00 | 17.19 | C |
| ATOM | 2049 | CD1 | PHE A | 353 | −47.459 | −2.635 | −11.573 | 1.00 | 14.98 | C |
| ATOM | 2050 | CE1 | PHE A | 353 | −46.627 | −1.571 | −11.246 | 1.00 | 11.47 | C |
| ATOM | 2051 | CZ | PHE A | 353 | −45.318 | −1.813 | −10.851 | 1.00 | 14.14 | C |
| ATOM | 2052 | CE2 | PHE A | 353 | −44.843 | −3.123 | −10.789 | 1.00 | 14.98 | C |
| ATOM | 2053 | CD2 | PHE A | 353 | −45.684 | −4.180 | −11.117 | 1.00 | 14.52 | C |
| ATOM | 2054 | C | PHE A | 353 | −48.621 | −6.712 | −13.673 | 1.00 | 19.49 | C |
| ATOM | 2055 | O | PHE A | 353 | −49.747 | −7.001 | −13.280 | 1.00 | 19.74 | O |
| ATOM | 2056 | N | ASP A | 354 | −47.860 | −7.552 | −14.375 | 1.00 | 20.86 | N |
| ATOM | 2057 | CA | ASP A | 354 | −48.242 | −8.947 | −14.620 | 1.00 | 21.44 | C |
| ATOM | 2058 | CB | ASP A | 354 | −47.205 | −9.653 | −15.501 | 1.00 | 20.80 | C |
| ATOM | 2059 | CG | ASP A | 354 | −47.237 | −9.180 | −16.946 | 1.00 | 22.05 | C |
| ATOM | 2060 | OD1 | ASP A | 354 | −48.265 | −8.610 | −17.374 | 1.00 | 20.38 | O |
| ATOM | 2061 | OD2 | ASP A | 354 | −46.224 | −9.376 | −17.657 | 1.00 | 23.66 | O |
| ATOM | 2062 | C | ASP A | 354 | −48.396 | −9.698 | −13.296 | 1.00 | 22.05 | C |
| ATOM | 2063 | O | ASP A | 354 | −47.658 | −9.424 | −12.348 | 1.00 | 22.32 | O |
| ATOM | 2064 | N | PRO A | 355 | −49.357 | −10.645 | −13.223 | 1.00 | 22.42 | N |
| ATOM | 2065 | CA | PRO A | 355 | −49.598 | −11.355 | −11.961 | 1.00 | 22.27 | C |
| ATOM | 2066 | CB | PRO A | 355 | −50.974 | −11.992 | −12.177 | 1.00 | 21.36 | C |
| ATOM | 2067 | CG | PRO A | 355 | −51.058 | −12.203 | −13.654 | 1.00 | 22.87 | C |
| ATOM | 2068 | CD | PRO A | 355 | −50.250 | −11.108 | −14.301 | 1.00 | 22.39 | C |
| ATOM | 2069 | C | PRO A | 355 | −48.522 | −12.412 | −11.716 | 1.00 | 21.99 | C |
| ATOM | 2070 | O | PRO A | 355 | −48.688 | −13.574 | −12.096 | 1.00 | 22.66 | O |
| ATOM | 2071 | N | ILE A | 356 | −47.429 | −11.998 | −11.078 | 1.00 | 21.54 | N |
| ATOM | 2072 | CA | ILE A | 356 | −46.209 | −12.814 | −10.987 | 1.00 | 21.20 | C |
| ATOM | 2073 | CB | ILE A | 356 | −45.033 | −12.034 | −10.324 | 1.00 | 20.97 | C |
| ATOM | 2074 | CG1 | ILE A | 356 | −44.720 | −10.757 | −11.114 | 1.00 | 18.83 | C |
| ATOM | 2075 | CD1 | ILE A | 356 | −43.695 | −9.846 | −10.448 | 1.00 | 20.77 | C |
| ATOM | 2076 | CG2 | ILE A | 356 | −43.781 | −12.904 | −10.236 | 1.00 | 18.65 | C |
| ATOM | 2077 | C | ILE A | 356 | −46.441 | −14.148 | −10.276 | 1.00 | 21.58 | C |
| ATOM | 2078 | O | ILE A | 356 | −45.931 | −15.185 | −10.704 | 1.00 | 20.42 | O |
| ATOM | 2079 | N | GLN A | 357 | −47.227 | −14.110 | −9.206 | 1.00 | 22.47 | N |
| ATOM | 2080 | CA | GLN A | 357 | −47.466 | −15.285 | −8.377 | 1.00 | 23.88 | C |
| ATOM | 2081 | CB | GLN A | 357 | −48.236 | −14.891 | −7.116 | 1.00 | 24.81 | C |
| ATOM | 2082 | CG | GLN A | 357 | −48.050 | −15.849 | −5.968 | 1.00 | 32.62 | C |
| ATOM | 2083 | CD | GLN A | 357 | −46.883 | −15.509 | −5.065 | 1.00 | 37.31 | C |
| ATOM | 2084 | OE1 | GLN A | 357 | −46.018 | −16.346 | −4.822 | 1.00 | 38.97 | O |
| ATOM | 2085 | NE2 | GLN A | 357 | −46.868 | −14.287 | −4.541 | 1.00 | 37.35 | N |
| ATOM | 2086 | C | GLN A | 357 | −48.194 | −16.395 | −9.146 | 1.00 | 22.96 | C |
| ATOM | 2087 | O | GLN A | 357 | −47.827 | −17.568 | −9.038 | 1.00 | 22.33 | O |
| ATOM | 2088 | N | GLU A | 358 | −49.206 | −16.016 | −9.928 | 1.00 | 22.62 | N |
| ATOM | 2089 | CA | GLU A | 358 | −49.931 | −16.956 | −10.784 | 1.00 | 23.97 | C |
| ATOM | 2090 | CB | GLU A | 358 | −51.166 | −16.296 | −11.403 | 1.00 | 23.50 | C |
| ATOM | 2091 | CG | GLU A | 358 | −52.309 | −16.029 | −10.447 | 1.00 | 27.77 | C |
| ATOM | 2092 | CD | GLU A | 358 | −53.549 | −15.511 | −11.169 | 1.00 | 29.54 | C |
| ATOM | 2093 | OE1 | GLU A | 358 | −54.259 | −16.332 | −11.801 | 1.00 | 36.28 | O |
| ATOM | 2094 | OE2 | GLU A | 358 | −53.810 | −14.285 | −11.099 | 1.00 | 37.58 | O |
| ATOM | 2095 | C | GLU A | 358 | −49.036 | −17.496 | −11.901 | 1.00 | 22.26 | C |
| ATOM | 2096 | O | GLU A | 358 | −49.057 | −18.693 | −12.191 | 1.00 | 22.58 | O |
| ATOM | 2097 | N | ILE A | 359 | −48.268 | −16.604 | −12.528 | 1.00 | 20.05 | N |
| ATOM | 2098 | CA | ILE A | 359 | −47.295 | −16.983 | −13.559 | 1.00 | 18.25 | C |
| ATOM | 2099 | CB | ILE A | 359 | −46.643 | −15.726 | −14.209 | 1.00 | 18.28 | C |
| ATOM | 2100 | CG1 | ILE A | 359 | −47.682 | −14.956 | −15.036 | 1.00 | 18.08 | C |
| ATOM | 2101 | CD1 | ILE A | 359 | −47.343 | −13.482 | −15.251 | 1.00 | 21.44 | C |
| ATOM | 2102 | CG2 | ILE A | 359 | −45.434 | −16.100 | −15.072 | 1.00 | 16.35 | C |
| ATOM | 2103 | C | ILE A | 359 | −46.234 | −17.933 | −12.984 | 1.00 | 17.75 | C |
| ATOM | 2104 | O | ILE A | 359 | −45.879 | −18.938 | −13.612 | 1.00 | 17.25 | O |
| ATOM | 2105 | N | ALA A | 360 | −45.755 | −17.625 | −11.780 | 1.00 | 17.36 | N |
| ATOM | 2106 | CA | ALA A | 360 | −44.760 | −18.457 | −11.105 | 1.00 | 17.15 | C |
| ATOM | 2107 | CB | ALA A | 360 | −44.304 | −17.803 | −9.812 | 1.00 | 16.29 | C |
| ATOM | 2108 | C | ALA A | 360 | −45.273 | −19.875 | −10.845 | 1.00 | 18.50 | C |
| ATOM | 2109 | O | ALA A | 360 | −44.505 | −20.842 | −10.954 | 1.00 | 19.19 | O |
| ATOM | 2110 | N | ASP A | 361 | −46.565 | −19.994 | −10.517 | 1.00 | 17.85 | N |
| | | | | | gad67.pdb | | | | | |
| ATOM | 2111 | CA | ASP A | 361 | −47.205 | −21.301 | −10.314 | 1.00 | 18.01 | C |
| ATOM | 2112 | CB | ASP A | 361 | −48.652 | −21.141 | −9.828 | 1.00 | 17.83 | C |
| ATOM | 2113 | CG | ASP A | 361 | −48.749 | −20.766 | −8.356 | 1.00 | 23.16 | C |
| ATOM | 2114 | OD1 | ASP A | 361 | −47.715 | −20.773 | −7.649 | 1.00 | 27.76 | O |
| ATOM | 2115 | OD2 | ASP A | 361 | −49.879 | −20.476 | −7.904 | 1.00 | 25.08 | O |
| ATOM | 2116 | C | ASP A | 361 | −47.193 | −22.107 | −11.604 | 1.00 | 17.53 | C |
| ATOM | 2117 | O | ASP A | 361 | −46.927 | −23.307 | −11.603 | 1.00 | 16.96 | O |
| ATOM | 2118 | N | ILE A | 362 | −47.494 | −21.437 | −12.708 | 1.00 | 17.22 | N |
| ATOM | 2119 | CA | ILE A | 362 | −47.481 | −22.085 | −14.007 | 1.00 | 17.74 | C |

TABLE A-continued

| | | | | | | | | | |
|---|---|---|---|---|---|---|---|---|---|
| ATOM | 2120 | CB | ILE A | 362 | −48.201 | −21.227 | −15.068 | 1.00 | 17.51 | C |
| ATOM | 2121 | CG1 | ILE A | 362 | −49.676 | −21.069 | −14.687 | 1.00 | 15.64 | C |
| ATOM | 2122 | CD1 | ILE A | 362 | −50.422 | −20.032 | −15.493 | 1.00 | 16.92 | C |
| ATOM | 2123 | CG2 | ILE A | 362 | −48.079 | −21.858 | −16.452 | 1.00 | 16.31 | C |
| ATOM | 2124 | C | ILE A | 362 | −46.044 | −22.461 | −14.414 | 1.00 | 18.78 | C |
| ATOM | 2125 | O | ILE A | 362 | −45.822 | −23.518 | −15.000 | 1.00 | 19.12 | O |
| ATOM | 2126 | N | CYS A | 363 | −45.079 | −21.610 | −14.069 | 1.00 | 19.58 | N |
| ATOM | 2127 | CA | CYS A | 363 | −43.661 | −21.885 | −14.331 | 1.00 | 21.50 | C |
| ATOM | 2128 | CB | CYS A | 363 | −42.802 | −20.667 | −13.996 | 1.00 | 20.61 | C |
| ATOM | 2129 | SG | CYS A | 363 | −42.973 | −19.339 | −15.164 | 1.00 | 21.60 | S |
| ATOM | 2130 | C | CYS A | 363 | −43.137 | −23.082 | −13.554 | 1.00 | 22.57 | C |
| ATOM | 2131 | O | CYS A | 363 | −42.344 | −23.863 | −14.079 | 1.00 | 22.29 | O |
| ATOM | 2132 | N | GLU A | 364 | −43.564 | −23.200 | −12.299 | 1.00 | 23.80 | N |
| ATOM | 2133 | CA | GLU A | 364 | −43.150 | −24.299 | −11.432 | 1.00 | 25.46 | C |
| ATOM | 2134 | CB | GLU A | 364 | −43.610 | −24.046 | −9.993 | 1.00 | 26.02 | C |
| ATOM | 2135 | CG | GLU A | 364 | −42.935 | −24.935 | −8.953 | 1.00 | 28.17 | C |
| ATOM | 2139 | C | GLU A | 364 | −43.715 | −25.617 | −11.952 | 1.00 | 25.17 | C |
| ATOM | 2140 | O | GLU A | 364 | −43.023 | −26.638 | −11.968 | 1.00 | 25.87 | O |
| ATOM | 2141 | N | LYS A | 365 | −44.970 | −25.572 | −12.392 | 1.00 | 24.69 | N |
| ATOM | 2142 | CA | LYS A | 365 | −45.668 | −26.736 | −12.926 | 1.00 | 24.45 | C |
| ATOM | 2143 | CB | LYS A | 365 | −47.137 | −26.387 | −13.180 | 1.00 | 23.44 | C |
| ATOM | 2144 | CG | LYS A | 365 | −48.001 | −27.544 | −13.637 | 1.00 | 25.60 | C |
| ATOM | 2145 | CD | LYS A | 365 | −49.435 | −27.095 | −13.853 | 1.00 | 27.97 | C |
| ATOM | 2146 | CE | LYS A | 365 | −50.278 | −28.204 | −14.455 | 1.00 | 32.77 | C |
| ATOM | 2147 | NZ | LYS A | 365 | −51.615 | −27.691 | −14.870 | 1.00 | 34.56 | N |
| ATOM | 2148 | C | LYS A | 365 | −45.024 | −27.265 | −14.208 | 1.00 | 24.30 | C |
| ATOM | 2149 | O | LYS A | 365 | −44.871 | −28.481 | −14.368 | 1.00 | 24.61 | O |
| ATOM | 2150 | N | TYR A | 366 | −44.646 | −26.356 | −15.109 | 1.00 | 23.90 | N |
| ATOM | 2151 | CA | TYR A | 366 | −44.112 | −26.741 | −16.422 | 1.00 | 23.98 | C |
| ATOM | 2152 | CB | TYR A | 366 | −44.794 | −25.942 | −17.537 | 1.00 | 23.23 | C |
| ATOM | 2153 | CG | TYR A | 366 | −46.265 | −26.261 | −17.699 | 1.00 | 23.62 | C |
| ATOM | 2154 | CD1 | TYR A | 366 | −46.682 | −27.400 | −18.395 | 1.00 | 22.02 | C |
| ATOM | 2155 | CE1 | TYR A | 366 | −48.033 | −27.696 | −18.545 | 1.00 | 22.73 | C |
| ATOM | 2156 | CZ | TYR A | 366 | −48.985 | −26.842 | −17.994 | 1.00 | 24.47 | C |
| ATOM | 2157 | OH | TYR A | 366 | −50.325 | −27.119 | −18.127 | 1.00 | 22.67 | O |
| ATOM | 2158 | CE2 | TYR A | 366 | −48.593 | −25.708 | −17.299 | 1.00 | 22.57 | C |
| ATOM | 2159 | CD2 | TYR A | 366 | −47.240 | −25.426 | −17.156 | 1.00 | 22.21 | C |
| ATOM | 2160 | C | TYR A | 366 | −42.590 | −26.642 | −16.554 | 1.00 | 24.56 | C |
| ATOM | 2161 | O | TYR A | 366 | −42.046 | −26.875 | −17.639 | 1.00 | 25.49 | O |
| ATOM | 2162 | N | ASN A | 367 | −41.915 | −26.316 | −15.450 | 1.00 | 25.08 | N |
| ATOM | 2163 | CA | ASN A | 367 | −40.457 | −26.101 | −15.425 | 1.00 | 26.16 | C |
| ATOM | 2164 | CB | ASN A | 367 | −39.676 | −27.423 | −15.574 | 1.00 | 27.26 | C |
| ATOM | 2165 | CG | ASN A | 367 | −38.192 | −27.278 | −15.221 | 1.00 | 30.78 | C |
| ATOM | 2166 | OD1 | ASN A | 367 | −37.776 | −26.293 | −14.606 | 1.00 | 32.53 | O |
| ATOM | 2167 | ND2 | ASN A | 367 | −37.393 | −28.264 | −15.613 | 1.00 | 32.45 | N |
| ATOM | 2168 | C | ASN A | 367 | −39.980 | −25.047 | −16.434 | 1.00 | 25.82 | C |
| ATOM | 2169 | O | ASN A | 367 | −39.183 | −25.335 | −17.336 | 1.00 | 26.47 | O |
| ATOM | 2170 | N | LEU A | 368 | −40.489 | −23.829 | −16.271 | 1.00 | 24.28 | N |
| ATOM | 2171 | CA | LEU A | 368 | −40.071 | −22.698 | −17.088 | 1.00 | 22.86 | C |
| ATOM | 2172 | CB | LEU A | 368 | −41.285 | −21.987 | −17.688 | 1.00 | 22.78 | C |
| ATOM | 2173 | CG | LEU A | 368 | −41.776 | −22.412 | −19.078 | 1.00 | 25.95 | C |
| ATOM | 2174 | CD1 | LEU A | 368 | −42.332 | −23.827 | −19.108 | 1.00 | 23.73 | C |
| ATOM | 2175 | CD2 | LEU A | 368 | −42.822 | −21.429 | −19.589 | 1.00 | 24.16 | C |
| ATOM | 2176 | C | LEU A | 368 | −39.258 | −21.716 | −16.265 | 1.00 | 21.09 | C |
| ATOM | 2177 | O | LEU A | 368 | −39.533 | −21.505 | −15.078 | 1.00 | 20.99 | O |
| ATOM | 2178 | N | TRP A | 369 | −38.248 | −21.128 | −16.900 | 1.00 | 18.83 | N |
| ATOM | 2179 | CA | TRP A | 369 | −37.474 | −20.050 | −16.298 | 1.00 | 16.51 | C |
| ATOM | 2180 | CB | TRP A | 369 | −36.239 | −19.749 | −17.153 | 1.00 | 15.98 | C |
| ATOM | 2181 | CG | TRP A | 369 | −35.351 | −18.641 | −16.630 | 1.00 | 14.08 | C |
| | | | | | gad67.pdb | | | | | |
| ATOM | 2182 | CD1 | TRP A | 369 | −35.612 | −17.297 | −16.644 | 1.00 | 12.90 | C |
| ATOM | 2183 | NE1 | TRP A | 369 | −34.559 | −16.606 | −16.096 | 1.00 | 14.49 | N |
| ATOM | 2184 | CE2 | TRP A | 369 | −33.587 | −17.497 | −15.725 | 1.00 | 13.55 | C |
| ATOM | 2185 | CD2 | TRP A | 369 | −34.050 | −18.790 | −16.050 | 1.00 | 13.67 | C |
| ATOM | 2186 | CE3 | TRP A | 369 | −33.233 | −19.894 | −15.764 | 1.00 | 12.08 | C |
| ATOM | 2187 | CZ3 | TRP A | 369 | −31.993 | −19.673 | −15.173 | 1.00 | 14.00 | C |
| ATOM | 2188 | CH2 | TRP A | 369 | −31.561 | −18.375 | −14.861 | 1.00 | 14.31 | C |
| ATOM | 2189 | CZ2 | TRP A | 369 | −32.341 | −17.276 | −15.126 | 1.00 | 14.51 | C |
| ATOM | 2190 | C | TRP A | 369 | −38.379 | −18.830 | −16.215 | 1.00 | 15.58 | C |
| ATOM | 2191 | O | TRP A | 369 | −39.021 | −18.466 | −17.201 | 1.00 | 16.07 | O |
| ATOM | 2192 | N | LEU A | 370 | −38.444 | −18.221 | −15.034 | 1.00 | 14.10 | N |
| ATOM | 2193 | CA | LEU A | 370 | −39.260 | −17.031 | −14.824 | 1.00 | 12.97 | C |
| ATOM | 2194 | CB | LEU A | 370 | −40.133 | −17.160 | −13.568 | 1.00 | 12.12 | C |
| ATOM | 2195 | CG | LEU A | 370 | −40.833 | −15.883 | −13.075 | 1.00 | 10.45 | C |
| ATOM | 2196 | CD1 | LEU A | 370 | −41.719 | −15.247 | −14.159 | 1.00 | 6.93 | C |
| ATOM | 2197 | CD2 | LEU A | 370 | −41.644 | −16.161 | −11.811 | 1.00 | 12.60 | C |
| ATOM | 2198 | C | LEU A | 370 | −38.380 | −15.801 | −14.721 | 1.00 | 12.93 | C |
| ATOM | 2199 | O | LEU A | 370 | −37.573 | −15.674 | −13.796 | 1.00 | 13.32 | O |
| ATOM | 2200 | N | HIS A | 371 | −38.540 | −14.903 | −15.685 | 1.00 | 13.72 | N |
| ATOM | 2201 | CA | HIS A | 371 | −37.841 | −13.633 | −15.660 | 1.00 | 13.61 | C |

TABLE A-continued

| ATOM | 2202 | CB | HIS A | 371 | −37.096 | −13.370 | −16.975 | 1.00 | 13.78 | C |
|---|---|---|---|---|---|---|---|---|---|---|
| ATOM | 2203 | CG | HIS A | 371 | −36.515 | −11.991 | −17.060 | 1.00 | 12.20 | C |
| ATOM | 2204 | ND1 | HIS A | 371 | −35.407 | −11.606 | −16.335 | 1.00 | 12.15 | N |
| ATOM | 2205 | CE1 | HIS A | 371 | −35.135 | −10.338 | −16.587 | 1.00 | 9.47 | C |
| ATOM | 2206 | NE2 | HIS A | 371 | −36.029 | −9.886 | −17.449 | 1.00 | 13.52 | N |
| ATOM | 2207 | CD2 | HIS A | 371 | −36.908 | −10.898 | −17.755 | 1.00 | 11.54 | C |
| ATOM | 2208 | C | HIS A | 371 | −38.831 | −12.521 | −15.395 | 1.00 | 13.71 | C |
| ATOM | 2209 | O | HIS A | 371 | −39.904 | −12.476 | −15.996 | 1.00 | 12.42 | O |
| ATOM | 2210 | N | VAL A | 372 | −38.467 | −11.625 | −14.486 | 1.00 | 14.49 | N |
| ATOM | 2211 | CA | VAL A | 372 | −39.293 | −10.461 | −14.217 | 1.00 | 13.73 | C |
| ATOM | 2212 | CB | VAL A | 372 | −39.677 | −10.350 | −12.720 | 1.00 | 13.37 | C |
| ATOM | 2213 | CG1 | VAL A | 372 | −40.403 | −9.045 | −12.443 | 1.00 | 12.45 | C |
| ATOM | 2214 | CG2 | VAL A | 372 | −40.551 | −11.539 | −12.305 | 1.00 | 11.54 | C |
| ATOM | 2215 | C | VAL A | 372 | −38.601 | −9.200 | −14.728 | 1.00 | 13.98 | C |
| ATOM | 2216 | O | VAL A | 372 | −37.521 | −8.839 | −14.264 | 1.00 | 13.84 | O |
| ATOM | 2217 | N | ASP A | 373 | −39.230 | −8.553 | −15.704 | 1.00 | 14.36 | N |
| ATOM | 2218 | CA | ASP A | 373 | −38.758 | −7.272 | −16.215 | 1.00 | 14.65 | C |
| ATOM | 2219 | CB | ASP A | 373 | −39.152 | −7.095 | −17.685 | 1.00 | 15.19 | C |
| ATOM | 2220 | CG | ASP A | 373 | −38.544 | −5.853 | −18.315 | 1.00 | 15.61 | C |
| ATOM | 2221 | OD1 | ASP A | 373 | −37.878 | −5.069 | −17.603 | 1.00 | 14.05 | O |
| ATOM | 2222 | OD2 | ASP A | 373 | −38.742 | −5.662 | −19.534 | 1.00 | 17.45 | O |
| ATOM | 2223 | C | ASP A | 373 | −39.288 | −6.123 | −15.358 | 1.00 | 14.29 | C |
| ATOM | 2224 | O | ASP A | 373 | −40.363 | −5.570 | −15.622 | 1.00 | 13.20 | O |
| ATOM | 2225 | N | ALA A | 374 | −38.515 | −5.772 | −14.335 | 1.00 | 14.80 | N |
| ATOM | 2226 | CA | ALA A | 374 | −38.853 | −4.675 | −13.435 | 1.00 | 14.98 | C |
| ATOM | 2227 | CB | ALA A | 374 | −38.687 | −5.123 | −11.968 | 1.00 | 13.55 | C |
| ATOM | 2228 | C | ALA A | 374 | −38.007 | −3.425 | −13.736 | 1.00 | 15.35 | C |
| ATOM | 2229 | O | ALA A | 374 | −37.714 | −2.628 | −12.841 | 1.00 | 13.83 | O |
| ATOM | 2230 | N | ALA A | 375 | −37.609 | −3.266 | −15.001 | 1.00 | 16.02 | N |
| ATOM | 2231 | CA | ALA A | 375 | −36.853 | −2.088 | −15.430 | 1.00 | 16.37 | C |
| ATOM | 2232 | CB | ALA A | 375 | −36.671 | −2.088 | −16.954 | 1.00 | 15.73 | C |
| ATOM | 2233 | C | ALA A | 375 | −37.529 | −.795 | −14.958 | 1.00 | 16.64 | C |
| ATOM | 2234 | O | ALA A | 375 | −36.880 | .079 | −14.391 | 1.00 | 17.40 | O |
| ATOM | 2235 | N | TRP A | 376 | −38.842 | −.712 | −15.166 | 1.00 | 16.83 | N |
| ATOM | 2236 | CA | TRP A | 376 | −39.648 | .451 | −14.794 | 1.00 | 16.39 | C |
| ATOM | 2237 | CB | TRP A | 376 | −40.702 | .694 | −15.882 | 1.00 | 15.16 | C |
| ATOM | 2238 | CG | TRP A | 376 | −41.728 | 1.793 | −15.633 | 1.00 | 16.12 | C |
| ATOM | 2239 | CD1 | TRP A | 376 | −43.081 | 1.691 | −15.812 | 1.00 | 12.91 | C |
| ATOM | 2240 | NE1 | TRP A | 376 | −43.692 | 2.883 | −15.524 | 1.00 | 13.52 | N |
| ATOM | 2241 | CE2 | TRP A | 376 | −42.741 | 3.796 | −15.150 | 1.00 | 15.59 | C |
| ATOM | 2242 | CD2 | TRP A | 376 | −41.484 | 3.147 | −15.209 | 1.00 | 14.77 | C |
| ATOM | 2243 | CE3 | TRP A | 376 | −40.330 | 3.874 | −14.870 | 1.00 | 14.16 | C |
| ATOM | 2244 | CZ3 | TRP A | 376 | −40.467 | 5.211 | −14.489 | 1.00 | 11.87 | C |
| ATOM | 2245 | CH2 | TRP A | 376 | −41.735 | 5.824 | −14.436 | 1.00 | 14.82 | C |
| ATOM | 2246 | CZ2 | TRP A | 376 | −42.880 | 5.135 | −14.757 | 1.00 | 12.00 | C |
| ATOM | 2247 | C | TRP A | 376 | −40.301 | .298 | −13.412 | 1.00 | 16.78 | C |
| ATOM | 2248 | O | TRP A | 376 | −40.278 | 1.223 | −12.597 | 1.00 | 17.71 | O |
| ATOM | 2249 | N | GLY A | 377 | −40.873 | −.871 | −13.145 | 1.00 | 17.19 | N |
| | | | | | gad67.pdb | | | | | |
| ATOM | 2250 | CA | GLY A | 377 | −41.564 | −1.115 | −11.878 | 1.00 | 17.71 | C |
| ATOM | 2251 | C | GLY A | 377 | −40.683 | −1.425 | −10.678 | 1.00 | 17.76 | C |
| ATOM | 2252 | O | GLY A | 377 | −41.168 | −1.425 | −9.547 | 1.00 | 17.93 | O |
| ATOM | 2253 | N | GLY A | 378 | −39.395 | −1.678 | −10.919 | 1.00 | 17.33 | N |
| ATOM | 2254 | CA | GLY A | 378 | −38.442 | −2.062 | −9.867 | 1.00 | 17.39 | C |
| ATOM | 2255 | C | GLY A | 378 | −38.225 | −1.033 | −8.771 | 1.00 | 18.67 | C |
| ATOM | 2256 | O | GLY A | 378 | −37.919 | −1.385 | −7.629 | 1.00 | 18.00 | O |
| ATOM | 2257 | N | GLY A | 379 | −38.384 | .242 | −9.116 | 1.00 | 19.22 | N |
| ATOM | 2258 | CA | GLY A | 379 | −38.283 | 1.322 | −8.139 | 1.00 | 20.05 | C |
| ATOM | 2259 | C | GLY A | 379 | −39.287 | 1.189 | −7.004 | 1.00 | 20.51 | C |
| ATOM | 2260 | O | GLY A | 379 | −39.029 | 1.646 | −5.885 | 1.00 | 20.81 | O |
| ATOM | 2261 | N | LEU A | 380 | −40.423 | .551 | −7.290 | 1.00 | 20.15 | N |
| ATOM | 2262 | CA | LEU A | 380 | −41.501 | .377 | −6.306 | 1.00 | 20.36 | C |
| ATOM | 2263 | CB | LEU A | 380 | −42.824 | .004 | −6.993 | 1.00 | 20.29 | C |
| ATOM | 2264 | CG | LEU A | 380 | −43.729 | 1.158 | −7.450 | 1.00 | 20.80 | C |
| ATOM | 2265 | CD1 | LEU A | 380 | −43.099 | 1.970 | −8.568 | 1.00 | 18.98 | C |
| ATOM | 2266 | CD2 | LEU A | 380 | −45.090 | .647 | −7.888 | 1.00 | 19.56 | C |
| ATOM | 2267 | C | LEU A | 380 | −41.155 | −.627 | −5.205 | 1.00 | 20.73 | C |
| ATOM | 2268 | O | LEU A | 380 | −41.822 | −.670 | −4.166 | 1.00 | 21.31 | O |
| ATOM | 2269 | N | LEU A | 381 | −40.112 | −1.422 | −5.439 | 1.00 | 19.97 | N |
| ATOM | 2270 | CA | LEU A | 381 | −39.581 | −2.331 | −4.429 | 1.00 | 20.25 | C |
| ATOM | 2271 | CB | LEU A | 381 | −38.510 | −3.249 | −5.029 | 1.00 | 19.28 | C |
| ATOM | 2272 | CG | LEU A | 381 | −38.914 | −4.348 | −6.018 | 1.00 | 19.56 | C |
| ATOM | 2273 | CD1 | LEU A | 381 | −37.689 | −4.893 | −6.760 | 1.00 | 19.51 | C |
| ATOM | 2274 | CD2 | LEU A | 381 | −39.676 | −5.486 | −5.330 | 1.00 | 19.35 | C |
| ATOM | 2275 | C | LEU A | 381 | −39.006 | −1.570 | −3.233 | 1.00 | 20.96 | C |
| ATOM | 2276 | O | LEU A | 381 | −38.917 | −2.116 | −2.135 | 1.00 | 21.39 | O |
| ATOM | 2277 | N | MET A | 382 | −38.620 | −.312 | −3.459 | 1.00 | 21.65 | N |
| ATOM | 2278 | CA | MET A | 382 | −38.067 | .563 | −2.421 | 1.00 | 21.83 | C |
| ATOM | 2279 | CB | MET A | 382 | −37.279 | 1.717 | −3.055 | 1.00 | 21.81 | C |
| ATOM | 2280 | CG | MET A | 382 | −36.168 | 1.296 | −4.013 | 1.00 | 22.10 | C |

TABLE A-continued

| | | | | | | | | | | |
|---|---|---|---|---|---|---|---|---|---|---|
| ATOM | 2281 | SD | MET A | 382 | −34.897 | .295 | −3.220 | 1.00 | 20.72 | S |
| ATOM | 2282 | CE | MET A | 382 | −34.022 | 1.538 | −2.272 | 1.00 | 19.69 | C |
| ATOM | 2283 | C | MET A | 382 | −39.146 | 1.146 | −1.502 | 1.00 | 22.20 | C |
| ATOM | 2284 | O | MET A | 382 | −38.832 | 1.752 | −.474 | 1.00 | 22.08 | O |
| ATOM | 2285 | N | SER A | 383 | −40.409 | .972 | −1.879 | 1.00 | 22.73 | N |
| ATOM | 2286 | CA | SER A | 383 | −41.526 | 1.514 | −1.113 | 1.00 | 23.86 | C |
| ATOM | 2287 | CB | SER A | 383 | −42.454 | 2.309 | −2.030 | 1.00 | 23.81 | C |
| ATOM | 2288 | OG | SER A | 383 | −43.670 | 2.623 | −1.376 | 1.00 | 22.51 | O |
| ATOM | 2289 | C | SER A | 383 | −42.309 | .423 | −.388 | 1.00 | 24.33 | C |
| ATOM | 2290 | O | SER A | 383 | −42.814 | −.506 | −1.018 | 1.00 | 24.69 | O |
| ATOM | 2291 | N | ARG A | 384 | −42.407 | .547 | .934 | 1.00 | 25.10 | N |
| ATOM | 2292 | CA | ARG A | 384 | −43.208 | −.370 | 1.753 | 1.00 | 25.84 | C |
| ATOM | 2293 | CB | ARG A | 384 | −43.051 | −.032 | 3.240 | 1.00 | 26.78 | C |
| ATOM | 2294 | CG | ARG A | 384 | −41.889 | −.747 | 3.928 | 1.00 | 30.81 | C |
| ATOM | 2295 | CD | ARG A | 384 | −41.052 | .199 | 4.787 | 1.00 | 36.59 | C |
| ATOM | 2296 | NE | ARG A | 384 | −41.848 | .944 | 5.761 | 1.00 | 42.33 | N |
| ATOM | 2297 | CZ | ARG A | 384 | −41.442 | 2.048 | 6.383 | 1.00 | 45.11 | C |
| ATOM | 2298 | NH1 | ARG A | 384 | −40.242 | 2.558 | 6.137 | 1.00 | 43.33 | N |
| ATOM | 2299 | NH2 | ARG A | 384 | −42.245 | 2.649 | 7.252 | 1.00 | 47.39 | N |
| ATOM | 2300 | C | ARG A | 384 | −44.684 | −.334 | 1.350 | 1.00 | 25.48 | C |
| ATOM | 2301 | O | ARG A | 384 | −45.360 | −1.366 | 1.335 | 1.00 | 25.47 | O |
| ATOM | 2302 | N | LYS A | 385 | −45.168 | .859 | 1.010 | 1.00 | 25.61 | N |
| ATOM | 2303 | CA | LYS A | 385 | −46.553 | 1.064 | .580 | 1.00 | 26.44 | C |
| ATOM | 2304 | CB | LYS A | 385 | −46.874 | 2.566 | .567 | 1.00 | 26.51 | C |
| ATOM | 2305 | CG | LYS A | 385 | −48.141 | 2.958 | −.190 | 1.00 | 28.82 | C |
| ATOM | 2306 | CD | LYS A | 385 | −48.252 | 4.469 | −.331 | 1.00 | 29.60 | C |
| ATOM | 2307 | CE | LYS A | 385 | −49.396 | 5.041 | .492 | 1.00 | 36.67 | C |
| ATOM | 2308 | NZ | LYS A | 385 | −50.703 | 4.888 | −.218 | 1.00 | 36.43 | N |
| ATOM | 2309 | C | LYS A | 385 | −46.869 | .433 | −.783 | 1.00 | 25.94 | C |
| ATOM | 2310 | O | LYS A | 385 | −47.988 | −.037 | −1.009 | 1.00 | 27.01 | O |
| ATOM | 2311 | N | HIS A | 386 | −45.884 | .410 | −1.680 | 1.00 | 24.59 | N |
| ATOM | 2312 | CA | HIS A | 386 | −46.124 | .001 | −3.066 | 1.00 | 23.18 | C |
| ATOM | 2313 | CB | HIS A | 386 | −45.720 | 1.127 | −4.021 | 1.00 | 22.63 | C |
| ATOM | 2314 | CG | HIS A | 386 | −46.620 | 2.318 | −3.963 | 1.00 | 20.88 | C |
| ATOM | 2315 | ND1 | HIS A | 386 | −47.833 | 2.365 | −4.613 | 1.00 | 20.28 | N |
| ATOM | 2316 | CE1 | HIS A | 386 | −48.406 | 3.534 | −4.388 | 1.00 | 23.47 | C |
| ATOM | 2317 | NE2 | HIS A | 386 | −47.606 | 4.248 | −3.618 | 1.00 | 23.78 | N |
| | | | | gad67.pdb | | | | | | |
| ATOM | 2318 | CD2 | HIS A | 386 | −46.484 | 3.509 | −3.334 | 1.00 | 21.98 | C |
| ATOM | 2319 | C | HIS A | 386 | −45.483 | −1.316 | −3.522 | 1.00 | 22.96 | C |
| ATOM | 2320 | O | HIS A | 386 | −45.836 | −1.827 | −4.586 | 1.00 | 23.54 | O |
| ATOM | 2321 | N | ARG A | 387 | −44.563 | −1.868 | −2.732 | 1.00 | 22.87 | N |
| ATOM | 2322 | CA | ARG A | 387 | −43.797 | −3.053 | −3.160 | 1.00 | 23.08 | C |
| ATOM | 2323 | CB | ARG A | 387 | −42.642 | −3.373 | −2.194 | 1.00 | 23.60 | C |
| ATOM | 2324 | CG | ARG A | 387 | −43.049 | −3.932 | −.839 | 1.00 | 25.33 | C |
| ATOM | 2325 | CD | ARG A | 387 | −41.904 | −4.703 | −.182 | 1.00 | 28.74 | C |
| ATOM | 2326 | NE | ARG A | 387 | −41.578 | −5.940 | −.902 | 1.00 | 36.57 | N |
| ATOM | 2327 | CZ | ARG A | 387 | −40.360 | −6.287 | −1.318 | 1.00 | 37.60 | C |
| ATOM | 2328 | NH1 | ARG A | 387 | −39.308 | −5.508 | −1.080 | 1.00 | 35.06 | N |
| ATOM | 2329 | NH2 | ARG A | 387 | −40.192 | −7.432 | −1.966 | 1.00 | 38.86 | N |
| ATOM | 2330 | C | ARG A | 387 | −44.642 | −4.297 | −3.436 | 1.00 | 22.59 | C |
| ATOM | 2331 | O | ARG A | 387 | −44.204 | −5.188 | −4.169 | 1.00 | 22.31 | O |
| ATOM | 2332 | N | HIS A | 388 | −45.848 | −4.342 | −2.862 | 1.00 | 21.72 | N |
| ATOM | 2333 | CA | HIS A | 388 | −46.770 | −5.473 | −3.038 | 1.00 | 20.81 | C |
| ATOM | 2334 | CB | HIS A | 388 | −48.037 | −5.278 | −2.193 | 1.00 | 20.68 | C |
| ATOM | 2335 | CG | HIS A | 388 | −48.887 | −4.136 | −2.647 | 1.00 | 18.92 | C |
| ATOM | 2336 | ND1 | HIS A | 388 | −49.933 | −4.295 | −3.530 | 1.00 | 20.36 | N |
| ATOM | 2337 | CE1 | HIS A | 388 | −50.490 | −3.120 | −3.761 | 1.00 | 18.77 | C |
| ATOM | 2338 | NE2 | HIS A | 388 | −49.836 | −2.205 | −3.070 | 1.00 | 16.43 | N |
| ATOM | 2339 | CD2 | HIS A | 388 | −48.827 | −2.814 | −2.368 | 1.00 | 16.87 | C |
| ATOM | 2340 | C | HIS A | 388 | −47.157 | −5.704 | −4.498 | 1.00 | 20.62 | C |
| ATOM | 2341 | O | HIS A | 388 | −47.543 | −6.811 | −4.875 | 1.00 | 21.24 | O |
| ATOM | 2342 | N | LYS A | 389 | −47.054 | −4.660 | −5.318 | 1.00 | 20.98 | N |
| ATOM | 2343 | CA | LYS A | 389 | −47.341 | −4.780 | −6.757 | 1.00 | 20.60 | C |
| ATOM | 2344 | CB | LYS A | 389 | −47.319 | −3.407 | −7.434 | 1.00 | 21.25 | C |
| ATOM | 2345 | CG | LYS A | 389 | −48.563 | −2.576 | −7.129 | 1.00 | 22.49 | C |
| ATOM | 2346 | CD | LYS A | 389 | −48.325 | −1.090 | −7.312 | 1.00 | 25.21 | C |
| ATOM | 2347 | CE | LYS A | 389 | −49.534 | −.280 | −6.848 | 1.00 | 26.73 | C |
| ATOM | 2348 | NZ | LYS A | 389 | −49.350 | 1.196 | −7.033 | 1.00 | 22.43 | N |
| ATOM | 2349 | C | LYS A | 389 | −46.397 | −5.766 | −7.448 | 1.00 | 19.85 | C |
| ATOM | 2350 | O | LYS A | 389 | −46.696 | −6.262 | −8.538 | 1.00 | 19.59 | O |
| ATOM | 2351 | N | LEU A | 390 | −45.277 | −6.065 | −6.787 | 1.00 | 19.31 | N |
| ATOM | 2352 | CA | LEU A | 390 | −44.292 | −7.028 | −7.289 | 1.00 | 19.38 | C |
| ATOM | 2353 | CB | LEU A | 390 | −42.887 | −6.398 | −7.345 | 1.00 | 18.82 | C |
| ATOM | 2354 | CG | LEU A | 390 | −42.645 | −5.166 | −8.229 | 1.00 | 18.30 | C |
| ATOM | 2355 | CD1 | LEU A | 390 | −42.830 | −3.881 | −7.426 | 1.00 | 10.49 | C |
| ATOM | 2356 | CO2 | LEU A | 390 | −41.249 | −5.188 | −8.872 | 1.00 | 11.87 | C |
| ATOM | 2357 | C | LEU A | 390 | −44.262 | −8.348 | −6.497 | 1.00 | 20.07 | C |
| ATOM | 2358 | O | LEU A | 390 | −43.312 | −9.120 | −6.620 | 1.00 | 20.25 | O |
| ATOM | 2359 | N | ASN A | 391 | −45.298 | −8.608 | −5.693 | 1.00 | 20.64 | N |

TABLE A-continued

| | | | | | | | | | | |
|---|---|---|---|---|---|---|---|---|---|---|
| ATOM | 2360 | CA | ASN A | 391 | −45.420 | −9.880 | −4.966 | 1.00 | 20.68 | C |
| ATOM | 2361 | CB | ASN A | 391 | −46.774 | −9.979 | −4.249 | 1.00 | 22.27 | C |
| ATOM | 2362 | CG | ASN A | 391 | −46.782 | −9.284 | −2.896 | 1.00 | 25.37 | C |
| ATOM | 2363 | OD1 | ASN A | 391 | −45.767 | −8.764 | −2.430 | 1.00 | 28.16 | O |
| ATOM | 2364 | ND2 | ASN A | 391 | −47.939 | −9.284 | −2.254 | 1.00 | 28.34 | N |
| ATOM | 2365 | C | ASN A | 391 | −45.233 | −11.093 | −5.876 | 1.00 | 18.89 | C |
| ATOM | 2366 | O | ASN A | 391 | −45.847 | −11.181 | −6.938 | 1.00 | 18.34 | O |
| ATOM | 2367 | N | GLY A | 392 | −44.378 | −12.017 | −5.453 | 1.00 | 18.63 | N |
| ATOM | 2368 | CA | GLY A | 392 | −44.050 | −13.197 | −6.253 | 1.00 | 18.60 | C |
| ATOM | 2369 | C | GLY A | 392 | −42.674 | −13.106 | −6.893 | 1.00 | 18.94 | C |
| ATOM | 2370 | O | GLY A | 392 | −42.111 | −14.122 | −7.313 | 1.00 | 19.78 | O |
| ATOM | 2371 | N | ILE A | 393 | −42.133 | −11.889 | −6.961 | 1.00 | 18.07 | N |
| ATOM | 2372 | CA | ILE A | 393 | −40.827 | −11.642 | −7.583 | 1.00 | 17.68 | C |
| ATOM | 2373 | CB | ILE A | 393 | −40.453 | −10.123 | −7.586 | 1.00 | 17.60 | C |
| ATOM | 2374 | CG1 | ILE A | 393 | −39.246 | −9.859 | −8.501 | 1.00 | 17.76 | C |
| ATOM | 2375 | CD1 | ILE A | 393 | −39.031 | −8.393 | −8.883 | 1.00 | 15.60 | C |
| ATOM | 2376 | CG2 | ILE A | 393 | −40.235 | −9.601 | −6.157 | 1.00 | 14.73 | C |
| ATOM | 2377 | C | ILE A | 393 | −39.721 | −12.481 | −6.941 | 1.00 | 18.33 | C |
| ATOM | 2378 | O | ILE A | 393 | −38.727 | −12.814 | −7.593 | 1.00 | 18.59 | O |
| ATOM | 2379 | N | GLU A | 394 | −39.917 | −12.833 | −5.669 | 1.00 | 18.00 | N |
| ATOM | 2380 | CA | GLU A | 394 | −38.954 | −13.639 | −4.920 | 1.00 | 18.25 | C |
| ATOM | 2381 | CB | GLU A | 394 | −39.318 | −13.687 | −3.425 | 1.00 | 19.51 | C |
| ATOM | 2382 | CG | GLU A | 394 | −40.500 | −14.604 | −3.053 | 1.00 | 21.81 | C |
| ATOM | 2383 | CD | GLU A | 394 | −41.872 | −13.955 | −3.231 | 1.00 | 29.92 | C |
| ATOM | 2384 | OE1 | GLU A | 394 | −42.885 | −14.669 | −3.046 | 1.00 | 35.16 | O |
| ATOM | 2385 | OE2 | GLU A | 394 | −41.954 | −12.744 | −3.548 | 1.00 | 29.48 | O |
| | | | | | gad67.pdb | | | | | |
| ATOM | 2386 | C | GLU A | 394 | −38.833 | −15.046 | −5.495 | 1.00 | 18.06 | C |
| ATOM | 2387 | O | GLU A | 394 | −37.900 | −15.778 | −5.158 | 1.00 | 18.66 | O |
| ATOM | 2388 | N | ARG A | 395 | −39.781 | −15.407 | −6.359 | 1.00 | 17.22 | N |
| ATOM | 2389 | CA | ARG A | 395 | −39.805 | −16.712 | −7.007 | 1.00 | 17.30 | C |
| ATOM | 2390 | CB | ARG A | 395 | −41.235 | −17.268 | −7.040 | 1.00 | 17.04 | C |
| ATOM | 2391 | CG | ARG A | 395 | −41.788 | −17.641 | −5.668 | 1.00 | 19.49 | C |
| ATOM | 2392 | CD | ARG A | 395 | −42.763 | −18.799 | −5.779 | 1.00 | 22.52 | C |
| ATOM | 2393 | NE | ARG A | 395 | −44.124 | −18.338 | −6.026 | 1.00 | 20.66 | N |
| ATOM | 2394 | CZ | ARG A | 395 | −45.091 | −19.091 | −6.538 | 1.00 | 18.68 | C |
| ATOM | 2395 | NH1 | ARG A | 395 | −44.851 | −20.347 | −6.889 | 1.00 | 16.08 | N |
| ATOM | 2396 | NH2 | ARG A | 395 | −46.298 | −18.579 | −6.720 | 1.00 | 20.13 | N |
| ATOM | 2397 | C | ARG A | 395 | −39.217 | −16.678 | −8.423 | 1.00 | 16.87 | C |
| ATOM | 2398 | O | ARG A | 395 | −39.131 | −17.712 | −9.087 | 1.00 | 16.73 | O |
| ATOM | 2399 | N | ALA A | 396 | −38.826 | −15.488 | −8.876 | 1.00 | 15.90 | N |
| ATOM | 2400 | CA | ALA A | 396 | −38.213 | −15.322 | −10.194 | 1.00 | 16.31 | C |
| ATOM | 2401 | CB | ALA A | 396 | −38.147 | −13.847 | −10.567 | 1.00 | 14.89 | C |
| ATOM | 2402 | C | ALA A | 396 | −36.819 | −15.937 | −10.225 | 1.00 | 16.34 | C |
| ATOM | 2403 | O | ALA A | 396 | −36.119 | −15.967 | −9.209 | 1.00 | 17.33 | O |
| ATOM | 2404 | N | ASN A | 397 | −36.427 | −16.432 | −11.392 | 1.00 | 16.48 | N |
| ATOM | 2405 | CA | ASN A | 397 | −35.066 | −16.908 | −11.606 | 1.00 | 16.30 | C |
| ATOM | 2406 | CB | ASN A | 397 | −35.049 | −17.997 | −12.681 | 1.00 | 16.79 | C |
| ATOM | 2407 | CG | ASN A | 397 | −35.897 | −19.202 | −12.305 | 1.00 | 15.82 | C |
| ATOM | 2408 | OD1 | ASN A | 397 | −37.003 | −19.378 | −12.814 | 1.00 | 16.98 | O |
| ATOM | 2409 | ND2 | ASN A | 397 | −35.391 | −20.025 | −11.397 | 1.00 | 14.25 | N |
| ATOM | 2410 | C | ASN A | 397 | −34.124 | −15.761 | −11.974 | 1.00 | 16.04 | C |
| ATOM | 2411 | O | ASN A | 397 | −32.918 | −15.842 | −11.749 | 1.00 | 16.47 | O |
| ATOM | 2412 | N | SER A | 398 | −34.688 | −14.694 | −12.537 | 1.00 | 15.79 | N |
| ATOM | 2413 | CA | SER A | 398 | −33.928 | −13.485 | −12.876 | 1.00 | 15.93 | C |
| ATOM | 2414 | CB | SER A | 398 | −33.220 | −13.624 | −14.236 | 1.00 | 15.54 | C |
| ATOM | 2415 | OG | SER A | 398 | −34.150 | −13.726 | −15.299 | 1.00 | 16.75 | O |
| ATOM | 2416 | C | SER A | 398 | −34.809 | −12.241 | −12.860 | 1.00 | 15.77 | C |
| ATOM | 2417 | O | SER A | 398 | −36.030 | −12.326 | −13.052 | 1.00 | 15.45 | O |
| ATOM | 2418 | N | VAL A | 399 | −34.178 | −11.093 | −12.626 | 1.00 | 16.07 | N |
| ATOM | 2419 | CA | VAL A | 399 | −34.864 | −9.808 | −12.547 | 1.00 | 15.81 | C |
| ATOM | 2420 | CB | VAL A | 399 | −35.152 | −9.396 | −11.068 | 1.00 | 16.80 | C |
| ATOM | 2421 | CG1 | VAL A | 399 | −35.800 | −8.006 | −10.995 | 1.00 | 16.79 | C |
| ATOM | 2422 | CG2 | VAL A | 399 | −36.032 | −10.431 | −10.363 | 1.00 | 14.88 | C |
| ATOM | 2423 | C | VAL A | 399 | −34.039 | −8.712 | −13.232 | 1.00 | 16.24 | C |
| ATOM | 2424 | O | VAL A | 399 | −32.852 | −8.551 | −12.949 | 1.00 | 15.65 | O |
| ATOM | 2425 | N | THR A | 400 | −34.675 | −7.981 | −14.146 | 1.00 | 16.11 | N |
| ATOM | 2426 | CA | THR A | 400 | −34.115 | −6.744 | −14.684 | 1.00 | 16.35 | C |
| ATOM | 2427 | CB | THR A | 400 | −34.443 | −6.565 | −16.187 | 1.00 | 16.52 | C |
| ATOM | 2428 | OG1 | THR A | 400 | −33.642 | −7.464 | −16.963 | 1.00 | 15.50 | O |
| ATOM | 2429 | CG2 | THR A | 400 | −34.168 | −5.141 | −16.650 | 1.00 | 16.76 | C |
| ATOM | 2430 | C | THR A | 400 | −34.657 | −5.566 | −13.873 | 1.00 | 16.64 | C |
| ATOM | 2431 | O | THR A | 400 | −35.858 | −5.480 | −13.612 | 1.00 | 16.49 | O |
| ATOM | 2432 | N | TRP A | 401 | −33.763 | −4.667 | −13.476 | 1.00 | 16.55 | N |
| ATOM | 2433 | CA | TRP A | 401 | −34.121 | −3.537 | −12.635 | 1.00 | 16.52 | C |
| ATOM | 2434 | CB | TRP A | 401 | −33.878 | −3.910 | −11.166 | 1.00 | 16.77 | C |
| ATOM | 2435 | CG | TRP A | 401 | −34.263 | −2.893 | −10.122 | 1.00 | 16.33 | C |
| ATOM | 2436 | CD1 | TRP A | 401 | −34.651 | −1.599 | −10.324 | 1.00 | 18.09 | C |
| ATOM | 2437 | NE1 | TRP A | 401 | −34.904 | −.984 | −9.121 | 1.00 | 15.16 | N |
| ATOM | 2438 | CE2 | TRP A | 401 | −34.659 | −1.871 | −8.107 | 1.00 | 16.55 | C |

TABLE A-continued

| ATOM | 2439 | CD2 | TRP A | 401 | −34.249 | −3.087 | −8.699 | 1.00 | 16.91 | C |
|---|---|---|---|---|---|---|---|---|---|---|
| ATOM | 2440 | CE3 | TRP A | 401 | −33.940 | −4.175 | −7.868 | 1.00 | 13.88 | C |
| ATOM | 2441 | CZ3 | TRP A | 401 | −34.039 | −4.013 | −6.488 | 1.00 | 17.19 | C |
| ATOM | 2442 | CH2 | TRP A | 401 | −34.448 | −2.786 | −5.926 | 1.00 | 16.90 | C |
| ATOM | 2443 | CZ2 | TRP A | 401 | −34.762 | −1.708 | −6.716 | 1.00 | 17.82 | C |
| ATOM | 2444 | C | TRP A | 401 | −33.266 | −2.352 | −13.065 | 1.00 | 16.28 | C |
| ATOM | 2445 | O | TRP A | 401 | −32.039 | −2.435 | −13.031 | 1.00 | 16.07 | O |
| ATOM | 2446 | N | ASN A | 402 | −33.918 | −1.270 | −13.495 | 1.00 | 16.50 | N |
| ATOM | 2447 | CA | ASN A | 402 | −33.229 | −.043 | −13.904 | 1.00 | 17.31 | C |
| ATOM | 2448 | CB | ASN A | 402 | −33.788 | .493 | −15.229 | 1.00 | 18.44 | C |
| ATOM | 2449 | CG | ASN A | 402 | −33.443 | −.378 | −16.429 | 1.00 | 21.24 | C |
| ATOM | 2450 | OD1 | ASN A | 402 | −32.932 | −1.492 | −16.296 | 1.00 | 22.89 | O |
| ATOM | 2451 | ND2 | ASN A | 402 | −33.740 | .136 | −17.621 | 1.00 | 21.93 | N |
| ATOM | 2452 | C | ASN A | 402 | −33.315 | 1.068 | −12.857 | 1.00 | 17.30 | C |
| ATOM | 2453 | O | ASN A | 402 | −34.299 | 1.810 | −12.823 | 1.00 | 15.87 | O |
| | | | gad67.pdb | | | | | | | |
| ATOM | 2454 | N | PRO A | 403 | −32.293 | 1.186 | −11.990 | 1.00 | 18.38 | N |
| ATOM | 2455 | CA | PRO A | 403 | −32.191 | 2.368 | −11.128 | 1.00 | 18.93 | C |
| ATOM | 2456 | CB | PRO A | 403 | −30.832 | 2.180 | −10.452 | 1.00 | 19.51 | C |
| ATOM | 2457 | CG | PRO A | 403 | −30.669 | .704 | −10.393 | 1.00 | 17.90 | C |
| ATOM | 2458 | CD | PRO A | 403 | −31.213 | .222 | −11.707 | 1.00 | 18.12 | C |
| ATOM | 2459 | C | PRO A | 403 | −32.248 | 3.707 | −11.872 | 1.00 | 19.28 | C |
| ATOM | 2460 | O | PRO A | 403 | −32.655 | 4.710 | −11.280 | 1.00 | 19.07 | O |
| ATOM | 2461 | N | HIS A | 404 | −31.867 | 3.724 | −13.151 | 1.00 | 18.42 | N |
| ATOM | 2462 | CA | HIS A | 404 | −31.904 | 4.965 | −13.930 | 1.00 | 18.91 | C |
| ATOM | 2463 | CB | HIS A | 404 | −30.898 | 4.961 | −15.108 | 1.00 | 18.62 | C |
| ATOM | 2464 | CG | HIS A | 404 | −31.307 | 4.126 | −16.280 | 1.00 | 16.93 | C |
| ATOM | 2465 | ND1 | HIS A | 404 | −32.315 | 4.496 | −17.144 | 1.00 | 18.17 | N |
| ATOM | 2466 | CE1 | HIS A | 404 | −32.441 | 3.581 | −18.089 | 1.00 | 16.13 | C |
| ATOM | 2467 | NE2 | HIS A | 404 | −31.546 | 2.634 | −17.874 | 1.00 | 16.73 | N |
| ATOM | 2468 | CD2 | HIS A | 404 | −30.817 | 2.957 | −16.756 | 1.00 | 16.59 | C |
| ATOM | 2469 | C | HIS A | 404 | −33.313 | 5.449 | −14.337 | 1.00 | 19.81 | C |
| ATOM | 2470 | O | HIS A | 404 | −33.460 | 6.546 | −14.880 | 1.00 | 20.56 | O |
| ATOM | 2471 | N | LLP A | 405 | −34.342 | 4.650 | −14.056 | 1.00 | 19.65 | N |
| ATOM | 2472 | CA | LLP A | 405 | −35.724 | 5.075 | −14.291 | 1.00 | 20.29 | C |
| ATOM | 2473 | CB | LLP A | 405 | −36.572 | 3.954 | −14.919 | 1.00 | 20.14 | C |
| ATOM | 2474 | CG | LLP A | 405 | −36.107 | 3.557 | −16.324 | 1.00 | 19.52 | C |
| ATOM | 2475 | CD | LLP A | 405 | −37.107 | 2.683 | −17.063 | 1.00 | 20.96 | C |
| ATOM | 2476 | CE | LLP A | 405 | −36.603 | 2.327 | −18.470 | 1.00 | 22.25 | C |
| ATOM | 2477 | NZ | LLP A | 405 | −37.710 | 1.874 | −19.369 | 1.00 | 23.14 | N |
| ATOM | 2478 | C4A | LLP A | 405 | −37.274 | 1.155 | −20.412 | 1.00 | 20.28 | C |
| ATOM | 2479 | C4 | LLP A | 405 | −37.689 | −.289 | −20.273 | 1.00 | 18.11 | C |
| ATOM | 2480 | C3 | LLP A | 405 | −38.906 | −.636 | −19.667 | 1.00 | 17.96 | C |
| ATOM | 2481 | O3 | LLP A | 405 | −39.661 | .237 | −19.242 | 1.00 | 17.79 | O |
| ATOM | 2482 | C2 | LLP A | 405 | −39.270 | −1.979 | −19.538 | 1.00 | 17.84 | C |
| ATOM | 2483 | C2A | LLP A | 405 | −40.568 | −2.370 | −18.889 | 1.00 | 15.06 | C |
| ATOM | 2484 | N1 | LLP A | 405 | −38.426 | −2.969 | −20.009 | 1.00 | 17.97 | N |
| ATOM | 2485 | CS | LLP A | 405 | −36.852 | −1.305 | −20.745 | 1.00 | 17.94 | C |
| ATOM | 2486 | C6 | LLP A | 405 | −37.225 | −2.642 | −20.606 | 1.00 | 18.71 | C |
| ATOM | 2487 | C5A | LLP A | 405 | −35.546 | −.997 | −21.408 | 1.00 | 14.80 | C |
| ATOM | 2488 | O4P | LLP A | 405 | −34.461 | −.425 | −20.650 | 1.00 | 14.85 | O |
| ATOM | 2489 | P | LLP A | 405 | −33.346 | .455 | −21.406 | 1.00 | 13.63 | P |
| ATOM | 2490 | O1P | LLP A | 405 | −32.417 | .827 | −20.319 | 1.00 | 13.87 | O |
| ATOM | 2491 | O2P | LLP A | 405 | −32.768 | −.463 | −22.408 | 1.00 | 12.01 | O |
| ATOM | 2492 | O3P | LLP A | 405 | −34.095 | 1.587 | −21.985 | 1.00 | 14.47 | O |
| ATOM | 2493 | C | LLP A | 405 | −36.365 | 5.689 | −13.031 | 1.00 | 21.82 | C |
| ATOM | 2494 | O | LLP A | 405 | −36.135 | 6.866 | −12.753 | 1.00 | 22.75 | O |
| ATOM | 2495 | N | MET A | 406 | −37.140 | 4.915 | −12.266 | 1.00 | 23.00 | N |
| ATOM | 2496 | CA | MET A | 406 | −37.864 | 5.475 | −11.106 | 1.00 | 23.65 | C . |
| ATOM | 2497 | CB | MET A | 406 | −38.848 | 4.470 | −10.493 | 1.00 | 23.90 | C |
| ATOM | 2498 | CG | MET A | 406 | −40.280 | 4.633 | −10.970 | 1.00 | 26.24 | C |
| ATOM | 2499 | SD | MET A | 406 | −40.929 | 6.320 | −10.892 | 1.00 | 28.82 | S |
| ATOM | 2500 | CE | MET A | 406 | −41.798 | 6.328 | −9.322 | 1.00 | 23.56 | C |
| ATOM | 2501 | C | MET A | 406 | −36.983 | 6.066 | −10.006 | 1.00 | 23.72 | C |
| ATOM | 2502 | O | MET A | 406 | −37.313 | 7.104 | −9.438 | 1.00 | 24.00 | O |
| ATOM | 2503 | N | MET A | 407 | −35.868 | 5.406 | −9.709 | 1.00 | 23.77 | N |
| ATOM | 2504 | CA | MET A | 407 | −34.959 | 5.871 | −8.662 | 1.00 | 23.47 | C |
| ATOM | 2505 | CB | MET A | 407 | −34.043 | 4.736 | −8.200 | 1.00 | 23.23 | C |
| ATOM | 2506 | CG | MET A | 407 | −34.808 | 3.587 | −7.544 | 1.00 | 24.88 | C |
| ATOM | 2507 | SD | MET A | 407 | −33.752 | 2.349 | −6.780 | 1.00 | 26.26 | S |
| ATOM | 2508 | CE | MET A | 407 | −33.393 | 1.323 | −8.174 | 1.00 | 32.95 | C |
| ATOM | 2509 | C | MET A | 407 | −34.166 | 7.104 | −9.095 | 1.00 | 22.17 | C |
| ATOM | 2510 | O | MET A | 407 | −33.513 | 7.756 | −8.277 | 1.00 | 21.78 | O |
| ATOM | 2511 | N | GLY A | 408 | −34.248 | 7.424 | −10.383 | 1.00 | 21.43 | N |
| ATOM | 2512 | CA | GLY A | 408 | −33.710 | 8.668 | −10.914 | 1.00 | 20.02 | C |
| ATOM | 2513 | C | GLY A | 408 | −32.201 | 8.762 | −10.926 | 1.00 | 19.25 | C |
| ATOM | 2514 | O | GLY A | 408 | −31.646 | 9.862 | −10.849 | 1.00 | 19.56 | O |
| ATOM | 2515 | N | VAL A | 409 | −31.535 | 7.612 | −11.004 | 1.00 | 18.24 | N |
| ATOM | 2516 | CA | VAL A | 409 | −30.095 | 7.583 | −11.236 | 1.00 | 17.81 | C |
| ATOM | 2517 | CB | VAL A | 409 | −29.484 | 6.171 | −10.983 | 1.00 | 17.78 | C |

TABLE A-continued

| | | | | | | | | | |
|---|---|---|---|---|---|---|---|---|---|
| ATOM | 2518 | CG1 | VAL A | 409 | −27.977 | 6.186 | −11.183 | 1.00 | 15.17 | C |
| ATOM | 2519 | CG2 | VAL A | 409 | −29.803 | 5.685 | −9.582 | 1.00 | 13.46 | C |
| ATOM | 2520 | C | VAL A | 409 | −29.856 | 8.031 | −12.678 | 1.00 | 18.50 | C |
| ATOM | 2521 | O | VAL A | 409 | −30.638 | 7.708 | −13.567 | 1.00 | 18.73 | O |
| | | | | | gad67.pdb | | | | | |
| ATOM | 2522 | N | LEU A | 410 | −28.796 | 8.800 | −12.900 | 1.00 | 18.79 | N |
| ATOM | 2523 | CA | LEU A | 410 | −28.449 | 9.254 | −14.245 | 1.00 | 18.61 | C |
| ATOM | 2524 | CB | LEU A | 410 | −27.282 | 10.252 | −14.184 | 1.00 | 18.86 | C |
| ATOM | 2525 | CG | LEU A | 410 | −27.598 | 11.720 | −13.847 | 1.00 | 17.95 | C |
| ATOM | 2526 | CD1 | LEU A | 410 | −28.184 | 11.909 | −12.445 | 1.00 | 19.05 | C |
| ATOM | 2527 | CD2 | LEU A | 410 | −26.374 | 12.588 | −14.020 | 1.00 | 17.41 | C |
| ATOM | 2528 | C | LEU A | 410 | −28.128 | 8.074 | −15.175 | 1.00 | 20.10 | C |
| ATOM | 2529 | O | LEU A | 410 | −27.517 | 7.085 | −14.751 | 1.00 | 19.73 | O |
| ATOM | 2530 | N | LEU A | 411 | −28.568 | 8.176 | −16.430 | 1.00 | 20.68 | N |
| ATOM | 2531 | CA | LEU A | 411 | −28.327 | 7.140 | −17.443 | 1.00 | 21.90 | C |
| ATOM | 2532 | CB | LEU A | 411 | −28.986 | 7.531 | −18.772 | 1.00 | 22.84 | C |
| ATOM | 2536 | C | LEU A | 411 | −26.827 | 6.888 | −17.660 | 1.00 | 21.50 | C |
| ATOM | 2537 | O | LEU A | 411 | −26.056 | 7.838 | −17.723 | 1.00 | 20.58 | O |
| ATOM | 2538 | N | GLN A | 412 | −26.398 | 5.628 | −17.765 | 1.00 | 22.19 | N |
| ATOM | 2539 | CA | GLN A | 412 | −27.240 | 4.433 | −17.639 | 1.00 | 22.38 | C |
| ATOM | 2540 | CB | GLN A | 412 | −26.933 | 3.439 | −18.767 | 1.00 | 22.77 | C |
| ATOM | 2541 | CG | GLN A | 412 | −27.479 | 3.804 | −20.145 | 1.00 | 23.99 | C |
| ATOM | 2542 | CD | GLN A | 412 | −27.143 | 2.759 | −21.204 | 1.00 | 23.36 | C |
| ATOM | 2543 | OE1 | GLN A | 412 | −26.002 | 2.300 | −21.304 | 1.00 | 27.10 | O |
| ATOM | 2544 | NE2 | GLN A | 412 | −28.137 | 2.387 | −22.002 | 1.00 | 27.86 | N |
| ATOM | 2545 | C | GLN A | 412 | −26.976 | 3.734 | −16.313 | 1.00 | 21.63 | C |
| ATOM | 2546 | O | GLN A | 412 | −25.856 | 3.753 | −15.804 | 1.00 | 21.64 | O |
| ATOM | 2547 | N | CYS A | 413 | −28.009 | 3.103 | −15.765 | 1.00 | 21.22 | N |
| ATOM | 2548 | CA | CYS A | 413 | −27.869 | 2.284 | −14.568 | 1.00 | 20.34 | C |
| ATOM | 2549 | CB | CYS A | 413 | −27.996 | 3.125 | −13.293 | 1.00 | 20.16 | C |
| ATOM | 2550 | SG | CYS A | 413 | −27.459 | 2.242 | −11.795 | 1.00 | 22.09 | S |
| ATOM | 2551 | C | CYS A | 413 | −28.907 | 1.169 | −14.589 | 1.00 | 19.48 | C |
| ATOM | 2552 | O | CYS A | 413 | −30.071 | 1.373 | −14.236 | 1.00 | 19.03 | O |
| ATOM | 2553 | N | SER A | 414 | −28.468 | −.009 | −15.018 | 1.00 | 18.72 | N |
| ATOM | 2554 | CA | SER A | 414 | −29.341 | −1.160 | −15.173 | 1.00 | 18.28 | C |
| ATOM | 2555 | CB | SER A | 414 | −29.756 | −1.313 | −16.632 | 1.00 | 18.82 | C |
| ATOM | 2556 | OG | SER A | 414 | −30.567 | −2.462 | −16.804 | 1.00 | 23.87 | O |
| ATOM | 2557 | C | SER A | 414 | −28.654 | −2.429 | −14.691 | 1.00 | 17.86 | C |
| ATOM | 2558 | O | SER A | 414 | −27.505 | −2.705 | −15.050 | 1.00 | 16.78 | O |
| ATOM | 2559 | N | ALA A | 415 | −29.366 | −3.199 | −13.875 | 1.00 | 16.77 | N |
| ATOM | 2560 | CA | ALA A | 415 | −28.841 | −4.450 | −13.354 | 1.00 | 17.03 | C |
| ATOM | 2561 | CB | ALA A | 415 | −28.805 | −4.417 | −11.827 | 1.00 | 17.36 | C |
| ATOM | 2562 | C | ALA A | 415 | −29.654 | −5.642 | −13.832 | 1.00 | 16.76 | C |
| ATOM | 2563 | O | ALA A | 415 | −30.877 | −5.564 | −13.958 | 1.00 | 16.29 | O |
| ATOM | 2564 | N | ILE A | 416 | −28.959 | −6.739 | −14.119 | 1.00 | 16.97 | N |
| ATOM | 2565 | CA | ILE A | 416 | −29.605 | −8.047 | −14.184 | 1.00 | 17.32 | C |
| ATOM | 2566 | CB | ILE A | 416 | −29.257 | −8.850 | −15.486 | 1.00 | 17.64 | C |
| ATOM | 2567 | CG1 | ILE A | 416 | −29.910 | −10.244 | −15.487 | 1.00 | 17.54 | C |
| ATOM | 2568 | CD1 | ILE A | 416 | −31.416 | −10.239 | −15.664 | 1.00 | 17.34 | C |
| ATOM | 2569 | CG2 | ILE A | 416 | −27.747 | −8.970 | −15.700 | 1.00 | 17.55 | C |
| ATOM | 2570 | C | ILE A | 416 | −29.263 | −8.815 | −12.904 | 1.00 | 17.18 | C |
| ATOM | 2571 | O | ILE A | 416 | −28.099 | −8.908 | −12.513 | 1.00 | 17.28 | O |
| ATOM | 2572 | N | LEU A | 417 | −30.296 | −9.316 | −12.236 | 1.00 | 16.54 | N |
| ATOM | 2573 | CA | LEU A | 417 | −30.131 | −10.103 | −11.025 | 1.00 | 15.70 | C |
| ATOM | 2574 | CB | LEU A | 417 | −31.012 | −9.559 | −9.894 | 1.00 | 15.61 | C |
| ATOM | 2575 | CG | LEU A | 417 | −30.956 | −8.056 | −9.579 | 1.00 | 15.23 | C |
| ATOM | 2576 | CD1 | LEU A | 417 | −31.992 | −7.688 | −8.523 | 1.00 | 14.28 | C |
| ATOM | 2577 | CD2 | LEU A | 417 | −29.565 | −7.606 | −9.143 | 1.00 | 16.31 | C |
| ATOM | 2578 | C | LEU A | 417 | −30.493 | −11.541 | −11.352 | 1.00 | 15.42 | C |
| ATOM | 2579 | O | LEU A | 417 | −31.500 | −11.799 | −12.013 | 1.00 | 14.92 | O |
| ATOM | 2580 | N | VAL A | 418 | −29.650 | −12.471 | −10.922 | 1.00 | 15.84 | N |
| ATOM | 2581 | CA | VAL A | 418 | −29.844 | −13.888 | −11.218 | 1.00 | 16.37 | C |
| ATOM | 2582 | CB | VAL A | 418 | −28.801 | −14.409 | −12.253 | 1.00 | 16.20 | C |
| ATOM | 2583 | CG1 | VAL A | 418 | −29.070 | −15.864 | −12.618 | 1.00 | 14.18 | C |
| ATOM | 2584 | CG2 | VAL A | 418 | −28.805 | −13.552 | −13.510 | 1.00 | 13.97 | C |
| ATOM | 2585 | C | VAL A | 418 | −29.774 | −14.679 | −9.907 | 1.00 | 17.64 | C |
| ATOM | 2586 | O | VAL A | 418 | −28.818 | −14.550 | −9.141 | 1.00 | 17.50 | O |
| ATOM | 2587 | N | LYS A | 419 | −30.804 | −15.478 | −9.650 | 1.00 | 19.89 | N |
| ATOM | 2588 | CA | LYS A | 419 | −30.938 | −16.195 | −8.380 | 1.00 | 21.61 | C |
| ATOM | 2589 | CB | LYS A | 419 | −32.307 | −16.884 | −8.292 | 1.00 | 21.71 | C |
| ATOM | 2590 | CG | LYS A | 419 | −32.495 | −17.745 | −7.047 | 1.00 | 23.42 | C |
| ATOM | 2591 | CD | LYS A | 419 | −33.790 | −17.417 | −6.327 | 1.00 | 27.75 | C |
| ATOM | 2592 | CE | LYS A | 419 | −34.991 | −18.084 | −6.960 | 1.00 | 31.76 | C |
| | | | | | gad67.pdb | | | | | |
| ATOM | 2593 | NZ | LYS A | 419 | −36.238 | −17.626 | −6.289 | 1.00 | 34.74 | N |
| ATOM | 2594 | C | LYS A | 419 | −29.802 | −17.192 | −8.156 | 1.00 | 22.33 | C |
| ATOM | 2595 | O | LYS A | 419 | −29.184 | −17.212 | −7.094 | 1.00 | 22.52 | O |
| ATOM | 2596 | N | GLU A | 420 | −29.526 | −17.998 | −9.173 | 1.00 | 23.54 | N |
| ATOM | 2597 | CA | GLU A | 420 | −28.498 | −19.020 | −9.088 | 1.00 | 25.60 | C |
| ATOM | 2598 | CB | GLU A | 420 | −28.936 | −20.252 | −9.880 | 1.00 | 25.20 | C |

TABLE A-continued

| ATOM | 2599 | CG | GLU A | 420 | −28.003 | −21.449 | −9.794 | 1.00 | 28.42 | C |
|---|---|---|---|---|---|---|---|---|---|---|
| ATOM | 2600 | CD | GLU A | 420 | −28.501 | −22.623 | −10.615 | 1.00 | 29.59 | C |
| ATOM | 2601 | OE1 | GLU A | 420 | −27.655 | −23.357 | −11.166 | 1.00 | 36.87 | O |
| ATOM | 2602 | OE2 | GLU A | 420 | −29.736 | −22.807 | −10.722 | 1.00 | 36.29 | O |
| ATOM | 2603 | C | GLU A | 420 | −27.165 | −18.488 | −9.602 | 1.00 | 25.05 | C |
| ATOM | 2604 | O | GLU A | 420 | −27.065 | −18.038 | −10.745 | 1.00 | 25.18 | O |
| ATOM | 2605 | N | LYS A | 421 | −26.150 | −18.545 | −8.745 | 1.00 | 25.51 | N |
| ATOM | 2606 | CA | LYS A | 421 | −24.803 | −18.098 | −9.082 | 1.00 | 26.77 | C |
| ATOM | 2607 | CB | LYS A | 421 | −23.992 | −17.874 | −7.801 | 1.00 | 26.38 | C |
| ATOM | 2608 | CG | LYS A | 421 | −22.666 | −17.145 | −7.998 | 1.00 | 30.94 | C |
| ATOM | 2609 | CD | LYS A | 421 | −22.038 | −16.769 | −6.661 | 1.00 | 31.31 | C |
| ATOM | 2610 | CE | LYS A | 421 | −20.534 | −16.510 | −6.790 | 1.00 | 39.53 | C |
| ATOM | 2611 | NZ | LYS A | 421 | −20.219 | −15.366 | −7.698 | 1.00 | 43.97 | N |
| ATOM | 2612 | C | LYS A | 421 | −24.105 | −19.112 | −9.989 | 1.00 | 25.55 | C |
| ATOM | 2613 | O | LYS A | 421 | −24.334 | −20.315 | −9.872 | 1.00 | 25.39 | O |
| ATOM | 2614 | N | GLY A | 422 | −23.265 | −18.618 | −10.897 | 1.00 | 25.12 | N |
| ATOM | 2615 | CA | GLY A | 422 | −22.489 | −19.487 | −11.780 | 1.00 | 23.32 | C |
| ATOM | 2616 | C | GLY A | 422 | −23.059 | −19.642 | −13.176 | 1.00 | 22.55 | C |
| ATOM | 2617 | O | GLY A | 422 | −22.354 | −20.091 | −14.081 | 1.00 | 22.44 | O |
| ATOM | 2618 | N | ILE A | 423 | −24.331 | −19.281 | −13.354 | 1.00 | 21.71 | N |
| ATOM | 2619 | CA | ILE A | 423 | −24.981 | −19.371 | −14.664 | 1.00 | 21.04 | C |
| ATOM | 2620 | CB | ILE A | 423 | −26.523 | −19.258 | −14.580 | 1.00 | 20.93 | C |
| ATOM | 2621 | CG1 | ILE A | 423 | −27.102 | −20.397 | −13.734 | 1.00 | 19.46 | C |
| ATOM | 2622 | CD1 | ILE A | 423 | −28.593 | −20.304 | −13.524 | 1.00 | 21.18 | C |
| ATOM | 2623 | CG2 | ILE A | 423 | −27.147 | −19.271 | −15.981 | 1.00 | 19.19 | C |
| ATOM | 2624 | C | ILE A | 423 | −24.420 | −18.335 | −15.637 | 1.00 | 21.60 | C |
| ATOM | 2625 | O | ILE A | 423 | −24.080 | −18.678 | −16.769 | 1.00 | 22.03 | O |
| ATOM | 2626 | N | LEU A | 424 | −24.314 | −17.082 | −15.190 | 1.00 | 21.66 | N |
| ATOM | 2627 | CA | LEU A | 424 | −23.753 | −16.008 | −16.013 | 1.00 | 22.57 | C |
| ATOM | 2628 | CB | LEU A | 424 | −23.845 | −14.652 | −15.298 | 1.00 | 22.42 | C |
| ATOM | 2629 | CG | LEU A | 424 | −25.208 | −13.983 | −15.083 | 1.00 | 24.91 | C |
| ATOM | 2630 | CD1 | LEU A | 424 | −25.063 | −12.747 | −14.193 | 1.00 | 23.27 | C |
| ATOM | 2631 | CD2 | LEU A | 424 | −25.879 | −13.613 | −16.408 | 1.00 | 22.09 | C |
| ATOM | 2632 | C | LEU A | 424 | −22.302 | −16.300 | −16.411 | 1.00 | 22.79 | C |
| ATOM | 2633 | O | LEU A | 424 | −21.927 | −16.119 | −17.570 | 1.00 | 22.58 | O |
| ATOM | 2634 | N | GLN A | 425 | −21.506 | −16.759 | −15.442 | 1.00 | 22.89 | N |
| ATOM | 2635 | CA | GLN A | 425 | −20.110 | −17.129 | −15.665 | 1.00 | 23.83 | C |
| ATOM | 2636 | CB | GLN A | 425 | −19.450 | −17.542 | −14.342 | 1.00 | 25.20 | C |
| ATOM | 2637 | CG | GLN A | 425 | −17.956 | −17.886 | −14.427 | 1.00 | 30.58 | C |
| ATOM | 2638 | CD | GLN A | 425 | −17.063 | −16.664 | −14.593 | 1.00 | 39.22 | C |
| ATOM | 2639 | OE1 | GLN A | 425 | −17.296 | −15.615 | −13.986 | 1.00 | 43.51 | O |
| ATOM | 2640 | NE2 | GLN A | 425 | −16.024 | −16.801 | −15.412 | 1.00 | 39.94 | N |
| ATOM | 2641 | C | GLN A | 425 | −19.988 | −18.248 | −16.696 | 1.00 | 23.17 | C |
| ATOM | 2642 | O | GLN A | 425 | −19.233 | −18.123 | −17.659 | 1.00 | 22.79 | O |
| ATOM | 2643 | N | GLY A | 426 | −20.740 | −19.329 | −16.490 | 1.00 | 22.10 | N |
| ATOM | 2644 | CA | GLY A | 426 | −20.725 | −20.476 | −17.392 | 1.00 | 20.60 | C |
| ATOM | 2645 | C | GLY A | 426 | −21.173 | −20.110 | −18.794 | 1.00 | 20.43 | C |
| ATOM | 2646 | O | GLY A | 426 | −20.567 | −20.533 | −19.786 | 1.00 | 19.61 | O |
| ATOM | 2647 | N | CYS A | 427 | −22.237 | −19.315 | −18.867 | 1.00 | 19.89 | N |
| ATOM | 2648 | CA | CYS A | 427 | −22.800 | −18.864 | −20.135 | 1.00 | 19.93 | C |
| ATOM | 2649 | CB | CYS A | 427 | −24.073 | −18.060 | −19.875 | 1.00 | 19.49 | C |
| ATOM | 2650 | SG | CYS A | 427 | −24.867 | −17.379 | −21.339 | 1.00 | 20.69 | S |
| ATOM | 2651 | C | CYS A | 427 | −21.822 | −18.027 | −20.962 | 1.00 | 20.57 | C |
| ATOM | 2652 | O | CYS A | 427 | −21.712 | −18.214 | −22.176 | 1.00 | 20.13 | O |
| ATOM | 2653 | N | ASN A | 428 | −21.108 | −17.120 | −20.296 | 1.00 | 20.73 | N |
| ATOM | 2654 | CA | ASN A | 428 | −20.390 | −16.048 | −20.982 | 1.00 | 21.42 | C |
| ATOM | 2655 | CB | ASN A | 428 | −20.776 | −14.693 | −20.377 | 1.00 | 21.35 | C |
| ATOM | 2656 | CG | ASN A | 428 | −22.183 | −14.266 | −20.759 | 1.00 | 23.65 | C |
| ATOM | 2657 | OD1 | ASN A | 428 | −22.572 | −14.342 | −21.923 | 1.00 | 26.47 | O |
| ATOM | 2658 | ND2 | ASN A | 428 | −22.952 | −13.817 | −19.778 | 1.00 | 24.49 | N |
| ATOM | 2659 | C | ASN A | 428 | −18.871 | −16.172 | −21.078 | 1.00 | 21.73 | C |
| ATOM | 2660 | O | ASN A | 428 | −18.270 | −15.576 | −21.964 | 1.00 | 21.89 | O |
| gad67.pdb | | | | | | | | | | |
| ATOM | 2661 | N | GLN A | 429 | −18.259 | −16.938 | −20.180 | 1.00 | 22.64 | N |
| ATOM | 2662 | CA | GLN A | 429 | −16.801 | −17.004 | −20.091 | 1.00 | 24.55 | C |
| ATOM | 2663 | CB | GLN A | 429 | −16.366 | −17.881 | −18.910 | 1.00 | 23.98 | C |
| ATOM | 2664 | CG | GLN A | 429 | −16.588 | −19.382 | −19.097 | 1.00 | 24.80 | C |
| ATOM | 2665 | CD | GLN A | 429 | −16.316 | −20.197 | −17.836 | 1.00 | 26.34 | C |
| ATOM | 2666 | OE1 | GLN A | 429 | −16.770 | −21.333 | −17.722 | 1.00 | 31.20 | O |
| ATOM | 2667 | NE2 | GLN A | 429 | −15.580 | −19.621 | −16.889 | 1.00 | 20.49 | N |
| ATOM | 2668 | C | GLN A | 429 | −16.123 | −17.457 | −21.391 | 1.00 | 25.65 | C |
| ATOM | 2669 | O | GLN A | 429 | −16.624 | −18.336 | −22.096 | 1.00 | 24.66 | O |
| ATOM | 2670 | N | MET A | 430 | −14.999 | −16.818 | −21.704 | 1.00 | 27.69 | N |
| ATOM | 2671 | CA | MET A | 430 | −14.118 | −17.259 | −22.783 | 1.00 | 30.88 | C |
| ATOM | 2672 | CB | MET A | 430 | −14.072 | −16.232 | −23.922 | 1.00 | 30.29 | C |
| ATOM | 2673 | CG | MET A | 430 | −15.316 | −16.249 | −24.811 | 1.00 | 32.37 | C |
| ATOM | 2674 | SD | MET A | 430 | −15.541 | −17.807 | −25.707 | 1.00 | 35.52 | S |
| ATOM | 2675 | CE | MET A | 430 | −17.334 | −17.879 | −25.801 | 1.00 | 29.77 | C |
| ATOM | 2676 | C | MET A | 430 | −12.721 | −17.571 | −22.242 | 1.00 | 32.72 | C |
| ATOM | 2677 | O | MET A | 430 | −11.878 | −18.117 | −22.959 | 1.00 | 32.75 | O |

TABLE A-continued

| | | | | | | | | | |
|---|---|---|---|---|---|---|---|---|---|
| ATOM | 2678 | N | CYS A | 431 | −12.505 | −17.228 | −20.967 | 1.00 | 35.33 | N |
| ATOM | 2679 | CA | CYS A | 431 | −11.298 | −17.584 | −20.196 | 1.00 | 38.24 | C |
| ATOM | 2680 | CB | CYS A | 431 | −11.292 | −19.079 | −19.839 | 1.00 | 38.57 | C |
| ATOM | 2681 | SG | CYS A | 431 | −12.831 | −19.694 | −19.116 | 1.00 | 42.36 | S |
| ATOM | 2682 | C | CYS A | 431 | −9.999 | −17.190 | −20.897 | 1.00 | 39.29 | C |
| ATOM | 2683 | O | CYS A | 431 | −9.045 | −17.970 | −20.963 | 1.00 | 39.39 | O |
| ATOM | 2684 | N | ALA A | 432 | −9.969 | −15.964 | −21.406 | 1.00 | 40.67 | N |
| ATOM | 2685 | CA | ALA A | 432 | −8.853 | −15.516 | −22.219 | 1.00 | 42.33 | C |
| ATOM | 2686 | CB | ALA A | 432 | −9.368 | −14.920 | −23.523 | 1.00 | 42.71 | C |
| ATOM | 2687 | C | ALA A | 432 | −7.951 | −14.517 | −21.511 | 1.00 | 43.35 | C |
| ATOM | 2688 | O | ALA A | 432 | −8.385 | −13.781 | −20.618 | 1.00 | 43.81 | O |
| ATOM | 2689 | N | GLY A | 433 | −6.682 | −14.516 | −21.904 | 1.00 | 43.84 | N |
| ATOM | 2690 | CA | GLY A | 433 | −5.878 | −13.319 | −21.764 | 1.00 | 44.61 | C |
| ATOM | 2691 | C | GLY A | 433 | −4.788 | −13.214 | −20.717 | 1.00 | 45.11 | C |
| ATOM | 2692 | O | GLY A | 433 | −4.368 | −14.225 | −20.154 | 1.00 | 45.34 | O |
| ATOM | 2693 | N | TYR A | 434 | −4.330 | −11.982 | −20.441 | 1.00 | 45.91 | N |
| ATOM | 2694 | CA | TYR A | 434 | −4.836 | −10.713 | −21.041 | 1.00 | 46.51 | C |
| ATOM | 2695 | CB | TYR A | 434 | −4.319 | −10.534 | −22.511 | 1.00 | 46.28 | C |
| ATOM | 2696 | CG | TYR A | 434 | −5.327 | −10.886 | −23.624 | 1.00 | 46.93 | C |
| ATOM | 2697 | CD1 | TYR A | 434 | −6.329 | −9.977 | −24.003 | 1.00 | 48.06 | C |
| ATOM | 2698 | CE1 | TYR A | 434 | −7.271 | −10.286 | −24.990 | 1.00 | 47.79 | C |
| ATOM | 2699 | CZ | TYR A | 434 | −7.211 | −11.508 | −25.636 | 1.00 | 48.20 | C |
| ATOM | 2700 | OH | TYR A | 434 | −8.146 | −11.786 | −26.617 | 1.00 | 45.32 | O |
| ATOM | 2701 | CE2 | TYR A | 434 | −6.221 | −12.434 | −25.296 | 1.00 | 47.63 | C |
| ATOM | 2702 | CD2 | TYR A | 434 | −5.279 | −12.116 | −24.295 | 1.00 | 47.94 | C |
| ATOM | 2703 | C | TYR A | 434 | −6.373 | −10.516 | −20.969 | 1.00 | 46.84 | C |
| ATOM | 2704 | O | TYR A | 434 | −6.930 | −9.830 | −21.839 | 1.00 | 48.96 | O |
| ATOM | 2705 | N | LEU A | 435 | −7.062 | −10.918 | −19.895 | 1.00 | 45.47 | N |
| ATOM | 2706 | CA | LEU A | 435 | −6.641 | −10.440 | −18.500 | 1.00 | 44.19 | C |
| ATOM | 2707 | CB | LEU A | 435 | −6.767 | −8.703 | −18.592 | 1.00 | 44.86 | C |
| ATOM | 2708 | CG | LEU A | 435 | −8.118 | −8.203 | −18.705 | 1.00 | 44.12 | C |
| ATOM | 2709 | CD1 | LEU A | 435 | −8.207 | −6.643 | −18.550 | 1.00 | 44.35 | C |
| ATOM | 2710 | CD2 | LEU A | 435 | −9.158 | −8.728 | −20.103 | 1.00 | 43.45 | C |
| ATOM | 2711 | C | LEU A | 435 | −7.722 | −10.734 | −17.445 | 1.00 | 42.58 | C |
| ATOM | 2712 | O | LEU A | 435 | −7.988 | −9.866 | −16.602 | 1.00 | 41.81 | O |
| ATOM | 2713 | N | PHE A | 436 | −8.297 | −11.926 | −17.362 | 1.00 | 41.16 | N |
| ATOM | 2714 | CA | PHE A | 436 | −7.869 | −13.122 | −16.613 | 1.00 | 40.82 | C |
| ATOM | 2715 | CB | PHE A | 436 | −9.250 | −13.733 | −16.329 | 1.00 | 39.99 | C |
| ATOM | 2716 | CG | PHE A | 436 | −10.389 | −12.867 | −16.887 | 1.00 | 39.08 | C |
| ATOM | 2717 | CD1 | PHE A | 436 | −10.807 | −13.008 | −18.215 | 1.00 | 38.83 | C |
| ATOM | 2718 | CE1 | PHE A | 436 | −11.809 | −12.185 | −18.750 | 1.00 | 36.14 | C |
| ATOM | 2719 | CZ | PHE A | 436 | −12.390 | −11.192 | −17.963 | 1.00 | 35.97 | C |
| ATOM | 2720 | CE2 | PHE A | 436 | −11.970 | −11.021 | −16.649 | 1.00 | 33.83 | C |
| ATOM | 2721 | CD2 | PHE A | 436 | −10.967 | −11.847 | −16.120 | 1.00 | 37.01 | C |
| ATOM | 2722 | C | PHE A | 436 | −7.004 | −14.211 | −17.269 | 1.00 | 41.13 | C |
| ATOM | 2723 | O | PHE A | 436 | −7.579 | −15.090 | −17.953 | 1.00 | 42.66 | O |
| ATOM | 2724 | N | GLN A | 437 | −5.684 | −14.298 | −17.024 | 1.00 | 40.31 | N |
| ATOM | 2725 | CA | GLN A | 437 | −4.940 | −14.189 | −15.726 | 1.00 | 38.38 | C |
| ATOM | 2726 | CB | GLN A | 437 | −4.307 | −12.814 | −15.458 | 1.00 | 38.18 | C |
| ATOM | 2727 | CG | GLN A | 437 | −3.314 | −12.349 | −16.511 | 1.00 | 34.72 | C |
| ATOM | 2728 | CD | GLN A | 437 | −3.749 | −11.035 | −17.115 | 1.00 | 33.87 | C | gad67.pdb

| | | | | | | | | | |
|---|---|---|---|---|---|---|---|---|---|
| ATOM | 2729 | OE1 | GLN A | 437 | −4.758 | −10.461 | −16.696 | 1.00 | 31.52 | O |
| ATOM | 2730 | NE2 | GLN A | 437 | −2.986 | −10.535 | −18.081 | 1.00 | 32.61 | N |
| ATOM | 2731 | C | GLN A | 437 | −5.469 | −14.825 | −14.434 | 1.00 | 37.85 | C |
| ATOM | 2732 | O | GLN A | 437 | −6.044 | −14.145 | −13.579 | 1.00 | 37.46 | O |
| ATOM | 2733 | N | PRO A | 438 | −5.223 | −16.141 | −14.280 | 1.00 | 37.93 | N |
| ATOM | 2734 | CA | PRO A | 438 | −5.498 | −16.880 | −13.046 | 1.00 | 38.18 | C |
| ATOM | 2735 | CB | PRO A | 438 | −5.546 | −18.348 | −13.507 | 1.00 | 38.21 | C |
| ATOM | 2736 | CG | PRO A | 438 | −5.246 | −18.344 | −15.001 | 1.00 | 38.87 | C |
| ATOM | 2737 | CD | PRO A | 438 | −4.656 | −17.016 | −15.323 | 1.00 | 38.04 | C |
| ATOM | 2738 | C | PRO A | 438 | −4.409 | −16.711 | −11.980 | 1.00 | 37.85 | C |
| ATOM | 2739 | O | PRO A | 438 | −4.696 | −16.846 | −10.787 | 1.00 | 38.41 | O |
| ATOM | 2740 | N | ASP A | 439 | −3.181 | −16.415 | −12.405 | 1.00 | 37.11 | N |
| ATOM | 2741 | CA | ASP A | 439 | −2.031 | −16.380 | −11.492 | 1.00 | 36.77 | C |
| ATOM | 2742 | CB | ASP A | 439 | −.802 | −17.080 | −12.115 | 1.00 | 36.55 | C |
| ATOM | 2743 | CG | ASP A | 439 | −.353 | −16.457 | −13.443 | 1.00 | 37.02 | C |
| ATOM | 2744 | OD1 | ASP A | 439 | −1.034 | −15.545 | −13.970 | 1.00 | 35.98 | O |
| ATOM | 2745 | OD2 | ASP A | 439 | .699 | −16.898 | −13.966 | 1.00 | 33.89 | O |
| ATOM | 2746 | C | ASP A | 439 | −1.678 | −14.992 | −10.944 | 1.00 | 36.35 | C |
| ATOM | 2747 | O | ASP A | 439 | −.505 | −14.622 | −10.858 | 1.00 | 37.38 | O |
| ATOM | 2748 | N | LYS A | 440 | −2.702 | −14.234 | −10.562 | 1.00 | 35.93 | N |
| ATOM | 2749 | CA | LYS A | 440 | −2.508 | −12.941 | −9.903 | 1.00 | 35.19 | C |
| ATOM | 2750 | CB | LYS A | 440 | −3.704 | −12.013 | −10.153 | 1.00 | 35.09 | C |
| ATOM | 2751 | CG | LYS A | 440 | −3.942 | −11.660 | −11.614 | 1.00 | 35.05 | C |
| ATOM | 2752 | CD | LYS A | 440 | −5.032 | −10.608 | −11.748 | 1.00 | 34.18 | C |
| ATOM | 2753 | CE | LYS A | 440 | −5.474 | −10.439 | −13.190 | 1.00 | 29.18 | C |
| ATOM | 2754 | NZ | LYS A | 440 | −6.281 | −9.208 | −13.369 | 1.00 | 25.06 | N |
| ATOM | 2755 | C | LYS A | 440 | −2.288 | −13.124 | −8.398 | 1.00 | 34.99 | C |
| ATOM | 2756 | O | LYS A | 440 | −2.571 | −14.187 | −7.842 | 1.00 | 34.54 | O |

TABLE A-continued

| | | | | | | | | | |
|---|---|---|---|---|---|---|---|---|---|
| ATOM | 2757 | N | GLN A | 441 | −1.789 | −12.075 | −7.749 | 1.00 | 34.96 | N |
| ATOM | 2758 | CA | GLN A | 441 | −1.499 | −12.098 | −6.311 | 1.00 | 35.32 | C |
| ATOM | 2759 | CB | GLN A | 441 | −.434 | −11.054 | −5.952 | 1.00 | 36.18 | C |
| ATOM | 2760 | CG | GLN A | 441 | −.120 | −10.055 | −7.062 | 1.00 | 40.28 | C |
| ATOM | 2761 | CD | GLN A | 441 | −1.118 | −8.923 | −7.166 | 1.00 | 40.90 | C |
| ATOM | 2762 | OE1 | GLN A | 441 | −1.156 | −8.031 | −6.317 | 1.00 | 42.01 | O |
| ATOM | 2763 | NE2 | GLN A | 441 | −1.919 | −8.940 | −8.225 | 1.00 | 41.98 | N |
| ATOM | 2764 | C | GLN A | 441 | −2.726 | −11.941 | −5.408 | 1.00 | 34.45 | C |
| ATOM | 2765 | O | GLN A | 441 | −2.655 | −12.232 | −4.210 | 1.00 | 35.00 | O |
| ATOM | 2766 | N | TYR A | 442 | −3.841 | −11.487 | −5.975 | 1.00 | 32.84 | N |
| ATOM | 2767 | CA | TYR A | 442 | −5.084 | −11.349 | −5.217 | 1.00 | 31.03 | C |
| ATOM | 2768 | CB | TYR A | 442 | −5.639 | −9.919 | −5.322 | 1.00 | 29.76 | C |
| ATOM | 2769 | CG | TYR A | 442 | −6.106 | −9.520 | −6.707 | 1.00 | 28.27 | C |
| ATOM | 2770 | CD1 | TYR A | 442 | −5.242 | −8.886 | −7.605 | 1.00 | 27.09 | C |
| ATOM | 2771 | CE1 | TYR A | 442 | −5.676 | −8.516 | −8.878 | 1.00 | 25.54 | C |
| ATOM | 2772 | CZ | TYR A | 442 | −6.987 | −8.779 | −9.256 | 1.00 | 25.88 | C |
| ATOM | 2773 | OH | TYR A | 442 | −7.436 | −8.425 | −10.508 | 1.00 | 26.55 | O |
| ATOM | 2774 | CE2 | TYR A | 442 | −7.857 | −9.402 | −8.380 | 1.00 | 25.73 | C |
| ATOM | 2775 | CD2 | TYR A | 442 | −7.417 | −9.764 | −7.116 | 1.00 | 25.48 | C |
| ATOM | 2776 | C | TYR A | 442 | −6.122 | −12.380 | −5.657 | 1.00 | 30.98 | C |
| ATOM | 2777 | O | TYR A | 442 | −5.948 | −13.045 | −6.682 | 1.00 | 31.39 | O |
| ATOM | 2778 | N | ASP A | 443 | −7.194 | −12.506 | −4.874 | 1.00 | 30.85 | N |
| ATOM | 2779 | CA | ASP A | 443 | −8.290 | −13.433 | −5.163 | 1.00 | 30.61 | C |
| ATOM | 2780 | CB | ASP A | 443 | −9.309 | −13.407 | −4.015 | 1.00 | 30.67 | C |
| ATOM | 2781 | CG | ASP A | 443 | −10.416 | −14.440 | −4.175 | 1.00 | 32.42 | C |
| ATOM | 2782 | OD1 | ASP A | 443 | −10.490 | −15.109 | −5.231 | 1.00 | 32.55 | O |
| ATOM | 2783 | OD2 | ASP A | 443 | −11.225 | −14.582 | −3.230 | 1.00 | 34.91 | O |
| ATOM | 2784 | C | ASP A | 443 | −8.955 | −13.071 | −6.491 | 1.00 | 30.21 | C |
| ATOM | 2785 | O | ASP A | 443 | −9.603 | −12.025 | −6.600 | 1.00 | 30.51 | O |
| ATOM | 2786 | N | VAL A | 444 | −8.798 | −13.940 | −7.493 | 1.00 | 29.78 | N |
| ATOM | 2787 | CA | VAL A | 444 | −9.249 | −13.628 | −8.863 | 1.00 | 29.60 | C |
| ATOM | 2788 | CB | VAL A | 444 | −8.448 | −14.383 | −9.974 | 1.00 | 29.43 | C |
| ATOM | 2789 | CG1 | VAL A | 444 | −7.013 | −13.887 | −10.026 | 1.00 | 28.95 | C |
| ATOM | 2790 | CG2 | VAL A | 444 | −8.506 | −15.896 | −9.781 | 1.00 | 31.48 | C |
| ATOM | 2791 | C | VAL A | 444 | −10.758 | −13.758 | −9.088 | 1.00 | 29.23 | C |
| ATOM | 2792 | O | VAL A | 444 | −11.266 | −13.390 | −10.154 | 1.00 | 28.81 | O |
| ATOM | 2793 | N | SER A | 445 | −11.465 | −14.279 | −8.085 | 1.00 | 28.61 | N |
| ATOM | 2794 | CA | SER A | 445 | −12.925 | −14.342 | −8.118 | 1.00 | 28.48 | C |
| ATOM | 2795 | CB | SER A | 445 | −13.461 | −15.188 | −6.958 | 1.00 | 28.81 | C |
| ATOM | 2796 | OG | SER A | 445 | −13.272 | −14.541 | −5.712 | 1.00 | 30.97 | O |
| | | | | | gad67.pdb | | | | | |
| ATOM | 2797 | C | SER A | 445 | −13.534 | −12.935 | −8.096 | 1.00 | 27.65 | C |
| ATOM | 2798 | O | SER A | 445 | −14.720 | −12.761 | −8.376 | 1.00 | 27.49 | O |
| ATOM | 2799 | N | TYR A | 446 | −12.702 | −11.944 | −7.779 | 1.00 | 27.24 | N |
| ATOM | 2800 | CA | TYR A | 446 | −13.090 | −10.533 | −7.806 | 1.00 | 27.50 | C |
| ATOM | 2801 | CB | TYR A | 446 | −12.345 | −9.752 | −6.718 | 1.00 | 28.00 | C |
| ATOM | 2802 | CG | TYR A | 446 | −12.801 | −10.065 | −5.310 | 1.00 | 28.22 | C |
| ATOM | 2803 | CD1 | TYR A | 446 | −13.852 | −9.359 | −4.728 | 1.00 | 29.28 | C |
| ATOM | 2804 | CE1 | TYR A | 446 | −14.278 | −9.639 | −3.434 | 1.00 | 29.92 | C |
| ATOM | 2805 | CZ | TYR A | 446 | −13.648 | −10.634 | −2.706 | 1.00 | 29.81 | C |
| ATOM | 2806 | OH | TYR A | 446 | −14.072 | −10.901 | −1.426 | 1.00 | 30.18 | O |
| ATOM | 2807 | CE2 | TYR A | 446 | −12.597 | −11.352 | −3.261 | 1.00 | 28.17 | C |
| ATOM | 2808 | CD2 | TYR A | 446 | −12.180 | −11.064 | −4.558 | 1.00 | 27.65 | C |
| ATOM | 2809 | C | TYR A | 446 | −12.869 | −9.874 | −9.175 | 1.00 | 27.80 | C |
| ATOM | 2810 | O | TYR A | 446 | −13.117 | −8.674 | −9.338 | 1.00 | 27.59 | O |
| ATOM | 2811 | N | ASP A | 447 | −12.381 | −10.652 | −10.144 | 1.00 | 27.83 | N |
| ATOM | 2812 | CA | ASP A | 447 | −12.371 | −10.235 | −11.548 | 1.00 | 27.04 | C |
| ATOM | 2813 | CB | ASP A | 447 | −11.130 | −10.755 | −12.281 | 1.00 | 27.10 | C |
| ATOM | 2814 | CG | ASP A | 447 | −9.855 | −10.027 | −11.877 | 1.00 | 28.10 | C |
| ATOM | 2815 | OD1 | ASP A | 447 | −9.933 | −9.051 | −11.095 | 1.00 | 27.88 | O |
| ATOM | 2816 | OD2 | ASP A | 447 | −8.768 | −10.432 | −12.349 | 1.00 | 25.22 | O |
| ATOM | 2817 | C | ASP A | 447 | −13.647 | −10.757 | −12.198 | 1.00 | 26.96 | C |
| ATOM | 2818 | O | ASP A | 447 | −13.781 | −11.953 | −12.467 | 1.00 | 26.59 | O |
| ATOM | 2819 | N | THR A | 448 | −14.573 | −9.839 | −12.455 | 1.00 | 26.77 | N |
| ATOM | 2820 | CA | THR A | 448 | −15.957 | −10.172 | −12.791 | 1.00 | 27.29 | C |
| ATOM | 2821 | CB | THR A | 448 | −16.919 | −9.306 | −11.920 | 1.00 | 28.01 | C |
| ATOM | 2822 | OG1 | THR A | 448 | −16.845 | −9.750 | −10.558 | 1.00 | 30.99 | O |
| ATOM | 2823 | CG2 | THR A | 448 | −18.364 | −9.395 | −12.387 | 1.00 | 30.86 | C |
| ATOM | 2824 | C | THR A | 448 | −16.281 | −10.075 | −14.295 | 1.00 | 26.46 | C |
| ATOM | 2825 | O | THR A | 448 | −17.351 | −10.502 | −14.734 | 1.00 | 25.07 | O |
| ATOM | 2826 | N | GLY A | 449 | −15.336 | −9.551 | −15.077 | 1.00 | 26.81 | N |
| ATOM | 2827 | CA | GLY A | 449 | −15.526 | −9.312 | −16.511 | 1.00 | 26.59 | C |
| ATOM | 2828 | C | GLY A | 449 | −15.924 | −10.480 | −17.400 | 1.00 | 26.84 | C |
| ATOM | 2829 | O | GLY A | 449 | −16.600 | −10.284 | −18.410 | 1.00 | 27.17 | O |
| ATOM | 2830 | N | ASP A | 450 | −15.517 | −11.695 | −17.036 | 1.00 | 26.95 | N |
| ATOM | 2831 | CA | ASP A | 450 | −15.751 | −12.861 | −17.895 | 1.00 | 28.08 | C |
| ATOM | 2832 | CB | ASP A | 450 | −14.735 | −13.976 | −17.607 | 1.00 | 28.56 | C |
| ATOM | 2833 | CG | ASP A | 450 | −14.232 | −14.663 | −18.877 | 1.00 | 30.61 | C |
| ATOM | 2834 | OD1 | ASP A | 450 | −14.548 | −14.198 | −19.998 | 1.00 | 30.01 | O |
| ATOM | 2835 | OD2 | ASP A | 450 | −13.503 | −15.670 | −18.749 | 1.00 | 30.10 | O |

TABLE A-continued

| | | | | | | | | | |
|---|---|---|---|---|---|---|---|---|---|
| ATOM | 2836 | C | ASP A | 450 | −17.190 | −13.398 | −17.862 | 1.00 | 28.10 | C |
| ATOM | 2837 | O | ASP A | 450 | −17.545 | −14.248 | −18.672 | 1.00 | 29.55 | O |
| ATOM | 2838 | N | LYS A | 451 | −18.015 | −12.903 | −16.942 | 1.00 | 27.50 | N |
| ATOM | 2839 | CA | LYS A | 451 | −19.435 | −13.283 | −16.896 | 1.00 | 26.73 | C |
| ATOM | 2840 | CB | LYS A | 451 | −19.909 | −13.462 | −15.448 | 1.00 | 26.40 | C |
| ATOM | 2841 | CG | LYS A | 451 | −20.048 | −12.171 | −14.666 | 1.00 | 27.41 | C |
| ATOM | 2842 | CD | LYS A | 451 | −19.722 | −12.375 | −13.207 | 1.00 | 31.13 | C |
| ATOM | 2843 | CE | LYS A | 451 | −20.960 | −12.521 | −12.363 | 1.00 | 33.02 | C |
| ATOM | 2844 | NZ | LYS A | 451 | −20.611 | −12.428 | −10.918 | 1.00 | 34.36 | N |
| ATOM | 2845 | C | LYS A | 451 | −20.325 | −12.284 | −17.647 | 1.00 | 26.01 | C |
| ATOM | 2846 | O | LYS A | 451 | −21.540 | −12.469 | −17.754 | 1.00 | 25.64 | O |
| ATOM | 2847 | N | ALA A | 452 | −19.704 | −11.227 | −18.161 | 1.00 | 25.52 | N |
| ATOM | 2848 | CA | ALA A | 452 | −20.390 | −10.221 | −18.963 | 1.00 | 25.20 | C |
| ATOM | 2849 | CB | ALA A | 452 | −19.755 | −8.855 | −18.738 | 1.00 | 25.00 | C |
| ATOM | 2850 | C | ALA A | 452 | −20.338 | −10.585 | −20.439 | 1.00 | 25.49 | C |
| ATOM | 2851 | O | ALA A | 452 | −19.509 | −11.393 | −20.852 | 1.00 | 23.81 | O |
| ATOM | 2852 | N | ILE A | 453 | −21.235 | −9.994 | −21.225 | 1.00 | 26.82 | N |
| ATOM | 2853 | CA | ILE A | 453 | −21.175 | −10.095 | −22.684 | 1.00 | 28.10 | C |
| ATOM | 2854 | CB | ILE A | 453 | −22.595 | −10.059 | −23.335 | 1.00 | 29.88 | C |
| ATOM | 2855 | CG1 | ILE A | 453 | −22.515 | −10.162 | −24.866 | 1.00 | 33.26 | C |
| ATOM | 2856 | CD1 | ILE A | 453 | −21.900 | −11.468 | −25.387 | 1.00 | 37.27 | C |
| ATOM | 2857 | CG2 | ILE A | 453 | −23.372 | −8.817 | −22.908 | 1.00 | 32.07 | C |
| ATOM | 2858 | C | ILE A | 453 | −20.263 | −9.002 | −23.245 | 1.00 | 27.24 | C |
| ATOM | 2859 | O | ILE A | 453 | −19.734 | −9.117 | −24.350 | 1.00 | 28.08 | O |
| ATOM | 2860 | N | GLN A | 454 | −20.082 | −7.942 | −22.462 | 1.00 | 26.25 | N |
| ATOM | 2861 | CA | GLN A | 454 | −19.146 | −6.878 | −22.793 | 1.00 | 24.39 | C |
| ATOM | 2862 | CB | GLN A | 454 | −19.456 | −5.624 | −21.976 | 1.00 | 24.26 | C |
| ATOM | 2863 | CG | GLN A | 454 | −20.689 | −4.872 | −22.412 | 1.00 | 22.53 | C |
| ATOM | 2864 | CD | GLN A | 454 | −20.987 | −3.689 | −21.516 | 1.00 | 23.19 | C | gad67.pdb

| | | | | | | | | | |
|---|---|---|---|---|---|---|---|---|---|
| ATOM | 2865 | OE1 | GLN A | 454 | −20.833 | −2.536 | −21.919 | 1.00 | 23.95 | O |
| ATOM | 2866 | NE2 | GLN A | 454 | −21.409 | −3.968 | −20.290 | 1.00 | 17.10 | N |
| ATOM | 2867 | C | GLN A | 454 | −17.735 | −7.327 | −22.471 | 1.00 | 23.60 | C |
| ATOM | 2868 | O | GLN A | 454 | −17.536 | −8.281 | −21.715 | 1.00 | 23.66 | O |
| ATOM | 2869 | N | CYS A | 455 | −16.761 | −6.640 | −23.058 | 1.00 | 22.39 | N |
| ATOM | 2870 | CA | CYS A | 455 | −15.384 | −6.738 | −22.611 | 1.00 | 21.87 | C |
| ATOM | 2871 | CB | CYS A | 455 | −14.419 | −6.760 | −23.799 | 1.00 | 22.08 | C |
| ATOM | 2872 | SG | CYS A | 455 | −12.695 | −6.824 | −23.311 | 1.00 | 21.94 | S |
| ATOM | 2873 | C | CYS A | 455 | −15.136 | −5.545 | −21.697 | 1.00 | 21.41 | C |
| ATOM | 2874 | O | CYS A | 455 | −15.282 | −5.655 | −20.482 | 1.00 | 21.63 | O |
| ATOM | 2875 | N | GLY A | 456 | −14.788 | −4.400 | −22.284 | 1.00 | 21.00 | N |
| ATOM | 2876 | CA | GLY A | 456 | −14.707 | −3.146 | −21.542 | 1.00 | 19.58 | C |
| ATOM | 2877 | C | GLY A | 456 | −16.086 | −2.750 | −21.053 | 1.00 | 19.32 | C |
| ATOM | 2878 | O | GLY A | 456 | −17.076 | −2.913 | −21.767 | 1.00 | 18.47 | O |
| ATOM | 2879 | N | ARG A | 457 | −16.160 | −2.246 | −19.826 | 1.00 | 19.55 | N |
| ATOM | 2880 | CA | ARG A | 457 | −17.451 | −1.873 | −19.236 | 1.00 | 19.25 | C |
| ATOM | 2881 | CB | ARG A | 457 | −18.042 | −3.030 | −18.409 | 1.00 | 18.68 | C |
| ATOM | 2882 | CG | ARG A | 457 | −19.374 | −2.714 | −17.730 | 1.00 | 19.29 | C |
| ATOM | 2883 | CD | ARG A | 457 | −20.069 | −3.970 | −17.216 | 1.00 | 19.26 | C |
| ATOM | 2884 | NE | ARG A | 457 | −19.352 | −4.628 | −16.125 | 1.00 | 20.12 | N |
| ATOM | 2885 | CZ | ARG A | 457 | −19.644 | −4.488 | −14.833 | 1.00 | 21.54 | C |
| ATOM | 2886 | NH1 | ARG A | 457 | −20.643 | −3.703 | −14.450 | 1.00 | 20.66 | N |
| ATOM | 2887 | NH2 | ARG A | 457 | −18.933 | −5.137 | −13.919 | 1.00 | 16.25 | N |
| ATOM | 2888 | C | ARG A | 457 | −17.339 | −.592 | −18.414 | 1.00 | 18.76 | C |
| ATOM | 2889 | O | ARG A | 457 | −16.467 | −.459 | −17.545 | 1.00 | 18.31 | O |
| ATOM | 2890 | N | HIS A | 458 | −18.231 | .347 | −18.714 | 1.00 | 18.33 | N |
| ATOM | 2891 | CA | HIS A | 458 | −18.275 | 1.636 | −18.045 | 1.00 | 18.38 | C |
| ATOM | 2892 | CB | HIS A | 458 | −19.222 | 2.577 | −18.796 | 1.00 | 18.62 | C |
| ATOM | 2893 | CG | HIS A | 458 | −19.247 | 3.971 | −18.255 | 1.00 | 21.47 | C |
| ATOM | 2894 | ND1 | HIS A | 458 | −18.300 | 4.915 | −18.586 | 1.00 | 22.48 | N |
| ATOM | 2895 | CE1 | HIS A | 458 | −18.569 | 6.045 | −17.955 | 1.00 | 22.69 | C |
| ATOM | 2896 | NE2 | HIS A | 458 | −19.658 | 5.868 | −17.228 | 1.00 | 20.10 | N |
| ATOM | 2897 | CD2 | HIS A | 458 | −20.101 | 4.579 | −17.397 | 1.00 | 18.87 | C |
| ATOM | 2898 | C | HIS A | 458 | −18.716 | 1.483 | −16.592 | 1.00 | 18.33 | C |
| ATOM | 2899 | O | HIS A | 458 | −19.555 | .640 | −16.268 | 1.00 | 18.08 | O |
| ATOM | 2900 | N | VAL A | 459 | −18.135 | 2.300 | −15.719 | 1.00 | 18.46 | N |
| ATOM | 2901 | CA | VAL A | 459 | −18.496 | 2.305 | −14.308 | 1.00 | 18.03 | C |
| ATOM | 2902 | CB | VAL A | 459 | −17.385 | 2.954 | −13.436 | 1.00 | 18.10 | C |
| ATOM | 2903 | CG1 | VAL A | 459 | −17.759 | 2.906 | −11.954 | 1.00 | 16.48 | C |
| ATOM | 2904 | CG2 | VAL A | 459 | −16.037 | 2.279 | −13.681 | 1.00 | 16.09 | C |
| ATOM | 2905 | C | VAL A | 459 | −19.833 | 3.034 | −14.120 | 1.00 | 18.78 | C |
| ATOM | 2906 | O | VAL A | 459 | −19.911 | 4.258 | −14.226 | 1.00 | 20.50 | O |
| ATOM | 2907 | N | ASP A | 460 | −20.888 | 2.273 | −13.864 | 1.00 | 18.46 | N |
| ATOM | 2908 | CA | ASP A | 460 | −22.196 | 2.856 | −13.595 | 1.00 | 18.86 | C |
| ATOM | 2909 | CB | ASP A | 460 | −23.280 | 2.141 | −14.411 | 1.00 | 19.62 | C |
| ATOM | 2910 | CG | ASP A | 460 | −23.134 | 2.355 | −15.912 | 1.00 | 23.98 | C |
| ATOM | 2911 | OD1 | ASP A | 460 | −22.646 | 3.425 | −16.332 | 1.00 | 24.80 | O |
| ATOM | 2912 | OD2 | ASP A | 460 | −23.525 | 1.448 | −16.678 | 1.00 | 27.81 | O |
| ATOM | 2913 | C | ASP A | 460 | −22.549 | 2.806 | −12.104 | 1.00 | 18.23 | C |
| ATOM | 2914 | O | ASP A | 460 | −23.561 | 3.372 | −11.685 | 1.00 | 18.86 | O |

TABLE A-continued

| | | | | | | | | | | |
|---|---|---|---|---|---|---|---|---|---|---|
| ATOM | 2915 | N | ILE A | 461 | −21.707 | 2.145 | −11.309 | 1.00 | 16.97 | N |
| ATOM | 2916 | CA | ILE A | 461 | −22.026 | 1.873 | −9.907 | 1.00 | 16.59 | C |
| ATOM | 2917 | CB | ILE A | 461 | −21.254 | .621 | −9.348 | 1.00 | 17.06 | C |
| ATOM | 2918 | CG1 | ILE A | 461 | −21.754 | .234 | −7.945 | 1.00 | 14.62 | C |
| ATOM | 2919 | CD1 | ILE A | 461 | −23.230 | −.136 | −7.869 | 1.00 | 14.40 | C |
| ATOM | 2920 | CG2 | ILE A | 461 | −19.737 | .850 | −9.333 | 1.00 | 13.93 | C |
| ATOM | 2921 | C | ILE A | 461 | −21.879 | 3.065 | −8.955 | 1.00 | 16.80 | C |
| ATOM | 2922 | O | ILE A | 461 | −22.711 | 3.246 | −8.063 | 1.00 | 16.57 | O |
| ATOM | 2923 | N | PHE A | 462 | −20.844 | 3.883 | −9.143 | 1.00 | 15.71 | N |
| ATOM | 2924 | CA | PHE A | 462 | −20.559 | 4.915 | −8.155 | 1.00 | 15.68 | C |
| ATOM | 2925 | CB | PHE A | 462 | −19.238 | 5.637 | −8.415 | 1.00 | 14.62 | C |
| ATOM | 2926 | CG | PHE A | 462 | −18.891 | 6.626 | −7.340 | 1.00 | 13.18 | C |
| ATOM | 2927 | CD1 | PHE A | 462 | −18.428 | 6.188 | −6.102 | 1.00 | 11.05 | C |
| ATOM | 2928 | CE1 | PHE A | 462 | −18.120 | 7.091 | −5.098 | 1.00 | 10.47 | C |
| ATOM | 2929 | CZ | PHE A | 462 | −18.282 | 8.446 | −5.319 | 1.00 | 14.03 | C |
| ATOM | 2930 | CE2 | PHE A | 462 | −18.757 | 8.894 | −6.547 | 1.00 | 14.79 | C |
| ATOM | 2931 | CD2 | PHE A | 462 | −19.062 | 7.983 | −7.546 | 1.00 | 11.22 | C |
| ATOM | 2932 | C | PHE A | 462 | −21.694 | 5.919 | −7.979 | 1.00 | 16.06 | C |
| | | | | | gad67.pdb | | | | | |
| ATOM | 2933 | O | PHE A | 462 | −22.076 | 6.224 | −6.847 | 1.00 | 15.51 | O |
| ATOM | 2934 | N | LYS A | 463 | −22.219 | 6.429 | −9.090 | 1.00 | 16.13 | N |
| ATOM | 2935 | CA | LYS A | 463 | −23.326 | 7.388 | −9.050 | 1.00 | 16.94 | C |
| ATOM | 2936 | CB | LYS A | 463 | −23.750 | 7.806 | −10.465 | 1.00 | 16.50 | C |
| ATOM | 2937 | CG | LYS A | 463 | −24.243 | 6.667 | −11.348 | 1.00 | 18.09 | C |
| ATOM | 2938 | CD | LYS A | 463 | −24.594 | 7.135 | −12.750 | 1.00 | 17.04 | C |
| ATOM | 2939 | CE | LYS A | 463 | −24.660 | 5.945 | −13.695 | 1.00 | 18.65 | C |
| ATOM | 2940 | NZ | LYS A | 463 | −24.773 | 6.354 | −15.121 | 1.00 | 19.82 | N |
| ATOM | 2941 | C | LYS A | 463 | −24.521 | 6.848 | −8.250 | 1.00 | 16.79 | C |
| ATOM | 2942 | O | LYS A | 463 | −25.123 | 7.579 | −7.467 | 1.00 | 16.26 | O |
| ATOM | 2943 | N | PHE A | 464 | −24.821 | 5.562 | −8.442 | 1.00 | 16.76 | N |
| ATOM | 2944 | CA | PHE A | 464 | −25.928 | 4.868 | −7.784 | 1.00 | 16.64 | C |
| ATOM | 2945 | CB | PHE A | 464 | −26.210 | 3.544 | −8.518 | 1.00 | 16.18 | C |
| ATOM | 2946 | CG | PHE A | 464 | −27.313 | 2.709 | −7.915 | 1.00 | 16.86 | C |
| ATOM | 2947 | CD1 | PHE A | 464 | −28.377 | 3.293 | −7.223 | 1.00 | 18.25 | C |
| ATOM | 2948 | CE1 | PHE A | 464 | −29.395 | 2.508 | −6.678 | 1.00 | 15.96 | C |
| ATOM | 2949 | CZ | PHE A | 464 | −29.369 | 1.128 | −6.843 | 1.00 | 16.60 | C |
| ATOM | 2950 | CE2 | PHE A | 464 | −28.321 | .534 | −7.547 | 1.00 | 17.27 | C |
| ATOM | 2951 | CD2 | PHE A | 464 | −27.306 | 1.326 | −8.082 | 1.00 | 16.36 | C |
| ATOM | 2952 | C | PHE A | 464 | −25.628 | 4.638 | −6.301 | 1.00 | 16.75 | C |
| ATOM | 2953 | O | PHE A | 464 | −26.438 | 4.988 | −5.437 | 1.00 | 17.55 | O |
| ATOM | 2954 | N | TRP A | 465 | −24.458 | 4.063 | −6.019 | 1.00 | 16.13 | N |
| ATOM | 2955 | CA | TRP A | 465 | −24.000 | 3.826 | −4.654 | 1.00 | 15.48 | C |
| ATOM | 2956 | CB | TRP A | 465 | −22.604 | 3.180 | −4.667 | 1.00 | 14.74 | C |
| ATOM | 2957 | CG | TRP A | 465 | −22.001 | 2.928 | −3.300 | 1.00 | 14.29 | C |
| ATOM | 2958 | CD1 | TRP A | 465 | −22.103 | 1.785 | −2.555 | 1.00 | 13.09 | C |
| ATOM | 2959 | NE1 | TRP A | 465 | −21.413 | 1.923 | −1.373 | 1.00 | 12.12 | N |
| ATOM | 2960 | CE2 | TRP A | 465 | −20.843 | 3.170 | −1.334 | 1.00 | 13.81 | C |
| ATOM | 2961 | CD2 | TRP A | 465 | −21.186 | 3.832 | −2.535 | 1.00 | 13.34 | C |
| ATOM | 2962 | CE3 | TRP A | 465 | −20.724 | 5.141 | −2.743 | 1.00 | 14.04 | C |
| ATOM | 2963 | CZ3 | TRP A | 465 | −19.938 | 5.742 | −1.753 | 1.00 | 13.57 | C |
| ATOM | 2964 | CH2 | TRP A | 465 | −19.614 | 5.055 | −.571 | 1.00 | 13.42 | C |
| ATOM | 2965 | CZ2 | TRP A | 465 | −20.054 | 3.771 | −.343 | 1.00 | 13.16 | C |
| ATOM | 2966 | C | TRP A | 465 | −24.000 | 5.122 | −3.838 | 1.00 | 15.92 | C |
| ATOM | 2967 | O | TRP A | 465 | −24.507 | 5.147 | −2.712 | 1.00 | 16.77 | O |
| ATOM | 2968 | N | LEU A | 466 | −23.445 | 6.190 | −4.411 | 1.00 | 14.93 | N |
| ATOM | 2969 | CA | LEU A | 466 | −23.376 | 7.491 | −3.734 | 1.00 | 15.70 | C |
| ATOM | 2970 | CB | LEU A | 466 | −22.544 | 8.497 | −4.538 | 1.00 | 14.65 | C |
| ATOM | 2971 | CG | LEU A | 466 | −22.014 | 9.725 | −3.793 | 1.00 | 13.60 | C |
| ATOM | 2972 | CD1 | LEU A | 466 | −20.974 | 9.347 | −2.737 | 1.00 | 11.75 | C |
| ATOM | 2973 | CD2 | LEU A | 466 | −21.433 | 10.743 | −4.775 | 1.00 | 15.46 | C |
| ATOM | 2974 | C | LEU A | 466 | −24.761 | 8.072 | −3.438 | 1.00 | 16.60 | C |
| ATOM | 2975 | O | LEU A | 466 | −24.977 | 8.642 | −2.368 | 1.00 | 16.91 | O |
| ATOM | 2976 | N | MET A | 467 | −25.684 | 7.927 | −4.388 | 1.00 | 16.40 | N |
| ATOM | 2977 | CA | MET A | 467 | −27.062 | 8.366 | −4.207 | 1.00 | 17.75 | C |
| ATOM | 2978 | CB | MET A | 467 | −27.854 | 8.189 | −5.500 | 1.00 | 17.81 | C |
| ATOM | 2979 | CG | MET A | 467 | −27.637 | 9.303 | −6.517 | 1.00 | 17.80 | C |
| ATOM | 2980 | SD | MET A | 467 | −28.455 | 8.981 | −8.089 | 1.00 | 18.60 | S |
| ATOM | 2981 | CE | MET A | 467 | −30.174 | 8.949 | −7.578 | 1.00 | 17.27 | C |
| ATOM | 2982 | C | MET A | 467 | −27.740 | 7.613 | −3.064 | 1.00 | 18.22 | C |
| ATOM | 2983 | O | MET A | 467 | −28.472 | 8.208 | −2.272 | 1.00 | 18.40 | O |
| ATOM | 2984 | N | TRP A | 468 | −27.475 | 6.308 | −2.983 | 1.00 | 17.69 | N |
| ATOM | 2985 | CA | TRP A | 468 | −28.023 | 5.466 | −1.928 | 1.00 | 17.44 | C |
| ATOM | 2986 | CB | TRP A | 468 | −27.724 | 3.990 | −2.204 | 1.00 | 17.03 | C |
| ATOM | 2987 | CG | TRP A | 468 | −28.716 | 3.031 | −1.589 | 1.00 | 17.29 | C |
| ATOM | 2988 | CD1 | TRP A | 468 | −29.363 | 3.163 | −.386 | 1.00 | 16.85 | C |
| ATOM | 2989 | NE1 | TRP A | 468 | −30.180 | 2.081 | −.164 | 1.00 | 17.58 | N |
| ATOM | 2990 | CE2 | TRP A | 468 | −30.069 | 1.217 | −1.222 | 1.00 | 18.37 | C |
| ATOM | 2991 | CD2 | TRP A | 468 | −29.152 | 1.783 | −2.140 | 1.00 | 17.99 | C |
| ATOM | 2992 | CE3 | TRP A | 468 | −28.861 | 1.087 | −3.322 | 1.00 | 16.94 | C |
| ATOM | 2993 | CZ3 | TRP A | 468 | −29.486 | −.136 | −3.547 | 1.00 | 17.52 | C |

TABLE A-continued

| | | | | | | | | | | |
|---|---|---|---|---|---|---|---|---|---|---|
| ATOM | 2994 | CH2 | TRP A | 468 | −30.392 | −.668 | −2.618 | 1.00 | 16.39 | C |
| ATOM | 2995 | CZ2 | TRP A | 468 | −30.697 | −.007 | −1.453 | 1.00 | 16.27 | C |
| ATOM | 2996 | C | TRP A | 468 | −27.482 | 5.881 | −.558 | 1.00 | 17.70 | C |
| ATOM | 2997 | O | TRP A | 468 | −28.231 | 5.924 | .417 | 1.00 | 18.12 | O |
| ATOM | 2998 | N | LYS A | 469 | −26.187 | 6.195 | −.496 | 1.00 | 17.50 | N |
| ATOM | 2999 | CA | LYS A | 469 | −25.569 | 6.747 | .717 | 1.00 | 17.40 | C |
| ATOM | 3000 | CB | LYS A | 469 | −24.049 | 6.895 | .555 | 1.00 | 16.67 | C |
| | | | | gad67.pdb | | | | | | |
| ATOM | 3001 | CG | LYS A | 469 | −23.281 | 5.592 | .369 | 1.00 | 19.05 | C |
| ATOM | 3002 | CD | LYS A | 469 | −23.285 | 4.725 | 1.624 | 1.00 | 23.32 | C |
| ATOM | 3003 | CE | LYS A | 469 | −22.100 | 5.029 | 2.523 | 1.00 | 24.13 | C |
| ATOM | 3004 | NZ | LYS A | 469 | −22.094 | 4.157 | 3.728 | 1.00 | 27.04 | N |
| ATOM | 3005 | C | LYS A | 469 | −26.167 | 8.102 | 1.098 | 1.00 | 17.53 | C |
| ATOM | 3006 | O | LYS A | 469 | −26.388 | 8.380 | 2.278 | 1.00 | 18.47 | O |
| ATOM | 3007 | N | ALA A | 470 | −26.426 | 8.934 | .093 | 1.00 | 17.08 | N |
| ATOM | 3008 | CA | ALA A | 470 | −26.908 | 10.297 | .309 | 1.00 | 16.77 | C |
| ATOM | 3009 | CB | ALA A | 470 | −26.656 | 11.147 | −.930 | 1.00 | 15.47 | C |
| ATOM | 3010 | C | ALA A | 470 | −28.382 | 10.351 | .687 | 1.00 | 17.07 | C |
| ATOM | 3011 | O | ALA A | 470 | −28.818 | 11.269 | 1.386 | 1.00 | 17.26 | O |
| ATOM | 3012 | N | LYS A | 471 | −29.144 | 9.375 | .207 | 1.00 | 17.56 | N |
| ATOM | 3013 | CA | LYS A | 471 | −30.587 | 9.360 | .392 | 1.00 | 18.11 | C |
| ATOM | 3014 | CB | LYS A | 471 | −31.291 | 8.983 | −.912 | 1.00 | 17.95 | C |
| ATOM | 3015 | CG | LYS A | 471 | −31.187 | 10.022 | −2.014 | 1.00 | 20.00 | C |
| ATOM | 3016 | CD | LYS A | 471 | −31.868 | 9.530 | −3.272 | 1.00 | 23.61 | C |
| ATOM | 3017 | CE | LYS A | 471 | −32.260 | 10.690 | −4.149 | 1.00 | 29.63 | C |
| ATOM | 3018 | NZ | LYS A | 471 | −32.945 | 10.238 | −5.383 | 1.00 | 36.71 | N |
| ATOM | 3019 | C | LYS A | 471 | −31.009 | 8.385 | 1.473 | 1.00 | 18.30 | C |
| ATOM | 3020 | O | LYS A | 471 | −31.963 | 8.644 | 2.209 | 1.00 | 17.92 | O |
| ATOM | 3021 | N | GLY A | 472 | −30.293 | 7.264 | 1.555 | 1.00 | 18.31 | N |
| ATOM | 3022 | CA | GLY A | 472 | −30.744 | 6.106 | 2.317 | 1.00 | 18.28 | C |
| ATOM | 3023 | C | GLY A | 472 | −31.924 | 5.469 | 1.603 | 1.00 | 19.10 | C |
| ATOM | 3024 | O | GLY A | 472 | −32.542 | 6.086 | .728 | 1.00 | 19.78 | O |
| ATOM | 3025 | N | THR A | 473 | −32.240 | 4.234 | 1.971 | 1.00 | 19.91 | N |
| ATOM | 3026 | CA | THR A | 473 | −33.413 | 3.544 | 1.437 | 1.00 | 20.55 | C |
| ATOM | 3027 | CB | THR A | 473 | −33.551 | 2.142 | 2.054 | 1.00 | 20.89 | C |
| ATOM | 3028 | OG1 | THR A | 473 | −32.340 | 1.406 | 1.828 | 1.00 | 22.68 | O |
| ATOM | 3029 | CG2 | THR A | 473 | −34.733 | 1.382 | 1.444 | 1.00 | 20.86 | C |
| ATOM | 3030 | C | THR A | 473 | −34.700 | 4.357 | 1.653 | 1.00 | 21.20 | C |
| ATOM | 3031 | O | THR A | 473 | −35.583 | 4.373 | .792 | 1.00 | 21.31 | O |
| ATOM | 3032 | N | VAL A | 474 | −34.783 | 5.039 | 2.796 | 1.00 | 21.51 | N |
| ATOM | 3033 | CA | VAL A | 474 | −35.938 | 5.873 | 3.140 | 1.00 | 22.21 | C |
| ATOM | 3034 | CB | VAL A | 474 | −35.871 | 6.357 | 4.628 | 1.00 | 22.95 | C |
| ATOM | 3035 | CG1 | VAL A | 474 | −36.962 | 7.383 | 4.935 | 1.00 | 25.35 | C |
| ATOM | 3036 | CG2 | VAL A | 474 | −35.981 | 5.166 | 5.581 | 1.00 | 23.40 | C |
| ATOM | 3037 | C | VAL A | 474 | −36.076 | 7.051 | 2.174 | 1.00 | 21.55 | C |
| ATOM | 3038 | O | VAL A | 474 | −37.191 | 7.441 | 1.818 | 1.00 | 22.04 | O |
| ATOM | 3039 | N | GLY A | 475 | −34.941 | 7.602 | 1.743 | 1.00 | 21.33 | N |
| ATOM | 3040 | CA | GLY A | 475 | −34.921 | 8.689 | .763 | 1.00 | 19.35 | C |
| ATOM | 3041 | C | GLY A | 475 | −35.564 | 8.303 | −.555 | 1.00 | 18.48 | C |
| ATOM | 3042 | O | GLY A | 475 | −36.412 | 9.024 | −1.070 | 1.00 | 18.97 | O |
| ATOM | 3043 | N | PHE A | 476 | −35.164 | 7.157 | −1.098 | 1.00 | 18.01 | N |
| ATOM | 3044 | CA | PHE A | 476 | −35.787 | 6.621 | −2.309 | 1.00 | 17.64 | C |
| ATOM | 3045 | CB | PHE A | 476 | −35.111 | 5.316 | −2.749 | 1.00 | 16.96 | C |
| ATOM | 3046 | CG | PHE A | 476 | −33.758 | 5.500 | −3.382 | 1.00 | 15.87 | C |
| ATOM | 3047 | CD1 | PHE A | 476 | −32.620 | 4.952 | −2.789 | 1.00 | 14.77 | C |
| ATOM | 3048 | CE1 | PHE A | 476 | −31.360 | 5.106 | −3.378 | 1.00 | 15.15 | C |
| ATOM | 3049 | CZ | PHE A | 476 | −31.235 | 5.813 | −4.577 | 1.00 | 14.02 | C |
| ATOM | 3050 | CE2 | PHE A | 476 | −32.366 | 6.358 | −5.180 | 1.00 | 12.65 | C |
| ATOM | 3051 | CD2 | PHE A | 476 | −33.620 | 6.196 | −4.582 | 1.00 | 15.08 | C |
| ATOM | 3052 | C | PHE A | 476 | −37.280 | 6.365 | −2.085 | 1.00 | 17.93 | C |
| ATOM | 3053 | O | PHE A | 476 | −38.101 | 6.708 | −2.933 | 1.00 | 17.46 | O |
| ATOM | 3054 | N | GLU A | 477 | −37.618 | 5.775 | −.938 | 1.00 | 18.84 | N |
| ATOM | 3055 | CA | GLU A | 477 | −39.006 | 5.446 | −.600 | 1.00 | 21.12 | C |
| ATOM | 3056 | CB | GLU A | 477 | −39.087 | 4.772 | .776 | 1.00 | 20.69 | C |
| ATOM | 3057 | CG | GLU A | 477 | −40.504 | 4.468 | 1.237 | 1.00 | 23.48 | C |
| ATOM | 3058 | CD | GLU A | 477 | −40.557 | 3.758 | 2.581 | 1.00 | 25.32 | C |
| ATOM | 3059 | OE1 | GLU A | 477 | −39.941 | 4.246 | 3.557 | 1.00 | 30.18 | O |
| ATOM | 3060 | OE2 | GLU A | 477 | −41.236 | 2.714 | 2.659 | 1.00 | 31.85 | O |
| ATOM | 3061 | C | GLU A | 477 | −39.917 | 6.671 | −.648 | 1.00 | 20.67 | C |
| ATOM | 3062 | O | GLU A | 477 | −40.957 | 6.649 | −1.305 | 1.00 | 20.45 | O |
| ATOM | 3063 | N | ASN A | 478 | −39.519 | 7.736 | .045 | 1.00 | 21.47 | N |
| ATOM | 3064 | CA | ASN A | 478 | −40.324 | 8.952 | .117 | 1.00 | 23.01 | C |
| ATOM | 3065 | CB | ASN A | 478 | −39.721 | 9.936 | 1.125 | 1.00 | 23.72 | C |
| ATOM | 3066 | CG | ASN A | 478 | −39.857 | 9.460 | 2.565 | 1.00 | 25.81 | C |
| ATOM | 3067 | OD1 | ASN A | 478 | −39.049 | 9.818 | 3.429 | 1.00 | 27.53 | O |
| ATOM | 3068 | ND2 | ASN A | 478 | −40.881 | 8.649 | 2.832 | 1.00 | 24.14 | N |
| | | | | gad67.pdb | | | | | | |
| ATOM | 3069 | C | ASN A | 478 | −40.483 | 9.615 | −1.243 | 1.00 | 23.32 | C |
| ATOM | 3070 | O | ASN A | 478 | −41.553 | 10.130 | −1.578 | 1.00 | 24.17 | O |
| ATOM | 3071 | N | GLN A | 479 | −39.402 | 9.590 | −2.015 | 1.00 | 23.19 | N |

TABLE A-continued

| | | | | | | | | | | |
|---|---|---|---|---|---|---|---|---|---|---|
| ATOM | 3072 | CA | GLN A | 479 | −39.381 | 10.115 | −3.371 | 1.00 | 23.01 | C |
| ATOM | 3073 | CB | GLN A | 479 | −37.948 | 10.073 | −3.897 | 1.00 | 23.41 | C |
| ATOM | 3074 | CG | GLN A | 479 | −37.758 | 10.502 | −5.331 | 1.00 | 24.25 | C |
| ATOM | 3075 | CD | GLN A | 479 | −36.298 | 10.501 | −5.715 | 1.00 | 26.84 | C |
| ATOM | 3076 | OE1 | GLN A | 479 | −35.459 | 11.057 | −5.004 | 1.00 | 30.24 | O |
| ATOM | 3077 | NE2 | GLN A | 479 | −35.981 | 9.872 | −6.838 | 1.00 | 24.63 | N |
| ATOM | 3078 | C | GLN A | 479 | −40.328 | 9.333 | −4.286 | 1.00 | 22.52 | C |
| ATOM | 3079 | O | GLN A | 479 | −41.125 | 9.926 | −5.008 | 1.00 | 22.65 | O |
| ATOM | 3080 | N | ILE A | 480 | −40.245 | 8.007 | −4.243 | 1.00 | 22.34 | N |
| ATOM | 3081 | CA | ILE A | 480 | −41.120 | 7.160 | −5.053 | 1.00 | 22.81 | C |
| ATOM | 3082 | CB | ILE A | 480 | −40.714 | 5.658 | −4.969 | 1.00 | 23.65 | C |
| ATOM | 3083 | CG1 | ILE A | 480 | −39.270 | 5.438 | −5.459 | 1.00 | 24.90 | C |
| ATOM | 3084 | CD1 | ILE A | 480 | −38.962 | 5.955 | −6.858 | 1.00 | 31.98 | C |
| ATOM | 3085 | CG2 | ILE A | 480 | −41.694 | 4.765 | −5.737 | 1.00 | 22.60 | C |
| ATOM | 3086 | C | ILE A | 480 | −42.594 | 7.369 | −4.674 | 1.00 | 22.62 | C |
| ATOM | 3087 | O | ILE A | 480 | −43.453 | 7.490 | −5.552 | 1.00 | 22.36 | O |
| ATOM | 3088 | N | ASN A | 481 | −42.868 | 7.437 | −3.372 | 1.00 | 22.17 | N |
| ATOM | 3089 | CA | ASN A | 481 | −44.229 | 7.624 | −2.856 | 1.00 | 21.90 | C |
| ATOM | 3090 | CB | ASN A | 481 | −44.243 | 7.563 | −1.323 | 1.00 | 20.90 | C |
| ATOM | 3091 | CG | ASN A | 481 | −44.084 | 6.151 | −.793 | 1.00 | 20.41 | C |
| ATOM | 3092 | OD1 | ASN A | 481 | −43.858 | 5.943 | .405 | 1.00 | 22.62 | O |
| ATOM | 3093 | ND2 | ASN A | 481 | −44.200 | 5.169 | −1.683 | 1.00 | 14.08 | N |
| ATOM | 3094 | C | ASN A | 481 | −44.930 | 8.895 | −3.333 | 1.00 | 22.39 | C |
| ATOM | 3095 | O | ASN A | 481 | −46.117 | 8.860 | −3.659 | 1.00 | 21.97 | O |
| ATOM | 3096 | N | LYS A | 482 | −44.203 | 10.012 | −3.379 | 1.00 | 23.48 | N |
| ATOM | 3097 | CA | LYS A | 482 | −44.796 | 11.283 | −3.822 | 1.00 | 24.68 | C |
| ATOM | 3098 | CB | LYS A | 482 | −43.974 | 12.500 | −3.365 | 1.00 | 25.05 | C |
| ATOM | 3099 | CG | LYS A | 482 | −42.488 | 12.434 | −3.638 | 1.00 | 31.95 | C |
| ATOM | 3100 | CD | LYS A | 482 | −42.109 | 13.107 | −4.956 | 1.00 | 39.96 | C |
| ATOM | 3101 | CE | LYS A | 482 | −40.603 | 13.103 | −5.168 | 1.00 | 38.99 | C |
| ATOM | 3102 | NZ | LYS A | 482 | −39.868 | 13.940 | −4.161 | 1.00 | 42.29 | N |
| ATOM | 3103 | C | LYS A | 482 | −45.107 | 11.338 | −5.321 | 1.00 | 23.90 | C |
| ATOM | 3104 | O | LYS A | 482 | −46.115 | 11.930 | −5.719 | 1.00 | 23.82 | O |
| ATOM | 3105 | N | CYS A | 483 | −44.252 | 10.718 | −6.136 | 1.00 | 22.89 | N |
| ATOM | 3106 | CA | CYS A | 483 | −44.485 | 10.585 | −7.576 | 1.00 | 22.05 | C |
| ATOM | 3107 | CB | CYS A | 483 | −43.307 | 9.877 | −8.247 | 1.00 | 21.65 | C |
| ATOM | 3108 | SG | CYS A | 483 | −41.803 | 10.864 | −8.385 | 1.00 | 23.11 | S |
| ATOM | 3109 | C | CYS A | 483 | −45.774 | 9.817 | −7.866 | 1.00 | 21.70 | C |
| ATOM | 3110 | O | CYS A | 483 | −46.547 | 10.192 | −8.746 | 1.00 | 21.19 | O |
| ATOM | 3111 | N | LEU A | 484 | −45.997 | 8.741 | −7.119 | 1.00 | 21.58 | N |
| ATOM | 3112 | CA | LEU A | 484 | −47.199 | 7.930 | −7.267 | 1.00 | 22.61 | C |
| ATOM | 3113 | CB | LEU A | 484 | −47.019 | 6.579 | −6.578 | 1.00 | 22.23 | C |
| ATOM | 3114 | CG | LEU A | 484 | −46.149 | 5.580 | −7.349 | 1.00 | 22.81 | C |
| ATOM | 3115 | CD1 | LEU A | 484 | −45.446 | 4.631 | −6.400 | 1.00 | 22.24 | C |
| ATOM | 3116 | CD2 | LEU A | 484 | −46.979 | 4.808 | −8.360 | 1.00 | 20.44 | C |
| ATOM | 3117 | C | LEU A | 484 | −48.435 | 8.657 | −6.739 | 1.00 | 23.30 | C |
| ATOM | 3118 | O | LEU A | 484 | −49.533 | 8.494 | −7.273 | 1.00 | 22.40 | O |
| ATOM | 3119 | N | GLU A | 485 | −48.233 | 9.466 | −5.702 | 1.00 | 24.85 | N |
| ATOM | 3120 | CA | GLU A | 485 | −49.279 | 10.302 | −5.131 | 1.00 | 27.75 | C |
| ATOM | 3121 | CB | GLU A | 485 | −48.767 | 10.988 | −3.860 | 1.00 | 27.53 | C |
| ATOM | 3122 | CG | GLU A | 485 | −49.852 | 11.584 | −2.974 | 1.00 | 34.09 | C |
| ATOM | 3123 | CD | GLU A | 485 | −49.311 | 12.180 | −1.671 | 1.00 | 34.17 | C |
| ATOM | 3124 | OE1 | GLU A | 485 | −48.071 | 12.261 | −1.501 | 1.00 | 41.72 | O |
| ATOM | 3125 | OE2 | GLU A | 485 | −50.139 | 12.571 | −.815 | 1.00 | 42.86 | O |
| ATOM | 3126 | C | GLU A | 485 | −49.784 | 11.334 | −6.146 | 1.00 | 26.50 | C |
| ATOM | 3127 | O | GLU A | 485 | −50.995 | 11.501 | −6.310 | 1.00 | 26.07 | O |
| ATOM | 3128 | N | LEU A | 486 | −48.870 | 12.009 | −6.844 | 1.00 | 26.36 | N |
| ATOM | 3129 | CA | LEU A | 486 | −49.304 | 13.004 | −7.831 | 1.00 | 26.29 | C |
| ATOM | 3130 | CB | LEU A | 486 | −48.307 | 14.170 | −7.994 | 1.00 | 27.49 | C |
| ATOM | 3131 | CG | LEU A | 486 | −46.859 | 14.032 | −8.450 | 1.00 | 30.60 | C |
| ATOM | 3132 | CD1 | LEU A | 486 | −46.738 | 14.548 | −9.853 | 1.00 | 36.96 | C |
| ATOM | 3133 | CD2 | LEU A | 486 | −45.955 | 14.853 | −7.550 | 1.00 | 31.61 | C |
| ATOM | 3134 | C | LEU A | 486 | −49.791 | 12.402 | −9.156 | 1.00 | 24.36 | C |
| ATOM | 3135 | O | LEU A | 486 | −50.483 | 13.075 | −9.921 | 1.00 | 24.18 | O |
| ATOM | 3136 | N | ALA A | 487 | −49.472 | 11.129 | −9.391 | 1.00 | 22.90 | N |
| | | | | | gad67.pdb | | | | | |
| ATOM | 3137 | CA | ALA A | 487 | −50.086 | 10.354 | −10.475 | 1.00 | 21.81 | C |
| ATOM | 3138 | CB | ALA A | 487 | −49.290 | 9.097 | −10.754 | 1.00 | 21.12 | C |
| ATOM | 3139 | C | ALA A | 487 | −51.541 | 10.000 | −10.151 | 1.00 | 22.23 | C |
| ATOM | 3140 | O | ALA A | 487 | −52.394 | 9.993 | −11.041 | 1.00 | 21.62 | O |
| ATOM | 3141 | N | GLU A | 488 | −51.809 | 9.698 | −8.880 | 1.00 | 22.74 | N |
| ATOM | 3142 | CA | GLU A | 488 | −53.177 | 9.497 | −8.389 | 1.00 | 24.99 | C |
| ATOM | 3143 | CB | GLU A | 488 | −53.178 | 9.039 | −6.924 | 1.00 | 24.56 | C |
| ATOM | 3144 | CG | GLU A | 488 | −52.613 | 7.640 | −6.698 | 1.00 | 29.30 | C |
| ATOM | 3145 | CD | GLU A | 488 | −52.404 | 7.310 | −5.223 | 1.00 | 29.88 | C |
| ATOM | 3146 | OE1 | GLU A | 488 | −51.315 | 6.791 | −4.877 | 1.00 | 34.36 | O |
| ATOM | 3147 | OE2 | GLU A | 488 | −53.326 | 7.567 | −4.412 | 1.00 | 35.80 | O |
| ATOM | 3148 | C | GLU A | 488 | −53.976 | 10.788 | −8.525 | 1.00 | 22.84 | C |
| ATOM | 3149 | O | GLU A | 488 | −55.135 | 10.768 | −8.939 | 1.00 | 22.99 | O |
| ATOM | 3150 | N | TYR A | 489 | −53.335 | 11.902 | −8.181 | 1.00 | 22.37 | N |

TABLE A-continued

| | | | | | | | | | | |
|---|---|---|---|---|---|---|---|---|---|---|
| ATOM | 3151 | CA | TYR A | 489 | −53.923 | 13.233 | −8.301 | 1.00 | 21.85 | C |
| ATOM | 3152 | CB | TYR A | 489 | −52.939 | 14.290 | −7.791 | 1.00 | 21.67 | C |
| ATOM | 3153 | CG | TYR A | 489 | −53.386 | 15.715 | −8.032 | 1.00 | 22.57 | C |
| ATOM | 3154 | CD1 | TYR A | 489 | −52.962 | 16.419 | −9.162 | 1.00 | 21.35 | C |
| ATOM | 3155 | CE1 | TYR A | 489 | −53.375 | 17.728 | −9.392 | 1.00 | 21.65 | C |
| ATOM | 3156 | CZ | TYR A | 489 | −54.222 | 18.346 | −8.480 | 1.00 | 22.72 | C |
| ATOM | 3157 | OH | TYR A | 489 | −54.633 | 19.639 | −8.691 | 1.00 | 24.64 | O |
| ATOM | 3158 | CE2 | TYR A | 489 | −54.656 | 17.669 | −7.352 | 1.00 | 22.24 | C |
| ATOM | 3159 | CD2 | TYR A | 489 | −54.237 | 16.359 | −7.133 | 1.00 | 21.86 | C |
| ATOM | 3160 | C | TYR A | 489 | −54.338 | 13.542 | −9.742 | 1.00 | 22.07 | C |
| ATOM | 3161 | O | TYR A | 489 | −55.444 | 14.039 | −9.985 | 1.00 | 22.30 | O |
| ATOM | 3162 | N | LEU A | 490 | −53.439 | 13.246 | −10.682 | 1.00 | 21.22 | N |
| ATOM | 3163 | CA | LEU A | 490 | −53.678 | 13.460 | −12.102 | 1.00 | 20.32 | C |
| ATOM | 3164 | CB | LEU A | 490 | −52.438 | 13.057 | −12.905 | 1.00 | 20.90 | C |
| ATOM | 3165 | CG | LEU A | 490 | −52.163 | 13.559 | −14.328 | 1.00 | 21.93 | C |
| ATOM | 3166 | CD1 | LEU A | 490 | −51.246 | 12.566 | −14.989 | 1.00 | 23.90 | C |
| ATOM | 3167 | CD2 | LEU A | 490 | −53.398 | 13.777 | −15.195 | 1.00 | 19.48 | C |
| ATOM | 3168 | C | LEU A | 490 | −54.862 | 12.621 | −12.564 | 1.00 | 19.86 | C |
| ATOM | 3169 | O | LEU A | 490 | −55.780 | 13.132 | −13.213 | 1.00 | 20.16 | O |
| ATOM | 3170 | N | TYR A | 491 | −54.826 | 11.332 | −12.236 | 1.00 | 19.57 | N |
| ATOM | 3171 | CA | TYR A | 491 | −55.882 | 10.413 | −12.623 | 1.00 | 20.74 | C |
| ATOM | 3172 | CB | TYR A | 491 | −55.597 | 8.998 | −12.096 | 1.00 | 20.88 | C |
| ATOM | 3173 | CG | TYR A | 491 | −56.690 | 7.989 | −12.400 | 1.00 | 20.66 | C |
| ATOM | 3174 | CD1 | TYR A | 491 | −57.416 | 7.388 | −11.371 | 1.00 | 19.35 | C |
| ATOM | 3175 | CE1 | TYR A | 491 | −58.417 | 6.466 | −11.644 | 1.00 | 16.73 | C |
| ATOM | 3176 | CZ | TYR A | 491 | −58.709 | 6.141 | −12.960 | 1.00 | 19.15 | C |
| ATOM | 3177 | OH | TYR A | 491 | −59.704 | 5.231 | −13.248 | 1.00 | 21.80 | O |
| ATOM | 3178 | CE2 | TYR A | 491 | −58.002 | 6.722 | −13.996 | 1.00 | 17.99 | C |
| ATOM | 3179 | CD2 | TYR A | 491 | −57.002 | 7.643 | −13.711 | 1.00 | 20.09 | C |
| ATOM | 3180 | C | TYR A | 491 | −57.244 | 10.919 | −12.152 | 1.00 | 21.53 | C |
| ATOM | 3181 | O | TYR A | 491 | −58.180 | 10.992 | −12.941 | 1.00 | 21.70 | O |
| ATOM | 3182 | N | ALA A | 492 | −57.334 | 11.298 | −10.879 | 1.00 | 22.48 | N |
| ATOM | 3183 | CA | ALA A | 492 | −58.580 | 11.801 | −10.297 | 1.00 | 24.16 | C |
| ATOM | 3184 | CB | ALA A | 492 | −58.426 | 11.989 | −8.791 | 1.00 | 23.74 | C |
| ATOM | 3185 | C | ALA A | 492 | −59.073 | 13.096 | −10.947 | 1.00 | 25.13 | C |
| ATOM | 3186 | O | ALA A | 492 | −60.282 | 13.335 | −11.018 | 1.00 | 25.25 | O |
| ATOM | 3187 | N | LYS A | 493 | −58.140 | 13.919 | −11.422 | 1.00 | 26.25 | N |
| ATOM | 3188 | CA | LYS A | 493 | −58.466 | 15.214 | −12.030 | 1.00 | 27.72 | C |
| ATOM | 3189 | CB | LYS A | 493 | −57.211 | 16.084 | −12.170 | 1.00 | 28.54 | C |
| ATOM | 3190 | CG | LYS A | 493 | −56.957 | 17.055 | −11.019 | 1.00 | 33.55 | C |
| ATOM | 3191 | CD | LYS A | 493 | −57.983 | 18.187 | −10.993 | 1.00 | 41.01 | C |
| ATOM | 3192 | CE | LYS A | 493 | −57.374 | 19.499 | −10.509 | 1.00 | 45.13 | C |
| ATOM | 3193 | NZ | LYS A | 493 | −56.498 | 20.130 | −11.549 | 1.00 | 46.61 | N |
| ATOM | 3194 | C | LYS A | 493 | −59.152 | 15.103 | −13.387 | 1.00 | 28.13 | C |
| ATOM | 3195 | O | LYS A | 493 | −60.020 | 15.912 | −13.712 | 1.00 | 29.46 | O |
| ATOM | 3196 | N | ILE A | 494 | −58.761 | 14.105 | −14.174 | 1.00 | 27.93 | N |
| ATOM | 3197 | CA | ILE A | 494 | −59.240 | 13.969 | −15.551 | 1.00 | 28.48 | C |
| ATOM | 3198 | CB | ILE A | 494 | −58.057 | 13.830 | −16.563 | 1.00 | 28.55 | C |
| ATOM | 3199 | CG1 | ILE A | 494 | −57.230 | 12.569 | −16.277 | 1.00 | 27.57 | C |
| ATOM | 3200 | CD1 | ILE A | 494 | −56.274 | 12.179 | −17.393 | 1.00 | 28.90 | C |
| ATOM | 3201 | CG2 | ILE A | 494 | −57.184 | 15.089 | −16.541 | 1.00 | 28.31 | C |
| ATOM | 3202 | C | ILE A | 494 | −60.225 | 12.809 | −15.718 | 1.00 | 28.93 | C |
| ATOM | 3203 | O | ILE A | 494 | −60.899 | 12.697 | −16.746 | 1.00 | 28.21 | O |
| ATOM | 3204 | N | LYS A | 495 | −60.293 | 11.964 | −14.690 | 1.00 | 30.42 | N |
| | | | | | gad67.pdb | | | | | |
| ATOM | 3205 | CA | LYS A | 495 | −61.143 | 10.769 | −14.644 | 1.00 | 32.88 | C |
| ATOM | 3206 | CB | LYS A | 495 | −61.169 | 10.233 | −13.206 | 1.00 | 33.01 | C |
| ATOM | 3207 | CG | LYS A | 495 | −61.644 | 8.800 | −13.044 | 1.00 | 34.92 | C |
| ATOM | 3208 | CD | LYS A | 495 | −61.422 | 8.307 | −11.611 | 1.00 | 35.23 | C |
| ATOM | 3209 | CE | LYS A | 495 | −62.465 | 8.845 | −10.631 | 1.00 | 39.15 | C |
| ATOM | 3210 | NZ | LYS A | 495 | −63.791 | 8.170 | −10.814 | 1.00 | 42.41 | N |
| ATOM | 3211 | C | LYS A | 495 | −62.581 | 10.980 | −15.144 | 1.00 | 33.11 | C |
| ATOM | 3212 | O | LYS A | 495 | −63.104 | 10.155 | −15.893 | 1.00 | 33.39 | O |
| ATOM | 3213 | N | ASN A | 496 | −63.208 | 12.079 | −14.724 | 1.00 | 33.45 | N |
| ATOM | 3214 | CA | ASN A | 496 | −64.616 | 12.336 | −15.037 | 1.00 | 34.78 | C |
| ATOM | 3215 | CB | ASN A | 496 | −65.469 | 12.280 | −13.758 | 1.00 | 35.15 | C |
| ATOM | 3216 | CG | ASN A | 496 | −65.433 | 10.916 | −13.088 | 1.00 | 36.29 | C |
| ATOM | 3217 | CD1 | ASN A | 496 | −65.085 | 10.805 | −11.912 | 1.00 | 37.81 | O |
| ATOM | 3218 | ND2 | ASN A | 496 | −65.790 | 9.871 | −13.834 | 1.00 | 36.88 | N |
| ATOM | 3219 | C | ASN A | 496 | −64.863 | 13.651 | −15.782 | 1.00 | 34.95 | C |
| ATOM | 3220 | O | ASN A | 496 | −65.877 | 14.321 | −15.565 | 1.00 | 35.58 | O |
| ATOM | 3221 | N | ARG A | 497 | −63.935 | 14.009 | −16.665 | 1.00 | 34.65 | N |
| ATOM | 3222 | CA | ARG A | 497 | −64.055 | 15.228 | −17.459 | 1.00 | 33.95 | C |
| ATOM | 3223 | CB | ARG A | 497 | −62.772 | 16.049 | −17.379 | 1.00 | 34.01 | C |
| ATOM | 3224 | CG | ARG A | 497 | −62.558 | 16.701 | −16.028 | 1.00 | 36.16 | C |
| ATOM | 3225 | CD | ARG A | 497 | −61.391 | 17.663 | −16.059 | 1.00 | 40.19 | C |
| ATOM | 3226 | NE | ARG A | 497 | −61.661 | 18.835 | −16.888 | 1.00 | 42.66 | N |
| ATOM | 3227 | CZ | ARG A | 497 | −60.865 | 19.898 | −16.971 | 1.00 | 43.47 | C |
| ATOM | 3228 | NH1 | ARG A | 497 | −59.737 | 19.954 | −16.270 | 1.00 | 42.85 | N |
| ATOM | 3229 | NH2 | ARG A | 497 | −61.201 | 20.912 | −17.757 | 1.00 | 45.18 | N |

TABLE A-continued

| | | | | | | | | | | |
|---|---|---|---|---|---|---|---|---|---|---|
| ATOM | 3230 | C | ARG A | 497 | −64.397 | 14.914 | −18.910 | 1.00 | 33.40 | C |
| ATOM | 3231 | O | ARG A | 497 | −63.881 | 13.949 | −19.485 | 1.00 | 34.11 | O |
| ATOM | 3232 | N | GLU A | 498 | −65.270 | 15.736 | −19.490 | 1.00 | 31.65 | N |
| ATOM | 3233 | CA | GLU A | 498 | −65.723 | 15.567 | −20.872 | 1.00 | 30.24 | C |
| ATOM | 3234 | CB | GLU A | 498 | −66.854 | 16.554 | −21.182 | 1.00 | 30.62 | C |
| ATOM | 3239 | C | GLU A | 498 | −64.592 | 15.740 | −21.889 | 1.00 | 28.76 | C |
| ATOM | 3240 | O | GLU A | 498 | −64.626 | 15.148 | −22.966 | 1.00 | 28.79 | O |
| ATOM | 3241 | N | GLU A | 499 | −63.596 | 16.551 | −21.533 | 1.00 | 27.50 | N |
| ATOM | 3242 | CA | GLU A | 499 | −62.457 | 16.839 | −22.407 | 1.00 | 27.14 | C |
| ATOM | 3243 | CB | GLU A | 499 | −61.664 | 18.043 | −21.882 | 1.00 | 26.91 | C |
| ATOM | 3244 | CG | GLU A | 499 | −62.467 | 19.333 | −21.716 | 1.00 | 30.64 | C |
| ATOM | 3245 | CD | GLU A | 499 | −63.121 | 19.469 | −20.341 | 1.00 | 35.64 | C |
| ATOM | 3246 | OE1 | GLU A | 499 | −63.470 | 18.436 | −19.727 | 1.00 | 36.39 | O |
| ATOM | 3247 | OE2 | GLU A | 499 | −63.291 | 20.619 | −19.874 | 1.00 | 38.60 | O |
| ATOM | 3248 | C | GLU A | 499 | −61.520 | 15.641 | −22.563 | 1.00 | 26.20 | C |
| ATOM | 3249 | O | GLU A | 499 | −60.781 | 15.548 | −23.546 | 1.00 | 26.08 | O |
| ATOM | 3250 | N | PHE A | 500 | −61.559 | 14.729 | −21.593 | 1.00 | 25.57 | N |
| ATOM | 3251 | CA | PHE A | 500 | −60.631 | 13.599 | −21.552 | 1.00 | 25.58 | C |
| ATOM | 3252 | CB | PHE A | 500 | −59.693 | 13.713 | −20.345 | 1.00 | 24.80 | C |
| ATOM | 3253 | CG | PHE A | 500 | −58.921 | 15.000 | −20.303 | 1.00 | 24.77 | C |
| ATOM | 3254 | CD1 | PHE A | 500 | −59.317 | 16.033 | −19.462 | 1.00 | 22.88 | C |
| ATOM | 3255 | CE1 | PHE A | 500 | −58.611 | 17.233 | −19.428 | 1.00 | 24.87 | C |
| ATOM | 3256 | CZ | PHE A | 500 | −57.495 | 17.407 | −20.248 | 1.00 | 24.62 | C |
| ATOM | 3257 | CE2 | PHE A | 500 | −57.091 | 16.381 | −21.093 | 1.00 | 24.69 | C |
| ATOM | 3258 | CD2 | PHE A | 500 | −57.804 | 15.186 | −21.120 | 1.00 | 24.75 | C |
| ATOM | 3259 | C | PHE A | 500 | −61.343 | 12.256 | −21.536 | 1.00 | 26.46 | C |
| ATOM | 3260 | O | PHE A | 500 | −62.458 | 12.133 | −21.027 | 1.00 | 27.71 | O |
| ATOM | 3261 | N | GLU A | 501 | −60.683 | 11.255 | −22.105 | 1.00 | 26.53 | N |
| ATOM | 3262 | CA | GLU A | 501 | −61.188 | 9.895 | −22.108 | 1.00 | 26.75 | C |
| ATOM | 3263 | CB | GLU A | 501 | −61.720 | 9.532 | −23.498 | 1.00 | 26.46 | C |
| ATOM | 3264 | CG | GLU A | 501 | −62.472 | 8.207 | −23.572 | 1.00 | 29.94 | C |
| ATOM | 3265 | CD | GLU A | 501 | −63.058 | 7.934 | −24.953 | 1.00 | 30.82 | C |
| ATOM | 3266 | OE1 | GLU A | 501 | −63.026 | 6.760 | −25.391 | 1.00 | 36.20 | O |
| ATOM | 3267 | OE2 | GLU A | 501 | −63.550 | 8.891 | −25.600 | 1.00 | 34.55 | O |
| ATOM | 3268 | C | GLU A | 501 | −60.054 | 8.964 | −21.697 | 1.00 | 25.19 | C |
| ATOM | 3269 | O | GLU A | 501 | −58.968 | 9.010 | −22.279 | 1.00 | 24.67 | O |
| ATOM | 3270 | N | MET A | 502 | −60.309 | 8.138 | −20.683 | 1.00 | 24.30 | N |
| ATOM | 3271 | CA | MET A | 502 | −59.333 | 7.156 | −20.225 | 1.00 | 23.62 | C |
| ATOM | 3272 | CB | MET A | 502 | −59.693 | 6.616 | −18.837 | 1.00 | 23.44 | C |
| ATOM | 3273 | CG | MET A | 502 | −59.837 | 7.678 | −17.738 | 1.00 | 25.29 | C |
| ATOM | 3274 | SD | MET A | 502 | −58.559 | 8.964 | −17.665 | 1.00 | 28.11 | S |
| ATOM | 3275 | CE | MET A | 502 | −57.098 | 8.012 | −17.261 | 1.00 | 23.09 | C |
| ATOM | 3276 | C | MET A | 502 | −59.224 | 6.016 | −21.226 | 1.00 | 23.04 | C |
| | | | | | gad67.pdb | | | | | |
| ATOM | 3277 | O | MET A | 502 | −60.231 | 5.543 | −21.755 | 1.00 | 24.34 | O |
| ATOM | 3278 | N | VAL A | 503 | −57.994 | 5.588 | −21.485 | 1.00 | 22.37 | N |
| ATOM | 3279 | CA | VAL A | 503 | −57.714 | 4.554 | −22.484 | 1.00 | 21.54 | C |
| ATOM | 3280 | CB | VAL A | 503 | −56.203 | 4.516 | −22.831 | 1.00 | 21.41 | C |
| ATOM | 3281 | CG1 | VAL A | 503 | −55.856 | 3.333 | −23.723 | 1.00 | 21.14 | C |
| ATOM | 3282 | CG2 | VAL A | 503 | −55.802 | 5.809 | −23.509 | 1.00 | 20.78 | C |
| ATOM | 3283 | C | VAL A | 503 | −58.234 | 3.181 | −22.053 | 1.00 | 21.09 | C |
| ATOM | 3284 | O | VAL A | 503 | −58.711 | 2.398 | −22.883 | 1.00 | 21.94 | O |
| ATOM | 3285 | N | PHE A | 504 | −58.150 | 2.899 | −20.756 | 1.00 | 20.47 | N |
| ATOM | 3286 | CA | PHE A | 504 | −58.650 | 1.639 | −20.210 | 1.00 | 20.06 | C |
| ATOM | 3287 | CB | PHE A | 504 | −57.523 | .602 | −20.102 | 1.00 | 19.47 | C |
| ATOM | 3288 | CG | PHE A | 504 | −56.448 | .956 | −19.101 | 1.00 | 18.71 | C |
| ATOM | 3289 | CD1 | PHE A | 504 | −55.421 | 1.833 | −19.434 | 1.00 | 18.46 | C |
| ATOM | 3290 | CE1 | PHE A | 504 | −54.425 | 2.153 | −18.515 | 1.00 | 17.30 | C |
| ATOM | 3291 | CZ | PHE A | 504 | −54.443 | 1.586 | −17.252 | 1.00 | 18.63 | C |
| ATOM | 3292 | CE2 | PHE A | 504 | −55.459 | .701 | −16.907 | 1.00 | 18.31 | C |
| ATOM | 3293 | CD2 | PHE A | 504 | −56.450 | .388 | −17.832 | 1.00 | 18.68 | C |
| ATOM | 3294 | C | PHE A | 504 | −59.328 | 1.861 | −18.864 | 1.00 | 20.75 | C |
| ATOM | 3295 | O | PHE A | 504 | −59.058 | 2.853 | −18.181 | 1.00 | 19.62 | O |
| ATOM | 3296 | N | ASN A | 505 | −60.214 | .936 | −18.498 | 1.00 | 22.44 | N |
| ATOM | 3297 | CA | ASN A | 505 | −60.933 | 1.007 | −17.230 | 1.00 | 24.35 | C |
| ATOM | 3298 | CB | ASN A | 505 | −62.315 | .343 | −17.357 | 1.00 | 25.84 | C |
| ATOM | 3299 | CG | ASN A | 505 | −63.181 | .530 | −16.112 | 1.00 | 31.90 | C |
| ATOM | 3300 | OD1 | ASN A | 505 | −62.972 | 1.450 | −15.315 | 1.00 | 35.66 | O |
| ATOM | 3301 | ND2 | ASN A | 505 | −64.165 | −.349 | −15.946 | 1.00 | 35.57 | N |
| ATOM | 3302 | C | ASN A | 505 | −60.119 | .367 | −16.109 | 1.00 | 24.30 | C |
| ATOM | 3303 | O | ASN A | 505 | −59.902 | −.849 | −16.097 | 1.00 | 24.75 | O |
| ATOM | 3304 | N | GLY A | 506 | −59.663 | 1.200 | −15.179 | 1.00 | 24.37 | N |
| ATOM | 3305 | CA | GLY A | 506 | −58.844 | .749 | −14.058 | 1.00 | 24.42 | C |
| ATOM | 3306 | C | GLY A | 506 | −57.975 | 1.857 | −13.497 | 1.00 | 25.21 | C |
| ATOM | 3307 | O | GLY A | 506 | −57.580 | 2.776 | −14.220 | 1.00 | 25.49 | O |
| ATOM | 3308 | N | GLU A | 507 | −57.690 | 1.777 | −12.201 | 1.00 | 25.60 | N |
| ATOM | 3309 | CA | GLU A | 507 | −56.777 | 2.715 | −11.551 | 1.00 | 25.68 | C |
| ATOM | 3310 | CB | GLU A | 507 | −56.933 | 2.669 | −10.028 | 1.00 | 25.52 | C |
| ATOM | 3311 | CG | GLU A | 507 | −58.254 | 3.234 | −9.507 | 1.00 | 30.36 | C |
| ATOM | 3315 | C | GLU A | 507 | −55.343 | 2.363 | −11.940 | 1.00 | 25.11 | C |

TABLE A-continued

| | | | | | | | | | |
|---|---|---|---|---|---|---|---|---|---|
| ATOM | 3316 | O | GLU A | 507 | −54.972 | 1.185 | −11.936 | 1.00 | 24.87 | O |
| ATOM | 3317 | N | PRO A | 508 | −54.540 | 3.378 | −12.302 | 1.00 | 24.61 | N |
| ATOM | 3318 | CA | PRO A | 508 | −53.132 | 3.167 | −12.627 | 1.00 | 24.45 | C |
| ATOM | 3319 | CB | PRO A | 508 | −52.622 | 4.586 | −12.892 | 1.00 | 24.09 | C |
| ATOM | 3320 | CG | PRO A | 508 | −53.826 | 5.325 | −13.338 | 1.00 | 25.76 | C |
| ATOM | 3321 | CD | PRO A | 508 | −54.923 | 4.790 | −12.468 | 1.00 | 24.91 | C |
| ATOM | 3322 | C | PRO A | 508 | −52.350 | 2.523 | −11.481 | 1.00 | 23.81 | C |
| ATOM | 3323 | O | PRO A | 508 | −52.481 | 2.941 | −10.328 | 1.00 | 23.38 | O |
| ATOM | 3324 | N | GLU A | 509 | −51.551 | 1.512 | −11.814 | 1.00 | 23.55 | N |
| ATOM | 3325 | CA | GLU A | 509 | −50.724 | .802 | −10.838 | 1.00 | 23.13 | C |
| ATOM | 3326 | CB | GLU A | 509 | −50.516 | −.652 | −11.268 | 1.00 | 22.67 | C |
| ATOM | 3327 | CG | GLU A | 509 | −51.804 | −1.441 | −11.471 | 1.00 | 23.87 | C |
| ATOM | 3328 | CD | GLU A | 509 | −51.550 | −2.904 | −11.785 | 1.00 | 23.89 | C |
| ATOM | 3329 | OE1 | GLU A | 509 | −51.552 | −3.272 | −12.980 | 1.00 | 22.82 | O |
| ATOM | 3330 | OE2 | GLU A | 509 | −51.337 | −3.689 | −10.836 | 1.00 | 23.81 | O |
| ATOM | 3331 | C | GLU A | 509 | −49.371 | 1.485 | −10.645 | 1.00 | 23.00 | C |
| ATOM | 3332 | O | GLU A | 509 | −48.706 | 1.289 | −9.627 | 1.00 | 23.59 | O |
| ATOM | 3333 | N | HIS A | 510 | −48.970 | 2.276 | −11.636 | 1.00 | 22.85 | N |
| ATOM | 3334 | CA | HIS A | 510 | −47.707 | 3.004 | −11.607 | 1.00 | 22.94 | C |
| ATOM | 3335 | CB | HIS A | 510 | −46.789 | 2.488 | −12.722 | 1.00 | 22.73 | C |
| ATOM | 3336 | CG | HIS A | 510 | −45.329 | 2.544 | −12.389 | 1.00 | 22.62 | C |
| ATOM | 3337 | ND1 | HIS A | 510 | −44.692 | 3.706 | −12.011 | 1.00 | 21.60 | N |
| ATOM | 3338 | CE1 | HIS A | 510 | −43.415 | 3.454 | −11.789 | 1.00 | 23.38 | C |
| ATOM | 3339 | NE2 | HIS A | 510 | −43.197 | 2.173 | −12.020 | 1.00 | 23.36 | N |
| ATOM | 3340 | CD2 | HIS A | 510 | −44.377 | 1.582 | −12.401 | 1.00 | 23.54 | C |
| ATOM | 3341 | C | HIS A | 510 | −48.002 | 4.502 | −11.769 | 1.00 | 22.80 | C |
| ATOM | 3342 | O | HIS A | 510 | −49.096 | 4.960 | −11.430 | 1.00 | 23.29 | O |
| ATOM | 3343 | N | THR A | 511 | −47.040 | 5.265 | −12.281 | 1.00 | 22.58 | N |
| ATOM | 3344 | CA | THR A | 511 | −47.248 | 6.696 | −12.519 | 1.00 | 21.99 | C |
| ATOM | 3345 | CB | THR A | 511 | −45.985 | 7.542 | −12.218 | 1.00 | 21.98 | C |
| ATOM | 3346 | OG1 | THR A | 511 | −44.939 | 7.204 | −13.138 | 1.00 | 21.89 | O |
| ATOM | 3347 | CG2 | THR A | 511 | −45.507 gad67.pdb | 7.321 | −10.782 | 1.00 | 17.80 | C |
| ATOM | 3348 | C | THR A | 511 | −47.761 | 6.980 | −13.933 | 1.00 | 21.90 | C |
| ATOM | 3349 | O | THR A | 511 | −48.066 | 8.127 | −14.273 | 1.00 | 22.40 | O |
| ATOM | 3350 | N | ASN A | 512 | −47.864 | 5.927 | −14.743 | 1.00 | 21.41 | N |
| ATOM | 3351 | CA | ASN A | 512 | −48.428 | 6.024 | −16.085 | 1.00 | 21.12 | C |
| ATOM | 3352 | CB | ASN A | 512 | −48.225 | 4.727 | −16.881 | 1.00 | 20.31 | C |
| ATOM | 3353 | CD | ASN A | 512 | −46.807 | 4.180 | −16.787 | 1.00 | 21.44 | C |
| ATOM | 3354 | OD1 | ASN A | 512 | −46.281 | 3.961 | −15.695 | 1.00 | 20.64 | O |
| ATOM | 3355 | ND2 | ASN A | 512 | −46.195 | 3.921 | −17.942 | 1.00 | 20.11 | N |
| ATOM | 3356 | C | ASN A | 512 | −49.917 | 6.339 | −16.025 | 1.00 | 21.54 | C |
| ATOM | 3357 | O | ASN A | 512 | −50.682 | 5.634 | −15.364 | 1.00 | 21.23 | O |
| ATOM | 3358 | N | VAL A | 513 | −50.314 | 7.411 | −16.703 | 1.00 | 21.56 | N |
| ATOM | 3359 | CA | VAL A | 513 | −51.726 | 7.755 | −16.862 | 1.00 | 21.08 | C |
| ATOM | 3360 | CB | VAL A | 513 | −52.125 | 9.029 | −16.064 | 1.00 | 21.27 | C |
| ATOM | 3361 | CG1 | VAL A | 513 | −53.606 | 9.344 | −16.249 | 1.00 | 20.14 | C |
| ATOM | 3362 | CG2 | VAL A | 513 | −51.804 | 8.867 | −14.576 | 1.00 | 17.78 | C |
| ATOM | 3363 | C | VAL A | 513 | −52.004 | 7.915 | −18.354 | 1.00 | 20.94 | C |
| ATOM | 3364 | O | VAL A | 513 | −51.475 | 8.823 | −19.004 | 1.00 | 21.23 | O |
| ATOM | 3365 | N | CYS A | 514 | −52.821 | 7.010 | −18.887 | 1.00 | 20.29 | N |
| ATOM | 3366 | CA | CYS A | 514 | −53.074 | 6.933 | −20.322 | 1.00 | 20.21 | C |
| ATOM | 3367 | CB | CYS A | 514 | −52.892 | 5.499 | −20.813 | 1.00 | 19.51 | C |
| ATOM | 3368 | SG | CYS A | 514 | −51.230 | 4.890 | −20.531 | 1.00 | 20.55 | S |
| ATOM | 3369 | C | CYS A | 514 | −54.451 | 7.464 | −20.697 | 1.00 | 20.41 | C |
| ATOM | 3370 | O | CYS A | 514 | −55.474 | 6.930 | −20.262 | 1.00 | 21.69 | O |
| ATOM | 3371 | N | PHE A | 515 | −54.465 | 8.506 | −21.524 | 1.00 | 20.07 | N |
| ATOM | 3372 | CA | PHE A | 515 | −55.695 | 9.225 | −21.844 | 1.00 | 20.21 | C |
| ATOM | 3373 | CB | PHE A | 515 | −55.973 | 10.291 | −20.771 | 1.00 | 19.83 | C |
| ATOM | 3374 | CG | PHE A | 515 | −54.921 | 11.370 | −20.697 | 1.00 | 18.98 | C |
| ATOM | 3375 | CD1 | PHE A | 515 | −55.078 | 12.563 | −21.401 | 1.00 | 18.75 | C |
| ATOM | 3376 | CE1 | PHE A | 515 | −54.109 | 13.562 | −21.340 | 1.00 | 19.70 | C |
| ATOM | 3377 | CZ | PHE A | 515 | −52.964 | 13.370 | −20.562 | 1.00 | 20.01 | C |
| ATOM | 3378 | CE2 | PHE A | 515 | −52.797 | 12.183 | −19.857 | 1.00 | 20.24 | C |
| ATOM | 3379 | CD2 | PHE A | 515 | −53.773 | 11.192 | −19.927 | 1.00 | 18.56 | C |
| ATOM | 3380 | C | PHE A | 515 | −55.653 | 9.879 | −23.225 | 1.00 | 20.91 | C |
| ATOM | 3381 | O | PHE A | 515 | −54.579 | 10.160 | −23.758 | 1.00 | 21.06 | O |
| ATOM | 3382 | N | TRP A | 516 | −56.838 | 10.112 | −23.785 | 1.00 | 21.01 | N |
| ATOM | 3383 | CA | TRP A | 516 | −57.012 | 10.930 | −24.978 | 1.00 | 20.62 | C |
| ATOM | 3384 | CB | TRP A | 516 | −58.059 | 10.307 | −25.903 | 1.00 | 19.53 | C |
| ATOM | 3385 | CD | TRP A | 516 | −57.666 | 9.044 | −26.611 | 1.00 | 18.11 | C |
| ATOM | 3386 | CD1 | TRP A | 516 | −56.801 | 8.924 | −27.664 | 1.00 | 15.14 | C |
| ATOM | 3387 | NE1 | TRP A | 516 | −56.720 | 7.613 | −28.063 | 1.00 | 15.66 | N |
| ATOM | 3388 | CE2 | TRP A | 516 | −57.549 | 6.856 | −27.276 | 1.00 | 16.59 | C |
| ATOM | 3389 | CD2 | TRP A | 516 | −58.169 | 7.727 | −26.354 | 1.00 | 16.24 | C |
| ATOM | 3390 | CE3 | TRP A | 516 | −59.077 | 7.196 | −25.426 | 1.00 | 18.06 | C |
| ATOM | 3391 | CZ3 | TRP A | 516 | −59.334 | 5.829 | −25.448 | 1.00 | 15.61 | C |
| ATOM | 3392 | CH2 | TRP A | 516 | −58.698 | 4.986 | −26.375 | 1.00 | 16.84 | C |
| ATOM | 3393 | CZ2 | TRP A | 516 | −57.804 | 5.477 | −27.294 | 1.00 | 16.76 | C |
| ATOM | 3394 | C | TRP A | 516 | −57.535 | 12.308 | −24.574 | 1.00 | 21.72 | C |

TABLE A-continued

| | | | | | | | | | | |
|---|---|---|---|---|---|---|---|---|---|---|
| ATOM | 3395 | O | TRP A | 516 | −58.297 | 12.429 | −23.608 | 1.00 | 21.48 | O |
| ATOM | 3396 | N | TYR A | 517 | −57.133 | 13.344 | −25.306 | 1.00 | 22.14 | N |
| ATOM | 3397 | CA | TYR A | 517 | −57.889 | 14.588 | −25.288 | 1.00 | 22.56 | C |
| ATOM | 3398 | CB | TYR A | 517 | −57.003 | 15.830 | −25.436 | 1.00 | 22.34 | C |
| ATOM | 3399 | CG | TYR A | 517 | −57.812 | 17.094 | −25.656 | 1.00 | 23.50 | C |
| ATOM | 3400 | CD1 | TYR A | 517 | −58.118 | 17.536 | −26.948 | 1.00 | 23.19 | C |
| ATOM | 3401 | CE1 | TYR A | 517 | −58.880 | 18.684 | −27.157 | 1.00 | 21.56 | C |
| ATOM | 3402 | CZ | TYR A | 517 | −59.341 | 19.405 | −26.072 | 1.00 | 22.90 | C |
| ATOM | 3403 | OH | TYR A | 517 | −60.089 | 20.541 | −26.283 | 1.00 | 23.11 | O |
| ATOM | 3404 | CE2 | TYR A | 517 | −59.059 | 18.987 | −24.777 | 1.00 | 22.62 | C |
| ATOM | 3405 | CD2 | TYR A | 517 | −58.302 | 17.831 | −24.577 | 1.00 | 23.78 | C |
| ATOM | 3406 | C | TYR A | 517 | −58.899 | 14.505 | −26.427 | 1.00 | 23.32 | C |
| ATOM | 3407 | O | TYR A | 517 | −58.521 | 14.282 | −27.579 | 1.00 | 22.56 | O |
| ATOM | 3408 | N | ILE A | 518 | −60.180 | 14.663 | −26.101 | 1.00 | 25.69 | N |
| ATOM | 3409 | CA | ILE A | 518 | −61.249 | 14.548 | −27.096 | 1.00 | 27.39 | C |
| ATOM | 3410 | CB | ILE A | 518 | −62.424 | 13.649 | −26.601 | 1.00 | 27.34 | C |
| ATOM | 3411 | CG1 | ILE A | 518 | −61.912 | 12.332 | −25.994 | 1.00 | 26.12 | C |
| ATOM | 3412 | CD1 | ILE A | 518 | −61.452 | 11.275 | −27.003 | 1.00 | 25.33 | C |
| ATOM | 3413 | CG2 | ILE A | 518 | −63.440 | 13.402 | −27.730 | 1.00 | 28.29 | C |
| ATOM | 3414 | C | ILE A | 518 | −61.764 | 15.942 | −27.443 | 1.00 | 28.98 | C |
| ATOM | 3415 | O | ILE A | 518 | −62.390 | 16.592 | −26.608 | 1.00 | 29.69 | O |
| | | | gad67.pdb | | | | | | | |
| ATOM | 3416 | N | PRO A | 519 | −61.491 | 16.414 | −28.674 | 1.00 | 30.91 | N |
| ATOM | 3417 | CA | PRO A | 519 | −61.965 | 17.744 | −29.054 | 1.00 | 33.60 | C |
| ATOM | 3418 | CB | PRO A | 519 | −61.263 | 17.999 | −30.393 | 1.00 | 33.22 | C |
| ATOM | 3419 | CG | PRO A | 519 | −61.008 | 16.644 | −30.951 | 1.00 | 31.36 | C |
| ATOM | 3420 | CD | PRO A | 519 | −60.759 | 15.750 | −29.770 | 1.00 | 31.19 | C |
| ATOM | 3421 | C | PRO A | 519 | −63.483 | 17.749 | −29.229 | 1.00 | 36.10 | C |
| ATOM | 3422 | O | PRO A | 519 | −64.075 | 16.698 | −29.510 | 1.00 | 36.56 | O |
| ATOM | 3423 | N | GLN A | 520 | −64.094 | 18.921 | −29.059 | 1.00 | 38.88 | N |
| ATOM | 3424 | CA | GLN A | 520 | −65.551 | 19.091 | −29.156 | 1.00 | 41.40 | C |
| ATOM | 3425 | CB | GLN A | 520 | −65.900 | 20.579 | −29.310 | 1.00 | 41.76 | C |
| ATOM | 3426 | CG | GLN A | 520 | −67.397 | 20.898 | −29.266 | 1.00 | 44.32 | C |
| ATOM | 3427 | CD | GLN A | 520 | −68.012 | 20.686 | −27.892 | 1.00 | 46.97 | C |
| ATOM | 3428 | OE1 | GLN A | 520 | −68.804 | 19.763 | −27.691 | 1.00 | 47.34 | O |
| ATOM | 3429 | NE2 | GLN A | 520 | −67.643 | 21.538 | −26.937 | 1.00 | 46.92 | N |
| ATOM | 3430 | C | GLN A | 520 | −66.183 | 18.271 | −30.288 | 1.00 | 42.60 | C |
| ATOM | 3431 | O | GLN A | 520 | −67.197 | 17.599 | −30.086 | 1.00 | 43.18 | O |
| ATOM | 3432 | N | SER A | 521 | −65.555 | 18.317 | −31.460 | 1.00 | 43.98 | N |
| ATOM | 3433 | CA | SER A | 521 | −66.033 | 17.638 | −32.666 | 1.00 | 45.45 | C |
| ATOM | 3434 | CB | SER A | 521 | −65.024 | 17.830 | −33.804 | 1.00 | 45.85 | C |
| ATOM | 3435 | OG | SER A | 521 | −64.345 | 19.073 | −33.690 | 1.00 | 47.76 | O |
| ATOM | 3436 | C | SER A | 521 | −66.297 | 16.141 | −32.476 | 1.00 | 46.58 | C |
| ATOM | 3437 | O | SER A | 521 | −67.178 | 15.573 | −33.129 | 1.00 | 47.06 | O |
| ATOM | 3438 | N | LEU A | 522 | −65.532 | 15.506 | −31.589 | 1.00 | 46.96 | N |
| ATOM | 3439 | CA | LEU A | 522 | −65.623 | 14.058 | −31.401 | 1.00 | 47.30 | C |
| ATOM | 3440 | CB | LEU A | 522 | −64.228 | 13.415 | −31.465 | 1.00 | 47.47 | C |
| ATOM | 3441 | CG | LEU A | 522 | −63.527 | 13.351 | −32.830 | 1.00 | 46.89 | C |
| ATOM | 3442 | CD1 | LEU A | 522 | −62.073 | 12.940 | −32.669 | 1.00 | 47.31 | C |
| ATOM | 3443 | CD2 | LEU A | 522 | −64.241 | 12.406 | −33.793 | 1.00 | 46.11 | C |
| ATOM | 3444 | C | LEU A | 522 | −66.380 | 13.637 | −30.133 | 1.00 | 47.79 | C |
| ATOM | 3445 | O | LEU A | 522 | −66.252 | 12.503 | −29.670 | 1.00 | 46.94 | O |
| ATOM | 3446 | N | ARG A | 523 | −67.177 | 14.552 | −29.587 | 1.00 | 48.83 | N |
| ATOM | 3447 | CA | ARG A | 523 | −68.045 | 14.243 | −28.450 | 1.00 | 49.94 | C |
| ATOM | 3448 | CB | ARG A | 523 | −67.899 | 15.301 | −27.347 | 1.00 | 49.66 | C |
| ATOM | 3449 | CG | ARG A | 523 | −66.470 | 15.554 | −26.881 | 1.00 | 48.05 | C |
| ATOM | 3450 | CD | ARG A | 523 | −66.386 | 16.816 | −26.034 | 1.00 | 44.84 | C |
| ATOM | 3451 | NE | ARG A | 523 | −65.027 | 17.352 | −25.981 | 1.00 | 42.68 | N |
| ATOM | 3452 | CZ | ARG A | 523 | −64.682 | 18.487 | −25.378 | 1.00 | 41.44 | C |
| ATOM | 3453 | NH1 | ARG A | 523 | −63.414 | 18.886 | −25.393 | 1.00 | 40.19 | N |
| ATOM | 3454 | NH2 | ARG A | 523 | −65.594 | 19.226 | −24.759 | 1.00 | 40.47 | N |
| ATOM | 3455 | C | ARG A | 523 | −69.504 | 14.169 | −28.924 | 1.00 | 51.12 | C |
| ATOM | 3456 | O | ARG A | 523 | −70.103 | 15.199 | −29.241 | 1.00 | 50.97 | O |
| ATOM | 3457 | N | GLY A | 524 | −70.079 | 12.967 | −28.991 | 1.00 | 52.38 | N |
| ATOM | 3458 | CA | GLY A | 524 | −69.412 | 11.711 | −28.638 | 1.00 | 53.68 | C |
| ATOM | 3459 | C | GLY A | 524 | −70.389 | 10.542 | −28.669 | 1.00 | 54.59 | C |
| ATOM | 3460 | O | GLY A | 524 | −71.398 | 10.561 | −27.963 | 1.00 | 55.35 | O |
| ATOM | 3461 | N | VAL A | 525 | −70.115 | 9.523 | −29.483 | 1.00 | 54.80 | N |
| ATOM | 3462 | CA | VAL A | 525 | −68.936 | 9.470 | −30.343 | 1.00 | 55.30 | C |
| ATOM | 3463 | CB | VAL A | 525 | −67.882 | 8.474 | −29.803 | 1.00 | 55.46 | C |
| ATOM | 3466 | C | VAL A | 525 | −69.354 | 9.172 | −31.796 | 1.00 | 55.60 | C |
| ATOM | 3467 | O | VAL A | 525 | −69.392 | 10.098 | −32.615 | 1.00 | 55.62 | O |
| ATOM | 3468 | N | PRO A | 526 | −69.648 | 7.892 | −32.138 | 1.00 | 55.47 | N |
| ATOM | 3469 | CA | PRO A | 526 | −69.340 | 6.600 | −31.509 | 1.00 | 54.84 | C |
| ATOM | 3470 | CB | PRO A | 526 | −70.559 | 5.734 | −31.864 | 1.00 | 54.83 | C |
| ATOM | 3471 | CG | PRO A | 526 | −71.386 | 6.549 | −32.858 | 1.00 | 55.46 | C |
| ATOM | 3472 | CD | PRO A | 526 | −70.528 | 7.696 | −33.300 | 1.00 | 55.93 | C |
| ATOM | 3473 | C | PRO A | 526 | −68.059 | 5.970 | −32.077 | 1.00 | 54.58 | C |
| ATOM | 3474 | O | PRO A | 526 | −67.595 | 6.375 | −33.149 | 1.00 | 54.34 | O |
| ATOM | 3475 | N | ASP A | 527 | −67.503 | 4.992 | −31.361 | 1.00 | 53.97 | N |

TABLE A-continued

| | | | | | | | | | | |
|---|---|---|---|---|---|---|---|---|---|---|
| ATOM | 3476 | CA | ASP A | 527 | −66.225 | 4.374 | −31.739 | 1.00 | 53.78 | C |
| ATOM | 3477 | CB | ASP A | 527 | −65.664 | 3.514 | −30.593 | 1.00 | 53.95 | C |
| ATOM | 3478 | CG | ASP A | 527 | −64.241 | 3.022 | −30.858 | 1.00 | 55.30 | C |
| ATOM | 3479 | OD1 | ASP A | 527 | −63.486 | 3.687 | −31.603 | 1.00 | 57.21 | O |
| ATOM | 3480 | OD2 | ASP A | 527 | −63.872 | 1.963 | −30.307 | 1.00 | 55.80 | O |
| ATOM | 3481 | C | ASP A | 527 | −66.325 | 3.560 | −33.029 | 1.00 | 53.19 | C |
| ATOM | 3482 | O | ASP A | 527 | −67.138 | 2.638 | −33.142 | 1.00 | 53.62 | O |
| ATOM | 3483 | N | SER A | 528 | −65.480 | 3.917 | −33.993 | 1.00 | 52.09 | N |
| ATOM | 3484 | CA | SER A | 528 | −65.470 | 3.305 | −35.318 | 1.00 | 51.00 | C |
| ATOM | 3485 | CB | SER A | 528 | −66.536 | 3.960 | −36.208 | 1.00 | 50.77 | C |
| ATOM | | | | | gad67.pdb | | | | | |
| ATOM | | | | | | | | | | |
| ATOM | 3486 | OG | SER A | 528 | −66.319 | 5.355 | −36.334 | 1.00 | 49.62 | O |
| ATOM | 3487 | C | SER A | 528 | −64.084 | 3.468 | −35.945 | 1.00 | 50.56 | C |
| ATOM | 3488 | O | SER A | 528 | −63.280 | 4.264 | −35.453 | 1.00 | 50.42 | O |
| ATOM | 3489 | N | PRO A | 529 | −63.785 | 2.703 | −37.017 | 1.00 | 50.37 | N |
| ATOM | 3490 | CA | PRO A | 529 | −62.536 | 2.929 | −37.755 | 1.00 | 49.81 | C |
| ATOM | 3491 | CB | PRO A | 529 | −62.589 | 1.885 | −38.880 | 1.00 | 49.98 | C |
| ATOM | 3492 | CG | PRO A | 529 | −64.025 | 1.486 | −38.980 | 1.00 | 50.85 | C |
| ATOM | 3493 | CD | PRO A | 529 | −64.554 | 1.579 | −37.585 | 1.00 | 50.49 | C |
| ATOM | 3494 | C | PRO A | 529 | −62.435 | 4.343 | −38.337 | 1.00 | 48.79 | C |
| ATOM | 3495 | O | PRO A | 529 | −61.333 | 4.887 | −38.430 | 1.00 | 49.21 | O |
| ATOM | 3496 | N | GLN A | 530 | −63.575 | 4.926 | −38.707 | 1.00 | 47.63 | N |
| ATOM | 3497 | CA | GLN A | 530 | −63.629 | 6.285 | −39.250 | 1.00 | 46.50 | C |
| ATOM | 3498 | CB | GLN A | 530 | −65.015 | 6.581 | −39.835 | 1.00 | 46.58 | C |
| ATOM | 3503 | C | GLN A | 530 | −63.256 | 7.340 | −38.207 | 1.00 | 45.56 | C |
| ATOM | 3504 | O | GLN A | 530 | −62.476 | 8.252 | −38.497 | 1.00 | 45.41 | O |
| ATOM | 3505 | N | ARG A | 531 | −63.809 | 7.201 | −37.000 | 1.00 | 43.93 | N |
| ATOM | 3506 | CA | ARG A | 531 | −63.535 | 8.118 | −35.889 | 1.00 | 42.37 | C |
| ATOM | 3507 | CB | ARG A | 531 | −64.553 | 7.915 | −34.751 | 1.00 | 42.53 | C |
| ATOM | 3508 | CG | ARG A | 531 | −63.964 | 7.988 | −33.346 | 1.00 | 40.95 | C |
| ATOM | 3509 | CD | ARG A | 531 | −64.896 | 8.627 | −32.344 | 1.00 | 40.21 | C |
| ATOM | 3510 | NE | ARG A | 531 | −64.268 | 8.664 | −31.024 | 1.00 | 42.24 | N |
| ATOM | 3511 | CZ | ARG A | 531 | −64.561 | 9.539 | −30.068 | 1.00 | 40.84 | C |
| ATOM | 3512 | NH1 | ARG A | 531 | −65.482 | 10.467 | −30.274 | 1.00 | 41.32 | N |
| ATOM | 3513 | NH2 | ARG A | 531 | −63.927 | 9.487 | −28.903 | 1.00 | 40.74 | N |
| ATOM | 3514 | C | ARG A | 531 | −62.095 | 8.023 | −35.369 | 1.00 | 41.29 | C |
| ATOM | 3515 | O | ARG A | 531 | −61.477 | 9.044 | −35.054 | 1.00 | 40.81 | O |
| ATOM | 3516 | N | ARG A | 532 | −61.580 | 6.796 | −35.284 | 1.00 | 40.41 | N |
| ATOM | 3517 | CA | ARG A | 532 | −60.212 | 6.534 | −34.833 | 1.00 | 40.05 | C |
| ATOM | 3518 | CB | ARG A | 532 | −59.955 | 5.026 | −34.710 | 1.00 | 39.90 | C |
| ATOM | 3519 | CG | ARG A | 532 | −60.576 | 4.381 | −33.473 | 1.00 | 41.54 | C |
| ATOM | 3520 | CD | ARG A | 532 | −60.276 | 2.887 | −33.400 | 1.00 | 41.69 | C |
| ATOM | 3525 | C | ARG A | 532 | −59.171 | 7.175 | −35.751 | 1.00 | 39.02 | C |
| ATOM | 3526 | O | ARG A | 532 | −58.105 | 7.590 | −35.291 | 1.00 | 38.27 | O |
| ATOM | 3527 | N | GLU A | 533 | −59.493 | 7.261 | −37.043 | 1.00 | 38.05 | N |
| ATOM | 3528 | CA | GLU A | 533 | −58.631 | 7.925 | −38.021 | 1.00 | 36.94 | C |
| ATOM | 3529 | CB | GLU A | 533 | −59.136 | 7.677 | −39.445 | 1.00 | 36.93 | C |
| ATOM | 3534 | C | GLU A | 533 | −58.505 | 9.428 | −37.747 | 1.00 | 35.69 | C |
| ATOM | 3535 | O | GLU A | 533 | −57.459 | 10.025 | −38.011 | 1.00 | 35.99 | O |
| ATOM | 3536 | N | LYS A | 534 | −59.570 | 10.028 | −37.217 | 1.00 | 34.17 | N |
| ATOM | 3537 | CA | LYS A | 534 | −59.562 | 11.444 | −36.839 | 1.00 | 33.14 | C |
| ATOM | 3538 | CB | LYS A | 534 | −60.987 | 12.008 | −36.771 | 1.00 | 33.69 | C |
| ATOM | 3539 | CG | LYS A | 534 | −61.528 | 12.539 | −38.093 | 1.00 | 37.97 | C |
| ATOM | 3540 | CD | LYS A | 534 | −62.228 | 11.459 | −38.915 | 1.00 | 40.74 | C |
| ATOM | 3541 | CE | LYS A | 534 | −63.716 | 11.372 | −38.587 | 1.00 | 42.66 | C |
| ATOM | 3542 | NZ | LYS A | 534 | −64.460 | 12.589 | −39.029 | 1.00 | 43.84 | N |
| ATOM | 3543 | C | LYS A | 534 | −58.857 | 11.677 | −35.507 | 1.00 | 31.67 | C |
| ATOM | 3544 | O | LYS A | 534 | −58.043 | 12.598 | −35.382 | 1.00 | 32.01 | O |
| ATOM | 3545 | N | LEU A | 535 | −59.183 | 10.843 | −34.518 | 1.00 | 29.70 | N |
| ATOM | 3546 | CA | LEU A | 535 | −58.616 | 10.954 | −33.173 | 1.00 | 27.23 | C |
| ATOM | 3547 | CB | LEU A | 535 | −59.298 | 9.966 | −32.219 | 1.00 | 26.71 | C |
| ATOM | 3548 | CG | LEU A | 535 | −58.937 | 9.992 | −30.727 | 1.00 | 24.93 | C |
| ATOM | 3549 | CD1 | LEU A | 535 | −59.081 | 11.387 | −30.122 | 1.00 | 24.38 | C |
| ATOM | 3550 | CD2 | LEU A | 535 | −59.787 | 8.985 | −29.964 | 1.00 | 26.29 | C |
| ATOM | 3551 | C | LEU A | 535 | −57.108 | 10.735 | −33.181 | 1.00 | 26.29 | C |
| ATOM | 3552 | O | LEU A | 535 | −56.374 | 11.377 | −32.425 | 1.00 | 25.89 | O |
| ATOM | 3553 | N | HIS A | 536 | −56.664 | 9.834 | −34.051 | 1.00 | 26.15 | N |
| ATOM | 3554 | CA | HIS A | 536 | −55.248 | 9.528 | −34.238 | 1.00 | 26.98 | C |
| ATOM | 3555 | CB | HIS A | 536 | −55.081 | 8.559 | −35.410 | 1.00 | 26.88 | C |
| ATOM | 3556 | CG | HIS A | 536 | −53.784 | 7.810 | −35.408 | 1.00 | 28.95 | C |
| ATOM | 3557 | ND1 | HIS A | 536 | −53.436 | 6.924 | −34.411 | 1.00 | 29.41 | N |
| ATOM | 3558 | CE1 | HIS A | 536 | −52.255 | 6.399 | −34.685 | 1.00 | 29.50 | C |
| ATOM | 3559 | NE2 | HIS A | 536 | −51.827 | 6.909 | −35.825 | 1.00 | 29.78 | N |
| ATOM | 3560 | CD2 | HIS A | 536 | −52.767 | 7.789 | −36.302 | 1.00 | 27.62 | C |
| ATOM | 3561 | C | HIS A | 536 | −54.401 | 10.777 | −34.473 | 1.00 | 26.62 | C |
| ATOM | 3562 | O | HIS A | 536 | −53.254 | 10.837 | −34.040 | 1.00 | 27.04 | O |
| ATOM | 3563 | N | LYS A | 537 | −54.979 | 11.774 | −35.137 | 1.00 | 26.88 | N |
| ATOM | 3564 | CA | LYS A | 537 | −54.248 | 12.987 | −35.518 | 1.00 | 27.87 | C |

TABLE A-continued

| | | | | | | | | | | |
|---|---|---|---|---|---|---|---|---|---|---|
| ATOM | 3565 | CB | LYS A | 537 | −54.857 | 13.599 | −36.786 | 1.00 | 28.12 | C |
| | | | | | gad67.pdb | | | | | |
| ATOM | 3566 | CG | LYS A | 537 | −54.963 | 12.626 | −37.968 | 1.00 | 30.91 | C |
| ATOM | 3567 | CD | LYS A | 537 | −55.672 | 13.251 | −39.178 | 1.00 | 31.72 | C |
| ATOM | 3568 | CE | LYS A | 537 | −54.816 | 14.313 | −39.866 | 1.00 | 38.50 | C |
| ATOM | 3569 | NZ | LYS A | 537 | −53.554 | 13.747 | −40.438 | 1.00 | 43.22 | N |
| ATOM | 3570 | C | LYS A | 537 | −54.170 | 14.039 | −34.408 | 1.00 | 26.12 | C |
| ATOM | 3571 | O | LYS A | 537 | −53.366 | 14.970 | −34.491 | 1.00 | 26.59 | O |
| ATOM | 3572 | N | VAL A | 538 | −54.996 | 13.885 | −33.374 | 1.00 | 24.72 | N |
| ATOM | 3573 | CA | VAL A | 538 | −55.101 | 14.876 | −32.291 | 1.00 | 22.58 | C |
| ATOM | 3574 | CB | VAL A | 538 | −56.336 | 14.607 | −31.374 | 1.00 | 22.83 | C |
| ATOM | 3575 | CG1 | VAL A | 538 | −56.410 | 15.622 | −30.227 | 1.00 | 18.69 | C |
| ATOM | 3576 | CG2 | VAL A | 538 | −57.634 | 14.625 | −32.191 | 1.00 | 20.86 | C |
| ATOM | 3577 | C | VAL A | 538 | −53.821 | 14.993 | −31.447 | 1.00 | 22.47 | C |
| ATOM | 3578 | O | VAL A | 538 | −53.234 | 16.075 | −31.356 | 1.00 | 22.98 | O |
| ATOM | 3579 | N | ALA A | 539 | −53.404 | 13.885 | −30.833 | 1.00 | 21.23 | N |
| ATOM | 3580 | CA | ALA A | 539 | −52.222 | 13.864 | −29.960 | 1.00 | 20.50 | C |
| ATOM | 3581 | CB | ALA A | 539 | −52.026 | 12.474 | −29.332 | 1.00 | 19.52 | C |
| ATOM | 3582 | C | ALA A | 539 | −50.923 | 14.357 | −30.626 | 1.00 | 20.07 | C |
| ATOM | 3583 | O | ALA A | 539 | −50.218 | 15.179 | −30.032 | 1.00 | 19.89 | O |
| ATOM | 3584 | N | PRO A | 540 | −50.592 | 13.852 | −31.840 | 1.00 | 20.04 | N |
| ATOM | 3585 | CA | PRO A | 540 | −49.407 | 14.371 | −32.544 | 1.00 | 21.35 | C |
| ATOM | 3586 | CB | PRO A | 540 | −49.392 | 13.588 | −33.871 | 1.00 | 21.07 | C |
| ATOM | 3587 | CG | PRO A | 540 | −50.711 | 12.946 | −33.977 | 1.00 | 20.41 | C |
| ATOM | 3588 | CD | PRO A | 540 | −51.230 | 12.759 | −32.593 | 1.00 | 19.77 | C |
| ATOM | 3589 | C | PRO A | 540 | −49.437 | 15.879 | −32.807 | 1.00 | 21.94 | C |
| ATOM | 3590 | O | PRO A | 540 | −48.398 | 16.528 | −32.737 | 1.00 | 22.92 | O |
| ATOM | 3591 | N | LYS A | 541 | −50.616 | 16.423 | −33.095 | 1.00 | 22.95 | N |
| ATOM | 3592 | CA | LYS A | 541 | −50.775 | 17.858 | −33.309 | 1.00 | 23.24 | C |
| ATOM | 3593 | CB | LYS A | 541 | −52.167 | 18.166 | −33.879 | 1.00 | 23.95 | C |
| ATOM | 3594 | CG | LYS A | 541 | −52.545 | 19.649 | −33.931 | 1.00 | 27.72 | C |
| ATOM | 3595 | CD | LYS A | 541 | −52.297 | 20.275 | −35.302 | 1.00 | 35.92 | C |
| ATOM | 3596 | CE | LYS A | 541 | −50.986 | 21.057 | −35.360 | 1.00 | 38.62 | C |
| ATOM | 3597 | NZ | LYS A | 541 | −50.956 | 21.983 | −36.540 | 1.00 | 39.33 | N |
| ATOM | 3598 | C | LYS A | 541 | −50.509 | 18.651 | −32.022 | 1.00 | 23.27 | C |
| ATOM | 3599 | O | LYS A | 541 | −49.745 | 19.621 | −32.038 | 1.00 | 23.35 | O |
| ATOM | 3600 | N | ILE A | 542 | −51.124 | 18.228 | −30.916 | 1.00 | 22.33 | N |
| ATOM | 3601 | CA | ILE A | 542 | −50.904 | 18.860 | −29.608 | 1.00 | 21.24 | C |
| ATOM | 3602 | CB | ILE A | 542 | −51.829 | 18.259 | −28.500 | 1.00 | 21.39 | C |
| ATOM | 3603 | CG1 | ILE A | 542 | −53.309 | 18.511 | −28.836 | 1.00 | 21.43 | C |
| ATOM | 3604 | CD1 | ILE A | 542 | −54.306 | 17.826 | −27.892 | 1.00 | 20.77 | C |
| ATOM | 3605 | CG2 | ILE A | 542 | −51.485 | 18.838 | −27.120 | 1.00 | 19.27 | C |
| ATOM | 3606 | C | ILE A | 542 | −49.435 | 18.779 | −29.181 | 1.00 | 21.44 | C |
| ATOM | 3607 | O | ILE A | 542 | −48.875 | 19.760 | −28.679 | 1.00 | 21.54 | O |
| ATOM | 3608 | N | LYS A | 543 | −48.822 | 17.614 | −29.387 | 1.00 | 21.93 | N |
| ATOM | 3609 | CA | LYS A | 543 | −47.402 | 17.410 | −29.080 | 1.00 | 22.76 | C |
| ATOM | 3610 | CB | LYS A | 543 | −46.998 | 15.946 | −29.319 | 1.00 | 22.75 | C |
| ATOM | 3611 | CG | LYS A | 543 | −45.513 | 15.619 | −29.127 | 1.00 | 22.32 | C |
| ATOM | 3612 | CD | LYS A | 543 | −45.008 | 15.966 | −27.728 | 1.00 | 25.79 | C |
| ATOM | 3613 | CE | LYS A | 543 | −43.607 | 15.419 | −27.486 | 1.00 | 23.39 | C |
| ATOM | 3614 | NZ | LYS A | 543 | −43.626 | 13.945 | −27.277 | 1.00 | 24.71 | N |
| ATOM | 3615 | C | LYS A | 543 | −46.517 | 18.364 | −29.884 | 1.00 | 23.29 | C |
| ATOM | 3616 | O | LYS A | 543 | −45.568 | 18.934 | −29.344 | 1.00 | 23.93 | O |
| ATOM | 3617 | N | ALA A | 544 | −46.846 | 18.545 | −31.163 | 1.00 | 23.75 | N |
| ATOM | 3618 | CA | ALA A | 544 | −46.124 | 19.480 | −32.032 | 1.00 | 24.43 | C |
| ATOM | 3619 | CB | ALA A | 544 | −46.667 | 19.419 | −33.451 | 1.00 | 23.96 | C |
| ATOM | 3620 | C | ALA A | 544 | −46.193 | 20.911 | −31.500 | 1.00 | 25.07 | C |
| ATOM | 3621 | O | ALA A | 544 | −45.201 | 21.642 | −31.533 | 1.00 | 25.10 | O |
| ATOM | 3622 | N | LEU A | 545 | −47.368 | 21.293 | −31.002 | 1.00 | 25.39 | N |
| ATOM | 3623 | CA | LEU A | 545 | −47.578 | 22.618 | −30.429 | 1.00 | 26.04 | C |
| ATOM | 3624 | CB | LEU A | 545 | −49.075 | 22.917 | −30.286 | 1.00 | 26.08 | C |
| ATOM | 3625 | CG | LEU A | 545 | −49.924 | 22.902 | −31.567 | 1.00 | 26.30 | C |
| ATOM | 3626 | CD1 | LEU A | 545 | −51.414 | 22.933 | −31.238 | 1.00 | 25.70 | C |
| ATOM | 3627 | CD2 | LEU A | 545 | −49.556 | 24.047 | −32.503 | 1.00 | 26.09 | C |
| ATOM | 3628 | C | LEU A | 545 | −46.854 | 22.792 | −29.091 | 1.00 | 26.51 | C |
| ATOM | 3629 | O | LEU A | 545 | −46.346 | 23.875 | −28.801 | 1.00 | 27.16 | O |
| ATOM | 3630 | N | MET A | 546 | −46.808 | 21.725 | −28.290 | 1.00 | 27.23 | N |
| ATOM | 3631 | CA | MET A | 546 | −46.045 | 21.704 | −27.034 | 1.00 | 27.96 | C |
| ATOM | 3632 | CB | MET A | 546 | −46.139 | 20.336 | −26.366 | 1.00 | 28.18 | C |
| ATOM | 3633 | CG | MET A | 546 | −47.345 | 20.135 | −25.499 | 1.00 | 29.91 | C |
| | | | | | gad67.pdb | | | | | |
| ATOM | 3634 | SD | MET A | 546 | −47.413 | 18.444 | −24.894 | 1.00 | 29.94 | S |
| ATOM | 3635 | CE | MET A | 546 | −48.949 | 18.526 | −23.985 | 1.00 | 30.91 | C |
| ATOM | 3636 | C | MET A | 546 | −44.578 | 22.000 | −27.271 | 1.00 | 27.12 | C |
| ATOM | 3637 | O | MET A | 546 | −43.987 | 22.842 | −26.601 | 1.00 | 27.26 | O |
| ATOM | 3638 | N | MET A | 547 | −43.999 | 21.283 | −28.228 | 1.00 | 26.74 | N |
| ATOM | 3639 | CA | MET A | 547 | −42.584 | 21.390 | −28.545 | 1.00 | 26.35 | C |
| ATOM | 3640 | CB | MET A | 547 | −42.160 | 20.240 | −29.465 | 1.00 | 25.93 | C |
| ATOM | 3641 | CG | MET A | 547 | −42.116 | 18.885 | −28.753 | 1.00 | 24.42 | C |
| ATOM | 3642 | SD | MET A | 547 | −41.697 | 17.461 | −29.787 | 1.00 | 28.53 | S |

TABLE A-continued

| | | | | | | | | | | |
|---|---|---|---|---|---|---|---|---|---|---|
| ATOM | 3643 | CE | MET A | 547 | −39.966 | 17.776 | −30.129 | 1.00 | 19.63 | C |
| ATOM | 3644 | C | MET A | 547 | −42.241 | 22.760 | −29.140 | 1.00 | 26.16 | C |
| ATOM | 3645 | O | MET A | 547 | −41.159 | 23.292 | −28.893 | 1.00 | 25.90 | O |
| ATOM | 3646 | N | GLU A | 548 | −43.176 | 23.331 | −29.898 | 1.00 | 25.99 | N |
| ATOM | 3647 | CA | GLU A | 548 | −43.017 | 24.672 | −30.455 | 1.00 | 25.72 | C |
| ATOM | 3648 | CB | GLU A | 548 | −44.124 | 24.975 | −31.471 | 1.00 | 26.30 | C |
| ATOM | 3649 | CG | GLU A | 548 | −43.829 | 24.477 | −32.879 | 1.00 | 28.78 | C |
| ATOM | 3653 | C | GLU A | 548 | −42.984 | 25.746 | −29.365 | 1.00 | 25.25 | C |
| ATOM | 3654 | O | GLU A | 548 | −42.145 | 26.648 | −29.398 | 1.00 | 24.48 | O |
| ATOM | 3655 | N | SER A | 549 | −43.896 | 25.646 | −28.401 | 1.00 | 25.05 | N |
| ATOM | 3656 | CA | SER A | 549 | −43.939 | 26.597 | −27.292 | 1.00 | 25.15 | C |
| ATOM | 3657 | CB | SER A | 549 | −45.328 | 26.614 | −26.646 | 1.00 | 25.69 | C |
| ATOM | 3658 | OG | SER A | 549 | −45.676 | 25.333 | −26.148 | 1.00 | 29.25 | O |
| ATOM | 3659 | C | SER A | 549 | −42.863 | 26.303 | −26.243 | 1.00 | 24.59 | C |
| ATOM | 3660 | O | SER A | 549 | −42.409 | 27.211 | −25.549 | 1.00 | 25.13 | O |
| ATOM | 3661 | N | GLY A | 550 | −42.463 | 25.034 | −26.137 | 1.00 | 23.71 | N |
| ATOM | 3662 | CA | GLY A | 550 | −41.432 | 24.605 | −25.189 | 1.00 | 22.70 | C |
| ATOM | 3663 | C | GLY A | 550 | −41.860 | 24.615 | −23.729 | 1.00 | 22.85 | C |
| ATOM | 3664 | O | GLY A | 550 | −41.017 | 24.579 | −22.833 | 1.00 | 22.36 | O |
| ATOM | 3665 | N | THR A | 551 | −43.170 | 24.657 | −23.488 | 1.00 | 22.83 | N |
| ATOM | 3666 | CA | THR A | 551 | −43.715 | 24.764 | −22.131 | 1.00 | 23.69 | C |
| ATOM | 3667 | CB | THR A | 551 | −45.179 | 25.246 | −22.147 | 1.00 | 24.02 | C |
| ATOM | 3668 | OG1 | THR A | 551 | −45.930 | 24.447 | −23.070 | 1.00 | 27.70 | O |
| ATOM | 3669 | CG2 | THR A | 551 | −45.263 | 26.714 | −22.558 | 1.00 | 24.21 | C |
| ATOM | 3670 | C | THR A | 551 | −43.668 | 23.433 | −21.382 | 1.00 | 23.34 | C |
| ATOM | 3671 | O | THR A | 551 | −43.453 | 23.399 | −20.167 | 1.00 | 23.18 | O |
| ATOM | 3672 | N | THR A | 552 | −43.896 | 22.347 | −22.118 | 1.00 | 22.94 | N |
| ATOM | 3673 | CA | THR A | 552 | −43.915 | 21.002 | −21.558 | 1.00 | 22.88 | C |
| ATOM | 3674 | CB | THR A | 552 | −45.255 | 20.711 | −20.817 | 1.00 | 22.86 | C |
| ATOM | 3675 | OG1 | THR A | 552 | −45.198 | 19.414 | −20.207 | 1.00 | 22.84 | O |
| ATOM | 3676 | CG2 | THR A | 552 | −46.447 | 20.782 | −21.774 | 1.00 | 22.48 | C |
| ATOM | 3677 | C | THR A | 552 | −43.661 | 19.959 | −22.649 | 1.00 | 22.30 | C |
| ATOM | 3678 | O | THR A | 552 | −43.679 | 20.282 | −23.839 | 1.00 | 22.65 | O |
| ATOM | 3679 | N | MET A | 553 | −43.399 | 18.722 | −22.233 | 1.00 | 21.78 | N |
| ATOM | 3680 | CA | MET A | 553 | −43.308 | 17.586 | −23.154 | 1.00 | 22.54 | C |
| ATOM | 3681 | CB | MET A | 553 | −41.855 | 17.267 | −23.506 | 1.00 | 21.66 | C |
| ATOM | 3682 | CG | MET A | 553 | −41.290 | 18.074 | −24.651 | 1.00 | 22.70 | C |
| ATOM | 3683 | SD | MET A | 553 | −39.562 | 17.670 | −24.938 | 1.00 | 24.91 | S |
| ATOM | 3684 | CE | MET A | 553 | −39.698 | 16.273 | −26.043 | 1.00 | 20.11 | C |
| ATOM | 3685 | C | MET A | 553 | −43.941 | 16.359 | −22.533 | 1.00 | 21.91 | C |
| ATOM | 3686 | O | MET A | 553 | −43.649 | 16.025 | −21.389 | 1.00 | 22.05 | O |
| ATOM | 3687 | N | VAL A | 554 | −44.813 | 15.700 | −23.291 | 1.00 | 21.91 | N |
| ATOM | 3688 | CA | VAL A | 554 | −45.394 | 14.422 | −22.885 | 1.00 | 22.18 | C |
| ATOM | 3689 | CB | VAL A | 554 | −46.764 | 14.598 | −22.129 | 1.00 | 22.25 | C |
| ATOM | 3690 | CG1 | VAL A | 554 | −47.802 | 15.298 | −22.998 | 1.00 | 23.52 | C |
| ATOM | 3691 | CG2 | VAL A | 554 | −47.303 | 13.259 | −21.613 | 1.00 | 20.66 | C |
| ATOM | 3692 | C | VAL A | 554 | −45.494 | 13.502 | −24.107 | 1.00 | 22.38 | C |
| ATOM | 3693 | O | VAL A | 554 | −45.701 | 13.968 | −25.228 | 1.00 | 22.55 | O |
| ATOM | 3694 | N | GLY A | 555 | −45.308 | 12.205 | −23.888 | 1.00 | 22.73 | N |
| ATOM | 3695 | CA | GLY A | 555 | −45.347 | 11.233 | −24.968 | 1.00 | 22.88 | C |
| ATOM | 3696 | C | GLY A | 555 | −46.751 | 10.851 | −25.387 | 1.00 | 22.97 | C |
| ATOM | 3697 | O | GLY A | 555 | −47.686 | 10.868 | −24.575 | 1.00 | 23.21 | O |
| ATOM | 3698 | N | TYR A | 556 | −46.892 | 10.517 | −26.667 | 1.00 | 22.32 | N |
| ATOM | 3699 | CA | TYR A | 556 | −48.114 | 9.925 | −27.199 | 1.00 | 22.91 | C |
| ATOM | 3700 | CB | TYR A | 556 | −48.864 | 10.911 | −28.106 | 1.00 | 21.76 | C |
| ATOM | 3701 | CG | TYR A | 556 | −48.189 | 11.165 | −29.432 | 1.00 | 21.36 | C |
| ATOM | 3702 | CD1 | TYR A | 556 | −47.311 | 12.237 | −29.598 | 1.00 | 20.49 | C |
| ATOM | 3703 | CE1 | TYR A | 556 | −46.677 | 12.463 | −30.819 | 1.00 | 20.56 | C |
| ATOM | 3704 | CZ | TYR A | 556 | −46.925 | 11.610 | −31.886 | 1.00 | 21.16 | C |
| | | | | | gad67.pdb | | | | | |
| ATOM | 3705 | OH | TYR A | 556 | −46.308 | 11.818 | −33.101 | 1.00 | 23.17 | O |
| ATOM | 3706 | CE2 | TYR A | 556 | −47.790 | 10.539 | −31.741 | 1.00 | 21.62 | C |
| ATOM | 3707 | CD2 | TYR A | 556 | −48.418 | 10.324 | −30.523 | 1.00 | 21.61 | C |
| ATOM | 3708 | C | TYR A | 556 | −47.745 | 8.662 | −27.972 | 1.00 | 23.89 | C |
| ATOM | 3709 | O | TYR A | 556 | −46.617 | 8.538 | −28.460 | 1.00 | 24.24 | O |
| ATOM | 3710 | N | GLN A | 557 | −48.694 | 7.735 | −28.086 | 1.00 | 23.88 | N |
| ATOM | 3711 | CA | GLN A | 557 | −48.478 | 6.482 | −28.815 | 1.00 | 24.57 | C |
| ATOM | 3712 | CB | GLN A | 557 | −47.415 | 5.596 | −28.127 | 1.00 | 24.23 | C |
| ATOM | 3713 | CG | GLN A | 557 | −47.814 | 4.944 | −26.806 | 1.00 | 25.18 | C |
| ATOM | 3714 | CD | GLN A | 557 | −47.980 | 5.946 | −25.678 | 1.00 | 28.16 | C |
| ATOM | 3715 | OE1 | GLN A | 557 | −49.098 | 6.221 | −25.245 | 1.00 | 31.08 | O |
| ATOM | 3716 | NE2 | GLN A | 557 | −46.872 | 6.513 | −25.214 | 1.00 | 27.85 | N |
| ATOM | 3717 | C | GLN A | 557 | −49.776 | 5.698 | −29.028 | 1.00 | 25.21 | C |
| ATOM | 3718 | O | GLN A | 557 | −50.720 | 5.834 | −28.244 | 1.00 | 24.72 | O |
| ATOM | 3719 | N | PRO A | 558 | −49.825 | 4.882 | −30.100 | 1.00 | 26.08 | N |
| ATOM | 3720 | CA | PRO A | 558 | −50.920 | 3.939 | −30.273 | 1.00 | 27.38 | C |
| ATOM | 3721 | CB | PRO A | 558 | −50.956 | 3.740 | −31.787 | 1.00 | 27.47 | C |
| ATOM | 3722 | CG | PRO A | 558 | −49.525 | 3.908 | −32.219 | 1.00 | 25.68 | C |
| ATOM | 3723 | CD | PRO A | 558 | −48.857 | 4.810 | −31.216 | 1.00 | 25.96 | C |
| ATOM | 3724 | C | PRO A | 558 | −50.622 | 2.610 | −29.569 | 1.00 | 29.39 | C |

TABLE A-continued

| | | | | | | | | | | |
|---|---|---|---|---|---|---|---|---|---|---|
| ATOM | 3725 | O | PRO A | 558 | −49.504 | 2.401 | −29.081 | 1.00 | 29.62 | O |
| ATOM | 3726 | N | GLN A | 559 | −51.621 | 1.732 | −29.513 | 1.00 | 30.69 | N |
| ATOM | 3727 | CA | GLN A | 559 | −51.453 | .380 | −28.990 | 1.00 | 32.39 | C |
| ATOM | 3728 | CB | GLN A | 559 | −51.484 | .374 | −27.459 | 1.00 | 32.13 | C |
| ATOM | 3729 | CG | GLN A | 559 | −50.884 | −.870 | −26.834 | 1.00 | 33.20 | C |
| ATOM | 3730 | CD | GLN A | 559 | −51.016 | −.893 | −25.322 | 1.00 | 34.45 | C |
| ATOM | 3731 | OE1 | GLN A | 559 | −50.021 | −.789 | −24.600 | 1.00 | 38.12 | O |
| ATOM | 3732 | NE2 | GLN A | 559 | −52.246 | −1.030 | −24.834 | 1.00 | 36.01 | N |
| ATOM | 3733 | C | GLN A | 559 | −52.562 | −.503 | −29.540 | 1.00 | 33.22 | C |
| ATOM | 3734 | O | GLN A | 559 | −53.744 | −.187 | −29.392 | 1.00 | 32.89 | O |
| ATOM | 3735 | N | GLY A | 560 | −52.178 | −1.606 | −30.177 | 1.00 | 34.59 | N |
| ATOM | 3736 | CA | GLY A | 560 | −53.139 | −2.510 | −30.804 | 1.00 | 35.98 | C |
| ATOM | 3737 | C | GLY A | 560 | −53.973 | −1.784 | −31.841 | 1.00 | 36.86 | C |
| ATOM | 3738 | O | GLY A | 560 | −53.453 | −1.350 | −32.869 | 1.00 | 37.38 | O |
| ATOM | 3739 | N | ASP A | 561 | −55.264 | −1.635 | −31.556 | 1.00 | 37.63 | N |
| ATOM | 3740 | CA | ASP A | 561 | −56.184 | −.934 | −32.452 | 1.00 | 38.26 | C |
| ATOM | 3741 | CB | ASP A | 561 | −57.459 | −1.762 | −32.669 | 1.00 | 39.17 | C |
| ATOM | 3742 | CG | ASP A | 561 | −58.321 | −1.874 | −31.410 | 1.00 | 43.97 | C |
| ATOM | 3743 | OD1 | ASP A | 561 | −57.774 | −1.794 | −30.281 | 1.00 | 45.52 | O |
| ATOM | 3744 | OD2 | ASP A | 561 | −59.556 | −2.053 | −31.555 | 1.00 | 47.74 | O |
| ATOM | 3745 | C | ASP A | 561 | −56.531 | .479 | −31.963 | 1.00 | 37.61 | C |
| ATOM | 3746 | O | ASP A | 561 | −57.259 | 1.212 | −32.640 | 1.00 | 38.06 | O |
| ATOM | 3747 | N | LYS A | 562 | −56.013 | .851 | −30.791 | 1.00 | 36.25 | N |
| ATOM | 3748 | CA | LYS A | 562 | −56.257 | 2.176 | −30.212 | 1.00 | 35.05 | C |
| ATOM | 3749 | CB | LYS A | 562 | −55.805 | 2.236 | −28.747 | 1.00 | 35.50 | C |
| ATOM | 3750 | CG | LYS A | 562 | −56.267 | 1.091 | −27.857 | 1.00 | 37.25 | C |
| ATOM | 3751 | CD | LYS A | 562 | −57.411 | 1.504 | −26.953 | 1.00 | 40.26 | C |
| ATOM | 3752 | CE | LYS A | 562 | −57.520 | .573 | −25.750 | 1.00 | 40.80 | C |
| ATOM | 3753 | NZ | LYS A | 562 | −57.970 | −.800 | −26.119 | 1.00 | 41.45 | N |
| ATOM | 3754 | C | LYS A | 562 | −55.510 | 3.248 | −31.000 | 1.00 | 33.27 | C |
| ATOM | 3755 | O | LYS A | 562 | −54.368 | 3.037 | −31.413 | 1.00 | 33.85 | O |
| ATOM | 3756 | N | ALA A | 563 | −56.163 | 4.389 | −31.205 | 1.00 | 30.45 | N |
| ATOM | 3757 | CA | ALA A | 563 | −55.530 | 5.555 | −31.816 | 1.00 | 28.84 | C |
| ATOM | 3758 | CB | ALA A | 563 | −56.593 | 6.546 | −32.269 | 1.00 | 28.74 | C |
| ATOM | 3759 | C | ALA A | 563 | −54.555 | 6.224 | −30.836 | 1.00 | 27.41 | C |
| ATOM | 3760 | O | ALA A | 563 | −54.672 | 6.036 | −29.621 | 1.00 | 27.48 | O |
| ATOM | 3761 | N | ASN A | 564 | −53.604 | 6.999 | −31.364 | 1.00 | 25.43 | N |
| ATOM | 3762 | CA | ASN A | 564 | −52.626 | 7.718 | −30.537 | 1.00 | 23.70 | C |
| ATOM | 3763 | CB | ASN A | 564 | −51.992 | 8.877 | −31.309 | 1.00 | 22.99 | C |
| ATOM | 3764 | CG | ASN A | 564 | −51.086 | 8.421 | −32.435 | 1.00 | 23.32 | C |
| ATOM | 3765 | OD1 | ASN A | 564 | −51.068 | 9.033 | −33.497 | 1.00 | 24.56 | O |
| ATOM | 3766 | ND2 | ASN A | 564 | −50.325 | 7.360 | −32.209 | 1.00 | 19.82 | N |
| ATOM | 3767 | C | ASN A | 564 | −53.256 | 8.281 | −29.272 | 1.00 | 22.78 | C |
| ATOM | 3768 | O | ASN A | 564 | −54.249 | 9.007 | −29.341 | 1.00 | 22.46 | O |
| ATOM | 3769 | N | PHE A | 565 | −52.689 | 7.936 | −28.122 | 1.00 | 21.52 | N |
| ATOM | 3770 | CA | PHE A | 565 | −53.124 | 8.520 | −26.855 | 1.00 | 20.91 | C |
| ATOM | 3771 | CB | PHE A | 565 | −53.942 | 7.520 | −26.019 | 1.00 | 19.66 | C |
| ATOM | 3772 | CG | PHE A | 565 | −53.283 gad67.pdb | 6.177 | −25.832 | 1.00 | 17.42 | C |
| ATOM | 3773 | CD1 | PHE A | 565 | −53.544 | 5.128 | −26.715 | 1.00 | 16.38 | C |
| ATOM | 3774 | CE1 | PHE A | 565 | −52.946 | 3.882 | −26.545 | 1.00 | 13.96 | C |
| ATOM | 3775 | CZ | PHE A | 565 | −52.080 | 3.669 | −25.470 | 1.00 | 16.03 | C |
| ATOM | 3776 | CE2 | PHE A | 565 | −51.822 | 4.707 | −24.573 | 1.00 | 13.75 | C |
| ATOM | 3777 | CD2 | PHE A | 565 | −52.426 | 5.949 | −24.757 | 1.00 | 16.73 | C |
| ATOM | 3778 | C | PHE A | 565 | −51.936 | 9.049 | −26.066 | 1.00 | 21.33 | C |
| ATOM | 3779 | O | PHE A | 565 | −50.800 | 8.625 | −26.284 | 1.00 | 21.27 | O |
| ATOM | 3780 | N | PHE A | 566 | −52.201 | 9.984 | −25.159 | 1.00 | 21.09 | N |
| ATOM | 3781 | CA | PHE A | 566 | −51.167 | 10.487 | −24.271 | 1.00 | 21.37 | C |
| ATOM | 3782 | CB | PHE A | 566 | −51.590 | 11.811 | −23.633 | 1.00 | 21.54 | C |
| ATOM | 3783 | CG | PHE A | 566 | −51.671 | 12.950 | −24.602 | 1.00 | 21.69 | C |
| ATOM | 3784 | CD1 | PHE A | 566 | −50.513 | 13.518 | −25.127 | 1.00 | 21.41 | C |
| ATOM | 3785 | CE1 | PHE A | 566 | −50.584 | 14.576 | −26.028 | 1.00 | 22.35 | C |
| ATOM | 3786 | CZ | PHE A | 566 | −51.819 | 15.076 | −26.414 | 1.00 | 20.73 | C |
| ATOM | 3787 | CE2 | PHE A | 566 | −52.983 | 14.515 | −25.897 | 1.00 | 23.33 | C |
| ATOM | 3788 | CD2 | PHE A | 566 | −52.902 | 13.457 | −24.993 | 1.00 | 22.51 | C |
| ATOM | 3789 | C | PHE A | 566 | −50.855 | 9.465 | −23.188 | 1.00 | 22.33 | C |
| ATOM | 3790 | O | PHE A | 566 | −51.764 | 8.844 | −22.620 | 1.00 | 21.94 | O |
| ATOM | 3791 | N | ARG A | 567 | −49.564 | 9.278 | −22.930 | 1.00 | 22.35 | N |
| ATOM | 3792 | CA | ARG A | 567 | −49.116 | 8.526 | −21.767 | 1.00 | 22.84 | C |
| ATOM | 3793 | CB | ARG A | 567 | −48.298 | 7.294 | −22.157 | 1.00 | 22.74 | C |
| ATOM | 3794 | CG | ARG A | 567 | −47.737 | 6.525 | −20.969 | 1.00 | 22.89 | C |
| ATOM | 3795 | CD | ARG A | 567 | −46.330 | 6.032 | −21.256 | 1.00 | 25.22 | C |
| ATOM | 3796 | NE | ARG A | 567 | −45.412 | 7.143 | −21.514 | 1.00 | 25.89 | N |
| ATOM | 3797 | CZ | ARG A | 567 | −44.136 | 7.007 | −21.857 | 1.00 | 27.02 | C |
| ATOM | 3798 | NH1 | ARG A | 567 | −43.393 | 8.088 | −22.064 | 1.00 | 22.37 | N |
| ATOM | 3799 | NH2 | ARG A | 567 | −43.602 | 5.797 | −21.990 | 1.00 | 25.01 | N |
| ATOM | 3800 | C | ARG A | 567 | −48.309 | 9.458 | −20.877 | 1.00 | 23.73 | C |
| ATOM | 3801 | O | ARG A | 567 | −47.119 | 9.708 | −21.106 | 1.00 | 23.39 | O |
| ATOM | 3802 | N | MET A | 568 | −48.987 | 9.988 | −19.870 | 1.00 | 23.83 | N |
| ATOM | 3803 | CA | MET A | 568 | −48.350 | 10.796 | −18.857 | 1.00 | 24.86 | C |

TABLE A-continued

| | | | | | | | | | | |
|---|---|---|---|---|---|---|---|---|---|---|
| ATOM | 3804 | CB | MET A | 568 | −49.412 | 11.622 | −18.132 | 1.00 | 25.12 | C |
| ATOM | 3805 | CG | MET A | 568 | −48.873 | 12.585 | −17.108 | 1.00 | 28.71 | C |
| ATOM | 3806 | SD | MET A | 568 | −47.903 | 13.945 | −17.773 | 1.00 | 29.12 | S |
| ATOM | 3807 | CE | MET A | 568 | −47.756 | 14.880 | −16.262 | 1.00 | 27.86 | C |
| ATOM | 3808 | C | MET A | 568 | −47.607 | 9.868 | −17.895 | 1.00 | 24.46 | C |
| ATOM | 3809 | O | MET A | 568 | −48.066 | 8.763 | −17.619 | 1.00 | 24.33 | O |
| ATOM | 3810 | N | VAL A | 569 | −46.446 | 10.314 | −17.426 | 1.00 | 24.42 | N |
| ATOM | 3811 | CA | VAL A | 569 | −45.633 | 9.573 | −16.460 | 1.00 | 24.90 | C |
| ATOM | 3812 | CB | VAL A | 569 | −44.558 | 8.652 | −17.134 | 1.00 | 25.04 | C |
| ATOM | 3813 | CG1 | VAL A | 569 | −45.126 | 7.278 | −17.434 | 1.00 | 22.70 | C |
| ATOM | 3814 | CG2 | VAL A | 569 | −43.977 | 9.293 | −18.391 | 1.00 | 25.98 | C |
| ATOM | 3815 | C | VAL A | 569 | −44.945 | 10.542 | −15.502 | 1.00 | 25.36 | C |
| ATOM | 3816 | O | VAL A | 569 | −44.666 | 11.687 | −15.858 | 1.00 | 25.45 | O |
| ATOM | 3817 | N | ILE A | 570 | −44.684 | 10.079 | −14.283 | 1.00 | 25.77 | N |
| ATOM | 3818 | CA | ILE A | 570 | −44.031 | 10.899 | −13.267 | 1.00 | 26.36 | C |
| ATOM | 3819 | CB | ILE A | 570 | −45.043 | 11.406 | −12.209 | 1.00 | 26.41 | C |
| ATOM | 3820 | CG1 | ILE A | 570 | −46.172 | 12.186 | −12.889 | 1.00 | 26.01 | C |
| ATOM | 3821 | CD1 | ILE A | 570 | −47.499 | 12.083 | −12.203 | 1.00 | 31.49 | C |
| ATOM | 3822 | CG2 | ILE A | 570 | −44.344 | 12.285 | −11.172 | 1.00 | 25.39 | C |
| ATOM | 3823 | C | ILE A | 570 | −42.888 | 10.136 | −12.594 | 1.00 | 27.57 | C |
| ATOM | 3824 | O | ILE A | 570 | −43.094 | 9.074 | −12.006 | 1.00 | 28.46 | O |
| ATOM | 3825 | N | SER A | 571 | −41.680 | 10.682 | −12.693 | 1.00 | 27.74 | N |
| ATOM | 3826 | CA | SER A | 571 | −40.517 | 10.102 | −12.027 | 1.00 | 28.15 | C |
| ATOM | 3827 | CB | SER A | 571 | −39.760 | 9.168 | −12.978 | 1.00 | 28.05 | C |
| ATOM | 3828 | OG | SER A | 571 | −39.160 | 9.892 | −14.042 | 1.00 | 30.41 | O |
| ATOM | 3829 | C | SER A | 571 | −39.585 | 11.186 | −11.485 | 1.00 | 27.42 | C |
| ATOM | 3830 | O | SER A | 571 | −38.607 | 10.891 | −10.796 | 1.00 | 28.52 | O |
| ATOM | 3831 | N | ASN A | 572 | −39.907 | 12.436 | −11.801 | 1.00 | 26.46 | N |
| ATOM | 3832 | CA | ASN A | 572 | −39.096 | 13.585 | −11.426 | 1.00 | 25.63 | C |
| ATOM | 3833 | CB | ASN A | 572 | −39.235 | 14.670 | −12.505 | 1.00 | 25.56 | C |
| ATOM | 3834 | CG | ASN A | 572 | −38.238 | 15.820 | −12.356 | 1.00 | 25.69 | C |
| ATOM | 3835 | OD1 | ASN A | 572 | −38.279 | 16.773 | −13.136 | 1.00 | 26.55 | O |
| ATOM | 3836 | ND2 | ASN A | 572 | −37.343 | 15.736 | −11.378 | 1.00 | 24.30 | N |
| ATOM | 3837 | C | ASN A | 572 | −39.529 | 14.113 | −10.058 | 1.00 | 24.77 | C |
| ATOM | 3838 | O | ASN A | 572 | −40.673 | 14.523 | −9.891 | 1.00 | 24.07 | O |
| ATOM | 3839 | N | PRO A | 573 | −38.620 | 14.085 | −9.063 | 1.00 | 24.77 | N |
| ATOM | 3840 | CA | PRO A | 573 | −38.925 | 14.675 | −7.756 | 1.00 | 24.24 | C |
| | | | | | gad67.pdb | | | | | |
| ATOM | 3841 | CB | PRO A | 573 | −37.683 | 14.347 | −6.920 | 1.00 | 24.13 | C |
| ATOM | 3842 | CG | PRO A | 573 | −36.610 | 14.078 | −7.908 | 1.00 | 26.05 | C |
| ATOM | 3843 | CD | PRO A | 573 | −37.282 | 13.465 | −9.085 | 1.00 | 24.43 | C |
| ATOM | 3844 | C | PRO A | 573 | −39.171 | 16.185 | −7.791 | 1.00 | 24.24 | C |
| ATOM | 3845 | O | PRO A | 573 | −39.695 | 16.744 | −6.822 | 1.00 | 24.51 | O |
| ATOM | 3846 | N | ALA A | 574 | −38.796 | 16.828 | −8.897 | 1.00 | 23.30 | N |
| ATOM | 3847 | CA | ALA A | 574 | −39.029 | 18.255 | −9.110 | 1.00 | 22.14 | C |
| ATOM | 3848 | CB | ALA A | 574 | −38.076 | 18.791 | −10.165 | 1.00 | 22.70 | C |
| ATOM | 3849 | C | ALA A | 574 | −40.476 | 18.554 | −9.507 | 1.00 | 22.24 | C |
| ATOM | 3850 | O | ALA A | 574 | −40.957 | 19.677 | −9.316 | 1.00 | 22.76 | O |
| ATOM | 3851 | N | ALA A | 575 | −41.160 | 17.558 | −10.069 | 1.00 | 21.10 | N |
| ATOM | 3852 | CA | ALA A | 575 | −42.568 | 17.692 | −10.448 | 1.00 | 21.57 | C |
| ATOM | 3853 | CB | ALA A | 575 | −43.047 | 16.454 | −11.194 | 1.00 | 20.91 | C |
| ATOM | 3854 | C | ALA A | 575 | −43.439 | 17.945 | −9.221 | 1.00 | 21.92 | C |
| ATOM | 3855 | O | ALA A | 575 | −43.276 | 17.296 | −8.189 | 1.00 | 22.01 | O |
| ATOM | 3856 | N | THR A | 576 | −44.336 | 18.918 | −9.336 | 1.00 | 22.56 | N |
| ATOM | 3857 | CA | THR A | 576 | −45.270 | 19.250 | −8.266 | 1.00 | 23.02 | C |
| ATOM | 3858 | CB | THR A | 576 | −45.013 | 20.662 | −7.671 | 1.00 | 22.89 | C |
| ATOM | 3859 | OG1 | THR A | 576 | −45.294 | 21.662 | −8.658 | 1.00 | 23.59 | O |
| ATOM | 3860 | CG2 | THR A | 576 | −43.575 | 20.811 | −7.180 | 1.00 | 21.65 | C |
| ATOM | 3861 | C | THR A | 576 | −46.702 | 19.178 | −8.793 | 1.00 | 23.17 | C |
| ATOM | 3862 | O | THR A | 576 | −46.927 | 19.084 | −10.000 | 1.00 | 22.40 | O |
| ATOM | 3863 | N | GLN A | 577 | −47.658 | 19.228 | −7.872 | 1.00 | 23.75 | N |
| ATOM | 3864 | CA | GLN A | 577 | −49.080 | 19.218 | −8.194 | 1.00 | 25.19 | C |
| ATOM | 3865 | CB | GLN A | 577 | −49.887 | 19.290 | −6.895 | 1.00 | 25.16 | C |
| ATOM | 3866 | CG | GLN A | 577 | −51.373 | 19.487 | −7.065 | 1.00 | 27.26 | C |
| ATOM | 3867 | CD | GLN A | 577 | −52.138 | 19.302 | −5.766 | 1.00 | 28.26 | C |
| ATOM | 3868 | OE1 | GLN A | 577 | −51.865 | 18.377 | −4.989 | 1.00 | 32.49 | O |
| ATOM | 3869 | NE2 | GLN A | 577 | −53.111 | 20.175 | −5.529 | 1.00 | 29.07 | N |
| ATOM | 3870 | C | GLN A | 577 | −49.463 | 20.349 | −9.165 | 1.00 | 24.34 | C |
| ATOM | 3871 | O | GLN A | 577 | −50.240 | 20.135 | −10.096 | 1.00 | 23.97 | O |
| ATOM | 3872 | N | SER A | 578 | −48.898 | 21.537 | −8.956 | 1.00 | 23.88 | N |
| ATOM | 3873 | CA | SER A | 578 | −49.133 | 22.669 | −9.856 | 1.00 | 24.93 | C |
| ATOM | 3874 | CB | SER A | 578 | −48.607 | 23.975 | −9.251 | 1.00 | 24.82 | C |
| ATOM | 3875 | OG | SER A | 578 | −47.207 | 23.920 | −9.066 | 1.00 | 29.61 | O |
| ATOM | 3876 | C | SER A | 578 | −48.572 | 22.446 | −11.274 | 1.00 | 24.23 | C |
| ATOM | 3877 | O | SER A | 578 | −49.105 | 22.990 | −12.236 | 1.00 | 24.36 | O |
| ATOM | 3878 | N | ASP A | 579 | −47.518 | 21.638 | −11.397 | 1.00 | 23.70 | N |
| ATOM | 3879 | CA | ASP A | 579 | −47.003 | 21.232 | −12.710 | 1.00 | 23.73 | C |
| ATOM | 3880 | CB | ASP A | 579 | −45.620 | 20.590 | −12.589 | 1.00 | 23.66 | C |
| ATOM | 3881 | CG | ASP A | 579 | −44.581 | 21.538 | −12.041 | 1.00 | 22.76 | C |
| ATOM | 3882 | OD1 | ASP A | 579 | −44.492 | 22.682 | −12.533 | 1.00 | 25.26 | O |

TABLE A-continued

| | | | | | | | | | |
|---|---|---|---|---|---|---|---|---|---|
| ATOM | 3883 | OD2 | ASP A | 579 | −43.842 | 21.133 | −11.123 | 1.00 | 24.29 | O |
| ATOM | 3884 | C | ASP A | 579 | −47.946 | 20.260 | −13.407 | 1.00 | 24.33 | C |
| ATOM | 3885 | O | ASP A | 579 | −47.965 | 20.174 | −14.637 | 1.00 | 24.06 | O |
| ATOM | 3886 | N | ILE A | 580 | −48.710 | 19.515 | −12.611 | 1.00 | 25.06 | N |
| ATOM | 3887 | CA | ILE A | 580 | −49.727 | 18.612 | −13.135 | 1.00 | 26.44 | C |
| ATOM | 3888 | CB | ILE A | 580 | −50.141 | 17.532 | −12.086 | 1.00 | 26.86 | C |
| ATOM | 3889 | CG1 | ILE A | 580 | −48.948 | 16.638 | −11.719 | 1.00 | 26.97 | C |
| ATOM | 3890 | CD1 | ILE A | 580 | −48.275 | 15.939 | −12.891 | 1.00 | 27.16 | C |
| ATOM | 3891 | CG2 | ILE A | 580 | −51.342 | 16.710 | −12.567 | 1.00 | 27.15 | C |
| ATOM | 3892 | C | ILE A | 580 | −50.934 | 19.422 | −13.597 | 1.00 | 26.99 | C |
| ATOM | 3893 | O | ILE A | 580 | −51.483 | 19.162 | −14.672 | 1.00 | 27.38 | O |
| ATOM | 3894 | N | ASP A | 581 | −51.330 | 20.402 | −12.781 | 1.00 | 27.34 | N |
| ATOM | 3895 | CA | ASP A | 581 | −52.382 | 21.357 | −13.134 | 1.00 | 28.15 | C |
| ATOM | 3896 | CB | ASP A | 581 | −52.609 | 22.364 | −11.998 | 1.00 | 28.27 | C |
| ATOM | 3897 | CG | ASP A | 581 | −53.173 | 21.718 | −10.738 | 1.00 | 30.34 | C |
| ATOM | 3898 | OD1 | ASP A | 581 | −53.647 | 20.564 | −10.810 | 1.00 | 30.19 | O |
| ATOM | 3899 | OD2 | ASP A | 581 | −53.144 | 22.372 | −9.672 | 1.00 | 33.92 | O |
| ATOM | 3900 | C | ASP A | 581 | −52.050 | 22.105 | −14.421 | 1.00 | 28.41 | C |
| ATOM | 3901 | O | ASP A | 581 | −52.907 | 22.259 | −15.290 | 1.00 | 29.33 | O |
| ATOM | 3902 | N | PHE A | 582 | −50.805 | 22.565 | −14.533 | 1.00 | 28.61 | N |
| ATOM | 3903 | CA | PHE A | 582 | −50.335 | 23.248 | −15.732 | 1.00 | 28.78 | C |
| ATOM | 3904 | CB | PHE A | 582 | −48.891 | 23.743 | −15.566 | 1.00 | 28.75 | C |
| ATOM | 3905 | CG | PHE A | 582 | −48.332 | 24.396 | −16.800 | 1.00 | 28.86 | C |
| ATOM | 3906 | CD1 | PHE A | 582 | −48.560 | 25.747 | −17.052 | 1.00 | 29.96 | C |
| ATOM | 3907 | CE1 | PHE A | 582 | −48.051 | 26.358 | −18.196 | 1.00 | 29.62 | C |
| ATOM | 3908 | CZ | PHE A | 582 | −47.312 | 25.613 | −19.106 | 1.00 | 29.72 | C | gad67.pdb

| | | | | | | | | | |
|---|---|---|---|---|---|---|---|---|---|
| ATOM | 3909 | CE2 | PHE A | 582 | −47.080 | 24.258 | −18.867 | 1.00 | 29.81 | C |
| ATOM | 3910 | CD2 | PHE A | 582 | −47.590 | 23.658 | −17.721 | 1.00 | 28.99 | C |
| ATOM | 3911 | C | PHE A | 582 | −50.446 | 22.376 | −16.980 | 1.00 | 28.99 | C |
| ATOM | 3912 | O | PHE A | 582 | −51.016 | 22.807 | −17.979 | 1.00 | 29.82 | O |
| ATOM | 3913 | N | LEU A | 583 | −49.900 | 21.160 | −16.921 | 1.00 | 29.32 | N |
| ATOM | 3914 | CA | LEU A | 583 | −49.892 | 20.264 | −18.085 | 1.00 | 29.86 | C |
| ATOM | 3915 | CB | LEU A | 583 | −49.193 | 18.938 | −17.777 | 1.00 | 29.19 | C |
| ATOM | 3916 | CG | LEU A | 583 | −49.262 | 17.978 | −18.975 | 1.00 | 30.23 | C |
| ATOM | 3917 | CD1 | LEU A | 583 | −47.938 | 17.875 | −19.706 | 1.00 | 30.53 | C |
| ATOM | 3918 | CD2 | LEU A | 583 | −49.749 | 16.616 | −18.554 | 1.00 | 28.60 | C |
| ATOM | 3919 | C | LEU A | 583 | −51.299 | 19.989 | −18.614 | 1.00 | 30.16 | C |
| ATOM | 3920 | O | LEU A | 583 | −51.528 | 20.015 | −19.825 | 1.00 | 30.16 | O |
| ATOM | 3921 | N | ILE A | 584 | −52.225 | 19.718 | −17.696 | 1.00 | 30.86 | N |
| ATOM | 3922 | CA | ILE A | 584 | −53.617 | 19.440 | −18.035 | 1.00 | 31.47 | C |
| ATOM | 3923 | CB | ILE A | 584 | −54.420 | 18.970 | −16.786 | 1.00 | 31.65 | C |
| ATOM | 3924 | CG1 | ILE A | 584 | −53.993 | 17.554 | −16.379 | 1.00 | 32.10 | C |
| ATOM | 3925 | CD1 | ILE A | 584 | −53.850 | 16.558 | −17.550 | 1.00 | 35.07 | C |
| ATOM | 3926 | CG2 | ILE A | 584 | −55.933 | 19.045 | −17.016 | 1.00 | 32.01 | C |
| ATOM | 3927 | C | ILE A | 584 | −54.261 | 20.645 | −18.707 | 1.00 | 31.81 | C |
| ATOM | 3928 | O | ILE A | 584 | −54.864 | 20.512 | −19.777 | 1.00 | 32.37 | O |
| ATOM | 3929 | N | GLU A | 585 | −54.105 | 21.816 | −18.091 | 1.00 | 32.20 | N |
| ATOM | 3930 | CA | GLU A | 585 | −54.605 | 23.068 | −18.657 | 1.00 | 33.70 | C |
| ATOM | 3931 | CB | GLU A | 585 | −54.374 | 24.232 | −17.686 | 1.00 | 34.16 | C |
| ATOM | 3932 | CG | GLU A | 585 | −55.339 | 24.248 | −16.499 | 1.00 | 37.48 | C |
| ATOM | 3933 | CD | GLU A | 585 | −54.779 | 24.958 | −15.268 | 1.00 | 44.14 | C |
| ATOM | 3934 | OE1 | GLU A | 585 | −55.474 | 24.976 | −14.228 | 1.00 | 45.22 | O |
| ATOM | 3935 | OE2 | GLU A | 585 | −53.648 | 25.493 | −15.330 | 1.00 | 47.53 | O |
| ATOM | 3936 | C | GLU A | 585 | −53.985 | 23.363 | −20.026 | 1.00 | 33.70 | C |
| ATOM | 3937 | O | GLU A | 585 | −54.673 | 23.841 | −20.930 | 1.00 | 34.08 | O |
| ATOM | 3938 | N | GLU A | 586 | −52.696 | 23.055 | −20.173 | 1.00 | 33.48 | N |
| ATOM | 3939 | CA | GLU A | 586 | −51.974 | 23.251 | −21.432 | 1.00 | 33.50 | C |
| ATOM | 3940 | CB | GLU A | 586 | −50.465 | 23.041 | −21.228 | 1.00 | 34.08 | C |
| ATOM | 3941 | CG | GLU A | 586 | −49.584 | 23.465 | −22.403 | 1.00 | 36.05 | C |
| ATOM | 3942 | CD | GLU A | 586 | −49.311 | 24.967 | −22.459 | 1.00 | 39.98 | C |
| ATOM | 3943 | OE1 | GLU A | 586 | −48.406 | 25.365 | −23.222 | 1.00 | 42.27 | O |
| ATOM | 3944 | OE2 | GLU A | 586 | −49.987 | 25.753 | −21.757 | 1.00 | 40.03 | O |
| ATOM | 3945 | C | GLU A | 586 | −52.496 | 22.341 | −22.543 | 1.00 | 32.90 | C |
| ATOM | 3946 | O | GLU A | 586 | −52.633 | 22.775 | −23.685 | 1.00 | 33.38 | O |
| ATOM | 3947 | N | ILE A | 587 | −52.783 | 21.085 | −22.203 | 1.00 | 31.80 | N |
| ATOM | 3948 | CA | ILE A | 587 | −53.349 | 20.129 | −23.155 | 1.00 | 31.19 | C |
| ATOM | 3949 | CB | ILE A | 587 | −53.462 | 18.705 | −22.544 | 1.00 | 31.02 | C |
| ATOM | 3950 | CG1 | ILE A | 587 | −52.067 | 18.075 | −22.418 | 1.00 | 30.23 | C |
| ATOM | 3951 | CD1 | ILE A | 587 | −52.037 | 16.690 | −21.790 | 1.00 | 29.64 | C |
| ATOM | 3952 | CG2 | ILE A | 587 | −54.389 | 17.818 | −23.382 | 1.00 | 27.94 | C |
| ATOM | 3953 | C | ILE A | 587 | −54.711 | 20.605 | −23.672 | 1.00 | 32.75 | C |
| ATOM | 3954 | O | ILE A | 587 | −54.974 | 20.559 | −24.876 | 1.00 | 32.53 | O |
| ATOM | 3955 | N | GLU A | 588 | −55.562 | 21.063 | −22.753 | 1.00 | 34.05 | N |
| ATOM | 3956 | CA | GLU A | 588 | −56.880 | 21.603 | −23.094 | 1.00 | 35.40 | C |
| ATOM | 3957 | CB | GLU A | 588 | −57.724 | 21.810 | −21.821 | 1.00 | 35.84 | C |
| ATOM | 3958 | CG | GLU A | 588 | −58.650 | 23.045 | −21.805 | 1.00 | 42.17 | C |
| ATOM | 3959 | CD | GLU A | 588 | −59.968 | 22.853 | −22.549 | 1.00 | 47.15 | C |
| ATOM | 3960 | OE1 | GLU A | 588 | −60.026 | 22.060 | −23.515 | 1.00 | 51.69 | O |
| ATOM | 3961 | OE2 | GLU A | 588 | −60.957 | 23.515 | −22.165 | 1.00 | 49.06 | O |

TABLE A-continued

| | | | | | | | | | |
|---|---|---|---|---|---|---|---|---|---|
| ATOM | 3962 | C | GLU A | 588 | −56.756 | 22.882 | −23.929 | 1.00 | 34.77 | C |
| ATOM | 3963 | O | GLU A | 588 | −57.492 | 23.066 | −24.898 | 1.00 | 34.01 | O |
| ATOM | 3964 | N | ARG A | 589 | −55.810 | 23.742 | −23.555 | 1.00 | 35.16 | N |
| ATOM | 3965 | CA | ARG A | 589 | −55.531 | 24.980 | −24.282 | 1.00 | 36.27 | C |
| ATOM | 3966 | CB | ARG A | 589 | −54.442 | 25.780 | −23.562 | 1.00 | 35.90 | C |
| ATOM | 3967 | CG | ARG A | 589 | −54.240 | 27.191 | −24.085 | 1.00 | 37.49 | C |
| ATOM | 3968 | CD | ARG A | 589 | −53.155 | 27.932 | −23.310 | 1.00 | 37.34 | C |
| ATOM | 3969 | NE | ARG A | 589 | −51.805 | 27.482 | −23.653 | 1.00 | 40.13 | N |
| ATOM | 3970 | CZ | ARG A | 589 | −51.110 | 27.898 | −24.711 | 1.00 | 41.44 | C |
| ATOM | 3971 | NH1 | ARG A | 589 | −51.629 | 28.776 | −25.561 | 1.00 | 41.64 | N |
| ATOM | 3972 | NH2 | ARG A | 589 | −49.887 | 27.426 | −24.927 | 1.00 | 43.46 | N |
| ATOM | 3973 | C | ARG A | 589 | −55.113 | 24.696 | −25.729 | 1.00 | 36.96 | C |
| ATOM | 3974 | O | ARG A | 589 | −55.657 | 25.278 | −26.672 | 1.00 | 37.56 | O |
| ATOM | 3975 | N | LEU A | 590 | −54.151 | 23.793 | −25.891 | 1.00 | 37.01 | N |
| ATOM | 3976 | CA | LEU A | 590 | −53.663 | 23.389 | −27.207 | 1.00 | 37.65 | C |
| ATOM | 3977 | CB | LEU A | 590 | −52.347 | 22.620 | −27.062 | 1.00 | 36.85 | C |
| ATOM | 3978 | CG | LEU A | 590 | −51.024 | 23.394 | −26.999 | 1.00 | 36.28 | C |
| ATOM | 3979 | CD1 | LEU A | 590 | −51.078 | 24.605 | −26.090 | 1.00 | 36.28 | C |
| ATOM | 3980 | CD2 | LEU A | 590 | −49.899 | 22.471 | −26.567 | 1.00 | 37.78 | C |
| ATOM | 3981 | C | LEU A | 590 | −54.694 | 22.542 | −27.954 | 1.00 | 38.67 | C |
| ATOM | 3982 | O | LEU A | 590 | −54.666 | 22.454 | −29.184 | 1.00 | 38.67 | O |
| ATOM | 3983 | N | GLY A | 591 | −55.609 | 21.940 | −27.197 | 1.00 | 39.66 | N |
| ATOM | 3984 | CA | GLY A | 591 | −56.639 | 21.062 | −27.742 | 1.00 | 41.75 | C |
| ATOM | 3985 | C | GLY A | 591 | −57.591 | 21.679 | −28.751 | 1.00 | 43.04 | C |
| ATOM | 3986 | O | GLY A | 591 | −58.012 | 21.005 | −29.694 | 1.00 | 43.08 | O |
| ATOM | 3987 | N | GLN A | 592 | −57.951 | 22.945 | −28.550 | 1.00 | 44.70 | N |
| ATOM | 3988 | CA | GLN A | 592 | −58.749 | 23.672 | −29.545 | 1.00 | 46.97 | C |
| ATOM | 3989 | CB | GLN A | 592 | −60.068 | 24.202 | −28.958 | 1.00 | 47.41 | C |
| ATOM | 3990 | CG | GLN A | 592 | −60.504 | 23.590 | −27.629 | 1.00 | 47.76 | C |
| ATOM | 3991 | CD | GLN A | 592 | −60.128 | 24.454 | −26.435 | 1.00 | 50.00 | C |
| ATOM | 3992 | OE1 | GLN A | 592 | −60.805 | 24.432 | −25.406 | 1.00 | 50.88 | O |
| ATOM | 3993 | NE2 | GLN A | 592 | −59.053 | 25.228 | −26.569 | 1.00 | 50.24 | N |
| ATOM | 3994 | C | GLN A | 592 | −57.925 | 24.812 | −30.149 | 1.00 | 48.05 | C |
| ATOM | 3995 | O | GLN A | 592 | −58.295 | 25.985 | −30.051 | 1.00 | 48.29 | O |
| ATOM | 3996 | N | ASP A | 593 | −56.797 | 24.450 | −30.761 | 1.00 | 49.30 | N |
| ATOM | 3997 | CA | ASP A | 593 | −55.877 | 25.414 | −31.362 | 1.00 | 50.23 | C |
| ATOM | 3998 | CB | ASP A | 593 | −54.984 | 26.051 | −30.291 | 1.00 | 50.54 | C |
| ATOM | 4002 | C | ASP A | 593 | −55.018 | 24.747 | −32.434 | 1.00 | 50.91 | C |
| ATOM | 4003 | O | ASP A | 593 | −54.233 | 25.407 | −33.119 | 1.00 | 51.61 | O |
| ATOM | 4004 | N | THR B | 93 | −20.401 | 21.651 | 11.097 | 1.00 | 45.50 | N |
| ATOM | 4005 | CA | THR B | 93 | −21.812 | 22.115 | 11.272 | 1.00 | 44.80 | C |
| ATOM | 4006 | CB | THR B | 93 | −21.958 | 23.051 | 12.497 | 1.00 | 45.25 | C |
| ATOM | 4009 | C | THR B | 93 | −22.399 | 22.786 | 10.016 | 1.00 | 43.52 | C |
| ATOM | 4010 | O | THR B | 93 | −23.523 | 23.303 | 10.051 | 1.00 | 44.04 | O |
| ATOM | 4011 | N | ASP B | 94 | −21.643 | 22.770 | 8.916 | 1.00 | 40.95 | N |
| ATOM | 4012 | CA | ASP B | 94 | −22.142 | 23.278 | 7.633 | 1.00 | 38.47 | C |
| ATOM | 4013 | CB | ASP B | 94 | −21.069 | 24.079 | 6.887 | 1.00 | 39.30 | C |
| ATOM | 4014 | CG | ASP B | 94 | −21.638 | 24.881 | 5.729 | 1.00 | 41.85 | C |
| ATOM | 4015 | OD1 | ASP B | 94 | −22.794 | 25.343 | 5.829 | 1.00 | 46.20 | O |
| ATOM | 4016 | OD2 | ASP B | 94 | −20.925 | 25.056 | 4.717 | 1.00 | 46.31 | O |
| ATOM | 4017 | C | ASP B | 94 | −22.687 | 22.137 | 6.766 | 1.00 | 35.15 | C |
| ATOM | 4018 | O | ASP B | 94 | −23.887 | 21.866 | 6.797 | 1.00 | 34.66 | O |
| ATOM | 4019 | N | PHE B | 95 | −21.812 | 21.467 | 6.012 | 1.00 | 31.06 | N |
| ATOM | 4020 | CA | PHE B | 95 | −22.210 | 20.292 | 5.228 | 1.00 | 28.39 | C |
| ATOM | 4021 | CB | PHE B | 95 | −21.144 | 19.914 | 4.192 | 1.00 | 28.19 | C |
| ATOM | 4022 | CG | PHE B | 95 | −21.162 | 20.775 | 2.961 | 1.00 | 28.89 | C |
| ATOM | 4023 | CD1 | PHE B | 95 | −20.051 | 21.536 | 2.617 | 1.00 | 28.81 | C |
| ATOM | 4024 | CE1 | PHE B | 95 | −20.064 | 22.340 | 1.482 | 1.00 | 28.35 | C |
| ATOM | 4025 | CZ | PHE B | 95 | −21.200 | 22.390 | .679 | 1.00 | 28.81 | C |
| ATOM | 4026 | CE2 | PHE B | 95 | −22.317 | 21.637 | 1.014 | 1.00 | 28.76 | C |
| ATOM | 4027 | CD2 | PHE B | 95 | −22.294 | 20.835 | 2.150 | 1.00 | 28.31 | C |
| ATOM | 4028 | C | PHE B | 95 | −22.534 | 19.089 | 6.106 | 1.00 | 26.19 | C |
| ATOM | 4029 | O | PHE B | 95 | −23.272 | 18.199 | 5.691 | 1.00 | 24.96 | O |
| ATOM | 4030 | N | SER B | 96 | −21.985 | 19.070 | 7.318 | 1.00 | 25.93 | N |
| ATOM | 4031 | CA | SER B | 96 | −22.268 | 18.002 | 8.281 | 1.00 | 26.55 | C |
| ATOM | 4032 | CB | SER B | 96 | −21.217 | 17.975 | 9.392 | 1.00 | 26.78 | C |
| ATOM | 4033 | OG | SER B | 96 | −21.108 | 19.235 | 10.025 | 1.00 | 31.22 | O |
| ATOM | 4034 | C | SER B | 96 | −23.681 | 18.079 | 8.867 | 1.00 | 25.90 | C |
| ATOM | 4035 | O | SER B | 96 | −24.135 | 17.145 | 9.527 | 1.00 | 26.16 | O |
| ATOM | 4036 | N | ASN B | 97 | −24.370 | 19.189 | 8.616 | 1.00 | 25.89 | N |
| ATOM | 4037 | CA | ASN B | 97 | −25.772 | 19.335 | 9.005 | 1.00 | 26.70 | C |
| ATOM | 4038 | CB | ASN B | 97 | −25.948 | 20.526 | 9.951 | 1.00 | 27.16 | C |
| ATOM | 4039 | CG | ASN B | 97 | −25.450 | 20.228 | 11.352 | 1.00 | 29.31 | C |
| ATOM | 4040 | OD1 | ASN B | 97 | −24.566 | 20.911 | 11.865 | 1.00 | 29.91 | O |
| ATOM | 4041 | ND2 | ASN B | 97 | −26.012 | 19.195 | 11.975 | 1.00 | 29.93 | N |
| ATOM | 4042 | C | ASN B | 97 | −26.706 | 19.453 | 7.806 | 1.00 | 26.09 | C |
| ATOM | 4043 | O | ASN B | 97 | −27.879 | 19.804 | 7.952 | 1.00 | 26.53 | O |
| ATOM | 4044 | N | LEU B | 98 | −26.174 | 19.140 | 6.627 | 1.00 | 24.78 | N |
| ATOM | 4045 | CA | LEU B | 98 | −26.931 | 19.199 | 5.385 | 1.00 | 23.97 | C | gad67.pdb

TABLE A-continued

| ATOM | 4046 | CB | LEU B | 98 | −26.285 | 20.174 | 4.397 | 1.00 | 24.73 | C |
|---|---|---|---|---|---|---|---|---|---|---|
| ATOM | 4047 | CG | LEU B | 98 | −26.322 | 21.672 | 4.704 | 1.00 | 29.23 | C |
| ATOM | 4048 | CD1 | LEU B | 98 | −25.539 | 22.440 | 3.645 | 1.00 | 31.79 | C |
| ATOM | 4049 | CD2 | LEU B | 98 | −27.754 | 22.199 | 4.813 | 1.00 | 32.69 | C |
| | | | | | gad67.pdb | | | | | |
| ATOM | 4050 | C | LEU B | 98 | −27.038 | 17.828 | 4.744 | 1.00 | 22.60 | C |
| ATOM | 4051 | O | LEU B | 98 | −26.130 | 17.000 | 4.864 | 1.00 | 22.30 | O |
| ATOM | 4052 | N | PHE B | 99 | −28.153 | 17.608 | 4.054 | 1.00 | 21.27 | N |
| ATOM | 4053 | CA | PHE B | 99 | −28.437 | 16.340 | 3.401 | 1.00 | 20.70 | C |
| ATOM | 4054 | CB | PHE B | 99 | −29.531 | 15.583 | 4.169 | 1.00 | 20.54 | C |
| ATOM | 4055 | CG | PHE B | 99 | −29.116 | 15.165 | 5.556 | 1.00 | 20.80 | C |
| ATOM | 4056 | CD1 | PHE B | 99 | −28.624 | 13.884 | 5.791 | 1.00 | 20.31 | C |
| ATOM | 4057 | CE1 | PHE B | 99 | −28.229 | 13.490 | 7.072 | 1.00 | 20.73 | C |
| ATOM | 4058 | CZ | PHE B | 99 | −28.321 | 14.388 | 8.134 | 1.00 | 22.51 | C |
| ATOM | 4059 | CE2 | PHE B | 99 | −28.806 | 15.675 | 7.913 | 1.00 | 23.00 | C |
| ATOM | 4060 | CD2 | PHE B | 99 | −29.205 | 16.057 | 6.629 | 1.00 | 21.74 | C |
| ATOM | 4061 | C | PHE B | 99 | −28.844 | 16.577 | 1.950 | 1.00 | 20.43 | C |
| ATOM | 4062 | O | PHE B | 99 | −29.214 | 17.695 | 1.580 | 1.00 | 20.25 | O |
| ATOM | 4063 | N | ALA B | 100 | −28.763 | 15.525 | 1.135 | 1.00 | 20.25 | N |
| ATOM | 4064 | CA | ALA B | 100 | −29.137 | 15.583 | −.281 | 1.00 | 20.35 | C |
| ATOM | 4065 | CB | ALA B | 100 | −28.922 | 14.228 | −.932 | 1.00 | 19.40 | C |
| ATOM | 4066 | C | ALA B | 100 | −30.579 | 16.057 | −.506 | 1.00 | 21.70 | C |
| ATOM | 4067 | O | ALA B | 100 | −30.872 | 16.724 | −1.504 | 1.00 | 22.16 | O |
| ATOM | 4068 | N | ARG B | 101 | −31.468 | 15.712 | .426 | 1.00 | 22.23 | N |
| ATOM | 4069 | CA | ARG B | 101 | −32.874 | 16.126 | .370 | 1.00 | 23.32 | C |
| ATOM | 4070 | CB | ARG B | 101 | −33.686 | 15.400 | 1.449 | 1.00 | 23.41 | C |
| ATOM | 4071 | CG | ARG B | 101 | −33.261 | 15.738 | 2.869 | 1.00 | 24.25 | C |
| ATOM | 4072 | CD | ARG B | 101 | −33.717 | 14.685 | 3.844 | 1.00 | 26.15 | C |
| ATOM | 4073 | NE | ARG B | 101 | −33.071 | 14.853 | 5.144 | 1.00 | 26.69 | N |
| ATOM | 4074 | CZ | ARG B | 101 | −33.084 | 13.946 | 6.118 | 1.00 | 24.67 | C |
| ATOM | 4075 | NH1 | ARG B | 101 | −33.716 | 12.793 | 5.955 | 1.00 | 22.39 | N |
| ATOM | 4076 | NH2 | ARG B | 101 | −32.459 | 14.196 | 7.259 | 1.00 | 26.16 | N |
| ATOM | 4077 | C | ARG B | 101 | −33.060 | 17.644 | .497 | 1.00 | 23.68 | C |
| ATOM | 4078 | O | ARG B | 101 | −34.125 | 18.171 | .175 | 1.00 | 24.49 | O |
| ATOM | 4079 | N | ASP B | 102 | −32.021 | 18.333 | .968 | 1.00 | 24.14 | N |
| ATOM | 4080 | CA | ASP B | 102 | −32.041 | 19.792 | 1.113 | 1.00 | 24.32 | C |
| ATOM | 4081 | CB | ASP B | 102 | −31.212 | 20.227 | 2.333 | 1.00 | 25.05 | C |
| ATOM | 4082 | CG | ASP B | 102 | −31.707 | 19.615 | 3.639 | 1.00 | 28.23 | C |
| ATOM | 4083 | OD1 | ASP B | 102 | −32.941 | 19.549 | 3.856 | 1.00 | 30.46 | O |
| ATOM | 4084 | OD2 | ASP B | 102 | −30.852 | 19.208 | 4.457 | 1.00 | 29.08 | O |
| ATOM | 4085 | C | ASP B | 102 | −31.545 | 20.528 | −.140 | 1.00 | 23.69 | C |
| ATOM | 4086 | O | ASP B | 102 | −31.693 | 21.746 | −.244 | 1.00 | 23.84 | O |
| ATOM | 4087 | N | LEU B | 103 | −30.956 | 19.790 | −1.081 | 1.00 | 22.60 | N |
| ATOM | 4088 | CA | LEU B | 103 | −30.478 | 20.376 | −2.342 | 1.00 | 21.48 | C |
| ATOM | 4089 | CB | LEU B | 103 | −29.284 | 19.583 | −2.889 | 1.00 | 20.35 | C |
| ATOM | 4090 | CG | LEU B | 103 | −28.084 | 19.309 | −1.975 | 1.00 | 18.94 | C |
| ATOM | 4091 | CD1 | LEU B | 103 | −27.053 | 18.465 | −2.703 | 1.00 | 19.77 | C |
| ATOM | 4092 | CD2 | LEU B | 103 | −27.444 | 20.596 | −1.449 | 1.00 | 20.44 | C |
| ATOM | 4093 | C | LEU B | 103 | −31.591 | 20.442 | −3.391 | 1.00 | 21.29 | C |
| ATOM | 4094 | O | LEU B | 103 | −32.668 | 19.869 | −3.198 | 1.00 | 21.11 | O |
| ATOM | 4095 | N | LEU B | 104 | −31.333 | 21.143 | −4.496 | 1.00 | 21.17 | N |
| ATOM | 4096 | CA | LEU B | 104 | −32.265 | 21.173 | −5.628 | 1.00 | 21.58 | C |
| ATOM | 4097 | CB | LEU B | 104 | −31.644 | 21.893 | −6.833 | 1.00 | 20.40 | C |
| ATOM | 4098 | CG | LEU B | 104 | −31.497 | 23.420 | −6.787 | 1.00 | 19.85 | C |
| ATOM | 4099 | CD1 | LEU B | 104 | −30.706 | 23.917 | −7.991 | 1.00 | 16.80 | C |
| ATOM | 4100 | CD2 | LEU B | 104 | −32.853 | 24.121 | −6.709 | 1.00 | 13.93 | C |
| ATOM | 4101 | C | LEU B | 104 | −32.666 | 19.743 | −5.999 | 1.00 | 22.50 | C |
| ATOM | 4102 | O | LEU B | 104 | −31.809 | 18.861 | −6.036 | 1.00 | 22.67 | O |
| ATOM | 4103 | N | PRO B | 105 | −33.959 | 19.503 | −6.293 | 1.00 | 23.63 | N |
| ATOM | 4104 | CA | PRO B | 105 | −35.077 | 20.423 | −6.520 | 1.00 | 24.67 | C |
| ATOM | 4105 | CB | PRO B | 105 | −36.072 | 19.554 | −7.285 | 1.00 | 24.71 | C |
| ATOM | 4106 | CG | PRO B | 105 | −35.852 | 18.187 | −6.746 | 1.00 | 25.07 | C |
| ATOM | 4107 | CD | PRO B | 105 | −34.382 | 18.094 | −6.431 | 1.00 | 23.81 | C |
| ATOM | 4108 | C | PRO B | 105 | −35.777 | 21.010 | −5.286 | 1.00 | 26.15 | C |
| ATOM | 4109 | O | PRO B | 105 | −36.783 | 21.709 | −5.447 | 1.00 | 26.14 | O |
| ATOM | 4110 | N | ALA B | 106 | −35.274 | 20.738 | −4.081 | 1.00 | 27.53 | N |
| ATOM | 4111 | CA | ALA B | 106 | −35.861 | 21.330 | −2.875 | 1.00 | 28.67 | C |
| ATOM | 4112 | CB | ALA B | 106 | −35.103 | 20.905 | −1.623 | 1.00 | 27.72 | C |
| ATOM | 4113 | C | ALA B | 106 | −35.879 | 22.848 | −3.013 | 1.00 | 30.19 | C |
| ATOM | 4114 | O | ALA B | 106 | −34.901 | 23.448 | −3.474 | 1.00 | 30.52 | O |
| ATOM | 4115 | N | LYS B | 107 | −37.003 | 23.454 | −2.636 | 1.00 | 31.80 | N |
| ATOM | 4116 | CA | LYS B | 107 | −37.228 | 24.895 | −2.809 | 1.00 | 33.01 | C |
| ATOM | 4117 | CB | LYS B | 107 | −38.509 | 25.330 | −2.087 | 1.00 | 33.29 | C |
| | | | | | gad67.pdb | | | | | |
| ATOM | 4122 | C | LYS B | 107 | −36.039 | 25.742 | −2.345 | 1.00 | 33.19 | C |
| ATOM | 4123 | O | LYS B | 107 | −35.514 | 25.543 | −1.243 | 1.00 | 33.26 | O |
| ATOM | 4124 | N | ASN B | 108 | −35.621 | 26.666 | −3.212 | 1.00 | 33.65 | N |
| ATOM | 4125 | CA | ASN B | 108 | −34.497 | 27.583 | −2.962 | 1.00 | 34.01 | C |
| ATOM | 4126 | CB | ASN B | 108 | −34.918 | 28.718 | −2.Q15 | 1.00 | 34.85 | C |
| ATOM | 4130 | C | ASN B | 108 | −33.198 | 26.917 | −2.481 | 1.00 | 33.92 | C |

TABLE A-continued

| | | | | | | | | | | |
|---|---|---|---|---|---|---|---|---|---|---|
| ATOM | 4131 | O | ASN B | 108 | −32.464 | 27.478 | −1.661 | 1.00 | 34.41 | O |
| ATOM | 4132 | N | GLY B | 109 | −32.920 | 25.722 | −3.003 | 1.00 | 33.30 | N |
| ATOM | 4133 | CA | GLY B | 109 | −31.701 | 24.989 | −2.663 | 1.00 | 31.91 | C |
| ATOM | 4134 | C | GLY B | 109 | −30.538 | 25.318 | −3.584 | 1.00 | 30.93 | C |
| ATOM | 4135 | O | GLY B | 109 | −29.516 | 24.639 | −3.556 | 1.00 | 29.52 | O |
| ATOM | 4136 | N | GLU B | 110 | −30.693 | 26.380 | −4.376 | 1.00 | 31.01 | N |
| ATOM | 4137 | CA | GLU B | 110 | −29.762 | 26.733 | −5.451 | 1.00 | 31.37 | C |
| ATOM | 4138 | CB | GLU B | 110 | −30.309 | 27.921 | −6.249 | 1.00 | 31.20 | C |
| ATOM | 4139 | CG | GLU B | 110 | −29.647 | 28.129 | −7.600 | 1.00 | 34.68 | C |
| ATOM | 4140 | CD | GLU B | 110 | −30.255 | 29.278 | −8.396 | 1.00 | 35.76 | C |
| ATOM | 4141 | OE1 | GLU B | 110 | −31.468 | 29.230 | −8.702 | 1.00 | 42.81 | O |
| ATOM | 4142 | OE2 | GLU B | 110 | −29.511 | 30.227 | −8.730 | 1.00 | 42.01 | O |
| ATOM | 4143 | C | GLU B | 110 | −28.324 | 27.001 | −4.991 | 1.00 | 29.41 | C |
| ATOM | 4144 | O | GLU B | 110 | −27.385 | 26.417 | −5.529 | 1.00 | 28.27 | O |
| ATOM | 4145 | N | GLU B | 111 | −28.161 | 27.876 | −4.001 | 1.00 | 28.24 | N |
| ATOM | 4146 | CA | GLU B | 111 | −26.831 | 28.283 | −3.530 | 1.00 | 27.66 | C |
| ATOM | 4147 | CB | GLU B | 111 | −26.932 | 29.488 | −2.590 | 1.00 | 28.21 | C |
| ATOM | 4152 | C | GLU B | 111 | −26.056 | 27.147 | −2.858 | 1.00 | 27.19 | C |
| ATOM | 4153 | O | GLU B | 111 | −24.838 | 27.029 | −3.033 | 1.00 | 26.28 | O |
| ATOM | 4154 | N | GLN B | 112 | −26.771 | 26.316 | −2.101 | 1.00 | 26.63 | N |
| ATOM | 4155 | CA | GLN B | 112 | −26.176 | 25.171 | −1.408 | 1.00 | 26.92 | C |
| ATOM | 4156 | CB | GLN B | 112 | −27.128 | 24.638 | −.334 | 1.00 | 26.65 | C |
| ATOM | 4157 | CG | GLN B | 112 | −27.403 | 25.636 | .784 | 1.00 | 31.76 | C |
| ATOM | 4158 | CD | GLN B | 112 | −28.372 | 25.116 | 1.833 | 1.00 | 30.51 | C |
| ATOM | 4159 | OE1 | GLN B | 112 | −29.260 | 24.307 | 1.544 | 1.00 | 36.40 | O |
| ATOM | 4160 | NE2 | GLN B | 112 | −28.211 | 25.591 | 3.062 | 1.00 | 36.38 | N |
| ATOM | 4161 | C | GLN B | 112 | −25.797 | 24.057 | −2.383 | 1.00 | 24.47 | C |
| ATOM | 4162 | O | GLN B | 112 | −24.789 | 23.377 | −2.193 | 1.00 | 25.12 | O |
| ATOM | 4163 | N | THR B | 113 | −26.622 | 23.874 | −3.411 | 1.00 | 22.22 | N |
| ATOM | 4164 | CA | THR B | 113 | −26.360 | 22.938 | −4.501 | 1.00 | 20.19 | C |
| ATOM | 4165 | CB | THR B | 113 | −27.552 | 22.892 | −5.485 | 1.00 | 19.36 | C |
| ATOM | 4166 | OG1 | THR B | 113 | −28.729 | 22.456 | −4.792 | 1.00 | 17.82 | O |
| ATOM | 4167 | CG2 | THR B | 113 | −27.273 | 21.958 | −6.651 | 1.00 | 13.73 | C |
| ATOM | 4168 | C | THR B | 113 | −25.089 | 23.349 | −5.244 | 1.00 | 20.58 | C |
| ATOM | 4169 | O | THR B | 113 | −24.209 | 22.519 | −5.493 | 1.00 | 21.05 | O |
| ATOM | 4170 | N | VAL B | 114 | −25.000 | 24.632 | −5.585 | 1.00 | 20.83 | N |
| ATOM | 4171 | CA | VAL B | 114 | −23.816 | 25.190 | −6.236 | 1.00 | 21.19 | C |
| ATOM | 4172 | CB | VAL B | 114 | −24.014 | 26.684 | −6.604 | 1.00 | 21.25 | C |
| ATOM | 4173 | CG1 | VAL B | 114 | −22.695 | 27.338 | −7.002 | 1.00 | 22.61 | C |
| ATOM | 4174 | CG2 | VAL B | 114 | −25.027 | 26.820 | −7.736 | 1.00 | 20.06 | C |
| ATOM | 4175 | C | VAL B | 114 | −22.565 | 24.978 | −5.375 | 1.00 | 21.66 | C |
| ATOM | 4176 | O | VAL B | 114 | −21.535 | 24.517 | −5.876 | 1.00 | 21.84 | O |
| ATOM | 4177 | N | GLN B | 115 | −22.672 | 25.281 | −4.082 | 1.00 | 21.39 | N |
| ATOM | 4178 | CA | GLN B | 115 | −21.540 | 25.129 | −3.167 | 1.00 | 21.64 | C |
| ATOM | 4179 | CB | GLN B | 115 | −21.829 | 25.746 | −1.794 | 1.00 | 22.11 | C |
| ATOM | 4180 | CG | GLN B | 115 | −21.679 | 27.269 | −1.745 | 1.00 | 26.11 | C |
| ATOM | 4181 | CD | GLN B | 115 | −20.373 | 27.767 | −2.366 | 1.00 | 32.13 | C |
| ATOM | 4182 | OE1 | GLN B | 115 | −20.388 | 28.590 | −3.289 | 1.00 | 33.28 | O |
| ATOM | 4183 | NE2 | GLN B | 115 | −19.240 | 27.264 | −1.871 | 1.00 | 32.33 | N |
| ATOM | 4184 | C | GLN B | 115 | −21.100 | 23.679 | −3.023 | 1.00 | 20.80 | C |
| ATOM | 4185 | O | GLN B | 115 | −19.902 | 23.392 | −3.054 | 1.00 | 20.91 | O |
| ATOM | 4186 | N | PHE B | 116 | −22.063 | 22.769 | −2.884 | 1.00 | 19.50 | N |
| ATOM | 4187 | CA | PHE B | 116 | −21.751 | 21.346 | −2.807 | 1.00 | 18.65 | C |
| ATOM | 4188 | CB | PHE B | 116 | −23.010 | 20.497 | −2.587 | 1.00 | 17.78 | C |
| ATOM | 4189 | CG | PHE B | 116 | −22.768 | 19.020 | −2.729 | 1.00 | 17.03 | C |
| ATOM | 4190 | CD1 | PHE B | 116 | −22.109 | 18.311 | −1.728 | 1.00 | 16.92 | C |
| ATOM | 4191 | CE1 | PHE B | 116 | −21.868 | 16.941 | −1.862 | 1.00 | 14.57 | C |
| ATOM | 4192 | CZ | PHE B | 116 | −22.280 | 16.274 | −3.006 | 1.00 | 15.39 | C |
| ATOM | 4193 | CE2 | PHE B | 116 | −22.937 | 16.969 | −4.015 | 1.00 | 16.00 | C |
| ATOM | 4194 | CD2 | PHE B | 116 | −23.176 | 18.339 | −3.874 | 1.00 | 17.81 | C |
| ATOM | 4195 | C | PHE B | 116 | −20.996 | 20.869 | −4.052 | 1.00 | 18.46 | C |
| ATOM | 4196 | O | PHE B | 116 | −19.935 | 20.253 | −3.937 | 1.00 | 18.72 | O |
| | | | | | gad67.pdb | | | | | |
| ATOM | 4197 | N | LEU B | 117 | −21.549 | 21.160 | −5.228 | 1.00 | 17.89 | N |
| ATOM | 4198 | CA | LEU B | 117 | −20.940 | 20.753 | −6.501 | 1.00 | 18.00 | C |
| ATOM | 4199 | CB | LEU B | 117 | −21.862 | 21.064 | −7.689 | 1.00 | 16.53 | C |
| ATOM | 4200 | CG | LEU B | 117 | −23.118 | 20.188 | −7.830 | 1.00 | 15.01 | C |
| ATOM | 4201 | CD1 | LEU B | 117 | −24.031 | 20.687 | −8.943 | 1.00 | 14.28 | C |
| ATOM | 4202 | CD2 | LEU B | 117 | −22.772 | 18.718 | −8.052 | 1.00 | 13.67 | C |
| ATOM | 4203 | C | LEU B | 117 | −19.545 | 21.343 | −6.705 | 1.00 | 18.60 | C |
| ATOM | 4204 | O | LEU B | 117 | −18.658 | 20.676 | −7.238 | 1.00 | 19.58 | O |
| ATOM | 4205 | N | LEU B | 118 | −19.351 | 22.582 | −6.258 | 1.00 | 19.58 | N |
| ATOM | 4206 | CA | LEU B | 118 | −18.029 | 23.219 | −6.280 | 1.00 | 19.70 | C |
| ATOM | 4207 | CB | LEU B | 118 | −18.139 | 24.715 | −5.973 | 1.00 | 19.89 | C |
| ATOM | 4208 | CG | LEU B | 118 | −18.646 | 25.620 | −7.103 | 1.00 | 20.93 | C |
| ATOM | 4209 | CD1 | LEU B | 118 | −18.882 | 27.024 | −6.584 | 1.00 | 21.69 | C |
| ATOM | 4210 | CD2 | LEU B | 118 | −17.682 | 25.638 | −8.285 | 1.00 | 20.61 | C |
| ATOM | 4211 | C | LEU B | 118 | −17.019 | 22.548 | −5.341 | 1.00 | 19.42 | C |
| ATOM | 4212 | O | LEU B | 118 | −15.821 | 22.503 | −5.640 | 1.00 | 18.53 | O |
| ATOM | 4213 | N | GLU B | 119 | −17.507 | 22.031 | −4.214 | 1.00 | 19.46 | N |

TABLE A-continued

| | | | | | | | | | |
|---|---|---|---|---|---|---|---|---|---|
| ATOM | 4214 | CA | GLU B | 119 | −16.678 | 21.241 | −3.300 | 1.00 | 19.81 | C |
| ATOM | 4215 | CB | GLU B | 119 | −17.376 | 21.031 | −1.949 | 1.00 | 20.98 | C |
| ATOM | 4216 | CG | GLU B | 119 | −17.530 | 22.293 | −1.090 | 1.00 | 26.57 | C |
| ATOM | 4217 | CD | GLU B | 119 | −16.203 | 22.867 | −.598 | 1.00 | 35.78 | C |
| ATOM | 4218 | OE1 | GLU B | 119 | −16.171 | 24.068 | −.269 | 1.00 | 40.80 | O |
| ATOM | 4219 | OE2 | GLU B | 119 | −15.191 | 22.134 | −.539 | 1.00 | 37.84 | O |
| ATOM | 4220 | C | GLU B | 119 | −16.288 | 19.890 | −3.904 | 1.00 | 18.79 | C |
| ATOM | 4221 | O | GLU B | 119 | −15.168 | 19.422 | −3.698 | 1.00 | 18.87 | O |
| ATOM | 4222 | N | VAL B | 120 | −17.216 | 19.269 | −4.633 | 1.00 | 17.89 | N |
| ATOM | 4223 | CA | VAL B | 120 | −16.930 | 18.042 | −5.383 | 1.00 | 17.75 | C |
| ATOM | 4224 | CB | VAL B | 120 | −18.203 | 17.448 | −6.051 | 1.00 | 17.91 | C |
| ATOM | 4225 | CG1 | VAL B | 120 | −17.849 | 16.237 | −6.928 | 1.00 | 15.87 | C |
| ATOM | 4226 | CG2 | VAL B | 120 | −19.253 | 17.073 | −5.006 | 1.00 | 16.02 | C |
| ATOM | 4227 | C | VAL B | 120 | −15.869 | 18.333 | −6.455 | 1.00 | 18.53 | C |
| ATOM | 4228 | O | VAL B | 120 | −14.852 | 17.651 | −6.522 | 1.00 | 18.68 | O |
| ATOM | 4229 | N | VAL B | 121 | −16.111 | 19.359 | −7.272 | 1.00 | 18.45 | N |
| ATOM | 4230 | CA | VAL B | 121 | −15.183 | 19.755 | −8.333 | 1.00 | 19.78 | C |
| ATOM | 4231 | CB | VAL B | 121 | −15.700 | 20.995 | −9.107 | 1.00 | 19.35 | C |
| ATOM | 4232 | CG1 | VAL B | 121 | −14.619 | 21.592 | −10.006 | 1.00 | 19.49 | C |
| ATOM | 4233 | CG2 | VAL B | 121 | −16.924 | 20.615 | −9.937 | 1.00 | 17.87 | C |
| ATOM | 4234 | C | VAL B | 121 | −13.762 | 19.965 | −7.803 | 1.00 | 21.62 | C |
| ATOM | 4235 | O | VAL B | 121 | −12.790 | 19.536 | −8.429 | 1.00 | 22.69 | O |
| ATOM | 4236 | N | ASP B | 122 | −13.656 | 20.592 | −6.635 | 1.00 | 22.87 | N |
| ATOM | 4237 | CA | ASP B | 122 | −12.367 | 20.868 | −6.003 | 1.00 | 24.12 | C |
| ATOM | 4238 | CB | ASP B | 122 | −12.576 | 21.697 | −4.740 | 1.00 | 26.11 | C |
| ATOM | 4239 | CG | ASP B | 122 | −11.528 | 22.789 | −4.566 | 1.00 | 34.61 | C |
| ATOM | 4240 | OD1 | ASP B | 122 | −10.353 | 22.650 | −5.247 | 1.00 | 43.33 | O |
| ATOM | 4241 | OD2 | ASP B | 122 | −11.893 | 23.844 | −3.747 | 1.00 | 39.53 | O |
| ATOM | 4242 | C | ASP B | 122 | −11.609 | 19.587 | −5.660 | 1.00 | 23.31 | C |
| ATOM | 4243 | O | ASP B | 122 | −10.386 | 19.527 | −5.810 | 1.00 | 23.20 | O |
| ATOM | 4244 | N | ILE B | 123 | −12.344 | 18.574 | −5.197 | 1.00 | 22.23 | N |
| ATOM | 4245 | CA | ILE B | 123 | −11.783 | 17.243 | −4.955 | 1.00 | 21.24 | C |
| ATOM | 4246 | CB | ILE B | 123 | −12.831 | 16.291 | −4.303 | 1.00 | 20.79 | C |
| ATOM | 4247 | CG1 | ILE B | 123 | −13.215 | 16.799 | −2.908 | 1.00 | 20.82 | C |
| ATOM | 4248 | CD1 | ILE B | 123 | −14.498 | 16.192 | −2.345 | 1.00 | 20.92 | C |
| ATOM | 4249 | CG2 | ILE B | 123 | −12.298 | 14.857 | −4.218 | 1.00 | 19.64 | C |
| ATOM | 4250 | C | ILE B | 123 | −11.237 | 16.639 | −6.254 | 1.00 | 20.58 | C |
| ATOM | 4251 | O | ILE B | 123 | −10.139 | 16.077 | −6.274 | 1.00 | 20.13 | O |
| ATOM | 4252 | N | LEU B | 124 | −12.005 | 16.787 | −7.333 | 1.00 | 19.79 | N |
| ATOM | 4253 | CA | LEU B | 124 | −11.651 | 16.228 | −8.636 | 1.00 | 20.36 | C |
| ATOM | 4254 | CB | LEU B | 124 | −12.864 | 16.225 | −9.576 | 1.00 | 19.45 | C |
| ATOM | 4255 | CG | LEU B | 124 | −14.176 | 15.632 | −9.037 | 1.00 | 17.59 | C |
| ATOM | 4256 | CD1 | LEU B | 124 | −15.314 | 15.831 | −10.031 | 1.00 | 13.49 | C |
| ATOM | 4257 | CD2 | LEU B | 124 | −14.023 | 14.161 | −8.670 | 1.00 | 12.13 | C |
| ATOM | 4258 | C | LEU B | 124 | −10.475 | 16.963 | −9.278 | 1.00 | 20.77 | C |
| ATOM | 4259 | O | LEU B | 124 | −9.623 | 16.341 | −9.914 | 1.00 | 20.61 | O |
| ATOM | 4260 | N | LEU B | 125 | −10.438 | 18.283 | −9.105 | 1.00 | 21.87 | N |
| ATOM | 4261 | CA | LEU B | 125 | −9.335 | 19.105 | −9.600 | 1.00 | 23.38 | C |
| ATOM | 4262 | CB | LEU B | 125 | −9.649 | 20.592 | −9.428 | 1.00 | 23.30 | C |
| ATOM | 4263 | CG | LEU B | 125 | −10.141 | 21.415 | −10.627 | 1.00 | 24.87 | C |
| ATOM | 4264 | CD1 | LEU B | 125 | −10.890 | 20.603 | −11.676 | 1.00 | 22.84 | C |
| | | | | | gad67.pdb | | | | | |
| ATOM | 4265 | CD2 | LEU B | 125 | −10.987 | 22.585 | −10.144 | 1.00 | 24.08 | C |
| ATOM | 4266 | C | LEU B | 125 | −8.007 | 18.742 | −8.933 | 1.00 | 24.11 | C |
| ATOM | 4267 | O | LEU B | 125 | −6.976 | 18.648 | −9.608 | 1.00 | 24.91 | O |
| ATOM | 4268 | N | ASN B | 126 | −8.040 | 18.523 | −7.619 | 1.00 | 23.65 | N |
| ATOM | 4269 | CA | ASN B | 126 | −6.862 | 18.047 | −6.890 | 1.00 | 24.58 | C |
| ATOM | 4270 | CB | ASN B | 126 | −7.140 | 17.959 | −5.386 | 1.00 | 25.09 | C |
| ATOM | 4271 | CG | ASN B | 126 | −5.930 | 17.470 | −4.593 | 1.00 | 30.96 | C |
| ATOM | 4272 | OD1 | ASN B | 126 | −5.967 | 16.401 | −3.987 | 1.00 | 34.51 | O |
| ATOM | 4273 | ND2 | ASN B | 126 | −4.848 | 18.247 | −4.608 | 1.00 | 33.33 | N |
| ATOM | 4274 | C | ASN B | 126 | −6.357 | 16.701 | −7.416 | 1.00 | 23.69 | C |
| ATOM | 4275 | O | ASN B | 126 | −5.149 | 16.486 | −7.537 | 1.00 | 24.81 | O |
| ATOM | 4276 | N | TYR B | 127 | −7.292 | 15.808 | −7.726 | 1.00 | 22.23 | N |
| ATOM | 4277 | CA | TYR B | 127 | −6.982 | 14.506 | −8.303 | 1.00 | 21.25 | C |
| ATOM | 4278 | CB | TYR B | 127 | −8.238 | 13.634 | −8.316 | 1.00 | 21.31 | C |
| ATOM | 4279 | CG | TYR B | 127 | −8.025 | 12.218 | −8.809 | 1.00 | 21.65 | C |
| ATOM | 4280 | CD1 | TYR B | 127 | −7.639 | 11.206 | −7.932 | 1.00 | 23.42 | C |
| ATOM | 4281 | CE1 | TYR B | 127 | −7.453 | 9.898 | −8.378 | 1.00 | 24.01 | C |
| ATOM | 4282 | CZ | TYR B | 127 | −7.659 | 9.598 | −9.719 | 1.00 | 23.16 | C |
| ATOM | 4283 | OH | TYR B | 127 | −7.479 | 8.313 | −10.170 | 1.00 | 23.52 | O |
| ATOM | 4284 | CE2 | TYR B | 127 | −8.048 | 10.588 | −10.609 | 1.00 | 22.45 | C |
| ATOM | 4285 | CD2 | TYR B | 127 | −8.229 | 11.887 | −10.150 | 1.00 | 19.15 | C |
| ATOM | 4286 | C | TYR B | 127 | −6.390 | 14.624 | −9.715 | 1.00 | 20.99 | C |
| ATOM | 4287 | O | TYR B | 127 | −5.458 | 13.898 | −10.056 | 1.00 | 19.86 | O |
| ATOM | 4288 | N | VAL B | 128 | −6.939 | 15.533 | −10.522 | 1.00 | 21.02 | N |
| ATOM | 4289 | CA | VAL B | 128 | −6.404 | 15.832 | −11.851 | 1.00 | 21.72 | C |
| ATOM | 4290 | CB | VAL B | 128 | −7.315 | 16.819 | −12.640 | 1.00 | 22.27 | C |
| ATOM | 4291 | CG1 | VAL B | 128 | −6.639 | 17.289 | −13.928 | 1.00 | 22.24 | C |
| ATOM | 4292 | CG2 | VAL B | 128 | −8.652 | 16.169 | −12.967 | 1.00 | 21.38 | C |

TABLE A-continued

| | | | | | | | | | |
|---|---|---|---|---|---|---|---|---|---|
| ATOM | 4293 | C | VAL B | 128 | −4.962 | 16.353 | −11.772 | 1.00 | 22.76 | C |
| ATOM | 4294 | O | VAL B | 128 | −4.097 | 15.881 | −12.516 | 1.00 | 22.58 | O |
| ATOM | 4295 | N | ARG B | 129 | −4.714 | 17.308 | −10.869 | 1.00 | 23.76 | N |
| ATOM | 4296 | CA | ARG B | 129 | −3.364 | 17.833 | −10.608 | 1.00 | 25.93 | C |
| ATOM | 4297 | CB | ARG B | 129 | −3.365 | 18.816 | −9.431 | 1.00 | 25.11 | C |
| ATOM | 4298 | CG | ARG B | 129 | −4.022 | 20.168 | −9.657 | 1.00 | 28.38 | C |
| ATOM | 4299 | CD | ARG B | 129 | −4.018 | 20.943 | −8.331 | 1.00 | 30.15 | C |
| ATOM | 4300 | NE | ARG B | 129 | −4.791 | 22.185 | −8.369 | 1.00 | 38.13 | N |
| ATOM | 4301 | CZ | ARG B | 129 | −4.283 | 23.383 | −8.659 | 1.00 | 42.29 | C |
| ATOM | 4302 | NH1 | ARG B | 129 | −5.068 | 24.455 | −8.660 | 1.00 | 44.23 | N |
| ATOM | 4303 | NH2 | ARG B | 129 | −2.993 | 23.519 | −8.949 | 1.00 | 40.81 | N |
| ATOM | 4304 | C | ARG B | 129 | −2.371 | 16.718 | −10.284 | 1.00 | 25.72 | C |
| ATOM | 4305 | O | ARG B | 129 | −1.290 | 16.647 | −10.873 | 1.00 | 26.05 | O |
| ATOM | 4306 | N | LYS B | 130 | −2.749 | 15.857 | −9.341 | 1.00 | 26.00 | N |
| ATOM | 4307 | CA | LYS B | 130 | −1.871 | 14.795 | −8.842 | 1.00 | 26.73 | C |
| ATOM | 4308 | CB | LYS B | 130 | −2.393 | 14.244 | −7.511 | 1.00 | 26.34 | C |
| ATOM | 4309 | CG | LYS B | 130 | −2.129 | 15.164 | −6.323 | 1.00 | 28.41 | C |
| ATOM | 4310 | CD | LYS B | 130 | −2.552 | 14.532 | −5.001 | 1.00 | 28.74 | C |
| ATOM | 4313 | C | LYS B | 130 | −1.645 | 13.660 | −9.837 | 1.00 | 26.76 | C |
| ATOM | 4314 | O | LYS B | 130 | −.665 | 12.923 | −9.725 | 1.00 | 27.36 | O |
| ATOM | 4315 | N | THR B | 131 | −2.552 | 13.528 | −10.802 | 1.00 | 26.89 | N |
| ATOM | 4316 | CA | THR B | 131 | −2.460 | 12.504 | −11.844 | 1.00 | 27.82 | C |
| ATOM | 4317 | CB | THR B | 131 | −3.733 | 12.506 | −12.731 | 1.00 | 27.83 | C |
| ATOM | 4318 | OG1 | THR B | 131 | −4.812 | 11.887 | −12.022 | 1.00 | 29.44 | O |
| ATOM | 4319 | CG2 | THR B | 131 | −3.509 | 11.758 | −14.026 | 1.00 | 27.61 | C |
| ATOM | 4320 | C | THR B | 131 | −1.209 | 12.688 | −12.708 | 1.00 | 27.97 | C |
| ATOM | 4321 | O | THR B | 131 | −.556 | 11.716 | −13.088 | 1.00 | 27.92 | O |
| ATOM | 4322 | N | PHE 8 | 132 | −.872 | 13.940 | −12.988 | 1.00 | 28.60 | N |
| ATOM | 4323 | CA | PHE B | 132 | .244 | 14.263 | −13.872 | 1.00 | 30.75 | C |
| ATOM | 4324 | CB | PHE B | 132 | −.126 | 15.459 | −14.755 | 1.00 | 29.79 | C |
| ATOM | 4325 | CG | PHE B | 132 | −1.331 | 15.213 | −15.619 | 1.00 | 28.51 | C |
| ATOM | 4326 | CD1 | PHE B | 132 | −1.196 | 14.615 | −16.867 | 1.00 | 25.62 | C |
| ATOM | 4327 | CE1 | PHE B | 132 | −2.312 | 14.376 | −17.667 | 1.00 | 25.85 | C |
| ATOM | 4328 | CZ | PHE B | 132 | −3.579 | 14.729 | −17.217 | 1.00 | 26.21 | C |
| ATOM | 4329 | CE2 | PHE B | 132 | −3.727 | 15.317 | −15.966 | 1.00 | 23.60 | C |
| ATOM | 4330 | CD2 | PHE B | 132 | −2.604 | 15.554 | −15.175 | 1.00 | 25.52 | C |
| ATOM | 4331 | C | PHE B | 132 | 1.557 | 14.502 | −13.116 | 1.00 | 32.67 | C |
| ATOM | 4332 | O | PHE B | 132 | 2.572 | 14.880 | −13.711 | 1.00 | 33.59 | O |
| ATOM | 4333 | N | ASP B | 133 | 1.522 | 14.259 | −11.807 | 1.00 | 34.03 | N |
| ATOM | 4334 | CA | ASP B | 133 | 2.682 | 14.385 | −10.933 | 1.00 | 35.36 | C |
| | | | | gad67.pdb | | | | | | |
| ATOM | 4335 | CB | ASP B | 133 | 2.257 | 15.046 | −9.614 | 1.00 | 35.91 | C |
| ATOM | 4336 | CG | ASP B | 133 | 3.428 | 15.361 | −8.697 | 1.00 | 40.16 | C |
| ATOM | 4337 | OD1 | ASP B | 133 | 4.594 | 15.065 | −9.048 | 1.00 | 43.84 | O |
| ATOM | 4338 | OD2 | ASP B | 133 | 3.175 | 15.914 | −7.606 | 1.00 | 43.88 | O |
| ATOM | 4339 | C | ASP B | 133 | 3.291 | 13.000 | −10.684 | 1.00 | 35.40 | C |
| ATOM | 4340 | O | ASP B | 133 | 2.629 | 12.107 | −10.158 | 1.00 | 35.52 | O |
| ATOM | 4341 | N | ARG B | 134 | 4.557 | 12.837 | −11.059 | 1.00 | 35.37 | N |
| ATOM | 4342 | CA | ARG B | 134 | 5.231 | 11.536 | −10.996 | 1.00 | 35.61 | C |
| ATOM | 4343 | CB | ARG B | 134 | 6.431 | 11.512 | −11.945 | 1.00 | 35.76 | C |
| ATOM | 4344 | CG | ARG B | 134 | 6.055 | 11.331 | −13.403 | 1.00 | 35.15 | C |
| ATOM | 4345 | CD | ARG B | 134 | 7.222 | 11.680 | −14.310 | 1.00 | 34.47 | C |
| ATOM | 4346 | NE | ARG B | 134 | 6.850 | 11.631 | −15.724 | 1.00 | 34.10 | N |
| ATOM | 4347 | CZ | ARG B | 134 | 6.233 | 12.613 | −16.377 | 1.00 | 32.69 | C |
| ATOM | 4348 | NH1 | ARG B | 134 | 5.905 | 13.734 | −15.747 | 1.00 | 30.63 | N |
| ATOM | 4349 | NH2 | ARG B | 134 | 5.940 | 12.472 | −17.664 | 1.00 | 29.78 | N |
| ATOM | 4350 | C | ARG B | 134 | 5.649 | 11.100 | −9.585 | 1.00 | 35.98 | C |
| ATOM | 4351 | O | ARG B | 134 | 6.044 | 9.947 | −9.377 | 1.00 | 36.10 | O |
| ATOM | 4352 | N | SER B | 135 | 5.562 | 12.020 | −8.626 | 1.00 | 35.71 | N |
| ATOM | 4353 | CA | SER B | 135 | 5.790 | 11.693 | −7.218 | 1.00 | 35.42 | C |
| ATOM | 4354 | CB | SER B | 135 | 6.045 | 12.962 | −6.403 | 1.00 | 35.39 | C |
| ATOM | 4356 | C | SER B | 135 | 4.609 | 10.911 | −6.629 | 1.00 | 35.27 | C |
| ATOM | 4357 | O | SER B | 135 | 4.766 | 10.179 | −5.644 | 1.00 | 35.81 | O |
| ATOM | 4358 | N | THR B | 136 | 3.434 | 11.074 | −7.237 | 1.00 | 34.14 | N |
| ATOM | 4359 | CA | THR B | 136 | 2.231 | 10.338 | −6.848 | 1.00 | 33.27 | C |
| ATOM | 4360 | CB | THR B | 136 | .964 | 10.963 | −7.480 | 1.00 | 33.80 | C |
| ATOM | 4361 | OG1 | THR B | 136 | .972 | 12.382 | −7.280 | 1.00 | 36.14 | O |
| ATOM | 4362 | CG2 | THR B | 136 | −.308 | 10.377 | −6.866 | 1.00 | 34.41 | C |
| ATOM | 4363 | C | THR B | 136 | 2.341 | 8.878 | −7.285 | 1.00 | 31.79 | C |
| ATOM | 4364 | O | THR B | 136 | 2.822 | 8.585 | −8.380 | 1.00 | 31.85 | O |
| ATOM | 4365 | N | LYS B | 137 | 1.904 | 7.967 | −6.420 | 1.00 | 30.20 | N |
| ATOM | 4366 | CA | LYS B | 137 | 1.852 | 6.546 | −6.761 | 1.00 | 29.09 | C |
| ATOM | 4367 | CB | LYS B | 137 | 1.631 | 5.693 | −5.506 | 1.00 | 28.58 | C |
| ATOM | 4368 | CG | LYS B | 137 | 2.897 | 5.422 | −4.693 | 1.00 | 29.82 | C |
| ATOM | 4369 | CD | LYS B | 137 | 2.578 | 4.891 | −3.290 | 1.00 | 30.71 | C |
| ATOM | 4370 | CE | LYS B | 137 | 2.084 | 3.452 | −3.302 | 1.00 | 36.30 | C |
| ATOM | 4371 | NZ | LYS B | 137 | 1.832 | 2.935 | −1.923 | 1.00 | 39.80 | N |
| ATOM | 4372 | C | LYS B | 137 | .743 | 6.275 | −7.775 | 1.00 | 27.20 | C |
| ATOM | 4373 | O | LYS B | 137 | −.299 | 6.942 | −7.768 | 1.00 | 26.74 | O |
| ATOM | 4374 | N | VAL B | 138 | .977 | 5.299 | −8.648 | 1.00 | 25.56 | N |

TABLE A-continued

| | | | | | | | | | | |
|---|---|---|---|---|---|---|---|---|---|---|
| ATOM | 4375 | CA | VAL B | 138 | −.034 | 4.850 | −9.605 | 1.00 | 23.86 | C |
| ATOM | 4376 | CB | VAL B | 138 | .543 | 3.818 | −10.610 | 1.00 | 22.71 | C |
| ATOM | 4377 | CG1 | VAL B | 138 | −.531 | 3.331 | −11.570 | 1.00 | 20.65 | C |
| ATOM | 4378 | CG2 | VAL B | 138 | 1.684 | 4.432 | −11.394 | 1.00 | 22.23 | C |
| ATOM | 4379 | C | VAL B | 138 | −1.237 | 4.282 | −8.853 | 1.00 | 24.06 | C |
| ATOM | 4380 | O | VAL B | 138 | −2.378 | 4.529 | −9.230 | 1.00 | 23.84 | O |
| ATOM | 4381 | N | LEU B | 139 | −.966 | 3.542 | −7.779 | 1.00 | 25.38 | N |
| ATOM | 4382 | CA | LEU B | 139 | −2.009 | 2.996 | −6.906 | 1.00 | 26.34 | C |
| ATOM | 4383 | CD | LEU B | 139 | −2.636 | 1.739 | −7.530 | 1.00 | 25.88 | C |
| ATOM | 4384 | CG | LEU B | 139 | −1.897 | .393 | −7.481 | 1.00 | 27.37 | C |
| ATOM | 4385 | CD1 | LEU B | 139 | −2.843 | −.735 | −7.868 | 1.00 | 24.67 | C |
| ATOM | 4386 | CD2 | LEU B | 139 | −.636 | .368 | −8.356 | 1.00 | 27.57 | C |
| ATOM | 4387 | C | LEU B | 139 | −1.471 | 2.670 | −5.511 | 1.00 | 27.20 | C |
| ATOM | 4388 | O | LEU B | 139 | −.294 | 2.350 | −5.347 | 1.00 | 27.64 | O |
| ATOM | 4389 | N | ASP B | 140 | −2.341 | 2.771 | −4.511 | 1.00 | 28.51 | N |
| ATOM | 4390 | CA | ASP B | 140 | −2.072 | 2.233 | −3.182 | 1.00 | 29.20 | C |
| ATOM | 4391 | CB | ASP B | 140 | −2.549 | 3.213 | −2.101 | 1.00 | 30.58 | C |
| ATOM | 4392 | CG | ASP B | 140 | −2.168 | 2.779 | −.685 | 1.00 | 35.75 | C |
| ATOM | 4393 | OD1 | ASP B | 140 | −1.201 | 2.003 | −.513 | 1.00 | 40.73 | O |
| ATOM | 4394 | OD2 | ASP B | 140 | −2.842 | 3.229 | .270 | 1.00 | 41.65 | O |
| ATOM | 4395 | C | ASP B | 140 | −2.826 | .909 | −3.105 | 1.00 | 28.60 | C |
| ATOM | 4396 | O | ASP B | 140 | −4.029 | .886 | −2.841 | 1.00 | 29.33 | O |
| ATOM | 4397 | N | PHE B | 141 | −2.124 | −.190 | −3.365 | 1.00 | 27.77 | N |
| ATOM | 4398 | CA | PHE B | 141 | −2.785 | −1.485 | −3.539 | 1.00 | 26.53 | C |
| ATOM | 4399 | CB | PHE B | 141 | −1.916 | −2.459 | −4.342 | 1.00 | 25.89 | C |
| ATOM | 4400 | CG | PHE B | 141 | −2.518 | −3.833 | −4.473 | 1.00 | 24.76 | C |
| ATOM | 4401 | CD1 | PHE B | 141 | −3.675 | −4.031 | −5.224 | 1.00 | 22.74 | C |
| ATOM | 4402 | CE1 | PHE B | 141 | −4.247 | −5.298 | −5.341 | 1.00 | 21.01 | C |
| ATOM | 4403 | CZ | PHE B | 141 | −3.657 | −6.384 | −4.706 | 1.00 | 23.74 | C |
| | | | | gad67.pdb | | | | | | |
| ATOM | 4404 | CE2 | PHE B | 141 | −2.498 | −6.200 | −3.952 | 1.00 | 26.18 | C |
| ATOM | 4405 | CD2 | PHE B | 141 | −1.936 | −4.926 | −3.838 | 1.00 | 25.30 | C |
| ATOM | 4406 | C | PHE B | 141 | −3.254 | −2.144 | −2.243 | 1.00 | 26.07 | C |
| ATOM | 4407 | O | PHE B | 141 | −2.515 | −2.228 | −1.261 | 1.00 | 26.20 | O |
| ATOM | 4408 | N | HIS B | 142 | −4.492 | −2.623 | −2.270 | 1.00 | 25.24 | N |
| ATOM | 4409 | CA | HIS B | 142 | −5.074 | −3.347 | −1.152 | 1.00 | 25.03 | C |
| ATOM | 4410 | CB | HIS B | 142 | −6.034 | −2.448 | −.361 | 1.00 | 24.49 | C |
| ATOM | 4411 | CG | HIS B | 142 | −5.401 | −1.191 | .143 | 1.00 | 24.70 | C |
| ATOM | 4412 | ND1 | HIS B | 142 | −4.738 | −1.122 | 1.348 | 1.00 | 27.23 | N |
| ATOM | 4413 | CE1 | HIS B | 142 | −4.274 | .103 | 1.524 | 1.00 | 29.02 | C |
| ATOM | 4414 | NE2 | HIS B | 142 | −4.612 | .832 | .475 | 1.00 | 28.13 | N |
| ATOM | 4415 | CD2 | HIS B | 142 | −5.316 | .045 | −.404 | 1.00 | 26.31 | C |
| ATOM | 4416 | C | HIS B | 142 | −5.805 | −4.577 | −1.674 | 1.00 | 24.66 | C |
| ATOM | 4417 | O | HIS B | 142 | −6.506 | −4.510 | −2.692 | 1.00 | 24.01 | O |
| ATOM | 4418 | N | HIS B | 143 | −5.621 | −5.699 | −.983 | 1.00 | 23.74 | N |
| ATOM | 4419 | CA | HIS B | 143 | −6.372 | −6.908 | −1.271 | 1.00 | 23.90 | C |
| ATOM | 4420 | CB | HIS B | 143 | −5.853 | −8.077 | −.430 | 1.00 | 23.76 | C |
| ATOM | 4421 | CG | HIS B | 143 | −4.510 | −8.575 | −.865 | 1.00 | 23.96 | C |
| ATOM | 4422 | ND1 | HIS B | 143 | −4.357 | −9.604 | −1.769 | 1.00 | 24.82 | N |
| ATOM | 4423 | CE1 | HIS B | 143 | −3.069 | −9.822 | −1.972 | 1.00 | 23.79 | C |
| ATOM | 4424 | NE2 | HIS B | 143 | −2.381 | −8.965 | −1.237 | 1.00 | 23.24 | N |
| ATOM | 4425 | CD2 | HIS B | 143 | −3.259 | −8.173 | −.536 | 1.00 | 23.46 | C |
| ATOM | 4426 | C | HIS B | 143 | −7.849 | −6.650 | −.999 | 1.00 | 24.44 | C |
| ATOM | 4427 | O | HIS B | 143 | −8.179 | −5.845 | −.118 | 1.00 | 23.91 | O |
| ATOM | 4428 | N | PRO B | 144 | −8.743 | −7.307 | −1.768 | 1.00 | 25.01 | N |
| ATOM | 4429 | CA | PRO B | 144 | −10.186 | −7.105 | −1.609 | 1.00 | 26.23 | C |
| ATOM | 4430 | CB | PRO B | 144 | −10.784 | −8.277 | −2.385 | 1.00 | 25.66 | C |
| ATOM | 4431 | CG | PRO B | 144 | −9.787 | −8.565 | −3.437 | 1.00 | 24.08 | C |
| ATOM | 4432 | CD | PRO B | 144 | −8.442 | −8.271 | −2.844 | 1.00 | 24.14 | C |
| ATOM | 4433 | C | PRO B | 144 | −10.651 | −7.121 | −.148 | 1.00 | 28.38 | C |
| ATOM | 4434 | O | PRO B | 144 | −11.387 | −6.219 | .266 | 1.00 | 28.83 | O |
| ATOM | 4435 | N | HIS B | 145 | −10.196 | −8.108 | .628 | 1.00 | 30.76 | N |
| ATOM | 4436 | CA | HIS B | 145 | −10.611 | −8.249 | 2.031 | 1.00 | 32.67 | C |
| ATOM | 4437 | CB | HIS B | 145 | −10.140 | −9.585 | 2.632 | 1.00 | 32.93 | C |
| ATOM | 4438 | CG | HIS B | 145 | −8.652 | −9.763 | 2.648 | 1.00 | 34.91 | C |
| ATOM | 4439 | ND1 | HIS B | 145 | −7.854 | −9.283 | 3.665 | 1.00 | 36.09 | N |
| ATOM | 4440 | CE1 | HIS B | 145 | −6.594 | −9.591 | 3.417 | 1.00 | 35.18 | C |
| ATOM | 4441 | NE2 | HIS B | 145 | −6.545 | −10.262 | 2.280 | 1.00 | 35.86 | N |
| ATOM | 4442 | CD2 | HIS B | 145 | −7.819 | −10.385 | 1.779 | 1.00 | 35.85 | C |
| ATOM | 4443 | C | HIS B | 145 | −10.215 | −7.071 | 2.923 | 1.00 | 34.24 | C |
| ATOM | 4444 | O | HIS B | 145 | −10.917 | −6.770 | 3.890 | 1.00 | 34.67 | O |
| ATOM | 4445 | N | GLN B | 146 | −9.116 | −6.395 | 2.584 | 1.00 | 35.83 | N |
| ATOM | 4446 | CA | GLN B | 146 | −8.662 | −5.213 | 3.327 | 1.00 | 37.59 | C |
| ATOM | 4447 | CB | GLN B | 146 | −7.293 | −4.736 | 2.834 | 1.00 | 37.66 | C |
| ATOM | 4448 | CG | GLN B | 146 | −6.153 | −5.731 | 2.990 | 1.00 | 38.51 | C |
| ATOM | 4449 | CD | GLN B | 146 | −4.811 | −5.144 | 2.573 | 1.00 | 39.32 | C |
| ATOM | 4450 | OE1 | GLN B | 146 | −4.065 | −5.753 | 1.804 | 1.00 | 42.75 | O |
| ATOM | 4451 | NE2 | GLN B | 146 | −4.501 | −3.950 | 3.076 | 1.00 | 42.66 | N |
| ATOM | 4452 | C | GLN B | 146 | −9.650 | −4.051 | 3.245 | 1.00 | 38.44 | C |
| ATOM | 4453 | O | GLN B | 146 | −9.915 | −3.392 | 4.250 | 1.00 | 39.51 | O |

TABLE A-continued

| ATOM | 4454 | N   | LEU B | 147 | −10.181 | −3.797 | 2.049  | 1.00 | 39.41 | N |
|------|------|-----|-------|-----|---------|--------|--------|------|-------|---|
| ATOM | 4455 | CA  | LEU B | 147 | −11.128 | −2.698 | 1.842  | 1.00 | 40.26 | C |
| ATOM | 4456 | CB  | LEU B | 147 | −11.185 | −2.285 | .368   | 1.00 | 39.97 | C |
| ATOM | 4457 | CG  | LEU B | 147 | −9.928  | −1.791 | −.360  | 1.00 | 39.29 | C |
| ATOM | 4458 | CD1 | LEU B | 147 | −10.233 | −1.581 | −1.835 | 1.00 | 36.47 | C |
| ATOM | 4459 | CD2 | LEU B | 147 | −9.369  | −.511  | .258   | 1.00 | 38.13 | C |
| ATOM | 4460 | C   | LEU B | 147 | −12.531 | −3.040 | 2.343  | 1.00 | 41.40 | C |
| ATOM | 4461 | O   | LEU B | 147 | −13.269 | −2.158 | 2.785  | 1.00 | 41.66 | O |
| ATOM | 4462 | N   | LEU B | 148 | −12.886 | −4.322 | 2.262  | 1.00 | 42.51 | N |
| ATOM | 4463 | CA  | LEU B | 148 | −14.167 | −4.837 | 2.756  | 1.00 | 44.09 | C |
| ATOM | 4464 | CB  | LEU B | 148 | −14.347 | −6.290 | 2.299  | 1.00 | 43.59 | C |
| ATOM | 4465 | CG  | LEU B | 148 | −15.471 | −6.722 | 1.343  | 1.00 | 43.14 | C |
| ATOM | 4466 | CD1 | LEU B | 148 | −15.005 | −7.919 | .518   | 1.00 | 42.07 | C |
| ATOM | 4467 | CD2 | LEU B | 148 | −15.978 | −5.614 | .427   | 1.00 | 41.29 | C |
| ATOM | 4468 | C   | LEU B | 148 | −14.325 | −4.751 | 4.278  | 1.00 | 45.64 | C |
| ATOM | 4470 | N   | GLU B | 149 | −13.202 | −4.689 | 4.987  | 1.00 | 48.44 | N |
| ATOM | 4471 | CA  | GLU B | 149 | −13.195 | −4.723 | 6.449  | 1.00 | 50.54 | C |
| ATOM | 4472 | CB  | GLU B | 149 | −12.045 | −5.606 | 6.951  | 1.00 | 50.54 | C | gad67.pdb

| ATOM | 4473 | CG  | GLU B | 149 | −12.298 | −7.104 | 6.811 | 1.00 | 52.20 | C |
|------|------|-----|-------|-----|---------|--------|-------|------|-------|---|
| ATOM | 4474 | CD  | GLU B | 149 | −11.018 | −7.931 | 6.811 | 1.00 | 54.23 | C |
| ATOM | 4475 | OE1 | GLU B | 149 | −9.925  | −7.364 | 7.044 | 1.00 | 54.91 | O |
| ATOM | 4476 | OE2 | GLU B | 149 | −11.105 | −9.154 | 6.567 | 1.00 | 54.00 | O |
| ATOM | 4477 | C   | GLU B | 149 | −13.120 | −3.340 | 7.103 | 1.00 | 51.66 | C |
| ATOM | 4478 | O   | GLU B | 149 | −13.007 | −3.234 | 8.326 | 1.00 | 52.35 | O |
| ATOM | 4479 | N   | GLY B | 150 | −13.192 | −2.288 | 6.290 | 1.00 | 52.52 | N |
| ATOM | 4480 | CA  | GLY B | 150 | −13.139 | −.916  | 6.796 | 1.00 | 53.51 | C |
| ATOM | 4481 | C   | GLY B | 150 | −11.739 | −.343  | 6.724 | 1.00 | 54.37 | C |
| ATOM | 4482 | O   | GLY B | 150 | −10.922 | −.554  | 7.623 | 1.00 | 54.43 | O |
| ATOM | 4483 | N   | MET B | 151 | −11.471 | .391   | 5.647 | 1.00 | 55.23 | N |
| ATOM | 4484 | CA  | MET B | 151 | −10.141 | .917   | 5.364 | 1.00 | 55.91 | C |
| ATOM | 4485 | CB  | MET B | 151 | −9.439  | .016   | 4.330 | 1.00 | 56.44 | C |
| ATOM | 4486 | CG  | MET B | 151 | −8.148  | .564   | 3.733 | 1.00 | 57.41 | C |
| ATOM | 4487 | SD  | MET B | 151 | −6.749  | .452   | 4.850 | 1.00 | 62.82 | S |
| ATOM | 4488 | CE  | MET B | 151 | −5.693  | 1.752  | 4.209 | 1.00 | 59.92 | C |
| ATOM | 4489 | C   | MET B | 151 | −10.213 | 2.382  | 4.889 | 1.00 | 55.93 | C |
| ATOM | 4490 | O   | MET B | 151 | −10.351 | 2.637  | 3.691 | 1.00 | 56.56 | O |
| ATOM | 4491 | N   | GLU B | 152 | −10.138 | 3.351  | 5.805 | 1.00 | 55.25 | N |
| ATOM | 4492 | CA  | GLU B | 152 | −10.067 | 3.143  | 7.254 | 1.00 | 54.77 | C |
| ATOM | 4493 | CB  | GLU B | 152 | −8.670  | 2.667  | 7.680 | 1.00 | 54.79 | C |
| ATOM | 4498 | C   | GLU B | 152 | −10.408 | 4.463  | 7.960 | 1.00 | 54.27 | C |
| ATOM | 4499 | O   | GLU B | 152 | −9.530  | 5.308  | 8.149 | 1.00 | 54.93 | O |
| ATOM | 4500 | N   | GLY B | 153 | −11.672 | 4.656  | 8.342 | 1.00 | 52.86 | N |
| ATOM | 4501 | CA  | GLY B | 153 | −12.741 | 3.687  | 8.117 | 1.00 | 50.92 | C |
| ATOM | 4502 | C   | GLY B | 153 | −13.673 | 4.101  | 6.991 | 1.00 | 49.18 | C |
| ATOM | 4503 | O   | GLY B | 153 | −14.683 | 4.777  | 7.216 | 1.00 | 49.10 | O |
| ATOM | 4504 | N   | PHE B | 154 | −13.315 | 3.698  | 5.774 | 1.00 | 46.73 | N |
| ATOM | 4505 | CA  | PHE B | 154 | −14.148 | 3.902  | 4.595 | 1.00 | 43.76 | C |
| ATOM | 4506 | CB  | PHE B | 154 | −13.272 | 3.839  | 3.334 | 1.00 | 43.64 | C |
| ATOM | 4507 | CG  | PHE B | 154 | −13.982 | 4.198  | 2.050 | 1.00 | 43.36 | C |
| ATOM | 4508 | CD1 | PHE B | 154 | −13.549 | 3.654  | .842  | 1.00 | 41.74 | C |
| ATOM | 4509 | CE1 | PHE B | 154 | −14.178 | 3.977  | −.356 | 1.00 | 40.46 | C |
| ATOM | 4510 | CZ  | PHE B | 154 | −15.257 | 4.853  | −.358 | 1.00 | 41.43 | C |
| ATOM | 4511 | CE2 | PHE B | 154 | −15.702 | 5.405  | .838  | 1.00 | 43.21 | C |
| ATOM | 4512 | CD2 | PHE B | 154 | −15.064 | 5.079  | 2.035 | 1.00 | 44.09 | C |
| ATOM | 4513 | C   | PHE B | 154 | −15.228 | 2.823  | 4.599 | 1.00 | 41.42 | C |
| ATOM | 4514 | O   | PHE B | 154 | −14.928 | 1.632  | 4.497 | 1.00 | 40.86 | O |
| ATOM | 4515 | N   | ASN B | 155 | −16.481 | 3.252  | 4.744 | 1.00 | 39.06 | N |
| ATOM | 4516 | CA  | ASN B | 155 | −17.610 | 2.334  | 4.892 | 1.00 | 37.02 | C |
| ATOM | 4517 | CB  | ASN B | 155 | −18.506 | 2.770  | 6.062 | 1.00 | 36.69 | C |
| ATOM | 4518 | CG  | ASN B | 155 | −19.687 | 1.829  | 6.290 | 1.00 | 37.32 | C |
| ATOM | 4519 | OD1 | ASN B | 155 | −19.564 | .604   | 6.174 | 1.00 | 38.20 | O |
| ATOM | 4520 | ND2 | ASN B | 155 | −20.838 | 2.405  | 6.623 | 1.00 | 33.76 | N |
| ATOM | 4521 | C   | ASN B | 155 | −18.424 | 2.176  | 3.606 | 1.00 | 35.42 | C |
| ATOM | 4522 | O   | ASN B | 155 | −19.130 | 3.098  | 3.185 | 1.00 | 34.48 | O |
| ATOM | 4523 | N   | LEU B | 156 | −18.326 | .992   | 3.003 | 1.00 | 33.84 | N |
| ATOM | 4524 | CA  | LEU B | 156 | −18.983 | .697   | 1.729 | 1.00 | 32.90 | C |
| ATOM | 4525 | CB  | LEU B | 156 | −18.168 | −.322  | .921  | 1.00 | 32.90 | C |
| ATOM | 4526 | CG  | LEU B | 156 | −16.762 | .093   | .471  | 1.00 | 32.94 | C |
| ATOM | 4527 | CD1 | LEU B | 156 | −16.065 | −1.062 | −.221 | 1.00 | 33.45 | C |
| ATOM | 4528 | CD2 | LEU B | 156 | −16.789 | 1.327  | −.432 | 1.00 | 32.01 | C |
| ATOM | 4529 | C   | LEU B | 156 | −20.426 | .220   | 1.874 | 1.00 | 32.20 | C |
| ATOM | 4530 | O   | LEU B | 156 | −21.174 | .197   | .895  | 1.00 | 32.25 | O |
| ATOM | 4531 | N   | GLU B | 157 | −20.813 | −.151  | 3.092 | 1.00 | 31.97 | N |
| ATOM | 4532 | CA  | GLU B | 157 | −22.157 | −.671  | 3.355 | 1.00 | 31.64 | C |
| ATOM | 4533 | CB  | GLU B | 157 | −22.249 | −1.262 | 4.765 | 1.00 | 32.25 | C |
| ATOM | 4534 | CG  | GLU B | 157 | −21.281 | −2.411 | 5.031 | 1.00 | 36.75 | C |
| ATOM | 4535 | CD  | GLU B | 157 | −21.522 | −3.616 | 4.140 | 1.00 | 39.54 | C |
| ATOM | 4536 | OE1 | GLU B | 157 | −22.670 | −4.108 | 4.095 | 1.00 | 42.53 | O |
| ATOM | 4537 | OE2 | GLU B | 157 | −20.557 | −4.078 | 3.496 | 1.00 | 41.44 | O |

TABLE A-continued

| | | | | | | | | | | |
|---|---|---|---|---|---|---|---|---|---|---|
| ATOM | 4538 | C | GLU B | 157 | −23.231 | .391 | 3.165 | 1.00 | 30.13 | C |
| ATOM | 4539 | O | GLU B | 157 | −22.985 | 1.575 | 3.389 | 1.00 | 30.99 | O |
| ATOM | 4540 | N | LEU B | 158 | −24.415 | −.049 | 2.746 | 1.00 | 28.58 | N |
| ATOM | 4541 | CA | LEU B | 158 | −25.561 | .828 | 2.534 | 1.00 | 27.11 | C |
| ATOM | 4542 | CB | LEU B | 158 | −26.225 | .511 | 1.190 | 1.00 | 26.58 | C |
| ATOM | 4543 | CG | LEU B | 158 | −25.327 | .551 | −.052 | 1.00 | 25.37 | C |
| ATOM | 4544 | CD1 | LEU B | 158 | −25.954 | −.217 | −1.203 | 1.00 | 23.82 | C |
| | | | gad67.pdb | | | | | | | |
| ATOM | 4545 | CD2 | LEU B | 158 | −24.993 | 1.987 | −.467 | 1.00 | 21.46 | C |
| ATOM | 4546 | C | LEU B | 158 | −26.564 | .671 | 3.675 | 1.00 | 27.04 | C |
| ATOM | 4547 | O | LEU B | 158 | −26.610 | −.377 | 4.325 | 1.00 | 26.90 | O |
| ATOM | 4548 | N | SER B | 159 | −27.365 | 1.708 | 3.916 | 1.00 | 26.82 | N |
| ATOM | 4549 | CA | SER B | 159 | −28.324 | 1.691 | 5.024 | 1.00 | 26.14 | C |
| ATOM | 4550 | CB | SER B | 159 | −27.684 | 2.249 | 6.299 | 1.00 | 26.30 | C |
| ATOM | 4551 | OG | SER B | 159 | −27.260 | 3.587 | 6.118 | 1.00 | 28.17 | O |
| ATOM | 4552 | C | SER B | 159 | −29.637 | 2.417 | 4.722 | 1.00 | 25.62 | C |
| ATOM | 4553 | O | SER B | 159 | −29.809 | 3.005 | 3.646 | 1.00 | 25.05 | O |
| ATOM | 4554 | N | ASP B | 160 | −30.556 | 2.353 | 5.688 | 1.00 | 24.85 | N |
| ATOM | 4555 | CA | ASP B | 160 | −31.888 | 2.945 | 5.587 | 1.00 | 24.07 | C |
| ATOM | 4556 | CB | ASP B | 160 | −32.749 | 2.518 | 6.781 | 1.00 | 25.17 | C |
| ATOM | 4557 | CG | ASP B | 160 | −33.066 | 1.035 | 6.779 | 1.00 | 29.34 | C |
| ATOM | 4558 | OD1 | ASP B | 160 | −32.877 | .378 | 5.733 | 1.00 | 32.91 | O |
| ATOM | 4559 | OD2 | ASP B | 160 | −33.514 | .522 | 7.828 | 1.00 | 34.68 | O |
| ATOM | 4560 | C | ASP B | 160 | −31.855 | 4.459 | 5.533 | 1.00 | 23.20 | C |
| ATOM | 4561 | O | ASP B | 160 | −32.655 | 5.077 | 4.828 | 1.00 | 23.03 | O |
| ATOM | 4562 | N | HIS B | 161 | −30.930 | 5.051 | 6.282 | 1.00 | 22.94 | N |
| ATOM | 4563 | CA | HIS B | 161 | −30.912 | 6.497 | 6.477 | 1.00 | 23.16 | C |
| ATOM | 4564 | CB | HIS B | 161 | −30.977 | 6.823 | 7.969 | 1.00 | 24.05 | C |
| ATOM | 4565 | CG | HIS B | 161 | −32.213 | 6.301 | 8.632 | 1.00 | 28.48 | C |
| ATOM | 4566 | ND1 | HIS B | 161 | −33.435 | 6.927 | 8.520 | 1.00 | 30.09 | N |
| ATOM | 4567 | CE1 | HIS B | 161 | −34.341 | 6.240 | 9.192 | 1.00 | 33.32 | C |
| ATOM | 4568 | NE2 | HIS B | 161 | −33.752 | 5.185 | 9.728 | 1.00 | 34.34 | N |
| ATOM | 4569 | CD2 | HIS B | 161 | −32.421 | 5.197 | 9.388 | 1.00 | 30.82 | C |
| ATOM | 4570 | C | HIS B | 161 | −29.740 | 7.208 | 5.801 | 1.00 | 22.17 | C |
| ATOM | 4571 | O | HIS B | 161 | −28.655 | 6.634 | 5.659 | 1.00 | 21.99 | O |
| ATOM | 4572 | N | PRO B | 162 | −29.969 | 8.463 | 5.367 | 1.00 | 21.18 | N |
| ATOM | 4573 | CA | PRO B | 162 | −28.970 | 9.258 | 4.659 | 1.00 | 20.61 | C |
| ATOM | 4574 | CB | PRO B | 162 | −29.741 | 10.525 | 4.288 | 1.00 | 20.41 | C |
| ATOM | 4575 | CG | PRO B | 162 | −30.839 | 10.608 | 5.292 | 1.00 | 19.68 | C |
| ATOM | 4576 | CD | PRO B | 162 | −31.240 | 9.199 | 5.524 | 1.00 | 20.11 | C |
| ATOM | 4577 | C | PRO B | 162 | −27.760 | 9.633 | 5.512 | 1.00 | 21.49 | C |
| ATOM | 4578 | O | PRO B | 162 | −27.880 | 9.812 | 6.733 | 1.00 | 21.72 | O |
| ATOM | 4579 | N | GLU B | 163 | −26.607 | 9.734 | 4.857 | 1.00 | 20.74 | N |
| ATOM | 4580 | CA | GLU B | 163 | −25.422 | 10.341 | 5.439 | 1.00 | 20.56 | C |
| ATOM | 4581 | CB | GLU B | 163 | −24.161 | 9.771 | 4.803 | 1.00 | 21.29 | C |
| ATOM | 4582 | CG | GLU B | 163 | −23.813 | 8.362 | 5.220 | 1.00 | 26.95 | C |
| ATOM | 4583 | CD | GLU B | 163 | −22.482 | 7.910 | 4.647 | 1.00 | 33.42 | C |
| ATOM | 4584 | OE1 | GLU B | 163 | −22.044 | 8.483 | 3.620 | 1.00 | 28.43 | O |
| ATOM | 4585 | OE2 | GLU B | 163 | −21.876 | 6.986 | 5.234 | 1.00 | 39.41 | O |
| ATOM | 4586 | C | GLU B | 163 | −25.467 | 11.830 | 5.145 | 1.00 | 19.41 | C |
| ATOM | 4587 | O | GLU B | 163 | −26.116 | 12.256 | 4.188 | 1.00 | 19.20 | O |
| ATOM | 4588 | N | SER B | 164 | −24.765 | 12.618 | 5.954 | 1.00 | 18.27 | N |
| ATOM | 4589 | CA | SER B | 164 | −24.634 | 14.046 | 5.692 | 1.00 | 17.91 | C |
| ATOM | 4590 | CB | SER B | 164 | −23.957 | 14.739 | 6.871 | 1.00 | 18.14 | C |
| ATOM | 4591 | OG | SER B | 164 | −22.568 | 14.437 | 6.904 | 1.00 | 20.14 | O |
| ATOM | 4592 | C | SER B | 164 | −23.823 | 14.271 | 4.414 | 1.00 | 17.64 | C |
| ATOM | 4593 | O | SER B | 164 | −23.062 | 13.394 | 3.988 | 1.00 | 16.56 | O |
| ATOM | 4594 | N | LEU B | 165 | −23.983 | 15.449 | 3.815 | 1.00 | 17.93 | N |
| ATOM | 4595 | CA | LEU B | 165 | −23.251 | 15.810 | 2.603 | 1.00 | 19.21 | C |
| ATOM | 4596 | CB | LEU B | 165 | −23.784 | 17.120 | 2.003 | 1.00 | 19.43 | C |
| ATOM | 4597 | CG | LEU B | 165 | −25.220 | 17.112 | 1.449 | 1.00 | 20.91 | C |
| ATOM | 4598 | CD1 | LEU B | 165 | −25.675 | 18.516 | 1.065 | 1.00 | 17.00 | C |
| ATOM | 4599 | CD2 | LEU B | 165 | −25.366 | 16.160 | .265 | 1.00 | 17.92 | C |
| ATOM | 4600 | C | LEU B | 165 | −21.751 | 15.908 | 2.864 | 1.00 | 20.15 | C |
| ATOM | 4601 | O | LEU B | 165 | −20.943 | 15.700 | 1.955 | 1.00 | 20.52 | O |
| ATOM | 4602 | N | GLU B | 166 | −21.383 | 16.219 | 4.105 | 1.00 | 21.09 | N |
| ATOM | 4603 | CA | GLU B | 166 | −19.980 | 16.229 | 4.499 | 1.00 | 22.84 | C |
| ATOM | 4604 | CB | GLU B | 166 | −19.807 | 16.796 | 5.912 | 1.00 | 23.38 | C |
| ATOM | 4605 | CG | GLU B | 166 | −18.366 | 16.817 | 6.441 | 1.00 | 30.50 | C |
| ATOM | 4606 | CD | GLU B | 166 | −17.393 | 17.547 | 5.522 | 1.00 | 40.52 | C |
| ATOM | 4607 | OE1 | GLU B | 166 | −17.744 | 18.627 | 4.992 | 1.00 | 43.22 | O |
| ATOM | 4608 | OE2 | GLU B | 166 | −16.267 | 17.037 | 5.339 | 1.00 | 45.03 | O |
| ATOM | 4609 | C | GLU B | 166 | −19.402 | 14.824 | 4.393 | 1.00 | 22.46 | C |
| ATOM | 4610 | O | GLU B | 166 | −18.281 | 14.643 | 3.913 | 1.00 | 23.00 | O |
| ATOM | 4611 | N | GLN B | 167 | −20.178 | 13.835 | 4.828 | 1.00 | 22.20 | N |
| ATOM | 4612 | CA | GLN B | 167 | −19.767 | 12.436 | 4.745 | 1.00 | 21.73 | C |
| | | | gad67.pdb | | | | | | | |
| ATOM | 4613 | CB | GLN B | 167 | −20.671 | 11.547 | 5.608 | 1.00 | 22.05 | C |
| ATOM | 4614 | CG | GLN B | 167 | −20.123 | 10.138 | 5.856 | 1.00 | 26.54 | C |
| ATOM | 4615 | CD | GLN B | 167 | −18.713 | 10.130 | 6.440 | 1.00 | 31.78 | C |

TABLE A-continued

| | | | | | | | | | |
|---|---|---|---|---|---|---|---|---|---|
| ATOM | 4616 | OE1 | GLN B | 167 | −18.444 | 10.762 | 7.466 | 1.00 | 33.79 | O |
| ATOM | 4617 | NE2 | GLN B | 167 | −17.808 | 9.405 | 5.787 | 1.00 | 31.16 | N |
| ATOM | 4618 | C | GLN B | 167 | −19.749 | 11.957 | 3.295 | 1.00 | 20.42 | C |
| ATOM | 4619 | O | GLN B | 167 | −18.934 | 11.110 | 2.928 | 1.00 | 20.66 | O |
| ATOM | 4620 | N | ILE B | 168 | −20.642 | 12.514 | 2.479 | 1.00 | 19.08 | N |
| ATOM | 4621 | CA | ILE B | 168 | −20.664 | 12.248 | 1.043 | 1.00 | 18.68 | C |
| ATOM | 4622 | CB | ILE B | 168 | −21.939 | 12.842 | .369 | 1.00 | 18.06 | C |
| ATOM | 4623 | CG1 | ILE B | 168 | −23.196 | 12.058 | .788 | 1.00 | 17.34 | C |
| ATOM | 4624 | CD1 | ILE B | 168 | −23.192 | 10.574 | .415 | 1.00 | 18.05 | C |
| ATOM | 4625 | CG2 | ILE B | 168 | −21.805 | 12.891 | −1.157 | 1.00 | 18.18 | C |
| ATOM | 4626 | C | ILE B | 168 | −19.383 | 12.763 | .374 | 1.00 | 19.29 | C |
| ATOM | 4627 | O | ILE B | 168 | −18.793 | 12.071 | −.457 | 1.00 | 19.48 | O |
| ATOM | 4628 | N | LEU B | 169 | −18.955 | 13.965 | .757 | 1.00 | 19.24 | N |
| ATOM | 4629 | CA | LEU B | 169 | −17.704 | 14.536 | .258 | 1.00 | 20.19 | C |
| ATOM | 4630 | CB | LEU B | 169 | −17.555 | 15.997 | .693 | 1.00 | 20.02 | C |
| ATOM | 4631 | CG | LEU B | 169 | −18.519 | 16.998 | .043 | 1.00 | 20.70 | C |
| ATOM | 4632 | CD1 | LEU B | 169 | −18.493 | 18.337 | .772 | 1.00 | 18.18 | C |
| ATOM | 4633 | CD2 | LEU B | 169 | −18.222 | 17.176 | −1.448 | 1.00 | 19.20 | C |
| ATOM | 4634 | C | LEU B | 169 | −16.491 | 13.716 | .695 | 1.00 | 20.38 | C |
| ATOM | 4635 | O | LEU B | 169 | −15.553 | 13.523 | −.083 | 1.00 | 20.07 | O |
| ATOM | 4636 | N | VAL B | 170 | −16.528 | 13.225 | 1.933 | 1.00 | 20.50 | N |
| ATOM | 4637 | CA | VAL B | 170 | −15.486 | 12.342 | 2.465 | 1.00 | 20.19 | C |
| ATOM | 4638 | CB | VAL B | 170 | −15.688 | 12.078 | 3.986 | 1.00 | 20.64 | C |
| ATOM | 4639 | CG1 | VAL B | 170 | −14.818 | 10.921 | 4.478 | 1.00 | 19.04 | C |
| ATOM | 4640 | CG2 | VAL B | 170 | −15.398 | 13.346 | 4.796 | 1.00 | 17.08 | C |
| ATOM | 4641 | C | VAL B | 170 | −15.430 | 11.028 | 1.679 | 1.00 | 21.15 | C |
| ATOM | 4642 | O | VAL B | 170 | −14.341 | 10.543 | 1.357 | 1.00 | 22.03 | O |
| ATOM | 4643 | N | ASP B | 171 | −16.601 | 10.467 | 1.367 | 1.00 | 21.09 | N |
| ATOM | 4644 | CA | ASP B | 171 | −16.695 | 9.243 | .569 | 1.00 | 21.55 | C |
| ATOM | 4645 | CB | ASP B | 171 | −18.144 | 8.765 | .461 | 1.00 | 21.82 | C |
| ATOM | 4646 | CG | ASP B | 171 | −18.702 | 8.268 | 1.786 | 1.00 | 24.88 | C |
| ATOM | 4647 | OD1 | ASP B | 171 | −17.908 | 7.896 | 2.679 | 1.00 | 27.66 | O |
| ATOM | 4648 | OD2 | ASP B | 171 | −19.945 | 8.249 | 1.931 | 1.00 | 22.61 | O |
| ATOM | 4649 | C | ASP B | 171 | −16.107 | 9.421 | −.831 | 1.00 | 21.42 | C |
| ATOM | 4650 | O | ASP B | 171 | −15.475 | 8.503 | −1.359 | 1.00 | 20.37 | O |
| ATOM | 4651 | N | CYS B | 172 | −16.329 | 10.598 | −1.420 | 1.00 | 21.21 | N |
| ATOM | 4652 | CA | CYS B | 172 | −15.757 | 10.948 | −2.716 | 1.00 | 21.69 | C |
| ATOM | 4653 | CB | CYS B | 172 | −16.296 | 12.294 | −3.202 | 1.00 | 21.55 | C |
| ATOM | 4654 | SG | CYS B | 172 | −18.025 | 12.275 | −3.741 | 1.00 | 20.81 | S |
| ATOM | 4655 | C | CYS B | 172 | −14.235 | 10.986 | −2.655 | 1.00 | 22.42 | C |
| ATOM | 4656 | O | CYS B | 172 | −13.562 | 10.406 | −3.507 | 1.00 | 23.11 | O |
| ATOM | 4657 | N | ARG B | 173 | −13.705 | 11.670 | −1.646 | 1.00 | 23.07 | N |
| ATOM | 4658 | CA | ARG B | 173 | −12.264 | 11.754 | −1.433 | 1.00 | 24.33 | C |
| ATOM | 4659 | CB | ARG B | 173 | −11.957 | 12.649 | −.231 | 1.00 | 25.07 | C |
| ATOM | 4660 | CG | ARG B | 173 | −10.488 | 13.037 | −.097 | 1.00 | 30.53 | C |
| ATOM | 4661 | CD | ARG B | 173 | −10.004 | 12.829 | 1.334 | 1.00 | 38.31 | C |
| ATOM | 4662 | NE | ARG B | 173 | −10.589 | 13.792 | 2.266 | 1.00 | 44.14 | N |
| ATOM | 4663 | CZ | ARG B | 173 | −10.827 | 13.551 | 3.554 | 1.00 | 45.86 | C |
| ATOM | 4664 | NH1 | ARG B | 173 | −10.548 | 12.364 | 4.084 | 1.00 | 46.11 | N |
| ATOM | 4665 | NH2 | ARG B | 173 | −11.357 | 14.500 | 4.314 | 1.00 | 45.98 | N |
| ATOM | 4666 | C | ARG B | 173 | −11.627 | 10.367 | −1.252 | 1.00 | 23.84 | C |
| ATOM | 4667 | O | ARG B | 173 | −10.600 | 10.075 | −1.868 | 1.00 | 24.07 | O |
| ATOM | 4668 | N | ASP B | 174 | −12.248 | 9.526 | −.421 | 1.00 | 23.55 | N |
| ATOM | 4669 | CA | ASP B | 174 | −11.756 | 8.169 | −.144 | 1.00 | 23.63 | C |
| ATOM | 4670 | CB | ASP B | 174 | −12.524 | 7.531 | 1.021 | 1.00 | 24.06 | C |
| ATOM | 4671 | CG | ASP B | 174 | −12.113 | 8.087 | 2.376 | 1.00 | 26.10 | C |
| ATOM | 4672 | OD1 | ASP B | 174 | −12.851 | 7.853 | 3.355 | 1.00 | 30.01 | O |
| ATOM | 4673 | OD2 | ASP B | 174 | −11.057 | 8.751 | 2.470 | 1.00 | 30.06 | O |
| ATOM | 4674 | C | ASP B | 174 | −11.812 | 7.243 | −1.355 | 1.00 | 22.96 | C |
| ATOM | 4675 | O | ASP B | 174 | −10.905 | 6.436 | −1.558 | 1.00 | 23.62 | O |
| ATOM | 4676 | N | THR B | 175 | −12.884 | 7.353 | −2.139 | 1.00 | 21.82 | N |
| ATOM | 4677 | CA | THR B | 175 | −13.056 | 6.563 | −3.357 | 1.00 | 21.52 | C |
| ATOM | 4678 | CB | THR B | 175 | −14.408 | 6.884 | −4.056 | 1.00 | 21.40 | C |
| ATOM | 4679 | OG1 | THR B | 175 | −15.492 | 6.465 | −3.218 | 1.00 | 24.00 | O |
| ATOM | 4680 | CG2 | THR B | 175 | −14.525 | 6.177 | −5.405 | 1.00 | 19.85 | C |
| | | | | gad67.pdb | | | | | | |
| ATOM | 4681 | C | THR B | 175 | −11.885 | 6.794 | −4.311 | 1.00 | 21.00 | C |
| ATOM | 4682 | O | THR B | 175 | −11.334 | 5.846 | −4.871 | 1.00 | 20.85 | O |
| ATOM | 4683 | N | LEU B | 176 | −11.498 | 8.055 | −4.476 | 1.00 | 21.05 | N |
| ATOM | 4684 | CA | LEU B | 176 | −10.387 | 8.406 | −5.356 | 1.00 | 21.88 | C |
| ATOM | 4685 | CB | LEU B | 176 | −10.431 | 9.891 | −5.718 | 1.00 | 20.96 | C |
| ATOM | 4686 | CG | LEU B | 176 | −11.573 | 10.317 | −6.643 | 1.00 | 19.91 | C |
| ATOM | 4687 | CD1 | LEU B | 176 | −11.722 | 11.828 | −6.638 | 1.00 | 17.77 | C |
| ATOM | 4688 | CD2 | LEU B | 176 | −11.366 | 9.788 | −8.061 | 1.00 | 18.00 | C |
| ATOM | 4689 | C | LEU B | 176 | −9.030 | 8.040 | −4.762 | 1.00 | 22.84 | C |
| ATOM | 4690 | O | LEU B | 176 | −8.085 | 7.756 | −5.502 | 1.00 | 23.26 | O |
| ATOM | 4691 | N | LYS B | 177 | −8.946 | 8.046 | −3.431 | 1.00 | 23.47 | N |
| ATOM | 4692 | CA | LYS B | 177 | −7.711 | 7.713 | −2.712 | 1.00 | 24.71 | C |
| ATOM | 4693 | CB | LYS B | 177 | −7.882 | 7.991 | −1.212 | 1.00 | 24.77 | C |
| ATOM | 4694 | CG | LYS B | 177 | −6.646 | 7.743 | −.356 | 1.00 | 24.98 | C |

TABLE A-continued

| | | | | | | | | | | |
|---|---|---|---|---|---|---|---|---|---|---|
| ATOM | 4695 | CD | LYS B | 177 | −6.917 | 8.088 | 1.102 | 1.00 | 26.62 | C |
| ATOM | 4696 | CE | LYS B | 177 | −5.653 | 8.006 | 1.957 | 1.00 | 33.85 | C |
| ATOM | 4697 | NZ | LYS B | 177 | −5.243 | 6.603 | 2.263 | 1.00 | 36.89 | N |
| ATOM | 4698 | C | LYS B | 177 | −7.295 | 6.259 | −2.932 | 1.00 | 24.50 | C |
| ATOM | 4699 | O | LYS B | 177 | −6.102 | 5.955 | −3.038 | 1.00 | 25.39 | O |
| ATOM | 4700 | N | TYR B | 178 | −8.285 | 5.373 | −3.012 | 1.00 | 24.01 | N |
| ATOM | 4701 | CA | TYR B | 178 | −8.034 | 3.937 | −3.079 | 1.00 | 23.22 | C |
| ATOM | 4702 | CB | TYR B | 178 | −8.888 | 3.213 | −2.033 | 1.00 | 23.25 | C |
| ATOM | 4703 | CG | TYR B | 178 | −8.501 | 3.576 | −.619 | 1.00 | 24.23 | C |
| ATOM | 4704 | CD1 | TYR B | 178 | −7.252 | 3.214 | −.106 | 1.00 | 23.92 | C |
| ATOM | 4705 | CE1 | TYR B | 178 | −6.882 | 3.546 | 1.187 | 1.00 | 24.95 | C |
| ATOM | 4706 | CZ | TYR B | 178 | −7.767 | 4.251 | 1.989 | 1.00 | 25.87 | C |
| ATOM | 4707 | OH | TYR B | 178 | −7.401 | 4.578 | 3.272 | 1.00 | 26.69 | O |
| ATOM | 4708 | CE2 | TYR B | 178 | −9.012 | 4.627 | 1.503 | 1.00 | 23.82 | C |
| ATOM | 4709 | CD2 | TYR B | 178 | −9.372 | 4.288 | .203 | 1.00 | 23.45 | C |
| ATOM | 4710 | C | TYR B | 178 | −8.217 | 3.330 | −4.473 | 1.00 | 22.67 | C |
| ATOM | 4711 | O | TYR B | 178 | −8.175 | 2.112 | −4.641 | 1.00 | 22.02 | O |
| ATOM | 4712 | N | GLY B | 179 | −8.408 | 4.188 | −5.469 | 1.00 | 22.63 | N |
| ATOM | 4713 | CA | GLY B | 179 | −8.534 | 3.742 | −6.849 | 1.00 | 23.40 | C |
| ATOM | 4714 | C | GLY B | 179 | −7.207 | 3.763 | −7.581 | 1.00 | 23.68 | C |
| ATOM | 4715 | O | GLY B | 179 | −6.174 | 4.109 | −7.008 | 1.00 | 24.46 | O |
| ATOM | 4716 | N | VAL B | 180 | −7.240 | 3.393 | −8.855 | 1.00 | 23.55 | N |
| ATOM | 4717 | CA | VAL B | 180 | −6.044 | 3.379 | −9.690 | 1.00 | 23.77 | C |
| ATOM | 4718 | CB | VAL B | 180 | −5.971 | 2.088 | −10.553 | 1.00 | 23.88 | C |
| ATOM | 4719 | CG1 | VAL B | 180 | −4.704 | 2.068 | −11.420 | 1.00 | 21.70 | C |
| ATOM | 4720 | CG2 | VAL B | 180 | −6.024 | .853 | −9.666 | 1.00 | 21.47 | C |
| ATOM | 4721 | C | VAL B | 180 | −6.028 | 4.622 | −10.577 | 1.00 | 24.25 | C |
| ATOM | 4722 | O | VAL B | 180 | −7.038 | 4.967 | −11.189 | 1.00 | 24.80 | O |
| ATOM | 4723 | N | ARG B | 181 | −4.882 | 5.297 | −10.627 | 1.00 | 24.29 | N |
| ATOM | 4724 | CA | ARG B | 181 | −4.723 | 6.475 | −11.476 | 1.00 | 24.37 | C |
| ATOM | 4725 | CB | ARG B | 181 | −3.657 | 7.422 | −10.916 | 1.00 | 24.52 | C |
| ATOM | 4726 | CG | ARG B | 181 | −4.097 | 8.130 | −9.655 | 1.00 | 26.41 | C |
| ATOM | 4727 | CD | ARG B | 181 | −3.010 | 9.029 | −9.104 | 1.00 | 33.64 | C |
| ATOM | 4728 | NE | ARG 8 | 181 | −3.428 | 9.673 | −7.859 | 1.00 | 37.53 | N |
| ATOM | 4729 | CZ | ARG B | 181 | −4.009 | 10.868 | −7.783 | 1.00 | 39.10 | C |
| ATOM | 4730 | NH1 | ARG B | 181 | −4.251 | 11.576 | −8.882 | 1.00 | 38.69 | N |
| ATOM | 4731 | NH2 | ARG B | 181 | −4.348 | 11.363 | −6.599 | 1.00 | 38.34 | N |
| ATOM | 4732 | C | ARG B | 181 | −4.406 | 6.058 | −12.907 | 1.00 | 23.66 | C |
| ATOM | 4733 | O | ARG B | 181 | −3.249 | 5.841 | −13.267 | 1.00 | 23.73 | O |
| ATOM | 4734 | N | THR B | 182 | −5.459 | 5.946 | −13.713 | 1.00 | 23.34 | N |
| ATOM | 4735 | CA | THR B | 182 | −5.349 | 5.492 | −15.097 | 1.00 | 22.29 | C |
| ATOM | 4736 | CB | THR B | 182 | −6.709 | 4.979 | −15.630 | 1.00 | 22.35 | C |
| ATOM | 4737 | OG1 | THR B | 182 | −7.688 | 6.024 | −15.552 | 1.00 | 23.94 | O |
| ATOM | 4738 | CG2 | THR B | 182 | −7.185 | 3.779 | −14.825 | 1.00 | 20.14 | C |
| ATOM | 4739 | C | THR B | 182 | −4.791 | 6.571 | −16.033 | 1.00 | 21.49 | C |
| ATOM | 4740 | O | THR B | 182 | −4.517 | 6.301 | −17.205 | 1.00 | 20.66 | O |
| ATOM | 4741 | N | GLY B | 183 | −4.626 | 7.784 | −15.509 | 1.00 | 20.52 | N |
| ATOM | 4742 | CA | GLY B | 183 | −4.069 | 8.897 | −16.275 | 1.00 | 19.54 | C |
| ATOM | 4743 | C | GLY B | 183 | −2.589 | 9.113 | −16.036 | 1.00 | 18.98 | C |
| ATOM | 4744 | O | GLY B | 183 | −1.955 | 9.904 | −16.730 | 1.00 | 20.02 | O |
| ATOM | 4745 | N | HIS B | 184 | −2.051 | 8.404 | −15.046 | 1.00 | 18.31 | N |
| ATOM | 4746 | CA | HIS B | 184 | −.657 | 8.515 | −14.627 | 1.00 | 17.89 | C |
| ATOM | 4747 | CB | HIS B | 184 | −.402 | 7.549 | −13.469 | 1.00 | 18.00 | C |
| ATOM | 4748 | CG | HIS B | 184 | .805 | 7.883 | −12.646 | 1.00 | 21.13 | C |
| | | | | | gad67.pdb | | | | | |
| ATOM | 4749 | ND1 | HIS B | 184 | 2.092 | 7.631 | −13.073 | 1.00 | 21.29 | N |
| ATOM | 4750 | CE1 | HIS B | 184 | 2.946 | 8.017 | −12.143 | 1.00 | 20.31 | C |
| ATOM | 4751 | NE2 | HIS B | 184 | 2.260 | 8.510 | −11.128 | 1.00 | 21.54 | N |
| ATOM | 4752 | CD2 | HIS B | 184 | .919 | 8.432 | −11.413 | 1.00 | 20.28 | C |
| ATOM | 4753 | C | HIS B | 184 | .298 | 8.212 | −15.784 | 1.00 | 18.01 | C |
| ATOM | 4754 | O | HIS B | 184 | .101 | 7.228 | −16.505 | 1.00 | 17.76 | O |
| ATOM | 4755 | N | PRO B | 185 | 1.332 | 9.059 | −15.975 | 1.00 | 17.70 | N |
| ATOM | 4756 | CA | PRO B | 185 | 2.336 | 8.849 | −17.025 | 1.00 | 17.39 | C |
| ATOM | 4757 | CB | PRO B | 185 | 3.420 | 9.868 | −16.672 | 1.00 | 17.59 | C |
| ATOM | 4758 | CG | PRO B | 185 | 2.689 | 10.964 | −16.001 | 1.00 | 17.14 | C |
| ATOM | 4759 | CD | PRO B | 185 | 1.600 | 10.291 | −15.210 | 1.00 | 17.65 | C |
| ATOM | 4760 | C | PRO B | 185 | 2.928 | 7.438 | −17.031 | 1.00 | 17.60 | C |
| ATOM | 4761 | O | PRO B | 185 | 3.322 | 6.938 | −18.087 | 1.00 | 17.70 | O |
| ATOM | 4762 | N | ARG B | 186 | 2.973 | 6.803 | −15.862 | 1.00 | 17.40 | N |
| ATOM | 4763 | CA | ARG B | 186 | 3.577 | 5.481 | −15.721 | 1.00 | 17.13 | C |
| ATOM | 4764 | CB | ARG B | 186 | 4.597 | 5.492 | −14.581 | 1.00 | 17.53 | C |
| ATOM | 4765 | CG | ARG B | 186 | 5.871 | 6.245 | −14.953 | 1.00 | 17.79 | C |
| ATOM | 4766 | CD | ARG B | 186 | 6.641 | 6.695 | −13.731 | 1.00 | 20.31 | C |
| ATOM | 4767 | NE | ARG B | 186 | 7.784 | 7.522 | −14.105 | 1.00 | 22.26 | N |
| ATOM | 4768 | CZ | ARG B | 186 | 8.729 | 7.929 | −13.263 | 1.00 | 24.92 | C |
| ATOM | 4769 | NH1 | ARG B | 186 | 8.676 | 7.591 | −11.978 | 1.00 | 23.33 | N |
| ATOM | 4770 | NH2 | ARG B | 186 | 9.732 | 8.676 | −13.710 | 1.00 | 25.10 | N |
| ATOM | 4771 | C | ARG B | 186 | 2.558 | 4.339 | −15.577 | 1.00 | 17.13 | C |
| ATOM | 4772 | O | ARG B | 186 | 2.895 | 3.242 | −15.132 | 1.00 | 17.19 | O |
| ATOM | 4773 | N | PHE B | 187 | 1.316 | 4.614 | −15.966 | 1.00 | 16.67 | N |

TABLE A-continued

| | | | | | | | | | |
|---|---|---|---|---|---|---|---|---|---|
| ATOM | 4774 | CA | PHE B | 187 | .286 | 3.588 | −16.074 | 1.00 | 16.57 | C |
| ATOM | 4775 | CB | PHE B | 187 | −1.090 | 4.162 | −15.715 | 1.00 | 16.20 | C |
| ATOM | 4776 | CG | PHE B | 187 | −2.212 | 3.156 | −15.781 | 1.00 | 17.50 | C |
| ATOM | 4777 | CD1 | PHE B | 187 | −2.390 | 2.218 | −14.767 | 1.00 | 18.00 | C |
| ATOM | 4778 | CE1 | PHE B | 187 | −3.432 | 1.295 | −14.825 | 1.00 | 14.61 | C |
| ATOM | 4779 | CZ | PHE B | 187 | −4.314 | 1.307 | −15.904 | 1.00 | 16.79 | C |
| ATOM | 4780 | CE2 | PHE B | 187 | −4.149 | 2.236 | −16.918 | 1.00 | 15.29 | C |
| ATOM | 4781 | CD2 | PHE B | 187 | −3.105 | 3.158 | −16.851 | 1.00 | 17.67 | C |
| ATOM | 4782 | C | PHE B | 187 | .285 | 3.031 | −17.496 | 1.00 | 15.95 | C |
| ATOM | 4783 | O | PHE B | 187 | −.127 | 3.719 | −18.436 | 1.00 | 14.71 | O |
| ATOM | 4784 | N | PHE B | 188 | .758 | 1.792 | −17.637 | 1.00 | 16.05 | N |
| ATOM | 4785 | CA | PHE B | 188 | .853 | 1.120 | −18.933 | 1.00 | 17.04 | C |
| ATOM | 4786 | CB | PHE B | 188 | 2.321 | .823 | −19.281 | 1.00 | 17.42 | C |
| ATOM | 4787 | CG | PHE B | 188 | 3.220 | 2.028 | −19.272 | 1.00 | 18.22 | C |
| ATOM | 4788 | CD1 | PHE B | 188 | 4.201 | 2.167 | −18.295 | 1.00 | 18.40 | C |
| ATOM | 4789 | CE1 | PHE B | 188 | 5.053 | 3.272 | −18.290 | 1.00 | 17.53 | C |
| ATOM | 4790 | CZ | PHE B | 188 | 4.928 | 4.250 | −19.272 | 1.00 | 17.06 | C |
| ATOM | 4791 | CE2 | PHE B | 188 | 3.958 | 4.118 | −20.257 | 1.00 | 19.46 | C |
| ATOM | 4792 | CD2 | PHE B | 188 | 3.110 | 3.010 | −20.254 | 1.00 | 18.64 | C |
| ATOM | 4793 | C | PHE B | 188 | .083 | −.203 | −18.940 | 1.00 | 17.97 | C |
| ATOM | 4794 | O | PHE B | 188 | .349 | −1.078 | −19.771 | 1.00 | 18.53 | O |
| ATOM | 4795 | N | ASN B | 189 | −.866 | −.346 | −18.017 | 1.00 | 18.19 | N |
| ATOM | 4796 | CA | ASN B | 189 | −1.526 | −1.630 | −17.774 | 1.00 | 18.46 | C |
| ATOM | 4797 | CB | ASN B | 189 | −2.208 | −1.614 | −16.401 | 1.00 | 18.52 | C |
| ATOM | 4798 | CG | ASN B | 189 | −2.328 | −2.994 | −15.790 | 1.00 | 19.06 | C |
| ATOM | 4799 | OD1 | ASN B | 189 | −1.323 | −3.639 | −15.495 | 1.00 | 19.18 | O |
| ATOM | 4800 | ND2 | ASN B | 189 | −3.558 | −3.452 | −15.591 | 1.00 | 16.53 | N |
| ATOM | 4801 | C | ASN B | 189 | −2.536 | −2.043 | −18.844 | 1.00 | 19.15 | C |
| ATOM | 4802 | O | ASN B | 189 | −2.767 | −3.232 | −19.058 | 1.00 | 19.36 | O |
| ATOM | 4803 | N | GLN B | 190 | −3.143 | −1.057 | −19.500 | 1.00 | 20.86 | N |
| ATOM | 4804 | CA | GLN B | 190 | −4.237 | −1.297 | −20.445 | 1.00 | 22.03 | C |
| ATOM | 4805 | CB | GLN B | 190 | −5.586 | −.810 | −19.876 | 1.00 | 21.98 | C |
| ATOM | 4806 | CG | GLN B | 190 | −5.925 | −1.215 | −18.436 | 1.00 | 26.08 | C |
| ATOM | 4807 | CD | GLN B | 190 | −6.176 | −2.709 | −18.252 | 1.00 | 31.10 | C |
| ATOM | 4808 | OE1 | GLN B | 190 | −5.738 | −3.304 | −17.267 | 1.00 | 37.44 | O |
| ATOM | 4809 | NE2 | GLN B | 190 | −6.888 | −3.316 | −19.192 | 1.00 | 34.60 | N |
| ATOM | 4810 | C | GLN B | 190 | −3.984 | −.611 | −21.792 | 1.00 | 23.04 | C |
| ATOM | 4811 | O | GLN B | 190 | −3.036 | .162 | −21.944 | 1.00 | 22.83 | O |
| ATOM | 4812 | N | LEU B | 191 | −4.848 | −.903 | −22.760 | 1.00 | 24.36 | N |
| ATOM | 4813 | CA | LEU B | 191 | −4.837 | −.242 | −24.061 | 1.00 | 26.30 | C |
| ATOM | 4814 | CB | LEU B | 191 | −5.599 | −1.086 | −25.091 | 1.00 | 25.74 | C |
| ATOM | 4815 | CG | LEU B | 191 | −4.786 | −2.046 | −25.982 | 1.00 | 27.02 | C |
| ATOM | 4816 | CD1 | LEU B | 191 | −3.685 | −2.783 | −25.238 | 1.00 | 22.98 | C |
| | | | | gad67.pdb | | | | | | |
| ATOM | 4817 | CD2 | LEU B | 191 | −5.693 | −3.033 | −26.694 | 1.00 | 25.70 | C |
| ATOM | 4818 | C | LEU B | 191 | −5.404 | 1.177 | −23.991 | 1.00 | 27.78 | C |
| ATOM | 4819 | O | LEU B | 191 | −5.048 | 2.033 | −24.799 | 1.00 | 28.75 | O |
| ATOM | 4820 | N | SER B | 192 | −6.288 | 1.415 | −23.027 | 1.00 | 29.03 | N |
| ATOM | 4821 | CA | SER B | 192 | −6.809 | 2.753 | −22.764 | 1.00 | 30.39 | C |
| ATOM | 4822 | CB | SER B | 192 | −8.319 | 2.708 | −22.541 | 1.00 | 30.44 | C |
| ATOM | 4823 | OG | SER B | 192 | −8.957 | 1.934 | −23.540 | 1.00 | 35.20 | O |
| ATOM | 4824 | C | SER B | 192 | −6.114 | 3.357 | −21.545 | 1.00 | 30.65 | C |
| ATOM | 4825 | O | SER B | 192 | −6.344 | 2.925 | −20.412 | 1.00 | 30.31 | O |
| ATOM | 4826 | N | THR B | 193 | −5.249 | 4.341 | −21.789 | 1.00 | 31.32 | N |
| ATOM | 4827 | CA | THR B | 193 | −4.526 | 5.042 | −20.720 | 1.00 | 31.86 | C |
| ATOM | 4828 | CB | THR B | 193 | −3.045 | 4.597 | −20.631 | 1.00 | 31.95 | C |
| ATOM | 4829 | OG1 | THR B | 193 | −2.358 | 4.966 | −21.833 | 1.00 | 35.31 | O |
| ATOM | 4830 | CG2 | THR B | 193 | −2.931 | 3.088 | −20.419 | 1.00 | 30.50 | C |
| ATOM | 4831 | C | THR B | 193 | −4.564 | 6.559 | −20.921 | 1.00 | 31.44 | C |
| ATOM | 4832 | O | THR B | 193 | −4.656 | 7.042 | −22.051 | 1.00 | 31.96 | O |
| ATOM | 4833 | N | GLY B | 194 | −4.488 | 7.304 | −19.821 | 1.00 | 30.56 | N |
| ATOM | 4834 | CA | GLY B | 194 | −4.436 | 8.758 | −19.886 | 1.00 | 28.73 | C |
| ATOM | 4835 | C | GLY B | 194 | −5.729 | 9.451 | −19.516 | 1.00 | 27.69 | C |
| ATOM | 4836 | O | GLY B | 194 | −6.788 | 8.825 | −19.448 | 1.00 | 27.74 | O |
| ATOM | 4837 | N | LEU B | 195 | −5.629 | 10.754 | −19.270 | 1.00 | 26.25 | N |
| ATOM | 4838 | CA | LEU B | 195 | −6.785 | 11.587 | −18.975 | 1.00 | 24.90 | C |
| ATOM | 4839 | CB | LEU B | 195 | −6.816 | 11.974 | −17.491 | 1.00 | 24.47 | C |
| ATOM | 4840 | CG | LEU B | 195 | −8.045 | 12.731 | −16.970 | 1.00 | 24.38 | C |
| ATOM | 4841 | CD1 | LEU B | 195 | −9.323 | 11.943 | −17.187 | 1.00 | 20.41 | C |
| ATOM | 4842 | CD2 | LEU B | 195 | −7.884 | 13.063 | −15.502 | 1.00 | 23.99 | C |
| ATOM | 4843 | C | LEU B | 195 | −6.774 | 12.831 | −19.859 | 1.00 | 24.84 | C |
| ATOM | 4844 | O | LEU B | 195 | −5.981 | 13.755 | −19.646 | 1.00 | 25.69 | O |
| ATOM | 4845 | N | ASP B | 196 | −7.651 | 12.838 | −20.858 | 1.00 | 23.48 | N |
| ATOM | 4846 | CA | ASP B | 196 | −7.801 | 13.985 | −21.740 | 1.00 | 22.06 | C |
| ATOM | 4847 | CB | ASP B | 196 | −8.352 | 13.552 | −23.094 | 1.00 | 22.11 | C |
| ATOM | 4848 | CG | ASP B | 196 | −8.260 | 14.649 | −24.131 | 1.00 | 24.11 | C |
| ATOM | 4849 | OD1 | ASP B | 196 | −9.113 | 15.560 | −24.113 | 1.00 | 23.29 | O |
| ATOM | 4850 | OD2 | ASP B | 196 | −7.336 | 14.596 | −24.967 | 1.00 | 28.24 | O |
| ATOM | 4851 | C | ASP B | 196 | −8.708 | 15.034 | −21.103 | 1.00 | 20.85 | C |
| ATOM | 4852 | O | ASP B | 196 | −9.861 | 14.748 | −20.770 | 1.00 | 20.13 | O |

TABLE A-continued

| | | | | | | | | | |
|---|---|---|---|---|---|---|---|---|---|
| ATOM | 4853 | N | ILE B | 197 | −8.177 | 16.246 | −20.952 | 1.00 | 19.69 | N |
| ATOM | 4854 | CA | ILE B | 197 | −8.875 | 17.338 | −20.270 | 1.00 | 18.80 | C |
| ATOM | 4855 | CB | ILE B | 197 | −7.940 | 18.565 | −20.055 | 1.00 | 18.97 | C |
| ATOM | 4856 | CG1 | ILE B | 197 | −6.687 | 18.160 | −19.254 | 1.00 | 18.98 | C |
| ATOM | 4857 | CD1 | ILE B | 197 | −6.963 | 17.494 | −17.884 | 1.00 | 20.33 | C |
| ATOM | 4858 | CG2 | ILE B | 197 | −8.695 | 19.731 | −19.391 | 1.00 | 14.62 | C |
| ATOM | 4859 | C | ILE B | 197 | −10.167 | 17.753 | −20.979 | 1.00 | 18.49 | C |
| ATOM | 4860 | O | ILE B | 197 | −11.187 | 17.997 | −20.330 | 1.00 | 18.03 | O |
| ATOM | 4861 | N | ILE B | 198 | −10.113 | 17.816 | −22.307 | 1.00 | 18.06 | N |
| ATOM | 4862 | CA | ILE B | 198 | −11.280 | 18.152 | −23.119 | 1.00 | 17.74 | C |
| ATOM | 4863 | CB | ILE B | 198 | −10.885 | 18.457 | −24.592 | 1.00 | 17.44 | C |
| ATOM | 4864 | CG1 | ILE B | 198 | −9.812 | 19.557 | −24.654 | 1.00 | 16.83 | C |
| ATOM | 4865 | CD1 | ILE B | 198 | −10.208 | 20.898 | −24.036 | 1.00 | 15.38 | C |
| ATOM | 4866 | CG2 | ILE B | 198 | −12.106 | 18.831 | −25.424 | 1.00 | 14.13 | C |
| ATOM | 4867 | C | ILE B | 198 | −12.321 | 17.036 | −23.051 | 1.00 | 17.81 | C |
| ATOM | 4868 | O | ILE B | 198 | −13.521 | 17.305 | −22.971 | 1.00 | 18.04 | O |
| ATOM | 4869 | N | GLY B | 199 | −11.846 | 15.791 | −23.075 | 1.00 | 17.30 | N |
| ATOM | 4870 | CA | GLY B | 199 | −12.702 | 14.622 | −22.891 | 1.00 | 16.35 | C |
| ATOM | 4871 | C | GLY B | 199 | −13.417 | 14.665 | −21.550 | 1.00 | 16.55 | C |
| ATOM | 4872 | O | GLY B | 199 | −14.604 | 14.345 | −21.466 | 1.00 | 15.00 | O |
| ATOM | 4873 | N | LEU B | 200 | −12.685 | 15.066 | −20.508 | 1.00 | 16.10 | N |
| ATOM | 4874 | CA | LEU B | 200 | −13.230 | 15.184 | −19.159 | 1.00 | 17.38 | C |
| ATOM | 4875 | CB | LEU B | 200 | −12.120 | 15.481 | −18.143 | 1.00 | 17.54 | C |
| ATOM | 4876 | CG | LEU B | 200 | −12.535 | 15.549 | −16.667 | 1.00 | 17.12 | C |
| ATOM | 4877 | CD1 | LEU B | 200 | −13.053 | 14.198 | −16.185 | 1.00 | 13.13 | C |
| ATOM | 4878 | CD2 | LEU B | 200 | −11.380 | 16.021 | −15.792 | 1.00 | 17.38 | C |
| ATOM | 4879 | C | LEU B | 200 | −14.321 | 16.250 | −19.076 | 1.00 | 17.87 | C |
| ATOM | 4880 | O | LEU B | 200 | −15.392 | 16.008 | −18.502 | 1.00 | 17.44 | O |
| ATOM | 4881 | N | ALA B | 201 | −14.039 | 17.422 | −19.647 | 1.00 | 17.41 | N |
| ATOM | 4882 | CA | ALA B | 201 | −15.017 | 18.495 | −19.755 | 1.00 | 17.67 | C |
| ATOM | 4883 | CB | ALA B | 201 | −14.405 | 19.707 | −20.442 | 1.00 | 17.78 | C |
| ATOM | 4884 | C | ALA B | 201 | −16.263 | 18.027 | −20.507 | 1.00 | 17.66 | C |
| ATOM | 4885 | O | ALA B | 201 | −17.391 | 18.282 | −20.070 | 1.00 | 17.56 | O |
| ATOM | 4886 | N | GLY B | 202 | −16.045 | 17.333 | −21.626 | 1.00 | 16.75 | N |
| ATOM | 4887 | CA | GLY B | 202 | −17.129 | 16.786 | −22.440 | 1.00 | 16.45 | C |
| ATOM | 4888 | C | GLY B | 202 | −18.008 | 15.833 | −21.657 | 1.00 | 16.42 | C |
| ATOM | 4889 | O | GLY B | 202 | −19.235 | 15.887 | −21.759 | 1.00 | 16.27 | O |
| ATOM | 4890 | N | GLU B | 203 | −17.368 | 14.970 | −20.869 | 1.00 | 15.81 | N |
| ATOM | 4891 | CA | GLU B | 203 | −18.058 | 14.020 | −19.999 | 1.00 | 16.50 | C |
| ATOM | 4892 | CB | GLU B | 203 | −17.054 | 13.100 | −19.302 | 1.00 | 17.86 | C |
| ATOM | 4893 | CG | GLU B | 203 | −16.507 | 11.967 | −20.163 | 1.00 | 23.21 | C |
| ATOM | 4894 | CD | GLU B | 203 | −17.479 | 10.812 | −20.318 | 1.00 | 33.82 | C |
| ATOM | 4895 | OE1 | GLU B | 203 | −18.690 | 11.059 | −20.528 | 1.00 | 37.18 | O |
| ATOM | 4896 | OE2 | GLU B | 203 | −17.026 | 9.651 | −20.248 | 1.00 | 36.19 | O |
| ATOM | 4897 | C | GLU B | 203 | −18.923 | 14.716 | −18.955 | 1.00 | 15.28 | C |
| ATOM | 4898 | O | GLU B | 203 | −20.068 | 14.316 | −18.730 | 1.00 | 15.47 | O |
| ATOM | 4899 | N | TRP B | 204 | −18.372 | 15.759 | −18.332 | 1.00 | 14.61 | N |
| ATOM | 4900 | CA | TRP B | 204 | −19.075 | 16.513 | −17.293 | 1.00 | 14.31 | C |
| ATOM | 4901 | CB | TRP B | 204 | −18.160 | 17.552 | −16.636 | 1.00 | 13.66 | C |
| ATOM | 4902 | CG | TRP B | 204 | −17.099 | 16.968 | −15.739 | 1.00 | 13.04 | C |
| ATOM | 4903 | CD1 | TRP B | 204 | −16.934 | 15.655 | −15.410 | 1.00 | 12.72 | C |
| ATOM | 4904 | NE1 | TRP B | 204 | −15.868 | 15.506 | −14.558 | 1.00 | 13.36 | N |
| ATOM | 4905 | CE2 | TRP B | 204 | −15.326 | 16.738 | −14.305 | 1.00 | 14.42 | C |
| ATOM | 4906 | CD2 | TRP B | 204 | −16.083 | 17.689 | −15.028 | 1.00 | 13.16 | C |
| ATOM | 4907 | CE3 | TRP B | 204 | −15.730 | 19.043 | −14.942 | 1.00 | 13.16 | C |
| ATOM | 4908 | CZ3 | TRP B | 204 | −14.644 | 19.402 | −14.139 | 1.00 | 14.37 | C |
| ATOM | 4909 | CH2 | TRP B | 204 | −13.913 | 18.430 | −13.426 | 1.00 | 13.83 | C |
| ATOM | 4910 | CZ2 | TRP B | 204 | −14.235 | 17.098 | −13.498 | 1.00 | 11.98 | C |
| ATOM | 4911 | C | TRP B | 204 | −20.324 | 17.181 | −17.839 | 1.00 | 14.65 | C |
| ATOM | 4912 | O | TRP B | 204 | −21.353 | 17.217 | −17.161 | 1.00 | 14.85 | O |
| ATOM | 4913 | N | LEU B | 205 | −20.228 | 17.696 | −19.065 | 1.00 | 14.60 | N |
| ATOM | 4914 | CA | LEU B | 205 | −21.367 | 18.305 | −19.748 | 1.00 | 14.57 | C |
| ATOM | 4915 | CB | LEU B | 205 | −20.907 | 19.067 | −21.000 | 1.00 | 14.25 | C |
| ATOM | 4916 | CG | LEU B | 205 | −21.975 | 19.882 | −21.740 | 1.00 | 13.33 | C |
| ATOM | 4917 | CD1 | LEU B | 205 | −21.377 | 21.155 | −22.287 | 1.00 | 13.92 | C |
| ATOM | 4918 | CD2 | LEU B | 205 | −22.649 | 19.071 | −22.848 | 1.00 | 11.46 | C |
| ATOM | 4919 | C | LEU B | 205 | −22.436 | 17.276 | −20.111 | 1.00 | 15.10 | C |
| ATOM | 4920 | O | LEU B | 205 | −23.626 | 17.514 | −19.895 | 1.00 | 15.36 | O |
| ATOM | 4921 | N | THR B | 206 | −22.001 | 16.149 | −20.673 | 1.00 | 14.95 | N |
| ATOM | 4922 | CA | THR B | 206 | −22.890 | 15.051 | −21.056 | 1.00 | 15.79 | C |
| ATOM | 4923 | CB | THR B | 206 | −22.090 | 13.846 | −21.613 | 1.00 | 16.17 | C |
| ATOM | 4924 | OG1 | THR B | 206 | −21.243 | 14.276 | −22.685 | 1.00 | 17.36 | O |
| ATOM | 4925 | CG2 | THR B | 206 | −23.022 | 12.777 | −22.124 | 1.00 | 15.39 | C |
| ATOM | 4926 | C | THR B | 206 | −23.743 | 14.586 | −19.872 | 1.00 | 15.67 | C |
| ATOM | 4927 | O | THR B | 206 | −24.948 | 14.372 | −20.012 | 1.00 | 14.58 | O |
| ATOM | 4928 | N | SER B | 207 | −23.103 | 14.440 | −18.713 | 1.00 | 16.13 | N |
| ATOM | 4929 | CA | SER B | 207 | −23.787 | 14.036 | −17.487 | 1.00 | 17.14 | C |
| ATOM | 4930 | CB | SER B | 207 | −22.776 | 13.774 | −16.372 | 1.00 | 16.55 | C |
| ATOM | 4931 | OG | SER B | 207 | −21.929 | 12.692 | −16.716 | 1.00 | 17.44 | O | gad67.pdb

TABLE A-continued

| ATOM | 4932 | C | SER B | 207 | −24.820 | 15.064 | −17.037 | 1.00 | 17.76 | C |
|---|---|---|---|---|---|---|---|---|---|---|
| ATOM | 4933 | O | SER B | 207 | −25.880 | 14.695 | −16.534 | 1.00 | 18.26 | O |
| ATOM | 4934 | N | THR B | 208 | −24.498 | 16.345 | −17.227 | 1.00 | 17.81 | N |
| ATOM | 4935 | CA | THR B | 208 | −25.404 | 17.451 | −16.915 | 1.00 | 18.18 | C |
| ATOM | 4936 | CB | THR B | 208 | −24.662 | 18.804 | −16.954 | 1.00 | 17.98 | C |
| ATOM | 4937 | OG1 | THR B | 208 | −23.453 | 18.704 | −16.189 | 1.00 | 17.39 | O |
| ATOM | 4938 | CG2 | THR B | 208 | −25.525 | 19.922 | −16.376 | 1.00 | 18.53 | C |
| ATOM | 4939 | C | THR B | 208 | −26.607 | 17.478 | −17.866 | 1.00 | 18.55 | C |
| ATOM | 4940 | O | THR B | 208 | −27.731 | 17.772 | −17.444 | 1.00 | 18.69 | O |
| ATOM | 4941 | N | ALA B | 209 | −26.359 | 17.159 | −19.137 | 1.00 | 18.40 | N |
| ATOM | 4942 | CA | ALA B | 209 | −27.406 | 17.092 | −20.156 | 1.00 | 18.36 | C |
| ATOM | 4943 | CB | ALA B | 209 | −26.791 | 17.031 | −21.547 | 1.00 | 17.52 | C |
| ATOM | 4944 | C | ALA B | 209 | −28.322 | 15.891 | −19.916 | 1.00 | 19.22 | C |
| ATOM | 4945 | O | ALA B | 209 | −29.524 | 15.959 | −20.187 | 1.00 | 20.06 | O |
| ATOM | 4946 | N | ASN B | 210 | −27.734 | 14.802 | −19.414 | 1.00 | 19.00 | N |
| ATOM | 4947 | CA | ASN B | 210 | −28.458 | 13.607 | −18.968 | 1.00 | 19.71 | C |
| ATOM | 4948 | CB | ASN B | 210 | −28.929 | 13.779 | −17.511 | 1.00 | 19.39 | C |
| ATOM | 4949 | CG | ASN B | 210 | −29.484 | 12.495 | −16.915 | 1.00 | 19.28 | C |
| ATOM | 4950 | OD1 | ASN B | 210 | −30.447 | 12.524 | −16.149 | 1.00 | 24.15 | O |
| ATOM | 4951 | ND2 | ASN B | 210 | −28.885 | 11.364 | −17.267 | 1.00 | 16.97 | N |
| ATOM | 4952 | C | ASN B | 210 | −29.624 | 13.192 | −19.872 | 1.00 | 19.70 | C | gad67.pdb

| ATOM | 4953 | O | ASN B | 210 | −30.793 | 13.290 | −19.483 | 1.00 | 18.98 | O |
|---|---|---|---|---|---|---|---|---|---|---|
| ATOM | 4954 | N | THR B | 211 | −29.294 | 12.729 | −21.074 | 1.00 | 19.80 | N |
| ATOM | 4955 | CA | THR B | 211 | −30.307 | 12.338 | −22.051 | 1.00 | 19.78 | C |
| ATOM | 4956 | CB | THR B | 211 | −30.586 | 13.490 | −23.069 | 1.00 | 20.01 | C |
| ATOM | 4957 | OG1 | THR B | 211 | −31.791 | 13.219 | −23.799 | 1.00 | 18.81 | O |
| ATOM | 4958 | CG2 | THR B | 211 | −29.412 | 13.688 | −24.039 | 1.00 | 18.22 | C |
| ATOM | 4959 | C | THR B | 211 | −29.985 | 11.005 | −22.751 | 1.00 | 20.77 | C |
| ATOM | 4960 | O | THR B | 211 | −28.877 | 10.474 | −22.613 | 1.00 | 21.05 | O |
| ATOM | 4961 | N | ASN B | 212 | −30.979 | 10.473 | −23.468 | 1.00 | 21.81 | N |
| ATOM | 4962 | CA | ASN B | 212 | −30.859 | 9.256 | −24.272 | 1.00 | 22.73 | C |
| ATOM | 4963 | CB | ASN B | 212 | −32.162 | 8.453 | −24.198 | 1.00 | 24.24 | C |
| ATOM | 4964 | CG | ASN B | 212 | −32.152 | 7.413 | −23.108 | 1.00 | 28.37 | C |
| ATOM | 4965 | OD1 | ASN B | 212 | −31.398 | 6.447 | −23.168 | 1.00 | 37.95 | O |
| ATOM | 4966 | ND2 | ASN B | 212 | −33.007 | 7.593 | −22.108 | 1.00 | 34.86 | N |
| ATOM | 4967 | C | ASN B | 212 | −30.586 | 9.578 | −25.739 | 1.00 | 22.63 | C |
| ATOM | 4968 | O | ASN B | 212 | −31.096 | 10.568 | −26.258 | 1.00 | 22.90 | O |
| ATOM | 4969 | N | MET B | 213 | −29.818 | 8.721 | −26.409 | 1.00 | 21.49 | N |
| ATOM | 4970 | CA | MET B | 213 | −29.518 | 8.888 | −27.837 | 1.00 | 21.51 | C |
| ATOM | 4971 | CB | MET B | 213 | −28.206 | 8.179 | −28.200 | 1.00 | 21.34 | C |
| ATOM | 4972 | CG | MET B | 213 | −26.929 | 8.904 | −27.790 | 1.00 | 20.13 | C |
| ATOM | 4973 | SD | MET B | 213 | −26.735 | 10.541 | −28.522 | 1.00 | 20.79 | S |
| ATOM | 4974 | CE | MET B | 213 | −26.634 | 10.179 | −30.271 | 1.00 | 17.41 | C |
| ATOM | 4975 | C | MET B | 213 | −30.617 | 8.407 | −28.800 | 1.00 | 21.78 | C |
| ATOM | 4976 | O | MET B | 213 | −30.527 | 8.659 | −30.005 | 1.00 | 22.86 | O |
| ATOM | 4977 | N | PHE B | 214 | −31.642 | 7.723 | −28.289 | 1.00 | 20.89 | N |
| ATOM | 4978 | CA | PHE B | 214 | −32.570 | 6.988 | −29.172 | 1.00 | 20.40 | C |
| ATOM | 4979 | CB | PHE B | 214 | −33.354 | 5.880 | −28.439 | 1.00 | 21.06 | C |
| ATOM | 4980 | CG | PHE B | 214 | −34.088 | 6.327 | −27.194 | 1.00 | 20.30 | C |
| ATOM | 4981 | CD1 | PHE B | 214 | −34.257 | 5.430 | −26.137 | 1.00 | 21.87 | C |
| ATOM | 4982 | CE1 | PHE B | 214 | −34.937 | 5.798 | −24.978 | 1.00 | 22.72 | C |
| ATOM | 4983 | CZ | PHE B | 214 | −35.468 | 7.083 | −24.868 | 1.00 | 23.29 | C |
| ATOM | 4984 | CE2 | PHE B | 214 | −35.320 | 7.985 | −25.921 | 1.00 | 20.31 | C |
| ATOM | 4985 | CD2 | PHE B | 214 | −34.632 | 7.603 | −27.076 | 1.00 | 19.42 | C |
| ATOM | 4986 | C | PHE B | 214 | −33.485 | 7.797 | −30.112 | 1.00 | 19.84 | C |
| ATOM | 4987 | O | PHE B | 214 | −33.955 | 7.259 | −31.116 | 1.00 | 20.18 | O |
| ATOM | 4988 | N | THR B | 215 | −33.727 | 9.068 | −29.798 | 1.00 | 18.27 | N |
| ATOM | 4989 | CA | THR B | 215 | −34.534 | 9.931 | −30.669 | 1.00 | 16.92 | C |
| ATOM | 4990 | CB | THR B | 215 | −36.001 | 10.087 | −30.169 | 1.00 | 17.00 | C |
| ATOM | 4991 | OG1 | THR B | 215 | −36.010 | 10.731 | −28.893 | 1.00 | 16.07 | O |
| ATOM | 4992 | CG2 | THR B | 215 | −36.710 | 8.739 | −30.062 | 1.00 | 14.79 | C |
| ATOM | 4993 | C | THR B | 215 | −33.929 | 11.319 | −30.802 | 1.00 | 15.99 | C |
| ATOM | 4994 | O | THR B | 215 | −33.265 | 11.803 | −29.887 | 1.00 | 15.83 | O |
| ATOM | 4995 | N | TYR B | 216 | −34.168 | 11.956 | −31.946 | 1.00 | 15.83 | N |
| ATOM | 4996 | CA | TYR B | 216 | −33.815 | 13.365 | −32.146 | 1.00 | 15.73 | C |
| ATOM | 4997 | CB | TYR B | 216 | −34.055 | 13.778 | −33.603 | 1.00 | 14.61 | C |
| ATOM | 4998 | CG | TYR B | 216 | −33.775 | 15.237 | −33.875 | 1.00 | 14.46 | C |
| ATOM | 4999 | CD1 | TYR B | 216 | −32.485 | 15.670 | −34.201 | 1.00 | 13.25 | C |
| ATOM | 5000 | CE1 | TYR B | 216 | −32.219 | 17.016 | −34.445 | 1.00 | 14.18 | C |
| ATOM | 5001 | CZ | TYR B | 216 | −33.252 | 17.940 | −34.359 | 1.00 | 13.71 | C |
| ATOM | 5002 | OH | TYR B | 216 | −33.001 | 19.271 | −34.589 | 1.00 | 12.81 | O |
| ATOM | 5003 | CE2 | TYR B | 216 | −34.539 | 17.533 | −34.034 | 1.00 | 13.88 | C |
| ATOM | 5004 | CD2 | TYR B | 216 | −34.794 | 16.188 | −33.799 | 1.00 | 11.99 | C |
| ATOM | 5005 | C | TYR B | 216 | −34.628 | 14.254 | −31.199 | 1.00 | 16.63 | C |
| ATOM | 5006 | O | TYR B | 216 | −34.159 | 15.298 | −30.749 | 1.00 | 17.21 | O |
| ATOM | 5007 | N | GLU B | 217 | −35.843 | 13.810 | −30.898 | 1.00 | 17.55 | N |
| ATOM | 5008 | CA | GLU B | 217 | −36.771 | 14.506 | −30.007 | 1.00 | 18.92 | C |
| ATOM | 5009 | CB | GLU B | 217 | −37.964 | 13.591 | −29.726 | 1.00 | 19.73 | C |
| ATOM | 5010 | CG | GLU B | 217 | −39.148 | 14.243 | −29.064 | 1.00 | 22.54 | C |

TABLE A-continued

| | | | | | | | | | | |
|---|---|---|---|---|---|---|---|---|---|---|
| ATOM | 5011 | CD | GLU B | 217 | −40.314 | 13.287 | −28.946 | 1.00 | 27.02 | C |
| ATOM | 5012 | OE1 | GLU B | 217 | −40.850 | 13.125 | −27.828 | 1.00 | 29.70 | O |
| ATOM | 5013 | OE2 | GLU B | 217 | −40.685 | 12.680 | −29.973 | 1.00 | 32.11 | O |
| ATOM | 5014 | C | GLU B | 217 | −36.140 | 14.985 | −28.692 | 1.00 | 18.06 | C |
| ATOM | 5015 | O | GLU B | 217 | −36.367 | 16.121 | −28.275 | 1.00 | 18.38 | O |
| ATOM | 5016 | N | ILE B | 218 | −35.355 | 14.125 | −28.045 | 1.00 | 17.46 | N |
| ATOM | 5017 | CA | ILE B | 218 | −34.741 | 14.481 | −26.758 | 1.00 | 16.95 | C |
| ATOM | 5018 | CB | ILE B | 218 | −35.279 | 13.600 | −25.545 | 1.00 | 17.48 | C |
| ATOM | 5019 | CG1 | ILE B | 218 | −34.595 | 12.220 | −25.407 | 1.00 | 18.95 | C |
| ATOM | 5020 | CD1 | ILE B | 218 | −34.369 | 11.435 | −26.662 | 1.00 | 22.95 | C |
| ATOM | 5021 | CG2 | ILE B | 218 | −36.823 | 13.558 | −25.519 | 1.00 | 14.88 | C |
| ATOM | 5022 | C | ILE B | 218 | −33.206 | 14.605 | −26.774 | 1.00 | 16.47 | C |
| ATOM | 5023 | O | ILE B | 218 | −32.600 | 14.930 | −25.756 | 1.00 | 17.54 | O |
| ATOM | 5024 | N | ALA B | 219 | −32.591 | 14.371 | −27.931 | 1.00 | 15.90 | N |
| ATOM | 5025 | CA | ALA B | 219 | −31.143 | 14.551 | −28.089 | 1.00 | 15.19 | C |
| ATOM | 5026 | CB | ALA B | 219 | −30.416 | 13.211 | −27.923 | 1.00 | 13.76 | C |
| ATOM | 5027 | C | ALA B | 219 | −30.782 | 15.199 | −29.432 | 1.00 | 15.14 | C |
| ATOM | 5028 | O | ALA B | 219 | −29.948 | 14.663 | −30.168 | 1.00 | 15.55 | O |
| ATOM | 5029 | N | PRO B | 220 | −31.391 | 16.365 | −29.748 | 1.00 | 14.87 | N |
| ATOM | 5030 | CA | PRO B | 220 | −31.251 | 16.931 | −31.094 | 1.00 | 14.76 | C |
| ATOM | 5031 | CB | PRO B | 220 | −32.058 | 18.232 | −31.021 | 1.00 | 14.09 | C |
| ATOM | 5032 | CG | PRO B | 220 | −32.182 | 18.545 | −29.573 | 1.00 | 12.55 | C |
| ATOM | 5033 | CD | PRO B | 220 | −32.218 | 17.225 | −28.880 | 1.00 | 14.71 | C |
| ATOM | 5034 | C | PRO B | 220 | −29.803 | 17.207 | −31.511 | 1.00 | 15.37 | C |
| ATOM | 5035 | O | PRO B | 220 | −29.388 | 16.791 | −32.593 | 1.00 | 15.46 | O |
| ATOM | 5036 | N | VAL B | 221 | −29.050 | 17.890 | −30.650 | 1.00 | 15.63 | N |
| ATOM | 5037 | CA | VAL B | 221 | −27.667 | 18.256 | −30.943 | 1.00 | 16.09 | C |
| ATOM | 5038 | CB | VAL B | 221 | −27.098 | 19.243 | −29.892 | 1.00 | 16.68 | C |
| ATOM | 5039 | CG1 | VAL B | 221 | −25.665 | 19.630 | −30.237 | 1.00 | 14.09 | C |
| ATOM | 5040 | CG2 | VAL B | 221 | −27.980 | 20.495 | −29.793 | 1.00 | 14.75 | C |
| ATOM | 5041 | C | VAL B | 221 | −26.778 | 17.020 | −31.044 | 1.00 | 16.13 | C |
| ATOM | 5042 | O | VAL B | 221 | −26.005 | 16.883 | −31.994 | 1.00 | 16.80 | O |
| ATOM | 5043 | N | PHE B | 222 | −26.906 | 16.119 | −30.073 | 1.00 | 16.04 | N |
| ATOM | 5044 | CA | PHE B | 222 | −26.063 | 14.921 | −30.006 | 1.00 | 15.74 | C |
| ATOM | 5045 | CB | PHE B | 222 | −26.265 | 14.183 | −28.680 | 1.00 | 14.91 | C |
| ATOM | 5046 | CG | PHE B | 222 | −25.953 | 15.015 | −27.458 | 1.00 | 15.13 | C |
| ATOM | 5047 | CD1 | PHE B | 222 | −24.783 | 15.773 | −27.386 | 1.00 | 10.46 | C |
| ATOM | 5048 | CE1 | PHE B | 222 | −24.492 | 16.532 | −26.253 | 1.00 | 13.92 | C |
| ATOM | 5049 | CZ | PHE B | 222 | −25.377 | 16.535 | −25.168 | 1.00 | 12.60 | C |
| ATOM | 5050 | CE2 | PHE B | 222 | −26.538 | 15.773 | −25.224 | 1.00 | 13.60 | C |
| ATOM | 5051 | CD2 | PHE B | 222 | −26.821 | 15.017 | −26.363 | 1.00 | 13.16 | C |
| ATOM | 5052 | C | PHE B | 222 | −26.276 | 13.968 | −31.181 | 1.00 | 15.99 | C |
| ATOM | 5053 | O | PHE B | 222 | −25.319 | 13.356 | −31.660 | 1.00 | 17.04 | O |
| ATOM | 5054 | N | VAL B | 223 | −27.525 | 13.845 | −31.634 | 1.00 | 15.41 | N |
| ATOM | 5055 | CA | VAL B | 223 | −27.863 | 13.021 | −32.798 | 1.00 | 15.34 | C |
| ATOM | 5056 | CB | VAL B | 223 | −29.391 | 12.970 | −33.038 | 1.00 | 15.44 | C |
| ATOM | 5057 | CG1 | VAL B | 223 | −29.717 | 12.417 | −34.426 | 1.00 | 12.71 | C |
| ATOM | 5058 | CG2 | VAL B | 223 | −30.088 | 12.149 | −31.949 | 1.00 | 16.41 | C |
| ATOM | 5059 | C | VAL B | 223 | −27.155 | 13.542 | −34.057 | 1.00 | 16.57 | C |
| ATOM | 5060 | O | VAL B | 223 | −26.612 | 12.757 | −34.842 | 1.00 | 16.89 | O |
| ATOM | 5061 | N | LEU B | 224 | −27.160 | 14.863 | −34.236 | 1.00 | 16.66 | N |
| ATOM | 5062 | CA | LEU B | 224 | −26.503 | 15.490 | −35.381 | 1.00 | 17.01 | C |
| ATOM | 5063 | CB | LEU B | 224 | −26.908 | 16.962 | −35.513 | 1.00 | 16.46 | C |
| ATOM | 5064 | CG | LEU B | 224 | −28.386 | 17.258 | −35.801 | 1.00 | 17.70 | C |
| ATOM | 5065 | CD1 | LEU B | 224 | −28.573 | 18.747 | −35.935 | 1.00 | 17.80 | C |
| ATOM | 5066 | CD2 | LEU B | 224 | −28.901 | 16.550 | −37.049 | 1.00 | 15.18 | C |
| ATOM | 5067 | C | LEU B | 224 | −24.986 | 15.346 | −35.305 | 1.00 | 17.38 | C |
| ATOM | 5068 | O | LEU B | 224 | −24.338 | 15.038 | −36.307 | 1.00 | 16.76 | O |
| ATOM | 5069 | N | MET B | 225 | −24.432 | 15.553 | −34.114 | 1.00 | 17.91 | N |
| ATOM | 5070 | CA | MET B | 225 | −23.004 | 15.331 | −33.875 | 1.00 | 19.08 | C |
| ATOM | 5071 | CB | MET B | 225 | −22.646 | 15.635 | −32.425 | 1.00 | 18.35 | C |
| ATOM | 5072 | CG | MET B | 225 | −22.514 | 17.096 | −32.134 | 1.00 | 17.47 | C |
| ATOM | 5073 | SD | MET B | 225 | −22.308 | 17.414 | −30.381 | 1.00 | 18.53 | S |
| ATOM | 5074 | CE | MET B | 225 | −22.107 | 19.193 | −30.404 | 1.00 | 15.34 | C |
| ATOM | 5075 | C | MET B | 225 | −22.566 | 13.912 | −34.232 | 1.00 | 19.97 | C |
| ATOM | 5076 | O | MET B | 225 | −21.512 | 13.720 | −34.834 | 1.00 | 20.55 | O |
| ATOM | 5077 | N | GLU B | 226 | −23.383 | 12.926 | −33.865 | 1.00 | 21.07 | N |
| ATOM | 5078 | CA | GLU B | 226 | −23.104 | 11.525 | −34.198 | 1.00 | 22.80 | C |
| ATOM | 5079 | CB | GLU B | 226 | −24.100 | 10.587 | −33.504 | 1.00 | 22.12 | C |
| ATOM | 5080 | CG | GLU B | 226 | −23.759 | 9.110 | −33.632 | 1.00 | 25.79 | C |
| ATOM | 5081 | CD | GLU B | 226 | −24.446 | 8.236 | −32.580 | 1.00 | 27.60 | C |
| ATOM | 5082 | OE1 | GLU B | 226 | −24.044 | 8.287 | −31.396 | 1.00 | 31.89 | O |
| ATOM | 5083 | OE2 | GLU B | 226 | −25.376 | 7.484 | −32.945 | 1.00 | 31.74 | O |
| ATOM | 5084 | C | GLU B | 226 | −23.093 | 11.300 | −35.713 | 1.00 | 21.99 | C |
| ATOM | 5085 | O | GLU B | 226 | −22.196 | 10.638 | −36.235 | 1.00 | 21.71 | O |
| ATOM | 5086 | N | GLN B | 227 | −24.081 | 11.864 | −36.407 | 1.00 | 21.59 | N |
| ATOM | 5087 | CA | GLN B | 227 | −24.183 | 11.751 | −37.859 | 1.00 | 22.65 | C |
| ATOM | 5088 | CB | GLN B | 227 | −25.482 | 12.399 | −38.346 | 1.00 | 22.29 | C |

TABLE A-continued

| ATOM | 5089 | CG | GLN B | 227 | −25.641 | 12.459 | −39.869 | 1.00 | 27.67 | C |
|------|------|-----|-------|-----|---------|--------|---------|------|-------|---|
| ATOM | 5090 | CD | GLN B | 227 | −26.868 | 13.246 | −40.305 | 1.00 | 27.90 | C |
| ATOM | 5091 | OE1 | GLN B | 227 | −26.761 | 14.228 | −41.044 | 1.00 | 34.33 | O |
| ATOM | 5092 | NE2 | GLN B | 227 | −28.041 | 12.818 | −39.846 | 1.00 | 34.95 | N |
| ATOM | 5093 | C | GLN B | 227 | −22.965 | 12.360 | −38.565 | 1.00 | 20.93 | C |
| ATOM | 5094 | O | GLN B | 227 | −22.398 | 11.745 | −39.469 | 1.00 | 20.41 | O |
| ATOM | 5095 | N | ILE B | 228 | −22.577 | 13.563 | −38.138 | 1.00 | 19.92 | N |
| ATOM | 5096 | CA | ILE B | 228 | −21.417 | 14.272 | −38.685 | 1.00 | 20.25 | C |
| ATOM | 5097 | CB | ILE B | 228 | −21.268 | 15.694 | −38.054 | 1.00 | 20.25 | C |
| ATOM | 5098 | CG1 | ILE B | 228 | −22.470 | 16.595 | −38.393 | 1.00 | 23.40 | C |
| ATOM | 5099 | CD1 | ILE B | 228 | −22.734 | 16.808 | −39.873 | 1.00 | 28.37 | C |
| ATOM | 5100 | CG2 | ILE B | 228 | −19.935 | 16.345 | −38.441 | 1.00 | 20.90 | C |
| ATOM | 5101 | C | ILE B | 228 | −20.128 | 13.480 | −38.455 | 1.00 | 19.66 | C |
| ATOM | 5102 | O | ILE B | 228 | −19.332 | 13.289 | −39.374 | 1.00 | 18.72 | O |
| ATOM | 5103 | N | THR B | 229 | −19.944 | 13.019 | −37.220 | 1.00 | 19.31 | N |
| ATOM | 5104 | CA | THR B | 229 | −18.731 | 12.316 | −36.811 | 1.00 | 19.38 | C |
| ATOM | 5105 | CB | THR B | 229 | −18.643 | 12.207 | −35.267 | 1.00 | 18.95 | C |
| ATOM | 5106 | OG1 | THR B | 229 | −18.828 | 13.504 | −34.696 | 1.00 | 18.83 | O |
| ATOM | 5107 | CG2 | THR B | 229 | −17.294 | 11.670 | −34.822 | 1.00 | 16.82 | C |
| ATOM | 5108 | C | THR B | 229 | −18.597 | 10.943 | −37.472 | 1.00 | 19.68 | C |
| ATOM | 5109 | O | THR B | 229 | −17.516 | 10.593 | −37.943 | 1.00 | 20.23 | O |
| ATOM | 5110 | N | LEU B | 230 | −19.691 | 10.181 | −37.526 | 1.00 | 19.98 | N |
| ATOM | 5111 | CA | LEU B | 230 | −19.669 | 8.865 | −38.181 | 1.00 | 19.85 | C |
| ATOM | 5112 | CB | LEU B | 230 | −20.993 | 8.116 | −38.012 | 1.00 | 18.41 | C |
| ATOM | 5113 | CG | LEU B | 230 | −21.331 | 7.571 | −36.622 | 1.00 | 19.47 | C |
| ATOM | 5114 | CD1 | LEU B | 230 | −22.778 | 7.130 | −36.596 | 1.00 | 16.57 | C |
| ATOM | 5115 | CD2 | LEU B | 230 | −20.407 | 6.435 | −36.191 | 1.00 | 16.30 | C |
| ATOM | 5116 | C | LEU B | 230 | −19.308 | 8.957 | −39.660 | 1.00 | 20.48 | C |
| ATOM | 5117 | O | LEU B | 230 | −18.532 | 8.139 | −40.159 | 1.00 | 20.08 | O |
| ATOM | 5118 | N | LYS B | 231 | −19.856 | 9.950 | −40.358 | 1.00 | 20.89 | N |
| ATOM | 5119 | CA | LYS B | 231 | −19.562 | 10.083 | −41.781 | 1.00 | 22.36 | C |
| ATOM | 5120 | CB | LYS B | 231 | −20.573 | 10.981 | −42.508 | 1.00 | 23.05 | C |
| ATOM | 5121 | CG | LYS B | 231 | −20.328 | 12.466 | −42.436 | 1.00 | 27.71 | C |
| ATOM | 5122 | CD | LYS B | 231 | −21.045 | 13.198 | −43.561 | 1.00 | 31.01 | C |
| ATOM | 5123 | CE | LYS B | 231 | −20.359 | 12.973 | −44.904 | 1.00 | 34.26 | C |
| ATOM | 5124 | NZ | LYS B | 231 | −20.689 | 14.065 | −45.868 | 1.00 | 36.52 | N |
| ATOM | 5125 | C | LYS B | 231 | −18.099 | 10.480 | −42.021 | 1.00 | 21.19 | C |
| ATOM | 5126 | O | LYS B | 231 | −17.471 | 10.014 | −42.970 | 1.00 | 21.29 | O |
| ATOM | 5127 | N | LYS B | 232 | −17.568 | 11.316 | −41.132 | 1.00 | 20.39 | N |
| ATOM | 5128 | CA | LYS B | 232 | −16.165 | 11.710 | −41.152 | 1.00 | 19.79 | C |
| ATOM | 5129 | CB | LYS B | 232 | −15.898 | 12.756 | −40.065 | 1.00 | 20.26 | C |
| ATOM | 5130 | CG | LYS B | 232 | −14.472 | 13.301 | −40.009 | 1.00 | 23.14 | C |
| ATOM | 5131 | CD | LYS B | 232 | −14.202 | 14.344 | −41.078 | 1.00 | 26.88 | C |
| ATOM | 5132 | CE | LYS B | 232 | −12.965 | 15.164 | −40.731 | 1.00 | 31.08 | C |
| ATOM | 5133 | NZ | LYS B | 232 | −12.659 | 16.170 | −41.784 | 1.00 | 33.52 | N |
| ATOM | 5134 | C | LYS B | 232 | −15.258 | 10.499 | −40.962 | 1.00 | 19.20 | C |
| ATOM | 5135 | O | LYS B | 232 | −14.234 | 10.366 | −41.639 | 1.00 | 18.78 | O |
| ATOM | 5136 | N | MET B | 233 | −15.644 | 9.617 | −40.042 | 1.00 | 18.21 | N |
| ATOM | 5137 | CA | MET B | 233 | −14.892 | 8.393 | −39.784 | 1.00 | 17.63 | C |
| ATOM | 5138 | CB | MET B | 233 | −15.432 | 7.668 | −38.548 | 1.00 | 17.23 | C |
| ATOM | 5139 | CG | MET B | 233 | −15.209 | 8.413 | −37.237 | 1.00 | 17.07 | C |
| ATOM | 5140 | SD | MET B | 233 | −16.142 | 7.710 | −35.854 | 1.00 | 18.67 | S |
| ATOM | 5141 | CE | MET B | 233 | −15.043 | 6.400 | −35.321 | 1.00 | 14.42 | C |
| ATOM | 5142 | C | MET B | 233 | −14.897 | 7.476 | −41.000 | 1.00 | 16.74 | C |
| ATOM | 5143 | O | MET B | 233 | −13.877 | 6.874 | −41.322 | 1.00 | 16.07 | O |
| ATOM | 5144 | N | ARG B | 234 | −16.043 | 7.392 | −41.676 | 1.00 | 16.98 | N |
| ATOM | 5145 | CA | ARG B | 234 | −16.186 | 6.605 | −42.903 | 1.00 | 17.05 | C |
| ATOM | 5146 | CB | ARG B | 234 | −17.650 | 6.535 | −43.341 | 1.00 | 16.12 | C |
| ATOM | 5147 | CG | ARG B | 234 | −18.545 | 5.736 | −42.394 | 1.00 | 16.88 | C |
| ATOM | 5148 | CD | ARG B | 234 | −19.884 | 5.401 | −43.026 | 1.00 | 14.74 | C |
| ATOM | 5149 | NE | ARG B | 234 | −20.694 | 6.591 | −43.293 | 1.00 | 15.97 | N |
| ATOM | 5150 | CZ | ARG B | 234 | −21.576 | 7.105 | −42.441 | 1.00 | 16.05 | C |
| ATOM | 5151 | NH1 | ARG B | 234 | −21.767 | 6.545 | −41.253 | 1.00 | 13.87 | N |
| ATOM | 5152 | NH2 | ARG B | 234 | −22.272 | 8.183 | −42.775 | 1.00 | 15.72 | N |
| ATOM | 5153 | C | ARG B | 234 | −15.320 | 7.155 | −44.038 | 1.00 | 18.52 | C |
| ATOM | 5154 | O | ARG B | 234 | −14.812 | 6.390 | −44.862 | 1.00 | 18.20 | O |
| ATOM | 5155 | N | GLU B | 235 | −15.161 | 8.478 | −44.072 | 1.00 | 19.98 | N |
| ATOM | 5156 | CA | GLU B | 235 | −14.281 | 9.133 | −45.041 | 1.00 | 23.38 | C |
| | | | | | gad67.pdb | | | | | |
| ATOM | 5157 | CB | GLU B | 235 | −14.495 | 10.649 | −45.036 | 1.00 | 23.45 | C |
| ATOM | 5158 | CG | GLU B | 235 | −15.809 | 11.081 | −45.685 | 1.00 | 27.26 | C |
| ATOM | 5159 | CD | GLU B | 235 | −16.184 | 12.535 | −45.400 | 1.00 | 28.77 | C |
| ATOM | 5160 | OE1 | GLU B | 235 | −17.131 | 13.031 | −46.055 | 1.00 | 36.81 | O |
| ATOM | 5161 | OE2 | GLU B | 235 | −15.551 | 13.179 | −44.527 | 1.00 | 34.89 | O |
| ATOM | 5162 | C | GLU B | 235 | −12.820 | 8.802 | −44.764 | 1.00 | 22.60 | C |
| ATOM | 5163 | O | GLU B | 235 | −12.059 | 8.522 | −45.683 | 1.00 | 22.94 | O |
| ATOM | 5164 | N | ILE B | 236 | −12.442 | 8.821 | −43.490 | 1.00 | 22.82 | N |
| ATOM | 5165 | CA | ILE B | 236 | −11.084 | 8.469 | −43.074 | 1.00 | 22.93 | C |
| ATOM | 5166 | CB | ILE B | 236 | −10.848 | 8.844 | −41.591 | 1.00 | 22.75 | C |
| ATOM | 5167 | CG1 | ILE B | 236 | −10.810 | 10.369 | −41.450 | 1.00 | 22.20 | C |

TABLE A-continued

| ATOM | 5168 | CD1 | ILE B | 236 | −11.219 | 10.879 | −40.090 | 1.00 | 25.00 | C |
|---|---|---|---|---|---|---|---|---|---|---|
| ATOM | 5169 | CG2 | ILE B | 236 | −9.554 | 8.239 | −41.064 | 1.00 | 21.97 | C |
| ATOM | 5170 | C | ILE B | 236 | −10.769 | 6.990 | −43.363 | 1.00 | 22.86 | C |
| ATOM | 5171 | O | ILE B | 236 | −9.646 | 6.655 | −43.755 | 1.00 | 23.09 | O |
| ATOM | 5172 | N | VAL B | 237 | −11.771 | 6.126 | −43.194 | 1.00 | 21.97 | N |
| ATOM | 5173 | CA | VAL B | 237 | −11.660 | 4.708 | −43.551 | 1.00 | 21.03 | C |
| ATOM | 5174 | CB | VAL B | 237 | −12.895 | 3.904 | −43.055 | 1.00 | 20.53 | C |
| ATOM | 5175 | CG1 | VAL B | 237 | −13.009 | 2.557 | −43.751 | 1.00 | 18.02 | C |
| ATOM | 5176 | CG2 | VAL B | 237 | −12.824 | 3.714 | −41.545 | 1.00 | 16.97 | C |
| ATOM | 5177 | C | VAL B | 237 | −11.434 | 4.534 | −45.063 | 1.00 | 22.21 | C |
| ATOM | 5178 | O | VAL B | 237 | −10.748 | 3.605 | −45.496 | 1.00 | 23.50 | O |
| ATOM | 5179 | N | GLY B | 238 | −11.997 | 5.443 | −45.854 | 1.00 | 21.84 | N |
| ATOM | 5180 | CA | GLY B | 238 | −11.787 | 5.441 | −47.297 | 1.00 | 21.78 | C |
| ATOM | 5181 | C | GLY B | 238 | −13.024 | 5.086 | −48.096 | 1.00 | 22.40 | C |
| ATOM | 5182 | O | GLY B | 238 | −12.933 | 4.851 | −49.305 | 1.00 | 22.41 | O |
| ATOM | 5183 | N | TRP B | 239 | −14.177 | 5.039 | −47.426 | 1.00 | 21.58 | N |
| ATOM | 5184 | CA | TRP B | 239 | −15.448 | 4.766 | −48.097 | 1.00 | 21.71 | C |
| ATOM | 5185 | CB | TRP B | 239 | −16.487 | 4.199 | −47.122 | 1.00 | 20.90 | C |
| ATOM | 5186 | CG | TRP B | 239 | −16.141 | 2.856 | −46.535 | 1.00 | 19.93 | C |
| ATOM | 5187 | CD1 | TRP B | 239 | −15.227 | 1.958 | −47.010 | 1.00 | 20.91 | C |
| ATOM | 5188 | NE1 | TRP B | 239 | −15.202 | .836 | −46.214 | 1.00 | 20.59 | N |
| ATOM | 5189 | CE2 | TRP B | 239 | −16.123 | .986 | −45.209 | 1.00 | 20.52 | C |
| ATOM | 5190 | CD2 | TRP B | 239 | −16.739 | 2.246 | −45.383 | 1.00 | 19.95 | C |
| ATOM | 5191 | CE3 | TRP B | 239 | −17.730 | 2.647 | −44.474 | 1.00 | 17.84 | C |
| ATOM | 5192 | CZ3 | TRP B | 239 | −18.070 | 1.785 | −43.435 | 1.00 | 21.22 | C |
| ATOM | 5193 | CH2 | TRP B | 239 | −17.439 | .538 | −43.291 | 1.00 | 20.30 | C |
| ATOM | 5194 | CZ2 | TRP B | 239 | −16.465 | .122 | −44.165 | 1.00 | 20.26 | C |
| ATOM | 5195 | C | TRP B | 239 | −15.979 | 6.030 | −48.773 | 1.00 | 23.25 | C |
| ATOM | 5196 | O | TRP B | 239 | −15.637 | 7.154 | −48.380 | 1.00 | 23.11 | O |
| ATOM | 5197 | N | SER B | 240 | −16.796 | 5.834 | −49.807 | 1.00 | 25.59 | N |
| ATOM | 5198 | CA | SER B | 240 | −17.365 | 6.940 | −50.574 | 1.00 | 28.05 | C |
| ATOM | 5199 | CB | SER B | 240 | −17.549 | 6.542 | −52.038 | 1.00 | 28.49 | C |
| ATOM | 5200 | OG | SER B | 240 | −18.655 | 5.671 | −52.194 | 1.00 | 31.81 | O |
| ATOM | 5201 | C | SER B | 240 | −18.696 | 7.386 | −49.991 | 1.00 | 28.94 | C |
| ATOM | 5202 | O | SER B | 240 | −19.407 | 6.589 | −49.376 | 1.00 | 28.82 | O |
| ATOM | 5203 | N | SER B | 241 | −19.026 | 8.659 | −50.207 | 1.00 | 30.36 | N |
| ATOM | 5204 | CA | SER B | 241 | −20.249 | 9.277 | −49.682 | 1.00 | 32.07 | C |
| ATOM | 5205 | CB | SER B | 241 | −20.223 | 10.786 | −49.935 | 1.00 | 32.94 | C |
| ATOM | 5206 | OG | SER B | 241 | −19.097 | 11.384 | −49.315 | 1.00 | 36.87 | O |
| ATOM | 5207 | C | SER B | 241 | −21.526 | 8.673 | −50.265 | 1.00 | 32.07 | C |
| ATOM | 5208 | O | SER B | 241 | −22.620 | 8.896 | −49.744 | 1.00 | 32.61 | O |
| ATOM | 5209 | N | LYS B | 242 | −21.370 | 7.914 | −51.346 | 1.00 | 32.25 | N |
| ATOM | 5210 | CA | LYS B | 242 | −22.465 | 7.194 | −51.997 | 1.00 | 32.45 | C |
| ATOM | 5211 | CB | LYS B | 242 | −21.891 | 6.275 | −53.080 | 1.00 | 32.72 | C |
| ATOM | 5212 | CG | LYS B | 242 | −22.898 | 5.382 | −53.790 | 1.00 | 35.83 | C |
| ATOM | 5213 | CD | LYS B | 242 | −22.380 | 4.919 | −55.154 | 1.00 | 40.85 | C |
| ATOM | 5214 | CE | LYS B | 242 | −21.347 | 3.798 | −55.048 | 1.00 | 45.15 | C |
| ATOM | 5215 | NZ | LYS B | 242 | −19.990 | 4.282 | −54.656 | 1.00 | 47.89 | N |
| ATOM | 5216 | C | LYS B | 242 | −23.306 | 6.388 | −51.002 | 1.00 | 31.97 | C |
| ATOM | 5217 | O | LYS B | 242 | −24.531 | 6.346 | −51.097 | 1.00 | 31.99 | O |
| ATOM | 5218 | N | ASP B | 243 | −22.636 | 5.751 | −50.049 | 1.00 | 30.92 | N |
| ATOM | 5219 | CA | ASP B | 243 | −23.312 | 4.913 | −49.076 | 1.00 | 30.43 | C |
| ATOM | 5220 | CB | ASP B | 243 | −23.201 | 3.439 | −49.490 | 1.00 | 30.82 | C |
| ATOM | 5221 | CG | ASP B | 243 | −24.482 | 2.652 | −49.224 | 1.00 | 33.06 | C |
| ATOM | 5222 | OD1 | ASP B | 243 | −25.213 | 2.981 | −48.266 | 1.00 | 35.90 | O |
| ATOM | 5223 | OD2 | ASP B | 243 | −24.757 | 1.695 | −49.978 | 1.00 | 34.77 | O |
| ATOM | 5224 | C | ASP B | 243 | −22.699 gad67.pdb | 5.158 | −47.701 | 1.00 | 28.47 | C |
| ATOM | 5225 | O | ASP B | 243 | −21.773 | 5.954 | −47.565 | 1.00 | 28.87 | O |
| ATOM | 5226 | N | GLY B | 244 | −23.221 | 4.494 | −46.679 | 1.00 | 26.17 | N |
| ATOM | 5227 | CA | GLY B | 244 | −22.638 | 4.619 | −45.356 | 1.00 | 23.34 | C |
| ATOM | 5228 | C | GLY B | 244 | −23.643 | 4.639 | −44.236 | 1.00 | 22.08 | C |
| ATOM | 5229 | O | GLY B | 244 | −24.728 | 5.216 | −44.355 | 1.00 | 20.99 | O |
| ATOM | 5230 | N | ASP B | 245 | −23.263 | 3.987 | −43.143 | 1.00 | 21.79 | N |
| ATOM | 5231 | CA | ASP B | 245 | −24.081 | 3.894 | −41.951 | 1.00 | 20.89 | C |
| ATOM | 5232 | CB | ASP B | 245 | −25.106 | 2.760 | −42.089 | 1.00 | 21.25 | C |
| ATOM | 5233 | CG | ASP B | 245 | −26.300 | 2.927 | −41.151 | 1.00 | 24.70 | C |
| ATOM | 5234 | OD1 | ASP B | 245 | −26.425 | 3.998 | −40.513 | 1.00 | 24.22 | O |
| ATOM | 5235 | OD2 | ASP B | 245 | −27.116 | 1.988 | −41.055 | 1.00 | 23.77 | O |
| ATOM | 5236 | C | ASP B | 245 | −23.168 | 3.641 | −40.760 | 1.00 | 20.20 | C |
| ATOM | 5237 | O | ASP B | 245 | −21.958 | 3.443 | −40.920 | 1.00 | 19.19 | O |
| ATOM | 5238 | N | GLY B | 246 | −23.753 | 3.653 | −39.569 | 1.00 | 18.98 | N |
| ATOM | 5239 | CA | GLY B | 246 | −23.011 | 3.419 | −38.353 | 1.00 | 18.58 | C |
| ATOM | 5240 | C | GLY B | 246 | −23.772 | 3.846 | −37.122 | 1.00 | 18.43 | C |
| ATOM | 5241 | O | GLY B | 246 | −24.779 | 4.548 | −37.214 | 1.00 | 18.61 | O |
| ATOM | 5242 | N | ILE B | 247 | −23.277 | 3.410 | −35.970 | 1.00 | 18.03 | N |
| ATOM | 5243 | CA | ILE B | 247 | −23.819 | 3.792 | −34.674 | 1.00 | 18.10 | C |
| ATOM | 5244 | CB | ILE B | 247 | −25.121 | 2.993 | −34.318 | 1.00 | 18.05 | C |
| ATOM | 5245 | CG1 | ILE B | 247 | −25.855 | 3.649 | −33.142 | 1.00 | 19.19 | C |
| ATOM | 5246 | CD1 | ILE B | 247 | −27.251 | 3.098 | −32.879 | 1.00 | 19.03 | C |

TABLE A-continued

| | | | | | | | | | |
|---|---|---|---|---|---|---|---|---|---|
| ATOM | 5247 | CG2 | ILE B | 247 | −24.817 | 1.502 | −34.058 | 1.00 | 18.02 | C |
| ATOM | 5248 | C | ILE B | 247 | −22.740 | 3.584 | −33.616 | 1.00 | 17.40 | C |
| ATOM | 5249 | O | ILE B | 247 | −21.846 | 2.749 | −33.785 | 1.00 | 17.21 | O |
| ATOM | 5250 | N | PHE B | 248 | −22.808 | 4.364 | −32.542 | 1.00 | 16.80 | N |
| ATOM | 5251 | CA | PHE B | 248 | −21.958 | 4.127 | −31.388 | 1.00 | 17.15 | C |
| ATOM | 5252 | CB | PHE B | 248 | −21.660 | 5.430 | −30.635 | 1.00 | 17.20 | C |
| ATOM | 5253 | CG | PHE B | 248 | −20.607 | 6.284 | −31.299 | 1.00 | 19.26 | C |
| ATOM | 5254 | CD1 | PHE B | 248 | −20.955 | 7.209 | −32.279 | 1.00 | 20.01 | C |
| ATOM | 5255 | CE1 | PHE B | 248 | −19.983 | 7.992 | −32.901 | 1.00 | 21.69 | C |
| ATOM | 5256 | CZ | PHE B | 248 | −18.645 | 7.849 | −32.549 | 1.00 | 20.59 | C |
| ATOM | 5257 | CE2 | PHE B | 248 | −18.285 | 6.929 | −31.569 | 1.00 | 22.01 | C |
| ATOM | 5258 | CD2 | PHE B | 248 | −19.264 | 6.152 | −30.955 | 1.00 | 21.05 | C |
| ATOM | 5259 | C | PHE B | 248 | −22.583 | 3.060 | −30.489 | 1.00 | 17.72 | C |
| ATOM | 5260 | O | PHE B | 248 | −23.809 | 2.992 | −30.340 | 1.00 | 17.62 | O |
| ATOM | 5261 | N | SER B | 249 | −21.726 | 2.215 | −29.922 | 1.00 | 17.85 | N |
| ATOM | 5262 | CA | SER B | 249 | −22.154 | 1.103 | −29.091 | 1.00 | 18.20 | C |
| ATOM | 5263 | CB | SER B | 249 | −21.977 | −.206 | −29.852 | 1.00 | 18.55 | C |
| ATOM | 5264 | OG | SER B | 249 | −20.626 | −.411 | −30.184 | 1.00 | 22.54 | O |
| ATOM | 5265 | C | SER B | 249 | −21.387 | 1.055 | −27.766 | 1.00 | 17.92 | C |
| ATOM | 5266 | O | SER B | 249 | −20.319 | 1.661 | −27.648 | 1.00 | 17.15 | O |
| ATOM | 5267 | N | PRO B | 250 | −21.927 | .330 | −26.765 | 1.00 | 17.70 | N |
| ATOM | 5268 | CA | PRO B | 250 | −21.266 | .233 | −25.460 | 1.00 | 17.14 | C |
| ATOM | 5269 | CB | PRO B | 250 | −22.386 | −.262 | −24.538 | 1.00 | 16.60 | C |
| ATOM | 5270 | CG | PRO B | 250 | −23.285 | −1.035 | −25.422 | 1.00 | 16.15 | C |
| ATOM | 5271 | CD | PRO B | 250 | −23.190 | −.435 | −26.799 | 1.00 | 17.22 | C |
| ATOM | 5272 | C | PRO B | 250 | −20.078 | −.740 | −25.452 | 1.00 | 16.88 | C |
| ATOM | 5273 | O | PRO B | 250 | −20.131 | −1.792 | −24.801 | 1.00 | 16.95 | O |
| ATOM | 5274 | N | GLY B | 251 | −19.015 | −.379 | −26.169 | 1.00 | 16.12 | N |
| ATOM | 5275 | CA | GLY B | 251 | −17.801 | −1.186 | −26.215 | 1.00 | 15.08 | C |
| ATOM | 5276 | C | GLY B | 251 | −17.593 | −1.848 | −27.558 | 1.00 | 14.90 | C |
| ATOM | 5277 | O | GLY B | 251 | −18.557 | −2.166 | −28.251 | 1.00 | 15.37 | O |
| ATOM | 5278 | N | GLY B | 252 | −16.330 | −2.060 | −27.917 | 1.00 | 14.49 | N |
| ATOM | 5279 | CA | GLY B | 252 | −15.960 | −2.651 | −29.206 | 1.00 | 14.90 | C |
| ATOM | 5280 | C | GLY B | 252 | −16.368 | −4.103 | −29.373 | 1.00 | 15.12 | C |
| ATOM | 5281 | O | GLY B | 252 | −16.519 | −4.590 | −30.497 | 1.00 | 15.21 | O |
| ATOM | 5282 | N | ALA B | 253 | −16.535 | −4.797 | −28.250 | 1.00 | 15.52 | N |
| ATOM | 5283 | CA | ALA B | 253 | −17.032 | −6.168 | −28.247 | 1.00 | 15.59 | C |
| ATOM | 5284 | CB | ALA B | 253 | −17.012 | −6.743 | −26.836 | 1.00 | 15.33 | C |
| ATOM | 5285 | C | ALA B | 253 | −18.441 | −6.201 | −28.818 | 1.00 | 15.51 | C |
| ATOM | 5286 | O | ALA B | 253 | −18.796 | −7.116 | −29.557 | 1.00 | 15.87 | O |
| ATOM | 5287 | N | ILE B | 254 | −19.230 | −5.184 | −28.483 | 1.00 | 15.71 | N |
| ATOM | 5288 | CA | ILE B | 254 | −20.609 | −5.081 | −28.958 | 1.00 | 15.81 | C |
| ATOM | 5289 | CB | ILE B | 254 | −21.502 | −4.294 | −27.955 | 1.00 | 16.45 | C |
| ATOM | 5290 | CG1 | ILE B | 254 | −21.663 | −5.126 | −26.676 | 1.00 | 16.82 | C |
| ATOM | 5291 | CD1 | ILE B | 254 | −22.548 | −4.516 | −25.627 | 1.00 | 22.40 | C |
| ATOM | 5292 | CG2 | ILE B | 254 | −22.865 | −3.927 | −28.576 | 1.00 | 15.93 | C |
| | | | | | gad67.pdb | | | | | |
| ATOM | 5293 | C | ILE B | 254 | −20.658 | −4.534 | −30.387 | 1.00 | 14.53 | C |
| ATOM | 5294 | O | ILE B | 254 | −21.535 | −4.902 | −31.162 | 1.00 | 14.80 | O |
| ATOM | 5295 | N | SER B | 255 | −19.701 | −3.676 | −30.735 | 1.00 | 13.86 | N |
| ATOM | 5296 | CA | SER B | 255 | −19.500 | −3.272 | −32.128 | 1.00 | 12.43 | C |
| ATOM | 5297 | CB | SER B | 255 | −18.359 | −2.267 | −32.247 | 1.00 | 12.16 | C |
| ATOM | 5298 | OG | SER B | 255 | −18.689 | −1.036 | −31.629 | 1.00 | 13.49 | O |
| ATOM | 5299 | C | SER B | 255 | −19.226 | −4.495 | −33.007 | 1.00 | 11.57 | C |
| ATOM | 5300 | O | SER B | 255 | −19.802 | −4.631 | −34.081 | 1.00 | 10.02 | O |
| ATOM | 5301 | N | ASN B | 256 | −18.353 | −5.386 | −32.538 | 1.00 | 12.61 | N |
| ATOM | 5302 | CA | ASN B | 256 | −18.079 | −6.648 | −33.234 | 1.00 | 13.26 | C |
| ATOM | 5303 | CB | ASN B | 256 | −16.962 | −7.420 | −32.532 | 1.00 | 13.04 | C |
| ATOM | 5304 | CG | ASN B | 256 | −15.571 | −6.832 | −32.796 | 1.00 | 16.14 | C |
| ATOM | 5305 | OD1 | ASN B | 256 | −14.595 | −7.229 | −32.163 | 1.00 | 17.99 | O |
| ATOM | 5306 | ND2 | ASN B | 256 | −15.480 | −5.895 | −33.732 | 1.00 | 11.29 | N |
| ATOM | 5307 | C | ASN B | 256 | −19.337 | −7.520 | −33.391 | 1.00 | 14.09 | C |
| ATOM | 5308 | O | ASN B | 256 | −19.587 | −8.075 | −34.466 | 1.00 | 13.52 | O |
| ATOM | 5309 | N | MET B | 257 | −20.126 | −7.612 | −32.317 | 1.00 | 14.06 | N |
| ATOM | 5310 | CA | MET B | 257 | −21.421 | −8.292 | −32.331 | 1.00 | 15.35 | C |
| ATOM | 5311 | CB | MET B | 257 | −22.080 | −8.196 | −30.947 | 1.00 | 14.57 | C |
| ATOM | 5312 | CG | MET B | 257 | −23.282 | −9.108 | −30.747 | 1.00 | 17.33 | C |
| ATOM | 5313 | SD | MET B | 257 | −24.008 | −8.994 | −29.090 | 1.00 | 19.57 | S |
| ATOM | 5314 | CE | MET B | 257 | −24.812 | −7.400 | −29.173 | 1.00 | 26.95 | C |
| ATOM | 5315 | C | MET B | 257 | −22.344 | −7.716 | −33.413 | 1.00 | 14.34 | C |
| ATOM | 5316 | O | MET B | 257 | −22.966 | −8.469 | −34.169 | 1.00 | 13.82 | O |
| ATOM | 5317 | N | TYR B | 258 | −22.416 | −6.385 | −33.483 | 1.00 | 14.14 | N |
| ATOM | 5318 | CA | TYR B | 258 | −23.167 | −5.685 | −34.531 | 1.00 | 15.51 | C |
| ATOM | 5319 | CB | TYR B | 258 | −22.937 | −4.167 | −34.460 | 1.00 | 17.16 | C |
| ATOM | 5320 | CG | TYR B | 258 | −23.898 | −3.387 | −33.589 | 1.00 | 19.89 | C |
| ATOM | 5321 | CD1 | TYR B | 258 | −25.225 | −3.196 | −33.976 | 1.00 | 24.01 | C |
| ATOM | 5322 | CE1 | TYR B | 258 | −26.106 | −2.466 | −33.184 | 1.00 | 23.65 | C |
| ATOM | 5323 | CZ | TYR B | 258 | −25.650 | −1.906 | −32.001 | 1.00 | 23.13 | C |
| ATOM | 5324 | OH | TYR B | 258 | −26.508 | −1.177 | −31.209 | 1.00 | 24.21 | O |
| ATOM | 5325 | CE2 | TYR B | 258 | −24.336 | −2.071 | −31.608 | 1.00 | 20.94 | C |

TABLE A-continued

| | | | | | | | | | |
|---|---|---|---|---|---|---|---|---|---|
| ATOM | 5326 | CD2 | TYR B | 258 | −23.469 | −2.800 | −32.404 | 1.00 | 19.15 | C |
| ATOM | 5327 | C | TYR B | 258 | −22.794 | −6.163 | −35.934 | 1.00 | 14.43 | C |
| ATOM | 5328 | O | TYR B | 258 | −23.671 | −6.434 | −36.749 | 1.00 | 14.28 | O |
| ATOM | 5329 | N | SER B | 259 | −21.494 | −6.256 | −36.209 | 1.00 | 13.50 | N |
| ATOM | 5330 | CA | SER B | 259 | −21.016 | −6.591 | −37.549 | 1.00 | 13.65 | C |
| ATOM | 5331 | CB | SER B | 259 | −19.488 | −6.453 | −37.654 | 1.00 | 13.38 | C |
| ATOM | 5332 | OG | SER B | 259 | −18.790 | −7.508 | −37.002 | 1.00 | 14.17 | O |
| ATOM | 5333 | C | SER B | 259 | −21.489 | −7.974 | −37.991 | 1.00 | 13.63 | C |
| ATOM | 5334 | O | SER B | 259 | −21.906 | −8.152 | −39.140 | 1.00 | 13.75 | O |
| ATOM | 5335 | N | ILE B | 260 | −21.442 | −8.931 | −37.065 | 1.00 | 13.20 | N |
| ATOM | 5336 | CA | ILE B | 260 | −21.869 | −10.306 | −37.322 | 1.00 | 13.36 | C |
| ATOM | 5337 | CB | ILE B | 260 | −21.447 | −11.262 | −36.169 | 1.00 | 13.60 | C |
| ATOM | 5338 | CG1 | ILE B | 260 | −19.919 | −11.265 | −36.005 | 1.00 | 11.84 | C |
| ATOM | 5339 | CD1 | ILE B | 260 | −19.408 | −11.882 | −34.708 | 1.00 | 10.80 | C |
| ATOM | 5340 | CG2 | ILE B | 260 | −21.963 | −12.684 | −36.428 | 1.00 | 12.12 | C |
| ATOM | 5341 | C | ILE B | 260 | −23.383 | −10.366 | −37.554 | 1.00 | 15.33 | C |
| ATOM | 5342 | O | ILE B | 260 | −23.853 | −11.079 | −38.447 | 1.00 | 15.94 | O |
| ATOM | 5343 | N | MET B | 261 | −24.132 | −9.597 | −36.762 | 1.00 | 15.65 | N |
| ATOM | 5344 | CA | MET B | 261 | −25.585 | −9.492 | −36.903 | 1.00 | 15.91 | C |
| ATOM | 5345 | CB | MET B | 261 | −26.173 | −8.649 | −35.764 | 1.00 | 15.23 | C |
| ATOM | 5346 | CG | MET B | 261 | −26.222 | −9.350 | −34.415 | 1.00 | 16.89 | C |
| ATOM | 5347 | SD | MET B | 261 | −26.921 | −8.344 | −33.074 | 1.00 | 18.88 | S |
| ATOM | 5348 | CE | MET B | 261 | −28.588 | −8.093 | −33.658 | 1.00 | 17.20 | C |
| ATOM | 5349 | C | MET B | 261 | −25.964 | −8.883 | −38.254 | 1.00 | 15.28 | C |
| ATOM | 5350 | O | MET B | 261 | −26.881 | −9.365 | −38.935 | 1.00 | 14.98 | O |
| ATOM | 5351 | N | ALA B | 262 | −25.256 | −7.819 | −38.629 | 1.00 | 14.15 | N |
| ATOM | 5352 | CA | ALA B | 262 | −25.453 | −7.163 | −39.923 | 1.00 | 14.16 | C |
| ATOM | 5353 | CB | ALA B | 262 | −24.623 | −5.887 | −40.006 | 1.00 | 13.23 | C |
| ATOM | 5354 | C | ALA B | 262 | −25.124 | −8.100 | −41.091 | 1.00 | 13.88 | C |
| ATOM | 5355 | O | ALA B | 262 | −25.899 | −8.205 | −42.037 | 1.00 | 13.87 | O |
| ATOM | 5356 | N | ALA B | 263 | −23.984 | −8.786 | −41.010 | 1.00 | 14.26 | N |
| ATOM | 5357 | CA | ALA B | 263 | −23.565 | −9.732 | −42.050 | 1.00 | 15.01 | C |
| ATOM | 5358 | CB | ALA B | 263 | −22.191 | −10.306 | −41.733 | 1.00 | 13.68 | C |
| ATOM | 5359 | C | ALA B | 263 | −24.587 | −10.855 | −42.234 | 1.00 | 15.02 | C |
| ATOM | 5360 | O | ALA B | 263 | −24.940 | −11.198 | −43.362 | 1.00 | 14.57 | O |
| | | | | | gad67.pdb | | | | | |
| ATOM | 5361 | N | ARG B | 264 | −25.062 | −11.405 | −41.118 | 1.00 | 15.39 | N |
| ATOM | 5362 | CA | ARG B | 264 | −26.075 | −12.461 | −41.134 | 1.00 | 15.97 | C |
| ATOM | 5363 | CB | ARG B | 264 | −26.260 | −13.054 | −39.729 | 1.00 | 15.30 | C |
| ATOM | 5364 | CG | ARG B | 264 | −27.284 | −14.184 | −39.649 | 1.00 | 15.18 | C |
| ATOM | 5365 | CD | ARG B | 264 | −27.402 | −14.758 | −38.250 | 1.00 | 16.26 | C |
| ATOM | 5366 | NE | ARG B | 264 | −27.839 | −13.782 | −37.254 | 1.00 | 16.62 | N |
| ATOM | 5367 | CZ | ARG B | 264 | −27.904 | −14.023 | −35.948 | 1.00 | 16.08 | C |
| ATOM | 5368 | NH1 | ARG B | 264 | −27.559 | −15.212 | −35.472 | 1.00 | 14.48 | N |
| ATOM | 5369 | NH2 | ARG B | 264 | −28.309 | −13.074 | −35.112 | 1.00 | 15.49 | N |
| ATOM | 5370 | C | ARG B | 264 | −27.413 | −11.979 | −41.717 | 1.00 | 16.19 | C |
| ATOM | 5371 | O | ARG B | 264 | −28.089 | −12.725 | −42.431 | 1.00 | 16.63 | O |
| ATOM | 5372 | N | TYR B | 265 | −27.787 | −10.737 | −41.423 | 1.00 | 16.61 | N |
| ATOM | 5373 | CA | TYR B | 265 | −29.008 | −10.162 | −41.996 | 1.00 | 16.90 | C |
| ATOM | 5374 | CB | TYR B | 265 | −29.425 | −8.880 | −41.275 | 1.00 | 17.44 | C |
| ATOM | 5375 | CG | TYR B | 265 | −30.780 | −8.385 | −41.721 | 1.00 | 18.96 | C |
| ATOM | 5376 | CD1 | TYR B | 265 | −30.898 | −7.294 | −42.583 | 1.00 | 18.46 | C |
| ATOM | 5377 | CE1 | TYR B | 265 | −32.143 | −6.849 | −43.008 | 1.00 | 19.71 | C |
| ATOM | 5378 | CZ | TYR B | 265 | −33.285 | −7.504 | −42.571 | 1.00 | 20.34 | C |
| ATOM | 5379 | OH | TYR B | 265 | −34.526 | −7.077 | −42.979 | 1.00 | 23.72 | O |
| ATOM | 5380 | CE2 | TYR B | 265 | −33.191 | −8.594 | −41.725 | 1.00 | 20.54 | C |
| ATOM | 5381 | CD2 | TYR B | 265 | −31.943 | −9.032 | −41.311 | 1.00 | 18.67 | C |
| ATOM | 5382 | C | TYR B | 265 | −28.913 | −9.909 | −43.499 | 1.00 | 16.85 | C |
| ATOM | 5383 | O | TYR B | 265 | −29.875 | −10.158 | −44.230 | 1.00 | 17.32 | O |
| ATOM | 5384 | N | LYS B | 266 | −27.766 | −9.403 | −43.950 | 1.00 | 17.37 | N |
| ATOM | 5385 | CA | LYS B | 266 | −27.516 | −9.169 | −45.376 | 1.00 | 18.14 | C |
| ATOM | 5386 | CB | LYS B | 266 | −26.115 | −8.568 | −45.585 | 1.00 | 19.13 | C |
| ATOM | 5387 | CG | LYS B | 266 | −25.507 | −8.745 | −46.988 | 1.00 | 20.93 | C |
| ATOM | 5388 | CD | LYS B | 266 | −25.522 | −7.467 | −47.819 | 1.00 | 29.46 | C |
| ATOM | 5389 | CE | LYS B | 266 | −26.848 | −7.244 | −48.537 | 1.00 | 34.30 | C |
| ATOM | 5390 | NZ | LYS B | 266 | −26.757 | −6.133 | −49.525 | 1.00 | 34.27 | N |
| ATOM | 5391 | C | LYS B | 266 | −27.687 | −10.450 | −46.196 | 1.00 | 18.10 | C |
| ATOM | 5392 | O | LYS B | 266 | −28.317 | −10.437 | −47.253 | 1.00 | 18.41 | O |
| ATOM | 5393 | N | TYR B | 267 | −27.135 | −11.550 | −45.692 | 1.00 | 18.23 | N |
| ATOM | 5394 | CA | TYR B | 267 | −27.104 | −12.814 | −46.423 | 1.00 | 19.26 | C |
| ATOM | 5395 | CB | TYR B | 267 | −25.801 | −13.555 | −46.133 | 1.00 | 20.54 | C |
| ATOM | 5396 | CG | TYR B | 267 | −24.603 | −12.947 | −46.819 | 1.00 | 24.11 | C |
| ATOM | 5397 | CD1 | TYR B | 267 | −24.443 | −13.050 | −48.201 | 1.00 | 27.76 | C |
| ATOM | 5398 | CE1 | TYR B | 267 | −23.340 | −12.490 | −48.840 | 1.00 | 28.01 | C |
| ATOM | 5399 | CZ | TYR B | 267 | −22.388 | −11.823 | −48.092 | 1.00 | 25.29 | C |
| ATOM | 5400 | OH | TYR B | 267 | −21.304 | −11.271 | −48.723 | 1.00 | 28.26 | O |
| ATOM | 5401 | CE2 | TYR B | 267 | −22.521 | −11.709 | −46.720 | 1.00 | 25.16 | C |
| ATOM | 5402 | CD2 | TYR B | 267 | −23.628 | −12.270 | −46.090 | 1.00 | 24.32 | C |
| ATOM | 5403 | C | TYR B | 267 | −28.294 | −13.729 | −46.154 | 1.00 | 18.96 | C |
| ATOM | 5404 | O | TYR B | 267 | −28.742 | −14.444 | −47.053 | 1.00 | 17.00 | O |

TABLE A-continued

| | | | | | | | | | |
|---|---|---|---|---|---|---|---|---|---|
| ATOM | 5405 | N | PHE B | 268 | −28.789 | −13.712 | −44.916 | 1.00 | 18.81 | N |
| ATOM | 5406 | CA | PHE B | 268 | −29.880 | −14.592 | −44.500 | 1.00 | 18.94 | C |
| ATOM | 5407 | CB | PHE B | 268 | −29.324 | −15.826 | −43.763 | 1.00 | 20.02 | C |
| ATOM | 5408 | CG | PHE B | 268 | −28.386 | −16.653 | −44.607 | 1.00 | 22.46 | C |
| ATOM | 5409 | CD1 | PHE B | 268 | −28.879 | −17.647 | −45.446 | 1.00 | 25.69 | C |
| ATOM | 5410 | CE1 | PHE B | 268 | −28.018 | −18.396 | −46.245 | 1.00 | 27.31 | C |
| ATOM | 5411 | CZ | PHE B | 268 | −26.650 | −18.145 | −46.215 | 1.00 | 24.14 | C |
| ATOM | 5412 | CE2 | PHE B | 268 | −26.149 | −17.149 | −45.389 | 1.00 | 24.77 | C |
| ATOM | 5413 | CD2 | PHE B | 268 | −27.017 | −16.410 | −44.591 | 1.00 | 23.10 | C |
| ATOM | 5414 | C | PHE B | 268 | −30.899 | −13.827 | −43.656 | 1.00 | 18.01 | C |
| ATOM | 5415 | O | PHE B | 268 | −31.004 | −14.050 | −42.446 | 1.00 | 17.92 | O |
| ATOM | 5416 | N | PRO B | 269 | −31.658 | −12.918 | −44.299 | 1.00 | 17.23 | N |
| ATOM | 5417 | CA | PRO B | 269 | −32.579 | −12.047 | −43.570 | 1.00 | 17.57 | C |
| ATOM | 5418 | CB | PRO B | 269 | −33.107 | −11.104 | −44.655 | 1.00 | 17.60 | C |
| ATOM | 5419 | CG | PRO B | 269 | −32.945 | −11.855 | −45.922 | 1.00 | 16.88 | C |
| ATOM | 5420 | CD | PRO B | 269 | −31.695 | −12.656 | −45.749 | 1.00 | 17.29 | C |
| ATOM | 5421 | C | PRO B | 269 | −33.730 | −12.795 | −42.907 | 1.00 | 17.82 | C |
| ATOM | 5422 | O | PRO B | 269 | −34.406 | −12.230 | −42.050 | 1.00 | 19.13 | O |
| ATOM | 5423 | N | GLU B | 270 | −33.928 | −14.056 | −43.281 | 1.00 | 18.38 | N |
| ATOM | 5424 | CA | GLU B | 270 | −34.999 | −14.884 | −42.731 | 1.00 | 19.17 | C |
| ATOM | 5425 | CB | GLU B | 270 | −35.322 | −16.069 | −43.662 | 1.00 | 19.56 | C |
| ATOM | 5426 | CG | GLU B | 270 | −34.188 | −17.083 | −43.870 | 1.00 | 22.46 | C |
| ATOM | 5427 | CD | GLU B | 270 | −33.306 | −16.798 | −45.094 | 1.00 | 26.81 | C |
| ATOM | 5428 | OE1 | GLU B | 270 | −33.083 | −15.615 | −45.439 | 1.00 | 23.21 | O |
| ATOM | 5429 | OE2 | GLU B | 270 | −32.826 | −17.777 | −45.712 | 1.00 | 29.18 | O |
| ATOM | 5430 | C | GLU B | 270 | −34.723 | −15.364 | −41.301 | 1.00 | 19.13 | C |
| ATOM | 5431 | O | GLU B | 270 | −35.639 | −15.818 | −40.617 | 1.00 | 19.93 | O |
| ATOM | 5432 | N | VAL B | 271 | −33.470 | −15.249 | −40.855 | 1.00 | 18.86 | N |
| ATOM | 5433 | CA | VAL B | 271 | −33.085 | −15.614 | −39.486 | 1.00 | 18.10 | C |
| ATOM | 5434 | CB | VAL B | 271 | −31.560 | −15.466 | −39.241 | 1.00 | 18.08 | C |
| ATOM | 5435 | CG1 | VAL B | 271 | −31.203 | −15.805 | −37.796 | 1.00 | 16.67 | C |
| ATOM | 5436 | CG2 | VAL B | 271 | −30.776 | −16.356 | −40.172 | 1.00 | 19.86 | C |
| ATOM | 5437 | C | VAL B | 271 | −33.827 | −14.768 | −38.456 | 1.00 | 17.70 | C |
| ATOM | 5438 | O | VAL B | 271 | −34.106 | −15.235 | −37.349 | 1.00 | 17.79 | O |
| ATOM | 5439 | N | LYS B | 272 | −34.140 | −13.529 | −38.833 | 1.00 | 17.71 | N |
| ATOM | 5440 | CA | LYS B | 272 | −34.773 | −12.574 | −37.933 | 1.00 | 17.30 | C |
| ATOM | 5441 | CB | LYS B | 272 | −34.933 | −11.217 | −38.622 | 1.00 | 17.02 | C |
| ATOM | 5442 | CG | LYS B | 272 | −35.319 | −10.080 | −37.678 | 1.00 | 17.83 | C |
| ATOM | 5443 | CD | LYS B | 272 | −35.437 | −8.746 | −38.399 | 1.00 | 16.74 | C |
| ATOM | 5444 | CE | LYS B | 272 | −36.032 | −7.695 | −37.469 | 1.00 | 16.53 | C |
| ATOM | 5445 | NZ | LYS B | 272 | −36.099 | −6.348 | −38.093 | 1.00 | 16.17 | N |
| ATOM | 5446 | C | LYS B | 272 | −36.121 | −13.105 | −37.449 | 1.00 | 17.90 | C |
| ATOM | 5447 | O | LYS B | 272 | −36.408 | −13.085 | −36.252 | 1.00 | 16.42 | O |
| ATOM | 5448 | N | THR B | 273 | −36.923 | −13.599 | −38.391 | 1.00 | 18.71 | N |
| ATOM | 5449 | CA | THR B | 273 | −38.250 | −14.134 | −38.092 | 1.00 | 19.57 | C |
| ATOM | 5450 | CB | THR B | 273 | −39.240 | −13.898 | −39.256 | 1.00 | 20.28 | C |
| ATOM | 5451 | OG1 | THR B | 273 | −38.698 | −14.429 | −40.476 | 1.00 | 21.16 | O |
| ATOM | 5452 | CG2 | THR B | 273 | −39.514 | −12.411 | −39.429 | 1.00 | 18.96 | C |
| ATOM | 5453 | C | THR B | 273 | −38.231 | −15.620 | −37.741 | 1.00 | 19.45 | C |
| ATOM | 5454 | O | THR B | 273 | −38.939 | −16.047 | −36.827 | 1.00 | 19.17 | O |
| ATOM | 5455 | N | LYS B | 274 | −37.404 | −16.393 | −38.443 | 1.00 | 19.23 | N |
| ATOM | 5456 | CA | LYS B | 274 | −37.444 | −17.858 | −38.348 | 1.00 | 19.95 | C |
| ATOM | 5457 | CB | LYS B | 274 | −37.342 | −18.482 | −39.743 | 1.00 | 19.18 | C |
| ATOM | 5458 | CG | LYS B | 274 | −38.562 | −18.249 | −40.623 | 1.00 | 21.46 | C |
| ATOM | 5459 | CD | LYS B | 274 | −38.378 | −18.864 | −42.003 | 1.00 | 24.05 | C |
| ATOM | 5460 | CE | LYS B | 274 | −39.677 | −18.821 | −42.812 | 1.00 | 32.02 | C |
| ATOM | 5461 | NZ | LYS B | 274 | −40.102 | −17.429 | −43.153 | 1.00 | 35.10 | N |
| ATOM | 5462 | C | LYS B | 274 | −36.411 | −18.497 | −37.413 | 1.00 | 19.61 | C |
| ATOM | 5463 | O | LYS B | 274 | −36.620 | −19.617 | −36.929 | 1.00 | 20.18 | O |
| ATOM | 5464 | N | GLY B | 275 | −35.301 | −17.805 | −37.172 | 1.00 | 18.55 | N |
| ATOM | 5465 | CA | GLY B | 275 | −34.251 | −18.321 | −36.298 | 1.00 | 18.66 | C |
| ATOM | 5466 | C | GLY B | 275 | −33.129 | −19.026 | −37.040 | 1.00 | 18.59 | C |
| ATOM | 5467 | O | GLY B | 275 | −33.235 | −19.280 | −38.241 | 1.00 | 18.50 | O |
| ATOM | 5468 | N | MET B | 276 | −32.058 | −19.340 | −36.311 | 1.00 | 18.60 | N |
| ATOM | 5469 | CA | MET B | 276 | −30.864 | −19.989 | −36.868 | 1.00 | 19.37 | C |
| ATOM | 5470 | CB | MET B | 276 | −29.725 | −20.010 | −35.840 | 1.00 | 18.08 | C |
| ATOM | 5471 | CG | MET B | 276 | −28.984 | −18.686 | −35.701 | 1.00 | 18.10 | C |
| ATOM | 5472 | SD | MET B | 276 | −28.051 | −18.207 | −37.178 | 1.00 | 16.48 | S |
| ATOM | 5473 | CE | MET B | 276 | −26.669 | −19.342 | −37.099 | 1.00 | 17.95 | C |
| ATOM | 5474 | C | MET B | 276 | −31.115 | −21.402 | −37.392 | 1.00 | 20.04 | C |
| ATOM | 5475 | O | MET B | 276 | −30.472 | −21.831 | −38.345 | 1.00 | 21.23 | O |
| ATOM | 5476 | N | ALA B | 277 | −32.051 | −22.117 | −36.774 | 1.00 | 20.71 | N |
| ATOM | 5477 | CA | ALA B | 277 | −32.415 | −23.470 | −37.214 | 1.00 | 21.23 | C |
| ATOM | 5478 | CB | ALA B | 277 | −33.268 | −24.170 | −36.148 | 1.00 | 20.25 | C |
| ATOM | 5479 | C | ALA B | 277 | −33.114 | −23.519 | −38.585 | 1.00 | 21.60 | C |
| ATOM | 5480 | O | ALA B | 277 | −33.323 | −24.603 | −39.129 | 1.00 | 22.51 | O |
| ATOM | 5481 | N | ALA B | 278 | −33.465 | −22.356 | −39.136 | 1.00 | 21.80 | N |
| ATOM | 5482 | CA | ALA B | 278 | −34.165 | −22.280 | −40.426 | 1.00 | 22.50 | C |
| ATOM | 5483 | CB | ALA B | 278 | −35.313 | −21.296 | −40.346 | 1.00 | 21.39 | C |

TABLE A-continued

| | | | | | | | | | |
|---|---|---|---|---|---|---|---|---|---|
| ATOM | 5484 | C | ALA B | 278 | −33.260 | −21.939 | −41.617 | 1.00 | 22.99 | C |
| ATOM | 5485 | O | ALA B | 278 | −33.732 | −21.840 | −42.752 | 1.00 | 23.65 | O |
| ATOM | 5486 | N | VAL B | 279 | −31.972 | −21.739 | −41.354 | 1.00 | 21.93 | N |
| ATOM | 5487 | CA | VAL B | 279 | −31.005 | −21.424 | −42.410 | 1.00 | 21.15 | C |
| ATOM | 5488 | CB | VAL B | 279 | −30.421 | −19.975 | −42.272 | 1.00 | 21.47 | C |
| ATOM | 5489 | CG1 | VAL B | 279 | −29.595 | −19.810 | −40.992 | 1.00 | 20.60 | C |
| ATOM | 5490 | CG2 | VAL B | 279 | −31.527 | −18.938 | −42.343 | 1.00 | 20.95 | C |
| ATOM | 5491 | C | VAL B | 279 | −29.886 | −22.461 | −42.403 | 1.00 | 20.51 | C |
| ATOM | 5492 | O | VAL B | 279 | −29.761 | −23.214 | −41.435 | 1.00 | 20.03 | O |
| ATOM | 5493 | N | PRO B | 280 | −29.068 | −22.510 | −43.477 | 1.00 | 20.77 | N |
| ATOM | 5494 | CA | PRO B | 280 | −27.922 | −23.427 | −43.495 | 1.00 | 20.62 | C |
| ATOM | 5495 | CB | PRO B | 280 | −27.250 | −23.121 | −44.839 | 1.00 | 20.47 | C |
| ATOM | 5496 | CG | PRO B | 280 | −28.302 | −22.504 | −45.671 | 1.00 | 20.77 | C | gad67.pdb

| | | | | | | | | | |
|---|---|---|---|---|---|---|---|---|---|
| ATOM | 5497 | CD | PRO B | 280 | −29.157 | −21.729 | −44.727 | 1.00 | 20.94 | C |
| ATOM | 5498 | C | PRO B | 280 | −26.930 | −23.166 | −42.352 | 1.00 | 20.53 | C |
| ATOM | 5499 | O | PRO B | 280 | −27.019 | −22.138 | −41.666 | 1.00 | 19.85 | O |
| ATOM | 5500 | N | LYS B | 281 | −25.999 | −24.097 | −42.154 | 1.00 | 20.04 | N |
| ATOM | 5501 | CA | LYS B | 281 | −24.956 | −23.943 | −41.150 | 1.00 | 21.02 | C |
| ATOM | 5502 | CB | LYS B | 281 | −24.176 | −25.249 | −40.972 | 1.00 | 20.80 | C |
| ATOM | 5503 | CG | LYS B | 281 | −23.545 | −25.419 | −39.592 | 1.00 | 24.79 | C |
| ATOM | 5504 | CD | LYS B | 281 | −22.739 | −26.703 | −39.525 | 1.00 | 28.87 | C |
| ATOM | 5505 | CE | LYS B | 281 | −22.687 | −27.304 | −38.138 | 1.00 | 32.94 | C |
| ATOM | 5506 | NZ | LYS B | 281 | −24.005 | −27.856 | −37.697 | 1.00 | 37.55 | N |
| ATOM | 5507 | C | LYS B | 281 | −24.019 | −22.797 | −41.541 | 1.00 | 21.53 | C |
| ATOM | 5508 | O | LYS B | 281 | −23.273 | −22.891 | −42.522 | 1.00 | 21.85 | O |
| ATOM | 5509 | N | LEU B | 282 | −24.085 | −21.712 | −40.774 | 1.00 | 21.94 | N |
| ATOM | 5510 | CA | LEU B | 282 | −23.266 | −20.524 | −41.010 | 1.00 | 21.18 | C |
| ATOM | 5511 | CB | LEU B | 282 | −24.040 | −19.265 | −40.612 | 1.00 | 21.14 | C |
| ATOM | 5512 | CG | LEU B | 282 | −24.979 | −18.538 | −41.589 | 1.00 | 22.30 | C |
| ATOM | 5513 | CD1 | LEU B | 282 | −25.573 | −19.432 | −42.679 | 1.00 | 21.82 | C |
| ATOM | 5514 | CD2 | LEU B | 282 | −26.082 | −17.819 | −40.818 | 1.00 | 21.99 | C |
| ATOM | 5515 | C | LEU B | 282 | −21.960 | −20.611 | −40.229 | 1.00 | 21.14 | C |
| ATOM | 5516 | O | LEU B | 282 | −21.960 | −20.958 | −39.043 | 1.00 | 20.47 | O |
| ATOM | 5517 | N | VAL B | 283 | −20.847 | −20.318 | −40.903 | 1.00 | 21.13 | N |
| ATOM | 5518 | CA | VAL B | 283 | −19.534 | −20.316 | −40.251 | 1.00 | 22.03 | C |
| ATOM | 5519 | CB | VAL B | 283 | −18.614 | −21.520 | −40.693 | 1.00 | 22.06 | C |
| ATOM | 5520 | CG1 | VAL B | 283 | −19.324 | −22.854 | −40.491 | 1.00 | 22.71 | C |
| ATOM | 5521 | CG2 | VAL B | 283 | −18.169 | −21.392 | −42.129 | 1.00 | 25.22 | C |
| ATOM | 5522 | C | VAL B | 283 | −18.811 | −18.966 | −40.384 | 1.00 | 21.92 | C |
| ATOM | 5523 | O | VAL B | 283 | −18.833 | −18.336 | −41.446 | 1.00 | 22.11 | O |
| ATOM | 5524 | N | LEU B | 284 | −18.195 | −18.537 | −39.281 | 1.00 | 20.56 | N |
| ATOM | 5525 | CA | LEU B | 284 | −17.436 | −17.289 | −39.202 | 1.00 | 19.63 | C |
| ATOM | 5526 | CB | LEU B | 284 | −17.770 | −16.515 | −37.922 | 1.00 | 18.95 | C |
| ATOM | 5527 | CG | LEU B | 284 | −19.183 | −16.206 | −37.447 | 1.00 | 20.45 | C |
| ATOM | 5528 | CD1 | LEU B | 284 | −19.860 | −17.434 | −36.883 | 1.00 | 19.83 | C |
| ATOM | 5529 | CD2 | LEU B | 284 | −19.075 | −15.135 | −36.378 | 1.00 | 21.15 | C |
| ATOM | 5530 | C | LEU B | 284 | −15.957 | −17.615 | −39.146 | 1.00 | 18.42 | C |
| ATOM | 5531 | O | LEU B | 284 | −15.570 | −18.706 | −38.720 | 1.00 | 18.88 | O |
| ATOM | 5532 | N | PHE B | 285 | −15.134 | −16.652 | −39.542 | 1.00 | 16.49 | N |
| ATOM | 5533 | CA | PHE B | 285 | −13.690 | −16.819 | −39.527 | 1.00 | 15.26 | C |
| ATOM | 5534 | CB | PHE B | 285 | −13.150 | −16.967 | −40.955 | 1.00 | 14.77 | C |
| ATOM | 5535 | CG | PHE B | 285 | −13.708 | −18.150 | −41.690 | 1.00 | 14.40 | C |
| ATOM | 5536 | CD1 | PHE B | 285 | −14.879 | −18.037 | −42.432 | 1.00 | 14.44 | C |
| ATOM | 5537 | CE1 | PHE B | 285 | −15.407 | −19.138 | −43.103 | 1.00 | 15.95 | C |
| ATOM | 5538 | CZ | PHE B | 285 | −14.757 | −20.367 | −43.038 | 1.00 | 14.94 | C |
| ATOM | 5539 | CE2 | PHE B | 285 | −13.588 | −20.490 | −42.301 | 1.00 | 14.96 | C |
| ATOM | 5540 | CD2 | PHE B | 285 | −13.070 | −19.386 | −41.631 | 1.00 | 14.97 | C |
| ATOM | 5541 | C | PHE B | 285 | −13.047 | −15.634 | −38.831 | 1.00 | 14.76 | C |
| ATOM | 5542 | O | PHE B | 285 | −13.476 | −14.493 | −39.006 | 1.00 | 15.19 | O |
| ATOM | 5543 | N | THR B | 286 | −12.026 | −15.921 | −38.033 | 1.00 | 14.68 | N |
| ATOM | 5544 | CA | THR B | 286 | −11.267 | −14.901 | −37.323 | 1.00 | 15.09 | C |
| ATOM | 5545 | CB | THR B | 286 | −11.999 | −14.444 | −36.022 | 1.00 | 15.31 | C |
| ATOM | 5546 | OG1 | THR B | 286 | −11.405 | −13.241 | −35.521 | 1.00 | 14.88 | O |
| ATOM | 5547 | CG2 | THR B | 286 | −11.966 | −15.528 | −34.948 | 1.00 | 14.30 | C |
| ATOM | 5548 | C | THR B | 286 | −9.882 | −15.461 | −37.018 | 1.00 | 15.90 | C |
| ATOM | 5549 | O | THR B | 286 | −9.690 | −16.672 | −37.021 | 1.00 | 16.91 | O |
| ATOM | 5550 | N | SER B | 287 | −8.922 | −14.577 | −36.770 | 1.00 | 18.26 | N |
| ATOM | 5551 | CA | SER B | 287 | −7.551 | −14.967 | −36.442 | 1.00 | 19.98 | C |
| ATOM | 5552 | CB | SER B | 287 | −6.667 | −13.720 | −36.391 | 1.00 | 20.53 | C |
| ATOM | 5553 | OG | SER B | 287 | −5.381 | −14.013 | −35.889 | 1.00 | 21.47 | O |
| ATOM | 5554 | C | SER B | 287 | −7.458 | −15.705 | −35.108 | 1.00 | 21.11 | C |
| ATOM | 5555 | O | SER B | 287 | −8.259 | −15.461 | −34.200 | 1.00 | 21.41 | O |
| ATOM | 5556 | N | GLU B | 288 | −6.468 | −16.593 | −34.998 | 1.00 | 21.78 | N |
| ATOM | 5557 | CA | GLU B | 288 | −6.098 | −17.223 | −33.726 | 1.00 | 23.93 | C |
| ATOM | 5558 | CB | GLU B | 288 | −4.896 | −18.151 | −33.911 | 1.00 | 23.65 | C |
| ATOM | 5559 | CG | GLU B | 288 | −5.215 | −19.509 | −34.504 | 1.00 | 28.20 | C |
| ATOM | 5560 | CD | GLU B | 288 | −3.963 | −20.326 | −34.822 | 1.00 | 28.36 | C |
| ATOM | 5561 | OE1 | GLU B | 288 | −2.846 | −19.749 | −34.834 | 1.00 | 32.26 | O |
| ATOM | 5562 | OE2 | GLU B | 288 | −4.106 | −21.548 | −35.074 | 1.00 | 33.27 | O |

TABLE A-continued

| | | | | | | | | | |
|---|---|---|---|---|---|---|---|---|---|
| ATOM | 5563 | C | GLU B | 288 | −5.744 | −16.194 | −32.653 | 1.00 | 23.07 | C |
| ATOM | 5564 | O | GLU B | 288 | −5.829 | −16.485 | −31.464 | 1.00 | 23.41 | O |
| | | | gad67.pdb | | | | | | | |
| ATOM | 5565 | N | GLN B | 289 | −5.333 | −15.003 | −33.082 | 1.00 | 22.71 | N |
| ATOM | 5566 | CA | GLN B | 289 | −4.921 | −13.941 | −32.160 | 1.00 | 22.34 | C |
| ATOM | 5567 | CB | GLN B | 289 | −3.481 | −13.517 | −32.461 | 1.00 | 22.30 | C |
| ATOM | 5568 | CG | GLN B | 289 | −2.473 | −14.645 | −32.218 | 1.00 | 22.55 | C |
| ATOM | 5569 | CD | GLN B | 289 | −1.032 | −14.236 | −32.465 | 1.00 | 23.42 | C |
| ATOM | 5570 | OE1 | GLN B | 289 | −.238 | −15.019 | −32.985 | 1.00 | 29.39 | O |
| ATOM | 5571 | NE2 | GLN B | 289 | −.687 | −13.012 | −32.093 | 1.00 | 24.38 | N |
| ATOM | 5572 | C | GLN B | 289 | −5.877 | −12.738 | −32.147 | 1.00 | 21.30 | C |
| ATOM | 5573 | O | GLN B | 289 | −5.544 | −11.667 | −31.631 | 1.00 | 21.03 | O |
| ATOM | 5574 | N | SER B | 290 | −7.071 | −12.932 | −32.704 | 1.00 | 19.82 | N |
| ATOM | 5575 | CA | SER B | 290 | −8.111 | −11.912 | −32.675 | 1.00 | 19.55 | C |
| ATOM | 5576 | CB | SER B | 290 | −9.166 | −12.201 | −33.737 | 1.00 | 20.01 | C |
| ATOM | 5577 | OG | SER B | 290 | −9.889 | −13.374 | −33.419 | 1.00 | 21.09 | O |
| ATOM | 5578 | C | SER B | 290 | −8.759 | −11.827 | −31.290 | 1.00 | 18.89 | C |
| ATOM | 5579 | O | SER B | 290 | −8.556 | −12.697 | −30.443 | 1.00 | 17.86 | O |
| ATOM | 5580 | N | HIS B | 291 | −9.537 | −10.772 | −31.070 | 1.00 | 18.17 | N |
| ATOM | 5581 | CA | HIS B | 291 | −10.185 | −10.545 | −29.781 | 1.00 | 17.71 | C |
| ATOM | 5582 | CB | HIS B | 291 | −10.725 | −9.115 | −29.709 | 1.00 | 17.27 | C |
| ATOM | 5583 | CG | HIS B | 291 | −11.128 | −8.689 | −28.333 | 1.00 | 17.43 | C |
| ATOM | 5584 | ND1 | HIS B | 291 | −12.434 | −8.732 | −27.892 | 1.00 | 19.94 | N |
| ATOM | 5585 | CE1 | HIS B | 291 | −12.491 | −8.298 | −26.646 | 1.00 | 16.37 | C |
| ATOM | 5586 | NE2 | HIS B | 291 | −11.269 | −7.977 | −26.262 | 1.00 | 18.32 | N |
| ATOM | 5587 | CD2 | HIS B | 291 | −10.397 | −8.213 | −27.297 | 1.00 | 15.63 | C |
| ATOM | 5588 | C | HIS B | 291 | −11.299 | −11.565 | −29.529 | 1.00 | 17.28 | C |
| ATOM | 5589 | O | HIS B | 291 | −12.032 | −11.935 | −30.447 | 1.00 | 15.21 | O |
| ATOM | 5590 | N | TYR B | 292 | −11.420 | −12.002 | −28.276 | 1.00 | 18.87 | N |
| ATOM | 5591 | CA | TYR B | 292 | −12.362 | −13.065 | −27.891 | 1.00 | 19.95 | C |
| ATOM | 5592 | CB | TYR B | 292 | −12.098 | −13.524 | −26.450 | 1.00 | 21.32 | C |
| ATOM | 5593 | CG | TYR B | 292 | −12.454 | −12.514 | −25.378 | 1.00 | 24.24 | C |
| ATOM | 5594 | CD1 | TYR B | 292 | −11.518 | −11.585 | −24.928 | 1.00 | 26.21 | C |
| ATOM | 5595 | CE1 | TYR B | 292 | −11.839 | −10.659 | −23.932 | 1.00 | 27.08 | C |
| ATOM | 5596 | CZ | TYR B | 292 | −13.105 | −10.668 | −23.373 | 1.00 | 27.62 | C |
| ATOM | 5597 | OH | TYR B | 292 | −13.427 | −9.759 | −22.391 | 1.00 | 28.68 | O |
| ATOM | 5598 | CE2 | TYR B | 292 | −14.051 | −11.585 | −23.797 | 1.00 | 28.49 | C |
| ATOM | 5599 | CD2 | TYR B | 292 | −13.721 | −12.505 | −24.792 | 1.00 | 28.19 | C |
| ATOM | 5600 | C | TYR B | 292 | −13.844 | −12.713 | −28.080 | 1.00 | 19.76 | C |
| ATOM | 5601 | O | TYR B | 292 | −14.717 | −13.583 | −27.964 | 1.00 | 19.60 | O |
| ATOM | 5602 | N | SER B | 293 | −14.119 | −11.444 | −28.372 | 1.00 | 19.43 | N |
| ATOM | 5603 | CA | SER B | 293 | −15.484 | −10.978 | −28.588 | 1.00 | 19.47 | C |
| ATOM | 5604 | CB | SER B | 293 | −15.539 | −9.450 | −28.648 | 1.00 | 19.39 | C |
| ATOM | 5605 | OG | SER B | 293 | −14.681 | −8.928 | −29.645 | 1.00 | 20.32 | O |
| ATOM | 5606 | C | SER B | 293 | −16.151 | −11.597 | −29.818 | 1.00 | 19.19 | C |
| ATOM | 5607 | O | SER B | 293 | −17.379 | −11.654 | −29.889 | 1.00 | 19.73 | O |
| ATOM | 5608 | N | ILE B | 294 | −15.350 | −12.066 | −30.775 | 1.00 | 17.83 | N |
| ATOM | 5609 | CA | ILE B | 294 | −15.881 | −12.785 | −31.938 | 1.00 | 17.07 | C |
| ATOM | 5610 | CB | ILE B | 294 | −14.814 | −12.987 | −33.062 | 1.00 | 17.61 | C |
| ATOM | 5611 | CG1 | ILE B | 294 | −14.145 | −11.652 | −33.455 | 1.00 | 15.28 | C |
| ATOM | 5612 | CD1 | ILE B | 294 | −15.083 | −10.581 | −34.028 | 1.00 | 16.05 | C |
| ATOM | 5613 | CG2 | ILE B | 294 | −15.429 | −13.692 | −34.280 | 1.00 | 14.83 | C |
| ATOM | 5614 | C | ILE B | 294 | −16.496 | −14.132 | −31.526 | 1.00 | 16.95 | C |
| ATOM | 5615 | O | ILE B | 294 | −17.639 | −14.425 | −31.876 | 1.00 | 17.09 | O |
| ATOM | 5616 | N | LYS B | 295 | −15.735 | −14.934 | −30.781 | 1.00 | 17.35 | N |
| ATOM | 5617 | CA | LYS B | 295 | −16.229 | −16.194 | −30.215 | 1.00 | 18.52 | C |
| ATOM | 5618 | CB | LYS B | 295 | −15.125 | −16.895 | −29.417 | 1.00 | 18.42 | C |
| ATOM | 5619 | CG | LYS B | 295 | −14.115 | −17.663 | −30.252 | 1.00 | 22.86 | C |
| ATOM | 5620 | CD | LYS B | 295 | −14.554 | −19.100 | −30.494 | 1.00 | 24.42 | C |
| ATOM | 5621 | CE | LYS B | 295 | −13.498 | −19.862 | −31.281 | 1.00 | 22.67 | C |
| ATOM | 5622 | NZ | LYS B | 295 | −13.887 | −21.277 | −31.531 | 1.00 | 21.79 | N |
| ATOM | 5623 | C | LYS B | 295 | −17.444 | −15.967 | −29.312 | 1.00 | 18.67 | C |
| ATOM | 5624 | O | LYS B | 295 | −18.418 | −16.727 | −29.355 | 1.00 | 18.96 | O |
| ATOM | 5625 | N | LYS B | 296 | −17.368 | −14.914 | −28.502 | 1.00 | 18.68 | N |
| ATOM | 5626 | CA | LYS B | 296 | −18.414 | −14.558 | −27.556 | 1.00 | 19.74 | C |
| ATOM | 5627 | CB | LYS B | 296 | −17.946 | −13.379 | −26.701 | 1.00 | 21.07 | C |
| ATOM | 5628 | CG | LYS B | 296 | −18.435 | −13.393 | −25.272 | 1.00 | 28.05 | C |
| ATOM | 5629 | CD | LYS B | 296 | −17.324 | −12.967 | −24.327 | 1.00 | 32.19 | C |
| ATOM | 5630 | CE | LYS B | 296 | −17.857 | −12.727 | −22.928 | 1.00 | 35.85 | C |
| ATOM | 5631 | NZ | LYS B | 296 | −16.817 | −12.905 | −21.869 | 1.00 | 37.05 | N |
| ATOM | 5632 | C | LYS B | 296 | −19.708 | −14.221 | −28.295 | 1.00 | 19.22 | C |
| | | | gad67.pdb | | | | | | | |
| ATOM | 5633 | O | LYS B | 296 | −20.789 | −14.683 | −27.911 | 1.00 | 18.44 | O |
| ATOM | 5634 | N | ALA B | 297 | −19.592 | −13.436 | −29.367 | 1.00 | 18.11 | N |
| ATOM | 5635 | CA | ALA B | 297 | −20.745 | −13.113 | −30.205 | 1.00 | 18.10 | C |
| ATOM | 5636 | CB | ALA B | 297 | −20.413 | −11.988 | −31.183 | 1.00 | 17.64 | C |
| ATOM | 5637 | C | ALA B | 297 | −21.240 | −14.356 | −30.948 | 1.00 | 17.89 | C |
| ATOM | 5638 | O | ALA B | 297 | −22.447 | −14.569 | −31.075 | 1.00 | 17.49 | O |
| ATOM | 5639 | N | GLY B | 298 | −20.305 | −15.175 | −31.424 | 1.00 | 16.44 | N |
| ATOM | 5640 | CA | GLY B | 298 | −20.637 | −16.467 | −32.016 | 1.00 | 16.28 | C |

TABLE A-continued

| | | | | | | | | | |
|---|---|---|---|---|---|---|---|---|---|
| ATOM | 5641 | C | GLY B | 298 | −21.543 | −17.292 | −31.120 | 1.00 | 16.68 | C |
| ATOM | 5642 | O | GLY B | 298 | −22.588 | −17.774 | −31.558 | 1.00 | 18.00 | O |
| ATOM | 5643 | N | ALA B | 299 | −21.148 | −17.442 | −29.858 | 1.00 | 16.56 | N |
| ATOM | 5644 | CA | ALA B | 299 | −21.943 | −18.172 | −28.870 | 1.00 | 15.32 | C |
| ATOM | 5645 | CB | ALA B | 299 | −21.161 | −18.333 | −27.576 | 1.00 | 14.83 | C |
| ATOM | 5646 | C | ALA B | 299 | −23.292 | −17.502 | −28.596 | 1.00 | 15.43 | C |
| ATOM | 5647 | O | ALA B | 299 | −24.335 | −18.161 | −28.619 | 1.00 | 15.83 | O |
| ATOM | 5648 | N | ALA B | 300 | −23.261 | −16.193 | −28.351 | 1.00 | 14.73 | N |
| ATOM | 5649 | CA | ALA B | 300 | −24.446 | −15.433 | −27.975 | 1.00 | 14.49 | C |
| ATOM | 5650 | CB | ALA B | 300 | −24.058 | −14.012 | −27.571 | 1.00 | 14.50 | C |
| ATOM | 5651 | C | ALA B | 300 | −25.507 | −15.403 | −29.065 | 1.00 | 14.58 | C |
| ATOM | 5652 | O | ALA B | 300 | −26.697 | −15.537 | −28.769 | 1.00 | 14.52 | O |
| ATOM | 5653 | N | LEU B | 301 | −25.067 | −15.242 | −30.315 | 1.00 | 13.72 | N |
| ATOM | 5654 | CA | LEU B | 301 | −25.966 | −15.050 | −31.462 | 1.00 | 13.42 | C |
| ATOM | 5655 | CB | LEU B | 301 | −25.283 | −14.210 | −32.554 | 1.00 | 12.62 | C |
| ATOM | 5656 | CG | LEU B | 301 | −24.762 | −12.817 | −32.161 | 1.00 | 14.06 | C |
| ATOM | 5657 | CD1 | LEU B | 301 | −23.902 | −12.208 | −33.267 | 1.00 | 11.72 | C |
| ATOM | 5658 | CD2 | LEU B | 301 | −25.874 | −11.860 | −31.751 | 1.00 | 9.82 | C |
| ATOM | 5659 | C | LEU B | 301 | −26.534 | −16.352 | −32.053 | 1.00 | 13.58 | C |
| ATOM | 5660 | O | LEU B | 301 | −27.356 | −16.320 | −32.978 | 1.00 | 14.08 | O |
| ATOM | 5661 | N | GLY B | 302 | −26.100 | −17.487 | −31.518 | 1.00 | 13.38 | N |
| ATOM | 5662 | CA | GLY B | 302 | −26.666 | −18.780 | −31.893 | 1.00 | 13.26 | C |
| ATOM | 5663 | C | GLY B | 302 | −25.918 | −19.534 | −32.974 | 1.00 | 13.45 | C |
| ATOM | 5664 | O | GLY B | 302 | −26.462 | −20.483 | −33.541 | 1.00 | 13.12 | O |
| ATOM | 5665 | N | PHE B | 303 | −24.685 | −19.110 | −33.266 | 1.00 | 14.18 | N |
| ATOM | 5666 | CA | PHE B | 303 | −23.821 | −19.793 | −34.236 | 1.00 | 14.34 | C |
| ATOM | 5667 | CB | PHE B | 303 | −22.725 | −18.854 | −34.761 | 1.00 | 14.12 | C |
| ATOM | 5668 | CG | PHE B | 303 | −23.235 | −17.738 | −35.626 | 1.00 | 14.22 | C |
| ATOM | 5669 | CD1 | PHE B | 303 | −23.334 | −17.902 | −37.001 | 1.00 | 13.12 | C |
| ATOM | 5670 | CE1 | PHE B | 303 | −23.794 | −16.872 | −37.805 | 1.00 | 13.55 | C |
| ATOM | 5671 | CZ | PHE B | 303 | −24.152 | −15.656 | −37.238 | 1.00 | 12.78 | C |
| ATOM | 5672 | CE2 | PHE B | 303 | −24.053 | −15.478 | −35.869 | 1.00 | 10.98 | C |
| ATOM | 5673 | CD2 | PHE B | 303 | −23.591 | −16.514 | −35.069 | 1.00 | 12.64 | C |
| ATOM | 5674 | C | PHE B | 303 | −23.146 | −21.011 | −33.624 | 1.00 | 14.64 | C |
| ATOM | 5675 | O | PHE B | 303 | −22.901 | −22.005 | −34.313 | 1.00 | 15.83 | O |
| ATOM | 5676 | N | GLY B | 304 | −22.830 | −20.917 | −32.335 | 1.00 | 14.08 | N |
| ATOM | 5677 | CA | GLY B | 304 | −22.012 | −21.917 | −31.658 | 1.00 | 14.12 | C |
| ATOM | 5678 | C | GLY B | 304 | −20.538 | −21.643 | −31.878 | 1.00 | 15.93 | C |
| ATOM | 5679 | O | GLY B | 304 | −20.128 | −21.288 | −32.988 | 1.00 | 16.53 | O |
| ATOM | 5680 | N | THR B | 305 | −19.737 | −21.805 | −30.824 | 1.00 | 16.42 | N |
| ATOM | 5681 | CA | THR B | 305 | −18.300 | −21.545 | −30.910 | 1.00 | 17.05 | C |
| ATOM | 5682 | CB | THR B | 305 | −17.618 | −21.533 | −29.524 | 1.00 | 17.27 | C |
| ATOM | 5683 | OG1 | THR B | 305 | −17.885 | −22.765 | −28.841 | 1.00 | 18.59 | O |
| ATOM | 5684 | CG2 | THR B | 305 | −18.113 | −20.358 | −28.682 | 1.00 | 16.00 | C |
| ATOM | 5685 | C | THR B | 305 | −17.577 | −22.536 | −31.834 | 1.00 | 18.16 | C |
| ATOM | 5686 | O | THR B | 305 | −16.508 | −22.217 | −32.369 | 1.00 | 17.77 | O |
| ATOM | 5687 | N | ASP B | 306 | −18.163 | −23.725 | −32.021 | 1.00 | 18.47 | N |
| ATOM | 5688 | CA | ASP B | 306 | −17.634 | −24.717 | −32.971 | 1.00 | 19.09 | C |
| ATOM | 5689 | CB | ASP B | 306 | −18.498 | −25.981 | −32.995 | 1.00 | 19.75 | C |
| ATOM | 5690 | CG | ASP B | 306 | −18.407 | −26.799 | −31.716 | 1.00 | 23.69 | C |
| ATOM | 5691 | OD1 | ASP B | 306 | −17.569 | −26.496 | −30.835 | 1.00 | 23.21 | O |
| ATOM | 5692 | OD2 | ASP B | 306 | −19.197 | −27.763 | −31.600 | 1.00 | 24.69 | O |
| ATOM | 5693 | C | ASP B | 306 | −17.581 | −24.159 | −34.388 | 1.00 | 18.64 | C |
| ATOM | 5694 | O | ASP B | 306 | −16.785 | −24.608 | −35.214 | 1.00 | 18.39 | O |
| ATOM | 5695 | N | ASN B | 307 | −18.447 | −23.186 | −34.658 | 1.00 | 18.09 | N |
| ATOM | 5696 | CA | ASN B | 307 | −18.596 | −22.620 | −35.989 | 1.00 | 17.82 | C |
| ATOM | 5697 | CB | ASN B | 307 | −20.075 | −22.591 | −36.376 | 1.00 | 18.03 | C |
| ATOM | 5698 | CG | ASN B | 307 | −20.687 | −23.979 | −36.406 | 1.00 | 17.30 | C |
| ATOM | 5699 | OD1 | ASN B | 307 | −20.184 | −24.873 | −37.088 | 1.00 | 17.24 | O |
| ATOM | 5700 | ND2 | ASN B | 307 | −21.771 | −24.169 | −35.660 | 1.00 | 13.88 | N |
| | | | | gad67.pdb | | | | | | |
| ATOM | 5701 | C | ASN B | 307 | −17.940 | −21.252 | −36.144 | 1.00 | 18.26 | C |
| ATOM | 5702 | O | ASN B | 307 | −18.190 | −20.539 | −37.121 | 1.00 | 18.68 | O |
| ATOM | 5703 | N | VAL B | 308 | −17.107 | −20.899 | −35.165 | 1.00 | 17.66 | N |
| ATOM | 5704 | CA | VAL B | 308 | −16.201 | −19.767 | −35.257 | 1.00 | 16.73 | C |
| ATOM | 5705 | CB | VAL B | 308 | −16.240 | −18.878 | −33.987 | 1.00 | 15.84 | C |
| ATOM | 5706 | CG1 | VAL B | 308 | −15.292 | −17.697 | −34.128 | 1.00 | 14.51 | C |
| ATOM | 5707 | CG2 | VAL B | 308 | −17.654 | −18.389 | −33.709 | 1.00 | 14.98 | C |
| ATOM | 5708 | C | VAL B | 308 | −14.807 | −20.366 | −35.470 | 1.00 | 18.03 | C |
| ATOM | 5709 | O | VAL B | 308 | −14.202 | −20.911 | −34.548 | 1.00 | 17.87 | O |
| ATOM | 5710 | N | ILE B | 309 | −14.320 | −20.274 | −36.705 | 1.00 | 19.22 | N |
| ATOM | 5711 | CA | ILE B | 309 | −13.120 | −20.987 | −37.128 | 1.00 | 19.36 | C |
| ATOM | 5712 | CB | ILE B | 309 | −13.280 | −21.539 | −38.580 | 1.00 | 20.09 | C |
| ATOM | 5713 | CG1 | ILE B | 309 | −14.523 | −22.438 | −38.710 | 1.00 | 21.08 | C |
| ATOM | 5714 | CD1 | ILE B | 309 | −14.469 | −23.767 | −37.932 | 1.00 | 23.12 | C |
| ATOM | 5715 | CG2 | ILE B | 309 | −12.003 | −22.252 | −39.053 | 1.00 | 16.62 | C |
| ATOM | 5716 | C | ILE B | 309 | −11.896 | −20.080 | −37.036 | 1.00 | 19.55 | C |
| ATOM | 5717 | O | ILE B | 309 | −11.872 | −18.999 | −37.617 | 1.00 | 19.47 | O |
| ATOM | 5718 | N | LEU B | 310 | −10.881 | −20.529 | −36.305 | 1.00 | 20.43 | N |
| ATOM | 5719 | CA | LEU B | 310 | −9.658 | −19.746 | −36.115 | 1.00 | 20.46 | C |

TABLE A-continued

| | | | | | | | | | |
|---|---|---|---|---|---|---|---|---|---|
| ATOM | 5720 | CB | LEU B | 310 | −9.022 | −20.049 | −34.753 | 1.00 | 20.30 | C |
| ATOM | 5721 | CG | LEU B | 310 | −9.906 | −19.964 | −33.497 | 1.00 | 20.69 | C |
| ATOM | 5722 | C01 | LEU B | 310 | −9.078 | −20.234 | −32.252 | 1.00 | 21.77 | C |
| ATOM | 5723 | CD2 | LEU B | 310 | −10.618 | −18.620 | −33.378 | 1.00 | 16.02 | C |
| ATOM | 5724 | C | LEU B | 310 | −8.647 | −19.964 | −37.239 | 1.00 | 20.78 | C |
| ATOM | 5725 | O | LEU 8 | 310 | −8.311 | −21.099 | −37.571 | 1.00 | 21.12 | O |
| ATOM | 5726 | N | ILE B | 311 | −8.177 | −18.860 | −37.817 | 1.00 | 20.86 | N |
| ATOM | 5727 | CA | ILE B | 311 | −7.209 | −18.881 | −38.913 | 1.00 | 20.88 | C |
| ATOM | 5728 | CB | ILE B | 311 | −7.471 | −17.726 | −39.917 | 1.00 | 20.93 | C |
| ATOM | 5729 | CG1 | ILE B | 311 | −8.914 | −17.784 | −40.430 | 1.00 | 20.63 | C |
| ATOM | 5730 | CD1 | ILE B | 311 | −9.438 | −16.447 | −40.943 | 1.00 | 23.13 | C |
| ATOM | 5731 | CG2 | ILE B | 311 | −6.485 | −17.775 | −41.090 | 1.00 | 17.58 | C |
| ATOM | 5732 | C | ILE B | 311 | −5.785 | −18.790 | −38.368 | 1.00 | 21.21 | C |
| ATOM | 5733 | O | ILE B | 311 | −5.507 | −17.991 | −37.475 | 1.00 | 21.46 | O |
| ATOM | 5734 | N | LYS B | 312 | −4.890 | −19.613 | −38.916 | 1.00 | 21.61 | N |
| ATOM | 5735 | CA | LYS B | 312 | −3.488 | −19.646 | −38.495 | 1.00 | 21.75 | C |
| ATOM | 5736 | CB | LYS B | 312 | −2.731 | −20.785 | −39.185 | 1.00 | 23.11 | C |
| ATOM | 5737 | CG | LYS B | 312 | −3.090 | −22.181 | −38.682 | 1.00 | 27.63 | C |
| ATOM | 5738 | CD | LYS B | 312 | −2.043 | −23.203 | −39.108 | 1.00 | 33.68 | C |
| ATOM | 5739 | CE | LYS B | 312 | −2.508 | −24.634 | −38.847 | 1.00 | 39.02 | C |
| ATOM | 5740 | NZ | LYS B | 312 | −3.549 | −25.071 | −39.826 | 1.00 | 39.69 | N |
| ATOM | 5741 | C | LYS B | 312 | −2.764 | −18.325 | −38.739 | 1.00 | 20.98 | C |
| ATOM | 5742 | O | LYS B | 312 | −2.975 | −17.662 | −39.753 | 1.00 | 19.37 | O |
| ATOM | 5743 | N | CYS B | 313 | −1.913 | −17.961 | −37.783 | 1.00 | 20.79 | N |
| ATOM | 5744 | CA | CYS B | 313 | −1.111 | −16.751 | −37.848 | 1.00 | 21.67 | C |
| ATOM | 5745 | CB | CYS B | 313 | −1.239 | −15.961 | −36.545 | 1.00 | 21.94 | C |
| ATOM | 5746 | SG | CYS B | 313 | −2.816 | −15.128 | −36.315 | 1.00 | 24.08 | S |
| ATOM | 5747 | C | CYS B | 313 | .355 | −17.091 | −38.083 | 1.00 | 22.11 | C |
| ATOM | 5748 | O | CYS B | 313 | .836 | −18.134 | −37.632 | 1.00 | 21.85 | O |
| ATOM | 5749 | N | ASN B | 314 | 1.067 | −16.208 | −38.776 | 1.00 | 22.17 | N |
| ATOM | 5750 | CA | ASN B | 314 | 2.506 | −16.375 | −38.951 | 1.00 | 22.88 | C |
| ATOM | 5751 | CB | ASN B | 314 | 2.992 | −15.684 | −40.236 | 1.00 | 22.62 | C |
| ATOM | 5752 | CG | ASN B | 314 | 2.829 | −14.166 | −40.201 | 1.00 | 23.43 | C |
| ATOM | 5753 | OD1 | ASN B | 314 | 2.653 | −13.562 | −39.141 | 1.00 | 22.87 | O |
| ATOM | 5754 | ND2 | ASN B | 314 | 2.902 | −13.544 | −41.371 | 1.00 | 21.25 | N |
| ATOM | 5755 | C | ASN B | 314 | 3.293 | −15.906 | −37.717 | 1.00 | 23.91 | C |
| ATOM | 5756 | O | ASN B | 314 | 2.702 | −15.516 | −36.704 | 1.00 | 24.44 | O |
| ATOM | 5757 | N | GLU B | 315 | 4.621 | −15.943 | −37.817 | 1.00 | 24.14 | N |
| ATOM | 5758 | CA | GLU B | 315 | 5.522 | −15.553 | −36.726 | 1.00 | 24.83 | C |
| ATOM | 5759 | CB | GLU B | 315 | 6.974 | −15.571 | −37.232 | 1.00 | 25.62 | C |
| ATOM | 5760 | CG | GLU B | 315 | 8.040 | −15.145 | −36.214 | 1.00 | 30.53 | C |
| ATOM | 5761 | CD | GLU B | 315 | 8.179 | −16.102 | −35.036 | 1.00 | 35.14 | C |
| ATOM | 5762 | OE1 | GLU B | 315 | 8.695 | −15.664 | −33.986 | 1.00 | 35.24 | O |
| ATOM | 5763 | OE2 | GLU B | 315 | 7.784 | −17.285 | −35.158 | 1.00 | 38.93 | O |
| ATOM | 5764 | C | GLU B | 315 | 5.185 | −14.186 | −36.116 | 1.00 | 23.98 | C |
| ATOM | 5765 | O | GLU B | 315 | 5.265 | −13.999 | −34.901 | 1.00 | 23.63 | O |
| ATOM | 5766 | N | ARG B | 316 | 4.801 | −13.247 | −36.977 | 1.00 | 23.68 | N |
| ATOM | 5767 | CA | ARG B | 316 | 4.495 | −11.874 | −36.581 | 1.00 | 23.52 | C |
| ATOM | 5768 | CB | ARG B | 316 | 4.834 | −10.919 | −37.730 | 1.00 | 23.61 | C |
| | | | | | gad67.pdb | | | | | |
| ATOM | 5769 | CG | ARG B | 316 | 6.314 | −10.886 | −38.094 | 1.00 | 26.24 | C |
| ATOM | 5770 | CD | ARG B | 316 | 6.543 | −10.147 | −39.397 | 1.00 | 28.71 | C |
| ATOM | 5771 | NE | ARG B | 316 | 6.167 | −8.737 | −39.304 | 1.00 | 35.89 | N |
| ATOM | 5772 | CZ | ARG B | 316 | 5.822 | −7.975 | −40.339 | 1.00 | 38.97 | C |
| ATOM | 5773 | NH1 | ARG B | 316 | 5.790 | −8.481 | −41.567 | 1.00 | 38.18 | N |
| ATOM | 5774 | NH2 | ARG B | 316 | 5.496 | −6.703 | −40.144 | 1.00 | 38.21 | N |
| ATOM | 5775 | C | ARG B | 316 | 3.042 | −11.660 | −36.125 | 1.00 | 22.70 | C |
| ATOM | 5776 | O | ARG B | 316 | 2.629 | −10.521 | −35.880 | 1.00 | 23.44 | O |
| ATOM | 5777 | N | GLY B | 317 | 2.281 | −12.750 | −36.021 | 1.00 | 21.17 | N |
| ATOM | 5778 | CA | GLY B | 317 | .912 | −12.717 | −35.505 | 1.00 | 20.31 | C |
| ATOM | 5779 | C | GLY B | 317 | −.129 | −12.239 | −36.497 | 1.00 | 20.21 | C |
| ATOM | 5780 | O | GLY B | 317 | −1.199 | −11.769 | −36.102 | 1.00 | 19.19 | O |
| ATOM | 5781 | N | LYS B | 318 | .191 | −12.359 | −37.785 | 1.00 | 20.25 | N |
| ATOM | 5782 | CA | LYS B | 318 | −.712 | −11.970 | −38.865 | 1.00 | 19.82 | C |
| ATOM | 5783 | CB | LYS B | 318 | .071 | −11.310 | −40.000 | 1.00 | 19.39 | C |
| ATOM | 5784 | CG | LYS B | 318 | .768 | −9.999 | −39.655 | 1.00 | 20.83 | C |
| ATOM | 5785 | CD | LYS B | 318 | 1.655 | −9.578 | −40.821 | 1.00 | 21.75 | C |
| ATOM | 5786 | CE | LYS B | 318 | 2.222 | −8.187 | −40.646 | 1.00 | 24.74 | C |
| ATOM | 5787 | NZ | LYS B | 318 | 1.217 | −7.122 | −40.926 | 1.00 | 24.93 | N |
| ATOM | 5788 | C | LYS B | 318 | −1.425 | −13.196 | −39.424 | 1.00 | 20.19 | C |
| ATOM | 5789 | O | LYS B | 318 | −.841 | −14.282 | −39.483 | 1.00 | 20.47 | O |
| ATOM | 5790 | N | ILE B | 319 | −2.678 | −13.018 | −39.848 | 1.00 | 19.80 | N |
| ATOM | 5791 | CA | ILE B | 319 | −3.404 | −14.063 | −40.575 | 1.00 | 20.13 | C |
| ATOM | 5792 | CB | ILE B | 319 | −4.838 | −13.599 | −40.993 | 1.00 | 19.83 | C |
| ATOM | 5793 | CG1 | ILE B | 319 | −5.857 | −13.961 | −39.912 | 1.00 | 19.54 | C |
| ATOM | 5794 | CD1 | ILE B | 319 | −7.256 | −13.389 | −40.152 | 1.00 | 19.00 | C |
| ATOM | 5795 | CG2 | ILE B | 319 | −5.268 | −14.223 | −42.329 | 1.00 | 19.22 | C |
| ATOM | 5796 | C | ILE B | 319 | −2.609 | −14.488 | −41.810 | 1.00 | 20.68 | C |
| ATOM | 5797 | O | ILE B | 319 | −2.089 | −13.635 | −42.542 | 1.00 | 20.65 | O |
| ATOM | 5798 | N | ILE B | 320 | −2.504 | −15.804 | −42.014 | 1.00 | 21.01 | N |

TABLE A-continued

| | | | | | | | | | |
|---|---|---|---|---|---|---|---|---|---|
| ATOM | 5799 | CA | ILE B | 320 | −1.946 | −16.379 | −43.245 | 1.00 | 21.43 | C |
| ATOM | 5800 | CB | ILE B | 320 | −1.191 | −17.716 | −42.982 | 1.00 | 21.31 | C |
| ATOM | 5801 | CG1 | ILE B | 320 | −.136 | −17.548 | −41.881 | 1.00 | 20.47 | C |
| ATOM | 5802 | CD1 | ILE B | 320 | .425 | −18.860 | −41.336 | 1.00 | 20.34 | C |
| ATOM | 5803 | CG2 | ILE B | 320 | −.559 | −18.249 | −44.279 | 1.00 | 20.00 | C |
| ATOM | 5804 | C | ILE B | 320 | −3.099 | −16.631 | −44.226 | 1.00 | 22.51 | C |
| ATOM | 5805 | O | ILE B | 320 | −3.890 | −17.558 | −44.025 | 1.00 | 23.25 | O |
| ATOM | 5806 | N | PRO B | 321 | −3.200 | −15.806 | −45.288 | 1.00 | 23.12 | N |
| ATOM | 5807 | CA | PRO B | 321 | −4.350 | −15.841 | −46.206 | 1.00 | 23.77 | C |
| ATOM | 5808 | CB | PRO B | 321 | −3.967 | −14.823 | −47.289 | 1.00 | 23.93 | C |
| ATOM | 5809 | CG | PRO B | 321 | −3.003 | −13.905 | −46.620 | 1.00 | 23.45 | C |
| ATOM | 5810 | CD | PRO B | 321 | −2.213 | −14.787 | −45.696 | 1.00 | 23.16 | C |
| ATOM | 5811 | C | PRO B | 321 | −4.616 | −17.216 | −46.833 | 1.00 | 24.21 | C |
| ATOM | 5812 | O | PRO B | 321 | −5.776 | −17.579 | −47.043 | 1.00 | 23.92 | O |
| ATOM | 5813 | N | ALA B | 322 | −3.551 | −17.965 | −47.119 | 1.00 | 24.78 | N |
| ATOM | 5814 | CA | ALA B | 322 | −3.666 | −19.308 | −47.696 | 1.00 | 25.01 | C |
| ATOM | 5815 | CB | ALA B | 322 | −2.291 | −19.869 | −48.029 | 1.00 | 24.78 | C |
| ATOM | 5816 | C | ALA B | 322 | −4.426 | −20.265 | −46.779 | 1.00 | 25.20 | C |
| ATOM | 5817 | O | ALA B | 322 | −5.132 | −21.149 | −47.256 | 1.00 | 25.16 | O |
| ATOM | 5818 | N | ASP B | 323 | −4.276 | −20.085 | −45.468 | 1.00 | 25.64 | N |
| ATOM | 5819 | CA | ASP B | 323 | −5.040 | −20.863 | −44.493 | 1.00 | 25.53 | C |
| ATOM | 5820 | CB | ASP B | 323 | −4.421 | −20.760 | −43.097 | 1.00 | 25.99 | C |
| ATOM | 5821 | CG | ASP B | 323 | −5.060 | −21.719 | −42.103 | 1.00 | 27.29 | C |
| ATOM | 5822 | OD1 | ASP B | 323 | −4.977 | −22.947 | −42.319 | 1.00 | 27.59 | O |
| ATOM | 5823 | OD2 | ASP B | 323 | −5.641 | −21.244 | −41.101 | 1.00 | 28.90 | O |
| ATOM | 5824 | C | ASP B | 323 | −6.501 | −20.420 | −44.457 | 1.00 | 24.37 | C |
| ATOM | 5825 | O | ASP B | 323 | −7.394 | −21.237 | −44.246 | 1.00 | 24.94 | O |
| ATOM | 5826 | N | PHE B | 324 | −6.733 | −19.129 | −44.668 | 1.00 | 23.82 | N |
| ATOM | 5827 | CA | PHE B | 324 | −8.086 | −18.571 | −44.706 | 1.00 | 23.41 | C |
| ATOM | 5828 | CB | PHE B | 324 | −8.039 | −17.031 | −44.719 | 1.00 | 21.92 | C |
| ATOM | 5829 | CG | PHE B | 324 | −9.370 | −16.365 | −44.978 | 1.00 | 19.65 | C |
| ATOM | 5830 | CD1 | PHE B | 324 | −9.450 | −15.281 | −45.844 | 1.00 | 17.54 | C |
| ATOM | 5831 | CE1 | PHE B | 324 | −10.671 | −14.648 | −46.092 | 1.00 | 18.88 | C |
| ATOM | 5832 | CZ | PHE B | 324 | −11.829 | −15.103 | −45.464 | 1.00 | 18.40 | C |
| ATOM | 5833 | CE2 | PHE B | 324 | −11.760 | −16.182 | −44.590 | 1.00 | 17.67 | C |
| ATOM | 5834 | CD2 | PHE B | 324 | −10.537 | −16.803 | −44.348 | 1.00 | 19.49 | C |
| ATOM | 5835 | C | PHE B | 324 | −8.885 | −19.142 | −45.882 | 1.00 | 23.77 | C |
| ATOM | 5836 | O | PHE B | 324 | −10.003 | −19.621 | −45.692 | 1.00 | 24.29 | O |
| | | | | gad67.pdb | | | | | | |
| ATOM | 5837 | N | GLU B | 325 | −8.303 | −19.116 | −47.080 | 1.00 | 24.04 | N |
| ATOM | 5838 | CA | GLU B | 325 | −8.940 | −19.718 | −48.256 | 1.00 | 25.09 | C |
| ATOM | 5839 | CB | GLU B | 325 | −8.154 | −19.417 | −49.535 | 1.00 | 25.27 | C |
| ATOM | 5840 | CG | GLU B | 325 | −8.813 | −19.963 | −50.808 | 1.00 | 26.81 | C |
| ATOM | 5841 | CD | GLU B | 325 | −8.172 | −19.457 | −52.092 | 1.00 | 26.77 | C |
| ATOM | 5842 | OE1 | GLU B | 325 | −8.626 | −19.878 | −53.180 | 1.00 | 27.73 | O |
| ATOM | 5843 | OE2 | GLU B | 325 | −7.227 | −18.640 | −52.021 | 1.00 | 29.56 | O |
| ATOM | 5844 | C | GLU B | 325 | −9.149 | −21.226 | −48.099 | 1.00 | 24.91 | C |
| ATOM | 5845 | O | GLU B | 325 | −10.185 | −21.756 | −48.506 | 1.00 | 25.53 | O |
| ATOM | 5846 | N | ALA B | 326 | −8.170 | −21.909 | −47.508 | 1.00 | 24.65 | N |
| ATOM | 5847 | CA | ALA B | 326 | −8.273 | −23.347 | −47.271 | 1.00 | 24.90 | C |
| ATOM | 5848 | CB | ALA B | 326 | −6.938 | −23.916 | −46.777 | 1.00 | 24.94 | C |
| ATOM | 5849 | C | ALA B | 326 | −9.409 | −23.696 | −46.299 | 1.00 | 25.06 | C |
| ATOM | 5850 | O | ALA B | 326 | −10.098 | −24.703 | −46.488 | 1.00 | 24.90 | O |
| ATOM | 5851 | N | LYS B | 327 | −9.597 | −22.864 | −45.271 | 1.00 | 24.89 | N |
| ATOM | 5852 | CA | LYS B | 327 | −10.669 | −23.067 | −44.287 | 1.00 | 24.64 | C |
| ATOM | 5853 | CB | LYS B | 327 | −10.491 | −22.158 | −43.059 | 1.00 | 26.22 | C |
| ATOM | 5854 | CG | LYS B | 327 | −9.255 | −22.436 | −42.192 | 1.00 | 26.69 | C |
| ATOM | 5855 | CD | LYS B | 327 | −9.468 | −23.566 | −41.200 | 1.00 | 30.40 | C |
| ATOM | 5856 | CE | LYS B | 327 | −8.168 | −23.963 | −40.496 | 1.00 | 32.17 | C |
| ATOM | 5857 | NZ | LYS B | 327 | −7.500 | −22.839 | −39.773 | 1.00 | 31.91 | N |
| ATOM | 5858 | C | LYS B | 327 | −12.039 | −22.839 | −44.919 | 1.00 | 23.81 | C |
| ATOM | 5859 | O | LYS B | 327 | −12.992 | −23.546 | −44.596 | 1.00 | 23.74 | O |
| ATOM | 5860 | N | ILE B | 328 | −12.128 | −21.854 | −45.816 | 1.00 | 23.17 | N |
| ATOM | 5861 | CA | ILE B | 328 | −13.351 | −21.594 | −46.586 | 1.00 | 23.49 | C |
| ATOM | 5862 | CB | ILE B | 328 | −13.196 | −20.376 | −47.543 | 1.00 | 23.61 | C |
| ATOM | 5863 | CG1 | ILE B | 328 | −12.994 | −19.078 | −46.756 | 1.00 | 22.64 | C |
| ATOM | 5864 | CD1 | ILE B | 328 | −12.661 | −17.884 | −47.629 | 1.00 | 22.04 | C |
| ATOM | 5865 | CG2 | ILE B | 328 | −14.409 | −20.251 | −48.487 | 1.00 | 21.97 | C |
| ATOM | 5866 | C | ILE B | 328 | −13.749 | −22.829 | −47.397 | 1.00 | 24.95 | C |
| ATOM | 5867 | O | ILE B | 328 | −14.875 | −23.323 | −47.276 | 1.00 | 24.40 | O |
| ATOM | 5868 | N | LEU B | 329 | −12.813 | −23.318 | −48.213 | 1.00 | 25.96 | N |
| ATOM | 5869 | CA | LEU B | 329 | −13.023 | −24.495 | −49.058 | 1.00 | 27.41 | C |
| ATOM | 5870 | CB | LEU B | 329 | −11.752 | −24.809 | −49.851 | 1.00 | 27.66 | C |
| ATOM | 5871 | CG | LEU B | 329 | −11.667 | −24.361 | −51.312 | 1.00 | 29.40 | C |
| ATOM | 5872 | CD1 | LEU B | 329 | −12.502 | −23.134 | −51.606 | 1.00 | 30.74 | C |
| ATOM | 5873 | CD2 | LEU B | 329 | −10.214 | −24.145 | −51.726 | 1.00 | 32.47 | C |
| ATOM | 5874 | C | LEU B | 329 | −13.456 | −25.714 | −48.255 | 1.00 | 28.08 | C |
| ATOM | 5875 | O | LEU B | 329 | −14.377 | −26.433 | −48.648 | 1.00 | 28.27 | O |
| ATOM | 5876 | N | GLU B | 330 | −12.790 | −25.926 | −47.125 | 1.00 | 28.69 | N |
| ATOM | 5877 | CA | GLU B | 330 | −13.112 | −27.005 | −46.202 | 1.00 | 29.82 | C |

TABLE A-continued

| ATOM | 5878 | CB  | GLU B | 330 | −12.107 | −26.997 | −45.053 | 1.00 | 29.31 | C |
| ATOM | 5879 | CG  | GLU B | 330 | −12.008 | −28.292 | −44.273 | 1.00 | 33.83 | C |
| ATOM | 5880 | CD  | GLU B | 330 | −11.118 | −28.166 | −43.041 | 1.00 | 33.11 | C |
| ATOM | 5881 | OE1 | GLU B | 330 | −10.096 | −27.441 | −43.104 | 1.00 | 36.49 | O |
| ATOM | 5882 | OE2 | GLU B | 330 | −11.444 | −28.798 | −42.010 | 1.00 | 38.67 | O |
| ATOM | 5883 | C   | GLU B | 330 | −14.544 | −26.891 | −45.663 | 1.00 | 29.16 | C |
| ATOM | 5884 | O   | GLU B | 330 | −15.213 | −27.904 | −45.464 | 1.00 | 29.30 | O |
| ATOM | 5885 | N   | ALA B | 331 | −15.011 | −25.662 | −45.447 | 1.00 | 28.57 | N |
| ATOM | 5886 | CA  | ALA B | 331 | −16.353 | −25.423 | −44.904 | 1.00 | 28.49 | C |
| ATOM | 5887 | CB  | ALA B | 331 | −16.494 | −23.983 | −44.418 | 1.00 | 27.42 | C |
| ATOM | 5888 | C   | ALA B | 331 | −17.461 | −25.760 | −45.898 | 1.00 | 28.43 | C |
| ATOM | 5889 | O   | ALA B | 331 | −18.457 | −26.390 | −45.536 | 1.00 | 27.92 | O |
| ATOM | 5890 | N   | LYS B | 332 | −17.291 | −25.336 | −47.145 | 1.00 | 28.50 | N |
| ATOM | 5891 | CA  | LYS B | 332 | −18.314 | −25.572 | −48.156 | 1.00 | 29.94 | C |
| ATOM | 5892 | CB  | LYS B | 332 | −18.355 | −24.459 | −49.214 | 1.00 | 29.91 | C |
| ATOM | 5893 | CG  | LYS B | 332 | −17.017 | −23.942 | −49.697 | 1.00 | 30.14 | C |
| ATOM | 5894 | CD  | LYS B | 332 | −17.159 | −22.522 | −50.246 | 1.00 | 30.04 | C |
| ATOM | 5895 | CE  | LYS B | 332 | −17.742 | −22.509 | −51.650 | 1.00 | 30.73 | C |
| ATOM | 5896 | NZ  | LYS B | 332 | −18.353 | −21.192 | −51.986 | 1.00 | 33.48 | N |
| ATOM | 5897 | C   | LYS B | 332 | −18.241 | −26.972 | −48.777 | 1.00 | 30.65 | C |
| ATOM | 5898 | O   | LYS B | 332 | −19.213 | −27.439 | −49.372 | 1.00 | 30.86 | O |
| ATOM | 5899 | N   | GLN B | 333 | −17.101 | −27.638 | −48.610 | 1.00 | 31.67 | N |
| ATOM | 5900 | CA  | GLN B | 333 | −16.955 | −29.033 | −49.013 | 1.00 | 33.19 | C |
| ATOM | 5901 | CB  | GLN B | 333 | −15.492 | −29.480 | −48.921 | 1.00 | 33.69 | C |
| ATOM | 5902 | CG  | GLN B | 333 | −15.161 | −30.740 | −49.718 | 1.00 | 37.40 | C |
| ATOM | 5906 | C   | GLN B | 333 | −17.845 | −29.919 | −48.140 | 1.00 | 33.49 | C |
| ATOM | 5907 | O   | GLN B | 333 | −18.374 | −30.933 | −48.606 | 1.00 | 34.06 | O | gad67.pdb

| ATOM | 5908 | N   | LYS B | 334 | −18.021 | −29.523 | −46.882 | 1.00 | 33.16 | N |
| ATOM | 5909 | CA  | LYS B | 334 | −18.879 | −30.272 | −45.967 | 1.00 | 33.35 | C |
| ATOM | 5910 | CB  | LYS B | 334 | −18.203 | −30.473 | −44.602 | 1.00 | 33.75 | C |
| ATOM | 5911 | CG  | LYS B | 334 | −17.831 | −29.209 | −43.854 | 1.00 | 37.03 | C |
| ATOM | 5912 | CD  | LYS B | 334 | −16.548 | −29.407 | −43.047 | 1.00 | 41.35 | C |
| ATOM | 5913 | CE  | LYS B | 334 | −16.632 | −30.585 | −42.087 | 1.00 | 44.08 | C |
| ATOM | 5914 | NZ  | LYS B | 334 | −15.277 | −30.999 | −41.627 | 1.00 | 45.47 | N |
| ATOM | 5915 | C   | LYS B | 334 | −20.299 | −29.704 | −45.847 | 1.00 | 32.41 | C |
| ATOM | 5916 | O   | LYS B | 334 | −21.061 | −30.090 | −44.960 | 1.00 | 32.21 | O |
| ATOM | 5917 | N   | GLY B | 335 | −20.648 | −28.803 | −46.765 | 1.00 | 32.15 | N |
| ATOM | 5918 | CA  | GLY B | 335 | −22.011 | −28.293 | −46.887 | 1.00 | 31.70 | C |
| ATOM | 5919 | C   | GLY B | 335 | −22.357 | −27.073 | −46.051 | 1.00 | 31.55 | C |
| ATOM | 5920 | O   | GLY B | 335 | −23.509 | −26.627 | −46.053 | 1.00 | 31.47 | O |
| ATOM | 5921 | N   | TYR B | 336 | −21.373 | −26.531 | −45.335 | 1.00 | 30.67 | N |
| ATOM | 5922 | CA  | TYR B | 336 | −21.586 | −25.331 | −44.524 | 1.00 | 29.55 | C |
| ATOM | 5923 | CB  | TYR B | 336 | −20.609 | −25.266 | −43.340 | 1.00 | 30.23 | C |
| ATOM | 5924 | CG  | TYR B | 336 | −20.508 | −26.519 | −42.484 | 1.00 | 31.29 | C |
| ATOM | 5925 | CD1 | TYR B | 336 | −19.418 | −26.704 | −41.637 | 1.00 | 33.22 | C |
| ATOM | 5926 | CE1 | TYR B | 336 | −19.300 | −27.839 | −40.841 | 1.00 | 32.89 | C |
| ATOM | 5927 | CZ  | TYR B | 336 | −20.276 | −28.817 | −40.896 | 1.00 | 33.63 | C |
| ATOM | 5928 | OH  | TYR B | 336 | −20.148 | −29.935 | −40.105 | 1.00 | 33.44 | O |
| ATOM | 5929 | CE2 | TYR B | 336 | −21.374 | −28.670 | −41.736 | 1.00 | 33.45 | C |
| ATOM | 5930 | CD2 | TYR B | 336 | −21.485 | −27.521 | −42.525 | 1.00 | 33.18 | C |
| ATOM | 5931 | C   | TYR B | 336 | −21.457 | −24.076 | −45.387 | 1.00 | 28.40 | C |
| ATOM | 5932 | O   | TYR B | 336 | −20.941 | −24.132 | −46.508 | 1.00 | 28.82 | O |
| ATOM | 5933 | N   | VAL B | 337 | −21.925 | −22.947 | −44.863 | 1.00 | 26.06 | N |
| ATOM | 5934 | CA  | VAL B | 337 | −21.905 | −21.691 | −45.603 | 1.00 | 24.06 | C |
| ATOM | 5935 | CB  | VAL B | 337 | −23.349 | −21.152 | −45.849 | 1.00 | 24.05 | C |
| ATOM | 5936 | CG1 | VAL B | 337 | −23.332 | −19.836 | −46.613 | 1.00 | 23.01 | C |
| ATOM | 5937 | CG2 | VAL B | 337 | −24.180 | −22.179 | −46.604 | 1.00 | 23.72 | C |
| ATOM | 5938 | C   | VAL B | 337 | −21.018 | −20.647 | −44.904 | 1.00 | 23.27 | C |
| ATOM | 5939 | O   | VAL B | 337 | −21.388 | −20.118 | −43.853 | 1.00 | 22.64 | O |
| ATOM | 5940 | N   | PRO B | 338 | −19.834 | −20.362 | −45.484 | 1.00 | 22.72 | N |
| ATOM | 5941 | CA  | PRO B | 338 | −18.969 | −19.269 | −45.028 | 1.00 | 21.92 | C |
| ATOM | 5942 | CB  | PRO B | 338 | −17.654 | −19.511 | −45.782 | 1.00 | 21.87 | C |
| ATOM | 5943 | CG  | PRO B | 338 | −17.785 | −20.847 | −46.433 | 1.00 | 22.36 | C |
| ATOM | 5944 | CD  | PRO B | 338 | −19.242 | −21.073 | −46.629 | 1.00 | 22.55 | C |
| ATOM | 5945 | C   | PRO B | 338 | −19.564 | −17.932 | −45.446 | 1.00 | 21.07 | C |
| ATOM | 5946 | O   | PRO B | 338 | −19.962 | −17.774 | −46.602 | 1.00 | 22.56 | O |
| ATOM | 5947 | N   | PHE B | 339 | −19.640 | −16.980 | −44.522 | 1.00 | 18.75 | N |
| ATOM | 5948 | CA  | PHE B | 339 | −20.321 | −15.721 | −44.815 | 1.00 | 17.21 | C |
| ATOM | 5949 | CB  | PHE B | 339 | −21.780 | −15.779 | −44.336 | 1.00 | 16.09 | C |
| ATOM | 5950 | CG  | PHE B | 339 | −21.947 | −15.511 | −42.866 | 1.00 | 15.65 | C |
| ATOM | 5951 | CD1 | PHE B | 339 | −22.411 | −14.276 | −42.421 | 1.00 | 14.30 | C |
| ATOM | 5952 | CE1 | PHE B | 339 | −22.563 | −14.018 | −41.065 | 1.00 | 13.17 | C |
| ATOM | 5953 | CZ  | PHE B | 339 | −22.247 | −14.996 | −40.138 | 1.00 | 14.81 | C |
| ATOM | 5954 | CE2 | PHE B | 339 | −21.782 | −16.239 | −40.569 | 1.00 | 15.55 | C |
| ATOM | 5955 | CD2 | PHE B | 339 | −21.636 | −16.490 | −41.924 | 1.00 | 13.84 | C |
| ATOM | 5956 | C   | PHE B | 339 | −19.634 | −14.502 | −44.215 | 1.00 | 16.45 | C |
| ATOM | 5957 | O   | PHE B | 339 | −20.008 | −13.372 | −44.524 | 1.00 | 16.98 | O |
| ATOM | 5958 | N   | TYR B | 340 | −18.641 | −14.730 | −43.360 | 1.00 | 15.73 | N |
| ATOM | 5959 | CA  | TYR B | 340 | −18.066 | −13.657 | −42.554 | 1.00 | 15.22 | C |

TABLE A-continued

| | | | | | | | | | | |
|---|---|---|---|---|---|---|---|---|---|---|
| ATOM | 5960 | CB | TYR B | 340 | −18.952 | −13.409 | −41.321 | 1.00 | 14.65 | C |
| ATOM | 5961 | CG | TYR B | 340 | −18.430 | −12.401 | −40.315 | 1.00 | 14.67 | C |
| ATOM | 5962 | CD1 | TYR B | 340 | −17.463 | −12.760 | −39.375 | 1.00 | 13.64 | C |
| ATOM | 5963 | CE1 | TYR B | 340 | −16.993 | −11.847 | −38.441 | 1.00 | 13.90 | C |
| ATOM | 5964 | CZ | TYR B | 340 | −17.504 | −10.565 | −38.421 | 1.00 | 14.08 | C |
| ATOM | 5965 | OH | TYR B | 340 | −17.034 | −9.674 | −37.479 | 1.00 | 14.68 | O |
| ATOM | 5966 | CE2 | TYR B | 340 | −18.482 | −10.183 | −39.329 | 1.00 | 11.99 | C |
| ATOM | 5967 | CD2 | TYR B | 340 | −18.939 | −11.102 | −40.269 | 1.00 | 13.79 | C |
| ATOM | 5968 | C | TYR B | 340 | −16.636 | −13.948 | −42.121 | 1.00 | 15.13 | C |
| ATOM | 5969 | O | TYR B | 340 | −16.318 | −15.054 | −41.666 | 1.00 | 14.17 | O |
| ATOM | 5970 | N | VAL B | 341 | −15.783 | −12.933 | −42.253 | 1.00 | 15.36 | N |
| ATOM | 5971 | CA | VAL B | 341 | −14.434 | −12.983 | −41.702 | 1.00 | 14.10 | C |
| ATOM | 5972 | CB | VAL B | 341 | −13.347 | −13.164 | −42.801 | 1.00 | 14.47 | C |
| ATOM | 5973 | CG1 | VAL B | 341 | −13.261 | −11.946 | −43.689 | 1.00 | 13.23 | C |
| ATOM | 5974 | CG2 | VAL B | 341 | −11.986 | −13.459 | −42.184 | 1.00 | 10.85 | C |
| ATOM | 5975 | C | VAL B | 341 | −14.167 | −11.725 | −40.889 | 1.00 | 14.47 | C |
| | | | | gad67.pdb | | | | | | |
| ATOM | 5976 | O | VAL B | 341 | −14.632 | −10.637 | −41.238 | 1.00 | 14.38 | O |
| ATOM | 5977 | N | ASN B | 342 | −13.427 | −11.889 | −39.797 | 1.00 | 14.55 | N |
| ATOM | 5978 | CA | ASN B | 342 | −12.947 | −10.759 | −39.016 | 1.00 | 15.32 | C |
| ATOM | 5979 | CB | ASN B | 342 | −13.309 | −10.929 | −37.533 | 1.00 | 14.80 | C |
| ATOM | 5980 | CG | ASN B | 342 | −12.584 | −9.942 | −36.637 | 1.00 | 15.21 | C |
| ATOM | 5981 | OD1 | ASN B | 342 | −12.732 | −8.732 | −36.779 | 1.00 | 17.50 | O |
| ATOM | 5982 | ND2 | ASN B | 342 | −11.791 | −10.460 | −35.712 | 1.00 | 15.26 | N |
| ATOM | 5983 | C | ASN B | 342 | −11.440 | −10.590 | −39.191 | 1.00 | 15.22 | C |
| ATOM | 5984 | O | ASN B | 342 | −10.672 | −11.508 | −38.904 | 1.00 | 15.15 | O |
| ATOM | 5985 | N | ALA B | 343 | −11.031 | −9.421 | −39.679 | 1.00 | 15.34 | N |
| ATOM | 5986 | CA | ALA B | 343 | −9.610 | −9.081 | −39.789 | 1.00 | 16.03 | C |
| ATOM | 5987 | CB | ALA B | 343 | −9.264 | −8.663 | −41.217 | 1.00 | 15.16 | C |
| ATOM | 5988 | C | ALA B | 343 | −9.238 | −7.979 | −38.794 | 1.00 | 15.67 | C |
| ATOM | 5989 | O | ALA B | 343 | −9.943 | −6.980 | −38.687 | 1.00 | 15.77 | O |
| ATOM | 5990 | N | THR B | 344 | −8.137 | −8.186 | −38.072 | 1.00 | 15.78 | N |
| ATOM | 5991 | CA | THR B | 344 | −7.573 | −7.229 | −37.104 | 1.00 | 17.07 | C |
| ATOM | 5992 | CB | THR B | 344 | −7.391 | −7.941 | −35.721 | 1.00 | 16.93 | C |
| ATOM | 5993 | OG1 | THR B | 344 | −8.336 | −9.010 | −35.575 | 1.00 | 16.46 | O |
| ATOM | 5994 | CG2 | THR B | 344 | −7.534 | −6.975 | −34.560 | 1.00 | 15.99 | C |
| ATOM | 5995 | C | THR B | 344 | −6.174 | −6.879 | −37.633 | 1.00 | 17.87 | C |
| ATOM | 5996 | O | THR B | 344 | −5.358 | −7.780 | −37.686 | 1.00 | 20.40 | O |
| ATOM | 5997 | N | ALA B | 345 | −5.795 | −5.649 | −37.999 | 1.00 | 20.05 | N |
| ATOM | 5998 | CA | ALA B | 345 | −6.325 | −4.314 | −37.650 | 1.00 | 18.82 | C |
| ATOM | 5999 | CB | ALA B | 345 | −7.817 | −4.241 | −37.749 | 1.00 | 21.18 | C |
| ATOM | 6000 | C | ALA B | 345 | −5.791 | −3.807 | −36.303 | 1.00 | 16.98 | C |
| ATOM | 6001 | O | ALA B | 345 | −6.261 | −2.806 | −35.766 | 1.00 | 16.36 | O |
| ATOM | 6002 | N | GLY B | 346 | −4.778 | −4.500 | −35.787 | 1.00 | 15.88 | N |
| ATOM | 6003 | CA | GLY B | 346 | −4.165 | −4.166 | −34.506 | 1.00 | 15.92 | C |
| ATOM | 6004 | C | GLY B | 346 | −4.626 | −5.104 | −33.413 | 1.00 | 15.96 | C |
| ATOM | 6005 | O | GLY B | 346 | −5.612 | −4.830 | −32.737 | 1.00 | 16.73 | O |
| ATOM | 6006 | N | THR B | 347 | −3.915 | −6.216 | −33.244 | 1.00 | 15.57 | N |
| ATOM | 6007 | CA | THR B | 347 | −4.292 | −7.229 | −32.256 | 1.00 | 15.20 | C |
| ATOM | 6008 | CB | THR B | 347 | −3.608 | −8.590 | −32.519 | 1.00 | 15.08 | C |
| ATOM | 6009 | OG1 | THR B | 347 | −2.183 | −8.424 | −32.532 | 1.00 | 16.24 | O |
| ATOM | 6010 | CG2 | THR B | 347 | −4.074 | −9.187 | −33.848 | 1.00 | 14.45 | C |
| ATOM | 6011 | C | THR B | 347 | −3.977 | −6.760 | −30.844 | 1.00 | 15.08 | C |
| ATOM | 6012 | O | THR B | 347 | −3.113 | −5.905 | −30.644 | 1.00 | 14.48 | O |
| ATOM | 6013 | N | THR B | 348 | −4.685 | −7.326 | −29.870 | 1.00 | 15.65 | N |
| ATOM | 6014 | CA | THR B | 348 | −4.622 | −6.871 | −28.477 | 1.00 | 15.79 | C |
| ATOM | 6015 | CB | THR B | 348 | −5.748 | −7.531 | −27.632 | 1.00 | 16.61 | C |
| ATOM | 6016 | OG1 | THR B | 348 | −7.014 | −7.262 | −28.241 | 1.00 | 20.30 | O |
| ATOM | 6017 | CG2 | THR B | 348 | −5.775 | −6.996 | −26.209 | 1.00 | 13.84 | C |
| ATOM | 6018 | C | THR B | 348 | −3.248 | −7.112 | −27.839 | 1.00 | 15.23 | C |
| ATOM | 6019 | O | THR B | 348 | −2.772 | −6.296 | −27.050 | 1.00 | 15.20 | O |
| ATOM | 6020 | N | VAL B | 349 | −2.610 | −8.223 | −28.196 | 1.00 | 14.62 | N |
| ATOM | 6021 | CA | VAL B | 349 | −1.323 | −8.580 | −27.608 | 1.00 | 14.94 | C |
| ATOM | 6022 | CB | VAL B | 349 | −1.274 | −10.081 | −27.211 | 1.00 | 15.58 | C |
| ATOM | 6023 | CG1 | VAL B | 349 | .083 | −10.456 | −26.622 | 1.00 | 14.49 | C |
| ATOM | 6024 | CG2 | VAL B | 349 | −2.393 | −10.397 | −26.220 | 1.00 | 12.38 | C |
| ATOM | 6025 | C | VAL B | 349 | −.130 | −8.140 | −28.483 | 1.00 | 15.63 | C |
| ATOM | 6026 | O | VAL B | 349 | .633 | −7.265 | −28.071 | 1.00 | 16.04 | O |
| ATOM | 6027 | N | TYR B | 350 | .013 | −8.706 | −29.682 | 1.00 | 15.66 | N |
| ATOM | 6028 | CA | TYR B | 350 | 1.135 | −8.356 | −30.579 | 1.00 | 16.17 | C |
| ATOM | 6029 | CB | TYR B | 350 | 1.261 | −9.369 | −31.720 | 1.00 | 16.05 | C |
| ATOM | 6030 | CG | TYR B | 350 | 1.985 | −10.659 | −31.390 | 1.00 | 15.79 | C |
| ATOM | 6031 | CD1 | TYR B | 350 | 2.470 | −11.481 | −32.412 | 1.00 | 17.91 | C |
| ATOM | 6032 | CE1 | TYR B | 350 | 3.132 | −12.672 | −32.130 | 1.00 | 15.14 | C |
| ATOM | 6033 | CZ | TYR B | 350 | 3.321 | −13.049 | −30.812 | 1.00 | 17.24 | C |
| ATOM | 6034 | OH | TYR B | 350 | 3.973 | −14.224 | −30.519 | 1.00 | 19.13 | O |
| ATOM | 6035 | CE2 | TYR B | 350 | 2.853 | −12.252 | −29.780 | 1.00 | 15.85 | C |
| ATOM | 6036 | CD2 | TYR B | 350 | 2.192 | −11.063 | −30.072 | 1.00 | 15.00 | C |
| ATOM | 6037 | C | TYR B | 350 | 1.033 | −6.957 | −31.181 | 1.00 | 16.65 | C |
| ATOM | 6038 | O | TYR B | 350 | 2.053 | −6.323 | −31.464 | 1.00 | 17.33 | O |

TABLE A-continued

| | | | | | | | | | |
|---|---|---|---|---|---|---|---|---|---|
| ATOM | 6039 | N | GLY B | 351 | −.195 | −6.484 | −31.390 | 1.00 | 16.72 | N |
| ATOM | 6040 | CA | GLY B | 351 | −.425 | −5.230 | −32.107 | 1.00 | 15.85 | C |
| ATOM | 6041 | C | GLY B | 351 | −.205 | −5.425 | −33.595 | 1.00 | 16.14 | C |
| ATOM | 6042 | O | GLY B | 351 | .130 | −4.479 | −34.313 | 1.00 | 15.11 | O |
| ATOM | 6043 | N | ALA B | 352 | −.395 | −6.666 | −34.042 | 1.00 | 16.62 | N |
| | | | | gad67.pdb | | | | | | |
| ATOM | 6044 | CA | ALA B | 352 | −.225 | −7.056 | −35.434 | 1.00 | 16.33 | C |
| ATOM | 6045 | CB | ALA B | 352 | −.067 | −8.556 | −35.534 | 1.00 | 15.49 | C |
| ATOM | 6046 | C | ALA B | 352 | −1.399 | −6.597 | −36.287 | 1.00 | 17.51 | C |
| ATOM | 6047 | O | ALA B | 352 | −2.504 | −6.382 | −35.778 | 1.00 | 17.13 | O |
| ATOM | 6048 | N | PHE B | 353 | −1.149 | −6.453 | −37.586 | 1.00 | 17.83 | N |
| ATOM | 6049 | CA | PHE B | 353 | −2.188 | −6.100 | −38.537 | 1.00 | 18.11 | C |
| ATOM | 6050 | CB | PHE B | 353 | −1.851 | −4.773 | −39.224 | 1.00 | 17.22 | C |
| ATOM | 6051 | CG | PHE B | 353 | −2.010 | −3.568 | −38.337 | 1.00 | 17.13 | C |
| ATOM | 6052 | CD1 | PHE B | 353 | −1.025 | −3.228 | −37.414 | 1.00 | 14.99 | C |
| ATOM | 6053 | CE1 | PHE B | 353 | −1.166 | −2.115 | −36.594 | 1.00 | 11.53 | C |
| ATOM | 6054 | CZ | PHE B | 353 | −2.298 | −1.314 | −36.698 | 1.00 | 14.19 | C |
| ATOM | 6055 | CE2 | PHE B | 353 | −3.290 | −1.639 | −37.622 | 1.00 | 15.08 | C |
| ATOM | 6056 | CD2 | PHE B | 353 | −3.138 | −2.763 | −38.436 | 1.00 | 14.66 | C |
| ATOM | 6057 | C | PHE B | 353 | −2.362 | −7.209 | −39.575 | 1.00 | 19.56 | C |
| ATOM | 6058 | O | PHE B | 353 | −1.421 | −7.540 | −40.304 | 1.00 | 19.54 | O |
| ATOM | 6059 | N | ASP B | 354 | −3.566 | −7.782 | −39.626 | 1.00 | 20.80 | N |
| ATOM | 6060 | CA | ASP B | 354 | −3.928 | −8.772 | −40.648 | 1.00 | 21.50 | C |
| ATOM | 6061 | CB | ASP B | 354 | −5.353 | −9.299 | −40.415 | 1.00 | 20.87 | C |
| ATOM | 6062 | CG | ASP B | 354 | −5.455 | −10.221 | −39.200 | 1.00 | 22.13 | C |
| ATOM | 6063 | OD1 | ASP B | 354 | −4.421 | −10.782 | −38.770 | 1.00 | 20.41 | O |
| ATOM | 6064 | OD2 | ASP B | 354 | −6.579 | −10.384 | −38.670 | 1.00 | 23.66 | O |
| ATOM | 6065 | C | ASP B | 354 | −3.815 | −8.148 | −42.041 | 1.00 | 21.95 | C |
| ATOM | 6066 | O | ASP B | 354 | −4.083 | −6.955 | −42.198 | 1.00 | 22.26 | O |
| ATOM | 6067 | N | PRO B | 355 | −3.411 | −8.946 | −43.052 | 1.00 | 22.40 | N |
| ATOM | 6068 | CA | PRO B | 355 | −3.229 | −8.410 | −44.409 | 1.00 | 22.23 | C |
| ATOM | 6069 | CB | PRO B | 355 | −2.389 | −9.487 | −45.099 | 1.00 | 21.20 | C |
| ATOM | 6070 | CG | PRO B | 355 | −2.752 | −10.748 | −44.411 | 1.00 | 22.77 | C |
| ATOM | 6071 | CD | PRO B | 355 | −3.118 | −10.391 | −42.988 | 1.00 | 22.45 | C |
| ATOM | 6072 | C | PRO B | 355 | −4.580 | −8.212 | −45.107 | 1.00 | 22.03 | C |
| ATOM | 6073 | O | PRO B | 355 | −5.049 | −9.096 | −45.827 | 1.00 | 22.60 | O |
| ATOM | 6074 | N | ILE B | 356 | −5.190 | −7.050 | −44.877 | 1.00 | 21.59 | N |
| ATOM | 6075 | CA | ILE B | 356 | −6.583 | −6.794 | −45.261 | 1.00 | 21.25 | C |
| ATOM | 6076 | CB | ILE B | 356 | −7.086 | −5.406 | −44.756 | 1.00 | 21.03 | C |
| ATOM | 6077 | CG1 | ILE B | 356 | −6.925 | −5.295 | −43.234 | 1.00 | 18.85 | C |
| ATOM | 6078 | CD1 | ILE B | 356 | −7.181 | −3.903 | −42.679 | 1.00 | 20.65 | C |
| ATOM | 6079 | CG2 | ILE B | 356 | −8.546 | −5.181 | −45.151 | 1.00 | 18.62 | C |
| ATOM | 6080 | C | ILE B | 356 | −6.830 | −6.939 | −46.762 | 1.00 | 21.64 | C |
| ATOM | 6081 | O | ILE B | 356 | −7.844 | −7.510 | −47.174 | 1.00 | 20.49 | O |
| ATOM | 6082 | N | GLN B | 357 | −5.894 | −6.434 | −47.563 | 1.00 | 22.48 | N |
| ATOM | 6083 | CA | GLN B | 357 | −6.021 | −6.439 | −49.019 | 1.00 | 23.82 | C |
| ATOM | 6084 | CB | GLN B | 357 | −4.872 | −5.647 | −49.651 | 1.00 | 24.90 | C |
| ATOM | 6085 | CG | GLN B | 357 | −5.171 | −5.107 | −51.043 | 1.00 | 32.63 | C |
| ATOM | 6086 | CD | GLN B | 357 | −5.830 | −3.737 | −51.030 | 1.00 | 37.37 | C |
| ATOM | 6087 | OE1 | GLN B | 357 | −6.894 | −3.544 | −51.623 | 1.00 | 38.93 | O |
| ATOM | 6088 | NE2 | GLN B | 357 | −5.190 | −2.771 | −50.368 | 1.00 | 37.49 | N |
| ATOM | 6089 | C | GLN B | 357 | −6.087 | −7.861 | −49.587 | 1.00 | 22.92 | C |
| ATOM | 6090 | O | GLN B | 357 | −6.926 | −8.149 | −50.447 | 1.00 | 22.19 | O |
| ATOM | 6091 | N | GLU B | 358 | −5.215 | −8.742 | −49.096 | 1.00 | 22.71 | N |
| ATOM | 6092 | CA | GLU B | 358 | −5.226 | −10.158 | −49.482 | 1.00 | 23.94 | C |
| ATOM | 6093 | CB | GLU B | 358 | −4.014 | −10.895 | −48.911 | 1.00 | 23.41 | C |
| ATOM | 6094 | CG | GLU B | 358 | −2.687 | −10.559 | −49.569 | 1.00 | 27.78 | C |
| ATOM | 6095 | CD | GLU B | 358 | −1.557 | −11.435 | −49.055 | 1.00 | 29.55 | C |
| ATOM | 6096 | OE1 | GLU B | 358 | −1.464 | −12.607 | −49.493 | 1.00 | 36.45 | O |
| ATOM | 6097 | OE2 | GLU B | 358 | −.762 | −10.953 | −48.212 | 1.00 | 37.63 | O |
| ATOM | 6098 | C | GLU B | 358 | −6.505 | −10.854 | −49.022 | 1.00 | 22.25 | C |
| ATOM | 6099 | O | GLU B | 358 | −7.099 | −11.635 | −49.772 | 1.00 | 22.65 | O |
| ATOM | 6100 | N | ILE B | 359 | −6.916 | −10.567 | −47.787 | 1.00 | 20.01 | N |
| ATOM | 6101 | CA | ILE B | 359 | −8.148 | −11.105 | −47.217 | 1.00 | 18.24 | C |
| ATOM | 6102 | CB | ILE B | 359 | −8.275 | −10.747 | −45.709 | 1.00 | 18.22 | C |
| ATOM | 6103 | CG1 | ILE B | 359 | −7.228 | −11.528 | −44.901 | 1.00 | 18.02 | C |
| ATOM | 6104 | CD1 | ILE B | 359 | −6.881 | −10.902 | −43.552 | 1.00 | 21.55 | C |
| ATOM | 6105 | CG2 | ILE B | 359 | −9.690 | −11.032 | −45.174 | 1.00 | 16.32 | C |
| ATOM | 6106 | C | ILE B | 359 | −9.360 | −10.627 | −48.018 | 1.00 | 17.74 | C |
| ATOM | 6107 | O | ILE B | 359 | −10.266 | −11.412 | −48.304 | 1.00 | 17.28 | O |
| ATOM | 6108 | N | ALA B | 360 | −9.350 | −9.348 | −48.397 | 1.00 | 17.40 | N |
| ATOM | 6109 | CA | ALA B | 360 | −10.419 | −8.755 | −49.200 | 1.00 | 17.16 | C |
| ATOM | 6110 | CB | ALA B | 360 | −10.197 | −7.263 | −49.363 | 1.00 | 16.26 | C |
| ATOM | 6111 | C | ALA B | 360 | −10.562 | −9.430 | −50.566 | 1.00 | 18.43 | C |
| | | | | gad67.pdb | | | | | | |
| ATOM | 6112 | O | ALA B | 360 | −11.684 | −9.632 | −51.038 | 1.00 | 19.22 | O |
| ATOM | 6113 | N | ASP B | 361 | −9.431 | −9.775 | −51.188 | 1.00 | 17.79 | N |
| ATOM | 6114 | CA | ASP B | 361 | −9.425 | −10.497 | −52.464 | 1.00 | 17.90 | C |
| ATOM | 6115 | CB | ASP B | 361 | −7.993 | −10.698 | −52.976 | 1.00 | 17.83 | C |
| ATOM | 6116 | CG | ASP B | 361 | −7.380 | −9.425 | −53.543 | 1.00 | 23.20 | C |

TABLE A-continued

| | | | | | | | | | |
|---|---|---|---|---|---|---|---|---|---|
| ATOM | 6117 | OD1 | ASP B | 361 | −8.113 | −8.431 | −53.745 | 1.00 | 27.84 | O |
| ATOM | 6118 | OD2 | ASP B | 361 | −6.155 | −9.421 | −53.797 | 1.00 | 25.14 | O |
| ATOM | 6119 | C | ASP B | 361 | −10.114 | −11.856 | −52.331 | 1.00 | 17.65 | C |
| ATOM | 6120 | O | ASP B | 361 | −10.912 | −12.250 | −53.188 | 1.00 | 16.87 | O |
| ATOM | 6121 | N | ILE B | 362 | −9.789 | −12.568 | −51.256 | 1.00 | 17.23 | N |
| ATOM | 6122 | CA | ILE B | 362 | −10.423 | −13.843 | −50.965 | 1.00 | 17.66 | C |
| ATOM | 6123 | CB | ILE B | 362 | −9.670 | −14.602 | −49.847 | 1.00 | 17.48 | C |
| ATOM | 6124 | CG1 | ILE B | 362 | −8.228 | −14.889 | −50.296 | 1.00 | 15.66 | C |
| ATOM | 6125 | CD1 | ILE B | 362 | −7.300 | −15.383 | −49.195 | 1.00 | 16.93 | C |
| ATOM | 6126 | CG2 | ILE B | 362 | −10.379 | −15.904 | −49.501 | 1.00 | 16.22 | C |
| ATOM | 6127 | C | ILE B | 362 | −11.925 | −13.654 | −50.663 | 1.00 | 18.72 | C |
| ATOM | 6128 | O | ILE B | 362 | −12.749 | −14.458 | −51.097 | 1.00 | 18.93 | O |
| ATOM | 6129 | N | CYS B | 363 | −12.274 | −12.578 | −49.962 | 1.00 | 19.37 | N |
| ATOM | 6130 | CA | CYS B | 363 | −13.680 | −12.280 | −49.657 | 1.00 | 21.47 | C |
| ATOM | 6131 | CB | CYS B | 363 | −13.795 | −11.104 | −48.684 | 1.00 | 20.60 | C |
| ATOM | 6132 | SG | CYS B | 363 | −13.285 | −11.497 | −47.028 | 1.00 | 21.37 | S |
| ATOM | 6133 | C | CYS B | 363 | −14.501 | −11.980 | −50.907 | 1.00 | 22.56 | C |
| ATOM | 6134 | O | CYS B | 363 | −15.656 | −12.404 | −51.016 | 1.00 | 22.22 | O |
| ATOM | 6135 | N | GLU B | 364 | −13.901 | −11.234 | −51.832 | 1.00 | 23.72 | N |
| ATOM | 6136 | CA | GLU B | 364 | −14.545 | −10.885 | −53.092 | 1.00 | 25.57 | C |
| ATOM | 6137 | CB | GLU B | 364 | −13.687 | −9.877 | −53.864 | 1.00 | 26.05 | C |
| ATOM | 6138 | CG | GLU B | 364 | −14.404 | −9.184 | −55.018 | 1.00 | 28.13 | C |
| ATOM | 6139 | CD | GLU B | 364 | −13.477 | −8.305 | −55.845 | 1.00 | 28.70 | C |
| ATOM | 6140 | OE1 | GLU B | 364 | −13.935 | −7.243 | −56.315 | 1.00 | 33.63 | O |
| ATOM | 6141 | OE2 | GLU B | 364 | −12.292 | −8.669 | −56.027 | 1.00 | 34.77 | O |
| ATOM | 6142 | C | GLU B | 364 | −14.783 | −12.136 | −53.935 | 1.00 | 25.01 | C |
| ATOM | 6143 | O | GLU B | 364 | −15.850 | −12.301 | −54.527 | 1.00 | 25.81 | O |
| ATOM | 6144 | N | LYS B | 365 | −13.785 | −13.013 | −53.966 | 1.00 | 24.63 | N |
| ATOM | 6145 | CA | LYS B | 365 | −13.858 | −14.268 | −54.704 | 1.00 | 24.52 | C |
| ATOM | 6146 | CB | LYS B | 365 | −12.505 | −14.989 | −54.654 | 1.00 | 23.37 | C |
| ATOM | 6147 | CG | LYS B | 365 | −12.409 | −16.243 | −55.515 | 1.00 | 25.52 | C |
| ATOM | 6148 | CD | LYS B | 365 | −11.023 | −16.856 | −55.403 | 1.00 | 27.94 | C |
| ATOM | 6149 | CE | LYS B | 365 | −10.943 | −18.204 | −56.093 | 1.00 | 32.77 | C |
| ATOM | 6150 | NZ | LYS B | 365 | −9.632 | −18.870 | −55.825 | 1.00 | 34.59 | N |
| ATOM | 6151 | C | LYS B | 365 | −14.972 | −15.179 | −54.182 | 1.00 | 24.22 | C |
| ATOM | 6152 | O | LYS B | 365 | −15.717 | −15.751 | −54.971 | 1.00 | 24.60 | O |
| ATOM | 6153 | N | TYR B | 366 | −15.083 | −15.309 | −52.862 | 1.00 | 23.81 | N |
| ATOM | 6154 | CA | TYR B | 366 | −16.016 | −16.265 | −52.264 | 1.00 | 23.92 | C |
| ATOM | 6155 | CB | TYR B | 366 | −15.320 | −17.080 | −51.165 | 1.00 | 23.19 | C |
| ATOM | 6156 | CG | TYR B | 366 | −14.241 | −18.003 | −51.683 | 1.00 | 23.55 | C |
| ATOM | 6157 | CD1 | TYR B | 366 | −14.564 | −19.232 | −52.255 | 1.00 | 22.03 | C |
| ATOM | 6158 | CE1 | TYR B | 366 | −13.576 | −20.077 | −52.737 | 1.00 | 22.68 | C |
| ATOM | 6159 | CZ | TYR B | 366 | −12.248 | −19.697 | −52.645 | 1.00 | 24.32 | C |
| ATOM | 6160 | OH | TYR B | 366 | −11.261 | −20.527 | −53.122 | 1.00 | 22.78 | O |
| ATOM | 6161 | CE2 | TYR B | 366 | −11.903 | −18.484 | −52.079 | 1.00 | 22.44 | C |
| ATOM | 6162 | CD2 | TYR B | 366 | −12.898 | −17.646 | −51.604 | 1.00 | 22.14 | C |
| ATOM | 6163 | C | TYR B | 366 | −17.314 | −15.642 | −51.737 | 1.00 | 24.47 | C |
| ATOM | 6164 | O | TYR B | 366 | −18.154 | −16.345 | −51.175 | 1.00 | 25.39 | O |
| ATOM | 6165 | N | ASN B | 367 | −17.477 | −14.336 | −51.942 | 1.00 | 25.05 | N |
| ATOM | 6166 | CA | ASN B | 367 | −18.623 | −13.569 | −51.436 | 1.00 | 26.03 | C |
| ATOM | 6167 | CB | ASN B | 367 | −19.928 | −13.935 | −52.164 | 1.00 | 27.24 | C |
| ATOM | 6168 | CG | ASN B | 367 | −21.058 | −12.933 | −51.903 | 1.00 | 30.79 | C |
| ATOM | 6169 | OD1 | ASN B | 367 | −20.836 | −11.834 | −51.387 | 1.00 | 32.30 | O |
| ATOM | 6170 | ND2 | ASN 8 | 367 | −22.278 | −13.318 | −52.264 | 1.00 | 32.55 | N |
| ATOM | 6171 | C | ASN B | 367 | −18.785 | −13.665 | −49.914 | 1.00 | 25.81 | C |
| ATOM | 6172 | O | ASN B | 367 | −19.805 | −14.146 | −49.402 | 1.00 | 26.33 | O |
| ATOM | 6173 | N | LEU B | 368 | −17.762 | −13.201 | −49.202 | 1.00 | 24.34 | N |
| ATOM | 6174 | CA | LEU B | 368 | −17.797 | −13.146 | −47.748 | 1.00 | 22.90 | C |
| ATOM | 6175 | CB | LEU B | 368 | −16.583 | −13.856 | −47.140 | 1.00 | 22.80 | C |
| ATOM | 6176 | CG | LEU B | 368 | −16.695 | −15.337 | −46.766 | 1.00 | 25.91 | C |
| ATOM | 6177 | CD1 | LEU B | 368 | −16.840 | −16.225 | −47.995 | 1.00 | 23.84 | C |
| ATOM | 6178 | CD2 | LEU B | 368 | −15.494 | −15.775 | −45.944 | 1.00 | 24.05 | C |
| ATOM | 6179 | C | LEU B | 368 | −17.842 | −11.705 | −47.278 | 1.00 | 21.04 | C |
| | | | | | gad67.pdb | | | | | |
| ATOM | 6180 | O | LEU B | 368 | −17.217 | −10.827 | −47.875 | 1.00 | 20.89 | O |
| ATOM | 6181 | N | TRP B | 369 | −18.593 | −11.471 | −46.207 | 1.00 | 18.79 | N |
| ATOM | 6182 | CA | TRP B | 369 | −18.612 | −10.177 | −45.543 | 1.00 | 16.49 | C |
| ATOM | 6183 | CB | TRP B | 369 | −19.734 | −10.144 | −44.511 | 1.00 | 16.05 | C |
| ATOM | 6184 | CG | TRP B | 369 | −19.874 | −8.856 | −43.748 | 1.00 | 13.94 | C |
| ATOM | 6185 | CD1 | TRP B | 369 | −19.049 | −8.388 | −42.760 | 1.00 | 12.97 | C |
| ATOM | 6186 | NE1 | TRP B | 369 | −19.520 | −7.188 | −42.277 | 1.00 | 14.55 | N |
| ATOM | 6187 | CE2 | TRP B | 369 | −20.676 | −6.867 | −42.941 | 1.00 | 13.63 | C |
| ATOM | 6188 | CD2 | TRP B | 369 | −20.928 | −7.897 | −43.880 | 1.00 | 13.59 | C |
| ATOM | 6189 | CE3 | TRP B | 369 | −22.062 | −7.806 | −44.699 | 1.00 | 11.98 | C |
| ATOM | 6190 | CZ3 | TRP B | 369 | −22.895 | −6.702 | −44.566 | 1.00 | 14.00 | C |
| ATOM | 6191 | CH2 | TRP B | 369 | −22.612 | −5.687 | −43.628 | 1.00 | 14.35 | C |
| ATOM | 6192 | CZ2 | TRP B | 369 | −21.511 | −5.752 | −42.810 | 1.00 | 14.34 | C |
| ATOM | 6193 | C | TRP B | 369 | −17.265 | −9.966 | −44.863 | 1.00 | 15.67 | C |
| ATOM | 6194 | O | TRP B | 369 | −16.789 | −10.827 | −44.112 | 1.00 | 16.05 | O |
| ATOM | 6195 | N | LEU B | 370 | −16.647 | −8.824 | −45.140 | 1.00 | 14.06 | N |

TABLE A-continued

| | | | | | | | | | | |
|---|---|---|---|---|---|---|---|---|---|---|
| ATOM | 6196 | CA | LEU B | 370 | −15.357 | −8.504 | −44.550 | 1.00 | 12.99 | C |
| ATOM | 6197 | CB | LEU B | 370 | −14.366 | −7.989 | −45.608 | 1.00 | 12.08 | C |
| ATOM | 6198 | CG | LEU B | 370 | −13.060 | −7.365 | −45.088 | 1.00 | 10.63 | C |
| ATOM | 6199 | CD1 | LEU B | 370 | −12.283 | −8.315 | −44.163 | 1.00 | 7.06 | C |
| ATOM | 6200 | CD2 | LEU B | 370 | −12.172 | −6.895 | −46.238 | 1.00 | 12.68 | C |
| ATOM | 6201 | C | LEU B | 370 | −15.523 | −7.488 | −43.438 | 1.00 | 12.83 | C |
| ATOM | 6202 | O | LEU B | 370 | −15.919 | −6.348 | −43.678 | 1.00 | 13.26 | O |
| ATOM | 6203 | N | HIS B | 371 | −15.224 | −7.913 | −42.218 | 1.00 | 13.63 | N |
| ATOM | 6204 | CA | HIS B | 371 | −15.233 | −7.006 | −41.084 | 1.00 | 13.62 | C |
| ATOM | 6205 | CB | HIS B | 371 | −16.073 | −7.556 | −39.927 | 1.00 | 13.70 | C |
| ATOM | 6206 | CG | HIS B | 371 | −15.960 | −6.742 | −38.676 | 1.00 | 12.14 | C |
| ATOM | 6207 | ND1 | HIS B | 371 | −16.549 | −5.504 | −38.540 | 1.00 | 12.23 | N |
| ATOM | 6208 | CE1 | HIS B | 371 | −16.264 | −5.011 | −37.348 | 1.00 | 9.55 | C |
| ATOM | 6209 | NE2 | HIS B | 371 | −15.502 | −5.881 | −36.709 | 1.00 | 13.48 | N |
| ATOM | 6210 | CD2 | HIS B | 371 | −15.290 | −6.969 | −37.521 | 1.00 | 11.49 | C |
| ATOM | 6211 | C | HIS B | 371 | −13.809 | −6.740 | −40.622 | 1.00 | 13.72 | C |
| ATOM | 6212 | O | HIS B | 371 | −12.999 | −7.656 | −40.509 | 1.00 | 12.30 | O |
| ATOM | 6213 | N | VAL B | 372 | −13.511 | −5.473 | −40.362 | 1.00 | 14.55 | N |
| ATOM | 6214 | CA | VAL B | 372 | −12.206 | −5.108 | −39.842 | 1.00 | 13.83 | C |
| ATOM | 6215 | CB | VAL B | 372 | −11.478 | −4.075 | −40.746 | 1.00 | 13.41 | C |
| ATOM | 6216 | CG1 | VAL B | 372 | −10.221 | −3.559 | −40.068 | 1.00 | 12.49 | C |
| ATOM | 6217 | CG2 | VAL B | 372 | −11.123 | −4.704 | −42.091 | 1.00 | 11.48 | C |
| ATOM | 6218 | C | VAL B | 372 | −12.344 | −4.620 | −38.402 | 1.00 | 14.00 | C |
| ATOM | 6219 | O | VAL B | 372 | −12.996 | −3.613 | −38.134 | 1.00 | 13.66 | O |
| ATOM | 6220 | N | ASP B | 373 | −11.741 | −5.368 | −37.481 | 1.00 | 14.37 | N |
| ATOM | 6221 | CA | ASP B | 373 | −11.687 | −4.978 | −36.081 | 1.00 | 14.61 | C |
| ATOM | 6222 | CB | ASP B | 373 | −11.596 | −6.213 | −35.175 | 1.00 | 15.24 | C |
| ATOM | 6223 | CG | ASP B | 373 | −11.732 | −5.875 | −33.693 | 1.00 | 15.46 | C |
| ATOM | 6224 | OD1 | ASP B | 373 | −11.772 | −4.680 | −33.335 | 1.00 | 14.30 | O |
| ATOM | 6225 | OD2 | ASP B | 373 | −11.792 | −6.814 | −32.877 | 1.00 | 17.40 | O |
| ATOM | 6226 | C | ASP B | 373 | −10.507 | −4.044 | −35.841 | 1.00 | 14.19 | C |
| ATOM | 6227 | O | ASP B | 373 | −9.405 | −4.483 | −35.514 | 1.00 | 13.12 | O |
| ATOM | 6228 | N | ALA B | 374 | −10.760 | −2.750 | −36.002 | 1.00 | 14.94 | N |
| ATOM | 6229 | CA | ALA B | 374 | −9.765 | −1.710 | −35.759 | 1.00 | 14.94 | C |
| ATOM | 6230 | CB | ALA B | 374 | −9.770 | −.700 | −36.911 | 1.00 | 13.69 | C |
| ATOM | 6231 | C | ALA B | 374 | −10.011 | −1.004 | −34.419 | 1.00 | 15.26 | C |
| ATOM | 6232 | O | ALA B | 374 | −9.695 | .178 | −34.264 | 1.00 | 14.16 | O |
| ATOM | 6233 | N | ALA B | 375 | −10.571 | −1.729 | −33.451 | 1.00 | 15.95 | N |
| ATOM | 6234 | CA | ALA B | 375 | −10.788 | −1.184 | −32.105 | 1.00 | 16.37 | C |
| ATOM | 6235 | CB | ALA B | 375 | −11.325 | −2.265 | −31.165 | 1.00 | 15.67 | C |
| ATOM | 6236 | C | ALA B | 375 | −9.509 | −.554 | −31.538 | 1.00 | 16.72 | C |
| ATOM | 6237 | O | ALA B | 375 | −9.542 | .552 | −31.003 | 1.00 | 17.48 | O |
| ATOM | 6238 | N | TRP B | 376 | −8.389 | −1.260 | −31.691 | 1.00 | 16.83 | N |
| ATOM | 6239 | CA | TRP B | 376 | −7.085 | −.814 | −31.202 | 1.00 | 16.45 | C |
| ATOM | 6240 | CB | TRP B | 376 | −6.328 | −2.018 | −30.615 | 1.00 | 15.18 | C |
| ATOM | 6241 | CG | TRP B | 376 | −4.890 | −1.803 | −30.167 | 1.00 | 16.16 | C |
| ATOM | 6242 | CD1 | TRP B | 376 | −3.823 | −2.606 | −30.463 | 1.00 | 12.81 | C |
| ATOM | 6243 | NE1 | TRP B | 376 | −2.684 | −2.121 | −29.877 | 1.00 | 13.60 | N |
| ATOM | 6244 | CE2 | TRP B | 376 | −2.988 | −.984 | −29.173 | 1.00 | 15.63 | C |
| ATOM | 6245 | CD2 | TRP B | 376 | −4.373 | −.748 | −29.329 | 1.00 | 14.89 | C |
| ATOM | 6246 | CE3 | TRP B | 376 | −4.945 | .368 | −28.696 | 1.00 | 14.14 | C |
| ATOM | 6247 | CZ3 | TRP B | 376 | −4.122 gad67.pdb | 1.202 | −27.936 | 1.00 | 11.92 | C |
| ATOM | 6248 | CH2 | TRP B | 376 | −2.746 | .941 | −27.809 | 1.00 | 14.88 | C |
| ATOM | 6249 | CZ2 | TRP B | 376 | −2.162 | −.141 | −28.416 | 1.00 | 11.96 | C |
| ATOM | 6250 | C | TRP B | 376 | −6.272 | −.096 | −32.295 | 1.00 | 16.85 | C |
| ATOM | 6251 | O | TRP B | 376 | −5.698 | .964 | −32.047 | 1.00 | 17.80 | O |
| ATOM | 6252 | N | GLY B | 377 | −6.244 | −.659 | −33.500 | 1.00 | 17.23 | N |
| ATOM | 6253 | CA | GLY B | 377 | −5.445 | −.099 | −34.593 | 1.00 | 17.63 | C |
| ATOM | 6254 | C | GLY B | 377 | −6.066 | 1.067 | −35.340 | 1.00 | 17.89 | C |
| ATOM | 6255 | O | GLY B | 377 | −5.390 | 1.717 | −36.141 | 1.00 | 18.10 | O |
| ATOM | 6256 | N | GLY B | 378 | −7.348 | 1.338 | −35.081 | 1.00 | 17.46 | N |
| ATOM | 6257 | CA | GLY B | 378 | −8.089 | 2.402 | −35.766 | 1.00 | 17.35 | C |
| ATOM | 6258 | C | GLY B | 378 | −7.548 | 3.807 | −35.554 | 1.00 | 18.66 | C |
| ATOM | 6259 | O | GLY B | 378 | −7.728 | 4.684 | −36.401 | 1.00 | 17.95 | O |
| ATOM | 6260 | N | GLY B | 379 | −6.895 | 4.026 | −34.414 | 1.00 | 19.32 | N |
| ATOM | 6261 | CA | GLY B | 379 | −6.259 | 5.307 | −34.127 | 1.00 | 20.11 | C |
| ATOM | 6262 | C | GLY B | 379 | −5.215 | 5.680 | −35.166 | 1.00 | 20.53 | C |
| ATOM | 6263 | O | GLY B | 379 | −5.004 | 6.864 | −35.441 | 1.00 | 20.98 | O |
| ATOM | 6264 | N | LEU B | 380 | −4.579 | 4.668 | −35.755 | 1.00 | 20.09 | N |
| ATOM | 6265 | CA | LEU B | 380 | −3.509 | 4.869 | −36.735 | 1.00 | 20.28 | C |
| ATOM | 6266 | CB | LEU B | 380 | −2.707 | 3.578 | −36.945 | 1.00 | 20.32 | C |
| ATOM | 6267 | CG | LEU B | 380 | −1.520 | 3.334 | −36.006 | 1.00 | 20.81 | C |
| ATOM | 6268 | CD1 | LEU B | 380 | −1.949 | 3.110 | −34.560 | 1.00 | 18.99 | C |
| ATOM | 6269 | CD2 | LEU B | 380 | −.684 | 2.161 | −36.493 | 1.00 | 19.53 | C |
| ATOM | 6270 | C | LEU B | 380 | −4.006 | 5.423 | −38.070 | 1.00 | 20.71 | C |
| ATOM | 6271 | O | LEU B | 380 | −3.209 | 5.906 | −38.881 | 1.00 | 21.43 | O |
| ATOM | 6272 | N | LEU B | 381 | −5.319 | 5.354 | −38.290 | 1.00 | 20.15 | N |
| ATOM | 6273 | CA | LEU B | 381 | −5.948 | 5.966 | −39.459 | 1.00 | 20.22 | C |
| ATOM | 6274 | CB | LEU B | 381 | −7.423 | 5.569 | −39.552 | 1.00 | 19.31 | C |

TABLE A-continued

| | | | | | | | | | |
|---|---|---|---|---|---|---|---|---|---|
| ATOM | 6275 | CG | LEU B | 381 | −7.808 | 4.129 | −39.919 | 1.00 | 19.64 | C |
| ATOM | 6276 | CD1 | LEU B | 381 | −9.287 | 3.863 | −39.612 | 1.00 | 19.62 | C |
| ATOM | 6277 | CD2 | LEU B | 381 | −7.505 | 3.807 | −41.377 | 1.00 | 19.22 | C |
| ATOM | 6278 | C | LEU B | 381 | −5.809 | 7.492 | −39.436 | 1.00 | 21.00 | C |
| ATOM | 6279 | O | LEU B | 381 | −5.848 | 8.137 | −40.485 | 1.00 | 21.48 | O |
| ATOM | 6280 | N | MET B | 382 | −5.638 | 8.054 | −38.239 | 1.00 | 21.61 | N |
| ATOM | 6281 | CA | MET B | 382 | −5.449 | 9.500 | −38.046 | 1.00 | 21.91 | C |
| ATOM | 6282 | CB | MET B | 382 | −5.732 | 9.891 | −36.589 | 1.00 | 21.78 | C |
| ATOM | 6283 | CG | MET B | 382 | −7.093 | 9.455 | −36.063 | 1.00 | 22.04 | C |
| ATOM | 6284 | SD | MET B | 382 | −8.435 | 10.177 | −37.002 | 1.00 | 20.77 | S |
| ATOM | 6285 | CE | MET B | 382 | −8.446 | 11.858 | −36.390 | 1.00 | 19.67 | C |
| ATOM | 6286 | C | MET B | 382 | −4.044 | 9.983 | −38.424 | 1.00 | 22.17 | C |
| ATOM | 6287 | O | MET B | 382 | −3.799 | 11.183 | −38.510 | 1.00 | 22.03 | O |
| ATOM | 6288 | N | SER B | 383 | −3.127 | 9.046 | −38.635 | 1.00 | 22.77 | N |
| ATOM | 6289 | CA | SER B | 383 | −1.744 | 9.378 | −38.950 | 1.00 | 23.86 | C |
| ATOM | 6290 | CB | SER B | 383 | −.793 | 8.605 | −38.033 | 1.00 | 23.78 | C |
| ATOM | 6291 | OG | SER B | 383 | .533 | 8.628 | −38.537 | 1.00 | 22.49 | O |
| ATOM | 6292 | C | SER B | 383 | −1.410 | 9.091 | −40.408 | 1.00 | 24.36 | C |
| ATOM | 6293 | O | SER B | 383 | −1.530 | 7.953 | −40.865 | 1.00 | 24.70 | O |
| ATOM | 6294 | N | ARG B | 384 | −.984 | 10.130 | −41.125 | 1.00 | 25.19 | N |
| ATOM | 6295 | CA | ARG B | 384 | −.497 | 9.995 | −42.504 | 1.00 | 25.98 | C |
| ATOM | 6296 | CB | ARG B | 384 | −.118 | 11.362 | −43.078 | 1.00 | 26.73 | C |
| ATOM | 6297 | CG | ARG B | 384 | −1.271 | 12.095 | −43.760 | 1.00 | 30.86 | C |
| ATOM | 6298 | CD | ARG B | 384 | −1.362 | 13.559 | −43.331 | 1.00 | 36.57 | C |
| ATOM | 6299 | NE | ARG B | 384 | −.114 | 14.292 | −43.530 | 1.00 | 42.31 | N |
| ATOM | 6300 | CZ | ARG B | 384 | .189 | 15.447 | −42.941 | 1.00 | 45.17 | C |
| ATOM | 6301 | NH1 | ARG B | 384 | −.658 | 16.021 | −42.093 | 1.00 | 43.39 | N |
| ATOM | 6302 | NH2 | ARG B | 384 | 1.354 | 16.027 | −43.196 | 1.00 | 47.43 | N |
| ATOM | 6303 | C | ARG B | 384 | .689 | 9.035 | −42.604 | 1.00 | 25.43 | C |
| ATOM | 6304 | O | ARG B | 384 | .790 | 8.271 | −43.560 | 1.00 | 25.43 | O |
| ATOM | 6305 | N | LYS B | 385 | 1.567 | 9.075 | −41.603 | 1.00 | 25.60 | N |
| ATOM | 6306 | CA | LYS B | 385 | 2.751 | 8.220 | −41.544 | 1.00 | 26.40 | C |
| ATOM | 6307 | CB | LYS B | 385 | 3.701 | 8.737 | −40.453 | 1.00 | 26.46 | C |
| ATOM | 6308 | CG | LYS B | 385 | 4.794 | 7.775 | −40.014 | 1.00 | 28.85 | C |
| ATOM | 6309 | CD | LYS B | 385 | 5.537 | 8.308 | −38.796 | 1.00 | 29.64 | C |
| ATOM | 6310 | CE | LYS B | 385 | 6.981 | 8.666 | −39.119 | 1.00 | 36.69 | C |
| ATOM | 6311 | NZ | LYS B | 385 | 7.847 | 7.453 | −39.149 | 1.00 | 36.39 | N |
| ATOM | 6312 | C | LYS B | 385 | 2.405 | 6.739 | −41.327 | 1.00 | 26.02 | C |
| ATOM | 6313 | O | LYS B | 385 | 3.065 | 5.852 | −41.886 | 1.00 | 27.00 | O |
| ATOM | 6314 | N | HIS B | 386 | 1.363 | 6.475 | −40.536 | 1.00 | 24.65 | N |
| ATOM | 6315 | CA | HIS B | 386 | 1.060 | 5.107 | −40.097 | 1.00 | 23.17 | C |
| | | | | | gad67.pdb | | | | | |
| ATOM | 6316 | CB | HIS B | 386 | 1.005 | 5.045 | −38.569 | 1.00 | 22.54 | C |
| ATOM | 6317 | CG | HIS B | 386 | 2.335 | 5.228 | −37.907 | 1.00 | 20.90 | C |
| ATOM | 6318 | ND1 | HIS B | 386 | 3.254 | 4.208 | −37.793 | 1.00 | 20.33 | N |
| ATOM | 6319 | CE1 | HIS B | 386 | 4.326 | 4.652 | −37.160 | 1.00 | 23.43 | C |
| ATOM | 6320 | NE2 | HIS B | 386 | 4.133 | 5.923 | −36.856 | 1.00 | 23.65 | N |
| ATOM | 6321 | CD2 | HIS B | 386 | 2.895 | 6.308 | −37.312 | 1.00 | 22.04 | C |
| ATOM | 6322 | C | HIS B | 386 | −.204 | 4.459 | −40.682 | 1.00 | 23.04 | C |
| ATOM | 6323 | O | HIS B | 386 | −.394 | 3.250 | −40.528 | 1.00 | 23.57 | O |
| ATOM | 6324 | N | ARG B | 387 | −1.055 | 5.238 | −41.353 | 1.00 | 22.82 | N |
| ATOM | 6325 | CA | ARG B | 387 | −2.352 | 4.716 | −41.826 | 1.00 | 23.05 | C |
| ATOM | 6326 | CB | ARG B | 387 | −3.275 | 5.832 | −42.348 | 1.00 | 23.57 | C |
| ATOM | 6327 | CG | ARG B | 387 | −2.866 | 6.456 | −43.673 | 1.00 | 25.34 | C |
| ATOM | 6328 | CD | ARG B | 387 | −4.043 | 7.152 | −44.359 | 1.00 | 28.85 | C |
| ATOM | 6329 | NE | ARG B | 387 | −5.057 | 6.201 | −44.824 | 1.00 | 36.56 | N |
| ATOM | 6330 | CZ | ARG B | 387 | −6.361 | 6.274 | −44.552 | 1.00 | 37.62 | C |
| ATOM | 6331 | NH1 | ARG B | 387 | −6.850 | 7.270 | −43.821 | 1.00 | 35.13 | N |
| ATOM | 6332 | NH2 | ARG B | 387 | −7.186 | 5.347 | −45.025 | 1.00 | 38.85 | N |
| ATOM | 6333 | C | ARG B | 387 | −2.258 | 3.563 | −42.838 | 1.00 | 22.64 | C |
| ATOM | 6334 | O | ARG B | 387 | −3.220 | 2.808 | −43.008 | 1.00 | 22.33 | O |
| ATOM | 6335 | N | HIS B | 388 | −1.100 | 3.429 | −43.486 | 1.00 | 21.60 | N |
| ATOM | 6336 | CA | HIS B | 388 | −.871 | 2.387 | −44.485 | 1.00 | 20.69 | C |
| ATOM | 6337 | CB | HIS B | 388 | .499 | 2.567 | −45.150 | 1.00 | 20.67 | C |
| ATOM | 6338 | CG | HIS B | 388 | 1.654 | 2.341 | −44.223 | 1.00 | 18.99 | C |
| ATOM | 6339 | ND1 | HIS B | 388 | 2.269 | 1.115 | −44.086 | 1.00 | 20.28 | N |
| ATOM | 6340 | CE1 | HIS B | 388 | 3.246 | 1.213 | −43.200 | 1.00 | 18.73 | C |
| ATOM | 6341 | NE2 | HIS B | 388 | 3.280 | 2.456 | −42.754 | 1.00 | 16.55 | N |
| ATOM | 6342 | CD2 | HIS B | 388 | 2.294 | 3.182 | −43.376 | 1.00 | 16.89 | C |
| ATOM | 6343 | C | HIS B | 388 | −.981 | .978 | −43.904 | 1.00 | 20.74 | C |
| ATOM | 6344 | O | HIS B | 388 | −1.208 | .013 | −44.639 | 1.00 | 21.20 | O |
| ATOM | 6345 | N | LYS B | 389 | −.810 | .860 | −42.589 | 1.00 | 21.00 | N |
| ATOM | 6346 | CA | LYS B | 389 | −.949 | −.432 | −41.909 | 1.00 | 20.65 | C |
| ATOM | 6347 | CB | LYS B | 389 | −.497 | −.322 | −40.450 | 1.00 | 21.26 | C |
| ATOM | 6348 | CG | LYS B | 389 | 1.023 | −.241 | −40.303 | 1.00 | 22.48 | C |
| ATOM | 6349 | CD | LYS B | 389 | 1.447 | .350 | −38.971 | 1.00 | 25.23 | C |
| ATOM | 6350 | CE | LYS B | 389 | 2.962 | .506 | −38.900 | 1.00 | 26.74 | C |
| ATOM | 6351 | NZ | LYS B | 389 | 3.415 | 1.131 | −37.623 | 1.00 | 22.48 | N |
| ATOM | 6352 | C | LYS B | 389 | −2.377 | −.980 | −42.020 | 1.00 | 19.92 | C |
| ATOM | 6353 | O | LYS B | 389 | −2.607 | −2.176 | −41.833 | 1.00 | 19.60 | O |

TABLE A-continued

| | | | | | | | | | |
|---|---|---|---|---|---|---|---|---|---|
| ATOM | 6354 | N | LEU B | 390 | −3.318 | −.097 | −42.357 | 1.00 | 19.36 | N |
| ATOM | 6355 | CA | LEU B | 390 | −4.721 | −.470 | −42.536 | 1.00 | 19.32 | C |
| ATOM | 6356 | CB | LEU B | 390 | −5.636 | .424 | −41.678 | 1.00 | 18.76 | C |
| ATOM | 6357 | CG | LEU B | 390 | −5.497 | .377 | −40.147 | 1.00 | 18.28 | C |
| ATOM | 6358 | CD1 | LEU B | 390 | −4.540 | 1.455 | −39.651 | 1.00 | 10.43 | C |
| ATOM | 6359 | CD2 | LEU B | 390 | −6.852 | .514 | −39.458 | 1.00 | 11.94 | C |
| ATOM | 6360 | C | LEU B | 390 | −5.172 | −.456 | −44.011 | 1.00 | 20.13 | C |
| ATOM | 6361 | O | LEU B | 390 | −6.370 | −.503 | −44.287 | 1.00 | 20.22 | O |
| ATOM | 6362 | N | ASN B | 391 | −4.218 | −.393 | −44.947 | 1.00 | 20.68 | N |
| ATOM | 6363 | CA | ASN B | 391 | −4.518 | −.472 | −46.385 | 1.00 | 20.71 | C |
| ATOM | 6364 | CB | ASN B | 391 | −3.227 | −.560 | −47.216 | 1.00 | 22.24 | C |
| ATOM | 6365 | CG | ASN B | 391 | −2.611 | .799 | −47.504 | 1.00 | 25.41 | C |
| ATOM | 6366 | OD1 | ASN B | 391 | −3.135 | 1.841 | −47.100 | 1.00 | 28.08 | O |
| ATOM | 6367 | ND2 | ASN B | 391 | −1.488 | .791 | −48.215 | 1.00 | 28.28 | N |
| ATOM | 6368 | C | ASN B | 391 | −5.431 | −1.651 | −46.739 | 1.00 | 18.92 | C |
| ATOM | 6369 | O | ASN B | 391 | −5.165 | −2.791 | −46.360 | 1.00 | 18.24 | O |
| ATOM | 6370 | N | GLY B | 392 | −6.501 | −1.362 | −47.470 | 1.00 | 18.69 | N |
| ATOM | 6371 | CA | GLY B | 392 | −7.496 | −2.370 | −47.816 | 1.00 | 18.55 | C |
| ATOM | 6372 | C | GLY B | 392 | −8.785 | −2.202 | −47.034 | 1.00 | 18.89 | C |
| ATOM | 6373 | O | GLY B | 392 | −9.827 | −2.739 | −47.428 | 1.00 | 19.78 | O |
| ATOM | 6374 | N | ILE B | 393 | −8.717 | −1.458 | −45.929 | 1.00 | 17.94 | N |
| ATOM | 6375 | CA | ILE B | 393 | −9.875 | −1.233 | −45.057 | 1.00 | 17.43 | C |
| ATOM | 6376 | CB | ILE B | 393 | −9.505 | −.391 | −43.796 | 1.00 | 17.67 | C |
| ATOM | 6377 | CG1 | ILE B | 393 | −10.646 | −.434 | −42.763 | 1.00 | 17.76 | C |
| ATOM | 6378 | CD1 | ILE B | 393 | −10.285 | .068 | −41.366 | 1.00 | 15.66 | C |
| ATOM | 6379 | CG2 | ILE B | 393 | −9.102 | 1.052 | −44.183 | 1.00 | 14.75 | C |
| ATOM | 6380 | C | ILE B | 393 | −11.044 | −.597 | −45.809 | 1.00 | 18.24 | C |
| ATOM | 6381 | O | ILE B | 393 | −12.202 | −.770 | −45.419 | 1.00 | 18.67 | O |
| ATOM | 6382 | N | GLU B | 394 | −10.733 | .117 | −46.894 | 1.00 | 17.89 | N |
| ATOM | 6383 | CA | GLU B | 394 | −11.739 | .779 | −47.721 | 1.00 | 18.27 | C |
| | | | | | gad67.pdb | | | | | |
| ATOM | 6384 | CB | GLU B | 394 | −11.078 | 1.753 | −48.710 | 1.00 | 19.59 | C |
| ATOM | 6385 | CG | GLU B | 394 | −10.416 | 1.112 | −49.934 | 1.00 | 21.82 | C |
| ATOM | 6386 | CD | GLU B | 394 | −9.002 | .606 | −49.681 | 1.00 | 29.86 | C |
| ATOM | 6387 | OE1 | GLU B | 394 | −8.423 | .013 | −50.616 | 1.00 | 35.01 | O |
| ATOM | 6388 | OE2 | GLU B | 394 | −8.462 | .793 | −48.567 | 1.00 | 29.52 | O |
| ATOM | 6389 | C | GLU B | 394 | −12.617 | −.235 | −48.454 | 1.00 | 18.05 | C |
| ATOM | 6390 | O | GLU B | 394 | −13.656 | .120 | −49.015 | 1.00 | 18.64 | O |
| ATOM | 6391 | N | ARG B | 395 | −12.185 | −1.494 | −48.438 | 1.00 | 17.34 | N |
| ATOM | 6392 | CA | ARG B | 395 | −12.927 | −2.596 | −49.050 | 1.00 | 17.30 | C |
| ATOM | 6393 | CB | ARG B | 395 | −11.975 | −3.516 | −49.822 | 1.00 | 16.97 | C |
| ATOM | 6394 | CG | ARG B | 395 | −11.336 | −2.857 | −51.038 | 1.00 | 19.46 | C |
| ATOM | 6395 | CD | ARG B | 395 | −11.043 | −3.888 | −52.111 | 1.00 | 22.51 | C |
| ATOM | 6396 | NE | ARG B | 395 | −9.728 | −4.498 | −51.948 | 1.00 | 20.68 | N |
| ATOM | 6397 | CZ | ARG B | 395 | −9.361 | −5.662 | −52.480 | 1.00 | 18.69 | C |
| ATOM | 6398 | NH1 | ARG B | 395 | −10.215 | −6.380 | −53.198 | 1.00 | 16.00 | N |
| ATOM | 6399 | NH2 | ARG B | 395 | −8.135 | −6.117 | −52.275 | 1.00 | 20.08 | N |
| ATOM | 6400 | C | ARG B | 395 | −13.736 | −3.402 | −48.027 | 1.00 | 16.75 | C |
| ATOM | 6401 | O | ARG B | 395 | −14.439 | −4.349 | −48.389 | 1.00 | 16.78 | O |
| ATOM | 6402 | N | ALA B | 396 | −13.629 | −3.031 | −46.755 | 1.00 | 15.79 | N |
| ATOM | 6403 | CA | ALA B | 396 | −14.397 | −3.686 | −45.694 | 1.00 | 16.32 | C |
| ATOM | 6404 | CB | ALA B | 396 | −13.884 | −3.272 | −44.321 | 1.00 | 14.85 | C |
| ATOM | 6405 | C | ALA B | 396 | −15.882 | −3.380 | −45.816 | 1.00 | 16.21 | C |
| ATOM | 6406 | O | ALA B | 396 | −16.267 | −2.317 | −46.295 | 1.00 | 17.44 | O |
| ATOM | 6407 | N | ASN B | 397 | −16.711 | −4.326 | −45.396 | 1.00 | 16.35 | N |
| ATOM | 6408 | CA | ASN B | 397 | −18.148 | −4.101 | −45.313 | 1.00 | 16.42 | C |
| ATOM | 6409 | CB | ASN B | 397 | −18.901 | −5.419 | −45.516 | 1.00 | 16.78 | C |
| ATOM | 6410 | CG | ASN B | 397 | −18.640 | −6.033 | −46.886 | 1.00 | 15.82 | C |
| ATOM | 6411 | OD1 | ASN B | 397 | −17.870 | −6.981 | −47.017 | 1.00 | 16.82 | O |
| ATOM | 6412 | ND2 | ASN B | 397 | −19.260 | −5.470 | −47.915 | 1.00 | 14.45 | N |
| ATOM | 6413 | C | ASN B | 397 | −18.537 | −3.447 | −43.986 | 1.00 | 16.07 | C |
| ATOM | 6414 | O | ASN B | 397 | −19.580 | −2.794 | −43.885 | 1.00 | 16.48 | O |
| ATOM | 6415 | N | SER B | 398 | −17.692 | −3.634 | −42.974 | 1.00 | 15.63 | N |
| ATOM | 6416 | CA | SER B | 398 | −17.875 | −3.005 | −41.666 | 1.00 | 15.88 | C |
| ATOM | 6417 | CB | SER B | 398 | −18.841 | −3.812 | −40.781 | 1.00 | 15.56 | C |
| ATOM | 6418 | OG | SER B | 398 | −18.329 | −5.100 | −40.483 | 1.00 | 16.69 | O |
| ATOM | 6419 | C | SER B | 398 | −16.540 | −2.815 | −40.957 | 1.00 | 15.70 | C |
| ATOM | 6420 | O | SER B | 398 | −15.569 | −3.519 | −41.244 | 1.00 | 15.28 | O |
| ATOM | 6421 | N | VAL B | 399 | −16.506 | −1.852 | −40.036 | 1.00 | 16.19 | N |
| ATOM | 6422 | CA | VAL B | 399 | −15.310 | −1.533 | −39.258 | 1.00 | 15.79 | C |
| ATOM | 6423 | CB | VAL B | 399 | −14.520 | −.338 | −39.882 | 1.00 | 16.76 | C |
| ATOM | 6424 | CG1 | VAL B | 399 | −13.303 | .041 | −39.026 | 1.00 | 16.74 | C |
| ATOM | 6425 | CG2 | VAL B | 399 | −14.076 | −.655 | −41.312 | 1.00 | 14.91 | C |
| ATOM | 6426 | C | VAL B | 399 | −15.690 | −1.211 | −37.810 | 1.00 | 16.28 | C |
| ATOM | 6427 | O | VAL B | 399 | −16.598 | −.416 | −37.561 | 1.00 | 15.71 | O |
| ATOM | 6428 | N | THR B | 400 | −15.009 | −1.855 | −36.865 | 1.00 | 16.17 | N |
| ATOM | 6429 | CA | THR B | 400 | −15.076 | −1.472 | −35.455 | 1.00 | 16.31 | C |
| ATOM | 6430 | CB | THR B | 400 | −15.056 | −2.704 | −34.518 | 1.00 | 16.54 | C |
| ATOM | 6431 | OG1 | THR B | 400 | −16.333 | −3.347 | −34.555 | 1.00 | 15.87 | O |
| ATOM | 6432 | CG2 | THR B | 400 | −14.760 | −2.306 | −33.071 | 1.00 | 16.85 | C |

TABLE A-continued

| ATOM | 6433 | C | THR B | 400 | −13.889 | −.565 | −35.154 | 1.00 | 16.53 | C |
|---|---|---|---|---|---|---|---|---|---|---|
| ATOM | 6434 | O | THR B | 400 | −12.762 | −.886 | −35.505 | 1.00 | 16.61 | O |
| ATOM | 6435 | N | TRP B | 401 | −14.152 | .562 | −34.503 | 1.00 | 16.53 | N |
| ATOM | 6436 | CA | TRP B | 401 | −13.128 | 1.553 | −34.206 | 1.00 | 16.48 | C |
| ATOM | 6437 | CB | TRP B | 401 | −13.163 | 2.636 | −35.297 | 1.00 | 16.82 | C |
| ATOM | 6438 | CG | TRP B | 401 | −12.120 | 3.715 | −35.227 | 1.00 | 16.38 | C |
| ATOM | 6439 | CD1 | TRP B | 401 | −11.245 | 3.962 | −34.206 | 1.00 | 18.09 | C |
| ATOM | 6440 | NE1 | TRP B | 401 | −10.460 | 5.046 | −34.508 | 1.00 | 15.21 | N |
| ATOM | 6441 | CE2 | TRP B | 401 | −10.831 | 5.542 | −35.731 | 1.00 | 16.55 | C |
| ATOM | 6442 | CD2 | TRP B | 401 | −11.878 | 4.729 | −36.215 | 1.00 | 16.94 | C |
| ATOM | 6443 | CE3 | TRP B | 401 | −12.439 | 5.023 | −37.468 | 1.00 | 13.89 | C |
| ATOM | 6444 | CZ3 | TRP B | 401 | −11.942 | 6.112 | −38.187 | 1.00 | 17.20 | C |
| ATOM | 6445 | CH2 | TRP B | 401 | −10.900 | 6.906 | −37.676 | 1.00 | 16.94 | C |
| ATOM | 6446 | CZ2 | TRP B | 401 | −10.331 | 6.638 | −36.456 | 1.00 | 17.84 | C |
| ATOM | 6447 | C | TRP B | 401 | −13.431 | 2.135 | −32.821 | 1.00 | 16.30 | C |
| ATOM | 6448 | O | TRP B | 401 | −14.526 | 2.647 | −32.593 | 1.00 | 15.98 | O |
| ATOM | 6449 | N | ASN B | 402 | −12.469 | 2.026 | −31.902 | 1.00 | 16.52 | N |
| ATOM | 6450 | CA | ASN B | 402 | −12.600 | 2.552 | −30.538 | 1.00 | 17.30 | C |
| ATOM | 6451 | CB | ASN B | 402 | −12.172 | 1.507 | −29.493 | 1.00 | 18.47 | C |
| ATOM | 6452 | CG | ASN B | 402 | −13.140 | .340 | −29.366 | 1.00 | 21.20 | C |
| ATOM | 6453 | OD1 | ASN B | 402 | −14.068 | .179 | −30.157 | 1.00 | 23.01 | O |
| ATOM | 6454 | ND2 | ASN B | 402 | −12.912 | −.489 | −28.357 | 1.00 | 21.88 | N |
| ATOM | 6455 | C | ASN B | 402 | −11.773 | 3.823 | −30.310 | 1.00 | 17.39 | C |
| ATOM | 6456 | O | ASN B | 402 | −10.587 | 3.744 | −29.983 | 1.00 | 16.05 | O |
| ATOM | 6457 | N | PRO B | 403 | −12.385 | 5.005 | −30.491 | 1.00 | 18.37 | N |
| ATOM | 6458 | CA | PRO B | 403 | −11.737 | 6.244 | −30.060 | 1.00 | 18.91 | C |
| ATOM | 6459 | CB | PRO B | 403 | −12.836 | 7.288 | −30.264 | 1.00 | 19.60 | C |
| ATOM | 6460 | CG | PRO B | 403 | −13.627 | 6.745 | −31.410 | 1.00 | 17.99 | C |
| ATOM | 6461 | CD | PRO B | 403 | −13.673 | 5.270 | −31.159 | 1.00 | 18.12 | C |
| ATOM | 6462 | C | PRO B | 403 | −11.262 | 6.246 | −28.599 | 1.00 | 19.37 | C |
| ATOM | 6463 | O | PRO B | 403 | −10.312 | 6.968 | −28.266 | 1.00 | 19.14 | O |
| ATOM | 6464 | N | HIS B | 404 | −11.902 | 5.450 | −27.741 | 1.00 | 18.46 | N |
| ATOM | 6465 | CA | HIS B | 404 | −11.491 | 5.376 | −26.335 | 1.00 | 18.97 | C |
| ATOM | 6466 | CB | HIS B | 404 | −12.636 | 4.903 | −25.407 | 1.00 | 18.69 | C |
| ATOM | 6467 | CG | HIS B | 404 | −12.929 | 3.434 | −25.468 | 1.00 | 16.97 | C |
| ATOM | 6468 | ND1 | HIS B | 404 | −12.092 | 2.481 | −24.928 | 1.00 | 18.18 | N |
| ATOM | 6469 | CE1 | HIS B | 404 | −12.615 | 1.282 | −25.109 | 1.00 | 16.08 | C |
| ATOM | 6470 | NE2 | HIS B | 404 | −13.770 | 1.423 | −25.734 | 1.00 | 16.77 | N |
| ATOM | 6471 | CD2 | HIS B | 404 | −13.995 | 2.759 | −25.960 | 1.00 | 16.62 | C |
| ATOM | 6472 | C | HIS B | 404 | −10.178 | 4.616 | −26.098 | 1.00 | 19.77 | C |
| ATOM | 6473 | O | HIS B | 404 | −9.635 | 4.626 | −24.991 | 1.00 | 20.51 | O |
| ATOM | 6474 | N | LLP B | 405 | −9.670 | 3.969 | −27.143 | 1.00 | 20.06 | N |
| ATOM | 6475 | CA | LLP B | 405 | −8.360 | 3.333 | −27.077 | 1.00 | 21.25 | C |
| ATOM | 6476 | CB | LLP B | 405 | −8.337 | 1.995 | −27.845 | 1.00 | 20.24 | C |
| ATOM | 6477 | CG | LLP B | 405 | −9.045 | .853 | −27.080 | 1.00 | 20.91 | C |
| ATOM | 6478 | CD | LLP B | 405 | −8.888 | −.517 | −27.739 | 1.00 | 21.29 | C |
| ATOM | 6479 | CE | LLP B | 405 | −9.051 | −1.674 | −26.734 | 1.00 | 22.00 | C |
| ATOM | 6480 | NZ | LLP B | 405 | −10.323 | −2.469 | −26.828 | 1.00 | 26.81 | N |
| ATOM | 6481 | C4A | LLP B | 405 | −10.093 | −3.787 | −26.663 | 1.00 | 22.87 | C |
| ATOM | 6482 | C4 | LLP B | 405 | −10.385 | −4.510 | −27.958 | 1.00 | 23.11 | C |
| ATOM | 6483 | C3 | LLP B | 405 | −9.338 | −4.752 | −28.861 | 1.00 | 22.37 | C |
| ATOM | 6484 | O3 | LLP B | 405 | −8.196 | −4.381 | −28.589 | 1.00 | 22.38 | O |
| ATOM | 6485 | C2 | LLP B | 405 | −9.589 | −5.406 | −30.071 | 1.00 | 19.61 | C |
| ATOM | 6486 | C2A | LLP B | 405 | −8.487 | −5.669 | −31.060 | 1.00 | 18.34 | C |
| ATOM | 6487 | N1 | LLP B | 405 | −10.874 | −5.813 | −30.372 | 1.00 | 20.94 | N |
| ATOM | 6488 | CS | LLP B | 405 | −11.682 | −4.934 | −28.283 | 1.00 | 19.57 | C |
| ATOM | 6489 | C6 | LLP B | 405 | −11.914 | −5.587 | −29.490 | 1.00 | 18.67 | C |
| ATOM | 6490 | C5A | LLP B | 405 | −12.849 | −4.727 | −27.364 | 1.00 | 17.70 | C |
| ATOM | 6491 | O4P | LLP B | 405 | −13.327 | −3.405 | −27.045 | 1.00 | 19.42 | O |
| ATOM | 6492 | P | LLP B | 405 | −14.105 | −3.143 | −25.660 | 1.00 | 18.92 | P |
| ATOM | 6493 | O1P | LLP B | 405 | −15.234 | −4.100 | −25.657 | 1.00 | 17.95 | O |
| ATOM | 6494 | O2P | LLP B | 405 | −14.503 | −1.726 | −25.823 | 1.00 | 14.83 | O |
| ATOM | 6495 | O3P | LLP B | 405 | −13.099 | −3.433 | −24.617 | 1.00 | 16.70 | O |
| ATOM | 6496 | C | LLP B | 405 | −7.252 | 4.331 | −27.480 | 1.00 | 22.54 | C |
| ATOM | 6497 | O | LLP B | 405 | −6.904 | 5.197 | −26.675 | 1.00 | 23.62 | O |
| ATOM | 6498 | N | MET B | 406 | −6.729 | 4.248 | −28.705 | 1.00 | 23.04 | N |
| ATOM | 6499 | CA | MET B | 406 | −5.580 | 5.077 | −29.110 | 1.00 | 23.64 | C |
| ATOM | 6500 | CB | MET B | 406 | −5.031 | 4.659 | −30.478 | 1.00 | 23.92 | C |
| ATOM | 6501 | CG | MET B | 406 | −3.826 | 3.727 | −30.418 | 1.00 | 26.29 | C |
| ATOM | 6502 | SD | MET B | 406 | −2.489 | 4.251 | −29.304 | 1.00 | 29.21 | S |
| ATOM | 6503 | CE | MET B | 406 | −1.392 | 5.133 | −30.406 | 1.00 | 23.56 | C |
| ATOM | 6504 | C | MET B | 406 | −5.807 | 6.586 | −29.098 | 1.00 | 23.73 | C |
| ATOM | 6505 | O | MET B | 406 | −4.903 | 7.343 | −28.750 | 1.00 | 24.15 | O |
| ATOM | 6506 | N | MET B | 407 | −7.001 | 7.020 | −29.489 | 1.00 | 23.65 | N |
| ATOM | 6507 | CA | MET B | 407 | −7.313 | 8.446 | −29.543 | 1.00 | 23.46 | C |
| ATOM | 6508 | CB | MET B | 407 | −8.489 | 8.707 | −30.485 | 1.00 | 23.34 | C |
| ATOM | 6509 | CG | MET B | 407 | −8.182 | 8.353 | −31.942 | 1.00 | 24.89 | C |
| ATOM | 6510 | SD | MET B | 407 | −9.464 | 8.850 | −33.102 | 1.00 | 26.38 | S |
| ATOM | 6511 | CE | MET B | 407 | −10.587 | 7.496 | −32.969 | 1.00 | 32.94 | C | gad67.pdb

TABLE A-continued

| | | | | | | | | | | |
|---|---|---|---|---|---|---|---|---|---|---|
| ATOM | 6512 | C | MET B | 407 | −7.555 | 9.035 | −28.150 | 1.00 | 22.16 | C |
| ATOM | 6513 | O | MET B | 407 | −7.680 | 10.250 | −27.986 | 1.00 | 21.89 | O |
| ATOM | 6514 | N | GLY B | 408 | −7.611 | 8.158 | −27.153 | 1.00 | 21.44 | N |
| ATOM | 6515 | CA | GLY B | 408 | −7.661 | 8.566 | −25.757 | 1.00 | 20.04 | C |
| ATOM | 6516 | C | GLY B | 408 | −8.925 | 9.281 | −25.335 | 1.00 | 19.17 | C |
| ATOM | 6517 | O | GLY B | 408 | −8.891 | 10.107 | −24.429 | 1.00 | 19.55 | O |
| ATOM | 6518 | N | VAL B | 409 | −10.038 | 8.977 | −25.998 | 1.00 | 18.32 | N |
| ATOM | 6519 | CA | VAL B | 409 | −11.336 | 9.466 | −25.555 | 1.00 | 17.72 | C |
| | | | gad67.pdb | | | | | | | |
| ATOM | 6520 | CB | VAL B | 409 | −12.426 | 9.313 | −26.645 | 1.00 | 17.90 | C |
| ATOM | 6521 | CG1 | VAL B | 409 | −13.776 | 9.835 | −26.152 | 1.00 | 15.07 | C |
| ATOM | 6522 | CG2 | VAL B | 409 | −12.017 | 10.043 | −27.917 | 1.00 | 13.49 | C |
| ATOM | 6523 | C | VAL B | 409 | −11.696 | 8.676 | −24.304 | 1.00 | 18.40 | C |
| ATOM | 6524 | O | VAL B | 409 | −11.363 | 7.499 | −24.191 | 1.00 | 18.72 | O |
| ATOM | 6525 | N | LEU B | 410 | −12.342 | 9.333 | −23.351 | 1.00 | 18.75 | N |
| ATOM | 6526 | CA | LEU B | 410 | −12.755 | 8.672 | −22.120 | 1.00 | 18.64 | C |
| ATOM | 6527 | CB | LEU B | 410 | −13.288 | 9.698 | −21.109 | 1.00 | 18.80 | C |
| ATOM | 6528 | CG | LEU B | 410 | −12.261 | 10.459 | −20.248 | 1.00 | 18.06 | C |
| ATOM | 6529 | CD1 | LEU B | 410 | −11.319 | 11.352 | −21.067 | 1.00 | 19.06 | C |
| ATOM | 6530 | CD2 | LEU B | 410 | −12.950 | 11.278 | −19.167 | 1.00 | 17.45 | C |
| ATOM | 6531 | C | LEU B | 410 | −13.774 | 7.560 | −22.385 | 1.00 | 20.00 | C |
| ATOM | 6532 | O | LEU B | 410 | −14.655 | 7.693 | −23.232 | 1.00 | 19.79 | O |
| ATOM | 6533 | N | LEU B | 411 | −13.602 | 6.454 | −21.668 | 1.00 | 20.62 | N |
| ATOM | 6534 | CA | LEU B | 411 | −14.519 | 5.309 | −21.629 | 1.00 | 22.17 | C |
| ATOM | 6535 | CB | LEU B | 411 | −14.154 | 4.515 | −20.382 | 1.00 | 23.01 | C |
| ATOM | 6536 | CG | LEU B | 411 | −13.779 | 3.050 | −20.404 | 1.00 | 27.01 | C |
| ATOM | 6537 | CD1 | LEU B | 411 | −12.519 | 2.900 | −19.563 | 1.00 | 27.10 | C |
| ATOM | 6538 | CD2 | LEU B | 411 | −14.923 | 2.220 | −19.853 | 1.00 | 28.60 | C |
| ATOM | 6539 | C | LEU B | 411 | −15.992 | 5.725 | −21.487 | 1.00 | 21.87 | C |
| ATOM | 6540 | O | LEU B | 411 | −16.295 | 6.571 | −20.651 | 1.00 | 21.58 | O |
| ATOM | 6541 | N | GLN B | 412 | −16.918 | 5.173 | −22.276 | 1.00 | 22.11 | N |
| ATOM | 6542 | CA | GLN B | 412 | −16.670 | 4.338 | −23.446 | 1.00 | 21.97 | C |
| ATOM | 6543 | CB | GLN B | 412 | −17.648 | 3.164 | −23.478 | 1.00 | 21.69 | C |
| ATOM | 6544 | CG | GLN B | 412 | −17.342 | 2.029 | −22.521 | 1.00 | 23.45 | C |
| ATOM | 6545 | CD | GLN B | 412 | −18.363 | .904 | −22.601 | 1.00 | 23.28 | C |
| ATOM | 6546 | OE1 | GLN B | 412 | −19.568 | 1.144 | −22.695 | 1.00 | 24.90 | O |
| ATOM | 6547 | NE2 | GLN B | 412 | −17.881 | −.334 | −22.549 | 1.00 | 27.56 | N |
| ATOM | 6548 | C | GLN B | 412 | −16.911 | 5.172 | −24.697 | 1.00 | 21.44 | C |
| ATOM | 6549 | O | GLN B | 412 | −17.696 | 6.118 | −24.672 | 1.00 | 21.36 | O |
| ATOM | 6550 | N | CYS B | 413 | −16.244 | 4.809 | −25.788 | 1.00 | 21.12 | N |
| ATOM | 6551 | CA | CYS B | 413 | −16.461 | 5.434 | −27.088 | 1.00 | 20.29 | C |
| ATOM | 6552 | CB | CYS B | 413 | −15.673 | 6.741 | −27.222 | 1.00 | 20.21 | C |
| ATOM | 6553 | SG | CYS B | 413 | −16.109 | 7.736 | −28.677 | 1.00 | 22.16 | S |
| ATOM | 6554 | C | CYS B | 413 | −16.064 | 4.451 | −28.181 | 1.00 | 19.47 | C |
| ATOM | 6555 | O | CYS B | 413 | −14.882 | 4.280 | −28.481 | 1.00 | 18.95 | O |
| ATOM | 6556 | N | SER B | 414 | −17.070 | 3.801 | −28.759 | 1.00 | 18.71 | N |
| ATOM | 6557 | CA | SER B | 414 | −16.864 | 2.756 | −29.747 | 1.00 | 18.30 | C |
| ATOM | 6558 | CB | SER B | 414 | −16.929 | 1.378 | −29.086 | 1.00 | 18.73 | C |
| ATOM | 6559 | OG | SER B | 414 | −16.774 | .359 | −30.057 | 1.00 | 23.86 | O |
| ATOM | 6560 | C | SER B | 414 | −17.915 | 2.847 | −30.837 | 1.00 | 17.84 | C |
| ATOM | 6561 | O | SER B | 414 | −19.114 | 2.947 | −30.553 | 1.00 | 16.73 | O |
| ATOM | 6562 | N | ALA B | 415 | −17.453 | 2.810 | −32.083 | 1.00 | 16.73 | N |
| ATOM | 6563 | CA | ALA B | 415 | −18.338 | 2.878 | −33.238 | 1.00 | 16.96 | C |
| ATOM | 6564 | CB | ALA B | 415 | −17.977 | 4.072 | −34.114 | 1.00 | 17.44 | C |
| ATOM | 6565 | C | ALA B | 415 | −18.282 | 1.604 | −34.056 | 1.00 | 16.73 | C |
| ATOM | 6566 | O | ALA B | 415 | −17.235 | .969 | −34.163 | 1.00 | 16.43 | O |
| ATOM | 6567 | N | ILE B | 416 | −19.428 | 1.225 | −34.609 | 1.00 | 17.04 | N |
| ATOM | 6568 | CA | ILE B | 416 | −19.462 | .281 | −35.714 | 1.00 | 17.32 | C |
| ATOM | 6569 | CB | ILE B | 416 | −20.413 | −.944 | −35.472 | 1.00 | 17.45 | C |
| ATOM | 6570 | CG1 | ILE B | 416 | −20.468 | −1.855 | −36.705 | 1.00 | 17.56 | C |
| ATOM | 6571 | CD1 | ILE B | 416 | −19.221 | −2.673 | −36.944 | 1.00 | 17.24 | C |
| ATOM | 6572 | CG2 | ILE B | 416 | −21.814 | −.507 | −35.076 | 1.00 | 17.57 | C |
| ATOM | 6573 | C | ILE B | 416 | −19.810 | 1.068 | −36.977 | 1.00 | 17.23 | C |
| ATOM | 6574 | O | ILE B | 416 | −20.786 | 1.828 | −37.008 | 1.00 | 17.21 | O |
| ATOM | 6575 | N | LEU B | 417 | −18.964 | .921 | −37.991 | 1.00 | 16.49 | N |
| ATOM | 6576 | CA | LEU B | 417 | −19.176 | 1.557 | −39.282 | 1.00 | 15.78 | C |
| ATOM | 6577 | CB | LEU B | 417 | −17.906 | 2.278 | −39.747 | 1.00 | 15.59 | C |
| ATOM | 6578 | CG | LEU B | 417 | −17.210 | 3.228 | −38.763 | 1.00 | 15.25 | C |
| ATOM | 6579 | CD1 | LEU B | 417 | −15.925 | 3.761 | −39.374 | 1.00 | 14.32 | C |
| ATOM | 6580 | CD2 | LEU B | 417 | −18.115 | 4.378 | −38.333 | 1.00 | 16.30 | C |
| ATOM | 6581 | C | LEU B | 417 | −19.574 | .482 | −40.273 | 1.00 | 15.34 | C |
| ATOM | 6582 | O | LEU B | 417 | −18.967 | −.583 | −40.304 | 1.00 | 14.86 | O |
| ATOM | 6583 | N | VAL B | 418 | −20.618 | .754 | −41.051 | 1.00 | 15.85 | N |
| ATOM | 6584 | CA | VAL B | 418 | −21.151 | −.209 | −42.016 | 1.00 | 16.37 | C |
| ATOM | 6585 | CB | VAL B | 418 | −22.524 | −.768 | −41.566 | 1.00 | 16.15 | C |
| ATOM | 6586 | CG1 | VAL B | 418 | −23.034 | −1.822 | −42.544 | 1.00 | 14.17 | C |
| ATOM | 6587 | CG2 | VAL B | 418 | −22.427 | −1.361 | −40.164 | 1.00 | 13.91 | C |
| | | | gad67.pdb | | | | | | | |
| ATOM | 6588 | C | VAL B | 418 | −21.260 | .466 | −43.382 | 1.00 | 17.71 | C |
| ATOM | 6589 | O | VAL B | 418 | −21.856 | 1.538 | −43.500 | 1.00 | 17.65 | O |

TABLE A-continued

| | | | | | | | | | | |
|---|---|---|---|---|---|---|---|---|---|---|
| ATOM | 6590 | N | LYS B | 419 | −20.670 | −.163 | −44.399 | 1.00 | 19.82 | N |
| ATOM | 6591 | CA | LYS B | 419 | −20.558 | .432 | −45.734 | 1.00 | 21.57 | C |
| ATOM | 6592 | CB | LYS B | 419 | −19.674 | −.432 | −46.641 | 1.00 | 21.72 | C |
| ATOM | 6593 | CG | LYS B | 419 | −19.610 | .042 | −48.092 | 1.00 | 23.39 | C |
| ATOM | 6594 | CD | LYS B | 419 | −18.177 | .204 | −48.569 | 1.00 | 27.73 | C |
| ATOM | 6595 | CE | LYS B | 419 | −17.576 | −1.107 | −49.034 | 1.00 | 31.79 | C |
| ATOM | 6596 | NZ | LYS B | 419 | −16.133 | −.937 | −49.357 | 1.00 | 34.73 | N |
| ATOM | 6597 | C | LYS B | 419 | −21.917 | .682 | −46.380 | 1.00 | 22.36 | C |
| ATOM | 6598 | O | LYS B | 419 | −22.176 | 1.769 | −46.889 | 1.00 | 22.63 | O |
| ATOM | 6599 | N | GLU B | 420 | −22.775 | −.331 | −46.336 | 1.00 | 23.59 | N |
| ATOM | 6600 | CA | GLU B | 420 | −24.098 | −.267 | −46.930 | 1.00 | 25.51 | C |
| ATOM | 6601 | CB | GLU B | 420 | −24.453 | −1.637 | −47.505 | 1.00 | 25.19 | C |
| ATOM | 6602 | CG | GLU B | 420 | −25.768 | −1.706 | −48.261 | 1.00 | 28.48 | C |
| ATOM | 6603 | CD | GLU B | 420 | −26.053 | −3.101 | −48.797 | 1.00 | 29.57 | C |
| ATOM | 6604 | OE1 | GLU B | 420 | −27.244 | −3.488 | −48.840 | 1.00 | 36.80 | O |
| ATOM | 6605 | OE2 | GLU B | 420 | −25.090 | −3.813 | −49.169 | 1.00 | 36.20 | O |
| ATOM | 6606 | C | GLU B | 420 | −25.130 | .177 | −45.895 | 1.00 | 25.02 | C |
| ATOM | 6607 | O | GLU B | 420 | −25.266 | −.433 | −44.834 | 1.00 | 25.05 | O |
| ATOM | 6608 | N | LYS B | 421 | −25.846 | 1.251 | −46.216 | 1.00 | 25.51 | N |
| ATOM | 6609 | CA | LYS B | 421 | −26.888 | 1.793 | −45.346 | 1.00 | 26.80 | C |
| ATOM | 6610 | CB | LYS B | 421 | −27.190 | 3.247 | −45.729 | 1.00 | 26.47 | C |
| ATOM | 6611 | CG | LYS B | 421 | −28.062 | 4.016 | −44.736 | 1.00 | 30.96 | C |
| ATOM | 6612 | CD | LYS B | 421 | −28.105 | 5.503 | −45.078 | 1.00 | 31.39 | C |
| ATOM | 6613 | CE | LYS B | 421 | −29.319 | 6.191 | −44.464 | 1.00 | 39.54 | C |
| ATOM | 6614 | NZ | LYS B | 421 | −29.311 | 6.146 | −42.975 | 1.00 | 43.97 | N |
| ATOM | 6615 | C | LYS B | 421 | −28.154 | .944 | −45.427 | 1.00 | 25.48 | C |
| ATOM | 6616 | O | LYS B | 421 | −28.459 | .370 | −46.469 | 1.00 | 25.31 | O |
| ATOM | 6617 | N | GLY B | 422 | −28.879 | .860 | −44.315 | 1.00 | 25.22 | N |
| ATOM | 6618 | CA | GLY B | 422 | −30.137 | .125 | −44.266 | 1.00 | 23.33 | C |
| ATOM | 6619 | C | GLY B | 422 | −30.034 | −1.279 | −43.706 | 1.00 | 22.55 | C |
| ATOM | 6620 | O | GLY B | 422 | −31.053 | −1.882 | −43.356 | 1.00 | 22.50 | O |
| ATOM | 6621 | N | ILE B | 423 | −28.814 | −1.810 | −43.627 | 1.00 | 21.61 | N |
| ATOM | 6622 | CA | ILE B | 423 | −28.602 | −3.154 | −43.071 | 1.00 | 21.16 | C |
| ATOM | 6623 | CB | ILE B | 423 | −27.199 | −3.725 | −43.405 | 1.00 | 20.86 | C |
| ATOM | 6624 | CG1 | ILE B | 423 | −27.023 | −3.854 | −44.918 | 1.00 | 19.45 | C |
| ATOM | 6625 | CD1 | ILE B | 423 | −25.636 | −4.293 | −45.342 | 1.00 | 21.21 | C |
| ATOM | 6626 | CG2 | ILE B | 423 | −26.997 | −5.080 | −42.749 | 1.00 | 19.14 | C |
| ATOM | 6627 | C | ILE B | 423 | −28.865 | −3.181 | −41.558 | 1.00 | 21.58 | C |
| ATOM | 6628 | O | ILE B | 423 | −29.596 | −4.042 | −41.072 | 1.00 | 21.94 | O |
| ATOM | 6629 | N | LEU B | 424 | −28.281 | −2.230 | −40.831 | 1.00 | 21.71 | N |
| ATOM | 6630 | CA | LEU B | 424 | −28.500 | −2.106 | −39.386 | 1.00 | 22.61 | C |
| ATOM | 6631 | CB | LEU B | 424 | −27.651 | −.969 | −38.796 | 1.00 | 22.38 | C |
| ATOM | 6632 | CG | LEU B | 424 | −26.124 | −1.132 | −38.714 | 1.00 | 24.94 | C |
| ATOM | 6633 | CD1 | LEU B | 424 | −25.481 | .160 | −38.239 | 1.00 | 23.24 | C |
| ATOM | 6634 | CD2 | LEU B | 424 | −25.697 | −2.297 | −37.822 | 1.00 | 22.04 | C |
| ATOM | 6635 | C | LEU B | 424 | −29.980 | −1.903 | −39.034 | 1.00 | 22.81 | C |
| ATOM | 6636 | O | LEU B | 424 | −30.497 | −2.548 | −38.117 | 1.00 | 22.63 | O |
| ATOM | 6637 | N | GLN B | 425 | −30.645 | −1.013 | −39.773 | 1.00 | 22.96 | N |
| ATOM | 6638 | CA | GLN B | 425 | −32.072 | −.740 | −39.611 | 1.00 | 23.81 | C |
| ATOM | 6639 | CB | GLN B | 425 | −32.511 | .385 | −40.556 | 1.00 | 25.12 | C |
| ATOM | 6640 | CG | GLN B | 425 | −33.967 | .829 | −40.408 | 1.00 | 30.54 | C |
| ATOM | 6641 | CD | GLN B | 425 | −34.223 | 1.647 | −39.148 | 1.00 | 39.20 | C |
| ATOM | 6642 | OE1 | GLN B | 425 | −33.402 | 2.477 | −38.748 | 1.00 | 43.49 | O |
| ATOM | 6643 | NE2 | GLN B | 425 | −35.374 | 1.422 | −38.523 | 1.00 | 39.95 | N |
| ATOM | 6644 | C | GLN B | 425 | −32.919 | −1.990 | −39.849 | 1.00 | 23.16 | C |
| ATOM | 6645 | O | GLN B | 425 | −33.747 | −2.347 | −39.012 | 1.00 | 22.64 | O |
| ATOM | 6646 | N | GLY B | 426 | −32.699 | −2.643 | −40.992 | 1.00 | 22.03 | N |
| ATOM | 6647 | CA | GLY B | 426 | −33.420 | −3.859 | −41.354 | 1.00 | 20.61 | C |
| ATOM | 6648 | C | GLY B | 426 | −33.218 | −4.972 | −40.345 | 1.00 | 20.42 | C |
| ATOM | 6649 | O | GLY B | 426 | −34.173 | −5.643 | −39.942 | 1.00 | 19.52 | O |
| ATOM | 6650 | N | CYS B | 427 | −31.965 | −5.153 | −39.935 | 1.00 | 19.90 | N |
| ATOM | 6651 | CA | CYS B | 427 | −31.591 | −6.175 | −38.964 | 1.00 | 19.93 | C |
| ATOM | 6652 | CB | CYS B | 427 | −30.068 | −6.189 | −38.796 | 1.00 | 19.48 | C |
| ATOM | 6653 | SG | CYS B | 427 | −29.451 | −7.374 | −37.607 | 1.00 | 20.55 | S |
| ATOM | 6654 | C | CYS B | 427 | −32.269 | −5.993 | −37.600 | 1.00 | 20.52 | C |
| ATOM | 6655 | O | CYS B | 427 | −32.766 | −6.958 | −37.019 | 1.00 | 20.08 | O | gad67.pdb

| | | | | | | | | | | |
|---|---|---|---|---|---|---|---|---|---|---|
| ATOM | 6656 | N | ASN B | 428 | −32.300 | −4.753 | −37.109 | 1.00 | 20.66 | N |
| ATOM | 6657 | CA | ASN B | 428 | −32.630 | −4.483 | −35.710 | 1.00 | 21.34 | C |
| ATOM | 6658 | CB | ASN B | 428 | −31.559 | −3.582 | −35.086 | 1.00 | 21.31 | C |
| ATOM | 6659 | CG | ASN B | 428 | −30.243 | −4.311 | −34.867 | 1.00 | 23.75 | C |
| ATOM | 6660 | OD1 | ASN B | 428 | −30.222 | −5.423 | −34.341 | 1.00 | 26.41 | O |
| ATOM | 6661 | ND2 | ASN B | 428 | −29.141 | −3.688 | −35.270 | 1.00 | 24.50 | N |
| ATOM | 6662 | C | ASN B | 428 | −34.024 | −3.929 | −35.405 | 1.00 | 21.64 | C |
| ATOM | 6663 | O | ASN B | 428 | −34.516 | −4.087 | −34.288 | 1.00 | 21.95 | O |
| ATOM | 6664 | N | GLN B | 429 | −34.659 | −3.290 | −36.383 | 1.00 | 22.10 | N |
| ATOM | 6665 | CA | GLN B | 429 | −35.936 | −2.610 | −36.144 | 1.00 | 23.57 | C |
| ATOM | 6666 | CB | GLN B | 429 | −36.426 | −1.897 | −37.407 | 1.00 | 23.57 | C |
| ATOM | 6667 | CG | GLN B | 429 | −36.953 | −2.819 | −38.500 | 1.00 | 24.69 | C |
| ATOM | 6668 | CD | GLN B | 429 | −37.253 | −2.100 | −39.801 | 1.00 | 26.10 | C |

TABLE A-continued

| | | | | | | | | | |
|---|---|---|---|---|---|---|---|---|---|
| ATOM | 6669 | OE1 | GLN B | 429 | −37.367 | −2.733 | −40.852 | 1.00 | 31.22 | O |
| ATOM | 6670 | NE2 | GLN B | 429 | −37.376 | −.775 | −39.742 | 1.00 | 20.47 | N |
| ATOM | 6671 | C | GLN B | 429 | −37.039 | −3.513 | −35.578 | 1.00 | 23.27 | C |
| ATOM | 6672 | O | GLN B | 429 | −37.189 | −4.665 | −35.990 | 1.00 | 23.01 | O |
| ATOM | 6673 | N | MET B | 430 | −37.785 | −2.973 | −34.616 | 1.00 | 22.07 | N |
| ATOM | 6674 | CA | MET B | 430 | −38.999 | −3.616 | −34.103 | 1.00 | 22.85 | C |
| ATOM | 6675 | CB | MET B | 430 | −38.842 | −4.022 | −32.636 | 1.00 | 21.29 | C |
| ATOM | 6676 | CG | MET B | 430 | −37.983 | −5.256 | −32.422 | 1.00 | 22.47 | C |
| ATOM | 6677 | SD | MET B | 430 | −38.666 | −6.764 | −33.152 | 1.00 | 30.70 | S |
| ATOM | 6678 | CE | MET B | 430 | −37.160 | −7.625 | −33.602 | 1.00 | 19.96 | C |
| ATOM | 6679 | C | MET B | 430 | −40.227 | −2.723 | −34.284 | 1.00 | 25.13 | C |
| ATOM | 6680 | O | MET B | 430 | −41.360 | −3.174 | −34.104 | 1.00 | 25.28 | O |
| ATOM | 6681 | N | CYS B | 431 | −39.987 | −1.460 | −34.640 | 1.00 | 30.40 | N |
| ATOM | 6682 | CA | CYS B | 431 | −41.046 | −.486 | −34.946 | 1.00 | 35.23 | C |
| ATOM | 6683 | CB | CYS B | 431 | −41.749 | −.841 | −36.268 | 1.00 | 35.72 | C |
| ATOM | 6684 | SG | CYS B | 431 | −40.616 | −1.171 | −37.649 | 1.00 | 41.32 | S |
| ATOM | 6685 | C | CYS B | 431 | −42.049 | −.357 | −33.800 | 1.00 | 37.41 | C |
| ATOM | 6686 | O | CYS B | 431 | −43.263 | −.283 | −34.015 | 1.00 | 38.42 | O |
| ATOM | 6687 | N | ALA B | 432 | −41.520 | −.323 | −32.581 | 1.00 | 39.95 | N |
| ATOM | 6688 | CA | ALA B | 432 | −42.341 | −.360 | −31.376 | 1.00 | 41.81 | C |
| ATOM | 6689 | CB | ALA B | 432 | −41.493 | −.723 | −30.171 | 1.00 | 41.42 | C |
| ATOM | 6690 | C | ALA B | 432 | −43.091 | .943 | −31.126 | 1.00 | 43.28 | C |
| ATOM | 6691 | O | ALA B | 432 | −42.552 | 2.035 | −31.338 | 1.00 | 42.92 | O |
| ATOM | 6692 | N | GLY B | 433 | −44.345 | .794 | −30.696 | 1.00 | 44.82 | N |
| ATOM | 6693 | CA | GLY B | 433 | −45.189 | 1.885 | −30.209 | 1.00 | 46.51 | C |
| ATOM | 6694 | C | GLY B | 433 | −45.067 | 3.220 | −30.916 | 1.00 | 47.70 | C |
| ATOM | 6695 | O | GLY B | 433 | −45.229 | 3.276 | −32.133 | 1.00 | 48.85 | O |
| ATOM | 6696 | N | TYR B | 434 | −44.764 | 4.303 | −30.191 | 1.00 | 48.07 | N |
| ATOM | 6697 | CA | TYR B | 434 | −44.398 | 4.339 | −28.754 | 1.00 | 48.93 | C |
| ATOM | 6698 | CB | TYR B | 434 | −44.565 | 2.985 | −28.034 | 1.00 | 49.84 | C |
| ATOM | 6699 | CG | TYR B | 434 | −43.370 | 2.551 | −27.215 | 1.00 | 53.01 | C |
| ATOM | 6700 | CD1 | TYR B | 434 | −43.153 | 3.050 | −25.933 | 1.00 | 54.41 | C |
| ATOM | 6701 | CE1 | TYR B | 434 | −42.044 | 2.657 | −25.195 | 1.00 | 54.41 | C |
| ATOM | 6702 | CZ | TYR B | 434 | −41.145 | 1.750 | −25.725 | 1.00 | 53.18 | C |
| ATOM | 6703 | OH | TYR B | 434 | −40.052 | 1.358 | −24.990 | 1.00 | 53.04 | O |
| ATOM | 6704 | CE2 | TYR B | 434 | −41.338 | 1.240 | −26.993 | 1.00 | 54.91 | C |
| ATOM | 6705 | CD2 | TYR B | 434 | −42.448 | 1.640 | −27.730 | 1.00 | 55.92 | C |
| ATOM | 6706 | C | TYR B | 434 | −43.005 | 4.944 | −28.541 | 1.00 | 48.14 | C |
| ATOM | 6707 | O | TYR B | 434 | −42.814 | 5.780 | −27.655 | 1.00 | 48.74 | O |
| ATOM | 6708 | N | LEU B | 435 | −42.042 | 4.522 | −29.354 | 1.00 | 46.67 | N |
| ATOM | 6709 | CA | LEU B | 435 | −40.725 | 5.143 | −29.363 | 1.00 | 45.48 | C |
| ATOM | 6710 | CB | LEU B | 435 | −39.658 | 4.179 | −28.828 | 1.00 | 45.57 | C |
| ATOM | 6711 | CG | LEU B | 435 | −38.364 | 4.779 | −28.258 | 1.00 | 44.61 | C |
| ATOM | 6712 | CD1 | LEU B | 435 | −38.637 | 5.729 | −27.093 | 1.00 | 45.52 | C |
| ATOM | 6713 | CD2 | LEU B | 435 | −37.409 | 3.681 | −27.823 | 1.00 | 44.83 | C |
| ATOM | 6714 | C | LEU B | 435 | −40.396 | 5.639 | −30.776 | 1.00 | 45.04 | C |
| ATOM | 6715 | O | LEU B | 435 | −39.751 | 6.680 | −30.941 | 1.00 | 44.83 | O |
| ATOM | 6716 | N | PHE B | 436 | −40.851 | 4.883 | −31.780 | 1.00 | 43.98 | N |
| ATOM | 6717 | CA | PHE B | 436 | −40.786 | 5.271 | −33.193 | 1.00 | 43.54 | C |
| ATOM | 6718 | CB | PHE B | 436 | −39.442 | 4.866 | −33.837 | 1.00 | 42.74 | C |
| ATOM | 6719 | CG | PHE B | 436 | −38.427 | 4.289 | −32.876 | 1.00 | 41.02 | C |
| ATOM | 6720 | CD1 | PHE B | 436 | −38.548 | 2.978 | −32.410 | 1.00 | 38.93 | C |
| ATOM | 6721 | CE1 | PHE B | 436 | −37.609 | 2.442 | −31.531 | 1.00 | 37.20 | C |
| ATOM | 6722 | CZ | PHE B | 436 | −36.522 | 3.212 | −31.124 | 1.00 | 38.44 | C |
| ATOM | 6723 | CE2 | PHE B | 436 | −36.384 | 4.519 | −31.588 | 1.00 | 36.35 | C |
| | | | | | gad67.pdb | | | | | |
| ATOM | 6724 | CD2 | PHE B | 436 | −37.330 | 5.046 | −32.465 | 1.00 | 39.22 | C |
| ATOM | 6725 | C | PHE B | 436 | −41.916 | 4.530 | −33.922 | 1.00 | 43.96 | C |
| ATOM | 6726 | O | PHE B | 436 | −41.708 | 3.385 | −34.331 | 1.00 | 44.95 | O |
| ATOM | 6727 | N | GLN B | 437 | −43.098 | 5.124 | −34.137 | 1.00 | 44.13 | N |
| ATOM | 6728 | CA | GLN B | 437 | −43.466 | 6.562 | −34.066 | 1.00 | 42.96 | C |
| ATOM | 6729 | CB | GLN B | 437 | −42.997 | 7.286 | −32.797 | 1.00 | 43.13 | C |
| ATOM | 6730 | CG | GLN B | 437 | −44.149 | 7.617 | −31.849 | 1.00 | 42.79 | C |
| ATOM | 6731 | CD | GLN B | 437 | −43.685 | 8.183 | −30.520 | 1.00 | 43.17 | C |
| ATOM | 6732 | OE1 | GLN B | 437 | −42.557 | 7.948 | −30.089 | 1.00 | 42.39 | O |
| ATOM | 6733 | NE2 | GLN B | 437 | −44.561 | 8.929 | −29.859 | 1.00 | 43.42 | N |
| ATOM | 6734 | C | GLN B | 437 | −43.160 | 7.335 | −35.353 | 1.00 | 41.68 | C |
| ATOM | 6735 | O | GLN B | 437 | −42.230 | 8.145 | −35.395 | 1.00 | 41.51 | O |
| ATOM | 6736 | N | PRO B | 438 | −43.965 | 7.081 | −36.408 | 1.00 | 40.16 | N |
| ATOM | 6737 | CA | PRO B | 438 | −43.764 | 7.658 | −37.735 | 1.00 | 38.95 | C |
| ATOM | 6738 | CB | PRO B | 438 | −44.353 | 6.589 | −38.659 | 1.00 | 39.32 | C |
| ATOM | 6739 | CG | PRO B | 438 | −45.456 | 5.962 | −37.851 | 1.00 | 40.20 | C |
| ATOM | 6740 | CD | PRO B | 438 | −45.139 | 6.184 | −36.382 | 1.00 | 40.22 | C |
| ATOM | 6741 | C | PRO B | 438 | −44.467 | 8.999 | −37.971 | 1.00 | 37.23 | C |
| ATOM | 6742 | O | PRO B | 438 | −44.125 | 9.702 | −38.924 | 1.00 | 37.29 | O |
| ATOM | 6743 | N | ASP B | 439 | −45.432 | 9.348 | −37.121 | 1.00 | 35.60 | N |
| ATOM | 6744 | CA | ASP B | 439 | −46.229 | 10.566 | −37.318 | 1.00 | 33.66 | C |
| ATOM | 6745 | CB | ASP B | 439 | −47.728 | 10.299 | −37.082 | 1.00 | 33.67 | C |
| ATOM | 6746 | CG | ASP B | 439 | −48.019 | 9.638 | −35.733 | 1.00 | 33.36 | C |
| ATOM | 6747 | OD1 | ASP B | 439 | −47.116 | 9.530 | −34.874 | 1.00 | 33.11 | O |

TABLE A-continued

| ATOM | 6748 | OD2 | ASP B | 439 | −49.175 | 9.219 | −35.537 | 1.00 | 30.92 | O |
|---|---|---|---|---|---|---|---|---|---|---|
| ATOM | 6749 | C | ASP B | 439 | −45.742 | 11.789 | −36.523 | 1.00 | 32.37 | C |
| ATOM | 6750 | O | ASP B | 439 | −46.506 | 12.731 | −36.280 | 1.00 | 32.65 | O |
| ATOM | 6751 | N | LYS B | 440 | −44.469 | 11.775 | −36.135 | 1.00 | 30.50 | N |
| ATOM | 6752 | CA | LYS B | 440 | −43.829 | 12.952 | −35.547 | 1.00 | 28.87 | C |
| ATOM | 6753 | CB | LYS B | 440 | −42.441 | 12.605 | −35.011 | 1.00 | 28.94 | C |
| ATOM | 6754 | CG | LYS B | 440 | −42.436 | 11.583 | −33.882 | 1.00 | 28.17 | C |
| ATOM | 6755 | CD | LYS B | 440 | −41.061 | 11.490 | −33.244 | 1.00 | 27.67 | C |
| ATOM | 6756 | CE | LYS B | 440 | −40.990 | 10.360 | −32.241 | 1.00 | 26.77 | C |
| ATOM | 6757 | NZ | LYS B | 440 | −39.736 | 10.417 | −31.449 | 1.00 | 29.35 | N |
| ATOM | 6758 | C | LYS B | 440 | −43.721 | 14.067 | −36.588 | 1.00 | 28.21 | C |
| ATOM | 6759 | O | LYS B | 440 | −43.706 | 13.800 | −37.790 | 1.00 | 28.18 | O |
| ATOM | 6760 | N | GLN B | 441 | −43.650 | 15.311 | −36.127 | 1.00 | 27.33 | N |
| ATOM | 6761 | CA | GLN B | 441 | −43.544 | 16.460 | −37.030 | 1.00 | 27.70 | C |
| ATOM | 6762 | CB | GLN B | 441 | −43.905 | 17.777 | −36.322 | 1.00 | 28.38 | C |
| ATOM | 6763 | CG | GLN B | 441 | −44.060 | 17.701 | −34.809 | 1.00 | 32.84 | C |
| ATOM | 6764 | CD | GLN B | 441 | −42.748 | 17.724 | −34.063 | 1.00 | 34.65 | C |
| ATOM | 6765 | OE1 | GLN B | 441 | −42.320 | 18.767 | −33.573 | 1.00 | 37.02 | O |
| ATOM | 6766 | NE2 | GLN B | 441 | −42.105 | 16.568 | −33.960 | 1.00 | 36.93 | N |
| ATOM | 6767 | C | GLN B | 441 | −42.197 | 16.586 | −37.752 | 1.00 | 26.74 | C |
| ATOM | 6768 | O | GLN B | 441 | −42.077 | 17.377 | −38.685 | 1.00 | 27.83 | O |
| ATOM | 6769 | N | TYR B | 442 | −41.197 | 15.818 | −37.323 | 1.00 | 25.23 | N |
| ATOM | 6770 | CA | TYR B | 442 | −39.886 | 15.813 | −37.976 | 1.00 | 23.51 | C |
| ATOM | 6771 | CB | TYR B | 442 | −38.783 | 16.235 | −36.992 | 1.00 | 22.35 | C |
| ATOM | 6772 | CG | TYR B | 442 | −38.518 | 15.229 | −35.892 | 1.00 | 20.33 | C |
| ATOM | 6773 | CD1 | TYR B | 442 | −39.161 | 15.329 | −34.657 | 1.00 | 18.77 | C |
| ATOM | 6774 | CE1 | TYR B | 442 | −38.923 | 14.405 | −33.648 | 1.00 | 16.94 | C |
| ATOM | 6775 | CZ | TYR B | 442 | −38.032 | 13.363 | −33.872 | 1.00 | 19.73 | C |
| ATOM | 6776 | OH | TYR B | 442 | −37.790 | 12.436 | −32.885 | 1.00 | 18.68 | O |
| ATOM | 6777 | CE2 | TYR B | 442 | −37.382 | 13.241 | −35.090 | 1.00 | 17.24 | C |
| ATOM | 6778 | CD2 | TYR B | 442 | −37.626 | 14.172 | −36.088 | 1.00 | 17.23 | C |
| ATOM | 6779 | C | TYR B | 442 | −39.561 | 14.455 | −38.610 | 1.00 | 23.59 | C |
| ATOM | 6780 | O | TYR B | 442 | −40.217 | 13.448 | −38.327 | 1.00 | 22.40 | O |
| ATOM | 6781 | N | ASP B | 443 | −38.539 | 14.452 | −39.466 | 1.00 | 24.69 | N |
| ATOM | 6782 | CA | ASP B | 443 | −38.039 | 13.253 | −40.147 | 1.00 | 25.54 | C |
| ATOM | 6783 | CB | ASP B | 443 | −36.908 | 13.653 | −41.103 | 1.00 | 26.27 | C |
| ATOM | 6784 | CG | ASP B | 443 | −36.423 | 12.504 | −41.967 | 1.00 | 27.88 | C |
| ATOM | 6785 | OD1 | ASP B | 443 | −37.056 | 11.425 | −41.977 | 1.00 | 25.20 | O |
| ATOM | 6786 | OD2 | ASP B | 443 | −35.395 | 12.694 | −42.650 | 1.00 | 32.96 | O |
| ATOM | 6787 | C | ASP B | 443 | −37.545 | 12.193 | −39.158 | 1.00 | 25.91 | C |
| ATOM | 6788 | O | ASP B | 443 | −36.466 | 12.328 | −38.575 | 1.00 | 25.48 | O |
| ATOM | 6789 | N | VAL B | 444 | −38.330 | 11.130 | −39.002 | 1.00 | 26.47 | N |
| ATOM | 6790 | CA | VAL B | 444 | −38.067 | 10.103 | −37.988 | 1.00 | 27.84 | C |
| ATOM | 6791 | CB | VAL B | 444 | −39.329 | 9.243 | −37.685 | 1.00 | 28.30 | C | gad67.pdb

| ATOM | 6792 | CG1 | VAL B | 444 | −40.442 | 10.119 | −37.118 | 1.00 | 29.16 | C |
|---|---|---|---|---|---|---|---|---|---|---|
| ATOM | 6793 | CG2 | VAL B | 444 | −39.799 | 8.475 | −38.923 | 1.00 | 26.66 | C |
| ATOM | 6794 | C | VAL B | 444 | −36.862 | 9.203 | −38.286 | 1.00 | 28.65 | C |
| ATOM | 6795 | O | VAL B | 444 | −36.496 | 8.366 | −37.460 | 1.00 | 27.90 | O |
| ATOM | 6796 | N | SER B | 445 | −36.255 | 9.378 | −39.461 | 1.00 | 29.70 | N |
| ATOM | 6797 | CA | SER B | 445 | −35.007 | 8.686 | −39.799 | 1.00 | 30.09 | C |
| ATOM | 6798 | CB | SER B | 445 | −34.690 | 8.815 | −41.295 | 1.00 | 29.96 | C |
| ATOM | 6799 | OG | SER B | 445 | −34.199 | 10.107 | −41.616 | 1.00 | 33.36 | O |
| ATOM | 6800 | C | SER B | 445 | −33.846 | 9.211 | −38.942 | 1.00 | 29.61 | C |
| ATOM | 6801 | O | SER B | 445 | −32.758 | 8.626 | −38.935 | 1.00 | 30.02 | O |
| ATOM | 6802 | N | TYR B | 446 | −34.094 | 10.317 | −38.238 | 1.00 | 27.86 | N |
| ATOM | 6803 | CA | TYR B | 446 | −33.174 | 10.852 | −37.233 | 1.00 | 27.46 | C |
| ATOM | 6804 | CB | TYR B | 446 | −33.327 | 12.369 | −37.113 | 1.00 | 27.28 | C |
| ATOM | 6805 | CG | TYR B | 446 | −32.724 | 13.110 | −38.275 | 1.00 | 27.83 | C |
| ATOM | 6806 | CD1 | TYR B | 446 | −31.379 | 13.466 | −38.273 | 1.00 | 27.27 | C |
| ATOM | 6807 | CE1 | TYR B | 446 | −30.819 | 14.140 | −39.343 | 1.00 | 27.85 | C |
| ATOM | 6808 | CZ | TYR B | 446 | −31.603 | 14.455 | −40.435 | 1.00 | 26.75 | C |
| ATOM | 6809 | OH | TYR B | 446 | −31.049 | 15.124 | −41.498 | 1.00 | 31.55 | O |
| ATOM | 6810 | CE2 | TYR B | 446 | −32.939 | 14.109 | −40.464 | 1.00 | 27.72 | C |
| ATOM | 6811 | CD2 | TYR B | 446 | −33.493 | 13.440 | −39.389 | 1.00 | 27.04 | C |
| ATOM | 6812 | C | TYR B | 446 | −33.350 | 10.192 | −35.865 | 1.00 | 27.16 | C |
| ATOM | 6813 | O | TYR B | 446 | −32.489 | 10.324 | −34.996 | 1.00 | 27.39 | O |
| ATOM | 6814 | N | ASP B | 447 | −34.470 | 9.498 | −35.671 | 1.00 | 26.59 | N |
| ATOM | 6815 | CA | ASP B | 447 | −34.618 | 8.601 | −34.531 | 1.00 | 26.78 | C |
| ATOM | 6816 | CB | ASP B | 447 | −36.087 | 8.321 | −34.210 | 1.00 | 26.50 | C |
| ATOM | 6817 | CG | ASP B | 447 | −36.848 | 9.573 | −33.801 | 1.00 | 27.18 | C |
| ATOM | 6818 | OD1 | ASP B | 447 | −36.211 | 10.608 | −33.510 | 1.00 | 29.71 | O |
| ATOM | 6819 | OD2 | ASP B | 447 | −38.090 | 9.523 | −33.767 | 1.00 | 26.34 | O |
| ATOM | 6820 | C | ASP B | 447 | −33.868 | 7.325 | −34.869 | 1.00 | 27.40 | C |
| ATOM | 6821 | O | ASP B | 447 | −34.375 | 6.443 | −35.567 | 1.00 | 28.35 | O |
| ATOM | 6822 | N | THR B | 448 | −32.643 | 7.254 | −34.366 | 1.00 | 27.53 | N |
| ATOM | 6823 | CA | THR B | 448 | −31.663 | 6.260 | −34.775 | 1.00 | 28.01 | C |
| ATOM | 6824 | CB | THR B | 448 | −30.233 | 6.895 | −34.728 | 1.00 | 28.41 | C |
| ATOM | 6825 | OG1 | THR B | 448 | −30.072 | 7.761 | −35.861 | 1.00 | 32.34 | O |
| ATOM | 6826 | CG2 | THR B | 448 | −29.122 | 5.852 | −34.741 | 1.00 | 30.54 | C |

TABLE A-continued

| ATOM | 6827 | C | THR B | 448 | −31.791 | 5.006 | −33.916 | 1.00 | 26.84 | C |
|---|---|---|---|---|---|---|---|---|---|---|
| ATOM | 6828 | O | THR B | 448 | −31.216 | 3.961 | −34.221 | 1.00 | 26.42 | O |
| ATOM | 6829 | N | GLY B | 449 | −32.595 | 5.115 | −32.865 | 1.00 | 26.91 | N |
| ATOM | 6830 | CA | GLY B | 449 | −32.728 | 4.065 | −31.865 | 1.00 | 26.57 | C |
| ATOM | 6831 | C | GLY B | 449 | −33.086 | 2.671 | −32.346 | 1.00 | 26.86 | C |
| ATOM | 6832 | O | GLY B | 449 | −32.645 | 1.685 | −31.758 | 1.00 | 27.28 | O |
| ATOM | 6833 | N | ASP B | 450 | −33.881 | 2.576 | −33.407 | 1.00 | 26.91 | N |
| ATOM | 6834 | CA | ASP B | 450 | −34.398 | 1.279 | −33.838 | 1.00 | 28.09 | C |
| ATOM | 6835 | CB | ASP B | 450 | −35.700 | 1.442 | −34.639 | 1.00 | 28.56 | C |
| ATOM | 6836 | CG | ASP B | 450 | −36.750 | .376 | −34.291 | 1.00 | 30.67 | C |
| ATOM | 6837 | OD1 | ASP B | 450 | −36.534 | −.426 | −33.350 | 1.00 | 30.21 | O |
| ATOM | 6838 | OD2 | ASP B | 450 | −37.806 | .345 | −34.960 | 1.00 | 30.25 | O |
| ATOM | 6839 | C | ASP B | 450 | −33.385 | .410 | −34.601 | 1.00 | 28.12 | C |
| ATOM | 6840 | O | ASP B | 450 | −33.638 | −.770 | −34.829 | 1.00 | 29.54 | O |
| ATOM | 6841 | N | LYS B | 451 | −32.245 | .983 | −34.984 | 1.00 | 27.41 | N |
| ATOM | 6842 | CA | LYS B | 451 | −31.180 | .215 | −35.641 | 1.00 | 26.72 | C |
| ATOM | 6843 | CB | LYS B | 451 | −30.515 | 1.039 | −36.751 | 1.00 | 26.45 | C |
| ATOM | 6844 | CG | LYS B | 451 | −29.634 | 2.173 | −36.261 | 1.00 | 27.45 | C |
| ATOM | 6845 | CD | LYS B | 451 | −29.662 | 3.345 | −37.217 | 1.00 | 31.13 | C |
| ATOM | 6846 | CE | LYS B | 451 | −28.460 | 3.366 | −38.128 | 1.00 | 32.98 | C |
| ATOM | 6847 | NZ | LYS B | 451 | −28.377 | 4.679 | −38.836 | 1.00 | 34.31 | N |
| ATOM | 6848 | C | LYS B | 451 | −30.144 | −.309 | −34.633 | 1.00 | 26.02 | C |
| ATOM | 6849 | O | LYS B | 451 | −29.201 | −1.014 | −35.000 | 1.00 | 25.72 | O |
| ATOM | 6850 | N | ALA B | 452 | −30.337 | .045 | −33.365 | 1.00 | 25.49 | N |
| ATOM | 6851 | CA | ALA B | 452 | −29.472 | −.399 | −32.279 | 1.00 | 25.23 | C |
| ATOM | 6852 | CB | ALA B | 452 | −29.361 | .690 | −31.214 | 1.00 | 25.03 | C |
| ATOM | 6853 | C | ALA B | 452 | −30.012 | −1.680 | −31.657 | 1.00 | 25.60 | C |
| ATOM | 6854 | O | ALA B | 452 | −31.188 | −2.009 | −31.819 | 1.00 | 23.80 | O |
| ATOM | 6855 | N | ILE B | 453 | −29.147 | −2.400 | −30.949 | 1.00 | 26.77 | N |
| ATOM | 6856 | CA | ILE B | 453 | −29.583 | −3.532 | −30.140 | 1.00 | 28.12 | C |
| ATOM | 6857 | CB | ILE B | 453 | −28.496 | −4.646 | −30.062 | 1.00 | 29.90 | C |
| ATOM | 6858 | CG1 | ILE B | 453 | −28.967 | −5.830 | −29.203 | 1.00 | 33.28 | C |
| ATOM | 6859 | CD1 | ILE B | 453 | −30.211 | −6.554 | −29.735 | 1.00 | 37.30 | C |
| | | | | | gad67.pdb | | | | | |
| ATOM | 6860 | CG2 | ILE B | 453 | −27.162 | −4.090 | −29.557 | 1.00 | 32.07 | C |
| ATOM | 6861 | C | ILE B | 453 | −30.027 | −3.049 | −28.751 | 1.00 | 27.32 | C |
| ATOM | 6862 | O | ILE B | 453 | −30.813 | −3.708 | −28.064 | 1.00 | 28.17 | O |
| ATOM | 6863 | N | GLN B | 454 | −29.522 | −1.883 | −28.358 | 1.00 | 26.18 | N |
| ATOM | 6864 | CA | GLN B | 454 | −29.940 | −1.220 | −27.132 | 1.00 | 24.42 | C |
| ATOM | 6865 | CB | GLN B | 454 | −28.919 | −.152 | −26.738 | 1.00 | 24.21 | C |
| ATOM | 6866 | CG | GLN B | 454 | −27.609 | −.687 | −26.222 | 1.00 | 22.56 | C |
| ATOM | 6867 | CD | GLN B | 454 | −26.626 | .415 | −25.897 | 1.00 | 23.15 | C |
| ATOM | 6868 | OE1 | GLN B | 454 | −26.373 | .711 | −24.730 | 1.00 | 23.98 | O |
| ATOM | 6869 | NE2 | GLN B | 454 | −26.073 | 1.036 | −26.929 | 1.00 | 17.10 | N |
| ATOM | 6870 | C | GLN B | 454 | −31.289 | −.546 | −27.339 | 1.00 | 23.66 | C |
| ATOM | 6871 | O | GLN B | 454 | −31.703 | −.299 | −28.476 | 1.00 | 23.61 | O |
| ATOM | 6872 | N | CYS B | 455 | −31.971 | −.258 | −26.236 | 1.00 | 22.27 | N |
| ATOM | 6873 | CA | CYS B | 455 | −33.095 | .662 | −26.258 | 1.00 | 21.86 | C |
| ATOM | 6874 | CB | CYS B | 455 | −34.226 | .175 | −25.345 | 1.00 | 22.13 | C |
| ATOM | 6875 | SG | CYS B | 455 | −35.668 | 1.277 | −25.284 | 1.00 | 22.05 | S |
| ATOM | 6876 | C | CYS B | 455 | −32.557 | 2.030 | −25.831 | 1.00 | 21.45 | C |
| ATOM | 6877 | O | CYS B | 455 | −32.159 | 2.832 | −26.676 | 1.00 | 21.55 | O |
| ATOM | 6878 | N | GLY B | 456 | −32.518 | 2.285 | −24.524 | 1.00 | 21.02 | N |
| ATOM | 6879 | CA | GLY B | 456 | −31.811 | 3.449 | −23.996 | 1.00 | 19.59 | C |
| ATOM | 6880 | C | GLY B | 456 | −30.325 | 3.372 | −24.321 | 1.00 | 19.34 | C |
| ATOM | 6881 | O | GLY B | 456 | −29.724 | 2.296 | −24.268 | 1.00 | 18.52 | O |
| ATOM | 6882 | N | ARG B | 457 | −29.735 | 4.511 | −24.672 | 1.00 | 19.45 | N |
| ATOM | 6883 | CA | ARG B | 457 | −28.323 | 4.569 | −25.046 | 1.00 | 19.13 | C |
| ATOM | 6884 | CB | ARG B | 457 | −28.147 | 4.437 | −26.568 | 1.00 | 18.64 | C |
| ATOM | 6885 | CG | ARG B | 457 | −26.695 | 4.470 | −27.051 | 1.00 | 19.36 | C |
| ATOM | 6886 | CD | ARG B | 457 | −26.535 | 3.955 | −28.485 | 1.00 | 19.13 | C |
| ATOM | 6887 | NE | ARG B | 457 | −27.179 | 4.809 | −29.484 | 1.00 | 20.14 | N |
| ATOM | 6888 | CZ | ARG B | 457 | −26.553 | 5.738 | −30.208 | 1.00 | 21.55 | C |
| ATOM | 6889 | NH1 | ARG B | 457 | −25.251 | 5.951 | −30.058 | 1.00 | 20.63 | N |
| ATOM | 6890 | NH2 | ARG B | 457 | −27.234 | 6.459 | −31.091 | 1.00 | 16.22 | N |
| ATOM | 6891 | C | ARG B | 457 | −27.659 | 5.837 | −24.516 | 1.00 | 18.77 | C |
| ATOM | 6892 | O | ARG B | 457 | −28.136 | 6.954 | −24.740 | 1.00 | 18.29 | O |
| ATOM | 6893 | N | HIS B | 458 | −26.555 | 5.640 | −23.803 | 1.00 | 18.35 | N |
| ATOM | 6894 | CA | HIS B | 458 | −25.779 | 6.730 | −23.233 | 1.00 | 18.44 | C |
| ATOM | 6895 | CB | HIS B | 458 | −24.712 | 6.166 | −22.292 | 1.00 | 18.49 | C |
| ATOM | 6896 | CG | HIS B | 458 | −23.937 | 7.215 | −21.561 | 1.00 | 21.52 | C |
| ATOM | 6897 | ND1 | HIS B | 458 | −24.420 | 7.847 | −20.436 | 1.00 | 22.37 | N |
| ATOM | 6898 | CE1 | HIS B | 458 | −23.529 | 8.727 | −20.014 | 1.00 | 22.61 | C |
| ATOM | 6899 | NE2 | HIS B | 458 | −22.489 | 8.691 | −20.828 | 1.00 | 20.09 | N |
| ATOM | 6900 | CD2 | HIS B | 458 | −22.717 | 7.752 | −21.803 | 1.00 | 18.75 | C |
| ATOM | 6901 | C | HIS B | 458 | −25.131 | 7.573 | −24.330 | 1.00 | 18.32 | C |
| ATOM | 6902 | O | HIS B | 458 | −24.693 | 7.043 | −25.350 | 1.00 | 17.96 | O |
| ATOM | 6903 | N | VAL B | 459 | −25.086 | 8.886 | −24.111 | 1.00 | 18.51 | N |
| ATOM | 6904 | CA | VAL B | 459 | −24.429 | 9.809 | −25.031 | 1.00 | 18.04 | C |
| ATOM | 6905 | CB | VAL B | 459 | −24.886 | 11.274 | −24.796 | 1.00 | 18.05 | C |

TABLE A-continued

| ATOM | 6906 | CG1 | VAL B | 459 | −24.252 | 12.211 | −25.820 | 1.00 | 16.48 | C |
|------|------|-----|-------|-----|---------|--------|---------|------|-------|---|
| ATOM | 6907 | CG2 | VAL B | 459 | −26.406 | 11.386 | −24.838 | 1.00 | 16.16 | C |
| ATOM | 6908 | C | VAL B | 459 | −22.908 | 9.699 | −24.884 | 1.00 | 18.76 | C |
| ATOM | 6909 | O | VAL B | 459 | −22.339 | 10.143 | −23.888 | 1.00 | 20.46 | O |
| ATOM | 6910 | N | ASP B | 460 | −22.263 | 9.089 | −25.873 | 1.00 | 18.43 | N |
| ATOM | 6911 | CA | ASP B | 460 | −20.811 | 8.971 | −25.902 | 1.00 | 18.83 | C |
| ATOM | 6912 | CB | ASP B | 460 | −20.391 | 7.530 | −26.227 | 1.00 | 19.55 | C |
| ATOM | 6913 | CG | ASP B | 460 | −20.761 | 6.537 | −25.124 | 1.00 | 23.97 | C |
| ATOM | 6914 | OD1 | ASP B | 460 | −20.816 | 6.926 | −23.936 | 1.00 | 24.70 | O |
| ATOM | 6915 | OD2 | ASP B | 460 | −20.984 | 5.351 | −25.451 | 1.00 | 27.72 | O |
| ATOM | 6916 | C | ASP B | 460 | −20.176 | 9.945 | −26.900 | 1.00 | 18.21 | C |
| ATOM | 6917 | O | ASP B | 460 | −18.952 | 10.076 | −26.954 | 1.00 | 18.80 | O |
| ATOM | 6918 | N | ILE B | 461 | −21.011 | 10.634 | −27.675 | 1.00 | 17.00 | N |
| ATOM | 6919 | CA | ILE B | 461 | −20.531 | 11.431 | −28.806 | 1.00 | 16.60 | C |
| ATOM | 6920 | CB | ILE B | 461 | −21.631 | 11.628 | −29.913 | 1.00 | 16.98 | C |
| ATOM | 6921 | CG1 | ILE B | 461 | −21.053 | 12.279 | −31.180 | 1.00 | 14.45 | C |
| ATOM | 6922 | CD1 | ILE B | 461 | −19.915 | 11.519 | −31.832 | 1.00 | 14.43 | C |
| ATOM | 6923 | CG2 | ILE B | 461 | −22.815 | 12.436 | −29.385 | 1.00 | 13.90 | C |
| ATOM | 6924 | C | ILE B | 461 | −19.895 | 12.770 | −28.428 | 1.00 | 16.78 | C |
| ATOM | 6925 | O | ILE B | 461 | −18.886 | 13.163 | −29.022 | 1.00 | 16.66 | O |
| ATOM | 6926 | N | PHE B | 462 | −20.473 | 13.473 | −27.457 | 1.00 | 15.67 | N |
| ATOM | 6927 | CA | PHE B | 462 | −20.033 | 14.833 | −27.197 | 1.00 | 15.69 | C |
| | | | | | gad67.pdb | | | | | |
| ATOM | 6928 | CB | PHE B | 462 | −20.903 | 15.554 | −26.167 | 1.00 | 14.51 | C |
| ATOM | 6929 | CG | PHE B | 462 | −20.514 | 16.988 | −25.975 | 1.00 | 13.24 | C |
| ATOM | 6930 | CD1 | PHE B | 462 | −20.812 | 17.938 | −26.951 | 1.00 | 10.98 | C |
| ATOM | 6931 | CE1 | PHE B | 462 | −20.431 | 19.258 | −26.796 | 1.00 | 10.44 | C |
| ATOM | 6932 | CZ | PHE B | 462 | −19.735 | 19.647 | −25.662 | 1.00 | 14.01 | C |
| ATOM | 6933 | CE2 | PHE B | 462 | −19.424 | 18.707 | −24.685 | 1.00 | 14.69 | C |
| ATOM | 6934 | CD2 | PHE B | 462 | −19.809 | 17.383 | −24.851 | 1.00 | 11.31 | C |
| ATOM | 6935 | C | PHE B | 462 | −18.555 | 14.918 | −26.816 | 1.00 | 16.19 | C |
| ATOM | 6936 | O | PHE B | 462 | −17.819 | 15.736 | −27.374 | 1.00 | 15.53 | O |
| ATOM | 6937 | N | LYS B | 463 | −18.134 | 14.068 | −25.881 | 1.00 | 16.17 | N |
| ATOM | 6938 | CA | LYS B | 463 | −16.750 | 14.049 | −25.415 | 1.00 | 16.95 | C |
| ATOM | 6939 | CB | LYS B | 463 | −16.546 | 12.974 | −24.338 | 1.00 | 16.50 | C |
| ATOM | 6940 | CG | LYS B | 463 | −16.814 | 11.547 | −24.801 | 1.00 | 18.02 | C |
| ATOM | 6941 | CD | LYS B | 463 | −16.601 | 10.529 | −23.682 | 1.00 | 17.03 | C |
| ATOM | 6942 | CE | LYS B | 463 | −17.303 | 9.220 | −24.010 | 1.00 | 18.69 | C |
| ATOM | 6943 | NZ | LYS B | 463 | −17.350 | 8.293 | −22.843 | 1.00 | 19.86 | N |
| ATOM | 6944 | C | LYS B | 463 | −15.774 | 13.856 | −26.582 | 1.00 | 16.83 | C |
| ATOM | 6945 | O | LYS B | 463 | −14.731 | 14.496 | −26.625 | 1.00 | 16.39 | O |
| ATOM | 6946 | N | PHE B | 464 | −16.145 | 12.989 | −27.526 | 1.00 | 16.94 | N |
| ATOM | 6947 | CA | PHE B | 464 | −15.339 | 12.680 | −28.706 | 1.00 | 16.66 | C |
| ATOM | 6948 | CB | PHE B | 464 | −15.839 | 11.372 | −29.339 | 1.00 | 16.11 | C |
| ATOM | 6949 | CG | PHE B | 464 | −15.118 | 10.967 | −30.605 | 1.00 | 16.87 | C |
| ATOM | 6950 | CD1 | PHE B | 464 | −13.774 | 11.284 | −30.817 | 1.00 | 18.17 | C |
| ATOM | 6951 | CE1 | PHE B | 464 | −13.125 | 10.900 | −31.985 | 1.00 | 15.96 | C |
| ATOM | 6952 | CZ | PHE B | 464 | −13.806 | 10.165 | −32.947 | 1.00 | 16.63 | C |
| ATOM | 6953 | CE2 | PHE B | 464 | −15.135 | 9.826 | −32.742 | 1.00 | 17.32 | C |
| ATOM | 6954 | CD2 | PHE B | 464 | −15.784 | 10.223 | −31.573 | 1.00 | 16.40 | C |
| ATOM | 6955 | C | PHE B | 464 | −15.349 | 13.836 | −29.706 | 1.00 | 16.58 | C |
| ATOM | 6956 | O | PHE B | 464 | −14.294 | 14.276 | −30.152 | 1.00 | 17.50 | O |
| ATOM | 6957 | N | TRP B | 465 | −16.541 | 14.320 | −30.043 | 1.00 | 16.06 | N |
| ATOM | 6958 | CA | TRP B | 465 | −16.717 | 15.466 | −30.936 | 1.00 | 15.47 | C |
| ATOM | 6959 | CB | TRP B | 465 | −18.210 | 15.789 | −31.093 | 1.00 | 14.76 | C |
| ATOM | 6960 | CG | TRP B | 465 | −18.519 | 16.979 | −31.956 | 1.00 | 14.25 | C |
| ATOM | 6961 | CD1 | TRP B | 465 | −18.755 | 16.976 | −33.305 | 1.00 | 13.10 | C |
| ATOM | 6962 | NE1 | TRP B | 465 | −19.010 | 18.252 | −33.743 | 1.00 | 12.17 | N |
| ATOM | 6963 | CE2 | TRP B | 465 | −18.943 | 19.111 | −32.678 | 1.00 | 13.83 | C |
| ATOM | 6964 | CD2 | TRP B | 465 | −18.640 | 18.343 | −31.532 | 1.00 | 13.37 | C |
| ATOM | 6965 | CE3 | TRP B | 465 | −18.514 | 18.991 | −30.297 | 1.00 | 14.01 | C |
| ATOM | 6966 | CZ3 | TRP B | 465 | −18.693 | 20.369 | −30.244 | 1.00 | 13.64 | C |
| ATOM | 6967 | CH2 | TRP B | 465 | −18.994 | 21.105 | −31.404 | 1.00 | 13.57 | C |
| ATOM | 6968 | CZ2 | TRP B | 465 | −19.125 | 20.496 | −32.626 | 1.00 | 13.17 | C |
| ATOM | 6969 | C | TRP B | 465 | −15.942 | 16.688 | −30.428 | 1.00 | 16.05 | C |
| ATOM | 6970 | O | TRP B | 465 | −15.212 | 17.323 | −31.195 | 1.00 | 16.68 | O |
| ATOM | 6971 | N | LEU B | 466 | −16.090 | 16.993 | −29.137 | 1.00 | 14.92 | N |
| ATOM | 6972 | CA | LEU B | 466 | −15.415 | 18.140 | −28.525 | 1.00 | 15.75 | C |
| ATOM | 6973 | CB | LEU B | 466 | −15.878 | 18.350 | −27.076 | 1.00 | 14.74 | C |
| ATOM | 6974 | CG | LEU B | 466 | −15.622 | 19.733 | −26.465 | 1.00 | 13.70 | C |
| ATOM | 6975 | CD1 | LEU B | 466 | −16.457 | 20.814 | −27.155 | 1.00 | 11.79 | C |
| ATOM | 6976 | CD2 | LEU B | 466 | −15.885 | 19.727 | −24.961 | 1.00 | 15.45 | C |
| ATOM | 6977 | C | LEU B | 466 | −13.893 | 18.023 | −28.582 | 1.00 | 16.59 | C |
| ATOM | 6978 | O | LEU B | 466 | −13.207 | 19.010 | −28.840 | 1.00 | 16.83 | O |
| ATOM | 6979 | N | MET B | 467 | −13.380 | 16.819 | −28.329 | 1.00 | 16.44 | N |
| ATOM | 6980 | CA | MET B | 467 | −11.950 | 16.549 | −28.424 | 1.00 | 17.83 | C |
| ATOM | 6981 | CB | MET B | 467 | −11.640 | 15.125 | −27.966 | 1.00 | 17.80 | C |
| ATOM | 6982 | CG | MET B | 467 | −11.560 | 14.966 | −26.462 | 1.00 | 17.76 | C |
| ATOM | 6983 | SD | MET B | 467 | −11.370 | 13.256 | −25.940 | 1.00 | 18.73 | S |
| ATOM | 6984 | CE | MET B | 467 | −9.792 | 12.835 | −26.683 | 1.00 | 17.24 | C |

TABLE A-continued

| | | | | | | | | | |
|---|---|---|---|---|---|---|---|---|---|
| ATOM | 6985 | C | MET B | 467 | −11.425 | 16.768 | −29.840 | 1.00 | 18.20 | C |
| ATOM | 6986 | O | MET B | 467 | −10.338 | 17.316 | −30.019 | 1.00 | 18.66 | O |
| ATOM | 6987 | N | TRP B | 468 | −12.206 | 16.344 | −30.833 | 1.00 | 17.65 | N |
| ATOM | 6988 | CA | TRP B | 468 | −11.856 | 16.518 | −32.238 | 1.00 | 17.38 | C |
| ATOM | 6989 | CB | TRP B | 468 | −12.839 | 15.765 | −33.137 | 1.00 | 17.02 | C |
| ATOM | 6990 | CG | TRP B | 468 | −12.269 | 15.350 | −34.471 | 1.00 | 17.38 | C |
| ATOM | 6991 | CD1 | TRP B | 468 | −11.365 | 16.041 | −35.239 | 1.00 | 16.86 | C |
| ATOM | 6992 | NE1 | TRP B | 468 | −11.093 | 15.346 | −36.392 | 1.00 | 17.58 | N |
| ATOM | 6993 | CE2 | TRP B | 468 | −11.825 | 14.188 | −36.398 | 1.00 | 18.41 | C |
| ATOM | 6994 | CD2 | TRP B | 468 | −12.581 | 14.156 | −35.202 | 1.00 | 18.05 | C |
| ATOM | 6995 | CE3 | TRP B | 468 | −13.418 | 13.058 | −34.960 | 1.00 | 17.00 | C |
| | | | | | gad67.pdb | | | | | |
| ATOM | 6996 | CZ3 | TRP B | 468 | −13.481 | 12.042 | −35.913 | 1.00 | 17.58 | C |
| ATOM | 6997 | CH2 | TRP B | 468 | −12.716 | 12.103 | −37.090 | 1.00 | 16.42 | C |
| ATOM | 6998 | CZ2 | TRP B | 468 | −11.885 | 13.165 | −37.349 | 1.00 | 16.31 | C |
| ATOM | 6999 | C | TRP B | 468 | −11.827 | 17.995 | −32.612 | 1.00 | 17.70 | C |
| ATOM | 7000 | O | TRP B | 468 | −10.950 | 18.426 | −33.366 | 1.00 | 18.26 | O |
| ATOM | 7001 | N | LYS B | 469 | −12.779 | 18.762 | −32.082 | 1.00 | 17.44 | N |
| ATOM | 7002 | CA | LYS B | 469 | −12.803 | 20.218 | −32.258 | 1.00 | 17.48 | C |
| ATOM | 7003 | CB | LYS B | 469 | −14.099 | 20.822 | −31.705 | 1.00 | 16.83 | C |
| ATOM | 7004 | CG | LYS B | 469 | −15.369 | 20.408 | −32.438 | 1.00 | 19.07 | C |
| ATOM | 7005 | CD | LYS B | 469 | −15.450 | 20.986 | −33.848 | 1.00 | 23.36 | C |
| ATOM | 7006 | CE | LYS B | 469 | −16.114 | 22.348 | −33.866 | 1.00 | 24.09 | C |
| ATOM | 7007 | NZ | LYS B | 469 | −16.221 | 22.872 | −35.255 | 1.00 | 27.05 | N |
| ATOM | 7008 | C | LYS B | 469 | −11.598 | 20.880 | −31.594 | 1.00 | 17.59 | C |
| ATOM | 7009 | O | LYS B | 469 | −10.999 | 21.800 | −32.155 | 1.00 | 18.58 | O |
| ATOM | 7010 | N | ALA B | 470 | −11.243 | 20.396 | −30.407 | 1.00 | 17.23 | N |
| ATOM | 7011 | CA | ALA B | 470 | −10.152 | 20.968 | −29.615 | 1.00 | 16.76 | C |
| ATOM | 7012 | CB | ALA B | 470 | −10.278 | 20.539 | −28.169 | 1.00 | 15.55 | C |
| ATOM | 7013 | C | ALA B | 470 | −8.767 | 20.611 | −30.143 | 1.00 | 17.19 | C |
| ATOM | 7014 | O | ALA B | 470 | −7.817 | 21.370 | −29.963 | 1.00 | 17.39 | O |
| ATOM | 7015 | N | LYS B | 471 | −8.653 | 19.449 | −30.774 | 1.00 | 17.74 | N |
| ATOM | 7016 | CA | LYS B | 471 | −7.366 | 18.960 | −31.248 | 1.00 | 18.02 | C |
| ATOM | 7017 | CB | LYS B | 471 | −7.210 | 17.475 | −30.931 | 1.00 | 17.90 | C |
| ATOM | 7018 | CG | LYS B | 471 | −7.100 | 17.158 | −29.461 | 1.00 | 19.95 | C |
| ATOM | 7019 | CD | LYS B | 471 | −7.047 | 15.666 | −29.235 | 1.00 | 23.71 | C |
| ATOM | 7020 | CE | LYS B | 471 | −6.416 | 15.355 | −27.898 | 1.00 | 29.64 | C |
| ATOM | 7021 | NZ | LYS B | 471 | −6.322 | 13.896 | −27.674 | 1.00 | 36.73 | N |
| ATOM | 7022 | C | LYS B | 471 | −7.188 | 19.168 | −32.745 | 1.00 | 18.35 | C |
| ATOM | 7023 | O | LYS B | 471 | −6.082 | 19.437 | −33.209 | 1.00 | 18.04 | O |
| ATOM | 7024 | N | GLY B | 472 | −8.280 | 19.032 | −33.494 | 1.00 | 18.29 | N |
| ATOM | 7025 | CA | GLY B | 472 | −8.206 | 18.898 | −34.944 | 1.00 | 18.30 | C |
| ATOM | 7026 | C | GLY B | 472 | −7.660 | 17.523 | −35.287 | 1.00 | 19.14 | C |
| ATOM | 7027 | O | GLY B | 472 | −7.066 | 16.856 | −34.437 | 1.00 | 19.72 | O |
| ATOM | 7028 | N | THR B | 473 | −7.858 | 17.093 | −36.530 | 1.00 | 19.83 | N |
| ATOM | 7029 | CA | THR B | 473 | −7.291 | 15.830 | −37.002 | 1.00 | 20.50 | C |
| ATOM | 7030 | CB | THR B | 473 | −7.671 | 15.563 | −38.474 | 1.00 | 20.91 | C |
| ATOM | 7031 | OG1 | THR B | 473 | −9.100 | 15.581 | −38.608 | 1.00 | 22.75 | O |
| ATOM | 7032 | CG2 | THR B | 473 | −7.144 | 14.215 | −38.947 | 1.00 | 20.77 | C |
| ATOM | 7033 | C | THR B | 473 | −5.766 | 15.801 | −36.806 | 1.00 | 21.20 | C |
| ATOM | 7034 | O | THR B | 473 | −5.195 | 14.763 | −36.457 | 1.00 | 21.34 | O |
| ATOM | 7035 | N | VAL B | 474 | −5.124 | 16.953 | −36.998 | 1.00 | 21.57 | N |
| ATOM | 7036 | CA | VAL B | 474 | −3.676 | 17.088 | −36.826 | 1.00 | 22.21 | C |
| ATOM | 7037 | CB | VAL B | 474 | −3.174 | 18.472 | −37.328 | 1.00 | 22.96 | C |
| ATOM | 7038 | CG1 | VAL B | 474 | −1.707 | 18.690 | −36.986 | 1.00 | 25.32 | C |
| ATOM | 7039 | CG2 | VAL B | 474 | −3.386 | 18.596 | −38.837 | 1.00 | 23.50 | C |
| ATOM | 7040 | C | VAL B | 474 | −3.253 | 16.835 | −35.377 | 1.00 | 21.52 | C |
| ATOM | 7041 | O | VAL B | 474 | −2.200 | 16.247 | −35.130 | 1.00 | 22.00 | O |
| ATOM | 7042 | N | GLY B | 475 | −4.085 | 17.267 | −34.428 | 1.00 | 21.34 | N |
| ATOM | 7043 | CA | GLY B | 475 | −3.846 | 17.016 | −33.001 | 1.00 | 19.30 | C |
| ATOM | 7044 | C | GLY B | 475 | −3.765 | 15.537 | −32.663 | 1.00 | 18.53 | C |
| ATOM | 7045 | O | GLY B | 475 | −2.821 | 15.099 | −32.002 | 1.00 | 18.91 | O |
| ATOM | 7046 | N | PHE B | 476 | −4.754 | 14.768 | −33.118 | 1.00 | 17.97 | N |
| ATOM | 7047 | CA | PHE B | 476 | −4.741 | 13.312 | −32.966 | 1.00 | 17.68 | C |
| ATOM | 7048 | CB | PHE B | 476 | −6.021 | 12.687 | −33.538 | 1.00 | 17.01 | C |
| ATOM | 7049 | CG | PHE B | 476 | −7.248 | 12.885 | −32.683 | 1.00 | 15.87 | C |
| ATOM | 7050 | CD1 | PHE B | 476 | −8.344 | 13.583 | −33.179 | 1.00 | 14.61 | C |
| ATOM | 7051 | CE1 | PHE B | 476 | −9.489 | 13.759 | −32.409 | 1.00 | 15.03 | C |
| ATOM | 7052 | CZ | PHE B | 476 | −9.553 | 13.230 | −31.124 | 1.00 | 13.92 | C |
| ATOM | 7053 | CE2 | PHE B | 476 | −8.469 | 12.524 | −30.614 | 1.00 | 12.67 | C |
| ATOM | 7054 | CD2 | PHE B | 476 | −7.322 | 12.351 | −31.398 | 1.00 | 15.09 | C |
| ATOM | 7055 | C | PHE B | 476 | −3.517 | 12.694 | −33.655 | 1.00 | 17.80 | C |
| ATOM | 7056 | O | PHE B | 476 | −2.854 | 11.830 | −33.090 | 1.00 | 17.32 | O |
| ATOM | 7057 | N | GLU B | 477 | −3.224 | 13.151 | −34.871 | 1.00 | 18.82 | N |
| ATOM | 7058 | CA | GLU B | 477 | −2.090 | 12.644 | −35.651 | 1.00 | 21.13 | C |
| ATOM | 7059 | CB | GLU B | 477 | −1.994 | 13.369 | −36.994 | 1.00 | 20.67 | C |
| ATOM | 7060 | CG | GLU B | 477 | −.799 | 12.934 | −37.842 | 1.00 | 23.48 | C |
| ATOM | 7061 | CD | GLU B | 477 | −.765 | 13.608 | −39.198 | 1.00 | 25.29 | C |
| ATOM | 7062 | OE1 | GLU B | 477 | −.880 | 14.856 | −39.255 | 1.00 | 30.18 | O |

TABLE A-continued

| | | | | | | | | | |
|---|---|---|---|---|---|---|---|---|---|
| ATOM | 7063 | OE2 | GLU B | 477 | −.619 | 12.885 | −40.208 | 1.00 | 31.79 | O |
| | | | | gad67.pdb | | | | | | |
| ATOM | 7064 | C | GLU B | 477 | −.759 | 12.758 | −34.908 | 1.00 | 20.69 | C |
| ATOM | 7065 | O | GLU B | 477 | −.006 | 11.785 | −34.817 | 1.00 | 20.43 | O |
| ATOM | 7066 | N | ASN B | 478 | −.484 | 13.948 | −34.377 | 1.00 | 21.48 | N |
| ATOM | 7067 | CA | ASN B | 478 | .772 | 14.219 | −33.678 | 1.00 | 23.07 | C |
| ATOM | 7068 | CB | ASN B | 478 | .914 | 15.717 | −33.380 | 1.00 | 23.68 | C |
| ATOM | 7069 | CG | ASN B | 478 | 1.148 | 16.545 | −34.635 | 1.00 | 25.71 | C |
| ATOM | 7070 | OD1 | ASN B | 478 | .817 | 17.728 | −34.677 | 1.00 | 27.38 | O |
| ATOM | 7071 | ND2 | ASN B | 478 | 1.716 | 15.922 | −35.667 | 1.00 | 24.20 | N |
| ATOM | 7072 | C | ASN B | 478 | .895 | 13.410 | −32.403 | 1.00 | 23.24 | C |
| ATOM | 7073 | O | ASN B | 478 | 1.969 | 12.907 | −32.073 | 1.00 | 24.27 | O |
| ATOM | 7074 | N | GLN B | 479 | −.225 | 13.285 | −31.702 | 1.00 | 23.14 | N |
| ATOM | 7075 | CA | GLN B | 479 | −.320 | 12.503 | −30.483 | 1.00 | 22.98 | C |
| ATOM | 7076 | CB | GLN B | 479 | −1.700 | 12.721 | −29.865 | 1.00 | 23.38 | C |
| ATOM | 7077 | CG | GLN B | 479 | −2.020 | 11.895 | −28.641 | 1.00 | 24.26 | C |
| ATOM | 7078 | CD | GLN B | 479 | −3.368 | 12.271 | −28.061 | 1.00 | 26.80 | C |
| ATOM | 7079 | OE1 | GLN B | 479 | −3.657 | 13.449 | −27.865 | 1.00 | 30.18 | O |
| ATOM | 7080 | NE2 | GLN B | 479 | −4.200 | 11.274 | −27.790 | 1.00 | 24.72 | N |
| ATOM | 7081 | C | GLN B | 479 | −.065 | 11.018 | −30.755 | 1.00 | 22.58 | C |
| ATOM | 7082 | O | GLN B | 479 | .721 | 10.379 | −30.049 | 1.00 | 22.72 | O |
| ATOM | 7083 | N | ILE B | 480 | −.724 | 10.477 | −31.778 | 1.00 | 22.44 | N |
| ATOM | 7084 | CA | ILE B | 480 | −.544 | 9.073 | −32.154 | 1.00 | 22.86 | C |
| ATOM | 7085 | CB | ILE B | 480 | −1.550 | 8.634 | −33.261 | 1.00 | 23.69 | C |
| ATOM | 7086 | CG1 | ILE B | 480 | −3.006 | 8.798 | −32.792 | 1.00 | 24.90 | C |
| ATOM | 7087 | CD1 | ILE B | 480 | −3.360 | 8.093 | −31.501 | 1.00 | 31.96 | C |
| ATOM | 7088 | CG2 | ILE B | 480 | −1.292 | 7.194 | −33.721 | 1.00 | 22.65 | C |
| ATOM | 7089 | C | ILE B | 480 | .904 | 8.810 | −32.587 | 1.00 | 22.61 | C |
| ATOM | 7090 | O | ILE B | 480 | 1.503 | 7.805 | −32.190 | 1.00 | 22.31 | O |
| ATOM | 7091 | N | ASN B | 481 | 1.462 | 9.730 | −33.376 | 1.00 | 22.22 | N |
| ATOM | 7092 | CA | ASN B | 481 | 2.840 | 9.605 | −33.877 | 1.00 | 21.96 | C |
| ATOM | 7093 | CB | ASN B | 481 | 3.184 | 10.740 | −34.848 | 1.00 | 20.87 | C |
| ATOM | 7094 | CG | ASN B | 481 | 2.561 | 10.546 | −36.216 | 1.00 | 20.51 | C |
| ATOM | 7095 | OD1 | ASN B | 481 | 2.548 | 11.462 | −37.037 | 1.00 | 22.71 | O |
| ATOM | 7096 | ND2 | ASN B | 481 | 2.045 | 9.352 | −36.471 | 1.00 | 13.96 | N |
| ATOM | 7097 | C | ASN B | 481 | 3.900 | 9.522 | −32.792 | 1.00 | 22.34 | C |
| ATOM | 7098 | O | ASN B | 481 | 4.827 | 8.724 | −32.902 | 1.00 | 21.99 | O |
| ATOM | 7099 | N | LYS B | 482 | 3.765 | 10.347 | −31.754 | 1.00 | 23.21 | N |
| ATOM | 7100 | CA | LYS B | 482 | 4.743 | 10.347 | −30.668 | 1.00 | 24.53 | C |
| ATOM | 7101 | CB | LYS B | 482 | 4.694 | 11.648 | −29.841 | 1.00 | 25.25 | C |
| ATOM | 7102 | CG | LYS B | 482 | 3.522 | 11.800 | −28.886 | 1.00 | 30.59 | C |
| ATOM | 7103 | CD | LYS B | 482 | 3.857 | 11.252 | −27.498 | 1.00 | 35.91 | C |
| ATOM | 7104 | CE | LYS B | 482 | 2.596 | 10.893 | −26.724 | 1.00 | 34.49 | C |
| ATOM | 7105 | NZ | LYS B | 482 | 2.879 | 9.908 | −25.629 | 1.00 | 30.24 | N |
| ATOM | 7106 | C | LYS B | 482 | 4.632 | 9.087 | −29.807 | 1.00 | 24.02 | C |
| ATOM | 7107 | O | LYS B | 482 | 5.652 | 8.568 | −29.347 | 1.00 | 24.51 | O |
| ATOM | 7108 | N | CYS B | 483 | 3.403 | 8.590 | −29.619 | 1.00 | 23.01 | N |
| ATOM | 7109 | CA | CYS B | 483 | 3.169 | 7.311 | −28.932 | 1.00 | 22.14 | C |
| ATOM | 7110 | CB | CYS B | 483 | 1.674 | 6.997 | −28.824 | 1.00 | 21.62 | C |
| ATOM | 7111 | SG | CYS B | 483 | .765 | 7.955 | −27.605 | 1.00 | 23.52 | S |
| ATOM | 7112 | C | CYS B | 483 | 3.873 | 6.167 | −29.665 | 1.00 | 21.73 | C |
| ATOM | 7113 | O | CYS B | 483 | 4.547 | 5.336 | −29.047 | 1.00 | 21.09 | O |
| ATOM | 7114 | N | LEU B | 484 | 3.713 | 6.139 | −30.985 | 1.00 | 21.62 | N |
| ATOM | 7115 | CA | LEU B | 484 | 4.356 | 5.129 | −31.819 | 1.00 | 22.68 | C |
| ATOM | 7116 | CB | LEU B | 484 | 3.743 | 5.120 | −33.220 | 1.00 | 22.30 | C |
| ATOM | 7117 | CG | LEU B | 484 | 2.377 | 4.427 | −33.304 | 1.00 | 22.82 | C |
| ATOM | 7118 | CD1 | LEU B | 484 | 1.528 | 5.009 | −34.414 | 1.00 | 22.21 | C |
| ATOM | 7119 | CD2 | LEU B | 484 | 2.550 | 2.935 | −33.492 | 1.00 | 20.44 | C |
| ATOM | 7120 | C | LEU B | 484 | 5.869 | 5.327 | −31.872 | 1.00 | 23.23 | C |
| ATOM | 7121 | O | LEU B | 484 | 6.624 | 4.35S | −31.905 | 1.00 | 22.55 | O |
| ATOM | 7122 | N | GLU B | 485 | 6.294 | 6.587 | −31.849 | 1.00 | 24.79 | N |
| ATOM | 7123 | CA | GLU B | 485 | 7.706 | 6.950 | −31.806 | 1.00 | 27.77 | C |
| ATOM | 7124 | CB | GLU B | 485 | 7.863 | 8.470 | −31.925 | 1.00 | 27.60 | C |
| ATOM | 7125 | CG | GLU B | 485 | 9.269 | 8.954 | −32.256 | 1.00 | 34.07 | C |
| ATOM | 7126 | CD | GLU B | 485 | 9.346 | 10.465 | −32.458 | 1.00 | 34.16 | C |
| ATOM | 7127 | OE1 | GLU B | 485 | 8.341 | 11.167 | −32.187 | 1.00 | 41.74 | O |
| ATOM | 7128 | OE2 | GLU B | 485 | 10.419 | 10.951 | −32.892 | 1.00 | 42.88 | O |
| ATOM | 7129 | C | GLU B | 485 | 8.377 | 6.431 | −30.530 | 1.00 | 26.46 | C |
| ATOM | 7130 | O | GLU B | 485 | 9.461 | 5.851 | −30.592 | 1.00 | 26.21 | O |
| ATOM | 7131 | N | LEU B | 486 | 7.737 | 6.614 | −29.378 | 1.00 | 26.26 | N |
| | | | | gad67.pdb | | | | | | |
| ATOM | 7132 | CA | LEU B | 486 | 8.347 | 6.138 | −28.132 | 1.00 | 26.31 | C |
| ATOM | 7133 | CB | LEU B | 486 | 7.974 | 7.010 | −26.915 | 1.00 | 27.52 | C |
| ATOM | 7134 | CG | LEU B | 486 | 6.564 | 7.219 | −26.384 | 1.00 | 30.60 | C |
| ATOM | 7135 | CD1 | LEU B | 486 | 6.397 | 6.421 | −25.126 | 1.00 | 37.04 | C |
| ATOM | 7136 | CD2 | LEU B | 486 | 6.353 | 8.685 | −26.057 | 1.00 | 31.71 | C |
| ATOM | 7137 | C | LEU B | 486 | 8.197 | 4.634 | −27.892 | 1.00 | 24.38 | C |
| ATOM | 7138 | O | LEU B | 486 | 8.901 | 4.068 | −27.061 | 1.00 | 24.32 | O |
| ATOM | 7139 | N | ALA B | 487 | 7.314 | 3.990 | −28.656 | 1.00 | 23.03 | N |
| ATOM | 7140 | CA | ALA B | 487 | 7.249 | 2.531 | −28.728 | 1.00 | 21.76 | C |

TABLE A-continued

| | | | | | | | | | |
|---|---|---|---|---|---|---|---|---|---|
| ATOM | 7141 | CB | ALA B | 487 | 5.937 | 2.086 | −29.332 | 1.00 | 21.18 | C |
| ATOM | 7142 | C | ALA B | 487 | 8.420 | 1.977 | −29.537 | 1.00 | 22.27 | C |
| ATOM | 7143 | O | ALA B | 487 | 8.973 | .927 | −29.194 | 1.00 | 21.51 | O |
| ATOM | 7144 | N | GLU B | 488 | 8.783 | 2.681 | −30.613 | 1.00 | 22.89 | N |
| ATOM | 7145 | CA | GLU B | 488 | 9.990 | 2.363 | −31.392 | 1.00 | 25.05 | C |
| ATOM | 7146 | CB | GLU B | 488 | 10.107 | 3.263 | −32.629 | 1.00 | 24.65 | C |
| ATOM | 7147 | CG | GLU B | 488 | 9.031 | 3.032 | −33.688 | 1.00 | 29.25 | C |
| ATOM | 7148 | CD | GLU B | 488 | 9.020 | 4.103 | −34.771 | 1.00 | 29.86 | C |
| ATOM | 7149 | OE1 | GLU B | 488 | 7.923 | 4.628 | −35.079 | 1.00 | 34.37 | O |
| ATOM | 7150 | OE2 | GLU B | 488 | 10.107 | 4.423 | −35.312 | 1.00 | 35.96 | O |
| ATOM | 7151 | C | GLU B | 488 | 11.231 | 2.517 | −30.520 | 1.00 | 22.88 | C |
| ATOM | 7152 | O | GLU B | 488 | 12.133 | 1.677 | −30.554 | 1.00 | 22.88 | O |
| ATOM | 7153 | N | TYR B | 489 | 11.249 | 3.593 | −29.734 | 1.00 | 22.50 | N |
| ATOM | 7154 | CA | TYR B | 489 | 12.326 | 3.874 | −28.786 | 1.00 | 21.92 | C |
| ATOM | 7155 | CB | TYR B | 489 | 12.053 | 5.190 | −28.048 | 1.00 | 21.70 | C |
| ATOM | 7156 | CG | TYR B | 489 | 13.027 | 5.488 | −26.925 | 1.00 | 22.66 | C |
| ATOM | 7157 | CD1 | TYR B | 489 | 12.723 | 5.151 | −25.604 | 1.00 | 21.44 | C |
| ATOM | 7158 | CE1 | TYR B | 489 | 13.615 | 5.422 | −24.568 | 1.00 | 21.66 | C |
| ATOM | 7159 | CZ | TYR B | 489 | 14.822 | 6.035 | −24.850 | 1.00 | 22.82 | C |
| ATOM | 7160 | OH | TYR B | 489 | 15.707 | 6.305 | −23.826 | 1.00 | 24.75 | O |
| ATOM | 7161 | CE2 | TYR B | 489 | 15.149 | 6.379 | −26.155 | 1.00 | 22.28 | C |
| ATOM | 7162 | CD2 | TYR B | 489 | 14.253 | 6.107 | −27.182 | 1.00 | 22.01 | C |
| ATOM | 7163 | C | TYR B | 489 | 12.509 | 2.737 | −27.791 | 1.00 | 22.01 | C |
| ATOM | 7164 | O | TYR B | 489 | 13.636 | 2.294 | −27.551 | 1.00 | 22.36 | O |
| ATOM | 7165 | N | LEU B | 490 | 11.395 | 2.284 | −27.212 | 1.00 | 21.24 | N |
| ATOM | 7166 | CA | LEU B | 490 | 11.385 | 1.177 | −26.262 | 1.00 | 20.37 | C |
| ATOM | 7167 | CB | LEU B | 490 | 9.958 | .906 | −25.782 | 1.00 | 20.90 | C |
| ATOM | 7168 | CG | LEU B | 490 | 9.649 | .177 | −24.469 | 1.00 | 21.93 | C |
| ATOM | 7169 | CD1 | LEU B | 490 | 8.256 | −.398 | −24.575 | 1.00 | 23.95 | C |
| ATOM | 7170 | CD2 | LEU B | 490 | 10.630 | −.923 | −24.099 | 1.00 | 19.54 | C |
| ATOM | 7171 | C | LEU B | 490 | 11.941 | −.079 | −26.911 | 1.00 | 19.73 | C |
| ATOM | 7172 | O | LEU B | 490 | 12.846 | −.713 | −26.369 | 1.00 | 20.15 | O |
| ATOM | 7173 | N | TYR B | 491 | 11.388 | −.434 | −28.067 | 1.00 | 19.60 | N |
| ATOM | 7174 | CA | TYR B | 491 | 11.796 | −1.638 | −28.787 | 1.00 | 20.73 | C |
| ATOM | 7175 | CB | TYR B | 491 | 11.010 | −1.784 | −30.098 | 1.00 | 20.76 | C |
| ATOM | 7176 | CG | TYR B | 491 | 11.435 | −2.962 | −30.958 | 1.00 | 20.72 | C |
| ATOM | 7177 | CD1 | TYR B | 491 | 12.021 | −2.765 | −32.210 | 1.00 | 19.33 | C |
| ATOM | 7178 | CE1 | TYR B | 491 | 12.412 | −3.846 | −32.998 | 1.00 | 16.66 | C |
| ATOM | 7179 | CZ | TYR B | 491 | 12.224 | −5.137 | −32.531 | 1.00 | 19.14 | C |
| ATOM | 7180 | OH | TYR B | 491 | 12.607 | −6.224 | −33.296 | 1.00 | 21.91 | O |
| ATOM | 7181 | CE2 | TYR B | 491 | 11.646 | −5.354 | −31.294 | 1.00 | 17.93 | C |
| ATOM | 7182 | CD2 | TYR B | 491 | 11.258 | −4.270 | −30.514 | 1.00 | 20.03 | C |
| ATOM | 7183 | C | TYR B | 491 | 13.306 | −1.652 | −29.034 | 1.00 | 21.55 | C |
| ATOM | 7184 | O | TYR B | 491 | 13.969 | −2.639 | −28.731 | 1.00 | 21.76 | O |
| ATOM | 7185 | N | ALA B | 492 | 13.836 | −.543 | −29.550 | 1.00 | 22.46 | N |
| ATOM | 7186 | CA | ALA B | 492 | 15.270 | −.399 | −29.814 | 1.00 | 24.24 | C |
| ATOM | 7187 | CB | ALA B | 492 | 15.543 | .918 | −30.534 | 1.00 | 23.71 | C |
| ATOM | 7188 | C | ALA B | 492 | 16.140 | −.508 | −28.553 | 1.00 | 25.26 | C |
| ATOM | 7189 | O | ALA B | 492 | 17.270 | −.999 | −28.620 | 1.00 | 25.21 | O |
| ATOM | 7190 | N | LYS B | 493 | 15.609 | −.054 | −27.416 | 1.00 | 26.34 | N |
| ATOM | 7191 | CA | LYS B | 493 | 16.343 | −.058 | −26.146 | 1.00 | 27.75 | C |
| ATOM | 7192 | CB | LYS B | 493 | 15.619 | .788 | −25.091 | 1.00 | 28.57 | C |
| ATOM | 7193 | CG | LYS B | 493 | 16.082 | 2.238 | −24.979 | 1.00 | 33.55 | C |
| ATOM | 7194 | CD | LYS B | 493 | 17.477 | 2.341 | −24.371 | 1.00 | 41.03 | C |
| ATOM | 7195 | CE | LYS B | 493 | 17.640 | 3.598 | −23.533 | 1.00 | 45.11 | C |
| ATOM | 7196 | NZ | LYS B | 493 | 16.928 | 3.481 | −22.219 | 1.00 | 46.62 | N |
| ATOM | 7197 | C | LYS B | 493 | 16.587 | −1.453 | −25.585 | 1.00 | 28.11 | C |
| ATOM | 7198 | O | LYS B | 493 | 17.640 | −1.711 | −25.006 | 1.00 | 29.51 | O |
| ATOM | 7199 | N | ILE B | 494 | 15.615 | −2.345 | −25.756 | 1.00 | 28.00 | N |
| | | | | | gad67.pdb | | | | | |
| ATOM | 7200 | CA | ILE B | 494 | 15.667 | −3.678 | −25.145 | 1.00 | 28.49 | C |
| ATOM | 7201 | CB | ILE B | 494 | 14.364 | −4.004 | −24.355 | 1.00 | 28.50 | C |
| ATOM | 7202 | CG1 | ILE B | 494 | 13.138 | −4.005 | −25.279 | 1.00 | 27.68 | C |
| ATOM | 7203 | CD1 | ILE B | 494 | 11.907 | −4.653 | −24.676 | 1.00 | 28.92 | C |
| ATOM | 7204 | CG2 | ILE B | 494 | 14.182 | −3.016 | −23.207 | 1.00 | 28.31 | C |
| ATOM | 7205 | C | ILE B | 494 | 15.972 | −4.780 | −26.158 | 1.00 | 28.84 | C |
| ATOM | 7206 | O | ILE B | 494 | 16.287 | −5.910 | −25.781 | 1.00 | 28.09 | O |
| ATOM | 7207 | N | LYS B | 495 | 15.884 | −4.419 | −27.437 | 1.00 | 30.48 | N |
| ATOM | 7208 | CA | LYS B | 495 | 16.089 | −5.319 | −28.584 | 1.00 | 32.90 | C |
| ATOM | 7209 | CB | LYS B | 495 | 16.185 | −4.484 | −29.867 | 1.00 | 32.99 | C |
| ATOM | 7210 | CG | LYS B | 495 | 15.972 | −5.245 | −31.166 | 1.00 | 34.91 | C |
| ATOM | 7211 | CD | LYS B | 495 | 15.877 | −4.281 | −32.352 | 1.00 | 35.17 | C |
| ATOM | 7212 | CE | LYS B | 495 | 17.237 | −3.735 | −32.775 | 1.00 | 39.09 | C |
| ATOM | 7213 | NZ | LYS B | 495 | 18.042 | −4.755 | −33.514 | 1.00 | 42.33 | N |
| ATOM | 7214 | C | LYS B | 495 | 17.315 | −6.233 | −28.475 | 1.00 | 33.11 | C |
| ATOM | 7215 | O | LYS B | 495 | 17.229 | −7.427 | −28.775 | 1.00 | 33.44 | O |
| ATOM | 7216 | N | ASN B | 496 | 18.446 | −5.670 | −28.053 | 1.00 | 33.42 | N |
| ATOM | 7217 | CA | ASN B | 496 | 19.704 | −6.419 | −28.000 | 1.00 | 34.74 | C |
| ATOM | 7218 | CB | ASN B | 496 | 20.704 | −5.852 | −29.020 | 1.00 | 35.06 | C |
| ATOM | 7219 | CG | ASN B | 496 | 20.207 | −5.958 | −30.454 | 1.00 | 36.29 | C |

TABLE A-continued

| ATOM | 7220 | OD1 | ASN B | 496 | 20.110 | −4.956 | −31.162 | 1.00 | 37.80 | O |
|---|---|---|---|---|---|---|---|---|---|---|
| ATOM | 7221 | ND2 | ASN B | 496 | 19.894 | −7.175 | −30.889 | 1.00 | 36.87 | N |
| ATOM | 7222 | C | ASN B | 496 | 20.340 | −6.483 | −26.604 | 1.00 | 34.96 | C |
| ATOM | 7223 | O | ASN B | 496 | 21.568 | −6.445 | −26.470 | 1.00 | 35.58 | O |
| ATOM | 7224 | N | ARG B | 497 | 19.504 | −6.583 | −25.572 | 1.00 | 34.57 | N |
| ATOM | 7225 | CA | ARG B | 497 | 19.985 | −6.678 | −24.193 | 1.00 | 33.92 | C |
| ATOM | 7226 | CB | ARG B | 497 | 19.272 | −5.668 | −23.298 | 1.00 | 33.98 | C |
| ATOM | 7227 | CG | ARG B | 497 | 19.661 | −4.227 | −23.584 | 1.00 | 36.23 | C |
| ATOM | 7228 | CD | ARG B | 497 | 19.089 | −3.275 | −22.554 | 1.00 | 40.21 | C |
| ATOM | 7229 | NE | ARG B | 497 | 19.665 | −3.484 | −21.227 | 1.00 | 42.69 | N |
| ATOM | 7230 | CZ | ARG B | 497 | 19.436 | −2.704 | −20.176 | 1.00 | 43.45 | C |
| ATOM | 7231 | NH1 | ARG B | 497 | 18.645 | −1.641 | −20.284 | 1.00 | 42.89 | N |
| ATOM | 7232 | NH2 | ARG B | 497 | 20.006 | −2.986 | −19.012 | 1.00 | 45.19 | N |
| ATOM | 7233 | C | ARG B | 497 | 19.808 | −8.086 | −23.644 | 1.00 | 33.40 | C |
| ATOM | 7234 | O | ARG B | 497 | 18.795 | −8.741 | −23.912 | 1.00 | 34.07 | O |
| ATOM | 7235 | N | GLU B | 498 | 20.799 | −8.544 | −22.881 | 1.00 | 31.62 | N |
| ATOM | 7236 | CA | GLU B | 498 | 20.785 | −9.889 | −22.295 | 1.00 | 30.21 | C |
| ATOM | 7237 | CB | GLU B | 498 | 22.131 | −10.191 | −21.630 | 1.00 | 30.67 | C |
| ATOM | 7242 | C | GLU B | 498 | 19.655 | −10.084 | −21.282 | 1.00 | 28.72 | C |
| ATOM | 7243 | O | GLU B | 498 | 19.160 | −11.196 | −21.103 | 1.00 | 28.79 | O |
| ATOM | 7244 | N | GLU B | 499 | 19.255 | −8.996 | −20.633 | 1.00 | 27.39 | N |
| ATOM | 7245 | CA | GLU B | 499 | 18.208 | −9.014 | −19.612 | 1.00 | 27.16 | C |
| ATOM | 7246 | CB | GLU B | 499 | 18.189 | −7.686 | −18.842 | 1.00 | 26.86 | C |
| ATOM | 7247 | CG | GLU B | 499 | 19.503 | −7.326 | −18.143 | 1.00 | 30.66 | C |
| ATOM | 7248 | CD | GLU B | 499 | 20.457 | −6.505 | −19.012 | 1.00 | 35.54 | C |
| ATOM | 7249 | OE1 | GLU B | 499 | 20.446 | −6.657 | −20.253 | 1.00 | 36.37 | O |
| ATOM | 7250 | OE2 | GLU B | 499 | 21.229 | −5.704 | −18.443 | 1.00 | 38.58 | O |
| ATOM | 7251 | C | GLU B | 499 | 16.819 | −9.281 | −20.202 | 1.00 | 26.32 | C |
| ATOM | 7252 | O | GLU B | 499 | 15.917 | −9.753 | −19.500 | 1.00 | 26.09 | O |
| ATOM | 7253 | N | PHE B | 500 | 16.659 | −8.978 | −21.489 | 1.00 | 25.53 | N |
| ATOM | 7254 | CA | PHE B | 500 | 15.363 | −9.066 | −22.153 | 1.00 | 25.57 | C |
| ATOM | 7255 | CB | PHE B | 500 | 14.877 | −7.675 | −22.565 | 1.00 | 24.83 | C |
| ATOM | 7256 | CG | PHE B | 500 | 14.803 | −6.704 | −21.427 | 1.00 | 24.77 | C |
| ATOM | 7257 | CD1 | PHE B | 500 | 15.800 | −5.749 | −21.247 | 1.00 | 22.92 | C |
| ATOM | 7258 | CE1 | PHE B | 500 | 15.738 | −4.847 | −20.184 | 1.00 | 24.86 | C |
| ATOM | 7259 | CZ | PHE B | 500 | 14.673 | −4.904 | −19.284 | 1.00 | 24.69 | C |
| ATOM | 7260 | CE2 | PHE B | 500 | 13.673 | −5.860 | −19.455 | 1.00 | 24.83 | C |
| ATOM | 7261 | CD2 | PHE B | 500 | 13.745 | −6.755 | −20.521 | 1.00 | 24.72 | C |
| ATOM | 7262 | C | PHE B | 500 | 15.383 | −9.990 | −23.359 | 1.00 | 26.48 | C |
| ATOM | 7263 | O | PHE B | 500 | 16.407 | −10.140 | −24.036 | 1.00 | 27.70 | O |
| ATOM | 7264 | N | GLU B | 501 | 14.237 | −10.612 | −23.616 | 1.00 | 26.51 | N |
| ATOM | 7265 | CA | GLU B | 501 | 14.072 | −11.492 | −24.760 | 1.00 | 26.73 | C |
| ATOM | 7266 | CB | GLU B | 501 | 14.076 | −12.953 | −24.312 | 1.00 | 26.39 | C |
| ATOM | 7267 | CG | GLU B | 501 | 14.097 | −13.964 | −25.450 | 1.00 | 29.99 | C |
| ATOM | 7268 | CD | GLU B | 501 | 14.171 | −15.407 | −24.968 | 1.00 | 30.81 | C |
| ATOM | 7269 | OE1 | GLU B | 501 | 13.533 | −16.273 | −25.611 | 1.00 | 36.25 | O |
| ATOM | 7270 | OE2 | GLU B | 501 | 14.866 | −15.676 | −23.956 | 1.00 | 34.43 | O |
| ATOM | 7271 | C | GLU B | 501 | 12.764 | −11.142 | −25.449 | 1.00 | 25.13 | C |
| | | | | | gad67.pdb | | | | | |
| ATOM | 7272 | O | GLU B | 501 | 11.710 | −11.109 | −24.809 | 1.00 | 24.79 | O |
| ATOM | 7273 | N | MET B | 502 | 12.843 | −10.858 | −26.745 | 1.00 | 24.29 | N |
| ATOM | 7274 | CA | MET B | 502 | 11.661 | −10.528 | −27.536 | 1.00 | 23.64 | C |
| ATOM | 7275 | CB | MET B | 502 | 12.051 | −9.884 | −28.872 | 1.00 | 23.46 | C |
| ATOM | 7276 | CG | MET B | 502 | 12.860 | −8.590 | −28.752 | 1.00 | 25.28 | C |
| ATOM | 7277 | SD | MET B | 502 | 12.290 | −7.439 | −27.475 | 1.00 | 28.24 | S |
| ATOM | 7278 | CE | MET B | 502 | 10.746 | −6.852 | −28.157 | 1.00 | 23.15 | C |
| ATOM | 7279 | C | MET B | 502 | 10.821 | −11.775 | −27.767 | 1.00 | 22.98 | C |
| ATOM | 7280 | O | MET B | 502 | 11.355 | −12.850 | −28.042 | 1.00 | 24.15 | O |
| ATOM | 7281 | N | VAL B | 503 | 9.507 | −11.624 | −27.640 | 1.00 | 22.27 | N |
| ATOM | 7282 | CA | VAL B | 503 | 8.575 | −12.745 | −27.755 | 1.00 | 21.55 | C |
| ATOM | 7283 | CB | VAL B | 503 | 7.173 | −12.360 | −27.206 | 1.00 | 21.42 | C |
| ATOM | 7284 | CG1 | VAL B | 503 | 6.142 | −13.442 | −27.477 | 1.00 | 21.03 | C |
| ATOM | 7285 | CG2 | VAL B | 503 | 7.266 | −12.104 | −25.721 | 1.00 | 20.84 | C |
| ATOM | 7286 | C | VAL B | 503 | 8.512 | −13.286 | −29.187 | 1.00 | 20.94 | C |
| ATOM | 7287 | O | VAL B | 503 | 8.425 | −14.491 | −29.396 | 1.00 | 21.83 | O |
| ATOM | 7288 | N | PHE B | 504 | 8.586 | −12.388 | −30.164 | 1.00 | 20.34 | N |
| ATOM | 7289 | CA | PHE B | 504 | 8.576 | −12.773 | −31.569 | 1.00 | 20.04 | C |
| ATOM | 7290 | CB | PHE B | 504 | 7.151 | −12.693 | −32.150 | 1.00 | 19.49 | C |
| ATOM | 7291 | CG | PHE B | 504 | 6.590 | −11.294 | −32.234 | 1.00 | 18.60 | C |
| ATOM | 7292 | CD1 | PHE B | 504 | 6.007 | −10.692 | −31.122 | 1.00 | 18.35 | C |
| ATOM | 7293 | CE1 | PHE B | 504 | 5.476 | −9.399 | −31.201 | 1.00 | 17.22 | C |
| ATOM | 7294 | CZ | PHE B | 504 | 5.524 | −8.703 | −32.405 | 1.00 | 18.56 | C |
| ATOM | 7295 | CE2 | PHE B | 504 | 6.099 | −9.300 | −33.528 | 1.00 | 18.23 | C |
| ATOM | 7296 | CD2 | PHE B | 504 | 6.622 | −10.588 | −33.437 | 1.00 | 18.49 | C |
| ATOM | 7297 | C | PHE B | 504 | 9.554 | −11.930 | −32.383 | 1.00 | 20.68 | C |
| ATOM | 7298 | O | PHE B | 504 | 9.899 | −10.811 | −31.996 | 1.00 | 19.54 | O |
| ATOM | 7299 | N | ASN B | 505 | 9.997 | −12.479 | −33.510 | 1.00 | 22.44 | N |
| ATOM | 7300 | CA | ASN B | 505 | 10.924 | −11.784 | −34.396 | 1.00 | 24.29 | C |
| ATOM | 7301 | CB | ASN B | 505 | 11.787 | −12.792 | −35.167 | 1.00 | 25.71 | C |
| ATOM | 7302 | CG | ASN B | 505 | 12.893 | −12.127 | −35.990 | 1.00 | 31.95 | C |

TABLE A-continued

| | | | | | | | | | |
|---|---|---|---|---|---|---|---|---|---|
| ATOM | 7303 | OD1 | ASN B | 505 | 13.293 | −10.982 | −35.729 | 1.00 | 35.70 | O |
| ATOM | 7304 | ND2 | ASN B | 505 | 13.397 | −12.852 | −36.989 | 1.00 | 35.51 | N |
| ATOM | 7305 | C | ASN B | 505 | 10.171 | −10.867 | −35.353 | 1.00 | 24.24 | C |
| ATOM | 7306 | O | ASN B | 505 | 9.424 | −11.332 | −36.215 | 1.00 | 24.79 | O |
| ATOM | 7307 | N | GLY B | 506 | 10.367 | −9.563 | −35.184 | 1.00 | 24.27 | N |
| ATOM | 7308 | CA | GLY B | 506 | 9.708 | −8.561 | −36.012 | 1.00 | 24.33 | C |
| ATOM | 7309 | C | GLY B | 506 | 9.555 | −7.234 | −35.295 | 1.00 | 25.24 | C |
| ATOM | 7310 | O | GLY B | 506 | 9.433 | −7.193 | −34.067 | 1.00 | 25.46 | O |
| ATOM | 7311 | N | GLU B | 507 | 9.573 | −6.147 | −36.065 | 1.00 | 25.61 | N |
| ATOM | 7312 | CA | GLU B | 507 | 9.345 | −4.811 | −35.526 | 1.00 | 25.67 | C |
| ATOM | 7313 | CB | GLU B | 507 | 9.794 | −3.734 | −36.516 | 1.00 | 25.44 | C |
| ATOM | 7314 | CG | GLU B | 507 | 11.301 | −3.646 | −36.715 | 1.00 | 30.43 | C |
| ATOM | 7318 | C | GLU B | 507 | 7.863 | −4.641 | −35.206 | 1.00 | 25.14 | C |
| ATOM | 7319 | O | GLU B | 507 | 7.009 | −5.015 | −36.014 | 1.00 | 24.90 | O |
| ATOM | 7320 | N | PRO B | 508 | 7.549 | −4.100 | −34.016 | 1.00 | 24.71 | N |
| ATOM | 7321 | CA | PRO B | 508 | 6.163 | −3.823 | −33.643 | 1.00 | 24.42 | C |
| ATOM | 7322 | CB | PRO B | 508 | 6.301 | −3.136 | −32.281 | 1.00 | 24.15 | C |
| ATOM | 7323 | CG | PRO B | 508 | 7.577 | −3.657 | −31.736 | 1.00 | 25.81 | C |
| ATOM | 7324 | CD | PRO B | 508 | 8.481 | −3.745 | −32.931 | 1.00 | 24.99 | C |
| ATOM | 7325 | C | PRO B | 508 | 5.459 | −2.900 | −34.638 | 1.00 | 23.85 | C |
| ATOM | 7326 | O | PRO B | 508 | 6.023 | −1.887 | −35.058 | 1.00 | 23.31 | O |
| ATOM | 7327 | N | GLU B | 509 | 4.233 | −3.266 | −35.007 | 1.00 | 23.64 | N |
| ATOM | 7328 | CA | GLU B | 509 | 3.424 | −2.484 | −35.941 | 1.00 | 23.14 | C |
| ATOM | 7329 | CB | GLU B | 509 | 2.504 | −3.402 | −36.748 | 1.00 | 22.73 | C |
| ATOM | 7330 | CG | GLU B | 509 | 3.222 | −4.504 | −37.522 | 1.00 | 23.87 | C |
| ATOM | 7331 | CD | GLU B | 509 | 2.276 | −5.316 | −38.385 | 1.00 | 23.92 | C |
| ATOM | 7332 | OE1 | GLU B | 509 | 1.860 | −6.411 | −37.949 | 1.00 | 22.71 | O |
| ATOM | 7333 | OE2 | GLU B | 509 | 1.939 | −4.845 | −39.494 | 1.00 | 23.82 | O |
| ATOM | 7334 | C | GLU B | 509 | 2.597 | −1.432 | −35.209 | 1.00 | 23.00 | C |
| ATOM | 7335 | O | GLU B | 509 | 2.147 | −.459 | −35.810 | 1.00 | 23.70 | O |
| ATOM | 7336 | N | HIS B | 510 | 2.397 | −1.640 | −33.911 | 1.00 | 22.78 | N |
| ATOM | 7337 | CA | HIS B | 510 | 1.637 | −.721 | −33.072 | 1.00 | 22.90 | C |
| ATOM | 7338 | CB | HIS B | 510 | .365 | −1.415 | −32.562 | 1.00 | 22.69 | C |
| ATOM | 7339 | CG | HIS B | 510 | −.801 | −.493 | −32.368 | 1.00 | 22.64 | C |
| ATOM | 7340 | ND1 | HIS B | 510 | −.750 | .616 | −31.551 | 1.00 | 21.47 | N |
| ATOM | 7341 | CE1 | HIS B | 510 | −1.917 | 1.232 | −31.572 | 1.00 | 23.42 | C |
| ATOM | 7342 | NE2 | HIS B | 510 | −2.730 | .557 | −32.364 | 1.00 | 23.51 | N |
| | | | | gad67.pdb | | | | | | |
| ATOM | 7343 | CD2 | HIS B | 510 | −2.057 | −.528 | −32.873 | 1.00 | 23.60 | C |
| ATOM | 7344 | C | HIS B | 510 | 2.536 | −.268 | −31.907 | 1.00 | 22.85 | C |
| ATOM | 7345 | O | HIS B | 510 | 3.765 | −.274 | −32.027 | 1.00 | 23.27 | O |
| ATOM | 7346 | N | THR B | 511 | 1.934 | .122 | −30.785 | 1.00 | 22.55 | N |
| ATOM | 7347 | CA | THR B | 511 | 2.705 | .507 | −29.607 | 1.00 | 21.98 | C |
| ATOM | 7348 | CB | THR B | 511 | 2.062 | 1.684 | −28.841 | 1.00 | 22.04 | C |
| ATOM | 7349 | OG1 | THR B | 511 | .834 | 1.259 | −28.241 | 1.00 | 22.03 | O |
| ATOM | 7350 | CG2 | THR B | 511 | 1.806 | 2.875 | −29.776 | 1.00 | 17.77 | C |
| ATOM | 7351 | C | THR B | 511 | 2.952 | −.671 | −28.667 | 1.00 | 22.02 | C |
| ATOM | 7352 | O | THR B | 511 | 3.656 | −.530 | −27.660 | 1.00 | 22.46 | O |
| ATOM | 7353 | N | ASN B | 512 | 2.381 | −1.830 | −29.005 | 1.00 | 21.47 | N |
| ATOM | 7354 | CA | ASN B | 512 | 2.622 | −3.068 | −28.263 | 1.00 | 21.12 | C |
| ATOM | 7355 | CB | ASN B | 512 | 1.689 | −4.204 | −28.721 | 1.00 | 20.44 | C |
| ATOM | 7356 | CG | ASN B | 512 | .239 | −3.767 | −28.872 | 1.00 | 21.44 | C |
| ATOM | 7357 | OD1 | ASN B | 512 | −.058 | −2.801 | −29.570 | 1.00 | 20.67 | O |
| ATOM | 7358 | ND2 | ASN B | 512 | −.672 | −4.500 | −28.237 | 1.00 | 20.21 | N |
| ATOM | 7359 | C | ASN B | 512 | 4.071 | −3.521 | −28.410 | 1.00 | 21.64 | C |
| ATOM | 7360 | O | ASN B | 512 | 4.577 | −3.666 | −29.531 | 1.00 | 21.31 | O |
| ATOM | 7361 | N | VAL B | 513 | 4.738 | −3.724 | −27.277 | 1.00 | 21.61 | N |
| ATOM | 7362 | CA | VAL B | 513 | 6.079 | −4.308 | −27.254 | 1.00 | 21.12 | C |
| ATOM | 7363 | CB | VAL B | 513 | 7.180 | −3.273 | −26.859 | 1.00 | 21.24 | C |
| ATOM | 7364 | CG1 | VAL B | 513 | 8.561 | −3.914 | −26.880 | 1.00 | 20.10 | C |
| ATOM | 7365 | CG2 | VAL B | 513 | 7.159 | −2.068 | −27.796 | 1.00 | 17.75 | C |
| ATOM | 7366 | C | VAL B | 513 | 6.052 | −5.502 | −26.303 | 1.00 | 21.00 | C |
| ATOM | 7367 | O | VAL B | 513 | 5.847 | −5.346 | −25.095 | 1.00 | 21.44 | O |
| ATOM | 7368 | N | CYS B | 514 | 6.236 | −6.694 | −26.865 | 1.00 | 20.23 | N |
| ATOM | 7369 | CA | CYS B | 514 | 6.088 | −7.938 | −26.118 | 1.00 | 20.19 | C |
| ATOM | 7370 | CB | CYS B | 514 | 5.168 | −8.899 | −26.869 | 1.00 | 19.52 | C |
| ATOM | 7371 | SG | CYS B | 514 | 3.492 | −8.259 | −27.094 | 1.00 | 20.58 | S |
| ATOM | 7372 | C | CYS B | 514 | 7.435 | −8.587 | −25.821 | 1.00 | 20.52 | C |
| ATOM | 7373 | O | CYS B | 514 | 8.183 | −8.942 | −26.741 | 1.00 | 21.80 | O |
| ATOM | 7374 | N | PHE B | 515 | 7.732 | −8.746 | −24.532 | 1.00 | 20.04 | N |
| ATOM | 7375 | CA | PHE B | 515 | 9.058 | −9.186 | −24.086 | 1.00 | 20.26 | C |
| ATOM | 7376 | CB | PHE B | 515 | 10.014 | −7.985 | −24.002 | 1.00 | 19.86 | C |
| ATOM | 7377 | CG | PHE B | 515 | 9.612 | −6.955 | −22.976 | 1.00 | 19.03 | C |
| ATOM | 7378 | CD1 | PHE B | 515 | 10.126 | −7.006 | −21.682 | 1.00 | 18.79 | C |
| ATOM | 7379 | CE1 | PHE B | 515 | 9.750 | −6.060 | −20.726 | 1.00 | 19.76 | C |
| ATOM | 7380 | CZ | PHE B | 515 | 8.858 | −5.048 | −21.066 | 1.00 | 20.02 | C |
| ATOM | 7381 | CE2 | PHE B | 515 | 8.340 | −4.986 | −22.356 | 1.00 | 20.32 | C |
| ATOM | 7382 | CD2 | PHE B | 515 | 8.717 | −5.937 | −23.301 | 1.00 | 18.61 | C |
| ATOM | 7383 | C | PHE B | 515 | 9.027 | −9.908 | −22.738 | 1.00 | 20.94 | C |
| ATOM | 7384 | O | PHE B | 515 | 8.127 | −9.688 | −21.918 | 1.00 | 21.03 | O |

TABLE A-continued

| | | | | | | | | | | |
|---|---|---|---|---|---|---|---|---|---|---|
| ATOM | 7385 | N | TRP B | 516 | 10.020 | −10.768 | −22.525 | 1.00 | 21.00 | N |
| ATOM | 7386 | CA | TRP B | 516 | 10.276 | −11.370 | −21.223 | 1.00 | 20.63 | C |
| ATOM | 7387 | CB | TRP B | 516 | 10.694 | −12.828 | −21.380 | 1.00 | 19.58 | C |
| ATOM | 7388 | CG | TRP B | 516 | 9.638 | −13.772 | −21.834 | 1.00 | 18.09 | C |
| ATOM | 7389 | CD1 | TRP B | 516 | 8.593 | −14.242 | −21.097 | 1.00 | 15.25 | C |
| ATOM | 7390 | NE1 | TRP B | 516 | 7.841 | −15.117 | −21.842 | 1.00 | 15.76 | N |
| ATOM | 7391 | CE2 | TRP B | 516 | 8.407 | −15.243 | −23.084 | 1.00 | 16.56 | C |
| ATOM | 7392 | CO2 | TRP B | 516 | 9.550 | −14.412 | −23.113 | 1.00 | 16.24 | C |
| ATOM | 7393 | CE3 | TRP B | 516 | 10.321 | −14.360 | −24.284 | 1.00 | 18.12 | C |
| ATOM | 7394 | CZ3 | TRP B | 516 | 9.928 | −15.134 | −25.381 | 1.00 | 15.60 | C |
| ATOM | 7395 | CH2 | TRP B | 516 | 8.783 | −15.949 | −25.318 | 1.00 | 16.94 | C |
| ATOM | 7396 | CZ2 | TRP B | 516 | 8.013 | −16.019 | −24.183 | 1.00 | 16.78 | C |
| ATOM | 7397 | C | TRP B | 516 | 11.431 | −10.633 | −20.549 | 1.00 | 21.72 | C |
| ATOM | 7398 | O | TRP B | 516 | 12.359 | −10.177 | −21.224 | 1.00 | 21.54 | O |
| ATOM | 7399 | N | TYR B | 517 | 11.382 | −10.523 | −19.223 | 1.00 | 22.11 | N |
| ATOM | 7400 | CA | TYR B | 517 | 12.597 | −10.251 | −18.470 | 1.00 | 22.55 | C |
| ATOM | 7401 | CB | TYR B | 517 | 12.356 | −9.409 | −17.214 | 1.00 | 22.35 | C |
| ATOM | 7402 | CG | TYR B | 517 | 13.583 | −9.336 | −16.314 | 1.00 | 23.51 | C |
| ATOM | 7403 | CD1 | TYR B | 517 | 13.753 | −10.233 | −15.256 | 1.00 | 23.14 | C |
| ATOM | 7404 | CE1 | TYR B | 517 | 14.880 | −10.180 | −14.438 | 1.00 | 21.65 | C |
| ATOM | 7405 | CZ | TYR B | 517 | 15.855 | −9.227 | −14.674 | 1.00 | 22.90 | C |
| ATOM | 7406 | OH | TYR B | 517 | 16.968 | −9.173 | −13.863 | 1.00 | 23.04 | O |
| ATOM | 7407 | CE2 | TYR B | 517 | 15.716 | −8.327 | −15.722 | 1.00 | 22.58 | C |
| ATOM | 7408 | CD2 | TYR B | 517 | 14.585 | −8.387 | −16.536 | 1.00 | 23.74 | C |
| ATOM | 7409 | C | TYR B | 517 | 13.213 | −11.585 | −18.091 | 1.00 | 23.20 | C |
| ATOM | 7410 | O | TYR B | 517 | 12.548 | −12.441 | −17.497 | 1.00 | 22.29 | O |
| | | | gad67.pdb | | | | | | | |
| ATOM | 7411 | N | ILE B | 518 | 14.488 | −11.740 | −18.437 | 1.00 | 24.45 | N |
| ATOM | 7412 | CA | ILE B | 518 | 15.240 | −12.953 | −18.141 | 1.00 | 25.41 | C |
| ATOM | 7413 | CB | ILE B | 518 | 16.136 | −13.386 | −19.346 | 1.00 | 25.59 | C |
| ATOM | 7414 | CG1 | ILE B | 518 | 15.371 | −13.304 | −20.681 | 1.00 | 24.20 | C |
| ATOM | 7415 | CD1 | ILE B | 518 | 14.157 | −14.249 | −20.803 | 1.00 | 24.50 | C |
| ATOM | 7416 | CG2 | ILE B | 518 | 16.744 | −14.771 | −19.109 | 1.00 | 25.09 | C |
| ATOM | 7417 | C | ILE B | 518 | 16.102 | −12.713 | −16.898 | 1.00 | 26.32 | C |
| ATOM | 7418 | O | ILE B | 518 | 17.037 | −11.908 | −16.935 | 1.00 | 26.51 | O |
| ATOM | 7419 | N | PRO B | 519 | 15.782 | −13.400 | −15.786 | 1.00 | 27.55 | N |
| ATOM | 7420 | CA | PRO B | 519 | 16.611 | −13.289 | −14.582 | 1.00 | 28.67 | C |
| ATOM | 7421 | CB | PRO B | 519 | 15.835 | −14.098 | −13.534 | 1.00 | 28.59 | C |
| ATOM | 7422 | CG | PRO B | 519 | 14.477 | −14.306 | −14.107 | 1.00 | 28.86 | C |
| ATOM | 7423 | CD | PRO B | 519 | 14.647 | −14.316 | −15.587 | 1.00 | 27.68 | C |
| ATOM | 7424 | C | PRO B | 519 | 17.983 | −13.914 | −14.808 | 1.00 | 29.34 | C |
| ATOM | 7425 | O | PRO B | 519 | 18.103 | −14.861 | −15.589 | 1.00 | 29.06 | O |
| ATOM | 7426 | N | GLN B | 520 | 18.995 | −13.387 | −14.122 | 1.00 | 30.47 | N |
| ATOM | 7427 | CA | GLN B | 520 | 20.381 | −13.854 | −14.245 | 1.00 | 31.49 | C |
| ATOM | 7428 | CB | GLN B | 520 | 21.239 | −13.262 | −13.118 | 1.00 | 31.39 | C |
| ATOM | 7429 | CG | GLN B | 520 | 22.725 | −13.581 | −13.203 | 1.00 | 34.38 | C |
| ATOM | 7430 | CD | GLN B | 520 | 23.405 | −12.881 | −14.360 | 1.00 | 36.52 | C |
| ATOM | 7431 | OE1 | GLN B | 520 | 23.781 | −13.512 | −15.348 | 1.00 | 36.33 | O |
| ATOM | 7432 | NE2 | GLN B | 520 | 23.557 | −11.566 | −14.250 | 1.00 | 37.70 | N |
| ATOM | 7433 | C | GLN B | 520 | 20.526 | −15.381 | −14.279 | 1.00 | 31.95 | C |
| ATOM | 7434 | O | GLN B | 520 | 21.302 | −15.914 | −15.074 | 1.00 | 31.44 | O |
| ATOM | 7435 | N | SER B | 521 | 19.768 | −16.072 | −13.429 | 1.00 | 33.17 | N |
| ATOM | 7436 | CA | SER B | 521 | 19.852 | −17.532 | −13.312 | 1.00 | 34.69 | C |
| ATOM | 7437 | CB | SER B | 521 | 19.066 | −18.027 | −12.090 | 1.00 | 35.01 | C |
| ATOM | 7438 | OG | SER B | 521 | 17.702 | −17.649 | −12.161 | 1.00 | 34.84 | O |
| ATOM | 7439 | C | SER B | 521 | 19.393 | −18.280 | −14.564 | 1.00 | 36.09 | C |
| ATOM | 7440 | O | SER B | 521 | 19.708 | −19.458 | −14.735 | 1.00 | 36.29 | O |
| ATOM | 7441 | N | LEU B | 522 | 18.657 | −17.598 | −15.438 | 1.00 | 37.41 | N |
| ATOM | 7442 | CA | LEU B | 522 | 18.139 | −18.231 | −16.647 | 1.00 | 38.90 | C |
| ATOM | 7443 | CB | LEU B | 522 | 16.634 | −17.965 | −16.804 | 1.00 | 38.91 | C |
| ATOM | 7444 | CG | LEU B | 522 | 15.673 | −18.577 | −15.774 | 1.00 | 38.89 | C |
| ATOM | 7445 | CD1 | LEU B | 522 | 14.258 | −18.064 | −15.996 | 1.00 | 39.58 | C |
| ATOM | 7446 | CD2 | LEU B | 522 | 15.696 | −20.102 | −15.799 | 1.00 | 38.51 | C |
| ATOM | 7447 | C | LEU B | 522 | 18.896 | −17.861 | −17.928 | 1.00 | 40.22 | C |
| ATOM | 7448 | O | LEU B | 522 | 18.697 | −18.486 | −18.967 | 1.00 | 40.65 | O |
| ATOM | 7449 | N | ARG B | 523 | 19.767 | −16.858 | −17.853 | 1.00 | 41.36 | N |
| ATOM | 7450 | CA | ARG B | 523 | 20.495 | −16.383 | −19.034 | 1.00 | 43.28 | C |
| ATOM | 7451 | CB | ARG B | 523 | 21.195 | −15.048 | −18.739 | 1.00 | 42.74 | C |
| ATOM | 7452 | CG | ARG B | 523 | 20.209 | −13.914 | −18.467 | 1.00 | 39.81 | C |
| ATOM | 7453 | CD | ARG B | 523 | 20.853 | −12.681 | −17.871 | 1.00 | 36.66 | C |
| ATOM | 7454 | NE | ARG B | 523 | 19.860 | −11.855 | −17.181 | 1.00 | 36.63 | N |
| ATOM | 7455 | CZ | ARG B | 523 | 20.111 | −10.689 | −16.588 | 1.00 | 34.13 | C |
| ATOM | 7456 | NH1 | ARG B | 523 | 19.130 | −10.030 | −15.988 | 1.00 | 32.06 | N |
| ATOM | 7457 | NH2 | ARG B | 523 | 21.335 | −10.174 | −16.592 | 1.00 | 34.28 | N |
| ATOM | 7458 | C | ARG B | 523 | 21.465 | −17.439 | −19.585 | 1.00 | 45.58 | C |
| ATOM | 7459 | O | ARG B | 523 | 22.443 | −17.805 | −18.930 | 1.00 | 45.90 | O |
| ATOM | 7460 | N | GLY B | 524 | 21.158 | −17.934 | −20.785 | 1.00 | 47.93 | N |
| ATOM | 7461 | CA | GLY B | 524 | 21.935 | −18.992 | −21.442 | 1.00 | 50.71 | C |
| ATOM | 7462 | C | GLY B | 524 | 21.859 | −20.349 | −20.755 | 1.00 | 52.39 | C |
| ATOM | 7463 | O | GLY B | 524 | 22.795 | −20.741 | −20.055 | 1.00 | 52.04 | O |

TABLE A-continued

| | | | | | | | | | |
|---|---|---|---|---|---|---|---|---|---|
| ATOM | 7464 | N | VAL B | 525 | 20.760 | −21.076 | −20.972 | 1.00 | 54.07 | N |
| ATOM | 7465 | CA | VAL B | 525 | 20.520 | −22.344 | −20.258 | 1.00 | 55.67 | C |
| ATOM | 7466 | CB | VAL B | 525 | 19.194 | −22.312 | −19.433 | 1.00 | 55.49 | C |
| ATOM | 7467 | CG1 | VAL B | 525 | 18.731 | −23.713 | −19.049 | 1.00 | 57.06 | C |
| ATOM | 7468 | CG2 | VAL B | 525 | 19.387 | −21.474 | −18.181 | 1.00 | 54.85 | C |
| ATOM | 7469 | C | VAL B | 525 | 20.706 | −23.655 | −21.060 | 1.00 | 56.71 | C |
| ATOM | 7470 | O | VAL B | 525 | 21.422 | −24.546 | −20.589 | 1.00 | 57.32 | O |
| ATOM | 7471 | N | PRO B | 526 | 20.089 | −23.791 | −22.259 | 1.00 | 57.26 | N |
| ATOM | 7472 | CA | PRO B | 526 | 19.228 | −22.925 | −23.060 | 1.00 | 57.53 | C |
| ATOM | 7473 | CB | PRO B | 526 | 19.717 | −23.215 | −24.483 | 1.00 | 58.26 | C |
| ATOM | 7474 | CG | PRO B | 526 | 20.189 | −24.672 | −24.433 | 1.00 | 57.61 | C |
| ATOM | 7475 | CD | PRO B | 526 | 20.332 | −25.060 | −22.972 | 1.00 | 56.98 | C |
| ATOM | 7476 | C | PRO B | 526 | 17.732 | −23.261 | −22.942 | 1.00 | 57.42 | C |
| ATOM | 7477 | O | PRO B | 526 | 17.289 | −23.759 | −21.904 | 1.00 | 57.52 | O |
| ATOM | 7478 | N | ASP B | 527 | 16.979 | −22.999 | −24.012 | 1.00 | 57.03 | N |
| | | | | | gad67.pdb | | | | | |
| ATOM | 7479 | CA | ASP B | 527 | 15.522 | −23.170 | −24.034 | 1.00 | 57.04 | C |
| ATOM | 7480 | CB | ASP B | 527 | 14.940 | −22.646 | −25.354 | 1.00 | 57.24 | C |
| ATOM | 7481 | CG | ASP B | 527 | 13.444 | −22.358 | −25.270 | 1.00 | 58.01 | C |
| ATOM | 7482 | CD1 | ASP B | 527 | 12.876 | −22.360 | −24.154 | 1.00 | 58.29 | O |
| ATOM | 7483 | OD2 | ASP B | 527 | 12.833 | −22.117 | −26.332 | 1.00 | 59.08 | O |
| ATOM | 7484 | C | ASP B | 527 | 15.068 | −24.611 | −23.791 | 1.00 | 56.75 | C |
| ATOM | 7485 | O | ASP B | 527 | 15.434 | −25.529 | −24.531 | 1.00 | 56.52 | O |
| ATOM | 7486 | N | SER B | 528 | 14.260 | −24.782 | −22.746 | 1.00 | 56.52 | N |
| ATOM | 7487 | CA | SER B | 528 | 13.738 | −26.082 | −22.335 | 1.00 | 55.99 | C |
| ATOM | 7488 | CB | SER B | 528 | 14.670 | −26.714 | −21.296 | 1.00 | 56.01 | C |
| ATOM | 7490 | C | SER B | 528 | 12.327 | −25.932 | −21.752 | 1.00 | 55.80 | C |
| ATOM | 7491 | O | SER B | 528 | 11.959 | −24.844 | −21.300 | 1.00 | 55.91 | O |
| ATOM | 7492 | N | PRO B | 529 | 11.522 | −27.016 | −21.775 | 1.00 | 55.24 | N |
| ATOM | 7493 | CA | PRO B | 529 | 10.217 | −27.015 | −21.100 | 1.00 | 54.43 | C |
| ATOM | 7494 | CB | PRO B | 529 | 9.688 | −28.431 | −21.354 | 1.00 | 54.75 | C |
| ATOM | 7495 | CG | PRO B | 529 | 10.393 | −28.879 | −22.587 | 1.00 | 55.55 | C |
| ATOM | 7496 | CD | PRO B | 529 | 11.767 | −28.292 | −22.474 | 1.00 | 55.41 | C |
| ATOM | 7497 | C | PRO B | 529 | 10.306 | −26.743 | −19.593 | 1.00 | 53.30 | C |
| ATOM | 7498 | O | PRO B | 529 | 9.367 | −26.190 | −19.016 | 1.00 | 53.73 | O |
| ATOM | 7499 | N | GLN B | 530 | 11.420 | −27.132 | −18.972 | 1.00 | 51.39 | N |
| ATOM | 7500 | CA | GLN B | 530 | 11.675 | −26.839 | −17.559 | 1.00 | 49.55 | C |
| ATOM | 7501 | CB | GLN B | 530 | 12.793 | −27.730 | −17.011 | 1.00 | 50.04 | C |
| ATOM | 7506 | C | GLN B | 530 | 12.042 | −25.369 | −17.362 | 1.00 | 48.11 | C |
| ATOM | 7507 | O | GLN B | 530 | 11.716 | −24.769 | −16.331 | 1.00 | 48.55 | O |
| ATOM | 7508 | N | ARG B | 531 | 12.728 | −24.803 | −18.354 | 1.00 | 45.02 | N |
| ATOM | 7509 | CA | ARG B | 531 | 13.079 | −23.385 | −18.361 | 1.00 | 42.80 | C |
| ATOM | 7510 | CB | ARG B | 531 | 14.143 | −23.103 | −19.431 | 1.00 | 42.58 | C |
| ATOM | 7511 | CG | ARG B | 531 | 13.969 | −21.793 | −20.173 | 1.00 | 41.44 | C |
| ATOM | 7512 | CD | ARG B | 531 | 15.277 | −21.067 | −20.366 | 1.00 | 39.56 | C |
| ATOM | 7513 | NE | ARG B | 531 | 15.093 | −19.901 | −21.224 | 1.00 | 41.69 | N |
| ATOM | 7514 | CZ | ARG B | 531 | 15.840 | −18.802 | −21.178 | 1.00 | 40.90 | C |
| ATOM | 7515 | NH1 | ARG B | 531 | 16.826 | −18.704 | −20.302 | 1.00 | 41.23 | N |
| ATOM | 7516 | NH2 | ARG B | 531 | 15.594 | −17.795 | −22.005 | 1.00 | 40.21 | N |
| ATOM | 7517 | C | ARG B | 531 | 11.848 | −22.489 | −18.539 | 1.00 | 41.68 | C |
| ATOM | 7518 | O | ARG B | 531 | 11.768 | −21.410 | −17.943 | 1.00 | 41.33 | O |
| ATOM | 7519 | N | ARG B | 532 | 10.895 | −22.949 | −19.347 | 1.00 | 40.61 | N |
| ATOM | 7520 | CA | ARG B | 532 | 9.661 | −22.205 | −19.602 | 1.00 | 39.94 | C |
| ATOM | 7521 | CB | ARG B | 532 | 8.904 | −22.794 | −20.795 | 1.00 | 40.47 | C |
| ATOM | 7522 | CG | ARG B | 532 | 9.559 | −22.517 | −22.138 | 1.00 | 42.07 | C |
| ATOM | 7523 | CD | ARG B | 532 | 8.586 | −22.742 | −23.279 | 1.00 | 44.63 | C |
| ATOM | 7524 | NE | ARG B | 532 | 9.157 | −22.329 | −24.560 | 1.00 | 50.21 | N |
| ATOM | 7525 | CZ | ARG B | 532 | 9.675 | −23.161 | −25.461 | 1.00 | 53.02 | C |
| ATOM | 7526 | NH1 | ARG B | 532 | 9.694 | −24.472 | −25.238 | 1.00 | 54.67 | N |
| ATOM | 7527 | NH2 | ARG B | 532 | 10.171 | −22.679 | −26.594 | 1.00 | 53.50 | N |
| ATOM | 7528 | C | ARG B | 532 | 8.753 | −22.139 | −18.375 | 1.00 | 38.76 | C |
| ATOM | 7529 | O | ARG B | 532 | 8.086 | −21.128 | −18.151 | 1.00 | 38.32 | O |
| ATOM | 7530 | N | GLU B | 533 | 8.740 | −23.212 | −17.585 | 1.00 | 37.59 | N |
| ATOM | 7531 | CA | GLU B | 533 | 7.951 | −23.271 | −16.354 | 1.00 | 36.42 | C |
| ATOM | 7532 | CB | GLU B | 533 | 7.931 | −24.697 | −15.795 | 1.00 | 36.73 | C |
| ATOM | 7537 | C | GLU B | 533 | 8.477 | −22.298 | −15.299 | 1.00 | 35.55 | C |
| ATOM | 7538 | O | GLU B | 533 | 7.706 | −21.739 | −14.514 | 1.00 | 35.70 | O |
| ATOM | 7539 | N | LYS B | 534 | 9.794 | −22.102 | −15.291 | 1.00 | 34.32 | N |
| ATOM | 7540 | CA | LYS B | 534 | 10.435 | −21.165 | −14.378 | 1.00 | 32.61 | C |
| ATOM | 7541 | ca | LYS B | 534 | 11.930 | −21.474 | −14.241 | 1.00 | 32.88 | C |
| ATOM | 7546 | C | LYS B | 534 | 10.229 | −19.734 | −14.855 | 1.00 | 31.37 | C |
| ATOM | 7547 | O | LYS B | 534 | 10.005 | −18.831 | −14.044 | 1.00 | 31.93 | O |
| ATOM | 7548 | N | LEU B | 535 | 10.303 | −19.537 | −16.172 | 1.00 | 29.28 | N |
| ATOM | 7549 | CA | LEU B | 535 | 10.143 | −18.215 | −16.780 | 1.00 | 27.39 | C |
| ATOM | 7550 | Ca | LEU B | 535 | 10.527 | −18.258 | −18.265 | 1.00 | 26.78 | C |
| ATOM | 7551 | CG | LEU B | 535 | 10.453 | −16.962 | −19.079 | 1.00 | 25.60 | C |
| ATOM | 7552 | CD1 | LEU B | 535 | 11.419 | −15.902 | −18.543 | 1.00 | 25.75 | C |
| ATOM | 7553 | CD2 | LEU B | 535 | 10.730 | −17.242 | −20.541 | 1.00 | 26.44 | C |
| ATOM | 7554 | C | LEU B | 535 | 8.716 | −17.693 | −16.604 | 1.00 | 26.68 | C |
| ATOM | 7555 | O | LEU B | 535 | 8.502 | −16.505 | −16.356 | 1.00 | 26.39 | O |

TABLE A-continued

| | | | | | | | | | | |
|---|---|---|---|---|---|---|---|---|---|---|
| ATOM | 7556 | N | HIS B | 536 | 7.757 | −18.605 | −16.724 | 1.00 | 26.37 | N |
| ATOM | 7557 | CA | HIS B | 536 | 6.334 | −18.326 | −16.553 | 1.00 | 27.25 | C |
| ATOM | 7558 | CB | HIS B | 536 | 5.560 | −19.648 | −16.588 | 1.00 | 27.22 | C |
| ATOM | 7559 | CG | HIS B | 536 | 4.081 | −19.493 | −16.752 | 1.00 | 29.74 | C |
| | | | | gad67.pdb | | | | | | |
| ATOM | 7560 | ND1 | HIS B | 536 | 3.502 | −19.056 | −17.925 | 1.00 | 29.70 | N |
| ATOM | 7561 | CE1 | HIS B | 536 | 2.188 | −19.037 | −17.784 | 1.00 | 30.08 | C |
| ATOM | 7562 | NE2 | HIS B | 536 | 1.893 | −19.452 | −16.564 | 1.00 | 29.51 | N |
| ATOM | 7563 | CD2 | HIS B | 536 | 3.058 | −19.749 | −15.900 | 1.00 | 28.73 | C |
| ATOM | 7564 | C | HIS B | 536 | 6.021 | −17.571 | −15.260 | 1.00 | 27.16 | C |
| ATOM | 7565 | O | HIS B | 536 | 5.126 | −16.731 | −15.234 | 1.00 | 27.96 | O |
| ATOM | 7566 | N | LYS B | 537 | 6.766 | −17.870 | −14.200 | 1.00 | 26.98 | N |
| ATOM | 7567 | CA | LYS B | 537 | 6.500 | −17.316 | −12.873 | 1.00 | 26.76 | C |
| ATOM | 7568 | CB | LYS B | 537 | 7.002 | −18.278 | −11.791 | 1.00 | 27.34 | C |
| ATOM | 7569 | CD | LYS B | 537 | 6.163 | −19.545 | −11.649 | 1.00 | 30.14 | C |
| ATOM | 7570 | CD | LYS B | 537 | 6.951 | −20.686 | −11.011 | 1.00 | 34.22 | C |
| ATOM | 7571 | CE | LYS B | 537 | 7.078 | −20.528 | −9.499 | 1.00 | 38.76 | C |
| ATOM | 7572 | NZ | LYS B | 537 | 5.795 | −20.805 | −8.787 | 1.00 | 43.85 | N |
| ATOM | 7573 | C | LYS B | 537 | 7.109 | −15.935 | −12.669 | 1.00 | 25.62 | C |
| ATOM | 7574 | O | LYS B | 537 | 6.767 | −15.242 | −11.710 | 1.00 | 26.01 | O |
| ATOM | 7575 | N | VAL B | 538 | 8.002 | −15.542 | −13.577 | 1.00 | 24.64 | N |
| ATOM | 7576 | CA | VAL B | 538 | 8.764 | −14.294 | −13.459 | 1.00 | 22.36 | C |
| ATOM | 7577 | CB | VAL B | 538 | 9.943 | −14.250 | −14.476 | 1.00 | 22.47 | C |
| ATOM | 7578 | CG1 | VAL B | 538 | 10.626 | −12.890 | −14.478 | 1.00 | 18.47 | C |
| ATOM | 7579 | CG2 | VAL B | 538 | 10.954 | −15.352 | −14.163 | 1.00 | 19.96 | C |
| ATOM | 7580 | C | VAL B | 538 | 7.886 | −13.045 | −13.580 | 1.00 | 22.14 | C |
| ATOM | 7581 | O | VAL B | 538 | 7.927 | −12.175 | −12.707 | 1.00 | 22.60 | O |
| ATOM | 7582 | N | ALA B | 539 | 7.093 | −12.968 | −14.649 | 1.00 | 21.12 | N |
| ATOM | 7583 | CA | ALA B | 539 | 6.218 | −11.812 | −14.892 | 1.00 | 20.48 | C |
| ATOM | 7584 | CB | ALA B | 539 | 5.546 | −11.907 | −16.266 | 1.00 | 19.61 | C |
| ATOM | 7585 | C | ALA B | 539 | 5.177 | −11.535 | −13.788 | 1.00 | 20.06 | C |
| ATOM | 7586 | O | ALA B | 539 | 5.078 | −10.399 | −13.327 | 1.00 | 19.99 | O |
| ATOM | 7587 | N | PRO B | 540 | 4.390 | −12.557 | −13.374 | 1.00 | 20.12 | N |
| ATOM | 7588 | CA | PRO B | 540 | 3.431 | −12.344 | −12.278 | 1.00 | 21.22 | C |
| ATOM | 7589 | CB | PRO B | 540 | 2.775 | −13.721 | −12.095 | 1.00 | 21.04 | C |
| ATOM | 7590 | CD | PRO B | 540 | 3.646 | −14.679 | −12.806 | 1.00 | 20.36 | C |
| ATOM | 7591 | CD | PRO B | 540 | 4.290 | −13.924 | −13.915 | 1.00 | 19.79 | C |
| ATOM | 7592 | C | PRO B | 540 | 4.059 | −11.868 | −10.967 | 1.00 | 22.05 | C |
| ATOM | 7593 | O | PRO B | 540 | 3.443 | −11.075 | −10.252 | 1.00 | 23.08 | O |
| ATOM | 7594 | N | LYS B | 541 | 5.270 | −12.335 | −10.666 | 1.00 | 23.12 | N |
| ATOM | 7595 | CA | LYS B | 541 | 6.000 | −11.914 | −9.468 | 1.00 | 23.21 | C |
| ATOM | 7596 | CB | LYS B | 541 | 7.210 | −12.827 | −9.226 | 1.00 | 23.97 | C |
| ATOM | 7597 | CD | LYS B | 541 | 8.184 | −12.358 | −8.140 | 1.00 | 27.68 | C |
| ATOM | 7598 | CD | LYS B | 541 | 7.938 | −13.029 | −6.795 | 1.00 | 35.85 | C |
| ATOM | 7599 | CE | LYS B | 541 | 7.155 | −12.145 | −5.842 | 1.00 | 38.55 | C |
| ATOM | 7600 | NZ | LYS B | 541 | 7.294 | −12.627 | −4.437 | 1.00 | 39.35 | N |
| ATOM | 7601 | C | LYS B | 541 | 6.424 | −10.445 | −9.557 | 1.00 | 23.25 | C |
| ATOM | 7602 | O | LYS B | 541 | 6.235 | −9.685 | −8.603 | 1.00 | 23.39 | O |
| ATOM | 7603 | N | ILE B | 542 | 6.988 | −10.051 | −10.700 | 1.00 | 22.37 | N |
| ATOM | 7604 | CA | ILE B | 542 | 7.395 | −8.659 | −10.933 | 1.00 | 21.22 | C |
| ATOM | 7605 | CB | ILE B | 542 | 8.165 | −8.493 | −12.276 | 1.00 | 21.30 | C |
| ATOM | 7606 | CG1 | ILE B | 542 | 9.505 | −9.242 | −12.225 | 1.00 | 21.36 | C |
| ATOM | 7607 | CD1 | ILE B | 542 | 10.290 | −9.235 | −13.529 | 1.00 | 20.87 | C |
| ATOM | 7608 | CG2 | ILE B | 542 | 8.386 | −7.011 | −12.598 | 1.00 | 19.26 | C |
| ATOM | 7609 | C | ILE B | 542 | 6.187 | −7.715 | −10.890 | 1.00 | 21.54 | C |
| ATOM | 7610 | O | ILE B | 542 | 6.253 | −6.639 | −10.288 | 1.00 | 21.53 | O |
| ATOM | 7611 | N | LYS B | 543 | 5.093 | −8.131 | −11.530 | 1.00 | 21.98 | N |
| ATOM | 7612 | CA | LYS B | 543 | 3.837 | −7.382 | −11.519 | 1.00 | 22.75 | C |
| ATOM | 7613 | CB | LYS B | 543 | 2.790 | −8.081 | −12.406 | 1.00 | 22.81 | C |
| ATOM | 7614 | CD | LYS B | 543 | 1.390 | −7.448 | −12.420 | 1.00 | 22.39 | C |
| ATOM | 7615 | CD | LYS B | 543 | 1.414 | −5.978 | −12.837 | 1.00 | 25.77 | C |
| ATOM | 7616 | CE | LYS B | 543 | .013 | −5.432 | −13.058 | 1.00 | 23.39 | C |
| ATOM | 7617 | NZ | LYS B | 543 | −.598 | −5.954 | −14.313 | 1.00 | 24.67 | N |
| ATOM | 7618 | C | LYS B | 543 | 3.311 | −7.184 | −10.089 | 1.00 | 23.31 | C |
| ATOM | 7619 | O | LYS B | 543 | 2.850 | −6.097 | −9.744 | 1.00 | 23.94 | O |
| ATOM | 7620 | N | ALA B | 544 | 3.391 | −8.232 | −9.268 | 1.00 | 23.82 | N |
| ATOM | 7621 | CA | ALA B | 544 | 2.994 | −8.163 | −7.858 | 1.00 | 24.36 | C |
| ATOM | 7622 | CB | ALA B | 544 | 3.145 | −9.525 | −7.201 | 1.00 | 23.99 | C |
| ATOM | 7623 | C | ALA B | 544 | 3.802 | −7.120 | −7.092 | 1.00 | 25.13 | C |
| ATOM | 7624 | O | ALA B | 544 | 3.256 | −6.388 | −6.256 | 1.00 | 25.23 | O |
| ATOM | 7625 | N | LEU B | 545 | 5.101 | −7.057 | −7.386 | 1.00 | 25.49 | N |
| ATOM | 7626 | CA | LEU B | 545 | 6.005 | −6.107 | −6.742 | 1.00 | 26.04 | C |
| ATOM | 7627 | CB | LEU B | 545 | 7.470 | −6.514 | −6.957 | 1.00 | 26.10 | C |
| | | | | gad67.pdb | | | | | | |
| ATOM | 7628 | CG | LEU B | 545 | 7.921 | −7.878 | −6.410 | 1.00 | 26.29 | C |
| ATOM | 7629 | CD1 | LEU B | 545 | 9.301 | −8.257 | −6.947 | 1.00 | 25.72 | C |
| ATOM | 7630 | CD2 | LEU B | 545 | 7.907 | −7.920 | −4.880 | 1.00 | 26.04 | C |
| ATOM | 7631 | C | LEU B | 545 | 5.756 | −4.682 | −7.228 | 1.00 | 26.53 | C |
| ATOM | 7632 | O | LEU B | 545 | 5.862 | −3.735 | −6.448 | 1.00 | 27.23 | O |
| ATOM | 7633 | N | MET B | 546 | 5.420 | −4.539 | −8.512 | 1.00 | 27.26 | N |

TABLE A-continued

| | | | | | | | | | |
|---|---|---|---|---|---|---|---|---|---|
| ATOM | 7634 | CA | MET B | 546 | 5.041 | −3.246 | −9.095 | 1.00 | 27.98 | C |
| ATOM | 7635 | CB | MET B | 546 | 4.655 | −3.402 | −10.565 | 1.00 | 28.21 | C |
| ATOM | 7636 | CG | MET B | 546 | 5.798 | −3.321 | −11.534 | 1.00 | 29.86 | C |
| ATOM | 7637 | SD | MET B | 546 | 5.235 | −3.664 | −13.202 | 1.00 | 29.98 | S |
| ATOM | 7638 | CE | MET B | 546 | 6.806 | −3.621 | −14.057 | 1.00 | 30.87 | C |
| ATOM | 7639 | C | MET B | 546 | 3.855 | −2.648 | −8.366 | 1.00 | 27.23 | C |
| ATOM | 7640 | O | MET B | 546 | 3.885 | −1.486 | −7.955 | 1.00 | 27.33 | O |
| ATOM | 7641 | N | MET B | 547 | 2.810 | −3.458 | −8.224 | 1.00 | 26.78 | N |
| ATOM | 7642 | CA | MET B | 547 | 1.564 | −3.036 | −7.600 | 1.00 | 26.41 | C |
| ATOM | 7643 | CB | MET B | 547 | .479 | −4.095 | −7.819 | 1.00 | 26.00 | C |
| ATOM | 7644 | CG | MET B | 547 | −.026 | −4.135 | −9.267 | 1.00 | 24.54 | C |
| ATOM | 7645 | SD | MET B | 547 | −1.253 | −5.408 | −9.621 | 1.00 | 28.69 | S |
| ATOM | 7646 | CE | MET B | 547 | −2.688 | −4.764 | −8.761 | 1.00 | 19.61 | C |
| ATOM | 7647 | C | MET B | 547 | 1.751 | −2.712 | −6.119 | 1.00 | 26.12 | C |
| ATOM | 7648 | O | MET B | 547 | 1.121 | −1.789 | −5.605 | 1.00 | 25.96 | O |
| ATOM | 7649 | N | GLU B | 548 | 2.633 | −3.460 | −5.452 | 1.00 | 25.96 | N |
| ATOM | 7650 | CA | GLU B | 548 | 2.961 | −3.219 | −4.046 | 1.00 | 25.70 | C |
| ATOM | 7651 | CB | GLU B | 548 | 3.818 | −4.357 | −3.482 | 1.00 | 26.34 | C |
| ATOM | 7656 | C | GLU B | 548 | 3.660 | −1.877 | −3.842 | 1.00 | 25.18 | C |
| ATOM | 7657 | O | GLU B | 548 | 3.317 | −1.134 | −2.925 | 1.00 | 24.45 | O |
| ATOM | 7658 | N | SER B | 549 | 4.629 | −1.569 | −4.702 | 1.00 | 25.05 | N |
| ATOM | 7659 | CA | SER B | 549 | 5.335 | −.292 | −4.647 | 1.00 | 25.15 | C |
| ATOM | 7660 | CB | SER B | 549 | 6.690 | −.394 | −5.355 | 1.00 | 25.66 | C |
| ATOM | 7661 | OG | SER B | 549 | 6.539 | −.776 | −6.714 | 1.00 | 29.38 | O |
| ATOM | 7662 | C | SER B | 549 | 4.510 | .860 | −5.234 | 1.00 | 24.57 | C |
| ATOM | 7663 | O | SER B | 549 | 4.682 | 2.016 | −4.839 | 1.00 | 25.18 | O |
| ATOM | 7664 | N | GLY B | 550 | 3.629 | .541 | −6.182 | 1.00 | 23.68 | N |
| ATOM | 7665 | CA | GLY B | 550 | 2.760 | 1.535 | −6.825 | 1.00 | 22.74 | C |
| ATOM | 7666 | C | GLY B | 550 | 3.459 | 2.476 | −7.793 | 1.00 | 22.82 | C |
| ATOM | 7667 | O | GLY B | 550 | 2.912 | 3.516 | −8.155 | 1.00 | 22.36 | O |
| ATOM | 7668 | N | THR B | 551 | 4.664 | 2.105 | −8.219 | 1.00 | 22.95 | N |
| ATOM | 7669 | CA | THR B | 551 | 5.488 | 2.956 | −9.084 | 1.00 | 23.70 | C |
| ATOM | 7670 | CB | THR B | 551 | 6.962 | 2.522 | −9.061 | 1.00 | 24.11 | C |
| ATOM | 7671 | OG1 | THR B | 551 | 7.046 | 1.110 | −9.315 | 1.00 | 27.71 | O |
| ATOM | 7672 | CG2 | THR B | 551 | 7.608 | 2.847 | −7.712 | 1.00 | 24.18 | C |
| ATOM | 7673 | C | THR B | 551 | 5.026 | 2.942 | −10.536 | 1.00 | 23.31 | C |
| ATOM | 7674 | O | THR B | 551 | 5.121 | 3.951 | −11.234 | 1.00 | 23.22 | O |
| ATOM | 7675 | N | THR B | 552 | 4.544 | 1.786 | −10.982 | 1.00 | 23.02 | N |
| ATOM | 7676 | CA | THR B | 552 | 4.108 | 1.589 | −12.365 | 1.00 | 22.87 | C |
| ATOM | 7677 | CB | THR B | 552 | 5.322 | 1.443 | −13.347 | 1.00 | 22.83 | C |
| ATOM | 7678 | OG1 | THR B | 552 | 4.850 | 1.323 | −14.695 | 1.00 | 22.87 | O |
| ATOM | 7679 | CG2 | THR B | 552 | 6.179 | .228 | −13.001 | 1.00 | 22.45 | C |
| ATOM | 7680 | C | THR B | 552 | 3.190 | .372 | −12.458 | 1.00 | 22.33 | C |
| ATOM | 7681 | O | THR B | 552 | 3.084 | −.401 | −11.503 | 1.00 | 22.74 | O |
| ATOM | 7682 | N | MET B | 553 | 2.520 | .224 | −13.599 | 1.00 | 21.91 | N |
| ATOM | 7683 | CA | MET B | 553 | 1.708 | −.958 | −13.901 | 1.00 | 22.60 | C |
| ATOM | 7684 | CB | MET B | 553 | .228 | −.724 | −13.570 | 1.00 | 21.61 | C |
| ATOM | 7685 | CG | MET B | 553 | −.161 | −.977 | −12.124 | 1.00 | 22.72 | C |
| ATOM | 7686 | SD | MET B | 553 | −1.911 | −.633 | −11.798 | 1.00 | 24.90 | S |
| ATOM | 7687 | CE | MET B | 553 | −2.681 | −2.180 | −12.261 | 1.00 | 20.24 | C |
| ATOM | 7688 | C | MET B | 553 | 1.843 | −1.317 | −15.375 | 1.00 | 21.94 | C |
| ATOM | 7689 | O | MET B | 553 | 1.702 | −.463 | −16.246 | 1.00 | 22.12 | O |
| ATOM | 7690 | N | VAL B | 554 | 2.120 | −2.587 | −15.644 | 1.00 | 21.94 | N |
| ATOM | 7691 | CA | VAL B | 554 | 2.153 | −3.105 | −17.007 | 1.00 | 22.13 | C |
| ATOM | 7692 | CB | VAL B | 554 | 3.590 | −3.037 | −17.644 | 1.00 | 22.24 | C |
| ATOM | 7693 | CG1 | VAL B | 554 | 4.606 | −3.822 | −16.831 | 1.00 | 23.51 | C |
| ATOM | 7694 | CG2 | VAL B | 554 | 3.580 | −3.521 | −19.092 | 1.00 | 20.64 | C |
| ATOM | 7695 | C | VAL B | 554 | 1.572 | −4.517 | −17.017 | 1.00 | 22.32 | C |
| ATOM | 7696 | O | VAL B | 554 | 1.759 | −5.283 | −16.071 | 1.00 | 22.53 | O |
| ATOM | 7697 | N | GLY B | 555 | .847 | −4.843 | −18.083 | 1.00 | 22.85 | N |
| ATOM | 7698 | CA | GLY B | 555 | .206 | −6.146 | −18.213 | 1.00 | 22.95 | C |
| ATOM | 7699 | C | GLY B | 555 | 1.155 | −7.258 | −18.615 | 1.00 | 22.97 | C | gad67.pdb

| | | | | | | | | | |
|---|---|---|---|---|---|---|---|---|---|
| ATOM | 7700 | O | GLY B | 555 | 2.152 | −7.027 | −19.304 | 1.00 | 23.21 | O |
| ATOM | 7701 | N | TYR B | 556 | .837 | −8.468 | −18.171 | 1.00 | 22.59 | N |
| ATOM | 7702 | CA | TYR B | 556 | 1.537 | −9.670 | −18.603 | 1.00 | 23.33 | C |
| ATOM | 7703 | CB | TYR B | 556 | 2.442 | −10.210 | −17.487 | 1.00 | 22.52 | C |
| ATOM | 7704 | CG | TYR B | 556 | 1.696 | −10.846 | −16.328 | 1.00 | 21.89 | C |
| ATOM | 7705 | CD1 | TYR B | 556 | 1.324 | −10.095 | −15.211 | 1.00 | 20.17 | C |
| ATOM | 7706 | CE1 | TYR B | 556 | .632 | −10.680 | −14.147 | 1.00 | 19.99 | C |
| ATOM | 7707 | CZ | TYR B | 556 | .314 | −12.028 | −14.198 | 1.00 | 20.91 | C |
| ATOM | 7708 | OH | TYR B | 556 | −.364 | −12.620 | −13.160 | 1.00 | 23.00 | O |
| ATOM | 7709 | CE2 | TYR B | 556 | .673 | −12.792 | −15.295 | 1.00 | 22.19 | C |
| ATOM | 7710 | CD2 | TYR B | 556 | 1.365 | −12.202 | −16.348 | 1.00 | 20.70 | C |
| ATOM | 7711 | C | TYR B | 556 | .505 | −10.716 | −19.021 | 1.00 | 24.30 | C |
| ATOM | 7712 | O | TYR B | 556 | −.632 | −10.691 | −18.546 | 1.00 | 24.92 | O |
| ATOM | 7713 | N | GLN B | 557 | .901 | −11.632 | −19.904 | 1.00 | 24.41 | N |
| ATOM | 7714 | CA | GLN B | 557 | .012 | −12.700 | −20.361 | 1.00 | 24.48 | C |
| ATOM | 7715 | CB | GLN B | 557 | −1.137 | −12.144 | −21.228 | 1.00 | 24.37 | C |
| ATOM | 7716 | CG | GLN B | 557 | −.756 | −11.662 | −22.630 | 1.00 | 25.49 | C |

TABLE A-continued

| | | | | | | | | | |
|---|---|---|---|---|---|---|---|---|---|
| ATOM | 7717 | CD | GLN B | 557 | .067 | −10.390 | −22.616 | 1.00 | 28.13 | C |
| ATOM | 7718 | OE1 | GLN B | 557 | 1.263 | −10.411 | −22.906 | 1.00 | 31.90 | O |
| ATOM | 7719 | NE2 | GLN B | 557 | −.565 | −9.276 | −22.261 | 1.00 | 28.05 | N |
| ATOM | 7720 | C | GLN B | 557 | .767 | −13.794 | −21.114 | 1.00 | 25.33 | C |
| ATOM | 7721 | O | GLN B | 557 | 1.825 | −13.531 | −21.692 | 1.00 | 24.93 | O |
| ATOM | 7722 | N | PRO B | 558 | .224 | −15.027 | −21.107 | 1.00 | 26.15 | N |
| ATOM | 7723 | CA | PRO B | 558 | .763 | −16.060 | −21.979 | 1.00 | 27.10 | C |
| ATOM | 7724 | CB | PRO B | 558 | .381 | −17.351 | −21.256 | 1.00 | 27.01 | C |
| ATOM | 7725 | CG | PRO B | 558 | −.887 | −17.018 | −20.528 | 1.00 | 25.30 | C |
| ATOM | 7726 | CD | PRO B | 558 | −.910 | −15.524 | −20.301 | 1.00 | 26.07 | C |
| ATOM | 7727 | C | PRO B | 558 | .090 | −15.992 | −23.349 | 1.00 | 28.91 | C |
| ATOM | 7728 | O | PRO B | 558 | −.839 | −15.200 | −23.541 | 1.00 | 29.08 | O |
| ATOM | 7729 | N | GLN B | 559 | .567 | −16.802 | −24.289 | 1.00 | 30.20 | N |
| ATOM | 7730 | CA | GLN B | 559 | −.057 | −16.920 | −25.602 | 1.00 | 31.94 | C |
| ATOM | 7731 | CB | GLN B | 559 | .287 | −15.714 | −26.480 | 1.00 | 32.15 | C |
| ATOM | 7732 | CG | GLN B | 559 | −.647 | −15.531 | −27.664 | 1.00 | 33.29 | C |
| ATOM | 7733 | CD | GLN B | 559 | −.124 | −14.526 | −28.663 | 1.00 | 34.94 | C |
| ATOM | 7734 | OE1 | GLN B | 559 | −.578 | −13.383 | −28.698 | 1.00 | 38.07 | O |
| ATOM | 7735 | NE2 | GLN B | 559 | .846 | −14.940 | −29.478 | 1.00 | 34.72 | N |
| ATOM | 7736 | C | GLN B | 559 | .419 | −18.199 | −26.266 | 1.00 | 33.01 | C |
| ATOM | 7737 | O | GLN B | 559 | 1.618 | −18.396 | −26.438 | 1.00 | 32.72 | O |
| ATOM | 7738 | N | GLY B | 560 | −.518 | −19.067 | −26.637 | 1.00 | 34.42 | N |
| ATOM | 7739 | CA | GLY B | 560 | −.168 | −20.358 | −27.223 | 1.00 | 35.57 | C |
| ATOM | 7740 | C | GLY B | 560 | .689 | −21.146 | −26.251 | 1.00 | 36.79 | C |
| ATOM | 7741 | O | GLY B | 560 | .282 | −21.377 | −25.112 | 1.00 | 37.35 | O |
| ATOM | 7742 | N | ASP B | 561 | 1.883 | −21.538 | −26.688 | 1.00 | 37.54 | N |
| ATOM | 7743 | CA | ASP B | 561 | 2.812 | −22.273 | −25.822 | 1.00 | 38.18 | C |
| ATOM | 7744 | CB | ASP B | 561 | 3.526 | −23.392 | −26.603 | 1.00 | 38.80 | C |
| ATOM | 7745 | CG | ASP B | 561 | 4.440 | −22.867 | −27.709 | 1.00 | 42.36 | C |
| ATOM | 7746 | OD1 | ASP B | 561 | 4.450 | −21.646 | −27.989 | 1.00 | 43.80 | O |
| ATOM | 7747 | OD2 | ASP B | 561 | 5.157 | −23.697 | −28.311 | 1.00 | 47.05 | O |
| ATOM | 7748 | C | ASP B | 561 | 3.824 | −21.363 | −25.108 | 1.00 | 37.46 | C |
| ATOM | 7749 | O | ASP B | 561 | 4.695 | −21.845 | −24.379 | 1.00 | 38.11 | O |
| ATOM | 7750 | N | LYS B | 562 | 3.698 | −20.053 | −25.325 | 1.00 | 36.03 | N |
| ATOM | 7751 | CA | LYS B | 562 | 4.582 | −19.064 | −24.707 | 1.00 | 34.75 | C |
| ATOM | 7752 | CB | LYS B | 562 | 4.487 | −17.713 | −25.425 | 1.00 | 35.12 | C |
| ATOM | 7753 | CG | LYS B | 562 | 4.608 | −17.766 | −26.936 | 1.00 | 37.15 | C |
| ATOM | 7754 | CD | LYS B | 562 | 5.927 | −17.214 | −27.419 | 1.00 | 39.69 | C |
| ATOM | 7755 | CE | LYS B | 562 | 5.869 | −16.926 | −28.911 | 1.00 | 40.91 | C |
| ATOM | 7756 | NZ | LYS B | 562 | 5.861 | −18.172 | −29.729 | 1.00 | 41.50 | N |
| ATOM | 7757 | C | LYS B | 562 | 4.223 | −18.861 | −23.240 | 1.00 | 33.25 | C |
| ATOM | 7758 | O | LYS B | 562 | 3.046 | −18.766 | −22.882 | 1.00 | 33.71 | O |
| ATOM | 7759 | N | ALA B | 563 | 5.249 | −18.784 | −22.399 | 1.00 | 31.13 | N |
| ATOM | 7760 | CA | ALA B | 563 | 5.082 | −18.455 | −20.989 | 1.00 | 28.99 | C |
| ATOM | 7761 | CB | ALA B | 563 | 6.341 | −18.816 | −20.221 | 1.00 | 29.20 | C |
| ATOM | 7762 | C | ALA B | 563 | 4.767 | −16.966 | −20.831 | 1.00 | 27.14 | C |
| ATOM | 7763 | O | ALA B | 563 | 5.025 | −16.178 | −21.744 | 1.00 | 26.40 | O |
| ATOM | 7764 | N | ASN B | 564 | 4.211 | −16.595 | −19.674 | 1.00 | 25.40 | N |
| ATOM | 7765 | CA | ASN B | 564 | 3.864 | −15.204 | −19.365 | 1.00 | 23.52 | C |
| ATOM | 7766 | CB | ASN B | 564 | 3.669 | −15.002 | −17.860 | 1.00 | 23.12 | C |
| ATOM | 7767 | CG | ASN B | 564 | 2.422 | −15.672 | −17.327 | 1.00 | 24.51 | C | gad67.pdb

| | | | | | | | | | |
|---|---|---|---|---|---|---|---|---|---|
| ATOM | 7768 | OD1 | ASN B | 564 | 2.470 | −16.354 | −16.304 | 1.00 | 27.11 | O |
| ATOM | 7769 | ND2 | ASN B | 564 | 1.297 | −15.475 | −18.006 | 1.00 | 21.34 | N |
| ATOM | 7770 | C | ASN B | 564 | 4.930 | −14.234 | −19.829 | 1.00 | 22.61 | C |
| ATOM | 7771 | O | ASN B | 564 | 6.105 | −14.394 | −19.494 | 1.00 | 21.81 | O |
| ATOM | 7772 | N | PHE B | 565 | 4.516 | −13.238 | −20.605 | 1.00 | 21.22 | N |
| ATOM | 7773 | CA | PHE B | 565 | 5.415 | −12.163 | −20.997 | 1.00 | 21.00 | C |
| ATOM | 7774 | CB | PHE B | 565 | 5.923 | −12.337 | −22.437 | 1.00 | 19.72 | C |
| ATOM | 7775 | CG | PHE B | 565 | 4.835 | −12.489 | −23.469 | 1.00 | 17.11 | C |
| ATOM | 7776 | CD1 | PHE B | 565 | 4.414 | −13.752 | −23.872 | 1.00 | 15.40 | C |
| ATOM | 7777 | CE1 | PHE B | 565 | 3.417 | −13.902 | −24.839 | 1.00 | 14.25 | C |
| ATOM | 7778 | CZ | PHE B | 565 | 2.839 | −12.780 | −25.416 | 1.00 | 14.69 | C |
| ATOM | 7779 | CE2 | PHE B | 565 | 3.261 | −11.515 | −25.033 | 1.00 | 14.70 | C |
| ATOM | 7780 | CD2 | PHE B | 565 | 4.259 | −11.373 | −24.066 | 1.00 | 16.01 | C |
| ATOM | 7781 | C | PHE B | 565 | 4.756 | −10.807 | −20.806 | 1.00 | 21.36 | C |
| ATOM | 7782 | O | PHE B | 565 | 3.529 | −10.701 | −20.783 | 1.00 | 21.41 | O |
| ATOM | 7783 | N | PHE B | 566 | 5.580 | −9.777 | −20.660 | 1.00 | 21.21 | N |
| ATOM | 7784 | CA | PHE B | 566 | 5.078 | −8.419 | −20.582 | 1.00 | 22.03 | C |
| ATOM | 7785 | CB | PHE B | 566 | 6.140 | −7.474 | −20.011 | 1.00 | 22.04 | C |
| ATOM | 7786 | CG | PHE B | 566 | 6.511 | −7.777 | −18.593 | 1.00 | 22.74 | C |
| ATOM | 7787 | CD1 | PHE B | 566 | 5.668 | −7.412 | −17.547 | 1.00 | 22.57 | C |
| ATOM | 7788 | CE1 | PHE B | 566 | 6.005 | −7.699 | −16.227 | 1.00 | 22.86 | C |
| ATOM | 7789 | CZ | PHE B | 566 | 7.196 | −8.360 | −15.948 | 1.00 | 21.89 | C |
| ATOM | 7790 | CE2 | PHE B | 566 | 8.042 | −8.732 | −16.985 | 1.00 | 23.01 | C |
| ATOM | 7791 | CD2 | PHE B | 566 | 7.697 | −8.443 | −18.300 | 1.00 | 23.55 | C |
| ATOM | 7792 | C | PHE B | 566 | 4.625 | −7.941 | −21.952 | 1.00 | 22.13 | C |
| ATOM | 7793 | O | PHE B | 566 | 5.323 | −8.131 | −22.953 | 1.00 | 21.85 | O |
| ATOM | 7794 | N | ARG B | 567 | 3.436 | −7.352 | −21.987 | 1.00 | 22.28 | N |
| ATOM | 7795 | CA | ARG B | 567 | 2.988 | −6.611 | −23.149 | 1.00 | 22.77 | C |

TABLE A-continued

| | | | | | | | | | |
|---|---|---|---|---|---|---|---|---|---|
| ATOM | 7796 | CB | ARG B | 567 | 1.638 | −7.111 | −23.657 | 1.00 | 22.75 | C |
| ATOM | 7797 | CG | ARG B | 567 | 1.079 | −6.306 | −24.834 | 1.00 | 22.91 | C |
| ATOM | 7798 | CD | ARG B | 567 | −.424 | −6.120 | −24.709 | 1.00 | 25.15 | C |
| ATOM | 7799 | NE | ARG B | 567 | −.776 | −5.388 | −23.492 | 1.00 | 25.81 | N |
| ATOM | 7800 | CZ | ARG B | 567 | −2.018 | −5.162 | −23.070 | 1.00 | 27.05 | C |
| ATOM | 7801 | NH1 | ARG B | 567 | −2.219 | −4.485 | −21.946 | 1.00 | 22.38 | N |
| ATOM | 7802 | NH2 | ARG B | 567 | −3.062 | −5.611 | −23.760 | 1.00 | 25.04 | N |
| ATOM | 7803 | C | ARG B | 567 | 2.919 | −5.140 | −22.764 | 1.00 | 23.74 | C |
| ATOM | 7804 | O | ARG B | 567 | 1.951 | −4.673 | −22.151 | 1.00 | 23.48 | O |
| ATOM | 7805 | N | MET B | 568 | 3.981 | −4.425 | −23.105 | 1.00 | 23.78 | N |
| ATOM | 7806 | CA | MET B | 568 | 4.025 | −2.993 | −22.932 | 1.00 | 24.88 | C |
| ATOM | 7807 | CB | MET B | 568 | 5.477 | −2.522 | −22.996 | 1.00 | 25.15 | C |
| ATOM | 7808 | CG | MET B | 568 | 5.689 | −1.063 | −22.722 | 1.00 | 28.71 | C |
| ATOM | 7809 | SD | MET B | 568 | 5.301 | −.538 | −21.050 | 1.00 | 29.30 | S |
| ATOM | 7810 | CE | MET B | 568 | 5.881 | 1.145 | −21.198 | 1.00 | 27.80 | C |
| ATOM | 7811 | C | MET B | 568 | 3.175 | −2.358 | −24.034 | 1.00 | 24.53 | C |
| ATOM | 7812 | O | MET B | 568 | 3.115 | −2.878 | −25.145 | 1.00 | 24.47 | O |
| ATOM | 7813 | N | VAL B | 569 | 2.496 | −1.263 | −23.702 | 1.00 | 24.50 | N |
| ATOM | 7814 | CA | VAL B | 569 | 1.685 | −.504 | −24.658 | 1.00 | 24.89 | C |
| ATOM | 7815 | CB | VAL B | 569 | .198 | −.973 | −24.703 | 1.00 | 25.01 | C |
| ATOM | 7816 | CG1 | VAL B | 569 | .007 | −2.089 | −25.717 | 1.00 | 22.66 | C |
| ATOM | 7817 | CG2 | VAL B | 569 | −.303 | −1.394 | −23.319 | 1.00 | 26.01 | C |
| ATOM | 7818 | C | VAL B | 569 | 1.728 | .978 | −24.307 | 1.00 | 25.34 | C |
| ATOM | 7819 | O | VAL B | 569 | 1.879 | 1.340 | −23.137 | 1.00 | 25.61 | O |
| ATOM | 7820 | N | ILE B | 570 | 1.596 | 1.827 | −25.323 | 1.00 | 25.68 | N |
| ATOM | 7821 | CA | ILE B | 570 | 1.622 | 3.275 | −25.137 | 1.00 | 26.43 | C |
| ATOM | 7822 | CB | ILE B | 570 | 2.971 | 3.885 | −25.603 | 1.00 | 26.45 | C |
| ATOM | 7823 | CG1 | ILE B | 570 | 4.139 | 3.224 | −24.860 | 1.00 | 26.06 | C |
| ATOM | 7824 | CD1 | ILE B | 570 | 5.409 | 3.100 | −25.661 | 1.00 | 31.50 | C |
| ATOM | 7825 | CG2 | ILE B | 570 | 2.984 | 5.391 | −25.364 | 1.00 | 25.47 | C |
| ATOM | 7826 | C | ILE B | 570 | .452 | 3.952 | −25.852 | 1.00 | 27.54 | C |
| ATOM | 7827 | O | ILE B | 570 | .298 | 3.828 | −27.067 | 1.00 | 28.49 | O |
| ATOM | 7828 | N | SER B | 571 | −.372 | 4.661 | −25.085 | 1.00 | 27.75 | N |
| ATOM | 7829 | CA | SER B | 571 | −1.486 | 5.428 | −25.638 | 1.00 | 28.12 | C |
| ATOM | 7830 | CB | SER B | 571 | −2.773 | 4.596 | −25.618 | 1.00 | 28.01 | C |
| ATOM | 7831 | OG | SER B | 571 | −3.222 | 4.383 | −24.292 | 1.00 | 30.46 | O |
| ATOM | 7832 | C | SER B | 571 | −1.688 | 6.748 | −24.890 | 1.00 | 27.35 | C |
| ATOM | 7833 | O | SER B | 571 | −2.513 | 7.573 | −25.280 | 1.00 | 28.53 | O |
| ATOM | 7834 | N | ASN B | 572 | −.923 | 6.936 | −23.820 | 1.00 | 26.46 | N |
| ATOM | 7835 | CA | ASN B | 572 | −1.027 | 8.113 | −22.961 | 1.00 | 25.69 | C |
| ATOM | 7836 | CB | ASN B | 572 | −.684 | 7.715 | −21.517 | 1.00 | 25.61 | C |
| ATOM | 7837 | CG | ASN B | 572 | −.997 | 8.799 | −20.491 | 1.00 | 25.63 | C |
| ATOM | 7838 | OD1 | ASN B | 572 | −.714 | 8.624 | −19.306 | 1.00 | 26.49 | O |
| ATOM | 7839 | ND2 | ASN B | 572 | −1.586 | 9.906 | −20.929 | 1.00 | 24.29 | N |
| ATOM | 7840 | C | ASN B | 572 | −.098 | 9.226 | −23.446 | 1.00 | 24.78 | C |
| ATOM | 7841 | O | ASN B | 572 | 1.117 | 9.052 | −23.445 | 1.00 | 24.05 | O |
| ATOM | 7842 | N | PRO B | 573 | −.668 | 10.375 | −23.868 | 1.00 | 24.80 | N |
| ATOM | 7843 | CA | PRO B | 573 | .156 | 11.520 | −24.266 | 1.00 | 24.22 | C |
| ATOM | 7844 | CB | PRO B | 573 | −.876 | 12.553 | −24.728 | 1.00 | 24.12 | C |
| ATOM | 7845 | CG | PRO B | 573 | −2.144 | 12.148 | −24.071 | 1.00 | 26.01 | C |
| ATOM | 7846 | CD | PRO B | 573 | −2.106 | 10.661 | −24.021 | 1.00 | 24.44 | C |
| ATOM | 7847 | C | PRO B | 573 | 1.013 | 12.084 | −23.123 | 1.00 | 24.34 | C |
| ATOM | 7848 | O | PRO B | 573 | 1.940 | 12.861 | −23.375 | 1.00 | 24.56 | O |
| ATOM | 7849 | N | ALA B | 574 | .698 | 11.691 | −21.886 | 1.00 | 23.54 | N |
| ATOM | 7850 | CA | ALA B | 574 | 1.466 | 12.084 | −20.703 | 1.00 | 22.41 | C |
| ATOM | 7851 | CB | ALA B | 574 | .617 | 11.940 | −19.444 | 1.00 | 22.13 | C |
| ATOM | 7852 | C | ALA B | 574 | 2.767 | 11.291 | −20.557 | 1.00 | 22.11 | C |
| ATOM | 7853 | O | ALA B | 574 | 3.691 | 11.732 | −19.871 | 1.00 | 21.72 | O |
| ATOM | 7854 | N | ALA B | 575 | 2.828 | 10.119 | −21.188 | 1.00 | 21.22 | N |
| ATOM | 7855 | CA | ALA B | 575 | 4.021 | 9.282 | −21.134 | 1.00 | 21.95 | C |
| ATOM | 7856 | CB | ALA B | 575 | 3.724 | 7.876 | −21.647 | 1.00 | 21.07 | C |
| ATOM | 7857 | C | ALA B | 575 | 5.154 | 9.925 | −21.931 | 1.00 | 22.29 | C |
| ATOM | 7858 | O | ALA B | 575 | 4.949 | 10.399 | −23.050 | 1.00 | 21.95 | O |
| ATOM | 7859 | N | THR B | 576 | 6.341 | 9.961 | −21.330 | 1.00 | 23.01 | N |
| ATOM | 7860 | CA | THR B | 576 | 7.521 | 10.531 | −21.974 | 1.00 | 23.34 | C |
| ATOM | 7861 | CB | THR B | 576 | 8.060 | 11.763 | −21.199 | 1.00 | 23.49 | C |
| ATOM | 7862 | OG1 | THR B | 576 | 8.549 | 11.353 | −19.915 | 1.00 | 24.44 | O |
| ATOM | 7863 | CG2 | THR B | 576 | 6.971 | 12.832 | −21.022 | 1.00 | 22.47 | C |
| ATOM | 7864 | C | THR B | 576 | 8.619 | 9.479 | −22.088 | 1.00 | 23.60 | C |
| ATOM | 7865 | O | THR B | 576 | 8.477 | 8.363 | −21.582 | 1.00 | 23.39 | O |
| ATOM | 7866 | N | GLN B | 577 | 9.710 | 9.846 | −22.755 | 1.00 | 24.33 | N |
| ATOM | 7867 | CA | GLN B | 577 | 10.896 | 9.001 | −22.865 | 1.00 | 25.35 | C |
| ATOM | 7868 | CB | GLN B | 577 | 11.979 | 9.745 | −23.648 | 1.00 | 25.74 | C |
| ATOM | 7869 | CG | GLN B | 577 | 13.364 | 9.108 | −23.620 | 1.00 | 28.08 | C |
| ATOM | 7870 | CD | GLN B | 577 | 14.359 | 9.853 | −24.494 | 1.00 | 28.35 | C |
| ATOM | 7871 | OE1 | GLN B | 577 | 14.000 | 10.396 | −25.542 | 1.00 | 33.97 | O |
| ATOM | 7872 | NE2 | GLN B | 577 | 15.619 | 9.873 | −24.070 | 1.00 | 29.78 | N |
| ATOM | 7873 | C | GLN B | 577 | 11.423 | 8.558 | −21.496 | 1.00 | 24.81 | C |
| ATOM | 7874 | O | GLN B | 577 | 11.738 | 7.383 | −21.300 | 1.00 | 24.79 | O | gad67.pdb

TABLE A-continued

| | | | | | | | | | | |
|---|---|---|---|---|---|---|---|---|---|---|
| ATOM | 7875 | N | SER B | 578 | 11.501 | 9.494 | −20.551 | 1.00 | 24.68 | N |
| ATOM | 7876 | CA | SER B | 578 | 12.003 | 9.193 | −19.207 | 1.00 | 25.27 | C |
| ATOM | 7877 | CB | SER B | 578 | 12.184 | 10.476 | −18.397 | 1.00 | 25.36 | C |
| ATOM | 7878 | OG | SER B | 578 | 10.933 | 11.082 | −18.132 | 1.00 | 29.57 | O |
| ATOM | 7879 | C | SER B | 578 | 11.101 | 8.212 | −18.452 | 1.00 | 24.49 | C |
| ATOM | 7880 | O | SER B | 578 | 11.576 | 7.440 | −17.621 | 1.00 | 24.46 | O |
| ATOM | 7881 | N | ASP B | 579 | 9.805 | 8.252 | −18.750 | 1.00 | 24.43 | N |
| ATOM | 7882 | CA | ASP B | 579 | 8.844 | 7.289 | −18.205 | 1.00 | 24.17 | C |
| ATOM | 7883 | CB | ASP B | 579 | 7.411 | 7.725 | −18.516 | 1.00 | 23.16 | C |
| ATOM | 7884 | CG | ASP B | 579 | 7.014 | 8.994 | −17.787 | 1.00 | 23.43 | C |
| ATOM | 7885 | OD1 | ASP B | 579 | 7.140 | 9.034 | −16.547 | 1.00 | 25.44 | O |
| ATOM | 7886 | OD2 | ASP B | 579 | 6.562 | 9.952 | −18.449 | 1.00 | 24.87 | O |
| ATOM | 7887 | C | ASP B | 579 | 9.102 | 5.882 | −18.743 | 1.00 | 24.14 | C |
| ATOM | 7888 | O | ASP B | 579 | 8.914 | 4.894 | −18.033 | 1.00 | 23.71 | O |
| ATOM | 7889 | N | ILE B | 580 | 9.532 | 5.801 | −20.001 | 1.00 | 25.31 | N |
| ATOM | 7890 | CA | ILE B | 580 | 9.923 | 4.524 | −20.607 | 1.00 | 26.27 | C |
| ATOM | 7891 | CB | ILE B | 580 | 10.038 | 4.624 | −22.158 | 1.00 | 26.58 | C |
| ATOM | 7892 | CG1 | ILE B | 580 | 8.683 | 4.976 | −22.789 | 1.00 | 28.05 | C |
| ATOM | 7893 | CD1 | ILE B | 580 | 7.494 | 4.157 | −22.282 | 1.00 | 28.31 | C |
| ATOM | 7894 | CG2 | ILE B | 580 | 10.616 | 3.342 | −22.772 | 1.00 | 27.16 | C |
| ATOM | 7895 | C | ILE B | 580 | 11.235 | 4.042 | −19.998 | 1.00 | 26.46 | C |
| ATOM | 7896 | O | ILE B | 580 | 11.373 | 2.865 | −19.669 | 1.00 | 26.22 | O |
| ATOM | 7897 | N | ASP B | 581 | 12.186 | 4.966 | −19.847 | 1.00 | 27.36 | N |
| ATOM | 7898 | CA | ASP B | 581 | 13.460 | 4.676 | −19.196 | 1.00 | 27.86 | C |
| ATOM | 7899 | CB | ASP B | 581 | 14.370 | 5.907 | −19.192 | 1.00 | 28.11 | C |
| ATOM | 7900 | CG | ASP B | 581 | 14.905 | 6.245 | −20.570 | 1.00 | 29.86 | C |
| ATOM | 7901 | OD1 | ASP B | 581 | 15.055 | 5.327 | −21.406 | 1.00 | 29.29 | O |
| ATOM | 7902 | OD2 | ASP B | 581 | 15.183 | 7.437 | −20.816 | 1.00 | 33.41 | O |
| ATOM | 7903 | C | ASP B | 581 | 13.224 | 4.190 | −17.774 | 1.00 | 27.97 | C |
| | | | | gad67.pdb | | | | | | |
| ATOM | 7904 | O | ASP B | 581 | 13.810 | 3.192 | −17.355 | 1.00 | 28.79 | O |
| ATOM | 7905 | N | PHE B | 582 | 12.353 | 4.886 | −17.043 | 1.00 | 28.11 | N |
| ATOM | 7906 | CA | PHE B | 582 | 11.982 | 4.465 | −15.695 | 1.00 | 28.65 | C |
| ATOM | 7907 | CB | PHE B | 582 | 10.954 | 5.412 | −15.059 | 1.00 | 28.85 | C |
| ATOM | 7908 | CG | PHE B | 582 | 10.480 | 4.960 | −13.702 | 1.00 | 28.58 | C |
| ATOM | 7909 | CD1 | PHE B | 582 | 11.235 | 5.223 | −12.563 | 1.00 | 30.51 | C |
| ATOM | 7910 | CE1 | PHE B | 582 | 10.808 | 4.796 | −11.305 | 1.00 | 30.21 | C |
| ATOM | 7911 | CZ | PHE B | 582 | 9.612 | 4.093 | −11.183 | 1.00 | 30.32 | C |
| ATOM | 7912 | CE2 | PHE B | 582 | 8.854 | 3.819 | −12.314 | 1.00 | 29.79 | C |
| ATOM | 7913 | CD2 | PHE B | 582 | 9.292 | 4.251 | −13.566 | 1.00 | 28.38 | C |
| ATOM | 7914 | C | PHE B | 582 | 11.462 | 3.030 | −15.669 | 1.00 | 28.66 | C |
| ATOM | 7915 | O | PHE B | 582 | 11.929 | 2.224 | −14.864 | 1.00 | 29.61 | O |
| ATOM | 7916 | N | LEU B | 583 | 10.507 | 2.714 | −16.544 | 1.00 | 28.70 | N |
| ATOM | 7917 | CA | LEU B | 583 | 9.879 | 1.390 | −16.554 | 1.00 | 29.47 | C |
| ATOM | 7918 | CB | LEU B | 583 | 8.759 | 1.301 | −17.595 | 1.00 | 29.31 | C |
| ATOM | 7919 | CG | LEU B | 583 | 8.145 | −.104 | −17.626 | 1.00 | 30.34 | C |
| ATOM | 7920 | CD1 | LEU B | 583 | 6.796 | −.148 | −16.925 | 1.00 | 30.42 | C |
| ATOM | 7921 | CD2 | LEU B | 583 | 8.052 | −.622 | −19.044 | 1.00 | 27.88 | C |
| ATOM | 7922 | C | LEU B | 583 | 10.883 | .257 | −16.778 | 1.00 | 30.11 | C |
| ATOM | 7923 | O | LEU B | 583 | 10.858 | −.746 | −16.061 | 1.00 | 30.33 | O |
| ATOM | 7924 | N | ILE B | 584 | 11.749 | .427 | −17.776 | 1.00 | 31.02 | N |
| ATOM | 7925 | CA | ILE B | 584 | 12.809 | −.536 | −18.081 | 1.00 | 31.55 | C |
| ATOM | 7926 | CB | ILE B | 584 | 13.683 | −.059 | −19.282 | 1.00 | 32.09 | C |
| ATOM | 7927 | CG1 | ILE B | 584 | 12.846 | .023 | −20.566 | 1.00 | 32.17 | C |
| ATOM | 7928 | CD1 | ILE B | 584 | 11.989 | −1.214 | −20.846 | 1.00 | 35.39 | C |
| ATOM | 7929 | CG2 | ILE B | 584 | 14.907 | −.959 | −19.488 | 1.00 | 32.01 | C |
| ATOM | 7930 | C | ILE B | 584 | 13.674 | −.797 | −16.850 | 1.00 | 32.08 | C |
| ATOM | 7931 | O | ILE B | 584 | 13.910 | −1.950 | −16.487 | 1.00 | 32.91 | O |
| ATOM | 7932 | N | GLU B | 585 | 14.117 | .281 | −16.205 | 1.00 | 32.79 | N |
| ATOM | 7933 | CA | GLU B | 585 | 14.939 | .202 | −14.998 | 1.00 | 33.50 | C |
| ATOM | 7934 | CB | GLU B | 585 | 15.478 | 1.587 | −14.621 | 1.00 | 34.01 | C |
| ATOM | 7935 | CG | GLU B | 585 | 16.503 | 2.150 | −15.596 | 1.00 | 36.29 | C |
| ATOM | 7939 | C | GLU B | 585 | 14.179 | −.404 | −13.817 | 1.00 | 33.44 | C |
| ATOM | 7940 | O | GLU B | 585 | 14.765 | −1.104 | −12.990 | 1.00 | 33.64 | O |
| ATOM | 7941 | N | GLU B | 586 | 12.875 | −.142 | −13.750 | 1.00 | 33.39 | N |
| ATOM | 7942 | CA | GLU B | 586 | 12.032 | −.684 | −12.683 | 1.00 | 33.75 | C |
| ATOM | 7943 | CB | GLU B | 586 | 10.680 | .040 | −12.633 | 1.00 | 34.10 | C |
| ATOM | 7944 | CG | GLU B | 586 | 9.777 | −.370 | −11.461 | 1.00 | 37.29 | C |
| ATOM | 7945 | CD | GLU B | 586 | 10.179 | .247 | −10.124 | 1.00 | 39.96 | C |
| ATOM | 7946 | OE1 | GLU B | 586 | 9.412 | .085 | −9.148 | 1.00 | 41.69 | O |
| ATOM | 7947 | OE2 | GLU B | 586 | 11.249 | .891 | −10.040 | 1.00 | 41.87 | O |
| ATOM | 7948 | C | GLU B | 586 | 11.838 | −2.198 | −12.796 | 1.00 | 32.88 | C |
| ATOM | 7949 | O | GLU B | 586 | 11.893 | −2.903 | −11.786 | 1.00 | 32.84 | O |
| ATOM | 7950 | N | ILE B | 587 | 11.613 | −2.690 | −14.018 | 1.00 | 32.01 | N |
| ATOM | 7951 | CA | ILE B | 587 | 11.489 | −4.132 | −14.271 | 1.00 | 31.30 | C |
| ATOM | 7952 | CB | ILE B | 587 | 11.087 | −4.440 | −15.745 | 1.00 | 30.99 | C |
| ATOM | 7953 | CG1 | ILE B | 587 | 9.669 | −3.925 | −16.028 | 1.00 | 29.43 | C |
| ATOM | 7954 | CD1 | ILE B | 587 | 9.174 | −4.140 | −17.447 | 1.00 | 29.61 | C |
| ATOM | 7955 | CG2 | ILE B | 587 | 11.202 | −5.945 | −16.047 | 1.00 | 26.94 | C |
| ATOM | 7956 | C | ILE B | 587 | 12.786 | −4.863 | −13.906 | 1.00 | 32.53 | C |

TABLE A-continued

| | | | | | | | | | |
|---|---|---|---|---|---|---|---|---|---|
| ATOM | 7957 | O | ILE B | 587 | 12.756 | −5.944 | −13.309 | 1.00 | 31.89 | O |
| ATOM | 7958 | N | GLU B | 588 | 13.918 | −4.256 | −14.258 | 1.00 | 33.62 | N |
| ATOM | 7959 | CA | GLU B | 588 | 15.229 | −4.814 | −13.943 | 1.00 | 35.69 | C |
| ATOM | 7960 | CB | GLU B | 588 | 16.324 | −3.988 | −14.610 | 1.00 | 36.16 | C |
| ATOM | 7961 | CG | GLU B | 588 | 17.505 | −4.807 | −15.080 | 1.00 | 41.98 | C |
| ATOM | 7962 | CD | GLU B | 588 | 18.349 | −4.085 | −16.119 | 1.00 | 47.11 | C |
| ATOM | 7963 | OE1 | GLU B | 588 | 17.789 | −3.275 | −16.896 | 1.00 | 48.25 | O |
| ATOM | 7964 | OE2 | GLU B | 588 | 19.574 | −4.339 | −16.159 | 1.00 | 49.00 | O |
| ATOM | 7965 | C | GLU B | 588 | 15.438 | −4.885 | −12.428 | 1.00 | 35.50 | C |
| ATOM | 7966 | O | GLU B | 588 | 15.804 | −5.938 | −11.903 | 1.00 | 34.74 | O |
| ATOM | 7967 | N | ARG B | 589 | 15.175 | −3.770 | −11.742 | 1.00 | 36.10 | N |
| ATOM | 7968 | CA | ARG B | 589 | 15.264 | −3.683 | −10.277 | 1.00 | 37.29 | C |
| ATOM | 7969 | CB | ARG B | 589 | 14.932 | −2.262 | −9.798 | 1.00 | 37.06 | C |
| ATOM | 7970 | CG | ARG B | 589 | 15.009 | −2.074 | −8.280 | 1.00 | 40.50 | C |
| ATOM | 7971 | CD | ARG B | 589 | 14.610 | −.663 | −7.841 | 1.00 | 39.82 | C |
| ATOM | 7972 | NE | ARG B | 589 | 13.160 | −.459 | −7.802 | 1.00 | 44.38 | N |
| ATOM | 7973 | CZ | ARG B | 589 | 12.385 | −.726 | −6.751 | 1.00 | 46.92 | C |
| ATOM | 7974 | NH1 | ARG B | 589 | 12.907 | −1.222 | −5.636 | 1.00 | 47.01 | N | gad67.pdb

| | | | | | | | | | |
|---|---|---|---|---|---|---|---|---|---|
| ATOM | 7975 | NH2 | ARG B | 589 | 11.078 | −.500 | −6.815 | 1.00 | 47.36 | N |
| ATOM | 7976 | C | ARG B | 589 | 14.363 | −4.702 | −9.572 | 1.00 | 36.41 | C |
| ATOM | 7977 | O | ARG B | 589 | 14.782 | −5.348 | −8.612 | 1.00 | 36.52 | O |
| ATOM | 7978 | N | LEU B | 590 | 13.132 | −4.839 | −10.056 | 1.00 | 36.01 | N |
| ATOM | 7979 | CA | LEU B | 590 | 12.174 | −5.789 | −9.495 | 1.00 | 35.64 | C |
| ATOM | 7980 | CB | LEU B | 590 | 10.755 | −5.429 | −9.933 | 1.00 | 35.46 | C |
| ATOM | 7981 | CG | LEU B | 590 | 9.889 | −4.542 | −9.029 | 1.00 | 35.95 | C |
| ATOM | 7982 | CD1 | LEU B | 590 | 10.692 | −3.618 | −8.120 | 1.00 | 35.04 | C |
| ATOM | 7983 | CD2 | LEU B | 590 | 8.910 | −3.748 | −9.877 | 1.00 | 34.56 | C |
| ATOM | 7984 | C | LEU B | 590 | 12.492 | −7.235 | −9.865 | 1.00 | 35.75 | C |
| ATOM | 7985 | O | LEU B | 590 | 12.115 | −8.159 | −9.148 | 1.00 | 35.10 | O |
| ATOM | 7986 | N | GLY B | 591 | 13.184 | −7.424 | −10.985 | 1.00 | 37.01 | N |
| ATOM | 7987 | CA | GLY B | 591 | 13.638 | −8.750 | −11.401 | 1.00 | 38.88 | C |
| ATOM | 7988 | C | GLY B | 591 | 14.789 | −9.259 | −10.550 | 1.00 | 40.11 | C |
| ATOM | 7989 | O | GLY B | 591 | 15.168 | −10.428 | −10.642 | 1.00 | 39.90 | O |
| ATOM | 7990 | N | GLN B | 592 | 15.341 | −8.366 | −9.728 | 1.00 | 41.52 | N |
| ATOM | 7991 | CA | GLN B | 592 | 16.406 | −8.690 | −8.779 | 1.00 | 43.19 | C |
| ATOM | 7992 | CB | GLN B | 592 | 17.510 | −7.628 | −8.839 | 1.00 | 42.74 | C |
| ATOM | 7993 | CG | GLN B | 592 | 18.173 | −7.495 | −10.202 | 1.00 | 43.50 | C |
| ATOM | 7994 | CD | GLN B | 592 | 19.162 | −6.341 | −10.290 | 1.00 | 44.11 | C |
| ATOM | 7995 | OE1 | GLN B | 592 | 19.771 | −6.122 | −11.335 | 1.00 | 44.60 | O |
| ATOM | 7996 | NE2 | GLN B | 592 | 19.324 | −5.597 | −9.197 | 1.00 | 44.59 | N |
| ATOM | 7997 | C | GLN B | 592 | 15.865 | −8.804 | −7.347 | 1.00 | 44.24 | C |
| ATOM | 7998 | O | GLN B | 592 | 16.629 | −8.765 | −6.378 | 1.00 | 44.95 | O |
| ATOM | 7999 | N | ASP B | 593 | 14.547 | −8.941 | −7.219 | 1.00 | 44.67 | N |
| ATOM | 8000 | CA | ASP B | 593 | 13.905 | −9.084 | −5.914 | 1.00 | 45.29 | C |
| ATOM | 8001 | CB | ASP B | 593 | 13.312 | −7.745 | −5.460 | 1.00 | 45.39 | C |
| ATOM | 8005 | C | ASP B | 593 | 12.837 | −10.179 | −5.935 | 1.00 | 45.57 | C |
| ATOM | 8006 | O | ASP B | 593 | 11.883 | −10.147 | −5.152 | 1.00 | 45.91 | O |
| ATOM | 8007 | N | LEU B | 594 | 13.026 | −11.156 | −6.822 | 1.00 | 45.95 | N |
| ATOM | 8008 | CA | LEU B | 594 | 12.065 | −12.247 | −7.035 | 1.00 | 46.38 | C |
| ATOM | 8009 | CB | LEU B | 594 | 12.461 | −13.089 | −8.260 | 1.00 | 46.19 | C |
| ATOM | 8010 | CG | LEU B | 594 | 12.540 | −12.416 | −9.638 | 1.00 | 46.20 | C |
| ATOM | 8011 | CD1 | LEU B | 594 | 11.159 | −12.068 | −10.188 | 1.00 | 45.31 | C |
| ATOM | 8012 | CD2 | LEU B | 594 | 13.299 | −13.295 | −10.625 | 1.00 | 45.86 | C |
| ATOM | 8013 | C | LEU B | 594 | 11.879 | −13.151 | −5.811 | 1.00 | 47.12 | C |
| ATOM | 8014 | O | LEU B | 594 | 10.882 | −13.872 | −5.713 | 1.00 | 47.53 | O |
| ATOM | 8015 | N | HIS B | 595 | 12.837 | −13.106 | −4.885 | 1.00 | 47.48 | N |
| ATOM | 8016 | CA | HIS B | 595 | 12.746 | −13.840 | −3.620 | 1.00 | 48.04 | C |
| ATOM | 8017 | CB | HIS B | 595 | 14.144 | −14.058 | −3.027 | 1.00 | 47.95 | C |
| ATOM | 8018 | CG | HIS B | 595 | 14.882 | −12.788 | −2.737 | 1.00 | 47.15 | C |
| ATOM | 8019 | ND1 | HIS B | 595 | 14.998 | −12.269 | −1.467 | 1.00 | 46.08 | N |
| ATOM | 8020 | CE1 | HIS B | 595 | 15.688 | −11.144 | −1.516 | 1.00 | 46.93 | C |
| ATOM | 8021 | NE2 | HIS B | 595 | 16.024 | −10.914 | −2.772 | 1.00 | 47.31 | N |
| ATOM | 8022 | CD2 | HIS B | 595 | 15.525 | −11.923 | −3.557 | 1.00 | 47.20 | C |
| ATOM | 8023 | C | HIS B | 595 | 11.830 | −13.134 | −2.607 | 1.00 | 48.59 | C |
| ATOM | 8024 | O | HIS B | 595 | 11.887 | −13.416 | −1.405 | 1.00 | 48.54 | O |
| ATOM | 8025 | N | HIS B | 596 | 10.989 | −12.229 | −3.116 | 1.00 | 49.43 | N |
| ATOM | 8026 | CA | HIS B | 596 | 10.035 | −11.431 | −2.333 | 1.00 | 49.67 | C |
| ATOM | 8027 | CB | HIS B | 596 | 9.160 | −12.309 | −1.426 | 1.00 | 49.63 | C |
| ATOM | 8033 | C | HIS B | 596 | 10.733 | −10.342 | −1.526 | 1.00 | 50.37 | C |
| ATOM | 8034 | O | HIS B | 596 | 10.871 | −9.207 | −1.988 | 1.00 | 50.72 | O |
| ATOM | 8035 | OW0 | HOH W | 2 | −40.980 | −2.811 | −15.683 | 1.00 | 7.45 | O |
| ATOM | 8036 | OW0 | HOH W | 3 | −19.232 | 12.924 | −16.086 | 1.00 | 15.93 | O |
| ATOM | 8037 | OW0 | HOH W | 4 | .229 | −3.646 | −20.593 | 1.00 | 12.95 | O |
| ATOM | 8038 | OW0 | HOH W | 5 | −25.640 | −16.576 | −12.562 | 1.00 | 8.97 | O |
| ATOM | 8039 | OW0 | HOH W | 6 | −43.666 | −2.925 | −21.354 | 1.00 | 13.56 | O |
| ATOM | 8040 | OW0 | HOH W | 7 | −24.485 | −20.290 | −30.027 | 1.00 | 14.99 | O |
| ATOM | 8041 | OW0 | HOH W | 8 | −10.175 | −9.012 | −33.325 | 1.00 | 4.61 | O |
| ATOM | 8042 | OW0 | HOH W | 9 | −27.521 | 19.116 | −26.314 | 1.00 | 10.78 | O |
| ATOM | 8043 | OW0 | HOH W | 10 | 2.799 | −3.588 | −31.850 | 1.00 | 15.46 | O |

TABLE A-continued

| | | | | | | | | | | |
|---|---|---|---|---|---|---|---|---|---|---|
| ATOM | 8044 | OW0 | HOH W | 11 | −33.293 | −15.251 | −34.892 | 1.00 | 14.66 | O |
| ATOM | 8045 | OW0 | HOH W | 12 | −29.109 | 17.470 | −27.641 | 1.00 | 7.74 | O |
| ATOM | 8046 | OW0 | HOH W | 13 | −44.475 | −9.703 | −20.059 | 1.00 | 15.61 | O |
| ATOM | 8047 | OW0 | HOH W | 14 | −21.999 | −3.023 | −45.452 | 1.00 | 13.51 | O |
| ATOM | 8048 | OW0 | HOH W | 15 | −25.617 | −.151 | −15.812 | 1.00 | 7.96 | O |
| ATOM | 8049 | OW0 | HOH W | 16 | −27.950 | −21.938 | −38.948 | 1.00 | 22.47 | O |
| ATOM | 8050 | OW0 | HOH W | 17 | −8.772 | −11.453 | −37.244 | 1.00 | 16.67 | O |
| | | | | | gad67.pdb | | | | | |
| ATOM | 8051 | OW0 | HOH W | 18 | −30.559 | 2.964 | −21.000 | 1.00 | 16.15 | O |
| ATOM | 8052 | OW0 | HOH W | 19 | −22.923 | −26.643 | −35.029 | 1.00 | 20.11 | O |
| ATOM | 8053 | OW0 | HOH W | 20 | −30.711 | −.209 | −23.794 | 1.00 | 18.05 | O |
| ATOM | 8054 | OW0 | HOH W | 21 | −26.456 | −.323 | −42.219 | 1.00 | 11.34 | O |
| ATOM | 8055 | OW0 | HOH W | 22 | −7.964 | 23.652 | −28.513 | 1.00 | 13.81 | O |
| ATOM | 8056 | OW0 | HOH W | 23 | −14.417 | 5.545 | −14.166 | 1.00 | 12.58 | O |
| ATOM | 8057 | OW0 | HOH W | 24 | −41.169 | 16.158 | −14.697 | 1.00 | 19.78 | O |
| ATOM | 8058 | OW0 | HOH W | 25 | −35.766 | 17.799 | −30.365 | 1.00 | 21.77 | O |
| ATOM | 8059 | OW0 | HOH W | 26 | −20.790 | 11.266 | −19.347 | 1.00 | 13.50 | O |
| ATOM | 8060 | OW0 | HOH W | 27 | −3.793 | −11.994 | −36.495 | 1.00 | 9.02 | O |
| ATOM | 8061 | OW0 | HOH W | 28 | −25.143 | 2.961 | −23.711 | 1.00 | 9.50 | O |
| ATOM | 8062 | OW0 | HOH W | 29 | −30.671 | 17.096 | −25.412 | 1.00 | 11.14 | O |
| ATOM | 8063 | OW0 | HOH W | 30 | −26.586 | 12.978 | −21.787 | 1.00 | 19.03 | O |
| ATOM | 8064 | OW0 | HOH W | 31 | −1.251 | −10.831 | −33.352 | 1.00 | 29.81 | O |
| ATOM | 8065 | OW0 | HOH W | 32 | −49.791 | 2.882 | −14.239 | 1.00 | 19.99 | O |
| ATOM | 8066 | OW0 | HOH W | 33 | −27.059 | −19.097 | −24.126 | 1.00 | 10.49 | O |
| ATOM | 8067 | OW0 | HOH W | 34 | −28.994 | −11.115 | −38.192 | 1.00 | 19.34 | O |
| ATOM | 8068 | OW0 | HOH W | 35 | −46.740 | −3.063 | −.194 | 1.00 | 30.63 | O |
| ATOM | 8069 | OW0 | HOH W | 36 | −27.119 | −22.606 | −35.114 | 1.00 | 20.25 | O |
| ATOM | 8070 | OW0 | HOH W | 37 | −6.848 | −9.219 | −30.806 | 1.00 | 11.09 | O |
| ATOM | 8071 | OW0 | HOH W | 38 | −21.727 | −16.351 | −12.321 | 1.00 | 24.74 | O |
| ATOM | 8072 | OW0 | HOH W | 39 | −12.461 | −14.793 | −31.047 | 1.00 | 15.61 | O |
| ATOM | 8073 | OW0 | HOH W | 40 | −.605 | −16.993 | −47.594 | 1.00 | 29.18 | O |
| ATOM | 8074 | OW0 | HOH W | 41 | −41.014 | −6.495 | −20.603 | 1.00 | 12.91 | O |
| ATOM | 8075 | OW0 | HOH W | 42 | −31.901 | 12.080 | −12.165 | 1.00 | 12.55 | O |
| ATOM | 8076 | OW0 | HOH W | 43 | .588 | 4.897 | −22.035 | 1.00 | 21.36 | O |
| ATOM | 8077 | OW0 | HOH W | 44 | −11.580 | 1.914 | −7.813 | 1.00 | 16.05 | O |
| ATOM | 8078 | OW0 | HOH W | 45 | −7.763 | −3.577 | −33.423 | 1.00 | 11.12 | O |
| ATOM | 8079 | OW0 | HOH W | 46 | −44.382 | 11.228 | −28.435 | 1.00 | 19.83 | O |
| ATOM | 8080 | OW0 | HOH W | 47 | −13.745 | 20.132 | −1.378 | 1.00 | 37.10 | O |
| ATOM | 8081 | OW0 | HOH W | 48 | −23.734 | 4.988 | −18.206 | 1.00 | 13.57 | O |
| ATOM | 8082 | OW0 | HOH W | 49 | −42.193 | 9.318 | −25.248 | 1.00 | 17.82 | O |
| ATOM | 8083 | OW0 | HOH W | 50 | −20.685 | −.057 | −20.546 | 1.00 | 13.72 | O |
| ATOM | 8084 | OW0 | HOH W | 51 | −27.074 | 13.361 | 2.134 | 1.00 | 16.74 | O |
| ATOM | 8085 | OW0 | HOH W | 52 | −20.404 | −.330 | −12.382 | 1.00 | 23.42 | O |
| ATOM | 8086 | OW0 | HOH W | 53 | −41.171 | −19.838 | −37.952 | 1.00 | 23.34 | O |
| ATOM | 8087 | OW0 | HOH W | 54 | −32.064 | 19.646 | −17.166 | 1.00 | 24.52 | O |
| ATOM | 8088 | OW0 | HOH W | 55 | −47.694 | 6.994 | −2.721 | 1.00 | 14.17 | O |
| ATOM | 8089 | OW0 | HOH W | 56 | 15.058 | 1.386 | −10.355 | 1.00 | 36.10 | O |
| ATOM | 8090 | OW0 | HOH W | 57 | −17.345 | −4.111 | −24.189 | 1.00 | 14.37 | O |
| ATOM | 8091 | OW0 | HOH W | 58 | −8.086 | 7.644 | −12.704 | 1.00 | 23.42 | O |
| ATOM | 8092 | OW0 | HOH W | 59 | −21.865 | −.980 | −15.833 | 1.00 | 17.71 | O |
| ATOM | 8093 | OW0 | HOH W | 60 | −26.903 | 4.177 | 2.566 | 1.00 | 13.33 | O |
| ATOM | 8094 | OW0 | HOH W | 61 | −54.194 | 5.200 | −17.036 | 1.00 | 28.88 | O |
| ATOM | 8095 | OW0 | HOH W | 62 | 3.409 | −5.857 | −34.062 | 1.00 | 19.12 | O |
| ATOM | 8096 | OW0 | HOH W | 63 | −20.856 | 6.039 | −11.584 | 1.00 | 18.23 | O |
| ATOM | 8097 | OW0 | HOH W | 64 | −52.930 | −1.910 | −14.851 | 1.00 | 14.83 | O |
| ATOM | 8098 | OW0 | HOH W | 66 | −30.804 | 13.142 | 1.890 | 1.00 | 17.40 | O |
| ATOM | 8099 | OW0 | HOH W | 67 | −12.402 | 19.601 | −35.755 | 1.00 | 20.68 | O |
| ATOM | 8100 | OW0 | HOH W | 68 | 6.220 | −7.548 | −36.669 | 1.00 | 22.37 | O |
| ATOM | 8101 | OW0 | HOH W | 69 | −48.503 | −6.883 | −19.468 | 1.00 | 19.10 | O |
| ATOM | 8102 | OW0 | HOH W | 70 | −10.700 | −23.381 | −34.985 | 1.00 | 22.05 | O |
| ATOM | 8103 | OW0 | HOH W | 71 | −26.368 | 6.390 | 4.065 | 1.00 | 17.45 | O |
| ATOM | 8104 | OW0 | HOH W | 72 | −44.662 | 10.550 | −21.701 | 1.00 | 17.43 | O |
| ATOM | 8105 | OW0 | HOH W | 73 | −15.432 | −.423 | −23.635 | 1.00 | 22.70 | O |
| ATOM | 8106 | OW0 | HOH W | 74 | −26.559 | −25.854 | −38.396 | 1.00 | 34.78 | O |
| ATOM | 8107 | OW0 | HOH W | 75 | −5.807 | 9.419 | −12.996 | 1.00 | 19.14 | O |
| ATOM | 8108 | OW0 | HOH W | 76 | −7.789 | 8.381 | −17.062 | 1.00 | 24.78 | O |
| ATOM | 8109 | OW0 | HOH W | 77 | −7.964 | 1.808 | −18.375 | 1.00 | 19.03 | O |
| ATOM | 8110 | OW0 | HOH W | 78 | −39.543 | 25.079 | −28.374 | 1.00 | 31.70 | O |
| ATOM | 8111 | OW0 | HOH W | 79 | −9.220 | 23.983 | −40.524 | 1.00 | 41.01 | O |
| ATOM | 8112 | OW0 | HOH W | 80 | 2.312 | 22.192 | −14.677 | 1.00 | 41.32 | O |
| ATOM | 8113 | OW0 | HOH W | 81 | 7.095 | −6.608 | −29.668 | 1.00 | 18.37 | O |
| ATOM | 8114 | OW0 | HOH W | 82 | −33.726 | 12.154 | −16.020 | 1.00 | 32.87 | O |
| ATOM | 8115 | OW0 | HOH W | 83 | −56.514 | −16.061 | −16.095 | 1.00 | 25.36 | O |
| ATOM | 8116 | OW0 | HOH W | 84 | −41.737 | 13.521 | −14.148 | 1.00 | 26.40 | O |
| ATOM | 8117 | OW0 | HOH W | 85 | −52.037 | 26.909 | −17.019 | 1.00 | 40.34 | O |
| ATOM | 8118 | OW0 | HOH W | 86 | −22.606 | −5.846 | −18.746 | 1.00 | 18.98 | O |
| | | | | | gad67.pdb | | | | | |
| ATOM | 8119 | OW0 | HOH W | 88 | −14.009 | −6.930 | −11.897 | 1.00 | 25.20 | O |
| ATOM | 8120 | OW0 | HOH W | 89 | 9.472 | −12.263 | −17.690 | 1.00 | 26.77 | O |
| ATOM | 8121 | OW0 | HOH W | 90 | −24.846 | −2.892 | 2.431 | 1.00 | 22.11 | O |

TABLE A-continued

| | | | | | | | | | | |
|---|---|---|---|---|---|---|---|---|---|---|
| ATOM | 8122 | OW0 | HOH W | 91 | −33.334 | −21.208 | −34.182 | 1.00 | 19.66 | O |
| ATOM | 8123 | OW0 | HOH W | 92 | −62.053 | 13.929 | −12.965 | 1.00 | 37.23 | O |
| ATOM | 8124 | OW0 | HOH W | 93 | −20.300 | 12.500 | −24.388 | 1.00 | 14.45 | O |
| ATOM | 8125 | OW0 | HOH W | 94 | −51.920 | .652 | −14.463 | 1.00 | 23.38 | O |
| ATOM | 8126 | OW0 | HOH W | 95 | −1.319 | −18.683 | −16.774 | 1.00 | 33.54 | O |
| ATOM | 8127 | OW0 | HOH W | 96 | −39.170 | −20.858 | −12.576 | 1.00 | 30.24 | O |
| ATOM | 8128 | OW0 | HOH W | 97 | −24.959 | −11.881 | −52.571 | 1.00 | 23.96 | O |
| ATOM | 8129 | OW0 | HOH W | 98 | −13.630 | −24.368 | −41.961 | 1.00 | 25.83 | O |
| ATOM | 8130 | OW0 | HOH W | 100 | 12.698 | −29.783 | −19.514 | 1.00 | 41.67 | O |
| ATOM | 8131 | OW0 | HOH W | 101 | −43.602 | 8.217 | 2.218 | 1.00 | 27.80 | O |
| ATOM | 8132 | OW0 | HOH W | 103 | −47.517 | 22.564 | −6.334 | 1.00 | 31.92 | O |
| ATOM | 8133 | OW0 | HOH W | 105 | −18.909 | −6.910 | −10.411 | 1.00 | 41.10 | O |
| ATOM | 8134 | OW0 | HOH W | 106 | −25.325 | 7.044 | −46.508 | 1.00 | 23.20 | O |
| ATOM | 8135 | OW0 | HOH W | 107 | −62.342 | 11.457 | −18.531 | 1.00 | 33.60 | O |
| ATOM | 8136 | OW0 | HOH W | 108 | −19.733 | 4.342 | −27.719 | 1.00 | 13.53 | O |
| ATOM | 8137 | OW0 | HOH W | 109 | −33.123 | 11.122 | 2.281 | 1.00 | 24.81 | O |
| ATOM | 8138 | OW0 | HOH W | 110 | −16.771 | −6.730 | −14.149 | 1.00 | 26.40 | O |
| ATOM | 8139 | OW0 | HOH W | 111 | −19.487 | 5.487 | −21.991 | 1.00 | 17.04 | O |
| ATOM | 8140 | OW0 | HOH W | 112 | −32.513 | 17.504 | 6.082 | 1.00 | 24.32 | O |
| ATOM | 8141 | OW0 | HOH W | 113 | −15.720 | −10.175 | −21.037 | 1.00 | 21.53 | O |
| ATOM | 8142 | OW0 | HOH W | 114 | .310 | −12.908 | −43.604 | 1.00 | 27.10 | O |
| ATOM | 8143 | OW0 | HOH W | 115 | −49.302 | −12.204 | −8.354 | 1.00 | 14.04 | O |
| ATOM | 8144 | OW0 | HOH W | 116 | −29.755 | 27.219 | −1.045 | 1.00 | 55.23 | O |
| ATOM | 8145 | OW0 | HOH W | 117 | −9.766 | 2.586 | −9.949 | 1.00 | 9.92 | O |
| ATOM | 8146 | OW0 | HOH W | 118 | −29.465 | 1.201 | −41.180 | 1.00 | 25.44 | O |
| ATOM | 8147 | OW0 | HOH W | 119 | −6.485 | 5.754 | −24.068 | 1.00 | 38.94 | O |
| ATOM | 8148 | OW0 | HOH W | 120 | 5.312 | −16.061 | −9.551 | 1.00 | 27.00 | O |
| ATOM | 8149 | OW0 | HOH W | 121 | −2.293 | −7.880 | −47.777 | 1.00 | 32.68 | O |
| ATOM | 8150 | OW0 | HOH W | 122 | −5.451 | 16.861 | −22.174 | 1.00 | 16.62 | O |
| ATOM | 8151 | OW0 | HOH W | 123 | 10.041 | 10.280 | −15.776 | 1.00 | 27.60 | O |
| ATOM | 8152 | OW0 | HOH W | 124 | −13.319 | 23.288 | −36.140 | 1.00 | 37.57 | O |
| ATOM | 8153 | OW0 | HOH W | 125 | −28.698 | −14.042 | −3.343 | 1.00 | 27.74 | O |
| ATOM | 8154 | OW0 | HOH W | 126 | −18.529 | −18.821 | −50.685 | 1.00 | 22.74 | O |
| ATOM | 8155 | OW0 | HOH W | 127 | −35.655 | 2.116 | −10.557 | 1.00 | 14.09 | O |
| ATOM | 8156 | OW0 | HOH W | 128 | −2.706 | 8.640 | −28.173 | 1.00 | 39.85 | O |
| ATOM | 8157 | OW0 | HOH W | 129 | −26.220 | −25.568 | −17.881 | 1.00 | 24.06 | O |
| ATOM | 8158 | OW0 | HOH W | 130 | .925 | 26.053 | −14.855 | 1.00 | 21.69 | O |
| ATOM | 8159 | OW0 | HOH W | 131 | −7.982 | 10.261 | −21.868 | 1.00 | 21.42 | O |
| ATOM | 8160 | OW0 | HOH W | 132 | −6.980 | .154 | −3.127 | 1.00 | 34.11 | O |
| ATOM | 8161 | OW0 | HOH W | 133 | 15.534 | −11.476 | −27.858 | 1.00 | 30.06 | O |
| ATOM | 8162 | OW0 | HOH W | 134 | −42.067 | −1.725 | −26.357 | 1.00 | 23.41 | O |
| ATOM | 8163 | OW0 | HOH W | 135 | −26.709 | 6.362 | −37.045 | 1.00 | 29.07 | O |
| ATOM | 8164 | OW0 | HOH W | 136 | .556 | 9.116 | −3.959 | 1.00 | 26.59 | O |
| ATOM | 8165 | OW0 | HOH W | 138 | −55.889 | −22.623 | −19.698 | 1.00 | 19.20 | O |
| ATOM | 8166 | OW0 | HOH W | 139 | −21.341 | −15.501 | −25.167 | 1.00 | 29.59 | O |
| ATOM | 8167 | OW0 | HOH W | 140 | −16.313 | −24.631 | −29.767 | 1.00 | 18.41 | O |
| ATOM | 8168 | OW0 | HOH W | 141 | −.810 | 26.892 | −17.008 | 1.00 | 55.12 | O |
| ATOM | 8169 | OW0 | HOH W | 142 | −49.063 | −.903 | −21.730 | 1.00 | 28.71 | O |
| ATOM | 8170 | OW0 | HOH W | 143 | −30.150 | 17.392 | −22.880 | 1.00 | 16.63 | O |
| ATOM | 8171 | OW0 | HOH W | 144 | −17.450 | 17.210 | −40.628 | 1.00 | 27.65 | O |
| ATOM | 8172 | OW0 | HOH W | 145 | −11.303 | 21.962 | −34.951 | 1.00 | 21.30 | O |
| ATOM | 8173 | OW0 | HOH W | 147 | −41.365 | −8.162 | −26.837 | 1.00 | 19.24 | O |
| ATOM | 8174 | OW0 | HOH W | 148 | −8.636 | 5.040 | −31.567 | 1.00 | 14.76 | O |
| ATOM | 8175 | OW0 | HOH W | 149 | −36.787 | −12.263 | −41.305 | 1.00 | 34.23 | O |
| ATOM | 8176 | OW0 | HOH W | 150 | −52.065 | −19.528 | −9.067 | 1.00 | 24.96 | O |
| ATOM | 8177 | OW0 | HOH W | 151 | −26.736 | −18.784 | −5.942 | 1.00 | 25.98 | O |
| ATOM | 8178 | OW0 | HOH W | 153 | 3.235 | −7.767 | −35.991 | 1.00 | 16.47 | O |
| ATOM | 8179 | OW0 | HOH W | 154 | 18.712 | −14.887 | −10.969 | 1.00 | 29.48 | O |
| ATOM | 8180 | OW0 | HOH W | 155 | −46.142 | 15.353 | −33.619 | 1.00 | 37.21 | O |
| ATOM | 8181 | OW0 | HOH W | 156 | −24.011 | −21.612 | −37.310 | 1.00 | 17.95 | O |
| ATOM | 8182 | OW0 | HOH W | 157 | .999 | 5.949 | −19.384 | 1.00 | 34.61 | O |
| ATOM | 8183 | OW0 | HOH W | 158 | −20.943 | −28.445 | −33.896 | 1.00 | 31.19 | O |
| ATOM | 8184 | OW0 | HOH W | 159 | 23.593 | −10.281 | −18.770 | 1.00 | 36.30 | O |
| ATOM | 8185 | OW0 | HOH W | 160 | −37.469 | 17.141 | −40.250 | 1.00 | 24.20 | O |
| ATOM | 8186 | OW0 | HOH W | 161 | 8.832 | −7.938 | −31.558 | 1.00 | 18.24 | O |
| | | | | gad67.pdb | | | | | | |
| ATOM | 8187 | OW0 | HOH W | 162 | −28.360 | 19.276 | −23.770 | 1.00 | 25.26 | O |
| ATOM | 8188 | OW0 | HOH W | 163 | −56.679 | 3.837 | −16.422 | 1.00 | 21.17 | O |
| ATOM | 8189 | OW0 | HOH W | 164 | 1.723 | 11.721 | −39.868 | 1.00 | 19.19 | O |
| ATOM | 8190 | OW0 | HOH W | 165 | −31.167 | 16.213 | −6.253 | 1.00 | 13.26 | O |
| ATOM | 8191 | OW0 | HOH W | 166 | −34.935 | 11.106 | −20.419 | 1.00 | 15.45 | O |
| ATOM | 8192 | OW0 | HOH W | 167 | −25.345 | −17.358 | −25.324 | 1.00 | 33.18 | O |
| ATOM | 8193 | OW0 | HOH W | 168 | −22.651 | −6.323 | 2.264 | 1.00 | 26.88 | O |
| ATOM | 8194 | OW0 | HOH W | 169 | −51.778 | 26.413 | −20.012 | 1.00 | 33.99 | O |
| ATOM | 8195 | OW0 | HOH W | 170 | −5.084 | 21.869 | −29.433 | 1.00 | 17.54 | O |
| ATOM | 8196 | OW0 | HOH W | 171 | −33.923 | 4.029 | −20.873 | 1.00 | 25.40 | O |
| ATOM | 8197 | OW0 | HOH W | 172 | −23.225 | 22.868 | −38.655 | 1.00 | 34.59 | O |
| ATOM | 8198 | OW0 | HOH W | 173 | −1.212 | −16.014 | −16.667 | 1.00 | 28.46 | O |
| ATOM | 8199 | OW0 | HOH W | 174 | −23.607 | 30.325 | −13.482 | 1.00 | 37.04 | O |
| ATOM | 8200 | OW0 | HOH W | 175 | −26.040 | −22.365 | −24.121 | 1.00 | 36.69 | O |

TABLE A-continued

| | | | | | | | | | |
|---|---|---|---|---|---|---|---|---|---|
| ATOM | 8201 | OW0 | HOH W | 176 | −42.373 | 14.358 | −7.941 | 1.00 | 45.61 | O |
| ATOM | 8202 | OW0 | HOH W | 177 | −8.036 | 2.957 | −47.146 | 1.00 | 26.00 | O |
| ATOM | 8203 | OW0 | HOH W | 178 | −9.694 | 4.922 | −11.218 | 1.00 | 18.17 | O |
| ATOM | 8204 | OW0 | HOH W | 179 | −20.018 | 7.017 | −46.018 | 1.00 | 29.19 | O |
| ATOM | 8205 | OW0 | HOH W | 180 | −7.758 | 2.849 | −31.314 | 1.00 | 26.20 | O |
| ATOM | 8206 | OW0 | HOH W | 181 | −30.006 | −16.274 | −4.639 | 1.00 | 21.40 | O |
| ATOM | 8207 | OW0 | HOH W | 182 | 7.600 | −14.232 | −17.449 | 1.00 | 16.46 | O |
| ATOM | 8208 | OW0 | HOH W | 183 | −42.117 | 12.059 | −16.323 | 1.00 | 28.70 | O |
| ATOM | 8209 | OW0 | HOH W | 184 | −42.206 | −20.710 | −35.676 | 1.00 | 31.13 | O |
| ATOM | 8210 | OW0 | HOH W | 185 | −43.488 | −7.033 | −28.113 | 1.00 | 34.92 | O |
| ATOM | 8211 | OW0 | HOH W | 186 | −28.831 | −19.206 | −1.045 | 1.00 | 45.83 | O |
| ATOM | 8212 | OW0 | HOH W | 187 | −33.667 | 23.498 | .721 | 1.00 | 35.48 | O |
| ATOM | 8213 | OW0 | HOH W | 190 | .614 | .326 | −4.065 | 1.00 | 22.29 | O |
| ATOM | 8214 | OW0 | HOH W | 191 | −60.429 | −7.628 | −19.180 | 1.00 | 34.02 | O |
| ATOM | 8215 | OW0 | HOH W | 192 | −30.620 | −15.051 | 3.568 | 1.00 | 34.11 | O |
| ATOM | 8216 | OW0 | HOH W | 193 | −5.709 | 26.528 | −35.436 | 1.00 | 26.15 | O |
| ATOM | 8217 | OW0 | HOH W | 194 | −34.665 | 17.569 | −41.278 | 1.00 | 25.76 | O |
| ATOM | 8218 | OW0 | HOH W | 195 | −3.352 | −5.878 | −18.420 | 1.00 | 23.47 | O |
| ATOM | 8219 | OW0 | HOH W | 196 | −9.098 | −11.038 | −1.021 | 1.00 | 26.62 | O |
| ATOM | 8220 | OW0 | HOH W | 197 | −43.779 | 3.396 | 1.910 | 1.00 | 27.11 | O |
| ATOM | 8221 | OW0 | HOH W | 198 | −38.118 | 10.773 | −27.348 | 1.00 | 18.55 | O |
| ATOM | 8222 | OW0 | HOH W | 199 | −32.079 | 28.105 | .897 | 1.00 | 36.11 | O |
| ATOM | 8223 | OW0 | HOH W | 200 | −43.122 | 25.755 | −18.435 | 1.00 | 33.81 | O |
| ATOM | 8224 | OW0 | HOH W | 201 | −6.724 | −16.221 | −7.094 | 1.00 | 27.10 | O |
| ATOM | 8225 | OW0 | HOH W | 202 | −29.847 | 15.540 | −4.110 | 1.00 | 27.17 | O |
| ATOM | 8226 | OW0 | HOH W | 203 | −13.904 | −30.483 | −46.086 | 1.00 | 39.52 | O |
| ATOM | 8227 | OW0 | HOH W | 204 | −1.274 | −8.471 | −16.152 | 1.00 | 22.30 | O |
| ATOM | 8228 | OW0 | HOH W | 205 | −30.804 | 18.208 | −19.465 | 1.00 | 15.35 | O |
| ATOM | 8229 | OW0 | HOH W | 206 | −8.187 | 6.721 | −8.167 | 1.00 | 39.20 | O |
| ATOM | 8230 | OW0 | HOH W | 207 | −6.294 | 12.066 | −25.992 | 1.00 | 28.69 | O |
| ATOM | 8231 | OW0 | HOH W | 208 | −8.654 | 11.801 | −3.095 | 1.00 | 24.36 | O |
| ATOM | 8232 | OW0 | HOH W | 209 | −26.021 | −23.257 | −37.430 | 1.00 | 23.11 | O |
| ATOM | 8233 | OW0 | HOH W | 210 | −42.396 | −12.830 | −36.343 | 1.00 | 20.74 | O |
| ATOM | 8234 | OW0 | HOH W | 211 | −23.254 | −10.374 | −7.415 | 1.00 | 12.30 | O |
| ATOM | 8235 | OW0 | HOH W | 212 | −10.671 | 5.772 | −8.774 | 1.00 | 26.22 | O |
| ATOM | 8236 | OW0 | HOH W | 213 | −30.774 | 29.361 | −2.900 | 1.00 | 21.76 | O |
| ATOM | 8237 | OW0 | HOH W | 214 | −19.209 | 9.049 | −15.823 | 1.00 | 21.28 | O |
| ATOM | 8238 | OW0 | HOH W | 215 | −2.587 | 7.571 | −6.194 | 1.00 | 37.40 | O |
| ATOM | 8239 | OW0 | HOH W | 216 | −10.513 | −14.330 | −13.081 | 1.00 | 36.51 | O |
| ATOM | 8240 | OW0 | HOH W | 217 | −35.197 | 19.054 | 2.709 | 1.00 | 27.45 | O |
| ATOM | 8241 | OW0 | HOH W | 218 | 4.391 | −6.345 | −30.185 | 1.00 | 13.04 | O |
| ATOM | 8242 | OW0 | HOH W | 219 | −4.859 | 3.962 | −4.677 | 1.00 | 27.06 | O |
| ATOM | 8243 | OW0 | HOH W | 220 | −46.219 | 24.827 | −11.468 | 1.00 | 23.27 | O |
| ATOM | 8244 | OW0 | HOH W | 221 | −8.358 | −12.827 | −13.498 | 1.00 | 27.23 | O |
| ATOM | 8245 | OW0 | HOH W | 222 | −36.006 | −21.256 | −31.876 | 1.00 | 24.80 | O |
| ATOM | 8246 | OW0 | HOH W | 223 | 4.063 | 23.227 | −21.055 | 1.00 | 47.82 | O |
| ATOM | 8247 | OW0 | HOH W | 224 | −12.414 | −14.137 | −21.562 | 1.00 | 53.62 | O |
| ATOM | 8248 | OW0 | HOH W | 225 | −10.123 | 5.319 | −50.571 | 1.00 | 28.84 | O |
| ATOM | 8249 | OW0 | HOH W | 227 | −31.212 | −8.528 | −46.109 | 1.00 | 20.90 | O |
| ATOM | 8250 | OW0 | HOH W | 228 | −15.057 | −13.172 | −14.505 | 1.00 | 27.22 | O |
| ATOM | 8251 | OW0 | HOH W | 229 | −2.842 | −23.995 | −43.532 | 1.00 | 35.20 | O |
| ATOM | 8252 | OW0 | HOH W | 230 | −55.924 | 13.047 | −28.048 | 1.00 | 19.04 | O |
| ATOM | 8253 | OW0 | HOH W | 232 | −48.447 | 28.564 | −20.755 | 1.00 | 37.47 | O |
| ATOM | 8254 | OW0 | HOH W | 233 | −21.750 | −4.316 | −47.687 | 1.00 | 38.38 | O |
| | | | | | gad67.pdb | | | | | |
| ATOM | 8255 | OW0 | HOH W | 234 | −7.756 | 32.331 | −17.738 | 1.00 | 32.92 | O |
| ATOM | 8256 | OW0 | HOH W | 235 | −17.302 | −6.091 | −16.644 | 1.00 | 24.29 | O |
| ATOM | 8257 | OW0 | HOH W | 236 | −11.950 | 4.490 | −7.107 | 1.00 | 20.80 | O |
| ATOM | 8258 | OW0 | HOH W | 237 | −3.398 | −15.614 | −18.150 | 1.00 | 29.99 | O |
| ATOM | 8259 | OW0 | HOH W | 238 | −33.780 | −7.893 | −46.194 | 1.00 | 23.18 | O |
| ATOM | 8260 | OW0 | HOH W | 239 | −6.369 | −11.537 | −2.058 | 1.00 | 31.12 | O |
| ATOM | 8261 | OW0 | HOH W | 240 | −54.931 | 11.312 | −30.057 | 1.00 | 22.88 | O |
| ATOM | 8262 | OW0 | HOH W | 241 | −32.136 | 13.420 | −2.485 | 1.00 | 15.84 | O |
| ATOM | 8263 | OW0 | HOH W | 242 | −33.353 | 10.747 | −7.871 | 1.00 | 22.52 | O |
| ATOM | 8264 | OW0 | HOH W | 243 | −17.743 | −22.181 | −25.970 | 1.00 | 31.43 | O |
| ATOM | 8265 | OW0 | HOH W | 244 | −47.602 | −14.117 | −30.601 | 1.00 | 28.00 | O |
| ATOM | 8266 | OW0 | HOH W | 245 | −20.843 | −8.272 | .154 | 1.00 | 33.43 | O |
| ATOM | 8267 | OW0 | HOH W | 246 | 3.654 | 14.197 | −35.802 | 1.00 | 44.37 | O |
| ATOM | 8268 | OW0 | HOH W | 247 | −59.581 | −12.751 | −18.569 | 1.00 | 36.35 | O |
| ATOM | 8269 | OW0 | HOH W | 248 | 2.728 | 14.515 | −16.633 | 1.00 | 31.37 | O |
| ATOM | 8270 | OW0 | HOH W | 249 | −3.902 | 20.491 | −31.454 | 1.00 | 21.83 | O |
| ATOM | 8271 | OW0 | HOH W | 250 | −6.355 | −3.126 | −7.361 | 1.00 | 42.59 | O |
| ATOM | 8272 | OW0 | HOH W | 251 | −3.765 | −10.731 | −29.508 | 1.00 | 16.75 | O |
| ATOM | 8273 | OW0 | HOH W | 252 | −6.832 | −5.481 | −15.537 | 1.00 | 25.37 | O |
| ATOM | 8274 | OW0 | HOH W | 253 | −10.578 | −11.234 | −56.078 | 1.00 | 27.12 | O |
| ATOM | 8275 | OW0 | HOH W | 254 | −47.808 | 7.195 | −33.714 | 1.00 | 14.88 | O |
| ATOM | 8276 | OW0 | HOH W | 255 | −26.212 | 10.183 | −21.486 | 1.00 | 9.91 | O |
| ATOM | 8277 | OW0 | HOH W | 257 | −31.383 | −18.096 | −11.601 | 1.00 | 26.18 | O |
| ATOM | 8278 | OW0 | HOH W | 258 | −26.556 | 10.667 | −18.372 | 1.00 | 25.99 | O |
| ATOM | 8279 | OW0 | HOH W | 259 | 18.239 | −11.035 | −12.214 | 1.00 | 38.24 | O |

TABLE A-continued

| | | | | | | | | | |
|---|---|---|---|---|---|---|---|---|---|
| ATOM | 8280 | OW0 | HOH W | 260 | −2.337 | −7.865 | −20.614 | 1.00 | 29.65 | O |
| ATOM | 8281 | OW0 | HOH W | 262 | −34.902 | 20.529 | −31.472 | 1.00 | 23.89 | O |
| ATOM | 8282 | OW0 | HOH W | 263 | −34.078 | −.046 | −30.046 | 1.00 | 14.38 | O |
| ATOM | 8283 | OW0 | HOH W | 264 | −27.874 | −11.538 | −1.856 | 1.00 | 26.64 | O |
| ATOM | 8284 | OW0 | HOH W | 265 | −39.502 | 7.831 | −34.749 | 1.00 | 34.98 | O |
| ATOM | 8285 | OW0 | HOH W | 266 | −3.009 | 11.631 | −19.301 | 1.00 | 33.29 | O |
| ATOM | 8286 | OW0 | HOH W | 267 | −15.763 | 4.494 | −16.487 | 1.00 | 23.13 | O |
| ATOM | 8287 | OW0 | HOH W | 268 | −51.868 | 3.897 | −16.986 | 1.00 | 25.00 | O |
| ATOM | 8288 | OW0 | HOH W | 269 | −29.940 | 21.149 | −22.963 | 1.00 | 34.37 | O |
| ATOM | 8289 | OW0 | HOH W | 270 | −17.936 | 8.419 | −46.617 | 1.00 | 28.11 | O |
| ATOM | 8290 | OW0 | HOH W | 271 | −51.577 | 14.634 | −36.999 | 1.00 | 23.13 | O |
| ATOM | 8291 | OW0 | HOH W | 272 | −27.125 | 31.290 | −5.430 | 1.00 | 49.33 | O |
| ATOM | 8292 | OW0 | HOH W | 274 | −40.077 | 27.517 | −10.698 | 1.00 | 28.42 | O |
| ATOM | 8293 | OW0 | HOH W | 275 | −8.027 | 9.706 | −14.718 | 1.00 | 23.50 | O |
| ATOM | 8294 | OW0 | HOH W | 276 | −45.665 | −12.692 | −32.146 | 1.00 | 29.62 | O |
| ATOM | 8295 | OW0 | HOH W | 277 | −21.540 | −25.915 | −24.784 | 1.00 | 29.59 | O |
| ATOM | 8296 | OW0 | HOH W | 278 | −33.438 | 12.127 | −.526 | 1.00 | 21.57 | O |
| ATOM | 8297 | OW0 | HOH W | 279 | −37.691 | 1.676 | −12.193 | 1.00 | 24.21 | O |
| ATOM | 8298 | OW0 | HOH W | 280 | 15.695 | 3.767 | −28.801 | 1.00 | 32.97 | O |
| ATOM | 8299 | OW0 | HOH W | 281 | 11.331 | 12.384 | −21.183 | 1.00 | 38.03 | O |
| ATOM | 8300 | OW0 | HOH W | 282 | −29.624 | 10.276 | 9.077 | 1.00 | 20.27 | O |
| ATOM | 8301 | OW0 | HOH W | 284 | −29.971 | 6.487 | −31.530 | 1.00 | 37.04 | O |
| ATOM | 8302 | OW0 | HOH W | 285 | −15.242 | 7.540 | 4.099 | 1.00 | 30.53 | O |
| ATOM | 8303 | OW0 | HOH W | 286 | 19.184 | −3.177 | −27.033 | 1.00 | 35.24 | O |
| ATOM | 8304 | OW0 | HOH W | 287 | −25.766 | −14.616 | −19.682 | 1.00 | 32.42 | O |
| ATOM | 8305 | OW0 | HOH W | 289 | −2.604 | −3.436 | −49.494 | 1.00 | 44.40 | O |
| ATOM | 8306 | OW0 | HOH W | 291 | −51.697 | −13.178 | −8.688 | 1.00 | 36.68 | O |
| ATOM | 8307 | OW0 | HOH W | 292 | −14.837 | 7.036 | −18.199 | 1.00 | 39.64 | O |
| ATOM | 8308 | OW0 | HOH W | 293 | −31.839 | 9.214 | −32.372 | 1.00 | 22.35 | O |
| ATOM | 8309 | OW0 | HOH W | 295 | −23.089 | −17.516 | −24.216 | 1.00 | 22.61 | O |
| ATOM | 8310 | OW0 | HOH W | 296 | −43.256 | 12.995 | −30.075 | 1.00 | 25.83 | O |
| ATOM | 8311 | OW0 | HOH W | 297 | .842 | 5.766 | −44.250 | 1.00 | 38.18 | O |
| ATOM | 8312 | OW0 | HOH W | 298 | −46.761 | 19.365 | −4.984 | 1.00 | 33.00 | O |
| ATOM | 8313 | OW0 | HOH W | 299 | −5.431 | 10.678 | −23.150 | 1.00 | 33.85 | O |
| ATOM | 8314 | OW0 | HOH W | 300 | −28.179 | 27.679 | −18.963 | 1.00 | 26.96 | O |
| ATOM | 8315 | OW0 | HOH W | 301 | −22.895 | −9.405 | −4.902 | 1.00 | 17.90 | O |
| ATOM | 8316 | OW0 | HOH W | 302 | −46.271 | 5.072 | −33.291 | 1.00 | 25.00 | O |
| ATOM | 8317 | OW0 | HOH W | 304 | −23.507 | 29.145 | −11.075 | 1.00 | 38.53 | O |
| ATOM | 8318 | OW0 | HOH W | 305 | −53.983 | −24.920 | −25.538 | 1.00 | 26.83 | O |
| ATOM | 8319 | OW0 | HOH W | 306 | 5.044 | −15.799 | −32.609 | 1.00 | 27.73 | O |
| ATOM | 8320 | OW0 | HOH W | 307 | −24.432 | 5.077 | 5.418 | 1.00 | 35.04 | O |
| ATOM | 8321 | OW0 | HOH W | 308 | −23.374 | 11.081 | 8.145 | 1.00 | 19.75 | O |
| ATOM | 8322 | OW0 | HOH W | 309 | −31.241 | 3.196 | −41.833 | 1.00 | 21.81 | O |
| | | | | | gad67.pdb | | | | | |
| ATOM | 8323 | OW0 | HOH W | 311 | −3.483 | −7.242 | −16.216 | 1.00 | 28.24 | O |
| ATOM | 8324 | OW0 | HOH W | 312 | −4.365 | 14.829 | −23.666 | 1.00 | 28.03 | O |
| ATOM | 8325 | OW0 | HOH W | 313 | −32.074 | −.489 | 3.684 | 1.00 | 25.01 | O |
| ATOM | 8326 | OW0 | HOH W | 314 | −33.935 | 12.424 | −10.372 | 1.00 | 22.69 | O |
| ATOM | 8327 | OW0 | HOH W | 315 | −43.017 | 21.165 | −33.219 | 1.00 | 16.34 | O |
| ATOM | 8328 | OW0 | HOH W | 316 | −31.503 | 15.248 | −16.154 | 1.00 | 34.79 | O |
| ATOM | 8329 | OW0 | HOH W | 317 | −41.031 | −3.993 | 3.226 | 1.00 | 27.55 | O |
| ATOM | 8330 | OW0 | HOH W | 318 | −11.432 | −22.995 | −32.419 | 1.00 | 30.19 | O |
| ATOM | 8331 | OW0 | HOH W | 319 | −35.243 | 11.562 | 3.935 | 1.00 | 28.82 | O |
| ATOM | 8332 | OW0 | HOH W | 320 | −1.975 | −8.520 | −13.564 | 1.00 | 35.83 | O |
| ATOM | 8333 | OW0 | HOH W | 321 | −5.747 | 33.894 | −25.064 | 1.00 | 53.13 | O |
| ATOM | 8334 | OW0 | HOH W | 322 | −37.095 | 6.509 | 9.506 | 1.00 | 39.40 | O |
| ATOM | 8335 | OW0 | HOH W | 323 | −19.431 | −16.742 | −11.063 | 1.00 | 25.92 | O |
| ATOM | 8336 | OW0 | HOH W | 325 | −6.259 | −19.142 | −30.181 | 1.00 | 32.22 | O |
| ATOM | 8337 | OW0 | HOH W | 326 | 5.633 | 7.744 | −35.402 | 1.00 | 27.29 | O |
| ATOM | 8338 | OW0 | HOH W | 327 | −5.772 | −24.535 | −38.080 | 1.00 | 36.63 | O |
| ATOM | 8339 | OW0 | HOH W | 328 | −41.208 | 9.789 | −15.864 | 1.00 | 43.38 | O |
| ATOM | 8340 | OW0 | HOH W | 329 | −22.730 | .908 | −19.301 | 1.00 | 22.05 | O |
| ATOM | 8341 | OW0 | HOH W | 330 | 9.015 | −17.087 | −28.814 | 1.00 | 29.40 | O |
| ATOM | 8342 | OW0 | HOH W | 331 | −32.765 | 22.421 | −30.636 | 1.00 | 31.91 | O |
| ATOM | 8343 | OW0 | HOH W | 332 | −20.424 | 28.182 | 4.803 | 1.00 | 26.52 | O |
| ATOM | 8344 | OW0 | HOH W | 333 | −58.865 | −16.086 | −17.805 | 1.00 | 28.10 | O |
| ATOM | 8345 | OW0 | HOH W | 334 | −33.058 | 11.738 | −18.605 | 1.00 | 25.26 | O |
| ATOM | 8346 | OW0 | HOH W | 335 | −21.714 | −16.377 | −49.949 | 1.00 | 30.35 | O |
| ATOM | 8347 | OW0 | HOH W | 336 | −17.782 | 26.064 | −33.349 | 1.00 | 42.36 | O |
| ATOM | 8348 | OW0 | HOH W | 337 | −32.321 | 24.035 | −22.893 | 1.00 | 41.82 | O |
| ATOM | 8349 | OW0 | HOH W | 338 | 2.903 | −15.461 | −44.186 | 1.00 | 34.51 | O |
| ATOM | 8350 | OW0 | HOH W | 340 | 4.381 | 13.936 | −33.122 | 1.00 | 31.03 | O |
| ATOM | 8351 | OW0 | HOH W | 342 | −19.502 | 6.217 | 4.523 | 1.00 | 33.06 | O |
| ATOM | 8352 | OW0 | HOH W | 343 | −1.318 | −11.051 | −30.325 | 1.00 | 30.80 | O |
| ATOM | 8353 | OW0 | HOH W | 344 | −45.755 | −7.552 | −11.204 | 1.00 | 31.61 | O |
| ATOM | 8354 | OW0 | HOH W | 345 | −17.245 | 8.798 | −17.771 | 1.00 | 27.11 | O |
| ATOM | 8355 | OW0 | HOH W | 346 | −16.637 | 27.350 | −11.406 | 1.00 | 22.80 | O |
| ATOM | 8356 | OW0 | HOH W | 347 | −2.973 | −5.620 | −46.803 | 1.00 | 31.22 | O |
| ATOM | 8357 | OW0 | HOH W | 348 | −3.788 | −4.254 | −44.236 | 1.00 | 28.15 | O |
| ATOM | 8358 | OW0 | HOH W | 349 | −55.252 | −1.038 | −13.425 | 1.00 | 29.05 | O |

TABLE A-continued

| | | | | | | | | | | |
|---|---|---|---|---|---|---|---|---|---|---|
| ATOM | 8359 | OW0 | HOH W | 350 | −18.897 | −9.688 | −28.784 | 1.00 | 29.57 | O |
| ATOM | 8360 | OW0 | HOH W | 351 | −35.435 | −21.598 | −35.822 | 1.00 | 33.91 | O |
| ATOM | 8361 | OW0 | HOH W | 352 | −38.682 | 9.061 | −8.330 | 1.00 | 29.26 | O |
| ATOM | 8362 | OW0 | HOH W | 353 | −31.383 | 2.688 | −29.176 | 1.00 | 18.49 | O |
| ATOM | 8363 | OW0 | HOH W | 354 | −4.212 | 13.063 | −21.711 | 1.00 | 41.35 | O |
| ATOM | 8364 | OW0 | HOH W | 355 | −23.344 | 5.763 | −27.423 | 1.00 | 20.41 | O |
| ATOM | 8365 | OW0 | HOH W | 356 | −25.074 | −5.158 | .825 | 1.00 | 12.47 | O |
| ATOM | 8366 | OW0 | HOH W | 357 | 18.847 | −9.326 | −5.597 | 1.00 | 34.71 | O |
| ATOM | 8367 | OW0 | HOH W | 358 | −18.846 | 14.900 | −41.501 | 1.00 | 20.09 | O |
| ATOM | 8368 | OW0 | HOH W | 359 | −33.853 | −23.539 | −31.955 | 1.00 | 36.36 | O |
| ATOM | 8369 | OW0 | HOH W | 360 | −29.933 | 4.698 | −29.699 | 1.00 | 23.74 | O |
| ATOM | 8370 | OW0 | HOH W | 361 | 7.730 | −19.522 | −23.515 | 1.00 | 33.48 | O |
| ATOM | 8371 | OW0 | HOH W | 362 | −15.308 | 28.572 | −9.378 | 1.00 | 28.15 | O |
| ATOM | 8372 | OW0 | HOH W | 364 | −23.481 | 9.725 | −40.963 | 1.00 | 23.28 | O |
| ATOM | 8373 | OW0 | HOH W | 365 | −6.063 | 13.325 | −5.152 | 1.00 | 29.83 | O |
| ATOM | 8374 | OW0 | HOH W | 366 | −30.954 | −12.300 | −39.723 | 1.00 | 36.33 | O |
| ATOM | 8375 | OW0 | HOH W | 368 | −19.445 | −30.012 | −30.510 | 1.00 | 26.74 | O |
| ATOM | 8376 | OW0 | HOH W | 369 | −11.490 | 33.988 | −23.529 | 1.00 | 34.84 | O |
| ATOM | 8377 | OW0 | HOH W | 370 | 1.344 | 16.451 | −38.268 | 1.00 | 24.65 | O |
| ATOM | 8378 | OW0 | HOH W | 371 | −58.847 | 4.347 | −30.505 | 1.00 | 40.90 | O |
| ATOM | 8379 | OW0 | HOH W | 372 | −23.073 | 7.341 | −17.178 | 1.00 | 23.88 | O |
| ATOM | 8380 | OW0 | HOH W | 374 | −27.031 | −6.122 | 2.403 | 1.00 | 16.64 | O |
| ATOM | 8381 | OW0 | HOH W | 377 | −25.074 | 30.150 | −26.525 | 1.00 | 25.84 | O |
| ATOM | 8382 | OW0 | HOH W | 378 | −3.824 | 7.573 | −2.573 | 1.00 | 30.46 | O |
| ATOM | 8383 | OW0 | HOH W | 379 | 18.960 | −19.599 | −22.862 | 1.00 | 51.14 | O |
| ATOM | 8384 | OW0 | HOH W | 380 | −20.588 | −18.410 | −48.997 | 1.00 | 18.70 | O |
| ATOM | 8385 | OW0 | HOH W | 381 | −56.852 | 8.959 | −7.735 | 1.00 | 32.34 | O |
| ATOM | 8386 | OW0 | HOH W | 382 | −30.051 | 13.097 | −4.213 | 1.00 | 39.06 | O |
| ATOM | 8387 | OW0 | HOH W | 383 | 1.551 | 24.683 | −21.788 | 1.00 | 31.36 | O |
| ATOM | 8388 | OW0 | HOH W | 384 | −34.809 | 16.962 | −11.112 | 1.00 | 27.97 | O |
| ATOM | 8389 | OW0 | HOH W | 385 | −17.796 | −25.224 | −38.660 | 1.00 | 22.67 | O |
| ATOM | 8390 | OW0 | HOH W | 386 | −19.833 | −17.067 | −24.172 | 1.00 | 43.83 | O |
| | | | | | gad67.pdb | | | | | |
| ATOM | 8391 | OW0 | HOH W | 387 | −32.698 | −7.066 | −25.830 | 1.00 | 26.72 | O |
| ATOM | 8392 | OW0 | HOH W | 388 | −43.563 | −20.715 | −32.031 | 1.00 | 25.41 | O |
| ATOM | 8393 | OW0 | HOH W | 389 | −33.787 | 15.338 | −9.088 | 1.00 | 34.87 | O |
| ATOM | 8394 | OE2 | GBA D | 1 | −5.814 | −6.121 | −22.382 | 1.00 | 35.93 | O |
| ATOM | 8395 | CD | GBA D | 1 | −5.904 | −4.877 | −22.271 | 1.00 | 31.02 | C |
| ATOM | 8396 | OE1 | GBA D | 1 | −5.137 | −4.228 | −21.531 | 1.00 | 30.07 | O |
| ATOM | 8397 | CG | GBA D | 1 | −6.969 | −4.147 | −23.068 | 1.00 | 29.73 | C |
| ATOM | 8398 | CB | GBA D | 1 | −7.657 | −3.080 | −22.221 | 1.00 | 28.06 | C |
| ATOM | 8399 | CA | GBA D | 1 | −8.653 | −2.252 | −23.021 | 1.00 | 28.04 | C |
| ATOM | 8400 | N | GBA D | 1 | −8.724 | −.916 | −22.454 | 1.00 | 27.53 | N |
| ATOM | 8401 | OE2 | GBA C | 1 | −40.986 | 5.089 | −23.829 | 1.00 | 43.01 | O |
| ATOM | 8402 | CD | GBA C | 1 | −40.425 | 5.654 | −22.867 | 1.00 | 40.97 | C |
| ATOM | 8403 | OE1 | GBA C | 1 | −40.832 | 6.747 | −22.420 | 1.00 | 42.68 | O |
| ATOM | 8404 | CG | GBA C | 1 | −39.223 | 4.988 | −22.230 | 1.00 | 40.86 | C |
| ATOM | 8405 | CB | GBA C | 1 | −38.177 | 6.029 | −21.842 | 1.00 | 38.58 | C |
| ATOM | 8406 | CA | GBA C | 1 | −37.021 | 5.418 | −21.066 | 1.00 | 39.25 | C |
| ATOM | 8407 | N | GBA C | 1 | −36.302 | 6.477 | −20.388 | 1.00 | 40.05 | N |

---

The claims defining the invention are as follows:

1. A crystal of a glutamic acid decarboxylase 65 (GAD65) polypeptide consisting of amino acids 84-585 of SEQ ID NO: 14 and a C-terminal hexahistidine tag, wherein the crystal has an orthorhombic C222$_1$ space group with unit cell dimensions of a=78.25±2.3 Å, b=99.05±2.3 Å and c=120.01±2.3 Å.

2. The crystal of claim 1, wherein the GAD65 polypeptide of the crystal has the GAD65 structure coordinates according to Table A.

* * * * *

SEQUENCE LISTING

<160> NUMBER OF SEQ ID NOS: 17

<210> SEQ ID NO 1
<211> LENGTH: 31
<212> TYPE: DNA
<213> ORGANISM: Artificial Sequence
<220> FEATURE:
<223> OTHER INFORMATION: GAD65-F283Y forward primer

<400> SEQUENCE: 1
catagtcatt attctctcaa gaagggagct g                          31

<210> SEQ ID NO 2
<211> LENGTH: 29
<212> TYPE: DNA
<213> ORGANISM: Artificial Sequence
<220> FEATURE:
<223> OTHER INFORMATION: GAD65-F283Y reverse primer

```
<400> SEQUENCE: 2
cttgagagaa taatgactat gttcagacg                                29

<210> SEQ ID NO 3
<211> LENGTH: 59
<212> TYPE: DNA
<213> ORGANISM: Artificial Sequence
<220> FEATURE:
<223> OTHER INFORMATION: GAD65-67loop forward primer

<400> SEQUENCE: 3
caaccaaatg tgtgccggat acctctttca gccagataaa cagtatgacc tgtcctatg    59

<210> SEQ ID NO 4
<211> LENGTH: 62
<212> TYPE: DNA
<213> ORGANISM: Artificial Sequence
<220> FEATURE:
<223> OTHER INFORMATION: GAD65-67loop reverse primer

<400> SEQUENCE: 4
caggtcatac tgtttatctg gctgaaagag gtatccggca cacatttggt tgcaattcca    60
tc                                                                  62

<210> SEQ ID NO 5
<211> LENGTH: 28
<212> TYPE: DNA
<213> ORGANISM: Artificial Sequence
<220> FEATURE:
<223> OTHER INFORMATION: GAD65-Y425F forward primer

<400> SEQUENCE: 5
gcctccttcc tctttcagca agataaac                                 28

<210> SEQ ID NO 6
<211> LENGTH: 28
<212> TYPE: DNA
<213> ORGANISM: Artificial Sequence
<220> FEATURE:
<223> OTHER INFORMATION: GAD65-Y425F reverse primer

<400> SEQUENCE: 6
ctgaaagagg aaggaggcat gcatttgg                                 28

<210> SEQ ID NO 7
<211> LENGTH: 30
<212> TYPE: DNA
<213> ORGANISM: Artificial Sequence
<220> FEATURE:
<223> OTHER INFORMATION: GAD67-Y292F forward primer

<400> SEQUENCE: 7
cagagtcact tttccataaa gaaagctggg                               30

<210> SEQ ID NO 8
<211> LENGTH: 31
<212> TYPE: DNA
<213> ORGANISM: Artificial Sequence
<220> FEATURE:
<223> OTHER INFORMATION: GAD67-Y292F reverse primer

<400> SEQUENCE: 8
ctttatggaa aagtgactct gttctgaggt g                             31

<210> SEQ ID NO 9
```

```
<211> LENGTH: 56
<212> TYPE: DNA
<213> ORGANISM: Artificial Sequence
<220> FEATURE:
<223> OTHER INFORMATION: GAD67-65loop forward primer

<400> SEQUENCE: 9
ccagatgcat gcatcctacc tcttccagca agacaagcat tatgatgtct cctacg        56

<210> SEQ ID NO 10
<211> LENGTH: 57
<212> TYPE: DNA
<213> ORGANISM: Artificial Sequence
<220> FEATURE:
<223> OTHER INFORMATION: GAD67-65loop reverse primer

<400> SEQUENCE: 10
gacatcataa tgcttgtctt gctggaagag gtaggatgca tgcatctggt tgcatcc       57

<210> SEQ ID NO 11
<211> LENGTH: 28
<212> TYPE: DNA
<213> ORGANISM: Artificial Sequence
<220> FEATURE:
<223> OTHER INFORMATION: GAD67-Y434F forward primer

<400> SEQUENCE: 11
gcaggattcc tcttccagcc agacaagc                                       28

<210> SEQ ID NO 12
<211> LENGTH: 26
<212> TYPE: DNA
<213> ORGANISM: Artificial Sequence
<220> FEATURE:
<223> OTHER INFORMATION: GAD67-Y434F reverse primer

<400> SEQUENCE: 12
ggaagaggaa tcctgcacac atctgg                                         26

<210> SEQ ID NO 13
<211> LENGTH: 594
<212> TYPE: PRT
<213> ORGANISM: Homo sapiens

<400> SEQUENCE: 13
```

Met Ala Ser Ser Thr Pro Ser Ser Ser Ala Thr Ser Ser Asn Ala Gly
1               5                   10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
            35                  40                  45

Gly Phe Leu Gln Arg Thr Asn Ser Leu Glu Glu Lys Ser Arg Leu Val
        50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

-continued

```
His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
            165                 170                 175

Lys Tyr Gly Val Arg Thr Gly His Pro Arg Phe Phe Asn Gln Leu Ser
        180                 185                 190

Thr Gly Leu Asp Ile Ile Gly Leu Ala Gly Glu Trp Leu Thr Ser Thr
    195                 200                 205

Ala Asn Thr Asn Met Phe Thr Tyr Glu Ile Ala Pro Val Phe Val Leu
210                 215                 220

Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Gly Ala Ile Ser Asn
            245                 250                 255

Met Tyr Ser Ile Met Ala Ala Arg Tyr Lys Tyr Phe Pro Glu Val Lys
        260                 265                 270

Thr Lys Gly Met Ala Ala Val Pro Lys Leu Val Leu Phe Thr Ser Glu
    275                 280                 285

Gln Ser His Tyr Ser Ile Lys Lys Ala Gly Ala Ala Leu Gly Phe Gly
290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
            325                 330                 335

Val Pro Phe Tyr Val Asn Ala Thr Ala Gly Thr Thr Val Tyr Gly Ala
        340                 345                 350

Phe Asp Pro Ile Gln Glu Ile Ala Asp Ile Cys Glu Lys Tyr Asn Leu
    355                 360                 365

Trp Leu His Val Asp Ala Ala Trp Gly Gly Gly Leu Leu Met Ser Arg
370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
            405                 410                 415

Leu Val Lys Glu Lys Gly Ile Leu Gln Gly Cys Asn Gln Met Cys Ala
        420                 425                 430

Gly Tyr Leu Phe Gln Pro Asp Lys Gln Tyr Asp Val Ser Tyr Asp Thr
    435                 440                 445

Gly Asp Lys Ala Ile Gln Cys Gly Arg His Val Asp Ile Phe Lys Phe
450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
            485                 490                 495

Arg Glu Glu Phe Glu Met Val Phe Asn Gly Glu Pro Glu His Thr Asn
        500                 505                 510

Val Cys Phe Trp Tyr Ile Pro Gln Ser Leu Arg Gly Val Pro Asp Ser
    515                 520                 525

Pro Gln Arg Arg Glu Lys Leu His Lys Val Ala Pro Lys Ile Lys Ala
530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
```

565                 570                 575
Gln Ser Asp Ile Asp Phe Leu Ile Glu Glu Ile Glu Arg Leu Gly Gln
                580                 585                 590

Asp Leu

<210> SEQ ID NO 14
<211> LENGTH: 585
<212> TYPE: PRT
<213> ORGANISM: Homo sapiens

<400> SEQUENCE: 14

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
                20                  25                  30

Ala Gln Lys Phe Thr Gly Gly Ile Gly Asn Lys Leu Cys Ala Leu Leu
            35                  40                  45

Tyr Gly Asp Ala Glu Lys Pro Ala Glu Ser Gly Gly Ser Gln Pro Pro
50                  55                  60

Arg Ala Ala Arg Lys Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Phe
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
290                 295                 300

Asp Glu Arg Gly Lys Met Ile Pro Ser Asp Leu Glu Arg Arg Ile Leu
305                 310                 315                 320

Glu Ala Lys Gln Lys Gly Pro Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

```
Ile Cys Lys Lys Tyr Lys Ile Trp Met His Val Asp Ala Ala Trp Gly
            355                 360                 365

Gly Gly Leu Leu Met Ser Arg Lys His Lys Trp Lys Leu Ser Gly Val
        370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510

Leu Arg Thr Leu Glu Asp Asn Glu Glu Arg Met Ser Arg Leu Ser Lys
        515                 520                 525

Val Ala Pro Val Ile Lys Ala Arg Met Met Glu Tyr Gly Thr Thr Met
    530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 15
<211> LENGTH: 497
<212> TYPE: PRT
<213> ORGANISM: Homo sapiens

<400> SEQUENCE: 15

Asn Tyr Ala Phe Leu His Ala Thr Asp Leu Leu Pro Ala Cys Asp Gly
1               5                   10                  15

Glu Arg Pro Thr Leu Ala Phe Leu Gln Asp Val Met Asn Ile Leu Leu
            20                  25                  30

Gln Tyr Val Val Lys Ser Phe Asp Arg Ser Thr Lys Val Ile Asp Phe
        35                  40                  45

His Tyr Pro Asn Glu Leu Leu Gln Glu Tyr Asn Trp Glu Leu Ala Asp
    50                  55                  60

Gln Pro Gln Asn Leu Glu Glu Ile Leu Met His Cys Gln Thr Thr Leu
65                  70                  75                  80

Lys Tyr Ala Ile Lys Thr Gly His Pro Arg Tyr Phe Asn Gln Leu Ser
                85                  90                  95

Thr Gly Leu Asp Met Val Gly Leu Ala Ala Asp Trp Leu Thr Ser Thr
            100                 105                 110

Ala Asn Thr Asn Met Phe Thr Tyr Glu Ile Ala Pro Val Phe Val Leu
        115                 120                 125

Leu Glu Tyr Val Thr Leu Lys Lys Met Arg Glu Ile Ile Gly Trp Pro
    130                 135                 140
```

Gly Gly Ser Gly Asp Gly Ile Phe Ser Pro Gly Gly Ala Ile Ser Asn
145                 150                 155                 160

Met Tyr Ala Met Met Ile Ala Arg Phe Lys Met Phe Pro Glu Val Lys
            165                 170                 175

Glu Lys Gly Met Ala Ala Leu Pro Phe Leu Ile Ala Phe Thr Ser Glu
            180                 185                 190

His Ser His Phe Ser Leu Lys Lys Gly Ala Ala Leu Gly Ile Gly
        195                 200                 205

Thr Asp Ser Val Ile Leu Ile Lys Cys Asp Glu Arg Gly Lys Met Ile
    210                 215                 220

Pro Ser Asp Leu Glu Arg Arg Ile Leu Glu Ala Lys Gln Lys Gly Pro
225                 230                 235                 240

Val Pro Phe Leu Val Ser Ala Thr Ala Gly Thr Thr Val Tyr Gly Ala
                245                 250                 255

Phe Asp Pro Leu Leu Ala Val Ala Asp Ile Cys Lys Lys Tyr Lys Ile
                260                 265                 270

Trp Met His Val Asp Ala Ala Trp Gly Gly Gly Leu Leu Met Ser Arg
            275                 280                 285

Lys His Lys Trp Lys Leu Ser Gly Val Glu Arg Ala Asn Ser Val Thr
            290                 295                 300

Trp Asn Pro His Lys Met Met Gly Val Pro Leu Gln Cys Ser Ala Leu
305                 310                 315                 320

Leu Val Arg Glu Glu Gly Leu Met Gln Asn Cys Asn Gln Met His Ala
                325                 330                 335

Ser Tyr Leu Phe Gln Gln Asp Lys His Tyr Asp Leu Ser Tyr Asp Thr
            340                 345                 350

Gly Asp Lys Ala Leu Gln Cys Gly Arg His Val Asp Val Phe Lys Leu
        355                 360                 365

Trp Leu Met Trp Arg Ala Lys Gly Thr Thr Gly Phe Glu Ala His Val
    370                 375                 380

Asp Lys Cys Leu Glu Leu Ala Glu Tyr Leu Tyr Asn Ile Ile Lys Asn
385                 390                 395                 400

Arg Glu Gly Tyr Glu Met Val Phe Asp Gly Lys Pro Gln His Thr Asn
                405                 410                 415

Val Cys Phe Trp Tyr Ile Pro Pro Ser Leu Arg Thr Leu Glu Asp Asn
                420                 425                 430

Glu Glu Arg Met Ser Arg Leu Ser Lys Val Ala Pro Val Ile Lys Ala
            435                 440                 445

Arg Met Met Glu Tyr Gly Thr Thr Met Val Ser Tyr Gln Pro Leu Gly
    450                 455                 460

Asp Lys Val Asn Phe Phe Arg Met Val Ile Ser Asn Pro Ala Ala Thr
465                 470                 475                 480

His Gln Asp Ile Asp Phe Leu Ile Glu Glu Ile Glu Arg Leu Gly Gln
                485                 490                 495

Asp

<210> SEQ ID NO 16
<211> LENGTH: 501
<212> TYPE: PRT
<213> ORGANISM: Homo sapiens

<400> SEQUENCE: 16

Thr Asp Phe Ser Asn Leu Phe Ala Arg Asp Leu Leu Pro Ala Lys Asn
1               5                   10                  15

```
Gly Glu Glu Gln Thr Val Gln Phe Leu Leu Glu Val Val Asp Ile Leu
             20                  25                  30

Leu Asn Tyr Val Arg Lys Thr Phe Asp Arg Ser Thr Lys Val Leu Asp
         35                  40                  45

Phe His His Pro His Gln Leu Leu Glu Gly Met Glu Gly Phe Asn Leu
 50                  55                  60

Glu Leu Ser Asp His Pro Glu Ser Leu Glu Gln Ile Leu Val Asp Cys
 65                  70                  75                  80

Arg Asp Thr Leu Lys Tyr Gly Val Arg Thr Gly His Pro Arg Phe Phe
             85                  90                  95

Asn Gln Leu Ser Thr Gly Leu Asp Ile Ile Gly Leu Ala Gly Glu Trp
            100                 105                 110

Leu Thr Ser Thr Ala Asn Thr Asn Met Phe Thr Tyr Glu Ile Ala Pro
        115                 120                 125

Val Phe Val Leu Met Glu Gln Ile Thr Leu Lys Lys Met Arg Glu Ile
        130                 135                 140

Val Gly Trp Ser Ser Lys Asp Gly Asp Gly Ile Phe Ser Pro Gly Gly
145                 150                 155                 160

Ala Ile Ser Asn Met Tyr Ser Ile Met Ala Ala Arg Tyr Lys Tyr Phe
                165                 170                 175

Pro Glu Val Lys Thr Lys Gly Met Ala Ala Val Pro Lys Leu Val Leu
                180                 185                 190

Phe Thr Ser Glu Gln Ser His Tyr Ser Ile Lys Lys Ala Gly Ala Ala
        195                 200                 205

Leu Gly Phe Gly Thr Asp Asn Val Ile Leu Ile Lys Cys Asn Glu Arg
210                 215                 220

Gly Lys Ile Ile Pro Ala Asp Phe Glu Ala Lys Ile Leu Glu Ala Lys
225                 230                 235                 240

Gln Lys Gly Tyr Val Pro Phe Tyr Val Asn Ala Thr Ala Gly Thr Thr
                245                 250                 255

Val Tyr Gly Ala Phe Asp Pro Ile Gln Glu Ile Ala Asp Ile Cys Glu
        260                 265                 270

Lys Tyr Asn Leu Trp Leu His Val Asp Ala Ala Trp Gly Gly Gly Leu
        275                 280                 285

Leu Met Ser Arg Lys His Arg His Lys Leu Asn Gly Ile Glu Arg Ala
290                 295                 300

Asn Ser Val Thr Trp Asn Pro His Lys Met Met Gly Val Leu Leu Gln
305                 310                 315                 320

Cys Ser Ala Ile Leu Val Lys Glu Lys Gly Ile Leu Gln Gly Cys Asn
                325                 330                 335

Gln Met Cys Ala Gly Tyr Leu Phe Gln Pro Asp Lys Gln Tyr Asp Val
            340                 345                 350

Ser Tyr Asp Thr Gly Asp Lys Ala Ile Gln Cys Gly Arg His Val Asp
        355                 360                 365

Ile Phe Lys Phe Trp Leu Met Trp Lys Ala Lys Gly Thr Val Gly Phe
        370                 375                 380

Glu Asn Gln Ile Asn Lys Cys Leu Glu Leu Ala Glu Tyr Leu Tyr Ala
385                 390                 395                 400

Lys Ile Lys Asn Arg Glu Glu Phe Glu Met Val Phe Asn Gly Glu Pro
            405                 410                 415

Glu His Thr Asn Val Cys Phe Trp Tyr Ile Pro Gln Ser Leu Arg Gly
        420                 425                 430

Val Pro Asp Ser Pro Gln Arg Arg Glu Lys Leu His Lys Val Ala Pro
        435                 440                 445
```

```
Lys Ile Lys Ala Leu Met Met Glu Ser Gly Thr Thr Met Val Gly Tyr
    450                 455                 460

Gln Pro Gln Gly Asp Lys Ala Asn Phe Phe Arg Met Val Ile Ser Asn
465                 470                 475                 480

Pro Ala Ala Thr Gln Ser Asp Ile Asp Phe Leu Ile Glu Glu Ile Glu
                485                 490                 495

Arg Leu Gly Gln Asp
            500

<210> SEQ ID NO 17
<211> LENGTH: 504
<212> TYPE: PRT
<213> ORGANISM: Homo sapiens

<400> SEQUENCE: 17

Thr Asp Phe Ser Asn Leu Phe Ala Arg Asp Leu Leu Pro Ala Lys Asn
1               5                   10                  15

Gly Glu Glu Gln Thr Val Gln Phe Leu Leu Glu Val Val Asp Ile Leu
            20                  25                  30

Leu Asn Tyr Val Arg Lys Thr Phe Asp Arg Ser Thr Lys Val Leu Asp
        35                  40                  45

Phe His His Pro His Gln Leu Leu Glu Gly Met Glu Gly Phe Asn Leu
    50                  55                  60

Glu Leu Ser Asp His Pro Glu Ser Leu Glu Gln Ile Leu Val Asp Cys
65                  70                  75                  80

Arg Asp Thr Leu Lys Tyr Gly Val Arg Thr Gly His Pro Arg Phe Phe
                85                  90                  95

Asn Gln Leu Ser Thr Gly Leu Asp Ile Ile Gly Leu Ala Gly Glu Trp
            100                 105                 110

Leu Thr Ser Thr Ala Asn Thr Asn Met Phe Thr Tyr Glu Ile Ala Pro
        115                 120                 125

Val Phe Val Leu Met Glu Gln Ile Thr Leu Lys Lys Met Arg Glu Ile
    130                 135                 140

Val Gly Trp Ser Ser Lys Asp Gly Asp Gly Ile Phe Ser Pro Gly Gly
145                 150                 155                 160

Ala Ile Ser Asn Met Tyr Ser Ile Met Ala Ala Arg Tyr Lys Tyr Phe
                165                 170                 175

Pro Glu Val Lys Thr Lys Gly Met Ala Ala Val Pro Lys Leu Val Leu
            180                 185                 190

Phe Thr Ser Glu Gln Ser His Tyr Ser Ile Lys Lys Ala Gly Ala Ala
        195                 200                 205

Leu Gly Phe Gly Thr Asp Asn Val Ile Leu Ile Lys Cys Asn Glu Arg
    210                 215                 220

Gly Lys Ile Ile Pro Ala Asp Phe Glu Ala Lys Ile Leu Glu Ala Lys
225                 230                 235                 240

Gln Lys Gly Tyr Val Pro Phe Tyr Val Asn Ala Thr Ala Gly Thr Thr
                245                 250                 255

Val Tyr Gly Ala Phe Asp Pro Ile Gln Glu Ile Ala Asp Ile Cys Glu
            260                 265                 270

Lys Tyr Asn Leu Trp Leu His Val Asp Ala Ala Trp Gly Gly Gly Leu
        275                 280                 285

Leu Met Ser Arg Lys His Arg His Lys Leu Asn Gly Ile Glu Arg Ala
    290                 295                 300

Asn Ser Val Thr Trp Asn Pro His Lys Met Met Gly Val Leu Leu Gln
305                 310                 315                 320
```

-continued

```
Cys Ser Ala Ile Leu Val Lys Glu Lys Gly Ile Leu Gln Gly Cys Asn
            325                 330                 335

Gln Met Cys Ala Gly Tyr Leu Phe Gln Pro Asp Lys Gln Tyr Asp Val
            340                 345                 350

Ser Tyr Asp Thr Gly Asp Lys Ala Ile Gln Cys Gly Arg His Val Asp
            355                 360                 365

Ile Phe Lys Phe Trp Leu Met Trp Lys Ala Lys Gly Thr Val Gly Phe
            370                 375                 380

Glu Asn Gln Ile Asn Lys Cys Leu Glu Leu Ala Glu Tyr Leu Tyr Ala
385                 390                 395                 400

Lys Ile Lys Asn Arg Glu Glu Phe Glu Met Val Phe Asn Gly Glu Pro
            405                 410                 415

Glu His Thr Asn Val Cys Phe Trp Tyr Ile Pro Gln Ser Leu Arg Gly
            420                 425                 430

Val Pro Asp Ser Pro Gln Arg Arg Glu Lys Leu His Lys Val Ala Pro
            435                 440                 445

Lys Ile Lys Ala Leu Met Met Glu Ser Gly Thr Thr Met Val Gly Tyr
    450                 455                 460

Gln Pro Gln Gly Asp Lys Ala Asn Phe Phe Arg Met Val Ile Ser Asn
465                 470                 475                 480

Pro Ala Ala Thr Gln Ser Asp Ile Asp Phe Leu Ile Glu Glu Ile Glu
            485                 490                 495

Arg Leu Gly Gln Asp Leu His His
            500
```